(12) United States Patent
Ammenn et al.

(10) Patent No.: US 7,229,987 B2
(45) Date of Patent: Jun. 12, 2007

(54) MULTICYCLIC COMPOUNDS FOR USE AS MELANIN CONCENTRATING HORMONE ANTAGONISTS IN THE TREATMENT OF OBESITY AND DIABETES

(75) Inventors: Jochen Ammenn, Hamburg (DE); James Ronald Gillig, Indianapolis, IN (US); Lawrence Joseph Heinz, Pittsboro, IN (US); Philip Arthur Hipskind, New Palestine, IN (US); Michael Dean Kinnick, Indianapolis, IN (US); Yen-Shi Lai, Chapel Hill, NC (US); John Michael Morin, Jr., Brownsburg, IN (US); James Arthur Nixon, Indianapolis, IN (US); Carsten Ott, Bad Segeberg (DE); Kenneth Allen Savin, Indianapolis, IN (US); Theo Schotten, Vierhoefen (DE); Lawrence John Slieker, Carmel, IN (US); Nancy June Snyder, Lizton, IN (US); Michael Alan Robertson, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 32 days.

(21) Appl. No.: 10/512,986

(22) PCT Filed: May 6, 2003

(86) PCT No.: PCT/US03/12123

§ 371 (c)(1),
(2), (4) Date: Apr. 28, 2005

(87) PCT Pub. No.: WO03/097047

PCT Pub. Date: Nov. 27, 2003

(65) Prior Publication Data

US 2005/0272718 A1    Dec. 8, 2005

Related U.S. Application Data

(60) Provisional application No. 60/380,351, filed on May 13, 2002.

(51) Int. Cl.
*A61K 31/5355* (2006.01)
*A61K 31/454* (2006.01)
*C07D 401/12* (2006.01)
*C07D 403/12* (2006.01)
*C07D 263/32* (2006.01)

(52) U.S. Cl. ............... 514/217.1; 514/227.8; 514/236.8; 514/326; 514/374; 514/378; 540/603; 544/60; 544/137; 546/208; 548/235; 548/247

(58) Field of Classification Search ......... 540/603
See application file for complete search history.

(56) References Cited

U.S. PATENT DOCUMENTS 2,641,601 A   6/1953   Rachlin et al.
2,858,318 A   10/1958  Graf et al.
3,708,598 A   1/1973   Griot
6,034,106 A   3/2000   Feng et al.

FOREIGN PATENT DOCUMENTS

WO   WO 00/06556   10/2000
WO   WO 02/10146   2/2002
WO   WO 02/32897   4/2002

OTHER PUBLICATIONS

STN International, HCAPLUS Database, Columbus, OH, Accession No. 2000:98534.
Gallagher, et al., "Regulation of stress-induced cytokine production by pyridinylimidazoles; inhibition of CSBP kinase," Bioorganic & Medicinal Chemistry, Elsevier Science Ltd, GB, vol. 5, No. 1, pp. 49-64; XP002094123 (1997).
Diwu, et al, "Fluorescent molecular probes II. The synthesis, spectral properties and use of dluorescent solvatochromic dapoxyl dyes," Photochemistry and Photobiology, Oxford, GB, vol. 66, No. 4, pp. 424-431; XP009003751 (1997).
Ni, et al., "Synthesis and Luminescent Properties of 2-Phenyl-5-{4'2-(6-substituent-2H-benz'De isoquinoline-1,3(2H)-dione-2-yl)polymethano-amino-{phenyl-1,3,4-oxadiazole," Chemistry Letters, Chemical Society of Japan, Tokyo, JP, No. 1, pp. 101-102; XP000671632 (1997).
De Laszlo S E, et al., "Pyrroles and other heterocycles as inhibitors of P38 kinase," Bioorganic & Medicinal Chemistry Letters, Oxford, GB, vol. 8, No. 19, pp. 2689-2694; XP004139602 (1998).
McLay, et al, "The discovery of RPR 200765A, a p38 MAP kinase inhibitor displaying a good oral anti-arthrititc efficacy," Bioorganic & Medicinal Chemistry Letters, vol. 9, pp. 537-554; XP002248371 (2001.
Meyer, et al., "Water-binding solid scintillators: synthesis, emission properties, and tests in 3H and 14C counting," Chem. Eur. J., vol. 6, No. 15, pp. 2809-2817; XP002248372 (2000).
Database Crossfire Beilstein Online, Beilstein Institut zur Forderung der Chemischen Wissenschaften, Frankfurt am Main, DE, Database accession No. BRN 567765; XP002248373; Abstract & Shevchenko, et al, Sov. Prog. Chem, vol. 44, No. 8, pp. 58-61 (1978).
Database Crossfire Beilstein Online, Beilstein Institut zur Forderung der Chemischen Wissenschaften, Frankfurt am Main, DE, Database accession No. BRN 6936668; XP002248374; Abstract & Litak, et al, J. Heterocycl. Chem., vol. 31, No. 2, pp. 457-480 (1994).
Database Crossfire Beilstein Online, Beilstein Institut zur Forderung der Chemischen Wissenschaften, Frankfurt am Main, DE, Database accession No. BRN 1507962, 1502375, 1512417; XP002248375; Abstract & Iyer & Gopalachari: Indian J. Chem., vol. 11, p. 1260 (1973).
Goff, et al., "The Preparation of 2,4-Disubstituted Thiazoles on Solid Support," Tetrahedron Letters, Elsevier Science Publishers, Amsterdam, NL, vol. 40, No. 3, pp. 423-426; XP004151347 (1999).
Penning, et al, Synthesis and Biological Evaluation of the 1,5-Diarylpyrazole Class of Cyclooxygenase-2 Inhibitors: Identification of 4-'5-(4-Methylphenyl)-3-(trifluoromethyl)-1 H-pyrazole-1-yl benzene-sulfonamide (SC-58635, Celecoxib), Journal of Medicinal Chemistry, American Chemical Society, Washington, US, vol. 40, pp. 1347-1365; XP002114833 (1997).

*Primary Examiner*—Kamal A. Saeed
*Assistant Examiner*—Andrew B. Freistein
(74) *Attorney, Agent, or Firm*—Francis O. Ginah

(57) ABSTRACT

The present invention relates to a melanin concentrating hormone antagonist compound of formula I: (I); or a pharmaceutically acceptable salt, solvate, enantiomer or prodrug thereof useful in the treatment, prevention or amelioration of symptoms associated with obesity and related diseases.

9 Claims, 1 Drawing Sheet

MULTICYCLIC COMPOUNDS FOR USE AS MELANIN CONCENTRATING HORMONE ANTAGONISTS IN THE TREATMENT OF OBESITY AND DIABETES

This is National filing under 35 U.S.C. § 371 of PCT/US03/1213, filed May 6, 2003, which claims priority from U.S. Provisional Application No. 60/380,351, filed May 13, 2002.

FIELD OF INVENTION

The present invention is in the field of medicine, particularly in the treatment of obesity and diseases caused by or exacerbated by obesity. More specifically, the present invention relates to antagonists of melanin concentrating hormone useful in the prevention and treatment of obesity and related diseases.

BACKGROUND OF THE INVENTION

The affluence of the 90's along with the exponential increase in food production particularly in Western and Asian economies has resulted in feeding patterns that lead to obesity. Obesity is defined as being excessively overweight. Excessive weight is generally characterized by excessive body fat, because unused energy is stored in the adipose tissues as fat.

Obesity has associated with it, economic and social costs. Obese people, an increasing proportion of developed and developing societies, are regarded as having out of control feeding habits often associated with low self-esteem. Moreover, obese persons are more likely to have medical problems associated with or exacerbated by the excess body weight. Examples of medical conditions caused, exacerbated or triggered by excessive weight include bone fractures, pains in the knee joints, arthritis, increased risk of hypertension, artherosclerosis, stroke, diabetes, etc.

BACKGROUND OF THE INVENTION

Melanin concentrating hormone (MCH) is a 19 amino acid neuropeptide produced in the lateral hypothalamic area and zona incerta, although MCH-expressing neurons project to numerous regions of the brain. MCH is processed from a larger pre-prohormone that also includes a second peptide, NEI, and possibly a third, NGE (Nahon, Crit Rev in Neurobiology, 8:221–262, 1994). MCH mediates its effects through at least two G protein-coupled receptors, MCHR1 and MCHR2 (Saito et al. Nature 400: 265–269, 1999; Hill et al., J Biol Chem 276: 20125–20129, 2001). Both receptors are expressed in regions of the brain consistent with MCH neuronal projection and known MCH physiologic function (Hervieu et al., Eur J Neuroscience 12: 1194–1216, 2000; Hill et al., J Biol Chem 276: 20125–20129, 2001; Sailer et al., Proc Nat Acad Sci 98: 7564–7569, 2001).

Extensive evidence exists to support the orexigenic activity of MCH. MCH mRNA is elevated in rodent models of obesity and in the fasted state (Qu et al., Nature 380: 243–247, 1996). Intracerebroventricularly administered MCH increases feeding and blocks the anorexic effect of α-melanocyte stimulating hormone (Ludwig et al., Am J Physiol 274: E627–E633, 1998). MCH knock-out mice (MCH$^{-/-}$ mice) are lean, hypophagic and hypometabolic (Shimada et al., Nature 396: 670–674, 1998), while MCH over-expressing transgenic mice are obese and insulin resistant (Ludwig et al., J Clin Invest 107: 379–386, 2001). MCHR1$^{-/-}$ mice have recently been reported to be lean and hypermetabolic, indicating that the R1 isoform mediates at least some of the metabolic effects of MCH (Marsh et al., Proc Nat Acad Sci 99: 3240–3245, 2002; Chen et al., Endocrinology, 2002, in press).

In addition to its effects on feeding, MCH has been implicated in regulation of the hypothalamic-pituitary-adrenal axis through modulation of CRF and ACTH release (Bluet-Pajot et al., J Neuroendocrinol 7: 297–303, 1995). MCH may also play a role in the modulation of reproductive function (Murray et al., J Neuroendocrinol 12: 217–223, 2000) and memory (Monzon et al., Peptides 20: 1517–1519, 1999).

The current preferred treatment for obesity as well as Type II non-insulin dependent diabetes is diet and exercise with a view toward weight reduction and improved insulin sensitivity for diabetics. Patient compliance, however, is usually poor. The problem is compounded by the fact that there are currently only two medications approved for the treatment of obesity (sibutramine, or Meridian and orlistat, or Xenical™.

PCT application number WO 01/21577 (JP00/06375) filed Sep. 19, 2000, discloses compounds reportedly useful as antagonists of the MCH receptor. In particular the WO 01/21577 application claims a compound of formula A

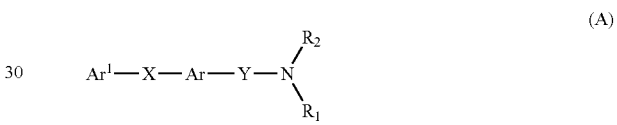

wherein:

Ar$^1$ is a cyclic group that may have substituents;

X is a spacer having a main chain of 1 to 6 atoms;

Y is a bond or a spacer having a main chain of 1 to 6 atoms;

Ar is a monocyclic aromatic ring which may be condensed with a 4 to 8 membered non-aromatic ring, and may have further substituents;

R$^1$ and R$^2$ are independently hydrogen atom or a hydrocarbon group which may have substituents;

R$^1$ and R$^2$ together with the adjacent nitrogen atom may form a nitrogen-containing hetero ring which may have Substituents; R$^2$ may form a spiro ring together with Ar; or R$^2$, together with the adjacent nitrogen atom and Y, may form a nitrogen-containing hetero ring which may have substituents; or salts thereof.

PCT application number WO 01/82925, filed Apr. 26, 2001, also discloses compounds reportedly useful as antagonists of the MCH receptor. In particular the WO 01/82925 application claims a compound of formula B

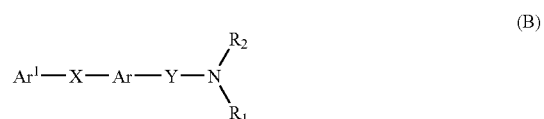

wherein:

Ar$^1$ is an optionally substituted cyclic group;

X and Y are independently a spacer having a C$_{1-6}$ main chain;

Ar is an optionally substituted fused polycyclic aromatic ring;

R¹ and R² are independently hydrogen atom or an optionally substituted hydrocarbon group; or alternatively R¹ and R² together with the nitrogen atom adjacent thereto may form a nitrogenous heterocycle, or R² together with the nitrogen atom adjacent thereto and Y may form an optionally substituted nitrogenous heterocycle, or R² together with the nitrogen atom adjacent thereto, Y, and Ar may form a fused ring.

PCT application number WO 01/87834, filed May 15, 2001, also discloses compounds reportedly useful as antagonists of the MCH receptor. In particular the WO 01/87834 application claims a compound of formula C.

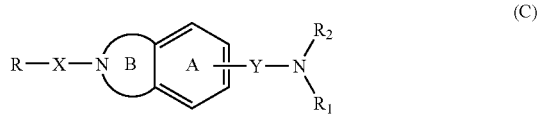

Wherein;

R represents hydrogen, halogen, or an optionally substituted cyclic group; X represents a bond or a spacer in which the main chain has one to ten atoms; Y represents a spacer in which the main chain has one to six atoms; ring A represents a benzene ring which may have other substituents; ring B represents a five- to nine-membered nitrogenous nonaromatic heterocycle which may have other substituents; and R¹ and R² are the same or different and each represents hydrogen, an optionally substituted hydrocarbon group, or an optionally substituted heterocyclic group, or R¹ and R² may form an optionally substituted nitrogenous heterocycle in cooperation with the adjacent nitrogen atom and R² may form an optionally substituted nitrogenous heterocycle in cooperation with the adjacent nitrogen atom and Y.

Japanese patent application number JP2001-226269A also discloses compounds reportedly useful as antagonists of the MCH receptor. In particular the JP2001-226269A application claims a compound of formula D.

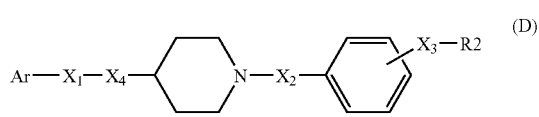

Wherein:

Ar is a substituted group-contg. arom. ring, $X_1$ is a substituted group-contg. divalent main chain of 1–5 atoms, $X_2$, $X_3$ and $X_4$ are linking arms, and R2 is a basic substituting group, and its salts.

Current treatments targeted at obesity have side effects. Examples of such treatments include phen-phen, and various over-the-counter appetite suppressants. These agents have not been proven effective for all patients and for sustainable periods of time. Similarly, the approved treatments, sibutramine (Meridia™) and orlistat (Xenical™) have been associated with side effects which may compromise compliance and may preclude long term use for sustained weight loss for certain patient populations.

Therefore, there is a need for new and/or improved therapeutically effective agents useful as antagonist of melanocortin releasing hormone to better control the dietary habits, minimize the preponderance of obesity and treat, prevent and/or ameliorate the effects of obesity including for example diabetes.

SUMMARY OF INVENTION

The present invention relates to a compound of formula I:

$$\text{Ar}^1\text{-L}^1\text{-Ar}^2\text{—Ar}^3\text{-L}^2\text{-Q} \tag{I}$$

or a pharmaceutically acceptable salt, solvate, enantiomer, diastereomer or mixture of diastereomers or prodrug thereof wherein:

$\text{Ar}^1$ is a cyclic group optionally substituted with one to five groups selected from $C_1$–$C_8$ alkyl, $C_2$–$C_8$ alkenyl, $C_2$–$C_8$ alkynyl, hydroxy, $C_1$–$C_8$ alkoxy, $C_1$–$C_8$ alkylaryl, phenyl, —O-aryl, heteroaryl, cycloalkyl, $C_1$–$C_8$ alkylcycloalkyl, cyano, —$(CH_2)_n NR^{16}$, $C_1$–$C_8$ haloalkyl, $C_1$–$C_8$ haloalkoxy, halo, $(CH_2)_n COR^6$, $(CH_2)_n NR^5 SO_2 R^6$, —$(CH_2)_n C(O)NR^6 R^6$, heterocyclic, and $C_1$–$C_8$ alkylheterocyclic; wherein the cycloalkyl, phenyl, aryl, and heterocyclic susbstitutents are each optionally substituted with one to three groups selected from hydroxy, $C_1$–$C_8$ alkoxyalkyl, $C_1$–$C_8$ haloalkoxy, $C_1$–$C_8$ alkyl, halo, $C_1$–$C_8$ haloalkyl, nitro, cyano, amino, carboxamido, phenyl, aryl, alkylheterocyclic, heterocyclic, and oxo;

$L^1$ is a bond or a divalent linker having a main chain of 1 to 10 atoms; or represented by the formula $X_2$—$(CR^3R^4)_m$—$X_3$ where $X_2$ is attached to $\text{Ar}^1$ and $X_3$ is attached to $\text{Ar}^2$ wherein $R^3$ and $R^4$ are independently selected from a bond, hydrogen, $C_1$–$C_8$ alkyl, $C_2$–$C_8$ alkylene, $C_2$–$C_8$ alkynyl, phenyl, aryl, $C_1$–$C_8$ alkylaryl; wherein the alkyl, alkenyl, phenyl, and aryl groups are optionally substituted with one to five substitutents independently selected from oxo, nitro, cyano, $C_1$–$C_8$ alkyl, aryl, halo, hydroxy, $C_1$–$C_8$ alkoxy, $C_1$–$C_8$ haloalkyl, $(CH_2)_n C(O)R^6$, and $(CH_2)_n CONR^6 R^6$;

$X_2$ is independently oxygen, —CH, —CONH$(CR^3R^4)_m$, —NHCO$(CR^3R^4)_m$, —$(CR^3R^4)_m$, —CHR$^6$, —NR$^5$, S, SO, SO$_2$, —O$(CR^3R^4)_m$, or —S$(CR^3R^4)_m$;

$X_3$ is independently oxygen, —C, —CH, —CHR$^6$, —$(CR^3R^4)_m$, —CONH$(CR^3R^4)_m$, —NHCO$(CR^3R^4)_m$, —NR$^5$, —NR$^5(CR^3R^4)_m$, S, SO$(CR^3R^4)_m$, SO$_2(CR^3R^4)_m$, S$(CR^3R^4)_m$, SO, or SO$_2$; —O$(CR^3R^4)_m$, or —S$(CR^3R^4)_m$;

$\text{AR}^2$ is a 5-member monocyclic heterocyclic aromatic group or positional isomer thereof, having 1, 2, or 3 heteroatoms independently selected from nitrogen, oxygen and sulfur; and optionally substituted with one to three substitutents selected from $C_1$–$C_8$ alkyl, $C_2$–$C_8$ alkenyl, $C_2$–$C_8$ alkynyl, hydroxy, $C_1$–$C_8$ alkoxy, $C_1$–$C_8$ alkylaryl, phenyl, aryl, $C_3$–$C_8$ cycloalkyl, $C_1$–$C_8$ alkylcycloalkyl, cyano, $C_1$–$C_8$ haloalkyl, halo, $(CH_2)_n C(O)R^6$, $(CH_2)_n C(O)OR^6$, $(CH_2)_n NR^5 SO_2 R^6$, $(CH_2)_n C(O)NR^6 R^6$, and $C_1$–$C_8$ alkylheterocyclic;

$\text{AR}^3$ is a 6-member monocyclic, aromatic, carbocyclic or heterocyclic ring having 0, 1, 2, or 3 heteroatoms selected from nitrogen, oxygen and sulfur and which is optionally substituted with one to three substitutents independently selected from $C_1$–$C_8$ alkyl, $C_2$–$C_8$ alkenyl, $C_2$–$C_8$ alkynyl, halo, —NWR$^5$, $C_1$–$C_8$ haloalkyl, $C_3$–$C_8$ cycloalkyl, hydroxy, alkoxy, $(CH_2)_n C(O)R^6$, $(CH_2)_n C(O)OR^6$, $(CH_2)_n NR^5 SO_2 R^6$, $(CH_2)_n C(O)NR^6 R^6$, phenyl, $C_1$–$C_8$ alkylaryl, and aryl;

$L^2$ is a divalent linker having a chain length of between 1 and 10 atoms in the main chain or is represented by the formula:

$$X_4\text{—}(CR^3R^4)_m\text{—}X_5;$$

wherein $X_4$ is attached to $AR^3$ and is selected from the group consisting of C, —CH, $CHR^6$, —CO, O, —$NR^5$, —NC(O)—, —NC(S), —C(O)$NR^5$—, —$N^6C(O)NR^6$, —$NR^6C(S)NR^6$, —$SO_2NR^7$, —$NRSO_2R^7$, and —$NR^6OC(NR^5)NR^6$;

$X_5$ is selected from the group consisting of —$CH_2$, —CH, —$O(CR^3R^4)_m$, $NR^3(CR^3R^4)_m$, SO, $SO_2$, S, and $SCH_2$; wherein the group $X_4$—$(CR^3R^4)_m$—$X_5$ imparts stability to the compound of formula (1) and may be a saturated or unsaturated chain or divalent linker.

Q is a basic group or a group represented by —$NR^1R^2$; wherein $R^1$ and $R^2$ are independently hydrogen, $C_1$–$C_8$ alkyl, $C_2$–$C_8$ alkenyl, $C_3$–$C_8$ cycloalkane, $C_1$–$C_8$ alkylaryl, —C(O)$C_1$–$C_8$ alkyl, —C(O)O$C_1$–$C_8$ alkyl, $C_1$–$C_8$ alkylcycloalkane, $(CH_2)_nC(O)OR^5$, $(CH_2)_nC(O)R^5$, $(CH_2)_nC(O)NR^6$, and $(CH_2)_nNSO_2R^5$; wherein each of the alkyl, alkenyl, aryl are each optionally substituted with one to five groups independently selected from $C_1$–$C_8$ alkyl, $C_2$–$C_8$ alkenyl, phenyl, and alkylaryl; and wherein $R^1$ and $R^2$ may combine together, and with the nitrogen atom to which they are attached or with 0, 1, 2 or 3 atoms adjacent to the nitrogen atom to form a nitrogen containing heterocycle which may have 1, or 2 substituents independently selected from $C_1$–$C_8$ alkyl, $C_2$–$C_8$ alkenyl, $C_3$–$C_8$ cycloalkane, $C_1$–$C_8$ alkylaryl, —C(O)$C_1$–$C_8$ alkyl, —C(O)O$C_1$–$C_8$ alkyl, $C_1$–$C_8$ alkylcycloalkane, oxo, halo amino, and $(CH_2)_nC(O)NR^6R^6$; provided that $L^2$-Q is not $CONH_2$; wherein $R^1$ and $R^2$ may combine with the nitrogen atom to which they are attached to form and imine; and provided that Q is not a subsituent on an amide;

$R^5$ is hydrogen, CN, $C_1$–$C_8$ alkyl, $C_2$–$C_8$ alkenyl, $C_5$–$C_8$ alkylaryl, $(CH_2)_nNSO_2C_1$–$C_8$ alkyl, $(CH_2)_nNSO_2$phenyl, $(CH_2)_nNSO_2$aryl, —C(O)$C_1$–$C_8$ alkyl, or —C(O)O$C_1$–$C_8$ alkyl; and $R^6$ and $R^{6'}$ are each independently hydrogen, $C_1$–$C_8$ alkyl, phenyl, aryl, $C_1$–$C_8$alkylaryl, or $C_3$–$C_8$cycloalkyl;

$R^7$ is hydrogen, $C_1$–$C_8$ alkyl, phenyl, aryl, $C_1$–$C_8$alkylaryl, or $C_3$–$C_8$cycloalkyl, and wherein m is an integer from 1 to 8; and n is an integer from 0 to 8.

The present invention also relates to pharmaceutical formulations containing, a compound of formula I.

In another embodiment, the pharmaceutical formulation of the present invention may be adapted for use in treating obesity and related diseases.

The present invention also relates to methods for treating obesity in a patient in need thereof, wherein such treatment comprises administering to said patient a therapeutically effective amount of a compound of formula I in association with a pharmaceutically acceptable carrier, diluent or excipient.

The present invention also relates to a method for antagonizing the binding of MCH to MCH receptors for the treatment of diseases caused, or exercabated by melanin concentrating hormone.

The present invention provides the use of a compound of formula I as an appetite suppressant and/or as a weight loss agent.

The present invention is related to the use of a compound of formula I for the manufacture of a medicament for treating obesity and related diseases.

DETAILED DESCRIPTION

Figure 1:
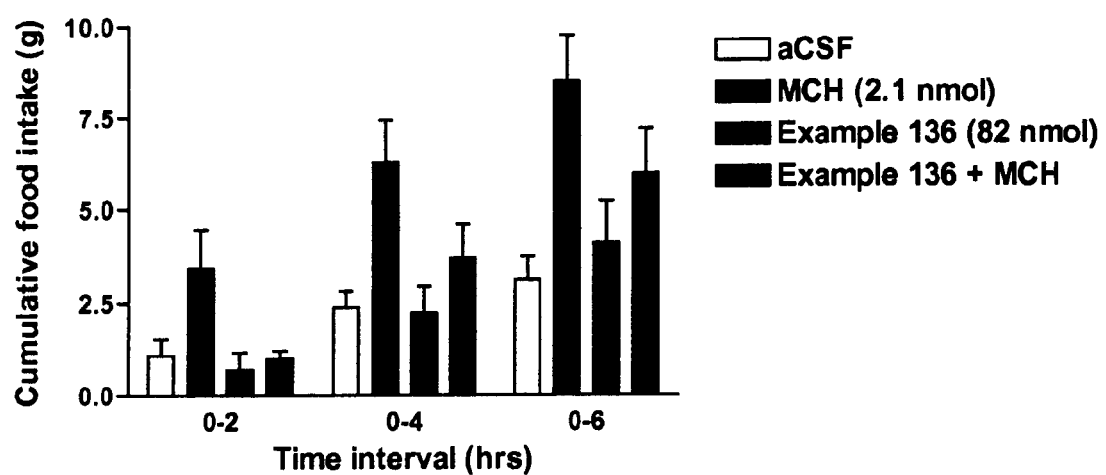
FIG. 1: Effect of compound from Example 136 on MCH-stimulated food intake in rats following ICV administration.

For the purposes of the present invention, as disclosed and claimed herein, the following terms are defined below.

The term "main chain" as used herein describes the number of atoms in the shortest distance between two ends of a variable or radical and includes the distance in number of atoms when traversing a straight chain, branched chain or atoms in a mono or bicyclic ring from one end of the variable or radical to the other.

The term "$C_1$–$C_8$ alkyl" represents a straight, branched hydrocarbon moiety having from one to eight carbon atoms, including but not limited to methyl, ethyl, n-propyl, isopropyl, n-butyl, isobutyl, sec-butyl, t-butyl, cyclobutyl, pentyl, hexyl, and the like.

The term "$C_3$–$C_8$ cycloalkyl" as used herein refers to a cyclic hydrocarbon radical or group having from 3 to 8 carbon atoms and having no double bonds. Examples of $C_3$–$C_8$ cycloalkyl groups include but are not limited to cyclopropyl, cyclobutyl, cyclopentyl, cyclohexyl, cycloheptyl, cyclooctyl.

The term "$C_3$–$C_8$ cycloalkenyl" as used herein referes to a cyclic hydrocarbon radical or group having from 3 to 8 carbon atoms and having from 1 to 3 double bonds. Specific examples of $C_{3-8}$ cycloalkenyl include cyclopropenyl, cyclobutenyl, cyclopentenyl, cyclohexenyl, cycloheptenyl, cyclooctenyl, tetrahydrothiophene, tetrahydrofuran, The term "halo" means halogens including iodo, chloro, bromo and fluoro.

The term "$C_1$–$C_4$ haloalkyl" refers to a $C_1$–$C_4$ alkyl group substituted with one, two or three halogen atoms as possible and appropriate. Examples of $C_1$–$C_4$ haloalkyl include but are not limited to trifluoromethyl, chloroethyl, and 2-chloropropyl. Similarly, a "$C_1$–$C_8$ haloalkyl" group is a $C_1$–$C_8$ alkyl moiety substituted with up to six halo atoms, preferably one to three halo atoms.

A "$C_1$–$C_8$ alkoxy" group is a $C_1$–$C_8$ alkyl moiety connected through an oxy linkage. The term includes "optionally halogenated $C_{1-8}$ alkoxy" groups including for example, $C_{1-8}$ alkoxy (e.g. methoxy, ethoxy, propoxy, butoxy, pentyloxy, etc.), which may have 1 to 5, preferably 1 to 3, halogen atoms (e.g. fluorine, chlorine, bromine, iodine, etc.). Concrete examples of alkoxy groups include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy.

The term "cyclic" as used herein refers to substituted or unsubstituted aromatic and non-aromatic ring structures containing hydrocarbon groups, and substituted or unsubstituted aromatic and non-aromatic heterocyclic groups. Cyclic groups may also be monocyclic, bicyclic or polycyclic unless otherwise specified. Examples of aromatic groups include, for example, benzene, thiophene, furan, pyrrole, imidazole, pyrazole, thiazole, isothiazole, oxazole, isoxazole, pyridine, pyrimidine, pyrazine, pyrimidine, pyridazine, napthyl, 1,2,4-oxadiazole, 1,3,4-oxadiazole, 1,2,4,-thiadiazole, 1,3,4-thiadiazole, pyrrolidine, imidazoline, imidazolidine, pyrazoline, pyrazolidine, tetrahydrothiazole, tetrahydroisothiazole, tetrahydrooxazole, tetrahydroisoxazole, piperidine, tetrahydropyridine, dihydropyridine, piperazine, morpholine, thiomorpholine, tetrahydropyrimidine, tetrahydropyridazine, hexamethyleneimine, benzofuran, benzimidazole, benzoxazole, benzothiophene, benzothiazole, benzisothiazole, naphtho[2,3-b]thiophene, isoquinoline, quinoline, indole, quinoxaline, phenanthridine, phenothiazine, phenoxathlin, phenoxazine, naphthylidene, quinazoline, carbazole, b-carboline, acridine, phenazine, phthalimide, and thioxanthene each of which may be optionally substituted.

The term alkylcycloalkyl" as used herein refers to an alkylgroup on which a cycloalkyl group is substituted. Exemplary of alkylcycloalkyl groups are methylcyclopropyl, methylcyclohexyl, methylcycloheptyl, ethylcyclopropyl, etc. The alkylcycloalkyl group may optionally be sustituted independently with one to five groups selected from $C_1$–$C_8$ alkyl, phenyl, aryl, halo, amino, alkysulfonyl, alkylsulfonamide, haloalkyl, carboxyalkyl, carboxamide, alkoxy, and perfluoroalkoxy.

The term "optionally substituted" as used herein and unless otherwise specified, means an optional substitution of one to five, preferably one to two groups independently selected from halo, hydroxy, oxo, cyano, nitro, phenyl, benzyl, triazolyl, tetrazolyl, 4,5-dihydrothiazolyl, halo, $C_1$–$C_6$ alkyl, $C_1$–$C_4$ haloalkyl, $C_1$–$C_6$ or a pharmaceutically acceptable salt, solvate, enantiomer, mixture of enatiomers or prodrug thereof wherein $Ar^1$ is a cyclic group optionally substituted with one to five groups selected from $C_1$–$C_8$ alkyl, $C_2$–$C_8$ alkenyl, $C_2$–$C_8$ alkynyl, hydroxy, $C_1$–$C_8$ alkoxy, $C_1$–$C_8$ alkylaryl, phenyl, —O-aryl, heteroaryl, cycloalkyl, $C_1$–$C_8$ alkylcycloalkyl, cyano, —$(CH_2)_nNR^6R^6$, $C_1$–$C_8$ haloalkyl, $C_1$–$C_8$ haloalkoxy, halo, $(CH_2)_nCOR^6$, $(CH_2)_nNR^5SO_2R^6$, —$(CH_2)_nC(O)NR^6R^6$, heterocyclic, and $C_1$–$C_8$ alkylheterocyclic; wherein the cycloalkyl, phenyl, aryl, and heterocyclic susbstitutents are each optionally substituted with one to three groups selected from hydroxy, $C_1$–$C_8$ alkoxyalkyl, $C_1$–$C_8$ haloalkoxy, $C_1$–$C_8$ alkyl, halo, $C_1$–$C_8$ haloalkyl, nitro, cyano, amino, carboxamido, phenyl, aryl, alkylheterocyclic, heterocyclic, and oxo;

$L^1$ is a bond or a divalent linker having a main chain of 1 to 10 atoms; or represented by the formula $X_2$—$(CR^3R^4)_m$—$X_3$ where $X_2$ is attached to $Ar^1$ and $X_3$ is attached to $AR^2$ wherein $R^3$ and $R^4$ are independently selected from a bond, hydrogen, $C_1$–$C_8$ alkyl, $C_2$–$C_8$ alkylene, $C_2$–$C_8$ alkynyl, phenyl, aryl, $C_1$–$C_8$ alkylaryl; wherein the alkyl, alkenyl, phenyl, and aryl groups are optionally substituted with one to five substitutents independently selected from oxo, nitro, cyano, $C_1$–$C_8$ alkyl, aryl, halo, hydroxy, $C_1$–$C_8$ alkoxy, $C_1$–$C_8$ halaoalkyl, $(CH_2)_nC(O)R^6$, and $(CH_2)_nCONR^6R^6$;

$X_2$ is independently oxygen, —CH, —$CONH(CR^3R^4)_m$, —$NHCO(CR^3R^4)_m$, —$(CR^3R^4)_m$, —$CHR^6$, —$NR^5$, S, SO, $SO_2$, —$O(CR^3R^4)_m$, or —$S(CR^3R^4)_m$;

$X_3$ is independently oxygen, —C, —CH, —$CHR^6$, —$(CR^3R^4)_m$, —$NR^5$, S, SO, or $SO_2$;

$AR^2$ is a 5-member monocyclic heterocyclic aromatic group or positional isomer thereof, having 1, 2, or 3 heteroatoms independently selected from nitrogen, oxygen and sulfur; and optionally substituted with one to three substitutents selected from $C_1$–$C_8$ alkyl, $C_2$–$C_8$ alkenyl, $C_2$–$C_8$ alkynyl, hydroxy, $C_1$–$C_8$ alkoxy, $C_1$–$C_8$ alkylaryl, phenyl, aryl, $C_3$–$C_8$ cycloalkyl, $C_1$–$C_8$ alkylcycloalkyl, cyano, $C_1$–$C_8$ haloalkyl, halo, $(CH_2)_nC(O)R^6$, $(CH_2)_nC(O)OR^6$, $(CH_2)NR^5SO_2R^6$, $(CH_2)_nC(O)NR^6R^6$, and $C_1$–$C_8$ alcylheterocyclic;

$AR^3$ is a 6-member monocyclic, aromatic, carbocyclic or heterocyclic ring having 0, 1, 2, or 3 heteroatoms selected from nitrogen, oxygen and sulfur and which is optionally substituted with one to three substitutents independently selected from $C_1$–$C_8$ alkyl, $C_2$–$C_8$ alkenyl, $C_2$–$C_8$ alkynyl, halo, —$NHR^5$, $C_1$–$C_8$ haloalkyl, $C_3$–$C_8$ cycloalkyl, hydroxy, alkoxy, $(CH_2)_nC(O)R^6$, $(CH_2)_nC(O)OR^6$, $(CH_2)_nNR^5SO_2R^6$, $(CH_2)_nC(O)NR^6R^6$, phenyl, $C_1$–$C_8$ alkylaryl, and aryl;

$L^2$ is a divalent linker having a chain length of between 1 and 10 atoms in the main chain or is represented by the formula:

$$X_4—(CR^3R^4)_m—X_5;$$

wherein $X_4$ is selected from the group consisting of C, —CH, $CHR^6$, —CO, O, —$NR^5$, —NC(O)—, —NC(S), —$C(O)NR^5$—, —$NR^6{}'C(O)NR^6$, —$NR^6{}'C(S)NR^6$, —$SO_2NR^7$, —$NRSO_2R^7$, and —$NR^6{}'C(NR^5)NR^6$;

$X_5$ is selected from the group consisting of —$CH_2$, —CH, —$O(CR^3R^4)_m$, $NR^3(CR^3R^4)_m$, SO, $SO_2$, S, and $SCH_2$; wherein the group $X_4$—$(CR^3R^4)_m$—$X_5$ imparts stability to the compound of formula (1) and may be a saturated or unsaturated chain or divalent linker.

Q is a basic group or a group represented by —$NR^1R^2$; wherein $R^1$ and $R^2$ are independently hydrogen, $C_1$–$C_8$ alkyl, $C_2$–$C_8$ alkenyl, $C_3$–$C_8$ cycloalkane, $C_1$–$C_8$ alkylaryl, —C(O) $C_1$–$C_8$ alkyl, —$C(O)OC_1$–$C_8$ alkyl, $C_1$–$C_8$ alkylcycloalkane, $(CH_2)_nC(O)OR^5$, $(CH_2)_nC(O)R^5$, $(CH_2)_nC(O)NR^6R^6$, and $(CH_2)_nNSO_2R^5$; wherein each of the alkyl, alkenyl, aryl are each optionally substituted with one to five groups independently selected from $C_1$–$C_8$ alkyl, $C_2$–$C_8$ alkenyl, phenyl, and alkylaryl; and wherein $R^1$ and $R^2$ may combine together, and with the nitrogen atom to which they are attached or with 0, 1, 2 or 3 atoms adjacent to the nitrogen atom to form a nitrogen containing heterocycle which may have 1, or 2 substituents independently selected from CL-CS alkyl, $C_2$–$C_8$ alkenyl, $C_3$–$C_8$ cycloalkane, $C_1$–$C_8$ alkylaryl, —$C(O)C_1$–$C_8$ alkyl, —$C(O)OC_1$–$C_8$ alkyl, $C_1$–$C_8$ alkylcycloalkane, oxo, halo amino, and $(CH_2)_nC(O)NR^6R^6$; provided that $L^2$-Q is not $CONH_2$; wherein $R^1$ and $R^2$ may combine with the nitrogen atom to which they are attached to form and imine; and provided that Q is not a subsituent on an amide;

$R^5$ is hydrogen, CN, $C_1$–$C_8$ alkyl, $C_2$–$C_8$ alkenyl, $C_5$–$C_8$ alkylaryl, $(CH_2)_nNSO_2C_1$–$C_8$ alkyl, $(CH_2)_nNSO_2$phenyl, $(CH_2)_nNSO_2$aryl, —$C(O)C_1$–$C_8$ alkyl, or —$C(O)OC_1$–$C_8$ alkyl; and $R^6$ and $R^{6'}$ are independently hydrogen, $C_1$–$C_9$ alkyl, phenyl, aryl, $C_1$–$C_8$alkylaryl, or $C_3$–$C_8$cycloalkyl; wherein m is an integer from 1 to 8; and n is an integer from 0 to 8. where $R^7$ is independently at each occurrence H, $C_1$–$C_6$ alkyl, phenyl or benzyl and $R^8$ is independently at each occurrence $C_1$–$C_6$ alkyl, phenyl or benzyl.

The term "heterocycle or heterocyclic" represents a stable, saturated, partially unsaturated, fully unsaturated or aromatic 4, 5, or 6 membered ring, said ring having from one to three heteroatoms that are independently selected from the group consisting of sulfur, oxygen, and nitrogen. The heterocycle may be attached at any point which affords a stable structure. Representative heterocycles include 1,3-dioxolane, 4,5-dihydro-1H-imidazole, 4,5-dihydrooxazole, furan, imidazole, imidazolidine, isothiazole, isoxazole, morpholine, oxadiazole, oxazole, oxazolidinedione, oxazolidone, piperazine, piperidine, pyrazine, pyrazole, pyrazoline, pyridazine, pyridine, pyrimidine, pyrrole, pyrrolidine, tetrazole, thiadiazole, thiazole, thiophene and triazole.

The heterocycle is further optionally substituted with one to three, preferably one or two groups independently selected from halo, hydroxy, oxo, cyano, nitro, phenyl, benzyl, triazolyl, tetrazolyl, 4,5-dihydrothiazolyl, $C_1$–$C_6$ alkyl, $C_1$–$C_4$ haloalkyl, $C_1$–$C_6$ alkoxy, $COR^7$, $CONR^7R^7$, $CO_2R$, $NR^7R^7$, $NR^7COR^7$, $NR^7SO_2R$, $OCOR^8$, $OCO_2R^7$, $OCONR^7R^7$, $SR^7$, $SOR^8$, $SO_2R$ and $SO_2(NR^7R^7)$, where $R^7$ is independently at each occurrence H, $C_1$–$C_6$ alkyl, phenyl or benzyl and R is independently at each occurrence $C_1$–$C_6$ alkyl, phenyl or benzyl.

The term "alkylheterocyclic" as used herein refers to an alkyl group further substitued with a heterocyclic group. Examples of alkylheterocycles include but are not limited to 2-methylimidazoline, N-methyhnorpholinyl, N-methylpyrrolyl and 2-methylindolyl.

The term "basic group" refers to an organic radical which is a proton acceptor. The term "basic group" also refers to an organic group containing one or more basic radicals. Illustrative basic radicals are amidino, guanidino, amino, piperidyl, pyridyl, etc, and excludes amides.

Suitable basic radicals contain one or more nitrogen atoms and include amino, imino, amidino, N-alkylamidines, N,N'-dialkylamidines, N-arylamidines, aminomethyleneamino, iminomethylamino, guanidino, aminoguanidino, alkylamino, dialkylamino, trialkylatnino, alkylideneamino, pyrrolyl, imidazolyl, pyrazolyl, pyridyl, pyrazinyl, pyrimidinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, amide, thioamide, benzamidino, pteridinyl, 4H-carbazolyl, carbazolyl, beta-carbolinyl, phenantrrridinyl, acridinyl, pyrimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, or any of the preceding substituted with amino, imino, amidino, aminomethyleneamino, iminomethylamino, guanidino, alkylamino, dialkylamino, trialkylamino, tetrahydroisoquinoline, dihydroisoindole, alkylideneamino, groups, or a group represented by the formula $NR^1R^2$.

The term "suitable solvent" refers to any solvent, or mixture of solvents, inert to the ongoing reaction, that sufficiently solubilizes the reactants to afford a medium within which to effect the desired reaction.

As used herein, the term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in an aquaculture. Also included are exotic animals used in food production such as alligators, water buffalo and ratites (e.g., emu, rheas or ostriches). The preferred patient of treatment is a human. The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof.

The terms "preventing", "prevention of", "prophylaxis", "prophylactic" and "prevent" are used herein interchangeably and refer to reducing the likelihood that the recipient of a compound of formula I will incur or develop any of the pathological conditions, or sequela thereof, described herein.

As used herein, the term "effective amount" means an amount of a compound of formula I that is sufficient for treating or preventing a condition, or detrimental effects thereof, herein described, or an amount of a compound of formula I that is sufficient for antagonizing the $MCHR^1$ receptor to achieve the objectives of the invention.

The term "pharmaceutically acceptable" is used herein as an adjective and means substantially non-deleterious to the recipient patient.

The term "formulation", as in pharmaceutical formulation, is intended to encompass a product comprising the active ingredient(s) (compound(s) of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier, or a compound of the formula I and a pharmaceutically acceptable co-antagonist of MCHR1 useful for the treatment and/or prevention of obesity or a related disease where antagonism of a MCH receptor may be beneficial.

The terms "diseases related to obesity" or "related diseases" as used herein refers to such symptoms, diseases or conditions caused by, exacerbated by, induced by, or adjunct to the condition of being obese. Such diseases, conditions and/or symptoms include but are not limited to eating disorders (bulima, anorexia nervosa, etc.), diabetes, diabetic complications, diabetic retinopathy, sexual/reproductive disorders, depression, anxiety, epileptic seizure, hypertension, cerebral hemorrhage, conjestive heart failure, sleeping disorders, atherosclerosis, rheumatoid arthritis, stroke, hyperlipidemia, hypertriglycemia, hyperglycemia, and hyperlipoproteinenamia.

The term "unit dosage form" refers to physically discrete units suitable as unitary dosages for human subjects and other non-human animals (as described above), each unit containing a predetermined quantity of active material calculated to produce the desired therapeutic effect, in association with a suitable pharmaceutical carrier. Because certain compounds of the invention contain an acidic moiety (e.g., carboxy), the compound of formula I may exist as a pharmaceutical base addition salt.

Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I may also exist as a pharmaceutical acid addition salt. Such salts include the salicylate, sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, oxalate, glycolate, maleate, tartrate, methanesulfonate, propanesulfonate, naphthalene-1-sulfonate, naphthalene-2-sulfonate, mandelate and like salts. Preferred acid addition salts include the hydrochloride and oxalate salts. Acid addition salts are typically formed by reacting an equivalent amount of acid (based on moles of available basic i.e free pairs of electrons on nitrogen atoms, or a slight excess thereof) with the free base compound of the invention. The addition salt product is often isolated as the crystallization product. The crystallization may be spontaneous or may be facilitated by cooling and/or seeding. Other methods of isolating the acid addition salts are known to one of skill in the art.

PREFERRED COMPOUNDS OF THE INVENTION

Certain compounds of the invention are particularly interesting and preferred. The following listing sets out several groups of preferred compounds. It will be understood that each of the listings may be combined with other listings to create additional groups of preferred compounds.

Preferred $Ar^1$

Preferred $Ar^1$ groups are cyclic groups selected from cycloallyl and cycloalkene groups such as the group consisting of cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl. Also preferred are groups selected from tetrahydrothiophene, tetrahydrofuran, pyrrolidine, imidazoline, imidazolidine, pyrazoline, pyrazolidine, tetrahydrothiazole, tetrahydroisothiazole, tetrahydrooxazole, phenyl, tetrahydroisoxazole, piperidine, tetrahydropyridine, benzothiophene, benzofuran, naphthyl, dihydropyridine, piperazine, morpholine, thiomorpholine, tetrahydropyrimidine, tetrahydropyridazine, hexamethyleneimine, each optionally substituted with $C_1$–$C_6$ alkyl, $C_1$–$C_6$ cycloalkyl, $C_1$–$C_6$ haloalkyl, hydroxy, alkoxyalkyl, cyano, halo, aryl, carboxamide, and $C_1$–$C_6$ carboxyalkyl. More preferred $Ar^1$ groups include cycloalkyl, cycloalkenyl, substituted or unsubstituted phenyl, benzothiophene, benzofuran and naphthyl.

Preferred $L^1$ Groups

Preferred as $L^1$ are groups having between 3 to 8 carbon atoms in the main chain. Also preferred are $L^1$ groups selected from the group consisting of —CH$_2$—, —CH$_2$CH$_2$—, —CH$_2$CH$_2$CH$_2$—, —SCH$_2$—, —OCH$_2$—, CH$_2$SCH$_2$—, —CH$_2$OCH$_2$—, —CH$_2$CH$_2$OCH$_2$—, —OCH$_2$CH$_2$OCH$_2$—, —O(CH$_2$)$_3$SCH$_2$—, —OCH(Et)CH$_2$CH$_2$SCH$_2$, —OCH(iPr)CH$_2$CH$_2$SCH$_2$, —OCH(CH$_3$)CH$_2$CH$_2$SCH$_2$, —O(CH$_2$)$_3$SCH(CH$_3$)—, —O(CH$_2$)$_2$SCH(CF$_3$)—, —OCH$_2$CH(NO$_2$)SCH$_2$—, —OCH(CN)CH$_2$SCH$_2$, —OCH$_2$CH(NH$_2$)SCH$_2$—, —CH$_2$O(CH$_2$)$_3$CH$_2$O—, and —CH$_2$O(CH$_2$)$_2$CH$_3$O—

Preferred $X_2$ Group

Also preferred is an $L^1$ group having the formula $X_2$—$(CR^3R^4)_m$—$X_3$ wherein a preferred $X_2$ group is selected from O, S, and —NR$^6$, and wherein R$^6$ is selected from the group consisting of hydrogen, $C_1$–$C_6$ alkyl, $C_2$–$C_6$ alkenyl, $C_3$–$C_8$ cycloalkyl, phenyl, benzyl, $C_1$–$C_8$ alkylamine, and aryl.

Preferred $X_3$ Groups

Also preferred is an $L^1$ group wherein, when $L^1$ is $X_2$—$(CR^3R^4)_m$—$X_3$; wherein $X_3$ is a group selected from —OCH$_2$, —SCH$_2$, —NR$^6$C(O)CH$_2$, —NHCH$_2$, wherein R$^6$ is selected from the group consisting of hydrogen, $C_1$–$C_6$ alkyl, $C_2$–$C_6$ alkenyl, $C_3$–$C_8$ cycloalkyl, phenyl, benzyl, and aryl. More preferred is an $X_3$ group selected from —OCH$_2$, and —SCH$_2$.

Also preferred is a compound of formula I wherein $L^1$ is $X_2$—$(CR^3R^4)_m$—$X_3$, and wherein the chain between $X_2$ and $X_3$ i.e., —$(CR^3R^4)_m$— is an alkyl chain of 3 to 8 carbon atoms, or an alkenyl chain of 3 to 8 carbon atoms and optionally contains an alkyl, phenyl, amino, or cycloalkyl group as a side chain.

Preferred $AR^2$ Groups

A preferred $Ar^2$ group is a 5-member monocyclic aromatic heterocyclic group having 1, 2, or 3 heteroatoms selected from oxygen, sulfur, and nitrogen. More preferred is a heterocyclic group selected from furan, thiophene, pyrrole, oxazole, thiazole, imidazole, imidazoline, imidazolidine, pyrazole, 2-pyraziline, pyrazolidine, isoxazole, isothiazole, 1,3,4-oxadiazole, 1,2,3-triazole, 1,3,4-thiadiazole and 1,3,4-oxadiazole. Most preferred $AR^2$ are the oxadiazolyl or oxazolyl groups, and positional isomers thereof.

Preferred $Ar^3$ Groups

Preferred $Ar^3$ group is a 6-member carbocyclic or heterocyclic group having 0, 1, 2, or 3 heteroatoms independently selected from oxygen, sulfur, and nitrogen and optionally substituted with one to two groups. More preferred is a cyclic group selected from phenyl, pyran, piperidine, pyridine, pyridazine, and piperazine. Most preferred $AR^3$ is phenyl.

Preferred $L^2$ Groups

Preferred $L^2$ groups include a divalent group having between 3 and 8 atoms in the main cahin. Also preferred are $L^2$ groups selected from the group consisting of —OCH$_2$CH$_2$—, —O(CH$_2$)$_3$—, —CH$_2$, —CH$_2$CH$_2$, —CH$_2$CH$_2$CH$_2$—, —CH=CH, —CH$_2$CH$_2$CH=CH— and $X_4$—$(CR^3R^4)_m$—$X_5$.

Preferred $X_4$ Groups

Preferred $X_4$ groups include divalent groups, radicals, or fragments of the formula —C(O)NR$^6$ wherein R$^6$ is selected from the group consisting of hydrogen, $C_1$–$C_6$ alkyl, $C_2$–$C_6$ alkenyl, $C_3$–$C_8$ cycloalkyl, phenyl, benzyl, $C_1$–$C_8$ alkylamine, and aryl.

Also preferred is an $X_4$ group selected from O, S, —NR$^6$C(O)NR$^6$, —C(S)NR$^6$, NR$^6$C(S)NR$^6$, NR$^6$C@4R$^6$)NR$^6$, —NR$^6$SO$_2$—, wherein R$^6$ is independently selected from the group consisting of hydrogen, $C_1$–$C_6$ alkyl, $C_2$–$C_6$ alkenyl, $C_3$–$C_8$ cycloalkyl, phenyl, benzyl, $C_1$–$C_8$ alkylamine, and aryl.

Preferred $X_5$ Groups

Preferred is an $X_5$ group selected from —OCH$_2$, —SCH$_2$, O, —NR$^6$C(O), —NR$^6$C(S), —C(O)NR$^6$, —C(S)NR$^6$, NR$^6$C(S)NR$^6$, NC(NR$^6$)N, NR$^6$C(O)NR$^6$, —NR$^6$SO$_2$ wherein R$^6$ is independently selected from the group consisting of hydrogen, $C_1$–$C_6$ alkyl, $C_2$–$C_6$ alkenyl, $C_3$–$C_8$ cycloalkyl, phenyl, benzyl, $C_1$–$C_8$ alkylamine, and aryl. More preferred is an $X_5$ group selected from OCH$_2$, SCH$_2$ and O.

Also preferred is a compound of formula I wherein the chain between $X_4$ and $X_5$ is preferably an alkyl chain of 2 to 8 carbon atoms, or an alkenyl chain of 2 to 8 carbon atoms and optionally containing an alkyl, phenyl, or cycloalkyl group as a side chain.

Preferred Q Groups:

The substituent Q of formula I is a basic group. A basic group is an organic group containing one or more basic radicals. Preferred Q groups are those represented by the formula —NR$^1$R$^2$ Preferred $R^1$ and $R^2$ Groups Preferred $R^1$ and $R^1$ groups are independently selected from the group consisting of hydrogen, $C_1$–$C_6$ alkyl, $C_2$–$C_6$ alkenyl, $C_3-C_8$ cycloalkyl, $C_3-C_{810}$ alkylcycloalkyl, phenyl, benzyl, $COR^9$, $SO_2R^9$, and $(CH_2)_nSO_2R^6$.

Also preferred are $R^1$ and $R^2$ groups which combine with each other, the nitrogen atom to which they are attached to form a heterocycle selected from morpholino, thiomorpholino, pyrrole, 2H-pyrrole, 2-pyrroline, pyrrolidine, oxazole, thiazole, imidazoline, imidazolidine, pyrazole, pyrazoline, piperazinyl, piperadinyl, pyrazinyl, pyrimidine each optionally substituted with a $C_1-C_8$ alkyl group.

Also preferred is a compound of the invention having $R^1$ and $R^2$ groups wherein the $R^1$ and $R^2$ groups combine with the nitrogen atom to which they are attached and with a carbon atom one or two atoms removed from the nitrogen atom to form a cycle such as for example, azepine, diazepine, pyridine, piperidine, indolyl, N-methylpyrrolidinyl, pyrrolidinyl, morpholino, piperidinyl, and the like.

Also preferred are compounds of formula I wherein $R^1$ and $R^2$ combine together with the nitrogen atom to which they are attached to form an imine or substituted imine.

Most preferred are $R_1$ and $R_2$ which singly or in combination with each other and/or the nitrogen atom to which they are attached form the groups independently selected from methyl, ethyl, propyl, isopropyl, isobutyl, cyclopentyl, cyclohexyl, N-morpholino, azepane, diazepine, pyridine, pyrrolidine, piperidine, N-methylpiperidine, and N-methylpiperazine.

Preferred $R^3$ and $R^4$ Groups:

Preferred $R^3$ and $R^4$ are independently selected from hydrogen, $C_1-C_8$ alkyl, $C_2-C_8$ alkylene, $C_2-C_8$ alkynyl, phenyl, aryl, $C_1-C_8$ alkylaryl, $(CH_2)_nNR^5SO_2R$, $(CH_2)_nC(O)R^6$, $(CH_2)_nCONR^6R^6$ and $(CH_2)_nC(O)OR^6$; wherein the alkyl, alkenyl, phenyl, and aryl groups are optionally substituted with one to three substituents independently selected from oxo, nitro, cyano, $C_1-C_8$ alkyl, aryl, halo, hydroxy, $C_1-C_8$ alkoxy, $C_1-C_8$ halaoalkyl, $(CH_2)_nC(O)R^6$, $(CH_2)_nCONR^6R^6$ and $(CH_2)_nC(O)OR^6$.

Most preferred $R^3$ and $R^4$ substituents are independently selected from hydrogen, $C_1-C_8$ alkyl, $C_2-C_8$ alkylene, $C_2-C_8$ alkynyl, phenyl, and benzyl; and wherein n is 0, or 1, and wherein $R^5$ is hydrogen, $C_1-C_8$ alkyl, phenyl or benzyl; and wherein $R^6$ is hydrogen, $C_1-C_8$ alkyl, phenyl or benzyl.

Preferred $R^5$ Groups

A preferred $R^5$ group is a group independently selected from hydrogen, $C_1-C_8$ alkyl, $C_1-C_8$ alkoxy, $C_2-C_8$ alkenyl, $C_5-C_8$ alkylaryl, $(CH_2)_nNSO_2C_1-C_8$ alkyl, $(CH_2)_nNSO_2$phenyl, $(CH_2)_nNSO_2$aryl, —$C(O)C_1-C_8$ alkyl, —$C(O)OC_1-C_8$ alkyl; and Preferred $R^6$ Groups A preferred $R^6$ or $R^{6'}$ is independently selected from hydrogen, $C_1-C_8$ alkyl, phenyl, aryl, alkylaryl, and $C_3-C_8$ cycloalkyl.

An example of a preferred compound of the present invention is a compound selected from the group consisting of: 1-{4-[2-(Benzofuran-2-ylmethoxymethyl)-oxazol-5-yl]-phenyl}-3-(2-dimethylamino-ethyl)-urea, 1-{4-[2-(Benzofuran-2-ylmethoxymethyl)-oxazol-5-yl]-phenyl}-3-(2-pyrrolidin-1-yl-ethyl)-urea, 1-{4-[2-(Benzofuran-2-ylmethoxymethyl)-oxazol-5-yl]-phenyl}-3-(2-piperidin-1-yl-ethyl)-urea, 1-(3-{4-[5-(Benzofuran-2-ylmethylsulfanylmethyl)-[1,3,4]oxadiazol-2-yl]-phenoxy}-propyl)-piperidine, Cyclohexyl-ethyl-(3-{4-[5-(2-phenoxy-ethylsulfanylmethyl)-[1,3,4]oxadiazol-2-yl]-phenyl}-allyl)-amine, 4-(3-{4-[5-(2-Phenoxy-ethylsulfanylmethyl)-[1,3,4]oxadiazol-2-yl]-phenyl}-allyl)-morpholine, 1-(3-{4-[2-(2-Phenoxy-ethylsulfanylmethyl)-oxazol-5-yl]-phenoxy}-propyl)-azepane, Diethyl-(3-{4-[5-(2-phenoxy-ethylsulfanylmethyl)-[1,3,4]oxadiazol-2-yl]-phenyl}-allyl)-amine, 1-(3-{4-[5-(2-Phenoxy-ethylsulfanylmethyl)-[1,3,4]oxadiazol-2-yl]-phenyl}-allyl)-piperidine, (3-{2-Chloro-4-[5-(2-phenoxy-ethylsulfanylmethyl)-[1,3,4]oxadiazol-2-yl]-phenoxy}-propyl)-dimethyl-amine, 1-Methyl-4-(3-{4-[5-(2-phenoxy-ethylsulfanylmethyl)-[1,3,4]oxadiazol-2-yl]-phenyl}-allyl)-piperazine, (3-{2-Fluoro-4-[5-(2-phenoxy-ethylsulfanylmethyl)-[1,3,4]oxadiazol-2-yl]-phenoxy}-propyl)-dimethyl-amine, Ethyl-isopropyl-(3-{4-[5-(2-phenoxy-ethylsulfanylmethyl)-[1,3,4]oxadiazol-2-yl]-phenyl}-allyl)-amine, Cyclopentyl-methyl-(3-{4-[5-(2-phenoxy-ethylsulfanylmethyl)-[1,3,4]oxadiazol-2-yl]-phenyl}-allyl)-amine, 1-(3-{4-[2-(2-Phenoxy-ethylsulfanylmethyl)-oxazol-5-yl]-phenoxy}-propyl)-azocane, Diethyl-(2-{4-[2-(2-phenoxy-ethylsulfanylmethyl)-oxazol-5-yl]-phenoxy}-ethyl)-amine, Dimethyl-(3-{4-[5-(2-phenoxy-ethylsulfanylmethyl)-[1,3,4]oxadiazol-2-yl]-phenyl}-allyl)-amine, Dimethyl-(3-{4-[2-(2-phenoxy-ethylsulfanylmethyl)-oxazol-4-yl]-phenoxy}-propyl)-amine, 2-{4-[2-(1-Methyl-pyrrolidin-2-yl)-ethoxy]-phenyl}-5-(2-phenoxy-ethylsulfanylmethyl)-[1,3,4]oxadiazole, 2-(2-Phenoxy-ethylsulfanylmethyl)-5-[4-(3-pyrrolidin-1-yl-propenyl)-phenyl]-[1,3,4]oxadiazole, Dimethyl-(3-{4-[5-(2-phenoxy-ethylsulfanylmethyl)-furan-2-yl]-phenoxy}-propyl)-amine, 4-Dimethylamino-N-{4-[5-(2-phenoxy-ethylsulfanylmethyl)-[1,3,4]oxadiazol-2-yl]-phenyl}-butyramide, 1-(2-Dimethylamino-ethyl)-3-{4-[5-(2-phenoxy-ethylsulfanylmethyl)-[1,3,4]oxadiazol-2-yl]-phenyl}-urea, 1-(3-Dimethylamino-propyl)-3-{4-[5-(2-phenoxy-ethylsulfanylmethyl)-[1,3,4]oxadiazol-2-yl]-phenyl}-urea, Dimethyl-(2-{4-[5-(2-phenoxy-ethylsulfanylmethyl)-[1,3,4]oxadiazol-2-yl]-phenoxy}-ethyl)-amine, 1-(2-{4-[5-(2-Phenoxy-ethylsulfanylmethyl)-[1,3,4]oxadiazol-2-yl]-phenoxy}-ethyl)-piperidine, Dimethyl-(5-{4-[5-(2-phenoxy-ethylsulfanylmethyl)-[1,3,4]oxadiazol-2-yl]-phenyl}-pent-4-enyl)-amine, 2-(2-Dimethylamino-ethoxy)-N-{4-[5-(2-phenoxy-ethylsulfanylmethyl)-[1,3,4]oxadiazol-2-yl]-phenyl}-acetamide, Dimethyl-(4-{4-[5-(2-phenoxy-ethylsulfanylmethyl)-[11,3,4]oxadiazol-2-yl]-phenoxy}-butyl)-amine, 1-(3-{4-[5-(2-Phenoxy-ethylsulfanylmethyl)-[1,3,4]oxadiazol-2-yl]-phenoxy}-propyl)-piperidine, Diethyl-(3-{4-[5-(2-phenoxy-ethylsulfanylmethyl)-[1,3,4]oxadiazol-2-yl]-phenoxy}-propyl)-amine, 1-(4-{4-[5-(2-Phenoxy-ethylsulfanylmethyl)-[1,3,4]oxadiazol-2-yl]-phenoxy}-butyl)-piperidine, 2-(2-Phenoxy-ethylsulfanylmethyl)-5-[4-(4-pyrrolidin-1-yl-butoxy)-phenyl]-[1,3,4]oxadiazole, 1-(3-{4-[5-(2-Phenoxy-ethylsulfanylmethyl)-[1,3,4]oxadiazol-2-yl]-phenoxy}-propyl)-azepane, 1-(2-{4-[5-(2-Phenoxy-ethylsulfanylmethyl)-[1,3,4]oxadiazol-2-yl]-phenoxy}-ethyl)-azepane, Methyl-(3-{4-[5-(2-phenoxy-ethylsulfanylmethyl)-[1,3,4]oxadiazol-2-yl]-phenoxy}-propyl)-amine, Diethyl-(2-{4-[5-(2-phenoxy-ethylsulfanylmethyl)-[1,3,4]oxadiazol-2-yl]-phenoxy}-ethyl)-amine, 1-(2-Dimethylamino-ethyl)-1-methyl-3-{4-[5-(2-phenoxy-ethylsulfanylmethyl)-[1,3,4]oxadiazol-2-yl]-phenyl}-urea, 2-(2-Phenoxy-ethylsulfanylmethyl)-5-[4-(3-pyrrolidin-1-yl-propoxy)-phenyl]-[1,3,4]oxadiazole, 1-(5-Dimethylamino-pentyl)-3-{4-[5-(2-phenoxy-ethylsulfanylmethyl)-[1,3,4]oxadiazol-2-yl]-phenyl}-urea,
1-{4-[5-(2-Phenoxy-ethylsulfanylmethyl)-[1,3,4]oxadiazol-2-yl]-phenyl}-3-(2-piperidin-1-yl-ethyl)-urea,
1-(4-{4-[5-(2-Phenoxy-ethylsulfanylmethyl)-[1,3,4]oxadiazol-2-yl]-phenoxy}-butyl)-azepane,
Diethyl-(4-{4-[5-(2-phenoxy-ethylsulfanylmethyl)-[1,3,4]oxadiazol-2-yl]-phenoxy}-butyl)-amine,
1-{4-[5-(2-Phenoxy-ethylsulfanylmethyl)-[1,3,4]oxadiazol-2-yl]-phenyl}-3-(2-pyrrolidin-1-yl-ethyl)-urea,
1-(2-Dimethylamino-ethyl)-3-{4-[5-(2-phenoxy-ethylsulfanylmethyl)-[1,3,4]oxadiazol-2-yl]-phenyl}-urea,
(3-{4-[S-(Benzofuran-2-ylmethylsulfanylmethyl)-[1,3,4]oxadiazol-2-yl]-phenoxy}-propyl)-dimethyl-amine,
2-(2-Phenoxy-ethylsulfanylmethyl)-5-[4-(5-pyrrolidin-1-yl-pent-1-enyl)-phenyl]-[1,3,4]oxadiazole,
1-(5-{4-[5-(2-Phenoxy-ethylsulfanylmethyl)-[1,3,4]oxadiazol-2-yl]-phenyl}-pent-4-enyl)-piperidine,
1-(3-{4-[5-(2-Phenoxy-ethylsulfanylmethyl)-[1,3,4]oxadiazol-2-yl]-phenoxy}-propyl)-piperidin-4-one,
2-(2-Phenoxy-ethylsulfanylmethyl)-5-[4-(2-pyrrolidin-1-yl-ethoxy)-phenyl]-oxazole,
Dimethyl-(2-{4-[2-(2-phenoxy-ethylsulfanylmethyl)-oxazol-5-yl]-phenoxy}-ethyl)-amine,
1-(2-{4-[2-(2-Phenoxy-ethylsulfanylmethyl)-oxazol-5-yl]-phenoxy}-ethyl)-piperidine,
1-(3-{4-[2-(2-Phenoxy-ethylsulfanylmethyl)-oxazol-5-yl]-phenoxy}-propyl)-piperidine,
2-(2-Phenoxy-ethylsulfanylmethyl)-5-[4-(3-pyrrolidin-1-yl-propoxy)-phenyl]-oxazole,
Dimethyl-(3-{4-[2-(2-phenoxy-ethylsulfanylmethyl)-oxazol-5-yl]-phenoxy}-propyl)-amine,
Dimethyl-(6-{4-[5-(2-phenoxy-ethylsulfanylmethyl)-[1,3,4]oxadiazol-2-yl]-phenyl}-hex-5-enyl)-amine,
Dimethyl-(4-{4-[5-(2-phenoxy-ethylsulfanylmethyl)-[1,3,4]oxadiazol-2-yl]-phenyl}-but-3-enyl)-amine,
Dimethyl-(3-{4-[4-(2-phenoxy-ethylsulfanylmethyl)-thiazol-2-yl]-phenoxy}-propyl)-amine,
(3-{4-[5-(Benzo[b]thiophen-2-ylmethylsulfanylmethyl)-[1,3,4]oxadiazol-2-yl]-phenoxy}-propyl)-dimethyl-amine,
Dimethyl-(3-{4-[5-(naphthalen-2-ylmethylsulfanylmethyl)-[1,3,4]oxadiazol-2-yl]-phenoxy}-propyl)-amine,
Dimethyl-(3-{4-[5-(2-phenoxy-ethylsulfanylmethyl)-[1,3,4]oxadiazol-2-yl]-phenoxy}-propyl)-amine,
2-(2-Phenoxy-ethylsulfanylmethyl)-5-[4-(2-pyrrolidin-1-yl-ethoxy)-phenyl]-[1,3,4]oxadiazole,
2-[4-(3-Azetidin-1-yl-propoxy)-phenyl]-5-(2-phenoxy-ethylsulfanylmethyl)-[1,3,4]oxadiazole,
1-{4-[2-(2-Phenoxy-ethylsulfanylmethyl)-oxazol-5-yl]-phenyl}-3-(2-piperidin-1-yl-ethyl)-urea,
1-{4-[2-(2-Phenoxy-ethylsulfanylmethyl)-oxazol-5-yl]-phenyl}-3-(2-pyrrolidin-1-yl-ethyl)-urea,
1-(2-Dimethylamino-ethyl)-3-{4-[2-(2-phenoxy-ethylsulfanylmethyl)-oxazol-5-yl]-phenyl}-urea,
1-(2-Dimethylamino-ethyl)-3-{4-[2-(2-phenoxy-ethylsulfanylmethyl)-oxazol-5-yl]-phenyl}-urea,
1-{4-[2-(2-Phenoxy-ethylsulfanylmethyl)-oxazol-5-yl]-phenyl}-3-(3-pyrrolidin-1-yl-propyl)-urea,
1-{4-[5-(2-Phenoxy-ethylsulfanylmethyl)-[1,3,4]oxadiazol-2-yl]-phenyl}-3-(3-pyrrolidin-1-yl-propyl)-urea,
N,N-dimethyl-N-{5-[5-(2-phenoxy-ethylsulfanylmethyl)-[1,3,4]oxadiazol-2-yl]-pyridin-2-yl}-ethane-1,2-diamine,
N,N-Dimethyl-N'-{5-[5-(2-phenoxy-ethylsulfanylmethyl)-[1,3,4]oxadiazol-2-yl]-pyridin-2-yl}-propane-1,3-diamine,
1-Methyl-3-{4-[5-(2-phenoxy-ethylsulfanylmethyl)-[1,3,4]oxadiazol-2-yl]-phenoxymethyl}-piperidine,
2-(2-Phenoxy-ethylsulfanylmethyl)-5-[4-(3-pyrrolidin-1-yl-propenyl)-phenyl]-oxazole,
1-(2-Diethylamino-ethyl)-3-{4-[5-(2-phenoxy-ethylsulfanylmethyl)-[1,3,4]oxadiazol-2-yl]-phenyl}-urea,
5-(2-Phenoxy-ethylsulfanylmethyl)-3-[4-(2-pyrrolidin-1-yl-ethoxy)-phenyl]-[1,2,4]oxadiazole,
Dimethyl-(2-{4-[5-(2-phenoxy-ethylsulfanylmethyl)-[1,2,4]oxadiazol-3-yl]-phenoxy}-ethyl)-amine, and pharmaceutically acceptable salts, solvates, enantiomers, diastereomers and mixture of enantiomers thereof.

A most preferred compound of the present invention is selected from the group consisting of:

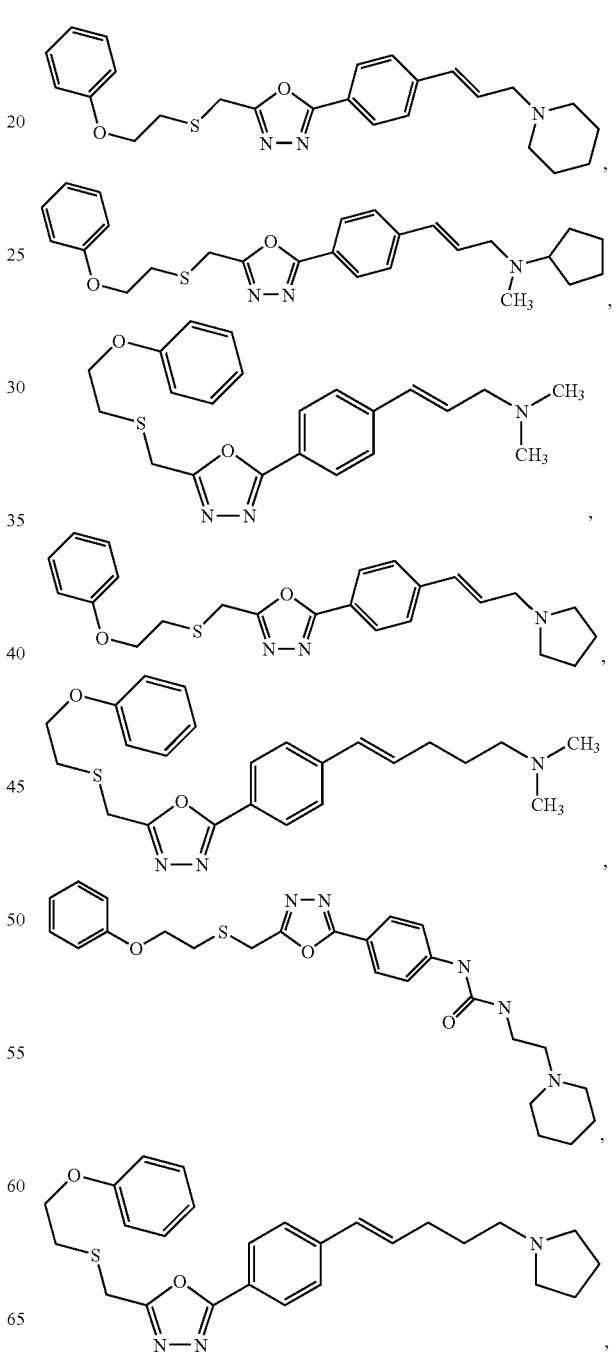

-continued

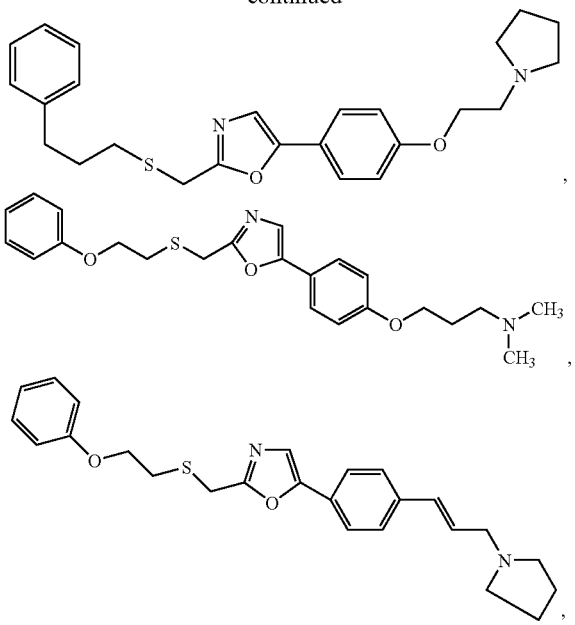

or a pharmaceutically acceptable salt, solvate, prodrug, enantiomer, or mixture of enantiomers thereof.

Preparing Compounds of the Invention

Compounds of formula I may be prepared as described in the following Schemes and Examples. Precursors to the compounds of the invention are prepared by methods known to one of skill in the art. The compounds employed as initial starting materials in the synthesis of the compounds of the invention are well known and, to the extent not commercially available, are readily synthesized by standard procedures commonly employed by those of ordinary skill in the art. More particularly, the compounds of the invention are produced in accordance with the General Methods 1 through 5 that are described in detail below, or analogous methods thereto. These reactions are often carried out in accordance with per se known methods, or analogous methods thereto. Examples of such known methods include the methods described in general reference texts such as Organic Functional Group Preparations, $2^{nd}$ Edition, 1989; Comprehensive Organic Transformations, VCH Publishers Inc, 1989; Compendium of Organic Synthetic Methods, Volumes 1–10, 1974–2002, Wiley Interscience; March's Advanced Organic Chemistry, Reactions Mechanisms, and Structure, $5^{th}$ Edition, Michael B. Smith and Jerry March, Wiley Interscience, 2001, Advanced Organic Chemistry, $4^{th}$ Edition, Part B, Reactions and Synthesis, Francis A. Carey and Richard J. Sundberg, Kluwer Academic/Plenum Publishers, 2000, etc., and references cited therein.

General Method 1: Coupling of the Basic Group

The compounds of Formula 3 can be prepared by the General Method 1, described in General Scheme 1, via coupling of a compound of Formula 2 containing a basic group with a group of Formula 1, where during the course of the coupling reaction the coupling groups are retained or lost to form the linker $L^2$ between the basic group and the phenyl ring. $Ar^1$, $L^1$, $Ar^2$, $L^2$, and basic group are defined as above. In the schemes that follow $AR^3$ of formula I has been depicted as a phenyl group for convenience only and is not intended to be limiting. Also, $L_a$ is defined as a group that when the coupling process occurs results in the formation of the linker $L^2$ defined above. Furthermore, in the schemes that follow, the group $L^1$ is depicted by the combination of group or groups interspacing or linking the groups $AR^1$ and $AR^2$. Similarly, the group $L^2$ is depicted by the combination of group or groups interspacing or linking the groups $AR^3$ and the basic group. The basic group of the compounds of the followoing schemes in general mean the group $—N(R^1R^2)$ unless otherwise indicated. Examples of the General Method 1 are a Displacement Process (Scheme 1a) and a Reductive Amination Process (Scheme 1b).

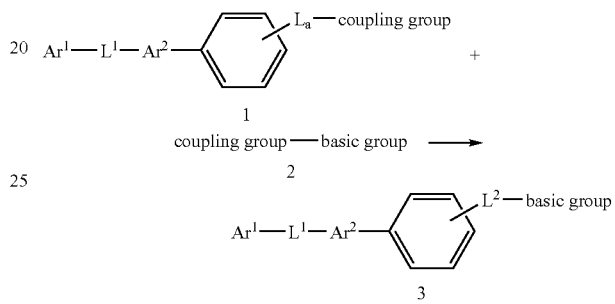

As outlined in Scheme 1a below, the coupling process of General Method 1 may consist of a displacement process whereby nucleophilic displacement of a leaving group, such as, but not limited to, halogen, triflate, tosylate, brosylate, mesylate, nosylate, nonaflate, tresylate, and the like, of Formula 4, by a nucleophilic basic group of Formula 5 affords the compounds of the invention. A leaving group is defined in one or more of the general reference texts described previously.

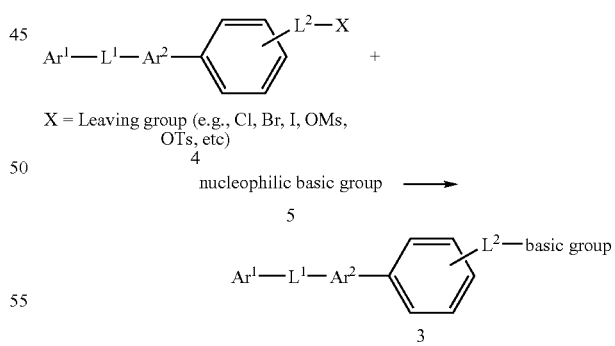

One to five equivalents of the nucleophilic basic group of Formula 5 and one to five equivalents of the reactive derivative of Formula 4 may be reacted in the presence, or absence, of an inert solvent. If necessary, the reaction may be carried out in the presence of a catalytic quantity to about five equivalents of a non-interfering base. A non-interfering base is a base suitable for the intended reaction by virtue of the base not deleteriously affecting the reaction. One to two equivalents of base is normally preferable. The reaction is normally carried out between 0° C. and 120° C. Reaction time is normally 4 to 24 hours.

Nucleophilic basic groups would include, but would not be limited to ammonia, primary and secondary amines, guanidines, and the like. Specific nucleophilic basic groups include ammonia, methylamine, dimethylamine, diethylamine, diisopropylamine, pyrrolidine, piperidine, morpholine, azetidine, thiomorpholine, piperazine, imidazole, and the like. Among the above nucleophilic basic groups dimethylamine, pyrrolidine, and piperidine are preferable.

If necessary, the reaction can be carried out with nucleophilic basic group synthon, i.e., a group that could readily be converted to a basic group by methods known to one skilled in the art. Nucleophilic basic group synthons would include, but would not be limited to, azide, phthalimide, protected amines, hexamethylenetetramine, cyanamide, cyanide anion, and the like. Following the displacement reaction, these groups would then be unmasked under standard conditions to afford the basic group. For example, displacement with potassium phthalimide followed by removal of the phthalimide group to afford the primary amine as in the Gabriel synthesis (see, March's Advanced Organic Chemistry, Reactions Mechanisms, and Structure, 5$^{th}$ Edition, Michael B. Smith and Jerry March, Wiley Interscience, 2001, Chapter 10, and references cited therein). Application of the synthon equivalent to the basic group applies to the processes described in all of the General Methods 1 through 5.

Examples of "inert solvent" includes amide solvents (preferably DMF or DMAC), sulfoxide solvents (preferably DMSO), sulfone solvents (preferably sulfolane or dimethylsulfone), nitrile solvents (preferably acetonitrile), halogenated hydrocarbon solvents (preferably dichloromethane), aromatic solvents (preferably toluene or benzene), ether solvents (preferably diethylether or THF), ketone solvents (preferably acetone), ester solvents preferably ethyl acetate), alcohol solvent (preferably MeOH or EtOH), etc. Two or more of the solvents can be mixed in an appropriate ratio for use. Among the above solvents, DMF and DMSO are preferable.

Examples of "base" include, for instance, hydrides of alkali metals and alkaline earth metals (e.g., lithium hydride, sodium hydride, potassium hydride, and the like), amides of alkali metals and alkaline earth metals (e.g., sodium amide, lithium diisopropyl amide, lithium hexamethyldisilazide, and the like), alkoxides (e.g. sodium methoxide, sodium ethoxide, potassium t-butoxide, and the like), inorganic bases, such as hydroxides of alkali metals or alkaline earth metals (e.g., sodium hydroxide, lithium hydroxide, potassium hydroxide, and the like), carbonates and hydrogen carbonates of alkali metals or alkaline earth metals (e.g., potassium carbonate, sodium bicarbonate, sodium carbonate, cesium carbonate, and the like), amine bases (such as, N-methylmorpholine, DBU, DBN, pyridine, 2,6-lutidine, triethylamine, diisopropylethylamine, and the like). Among the above bases, sodium hydride, potassium carbonate, and cesium carbonate are preferable.

As outlined in Scheme 1b below, the coupling process can consist of a Reductive Amination Process. A compound of Formula 6 is condensed with ammonia, or a primary, or secondary amine under dehydration/reduction conditions. Scheme 1b is a process analogous to that described in for example, Chem Pharm Bull 1999, 47 (8), 1154–1156; Synlett 1999, (11), 1781–1783; and J Med Chem 1999, 42 (26), 5402–5414 and references cited therein.

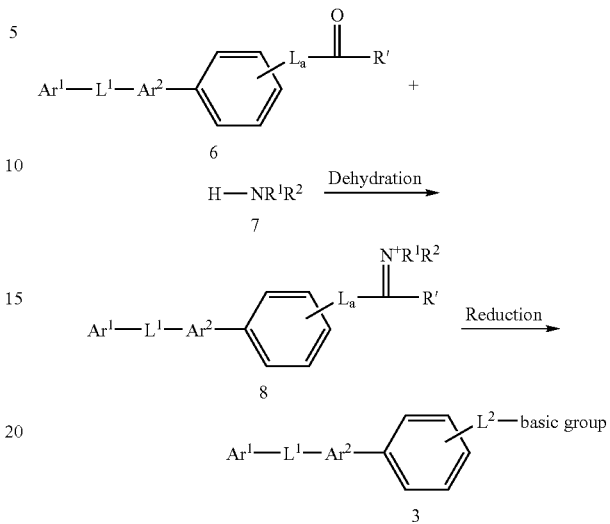

Scheme 1b: Reductive Amination Process

The carbonyl compound of Formula 6 is reacted with an amine of Formula 7 in an inert solvent under conditions that form the iminium species of Formula 8. The iminium species is reduced in-situ to form the compounds of Formula 3. The reaction is normally done in the presence of a dehydrating agent and a reducing agent. Amines of Formula 7 include, but are not limited to ammonia, primary and secondary amines, and the like. Specific amine groups include ammonia, methylamine, dimethylamine, diethylamine, diisopropylamine, pyrrolidine, piperidine, morpholine, azetidine, thiomorpholine, piperazine, imidazole, and the like. One to five equivalents of the amine group of Formula 7 and one to five equivalents of the reactive derivative of Formula 6 are reacted in the presence, or absence, of an inert solvent. The use of an excess of dehydrating agent is normally preferable. The reaction is carried out in the presence of one to hundred equivalents of a reducing agent. One to three equivalents of reducing agent is preferable. The reaction is normally carried out between 0° C. and 120° C. Reaction time is normally 4 to 24 hours. For the above amination reaction, MeOH and EtOH are preferable as inert solvents.

Examples of "dehydrating agents" may be anhydrous molecular sieves beads, anhydrous molecular sieve pellets, powdered anhydrous molecular sieves, anhydrous molecular sieves on supports (such as zeolite), anhydrous magnesium sulfate, anhydrous sodium sulfate, and the like. Among the above dehydrating agents, anhydrous molecular sieves pellets and powdered anhydrous molecular sieves are preferable.

Examples of "reducing agents" include hydrogen gas or hydrogen gas precursor and a hydrogenation catalyst. Other "reducing agents" include sodium cyanoborohydride, sodium triacetoxyborohydride, sodium borohydride, sodium borohydride/Ti (Oi-Pr)4, borohydride-exchange resin, and the like. Examples of "hydrogen gas precursors" include formic acid, 1,4-cyclohexadiene, and the like. Examples of "hydrogenation catalyst" include palladium on carbon, platinum on carbon, rhodium, ruthenium, nickel and the like. The metal can be used as a finely dispersed solid or absorbed on a support, such as carbon or alumina. Among the above reducing agents, sodium cyanoborohydride and sodium triacetoxyborohydride are preferred.

General Method 2: Coupling of the Linker Group

The compounds of Formula 3 can be prepared by the General Method 2, described in General Scheme 2, via reaction of the coupling group of Formula 9 with a coupling group of Formula 10.

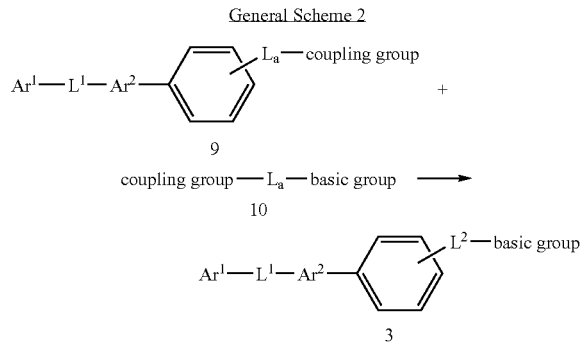

Examples of the General Method 2 are an Ether/Thioether Alkylation Process (Scheme 2a), an Acylation/Sulfonylation Process (Scheme 2b), Urea/Thiourea/Guanidine Coupling Process (Scheme 2c1, 2c2, 2c3), an Organometallic Process (Scheme 2d), and a Wittig-type Coupling (Scheme 2e). As outlined in Scheme 2a below, the coupling process of General Method 2 can consist of a Ether/Thioether Alkylation Process. Nucleophilic displacement by an alcohol or thiol-containing compound of Formula 11 (or Formula 11') with a compound of Formula 12 (or Formula 12') containing a leaving group affords the ether and thioether compounds of Formula 13. Scheme 2a is a process analogous to that described in The Chemistry of the Ether Linkage; Patai, Wiley, 1967, 446, 460; and in March's Advanced Organic Chemistry, Reactions Mechanisms, and Structure, 5$^{th}$ Edition, Michael B. Smith and Jerry March, Wiley Interscience, 2001, Chapter 10.

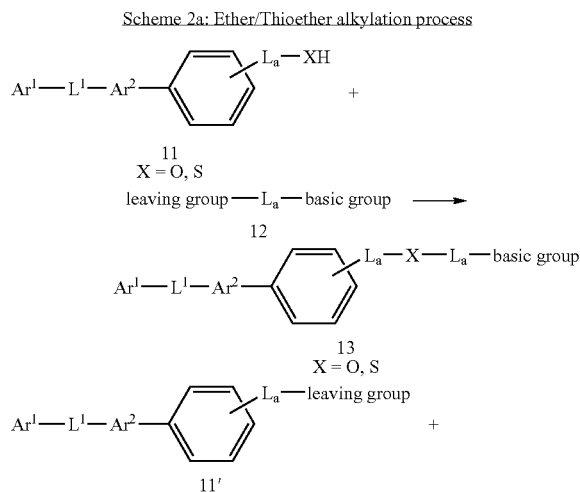

One to five equivalents of the alcohol or thiol of Formula 11 (or Formula 11') and one to five equivalents of the reactive derivative of Formula 12 (or Formula 12') are reacted in the presence, or absence, of an inert solvent. If necessary, the reaction can be carried out in the presence of a catalytic quantity to ten equivalents of a non-interfering base. One to three equivalents of base is normally preferable. The reaction is typically carried out between 0° C. and 120° C. Reaction time is typically 4 to 24 hours, but may be longer depending on the particular substrate. Preferred bases for the above reaction include sodium hydride, potassium carbonate and cesium carbonate. If necessary, the reaction may be carried out with basic group synthon incorporated as the basic group in Formula 12, i.e., a group that could readily be converted to a basic group by methods known to one skilled in the art. Basic group synthons would include, but not be limited to, halogen, protected amine, nitrile, aldehyde, and the like. Following the ether/thioether alkylation reaction, these groups would then be unmasked or converted under standard conditions to afford the basic group. For example, alkylation with 1-iodo-4-chloro-butane would give a 4-chlorobutane derivative of compound 11. The chloride could then be converted by the Displacement Process, described above in Scheme 1a, into the basic group of a compound of Formula 13. Among the inert solvents, DMF and DMSO are preferable.

As outlined in Scheme 2b below, the coupling process of General Method 2 can consist of a Acylation/Sulfonylation Process. Acylation or sulfonylation of an alcohol or amine compound of Formula 14 with a carboxylic acid or sulfonic acid compound of Formula 15, affords the ester, amide, sulfonic ester, or sulfonamide compounds of Formula 16. Alternatively, acylation or sulfonylation of an alcohol or amine compound of Formula 18 with a carboxylic acid or sulfonic acid compound of Formula 17 affords the ester, amide, sulfonic ester, or sulfonamide compounds of Formula 19. If necessary, the reaction can be carried out with a basic group synthon incorporated as the basic group in Formula 15 or Formula 18, i.e., a group that could readily be converted to a basic group by methods known to one skilled in the art. Basic group synthons would include, but not be limited to, halogen, protected amine, nitrile, aldehyde, and the like. Following the Acylation/Sulfonylation reaction, these groups would then be unmasked or converted under standard conditions to afford the basic group.

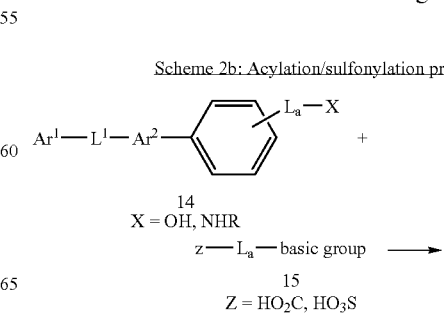

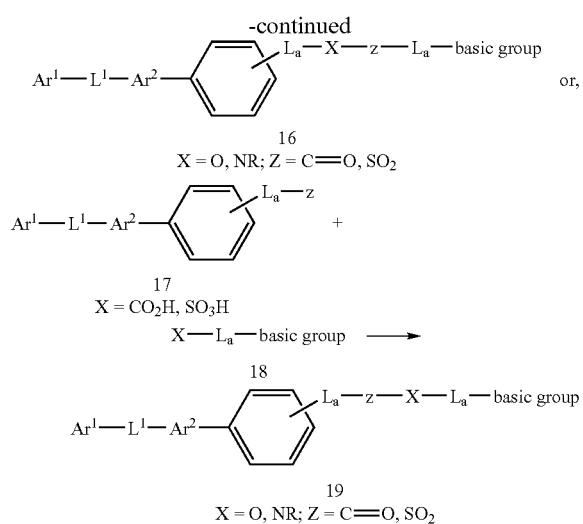

-continued

16
X = O, NR; Z = C=O, SO₂

17
X = CO₂H, SO₃H

X—L$_a$—basic group →

18

19
X = O, NR; Z = C=O, SO₂

The carboxylic acid (or sulfonic acid) residue of compound 15 (or compound 17) is activated for coupling as a "reactive acylating agent." "Reactive acylating agents" are described in detail in Advanced Organic Chemistry, 4$^{th}$ Edition, Part B, Reactions and Synthesis, Francis A. Carey and Richard J. Sundberg, Kluwer Academic/Plenum Publishers, 2000, Chapter 3, and references cited therein. The "reactive acylating agent" can be formed and isolated, then reacted with the compound of Formula 14 (or 18), or formed in situ and reacted with the compound of Formula 14 (or 18), to form the compound of Formula 16 (or 19).

One to five equivalents of the "reactive acylating agent" of compound 15 (or compound 17) and one to five equivalents of compound of Formula 14 (or 18) are reacted in an inert solvent. If necessary the reaction may be carried out in the presence of one to five equivalents of 1-hydroxybenzotriazole, 1-hydroxy-7-azabenzotriazole, and (or) a catalytic quantity to five equivalents of a base. The reaction is normally carried out between 0° C. and 120° C. Reaction time is normally 4 to 48 hours.

Examples of "reactive acylating agent" of compound 15 (or compound 17) include acid halides (e.g., acid chloride, acid bromide, and the like), mixed acid anhydrides (e.g., acid anhydrides with C$_1$–C$_6$ alkyl-carboxylic acid, C$_6$–C$_{10}$ aryl-carboxylic acid, and the like), activated esters (e.g., esters with phenol which may have substituents, 1-hydroxybenzotriazole, N-hydroxysuccinimide, 1-hydroxy-7-azabenzotriazole, and the like), thioesters (such as, 2-pyridinethiol, 2-imidazolethiol, and the like), N-acylimidazoles (e.g., imidazole, and the like), etc.

A "reactive acylation agent" may also be formed reacting the carboxylic acid (or sulfonic acid) residue of compound 15 (or compound 17) with a dehydration/condensation agent. Examples of a "dehydration/condensation agent" include dicyclohexylcarbodimide (DCC), 1-ethyl-3-(3-dimethylaminopropyl)carbodimide (EDCI), (2-ethoxy-1-ethoxycarbonyl-1,2-dihydroquinoline (EEDQ), and the like. Preferred solvents for the above reaction include acetonitrile, THF, and dichloromethane. Preferred bases for the above reaction include triethylamine, pyridine, and dimethylaminopyridine are preferable.

As outlined in Scheme 2c1, Scheme 2c2, and Scheme 2c3 below, the coupling process of General Method 2 can consist of a Urea/Thiourea/Guanidine/Carbamate-Type Coupling Process. The processes described are analogous to that described in U.S. Pat. Nos. 5,849,769 and 5,593,993, and references cited therein.

Scheme 2c1: Urea/Thiourea/Guanidine/Carbamate-Type coupling

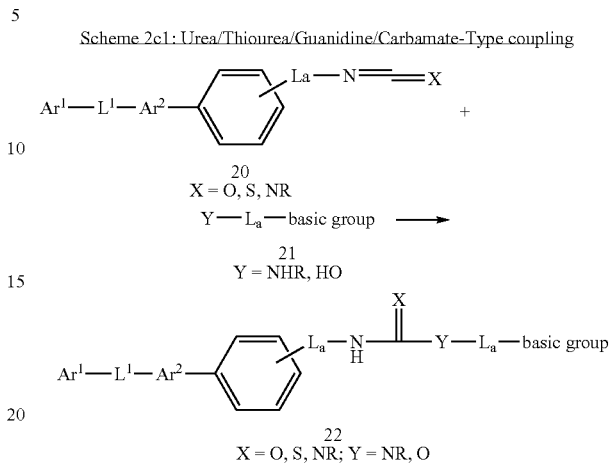

20
X = O, S, NR

21
Y = NHR, HO

22
X = O, S, NR; Y = NR, O

One to five equivalents of the isocyanate, isothiocyanate, carbodiimide of Formula 20 and one to five equivalents of compound of Formula 21 are reacted in an inert solvent. The reaction is typically carried out between 0° C. and 150° C. Preferred reaction time is between 4 to 48 hours. Preferred solvents for the above reaction include acetonitrile, DMF, DMSO, THF, and dichloromethane.

If necessary, the reaction can be carried out with a basic group synthon incorporated as the basic group wherein a synthon is as described ealier. Following the Urea/Thiourea/Guanidine/Carbamate-Type Coupling Process, these groups would then be unmasked or converted under standard conditions to afford the basic group.

Scheme 2c2: Urea/Thiourea/Guanidine/Carbamate-Type coupling

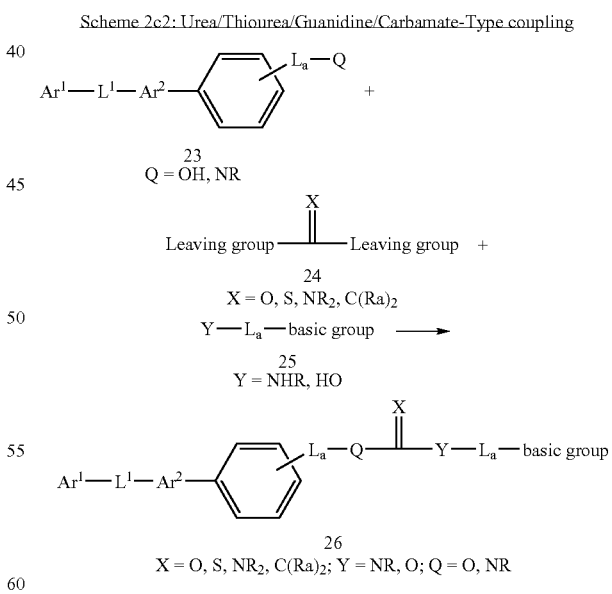

23
Q = OH, NR

24
X = O, S, NR₂, C(Ra)₂

25
Y = NHR, HO

26
X = O, S, NR₂, C(Ra)₂; Y = NR, O; Q = O, NR

Approximately one equivalent of the compound of Formula 23 and one equivalent of compound of Formula 24 and one equivalent of the compound of Formula 25 are reacted in an inert solvent. The reaction is typically carried out between 0° C. and 150° C. Reaction time is normally 4 to 48 hours. The sequence of addition depends upon the reactivity of the individual reagents. The intermediate addition product may be isolated and subsequently be condensed with the second reagent. The reaction may or may not require the addition of a catalyst. Prefered solvents for the above reaction include acetonitrile, DMF, DMSO, TBT, toluene, isopropanol, and dichloromethane. Acids and bases as described previously may be used to catalyze the above reaction.

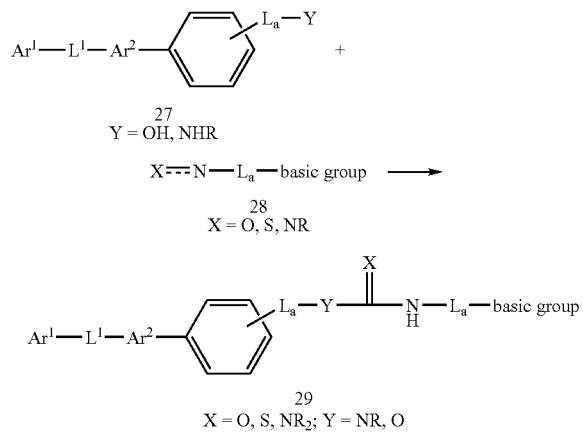

One to five equivalents of the isocyanate, isothiocyanate, carbodiimide of Formula 28 and one to five equivalents of compound of Formula 27 are reacted in an inert solvent. The reaction is normally carried out between 0° C. and 150° C. Reaction time is normally 4 to 48 hours.

As outlined in Schemes 2d below, the coupling process of General Method 2 may consist of a Organometallic Coupling Process.

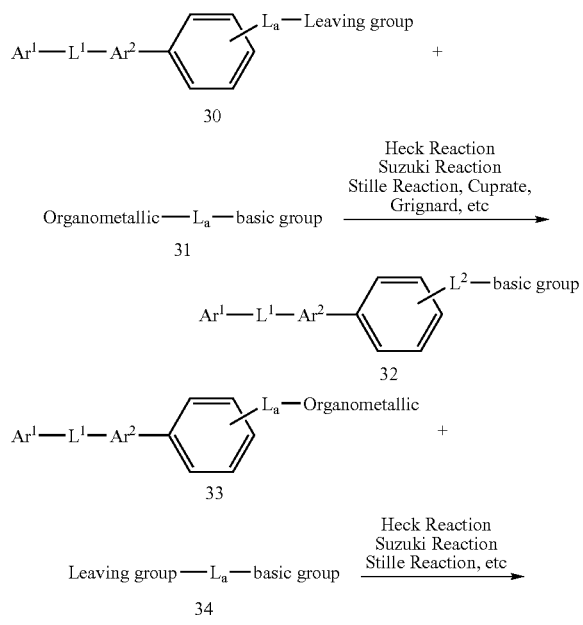

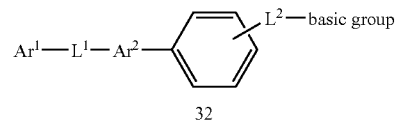

The compound of Formula 30 (or Formula 34) is coupled with an organometallic compound of Formula 31 (or Formula 33) (containing a basic group, or basic group precursor) in an Organometallic Coupling Process to afford the compounds of the invention of Formula 32.

"Organometallic Coupling Processes" include "palladium-catalyzed cross coupling reactions," such as, Heck-type coupling reactions, Suzuki-type coupling reactions and Stille-type coupling reactions. Other organometallic coupling reactions include, organocuprate coupling reactions, Grignard coupling reactions, and the like. A general description of Organometallic Coupling is given in detail in Advanced Organic Chemistry, 4$^{th}$ Edition, Part B, Reactions and Synthesis, Francis A. Carey and Richard J. Sundberg, Kluwer Academic/Plenum Publishers, 2000, Chapters 7 and 8, and references cited therein.

In Scheme 2d. the compound of Formula 30 (or Formula 34) is coupled with the organometallic reagent of Formula 31 (or Formula 33) in the presence, or absence, of a transition metal catalyst, and/or a phosphine or arsine, and/or a base in an inert solvent. Other additives, such as, copper salts, silver salts, and the like may be added. Approximately one equivalent of the compound of Formula 30 (or Formula 34) is reacted with one to five equivalents of the compound of Formula 31 (or Formula 33) with the appropriate additives in an inert solvent. The reaction is normally carried out between −78° C. and 200° C. for between 4 to 72 hours.

Examples of "organometallic reagents" include, organo-magnesium, organozinc, mixed organocuprate, organostannane, or organoboron compounds, and the like. Examples of "transition metal catalysts" include, palladium and nickel catalysts, such as, $Pd(OAc)_2$, $Pd(PPh_3)_4$, $PdCl_2$, $Pd(PPh_3)Cl_2$, $Pd(OCOCF_3)_2$, $(CH_3C_4H_5P)_2PdCl_2$, $[(CH_3CH_2)_3P]_2PdCl_2$, $[(C_6H_{11})_3P_{12}PdCl_2$, $[(C_6H_5)_3P]_2PdBr_2$, $Ni(PPh_3)_4$, $(C_6H_4CH=CHCOCH=CHC_6H_5)_3Pd$, and the like. Among the above transition metal catalysts, $Pd(OAc)_2$, $Ni(PPh_3)_4$, and $Pd(PPh_3)_4$ are preferable.

Examples of "phosphines or arsines" include, a trialkyl or triarylphosphine or arsine, such as triisopropylphosphine, triethylphosphine, tricyclopentylphosphine, triphenylphosphine, triphenylarsine, 2-furylphosphine, tri-o-tolylphosphine, tricyclohexylphosphine, 1,2-bis(diphenylphosphino)ethane, 1,3-bis(diphenylphosphino)propane, 1,4-bis(diphenylphosphino)butane, 2-(Di-t-butylphosphino)biphenyl, and the like. Among the above "phosphines and arsines," tri-o-tolylphosphine, triphenylarsine, and tricyclohexylphosphine are preferable.

Examples of "other additives" include, copper salts, zinc salts, lithium salts, ammonium salts and the like. Among the above "other additives," CuI, LiCl, and $n-Bu_4N^+Cr$ are preferable. If necessary, the reaction can be carried out with a basic group synthon incorporated as the basic group as described previously. As outlined in Schemes 2e below, the coupling process of General Method 2 can consist of a Wittig-type Coupling Process. The compound of Formula 33 (or Formula 37) is coupled with the phosphorus ylene (or ylide) reagent of Formula 34 (or Formula 36) to afford the compounds of Formula 35 of the invention. A general description of Wittig-type Coupling Reactions is given in detail in general reference texts such as Advanced Organic Chemistry, 4$^{th}$ Edition, Part B, Reactions and Synthesis, Francis A. Carey and Richard J. Sundberg, Kluwer Academic/Plenum Publishers, 2000, Chapter 2, and references cited therein.

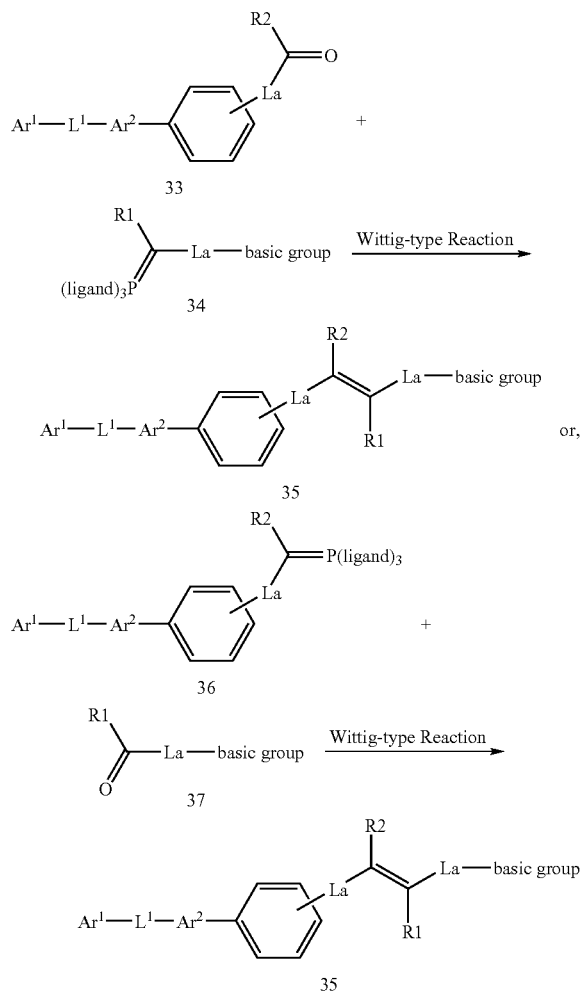

The compound of Formula 33 (or Formula 37) is coupled with the phosphorus ylene (or ylide) reagent of Formula 34 (or Formula 36) in the presence, or absence, a base in an inert solvent to form the compounds of the invention of Formula 35. Other additives, such as, lithium salts, sodium salts, potassium salts, and the like may be added. Approximately one to five equivalents of the compound of Formula 33 (or Formula 37) is reacted with one to five equivalents of the compound of Formula 34 (or Formula 36) with the appropriate additives an inert solvent. The reaction is normally carried out between −78° C. and 120° C. for between 2 to 72 hours. The Wittig reaction product may be reduced to form other compounds of the invention using reducing agents known to one of skill in the art and/or described previously. Preferred bases for the above organometallic reactions include, sodium hydride, DBU, potassium t-butoxide, and lithium hexamethyldisilazide.

General Method 3: Coupling of the Five-membered Ring Heterocycle and Phenyl Groups The compounds of Formula 3 can be prepared by the General Method 3, described in General Scheme 3, via coupling of the compounds of Formula 38 with a compound of Formula 39. An example of the General Method 3 is a Aryl Coupling Process (Scheme 3a). The aryl-coupling reaction is carried out in accordance with per se known methods, or analogous methods thereto, such as those described in the general reference texts discussed previously.

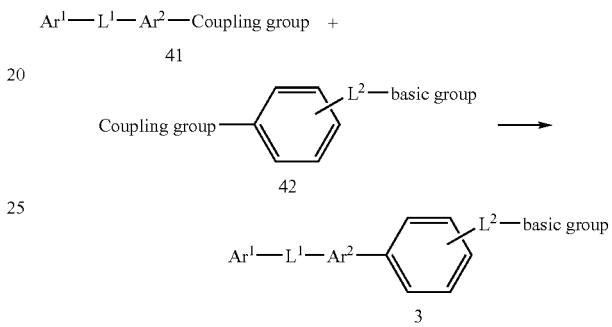

The compound of Formula 44 (or Formula 45) is coupled with an organometallic compound of Formula 43 (or Formula 46) in an Aryl Coupling Process to afford the compounds of the invention of Formula 3.

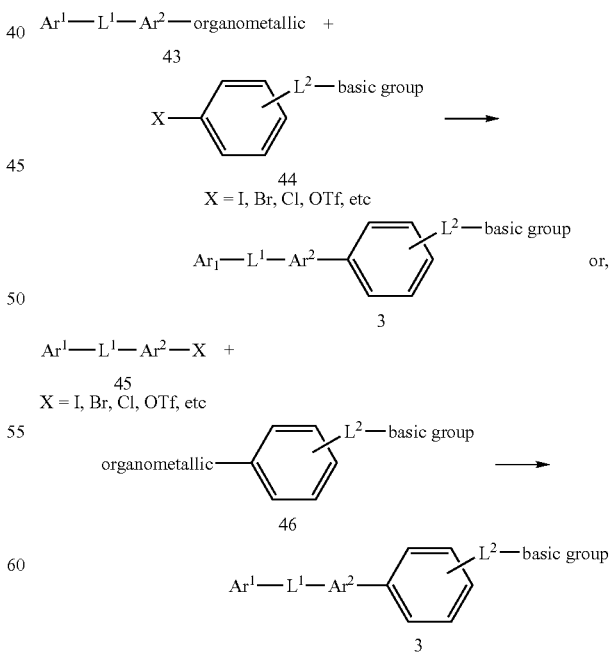

The compound of Formula 44 (or Formula 45) is coupled with the organometallic reagent of Formula 43 (Formula 46)

in the presence, or absence, of a transition metal catalyst, and (or) a phosphine or arsine, and (or) a base in an inert solvent. Other additives, such as, copper salts, silver salts, and the like may be added. Approximately one equivalent of the compound of Formula 44 (or Formula 45) is reacted with one to five equivalents of the compound of Formula 43 (Formula 46) with the appropriate additives an inert solvent. The reaction is normally carried out between −78° C. and 200° C. for between 4 to 72 hours. Examples of "organometallic reagents", "transition metal catalysts" "phosphines or arsines" "other additives" and "base" have been described previously.

General Method 4: Heterocycle Formation

The compounds of Formula 3 can be prepared by the General Method 4, described in General Scheme 4, via reaction of the compound of Formula 47 containing a coupling group with a compound of Formula 48 containing a coupling group, where during the course of the coupling reaction the coupling groups form the 5-membered ring heterocycle between the linker $L^1$ and the phenyl ring. $Ar^1$, $L^1$, $Ar^2$, $L^2$, and basic group are defined as above. Examples of heterocyclic ring forming reactions are given in Comprehensive Heterocyclic Chemistry, Volumes 1–8, A. P. Katritzky and C. W. Rees Eds, Pergamon Press, 1984; Heterocyclic Chemistry, $3^{rd}$ Ed, Thomas L. Gilchrist, Addison-Wesley-Longman Ltd, 1997; An Introduction to the Chemistry of Heterocyclic Compounds, $3^{rd}$ Ed, R. M. Acheson, Wiley Interscience, 1976; etc, and references cited therein. Specific examples of the General Method 4 include an Oxadiazole Process (Schemes 4a and 4b), a Thiadiazole

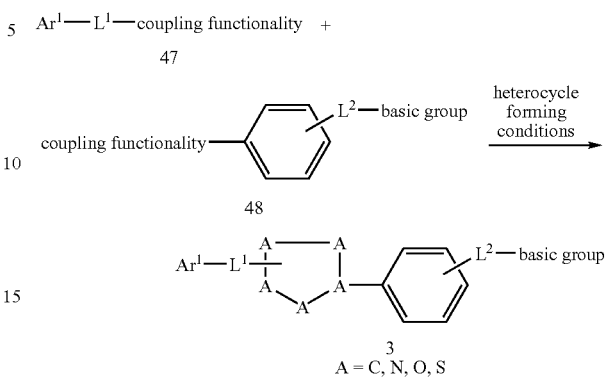

As outlined in Scheme 4a below, the coupling process of General Method 4 can consist of a Oxadiazole Process. The diacylhydrazide compound of Formula 51 is produced by acylation of an acylhydrazide of Formula 50 (or Formula 53) by a carboxylic acid derivative of Formula 49 (or Formula 54). The acylation process is carried out in accordance with the above Acylation/Sulfonylation Process of the General Method 2. The diacylhydrazide is cyclized to the oxadiazole compounds of the invention of Formula 52 utilizing dehydration processes analogous to that described in J Org Chem 1999, 64 (19), 6989–6992; and Chem Heterocycl Compd 1999, 35 (3), 275–280.

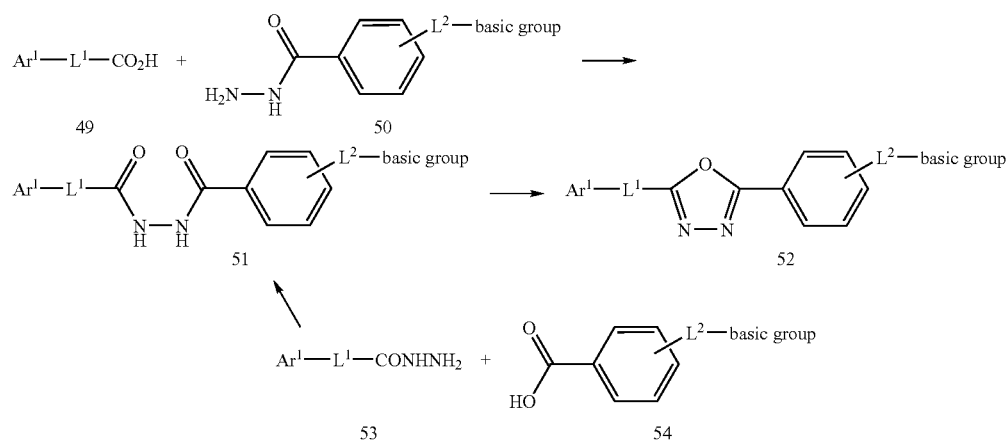

Process (Scheme 4c), and an Oxazole Process (Scheme 6 a-e). If necessary, the reaction can be carried out with a basic group synthon incorporated as the basic group, i.e., a group that could readily be converted to a basic group by methods known to one skilled in the art. Basic group synthons would include, but not be limited to, halogen, protected amine, nitrile, aldehyde, and the like. Following the Heterocycle Formation Process, these groups would then be unmasked or converted under standard conditions to afford the basic group.

One equivalent of compound of Formula 51 is reacted with one to equivalents of a dehydrating agent in the presence, or absence, a base in an inert solvent. The reaction is normally carried out between 25° C. and 250° C. for between 4 to 72 hours. Examples of "dehydrating agents" include, $SOCl_2$, $H_3PO_4$, $POCl_3$, $PCl_5$, $Tf_2O$, $Ac_2O$, $PPh_3$-$I_2$, $PPh_3$—$Br_2$, $PPh_3$—$Cl_2$, $PPh_3$–$CBr_4$, $PPh_3$–$CCl_4$, PPA, $NH(Tms)_2$, $P_2O_5$, $Me_2SiCl_2$, $PhOPCl_2$, $H_2SO_4$, and the like.

As outlined in Scheme 4b below, an alternative Oxadiazole Process may be utilized to prepare the oxadiazole compounds of the invention of Formula 52. The carboxylic acid derivative of Formula 49 (or 54) is activated for coupling as a "reactive acylating agent." The acylation process is carried out in accordance with the above Acylation/Sulfonylation Process of the General Method 2. The acylated intermediate is converted to the oxadiazole compounds of the invention of Formula 52. The process is analogous to that described in Synth Commun 1994, 24 (11), 1575–1582; J Org Chem 1961, 26, 2372; Synthetic Commun 24 (11), 1575–1582 (1994); etc, and references cited therein.

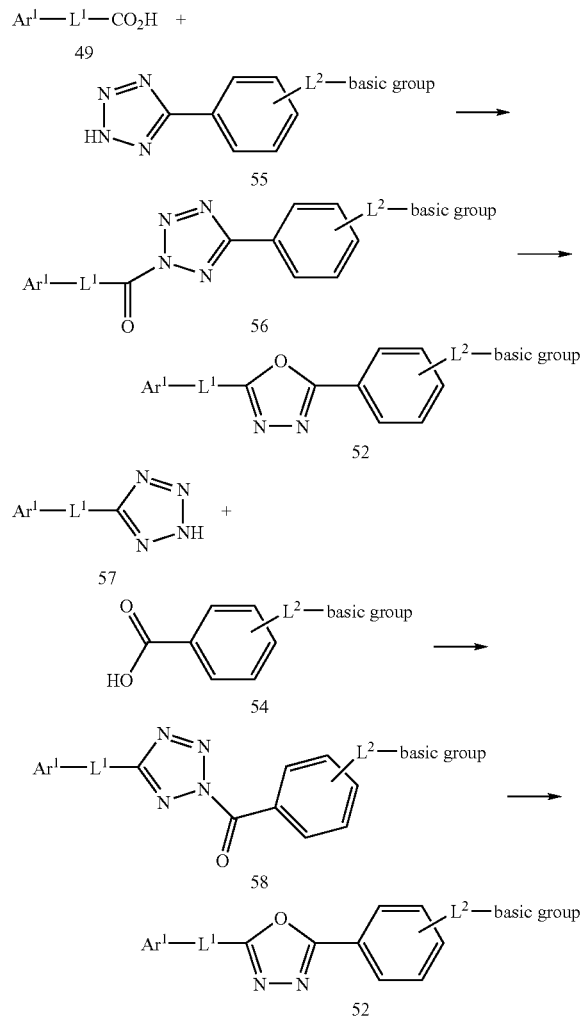

One to five equivalents of the "reactive acylating agent" of compound 49 (or compound 54) and one to five equivalents of compound of Formula 55 (or 57) are reacted in an inert solvent. If necessary the reaction can be carried out in the presence of a one to five equivalents of 1-hydroxybenzotriazole, 1-hydroxy-7-azabenzotriazole, and (or) a catalytic quantity to five equivalents of a base. The reaction intermediate of Formula 56 (or 58) may, or may not, be isolated. The reaction is normally carried out between 0° C. and 200° C. Reaction time is normally 4 to 48 hours. Reactive acylation agents have been described and may similarly be prepared for compounds 49 and/or 55 as described previously.

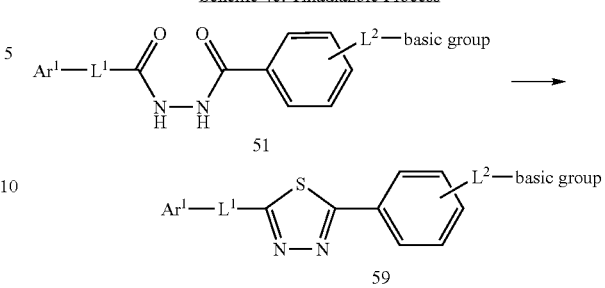

One equivalent of compound of Formula 51 is reacted with one to five equivalents of a thiol dehydrating agent in the presence, or absence, a base in an inert solvent. The reaction is normally carried out between 25° C. and 250° C. for between 4 to 72 hours. Examples of "thiol dehydrating agents" include, $P_2S_5$, Lawesson reagent, and the like.

General Method 5: Coupling of the Linker Group $L^1$

The compounds of Formula 3 can be prepared by the General Method 5, described in General Scheme 5, via reaction of the coupling group of Formula 62 with a coupling group of Formula 63, where during the course of the coupling reaction the coupling groups are retained, or lost, to form the linker $L^1$ between the 5-membered ring heterocyclic group and $Ar^1$. $Ar^1$, $L^1$, $AR^2$, $L^2$, and basic group are defined as above. La is defined as a group that when the coupling process occurs results in the formation of the linker $L^2$ defined above. Examples of the General Method 5 are an Ether/Thioether Alkylation Process (Scheme 5a), an Acylation/Sulfonylation Process Process (Scheme 5b), an Urea/Thiourea/Guanadine Coupling Process (Scheme 5c1, 5c2, 5c3), an Organometallic Process (Scheme 5d), and a Wittig-type Coupling (Scheme 5e).

If necessary, the reactions below may be carried out with a basic group synthon incorporated as the basic group, as described previously. Following the Coupling of the Linker Group ($L^1$) Process, these groups would then be unmasked or converted under standard conditions to afford the basic group.

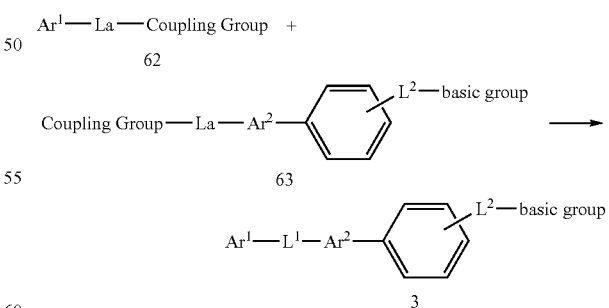

As outlined in Scheme 5a below, the coupling process of General Method 5 can consist of a Ether/Thioether Alkylation Process. Nucleophilic displacement by an alcohol or thiol-containing compound of Formula 64 (or Formula 68) with a compound of Formula 65 (or Formula 67) containing a leaving group affords the ether and thioether compounds of Formula 66 of the invention. The processes are analogous to the process described for the General Method 2, described in Scheme 2a, and carried out in accordance with the above method.

Scheme 5a: Ether/Thioether alkylation process

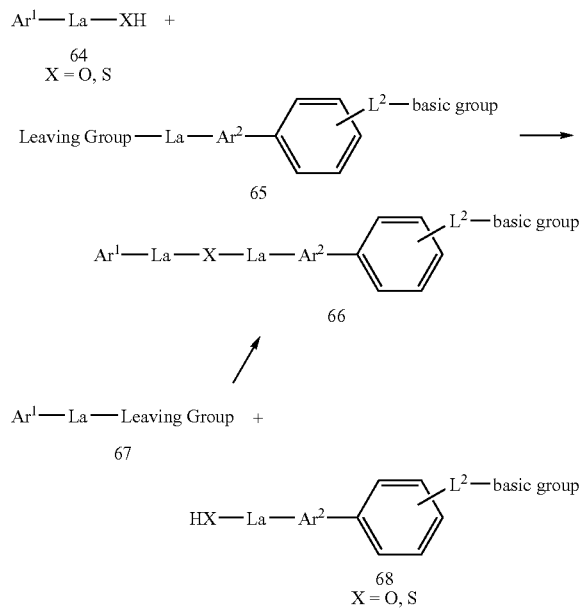

As outlined in Scheme 5b below, the coupling process of General Method 5 can consist of an Acylation/Sulfonylation Process. Acylation or sulfonylation of an alcohol or amine compound of Formula 70 with a carboxylic acid or sulfonic acid compound of Formula 69, affords the ester, amide, sulfonic ester, or sulfonamide compounds of Formula 71. Alternatively, acylation or sulfonylation of an alcohol or amine compound of Formula 72 with a carboxylic acid or sulfonic acid compound of Formula 73 affords the ester, amide, sulfonic ester, or sulfonamide compounds of Formula 74. The processes are analogous to the process described for the General Method 2, described in Scheme 2b, is carried out in accordance with the above method.

Scheme 5b: Acylation/Sulfonylation Process

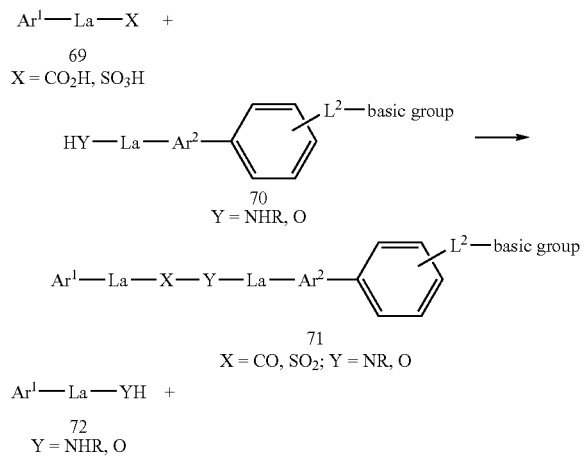

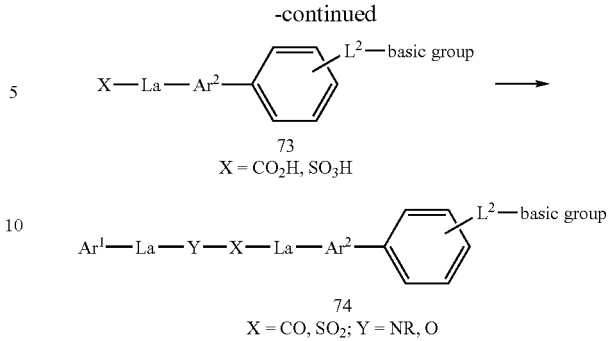

As outlined in Schemes 5c1, 5c2, and 5c3, below, the coupling process of General Method 5 can consist of a Urea/Thiourea/Guanidine/Carbamate-Type Coupling Process to afford the compounds of Formula 77, 81, and 84 of the invention. The processes are analogous to the processes described for the General Method 2, described in Schemes 2c1, 2c2, and 2c3, are carried out in accordance with the above method.

Scheme 5c1: Urea/Thiourea/Guanidine/Carbamate-Type Coupling

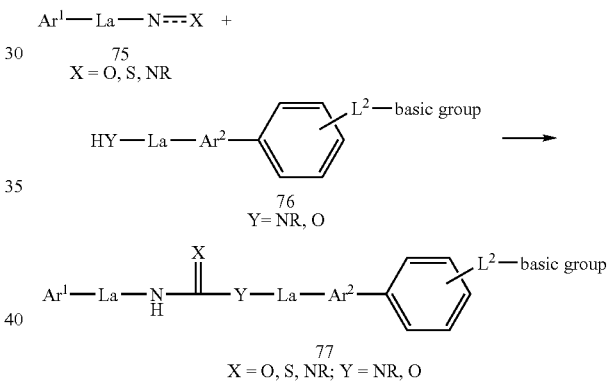

Scheme 5c2: Urea/Thiourea/Guanidine/Carbamate-Type Coupling

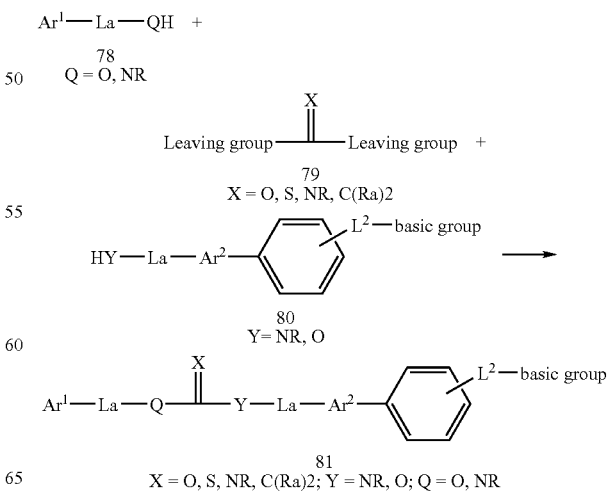

Scheme 5c3: Urea/Thiourea/Guadidine/Carbamate-Type Coupling

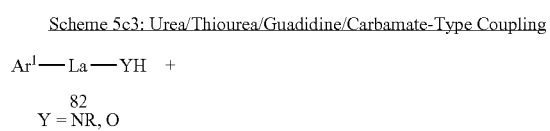

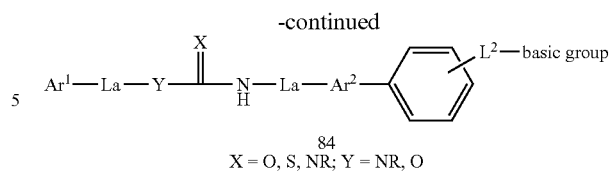

As outlined in Schemes 5d below, the coupling process of General Method 5 can consist of a Organometallic Coupling Process. The compound of Formula 86 (or Formula 87) is coupled with an organometallic compound of Formula 85 (or Formula 88) in an Organometallic Coupling Process to afford the compounds of Formula 3 of the invention. The processes are analogous to the processes described for the General Method 2, described in Scheme 2d, and are carried out in accordance with the above methods.

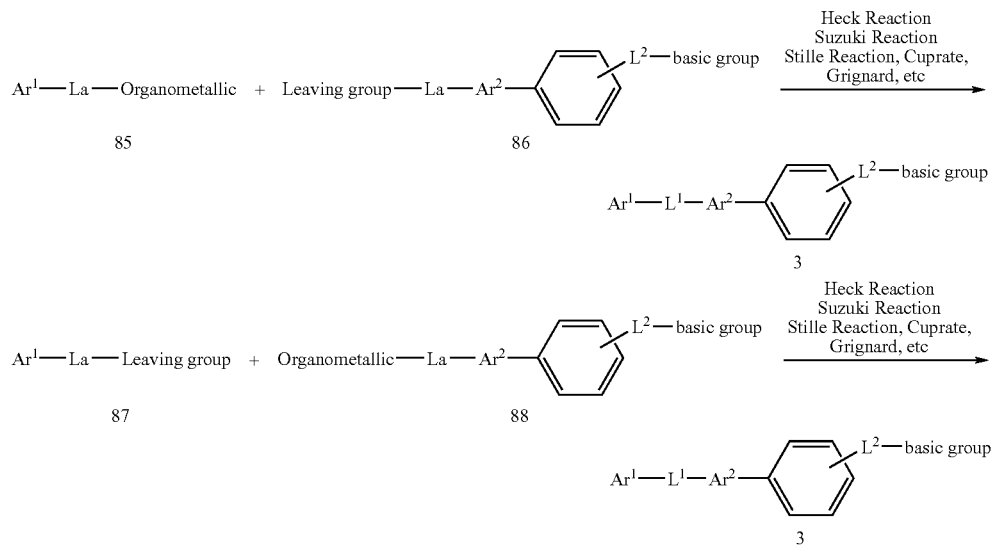

As outlined in Schemes 5e below, the coupling process of General Method 2 can consist of a Wittig-type Coupling Process. The compound of Formula 89 (or Formula 93) is coupled with the phosphorus ylene (or ylide) reagent of Formula 90 (Formula 92) to afford the compounds of Formula 91 of the invention. The processes are analogous to the processes described for the General Method 2, described in Scheme 2e, and are carried out in accordance with the above methods.

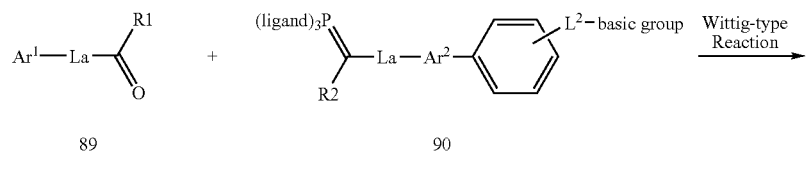

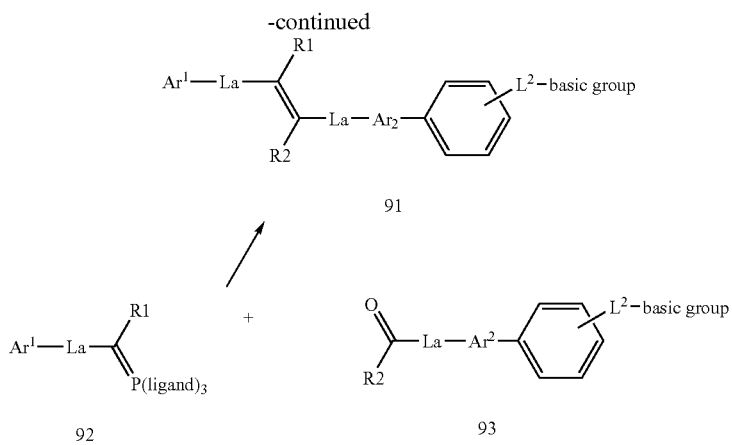

Preparation of Oxazole and Oxathiazole Compounds

As outlined in schemes 6a-c (below) the formation of oxazoles and thiazoles require elevated temperatures from 80–120° C. in solvents like dimethylformamide (scheme 6a+b) or phosphoryl chloride (scheme 6c).

These heterocyclic cyclisations result either in chloromethyl substituted oxazoles and thiazoles (scheme 6a+c) or in vinyl substituted oxazole (scheme 6b). After cis-hydroxylation of the later vinyl substituted oxazole, followed by diol cleavage, as known to the artesian, the resulting formyl substituted oxazole can be converted via reduction and substitution to the chloro methyl substituted oxazole (scheme 6b). The cyclisation of □-bromoketone with acrylamide (scheme 6b) is preferably performed in the presence of a stabiliser (such as 2,6 di-tert.-butyl-4-methyl-phenol) to prevent polymerisation of the acrylamide. As outlined in scheme 6c, the condensation of 2-chloro acetyl chloride with an □-aminoketone in presence of a base such as, for example, triethylamine, affords a product in high yield that can be cyclised in phosphoryl chloride to result in formation of an

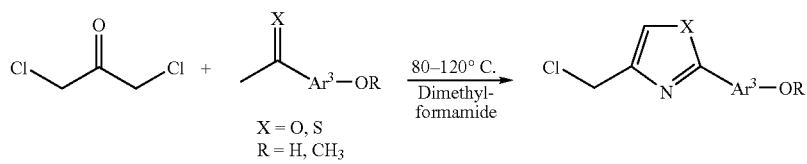

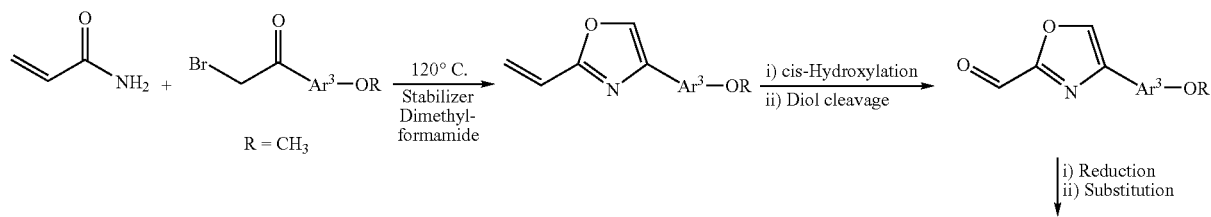

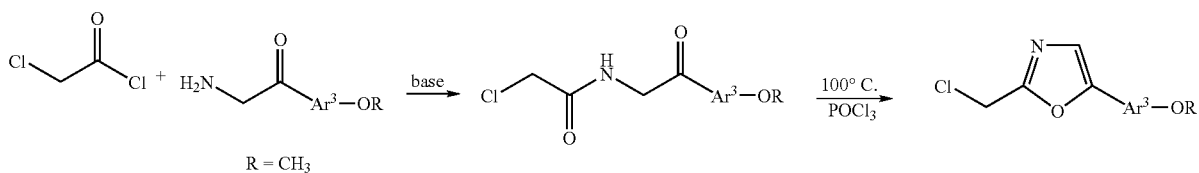

oxazole. Unlike general scheme 4, these heterocyclic formations of oxazoles and thiazoles do not work as desired in the presence of Ar¹-L¹- nor in the presence of -L²-basic group, so that these groups have to be introduced later, as outlines in schemes 6d and 6e.

Scheme 6d: Formation of the Linker Group $L_1$

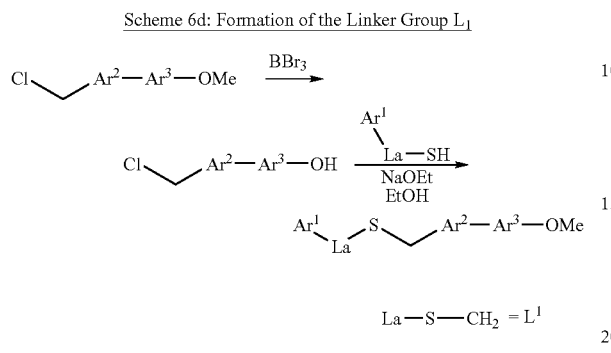

Scheme 6e: Formation of the Linker Group $L_2$

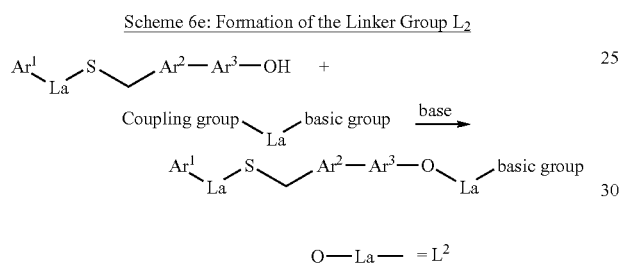

In order to achieve formation of the linker $L^1$, the chloromethyl substituted oxazoles or thiazoles from scheme 6a-c can be used as alkylation substrates for thiolates (scheme 6d). Therefore, a thiol is treated with a base, like sodium ethoxide in ethanol, before addition of the chloro methyl substituted oxazole. This alkylation proceeds in the presence of an unprotected phenol. The unprotected phenol can be incorporated into linker $L^2$ in a subsequent reaction, as outlined in scheme 6e in solvents such as dimethylformamide and involving bases such as potassium carbonate. As outlined in scheme 6d, the phenol may be obtained from the Lewis-acid mediated cleavage of a methylether with Lewis-acids, preferably, borontribromide in solvents such as dichloromethane.

For compounds wherein $AR^2$ is oxazole, positional isomers of the oxazole group (e.g isoxazole) may be made as shown in Scheme 7.

Scheme 7

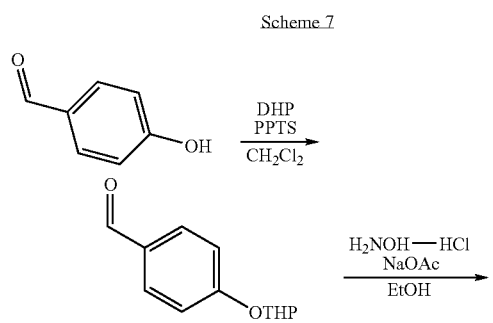

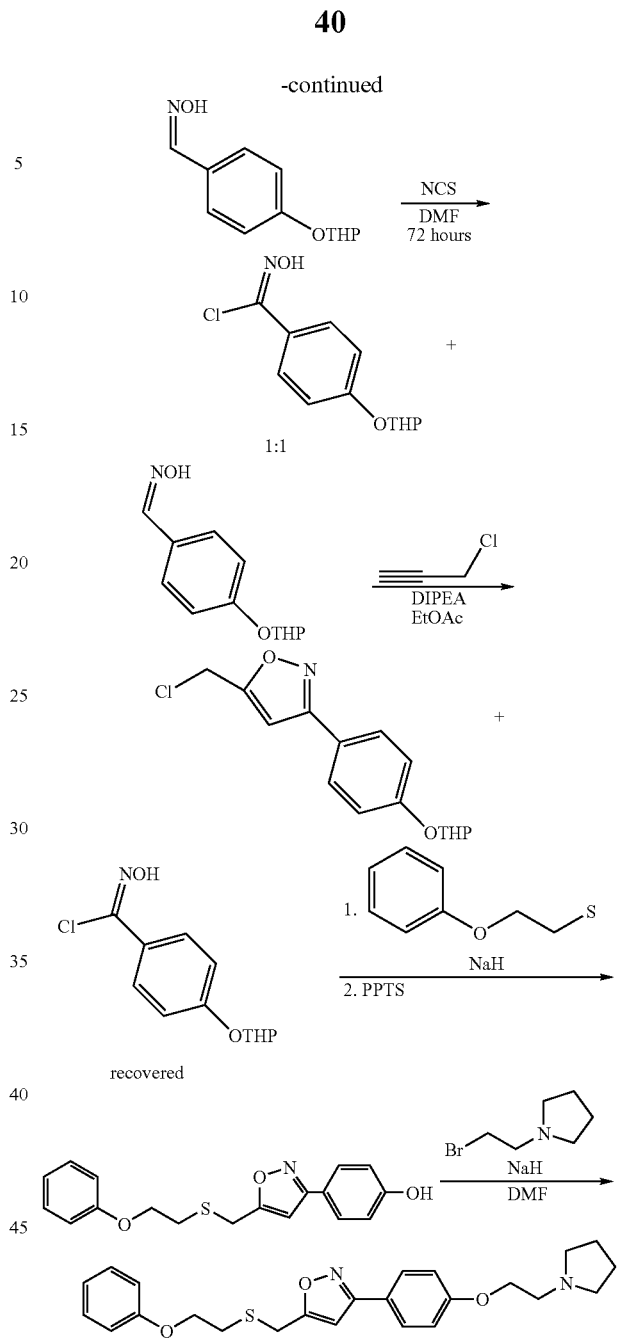

4-Hydroxy-benzaldehyde is protected as the tetrahydropyran (THP) ether, using dihydropyran and p-toluenesulfonic acid (PPTS) in dichloromethane. The aldehyde functionality is converted to an oxime with hydroxylamine hydrochloride and sodium acetate in ethanol. The oxine is then converted to a chloro-oxime with NCS in DMF. Dipolar cycloaddition of the chloro-oxime and 3-chloropropyne in ethyl acetate using DIPEA as catalyst gives the intermediate 5-chloromethyl-3-[4-(tetrahydro-pyran-2-yloxy)-phenyl]-isoxazole. This is then used to alkylate 2-phenoxy-ethanethiol. This intermediate is deprotected with PPTS to give 4-[5-(2-phenoxy-ethylsulfanylmethyl)-isoxazol-3-yl]-phenol. The phenol is alkyated with 1-(2-chloro-ethyl)-pyrrolidine hydrochloride to give the final product, 5-(2-phenoxy-ethylsulfanylmethyl)-3-[4-(2-pyrrolidin-1-yl-ethoxy)-phenyl]-isoxazole.

The 1,2,4-oxadiazole simer may be prepared following the procedure of Scheme as shown in Scheme 8 for the particular example.

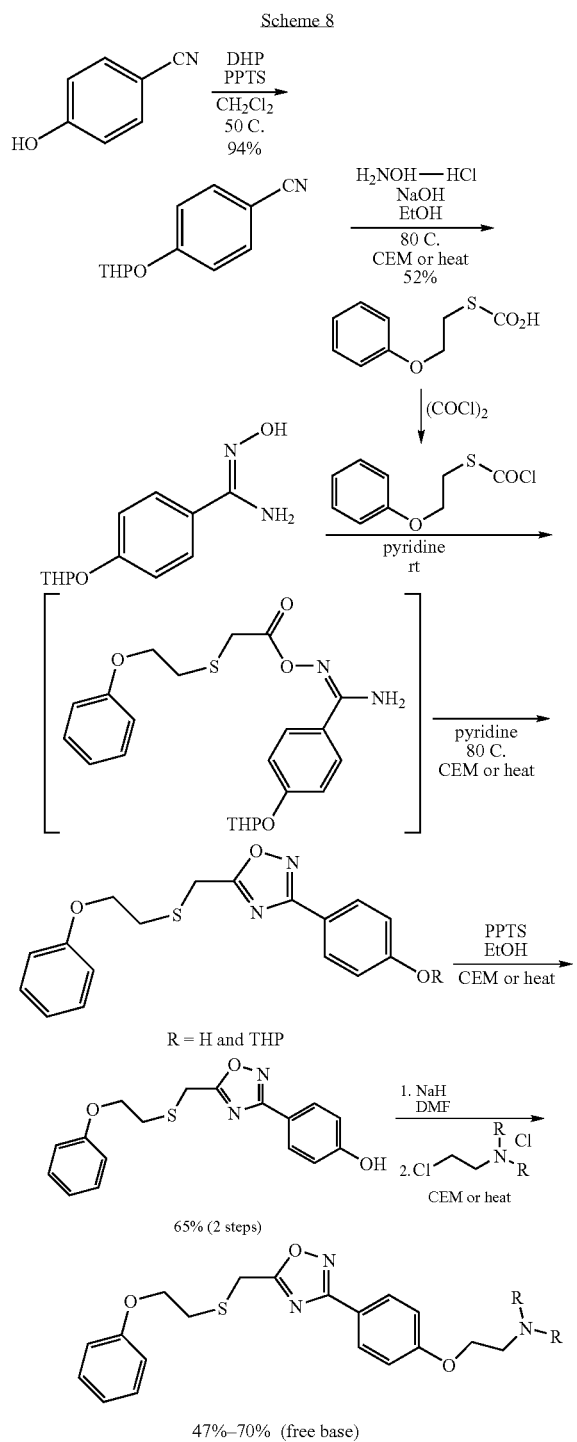

As shown, 4-Cyanophenol is protected as the Tetrahydropyran (THP) ether using dihyropyran and dihydropyran and p-toluenesulfonic acid (PPTS) in dichloromethane. The cyano functionality is converted to an amidoxime functionality by reaction with hydroxylamine hydrochloride and NaOH in ethanol in a microwave chamber at 80 C. A mixture of the amidoxime and (2-phenoxy-ethylsulfanyl)-acetyl chloride in pyridine is microwaved at 80 C to give the isoxazole intermediate as a mixture of protected THP ether and deprotected phenol. After removal of pyridine under vacuum, the reaction products are treated with PPTS in ethanol and microwaved at 75 C to deprotect any remaining THP ether, giving 4-[5-(2-phenoxy-ethylsulfanylmethyl)-[1, 2,4]oxadiazol-3-yl]-phenol. The phenol is alkyated with 1-(2-chloro-ethyl)-pyrrolidine hydrochloride to give the final product, 5-(2-phenoxy-ethylsulfanylmethyl)-3-[4-(2-pyrrolidin-1-yl-ethoxy)-phenyl]-[1,2,4]oxadiazole hydrochloride.

One of skill in the art is aware that other compounds within the scope of the invention may be made as shown or by modifications to the procedures provided which are not cumbersome and are known to one of skill in the art or accessible in the general reference texts or literature available to one of skill in the art. Futhermore, in addition to the discussive procedures herein, detailed examples are provided which would further assist one of skill in the art to make the appropriate modifications to arrive at compounds within the scope that are not specifically exemplified.

Demonstration of Function

In order to demonstrate that compounds of the present invention have the capacity to bind to and inhibit the function of MCHR1, binding and functional assays were established. All ligands, radioligands, solvents and reagents employed in these assays are readily available from commercial sources or can be readily prepared by those skilled in the art.

The full-length cDNA for human MCHR1 was cloned from a human adult brain cDNA library (Edge Biosystems, Cat. 38356) by standard polymerase chain reaction (PCR) methodology employing the following primers: sense, 5'-GCCACCATGGACCT GGAAGCCTCGCTGC-3'; antisense, 5'-TGGTGCCCTGACTTGGAGGTGTGC-3'.

The PCR reaction was performed in a final volume of 50 μl containing 5 μl of a 10× stock solution of PCR buffer, 1 μl of 10 mM dNTP mixture (200 μM final), 2 μl of 50 mM Mg(SO$_4$) (2 mM final), 0.5 μl of 20 μM solutions of each primer (0.2 μM final), 5 μl of template cDNA containing 0.5 ng DNA, 0.5 μl of Platinum Taq High Fidelity DNA polymerase (Gibco Life Technologies) and 36 μl of H$_2$O. PCR amplification was performed on a Perkin Elmer 9600 thermocycler. After denaturation for 90 sec at 94° C., the amplification sequence consisting of 94° C. for 25 sec, 55° C. for 25 sec and 72° C. for 2 min was repeated 30 times, followed by a final elongation step at 72° C. for 10 min. The desired PCR product (1.1 Kb) was confirmed by agarose gel electrophoresis and the band was extracted from the gel by Geneclean (Bio 1) following the manufacturer's instructions. Following extraction, the cDNA fragment was cloned into pCR2.1-TOPO plasmid (Invitrogen) to confirm the identity and sequence.

In order to generate cell lines stably expressing MCHR1, the insert was then subcloned into the Xba I and Not I sites of pcDNA(+)-3.1-neomycin (Invitrogen). After purification by Qiagen Maxi-prep kit (QIAGEN, Inc.), the plasmid was transfected by Fugene 6 (Roche Applied Science) into AV12 cells that had been previously transfected with the promiscuous G protein G$_{\alpha15}$. The transfected cells were selected by G418 (800 μg/ml) for 10–14 days and single colonies were isolated from culture plates. The G418-resistant colonies were further selected for MCHR1 expression by measuring MCH-stimulated Ca transients with a fluorometric imaging plate reader (FLIPR, Molecular Devices).

Typically, individual clones are plated out in 96-well plates at 60,000 cells per well in 100 μl of growth medium (Dulbecco's modified Eagle's medium (DMEM), 5% fetal bovine serum, 2 mM L-glutamine, 10 mM HEPES, 1 nmM sodium pyruvate, 0.5 mg/ml Zeocin, and 0.5 mg/ml Geneticin). After 24 hrs at 37° C., medium is removed and replaced with 50 μl of dye loading buffer (Hank's balanced salt solution (HBSS) containing 25 mM HEPES, 0.04% Pluronate 127 and 8 μM Fluo3 Both from Molecular Probes)). After a 60 min loading period at room temperature, dye loading buffer is aspirated and replaced with 100 μl of HEPES/HBBS. Plate is placed in FLIPR and basal readings are taken for 10 sec, at which point 100 μl of buffer containing 2 μM MCH (1 μM final) is added and measurements are taken over 105 sec. To correct for variations between clones in numbers of cells per well, the MCH response is normalized to the response induced by epinephrine.

Both the $^{125}$I-MCH binding and functional GTPγ$^{35}$S binding assays employed membranes isolated from a clone designated as clone 43. Typically, cells from 20 confluent T225 flasks were processed by washing the monolayers in cold phosphate-buffered saline (PBS), scraping the cells into same and re-suspending the cell pellet in 35 ml of 250 mM Sucrose, 50 mM HEPES, pH 7.5, 1 mM MgCl$_2$, 24 μg/ml DNase I, and protease inhibitors (1 Complete® tablet, per 50 ml of buffer prepared, Roche Diagnostics). After incubation on ice for 5 min, cells were disrupted with 20–25 strokes of a Teflon/Glass homogenizer attached to an overhead motorized stirrer, and the homogenate was centrifuged at 40,000 rpm in Beckman Type 70.1 Ti rotor. The pellets were re-suspended in 250 mM Sucrose, 50 mM HEPES, pH 7.5, 1.5 mM CaCl$_2$, 1 mM MgSO$_4$ and protease inhibitors by Teflon/Glass homogenization to achieve a protein concentration of ~3–5 mg/ml (Pierce BCA assay with Bovine serum albumin as standard).

Aliquots were stored at –70° C. Binding of compounds to MCHR1 was assessed in a competitive binding assay employing $^{125}$I-MCH, compound and clone 43 membranes. Briefly, assays are carried out in 96-well Costar 3632 white opaque plates in a total volume of 200 μl containing 25 mM HEPES, pH 7.5, 10 mM CaCl$_2$, 2 mg/ml bovine serum albumin, 0.5% dimethyl sulfoxide (DMSO), 4 μg of clone 43 membranes, 100 μM $^{125}$I-MCH (NEN), 1.0 mg of wheat germ agglutinin scintillation proximity assay beads (WGA-SPA beads, Amersham) and a graded dose of test compound. Non-specific binding is assessed in the presence of 1 μM unlabeled MCH. Bound $^{125}$I-MCH is determined by placing sealed plates in a Microbeta Trilux (Wallac) and counting after a 5 hr delay.

IC$_{50}$ values (defined as the concentration of test compound required to reduce specific binding of $^{125}$I-MCH by 50%) are determined by fitting the concentration-response data to a 4-parameter model (max response, min response, Hill coefficient, IC$_{50}$) using Excel. K$_i$ values are calculated from IC$_{50}$ values using the Cheng-Prusoff approximation as described by Cheng et al. (Relationship between the inhibition constant (K$_i$) and the concentration of inhibitor which causes 50% inhibition (IC$_{50}$) of an enzymatic reaction, Biochem. Pharmacol., 22: 3099–3108 (1973)). The K$_d$ for $^{125}$I-MCH is determined independently from a saturation binding isotherm.

Functional antagonism of MCH activity is assessed by measuring the ability of test compound to inhibit MCH-stimulated binding of GTPγ$^{35}$S to clone 43 membranes. Briefly, assays are carried out in Costar 3632 white opaque plates in a total volume of 200 μl containing 25 mM Hepes, pH 7.5, 5 mM MgCl$_2$, 10 μg/ml saponin, 100 mM NaCl, 3 μM GDP, 0.3 nM GTPγ$^{35}$S, 40 nM MCH (approximately equal to EC$_{90}$), 20 μg of clone 43 membranes, 1.0 mg of wheat germ agglutinin scintillation proximity assay beads (WGA-SPA beads, Amersham) and a graded dose of test compound. The plates are sealed and left for 16–18 hrs at 4° C. After a 1 hr delay to allow plates to equilibrate to ambient temperature, bound GTPγ$^{35}$S is determined by counting in a Microbeta Trilux (Wallac).

IC$_{50}$ values (defined as the concentration of test compound required to reduce MCH-stimulated GTPγ$^{35}$S binding by 50%) are determined by fitting the concentration-response data to a 4-parameter model (max response, min response, Hill coefficient, IC$_{50}$) using Excel. K$_b$ values are calculated from IC$_{50}$ values using a modification of the Cheng-Prusoff approximation as described by Leff and Dougal (Further concerns over Cheng-Prusoff analysis, Trends Pharmacol. Sci. 14: 110–112 (1993)) after verifying competitive antagonism by Schild analysis. The EC$_{50}$ for MCH alone is determined independently. The MCHR1 binding and functional activities of 24 compounds in the oxadiazole series (tested in duplicate) are shown in Table 1

TABLE 1

| Structure | K$_i$ (nM) | K$_b$ (nM) |
|---|---|---|
| 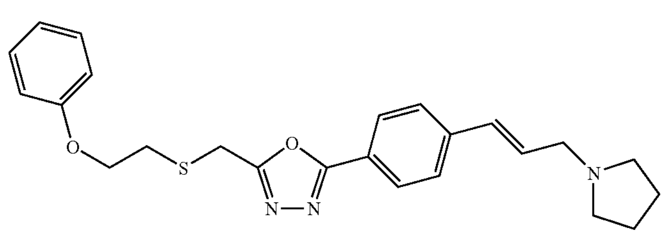 | 1.9 | 6.0 |

TABLE 1-continued
| Structure | $K_i$ (nM) | $K_b$ (nM) |
|---|---|---|
| 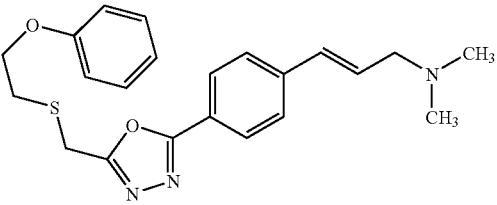 | 3.7 | 11.6 |
| 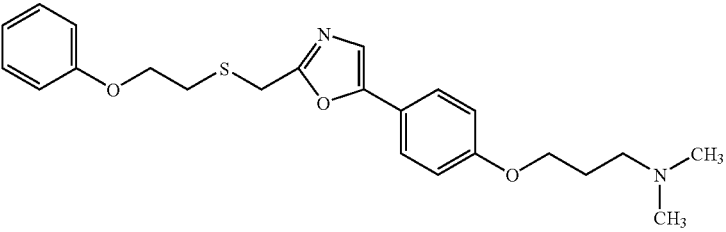 | 4.3 | 15.0 |
| 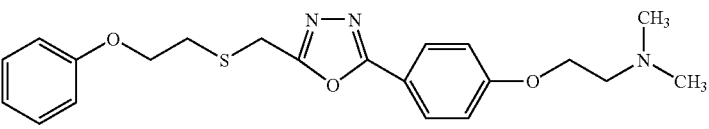 | 5.3 | 13.6 |
| 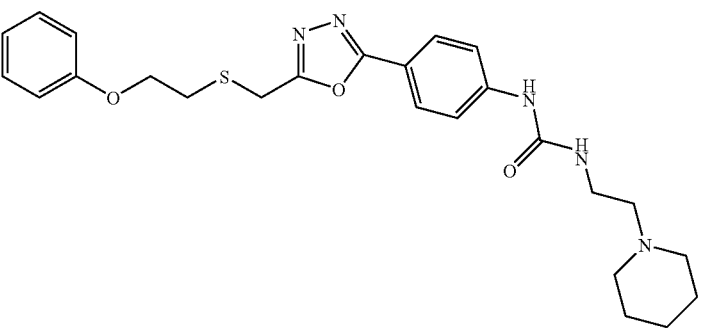 | 5.6 | 14.7 |
| 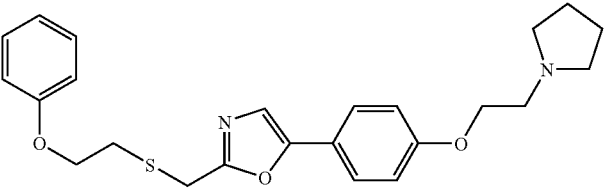 | 5.8 | 12.0 |
| 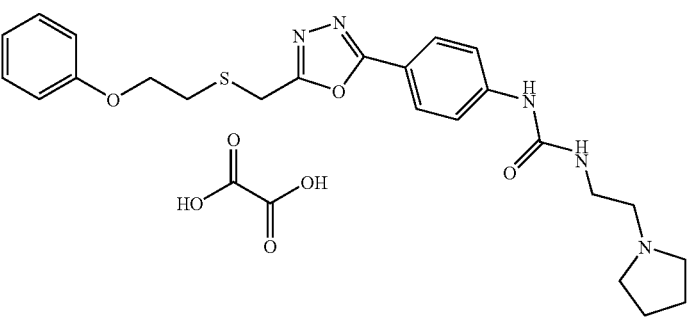 | 9 | 20.0 |

TABLE 1-continued
| Structure | $K_i$ (nM) | $K_b$ (nM) |
|---|---|---|
| 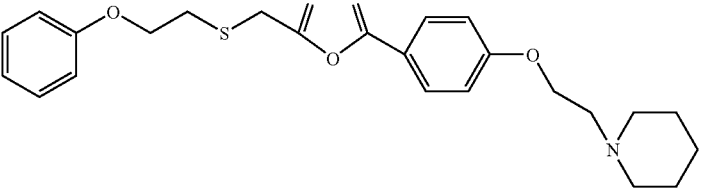 | 9.2 | 19.8 |
| 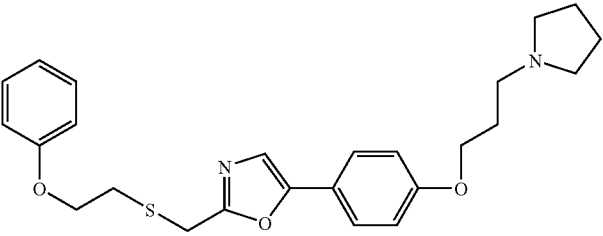 | 10.2 | 16.5 |
| 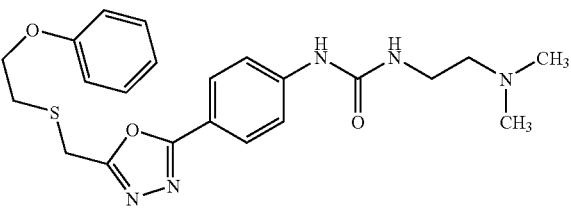 | 10.4 | 16.2 |
| 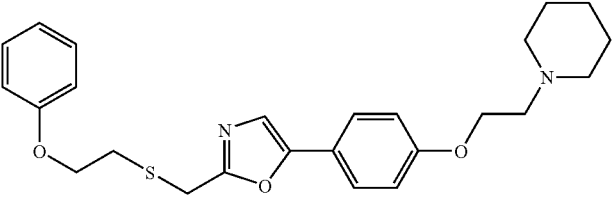 | 11.6 | 7.3 |
| 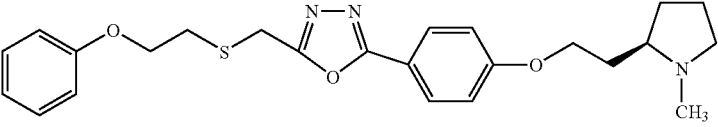 | 12.9 | 39.6 |
| 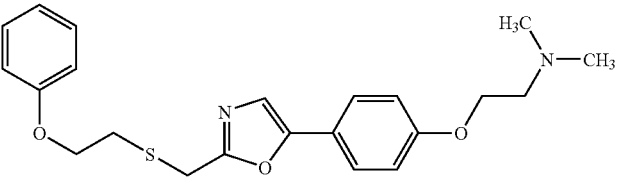 | 13.3 | 9.4 |
| 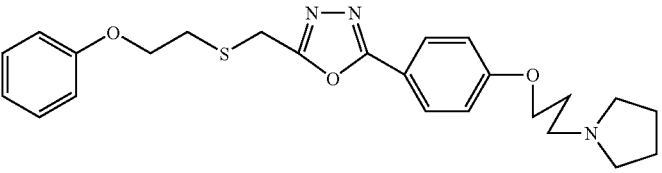 | 14.3 | 18.1 |
| 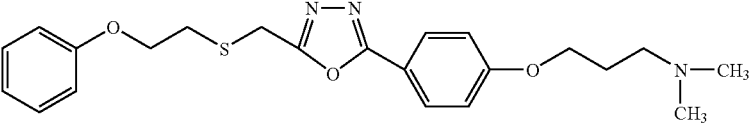 | 16 | 11.9 |

TABLE 1-continued
| Structure | $K_i$ (nM) | $K_b$ (nM) |
|---|---|---|
| 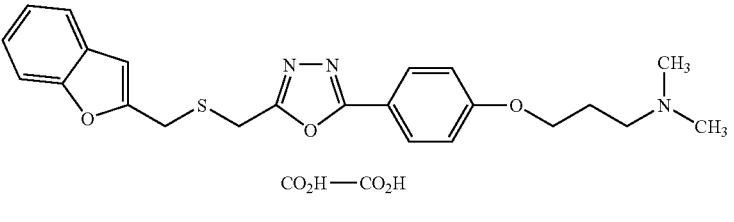 | 16.1 | 35.4 |
| 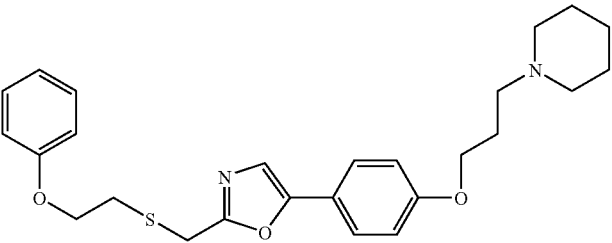 | 17.9 | 15.9 |
| 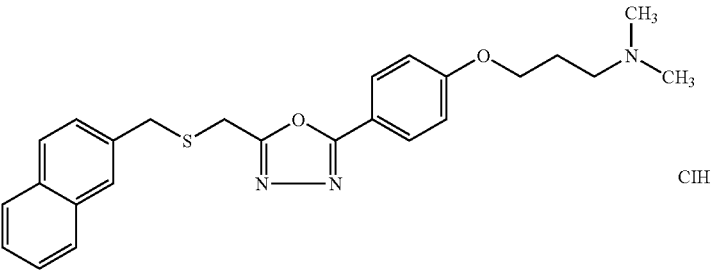 | 22.4 | 50.6 |
| 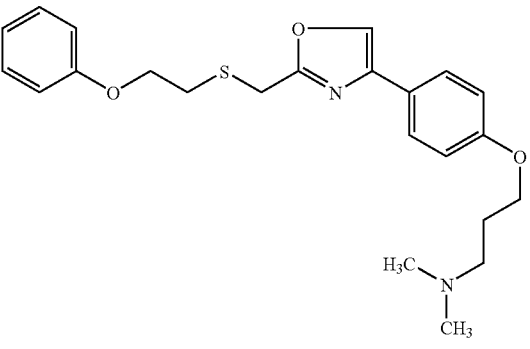 | 35 | 41.5 |
| 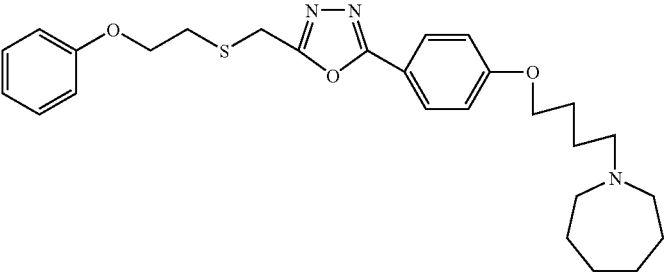 | 37.9 | 31.3 |

TABLE 1-continued

| Structure | $K_i$ (nM) | $K_b$ (nM) |
|---|---|---|
| 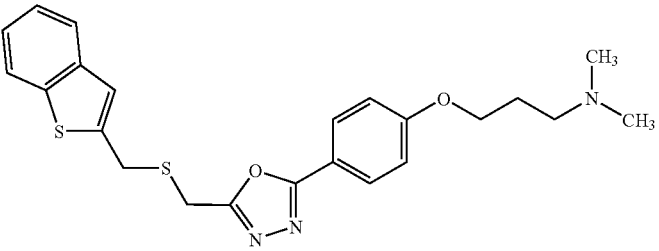 | 48.4 | 139.5 |
| 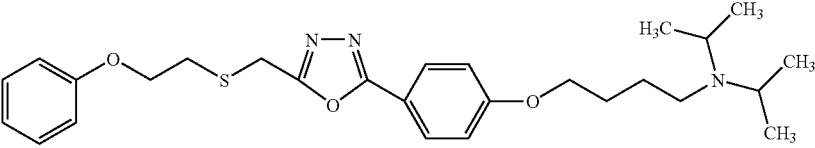 | 63.3 | 52.1 |
| 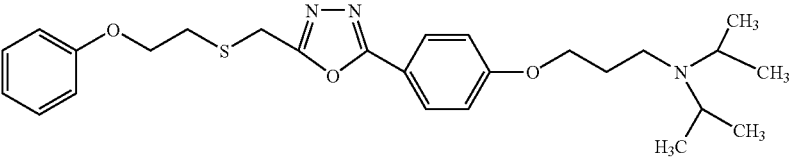 | 140 | 145.2 |
| 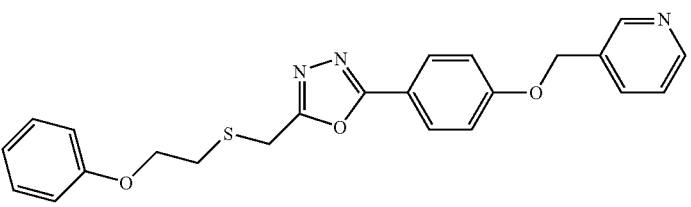 | 2898 | 6889 |

In order to demonstrate in vivo efficacy of this series of compounds, compound of example 136 was injected intracerebro-ventricularly in the absence or presence of 2.1 nmol MCH, and its ability to block the effect of exogenous MCH was assessed. Diet-induced obese male Long-Evans rats (Harlan, Ind.) weighing 500–550 g at time of surgery were anesthetized with isoflurane. Stainless steel cannula guides (5 mm length, 26 gauge, Plastics One, Va.) were stereotaxically implanted in the lateral ventricle anteroposteriority: 0.8 mm caudal to bregma; and lateral: 1.5 mm from midline suture. Animals were individually housed in a temperature regulated room (24° C.) with a reverse 12 hour light/dark cycle (dark 10:00/22:00). Water and food (Teklad 95217, Harlan, Wis.) were available ad libitum. After surgery, animals were allowed to recover 7 days before experimental use. On test day, food was removed 1 hr prior to testing and animals (4 groups, n=6 per group) were injected between 0900 and 1000 with 5 µl of vehicle (artificial CSF), 2.1 nmol MCH, 82 nmol of compound of example 136, and MCH plus compound of example 136. Cumulative food intake was measured at 2, 4 and 6 hours after injection. The results are shown in FIG. 1. Treatment with compound of example 136 completely blocked the orexigenic effect of exogenous MCH (*$p<0.05$ vs. MCH alone).

Utility

As antagonists of the MCHR1 binding, a compound of the present invention is useful in treating conditions in human and non-human animals in which the the MCHR1 receptor has been demonstrated to play a role. The diseases, disorders or conditions for which compounds of the present invention are useful in treating or preventing include, but are not limited to, diabetes mellitus, hyperglycemia, obesity, hyperlipidemia, hypertriglyceridemia, hypercholesterolemia, atherosclerosis of coronary, cerebrovascular and peripheral arteries, gastrointestinal disorders including peptid ulcer, esophagitis, gastritis and duodenitis, (including that induced by H. pylori), intestinal ulcerations (including inflammatory bowel disease, ulcerative colitis, Crohn's disease and proctitis) and gastrointestinal ulcerations, neurogenic inflammation of airways, including cough, asthma, depression, prostate diseases such as benign prostate hyperplasia, irritable bowel syndrome and other disorders needing decreased gut motility, diabetic retinopathy, neuropathic bladder dysfunction, elevated intraocular pressure and glaucoma and non-specific diarrhea dumping syndrome. By inhibiting the MCH activity the compounds of the invention provide anorexic effects. That is, the compounds of the invention are useful as appetite suppressants and/or weightless agents. Compounds of the present invention have also shown some affinity for the R2 isoform of MCHR. The compounds of the invention may also be used in combination with other approved therapeutic agents for the treatment and/or prevention of obesity and related diseases. In this format, the compounds of the present invention enhance the positive effects of such combination treatments while minimizing the side effects due to the potential requirement of lower doses of such combination compounds. Such combination therapies may be delivered individually or in a combined formulation. Examples of compounds potentially useful in combination with compounds of formula I include weight loss agents (Mevidia™, Xenical™), cholesterol lowering agents, glucose level control or modulating agents and the like.

In treating non-human, non-companion animals, the compounds of the present invention are useful for reducing weight gain and/or improving the feed utilization efficiency and/or increasing lean body mass.

Formulation

The compound of formula I is preferably formulated in a unit dosage form prior to administration. Therefore, yet another embodiment of the present invention is a pharmaceutical formulation comprising a compound of formula I and a pharmaceutical carrier.

The present pharmaceutical formulations are prepared by known procedures using well-known and readily available ingredients. In making the formulations of the present invention, the active ingredient (formula I compound) will usually be mixed with a carrier, or diluted by a carrier, or enclosed within a carrier which may be in the form of a liquid, tablet, capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

FORMULATION EXAMPLES

Formulation 1
Tablets

| Ingredient | Quantity (mg/tablet) |
| --- | --- |
| Active Ingredient | 5–500 |
| Cellulose, microcrystalline | 200–650 |
| Silicon dioxide, fumed | 10–650 |
| Stearate acid | 5–15 |

The components are blended and compressed to form tablets.

Formulation 2
Suspensions

| Ingredient | Quantity (mg/5 ml) |
| --- | --- |
| Active Ingredient | 5–500 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve (approximately 355 micron opening) and mixed with the sodium carboxymethyl cellulose and syrup to form a smooth paste. The benzoic acid solution, flavor, and color are diluted with some of the water and added, with stirring. Sufficient water is then added to produce the required volume.

Formulation 3
Intravenous Solution

| Ingredient | Quantity |
| --- | --- |
| Active Ingredient | 25 mg |
| Isotonic saline | 1,000 ml |

The solution of the above ingredients is intravenously administered to a patient at a rate of about 1 ml per minute.

Dose

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. However, it will be understood that the therapeutic dosage administered will be determined by the physician in the light of the relevant circumstances, or by the vetrinarian for non-human recipients.

Generally, an effective minimum daily dose of a compound of formula I is about 5, 10, 15, or 20 mg. Typically, an effective maximum dose is about 500, 100, 60, 50, or 40 mg. Most typically, the dose ranges between 5 mg and 60 mg. The exact dose may be determined, in accordance with the standard practice in the medical arts of "dose titrating" the recipient; that is, initially administering a low dose of the compound, and gradually increasing the does until the desired therapeutic effect is observed.

Route of Administration

The compounds may be administered by a variety of routes including the oral, rectal, transdermal, subcutaneous, topical, intravenous, intramuscular or intranasal routes.

Combination Therapy

A compound of formula I may be used in combination with other drugs or therapies that are used in the treatment/ prevention/suppression or amelioration of the diseases or conditions for which compounds of formula I are useful. Such other drug(s) may be administered, by a route and in an amount commonly used therefor, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I. Examples of other active ingredients that may be combined with a compound of formula I, either administered separately or in the same pharmaceutical compositions, include, but are not limited to:
  (a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847;
    (ii) biguanides such as metformin and phenformin;
  (b) insulin or insulin mimetics;
  (c) sulfonylureas such as tolbutamide and glipizide;
  (d) alpha-glucosidase inhibitors (such as acarbose);
  (e) cholesterol lowering agents such as
    i. HMG-CoA reductase inhibitors (lovastatin, simvastatin and pravastatin, fluvastatin, atorvastatin, and other statins),
    ii. sequestrants (cholestyramine, colestipol and a dialkylaminoalkyl derivatives of a cross-linked dextran),
    iii. nicotinyl alcohol nicotinic acid or a salt thereof,
    iv. proliferator-activator receptor a agonists such as fenofibric acid derivatives (gemfibrozil, clofibrat, fenofibrate and benzafibrate),
    v. inhibitors of cholesterol absorption for example P-sitosterol and (acyl CoA:cholesterol acyltransferase) inhibitors for example melinamide,
    vi. probucol,
    vii. vitamin E, and
    viii. thyromimetics;
  (f) PPARδ agonists such as those disclosed in WO97/28149;
  (g) antiobesity compounds such as fenfluramine, dexfenfluramine, phentermine, sibutramine, orlistat, and other P3 adrenergic receptor agonists;
  (h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;
  (i) PPARα agonists such as described in WO 97/36579 by Glaxo;
  (j) PPARγ antagonists as described in WO97/10813; and
  (k) serotonin reuptake inhibitors such as fluoxetine and sertraline
  (l) antipsychotic agents such as for example olanzapine.

EXAMPLES

The following examples are only illustrative of the prepration protocols and Applicants' ability to prepare compounds of the present invention based on the schemes presented or modifications thereof. The examples are not intended to be exclusive or exhaustive of compounds made or obtainable.

Example 1

Preparation of N-(3-Dimethylaminopropyl)-4-[5-(3-phenylpropoxymethyl)-[1,3,4]oxadiazol-2-yl]benzamide from 3-phenyl-1-propanol

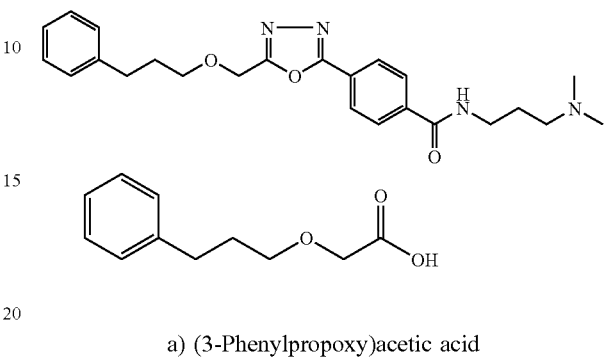

a) (3-Phenylpropoxy)acetic acid

To a solution of 3-phenyl-1-propanol (5.0 g, 36.7 mmol) in 36 mL THF at room temperature was added, in portions, sodium hydride (1.54 g, 38.5 mmol). After 30 minutes, a solution of methyl bromoacetate (6.18 g, 40.4 mmol) in 18 mL THF was added and the resultant mixture stirred at room temperature for 4.1 hours. Next, the mixture was diluted with 20 mL $H_2O$, then lithium hydroxide (2.64 g, 110 mmol) was added and the biphasic solution was heated at 60° C. for 1.5 hours. The mixture was then cooled to room temperature, diluted with $Et_2O$ and washed three times with $H_2O$. The combined aqueous phases were acidified with concentrated HCl until pH<2. The resultant mixture was extracted three times with $Et_2O$. The organic extracts were washed with brine, dried over sodium sulfate, filtered and concentrated to afford an oil. Purification by flash filtration chromatography on silica gel (elution with $CH_2Cl_2$ followed by 9:1 $CH_2Cl_2$:MeOH) afforded 2.7 g (38%) of(3-phenylpropoxy)acetic acid as an oil.

$^1$HNMR (DMSO-d6) δ 7.30–7.15 (m, 5H), 3.99 (s, 2H), 3.5 (t, 2H, J=6 Hz), 2.63 (t, 2H, J=7 Hz), 1.76–1.85 (m, 2H). IR ($CHCl_3$, $cm^{-1}$) 3027, 3019, 3013, 2948, 1779, 1732, 1454, 1246, and 1136.MS (ES) m/e 193. Anal. Calcd for $C_{11}H_{14}O_3$: C, 68.02; H, 7.27. Found C, 68.58; H, 6.91 b) 4-[5-(3-Phenylpropoxymethyl)-[1,3,4]oxadiazol-2-yl]benzoic acid methyl ester

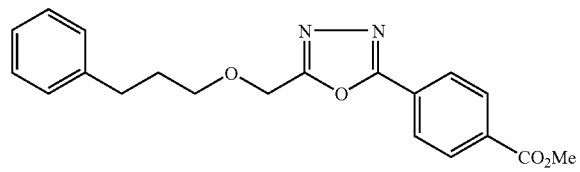

To a solution of (3-phenylpropoxy)acetic acid (1.11 g, 5.7 mmol) in 14.6 mL toluene at room temperature was added 1,3-dicyclohexylcarbodiimide (1.11 g, 5.7 mmol). After five minutes, 4-(1H-tetrazole-5-yl)benzoic acid methyl ester (1.16 g, 5.7 mmol) was added and the suspension was heated at 100° C. for thirty minutes, then at 130° C. for thirty minutes. The mixture was cooled to room temperature then diluted with $CH_2Cl_2$ and filtered. Concentration of the filtrate afforded a solid. Purification by radial chromatography on silica gel (elution with 50% EtOAc:hexane) followed by crystallization of the isolated material from Et$_2$O:hexane afforded 0.921 g (46%) of 4-[5-(3-Phenylpropoxymethyl)-[1,3,4]oxadiazol-2-yl]benzoic acid methyl ester.

$^1$HNMR (DMSO-d6) δ 8.17 (s, 4H), 7.1–7.3 (m, 5H), 4.8 (s, 2H), 3.9 (s, 3H), 3.6 (t, 2H, J=6 Hz), 2.6 (t, 2H, J=8 Hz), 1.8–1.9 (m, 2H). IR (CHCl$_3$, cm$^{-1}$) 1722, 1438, 1283, 1111. MS (ES) m/e 353. Anal. Calcd for C$_{20}$H$_{20}$N$_2$O$_4$: C, 68.17; H, 5.72; N, 7.95. Found C, 67.78; H, 5.69; N, 7.74.

c) 4-[5-(3-Phenylpropoxymethyl)-[1,3,4]oxadiazol-2-yl]benzoic acid

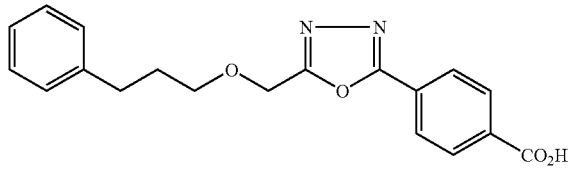

A mixture of 4-[5-(3-phenylpropoxymethyl)-[1,3,4]oxadiazol-2-yl]benzoic acid methyl ester (0.866 g, 2.5 mmol) and lithium hydroxide (0.177 g, 7.4 mmol) in 3.85 mL THF and 1.65 mL H$_2$O was stirred at 60° C. for 1 hour. Upon cooling to room temperature the mixture was acidified with concentrated HCl (0.421 mL) and reduced in volume to remove the THF. The resulting insoluble material was collected by filtration to afford 0.760 g (91%) of 4-[5-(3-phenylpropoxymethyl)-[1,3,4]oxadiazol-2-yl]benzoic acid.

$^1$H NMR (DMSO-d6) δ 8.1 (m, 4H), 7.1–7.3 (m, 5H), 4.8 (s, 2H), 3.6 (t, 2H, J=6 Hz) 2.6 (t, 2H, J=7 Hz), 1.8–1.9 (m, 2H). IR (CHCl$_3$, cm$^{-1}$) 3097, 3028, 2944, 2856, 2675, 2559, 1706, 1685, 1583, 1551, 1433, 1292, 1108, 874, 719. MS (ES) m/e 339, 337 Anal. Calcd for C$_{19}$H$_{18}$N$_2$O$_4$: C, 67.45; H, 5.36; N, 8.28. Found C, 66.34; H, 5.31; N, 8.18.

d) N-(3-Dimethylaminopropyl)-4-[5-(3-phenylpropoxymethyl)-[1,3,4]oxadiazol-2-yl]benzamide

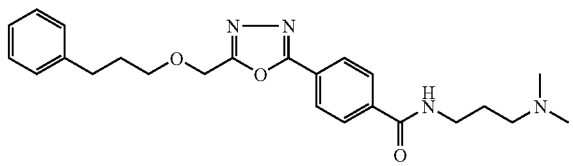

A mixture of 4-[5-(3-phenylpropoxymethyl)-[1,3,4]oxadiazol-2-yl]benzoic acid (0.730 g, 2.2 mmol) and 1,1'-carbonyldi-imidazole (0.367 g, 2.3 mmol) was stirred in 18 mL THF at 60° C. for 45 minutes. After stirring an additional 45 minutes at room temperature, 3-(dimethylamino)propylamine (0.265 g, 2.59 mmol) was added. After stirring approximately 24 h at room temperature, the mixture was concentrated to an oil. The oil was treated with Et$_2$O and the resultant suspension was filtered. The filtrate was treated with hexane and the resultant crystals were collected by filtration to afford 0.451 g (49%) of N-(3-dimethylaminopropyl)-4-[5-(3-phenylpropoxymethyl)-[1,3,4]oxadiazol-2-yl]benzamide.

$^1$H NMR (DMSO-d6) δ 8.7 (d, 1H, J=5 Hz), 8.1 (d, 2H, J=8 Hz), 8.0 (d, 2H, J=8 Hz), 7.1–7.3 (m, 5H), 4.8 (s, 2H), 3.5 (t, 2H, J=6 Hz), 3.32 (m, 2H), 2.62 (t, 2H, J=7 Hz), 2.27 (t, 2H, J=7 Hz), 2.14 (s, 6H), 1.86 (m, 2H), 1.67 (m, 2H). MS (ES) m/e, 423, 421. Anal. Calcd for C$_{24}$H$_{30}$N$_4$O$_3$: C, 68.22; H, 7.16; N, 13.26. Found C, 67.89; H, 7.09; N, 13.15. Mp(° C.)=90.

Example 2

N-(3-Dimethylaminopropyl)-4-[5-(2-phenethyloxyethyl)-[1,3,4-oxadiazol-2-yl]benzamide from 3-Phenethyloxypropionic acid

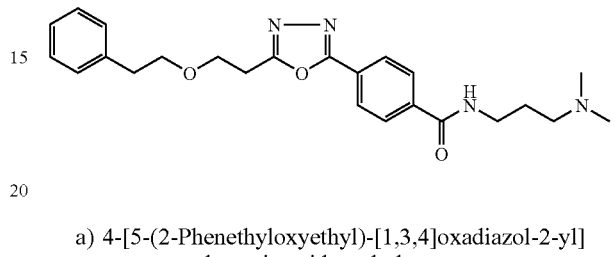

a) 4-[5-(2-Phenethyloxyethyl)-[1,3,4]oxadiazol-2-yl]benzoic acid methyl ester

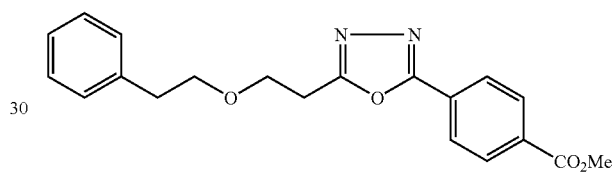

The above compound was prepared in a manner similar to that exemplified for the preparation of Example 1b, from 3-Phenethyloxypropionic acid (1.02 g, 5.3 mmol), 1,3-dicyclohexylcarbodiimide (1.08 g, 5.3 mmol) and 4-(1H-tetrazole-5-yl)benzoic acid methyl ester (1.06 g, 5.2 mmol) to afford 0.79 g (43%) of 4-[5-(2-Phenethyloxyethyl)-[1,3,4]oxadiazol-2-yl]benzoic acid methyl ester as a crystalline solid.

$^1$HNMR (DMSO-d6) δ 8.09–8.18 (m, 4H), 7.07–7.17 (m, 5H), 3.91 (s, 3H), 3.85 (t, 2H, J=6 Hz), 3.65 (t, 2H, J=7 Hz), 3.20 (t, 2H, J=6 Hz), 2.78 (t, 2H, J=7 Hz). IR (CHCl$_3$, cm$^{-1}$) 3009, 2954, 2871, 1721, 1438, 1282, 1111. MS (ES) m/e, 353. Anal. Calcd for C$_{20}$H$_{20}$N$_2$O$_4$: C, 68.17; H, 5.72; N, 7.95. Found C, 68.38; H, 5.66; N, 8.01.

b) 4-[5-(2-Phenethyloxyethyl)-[1,3,4]oxadiazol-2-yl]benzoic acid

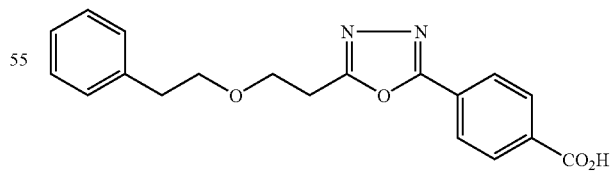

The above compound was prepared in a manner similar to that exemplified for the preparation of Example 1c, from 4-[5-(2-Phenethyloxyethyl)-[1,3,4]oxadiazol-2-yl]benzoic acid methyl ester 0.724 g, 2.1 mmol) and lithium hydroxide (0.148 g, 6.2 mmol) to afford 0.558 g (80%) of 4-[5-(2-Phenethyloxyethyl)-[1,3,4]oxadiazol-2-yl]benzoic acid as solid.

$^1$H NMR (DMSO-d6) δ8.05–8.16 (m, 4H), 7.07–7.17 (m, 5H), 3.85 (t, 2H, J=6 Hz), 3.65 (t, 2H, J=7 Hz), 3.20 (t, 2H, J=6 Hz), 2.78 (t, 2H, J=7 Hz). IR (KBr, cm$^{-1}$) 3431, 1705, 1685, 1434, 1290, 1118, 715. MS (ES) m/e, 339, 337. Anal. Calcd for $C_{19}H_{18}N_2O_4$: C, 67.45; H, 5.36; N, 8.28. Found C, 64.37; H, 5.08; N, 9.05.

c) N-(3-Dimethylaminopropyl)-4-[5-(2-phenethyloxyethyl)-[1,3,4-oxadiazol-2-yl]benzamide

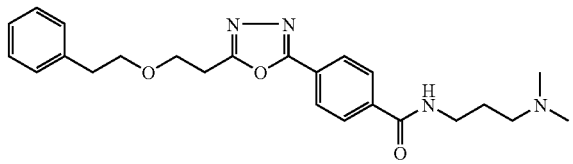

The above compound was prepared in a manner similar to that exemplified for the preparation of Example 1d, from 4-[5-(2-Phenethyloxyethyl)-[1,3,4]oxadiazol-2-yl]benzoic acid (0.528 g, 1.6 mmol), 1,1'-carbonyldiimidazole (0.266 g, 1.6 mmol) and 3-(dimethylamino)propylamine (0.392 g, 3.8 mmol) to afford 0.309 g (47%) of N-(3-Dimethylaminopropyl)-4-[5-(2-phenethyloxyethyl)-[1,3,4-oxadiazol-2-yl]benzamide as a crystalline solid.

$^1$H NMR (DMSO-d6) δ8.71 (t, 1H, J=5 Hz), 8.05 (d, 2H, J=9 Hz), 8.02 (d, 2H, J=9 Hz), 7.09–7.17 (m, 5H), 3.85 (t, 2H, J=9 Hz), 3.65 (t, 2H, J=7 Hz), 3.29 (m, 2H), 3.19 (t, 2H, J=6 Hz), 2.78 (t, 2H, J=7 Hz), 2.26 (t, 2H, J=7 Hz), 2.14 (s, 6H), 1.66 (m, 2H). IR (CHCl$_3$, cm$^{-1}$) 3307, 2942, 2879, 2761, 1631, 1540, 1116, 858, 699. MS (ES) m/e, 423, 421. Anal. Calcd for $C_{24}H_{30}N_4O_3$: C, 68.22; H, 7.16; N, 13.26. Found C, 67.83; H, 7.24; N, 13.19. Mp(° C.)=92.

Example 3

Preparation of 4-[5-(3-Benzyloxypropyl)-[1,3,4] oxadiazol-2-yl]-N-(3 dimethylaminopropyl)benzamide from 4-benzyloxybutyric acid

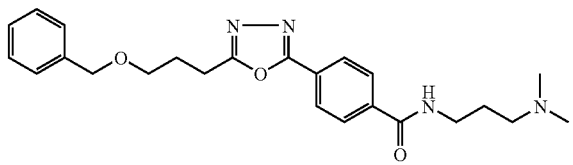

a) 4-[5-(3-Benzyloxypropyl)-[1,3,4]oxadiazol-2-yl]-N-(3-dimethylaminopropyl)benzoic acid methyl ester

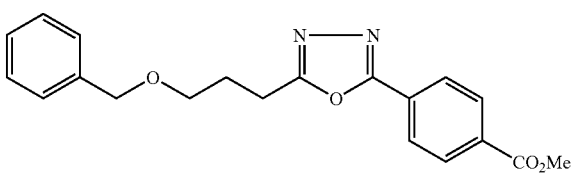

The above compound was prepared in a manner similar to that exemplified for the preparation of Example 1b, from 4-benzyloxybutyric acid (0.725 g, 3.7 mmol), 1,3-dicyclohexylcarbodiimide (0.771 g, 3.7 mmol) and 4-(1H-tetrazole-5-yl)benzoic acid methyl ester (0.755 g, 3.7 mmol) to afford 0.733 g (56%) of 4-[5-(3-benzyloxypropyl)-[1,3,4]oxadiazol-2-yl]-N-(3-dimethylaminopropyl)benzoic acid methyl ester as a crystalline solid.

$^1$HNMR (DMSO-d6) δ8.09–8.16 (m, 4H), 7.23–7.30 (m, 5H), 4.46 (s, 2H), 3.90 (s, 3H), 3.56 (t, 2H, J=6 Hz), 3.03 (t, 2H, J=7 Hz), 2.07 (m, 2H). IR (CHCl$_3$, cm$^{-1}$) 1721, 1438, 1282, 1111. MS (ES) m/e, 353. Anal. Calcd for $C_{20}H_{20}N_2O_4$: C, 68.17; H, 5.72; N, 7.95. Found C, 68.10; H, 5.79; N, 8.03.

b) 4-[5-(3-Benzyloxypropyl)-[1,3,4]oxadiazol-2-yl]-N-(3-dimethylaminopropyl)benzoic acid

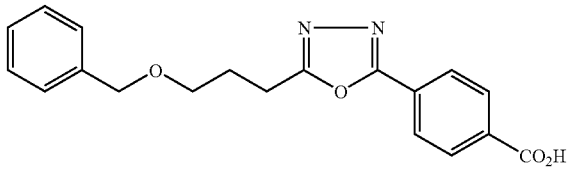

The above compound was prepared in a manner similar to that exemplified for the preparation of Example 1c, from 4-[5-(3-benzyloxypropyl)-[1,3,4]oxadiazol-2-yl]-N-(3-dimethyl aminopropyl)benzoic acid methyl ester (0.669 g, 1.9 mmol) and lithium hydroxide (0.136 g, 5.7 mmol) to afford 0.610 g (95%) 4-[5-(3-benzyloxypropyl)-[1,3,4]oxadiazol-2-yl]-N-(3-dimethylaminopropyl)benzoic acid as a solid.

$^1$H NMR (DMSO-d6) δ 8.06–8.14 (m, 4H), 7.23–7.29 (m, 5H), 4.46 (s, 2H), 3.56 (t, 2H, J=6 Hz), 3.03 (t, 2H, J=7 Hz), 2.02–2.11 (m, 2H). IR (KBr, cm$^{-1}$) 2859, 1681, 1428, 1321, 1292, 1119, 720. MS (ES) m/e, 339, 337. Anal. Calcd for $C_{19}H_{18}N_2O_4$: C, 67.45; H, 5.36; N, 8.28. Found C, 67.15; H, 5.36; N, 8.32.

c) 4-[5-(3-Benzyloxypropyl)-[1,3,4]oxadiazol-2-yl]-N-(3-dimethylaminopropyl)benzamide

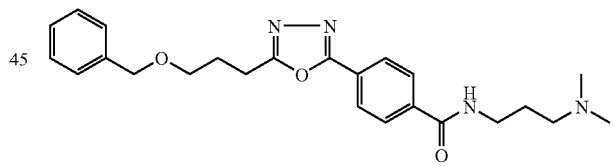

The above compound was prepared in a manner similar to that exemplified for the preparation of Example 1d, from (4-[5-(3-Benzyloxypropyl)-[1,3,4]oxadiazol-2-yl]-N-(3-dimethyl aminopropyl)benzoic acid (0.580 g, 1.7 mmol), 1,1'-carbonyl diimidazole (0.291 g, 1.8 mmol) and 3-(dimethylamino)propyl amine (0.210 g, 2.1 mmol) to afford 0.408 g (56%) 4-[5-(3-benzyloxypropyl)-[1,3,4]oxadiazol-2-yl]-N-(3-dimethyl aminopropyl)benzamide as a crystalline material.

$^1$H NMR (DMSO-d6) 68.69 (m, 1H), 7.99–8.07 (m, 4H), 7.28 (m, 5H), 4.46 (s, 2H), 3.55 (t, 2H, J=6 Hz), 3.30 (m, 2H), 3.02 (t, 2H, J=7 Hz), 2.26 (t, 2H, J=7 Hz), 2.14 (s, 6H), 2.06 (m, 2H), 1.66 (m, 2H). IR (CHCl$_3$, cm$^{-1}$) 3008, 2864, 2827, 1651, 1587, 1556, 1494, 1093. MS (ES) m/e, 423, 421. Anal. Calcd for $C_{24}H_{30}N_4O_3$: C, 68.22; H, 7.16; N, 13.26. Found C, 67.24; H, 6.01; N, 12.84. Analytical HPLC: 100% purity. Mp(° C.)=106

Example 4

Preparation of N-(3-Dimethylaminopropyl)4-[5-(4-phenoxybutyl)-[1,3,4]oxadiazol-2-yl]benzamide from 5-phenoxypentanoic acid

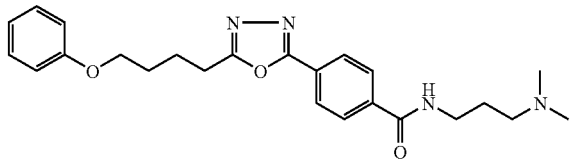

a) 4-[5-(4-Phenoxybutyl)-[1,3,4]oxadiazol-2-yl]benzoic acid methyl ester

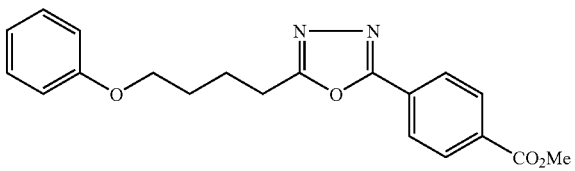

The above compound was prepared in a manner similar to that exemplified for the preparation of Example 1b, from 5-phenoxypentanoic acid (1.02 g, 5.3 mmol), 1,3-dicyclohexylcarbodiimide (1.08 g, 5.3 mmol) and 4-(1H-tetrazole-5-yl)benzoic acid methyl ester (1.06 g, 5.2 mmol) to afford 0.639 g (38%) of 4-[5-(4-Phenoxybutyl)-[1,3,4]oxadiazol-2-yl]benzoic acid methyl ester as a crystalline material.

$^1$HNMR (DMSO-d6) δ8.10 (m, 4H), 7.23–7.29 (m, 2H), 6.88–6.94 (m, 3H), 4.02 (t, 2H, J=6 Hz), 3.90 (s, 3H), 3.04 (t, 2H, J=7 Hz), 1.83–1.98 (m, 4H). IR (CHCl$_3$, cm$^{-1}$) 1721, 1587, 1498, 1438, 1283, 1245, 1111. MS (ES) m/e, 353. Anal. Calcd for C$_{20}$H$_{20}$N$_2$O$_4$: C, 68.17; H, 5.72; N, 7.95. Found C, 67.89; H, 5.58; N, 7.91.

b) 4-[5-(4-Phenoxybutyl)-[1,3,4]oxadiazol-2-yl]benzoic acid

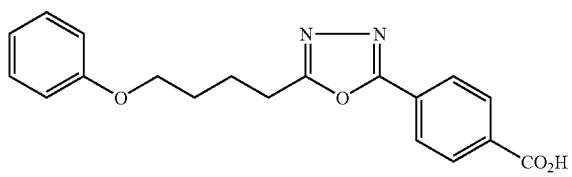

The above compound was prepared in a manner similar to that exemplified for the preparation of Example 1c, from 4-[5-(4-Phenoxybutyl)-[1,3,4]oxadiazol-2-yl]benzoic acid methyl ester (0.560 g, 1.6 mmol) and lithium hydroxide (0.114 g, 4.8 mmol) to afford 0.491 g (91%) of 4-[5-(4-Phenoxybutyl)-[1,3,4]oxadiazol-2-yl]benzoic acid as a solid.

$^1$H NMR (DMSO-d6) δ8.08–8.15 (m, 4H), 7.23–7.30 (m, 2H), 6.88–6.94 (m, 3H), 4.02 (t, 2H, J=6 Hz), 3.04 (t, 2H, J=7 Hz), 1.81–2.00 (m, 4H). IR (KBr, cm$^{-1}$) 1684, 1585, 1501, 1321, 1292, 1256, 723. MS (ES) m/e, 339, 337. Anal. Calcd for C$_{19}$H$_{18}$N$_2$O$_4$: C, 67.45; H, 5.36; N, 8.28. Found C, 66.79; H, 5.40; N, 8.27.

c) N-(3-Dimethylaminopropyl)4-[5-(4-phenoxybutyl)-[1,3,4]oxadiazol-2-yl]benzamide

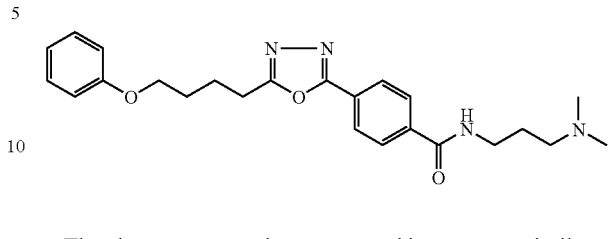

The above compound was prepared in a manner similar to that exemplified for the preparation of Example 1d, from 4-[5-(4-Phenoxybutyl)-[1,3,4]oxadiazol-2-yl]benzoic acid (0.461 g, 1.4 mmol), 1,1'-carbonyldiimidazole (0.231 g, 1.4 mmol) and 3-(dimethylamino)propylamine (0.167 g, 1.6 mmol) to afford the title compound as a crude mixture. Crystallization of the material from EtOAc afforded 0.237 g (40%) of N-(3-dimethyl-aminopropyl)4-[5-(4-phenoxybutyl)-[1,3,4]oxadiazol-2-yl]benzamide.

$^1$H NMR (DMSO-d6) δ8.70 (m, 1H), 8.00–8.08 (m, 4H), 7.23–7.30 (m, 2H), 6.88–6.94 (m, 3H), 4.02 (t, 2H, J=6 Hz), 3.32 (m, 2H), 2.26 (t, 2H, J=7 Hz), 2.14 (s, 6H), 1.83–1.98 (m, 4H), 1.62–1.72 (m, 2H). IR (KBr, cm$^{-1}$) 3310, 2953, 2763, 1634, 1563, 1540, 1498, 1253, 1249, 1010, 855, 749. MS (ES) m/e, 423, 421. Anal. Calcd for C$_{24}$H$_{30}$N$_4$O$_3$: C, 68.22; H, 7.16; N, 13.26. Found C, 68.25; H, 7.21; N, 12.82. Analytical HPLC: 100% purity. Mp(° C.)=114.

Example 5

Preparation of N-(Dimethylaminopropyl)4-[5-(2-phenoxy-ethoxymethyl)-[1,3,4]oxadiazol-2-yl]benzamide from 2-phenoxyethanol

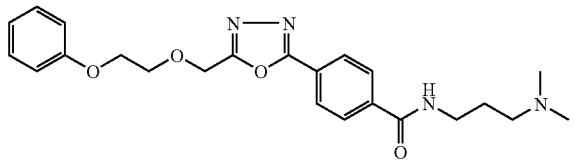

a) 2-(Phenoxyethoxy)acetic acid

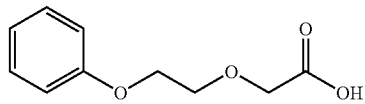

The above compound was prepared in a manner similar to that exemplified for the preparation of Example 1a, from 2-phenoxyethanol (5.4 g, 38.9 mmol) and methyl bromoacetate (6.55 g, 42.8 mmol), then, using lithium hydroxide (2.78 g 116.1 mmol) to afford 5.9 g (77%) of 2-(phenoxyethoxy)acetic acid as an oil.

$^1$H NMR (DMSO-d6) δ7.25–7.31 (m, 2H), 6.93 (m, 3H), 4.11 (m, 4H), 3.81 (m, 2H). IR (CHCl$_3$, cm$^{-1}$) 1733, 1600, 1589, 1498, 1245, 1144. MS (S) m/e, 197, 195. Anal. Calcd for C$_{10}$H$_{12}$O$_4$: C, 61.22; H, 6.16. Found C, 61.49; H, 5.70.

b) 4-[5-(2-Phenoxyethoxymethyl)-[1,3,4]oxadiazol-2-yl]benzoic acid methyl ester

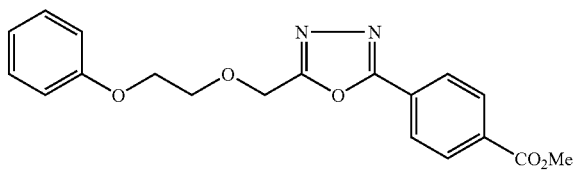

The above compound was prepared in a manner similar to that exemplified for the preparation of Example 1b, from 2-(phenoxyethoxy)acetic acid (1.08 g, 5.5 mmol), 1,3-dicyclohexylcarbodiimide (0.957 g, 4.6 mmol) and 4-(1H-tetrazole-5-yl)benzoic acid methyl ester (0.938 g, 4.6 mmol) to afford 0.559 g (35%) of 4-[5-(2-Phenoxyethoxymethyl)-[1,3,4]oxadiazol-2-yl]benzoic acid methyl ester as a crystalline solid contaminated with 1,3-dicyclohexylurea.

$^1$H NMR (DMSO-d6) $\delta$8.15 (m, 4H), 7.22–7.29 (m, 2H), 6.89–6.94 (m, 3H), 4.92 (s, 2H), 4.15 (m, 2H), 3.92–4.17 (m, 2H), 3.91 (s, 3H). IR (CHCl$_3$, cm$^{-1}$) 3328, 2850, 1719, 1601, 1565, 1441, 1296, 1282, 1254, 1146, 1137, 1112, 759, 715. MS (ES) m/e,
355. Anal. Calcd for C$_{19}$H$_{18}$N$_2$O$_5$: C, 64.40; H, 5.12; N, 7.91. Found C, 64.72; H, 5.66; N, 8.37.

c) 4-[5-(2-Phenoxyethoxymethyl)-[1,3,4]oxadiazol-2-yl]benzoic acid

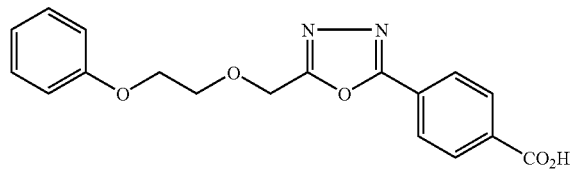

The above compound was prepared in a manner similar to that exemplified for the preparation of Example 1c, from 4-[5-(2-Phenoxyethoxymethyl)-[1,3,4]oxadiazol-2-yl]benzoic acid methyl ester (0.500 g, 1.4 mmol) and lithium hydroxide (0.101 g, 4.2 mmol) to afford 0.366 g (76%) as a solid contaminated with 1,3-dicyclohexylurea $^1$H NMR DMSO-d6) $\delta$7.95–8.06 (m, 4H), 7.26–7.32 (m, 2H), 6.91–6.98 (m, 3H), 4.14–4.19 (m, 4H), 3.88 (m, 2H).

IR (KBr, cm$^{-1}$) 3327, 2928, 2850, 1700, 1685, 1625, 1608, 1246, 1132, 691. MS (ES) m/e, 339. Anal. Calcd for C$_{18}$H$_{16}$N$_2$O$_5$: C, 63.53; H, 4.74; N, 8.23. Found C, 61.01; H, 5.65; N, 8.32.

d) N-(Dimethylaminopropyl)4-[5-(2-phenoxyethoxymethyl)-[1,3,4]oxadiazol-2-yl]benzamide

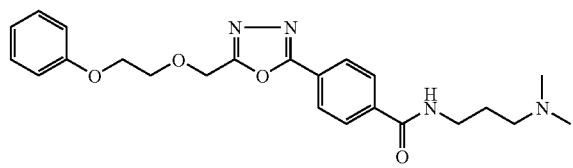

The above compound was prepared in a manner similar to that exemplified for the preparation of Example 1d, from 4-[5-(2-Phenoxyethoxymethyl)-[1,3,4]oxadiazol-2-yl]benzoic acid 0.333 g, 0.98 mmol), 1,1'-carbonyldiimidazole (0.160 g, 0.99 mmol) and 3-(dimethylamino)propylamine (0.099 g, 1.0 mmol) to afford the title compound as a crude mixture. Purification by radial chromatography on silica gel (eluted with 10% 2M NH$_3$ in MeOH:CHCl$_3$) afforded 0.03 g (7%) of N-(dimethylamino propyl)4-[5-(2-phenoxyethoxymethyl)-[1,3,4]oxadiazol-2-yl]benzamide as a solid.

$^1$H NMR (DMSO-d6) $\delta$8.72 (t, 1H, J=5 Hz), 8.01–8.10 (m, 4H), 7.23–7.29 (m, 2H), 6.89–6.96 (m, 3H), 4.19 (s, 2H), 4.15 (m, 2H), 3.93 (m, 2H), 3.31 (m, 2H), 2.26 (t, 2H, J=7 Hz), 2.14 (s, 6H), 1.62–1.72 (m, 2H) IR (CHCl$_3$, cm$^{-1}$) 4446, 2936, 2763, 1637, 1530, 1490, 1253, 1047, 752. MS (ES) m/e, 425, 423. Anal. Calcd for C$_{23}$H$_{28}$N$_4$O$_4$: C, 65.08; H, 6.65; N, 13.20. Found C, 64.74; H, 6.58; N, 12.98. Mp (° C.)=146.

Example 6

Preparation of N-(3-Dimethylaminopropyl)-4-(5-phenyl-[1,3,4]oxadiazol-2-yl)benzamide from benzoyl chloride

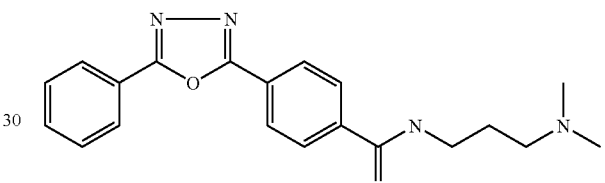

a) 4-(5-phenyl-[1,3,4]oxadiazol-2-yl)benzoic acid methyl ester

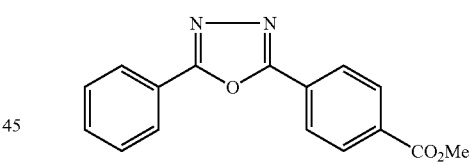

A suspension of 4-(1H-tetrazole-5-yl)benzoic acid methyl ester (1.00 g, 4.9 mmol) and pyridine (0.391 g, 5.0 mmol) in 7.3 mL toluene stirring at room temperature was added benzoyl chloride. The resultant heavy white suspension was heated at 100□ C. for twenty minutes then at 140 DC for twenty minutes. After cooling to room temperature the mixture was treated with EtOAc and H$_2$O. The suspension was triterated then filtered to afford 0.652 g (48%) of 4-(5-phenyl-[1,3,4]oxadiazol-2-yl)benzoic acid methyl ester. The filtrate phases were separated. The organic phase was dried over sodium sulfate, filtered, concentrated to afford a solid. The solid was crystallized from acetone:diethyl ether to afford 0.371 (27%) of 4-(5-phenyl-[1,3,4] oxadiazol-2-yl)benzoic acid methyl ester.

$^1$HNMR (DMSO-d6) $\delta$ 8.27 (m, 2H), 8.16 (m, 4H), 7.62–7.71 (m, 3H), 3.91 (s, 3H). IR (KBr, cm$^{-1}$) 1723, 1545, 1447, 1442, 1280, 1118, 1110, 1018, 780, 717, 688. MS (ES) m/e, 281. Anal. Calcd for C$_{16}$H$_{12}$N$_2$O$_3$: C, 68.57; H, 4.32; N, 9.99. Found C, 68.47; H, 4.42; N, 10.03.

b) 4-(5-phenyl-[1,3,4]oxadiazol-2-yl)benzoic acid

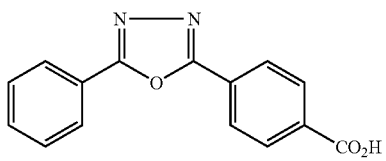

The above compound was prepared in a manner similar to that exemplified for the preparation of Example 1c, from 4-(5-phenyl-[1,3,4]oxadiazol-2-yl)benzoic acid methyl ester (0.938 g, 3.3 mmol) and lithium hydroxide (0.240 g, 10.0 mmol) to afford 0.889 g (100%) of 4-(5-phenyl-[1,3,4]oxadiazol-2-yl)benzoic acid as a solid.

$^1$HNMR (DMSO-d6) 813.29 (bs, 1H), 8.21–8.28 (m, 2H), 8.13–8.19 (m, 4H), 7.61–7.69 (m, 3H). IR (KBr, cm$^{-1}$) 3436, 1683, 1547, 1425, 1287, 718, 689. MS (ES) m/e, 267, 265. Anal. Calcd for $C_{15}H_{10}N_2O_3$: C, 67.67; H, 3.79; N, 10.52. Found C, 64.26; H, 3.76; N, 9.94.

c) N-(3-Dimethylaminopropyl)-4-(5-phenyl-[1,3,4]oxadiazol-2-yl)benzamide

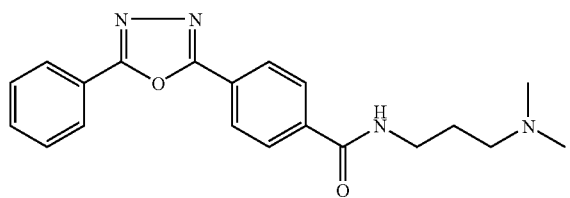

The above compound was prepared in a manner similar to that exemplified for the preparation of Example 1d, from 4-(5-phenyl-[1,3,4]oxadiazol-2-yl)benzoic acid (0.536 g, 2.0 mmol), 1,1'-carbonyldiimidazole (0.3300 g, 2.0 mmol) and 3-(dimethylamino)propylamine (0.412 g, 4.0 mmol) and 1.3 mL DMF to afford a solid. Crystallization from methanol:diethyl ether afforded 0.286 g (41%) of N-(3-Dimethylaminopropyl)-4-(5-phenyl-[1,3,4]oxadiazol-2-yl)benzamide.

$^1$H NMR (DMSO-d6) δ8.73 (t, 1H, J=5 Hz), 8.23 (d, 2H, J=7 Hz), 8.15–8.20 (m, 2H), 8.05 (d, 2H, J=7 Hz), 7.61–7.69 (m, 3H), 3.31 (m, 2H), 2.27 (t, 2H, J=7 Hz), 3.31 (m, 2H), 1.63–1.73 (m, 2H). IR (KBr, cm$^{-1}$) 3330, 2941, 2763, 1667, 1646, 1547, 1492, 715. MS (S) m/e, 351, 349. Anal. Calcd for $C_{20}H_{22}N_4O_2$: C, 68.55; H, 6.33; N, 15.99. Found C, 68.08; H, 6.29; N, 15.90. Mp(° C.)=130.

Example 7

Preparation of 4-(5-Benzyl-[1,3,4]oxadiazol-2-yl)-N-(3-dimethylaminopropyl)benzamide from phenylacetic acid

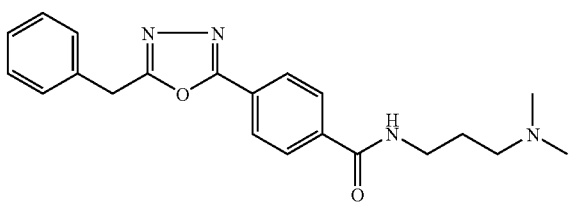

a) 4-(5-Benzyl-[1,3,4]oxadiazol-2-yl)benzoic acid methyl ester

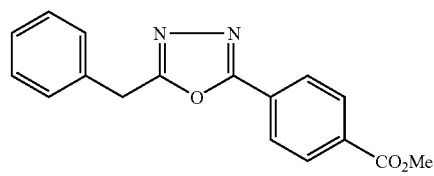

The above compound was prepared in a manner similar to that exemplified for the preparation of Example 1b, from phenyl acetic acid (0.470 g, 3.5 mmol), 1,3-dicyclohexyl-carbodiimide (0.710 g, 3.5 mmol) and 4-(1H-tetrazole-5-yl)benzoic acid methyl ester (0.700 g, 3.5 mmol) to afford the title compound as a crude mixture. Purification by radial chromatography on silica gel (elution with 25% to 50% EtOAc:hexane) followed by crystallization of the isolated material from diethyl ether afforded 0.421 g (69%) of 4-(5-Benzyl-[1,3,4]oxadiazol-2-yl)benzoic acid methyl ester.

$^1$H NMR (DMSO-d6) δ 8.08–8.16 (m, 4H), 7.28–7.41 (m, 5H), 4.39 9s, 2H), 3.89 (s, 3H). IR (KBr, cm$^{-1}$) 1716, 1559, 1551, 1435, 1276, 1111, 779, 728, 723, 710. MS (ES) m/e, 295. Anal. Calcd for $C_{17}H_{14}N_2O_3$: C, 69.38; H, 4.79; N, 9.52. Found C, 69.27; H, 4.78; N, 9.52.

b) 4-(5-Benzyl-[1,3,4]oxadiazol-2-yl)benzoic acid

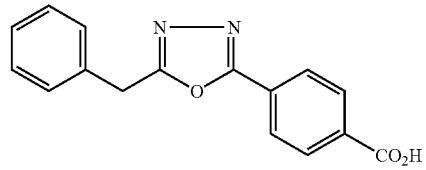

A mixture of 4-(5-Benzyl-[1,3,4]oxadiazol-2-yl)benzoic acid methyl ester (0.413 g, 1.4 mmol) and lithium hydroxide (0.125 g, 5.2 mmol) in 4.1 mL THF and 1.8 mL H$_2$O was stirred at room temperature for fours hours. Next, concentrated HCl (450 uL, 5.2 mmol) was added. The resultant suspension was reduced in volume then filtered to afford 0.393 g (85%) of 4-(5-Benzyl-[1,3,4]oxadiazol-2-yl)benzoic acid.

$^1$H NMR (DMSO-d6) δ13.33 (bs, 1H), 8.06–8.14 (m, 4H), 7.27–7.42 (m, 5H), 4.39 (s, 2H). IR (KBr, cm$^{-1}$) 1706, 1685, 1583, 1563, 1552, 1432, 1323, 1290, 872, 716, 706. MS (ES) m/e, 281, 279. Anal. Calcd for $C_{16}H_{12}N_2O_3$: C, 68.57; H, 4.32; N, 9.99. Found C, 68.38; H, 4.43; N, 9.99.

c) 4-(5-Benzyl-[1,3,4]oxadiazol-2-yl)-N-(3-dimethylaminopropyl)benzamide

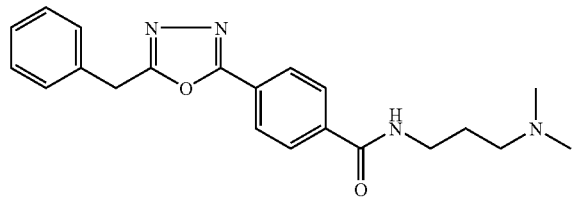

A suspension of 4-(5-Benzyl-[1,3,4]oxadiazol-2-yl)benzoic acid (0.255 g, 0.91 mmol), 1-hydroxybenzotriazole (0.123 g, 0.91 mmol), 4-dimethylamino pyridine (0.011 g, 0.09 mmol) and 1,3-dicyclohexylcarbodiimide (0.206 g, 1.00 mmol) in 26 mL $CH_2Cl_2$ was stirred at room temperature for fifteen minutes. Next, 3-(dimethylamino)propyl amine (0.093 g, 0.91 mmol) was added and the reaction was stirred 21 hours at room temperature. The suspension was filtered and the filtrate was reduced in volume. Purification by radial chromatography on silica gel (elution with 90:10:1 $CH_2Cl_2$:MeOH:$NH_4OH$) followed by crystallization of the isolated material from ethanol:diethyl ether afforded 0.054 g (16%) of 4-(5-Benzyl-[1,3,4]oxadiazol-2-yl)-N-(3-dimethylaminopropyl)benzamide. A second lot of crystals was obtained to afford 0.017 g (5%) of 4-(5-Benzyl-[1,3,4]oxadiazol-2-yl)-N-(3-dimethylamino-propyl)benzamide.

$^1$H NMR (DMSO-d6) δ8.70 (t, 1H, J=5 Hz), 8.04 (d, 2H, J=9 Hz), 8.00 (d, 2H, J=9 Hz), 7.29–7.41 (m, 5H), 4.38 (s, 2H), 3.31 (m, 2H), 2.25 (t, 2H, J=7 Hz), 2.13 (s, 6H), 1.61–1.70 (m, 2H). IR (KBr, cm$^{-1}$) 3298, 2943, 2768, 1937, 1636, 1555, 1324, 1087, 863, 721, 706. MS (ES) m/e, 365, 363. Anal. Calcd for $C_{21}H_{24}N_4O_2$: C, 69.21; H, 6.64; N, 15.37. Found C, 68.91; H, 6.71; N, 15.38. Mp(° C.)=110.

Example 8

Preparation of N-(3-dimethylaminopropyl)-4-(5-phenethyl-[1,3,4]oxadiazol-2-yl)benzamide from hydrocinnamoyl chloride

a) 4-(5-phenethyl-[1,3,4]oxadiazol-2-yl)benzoic acid methyl ester

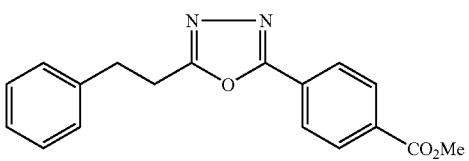

A solution of 4-(1H-tetrazole-5-yl)benzoic acid methyl ester (1.00 g, 4.9 mmol) and hydrocinnamoyl chloride (0.826 g, 4.9 mmol) in 10 mL toluene was heated at 100° C. for five hours. The mixture was then concentrated to an oil. The oil was dissolved into $CH_2Cl_2$ and washed with 0.1 N HCl. The aqueous phase was extracted with $CH_2Cl_2$. The combined organic phases were dried over sodium sulfate, filtered and concentrated to afford a solid. Purification by HPLC on silica gel (eluted with a linear gradient of 10 to 25% EtOAc:toluene over a thirty minute period) afforded 0.604 g (40%) of 4-(5-phenethyl-[1,3,4]oxadiazol-2-yl)benzoic acid methyl ester as a white solid.

$^1$H NMR (DMSO-d6) δ 8.15 (d, 2H, J=9 Hz), 8.09 (d, 2H, J=9 Hz), 7.18–7.31 (m, 5H), 3.90 (s, 3H), 3.28 (t, 2H, J=7 Hz), 3.12 (t, 2H, J=7 Hz). IR (KBr, cm$^{-1}$) 1714, 1415, 1278, 1111, 774, 713, 696. MS (ES) m/e, 309. Anal. Calcd for $C_{18}H_{16}N_2O_3$: C, 70.12; H, 5.23; N, 9.09. Found C, 69.55; H, 5.14; N, 9.03.

b) 4-(5-phenethyl-[1,3,4]oxadiazol-2-yl)benzoic acid

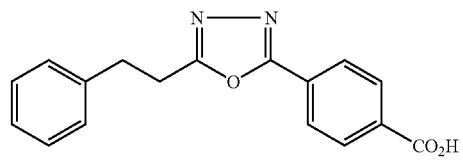

The above compound was prepared in a manner similar to that exemplified for the preparation of Example 7b, from 4-(5-phenethyl-[1,3,4]oxadiazol-2-yl)benzoic acid methyl ester (0.600 g, 2.0 mmol) and lithium hydroxide (0.140 g, 5.8 mmol), to afford 0.510 g (89%) of 4-(5-phenethyl-[1,3,4]oxadiazol-2-yl)benzoic acid.

$^1$HNMR (DMSO-d6) δ 13.33 (bs, 1H), 8.13 (d, 2H, J=9 Hz), 8.07 (d, 2H, J=9 Hz), 7.18–7.33 (m, 5H), 3.28 (t, 2H, J=7 Hz), 3.12 (t, 2H, J=7 Hz). IR (CHCl$_3$, cm$^{-1}$) 1670, 1568, 1555, 1420, 1280, 1017. MS (ES) m/e, 295, 293. Anal. Calcd for $C_{17}H_{14}N_2O_3$: C, 69.38; H, 4.79; N, 9.52. Found C, 68.95; H, 4.57; N, 9.40.

c) N-(3-dimethylaminopropyl)-4-(5-phenethyl-[1,3,4]oxadiazol-2-yl)benzamide

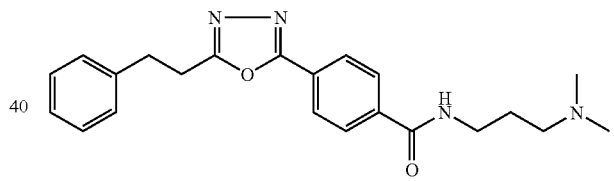

A suspension of 4-(5-phenethyl-[1,3,4]oxadiazol-2-yl) benzoic acid (0.480 g, 1.6 mmol), 1-hydroxybenzotriazole (0.337 g, 2.5 mmol), 3-(dimethylamino)propyl amine (0.286 g, 2.8 mmol) and 1-(3-dimethylaminopropyl)-3-ethylcarbodiimide (0.597 g, 3.11 mmol) in 46 mL THF was stirred at room temperature for twenty four hours. The resultant suspension was filtered and the filtrate was concentrated to an oil. The oil was dissolved into EtOAc then washed with 2N sodium hydroxide (2×25 ml), water then brine. The organic phase was dried over sodium sulfate, filtered, concentrated to afford a white solid. Crystallization of this material from methanol:diethyl ether affored 0.354 g (57%) of N-(3-dimethylaminopropyl)-4-(5-phenethyl)-[1,3,4]oxadiazol-2-yl)benzamide.

$^1$H NMR (DMSO-d6) δ8.70 (t, 1H, J=5 Hz), 8.04 (d, 2H, J=9 Hz), 8.01 (d, 2H, J=9 Hz), 7.19–7.30 (m, 5H), 3.26–3.33 (m, 4H), 3.12 (t, 2H, J=8 Hz), 2.26 (t, 2H, J=7 Hz), 2.14 (s, 6H), 1.62–1.71 (m, 2H). IR (CHCl$_3$, cm$^{-1}$) 3346, 2973, 2942, 2813, 2764, 1636, 1585, 1564, 1552, 1530, 1496, 1496, 1287. MS (ES) m/e, 379, 377. Anal. Calcd for $C_{22}H_{26}N_4O_2$: C, 69.82; H, 6.92; N, 14.80. Found C, 69.62; H, 6.84; N, 14.80. Mp(° C.)=126.

Example 9

Preparation of N-(3-dimethylaminopropyl)4-(5-phenylpropyl)-[1,3,4]oxadiazol-2-yl)benzamide from 4phenylbutyric acid

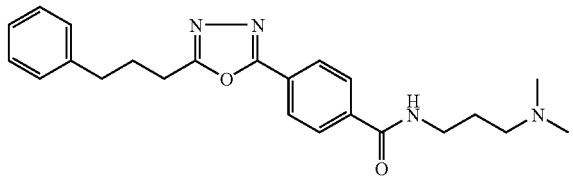

a) 4-[5-(3-phenylpropyl)-[1,3,4]oxadiazol-2-yl)benzoic acid methyl ester

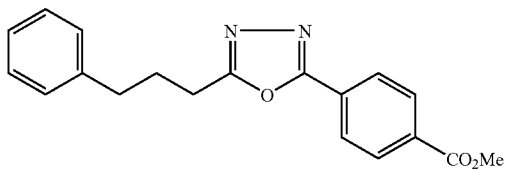

The above compound was prepared in a manner similar to that exemplified for the preparation of Example 1b, from 4-phenylbutyric acid (0.470 g, 3.5 mmol), 1,3-dicyclohexylcarbodiimide (0.710 g, 3.5 mmol), 4-(1H-tetrazole-5-yl)benzoic acid methyl ester (0.700 g, 3.4 mmol) and 5.1 mL toluene to afford the title compound as a crude material. Purification by radial chromatography on silica gel (elution with 25% to 50% EtOAc:hexane) followed by crystallization of the isolated material from diethyl ether afforded 0.554 g (50%) of 4-[5-(3-phenylpropyl)-[1,3,4]oxadiazol-2-yl)-benzoic acid methyl ester.

$^1$H NMR (DMSO-d6), δ 8.14 (d, 2H, J=6 Hz), 8.11 (d, 2H, J=6 Hz), 7.15–7.32 (m, 5H), 3.90 (s, 3H), 2.95 (t, 2H, J=7 Hz), 2.72 (t, 2H, J=7 Hz), 2.04–2.14 (m, 2H). IR (KBr, cm$^{-1}$) 1724, 1713, 1587, 1572, 1415, 1281, 1275, 1114, 1107, 751, 718. MS (ES) m/e, 323. Anal. Calcd for $C_{19}H_{18}N_2O_3$: C, 70.79; H, 5.63; N, 8.69. Found C, 70.60; H, 5.65; N, 8.71.

b) 4-[5-(3-phenylpropyl)-[1,3,4]oxadiazol-2-yl)benzoic acid

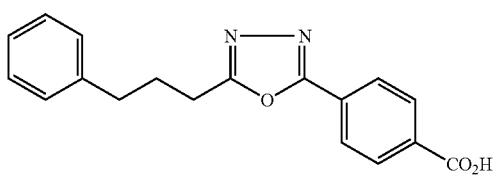

The above compound was prepared in a manner similar to that exemplified for the preparation of Example 7b, from 4-[5-(3-phenylpropyl)-[1,3,4]oxadiazol-2-yl)benzoic acid methyl ester (0.512 g, 1.6 mmol) and lithium hydroxide (0.092 g, 3.8 mmol) to afford 0.333 g (85%) of 4-[5-(3-phenylpropyl)-[1,3,4]oxadiazol-2-yl)benzoic acid.

$^1$H NMR (DMSO-d6) δ13.33 (bs, 1H), 8.12 (d, 2H, J=9 Hz), 8.08 (d, 2H, J=$$ 9 Hz), 7.15–7.32 (m, 5H), 2.95 (t, 2H, J=7 Hz), 2.72 (t, 2H, J=7 Hz), 2.04–2.14 (m, 2H). IR (KBr, cm$^{-1}$) 1685, 1565, 1322, 1302, 1287, 722. MS (ES) m/e, 309, 307. Anal. Calcd for $C_{18}H_{16}N_2O_3$: C, 70.12; H, 5.23; N, 9.09. Found C, 70.05; H, 5.20; N, 9.00.

c) N-(3-dimethylaminopropyl)-4-(5-phenylpropyl)-[1,3,4]oxadiazol-2-yl)benzamide

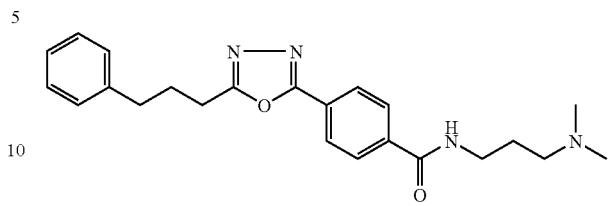

The above compound was prepared in a manner similar to that exemplified for the preparation of Example 7c, from 4-[5-(3-phenylpropyl)-[1,3,4]oxadiazol-2-yl)benzoic acid (0.430 g, 1.39 mmol), 1-hydroxybenzotriazole (0.188 g, 1.39 mmol), 4-dimethylamino pyridine 0.150 g, 1.46 mmol), 3-(dimethylamino)propylamine (0.150 g, 1.46 mmol) to afford the title compound as a crude mixture. Purification by radial chromatography on silica gel (elutted with 10% 2M ammonium: CH$_2$Cl$_2$) followed by crystallization from the isolated material from ethanol:diethyl ether afforded 0.274 g (50%) of N-(3-dimethylaminopropyl)-4-(5-phenylpropyl)-[1,3,4]oxadiazol-2-yl)benzamide.

$^1$H NMR (DMSO-d6) δ 8.70 (t, 1H, J=5 Hz), 7.99-8.08 (m, 4H), 7.16–7.33 (m, 5H), 3.53 (m, 2H), 3.30 (t, 2H, J=7 Hz), 2.72 (t, 2H, J=7 Hz), 2.27 (t, 2H, J=7 Hz), 2.13 (s, 6H), 2.04–2.11 (m, 2H), 1.63–1.72 (m, 2H). IR (CHCl$_3$, cm$^{-1}$) 3008, 2950, 2827, 1652, 1586, 1567, 1557, 1529, 1495, 1243, 1089. MS (ES) m/e, 393, 391. Anal. Calcd for $C_{23}H_{28}N_4O_4$: C, 70.38; H, 7.19; N, 14.27. Found C, 69.78; H, 7.04; N, 14.04. Analytical HPLC: 100% purity. Mp(° C.)>200.

Example 10

Preparation of N-(3-dimethylaminopropyl)-4-(5-phenylbutyl)-[1,3,4]oxadiazol-2-yl)benzamide from 5-phenylvaleric acid

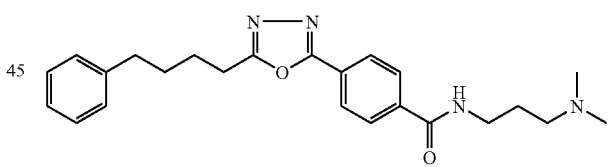

a) 4-[5-(3-phenylbutyl)-[1,3,4]oxadiazol-2-yl)benzoic acid methyl ester

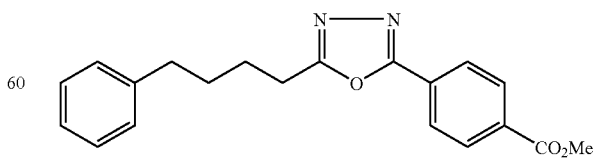

The above compound was prepared in a manner similar to that exemplified for the preparation of Example 1b, from 5-phenylvaleric acid (0.620 g, 3.5 mmol), 1,3-dicyclohexylcarbodiimide (0.710 g, 3.5 mmol), 4-(1H-tetrazole-5-yl)benzoic acid methyl ester (0.700 g, 3.4 mmol) and 5.1 mL toluene to afford the title compound as a crude mixture. Purification by radial chromatography on silica gel (elution with 25% to 50% EtOAc:hexane) followed by crystallization of the isolated material from diethyl ether afforded 0.463 g (40%) of 4-[5-(3-phenylbutyl)-[1,3,4]oxadiazol-2-yl)benzoic acid methyl ester.

$^1$HNMR (DMSO-d6) δ8.09–8.17 (m, 4H), 7.14–7.30 (m, 5H), 3.90 (s, 3H), 2.99 (t, 2H, J=7 Hz), 2.64 (t, 2H, J=7 Hz), 1.65–1.85 (m, 4H). IR (KBr, cm$^{-1}$) 1723, 1568, 1413, 1277, 1111, 716, 697. MS (ES) m/e, 337. Anal. Calcd for $C_{20}H_{20}N_2O_3$: C, 71.41; H, 5.99; N, 8.33. Found C, 71.36; H, 5.90; N, 8.29.

b)
4-[5-(3-phenylbutyl)-[1,3,4]oxadiazol-2-yl)benzoic acid

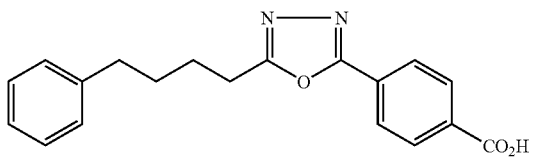

The above compound was prepared in a manner similar to that exemplified for the preparation of Example 7b, using 4-[5-(3-phenylbutyl)-[1,3,4]oxadiazol-2-yl)benzoic acid methyl ester (0.380 g, 1.16 mmol) and lithium hydroxide (0.081 g, 3.4 mmol) to afford 0.360 g (99%) of 4-[5-(3-phenylbutyl)-[1,3,4]oxa-diazol-2-yl)benzoic acid.

$^1$H NMR (DMSO-d6) δ13.38 (bs, 1H), 8.04–8.14 (m, 4H), 7.14–7.30 (m, 5H), 2.99 (t, 2H, J=7 Hz), 2.64 (t, 2H, J=7 Hz), 1.64–1.85 (m, 4H). IR (KBr, cm$^{-1}$) 2946, 1686, 1586, 1567, 1551, 1429, 1413, 1320, 1288, 740, 716. MS (ES) m/e, 323, 321. Anal. Calcd for $C_{19}H_{18}N_2O_3$: C, 70.79; H, 5.63; N, 8.69. Found C, 70.33; H, 5.38; N, 8.41.

c) 4[5-(3-dimethylaminopropyl)-4-(5-phenylbutyl)-[1,3,4]oxadiazol-2-yl)benzamide

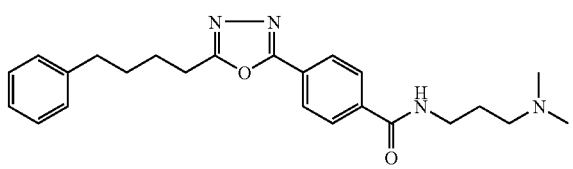

The above compound was prepared in a manner similar to that exemplified for the preparation of Example 7c, from 4-[5-(3-phenylbutyl)-[1,3,4]oxadiazol-2-yl)benzoic acid (0.342 g, 1.0 mmol), 1-hydroxybenzotriazole 0.136 g, 1.0 mmol), 4-dimethylamino pyridine (0.012 g, 0.10 mmol), 3-(dimethylamino)propylamine (0.108 g, 1.06 mmol) and 29 mL $CH_2Cl_2$. Purification by radial chromatography on silica gel (eluted with 10% 2M ammonium:$CH_2Cl_2$) followed by crystallization of the iosolated material from ethanol:diethyl ether afforded 0.226 g (55%) of 4[5-(3-dimethylaminopropyl)-4-(5-phenylbutyl)-[1,3,4]oxadiazol-2-yl)benzamide.

$^1$HNMR (DMSO-d6) δ8.71 (t, 1H, J=5 Hz), 7.99–8.06 (m, 4H), 7.14–7.30 (m, 5H), 3.32 (m, 2H), 2.98 (t, 2H, J=7 Hz), 2.64 (t, 2H, J=7 Hz), 2.26 (t, 2H, J=7 Hz), 2.14 (s, 6H), 1.62–1.82 (m, 6H). IR (CHCl$_3$, cm$^{-1}$) 3008, 2947, 1652, 1586, 1567, 1556, 1529, 1495. MS (ES) m/e, 407, 405. Anal. Calcd for $C_{24}H_{30}N_4O_2$: C, 70.91; H, 7.44; N, 13.78. Found C, 70.66; H, 7.35; N, 13.67. Mp(° C.)=84.

Example 11

Preparation of N-(3-dimethylaminopropyl)-4-(5-phenylpentyl)-[1,3,4]oxadiazol-2-yl)benzamide from 6-phenylhexanoic acid

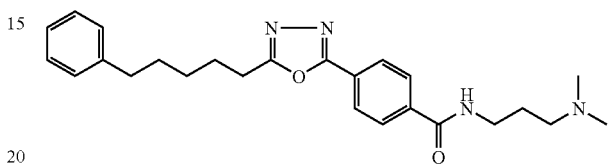

a) 4-[5-(3-phenylpentyl)-[1,3,4]oxadiazol-2-yl)benzoic acid methyl ester

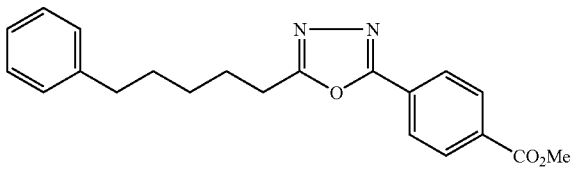

The above compound was prepared in a manner similar to that exemplified for the preparation of Example 1b, from 6-phenylhexanoic acid (0.960 g, 5.0 mmol), 1,3-dicyclohexylcarbodiimide (1.01 g, 5.0 mmol) and 4-(1H-tetrazole-5-yl)benzoic acid methyl ester (1.01 g, 4.95 mmol) to afford the title compound as a crude mixture. Purification by radial chromatography on silica gel (elution with 25% to 50% EtOAc:hexane) afforded 0.766 g (44%) of 4-[5-(3-phenylpentyl)-[1,3,4]oxadiazol-2-yl)benzoic acid methyl ester.

$^1$H NMR (DMSO-d6) δ8.10–8.17 (m, 4H), 7.11–7.28 (m, 5H), 3.90 (s, 3), 2.95 (t, 2H, J=7 Hz), 2.59 (t, 2H, J=8 Hz), 1.81 (dt, 2H, J=8 Hz), 1.63 (dt, 2H, J=8 Hz), 1.35–1.45 (m, 2H). IR (CHCl$_3$, cm$^{-1}$) 3010, 2938, 2860, 1721, 1569, 1438, 1282, 1119, 1111. MS (ES) m/e, 351. Anal. Calcd for $C_{21}H_{22}N_2O_3$: C, 71.98; H, 6.33; N, 7.99. Found C, 72.04; H, 6.32; N, 8.00.

b) 4-[5-(3-phenylpentyl)-[1,3,4]oxadiazol-2-yl)benzoic acid

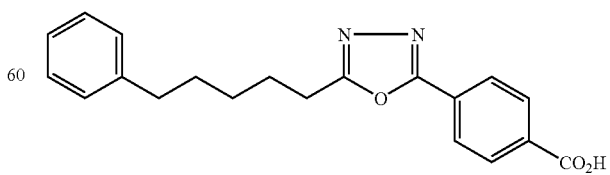

The above compound was prepared in a manner similar to that exemplified for the preparation of Example 7b, from 4-[5-(3-phenylpentyl)-[1,3,4]oxadiazol-2-yl)benzoic acid methyl ester (0.7.25 g, 2.1 mmol), lithium hydroxide (0.149 g, 6.2 mmol) to afford 0.685 g (98%) of 4-[5-(3-phenylpentyl)-[1,3,4]oxadiazol-2-yl)benzoic acid.

$^1$H NMR (DMSO-d6) δ13.33 (bs, 1H), 8.07–8.15 (m, 4H), 7.12–7.28 (m, 5H), 2.95 (t, 2H, J=7 Hz), 2.59 (t, 2H, J=7 Hz), 1.74–1.86 (m, 2H), 1.56–1.70 (m, 2H), 1.35–1.45 (m, 2H). IR (KBr, cm$^{-1}$) 2949, 2919, 2856, 1683, 1570, 1321, 1291, 732, 720. MS (ES) m/e, 337, 335. Anal. Calcd for $C_{20}H_{20}N_2O_3$: C, 71.41; H, 5.99; N, 8.33. Found C, 70.86; H, 5.96; N, 8.26.

c) 4[5-(3-dimethylaminopropyl)-4-(5-phenylpentyl)-[1,3,4]oxadiazol-2-yl)benzamide

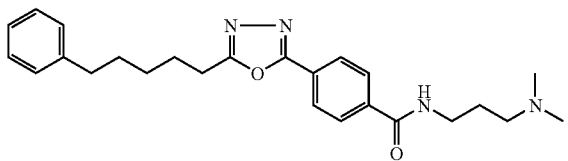

The above compound was prepared in a manner similar to that exemplified for the preparation of Example 7c, from 4-[5-(3-phenylpentyl)-[1,3,4]oxadiazol-2-yl)benzoic acid (0.500 g, 1.49 mmol), 1-hydroxybenzotriazole (0.201 g, 1.49 mmol), 4-dimethylamino pyridine (0.018 g, 0.15 mmol), and 3-(dimethylamino)propylamine (0.159 g, 1.56 mmol) to afford the title compound as a crude mixture. Purification by chromatography on silica gel (eltuted with a linear gradient of 2 to 10% 2M ammonium:CH$_2$Cl$_2$ over a thirty minute period) followed by crystallization of the isolated material from ethanol:diethyl ether afforded 0.209 g (33%) of 4[5-(3-dimethylaminopropyl)-4-(S-phenylpentyl)-[1,3,4]oxadiazol-2-yl)benzamide. A second crop of crystals afforded 0.085 g (13%) of the title compound.

$^1$H NMR (DMSO-d6) δ8.71 (t, 1H, J=5 Hz), 8.00–8.07 (m, 4H), 7.12–7.28 (m, 5H), 3.30 (m, 2H), 2.94 (t, 2H, J=7 Hz), 2.59 (t, 2H, J=7 Hz), 2.26 (t, 2H, J=7 Hz), 2.14 (s, 6H), 1.76–1.86 (m, 2H), 1.58–1.71 (m, 4H), 1.37–1.45 (m, 2H). IR (CHCl$_3$, cm$^{-1}$) 3007, 1652, 1586, 1555, 1529, 1494. MS (ES) m/e, 421, 419. Anal. Calcd for $C_{25}H_{32}N_4O_2$: C, 71.40; H, 7.67; N, 13.32. Found C, 71.16; H, 7.64; N, 13.23. Mp(° C.)=116.

Example 12

Preparation of N-(3-dimethylaminopropyl)-4-(5-phenylpentyl)-[1,3,4]oxadiazol-2-yl)benzamide from 7-phenylheptanoic acid a) 4-[5-(3-phenylhexyl)-[1,3,4]oxadiazol-2-yl)benzoic acid methyl ester

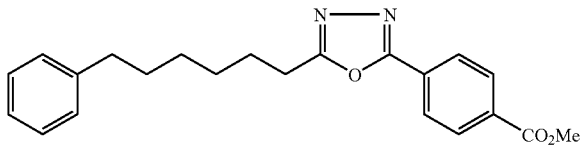

The above compound was prepared in a manner similar to that exemplified for the preparation of Example 1b, from 7-phenylheptanoic acid (0.714 g, 3.46 mmol), 1,3-dicyclohexylcarbodiimide (0.714 g, 3.46 mmol), 4-(1H-tetrazole-5-yl)benzoic acid methyl ester (0.700 g, 3.43 mmol) and 5.1 mL toluene to afford the title compound as a crude mixture. Purification by radial chromatography on silica gel (elution with 25% to 50% EtOAc:hexane) afforded 0.738 g (59%) of 4-[5-(3-phenylhexyl)-[1,3,4]oxadiazol-2-yl)benzoic acid methyl ester.

$^1$H NMR (DMSO-d6) δ8.10–8.17 (m, 4H), 7.12–7.28 (m, 5H), 3.90 (s, 3H), 2.94 (t, 2H, J=7 Hz), 2.56 (t, 2H, J=7 Hz), 1.72–1.82 (m, 2H), 1.53–1.63 (m, 2H), 1.28–1.46 (m, 4H). IR (KBr, cm$^{-1}$) 2952, 2930, 2856, 1723, 1565, 1414, 1280, 1264, 1110, 778, 717, 698. MS (ES) m/e, 365. Anal. Calcd for $C_{22}H_{24}N_2O_3$: C, 72.51; H, 6.64; N, 7.69. Found C, 72.83; H, 6.59; N, 7.62.

b) 4-[5-(3-phenylhexyl)-[1,3,4]oxadiazol-2-yl)benzoic acid

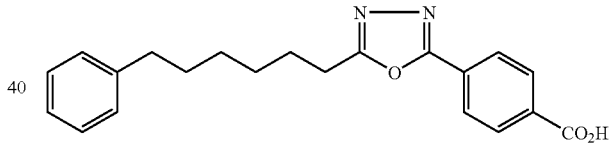

The above compound was prepared in a manner similar to that exemplified for the preparation of Example 7b, from 4-[5-(3-phenylhexyl)-[1,3,4]oxadiazol-2-yl)benzoic acid methyl ester (0.676 g, 1.93 mmol) and lithium hydroxide (0.139 g, 5.79 mmol) to afford 0.616 g (95%) of 4-[5-(3-phenylhexyl)-[1,3,4]oxadiazol-2-yl)benzoic acid.

$^1$HNMR (DMSO-d6) δ8.05–8.13 (m, 4H), 7.12–7.28 (m, 5H), 2.93 (t, 2H, J=7 Hz), 2.56 (t, 2H, J=8 Hz), 1.72–1.82 (m, 2H), 1.50–1.63 (m, 2H), 1.26–1.46 (m, 4H). IR (KBr, cm$^{-1}$) 2942, 2924, 2853, 1686, 1573, 1429, 1287, 715. MS (ES) m/e, 351, 349. Anal. Calcd for $C_{21}H_{22}N_2O_3$: C, 71.98; H, 6.33; N, 7.99. Found C, 71.59; H, 6.45; N, 7.86.

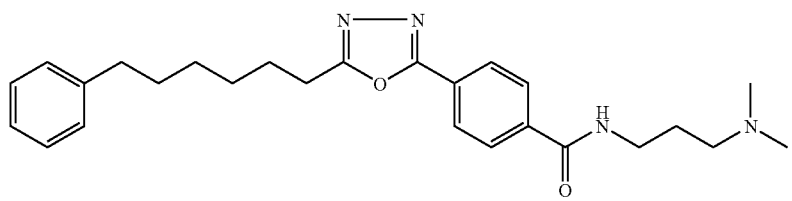

c) 4[5-(3-dimethylaminopropyl)-4-(5-phenylhexyl)-[1,3,4]oxadiazol-2-yl)benzamide

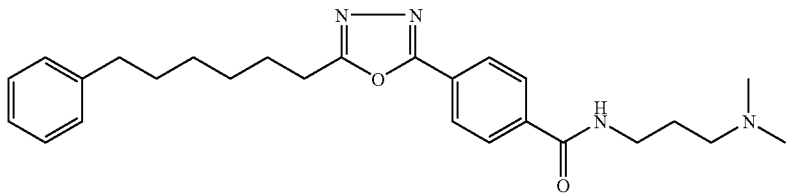

The above compound was prepared in a manner similar to that exemplified for the preparation of Example 7c, from 4-[5-(3-phenylhexyl)-[1,3,4]oxadiazol-2-yl)benzoic acid (0.488 g, 1.39 mmol), 1-hydroxybenzotriazole (0.188 g, 1.39 mmol), 4-dimethylamino pyridine (0.017 g, 0.14 mmol) and 3-(dimethylamino)propylamine (0.149 g, 1.46 mmol) to afford the title compound as a crude mixture. Purification by radial chromatography on silica gel (eltuted with a 10% 2M ammonium:$CH_2Cl_2$) followed by crystallization of the isolated material from ethanol:diethyl ether afforded 0.152 g (25%) of 4[5-(3-dimethylaminopropyl)-4-(5-phenylhexyl)-[1,3,4]oxadiazol-2-yl)benzamide.

$^1$H NMR (DMSO-d6) $\delta$8.71 (t, 1H, J=5 Hz), 8.00–8.08 (m, 4H), 7.12–7.238 (m, 5H), 3.31 (m, 2H), 2.93 (t, 2H, J=7 Hz), 2.56 (t, 2H, J=8 Hz), 2.27 (t, 2H, J=7 Hz), 2.13 (s, 6H), 1.53–1.79 (m, 6H), 1.30–1.44 (m, 4H). IR (KBr, cm$^{-1}$) 2936, 2861, 1652, 1586, 1567, 1556, 1529, 1495, 1302. MS (ES) m/e, 435, 433. Anal. Calcd for $C_{26}H_{34}N_4O_2$: C, 71.86; H, 7.89; N, 12.89. Found C, 71.59; H, 7.69; N, 12.72. Mp(° C.)=91.

Example 13

Preparation of N-(3-dimethylaminopropyl)-4-(5-phenylheptyl)-[1,3,4]oxadiazol-2-yl)benzamide from 8-phenyloctanoic acid

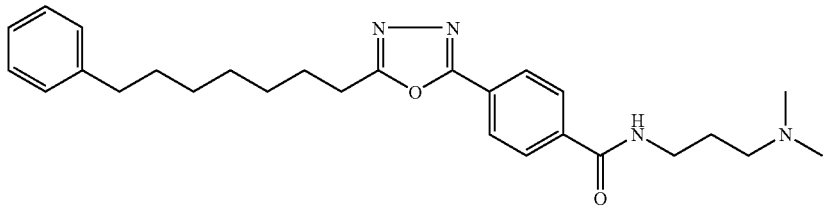

a) 4-[5-(3-phenylheptyl)-[1,3,4]oxadiazol-2-yl)benzoic acid methyl ester

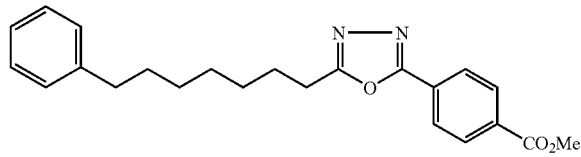

The above compound was prepared in a manner similar to that exemplified for the preparation of Example 1b, from 8-phenyloctanoic acid (0.763 g, 3.46 mmol), 1,3-dicyclohexylcarbodiimide (0.714 g, 3.46 mmol) and 4-(1H-tetrazole-5-yl)benzoic acid methyl ester (0.700 g, 3.43 mmol) to afford the title compound as a crude mixture. Purification by radial chromatography on silica gel (elution with 25% to 50% EtOAc:hexane) followed by crystallization of the isolated material from diethyl ether afforded 0.522 g (40%) of 4-[5-(3-phenylheptyl)-[1,3,4]oxadiazol-2-yl)benzoic acid methyl ester.

$^1$H NMR (DMSO-d6) $\delta$8.13 (m, 4H), 7.12–7.28 (m, 5H), 3.90 (s, 3H), 2.94 (t, 2H, J=7 Hz), 2.56 (t, 2H, J=7 Hz), 1.63–1.81 (m, 2H), 1.44–1.61 (m, 21), 1.22–1.41 (m, 6H). IR (KBr, cm$^{-1}$) 2926, 1724, 1570, 1437, 1280, 1110, 712. MS (ES) m/e, 379. Anal. Calcd for $C_{23}H_{26}N_2O_3$: C, 72.99; H, 6.92; N, 7.40. Found C, 73.11; H, 7.08; N, 7.68.

b) 4-[5-(3-phenylheptyl)-[1,3,4]oxadiazol-2-yl)benzoic acid

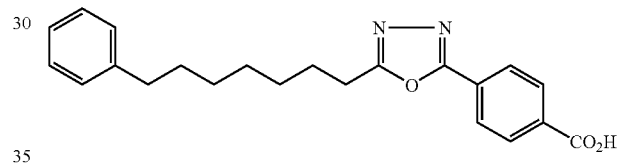

Preparation of N-(3-dimethylaminopropyl)-4-[5-(3-phenylpropylsulfanylmethyl)-[1,3,4]oxadiazol-2-yl]benzamide from 3-phenylpropylmercaptan

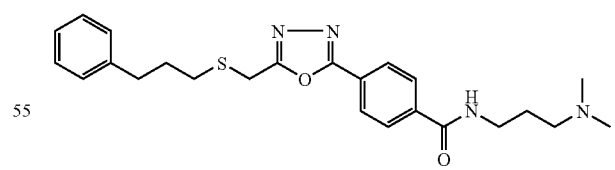

a) (3-phenylpropylsulfanyl)acetic acid

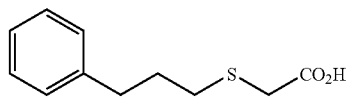

The above compound was prepared in a manner similar to that exemplified for the preparation of Example 1a, from 3-phenylpropylmercaptan (3.13 g, 20.6 mmol), sodium hydride (0.823 g, 20.6 mmol), and methyl bromoacetate (2.86 g, 18.7 mmol) to afford the title compound as a crude mixture. Purification by flash filtration chromatography on silica gel (elution with 4×250 mL 15% EtOAc:hexane followed by 3×250 mL EtOAc) afforded 3.83 g, (89%) of (3-phenylpropylsulfanyl)acetic acid.

$^1$HNMR (DMSO-d6) $\delta$12.51 (bs, 1H), 7.15–7.30 (m, 5H), 3.23 (s, 2H), 2.65 (t, 2H, J=8 Hz), 2.58 (t, 2H, J=7 Hz), 1.78–1.88 (m, 2H). IR (CHCl$_3$, cm$^{-1}$) 3029, 3011, 1710, 1601, 1454, 1423, 1295, 1197. MS (ES) m/e, 209. Anal. Calcd for C$_1$H$_{14}$O$_2$S: C, 62.83; H, 6.71. Found C, 62.70; H, 6.52.

b) 4-[5-(3-phenylpropylsulfanylmethyl)-[1,3,4]oxa-diazol-2-yl]benzoic acid methyl ester

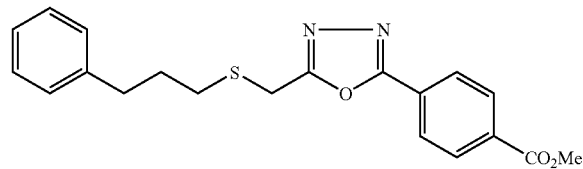

The above compound was prepared in a manner similar to that exemplified for the preparation of Example 1b, from (3-phenylpropylsulfanyl)acetic acid (0.975 g, 4.6 nM), 1,3-dicyclohexylcarbodiimide (0.957 g, 4.6 mmol), and 4-(1H-tetrazole-5-yl)benzoic acid methyl ester (0.789 g, 3.9 mmol) to afford the title compound as a crude mixture.

Purification by radial chromatography on silica gel followed by crystallization from diethyl ether afforded a total of 0.668 g (47%) of 4-[5-(3-phenylpropylsulfanylmethyl) [1,3,4]oxadiazol-2-yl]benzoic acid methyl ester.

$^1$H NMR (DMSO-d6) $\delta$8.09–8.18 (m, 4H), 7.12–7.26 (m, 5H), 4.14 (s, 2H), 3.91 (s, 3H), 2.62–2.67 (m, 4H), 1.80–1.90 (m, 2H). IR (CHCl$_3$, cm$^{-1}$) 1721, 1554, 1438, 1299, 1283, 1119, 1111. MS (ES) m/e, 369. Anal. Calcd for C$_{20}$H$_{20}$N$_2$O$_3$S: C, 65.20; H, 5.47; N, 7.60. Found C, 65.05; H, 5.48; N, 7.67.

c) 4-[5-(3-phenylpropylsulfanylmethyl)-[1,3,4]oxa-diazol-2-yl]benzoic acid

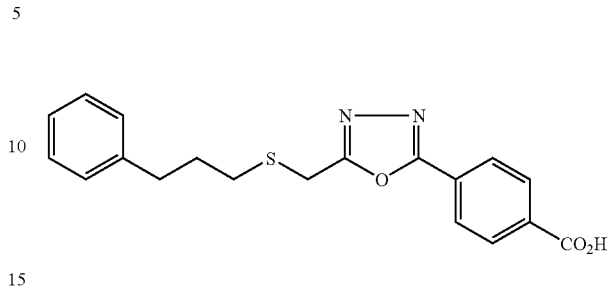

The above compound was prepared in a manner similar to that exemplified for the preparation of Example 1c, from 4-[5-(3-phenylpropylsulfanylmethyl)-[1,3,4]oxadiazol-2-yl] benzoic acid methyl ester (0.600 g, 1.63 mmol) and lithium hydroxide (0.117 g, 4.89 mmol) to afford 0.522 g (90%) of 4-[5-(3-phenylpropylsulfanylmethyl)-[1,3,4]oxadiazol-2-yl] benzoic acid.

$^1$H NMR (DMSO-d6) $\delta$8.03–8.16 (m, 4H), 7.11–7.28 (m, 5H), 4.14 (s, 2H), 2.66 (dt, 4H, J=7 Hz), 1.79–1.88 (m, 2H). IR (KBr, cm$^{-1}$) 1706, 1685, 1551, 1433, 1324, 1293, 715, 699.

MS (ES) m/e, 355, 353. Anal. Calcd for Cl$_9$H$_{18}$N$_2$O$_3$S: C, 64.39; H, 5.12; N, 7.90. Found C, 63.29; H, 4.95; N, 7.81.

d) N-(3-dimethylaminopropyl)-4-[5-(3-phenylpro-pylsulfanylmethyl)-[1,3,4]oxadiazol-2-yl]benzamide The above compound was prepared in a manner similar to that exemplified for the preparation of Example 7b, from 4-[5-(3-phenyl heptyl)-[1,3,4]oxadiazol-2-yl)benzoic acid methyl ester (0.467 g, 1.23 mmol) and lithium hydroxide (0.089 g, 3.70 mmol), in THF (5.4 mL) and water (1.0 mL) to afford 0.435 g (97%) of 4-[5-(3-phenylheptyl)-[1,3,4]-oxadiazol-2-yl)benzoic acid.

$^1$H NMR (DMSO-d6) $\delta$8.06–8.14 (m, 4H), 7.12–7.28 (m, 5H), 2.94 (t, 2H, J=7 Hz), 2.56 (t, 2H, J=7 Hz), 1.69–1.81 (m, 2H), 1.50–1.61 (m, 2H), 1.23–1.41 (m, 6H). IR (KBr, cm$^{-1}$) 2928, 2922, 2850, 1688, 1585, 1571, 1434, 1321, 1291, 722. MS (ES) m/e, 365, 363. Anal. Calcd for C$_{22}$H$_{24}$N$_2$O$_3$: C, 72.51; H, 6.64; N, 7.69. Found C, 69.19; H, 6.35; N, 7.47.

c) 4[5-(3-dimethylaminopropyl)-4-(5-phenylheptyl)-[1,3,4]oxadiazol-2-yl)benzamide

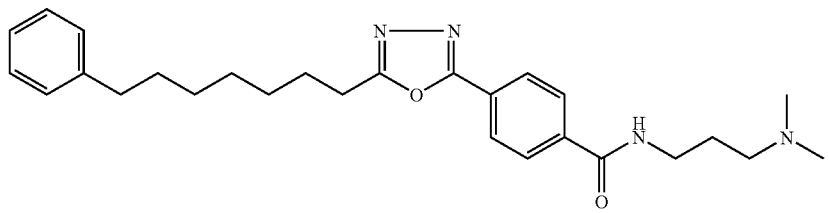

The above compound was prepared in a manner similar to that exemplified for the preparation of Example 7c, from 4-[5-(3-phenylheptyl)-[1,3,4]oxadiazol-2-yl)benzoic acid (0.399 g, 1.14 mmol), 1-hydroxybenzotriazole (0.154 g, 1.14 mmol), 4-dimethylamino pyridine (0.014 g, 0.11 mmol) and 3-(dimethylamino)propylamine (0.122 g, 1.20 mmol) to afford the title compound as a crude mixture. Purification by silica gel radial chromatography (eltuted with a 10% 2M ammonium: $CH_2Cl_2$) followed by crystallization of the isolated material from ethanol:diethyl ether afforded 0.103 g (20%) of 4[5-(3-dimethylaminopropyl)-4-(5-phenylhexyl)-[1,3,4]oxadiazol-2-yl)benzamide.

$^1$H NMR (DMSO-d6) 8.71 (t, 1H, J=5 Hz), 8.00–8.08 (m, 4H), 7.12–7.28 (m, 5H), 3.32 (m, 2H), 2.93 (t, 2H, J=7 Hz), 2.56 (t, 2H, J=8 Hz), 2.26 (t, 2H, J=7 Hz), 2.14 (s, 6H), 1.44–1.77 (m, 6H), 1.27–1.40 (m, 6H). IR (CHCl$_3$, cm$^{-1}$) 3008, 2934, 2859, 2827, 1652, 1586, 1556, 1495. MS (ES) m/e, 449. Anal. Calcd for $C_{27}H_{36}N_4O_2$: C, 72.29; H, 8.09; N, 12.49. Found C, 72.21; H, 8.05; N, 12.50. Mp(° C.)=108.

Example 14

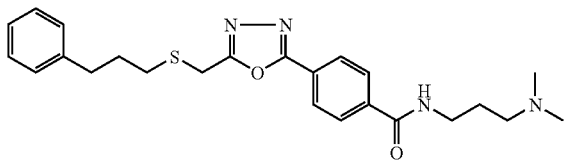

The above compound was prepared in a manner similar to that exemplified for the preparation of Example 1d, from 4-[5-(3-phenylpropylsulfanylmethyl)-[1,3,4]oxadiazol-2-yl]benzoic acid (0.492 g, 1.39 mmol), 1,1'-carbonyldiimidazole (0.236 g, 1.46 mmol) and 3-(dimethylamino)propylamine (0.170 g, 1.67 mmol) to afford the title compound as a crude mixture. Purification by radial chromatography on silica gel (elution with 10% 2M ammonia in MeOH:CHCl$_3$) afforded 0.392 g (64%) of N-(3-dimethylaminopropyl)-4-[5-(3-phenylpropylsulfanylmethyl)-[1,3,4]oxadiazol-2-yl]benzamide.

$^1$H NMR (DMSO-d6) 8.72 (t, 1H, J=5 Hz), 8.01–8.07 (m, 4H), 7.12–7.26 (m, 5H), 4.13 (s, 2H), 2.62–2.67 (m, 4H), 2.27 (t, 2H, J=7 Hz), 2.14 (s, 6H), 1.75–1.86 (m, 2H), 1.63–1.72 (m, 2H). IR (KBr, cm$^{-1}$) 3338, 2939, 2813, 2761, 1638, 1581, 1552, 1534, 1496, 1456, 1288, 712. MS (ES) m/e, 439, 437. Anal. Calcd for $C_{24}H_{30}N_4O_2S$: C, 65.73; H, 6.89; N, 12.77. Found C, 65.82; H, 6.94; N, 12.74. Mp(° C.)=112.

Example 15

Preparation of N-(3-dimethylaminopropyl)-4-[5-(3-phenylpropane-1-sulfinylmethyl)-[1,3,4]oxadiazol-2-yl]benzamide from 4-[5-(3-phenylpropylsulfanylmethyl)-[1,3,4]oxadiazol-2-yl]benzoic acid methyl ester

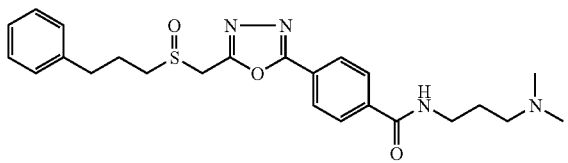

a) 4-[5-(3-phenylpropane-1-sulfinylmethyl)-[1,3,4]oxadiazol-2-yl]benzoic acid methyl ester

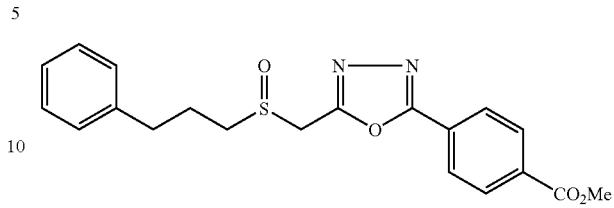

A solution of 4-[5-(3-phenylpropylsulfanylmethyl)-[1,3,4]oxadiazol-2-yl]benzoic acid methyl ester (0.870 g, 2.4 mmol) in 12 mL $CH_2Cl_2$ stirring at 0° C. was added dropwise and peracetic acid (0.673 g, 2.8 mmol). After 2.1 hours the mixture was stirred at room temperature for 20 minutes before additional peracetic acid (0.036 g, 0.47 mmol) was added. Fifty minutes later additional peracetic acid (0.036 g, 0.47 mmol) was added. Twenty minutes after the second addition, the reaction was quenched with 5 mL saturated aqueous solution of sodium sulfite. The mixture was diluted with water then extracted with $CH_2Cl_2$. The organic phase was washed twice with $H_2O$, once with brine, dried over sodium sulfate, filtered, concentrated to afford a solid. Crystallization form acetone afforded 0.660 g (73%) of 4-[5-(3-phenylpropane-1-sulfinylmethyl)-[1,3,4]oxadiazol-2-yl]benzoic acid methyl ester.

$^1$H NMR (DMSO-d6) 8.11–8.20 (m, 4H), 7.16–7.32 (m, 5H), 4.73–4.78 (m, 1H), 4.51–4.56 (m, 1H), 3.90 (s, 31), 2.88–3.05 (m, 2H), 2.72–2.77 (m, 2H), 1.95–2.05 (m, 2H). IR (CHCl$_3$, cm$^{-1}$) 1722, 1551, 1438, 1283, 1111. MS (ES) m/e, 385. Anal. Calcd for $C_{20}H_{20}N_2O_4S$: C, 62.16; H, 5.74; N, 7.25. Found C, 62.11; H, 5.22; N, 7.31.

b) 4-[5-(3-phenylpropane-1-sulfinylmethyl)[1,3,4]oxadiazol-2-yl]benzoic acid

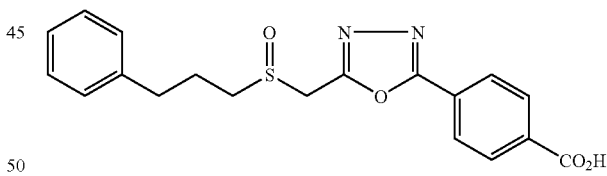

The above compound was prepared in a manner similar to that exemplified for the preparation of Example 1c, from 4-[5-(3-phenylpropane-1-sulfinylmethyl)-[1,3,4]oxadiazol-2-yl]benzoic acid methyl ester (0.599 g, 1.56 mmol) and lithium hydroxide (0.112 g, 4.67 mmol) to afford 0.457 g (79%) of 4-[5-(3-phenylpropane-1-sulfinylmethyl)[1,3,4]oxadiazol-2-yl]benzoic acid.

$^1$HNMR(DMSO-d6) 13.40 (bs, 1H), 8.03–8.17 (m, 4H), 7.16–7.23 (m, 5H), 4.75 (d, 1H, J=14 Hz), 4.54 (d, 1H, J=14 Hz), 2.88–3.05 (m, 2H), 2.70–2.80 (m, 2H), 1.96–2.09 (m, 2H). IR (KBr, cm$^{-1}$) 2923, 1706, 1685, 1554, 1434, 1324, 1292, 1044, 1012, 873, 716, 697. MS (ES) m/e, 371. Anal. Calcd for $C_{19}H_{20}N_2O_4S$: C, 61.27; H, 5.41; N, 7.52. Found C, 60.74; H, 4.79; N, 7.43.

c) N-(3-dimethylaminopropyl)-4-[5-(3-phenylpropane-1-sulfinylmethyl)-[1,3,4]oxadiazol-2-yl]benzamide

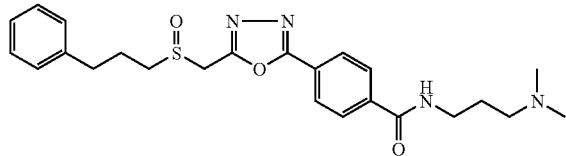

The above compound was prepared in a manner similar to that exemplified for the preparation of Example 1d, from 4-[5-(3-phenylpropane-1-sulfinylmethyl)[1,3,4]oxadiazol-2-yl]benzoic acid (0.448 g, 1.20 mmol), 1,1'-carbonyldiimidazole (0.205 g, 1.26 mmol) and 3-(dimethylamino)propylamine (0.147 g, 1.44 mmol) to afford the title compound as a crude mixture. Crystallization of the crude material from methanol:diethyl ether afforded 0.284 g (45%) of N-(3-dimethylaminopropyl)-4-[5-(3-phenylpropane-1-sulfinylmethyl)-[1,3,4]oxadiazol-2-yl]benzamide.

$^1$H NMR (DMSO-d6) δ8.73 (t, 1H, J=5 Hz), 8.05 (m, 4H), 7.17–7.32 (m, 5H), 4.73 (d, 1H, J=14 Hz), 4.52 (d, 1H, J=14 Hz), 3.32 (m, 2H), 2.84–3.03 (m, 2H), 2.62–2.70 (m, 2H), 2.27 (t, 2H, J=7 Hz), 2.14 (s, 6H), 1.94–2.06 (m, 2H), 1.62–1.72 (m, 2H). IR (KBr, cm$^{-1}$) 3334, 1645, 1585, 1554, 1536, 1304, 1047, 859 MS (ES) m/e, 455, 453. Anal. Calcd for C$_{24}$H$_{30}$N$_4$O$_3$S: C, 63.41; H, 6.65; N, 12.32. Found C, 62.86; H, 6.58; N, 12.14. Analytical HPLC: 100% Purity. Mp(° C.)=127.

Example 16

Preparation of N-(3-dimethylaminopropyl)-4-[5-(3-phenylpropane-1-sulfonylmethyl)-[1,3,4]oxadiazol-2-yl]benzamide from 4-[5-(3-phenylpropylsulfanylmethyl)-[1,3,4]oxadiazol-2-yl]benzoic acid methyl ester

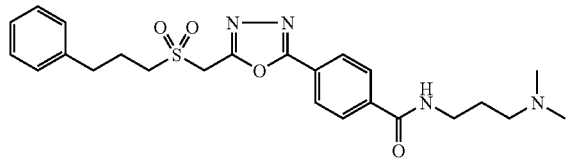

a) 4-[5-(3-phenylpropane-1-sulfonylmethyl)-[1,3,4]oxadiazol-2-yl]benzoic acid methyl ester

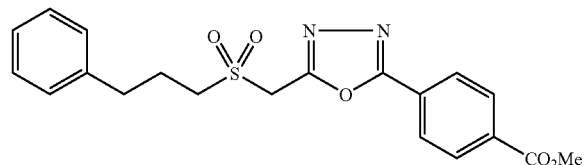

A solution of 4-[5-(3-phenylpropylsulfanylmethyl)-[1,3,4]oxadiazol-2-yl]benzoic acid methyl ester (0.970 g, 2.63 mmol) and m-chloroperoxybenzoic acid (1.82 g, 5.8 mmol) in 14 mL CH$_2$Cl$_2$ was stirred at room temperature for 4.5 hours. The mixture was then quenched with 5 mL saturated aqueous solution of sodium sulfite. The mixture was diluted with water then extracted with CH$_2$Cl$_2$. The organic phase was washed twice with H$_2$O, once with brine, dried over sodium sulfate, filtered, concentrated to afford a solid. Crystallization form acetone afforded 0.733 g (70%) of 4-[5-(3-phenylpropane-1-sulfonylmethyl)-[1,3,4]oxadiazol-2-yl]benzoic acid methyl ester.

$^1$H NMR (DMSO-d6) δ8.11–8.20 (m, 4H), 7.18–7.33 (m, 5H), 5.25 (s, 2H), 3.91 (s, 3H), 3.38 (t, 2H, J=8 Hz), 2.74 (t, 2H, J=8 Hz), 2.02–2.13 (m, 2H). IR (CHCl$_3$, cm$^{-1}$) 1722, 1438, 1333, 1299, 1284, 1112. MS (ES) m/e, 401, 399. Anal. Calcd for C$_{20}$H$_{20}$N$_2$O$_5$S: C, 59.99; H, 5.03; N, 7.00. Found C, 59.93; H, 5.12; N, 6.95.

b) 4-[5-(3-phenylpropane-1-sulfonylmethyl)[1,3,4]oxadiazol-2-yl]benzoic acid

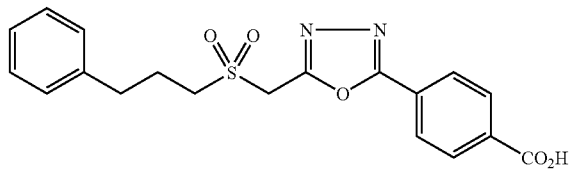

The above compound was prepared in a manner similar to that exemplified for the preparation of Example 1c, from 4-[5-(3-phenylpropane-1-sulfonylmethyl)-[1,3,4]oxadiazol-2-yl]benzoic acid methyl ester (0.667 g, 1.67 mmol) and lithium hydroxide (0.120 g, 5.00 mmol) to afford 0.559 g (87%) of 4-[5-(3-phenylpropane-1-sulfonylmethyl)[1,3,4]oxadiazol-2-yl]benzoic acid.

$^1$H NMR (DMSO-d6) δ13.38 (bs, 1H), 8.08–8.18 (m, 4H), 7.18–7.34 (m, 5H), 5.25 (s, 2H), 3.38 (t, 2H, J=8 Hz), 2.75 (t, 2H, J=8 Hz), 2.01–2.13 (m, 2H). IR (KBr, cm$^{-1}$) 2995, 2675, 2555, 1706, 1685, 1551, 1433, 1321, 1294, 1137, 1131, 1121, 717. MS (ES) m/e, 387. Anal. Calcd for C$_{19}$H$_{18}$N$_2$O$_5$S: C, 59.06; H, 4.70; N, 7.25. Found C, 58.42; H, 4.69; N, 7.11.

c) N-(3-dimethylaminopropyl)-4-[5-(3-phenylpropane-1-sulfonylmethyl)-[1,3,4]oxadiazol-2-yl]benzamide

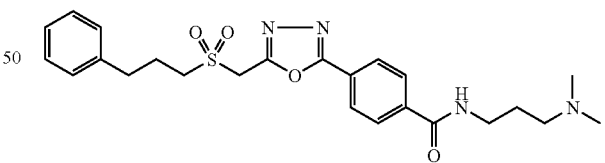

The above compound was prepared in a manner similar to that exemplified for the preparation of Example 1d, from 4-[5-(3-phenylpropane-1-sulfonylmethyl)[1,3,4]oxadiazol-2-yl]benzoic acid (0.550 g, 1.42 mmol), 1,1'-carbonyldiimidazole (0.242 g, 1.49 mmol) and 3-(dimethylamino)propylamine (0.175 g, 1.71 mmol) to afford the title compound as a crude mixture. Crystallization of the crude material from methanol:diethyl ether afforded 0.378 g (56%) of N-(3-dimethylaminopropyl)-4-[5-(3-phenylpropane-1-sulfonylmethyl)-[1,3,4]oxadiazol-2-yl]benzamide.

$^1$HNMR (DMSO-d6) δ8.74 (t, 1H, J=5 Hz), 8.05 (m, 4H), 7.18–7.34 (m, 5H), 5.23 (s, 2H), 3.28–3.40 (m, 4H), 2.74 (t,

2H, J=8 Hz), 2.27 (t, 2H, J=7 Hz), 2.14 (s, 6H), 2.02–2.10 (m, 2H), 1.63–1.72 (m, 2H). IR (KBr, cm$^{-1}$) 3264, 2941, 2763, 1634, 1555, 1320, 1166, 1115, 697. MS (ES) m/e, 469. Anal. Calcd for $C_{24}H_{30}N_4O_4S$: C, 61.26; H, 6.43; N, 11.91. Found C, 61.38; H, 6.52; N, 11.94. Mp(° C.)=157.

Example 17

Preparation of N-(3-dimethylaminopropyl)-4-[5-(2-phenoxypropylsulfanylmethyl)-[1,3,4]oxadiazol-2-yl]benzamide from 2-phenoxypropanol

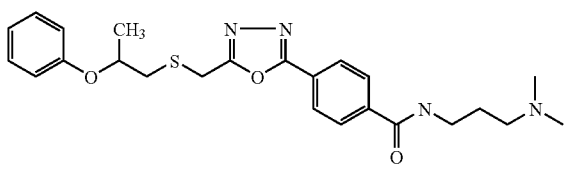

a) (2-Bromo-1-methylethoxy)benzene

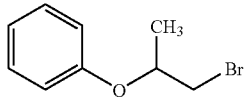

A solution of triphenylphosphine (8.63 g, 32.9 mmol) in 94 mL CH$_2$Cl$_2$ stirring at room temperature was added dropwise, bromine (5.26 g, 32.9 mmol) over a twenty minute period. The resultant suspension was stirred at room temperature for 15 minutes then a solution of 2-phenoxypropanol (5.01 g, 32.9 mmol) and imidazole (2.69 g, 39.5 mmol) in 70 mL CH$_2$Cl$_2$ was added over a 15 minute period. The mixture was stirred at room temperature for 2.5 hours then subjected to filtration. The filtrate was concentrated in vacuo to afford an oil. Purification by flash filtration chromatography on silica gel (elution with 15% EtOAc:hexane) afforded 4.80 g (68%) of (2-Bromo-1-methylethoxy)benzene.

$^1$H NMR (DMSO-d6) δ7.32–7.39 (m, 2H), 6.92–6.99 (m, 3H), 4.63–4.72 (m, 1H), 3.69 (ddd, 2H, J=5, 11 and 22 Hz), 1.33 (d, 3H, J=6 Hz). IR (CHCl$_3$, cm$^{-1}$) 1600, 1588, 1495, 1062. MS (ES) m/e, 214. Anal. Calcd for C$_9$H$_{11}$BrO: C, 50.26; H, 5.15. Found C, 44.83; H, 4.51.

b) (2-Phenoxypropylsulfanyl)acetic acid methyl ester

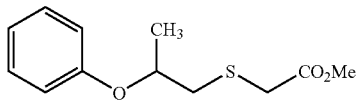

A solution of methyl thioglycolate (1.64 g, 15.4 mmol) in 61 mL THF stirring at room temperature was added sodium hydride (0.62 g, 15.4 mmol). The mixture was stirred fifteen minutes before a solution of 2-bromo-1-methylethoxy)benzene (3.02 g, 14.0 mmol) in 3.0 mL THF was added. The mixture was stirred at room temperature for two days. The reaction mixture was diluted with 100 mL EtOAc then washed three times with water, brine, dried over sodium sulfate, filtered, concentrated to afford an oil. Purification by chromatography on silica gel (elution with a linear gradient of 10 to 25% Et$_2$O:hexane) afforded 2.20 g (65%)(2-phenoxypropylsulfanyl)acetic acid methyl ester.

$^1$H NMR (DMSO-d6) δ7.24–7.30 (m, 2H), 6.90–6.94 (m, 3H), 4.60–4.66 (m, 1H), 3.61 (s, 3H), 3.45 (d, 2H, J=3 Hz), 2.76 (ddd, 2H, J=6, 14, 38 Hz), 1.30 (d, 3H, J=6 Hz). IR (CHCl$_3$, cm$^{-1}$) 1735, 1599, 1587, 1495, 1438, 1289, 1173, 1132. MS (ES) m/e, 241. Anal. Calcd for C$_{12}$H$_{16}$O$_3$S: C, 59.97; H, 6.71. Found C, 49.24; H, 5.39.

c) (2-Phenoxypropylsulfanyl)acetic acid

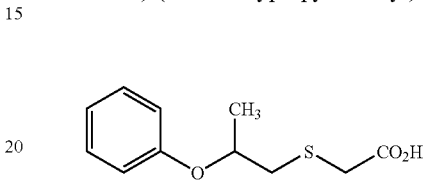

A mixture of 2-phenoxypropylsulfanyl)acetic acid methyl ester (1.93 g, 8.0 mmol) and lithium hydroxide (0.577 g, 24.1 mmol) was stirred at room temperature for 5.5 hours. The reaction mixture was quenched with concentrated HCl (2.02 mL, 8.0 mmol), diluted with EtOAc and water. The phases were separated and the aqueous phase extracted once with EtOAc. The combined organic phases were washed with brine, dried over sodium sulfate, filtered, concentrated to afford 1.22 g (67%) of (2-Phenoxypropylsulfanyl)acetic acid.

$^1$HNMR (DMSO-d6) δ7.24–7.31 (m, 2H), 6.89–6.96 (m, 3H), 4.59–4.69 (m, 1H), 3.28–3.39 (m, 2H), 2.76–2.95 (m, 2H), 1.30 (d, 3H, J=6 Hz). IR (CHCl$_3$, cm$^{-1}$) 2982, 2931, 1711, 1599, 1587, 1495, 1291, 1239, 1173, 1131. MS (ES) m/e, 227, 225. Anal. Calcd for C$_{11}$H$_{14}$O$_3$S: C, 58.38; H, 6.24. Found C, 58.80; H, 6.00.

d) 4-[5-(2-phenoxypropylsulfanylmethyl)-[1,3,4]oxadiazol-2-yl]benzoic acid methyl ester

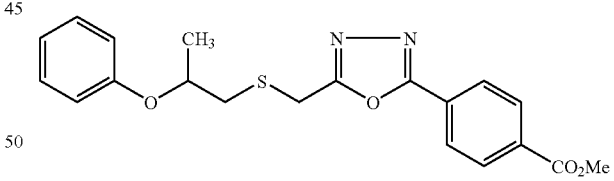

The above compound was prepared in a manner similar to that exemplified for the preparation of Example 1b, from (2-phenoxypropylsulfanyl)acetic acid (0.950 g, 4.2 nM), 1,3-dicyclohexylcarbodiimide (0.866 g, 4.2 mmol), and 4-(1H-tetrazole-5-yl)benzoic acid methyl ester (0.857 g, 4.2 mmol) to afford the title compound as a crude mixture.

Purification three times by radial chromatography on silica gel (elution with 50% EtOAc:hexane) afforded 0.631 g (39%) of 4-[5-(2-phenoxypropyl sulfanylmethyl)-[1,3,4] oxadiazol-2-yl]benzoic acid methyl ester as an oil that slowly crystallized out.

$^1$HNMR (DMSO-d6) δ8.07–8.16 (m, 4H), 7.20–7.27 (m, 2H), 6.86–6.94 (m, 3H), 4.62–4.68 (m, 1H), 4.16–4.27 (m, 2H), 3.91 (s, 3H), 2.89–2.95 (m, 2H), 1.29 (d, 2H, J=6 Hz).

e) 4-[5-(2-phenoxypropylsulfanylmethyl)-[1,3,4]oxadiazol-2-yl]benzoic acid

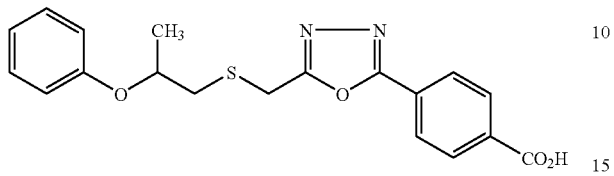

The above compound was prepared in a manner similar to that exemplified for the preparation of Example 17c, from 4-[5-(2-phenoxypropylsulfanylmethyl)-[1,3,4]oxadiazol-2-yl]benzoic acid methyl ester (0.611 g, 1.59 mmol) and lithium hydroxide (0.114 g, 4.76 mmol) to afford 0.573 g (97%) of 4-[5-(2-phenoxypropylsulfanylmethyl)-[1,3,4]oxadiazol-2-yl]benzoic acid.

$^1$H NMR (DMSO-d6) δ13.35 (bs, 1H) 8.04–8.14 (m, 4H), 7.21–7.30 (m, 3H), 6.87–6.94 (m, 3H), 4.58–4.71 (m, 2H), 4.16–4.27 (m, 2H), 2.88–3.00 (m, 2H), 1.29 (d, 3H, J=6 Hz). IR (CHCl$_3$, Cm$^{-1}$) 1700, 1587, 1495, 1240. MS (ES) m/e, 371, 369.

f) N-(3-dimethylaminopropyl)-4-[5-(2-phenoxypropyl sulfanylmethyl)-[1,3,4]oxadiazol-2-yl]benzamide

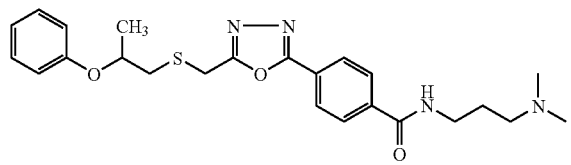

The above compound was prepared in a manner similar to that exemplified for the preparation of Example 1d, from 4-[5-(2-phenoxypropylsulfanylmethyl)-[1,3,4]oxadiazol-2-yl]benzoic acid (0.541 g, 1.46 mmol), 1,1'-carbonyldiimidazole (0.249 g, 1.53 mmol) and 3-(dimethylamino)propylamine (0.157 g, 1.53 mmol) to afford the title compound as a crude material. Purification by silica gel radial chromatography (elution with 10% 2M NH$_3$ in MeOH:CH$_2$Cl$_2$) followed by treatment of the isolated material with oxalic acid in acetone afforded the oxalate salt of N-(3-dimethylaminopropyl)-4-[5-(2-phenoxy propylsulfanylmethyl)-[1,3,4]oxadiazol-2-yl]benzamide.

$^1$H NMR (DMSO-d6) δ8.85 (t, 1H, J=6 Hz), 8.04 (s, 4H), 7.18–7.27 (m, 2H), 6.87–6.93 (m, 3H), 4.63–4.69 (m, 1H), 4.16–4.27 (m, 2H), 3.32–3.39 (q, 2H, J=6 Hz), 3.00–3.10 (m, 2H), 2.87–2.98 (m, 2H), 2.75 (s, 6H), 1.86–1.95 (m, 2H), 1.29 (d, 2H, J=6 Hz). IR (CHCl$_3$, cm$^{-1}$) 3009, 1778, 1656, 1599, 1586, 1495, 1302, 1239, 1012. MS (ES) m/e, 455, 453. Anal. Calcd for C$_{24}$H$_{30}$N$_4$O$_3$S.C$_2$H$_2$O$_4$: C, 57.34; H, 5.92, N, 10.29. Found C, 56.92; H, 5.81; N, 10.22. Mp(° C.)=117.

MS (ES) m/e, 385. Anal. Calcd for C$_{20}$H$_{20}$N$_2$O$_4$S: C, 62.48; H, 5.24; N, 7.29. Found C, 62.25; H, 5.00; N, 6.71.

Example 18

Preparation of N-(3-dimethylaminopropyl)-4-[5-(1-methyl-2-phenoxyethylsulfanylmethyl)-[1,3,4]oxadiazol-2-yl]benzamide from 1-phenoxy-2-propanol

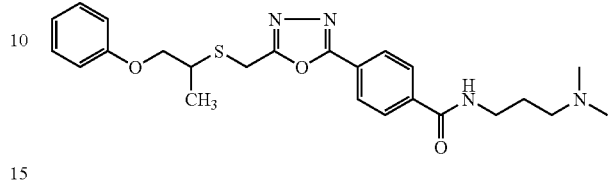

a) (2-bromopropoxy)benzene

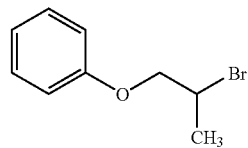

The above compound was prepared in a manner similar to that exemplified for the preparation of Example 17a, from 1-phenoxy-2-propanol (7.01 g, 46.1 mmol)(containing approximately 10% 2-phenoxypropanol), triphenylphosphine (12.08 g, 46.1 mmol), bromine (7.36 g, 46.1 mM) and imidazole (3.76 g, 55.3 mmol) to afford 9.23 g (93%) of (2-bromopropoxy)benzene as an oil which is contaminated with approximately 10% (2-bromo-1-methylethoxy)benzene.

$^1$H NMR (DMSO-d6) δ7.26–7.33 (m, 2H), 6.92–6.98 (m, 3H), 4.47–4.56 (m, 1H), 4.13–4.24 (m, 2H), 1.72 (d, 3H, J=7 Hz). IR (CHCl$_3$, cm$^{-1}$) 15600, 1588, 1497, 1244, 1035. MS (ES) m/e, 216, 214. Anal. Calcd for C$_9$H$_{11}$BrO: C, 50.26; H, 5.15. Found C, 41.53; H, 4.64.

b) (1-Methyl-2-phenoxyethylsulfanyl)acetic acid methyl ester

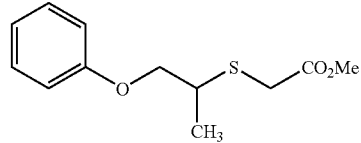

The above compound was prepared in a manner similar to that exemplified for the preparation of Example 17b, from (2-bromopropoxy)benzene (3.90 g, 18.1 mmol), methylthioglycolate (2.12 g, 19.9 mmol), and sodium hydride (0.798 g, 19.9 mmol) to afford 2.30 g (53%) of (1-Methyl-2-phenoxyethylsulfanyl)acetic acid methyl ester as an oil.

$^1$H NMR (DMSO-d6) δ7.25–7.32 (m, 2H), 6.90–6.96 (m, 3H), 4.10 (dd, 1H, J=6, 10 Hz), 3.94 (dd, 1H, J=7, 10 Hz), 3.44–3.62 (m, 5H), 3.24–3.31 (m, 1), 1.29 (d, 3H, J=7 Hz). IR (CHCl$_3$, cm$^{-1}$) 1735, 1600, 1497, 1289, 1243. MS (ES) m/e, 241. Anal. Calcd for C$_{12}$H$_{16}$O$_3$S: C, 59.97; H, 6.71. Found C, 59.61; H, 6.63.

c) (1-Methyl-2-phenoxyethylsulfanyl)acetic acid

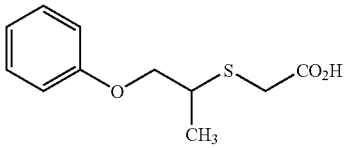

The above compound was prepared in a manner similar to that exemplified for the preparation of Example 17c, from (1-Methyl-2-phenoxyethylsulfanyl)acetic acid methyl ester (2.01 g, 8.36 mmol) and lithium hydroxide (0.601 g, 25.1 mmol) to afford 1.84 g (97%) of (1-Methyl-2-phenoxyethylsulfanyl)acetic acid as an oil.

$^1$H NMR (DMSO-d6) δ 12.51 (bs, 1H), 7.24–7.32 (m, 2H), 6.90–6.95 (m, 3H), 4.11 (dd, 1H, J=5, 10 Hz), 3.93 (dd, 1H, J=7, 10 Hz), 3.23–3.48 (m, 3H), 1.33 (d, 3H, J=11 Hz). IR (CHCl$_3$, cm$^{-1}$) 3010, 1712, 1600, 1587, 1497, 1300, 1291, 1243. MS (ES) m/e, 225. Anal. Calcd for C$_{11}$H$_{14}$O$_3$S: C, 58.38; H, 6.24. Found C, 58.34; H, 6.08.

d) 4-[5-(1-methyl-2-phenoxyethylsulfanylmethyl)-[1,3,4]oxadiazol-2-yl]benzoic acid methyl ester

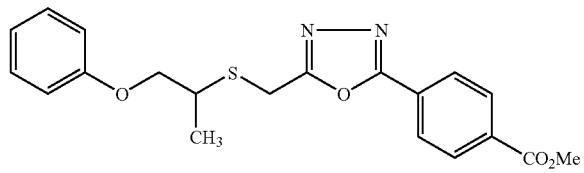

The above compound was prepared in a manner similar to that exemplified for the preparation of Example 1b, from (1-Methyl-2-phenoxyethylsulfanyl)acetic acid (1.44 g, 6.4 nM), 1,3-dicyclohexylcarbodiimide (1.31 g, 6.4 mmol), and 4-(1H-tetrazole-5-yl)benzoic acid methyl ester (1.30 g, 6.4 mmol) to afford the title compound as a crude mixture. Purification by radial chromatography on silica gel (elution with 50% EtOAc:hexane) afforded 1.21 g (49%) of 4-[5-(1-methyl-2-phenoxyethylsulfanylmethyl)-[1,3,4]oxadiazol-2-yl]benzoic acid methyl ester as an oil that crystallizes out.

$^1$H NMR (DMSO-d6) δ 8.07–8.16 (m, 4H), 7.20–7.31 (m, 2H), 6.89–6.96 (m, 3H), 4.29 (m, 2H), 4.11–4.15 (m, 1H), 4.00 (dd, 1H, J=7, 10 Hz), 3.91 (s, 3H), 3.21–3.33 (m, 1H), 1.33 (d, 3H, J=7 Hz). MS (ES) m/e, 385, 383. Anal. Calcd for C$_{20}$H$_{20}$N$_2$O$_4$S: C, 62.48; H, 5.24, N, 7.29. Found C, 63.52; H, 5.95; N, 6.91.

e) 4-[5-(1-methyl-2-phenoxyethylsulfanylmethyl)-[1,3,4]oxadiazol-2-yl]benzoic acid

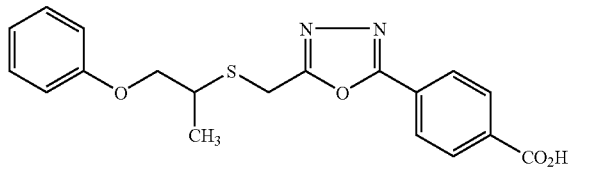

The above compound was prepared in a manner similar to that exemplified for the preparation of Example 17c, from 4-[5-(1-methyl-2-phenoxyethylsulfanylmethyl)-[1,3,4]oxadiazol-2-yl]benzoic acid methyl ester (1.19 g, 3.1 mmol), and lithium hydroxide (0.222 g, 9.3 mmol) to afford 1.06 g (92%) of (4-[5-(1-methyl-2-phenoxyethylsulfanylmethyl)-[1,3,4]oxadiazol-2-yl]benzoic acid as a solid.

$^1$H NMR (DMSO-d6) δ13.36 (bs, 1H), 8.05–8.14 (M, 4 h), 7.20–7.28 (m, 2H), 6.88–6.96 (m, 3H), 4.22–4.37 (m, 2H), 4.13 (dd, 1H, J=6, 10 Hz), 4.00 (dd, 1H, J=6, 10 Hz), 3.25–3.37 (m, 1H), 1.34 (d, 3H, J=7 Hz). IR (CHCl$_3$, cm$^{-1}$) 3010, 2934, 2859, 1700, 1600, 1587, 1497, 1286, 1266, 1242. MS (ES) m/e, 371, 369.

f) N-(3-dimethylaminopropyl)-4-[5-(1-methyl-2-phenoxyethylsulfanylmethyl)-[1,3,4]oxadiazol-2-yl]benzamide

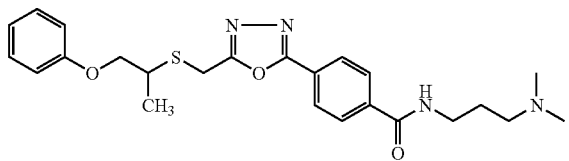

The above compound was prepared in a manner similar to that exemplified for the preparation of Example 1d, from 4-[5-(1-methyl-2-phenoxyethylsulfanylmethyl)-[1,3,4]oxadiazol-2-yl]benzoic acid (1.04 g, 2.8 mmol), 1,1'-carbonyldiimidazole (0.477 g, 2.9 mmol) and 3-(dimethylamino)propylamine (0.301 g, 2.9 mmol) to afford the title compound as a crude mixture. Purification by radial chromatography on silica gel (elution with 10% 2M NH$_3$ in MeOH:CH$_2$Cl$_2$) followed by crystallization with EtOH:Et2O afforded 0.404 g (32%) of N-(3-dimethylamino propyl)-4-[5-(1-methyl-2-phenoxyethylsulfanylmethyl)-[1,3,4]oxadiazol-2-yl]benzamide.

$^1$H NMR (DMSO-d6) δ8.72 (t, 1H, J=5 Hz), 7.99–8.06 (m, 4H), 7.23–7.28 (m, 2H), 6.89–6.94 (m, 3H), 4.22–4.37 (m, 2H), 4.14 (dd, 1H, J=6 and 10 Hz), 4.01 (dd, 1H, J=7 and 10 Hz), 3.27–3.38 (m, 4H), 2.27 (t, 2H, J=7 Hz), 2.14 (s, 6H), 1.62–1.72 (m, 2H), 1.33 (d, 3H, J=7 Hz). IR (CHCl$_3$, cm$^{-1}$) 307, 2951, 2827, 1652, 1585, 1550, 1496, 1243, 1012. MS (ES) m/e, 455, 453. Anal. Calcd for C$_{24}$H$_{30}$N$_4$O$_3$S: C, 63.41; H, 6.65, N, 12.32. Found C, 63.57; H, 6.62; N, 12.28. Mp(° C.)=84.

Example 19

Preparation of 3-{4-[5–1,1-dimethyl-2-phenoxyethyl sulfanylmethyl)-[1,3,4]oxadiazol-2-yl]phenoxy}propyl)dimethylamine from isobutylene sulfide

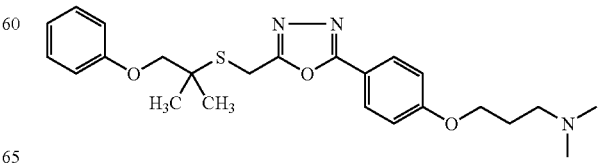

a) (1,1-dimethyl-2-phenoxyethylsulfanyl)acetic acid methyl ester

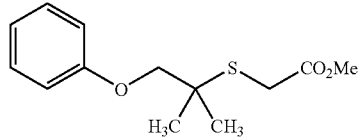

A suspension of sodium hydride (0.416 g, 10.4 mmol) (washed twice with hexane) in 30 mL THF stirring at room temperature was added dropwise a solution of phenol (0.978 g, 10.4 mmol) in 3.5 mL THF. The resultant solution was added to a suspension of chloro(triphenylphosphine)gold (5.14 g, 10.4 mmol) in 30 mL THF over an 80 minute period. The temperature of the mixture was maintained between −30° C. and 10° C. (dry ice/CH$_3$CN) during the addition of the sodium phenolate. The reaction was then stirred at room temperature for 3.5 hours before isobutylene sulfide (0.962 g, 10.9 mmol) was added. The reaction continued stirring at room temperature for approximately 4 hours then methyl boromacetate (1.75 g, 11.4 mmol) was added. The reaction was stirred overnight at room temperature. The suspension was treated with Celite, filtered through a pad of Celite and rinsed with diethyl ether. The filtrate was concentrated to an oil which slowly turns into a suspension. The suspension was diluted with hexane, filtered and the filtrate concentrated to a yellow oil. Purification by chromatography on silica gel (elution with CH$_2$Cl$_2$) afforded 1.66 g (54%) of (1,1-dimethyl-2-phenoxyethylsulfanyl)acetic acid methyl ester a yellow oil.

$^1$H NMR (DMSO-d6) δ7.26–7.31 (m, 2 h), 6.91–6.96 (m, 3H), 3.91 (s, 2H), 3.57 (s, 3H), 3.51 (s, 2H), 1.35 (s, 6H).
IR (CHCl$_3$, cm$^{-1}$) 3004, 2954, 2932, 2869, 1736, 1600, 1498, 1466, 1290, 1245, 1172, 1135. MS (ES) m/e, 255. Anal. Calcd for C$_{13}$H$_{18}$O$_3$S: C, 61.39; H, 7.13. Found C, 61.40; H, 7.17.

b) (1,1-dimethyl-2-phenoxyethylsulfanyl)acetic acid

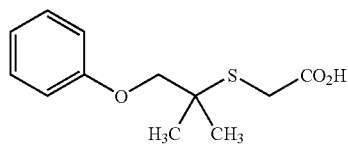

The above compound was prepared in a manner similar to that exemplified for the preparation of Example 7b, from 1,1-dimethyl-2-phenoxyethylsulfanyl)acetic acid methyl ester (1.85 g, 7.3 mmol), lithium hydroxide (0.522 g, 21.8 mmol) to afford 1.28 g (73%) of (1,1-dimethyl-2-phenoxyethyl sulfanyl)acetic acid as an oil.

$^1$HNMR (DMSO-d6) δ7.25–7.31 (m, 2H), 6.91–6.95 (m, 3H), 3.92 (s, 2H), 3.40 (s, 2H), 1.35 (s, 6H). IR (CHCl$_3$, cm$^{-1}$) 2969, 2930, 2871, 1713, 1600, 1587, 1498, 1466, 1301, 1291, 1245, 1173. MS (ES) m/e, 240, 239. Anal. Calcd for C$_{12}$H$_{16}$O$_3$S: C, 59.97; H, 6.71. Found C, 43.43; H, 4.94.

c) 4-Hydroxybenzoic acid-N-[2-(1,1-dimethyl-2-phenoxyethyl sulfanyl)acetyl]hydrazide

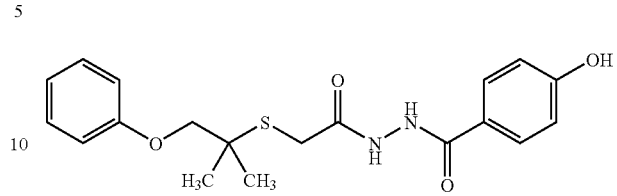

A solution of (1,1-dimethyl-2-phenoxyethylsulfanyl)acetic acid (1.19 g, 4.95 mmol) and 2-ethoxy-1-ethoxycarbonyl-1,2-dihydroquinoline (1.22 g, 4.95 mmol) in 25 mL CH$_3$CN and 6 mL THF was stirred at room temperature for 1 hour. The mixture was then treated with 4-hydroxybenzoic hydrazide (0.753 g, 4.95 mM). The suspension was stirred at room temperature for 28 hours. The suspension was filtered, insolubles rinsed with CH$_3$CN and the filtrate concentrated to an oil. Purification by chromatography on silica gel (elution with 50% EtOAc:hexane followed by 75% EtOAc:hexane) afforded 0.910 g (49%) of 4-Hydroxybenzoic acid-N-[2-(1,1-dimethyl-2-phenoxyethylsulfanyl)acetyl]hydrazide as a white foam.

$^1$H NMR (DMSO-d6) δ9.98–10.15 (m, 2H), 7.75 (d, 2H, J=9 Hz), 7.25–7.31 (m, 2H), 6.91–7.00 (m, 3H), 6.81 (d, 2H, J=9 Hz), 3.96 (s, 21), 3.40 (s, 2H), 1.39 (s, 6H). IR(CHCl$_3$, cm$^{-1}$) 1685, 1632, 1610, 1600, 1588, 1498, 1467, 1456, 1245, 1172. MS (ES) m/e, 375, 373. Anal. Calcd for C$_{19}$H$_{22}$N$_2$O$_4$S: C, 60.94; H, 5.92, N, 7.48. Found C, 60.76; H, 5.91; N, 7.24.

d) 4-[5–1,1-dimethyl-2-phenoxyethylsulfanylmethyl)-[1,3,4]oxadiazol-2-yl]phenol

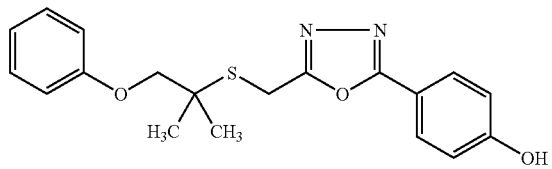

A mixture of 4-Hydroxybenzoic acid-N-[2-(1,1-dimethyl-2-phenoxyethylsulfanyl)acetyl]hydrazide (0.860 g, 2.3 mmol), triphenylphosphine (1.21 g, 4.6 mmol), triethyl amine (0.837 g, 8.3 mmol) and carbon tetrachloride (1.45 g, 8.3 mmol) in 24 mL CH$_3$CN was stirred at room temperature for 6.25 hours. The mixture was then concentrated to an oil. The oil was dissolved into EtOAc and washed three times with water and once with brine. The organic phase was dried over sodium sulfate, filtered, concentrated in vacuo to afford an oil. Purification by silica gel chromatography (elution with a linear gradient of 0 to 5% methanol:CHCl$_3$ over a twenty minute period) afforded 4-[5–1,1-dimethyl-2-phenoxyethylsulfanylmethyl)-[1,3,4]oxadiazol-2-yl]phenol and triphenyl phosphine oxide as an oil that slowly crystallizes out. The mixture was duiluted with diethyl ether then filtered. The filtrate was concentrated to an oil. Purification by slicia gel radial chromatography (elution with 50% Et$_2$O:hexane) followed by crystallization from MeOH:Et$_2$O afforded 0.499 g (61%) of 4-[5–1,1-dimethyl-2-phenoxyethylsulfanylmethyl)-[1,3,4]oxadiazol-2-yl]phenol.

$^1$H NMR (DMSO-d6) δ10.30 (bs, 11H), 7.76 (m, 2H), 7.73 (m, 2H), 7.21–7.28 (m, 2H), 6.90–6.94 (m, 3H), 4.23 (s, 2H), 3.96 (s, 2H), 1.40 (s, 6H). IR (KBr, cm$^{-1}$) 3158, 1610, 1598, 1588, 1499, 1467, 1286, 1244, 1173, 757. MS (ES) m/e, 357, 355. Anal. Calcd for $C_{19}H_{20}N_2O_3S$: C, 64.02; H, 5.66; N, 7.86. Found C, 63.91; H, 5.65; N, 7.77.

e) 3-{4-[5–1,1-dimethyl-2-phenoxyethylsulfanylmethyl)-[1,3,4]oxadiazol-2-yl]phenoxy}propyl)dimethylamine

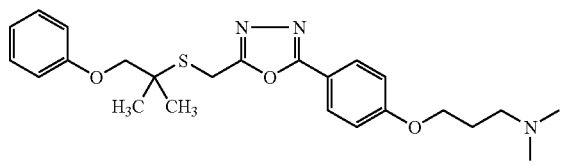

To a solution of 4-[5–1,1-dimethyl-2-phenoxyethylsulfanylmethyl)-[1,3,4]oxadiazol-2-yl]phenol (0.205 g, 1.3 mmol) in 16.4 mL DMF stirring at room temperature was added sodium hydride (0.109 g, 2.7 mmol). The mixture was stirred 5 minutes then 3-chloro-N,N-dimethylpropyl amine hydrochloride (0.205 g, 1.3 mmol) was added. The reaction was heated at 100° C. for 1.45 hours. After cooling to room temperature, the mixture was diluted with 50% EtOAc:hexane and 50% brine:H$_2$O. The phases were separated and the aqueous phase was extracted with 50% EtOAc:hexane. The combined organic phases were washed with 50% brine:H$_2$O the brine. The organic phase was dried over sodium sulfate, filtered, concentrated to afford 0.533 g an oil. The oil was dissolved into diethyl ether. To this solution was added dropwise a solution of EtOH in Et$_2$O that was treated with 0.103 mL acetyl chloride. The resultant precipitate was collected by filtration to afford 0.154 g (27%) of 3-{4-[5–1,1-dimethyl-2-phenoxyethylsulfanylmethyl)-[1,3,4]oxadiazol-2-yl]phenoxy}propyl)dimethylamine as the hydrochloride salt.

$^1$H NMR (DMSO-d6) δ7.86–7.88 (m, 2H), 7.210–7.28 (m, 2H), 7.10–7.15 (m, 2H), 6.90–6.94 (m, 3H), 4.25 (s, 2H), 4.16 (t, 2H, J=6 Hz), 3.96 (s, 2H), 3.19–3.24 (m, 2H), 2.79 (s, 6H), 2.13–2.22 (m, 2H), 1.40 (s, 6H). IR (CHCl$_3$, cm$^{-1}$) 2970, 1615, 1500, 1245, 1224, 1175. MS (ES) m/e, 442. Anal. Calcd for $C_{24}H_{31}N_3O_3S\cdot HCl$: C, 60.30; H, 6.75; N, 8.79. Found C, 59.96; H, 6.59; N, 8.64. Mp(° C.)=134.

Example 20

Preparation of 1-{5-[4-(3-Dimethylaminopropoxy)phenyl]-[1,3,4]oxadiazol-2-yl}-4-phenoxybutan-2-ol from 3-Oxo-5-phenoxypentanoic acid ethyl ester

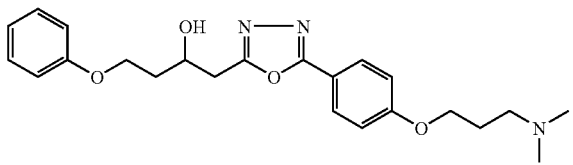

a) 3-hydroxy-5-phenoxypentanoic acid ethyl ester

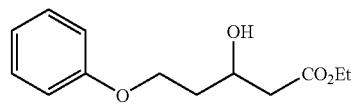

A solution of 3-Oxo-5-phenoxypentanoic acid ethyl ester 910.23 g, 43.3 mmol) in 122 mL EtOH and sodium borohydride (0.573 g, 15.2 mmol) was stirred at room temperature for 2.0 hours. The mixture was then treated with H$_2$O and reduced in volume.

EtOAc and 1N HCl were added, phases separated and the organic phase was washed with brine, dried over sodium sulfate, filtered, concentrated to afford an oil. Purification by HPLC on silica gel (elution with a linear gradient of 20 to 35% EtOAc:hexane over a 30 minute period) afforded 6.55 g (63%) of 3-hydroxy-5-phenoxypentanoic acid ethyl ester as an oil.

$^1$H NMR (DMSO-d6) δ7.24–7.31 (m, 2H), 6.88–6.93 (m, 3H), 4.90 (d, 1H, J=6 Hz), 3.94–4.11 (m, 5H), 2.50 (dd, 1H, J=5 and 15 Hz), 2.37 (dd, 1H, J=8 and 15 Hz), 1.71–1.88 (m, 2H), 1.18 (t, 3H, J=7 Hz). IR (CHCl$_3$, cm$^{-1}$) 3554, 3003, 2983, 2932, 1718, 1600, 1498, 1470, 1301, 1245, 1173. MS (ES) m/e, 239. Anal. Calcd for $Cl_3H_{18}O_4$: C, 65.53; H, 7.61. Found C, 65.32; H, 7.42.

b) 3-hydroxy-5-phenoxypentanoic acid

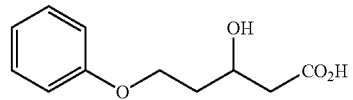

The above compound was prepared in a manner similar to that exemplified for the preparation of Example 8b, from 3-hydroxy-5-phenoxypentanoic acid ethyl ester (6.35 g, 26.6 mmol) and lithium hydroxide 1.91 g, 79.9 mmol) to afford 5.08 g (91%) of 3-hydroxy-5-phenoxypentanoic acid as a white solid.

$^1$H NMR (DMSO-d6) δ7.24–7.31 (m, 2H), 6.88–6.94 (m, 3H), 3.94–4.09 (m, 3H), 2.41 (dd, 1H, J=5, 15 Hz), 2.30 (dd, 1H, J=8, 15 Hz), 1.65–1.93 (m, 2H). IR (CHCl$_3$, cm$^{-1}$) 3516, 3028, 2952, 2932, 2883, 1710, 1600, 1498, 1423, 1244, 1230, 1173. MS (ES) m/e, 211, 209. Anal. Calcd for $C_{11}H_{14}O_4$: C, 62.85; H, 6.71. Found C, 63.03; H, 6.59.

c) 4-Hydroxybenzoic acid-N-(3-hydroxy-5-phenoxypentanoyl)hydrazide

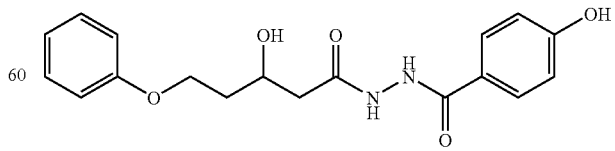

The above compound was prepared in a manner similar to that exemplified for the preparation of Example 19c, from 3-hydroxy-5-phenoxypentanoic acid (2.35 g, 8.0 mmol), 2-ethoxy-1-ethoxycarbonyl-1,2-dihydroquinoline (1.97 g, 8.0 mmol) and 4-hydroxybenzoic hydrazide (1.21 g, 8.0 mmol) to afford 2.33 g (85%) of 4-Hydroxybenzoic acid-N-(3-hydroxy-5-phenoxy pentanoyl)hydrazide as a solid.

$^1$H NMR (DMSO-d6) δ10.07 (bs, 2H), 9.77 (bs, 1H), 7.74 (d, 2H, J=9 Hz), 7.22–7.31 (m, 2H), 6.89–6.95 (m, 3H), 6.89–6.95 (m, 3H), 6.80 (d, 2H, J=9 Hz), 4.84 (d, 1H, J=5 Hz), 4.01–4.16 (m, 3H), 2.29–2.43 (m, 2H), 1.89–2.02 (m, 1H), 1.68–1.82 (m, 1H). IR (KBr, cm$^{-1}$) 3413, 3207, 2949, 2875, 1661, 1601, 1579, 1475, 1469, 1244, 1056, 835. MS (ES) m/e, 345, 343. Anal. Calcd for $C_{18}H_{20}N_2O_5$: C, 62.78; H, 5.85, N, 8.13. Found C, 62.68; H. 5.83; N, 8.26.

d) 4-[5-(2-Hydroxy-4-phenoxybutyl)-[1,3,4]oxadiazol-2-yl]phenol

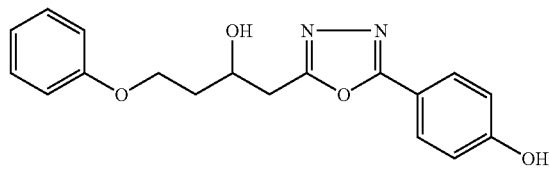

To a heavy suspension of 4-Hydroxybenzoic acid-N-(3-hydroxy-5-phenoxypentanoyl)hydrazide (0.900 g, 2.6 mmol) in 6 mL chlorobenzene stirring at room temperature was added 1,1,3,3-hexamethyldisilazane (1.31 g, 8.1 mmol) followed by trifluoromethane sulfonic acid (0.392 g, 2.6 mmol). The mixture was then heated at 120° C. for 6 hours. After cooling to room temperature the suspension was filtered. The filtrate was treated with methanol then concentrated to an oil. The oil was dissolved into EtOAc and washed twice with 5N HCl. The aqueous phases were combined then extracted twice with EtOAc. The organic phases were combined, dried over sodium sulfate, filtered and concentrated to afford an oil. Purification by chromatography on silica gel (elution with 50% EtOAc:hexane) afforded 0.280 g (33%) of 4-[5-(2-Hydroxy-4-phenoxybutyl)-[1,3,4]oxadiazol-2-yl]phenol as a solid.

$^1$H NMR (DMSO-d6) δ10.24 (bs, 1H), 7.78–7.82 (m, 2H), 7.24–7.31 (m, 2H), 6.89–6.96 (m, 5H), 5.14 (d, 1H, J=6 Hz), 4.02–4.21 (m, 3H), 3.11 (dd, 1H, J=5, 15 Hz), 2.99 (dd, 1H, J=8, 15 Hz), 1.74–2.05 (m, 2H). IR (CHCl$_3$, cm$^{-1}$) 3204, 1617, 1599, 1587, 1501, 1473, 1279, 1244, 1173, 844, 754, 739. MS (ES) m/e, 327. Anal. Calcd for $C_{18}H_{18}N_2O_4$: C, 66.25; H, 5.56; N, 8.58. Found C, 60.90; H, 4.97; N, 6.95.

e) 1-{5-[4-(3-Dimethylaminopropoxy)phenyl]-[1,3,4]oxadiazol-2-yl}-4-phenoxybutan-2-ol

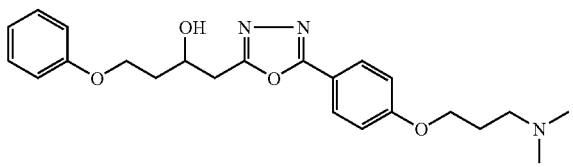

The above compound was prepared in a manner similar to that exemplified for the preparation of Example 19d, from 4-[5-(2-Hydroxy-4-phenoxybutyl)-[1,3,4]oxadiazol-2-yl]phenol (0.260 g 0.8 mmol), sodium hydride (0.064 g, 1.6 mmol) and 3-chloro-N,N-dimethylpropyl amine hydrochloride (0.126 g, 0.8 mmol) to afford the title compound as a crude mixture. Purification by chromatography on silica gel (elution with 10% 2M NH$_3$ in MeOH:Et$_2$O) followed by crystallization from MeOH:Et2O afforded 0.129 g (39%) of 1-{5-[4-(3-Dimethylaminopropoxy)phenyl]-[1,3,4]oxadiazol-2-yl}-4-phenoxybutan-2-ol.

$^1$H NMR (DMSO-d6) δ7.88–7.91 (m, 2H), 7.24–7.30 (m, 2H), 7.12 (d, 2H, J=9 Hz), 6.89–6.95 (m, 3H), 5.15 (d, 1H, J=6 Hz), 4.07–4.21 (m, 5H), 3.12 (dd, 1H, J=5, 15 Hz), 3.00 (dd, 1H, J=8, 15 Hz), 2.35 (t, 2H, J=7 Hz), 2.14 (s, 6H), 1.77–2.05 (m, 4H). IR (CHCl$_3$, cm$^{-1}$) 3535, 3019, 2953, 2825, 2777, 1614, 1500, 1470, 1255, 1174. MS (ES) m/e, 412. Anal. Calcd for $C_{23}H_{29}N_3O_4$: C, 67.13; H, 7.10, N, 10.21. Found C, 66.98; H, 6.96; N, 10.19. Mp(° C.)=93.

Example 21

Preparation of Dimethyl-(3-{4-[5-(5-phenoxypent-1-enyl)-[1,3,4]-oxadiazol-2-yl]phenoxy}propyl)amine from 4-Phenoxybutan-1-o1

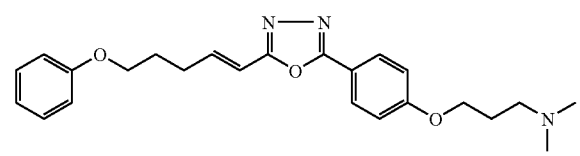

a) 6-Phenoxyhex-2-enoic acid ethyl ester

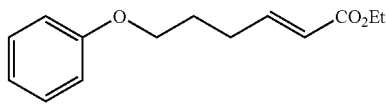

To a solution of oxalyl chloride (5.39 g, 42.5 mmol) in 500 mL CH$_2$Cl$_2$ at −78° C. was added dimethyl sulfoxide (6.64 g, 85.0 mmol). The reaction was stirred 10 minutes before a solution of 4-Phenoxybutan-1-o1 (6.42 g, 38.6 mmol) in 40 mL CH$_2$Cl$_2$ was added dropwise over a 25 minute period. The reaction was continued stirring at −78° C. for 30 minutes before triethylamine (19.54 g, 193.1 mmol) was added. The cooling bath was removed allowing the reaction to gradually warm to room temperature. Upon warming, at approximately −40° C. (carboethoxymethylene) triphenylphosphorane was added directly followed by 250 mL CH$_2$Cl$_2$. The resultant solution was stirred approximately 18 hours at room temperature before being concentrated to an oil. Treatment of the oil with diethyl ether followed by sonication resulted in crystal formation. Crystals were collected by filtration and discarded. The filtrate was concentrated to an oil and the above process was repeated to remove additional triphenylphosphine oxide. Purification by chromatography on silica gel (elution with 10% Et$_2$O:hexane) afforded 7.05 g (78%) of trans-6-Phenoxyhex-2-enoic acid ethyl ester and 0.520 g (6%) of cis-6-Phenoxyhex-2-enoic acid ethyl ester as oils.

$^1$H NMR (DMSO-d6) δ7.24–7.31 (m, 2H), 6.89–7.00 (m, 4H), 5.88 (dt, 1H, J=1 and 15 Hz), 4.10 (q, 2H, J=7 Hz), 3.96 (t, 2H, J=6 Hz), 2.36 (ddd, 2H, J=1, 7 and 16 Hz), 1.82–1.92 (m, 2H), 1.20 (t, 3H, J=7 Hz). IR (CHCl$_3$, cm$^{-1}$) 1711, 1600, 1498, 1277, 1246, 1172, 1041. MS (ES) m/e, 235. Anal. Calcd for $C_{14}H_{18}O_3$: C, 71.77; H, 7.74. Found C, 71.30; H, 7.73.

b) trans-6-Phenoxyhex-2-enoic acid

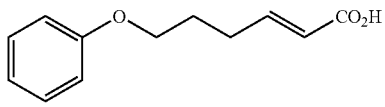

A solution of trans-6-Phenoxyhex-2-enoic acid ethyl ester (2.25 g, 9.6 mmol) in 48 mL acetone and 48 mL 1N lithium hydroxide was stirred at room temperature for 2.5 hours. The mixture was then quenched with 4.14 mL concentrated HCl, reduced in volume and set aside at 5° C. to allow for crystal formation. Collection of the crystals by filtration afforded 1.43 g (72%) of trans-6-phenoxyhex-2-enoic acid.

$^1$H NMR (DMSO-d6) δ12.10 (bs, 1H), 7.24–7.31 (m, 2H), 6.83–6.93 (m, 4H), 5.77–5.83 (m, 1H), 3.96 (t, 2H, J=6 Hz), 2.30–2.38 (m, 2H), 1.81–1.91 (m, 2H). IR (KBr, cm$^{-1}$) 3441, 2942, 1693, 1642, 1291, 1252, 1242, 758. MS (ES) m/e, 205. Anal. Calcd for $C_{12}H_{14}O_3$: C, 69.89; H, 6.84. Found C, 70.02; H, 7.06.

c) 4-Hydroxybenzoic acid-N-(6-phenoxyhex-2-enoyl)hydrazide

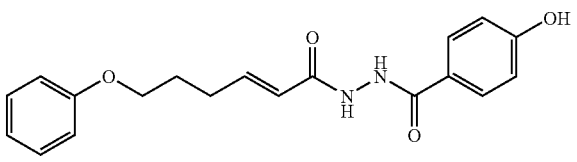

The above compound was prepared in a manner similar to that exemplified for the preparation of Example 19c, from trans-6-phenoxyhex-2-enoic acid (1.30 g, 6.3 mmol), 2-ethoxy-1-ethoxycarbonyl-1,2-dihydroquinoline (1.56 g, 6.3 mmol) and 4-hydroxybenzoic hydrazide (0.959 g, 6.3 mmol) to afford the title compound as a crude mixture. Purification by crystallization (MeOH:Et$_2$O) afforded 1.05 g (49%) of 4-Hydroxybenzoic acid-N-(6-phenoxyhex-2-enoyl)hydrazide.

$^1$H NMR (DMSO-d6) δ10.09 (bs, 2H), 9.87 (bs, 1H), 7.74 (d, 2H, J=9 Hz), 7.22–7.32 (m, 2H), 6.89–6.95 (m, 3H), 6.76–6.86 (m, 3H), 6.02–6.07 (m, 1H), 3.99 (t, 2H, J=6 Hz), 2.35 (q, 2H, J=7 Hz), 1.88 (m, 2H). IR (KBr, cm$^{-1}$) 3284, 3210, 3007, 1693, 1618, 1610, 1600, 1585, 1518, 1492, 1291, 1245, 1173, 937, 758. MS (ES) m/e, 341, 339. Anal. Calcd for $C_{19}H_{20}N_2O_4$: C, 67.05; H, 5.92; N, 8.23. Found C, 66.90; H, 6.03; N, 8.57.

d) 4-[5-(5-phenoxypent-1-enyl)-[1,3,4]oxadiazol-2-yl]phenol

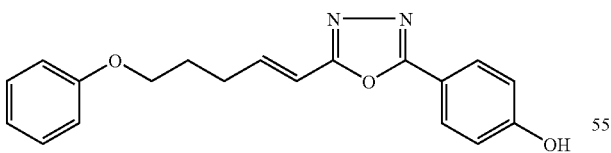

The above compound was prepared in a manner similar to that exemplified for the preparation of Example 19d, from 4-Hydroxybenzoic acid-N-(6-phenoxyhex-2-enoyl)hydrazide (0.915 g, 2.7 mmol), triphenylphosphine (1.41 g, 5.4 mmol), triethyl amine (0.544 g, 5.4 mmol) and carbon tetrabromide (1.78 g, 5.4 mmol) to afford the title compound as a crude mixture. Crystallization of this material from EtOAc afforded 0.224 g (26%) of 4-[5-(5-phenoxypent-1-enyl)-[1,3,4]oxadiazol-2-yl]phenol.

$^1$H NMR (DMSO-d6) δ10.31 (bs, 1H), 7.84–7.89 (m, 2H), 7.25–7.31 (m, 2H), 6.89–6.99 (m, 6H), 6.54–6.59 (m, 1H), 4.03 (t, 2H, J=6 Hz), 2.45–2.50 (m, 2H), 1.91–2.00 (m, 2H). IR (KBr, cm$^{-1}$) 2945, 2612, 1656, 1588, 1441, 1288, 1243, 1173, 1034, 845. MS (ES) m/e, 323, 321. Anal. Calcd for $C_{19}H_{18}N_2O_3$: C, 70.79; H, 5.63; N, 8.64. Found C, 70.70; H, 5.78; N, 8.64.

e) Dimethyl-(3-{4-[5-(5-phenoxypent-1-enyl)-[1,3,4]-oxadiazol-2-yl]phenoxy}propyl)amine from 4-Phenoxybutan-1-01

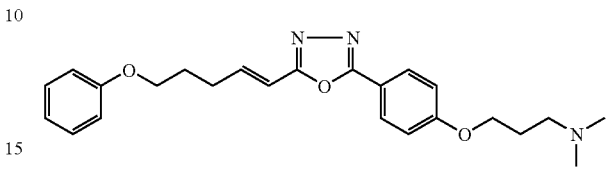

A suspension of 4-[5-(5-phenoxypent-1-enyl)-[1,3,4]oxadiazol-2-yl]phenol (0.207 g 0.6 mmol), cesium carbonate (0.418 g, 1.3 mmol) and 3-chloro-N,N-dimethylpropyl amine hydrochloride (0.102 g, 0.6 mmol) in 8.5 mL DMF was heated at 90° C. for 3.5 hours. After cooling to room temperature the reaction was diluted with water then extracted three times with EtOAc. The organic phases were combined, washed with brine then concentrated an oil. Purification by radial chromatography on silica gel (elution with 10% 2M NH3 in MeOH:CHCl$_3$) afforded 0.153 g of the title compound as an oil. Treatment of the oil, dissolved in acetone, with oxalic acid afforded 0.147 g (46%) of the oxalate salt of dimethyl-(3-{4-[5-(5-phenoxypent-1-enyl)-[1,3,4]-oxadiazol-2-yl]phenoxy}propyl)amine.

$^1$H NMR (DMSO-d6) δ7.97 (d, 2H, J=9 Hz), 7.23–7.31 (m, 2H), 7.15 (d, 2H, J=9 Hz), 6.90–7.03 (m, 4H), 6.56–6.62 (m, 1H), 4.15 (t, 2H, J=6 Hz), 4.01–4.05 (m, 2H), 2.76 (s, 6H), 2.04–2.17 (m, 2H), 1.87–1.99 (m, 2H). IR (CHCl$_3$, cm$^{-1}$) 1776, 1658, 1609, 1493, 1471, 1255, 1172. MS (ES) m/e, 408. Anal. Calcd for $C_{24}H_{29}N_3O_3 \cdot C_2H_2O_4$: C, 62.77; H, 6.28, N, 8.45. Found C, 62.47; H, 6.26; N, 8.32. Mp(° C.)=163.

Example 22

Preparation of Dimethyl(3-{4-[5-(5-phenoxypent-2-enyl)-[1,3,4]oxadiazol-2-yl]phenoxy}propyl)amine from Hex-3-enedioic acid monomethyl ester

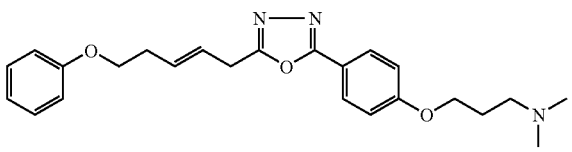

a) 6-Hydroxyhex-3-enoic acid methyl ester

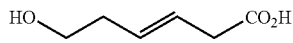

To a solution of hex-3-enedioic acid monomethyl ester (8.49 g, 53.7 mmol) in 23 mL THF at −10° C. was added a 1.0 M solution of borane in THF over a 140 minute period. The resultant suspension was stirred at room temperature approximately 24 hours. Next, the mixture was treated with 1:1 Acetic acid:H$_2$O then concentrated to an oil. The oil was added dropwise to a 100 mL saturated solution of sodium bicarbonate. This mixture was extracted with EtOAc. The organic phase was washed twice with the saturated solution of sodium bicarbonate. The combined aqueous phases were acidified with 5N HCl then extracted three times with EtOAc. The combined organic phases were washed with brine, dried over sodium sulfate, filtered, concentrated in vacuo to afford 4.09 g (53%) of 6-Hydroxyhex-3-enoic acid methyl ester as an oil.

$^1$H NMR (DMSO-d6) δ5.45–5.60 (m, 2H), 4.47 (t, 1H, J=5 Hz), 3.59 (s, 3H), 3.40 (ddd, 2H, J=5, 7, 12 Hz), 3.04 (d, 2H, J=6 Hz), 2.14 (q, 2H, J=6 Hz). IR (CHCl$_3$, cm$^{-1}$) 3620, 3465, 3023, 2955, 2884, 1733, 1438, 1169, 1044, 971. MS (ES) m/e, 126. Anal. Calcd for C$_7$H$_{12}$O$_3$: C, 58.32; H, 8.39. Found C, 57.43; H, 7.99.

b) 6-Phenxoyhex-3-enoic acid methyl ester

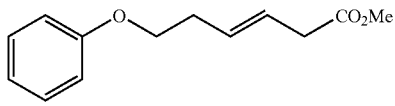

To a solution of 6-hydroxyhex-3-enoic acid methyl (1.30 g, 9.0 mmol) and phenol (1.27 g, 13.5) in 81 mL THF stirring at room temperature was added, in portions, 3,3-dimethyl-1,2,5-thiadiazolidine-1,1-dioxide triphenylphosphine adduct (reference: Castro, J. L., Matassa, V. G., *J. Org. Chem.* 1994, 59, 2289–2291) over a twenty minute period. After stirring approximately 24 hours, the reaction was diluted with EtOAc then washed three times with 1N sodium hydroxide, brine, dried over sodium sulfate, filtered, concentrated to a solid. Purification by chromatography on silica gel (elution with 10% Et$_2$O:hexane) afforded 0.987 g (50%) of 6-phenxoyhex-3-enoic acid methyl ester as an oil.

$^1$H NMR (DMSO-d6) δ7.24–7.31 (m, 2H), 6.89–6.94 (m, 3H), 5.62–5.65 (m, 2H), 3.97 (t, 2H, J=7 Hz), 3.60 (s, 3H), 3.09 (m, 2H), 2.42–2.49 (m, 2H). IR (KBr, cm$^{-1}$) 3013, 2954, 1734, 1601, 1497, 1438, 1290, 1245, 1173, 1037, 970. MS (ES) m/e, 220. Anal. Calcd for C$_{13}$H$_{16}$O$_3$: C, 70.89; H, 7.32. Found C, 56.90; H, 5.84.

c) 6-Phenxoyhex-3-enoic acid

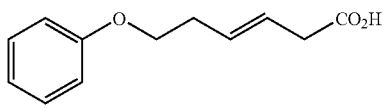

The above compound was prepared in a manner similar to that exemplified for the preparation of Example 17c, from 6-phenxoyhex-3-enoic acid methyl ester (0.960 g, 4.4 mmol) and lithium hydroxide (0.313 g, 13.1 mmol) to afford 0.760 g (85%) of 6-phenxoyhex-3-enoic acid as an oil that slowly crystallized out upon standing.

$^1$H NMR (DMSO-d6) δ12.29 (bs, 1H), 7.20–7.32 (m, 2H), 6.88–6.96 (m, 3H), 5.54–5.66 (m, 2H), 3.97 (t, 2H, J=7 Hz), 2.99 (m, 2H), 2.43–2.48 (m, 2H). IR (KBr, cm$^{-1}$) 1713, 1601, 1471, 1398, 1246, 1225, 1039, 968, 758, 694. MS (ES) m/e, 205. Anal. Calcd for C$_{12}$H$_{14}$O$_3$: C, 69.89; H, 6.84. Found C, 69.30; H, 6.64.

d) 4-(3-Dimethylaminopropoxy)benzoic acid-N-(6-phenoxyhex-3-enoyl)hydrazide

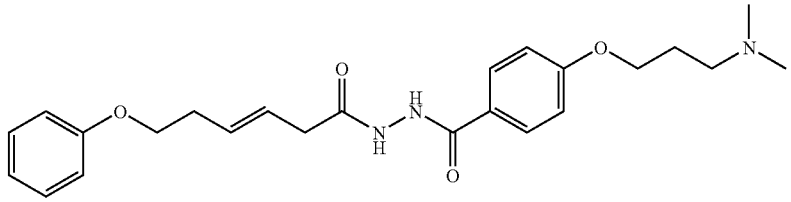

The above compound was prepared in a manner similar to that exemplified for the preparation of Example 19c, from 6-phenxoyhex-3-enoic acid (0.760 g, 3.7 mmol), 2-ethoxy-1-ethoxycarbonyl-1,2-dihydroquinoline (0.911 g, 3.7 mmol) and 4-(3-dimethylaminopropoxy)benzoic hydrazide (0.874 g, 3.7 mmol) to afford the title compound as an oil. Treatment of the oil with EtOAc followed by 1N HCl resulted in crystal formation in the aqueous phase. The crystals were collected by filtration to afford 0.364 g (23%) of 4-(3-Dimethyl aminopropoxy)benzoic acid-N-(6-phenoxyhex-3-enoyl)hydrazide.

$^1$H NMR (DMSO-d6) δ10.17 (s, 1H), 9.86 (s, 1H), 7.85 (d, 2H, J=9 Hz), 7.24–7.31 (m, 2H), 7.03 (d, 2H, J=9 Hz), 6.90–6.95 (m, 3H), 5.57–5.69 (m, 2H), 4.13 (t, 2H, J=6 Hz), 3.99 (t, 2H, J=7 Hz), 3.17–3.23 (m, 2H); 2.96 (d, 2H, J=3 Hz), 2.44–2.48 (m, 2H), 2.11–2.20 (m, 2H). IR (KBr, cm$^{-1}$) 3201, 3010, 2591, 2563, 2519, 2468, 1683, 1666, 1642, 1609, 1493, 1477, 1467, 1307, 1263, 1166, 978, 762. MS (ES) m/e, 426, 424. Anal. Calcd for C$_{24}$H$_{31}$N$_3$O$_4$: C, 62.40; H, 6.98; N, 9.10. Found C, 61.74; H, 6.83; N, 8.72.

e) Dimethyl(3-{4-[5-(5-phenoxypent-2-enyl)-[1,3,4]oxadiazol-2-yl]phenoxy}propyl)amine

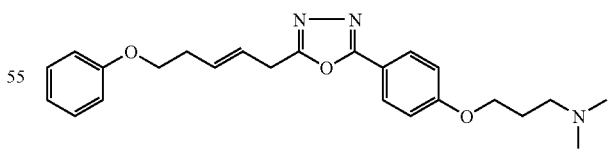

The above compound was prepared in a manner similar to that exemplified for the preparation of Example 19d, from 4-(3-Dimethylaminopropoxy)benzoic acid-N-(6-phenoxyhex-3-enoyl)hydrazide (0.348 g, 0.8 mmol), triphenylphosphine (0.217 g, 0.8 mmol), triethyl amine (0.160 g, 1.6 mmol) and carbon tetrabromide (0.275 g, 0.8 mmol) to afford the title compound as a crude mixture. Purification by radial chromatography on silica gel (10% 2M NH$_3$ in MeO- H:CHCl₃) afforded 0.224 g of material. The material was dissolved into diethyl ether. To this solution was added dropwise a solution of EtOH in Et2O that was treated with 0.047 mL acetyl chloride. The resultant precipitate was collected by filtration to afford 0.176 g (53%) of dimethyl (3-{4-[5-(5-phenoxypent-2-enyl)-[1,3,4]oxadiazol-2-yl]-phenoxy}propyl)amine as the hydrochloride salt.

$^1$H NMR (DMSO-d6) δ7.87–7.93 (m, 2H), 7.23–7.29 (m, 2H), 7.11–7.16 (m, 2H), 6.89–6.94 (m, 3H), 5.78–5.82 (m, 2H), 4.16 (t, 2H, J=6 Hz), 4.01 (t, 2H, J=7 Hz), 3.71 (d, 2H, J=5 Hz), 3.18–3.24 (m, 2H), 2.78 (s, 6H), 2.47–2.53 (m, 2H), 2.13–2.22 (m, 2H). IR (KBr, cm$^{-1}$) 2936, 2675, 2658, 2614, 2477, 1617, 1501, 1473, 1257, 1175, 972, 839, 769. MS (ES) m/e, 408. Anal. Calcd for C$_{24}$H$_{29}$N$_3$O$_3$.HCl: C, 64.93; H, 6.81, N, 9.46. Found C, 63.76; H, 6.75; N, 9.24. Analytical HPLC: 100% Purity. Mp(° C.)=145.

Example 23

Preparation of Dimethyl-[3(4-{5-[2-(2-phenoxy-ethyl)cyclopropyl]-[1,3,4]oxadiazol-2-yl}phenoxy)propyl]amine from 4-phenoxybutene

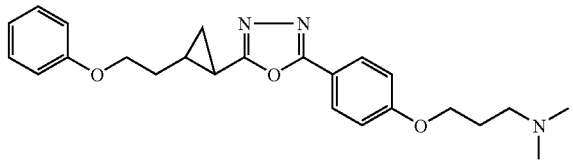

a) 2-(2-Phenoxyethyl)cyclopropanecarboxylic acid methyl ester

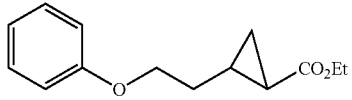

To a light suspension of 4-phenoxybutene (4.95 g, 33.4 mmol) and rhodium acetate (0.147 g, 0.33 mmol) in 295 mL CH$_2$Cl$_2$ stirring at room temperature was added a solution of ethyl diazo acetate (3.81 g, 33.4 mmol) in 48 mL CH$_2$Cl$_2$ over a four hour period. Stirring continued for an additional 30 minutes before the mixture was washed twice with 1N HCl, brine, dried over sodium sulfate, filtered, concentrated to afford an oil. Purification by chromatography on silica gel (elution with CH$_2$Cl$_2$) afforded 1.29 g (16%) of 2-(2-phenoxyethyl)cyclopropanecarboxylic acid methyl ester.

$^1$H NMR (CDCl₃) δ7.28 (m, 2H), 6.90–6.94 (m, 3H), 4.12 (m, 2H), 4.02 (ddd, 2H, J=7, 9, 13 Hz), 1.82 (ddd, 1H, J=7, 14, 21 Hz), 1.76 (ddd, 1H, J=6, 13, 21 Hz), 1.55 (m; 1H), 1.48 (dd, 1H, J=5, 8 Hz), 1.26 (t, 3H), 1.22 (ddd, 1H, 4, 4, 9 Hz), 0.79 (ddd, 1H, J=4, 6, 8 Hz). IR (CHCl₃, cm$^{-1}$) 3009, 2984, 2941, 2873, 1717, 1600, 1498, 1302, 1246, 1182, 1039. MS (EI) m/e, 234. Anal. Calcd for C$_{14}$H$_{18}$O$_3$: C, 71.77; H, 7.74. Found C, 69.01; H, 7.53.

b) 2-(2-Phenoxyethyl)cyclopropanecarboxylic acid

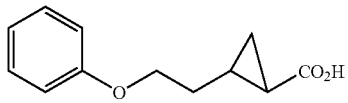

The above compound was prepared in a manner similar to that exemplified for the preparation of Example 1c, from 2-(2-Phenoxyethyl)cyclopropanecarboxylic acid methyl ester (1.07 g, 4.5 mmol) and lithium hydroxide (0.33 g, 13.6 mmol) to afford the title compound as a crude mixture. The material was treated with water then extracted twice with EtOAc. The organic phases were combined, dried over sodium sulfate, filtered, concentrated to afford 0.771 g (82%) 2-(2-Phenoxyethyl)cyclopropanecarboxylic acid as a solid.

$^1$H NMR (DMSO-d6) δ12.13 (bs, 1H), 7.24–7.31 (m, 2H), 6.89–6.95 (m, 3H), 3.94–4.06 (m, 2H), 1.66–1.75 (q, 2H, J=7 Hz), 1.31–1.45 (m, 2H), 1.00 (ddd, 1H, J=4, 8, 17 Hz), 0.78 (ddd, 1H, J=4, 6, 8 Hz). IR (CHCl₃, cm$^{-1}$) 3020, 2943, 1696, 1600, 1498, 1246. MS (ES) m/e, 205. Anal. Calcd for Cl$_2$H$_{14}$O$_3$: C, 69.89; H, 6.84. Found C, 69.50; H, 6.90.

c) 4-Hydroxybenzoic acid-N-[2-(2-phenoxyethyl)cyclopropane carbonyl]hydrazide

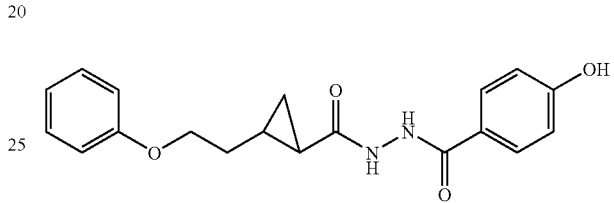

The above compound was prepared in a manner similar to that exemplified for the preparation of Example 19c, from 2-(2-Phenoxyethyl)cyclopropanecarboxylic acid (0.750 g, 3.6 mmol), 2-ethoxy-1-ethoxycarbonyl-1,2-dihydroquinoline (0.899 g, 3.6 mmol) and 4-hydroxybenzoic hydrazide (0.553 g, 3.6 mmol) to afford the title compound as a crude mixture. Purification by radial chromatography on silica gel (elution with 10% MeOH:CHCl₃) followed by crystallization from MeOH:EtOAc afforded 0.336 g (27%) of 4-hydroxybenzoic acid-N-[2-(2-phenoxyethyl)-cyclopropanecarbonyl]hydrazide.

$^1$H NMR (DMSO-d6) δ 10.06–9.97 (M, 3H), 7.80–7.71 (m, 2H), 7.32–7.21 (m, 2H), 6.90–6.96 (m, 3H), 6.79–6.83 (m, 2H),4.02 (t, 2H, J=6 Hz), 1.68–1.79 (m, 2H), 1.55–1.61 (m, 1H), 1.28–1.36 (m, 1H), 0.92–0.98 (m, 1H), 0.74–0.80 (m, 1H). IR (KBr, cm$^{-1}$) 3301, 3226, 1696, 1620, 1610, 1584, 1518, 1498, 1290, 1248, 1173, 756. MS (ES) m/e, 341, 339. Anal. Calcd for C$_{19}$H$_{20}$N$_2$O$_4$: C, 67.05; H, 5.92; N, 8.23. Found C, 66.78; H, 5.76; N, 8.26.

d) 4-{5-[2-(2-Phenoxyethyl)cyclopropyl]-[1,3,4] oxadiazol-2-yl}phenol

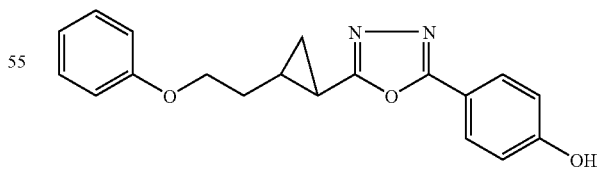

The above compound was prepared in a manner similar to that exemplified for the preparation of Example 19d, from 4-hydroxybenzoic acid-N-[2-(2-phenoxyethyl)cyclopropanecarbonyl]hydrazide (0.308 g, 0.9 mmol), triphenylphosphine (0.285 g, 1.1 mmol), triethyl amine (0.110 g, 1.1 mmol) and carbon tetrabromide (0.360 g, 1.1 mmol) to afford the title compound as a crude mixture. Purification by radial chromatography on silica gel (elution with EtOAc) afforded 0.247 mg (85%) of (4-{5-[2-(2-Phenoxyethyl)cyclopropyl]-[1,3,4]oxadiazol-2-yl}phenol 0.247 g (85%) as a white foam.

$^1$H NMR (DMSO-d6) δ10.23 (bs, 1H), 7.73–7.81 (m, 2H), 7.24–7.31 (m, 2H), 6.88–6.96 (m, 5H, 4.05–4.12 (m, 2H), 2.16–2.22 (m, 1H), 1.77–1.90 (m, 2H), 1.56–1.64 (m, 1H), 1.26–1.32 (m, 1H), 1.06–1.14 (m, 1H). IR (KBr, cm$^{-1}$) 3422, 3092, 3027, 2954, 2813, 2684, 2606, 1615, 1601, 1585, 1565, 1500, 1478, 1381, 1287, 1269, 1249, 1175, 1167, 1078, 1032, 1008, 835, 752, 741, 689. MS (ES) m/e, 323, 321. Anal. Calcd for $C_{19}H_{18}N_2O_3$: C, 70.79; H, 5.63; N, 8.69. Found C, 69.53; H, 5.51; N, 8.28.

e) Dimethyl-[3(4-{5-[2-(2-phenoxyethyl)cyclopropyl]-[1,3,4]oxadiazol-2-yl}phenxoy)propyl]amine

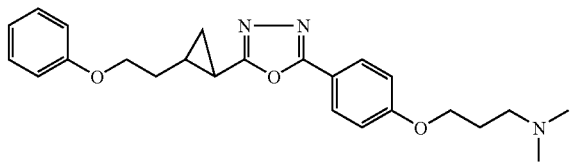

The above compound was prepared in a manner similar to that exemplified for the preparation of Example 21e, from 4-{5-[2-(2-Phenoxyethyl)cyclopropyl]-[1,3,4]oxadiazol-2-yl}phenol (0.227 g 0.7 mmol), cesium carbonate (0.459 g, 1.4 mmol) and 3-chloro-N,N-dimethylpropyl amine hydrochloride (0.111 g, 0.7 mmol) to afford the title compound as a crude mixture. Purification by radial chromatography on silica gel (elution with 10% 2M NH$_3$ in MeOH:Et$_2$O) afforded an oil. Treatment of the oil, in acetone, with oxalic acid afforded 0.214 g (61%) of dimethyl-[3(4-{5-[2-(2-phenoxyethyl)cyclopropyl]-[1,3,4]oxadiazol-2-yl}phenxoy)propyl]amine as the oxalate salt.

$^1$H NMR (DMSO-d6) δ7.87 (d, 2H, J=9 Hz), 7.24–7.31 (m, 2H), 7.11 (d, 2H, J=9 Hz), 6.89–6.96 (m, 3H), 4.05–4.15 (m, 4H), 3.13–3.18 (m, 2H), 2.75 (s, 6H), 2.01–2.20 (m, 3H), 1.78–1.90 (m, 2H), 1.54–1.68 (m, 1H), 1.28–1.34 (m, 1H), 1.15 (ddd, 1H, J=5, 6, 8 Hz). IR (CHCl$_3$, cm$^{-1}$) 3000, 1777, 1655, 1615, 1501, 1302, 1250, 1224, 1175. MS (ES) m/e, 408. Anal. Calcd for $C_{24}H_{29}N_3O_3$: C, 62.77; H, 6.28, N, 8.45. Found C, 62.58; H, 6.28; N, 8.44. Mp(° C.)=148.

Example 24

Dimethyl-(3-{4-[5-(2-phenylsulfanylethoxymethyl)-[1,3,4]oxadiazol-2-yl]phenoxy}propyl)amine from 2-(phenylthio)ethanol

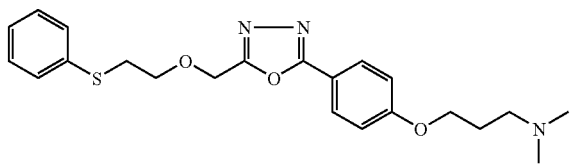

a) (2-Phenylsulfanylethoxy)acetic acid

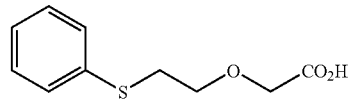

A suspension of sodium hydride (1.15 g, 28.9 mmol) (washed once with hexane) and 2-(phenylthio)ethanol (4.45 g, 28.9 mmol) in 104 mL DMF was stirred at room temperature for 30 minutes. Next, methyl bromoacetate (4.86 g, 31.7 mmol) was added and the stirring continued for 6.5 hours. The reaction was quenched with water then extracted twice with both hexane followed by EtOAc. The organic phases were combined, washed twice with water, once with brine, dried over sodium sulfate, filtered, concentrated to an oil. The oil was dissolved into 40 mL THF and 20 mL water then treated with lithium hydroxide (2.07 g, 86.6 mmol). The biphasic solution was heated with stirring at 60° C. for 1 hour. Upon cooling to room temperature the reaction was quenched with 7.56 mL concentrated HCl. The reaction was extracted with EtOAc then the organic phase was washed twice with water, once with brine, dried over sodium sulfate, filtered, concentrated to afford an oil. Purification by chromatography on silica gel (elution with 10% MeOH containing 1% AcOH:CH$_2$Cl$_2$) afforded 0.903 g (15%) of (2-phenylsulfanylethoxy)acetic acid.

$^1$H NMR (DMSO-d6) δ7.29–7.36 (m, 4H), 7.16–7.24 (m, 1H), 3.77 (s, 2H), 3.63 (t, 2H, J=7 Hz), 3.14 (t, 2H, J=7 Hz).

IR (CHCl$_3$, cm$^{-1}$) 3051, 1603, 1481, 1440, 1428, 1409, 1116.

MS (ES) m/e, 211. Anal. Calcd for $C_{10}H_{12}O_3S$: C, 56.58; H, 5.70. Found C, 52.81; H, 5.54.

b) 4-Hydroxybenzoic acid N'-[2-(2-phenylsulfanylethoxy]hydrazide

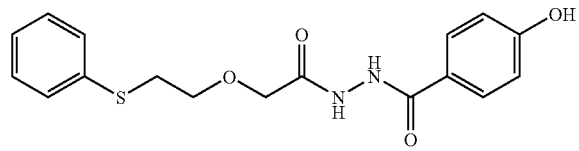

The above compound was prepared in a manner similar to that exemplified for the preparation of Example 19c, from (2-Phenylsulfanylethoxy)acetic acid (0.800 g, 3.8 mmol), 2-ethoxy-1-ethoxycarbonyl-1,2-dihydroquinoline (0.932 g, 3.8 mmol) and 4-hydroxybenzoic hydrazide (0.573 g, 3.8 mmol) to afford the title compound as a crude mixture. Purification by HPLC on silica gel (elution with a linear gradient of 2 to 5% MeOH:CHCl$_3$) afforded 0.183 g (14%) of 4-hydroxybenzoic acid N'-[2-(2-phenylsulfanylethoxy]hydrazide.

$^1$H NMR (DMSO-d6) δ10.07 (bs, 2H), 9.68 (bs, 1H), 7.74 (d, 2H, J=9 Hz), 7.30–7.40 (m, 4H), 7.16–7.22 (m, 1H), 6.81 (d, 2H, J=8 Hz), 4.04 (s, 2H), 3.71 (t, 2H, J=7 Hz), 3.23 (t, 2H, J=7 Hz). IR (KBr, cm$^{-1}$) 3209, 1692, 1640, 1608, 1507, 1439, 1281, 1236, 1173, 1127, 850, 742, 692. MS (ES) m/e, 347, 345. Anal. Calcd for $C_{17}H_{18}N_2O_4S$: C, 58.94; H, 5.24; N, 8.09. Found C, 58.52; H, 4.96; N, 8.01.

c) 4-[5-(2-Phenylsulfanylethoxymethyl)-[1,3,4]oxa-diazol-2-yl]phenol

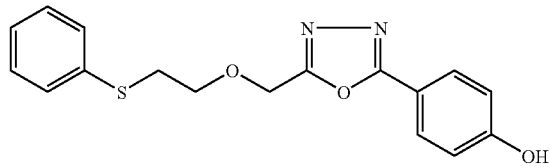

The above compound was prepared in a manner similar to that exemplified for the preparation of Example 19d, from 4-Hydroxybenzoic acid N'-[2-(2-phenylsulfanylethoxy]hydrazide (0.161 g, 0.7 mmol), triphenylphosphine (0.244 g, 0.9 mmol), triethyl amine (0.094 g, 0.9 mmol) and carbon tetrabromide (0.308 g, 0.9 mmol) to afford the title compound as a crude mixture. Purification by radial chromatography on silica gel (elution with 75% EtOAc:hexane) afforded 0.135 g (88%) of 4-[5-(2-Phenylsulfanylethoxymethyl)-[1,3,4]oxadiazol-2-yl]phenol.

$^1$H NMR (DMSO-d6) $\delta$10.35 (bs, 1H), 7.82 (d, 2H, J=9 Hz), 7.25–7.36 (m, 4H), 7.14–7.20 (m, 1H), 6.95 (d, 2H, J=9 Hz), 4.78 (s, 2H), 3.73 (t, 2H, J=7 Hz), 3.20 (t, 2H, J=7 Hz).

IR (KBr, cm$^{-1}$) 3586, 3005, 1615, 1603, 1505, 1498, 1482, 1440, 1283, 1171, 1112, 1085, 843. MS (ES) m/e, 329, 327. Anal. Calcd for $C_{17}H_{16}N_2O_3S$: C, 62.18; H, 4.91; N, 8.53. Found C, 61.90; H, 4.88; N, 8.35.

d) Dimethyl-(3-{4-[5-(2-phenylsulfanylethoxymethyl)-[1,3,4]oxadiazol-2-yl]phenoxy}propyl)amine

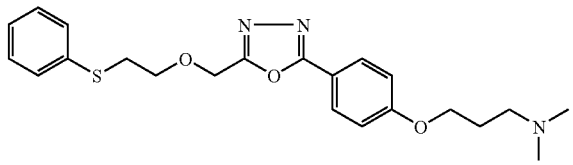

The above compound was prepared in a manner similar to that exemplified for the preparation of Example 21e, from 4-[5-(2-phenylsulfanylethoxymethyl)-[1,3,4]oxadiazol-2-yl]phenol (0.114 g 0.4 mmol), cesium carbonate (0.226 g, 0.7 mmol) and 3-chloro-N,N-dimethylpropyl amine hydrochloride (0.055 g, 0.4 mmol) to afford the title compound as a crude mixture. Purification by radial chromatography on silica gel (elution with 10% 2M NH$_3$ in MeOH:CHCl$_3$) followed by treatment of the isolated material with oxalic acid in acetone afforded 0.130 g (74%) of Dimethyl-(3-{4-[5-(2-phenylsulfanylethoxymethyl)-[1,3,4]oxadiazol-2-yl]phenoxy}propyl)amine as the oxalate salt.

$^1$H NMR (DMSO-d6) $\delta$7.93 (d, 2H, J=7 Hz), 7.25–7.36 (m, 4H), 7.13–7.20 (m, 3H), 4.80 (s, 2H), 4.15 (t, 2H, J=6 Hz), 3.74 (t, 2H, J=6 Hz), 3.14–3.23 (m, 4H), 2.76 (s, 6H), 2.09–2.18 (m, 2H). IR (KBr, cm$^{-1}$) 3432, 3037, 2930, 2874, 1726, 1611, 1496, 1258, 1109, 742. MS (ES) m/e, 414. Anal. Calcd for $C_{22}H_{27}N_3O_3S \cdot C_2H_2O_4$: C, 57.24; H, 5.80; N, 8.34. Found C, 57.14; H, 5.71; N, 8.27. Mp(° C.)=143.

Example 25

Preparation of (3-{4-[5-(Benzooxazol-2-ylmethylsulfanylmethyl)-[1,3,4]oxadizol-2-yl]phenoxy}propyl)dimethylamine from 2-Chloromethylbenzoxazole

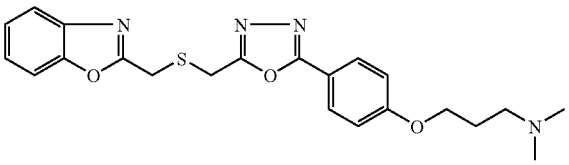

a) (Benzooxazol-2-ylmethylsulfanyl)acetic acid

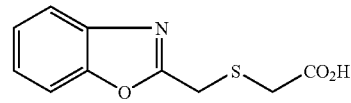

The above compound was prepared in a manner similar to that exemplified for the preparation of Example 17b, from 2-Chloromethylbenzoxazole (1.57 g, 9.4 mmol), methylthio-glycolate (0.994 g, 9.4 mmol), and sodium hydride (0.375 g, 9.4 mmol) to afford the title compound as a crude mixture. Purification by crystallization with Et2O afforded 1.12 g (54%) of (Benzo-oxazol-2-ylmethylsulfanyl)acetic acid.

$^1$H NMR DMSO-d6) $\delta$12.71 (bs, 1H), 7.68–7.75 (m, 2H), 7.34–7.43 (m, 2H), 4.14 (s, 2H), 3.45 (s, 2H). IR (KBr, cm$^{-1}$) 2933, 2542, 1725, 1606, 1571, 1454, 1236, 1191, 1133, 840, 767. MS (ES) m/e, 224. Anal. Calcd for $C_{10}H_9NO_3S$: C, 53.80; H, 4.06; N, 6.27. Found C, 53.53; H, 4.02; N, 6.17.

b) 4-Hydroxybenzoic acid-N'-[2-benzooxazol-2-ylmethylsulfanyl)acetyl]hydrazide

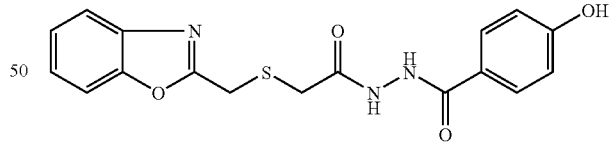

The above compound was prepared in a manner similar to that exemplified for the preparation of Example 19c, from (benzooxazol-2-ylmethylsulfanyl)acetic acid (0.822 g, 3.7 mmol), 2-ethoxy-1-ethoxycarbonyl-1,2-dihydroquinoline (0.911 g, 3.7 mmol) and 4-hydroxybenzoic hydrazide (0.560 g, 3.7 mmol) to afford the title compound as a crude material. Purification by HPLC on silica gel (elution with a linear gradient of 2 to 10% 2M NH$_3$ in MeOH:CHCl$_3$) afforded 0.190 g (14%) of 4-hydroxy benzoic acid-N'-[2-benzooxazol-2-ylmethylsulfanyl)acetyl]hydrazide as a white foam.

$^1$H NMR (DMSO-d6) $\delta$10.27 (bs, 1H), 9.83 (bs, 1H), 9.38 (bs, 1H), 7.71–7.86 (m, 3H), 6.68–6.94 (m, 5H), 4.20 (s, 2H), 3.61 (s, 2H). IR (KBr, cm$^{-1}$) 3208, 1658, 1612, 1598, 1497, 1456, 1368, 1282, 1239, 1172, 843, 752. MS (ES) m/e, 358, 356. Anal. Calcd for $C_{17}H_{15}N_3O_4S$: C, 57.13; H, 4.23; N, 11.76. Found C, 56.82; H, 4.08; N, 11.71.

c) 4-[5-(Benzooxazol-2-ylmethylsulfanylmethyl)-[1,3,4]oxadiazol-2-yl]phenol

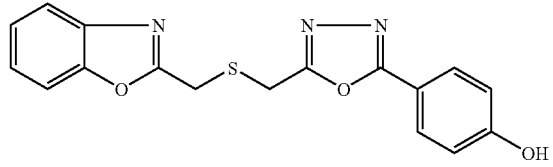

The above compound was prepared in a manner similar to that exemplified for the preparation of Example 19d, from 4-hydroxybenzoic acid-N'-[2-benzooxazol-2-ylmethylsulfanyl)acetyl]hydrazide (0.190 g, 0.5 mmol), triphenylphosphine (0.279 g, 1.1 mmol), triethyl amine (0.108 g, 1.1 mmol) and carbon tetrabromide (0.353 g, 1.1 mmol) to afford the title compound as a crude mixture. Purification by radial chromatography on silica gel (elution with 50% EtOAc:hexane) afforded 0.150 g of 4-[5-(Benzooxazol-2-ylmethylsulfanylmethyl)-[1,3,4]oxadiazol-2-yl]phenol along with triphenylphosphine as a contaminant.

$^1$H NMR (DMSO-d6) $\delta$10.29 (bs, 1H), 7.52 (m, 4H), 7.30–7.39 (m, 2H), 6.88–6.93 (m, 2H), 4.24 (d, 4H). IR (KBr, cm$^{-1}$) 3227, 1609, 1561, 1497, 1452. MS (ES) m/e, 340, 338. Anal. Calcd for $C_{17}H_{13}N_3O_3S$: C, 60.17; H, 3.86; N, 12.38. Found C, 63.51; H, 4.23; N, 9.32.

d) (3-{4-[5-(Benzooxazol-2-ylmethylsulfanyl methyl)-[1,3,4]oxadizol-2-yl]phenoxy}propyl)dimethylamine

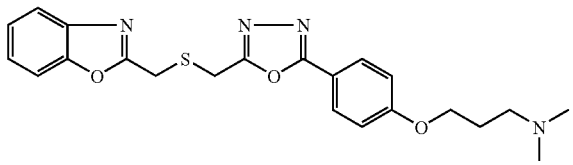

The above compound was prepared in a manner similar to that exemplified for the preparation of Example 21e, from 4-[5-(Benzooxazol-2-ylmethylsulfanylmethyl)-[1,3,4]oxadiazol-2-yl]phenol (0.131 g, 0.4 mmol), cesium carbonate (0.252 g, 0.8 mmol) and 3-chloro-N,N-dimethylpropyl amine hydrochloride (0.061 g, 0.4 mmol) to afford the title compound as a crude material. Purification by radial chromatography on silica gel (elution with 10% 2M NH3 in MeOH:CHCl$_3$) followed by treatment of the isolated, material with oxalic acid in acetone afforded 0.026 g (13%) of (3-{4-[5-(Benzooxazol-2-ylmethylsulfanylmethyl)-[1,3,4] oxadizol-2-yl]phenoxy}propyl)dimethylamine as the oxalate salt.

$^1$H NMR DMSO-d6) $\delta$7.81 (d, 2H, J=9 Hz), 7.60–7.64 (m, 2H), 7.29–7.38 (m, 2H), 7.10 (d, 2H, J=9 Hz), 4.25 (d, 4H), 4.14 (t, 2H, J=6 Hz), 3.15–3.20 (m, 2H), 2.77 (s, 6H), 2.08–2.17 (m, 2H). IR (KBr, cm$^{-1}$) 3007, 1777, 1656, 1614, 1500, 1455, 1302, 1254, 1176, 839. MS (ES) m/e, 425. Anal. Calcd for $C_{22}H_{24}N_4O_3S \cdot C_2H_2O_4$: C, 56.02; H, 5.09; N, 10.89. Found C, 55.28; H, 4.84; N, 10.74. Mp($^\circ$ C.)=120.

Example 26

Preparation of (3-{4-[5-Benzofuran-2-ylmethylsulfanylmethyl)-[1,3,4]oxadiazol-2-yl]phenoxy}propyl) dimethylamine from 2-Bromomethylbenzofuran

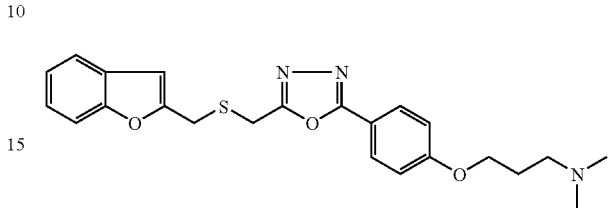

a) (Benzofuran-2-ylmethylsulfanyl)acetic acid

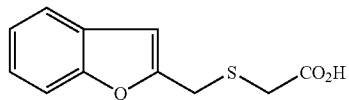

The above compound was prepared in a manner similar to that exemplified for the preparation of Example 17b, from 2-Bromomethylbenzofuran (3.34 g, 15.8 mmol), methylthioglycolate (2.02 g, 19.0 mmol), and sodium hydride (0.760 g, 19.0 mmol) to afford the title compound as a crude material. Purification by HPLC on silica gel (elution with a linear gradient of 2 to 10% MeOH:CHCl$_3$) afforded 1.46 g of (Benzofuran-2-ylmethylsulfanyl)acetic acid along with other coeluting impurities. Material was taken on to next step without further purification.

b) 4-Hydroxybenzoic acid-N'-[2-benzofuran-2-ylmethylsulfanyl)acetyl]hydrazide

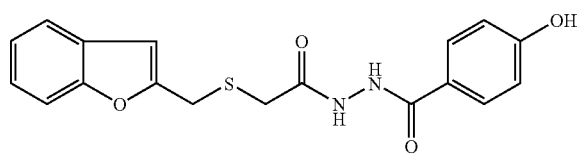

To a solution of benzofuran-2-ylmethylsulfanyl)acetic acid (1.46 g, 6.6 mmol) in 100 mL THF stirring at room temperature was added 1,1'-carbonyldiimidazole (1.07 g, 6.6 mmol). The reaction was heated at 60° C. for one hour. After cooling to room temperature, the mixture was treated with and 4-hydroxybenzoic hydrazide (1.50 g, 9.9 mmol). After stirring for approximately 4 hours the reaction was concentrated to a solid material. The material was partitioned between EtOAc and 1N HCl. The phases were separated and the organic phase was washed twice with 1N HCl, brine, dried over sodium sulfate, filtered, concentrated to afford an oil. Treatment of the oil with CHCl$_3$ followed by sonication afforded 0.854 g (36%) of 4-Hydroxybenzoic acid-N'-[2-benzofuran-2-ylmethylsulfanyl)acetyl]hydrazide as a filterable solid.

¹H NMR (DMSO-d6) δ10.02 (bs, 1H), 7.76 (d, 2H, J=8 Hz), 7.53–7.61 (m, 2H), 7.20–7.31 (m, 2H), 6.83 (m, 3H), 4.09 (s, 2H), 3.27 (s, 2H). IR (KBr, cm⁻¹) 3296, 3211, 3007, 1687, 1625, 1584, 1515, 1452, 1281, 1173, 956, 745. MS (ES) m/e, 357, 355. Anal. Calcd for $C_{18}H_{16}N_2O_4S$: C, 60.66; H, 4.53; N, 7.86. Found C, 58.53; H, 4.43; N, 7.93.

c) 4-[5-(benzofuran-2-ylmethylsulfanylmethyl)[1,3,4]oxadiazol-2-yl]phenol

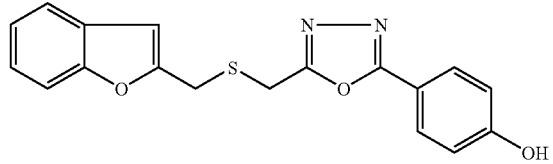

The above compound was prepared in a manner similar to that exemplified for the preparation of Example 19d, from 4-hydroxybenzoic acid-N'-[2-benzofuran-2-ylmethylsulfanyl)acetyl]hydrazide (0.753 g, 2.1 mmol), triphenylphosphine (0.665 g, 2.5 mmol), triethyl amine (0.256 g, 2.5 mmol) and carbon tetrabromide (0.841 g, 2.5 mmol) to afford the title compound as a crude material. Purification by radial chromatography on silica gel (elution with 75% EtOAc:hexane) afforded 0.550 g (77%) of 4-[5-(benzofuran-2-ylmethyl sulfanylmethyl)[1,3,4]oxadiazol-2-yl]phenol as an oil that slowly crystallized out.

¹H NMR (DMSO-d6) δ10.29 (s, 1H), 7.72 (d, 2H, J=8 Hz), 7.46–7.57 (m, 2H), 7.17–7.28 (m, 2H), 6.79 (s, 11H), 6.79 (s, 1H), 4.10 (s, 2H), 4.08 (s, 2H). IR (KBr, cm⁻¹) 3429, 3053, 2936, 1611, 1595, 1575, 1452, 1293, 1176, 1097, 953, 844, 757. MS (ES) m/e, 339, 337. Anal. Calcd for $C_{18}H_{14}N_2O_3S$: C, 63.89; H, 4.17; N, 8.28. Found C, 63.05; H, 4.34; N, 7.26.

d) (3-{4-[5-Benzofuran-2-ylmethylsulfanylmethyl)-[1,3,4]oxadiazol-2-yl]phenoxy}propyl)dimethylamine

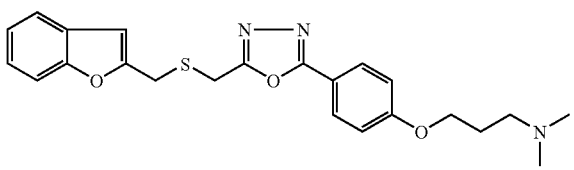

The above compound was prepared in a manner similar to that exemplified for the preparation of Example 21e, from 4-[5-(Benzofuran-2-ylmethylsulfanylmethyl)[1,3,4]oxadiazol-2-yl]phenol (0.510 g, 1.5 mmol), cesium carbonate (0.982 g, 3.0 mmol) and 3-chloro-N,N-dimethylpropyl amine hydrochloride (0.238 g, 1.5 mmol) to afford the title compound as a crude material. Purification by radial chromatography on silica gel (elution with 10% 2M NH₃ in MeOH:CHCl₃) followed by treatment of the isolated material with oxalic acid in acetone afforded 0.364 g (47%) of (3-{4-[5-Benzofuran-2-ylmethylsulfanylmethyl)-[1,3,4]oxadiazol-2-yl]phenoxy}propyl)dimethylamine as the oxalate salt.

¹H NMR (DMSO-d6) δ7.83 (d, 2H, J=9 Hz), 7.45–7.56 (m, 2H), 7.17–7.27 (m, 2H), 7.10 (d, 2H, J=9 Hz), 6.79 (s, 1H), 4.09–4.16 (m, 6H), 3.15–3.20 (m, 2H), 2.77 (s, 6H), 2.09–2.18 (m, 2H). IR (KBr, cm⁻¹) 1615, 1500, 1255, 1175, 949, 754, 707. MS (ES) m/e, 424. Anal. Calcd for $C_{23}H_{25}N_3O_3S.C_2H_2O_4$: C, 58.47; H, 5.30; N, 8.18. Found C, 58.08; H, 5.22; N, 8.08. Mp(° C.)=144.

Example 27

Preparation of (3-{4-[5-Benzo[b]thiophene-2-ylmethylsulfanylmethyl)-[1,3,4]oxadiazol-2-yl]phenoxy}propyl)dimethylamine from 2-bromomethylbenzo[b]thiophene

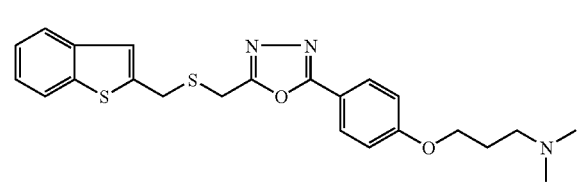

a) (Benzo[b]thiophene-2-ylmethylsulfanyl)acetic acid

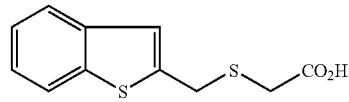

The above compound was prepared in a manner similar to that exemplified for the preparation of Example 17b, from 2-bromomethylbenzo[b]thiophene (2.21 g, 9.7 mmol), methylthioglycolate (1.03 g, 9.7 mmol), and sodium hydride (0.389 g, 9.7 mmol) to afford the title compound as a crude mixture. Purification by HPLC on silica gel (elution with a linear gradient of 2 to 10% MeOH:CHCl₃) followed by crystallization of the isolated material from Et₂O:hexane afforded 1.16 g (50%) of (benzo[b]thiophene-2-ylmethylsulfanyl)acetic acid.

¹H NMR (DMSO-d6) δ12.65 (bs, 1H), 7.89–7.92 (m, 1H), 7.76–7.80 (m, 1H), 7.29–7.38 (m, 3H), 4.16 (s, 2H), 3.24 (s, 2H). IR (CHCl₃, cm⁻¹) 3010, 2917, 2673, 2568, 1710, 1458, 1436, 1297, 1132. MS (ES) m/e, 237. Anal. Calcd for $C_{11}H_{10}O_2S_2$: C, 55.44; H, 4.23. Found C, 55.41; H, 4.13.

b) 4-Hydroxybenzoic acid-N'-[2-benzo[b]thiophen-2-ylmethylsulfanyl)acetyl]hydrazide

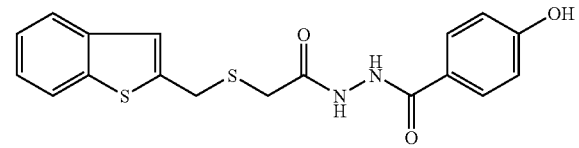

The above compound was prepared in a manner similar to that exemplified for the preparation of Example 19c, from (benzo[b]thiophene-2-ylmethylsulfanyl)acetic acid (1.00 g, 4.2 mmol), 2-ethoxy-1-ethoxycarbonyl-1,2-dihydroquinoline (1.04 g, 4.2 mmol) and 4-hydroxybenzoic hydrazide (0.638 g, 4.2 mmol) to afford the title compound. The resultant crystals that had formed upon concentration of the crude material were collected by filtration to afford 0.982 g (63%) of 4-Hydroxybenzoic acid-N'-[2-benzo[b]thiophen-2-ylmethylsulfanyl)acetyl]hydrazide.

$^1$H NMR (DMSO-d6) δ10.17 (bs, 1H), 10.09 (bs, 1H), 9.99 (bs, 1H), 7.89–7.93 (m, 1H), 7.75–7.79 (m, 3H), 7.22–7.38 (m, 3H), 6.82 (d, 2H, J=9 Hz), 4.24 (s, 2H), 3.24 (s, 2H).

IR (KBr, cm$^{-1}$) 3311, 3200, 3004, 1685, 1624, 1610, 1585, 1547, 1518, 1495, 1331, 1285, 1234, 1175, 1109, 747. MS (ES) m/e, 373. Anal. Calcd for $C_{18}H_{18}N_2O_3S_2$: C, 57.73; H, 4.84; N, 7.48. Found C, 57.95; H, 4.09; N, 7.29.

c) 4-[5-(benzo[b]thiophene-2-ylmethylsulfanylmethyl)[1,3,4]oxadiazol-2-yl]phenol

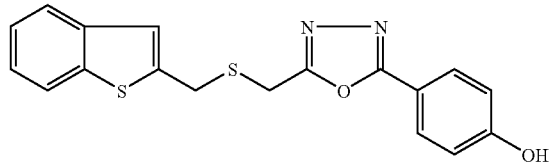

The above compound was prepared in a manner similar to that exemplified for the preparation of Example 19d, from 4-hydroxybenzoic acid-N'-[2-benzo[b]thiophen-2-ylmethylsulfanyl)acetyl]hydrazide (0.611 g, 1.6 mmol), triphenylphosphine (0.860 g, 3.3 mmol), triethyl amine (0.332 g, 3.3 mmol) and carbon tetrabromide (1.09 g, 3.3 mmol) to afford the title compound as a crude mixture. Purification by radial chromatography on silica gel (elution with 50% EtOAc:hexane) followed by the filtration of the resultant crystals in the eluent afforded 0.208 g (36%) of 4-[5-(benzo[b]thiophene-2-ylmethylsulfanylmethyl)[1,3,4]oxadiazol-2-yl]phenol.

$^1$H NMR (DMSO-d6) δ10.29 (s, 1H), 7.87–7.90 (m, 1H), 7.72–7.78 (m, 3H), 7.28–7.37 (m, 3H), 6.92 (d, 2H, J=9 Hz), 4.22 (s, 2H), 4.04 (s, 2H). IR (KBr, cm$^{-1}$) 3160, 2982, 2932, 1609, 1599, 1565, 1498, 1457, 1282, 1221, 1175, 742. MS (ES) m/e, 355. Anal. Calcd for $C_{15}H_{16}N_2O_3S_2$: C, 60.65; H, 4.52; N, 7.86. Found C, 61.72; H, 4.26; N, 7.31.

d) (3-{4-[5-Benzo[b]thiophene-2-ylmethylsulfanylmethyl)-[1,3,4]oxadiazol-2-yl]phenoxy}propyl)dimethylamine

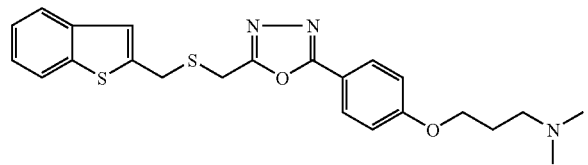

The above compound was prepared in a manner similar to that exemplified for the preparation of Example 21e, from 4-[5-(benzo[b]thiophene-2-ylmethylsulfanylmethyl)[1,3,4]oxadiazol-2-yl]phenol (0.178 g, 0.5 mmol), cesium carbonate (0.325 g, 1.0 mmol) and 3-chloro-N,N-dimethylpropyl amine hydrochloride (0.079 g, 0.5 mmol) to afford the title compound as a crude mixture. Purification by radial chromatography on silica gel (elution with 10% 2M NH3 in MeOH:CHCl$_3$) followed by crystallization of the isolated material from Et2O afforded 0.115 g (52%) of (3–1{4[5-benzo[b]thiophene-2-ylmethylsulfanylmethyl)-[1,3,4]oxadiazol-2-yl]phenoxy}propyl)dimethylamine.

$^1$H NMR (DMSO-d6) δ7.74–7.89 (m, 4H), 7.27–7.36 (m, 3H), 7.08 (d, 2H, J=9 Hz), 4.23 (s, 2H), 4.05–4.11 (m, 4H), 2.36 (t, 2H, J=7 Hz), 2.15 (s, 6H), 1.88 (m, 2H). IR (KBr, cm$^{-1}$) 3432, 2940, 2814, 2761, 1587, 1616, 1563, 1500, 1469, 1428, 1305, 1256, 1177, 1153, 1088, 1051, 821, 740, 728. MS (ES) m/e, 438. Anal. Calcd for $C_{23}H_{25}N_3O_3S_2$: C, 62.15; H, 5.62; N, 9.24. Found C, 62.84; H, 5.73; N, 9.56. Mp(° C.)=93.

Example 28

Preparation of Dimethyl-(3-{4-[5(naphthalen-2-ylmethylsulfanylmethyl)-[1,3,4]oxadiazol-2-yl]phenoxy}propyl)amine from 2-Bromomethylnaphthalene

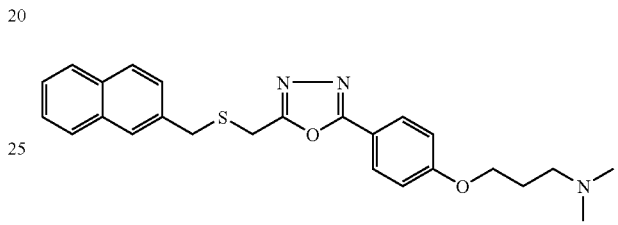

a) (Naphthalen-2ylmethylsulfanyl)acetic acid

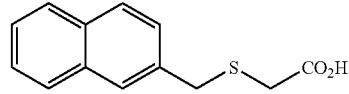

The above compound was prepared in a manner similar to that exemplified for the preparation of Example 17b, from 2-bromomethylnaphthalene (1.86 g, 8.4 mmol), methylthioglycolate (0.982 g, 9.3 mmol), and sodium hydride (0.370 g, 9.3 mmol) to afford the title compound as a crude mixture. Crystallization from Et$_2$O afforded 1.01 g (52%) of (Naphthalen-2ylmethylsulfanyl)acetic acid.

$^1$H NMR (DMSO-d6) δ12.60 (bs, 1H), 7.86–7.91 (m, 3H), 7.78 (s, 1H), 7.46–7.54 (m, 3H), 3.98 (s, 2H), 3.13 (s, 2H).

IR (CHCl$_3$, cm$^{-1}$) 3059, 3019, 3010, 1709, 1601, 1510, 1422, 1295, 1230, 1126, 820. MS (ES) m/e, 231. Anal. Calcd for $C_{13}H_{12}O_2S$: C, 67.22; H, 5.21. Found C, 73.11; H, 4.83.

b) 4-Hydroxybenzoic acid-N'-[2-(naphthalen2-ylmethylsulfanyl)acetyl]hydrazide

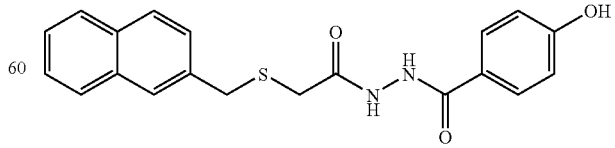

The above compound was prepared in a manner similar to that exemplified for the preparation of Example 19c, from (Naphthalen-2-ylmethylsulfanyl)acetic acid (1.00 g, 4.3 mmol), 2-ethoxy-1-ethoxycarbonyl-1,2-dihydroquinoline (1.06 g, 4.3 mmol) and 4-hydroxybenzoic hydrazide (0.655 g, 4.3 mmol) to afford the title compound. The resultant crystals that had formed upon concentration of the crude material were collected by filtration to afford 0.761 g (48%) of 4-hydroxybenzoic acid-N'-[2-(naphthalen-2-ylmethylsulfanyl)acetyl]hydrazide $^1$H NMR (DMSO-d6) $\delta$10.18 (bs, 1H), 10.09 (bs, 1H), 9.99 (bs, 1H), 7.83–7.97 (m, 4H), 7.77 (d, 2H, J=9 Hz), 7.45–7.55 (m, 3H), 6.83 (d, 2H, J=9 Hz), 4.06 (s, 2H), 3.15 (s, 2H). IR (KBr, cm$^{-1}$) 3206, 3055, 3005, 1688, 1622, 1610, 1584, 1549, 1517, 1495, 1289, 1234, 1173, 750. MS (ES) m/e, 367, 365. Anal. Calcd for $C_{20}H_{18}N_2O_3S$: C, 65.56; H, 4.95; N, 7.64. Found C, 65.74; H, 4.69; N, 7.58.

c) 4-[5-(Naphthalen-2-ylmethylsulfanylmethyl)-[1,3,4]oxadiazol-2-yl]phenol

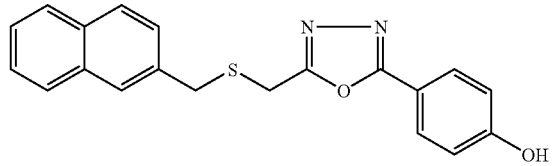

The above compound was prepared in a manner similar to that exemplified for the preparation of Example 19d, from 4-hydroxybenzoic acid-N'-[2-(naphthalen-2-ylmethylsulfanyl)acetyl]hydrazide (0.562 g, 1.5 mmol), triphenylphosphine (0.805 g, 3.1 mmol), triethyl amine (0.310 g, 3.1 mmol) and carbon tetrabromide (1.02 g, 3.1 mmol) to afford the title compound as a crude mixture. Attempts to purify material by silica gel radial chromatography failed. Material taken on to next step without further purification.

d) Dimethyl-(3-{4-[5(naphthalen-2-ylmethylsulfanylmethyl)-[1,3,4]oxadiazol-2-yl]phenoxy}propyl)amine

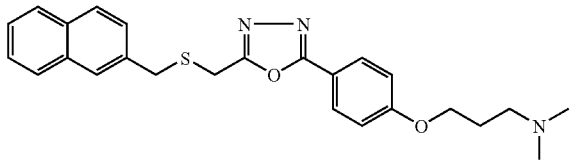

The above compound was prepared in a manner similar to that exemplified for the preparation of Example 21e, from 4-[5-(Naphthalen-2-ylmethylsulfanylmethyl)-[1,3,4]oxadiazol-2-yl]phenol (0.534 g, 1.5 mmol), cesium carbonate (0.999 g, 3.1 mmol) and 3-chloro-N,N-dimethylpropyl amine hydrochloride (0.242 g, 1.5 mmol) to afford the title compound. Purification by radial chromatography on silica gel (elution with 10% 2M NH$_3$ in MeOH:CHCl$_3$) afforded 0.155 g of the title compound as a solid. This material was dissolved into Et2O then treated with a solution of EtOH that was treated with acetyl chloride (0.030 mL, 0.43 mmol). The resultant precipitate was collected by filtration to afford 0.103 g (16%) of dimethyl-(3-{4-[5(naphthalen-2-ylmethylsulfanylmethyl)-[1,3,4]oxadiazol-2-yl]phenoxy}propyl) amine as the hydrochloride salt.

$^1$H NMR (DMSO-d6) $\delta$7.89–7.82 (m, 6H), 7.46–7.53 (m, 3H), 7.11 (d, 2H, J=9 Hz), 4.16 (t, 2H, J=6 Hz), 4.05 9s, 2H), 3.99 (s, 2H), 3.21 (m, 2H), 2.78 (s, 6H), 2.13–2.22 (m, 2H).

IR (KBr, cm$^{-1}$) 3428, 3015, 2956, 2605, 2482, 1613, 1567, 1498, 1486, 1473, 1473, 1428, 1392, 1309, 1260, 1243, 1182, 1088, 1055, 941, 832, 752, 734. MS (ES) m/e, 434. Anal. Calcd for $C_{25}H_{27}N_3O_2S\cdot HCl$: C, 63.88; H, 6.00; N, 8.94. Found C, 63.05; H, 5.88; N, 8.65. Analytical HPLC: 100% Purity. Mp(° C.)=194.

Example 29

Preparation of Dimethyl-(3-{4-[5(naphthalen-1-ylmethylsulfanylmethyl)-[1,3,4]oxadiazol-2-yl]phenoxy}propyl)amine from 1-bromomethylnaphthalene

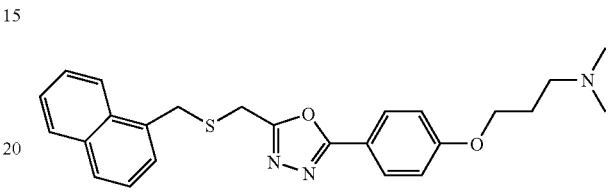

a) (Naphthalen-2ylmethylsulfanyl)acetic acid

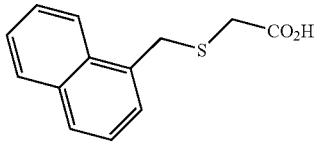

The above compound was prepared in a manner similar to that exemplified for the preparation of Example 17b, from 1-bromomethylnaphthalene (10.71 g, 48.4 mmol), methylthio glycolate (3.57 g, 38.3 mmol), and sodium hydride (3.10 g, 77.5 mmol) to afford the title compound as a crude mixture. Purification by flash filtration chromatography on silica gel (elution with 3×500 mL CH$_2$Cl$_2$, 3×500 mL 10% MeOH:CH$_2$Cl$_2$) afforded 6.76 g (75%) of (naphthalen-1ylmethylsulfanyl)acetic acid.

$^1$H NMR (DMSO-d6) $\delta$12.68 (bs, 11H), 8.16–8.20 (m, 11H), 7.90–7.97 (m, 1H), 7.83–7.88 (m, 1H), 7.50–7.60 (m, 2H), 7.41–7.48 (m, 2H), 4.30 (s, 2H), 3.20 (s, 2H). IR (KBr, cm$^{-1}$) 3065, 3050, 3001, 2928, 1709, 1597, 1512, 1426, 1399, 1295, 802. MS (EI) m/e, 232 b) 4-Hydroxybenzoic acid-N'-[2-(naphthalen2-ylmethylsulfanyl)acetyl]hydrazide

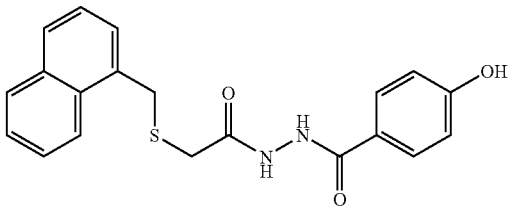

The above compound was prepared in a manner similar to that exemplified for the preparation of Example 19c, from (Naphthalen-1ylmethylsulfanyl)acetic acid (1.77 g, 7.6 mmol), 2-ethoxy-1-ethoxycarbonyl-1,2-dihydroquinoline (1.89 g, 7.6 mmol) and 4-hydroxybenzoic hydrazide (1.16 g, 7.6 mmol) to afford the title compound as a crude mixture. Crystallization from MeOH:Et2O afforded 1.57 g (56%) of 4-hydroxybenzoic acid-N'-[2-(naphthalen-1-ylmethylsulfanyl)acetyl]hydrazide.

$^1$H NMR (DMSO-d6) δ10.24–10.04 (m, 3H), 8.22 (d, 1H, J=8 Hz), 7.94 (d, 1H, J=8 Hz), 7.85 (d, 1H, J=8 Hz), 7.78 (d, 2H, J=9 Hz), 7.43–7.61 (m, 4H), 6.83 (d, 2H, J=9 Hz), 4.40 (s, 2H), 3.22 (s, 2H). IR (KBr, cm$^{-1}$) 3364, 3173, 3017, 1693, 1654, 1610, 1571, 1511, 1495, 1294, 1285, 1237, 1175, 778. MS (ES) m/e, 367, 365. Anal. Calcd for $C_{20}H_{18}N_3O_3S$: C, 65.56; H, 4.95; N, 7.64. Found C, 63.99; H, 4.74; N, 7.33.

c) 4-[5-(Naphthalen-2-ylmethylsulfanylmethyl)-[1,3,4]oxadiazol-2-yl]phenol

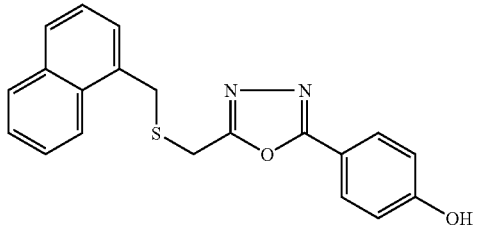

The above compound was prepared in a manner similar to that exemplified for the preparation of Example 19d, using 4-hydroxybenzoic acid-N'-[2-(naphthalen-1-ylmethylsulfanyl)acetyl]hydrazide (0.898 g, 2.5 mmol), triphenylphosphine (1.93 g, 7.4 mmol), triethyl amine (0.744 g, 7.4 mmol) and carbon tetrabromide (2.44 g, 7.4 mmol) to afford the title compound. Purification by silica gel flash filtration (elution with 50% Et$_2$O:hexane followed by Et$_2$O) afforded 0.420 g (49%) of 4-[5-(Naphthalen-1-ylmethylsulfanylmethyl)-[1,3,4]oxadiazol-2-yl]phenol as a white solid.

$^1$H NMR DMSO-d6) δ10.31 9s, 1H), 8.13–8.17 (m, 1H), 7.91–7.95 (m, 1H), 7.84 (d, 1H, J=8 Hz), 7.77 (d, 2H, J=8 Hz), 7.38–7.57 (m, 4H), 6.94 (d, 2H, J=8 Hz), 4.35 (s, 2H), 4.01 (s, 2H). IR (KBr, cm$^{-1}$) 3057, 1613, 1594, 1577, 1446, 1293, 1177, 773. MS (ES) m/e, 349, 347. Anal. Calcd for $C_{20}H_{16}N_2O_2S$: C, 68.95; H, 4.63; N, 8.04. Found C, 67.72; H, 4.54; N, 7.74.

d) Dimethyl-(3-{4-[5(naphthalen-1-ylmethylsulfanylmethyl)-[1,3,4]oxadiazol-2-yl]phenoxy}propyl)amine

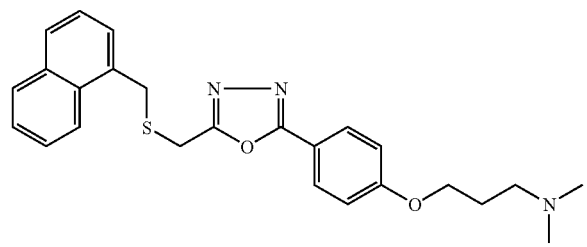

The above compound was prepared in a manner similar to that exemplified for the preparation of Example 21e, from 4-[5-(Naphthalen-1-ylmethylsulfanylmethyl)-[1,3,4]oxadiazol-2-yl]phenol (0.400 g, 1.1 mmol), cesium carbonate (0.748 g, 2.3 mmol) and 3-chloro-N,N-dimethylpropyl amine hydrochloride (0.181 g, 1.1 mmol) to afford the title compound. Purification by silica gel radial chromatography (elution with 5% 2M NH$_3$ in MeOH:CHCl$_3$) afforded 0.374 g of the title compound as a solid. Crystallization from Et2O afforded 0.374 g (75%) of Dimethyl-(3-{4-[5(naphthalen-1-ylmethylsulfanylmethyl)-[1,3,4]oxadiazol-2-yl]phenoxy}propyl)amine.

$^1$H NMR (DMSO-d6) δ 8.16–8.13 (m, 1H), 7.92–7.95 (m, 1H), 7.84–7.88 (m, 3H), 7.41–7.57 (m, 4H), 7.12 (d, 2H, J=9 Hz), 4.36 (s, 2H), 4.10 (t, 2H, J=7 Hz), 2.15 (s, 6H), 1.84–1.93 (m, 2H). IR (KBr, cm$^{-1}$) 1614, 1500, 1469, 1257, 1175, 839. MS (ES) m/e, 434. Anal. Calcd for $C_{25}H_{27}N_3O_2S$: C, 69.26; H, 6.28; N, 9.69. Found C, 68.35; H, 6.16; N, 9.59. Mp(° C.)=96.

Example 30

Preparation of Dimethyl-(3-{4-[5-(3-phenylpropylsulfanyl methyl)-[1,3,4]oxadiazol-2-yl]phenoxy}propyl)amine from 3-Phenylpropyl mercaptan

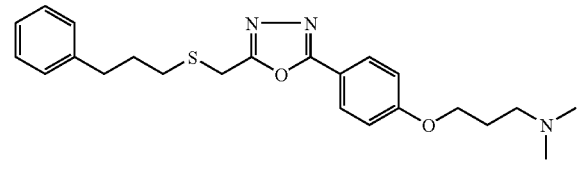

a) 4-Hydroxybenzoic acid N'-[2(3-phenylpropylsulfanyl)acetyl]hydrazide

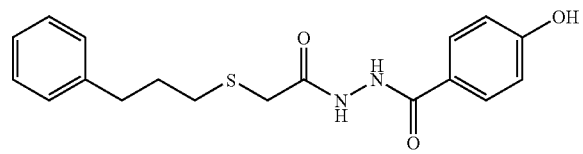

The above compound was prepared in a manner similar to that exemplified for the preparation of Example 19c, from (3-phenyl propylsulfanyl)acetic acid (2.00 g, 9.5 mmol), 4-hydroxy benzoic hydrazide (1.45 g, 9.5 mmol) and 2-ethoxy-1-ethoxycarbonyl-1,2-dihydroquinoline (2.35 g, 9.5 mmol) to afford the title compound as a crude mixture. Crystallization from methanol and diethyl ether afforded 2.15 g (66%) of 4-hydroxybenzoic acid N'-[2(3-phenyl propyl sulfanyl)acetyl]hydrazide.

$^1$H NMR (DMSO-d6) δ10.02–10.13 (m, 2H), 9.94–9.97 (bs, 1H), 7.74 (d, 2H, J=8 Hz), 7.14–7.31 (m, 5H), 6.81 (d, 2H, J=9 Hz), 3.21 (s, 2H), 2.63–2.69 (m, 4H), 1.80–1.92 (m, 2H).

IR (KBr, cm$^{-1}$) 3311, 3208, 2859, 1695, 1625, 1609, 1585, 1517, 1495, 1284, 1175, 1115, 848, 694, 567. MS (ES) m/e, 345, 343. Anal. Calcd for $C_{18}H_{20}N_2O_3S$: C, 62.77; H, 5.85; N, 8.13. Found C, 62.37; H, 5.86; N, 8.03.

b) 4-[5(3-Phenylpropylsulfanylmethyl)-[1,3,4]oxa-diazol-2-yl]phenol

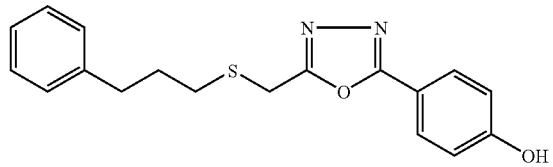

The above compound was prepared in a manner similar to that exemplified for the preparation of Example 19d, from 4-hydroxybenzoic acid-N'-[2(3-phenylpropyl sulfanyl) acetyl]hydrazide (1.94 g, 5.6 mmol), triphenyl phosphine (2.95 g, 11.3 mmol), triethylamine (2.05 g, 20.2 mmol) and carbon tetrabromide (3.55 g, 23.1 mmol) to afford the title compound as a crude material. Purification by flash filtration chromatography on silica gel (elution with 50% acetone: hexane) followed by crystallization of the isolated product from EtOH afforded 0.973 g (53%) of 4-[5(3-phenylpropyl sulfanyl methyl)-[1,3,4]oxadiazol-2-yl]phenol.

$^1$H NMR (DMSO-d6) δ10.31 (s, 1H), 7.78 (d, 2H, J=9 Hz), 7.14–7.27 (m, 5 Hz), 6.94 (d, 2H, J=9 Hz), 4.07 (s, 2H), 2.60–2.67 (m, 4H), 1.79–1.89 (m, 2H). IR (KBr, cm$^{-1}$) 3143, 3024, 2938, 1611, 1601, 1499, 1232. MS (ES) m/e, 327, 325. Anal. Calcd for $C_{18}H_{18}N_2O_2S$: C, 66.23; H, 5.56; N, 8.58. Found C, 65.87; H, 5.47; N, 8.44.

c) Dimethyl-(3-{4-[5-(3-phenylpropylsulfanyl methyl)-[1,3,4]oxadiazol-2-yl]phenoxy}propyl) amine

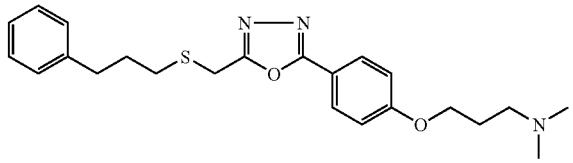

The above compound was prepared in a manner similar to that exemplified for the preparation of Example 19e, from 4-[5(3-phenylpropyl sulfanylmethyl)-[1,3,4]oxadiazol-2-yl] phenol (0.800 g, 2.5 mmol), sodium hydride (0.225 g, 5.6 mmol), and 3-chloro-N,N-dimethylpropylamine HCl (0.426 g, 2.7 mmol) to afford the title compound as a crude material. Purification by radial chromatography on silica gel (elution with 10% 2M NH$_3$ IN MeOH:CHCl$_3$) afforded 0.602 g of an oil. The oil was dissolved in diethyl ether. To this solution was added dropwise, a solution of EtOH in Et2O that was treated with 0.116 mL acetyl chloride. The resultant precipitate was collected by filtration to afford 0.533 g (50%) of dimethyl-(3-{4-[5-(3-phenylpropylsulfa-nyl methyl)-[1,3,4]oxadiazol-2-yl]phenoxy}propyl)amine as the hydrochloride salt.

$^1$H NMR (DMSO-d6) δ7.90 (d, 2H, J=9 Hz), 7.22–7.27 (m, 2H), 7.13–7.18 (m, 5H), 4.17 (t, 2H, J=6 Hz), 4.09 (s, 2H), 3.19–3.21 (m, 2H), 2.78 (s, 6H), 2.60–2.67 (m, 4H), 2.13–2.22 (m, 2H), 1.79–1.89 (m, 2H). IR (CHCl$_3$, cm$^{-1}$) 2970, 2337, 1615, 1570, 1500, 1474, 1254, 1176. MS (ES) m/e, 412. Anal. Calcd for $C_{23}H_{29}N_3O_2S \cdot HCl$: C, 61.66; H, 6.75; N, 9.38. Found C, 61.30; H, 6.76; N, 9.13. Mp(° C.)=148.

Example 31

Preparation of Dimethyl-(3-{4-[5-(2-phenoxy-ethoxymethyl)-[1,3,4]oxadiazol-2-yl] phenoxy}propyl)amine from 2-(Phenoxyethoxy) acetic acid

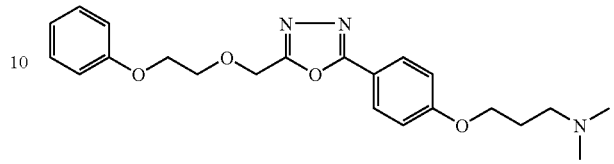

a) 4-Hydroxybenzoic acid N'-[2-(2-phenoxyethoxy)acetyl]hydrazide

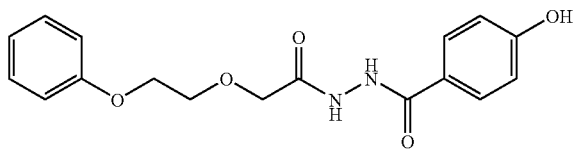

The above compound was prepared in a manner similar to that exemplified for the preparation of Example 19c, from 2-(phenoxyethoxy)acetic acid (2.0 g, 10.2 mmol), 4-hydroxybenzoic hydrazide (1.55 g, 10.2 mmol) and 2-ethoxy-1-ethoxycarbonyl-1,2-dihydroquinoline (2.52 g, 10.2 mmol) to afford the title compound as a crude mixture. Purification by HPLC on silica gel (elution with a linear gradient of 0 to 10% MeOH:CHCl$_3$ over a thirty minute period) followed by crystallization of the isolated material from MeOH:Et$_2$O afforded 1.02 g (30%) of 4-hydroxybenzoic acid N'-[2-(2-phenoxyethoxy)acetyl]hydrazide.

$^1$H NMR (DMSO-d6) δ10.08 (bs, 2H), 9.76 (bs, 1H), 7.74 (d, 2H, J=9 Hz), 7.24–7.32 (m, 2H), 6.91–6.97 (m, 3H), 6.81 (d, 2H, J=9 Hz), 4.16–4.19 (m, 2H), 4.11 (s, 2H), 3.85–3.89 (m, 2H). IR (KBr, cm$^{-1}$) 3229, 1695, 1647, 1627, 1609, 1588, 1574, 1507, 1498, 1246, 1140, 755. MS (ES) m/e, 331, 329. Anal. Calcd for $C_{17}H_{18}N_2O_5$: C, 61.81; H, 5.49; N, 8.48. Found C, 61.26; H, 5.51; N, 8.46.

b) 4-[5-(2-Phenoxyethoxymethyl)-[1,3,4]-oxadiazol-2-yl]phenol

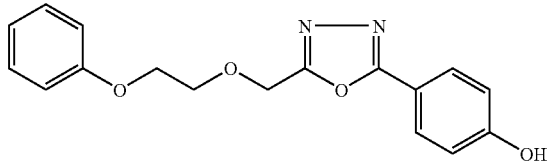

The above compound was prepared in a manner similar to that exemplified for the preparation of Example 19d, from 4-hydroxybenzoic acid N'-[2-(2-phenoxyethoxy) acetyl]hy-drazide (0.961 g, 2.9 mmol), triphenylphosphine (1.53 g, 5.8 mmol), triethylamine (1.06 g, 10.5 mmol) and carbon tetrabromide (1.83 g, 11.9 mmol) to afford the title compound as a crude mixture. Purification by flash filtration chromatography on silica gel (elution with 50% acetone:hexane) followed by crystallization of the isolated product from EtOH afforded 0.473 g (52%) of 4-[5-(2-phenoxyethoxymethyl)-[1,3,4]-oxadiazol-2-yl]phenol.

$^1$H NMR (DMSO-d6) δ10.32 (bs, 1H), 7.81 (d, 2H, J=9 Hz), 7.23–7.30 (m, 2H), 6.89–6.97 (m, 5H), 4.85 (s, 2H), 4.13–4.16 (m, 2H), 3.89–3.92 (m, 2H). IR (KBr, cm⁻¹) 3120, 1609, 1600, 1497, 1218, 1244, 1251, 1116, 753. MS (ES) m/e, 313, 311. Anal. Calcd for $C_{17}H_{16}N_2O_4$: C, 65.38; H, 5.16; N, 8.97. Found C, 65.00; H, 5.10; N, 8.65.

c) Preparation of Dimethyl-(3-{4-[5-(2-phenoxyethoxymethyl)-[1,3,4]oxadiazol-2-yl]phenoxy}propyl)amine

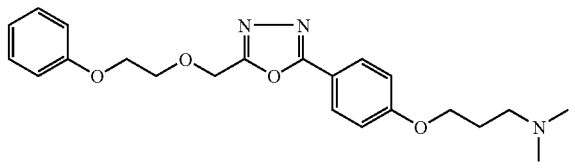

The above compound was prepared in a manner similar to that exemplified for the preparation of Example 19e, from 4-[5-(2-phenoxyethoxy methyl)-[1,3,4]-oxadiazol-2-yl]phenol (0.420 g, 1.3 mmol), sodium hydride (0.124 g, 3.1 mmol), and 3-chloro-N,N-dimethylpropylamine HCl (0.234 g, 1.5 mmol) to afford the title compound as a crude mixture. Crystallization from hexane:Et₂O afforded 0.321 g (60%) of dimethyl-(3-{4-[5-(2-phenoxyethoxymethyl)-[1,3,4]oxadiazol-2-yl]phenoxy}propyl)amine.

¹H NMR (DMSO-d6) δ 7.90 (d, 2H, J=9 Hz), 7.24–7.29 (m, 2H), 7.12 (d, 2H, J=9 Hz), 6.89–6.94 (m, 3H), 4.86 (s, 2H), 4.07–4.16 (m, 4H), 3.90–3.93 (m, 2H), 2.36 (t, 2H, J=7 Hz), 2.14 (s, 6H), 1.83–1.92 (m, 2H). IR (CHCl₃, cm⁻¹) 2948, 2824, 2777, 1614, 1600, 1589, 1499, 1469, 1302, 1256, 1175, 1087, 839. MS (FD) m/e, 397. Anal. Calcd for $C_{22}H_{27}N_3O_4$: C, 66.48; H, 6.85; N, 10.57. Found C, 66.10; H, 6.83; N, 10.44. Mp(° C.)=77.

Example 32

Preparation of N-(3-Dimethylaminopropyl)-4-[5-(2-phenoxyethoxysulfanylmethyl)-[1,3,4]oxadiazol-2-yl]benzamide from (2-Phenoxyethylthio)acetic acid

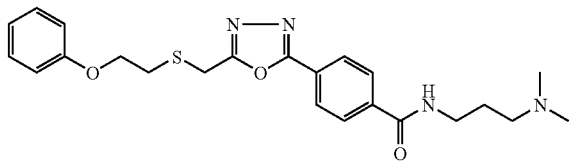

a) 4-[5-(2-Phenoxyethoxysulfanylmethyl)-[1,3,4]oxadiazol-2-yl]benzoic acid methyl ester

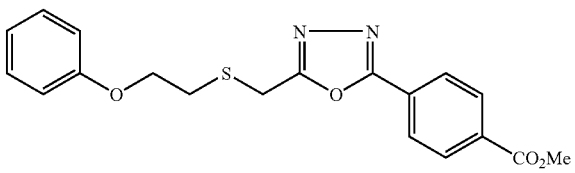

The above compound was prepared in a manner similar to that exemplified for the preparation of Example 1b, from (2-phenoxyethylthio)acetic acid (2.21 g, 10.4 mmol), 1,3-dicyclohexylcarbodiimide (2.15 g, 10.4 mmol) and 4-(1H-tetrazole-5-yl)benzoic acid methyl ester (2.13 g, 104 mmol) to afford the title compound as a crude mixture. Purification by flash filtration chromatography on silica gel (elution with 1×250 mL CH₂Cl₂, 3×250 mL 50% EtOAc:hexane) afforded 0.990 g (26%) of 4-[5-(2-phenoxyethoxy sulfanyl methyl)-[1,3,4]oxadiazol-2-yl]benzoic acid methyl ester as a crystalline solid. Purification of the remaining contaminated fractions by HPLC on silica gel (elution with a linear gradient of 25 to 40% EtOAc:hexane over a thirty minute period) afforded 0.841 g (22%) of 4-[5-(2-phenoxy ethoxy sulfanyl methyl)-[1,3,4]oxadiazol-2-yl]benzoic acid methyl ester.

¹H NMR (DMSO-d6) δ8.09–8.16 (m, 4H), 7.23–7.30 (m, 2H), 6.90–6.94 (m, 3H), 4.26 (s, 2H), 4.20 (t, 2H, J=6 Hz), 3.91 (s, 3H), 3.04 (t, 2H, J=6 Hz). IR (CHCl₃, cm⁻¹) 1721, 1498, 1283, 1243. MS (ES) m/e, 371. Anal. Calcd for $C_{19}H_{18}N_2O_4S$: C, 61.61; H, 4.90; N, 7.56. Found C, 61.54; H, 4.91; N, 7.56.

b) 4-[5-(2-Phenoxyethoxysulfanylmethyl)-[1,3,4]oxadiazol-2-yl]benzoic acid

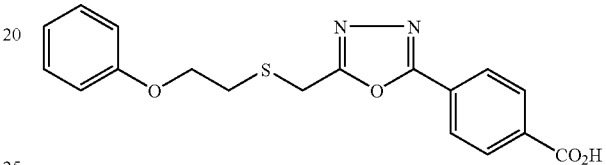

The above compound was prepared in a manner similar to that exemplified for the preparation of Example 1c, from 4-[5-(2-phenoxy ethoxy sulfanyl methyl)-[1,3,4]oxadiazol-2-yl]benzoic acid methyl ester (1.00 g, 2.7 mmol), and lithium hydroxide (0.194 g, 8.1 mmol) to afford 0.868 g (90%) of 4-[5-(2-phenoxyethoxy sulfanylmethyl)-[1,3,4] oxadiazol-2-yl]benzoic acid as a white solid.

¹H NMR (DMSO-d6) δ13.35 (bs, 1H), 8.06–8.14 (m, 4H), 7.23–7.30 (m, 2H), 6.90–6.98 (m, 3H), 4.26 (s, 2H), 4.20 (t, 2H, J=6 Hz), 3.04 (t, 2H, J=6 Hz). IR (CHCl₃, cm⁻¹) 1700, 1587, 1497, 1243. MS (ES) m/e, 357, 355. Anal. Calcd for $C_{18}H_{16}N_2O_4S$: C, 60.66; H, 4.53; N, 7.86. Found C, 60.29; H, 4.51; N, 7.80.

c) N-(3-Dimethylaminopropyl)-4-[5-(2-phenoxyethoxysulfanyl methyl)-[1,3,4]oxadiazol-2-yl]benzamide

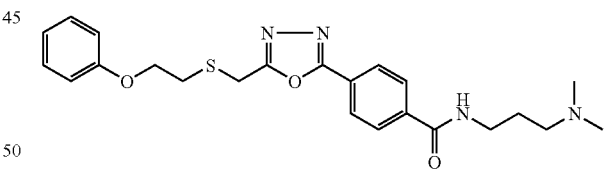

The above compound was prepared in a manner similar to that exemplified for the preparation of Example 7c, from 4-[5-(2-phenoxyethoxy sulfanylmethyl)-[1,3,4]oxadiazol-2-yl]benzoic acid (0.600 g, 1.68 mmol), 1-hydroxybenzotriazole (0.227 g, 1.68 mmol), 4-dimethylamino pyridine (0.021 g, 0.17 mmol), 3-(dimethylamino)propyl amine (0.181 g, 1.77 mmol) and 1,3-dicyclohexyl carbodiimide (0.365 g, 1.77 mmol) to afford the title compound as a crude mixture. Purification by radial chromatography on silica gel (elution with 10% 2M NH₃ in MeOH:CH₂Cl₂) followed by crystallization of the isolated material from EtOH:Et₂O afforded 0.335 g (45%) of N-(3-dimethylaminopropyl)-4-[5-(2-phenoxyethoxysulfanyl methyl)-[1,3,4]oxadiazol-2-yl]benzamide.

¹H NMR (DMSO-d6) δ8.72 (t, 1H, J=5 Hz), 8.00–8.07 (m, 4H), 7.23–7.29 (m, 2H), 6.90–6.94 (m, 3H), 4.25 (s,

2H), 4.20 (t, 2H, J=6 Hz), 3.30 (q, 2H, J=6 Hz), 3.04 (t, 2H, J=6 Hz), 2.66 (t, 2H, J=7 Hz), 2.14 (s, 6H), 1.62–1.72 (m, 2H). IR (CHCl$_3$, cm$^{-1}$) 3008, 2951, 2827, 1652, 1585, 1555, 1497, 1243, 1011. MS (ES) m/e, 441, 439. Anal. Calcd for C$_{23}$H$_{28}$N$_4$O$_3$S: C, 62.70; H, 6.41; N, 12.72. Found C, 62.33; H, 6.31; N, 12.62. Mp(° C.)=96.

Example 33

Preparation of Dimethyl-(3-{4-[5-(4-phenoxybutyl)-[1,3,4]oxadiazol-2-yl]phenoxy}propyl)amine from 5-phenoxypentanoic acid

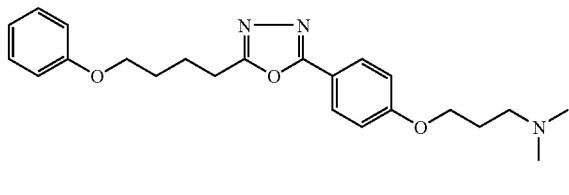

a) 4-Hydroxybenzoic acid-1V-(5-phenoxypentainoyl)hydrazide

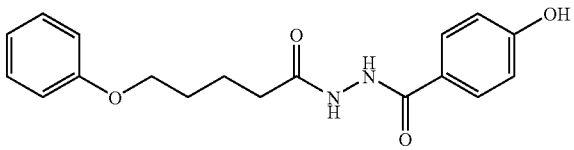

The above compound was prepared in a manner similar to that exemplified for the preparation of Example 19c, from 5-phenoxypentanoic acid (2.00 g, 10.3 mmol), 4-hydroxybenzoic hydrazide (1.57 g, 10.3 mmol) and 2-ethoxy-1-ethoxycarbonyl-1,2-dihydroquinoline (2.55 g, 10.3 mmol) to afford the title compound as a crude mixture. Purification by HPLC on silica gel (elution with a linear gradient of 0 to 10% MeOH:CHCl$_3$ over a thirty minute period) afforded 2.03 g (60%) of 4-hydroxybenzoic acid-N'-(5-phenoxypentanoyl)hydrazide as a white foam.

$^1$H NMR (DMSO-d6) δ10.06 (bs, 1H), 10.02 (bs, 1H), 9.75 (bs, 1H), 7.74 (d, 2H, J=9 Hz), 7.21–7.31 (m, 2H), 6.87–6.95 (m, 3H), 6.81 (d, 2H, J=9 Hz), 3.98 (t, 2H, J=6 Hz), 2.24 (t, 2H, J=7 Hz), 1.62–1.83 (m, 4H). IR (KBr, cm$^{-1}$) 3269, 1663, 1608, 1577, 1496, 1472, 1280, 1248, 848, 754. MS (ES) m/e, 329, 327. Anal. Calcd for C$_{18}$H$_{20}$N$_2$O$_4$: C, 65.84; H, 6.14; N, 8.53. Found C, 65.53; H, 6.19; N, 8.36.

b) 4-[5-(4-Phenoxybutyl)-[1,3,4]oxadiazol-2-yl]phenol

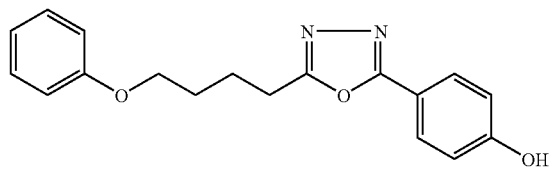

The above compound was prepared in a manner similar to that exemplified for the preparation of Example 19d, from 4-hydroxybenzoic acid-N'-(5-phenoxypentanoyl)hydrazide (1.90 g, 5.8 mmol), triphenyl phosphine (11.6 g, 3.04 mmol), triethylamine (2.11 g, 20.8 mmol) and carbon tetrachloride (3.65 g, 23.7 mmol) to afford the title compound as a crude mixture. Purification by flash filtration chromatography on silica gel (elution with 50% acetone:hexane) followed by crystallization of the isolated product from ethanol afforded 1.71 g (65%) of 4-[5-(4-phenoxy butyl)-[1,3,4]oxadiazol-2-yl]phenol.

$^1$H NMR (DMSO-d6) δ10.25 (bs, 1H), 7.78–7.82 (m, 2H), 7.23–7.31 (m, 2H), 6.88–6.96 (m, 5H), 4.02 (t, 2H, J=6 Hz), 2.98 (t, 2H, J=7 Hz), 1.78–1.97 (m, 4H). IR (KBr, cm$^{-1}$) 3061, 2935, 2870, 1611, 1601, 1499, 1283, 1245, 1229, 1174, 1035, 750, 689. MS (ES) m/e, 311, 309. Anal. Calcd for C$_{18}$H$_{18}$N$_2$O$_3$: C, 69.66; H, 5.85; N, 9.03. Found C, 69.81; H, 5.85; N, 8.76.

c) Dimethyl-(3-{4-[5-(4-phenoxybutyl)-[1,3,4]oxadiazol-2-yl]phenoxy}propyl)amine

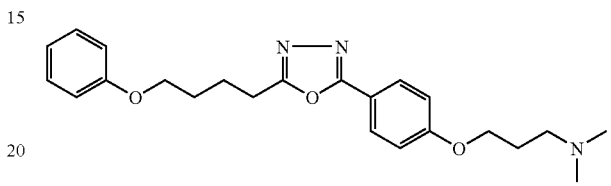

The above compound was prepared in a manner similar to that exemplified for the preparation of Example 19e, from 4-[5-(4-phenoxy butyl)-[1,3,4]oxadiazol-2-yl]phenol (0.865 g, 2.8 mmol), sodium hydride (0.256 g, 6.4 mmol), and 3-chloro-N,N-dimethyl propylamine HCl (0.485 g, 3.1 mmol) to afford the title compound as a crude mixture. Crystallization from hexane:Et$_2$O afforded 0.769 g (70%) of dimethyl-(3-{4-[5-(4-phenoxybutyl)-[1,3,4]oxadiazol-2-yl]phenoxy}propyl)amine.

$^1$H NMR (DMSO-d6) δ7.88 (d, 2H, J=9 Hz), 7.23–7.30 (m, 2H), 7.10 (d, 2H, J=9 Hz), 6.89–6.94 (m, 3H), 4.08 (t, 2H, J=7 Hz), 4.02 (t, 2H, J=6 Hz), 2.99 (t, 2H, J=7 Hz), 2.35 (t, 2H, J=7 Hz), 2.14 (s, 6H), 1.81–1.95 (m, 6H). IR (CHCl$_3$, cm$^{-1}$) 2952, 2873, 2825, 2777, 1615, 1589, 1500, 1470, 1248, 1174. MS (FD) m/e, 395. Anal. Calcd for C$_{23}$H$_{29}$N$_3$O$_3$: C, 69.85; H, 7.39; N, 10.62. Found C, 69.87; H, 7.54; N, 10.26. Mp(° C.)=78.

Example 34

Preparation of 4-[5-(2-Phenoxy-ethylsulfanylmethyl)-[1,3,4]oxadiazol-2-yl]-N-(2-pyrrolidin-1-yl-ethyl)-benzamide from 4-[5-(Phenoxyethylsulfanyl-methyl)-[1,3,4]oxadiazol-2-yl]benzoic acid and N-(2-aminoethyl)pyrrolidine

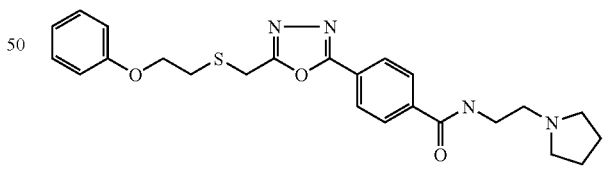

To a slurry of the 4-[5-(Phenoxyethylsulfanylmethyl)-[1,3,4]oxadiazol-2-yl]benzoic acid (0.054 g, 0.15 mmole), 1-hydroxybenzotriazole hydrate (0.024 g, 0.18 mmole), and N-(2-aminoethyl)pyrrolidine (0.023 ml, 0.18 mmole) in 2 ml dichloromethane at room temperature was added diisopropylcarbodiimide (0.047 ml, 0.30 mmole). The reaction was stirred 16 h at ambient temperature, then polystyrene methylisocyanate (0.06 mmole) and dichloromethane were added and the reaction was stirred at room temperature overnight. The reaction mixture was evaporated, taken up in 3 ml methanol, and purified over an SCX column (elution with 2 M ammonia in methanol) to afford 0.067 g (99%) of 4-[5-(2-Phenoxy-ethylsulfanylmethyl)-[1,3,4]oxadiazol-2-yl]-N-(2-pyrrolidin-1-yl-ethyl)-benzamide.

$^1$H NMR(CDCl$_3$) δ 8.08(d, 2H, J=9), 7.90(d, 2H, J=9), 7.26(m, 2H), 7.01(m, 1H), 6.94(t, 1H, J=8), 6.88(d, 2H, J=9), 4.22(t, 2H, J=6), 4.07(s, 2H), 3.57(q, 2H, J=6), 3.06(t, 2H, J=6), 2.74(t, 2H, J=6), 2.60(m, 4H), 1.80(m, 4H). MS (ES) m/e, 452.19 (C$_{24}$H$_{28}$N$_4$O$_3$S).

Example 35

Preparation of 4-[5-(2-Phenoxy-ethylsulfanylmethyl)-[1,3,4]oxadiazol-2-yl]-N-(3-pyrrolidin-1-yl-propyl)-benzamide from 4-[5-(Phenoxyethylsulfanylmethyl)-[1,3,4]oxadiazol-2-yl]benzoic acid and N-(3-aminopropyl)pyrrolidine The above compound was prepared in a manner similar to that exemplified for the preparation of Example 34, from 4-[5-(Phenoxyethylsulfanylmethyl)-[1,3,4]oxadiazol-2-yl] benzoic acid and N-(4-aminobutyl)pyrrolidine to afford 4-[5-(2-Phenoxy-ethylsulfanylmethyl)-[1,3,4]oxadiazol-2-yl]-N-(4-pyrrolidin-1-yl-butyl)-benzamide.

$^1$H NMR(CDCl$_3$) δ 8.25(m, 1H), 8.09(d, 2H, J=8), 7.88(d, 2H, J=8), 7.28(m, 2H), 6.95(t, 1H, J=7), 6.89(d, 2H, J=8), 4.22(t, 2H, J=7), 4.07(s, 2H), 3.47(q, 2H, J=7), 3.06(t, 2H, J=6), 2.48(m, 6H), 1.71(m, 8H). MS (ES) m/e, 480.22. Anal. Calcd for C$_{25}$H$_{30}$N$_4$O$_3$S.0.33H$_2$O: C, 64.17; H, 6.77; N, 11.51. Found C, 64.16; N, 6.58; H, 11.59.

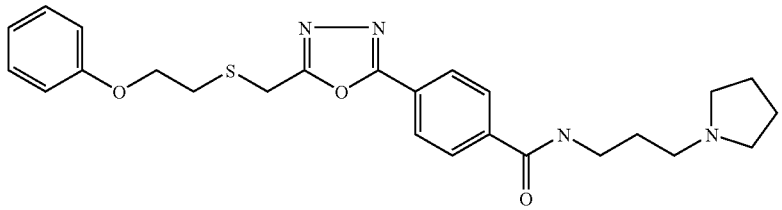

The above compound was prepared in a manner similar to that exemplified for the preparation of Example 34, from 4-[5-(Phenoxyethylsulfanylmethyl)-[1,3,4]oxadiazol-2-yl] benzoic acid and N-(3-aminopropyl)pyrrolidine to afford 4-[5-(2-Phenoxy-ethylsulfanylmethyl)-[1,3,4]oxadiazol-2-yl]-N-(3-pyrrolidin-1-yl-propyl)-benzamide.

$^1$H NMR(CDCl3) δ 9.29(m, 1H), 8.08(d, 2H, J=9), 7.99 (d, 2H, J=9), 7.27(m, 2H), 6.98(t, 1H, J=8), 6.89(d, 2H, J=7), 4.21(t, 2H, J=7), 4.07(s, 2H), 3.62(q, 2H, J=6), 3.06(t, 2H, J=6), 2.74(t, 2H, J=6), 2.59(m, 4H), 1.83(m, 6H).

MS (ES) m/e, 466.20. Anal. Calcd for C$_{25}$H$_{30}$N$_4$O$_3$S.0.5H$_2$O: C, 63.13; H, 6.75; N, 11.78. Found C, 63.33; H, 6.26; N, 11.95.

Example 36

Preparation 4-[5-(2-Phenoxy-ethylsulfanylmethyl)-[1,3,4]oxadiazol-2-yl]-N-(4-pyrrolidin-1-yl-butyl)-benzamide from 4-[5-(Phenoxyethylsulfanylmethyl)-[1,3,4]oxadiazol-2-yl]benzoic acid and N-(4-aminobutyl)pyrrolidine

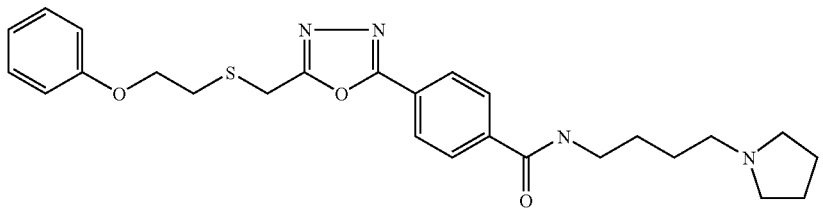

Example 37

Preparation N-[3-(4-Methyl-piperazin-1-yl)-propyl]-4-[5-(2-phenoxy-ethylsulfanylmethyl)-[1,3,4]oxadiazol-2-yl]-benzamide from 4-[5-(Phenoxyethylsulfanylmethyl)-[1,3,4]oxadiazol-2-yl]benzoic acid and 3-(4-Methyl-piperazin-1-yl)-propylamine

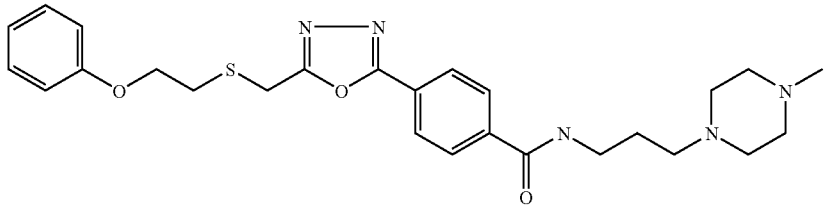

The above compound was prepared in a manner similar to that exemplified for the preparation of Example 34, from 4-[5-(Phenoxyethylsulfanylmethyl)-[1,3,4]oxadiazol-2-yl]benzoic acid and 3-(4-Methyl-piperazin-1-yl)-propylamine to afford N-[3-(4-Methyl-piperazin-1-yl)-propyl]-4-[5-(2-phenoxy-ethylsulfanyl methyl)-[1,3,4]oxadiazol-2-yl]-benzamide.

$^1$H NMR(CDCl$_3$) δ 8.09(m, 4H), 7.26(m, 2H), 6.95(t, 1H, J=8), 6.89(d, 2H, J=9), 4.22(t, 2H, J=8), 4.07(s, 2H), 4.00(m, 1H), 3.82(m, 1H), 3.64(q, 2H, J=7), 3.40(m, 1H), 3.06(t, 2H, J=6), 2.97(m, 6H), 2.51(m, 2H), 2.12(m, 1H), 1.77(m, 5H). MS (ES) m/e, 495.23. Anal. Calcd for C$_{26}$H$_{33}$N$_5$O$_3$S.HCl.H$_2$O: C, 56.77; H, 6.60; N, 12.73. Found C, 56.71; H, 6.82; N, 13.57.

Example 38

Preparation N-(1-Benzyl-piperidin-4-yl)-4-[5-(2-phenoxy-ethylsulfanylmethyl)-[1,3,4]oxadiazol-2-yl]-benzamide from 4-[5-(Phenoxyethylsulfanylmethyl)-[1,3,4]oxadiazol-2-yl]benzoic acid and 1-Benzyl-piperidin-4-ylamine

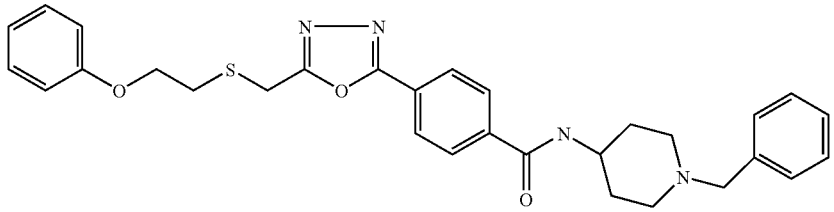

The above compound was prepared in a manner similar to that exemplified for the preparation of Example 34, from 4-[5-(phenoxyethylsulfanylmethyl)-[1,3,4]oxadiazol-2-yl] benzoic acid and 1-Benzyl-piperidin-4-ylamine to afford N-(1-Benzyl-piperidin-4-yl)-4-[5-(2-phenoxyethylsulfanylmethyl)-[1,3,4]oxadiazol-2-yl]-benzamide.

$^1$H NMR(CDCl$_3$) δ 8.09(d, 2H, J=9), 7.86(d, 2H, J=9), 7.31(m, 2H), 7.24(m, 5H), 6.95(t, 1H, J=8), 6.89(d, 2H, J=9), 4.21(d, 1H, J=7), 4.07(s, 2H), 4.03(m, 1H), 3.52(s, 2H), 3.06(t, 2H, J=7), 2.88(d, 2H, J=11), 2.14(t, 2H, J=10), 2.04(d, 2H, J=13), 1.58(m, 2H). MS (ES) m/e, 528.22. Anal. Calcd for C$_{30}$H$_{32}$N$_4$O$_3$S: C, 68.16; H, 6.10; N, 10.60. Found C, 67.78; H, 6.11; N, 10.53.

Example 39

Preparation N-(2-Morpholin-4-yl-ethyl)-4-[5-(2-phenoxy-ethylsulfanylmethyl)-[1,3,4]oxadiazol-2-yl]-benzamide from 4-[5-(Phenoxyethylsulfanylmethyl)-[1,3,4]oxadiazol-2-yl]benzoic acid and 2-Morpholin-4-yl-ethylamine

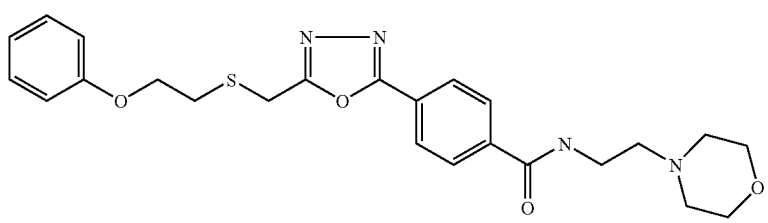

The above compound was prepared in a manner similar to that exemplified for the preparation of Example 34, from 4-[5-(Phenoxyethylsulfanylmethyl)-[1,3,4]oxadiazol-2-yl] benzoic acid and 2-morpholin-4-yl-ethylamine to afford N-(2-Morpholin-4-yl-ethyl)-4-[5-(2-phenoxy-ethylsulfanyl-methyl)-[1,3,4]oxadiazol-2-yl]-benzamide.

$^1$H NMR(CDCl$_3$) δ 8.11(d, 2H, J=9), 7.90(d, 2H, J=9), 7.28(m, 2H), 6.94(t, 1H, J=9), 6.89(d, 2H, J=8), 6.85(m, 1H), 4.21(t, 2H, J=7), 4.08(s, 2H), 3.75(t, 4H, J=2), 3.58(q, 2H, J=6), 3.06(t, 2H, J=6), 2.63(t, 2H, J=3), 2.52(m, 4H). MS (ES) m/e, 468.18. Anal. Calcd for C$_{24}$H$_{28}$N$_4$O$_4$S: C, 61.52; H, 6.02; N, 11.96. Found C, 61.36; H, 5.94; 11.95.

Example 40

Preparation N-(3-Morpholin-4-yl-propyl)-4-[5-(2-phenoxy-ethylsulfanylmethyl)-[1,3,4]oxadiazol-2-yl]-benzamide from 4-[5-(Phenoxyethylsulfanylmethyl)-[1,3,4]oxadiazol-2-yl]benzoic acid and 3-Morpholin-4-yl-propylamine

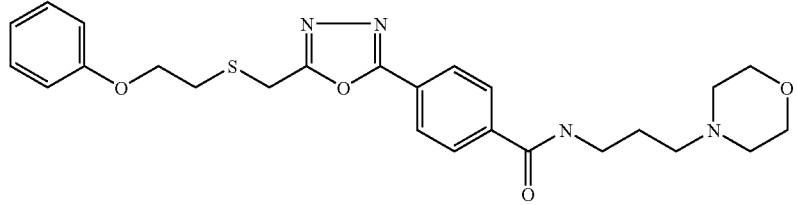

The above compound was prepared in a manner similar to that exemplified for the preparation of Example 34, from 4-[5-(Phenoxyethylsulfanylmethyl)-[1,3,4]oxadiazol-2-yl] benzoic acid and 3-morpholin-4-yl-propylamine to afford N-(3-Morpholin-4-yl-propyl)-4-[5-(2-phenoxyethylsulfa-nylmethyl)-[1,3,4]oxadiazol-2-yl]-benzamide.

$^1$H NMR(CDCl$_3$) δ 8.29(m, 1H), 8.12(d, 2H, J=9), 7.95(d, 2H, J=9), 7.25(m, 2H), 6.95(t, 1H, J=8), 6.89(d, 2H, J=9), 4.22(t, 2H, J=6), 4.08(s, 2H), 3.70(t, 4H, J=6), 3.61(q, 2H, J=5), 3.06(t, 2H, J=8), 2.58(t, 2H, J=7), 2.51(m, 4H), 1.81 (m, 2H, J=6). MS (ES) m/e, 482.20. Anal. Calcd for C$_{25}$H$_{30}$N$_4$O$_4$S.2.33H$_2$O: C, 57.23; H, 6.66; N, 10.68. Found C, 57.12; H, 5.69; N, 10.74.

Example 41

Preparation N-(3-Imidazol-1-yl-propyl)-4-[5-(2-phenoxy-ethylsulfanylmethyl)-[1,3,4]oxadiazol-2-yl]-benzamide from 4-[5-(Phenoxyethylsulfanylmethyl)-[1,3,4]oxadiazol-2-yl]benzoic acid and 3-Imidazol-1-yl-propylamine

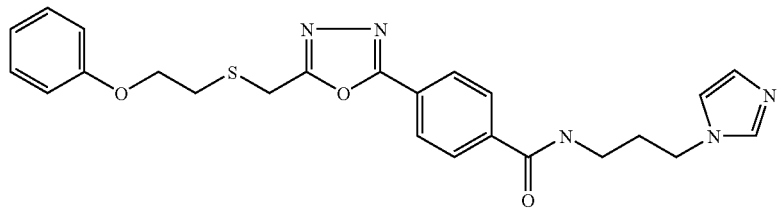

The above compound was prepared in a manner similar to that exemplified for the preparation of Example 34, from 4-[5-(Phenoxyethylsulfanylmethyl)-[1,3,4]oxadiazol-2-yl] benzoic acid and 3-imidazol-1-yl-propylamine to afford N-(3-Imidazol-1-yl-propyl)-4-[5-(2-phenoxy-ethylsulfanyl-methyl)-[1,3,4]oxadiazol-2-yl]-benzamide.

$^1$H NMR(CDCl$_3$) δ 8.08(d. 2H, J=9), 7.85(d, 2H, J=9), 7.56(s, 1H), 7.26(m, 2H), 7.07(s, 1H), 6.98(s, 1H), 6.95(t, 1H, J=8), 6.89(d, 2H, J=9), 6.43(t, 1H, J=6), 4.21(t, 2H, J=7), 4.07(t, 4H, J=7), 3.51(q, 2H, J=7), 3.05(t, 2H, J=7), 2.18(m, 2H, J=7). MS (ES) m/e, 463.17.

Example 42

Preparation N-(3-Dimethylamino-propyl)-N-methyl-4-[5-(2-phenoxy-ethylsulfanylmethyl)-[1,3,4]oxadia-zol-2-yl]-benzamide from 4-[5-(Phenoxyethylsulfa-nylmethyl)-[1,3,4]oxadiazol-2-yl]benzoic acid and N,N,N'-Trimethyl-propane-1,3-diamine

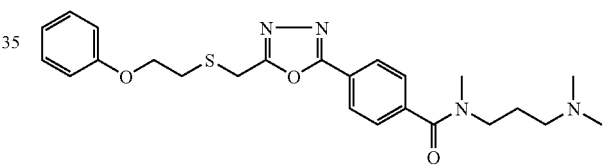

The above compound was prepared in a manner similar to that exemplified for the preparation of Example 34, from 4-[5-(Phenoxyethylsulfanylmethyl)-[1,3,4]oxadiazol-2-yl] benzoic acid and N,N,N'-Trimethyl-propane-1,3-diamine to afford N-(3-Dimethylamino-propyl)-N-methyl-4-[5-(2-phe-noxy-ethylsulfanylmethyl)-[1,3,4]oxadiazol-2-yl]-benza-mide.

$^1$H NMR(CDCl$_3$) δ8.06(d, 2H, J=9), 7.52(d, 2H, J=9), 7.25(m, 2H), 6.94(t, 1H, J=9), 6.89(d, 2H, J=9), 4.21(t, 2H, J=7), 4.07(s, 2H), 3.59(t, 1H, J=7), 3.28(t, 1H, J=8), 3.08(q, 2H, J=7), 3.06(s, 1.5H), 2.96(s, 1.5H), 2.36(t, 1H, J=9), 2.26(s, 3H), 2.10(m, 1H), 2.09(s, 3H), 1.85(m, 1H), 1.69(m, 1H). MS (ES) m/e, 454.20. Anal. Calcd for C$_{24}$H$_{30}$N$_4$O$_3$S.0.33H$_2$O: C, 62.59; H, 6.71; N, 12.16. Found C, 62.44; H, 6.54; N, 12.48.

Example 43

Preparation N-[3-(ethyl-phenyl-amino)-propyl]-4-[5-(2-phenoxy-ethylsulfanylmethyl)-[1,3,4]oxadiazol-2-yl]-benzamide from 4-[5-(Phenoxyethylsulfanylmethyl)-[1,3,4]oxadiazol-2-yl]benzoic acid and N1-Methyl-N1-phenyl-propane-1,3-diamine

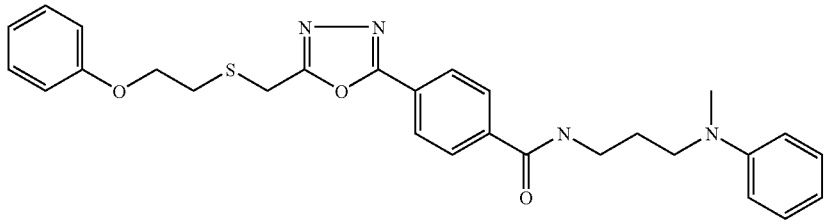

The above compound was prepared in a manner similar to that exemplified for the preparation of Example 34, from 4-[5-(Phenoxyethylsulfanylmethyl)-[1,3,4]oxadiazol-2-yl] benzoic acid and N1-Methyl-N1-phenyl-propane-1,3-diamine to afford N-[3-(Methyl-phenyl-amino)-propyl]-4-[5-(2-phenoxy-ethylsulfanylmethyl)-[1,3,4]oxadiazol-2-yl]-benzamide.

$^1$H NMR(CDCl$_3$) δ 8.04(d, 2H, J=9), 7.84(d, 2H, J=9), 7.26(m, 4H), 6.95(t, 1H, J=8), 6.87(d, 2H, J=9), 6.77(m, 3H), 6.53(t, 11H, J=7), 4.21(t, 2H, J=6), 4.07(s, 2H), 3.57(q, 2H, J=7), 3.47(t, 2H, J=7), 3.06(t, 2H, J=6), 2.93(s, 3H), 1.95(m, 2H, J=7). MS (ES) m/e, 502.20. Anal. Calcd for C$_{28}$H$_{30}$N$_4$O$_3$S.0.33H$_2$O: C, 66.12; H, 6.08; N, 11.01. Found C, 66.91; H, 5.71; N, 11.03.

Example 44

Preparation of 4-{5-[2-(2,4-dichlorophenoxy)-ethylsulfanylmethyl]-[1,3,4]-oxadiazol-2-yl}-N-(3-dimethylaminopropyl)-benzamide

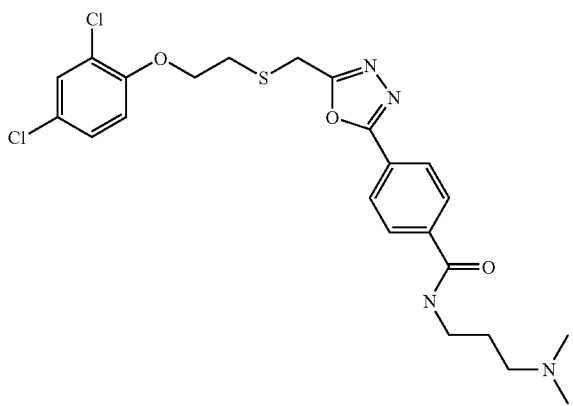

a) 4-N'-{2-[2-(2,4-dichlorophenoxy)-ethylsulfanyl]-acetyl}-hydrazinocarbonyl)-benzoic acid methyl ester

A solution of 2-[[2-(2,4-dichlorophenoxy)ethyl]-[thio] acetic acid hydrazide (1.48 g, 5.0 mmol), terephthalic acid, monomethyl ester chloride (0.993 g, 5.0 mmol), and triethylamine (0.836 mL, 6.0 mmol) in 35 mL THF was stirred at room temperature for 6 h. The resultant precipitate was collected by filtration, washed with THF, and the filtrate was concentrated in vacuo to afford an off-white solid, which was crystallized from ethanol to afford 1.94 g (85%) of 4-(N'-{2-[2-(2,4-dichlorophenoxy)-ethylsulfanyl]-acetyl}-hydrazinocarbonyl)-benzoic acid methyl ester as a white solid (1156–157° C., MW 456.03).

$^1$H NMR (CDCl$_3$) δ 9.30 (d, 1H, J=6 Hz), 8.82 (d, 1H, J=6 Hz), 8.11 (d, 2H, J=8 Hz), 7.84 (d, 2H, J=8 Hz), 7.36 (d, 1H, J=2 Hz), 7.17 (dd, 1H, J=2 and 9 Hz), 6.87 (d, 1H, J=9 Hz), 4.30 (t, 2H, J=6 Hz), 3.95 (s, 3H), 3.59 (s, 2H), and 3.16 (t, 2H, J=6 Hz). IR KBr, cm$^{-1}$) 3193, 1714, 1604, 1568, 1481, 1465, 1295, 1105, and 869. MS (ESI) m/e 455, 457, 459, 461. Anal. Calcd for C$_{19}$H$_{18}$Cl$_2$N$_2$O$_5$S: C, 49.90; H, 3.97; Cl, 15.50; N, 6.13; S, 7.01. Found C, 49.99; H, 3.98; Cl, 15.79; N, 6.15; S, 7.37.

b) 4-{5-[2-(2,4-dichlorophenoxy)-ethylsulfanylmethyl]-[1,3,4]oxadiazol-2-yl}-benzoic acid methyl ester

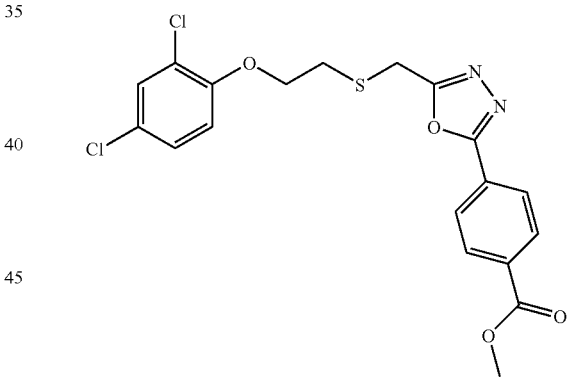

A heterogeneous mixture of 4-(N'-{2-[2-(2,4-dichlorophenoxy)-ethylsulfanyl]-acetyl}-hydrazinocarbonyl)-benzoic acid methyl ester (0.228 g, 0.5 mmol), triphenylphosphine (0.265 g, 1.0 mmol), triethylamine (0.251 mL, 1.8 mmol) and carbon tetrachloride (0.202 mL, 2.06 mmol) in 4 mL acetonitrile was stirred at room temperature for 4 h. The resultant precipitate was collected by filtration, washed with acetonitrile and diethyl ether, and the solid was dried in vacuo at 40° C. for 2 h to afford 0.153 g (70%) of 4-{5-[2-(2,4-dichlorophenoxy)-ethylsulfanylmethyl]-[1,3,4] oxadiazol-2-yl}-benzoic acid methyl ester as a white solid (MP 148–152° C., MW 438.02).

$^1$H NMR (CDCl$_3$) δ 8.17 (d, 2H, J=8 Hz), 8.10 (d, 2H, J=8 Hz), 7.34 (d, 1H, J=2 Hz), 7.17 (dd, 1H, J=2 and 9 Hz), 6.84 (d, 1H, J=9 Hz), 4.26 (t, 2H, J=6 Hz), 4.18 (s, 2H), 3.97 (s, 3H), and 3.12 (t, 2H, J=6 Hz). IR (KBr, cm$^{-1}$) 2940, 1717, 1485, 1470, 1437, 1432, 1287, 1252, 1236, 1114, 1062, 1010, 776, 719, and 715. MS (ES) m/e 437, 439, 441, 443.

Anal. Calcd for $C_{19}H_{16}Cl_2N_2O_4S$: C, 51.95; H, 3.67; Cl, 16.14; N, 6.38; S, 7.30. Found C, 52.32; H, 3.69; Cl, 15.86; N, 6.38; S, 7.33.

c) 4-f{5-[2-(2,4-dichlorophenoxy)-ethylsulfanylmethyl]-[1,3,4]oxadiazol-2-yl}-benzoic acid

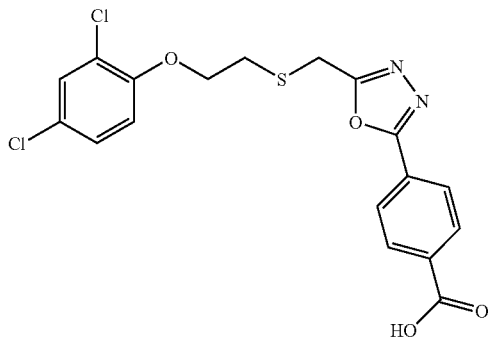

A suspension of 4-{5-[2-(2,4-dichlorophenoxy)-ethylsulfanylmethyl]-[1,3,4]oxadiazol-2-yl}-benzoic acid methyl ester (0.22 g, 0.5 mmol), and lithium hydroxide (0.036 g, 1.5 mmol) in 3.5 mL THF and 1.5 mL $H_2O$ was stirred at room temperature for 5 h. The THF was removed in vacuo, and the remaining aqueous solution adjusted to pH 1.7 with concentrated HCl. The resultant precipitate was collected by filtration, washed with $H_2O$, and dried in vacuo at 40° C. to afford 0.134 g (63%) of 4-{5-[2-(2,4-dichlorophenoxy)-ethylsulfanylmethyl]-[1,3,4]oxadiazol-2-yl}-benzoic acid as a white solid (1161–163° C., MW 424.01).

$^1$H NMR (DMSO-$d_6$) δ 13.30 (bs, 1H), 8.11 (d, 2H, J=9 Hz), 8.04 (d, 2H, J=9 Hz), 7.52 (d, 1H, J=2 Hz), 7.33 (dd, H, J=2 and 9 Hz), 7.17 (d, 1H, J=9 Hz), 4.28 (t, 2H, J=6 Hz), 4.27 (s, 2H), and 3.05 (t, 2H, J=6 Hz). IR (KBr, cm$^{-1}$) 2910, 2670, 2550, 1704, 1686, 1551, 1485, 1433, 1291, 1262, 1072, 871, and 714. MS (ESI) m/e 423, 425, 427, 429. Anal. Calcd for $C_{18}H_{14}Cl_2N_2O_4S$: C, 50.84; H, 3.32; Cl, 16.67; N, 6.59; S, 7.54. Found C, 50.78; H, 3.40; Cl, 16.83; N, 6.55; S, 7.74.

d) 4-{5-[2-(2,4-dichlorophenoxy)-ethylsulfanylmethyl]-[1,3,4]-oxadiazol-2-yl}-N-(3-dimethylaminopropyl)-benzamide

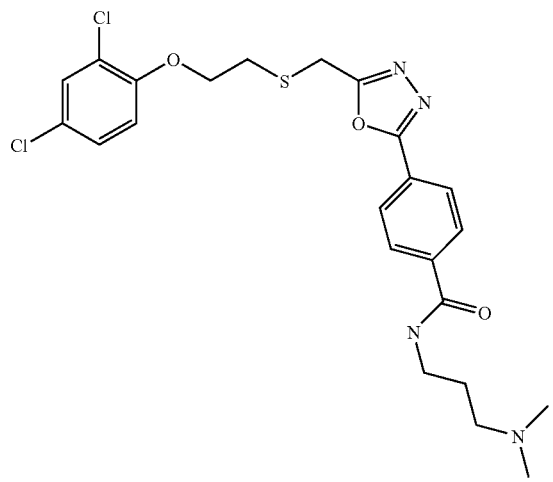

A solution of 4-{5-[2-(2,4-dichlorophenoxy)-ethylsulfanylmethyl]-[1,3,4]oxadiazol-2-yl}-benzoic acid (0.361 g, 0.85 mmol), and 1,1'-carbonyldiimidazole (0.139 g, 0.86 mmol) in 10.0 mL THF was stirred at 60° C. for 0.5 h. The reaction solution was allowed to cool to ambient temperature followed by addition of 3-(dimethylamino)propylamine (0.129 mL, 1.02 mmol), then stirred at room temperature for 3 h. The THF was concentrated in vacuo and the resultant precipitate was collected by filtration, washed with ethyl acetate and diethyl ether, and dried in vacuo at 40° C. to afford 0.25 g (57%) of 4-{5-[2-(2,4-dichlorophenoxy)-ethylsulfanylmethyl]-[1,3,4]-oxadiazol-2-yl}-N-(3-dimethylaminopropyl)-benzamide as a white solid (MP 140–141° C., MW 508.11).

$^1$H NMR (CDCl$_3$) δ 8.86 (bs, 1H), 8.09 (d, 2H, J=9 Hz), 7.92 (d, 2H, J=9 Hz), 7.34 (d, 1H, J=2 Hz), 7.17 (dd, 1H, J=2 and 9 Hz), 6.84 (d, 1H, J=9 Hz), 4.26 (t, 2H, J=6 Hz), 4.17 (s, 2H), 3.61 (m, 2H), 3.11 (t, 2H, J=6 Hz), 2.61 (m, 2H), 2.38 (bs, 6H), 1.83 (m, 2H). IR (KBr, cm$^{-1}$) 3335, 2942, 2761, 2722, 1635, 1555, 1484, 1105, and 803. MS (ESI) m/e 507, 509, 511, 513. Anal. Calcd for $C_{23}H_{26}Cl_2N_4O_3S$: C, 54.23; H, 5.14; Cl, 13.92; N, 11.00; S, 6.29. Found C, 54.03; H, 5.15; Cl, 13.98; N, 10.98; S, 6.25.

Example 45

Preparation of N-(3-dimethylaminopropyl)-4-[5-(2-phenoxyethanesulfinylmethyl)-[1,3,4]oxadiazol-2-yl]-benzamide

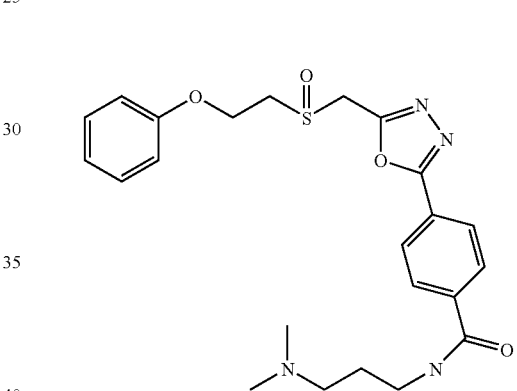

A solution of the N-(3-dimethylaminopropyl)4-[5-(2-phenoxyethylsulfanylmethyl)-[1,3,4]oxadiazol-2-yl]-benzamide (0.044 g, 0.1 mmol) prepared in Example 32, glacial acetic acid (1.14 mL, 20.0 mmol), and 3-chloroperoxybenzoic acid (0.022 g, 0.1 mmol) in 1 mL of dichloromethane was stirred at room temperature for 1 h. The mixture was quenched with 3 mL saturated sodium sulfite followed by addition of 6 mL $H_2O$ and 1 mL dichloromethane. The resultant biphasic solution was adjusted to pH 10.3 with 1N NaOH, the solvent layers separated, and the aqueous phase back extracted with 6×10 mL dichloromethane. The combined dichloromethane extracts were washed with $H_2O$ and brine, dried over anhydrous sodium sulfate, filtered, and concentrated in vacuo to afford 0.043 g (95%) of N-(3-dimethylaminopropyl)-4-[5-(2-phenoxyethanesulfinylmethyl)-[1,3,4]oxadiazol-2-yl]-benzamide as a white solid WP 112–114° C., MW 456.57). Analytical HPLC: 93% purity.

$^1$H NMR (CDCl$_3$) δ 8.88 (bs, 1H), 8.12 (d, 2H, J=8 Hz), 7.95 (d, 2H, J=8 Hz), 7.30 (t, 2H, J=8 Hz), 7.01 (t, 1H, J=7 Hz), 6.93 (d, 2H, J=8 Hz), 4.62 (d, 1H, J=14 Hz), 4.48 (m, 2H), 4.36 (d, 1H, J=14 Hz), 3.61 (m, 2H), 3.40 (m, 2H), 2.65 (m, 2H), 2.41 (bs, 6H), and 1.86 (m, 2H). IR (KBr, cm$^{-1}$) 3344, 2922, 2761, 1636, 1549, 1497, 1251, and 1044. MS (ESI) m/e 457, 455. Anal. Calcd for $C_{23}H_{28}N_4O_4S$: C, 60.51; H, 6.18; N, 12.27; S, 7.02. Found C, 59.91; H, 6.16; N, 11.61; S, 6.50.

Example 46

Preparation of N-(3-dimethylaminopropyl)-4-[5-(2-phenoxyethanesulfonylmethyl)-[1,3,4]oxadiazol-2-yl]-benzamide

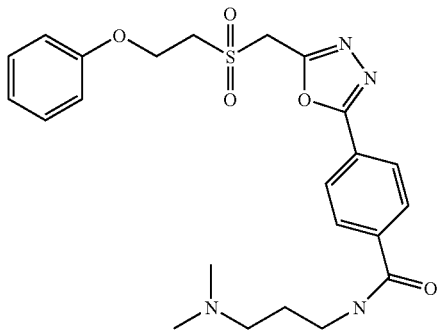

A solution of the N-(3-dimethylaminopropyl)-4-[5-(2-phenoxyethylsulfanylmethyl)-[1,3,4]oxadiazol-2-yl]-benzamide (0.022 g, 0.05 mmol) prepared in Example 32, glacial acetic acid (0.58 mL, 10.0 mmol), and 3-chloroperoxybenzoic acid (0.022 g, 0.1 mmol) in 1 mL of dichloromethane was stirred at room temperature for 19 h. The mixture was quenched with 3 mL saturated sodium sulfite followed by addition of 2 mL H$_2$O and 4 mL dichloromethane. The resultant biphasic solution was adjusted to pH 10.3 with 1N NaOH, the solvent layers separated, and the aqueous phase back extracted with 3×15 mL dichloromethane. The combined dichloromethane extracts were washed with H$_2$O and brine, dried over anhydrous sodium sulfate, filtered, and concentrated in vacuo to afford 0.017 g (73%) of a mixture composed primarily of N-(3-dimethylaminopropyl)-4-[5-(2-phenoxyethanesulfonylmethyl)-[1,3,4]oxadiazol-2-yl]-benzamide and a minor amount of N-(3-dimethylaminopropyl)-4-[5-(2-phenoxyethanesulfinylmethyl)-[1,3,4]oxadiazol-2-yl]-benzamide as a white solid. A solution of the preceding mixture (0.015 g, ~0.03 mmol), osmium tetroxide (2.5 weight percent solution in 2-methyl-2-propanol, 0.003 mL, 0.25 □M), and 4-methylmorpholine N-oxide (0.003 g, 0.025 mmol) in 1 mL of THF and 0.5 mL dichloromethane was stirred at room temperature for 1 h. The THF was removed in vacuo, the resultant gum redissolved in dichloromethane, washed with H$_2$O and brine, dried over anhydrous sodium sulfate, filtered, and concentrated in vacuo to afford 0.008 g of a black solid. Purification by column chromatography on silica gel (isocratic elution with 8:2 CHCl$_3$/2.0 M ammonia in methanol) afforded 0.003 g (13%) of N-(3-dimethylaminopropyl)-4-[5-(2-phenoxyethanesulfonylmethyl)-[1,3,4]oxadiazol-2-yl]-benzamide as an off-white solid (MW 472.57).

$^1$H NMR (CDCl$_3$) δ 8.88 (bs, 1H), 8.11 (d, 2H, J=8 Hz), 7.95 (d, 2H, J=8 Hz), 7.33 (t, 2H, J=8 Hz), 7.04 (t, 1H, J=7 Hz), 6.97 (d, 2H, J=8 Hz), 4.86 (s, 2H), 4.53 (t, 2H, J=5 Hz), 3.71 (t, 2H, J=5 Hz), 3.61 (m, 2H), 2.65 (m, 2H), 2.41 (bs, 6H), and 1.87 (m, 2H). MS (ES) m/e 471, 473.

Example 47

Preparation of N-(3-dimethylaminopropyl)-4-[5-(3-phenoxypropylsulfanylmethyl)-[1,3,4]oxadiazol-2-yl]-benzamide

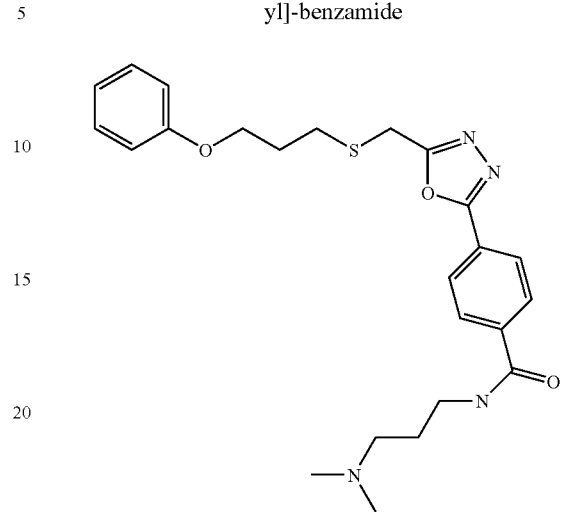

a) 3-chloropropoxy benzene

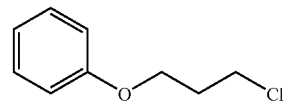

A solution of phenol (9.41 g, 0.1 M), 1-bromo-3-chloropropane (15.74 g, 0.1 M) and potassium carbonate (13.8 g, 0.1 M) in 150 mL of DMF was stirred at room temperature for 48 h, then sonicated at 50–60° C. for 12 h. The DMF was removed in vacuo, the residue diluted with EtOAc, washed with water, 5 N NaOH, and brine, dried over anhydrous magnesium sulfate, filtered and concentrated to afford 14.4 g (84%) of 3-chloropropoxy benzene as a clear oil.

$^1$H NMR (DMSO-d6) δ 7.3 (m, 2H), 6.9 (m, 3H), 4.1 (t, 2H, J=6 Hz), 3.6 (t, 2H, J=6 Hz), and 2.1 (quintet, 2H, J=6 Hz). IR (CHCl$_3$, cm$^{-1}$) 1600, 1587, 1498, 1470, 1244, 1226, 1172, and 1039. MS (EI) m/e 170. Anal. Calcd for C$_9$H$_9$H$_{11}$ClO: C, 63.35; H, 6.50; Cl, 20.78. Found C, 65.60; H, 6.57; Cl, 17.41.

b) (3-phenoxypropylsulfanyl)-acetic acid methyl ester

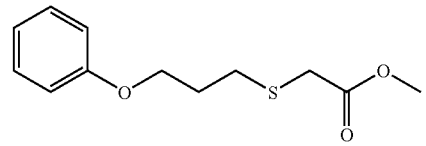

A solution of 3-chloropropoxy benzene (1.00 g, 5.86 mmol), thioglycolate methyl ester (0.622 g, 5.86 mmol) and potassium carbonate (1.00 g, 7.25 mmol) in 5 mL of DMF was stirred at room temperature for 48 h, then sonicated at 50–60° C. for 8 h, then stirred at room temperature for an additional 64 h. The mixture was diluted with EtOAc, washed with water and brine, dried over anhydrous magnesium sulfate, filtered and concentrated to afford 1.29 g (92%) of (3-phenoxypropylsulfanyl)-acetic acid methyl ester as a clear oil.

$^1$H NMR (DMSO-d6) δ 7.3 (m, 2H), 6.9 (m, 3H), 4.0 (t, 2H, J=6 Hz), 3.65 (s, 3H), 3.4 (s, 2H), 2.7 (t, 2H, J=7 Hz), and 1.9 (m, 2H). IR (CHCl₃, cm⁻¹) 2954, 1734, 1600, 1587, 1497, 1469, 1437, 1289, and 1244. MS (FD) m/e 241. Anal. Calcd for $C_{12}H_{16}O_3S$: C, 59.98; H, 6.71. Found C, 58.81; H, 6.24.

c) (3-phenoxypropylsulfanyl)-acetic acid

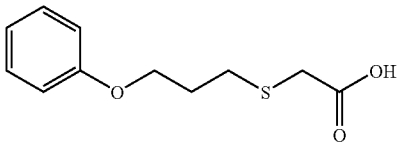

A solution of (3-phenoxypropylsulfanyl)-acetic acid methyl ester (1.20 g, 5.0 mmol) and 1 N NaOH (15.0 mL, 15 mmol) in 15 mL of methanol was stirred at room temperature for 48 h. The solvent was removed in vacuo, the residue triturated with EtOAc, then dissolved in 1 N HCl and EtOAc. The organic layer was washed with water and brine, dried over anhydrous magnesium sulfate, filtered and concentrated to afford 0.853 g (75%) of 3-phenoxypropylsulfanyl)-acetic acid as a clear oil.

¹H NMR (DMSO-d6) δ 12.5 (br s, 1H), 7.3 (m, 2H), 6.9 (m, 3H), 4.0 (t, 2H, J=6 Hz), 3.3 (s, 2H), 2.7 (t, 2H, J=7 Hz), and 2.0 (quintet, 2H, J=6 Hz). IR (CHCl₃, cm⁻¹) 3010, 2944, 1711, 1601, 1497, 1301, 1290, 1244, and 1172. MS (ESI) m/e 227, 225. Anal. Calcd for $C_{11}H_{14}O_3S$: C, 58.38; H, 6.23; S, 14.17. Found C, 58.16; H, 6.20; S, 13.78.

d) 4-[5-(3-phenoxypropylsulfanylmethyl)-[1,3,4]oxadiazol-2-yl]-benzoic acid methyl ester

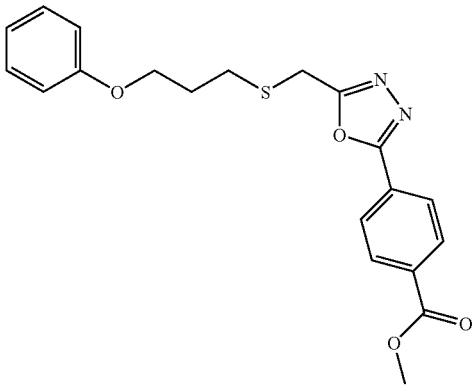

The above compound was prepared in a manner similar to that exemplified for the preparation of Example 1b, from 4-(1H-tetrazol-5-yl)-benzoic acid methyl ester (0.714 g, 3.5 mmol) and (3-phenoxypropylsulfanyl)-acetic acid (0.8 g, 3.54 mmol). Purification by column chromatography on silica gel (elution with linear gradient of 15–100% ethyl acetate/hexane) afforded 0.985 g (73%) of 4-[5-(3-phenoxypropylsulfanylmethyl)-[1,3,4]oxadiazol-2-yl]-benzoic acid methyl ester as a tan solid (W 97–100° C., MW 384.46).

¹H NMR (CDCl₃) δ 8.17 (d, 2H, J=9 Hz), 8.12 (d, 2H, J=9 Hz), 7.26 (t, 2H, J=8 Hz), 6.94 (t, 1H, J=8 Hz), 6.87 (d, 2H, J=8 Hz), 4.06 (t, 2H, J=6 Hz), 3.97 (s, 31), 3.96 (s, 2H), 2.86 (t, 2H, J=7 Hz), and 2.11 (m, 2H). IR (KBr, cm⁻¹) 2920, 1718, 1604, 1439, 1280, 1254, 1109, 755, and 709. MS (ES) m/e 385, 383. Anal. Calcd for $C_{20}H_{20}N_2O_4S$: C, 62.48; H, 5.24; N, 7.29; S, 8.34. Found C, 62.90; H, 5.77; N, 7.30; S, 8.81.

e) 4-[5-(3-phenoxypropylsulfanylmethyl)-[1,3,4]oxadiazol-2-yl]-benzoic acid

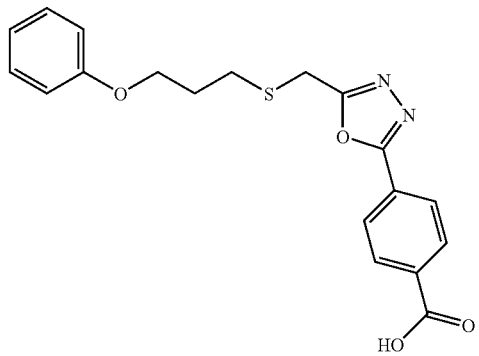

A suspension of 4-[5-(3-phenoxypropylsulfanylmethyl)-[1,3,4]oxadiazol-2-yl]-benzoic acid methyl ester (0.961 g, 2.5 mmol), and lithium hydroxide (0.183 g, 7.5 mmol) in 9 mL THF and 4 mL H₂O was stirred at room temperature for 4 h. The THF was removed in vacuo, an additional 10 mL of H₂O was added, and the heterogeneous aqueous mixture was adjusted to pH 1.8 with concentrated HCl. The resultant precipitate was collected by filtration, washed with H₂O, and dried in vacuo at 40° C. to afford 0.917 g (99%) of 4-[5-(3-phenoxypropylsulfanylmethyl)-[1,3,4]oxadiazol-2-yl]-benzoic acid as an off-white solid (M 180–185° C., MW 370.43).

¹H NMR (DMSO-d6) δ13.30 (bs, 1H), 8.11 (d, 2H, J=9 Hz), 8.07 (d, 2H, J=9 Hz), 7.23 (t, 2H, J=8 Hz), 6.88 (m, 3H), 4.15 (s, 2H), 4.01 (t, 2H, J=6 Hz), 2.78 (t, 2H, J=7 Hz), and 1.99 (m; 2H). IR (KBr, cm⁻¹) 2997, 2643, 2522, 1709, 1471, 1267, 1242, 753, and 714. MS (ESI) m/e 371, 369. Anal. Calcd for $C_{19}H_{18}N_2O_4S$: C, 61.61; H, 4.90; N, 7.56; S, 8.66. Found C, 62.26; H, 5.52; N, 7.54; S, 8.29.

f) N-(3-dimethylaminopropyl)-4-[5-(3-phenoxypropylsulfanylmethyl)-[1,3,4]oxadiazol-2-yl]-benzamide

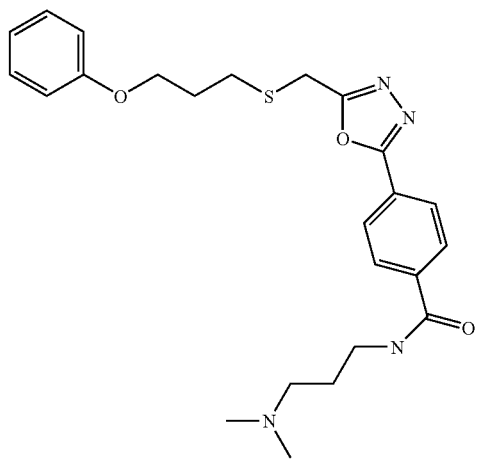

A solution of 4-[5-(3-phenoxypropylsulfanylmethyl)-[1,3,4]oxadiazol-2-yl]-benzoic acid (0.37 g, 1.0 mmol), and 1,1'-carbonyldiimidazole (0.164 g, 1.01 mmol) in 10.0 mL THF was stirred at 60° C. for 0.5 h. The reaction solution was allowed to cool to ambient temperature followed by addition of 3-(dimethylamino)propylamine (0.152 mL, 1.2 mmol), then stirred at room temperature for 6 h. The THF was concentrated in vacuo, and the oily residue redissolved in ethyl acetate/H₂O. The solvent layers were separated, and the ethyl acetate layer was washed with H$_2$O and brine, dried over anhydrous sodium sulfate, filtered, concentrated in vacuo to afford 0.342 g of a tan solid. Purification by column chromatography on silica gel (isocratic elution with 1:1 toluene/ethyl acetate followed by 9:1 CHCl$_3$/2.0 M ammonia in methanol) afforded 0.256 g (56%) of N-(3-dimethylaminopropyl)-4-[5-(3-phenoxypropylsulfanylmethyl)-[1,3,4]oxadiazol-2-yl]-benzamide as an off-white solid (MP 77–80° C., MW 454.60).

$^1$H NMR (CDCl$_3$) δ 8.79 (bs, 1H), 8.12 (d, 2H, J=8 Hz), 8.01 (d, 2H, J=8 Hz), 7.26 (t, 2H, J=8 Hz), 6.92 (t, 1H, J=7 Hz), 6.88 (d, 2H, J=8 Hz), 4.06 (t, 2H, J=6 Hz), 3.95 (s, 2H), 3.64 (m, 2H), 2.86 (t, 2H, J=7 Hz), 2.77 (m, 2H), 2.52 (bs, 6H), 2.11 (m, 2H), and 1.96 (m, 2H). IR (KBr, c$^{-1}$) 3304, 3063, 2937, 2814, 2762, 1633, 1586, 1561, 1554, 1541, 1499, 1469, 1245, 1183, 853, and 751. MS (ESI) m/e 455, 453. Anal. Calcd for C$_{24}$H$_{30}$N$_4$O$_3$S: C, 63.41; H, 6.65; N, 12.32; S, 7.05. Found C, 63.29; H, 6.67; N, 12.34; S, 7.03.

Example 48

Preparation of N-(3-dimethylaminopropyl)-4-[5-(4-phenoxybutylsulfanylmethyl)-[1,3,4]oxadiazol-2-yl]-benzamide

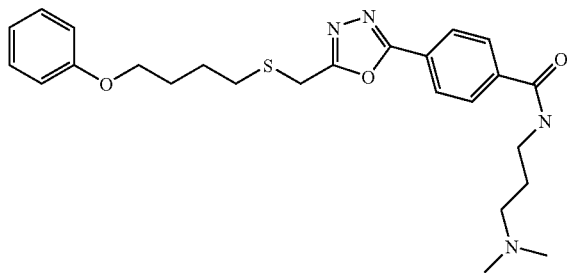

a) 4-chlorobutoxy benzene

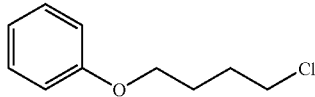

The above compound was prepared in a manner similar to that exemplified for the preparation of Example 47a, from phenol (4.75 g, 50.0 mmol) and 1-bromo-4-chlorobutane (5.82 mL, 50.0 mmol) to afford 9.5 g (quantitative) of 4-chlorobutoxy benzene as a colorless oil (MW 184.67).

$^1$H NMR (CDCl$_3$) δ 7.28 (t, 2H, J=8 Hz), 6.94 (t, 1H, J=8 Hz), 6.89 (d, 2H, J=8 Hz), 4.00 (t, 2H, J=6 Hz), 3.62 (t, 2H, J=6 Hz), and 1.97 (m, 4H). IR (CHCl$_3$, cm$^{-1}$) 3012, 2960, 2875, 1599, 1587, 1498, 1471, 1244, and 1172. MS (EI) m/e 184. Anal. Calcd for C$_{10}$H$_{13}$ClO: C, 65.04; H, 7.10; Cl, 19.20. Found C, 64.96; H, 7.03; Cl, 18.91.

b) (4-phenoxybutylsulfanyl)-acetic acid methyl ester

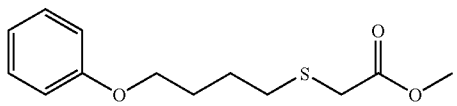

The above compound was prepared in a manner similar to that exemplified for the preparation of Example 47b, from 4-chlorobutoxybenzene (1.85 g, 10.0 mmol) and methyl thioglycolate (1.03 mL, 11.0 mmol) to afford 2.46 g (96%) of (4-phenoxybutylsulfanyl)-acetic acid methyl ester as a colorless oil (MW 254.35).

$^1$H NMR (CDCl$_3$) δ 7.28 (t, 2H, J=8 Hz), 6.93 (t, 1H, J=8 Hz), 6.89 (d, 2H, J=8 Hz), 3.98 (t, 2H, =6 Hz), 3.73 (s, 3H), 3.24 (s, 2H), 2.72 (t, 2H, J=7 Hz), and 1.86 (m, 4H). IR (CHCl$_3$, cm$^{-1}$) 3012, 2930, 1733, 1600, 1497, 1287, and 1244. MS (FD) m/e 254. Anal. Calcd for C$_{13}$H$_{18}$O$_3$S: C, 61.39; H, 7.13; S, 12.61. Found C, 60.43; H, 7.06; S, 10.84.

c) (4-phenoxybutylsulfanyl)-acetic acid

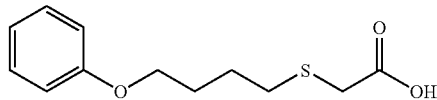

The above compound was prepared in a manner similar to that exemplified for the preparation of Example 47c, from 4-phenoxybutylsulfanyl)-acetic acid methyl ester (2.29 g, 9.0 mmol) and 2NaOH (13.5 mL, 27.0 mmol) to afford 2.04 g (94%) of (4-phenoxybutylsulfanyl)-acetic acid as a pale yellow solid (MP 48–50° C., MW 240.32).

$^1$H NMR (CDCl$_3$) δ 7.28 (t, 2H, J=8 Hz), 6.94 (t, 1H, J=8 Hz), 6.89 (d, 2H, J=8 Hz), 3.98 (t, 2H, J=6 Hz), 3.28 (s, 2H), 2.74 (t, 2H, J=7 Hz), and 1.86 (m, 4H). IR (CHCl$_3$, cm$^{-1}$) 3010, 2944, 1710, 1600, 1497, 1300, 1291, 1244, and 1172. MS (ESI) m/e 241, 239. Anal. Calcd for C$_{12}$H$_{16}$O$_3$S: C, 59.97; H, 6.71; S, 13.34. Found C, 58.55; H, 6.66; S, 16.01.

d) 4-[5-(4-phenoxybutylsulfanylmethyl)-[1,3,4]oxadiazol-2-yl]-benzoic acid methyl ester

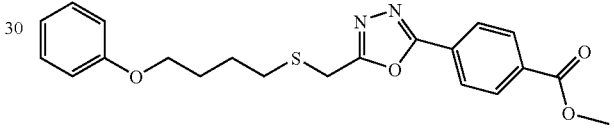

The above compound was prepared in a manner similar to that exemplified for the preparation of Example 47d, from 4-(1H-tetrazol-5-yl)-benzoic acid methyl ester (0.817 g, 4.0 mmol) and (4-phenoxybutylsulfanyl)-acetic acid (0.971 g, 4.04 mmol). Purification by column chromatography on silica gel (elution with linear gradient of 10–100% ethyl acetate/hexane) afforded 1.08 g (68%) of 4-[5-(4-phenoxybutylsulfanylmethyl)-[1,3,4]oxadiazol-2-yl]-benzoic acid methyl ester as an off-white solid (MP 98–105° C., MW 398.48).

$^1$H NMR (CDCl$_3$) δ 8.17 (d, 2H, J=9 Hz), 8.13 (d, 2H, J=9 Hz), 7.26 (t, 2H, J=8 Hz), 6.92 (t, 1H, J=8 Hz), 6.86 (d, 2H, J=8 Hz), 3.96 (m, 7H), 2.73 (t, 2H, J=7 Hz), and 1.87 (m, 4H). IR (KBr, cm$^{-1}$) 2930, 1713, 1554, 1498, 1426, 1289, 1283, 1241, 1119, 1112, 754, and 713. MS (ESI) m/e 399, 397. Anal. Calcd for C$_{21}$H$_{22}$N$_2$O$_4$S: C, 63.30; H, 5.56; N, 7.03; S, 8.05. Found C, 63.41; H, 6.04; N, 6.82; S, 7.97.

e) 4-[5-(4-phenoxybutylsulfanylmethyl)-[1,3,4]oxadiazol-2-yl]-benzoic acid

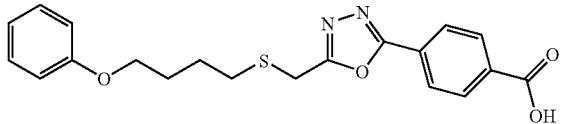

The above compound was prepared in a manner similar to that exemplified for the preparation of Example 47e, from 4-[5-(4-phenoxybutylsulfanylmethyl)-[1,3,4]oxadiazol-2-yl]-benzoic acid methyl ester (1.04 g, 2.6 mmol), and lithium hydroxide (0.191 g, 7.8 mmol) to afford 1.0 g (quantitative) of 4-[5-(4-phenoxybutylsulfanylmethyl)-[1,3,4]oxadiazol-2-yl]-benzoic acid as an off-white solid (P 153–160° C., MW 384.46).

¹H NMR (DMSO-d₆) δ13.25 (bs, 1H), 8.11 (d, 2H, J=9 Hz), 8.08 (d, 2H, J=9 Hz), 7.22 (t, 2H, J=8 Hz), 6.87 (m, 3H), 4.12 (s, 2H), 3.93 (t, 2H, J=6 Hz), 2.69 (t, 2H, J=7 Hz), and 1.73 (m, 4H). IR (KBr, cm⁻¹) 3314, 2925, 2851, 1705, 1684, 1498, 1293, 1247, 748, and 715. MS (ESI) m/e 385, 383. Anal. Calcd for $C_{20}H_{20}N_2O_4S$: C, 62.48; H, 5.24; N, 7.29; S, 8.34. Found C, 63.19; H, 5.99; N, 7.13; S, 8.37.

f) N-(3-dimethylaminopropyl)-4-[5-(4-phenoxybutylsulfanylmethyl)-[1,3,4]oxadiazol-2-yl]-benzamide

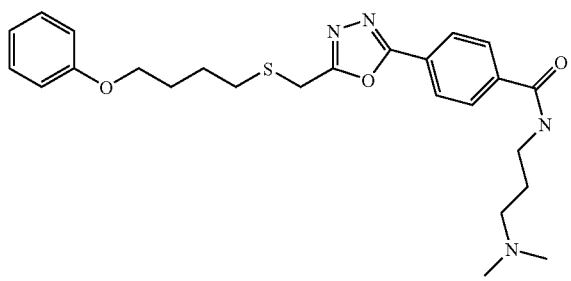

A solution of 4-[5-(4-phenoxybutylsulfanylmethyl)-[1,3,4]oxadiazol-2-yl]-benzoic acid (0.384 g, 1.0 mmol), and 1,1'-carbonyldiimidazole (0.164 g, 1.01 mmol) in 8.0 mL THF was stirred at 65° C. for 0.5 h. The reaction solution was allowed to cool to ambient temperature followed by addition of 3-(dimethylamino)propylamine (0.152 mL, 1.2 mmol), then stirred at room temperature for 4.5 h. The TIE was concentrated in vacuo, and the oily residue redissolved in 5–10% THF/ethyl acetate and H₂O. The solvent layers were separated, and the ethyl acetate/THF layer was washed with H₂O, saturated aqueous NaHCO₃ solution, and brine, dried over anhydrous sodium sulfate, filtered, concentrated in vacuo to afford 0.334 g of a tan solid. Crystallization from EtOH/diethyl ether afforded 0.182 g (39%) of N-(3-dimethylaminopropyl)-4-[5-(4-phenoxybutylsulfanylmethyl)-[1,3,4]oxadiazol-2-yl]-benzamide as an off-white solid (MP 87–93° C., MW 468.62).

¹H NMR (CDCl₃) δ 8.75 (bs, 1H), 8.12 (d, 2H, J=8 Hz), 8.03 (d, 2H, J=8 Hz), 7.26 (t, 2H, J=8 Hz), 6.92 (t, 1H, J=7 Hz), 6.86 (d, 2H, J=8 Hz), 3.96 (t, 2H, J=6 Hz), 3.94 (s, 2H), 3.64 (m, 2H), 2.83 (m, 2H), 2.73 (t, 2H, J=7 Hz), 2.56 (bs, 6H), 1.99 (m, 2H), and 1.86 (m, 4H). IR (KBr, cm⁻¹) 3341, 2941, 2764, 1640, 1552, 1536, and 1244. MS (ESI) m/e 467,469. Anal. Calcd for $C_{25}H_{32}N_4O_3S$: C, 64.08; H, 6.88; N, 11.96; S, 6.84. Found C, 63.76; H, 6.97; N, 11.56; S, 6.72.

Example 49

Preparation of dimethyl-(3-{4-[5-(3-phenoxypropylsulfanylmethyl)-[1,3,4]oxadiazol-2-yl]-phenoxy}-propyl)-amine, oxalic acid salt

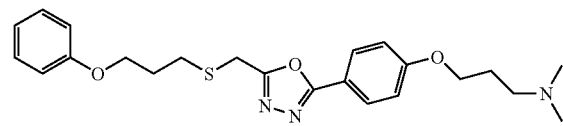

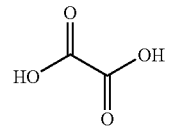

a) 3-chloropropoxy benzene

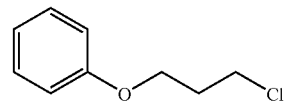

The above compound was prepared as exemplified in Example 47a.

b) (3-phenoxypropylsulfanyl)-acetic acid methyl ester

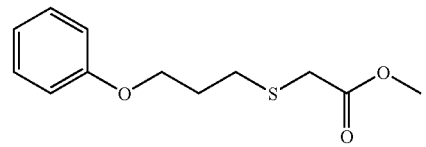

The above compound was prepared as exemplified in Example 47b from 3-chloropropoxy benzene (3.41 g, 20.0 mmol) and methyl thioglycolate (2.07 mL, 22.0 mmol). Purification by column chromatography on silica gel (isocratic elution with 10% ethyl acetate/toluene) afforded 2.95 g (61%) of (3-phenoxypropylsulfanyl)-acetic acid methyl ester as a colorless oil (MW 240.32).

¹H NMR (CDCl₃) δ 7.28 (t, 2H, J=8 Hz), 6.93 (t, 1H, J=8 Hz), 6.89 (d, 2H, J=8 Hz), 4.06 (t, 2H, J=6 Hz), 3.73 (s, 3H), 3.25 (s, 2H), 2.84 (t, 2H, J=7 Hz), and 2.08 (m, 2H). IR (CHCl₃, cm⁻¹) 3010, 2954, 1734, 1601, 1497, 1437, 1288, 1244, and 1225. MS (ES) m/e 241. Anal. Calcd for $C_{12}H_{16}O_3S$: C, 59.97; H, 6.71; S, 13.34. Found C, 59.22; H, 6.71; S, 18.00.

c) (3-phenoxypropylsulfanyl)-acetic acid

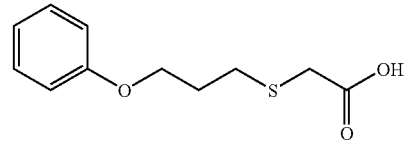

The above compound was prepared as exemplified in Example 47c from (3-phenoxypropylsulfanyl)-acetic acid methyl ester (2.64 g, 11.0 mmol) and 2N NaOH (16.5 mL, 33.0 mmol) to afford 2.33 g (94%) of (3-phenoxypropylsulfanyl)-acetic acid as a white crystalline solid (O 35–37° C., MW 226.30).

¹H NMR (CDCl₃) δ 7.28 (t, 2H, J=8 Hz), 6.94 (t, 1H, J=8 Hz), 6.89 (d, 2H, J=8 Hz), 4.06 (t, 2H, J=6 Hz), 3.28 (s, 2H), 2.87 (t, 2H, J=7 Hz), and 2.11 (m, 2H). IR (CHCl₃, cm⁻¹)

3041, 2927, 2674, 2565, 1710, 1601, 1498, 1244, 1172 and 1040. MS (ESI) m/e 227, 225. Anal. Calcd for $C_{11}H_{14}O_3S$: C, 58.38; H, 6.24; S, 14.17. Found C, 57.95; H, 6.08; S, 14.11.

d) 4-hydroxy-benzoic acid N'-[2-(3-phenoxypropyl-sulfanyl)-acetyl]-hydrazide

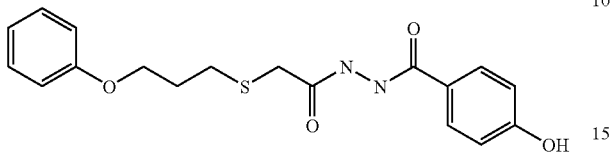

A solution of (3-phenoxypropylsulfanyl)-acetic acid (1.13 g, 5.0 mmol), and 2-ethoxy-1-ethoxycarbonyl-1,2-dihydroquinoline (EEDQ) (1.25 g, 5.0 mmol) in 5.0 mL THF and 20.0 mL acetonitrile was stirred at ambient temperature for 1.0 h followed by addition of 4-hydroxybenzoic hydrazide (0.776 g, 5.0 mmol), then stirred at room temperature for 66 h. The THF/acetonitrile were concentrated in vacuo and the resultant off-white solid redissolved in 20% THF/ethyl acetate. The ethyl acetate/THF solution was washed with 1N HCl, $H_2O$, saturated aqueous $NaHCO_3$ solution, and brine, dried over anhydrous magnesium sulfate, filtered, and concentrated in vacuo to afford an off-white solid. The solid was triturated with a mixture of $CH_2Cl_2$/diethyl ether/n-hexane, filtered, and the collected solid washed with diethyl ether and n-hexane to afford 1.53 g (85%) of 4-hydroxy-benzoic acid N'-[2-(3-phenoxypropylsulfanyl)-acetyl]-hydrazide as an amorphous white solid (MP 146–151° C., MW 360.44).

$^1$H NMR (DMSO-$d_6$) δ 10.14 (s, 1H), 10.07 (s, 1H), 9.96 (s, 1H), 7.73 (d, 2H, J=9 Hz), 7.26 (t, 2H, J=8 Hz), 6.91 (m, 3H), 6.79 (d, 2H, J=8 Hz), 4.02 (t, 2H, J=6 Hz), 3.22 (s, 2H), 2.78 (t, 2H, J=7 Hz), and 2.00 (m, 2H). IR (KBr, cm$^{-1}$) 3304, 3228, 1667, 1607, 1575, 1514, 1498, 1468, 1277, 1250, 1235, and 755. MS (ESI) m/e 361, 359. Anal. Calcd for $C_{18}H_{20}N_2O_4S$: C, 59.98; H, 5.59; N, 7.77; S, 8.90. Found C, 59.94; H, 5.62; N, 7.73; S, 8.92.

e) 4-[5-(3-phenoxypropylsulfanylmethyl)-[1,3,4]oxadiazol-2-yl]-phenol

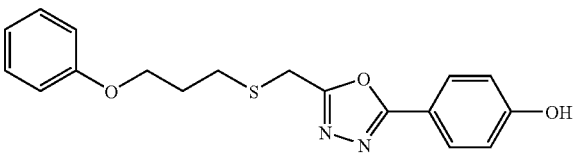

A heterogeneous mixture of 4-hydroxy-benzoic acid N'-[2-(3-phenoxypropylsulfanyl)-acetyl]-hydrazide (1.44 g, 4.0 mmol), triphenylphosphine (2.12 g, 8.0 mmol), triethylamine (2.0 mL, 14.4 mmol) and carbon tetrachloride (1.61 mL, 16.5 mmol) in 20 mL acetonitrile was stirred at room temperature for 2.5 h. The resultant precipitate was collected by filtration, washed with acetonitrile and discarded. The filtrate was concentrated in vacuo and the resultant solid redissolved in 10% THF/ethyl acetate.

The ethyl acetate/THF solution was washed with 1N HCl, $H_2O$, saturated aqueous $NaHCO_3$ solution, and brine, dried over anhydrous magnesium sulfate, filtered, and concentrated in vacuo to afford 3.92 g of a yellow oil. Purification by column chromatography on silica gel (elution with linear gradient of 0–100% ethyl acetate/toluene) afforded 1.15 g (83%) of 4-[5-(3-phenoxypropylsulfanylmethyl)-[1,3,4] oxadiazol-2-yl]-phenol as a white solid (MP 122–127° C., MW 342.42).

$^1$H NMR (CDCl$_3$) δ 7.95 (d, 2H, J=9 Hz), 7.26 (t, 2H, J=8 Hz), 6.96 (d, 2H, J=9 Hz), 6.93 (t, 1H, J=8 Hz), 6.87 (d, 2H, J=8 Hz), 4.05 (t, 2H, J=6 Hz), 3.92 (s, 2H), 2.85 (t, 2H, J=7 Hz), and 2.10 (m, 2H). IR (KBr, cm$^{-1}$) 3442, 3127, 2944, 1609, 1599, 1586, 1497, 1472, 1246, 1229, 1174, and 756. MS (ESI) m/e 343, 341. Anal. Calcd for $C_{18}H_{18}N_2O_3S$: C, 63.14; H, 5.30; N, 8.18; S, 9.36. Found C, 63.31; H, 5.32; N, 8.14; S, 9.17.

f) Dimethyl-(3-{4-[5-(3-phenoxypropylsulfanylmethyl)-[1,3,4]oxadiazol-2-yl]-phenoxy}-propyl)-amine, oxalic acid salt

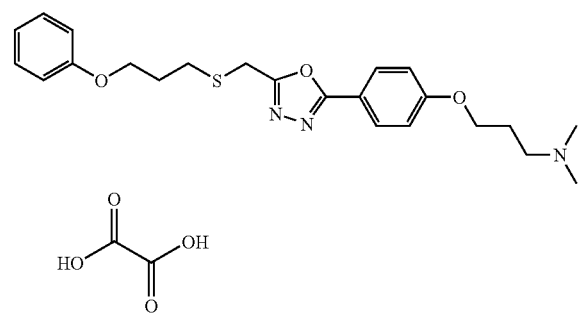

A heterogeneous mixture of 4-[5-(3-phenoxypropylsulfanylmethyl)-[1,3,4]oxadiazol-2-yl]-phenol (0.342 g, 1.0 mmol), 3-chloro-N,N-dimethylpropylamine hydrochloride (0.174 g, 1.1 mmol), and sodium hydride (0.092 g, 2.3 mmol) in 10 mL DMF was stirred at 100° C. for 2.5 h. The reaction mixture was allowed to cool to room temperature and diluted with ethyl acetate/$H_2O$. The solvent layers were separated, the aqueous layer back extracted with ethyl acetate, the combined organic extracts washed with water and brine, dried over anhydrous sodium sulfate, filtered, and concentrated in vacuo to afford 0.332 g of a yellow oil. Purification by column chromatography on silica gel (isocratic elution with 1:1 toluene/ethyl acetate followed by 9:1 CHCl$_3$/2.0 M ammonia in methanol) afforded 0.188 g (44%) of dimethyl-(3-{4-[5-(3-phenoxypropylsulfanylmethyl)-[1,3,4]oxadiazol-2-yl]-phenoxy}-propyl)-amine as an oily gum. The gum (0.182 g, 0.426 mmol) was dissolved in 2 mL acetone, and oxalic acid (0.042 g, 0.468 mmol), dissolved in 1 mL acetone, was added with rapid stirring at room temperature. Filtered the resultant thick precipitate, washed the collected solid with acetone and diethyl ether, and dried in vacuo at 40° C. to afford 0.205 g (93%) of dimethyl-(3-{4-[5-(3-phenoxypropylsulfanylmethyl)-[1,3,4]oxadiazol-2-yl]-phenoxy}-propyl)-amine, oxalic acid salt as a white solid (MP 131–133° C., MW oxalate salt 517.61, MW free amine 427.57).

$^1$H NMR (DMSO-$d_6$) δ 7.91 (d, 2H, J=9 Hz), 7.24 (t, 2H, J=8 Hz), 7.12 (d, 2H, J=9 Hz), 6.89 (m, 3H), 4.12 (t, 2H, J=6 Hz), 4.09 (s, 2H), 4.01 (t, 2H, J=6 Hz), 3.13 (m, 2H), 2.76 (t, 2H, J=7 Hz), 2.74 (s, 6H), 2.10 (m, 2H), and 1.99 (t, 2H, J=7 Hz). IR (KBr, cm$^{-1}$) 3042, 2928, 1723, 1611, 1499, 1472, 1259, 1248, 1177, 756, and 696. MS (ES) m/e 428. Anal. Calcd for $C_{23}H_{29}N_3O_3S \cdot C_2H_2O_4$: C, 58.01; H, 6.04; N, 8.12; S, 6.19. Found C, 57.72; H, 6.01; N, 7.78; S, 6.55.

Example 50

Preparation of dimethyl-(3-{4-[5-(4-phenoxybutyl-sulfanylmethyl)-[1,3,4]oxadiazol-2-yl]-phenoxy}-propyl)-amine

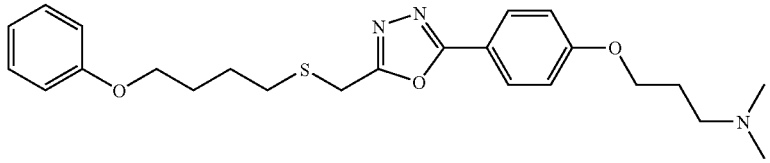

a) 4-chlorobutoxy benzene

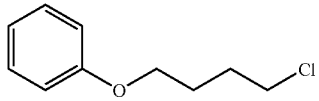

The above compound was prepared in a manner similar to that exemplified for the preparation of Example 47a, from phenol (4.75 g, 50.0 mmol) and 1-bromo-4-chlorobutane (5.82 mL, 50.0 mmol) to afford 9.5 g (quantitative) of 4-chlorobutoxy benzene as a colorless oil (MW 184.67).

$^1$H NMR (CDCl$_3$) δ 7.28 (t, 2H, J=8 Hz), 6.94 (t, 1H, J=8 Hz), 6.89 (d, 2H, J=8 Hz), 4.00 (t, 2H, J=6 Hz), 3.62 (t, 2H, J=6 Hz), and 1.97 (m, 4H). IR (CHCl$_3$, cm$^{-1}$) 3012, 2960, 2875, 1599, 1587, 1498, 1471, 1244, and 1172. MS (EI) m/e 184. Anal. Calcd for C$_{10}$H$_{13}$ClO: C, 65.04; H, 7.10; Cl, 19.20. Found C, 64.96; H, 7.03; Cl, 18.91.

b) (4-phenoxybutylsulfanyl)-acetic acid methyl ester

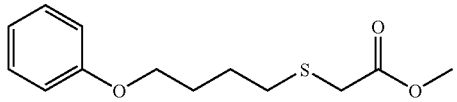

The above compound was prepared in a manner similar to that exemplified for the preparation of Example 47b, from 4-chlorobutoxy benzene (1.85 g, 10.0 mmol) and methyl thioglycolate (1.03 mL, 11.0 mmol) to afford 2.46 g (96%) of (4-phenoxybutylsulfanyl)-acetic acid methyl ester as a colorless oil (MW 254.35).

$^1$H NMR (CDCl$_3$) δ 7.28 (t, 2H, J=8 Hz), 6.93 (t, 1H, J=8 Hz), 6.89 (d, 2H, J=8 Hz), 3.98 (t, 2H, J=6 Hz), 3.73 (s, 3H), 3.24 (s, 2H), 2.72. (t, 2H, J=7 Hz), and 1.86 (m, 4H). IR (CHCl$_3$, cm$^{-1}$) 3012, 2930, 1733, 1600, 1497, 1287, and 1244. MS (FD) m/e 254. Anal. Calcd for C$_{13}$H$_{18}$O$_3$S: C, 61.39; H, 7.13; S, 12.61. Found C, 60.43; H, 7.06; S, 10.84.

c) (4-phenoxybutylsulfanyl)-acetic acid

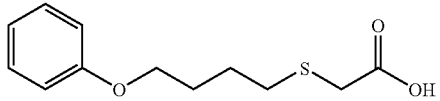

The above compound was prepared in a manner similar to that exemplified for the preparation of Example 47c, from 4-phenoxybutylsulfanyl)-acetic acid methyl ester (2.29 g, 9.0 mmol) and 2N NaOH (13.5 mL, 27.0 mmol) to afford 2.04 g (94%) of (4-phenoxybutylsulfanyl)-acetic acid as a pale yellow solid (MP 48–50° C., MW 240.32).

$^1$H NMR (CDCl$_3$) δ 7.28 (t, 2H, J=8 Hz), 6.94 (t, 1H, J=8 Hz), 6.89 (d, 2H, J=8 Hz), 3.98 (t, 2H, J=6 Hz), 3.28 (s, 2H), 2.74 (t, 2H, J=7 Hz), and 1.86 (m, 4H). IR (CHCl$_3$, cm$^{-1}$) 3010, 2944, 1710, 1600, 1497, 1300, 1291, 1244, and 1172. MS (ESI) m/e 241, 239. Anal. Calcd for C$_{12}$H$_{16}$O$_3$S: C, 59.97; H, 6.71; S, 13.34. Found C, 58.55; H, 6.66; S, 16.01.

d) 4-hydroxy-benzoic acid N'-[2-(4-phenoxybutyl-sulfanyl)-acetyl]-hydrazide

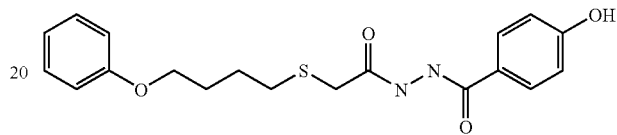

The above compound was prepared in a manner similar to that exemplified for the preparation of Example 49d, from (4-phenoxybutylsulfanyl)-acetic acid (0.961 g, 4.0 mmol), 2-ethoxy-1-ethoxycarbonyl-1,2-dihydroquinoline (EEDQ) (0.999 g, 4.0 mmol), and 4-hydroxybenzoic hydrazide (0.621 g, 4.0 mmol) to afford 1.14 g (76%) of 4-hydroxy-benzoic acid N'-[2-(4-phenoxybutylsulfanyl)-acetyl]-hydrazide as an amorphous white solid (MP 113–115° C., MW 374.46).

$^1$H NMR(DMSO-d$_6$) δ 10.13 (s, 1H), 10.07 (s, 1H), 9.94 (s, 1H), 7.73 (d, 2H, J=9 Hz), 7.25 (t, 2H, J=8 Hz), 6.89 (m, 3H), 6.79 (d, 2H, J=8 Hz), 3.96 (t, 2H, J=6 Hz), 3.19 (s, 2H), 2.70 (t, 2H, J=7 Hz), and 1.74 (m, 4H). IR (CHCl$_3$, cm$^{-1}$) 3281, 3003, 2940, 1631, 1609, 1587, 1497, 1470, 1387, 1279, 1244, and 1171. MS (ESI) m/e 375, 373. Anal. Calcd for C$_{19}$H$_{22}$N$_2$O$_4$S: C, 60.94; H, 5.92; N, 7.48; S, 8.56. Found C, 60.24; H, 5.92; N, 7.50; S, 9.12.

e) 4-[5-(4-phenoxybutylsulfanylmethyl)-[1,3,4]oxa-diazol-2-yl]-phenol

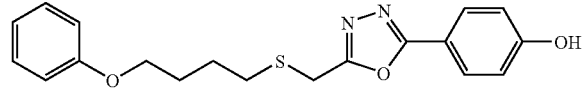

The above compound was prepared in a manner similar to that exemplified for the preparation of Example 49e, using 4-hydroxybenzoic acid N'-[2-(4-phenoxybutylsulfanyl)-acetyl]-hydrazide (1.09 g, 2.9 mmol), triphenylphosphine (1.54 g, 5.8 mmol), and triethylamine (1.46 mL, 10.44 mmol) to afford 0.831 g (80%) of 4-[5-(4-phenoxybutylsulfanylmethyl)-[1,3,4]oxadiazol-2-yl]-phenol as a white solid (MP 129–130° C., MW 356.45).

$^1$H NMR (CDCl$_3$) δ 7.95 (d, 2H, J=9 Hz), 7.26 (t, 2H, J=8 Hz), 6.95 (d, 2H, J=9 Hz), 6.93 (t, 1H, J=8 Hz), 6.86 (d, 2H, J=8 Hz), 3.96 (t, 2H, J=6 Hz), 3.91 (s, 2H), 2.71 (t, 2H, J=7 Hz), and 1.85 (m, 4H—). IR (KBr, cm$^{-1}$) 3096, 2935, 1610, 1600, 1567, 1498, 1475, 1456, 1284, 1275, 1237, 1178, 757, and 691. MS (ESI) m/e 357, 355. Anal. Calcd for C$_{19}$H$_{20}$N$_2$O$_3$S: C, 64.02; H, 5.66; N, 7.86; S, 9.00. Found C, 63.81; H, 5.68; N, 7.84; S, 9.09.

f) [Dimethyl-(3-{4-[5-(4-phenoxybutylsulfanylmethyl)-1,3,4]oxadiazol-2-yl]-phenoxy}-propyl)-amine

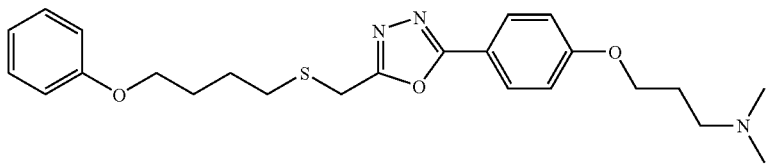

A heterogeneous mixture of 4-[5-(4-phenoxybutylsulfanyl methyl)-[1,3,4]oxadiazol-2-yl]-phenol (0.178 g, 0.5 mmol), 3-chloro-N,N-dimethylpropylamine hydrochloride (0.087 g, 0.55 mmol), and sodium hydride (0.046 g, 1.15 mmol) in 5 mL DMF was stirred at 100° C. for 2.5 h. The reaction mixture was allowed to cool to room temperature and diluted with ethyl acetate/H$_2$O. The solvent layers were separated, the aqueous layer back extracted with ethyl acetate, the combined organic extracts washed with water and brine, dried over anhydrous sodium sulfate, filtered, and concentrated in vacuo to afford 0.223 g of a tan solid. Purification by column chromatography on silica gel (isocratic elution with 1:1 toluene/ethyl acetate followed by 9:1 CHCl$_3$/2.0M ammonia in methanol) afforded 0.15 g (68%) of dimethyl-(3-{4-[5-(4-phenoxybutylsulfanylmethyl)-[1,3,4]oxadiazol-2-yl]-phenoxy})-propyl)-amine as a white solid (MP 69–73° C., MW 441.60).

$^1$H NMR (CDCl$_3$) δ 7.98 (d, 2H, J=9 Hz), 7.26 (t, 2H, J=8 Hz), 6.97 (d, 2H, J=9 Hz), 6.92 (t, 1H, J=7 Hz), 6.87 (d, 2H, J=8 Hz) 4.13 (t, 2H, J=6 Hz), 3.96 (t, 2H, J=6 Hz), 3.91 (s, 2H), 2.92 (m, 2H), 2.72 (t, 2H, J=7 Hz), 2.60 (1's, 6H), 2.25 (m, 2H), and 1.84 (m, 4H). IR (KBr, cm$^{-1}$) 2947, 1612, 1501, 1468, 1258, and 749. MS (ESI) m/e 442, 440. Anal. Calcd for C$_{24}$H$_{31}$N$_3$O$_3$S: C, 65.28; H, 7.08; N, 9.52; S, 7.26. Found C, 65.36; H, 7.12; N, 9.38; S, 7.39.

Example 51

Preparation of dimethyl-(3-{4-[5-(5-phenylpentyl)-[1,3,4]oxadiazol-2-yl]-phenoxy}-propyl)-amine

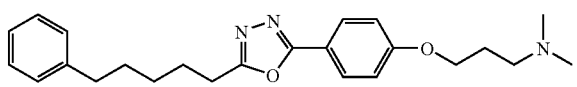

a) 4-hydroxybenzoic acid N'-(6-phenylhexanoyl)-hydrazide

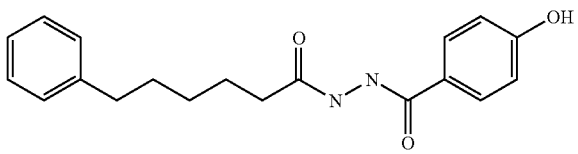

A solution of 6-phenylhexanoic acid (0.961 g, 5.0 mmol), and 2-ethoxy-1-ethoxycarbonyl-1,2-dihydroquinoline (EEDQ) (1.25 g, 5.0 mmol) in 5.0 mL THF and 20.0 ml acetonitrile was stirred at ambient temperature for 1.0 h followed by addition of 4-hydroxy-benzoic hydrazide (0.776 g, 5.0 mmol), then stirred at room temperature for 18 h followed by heating at 65° C. for 1.5 h. The reaction mixture was allowed to cool to room temperature, the THF/acetonitrile were concentrated in vacuo, and the resultant gold oil redissolved in ethyl acetate. The ethyl acetate solution was washed with 1N HCl, H$_2$O, saturated aqueous NaHCO$_3$ solution, and brine, dried over anhydrous magnesium sulfate, filtered, and concentrated in vacuo to afford an off-white solid. The solid was triturated with a mixture of CH$_2$Cl$_2$/diethyl ether/n-hexane, filtered, and the collected solid washed with diethyl ether and n-hexane to afford 1.16 g (71%) of 4-hydroxy-benzoic acid N'-(6-phenylhexanoyl)-hydrazide as an amorphous white solid (MP 155–160° C., MW 326.40).

$^1$H NMR (DMSO-d$_6$) δ 10.04 (s, 1H), 9.98 (s, 1H), 9.69 (s, 1H), 7.72 (d, 2H, J=9 Hz), 7.25 (t, 2H, J=8 Hz), 7.16 (m, 3H), 6.79 (d, 2H, J=8 Hz), 2.55 (t, 2H, J=8 Hz), 2.14 (t, 2H, J=7 Hz), 1.56 (m, 4H) and 1.32 (m, 2H). IR (KBr, cm$^{-1}$) 3314, 3222, 3023, 2930, 2856, 1699, 1626, 1609, 1584, 1517, 1492, 1287, 1237, and 697. MS (ESI) m/e 327, 325. Anal. Calcd for C$_{19}$H$_{22}$N$_2$O$_3$: C, 69.92; H, 6.79; N, 8.58. Found C, 69.83; H, 6.66; N, 8.43.

b) 4-[5-(5-phenylpentyl)-[1,3,4]oxadiazol-2-yl]-phenol

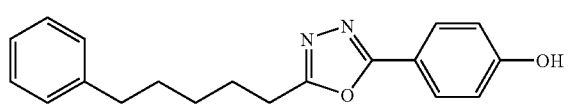

The above compound was prepared in a manner similar to that exemplified for the preparation of Example 49e, from 4-hydroxy-benzoic acid N'-(6-phenylhexanoyl)-hydrazide (1.1 g, 3.4 mmol), triphenylphosphine (1.8 g, 6.8 mmol), and triethylamine (1.71 mL, 12.24 mmol) to afford 0.841 g (80%) of 4-[5-(5-phenylpentyl)-[1,3,4]oxadiazol-2-yl]-phenol as a white solid (MP 118–123° C., MW 308.38).

$^1$H NMR (CDCl$_3$) δ 7.94 (d, 2H, J=9 Hz), 7.27 (t, 2H, J=8 Hz), 7.17 (m, 3H), 6.98 (d, 2H, J=8 Hz), 2.91 (t, 2H, J=7 Hz), 2.63 (t, 2H, J=8 Hz), 1.86 (m, 2H), 1.68 (m, 2H), and 1.48 (m, 2H). IR (KBr, cm$^{-1}$) 2921, 1610, 1600, 1496, 1283, and 1231. MS (ESI) m/e 309, 307. Anal. Calcd for C$_{19}$H$_{20}$N$_2$O$_2$: C, 74.00; H, 6.54; N, 9.08. Found C, 73.52; H, 6.40; N, 8.66.

c) Dimethyl-(3-{4-[5-(5-phenylpentyl)-[1,3,4]oxadiazol-2-yl]-phenoxy}-propyl)-amine

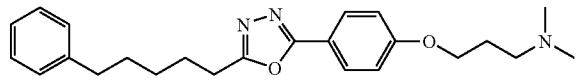

The above compound was prepared in a manner similar to that exemplified for the preparation of Example 50f, from 4-[5-(5-phenylpentyl)-[1,3,4]oxadiazol-2-yl]-phenol (0.154 g, 0.5 mmol) to afford 0.119 g (60%) of dimethyl-(3-{4-[5-(5-phenylpentyl)-[1,3,4]oxadiazol-2-yl]-phenoxy}-propyl)-amine as a white solid (NV 49–50° C., MW 393.53).

$^1$H NMR (CDCl$_3$) δ 7.95 (d, 2H, J=9 Hz), 7.27 (t, 2H, J=7 Hz), 7.18 (m, 3H), 6.98 (d, 2H, J=9 Hz), 4.13 (t, 2H, J=6 Hz), 2.91 (t, 2H, J=7 Hz), 2.88 (m, 2H), 2.63 (t, 2H, J=8 Hz), 2.56 (bs, 6H), 2.23 (m, 2H), 1.87 (m, 2H), 1.68 (m, 2H), and 1.49 (m, 2H). IR (KBr, cm$^{-1}$) 3083, 3026, 2938, 2859, 2764, 1612, 1574, 1502, 1466, 1259, 1176, and 999. MS (ESI) m/e 394, 392. Anal. Calcd for C$_{24}$H$_{31}$N$_3$O$_2$: C, 73.25; H, 7.94; N, 10.68. Found C, 72.94; H, 7.99; N, 10.52.

Example 52

Preparation of dimethyl-(3-{4-[5-(6-phenylhexyl)-[1,3,4]oxadiazol-2-yl]-phenoxy}-propyl)-amine, oxalic acid salt

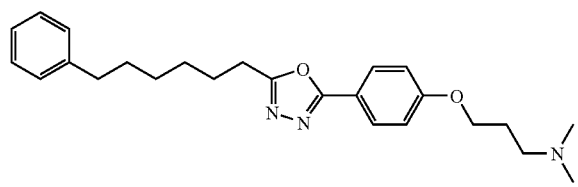

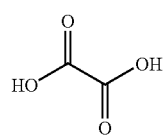

a) 4-hydroxy-benzoic acid N'-(7-phenylheptanoyl)-hydrazide

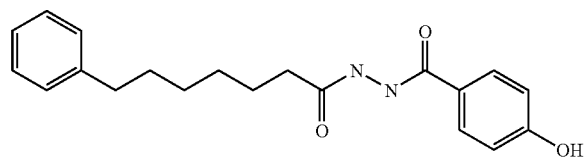

The above compound was prepared in a manner similar to that exemplified for the preparation of Example 51a, from 7-phenylheptanoic acid (1.06 g, 5.0 mmol) to afford 1.39 g (81%) of 4-hydroxy-benzoic acid N'-(7-phenylheptanoyl)-hydrazide as a white solid (154–158° C., MW 340.43).

$^1$H NMR (DMSO-d$_6$) δ 10.04 (s, 1H), 9.97 (s, 1H), 9.68 (s, 1H), 7.72 (d, 2H, J=9 Hz), 7.25 (t, 2H, J=7 Hz), 7.15 (m, 3H), 6.79 (d, 2H, J=9 Hz), 2.55 (t, 2H, J=8 Hz), 2.13 (t, 2H, J=8 Hz), 1.53 (m, 4H) and 1.29 (m, 4H). IR (KBr, cm$^{-1}$) 3213, 3024, 2931, 2855, 1765, 1684, 1670, 1646, 1610, 1583, 1506, 1492, 1464, 1453, 1308, 1279, 1254, 1225, 1174, and 699. MS (ES) m/e 341, 339. Anal. Calcd for C$_{20}$H$_{24}$N$_2$O$_3$: C, 70.57; H, 7.11; N, 8.23. Found C, 69.87; H, 7.05; N, 8.00.

b) 4-[5-(6-phenylhexyl)-[1,3,4]oxadiazol-2-yl]-phenol

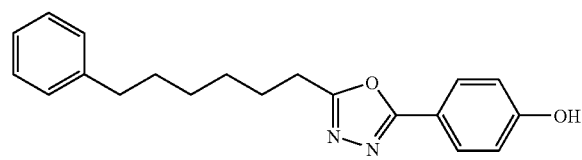

The above compound was prepared in a manner similar to that exemplified for the preparation of Example 49e, from 4-hydroxy-benzoic acid N'-(7-phenylheptanoyl)-hydrazide (1.3 g, 3.82 mmol), triphenylphosphine (2.02 g, 7.64 mmol), and triethylamine (1.92 mL, 13.75 mmol) to afford 0.883 g (71%) of 4-[5-(6-phenylhexyl)-[1,3,4]oxadiazol-2-yl]-phenol as a white solid (MP 125–129° C., MW 322.41).

$^1$H NMR (CDCl$_3$) δ 7.94 (d, 2H, J=9 Hz), 7.27 (t, 2H, J=8 Hz), 7.17 (m, 3H), 6.98 (d, 2H, J=8 Hz), 2.90 (t, 2H, J=7 Hz), 2.60 (t, 2H, J=8 Hz), 1.84 (m, 2H), 1.64 (m, 2H), and 1.43 (m, 4H). IR (KBr, cm$^{-1}$) 3061, 3020, 2925, 2852, 2809, 2686, 2608, 2481, 1612, 1600, 1577, 1498, 1466, 1375, 1286, 1239, and 1174. MS (ESI) m/e 323, 321. Anal. Calcd for C$_{20}$H$_{22}$N$_2$O$_2$: C, 74.51; H, 6.88; N, 8.69. Found C, 74.27; H, 6.76; N, 8.61.

c) Dimethyl-(3-{4-[5-(6-phenylhexyl)-[1,3,4]oxadiazol-2-yl]-phenoxy}-propyl)-amine, oxalic acid salt

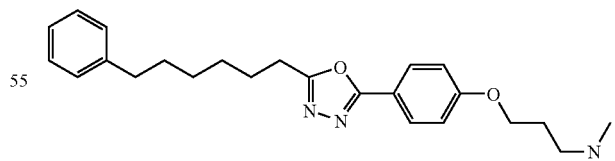

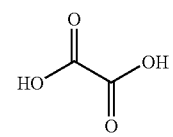

The above compound was prepared in a manner similar to that exemplified for the preparation of Example 50f, from 4-[5-(6-phenylhexyl)-[1,3,4]oxadiazol-2-yl]-phenol (0.161 g, 0.5 mmol) to afford 0.153 g (75%) of dimethyl-(3-{4-[5-(6-phenylhexyl)-[1,3,4]oxadiazol-2-yl]-phenoxy}-propyl)-amine as an oily gum. The gum (0.151 g, 0.37 mmol) was dissolved in 2 mL acetone, and oxalic acid (0.037 g, 0.41 mmol), dissolved in 1 mL acetone, was added with rapid stirring at room temperature. Filtered the resultant thick precipitate, washed the collected solid with acetone and diethyl ether, and dried in vacuo at 40° C. to afford 0.18 g (97%) of dimethyl-(3-{4-[5-(6-phenylhexyl)-[1,3,4]oxadiazol-2-yl]-phenoxy}-propyl)-amine, oxalic acid salt as a white solid (M 147–152° C., MW oxalate salt 497.60, MW free amine 407.56).

$^1$H NMR (DMSO-$d_6$) δ 7.90 (d, 2H, J=9 Hz), 7.24 (t, 2H, J=7 Hz), 7.15 (m, 3H), 7.11 (d, 2H, J=9 Hz), 4.12 (t, 2H, J=6 Hz), 3.13 (t, 2H, J=7 Hz), 2.87 (t, 2H, J=7 Hz), 2.74 (s, 6H), 2.54 (t, 2H, J=8 Hz), 2.08 (m, 2H), 1.72 (m, 2H), 1.55 (m, 2H), and 1.34 (m, 4H). IR (KBr, cm$^{-1}$) 2970, 2925, 2854, 2676, 1721, 1612, 1590, 1496, 1311, 1232, 1177, 1040, and 842. MS (ESI) m/e 408, 408.5. Anal. Calcd for $C_{25}H_{33}N_3O_2 \cdot C_2H_2O_4$: C, 65.17; H, 7.09; N, 8.44. Found C, 64.95; H, 6.94; N, 8.39.

Example 53

Preparation of dimethyl-(3-{4-[5-(7-phenylheptyl)-[1,3,4]oxadiazol-2-yl]-phenoxy}-propyl)-amine

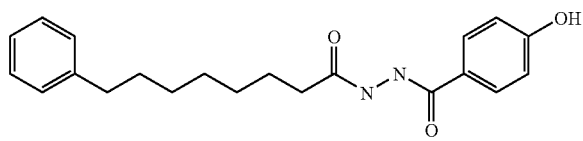

a) 4-hydroxy-benzoic acid N'-(8-phenyloctanoyl)-hydrazide

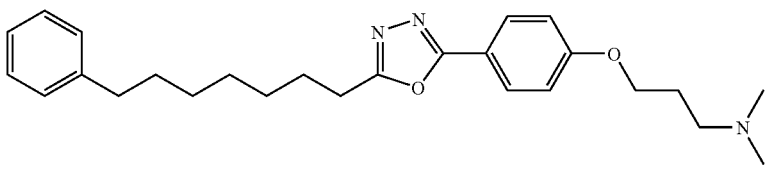

The above compound was prepared in a manner similar to that exemplified for the preparation of Example 51aa, from 8-phenyloctanoic acid (1.14 g, 5.0 mmol) to afford 1.27 g (71%) of 4-hydroxy-benzoic acid N'-(8-phenyloctanoyl)-hydrazide as a white solid (MP 150–152° C., MW 354.45).

$^1$H NMR (DMSO-$d_6$) δ 10.04 (s, 1H), 9.97 (s, 1H), 9.68 (s, 1H), 7.72 (d, 2H, J=9 Hz), 7.24 (t, 2H, J=7 Hz), 7.15 (m, 3H), 6.79 (d, 2H, J=9 Hz), 2.55 (t, 2H, J=8 Hz), 2.13 (t, 2H, J=8 Hz), 1.53 (m, 4H) and 1.28 (bs, 6H). IR (KBr, cm$^{-1}$) 3280, 3023, 2927, 2852, 1759, 1659, 1607, 1575, 1515, 1494, 1277, 1237, 1181, 845, and 698. MS (ESI) m/e 355, 353. Anal. Calcd for $C_{21}H_{26}N_2O_3$: C, 71.16; H, 7.39; N, 7.90. Found C, 70.45; H, 7.34; N, 7.69.

b) 4-[5-(7-phenylheptyl)-[1,3,4]oxadiazol-2-yl]-phenol

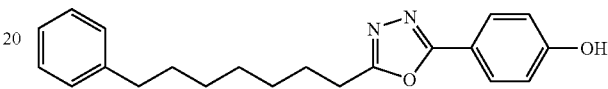

The above compound was prepared in a manner similar to that exemplified for the preparation of Example 49e, from 4-hydroxy-benzoic acid N'-(8-phenyloctanoyl)-hydrazide (1.2 g, 3.4 mmol), triphenylphosphine (1.8 g, 6.8 mmol), and triethylamine (1.71 mL, 12.24 mmol) to afford 0.935 g (82%) of 4-[5-(7-phenylheptyl)-[1,3,4]oxadiazol-2-yl]-phenol as a white solid (MP 138–140° C., MW 336.44).

$^1$H NMR (CDCl$_3$) δ 7.95 (d, 2H, J=9 Hz), 7.27 (t, 2H, J=8 Hz), 7.17 (m, 3H), 6.99 (d, 2H, J=9 Hz), 2.90 (t, 2H, J=8 Hz), 2.59 (t, 2H, J=8 Hz), 1.82 (m, 2H), 1.61 (m, 2H), and 1.37 (m, 6H). IR (KBr, cm$^{-1}$) 3083, 3063, 3024, 2925, 2852, 1611, 1599, 1576, 1497, 1467, 1454, 1287, 1234, 1174, 862, 819, 739, and 695. MS (ESI) m/e 337, 335. Anal. Calcd for $C_{21}H_{24}N_2O_2$: C, 74.97; H, 7.19; N, 8.33. Found C, 74.90; H, 7.05; N, 8.36.

c) Dimethyl-(3-{4-[5-(7-phenylheptyl)-[1,3,4]oxadiazol-2-yl]-phenoxy}-propyl)-amine The above compound was prepared in a manner similar to that exemplified for the preparation of Example 50f, using 4-[5-(7-phenylheptyl)-[1,3,4]oxadiazol-2-yl]-phenol (0.168 g, 0.5 mmol) to afford 0.198 g (94%) of dimethyl-(3-{4-[5-(7-phenylheptyl)-[1,3,4]oxadiazol-2-yl]-phenoxy}-propyl)-amine as an off-white solid (AD 36–39° C., MW 421.59).

$^1$H NMR (CDCl$_3$) δ 7.95 (d, 2H, J=9 Hz), 7.27 (t, 2H, J=7 Hz), 7.17 (m, 3H), 6.98 (d, 2H, J=9 Hz), 4.12 (t, 2H, J=6 Hz), 2.89 (t, 2H, J=8 Hz), 2.74 (m, 2H, 2.59 (t, 2H, J=8 Hz), 2.48 (bs, 6H), 2.16 (m, 2H), 1.81 (m, 2H), 1.62 (m, 2H), and 1.37 (m, 6H). IR (KBr, cm$^{-1}$) 2925, 2853, 2765, 1613, 1500, 1468, 1254, 1174, and 836. MS (ESI) m/e 420, 422. Anal. Calcd for C$_{26}$H$_{35}$N$_3$O$_2$: C, 74.07; H, 8.37; N, 9.97. Found C, 73.88; H, 8.44; N, 9.90.

Example 54

Preparation of N-(2-dimethylaminoethyl)-4-[5-(2-phenoxyethylsulfanylmethyl)-[1,3,4]oxadiazol-2-yl]-benzamide

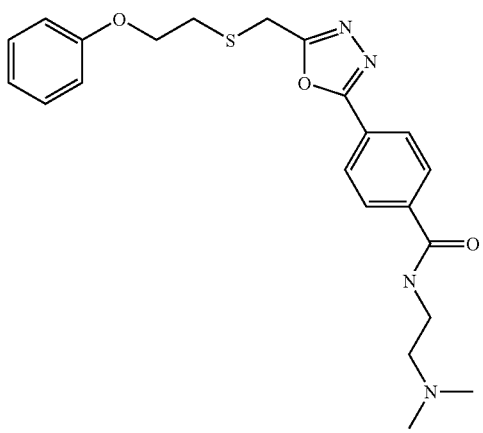

The above compound was prepared in a manner similar to that exemplified for the preparation of Example 47f, from 4-[5-(2-phenoxyethylsulfanylmethyl)-[1,3,4]oxadiazol-2-yl]-benzoic acid (0.178 g, 0.5 mmol), 1,1'-carbonyldiimidazole (0.082 g, 0.505 mmol), and 2-(dimethylamino)ethylamine (0.069 mL, 0.6 mmol) to afford 0.128 g (60%) of N-(2-dimethylaminoethyl)-4-[5-(2-phenoxyethylsulfanylmethyl)-[1,3,4]oxadiazol-2-yl]-benzamide as a white solid (MP 94–100° C., MW 426.54).

$^1$H NMR (CDCl$_3$) δ 8.15 (t, 1H, J=7 Hz), 8.12 (s, 4H), 7.27 (t, 2H, J=8 Hz), 6.95 (t, 1H, J=7 Hz), 6.89 (d, 2H, J=8 Hz), 4.22 (t, 2H, J=6 Hz), 4.08 (s, 2H), 3.79 (m, 2H), 3.07 (t, 2H, J=6 Hz), 2.99 (m, 2H), and 2.67 (bs, 6H). IR (KBr, cm$^{-1}$) 3350, 2943, 2819, 2766, 1643, 1554, 1538, 1494, 1245, 1033, 863, and 750. MS (ESI) m/e 427, 425. Anal. Calcd for C$_{22}$H$_{26}$N$_4$O$_3$S: C, 61.95; H, 6.14; N, 13.14; S, 7.52. Found C, 61.40; H, 5.90; N, 13.00; S, 7.59. Analytical HPLC: 97% purity.

Example 55

Preparation of N-(4-dimethylaminobutyl)-4-[5-(2-phenoxyethylsulfanylmethyl)-[1,3,4]oxadiazol-2-yl]-benzamide

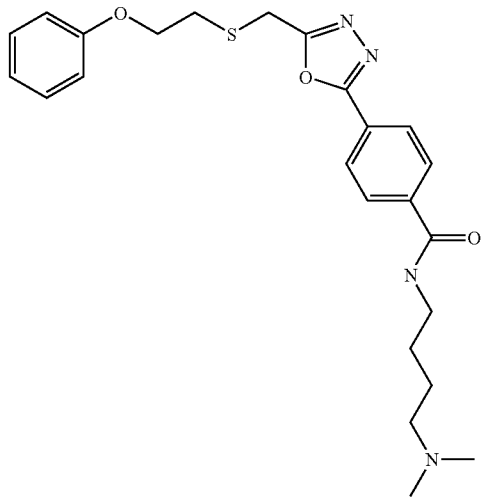

The above compound was prepared in a manner similar to that exemplified for the preparation of Example 47f, from 4-[5-(2-phenoxyethylsulfanylmethyl)-[1,3,4]oxadiazol-2-yl]-benzoic acid (0.178 g, 0.5 mmol), 1,1'-carbonyldiimidazole (0.082 g, 0.505 mmol), and 4-(dimethylamino)butylamine (0.07 g, 0.6 mmol) to afford 0.136 g (60%) of N-(4-dimethylaminobutyl)-4-[5-(2-phenoxyethylsulfanylmethyl)-[1,3,4]oxadiazol-2-yl]-benzamide as an off-white waxy solid (MP 71–78° C., MW 454.60).

$^1$H NMR (CDCl$_3$) δ 8.11 (bs, 1H), 8.09 (d, 2H, J=9 Hz), 8.05 (d, 2H, J=9 Hz), 7.27 (t, 2H, J=8 Hz), 6.95 (t, 1H, J=7 Hz), 6.89 (d, 2H, J=8 Hz), 4.22 (t, 2H, J=6 Hz), 4.07 (s, 2H), 3.53 (m, 2H), 3.06 (t, 2H, J=6 Hz), 2.78 (m, 2H), 2.56 (bs, 6H), and 1.83 (m, 4H). IR (KBr, cm$^{-1}$) 3338, 2943, 1643, 1602, 1554, 1533, 1494, 1468, 1289, 1246, 749, and 691. MS (ESI) m/e 453, 455. Anal. Calcd for C$_{24}$H$_{30}$N$_4$O$_3$S: C, 63.41; H, 6.65; N, 12.32; S, 7.05. Found C, 62.75; H, 6.77; N, 12.53; S, 6.93. Analytical HPLC: 97% purity.

Example 56

Preparation of N-(5-dimethylaminopentyl)-4-[5-(2-phenoxyethylsulfanylmethyl)-[1,3,4]oxadiazol-2-yl]-benzamide

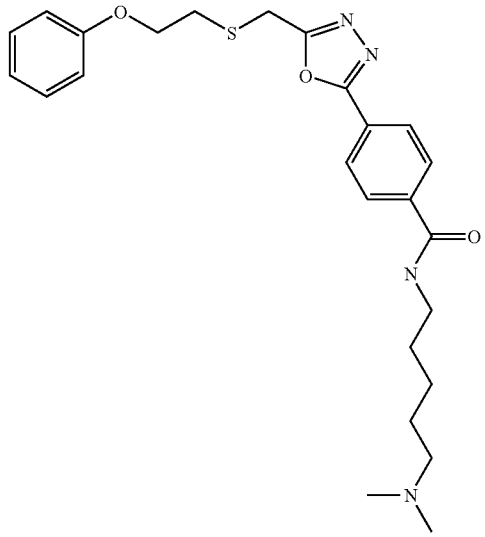

Example 57

Preparation of N-(6-dimethylaminohexyl)-4-[5-(2-phenoxyethylsulfanylmethyl)-[1,3,4]oxadiazol-2-yl]-benzamide The above compound was prepared in a manner similar to that exemplified for the preparation of Example 47f, from 4-[5-(2-phenoxyethylsulfanylmethyl)-[1,3,4]oxadiazol-2-yl]-benzoic acid (0.178 g, 0.5 mmol), 1,1'-carbonyldiimidazole (0.082 g, 0.505 mmol), and 5-(dimethylamino)pentylamine (0.078 g, 0.6 mmol) to afford 0.126 g (53%) of N-(5-dimethylaminopentyl)-4-[5-(2-phenoxyethylsulfanylmethyl)-[1,3,4]oxadiazol-2-yl]-benzamide as an off-white waxy solid (MP 83–89° C., MW 468.62).

$^1$H NMR (CDCl$_3$) δ 8.11 (bs, 1H), 8.09 (d, 2H, J=8 Hz), 7.98 (d, 2H, J=8 Hz), 7.27 (m, 2H), 6.93 (t, 1H, J=7 Hz), 6.89 (d, 2H, J=8 Hz), 4.22 (t, 2H, J=6 Hz), 4.07 (s, 2H), 3.52 (m, 2H), 3.06 (t, 2H, J=6 Hz), 2.62 (m, 2H), 2.48 (bs, 6H), 1.71 (m, 4H), and 1.54 (m, 2H). IR (KBr, cm$^{-1}$) 3346, 2942, 2761, 1717, 1644, 1554, 1533, and 1246. MS (ES) m/e 467, 469. Anal. Calcd for C$_{25}$H$_{32}$N$_4$O$_3$S: C, 64.08; H, 6.88; N, 11.96; S, 6.84. Found C, 63.05; H, 6.78; N, 11.71; S, 6.47. Analytical HPLC: 96% purity.

Example 57

Preparation of N-(6-dimethylaminohexyl)-4-[5-(2-phenoxyethylsulfanylmethyl)-[1,3,4]oxadiazol-2-yl]-benzamide

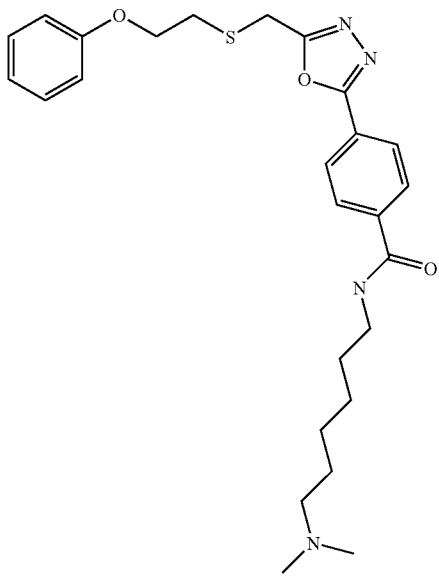

The above compound was prepared in a manner similar to that exemplified for the preparation of Example 47f, from 4-[5-(2-phenoxyethylsulfanylmethyl)-[1,3,4]oxadiazol-2-yl]-benzoic acid (0.178 g, 0.5 mmol), 1,1'-carbonyldiimidazole (0.082 g, 0.505 mmol), and 6-(dimethylamino)hexylamine (0.087 g, 0.6 mmol) to afford 0.148 g (61%) of N-(6-dimethylaminohexyl)-4-[5-(2-phenoxyethylsulfanylmethyl)-[1,3,4]oxadiazol-2-yl]-benzamide as an off-white solid (MP 86–93° C., MW 482.65).

$^1$H NMR (CDCl$_3$) δ 8.13 (bs, 1H), 8.10 (d, 2H, J=9 Hz), 8.02 (d, 2H, J=9 Hz), 7.27 (t, 2H, J=8 Hz), 6.95 (t, 1H, J=8 Hz), 6.89 (d, 2H, J=8 Hz), 4.22 (t, 2H, J=6 Hz), 4.07 (s, 2H), 3.51 (m, 2H), 3.06 (t, 2H, J=6 Hz), 2.87 (m, 2H), 2.70 (bs, 6H), 1.83 (m, 2H), 1.71 (m, 2H) and 1.47 (m, 4H). R (KBr, cm$^{-1}$) 3339, 2929, 2854, 2815, 2776, 1642, 1602, 1580, 1554, 1532, 1492, 1468, 1247, 1017, 749, and 691. MS (ESI) m/e 481, 483. Anal. Calcd for C$_{26}$H$_{34}$N$_4$O$_3$S: C, 64.70; H, 7.10; N, 11.61; S, 6.64. Found C, 63.86; H, 7.13; N, 12.19; S, 6.76. Analytical HPLC: 97% purity.

Example 58

Preparation of {3-[4-(5-biphenyl-4-yl-[1,3,4]oxadiazol-2-yl)-phenoxy]-propyl}-dimethylamine

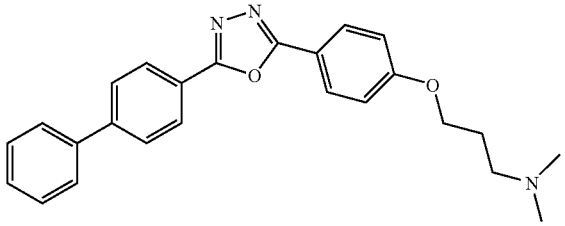

a) 4-hydroxy-benzoic acid N'-(biphenyl-4-carbonyl)-hydrazide

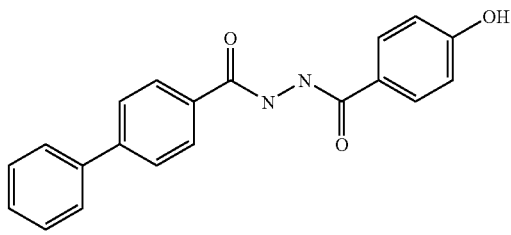

The above compound was prepared in a manner similar to that exemplified for the preparation of Example 51a, from 4-biphenylcarboxylic acid (1.04 g, 5.0 mmol) to afford 1.52 g (91%) of 4-hydroxy-benzoic acid N'-(biphenyl-4-carbonyl)-hydrazide as an off-white solid (279–281° C., MW 332.36).

$^1$H NMR (DMSO-d6) δ 10.44 (s, 1H), 10.24 (s, 1H), 10.09 (s, 1H), 8.00 (d, 2H, J=9 Hz), 7.81 (d, 2H, J=8 Hz), 7.79 (d, 2H, J=9 Hz), 7.74 (d, 2H, J=8 Hz), 7.49 (t, 2H, J=8 Hz), 7.40 (t, 1H, J=7 Hz), and 6.84 (d, 2H, J=9 Hz). IR (KBr, cm$^{-1}$) 3272, 1674, 1622, 1608, 1582, 1513, 1492, 1484, 1284, 1277, 1236, 847, and 745. MS (ESI) m/e 331, 333. Anal. Calcd for C$_{20}$H$_{16}$N$_2$O$_3$: C, 72.28; H, 4.85; N, 8.43. Found C, 72.52; H, 4.99; N, 8.27.

b) 4-(5-biphenyl-4-yl-[1,3,4]oxadiazol-2-yl)-phenol

The above compound was prepared in a manner similar to that exemplified for the preparation of Example 49e, from 4-hydroxy-benzoic acid N'-(biphenyl-4-carbonyl)-hydrazide (1.33 g, 4.0 mmol), triphenylphosphine (2.12 g, 8.0 mmol), and triethylamine (2.0 mL, 14.4 mmol) to afford 0.343 g (27%) of 4-(5-biphenyl-4-yl-[1,3,4]oxadiazol-2-yl)-phenol as an off-white solid (UT 256–260° C., MW 314.35).

$^1$H NMR (DMSO-d$_6$) δ 10.34 (s, 1H), 8.17 (d, 2H, J=8 Hz), 7.97 (d, 2H, J=8 Hz), 7.92 (d, 2H, J=8 Hz), 7.77 (d, 2H, J=8 Hz), 7.51 (t, 2H, J=8 Hz), 7.42 (t, 1H, J=8 Hz), and 6.97 (d, 2H, J=8 Hz). IR (KBr, cm$^{-1}$) 3110, 1613, 1498, 1483, 1293, 1176, 1074, 838, and 739. MS (ESI) m/e 313, 315. Anal. Calcd for C$_{20}$H$_{14}$N$_2$O$_2$: C, 76.42; H, 4.49; N, 8.91. Found C, 76.34; H, 4.75; N, 8.35.

c) {3-[4-(5-biphenyl-4-yl-[1,3,4]oxadiazol-2-yl)-phenoxy]-propyl}-dimethylamine

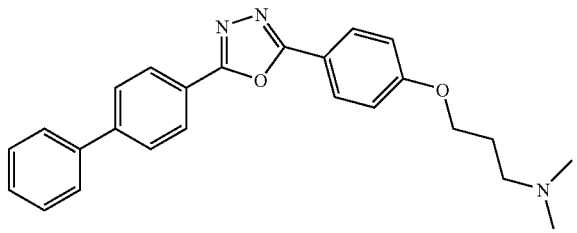

The above compound was prepared in a manner similar to that exemplified for the preparation of Example 50f, from 4-(5-biphenyl-4-yl-[1,3,4]oxadiazol-2-yl)-phenol (0.157 g, 0.5 mmol) to afford 0.162 g (81%) of {3-[4-(5-biphenyl-4-yl-[1,3,4]oxadiazol-2-yl)-phenoxy]-propyl}-dimethylamine as a white solid (MP 130–132° C., MW 399.50).

$^1$H NMR (CDCl$_3$) δ 8.19 (d, 2H, J=9 Hz), 8.09 (d, 2H, J=9 Hz), 7.76 (d, 2H, J=9 Hz), 7.66 (d, 2H, J=8 Hz), 7.49 (t, 2H, J=7 Hz), 7.41 (t, 1H, J=7 Hz), 7.03 (d, 2H, J=8 Hz), 4.18 (t, 2H, J=6 Hz), 3.07 (m, 2H), 2.72 (bs, 6H), and 2.36 (m, 2H). IR (KBr, cm$^{-1}$) 2940, 2752, 1613, 1473, 1464, 1257, 1006, 842, and 740. MS (ESI) m/e 400. Anal. Calcd for C$_{25}$H$_{25}$N$_3$O$_2$: C, 75.16; H, 6.31; N, 10.52. Found C, 73.89; H, 6.33; N, 10.35. Analytical HPLC: 95% purity.

Example 59

Preparation of Dimethyl-(3-{4-[5-(2-phenoxyethylsulfanylmethyl)-[1,3,4]thiadiazol-2-yl]-phenoxy}-propyl)-amine

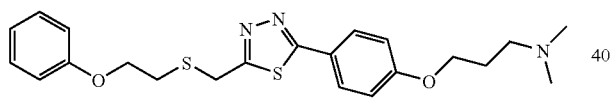

a) 4-[5-(2-phenoxyethylsulfanylmethyl)-[1,3,4]thiadiazol-2-yl]-phenol

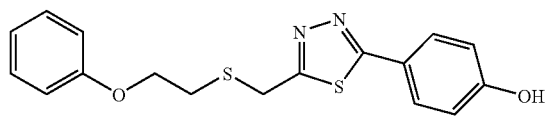

A heterogeneous mixture of 4-hydroxy-benzoic acid N'-[2-(2-phenoxyethylsulfanyl)-acetyl]-hydrazide (1.04 g, 3.0 mmol), and 2,4-bis(4-methoxyphenyl)-1,3-dithia-2,4-diphosphetane-2,4-disulfide (Lawesson's Reagent) (1.25 g, 3.0 mmol) in 30 mL toluene was stirred at reflux temperature (111° C.) for 1.5 h. The reaction mixture was allowed to cool to room temperature and concentrated in vacuo to afford 2.37 g of a yellow solid. Purification by column chromatography on silica gel (elution with linear gradient of 0–100% ethyl acetate/hexane followed by isocratic elution with 5% methanol/ethyl acetate) afforded 0.144 g (14%) of 4-[5-(2-phenoxyethylsulfanylmethyl)-[1,3,4]thiadiazol-2-yl]-phenol as a white solid (MP 127–128° C., MW 344.416).

$^1$H NMR (DMSO-d$_6$) δ 10.17 (s, 1H), 7.76 (d, 2H, J=9 Hz), 7.25 (t, 2H, J=8 Hz), 6.90 (m, 5H), 4.32 (s, 2H), 4.14 (t, 2H, J=6 Hz), and 2.93 (t, 2H, J=6 Hz). IR (KBr, cm$^{-1}$) 3415, 3125, 2920, 1600, 1586, 1496, 1243, 1177, 1032, 754, and 690. MS (ESI) m/e 345, 343. Anal. Calcd for C$_{17}$H$_{16}$N$_2$O$_2$S$_2$: C, 59.28; H, 4.68; N, 8.13; S, 18.62. Found C, 59.24; H, 4.71; N, 8.20; S, 18.36.

b) Dimethyl-(3-{4-[5-(2-phenoxyethylsulfanylmethyl)-[1,3,4]thiadiazol-2-yl]-phenoxy}-propyl)-amine

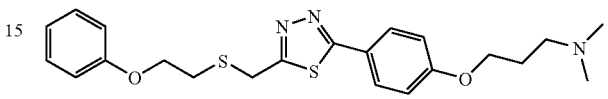

The above compound was prepared as exemplified in Example 50f, using 4-[5-(2-phenoxyethylsulfanylmethyl)-[1,3,4]thiadiazol-2-yl]-phenol (0.12 g, 0.35 mmol) to afford 0.038 g (25%) of dimethyl-(3-{4-[5-(2-phenoxyethylsulfanylmethyl)-[1,3,4]thiadiazol-2-yl]-phenoxy}-propyl)-amine as a white solid (MP 72–73° C., MW 429.61).

$^1$H NMR (CDCl$_3$) δ 7.87 (d, 2H, J=9 Hz), 7.26 (t, 2H, J=8 Hz), 6.95 (d, 2H, J=9 Hz), 6.91 (t, 1H, J=8 Hz), 6.88 (d, 2H, J=8 Hz), 4.22 (s, 2H), 4.18 (m, 4H), 3.25 (m, 2H), 2.99 (t, 2H, J=6 Hz), 2.87 (s, 3H), 2.86 (s, 3H), and 2.47 (m, 2H). IR (KBr, cm$^{-1}$) 2948, 2923, 2873, 2825, 2779, 1602, 1499, 1465, 1452, 1253, 1178, 1057, 955, 842, and 757. MS (ESI) m/e 428, 430. Anal. Calcd for C$_{22}$H$_{27}$N$_3$O$_2$S$_2$: C, 61.51; H, 6.33; N, 9.78; S, 14.93. Found C, 61.89; H, 6.68; N, 9.19; S, 13.88. Analytical HPLC: 91% purity.

Example 60

Preparation of N-(2-Dimethylamino-ethyl)3-[5-(2-phenoxy-ethylsulfanylmethyl)-[1,3,4]oxadiazol-2-yl]-benzamide

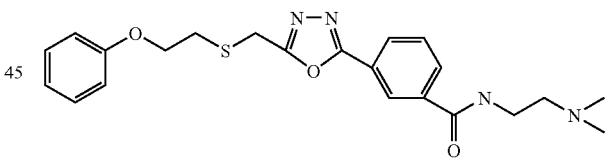

a) 3-(1H-Tetrazol-5-yl)-benzoic acid ethyl ester

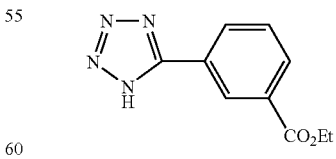

A solution of 3-cyano-benzoic acid ethyl ester (2.00 g, 11.4 mmol), sodium azide (2.22 g, 34.2 mmol), and triethylamine hydrochloride (4.71 g, 34.2 mmol) in 40 mL toluene was heated to 100° C. for 4.5 h. The mixture was cooled to room temperature and 150 mL of H$_2$O was added. The suspension was stirred for 10 min. and transferred to a separatory funnel and separated. The aqueous layer was transferred to a round-bottom flask with H$_2$O (50 mL), cooled to 0° C. and acidified with HCl (conc). The resultant precipitate was collected by filtration, washed with H$_2$O, and dried in vacuo to afford 2.36 g (95%) of 3-(1H-Tetrazol-5-yl)-benzoic acid ethyl ester as a white solid.

$^1$H NMR (DMSO-d6) δ 8.62 (s, 1H), 8.30 (d, 1H, J=8 Hz), 8.13 (d, 1H, J=8 Hz), 7.76 (t, 1H, J=8 Hz), 4.36 (q, 2H, J=7 Hz) and 1.3 (t, 3H, J=7 Hz). IR (KBr, cm$^{-1}$) 3153, 3102, 2924, 1690, 1295, 1277, and 733. MS (ESI) m/e 217. Anal. Calcd for C$_{10}$H$_{10}$N$_4$O$_2$Cl: C, 55.04; H, 4.62; N, 25.67. Found C, 55.09; H, 4.64; N, 25.39.

b) 3-[5-(2-Phenoxy-ethylsulfanylmethyl)-[1,3,4]oxadiazol-2-yl]-benzoic acid ethyl ester

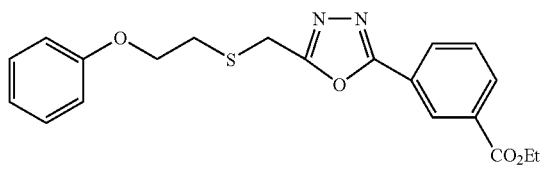

To a solution of thioacetic acid (0.65 g, 3.1 mmol) and 1,3-dicyclohexylocarbodiimide (0.64 g, 3.1 mmol) in 5 mL of toluene was added 3-(1H-Tetrazol-5-yl)-benzoic acid ethyl ester (0.67 g, 3.1 mmol). The reaction mixture was heated to 111° C. for 20 min., concentrated in vacuo and titurated with CH$_2$Cl$_2$ (5 mL). The resultant precipitate was collected by filtration and the filtrate concentrated in vacuo. The filtrate was purified directly by column chromatography on silica gel (elution with 1/1 ethyl acetate and toluene) to afford 0.880 g (75%) of 3-[5-(2-phenoxy-ethylsulfanylmethyl)-[1,3,4]oxadiazol-2-yl]-benzoic acid ethyl ester.

$^1$H NMR (CDCl$_3$) δ 8.7 (s, 1H), 8.2 (m, 2H), 7.6 (t, 1H, J=8 Hz), 7.3 (m, 3H), 6.9 (m, 2H), 4.4 (q, 2H, J=7 Hz), 4.2 (t, 2H, 6 Hz), 4.086 (s, 2H), 3.1 (t, 2H, J=6 Hz), and 1.4 (t, 3H, J=7 Hz). IR (KBr, cm$^{-1}$) 2935, 1719, 1601, 1498, 1303, 1244. MS (ESI) m/e 385. Anal. Calcd for C$_{20}$H$_{20}$N$_2$O$_4$S: C, 62.48; H, 5.24; N, 7.29. Found C, 61.7; H, 5.34; N, 6.83.

c) 3-[5-(2-Phenoxy-ethylsulfanylmethyl)-[1,3,4]oxadiazol-2-yl]-benzoic acid

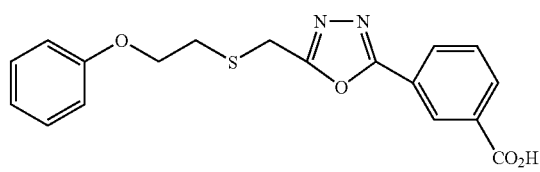

A solution of 3-[5-(2-Phenoxy-ethylsulfanylmethyl)-[1,3,4]oxadiazol-2-yl]-benzoic acid ethyl ester (0.880 g, 2.29 mmol) and lithium hydroxide (0.164 g, 6.87 mmol) in water (3 mL) and THF (7 mL) was stirred at room temperature overnight. Concentrated HCl (0.59 mL) was added and the resulting precipitate was collected by filtration and dried in vacuo to afford 0.694 g (85%) of 3-[5-(2-Phenoxy-ethylsulfanylmethyl)-[1,3,4]oxadiazol-2-yl]-benzoic acid as a gold solid.

$^1$H NMR (DMSO-d6) δ8.5 (s, 11H), 8.1 (m, 2H), 7.7 (t, 1H, J=7.7 Hz), 7.25 (m, 2H), 6.9 (m, 3H), 4.2 (s, 2H), 4.2 (t, 2H, J=6.2 Hz), and 3.0 (t, 2H, J=6.3 Hz). IR (KBr, cm$^{-1}$) 3419, 3295, 2928, 2852, 1717, 1600, 1498, 1246, 757, 714, and 690. MS (ESI) m/e 357, 355. Anal. Calcd for C$_{18}$H$_{16}$N$_2$O$_4$S: C, 60.66; H, 4.53; N, 7.86. Found C, 58.25; H, 5.16; N, 6.99.

d) N-(2-Dimethylamino-ethyl)-3-[5-(2-phenoxy-ethylsulfanylmethyl)-[1,3,4]oxadiazol-2-yl]-benzamide

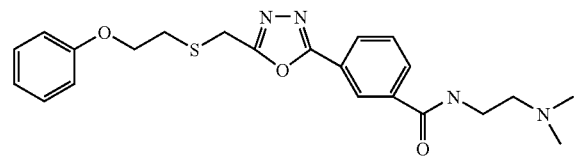

3-[5-(2-Phenoxy-ethylsulfanylmethyl)-[1,3,4]oxadiazol-2-yl]-benzoic acid was added to a nitrogen flushed vessal with CH$_2$Cl$_2$ (5 mL) followed by the addition of oxalyl chloride (0.397 g, 3.13 mmol) and DMF (2 drops). The mixture was stirred at room temperature for 35 min., concentrated in vacuo and azeotroped with CH$_2$Cl$_2$ (3×5 mL) to give 3-[5-(2-phenoxy-ethylsulfanylmethyl)-[1,3,4]oxadiazol-2-yl]-benzoyl chloride. N1,N1-Dimethyl-ethane-1,2-diamine was dissolved in CH$_2$Cl$_2$ (1 mL) and added to a nitrogen flushed vessal. 3-[5-(2-phenoxy-ethylsulfanylmethyl)-[1,3,4]oxadiazol-2-yl]-benzoyl chloride was dissolved in CH$_2$Cl$_2$ (3 mL) and added dropwise. The reaction was stirred at room temperature overnight and diluted with water, CH$_2$Cl$_2$, and NaOH (1N). The aqueous layer was extracted 2 times with CH$_2$Cl$_2$. The combined organic extracts were washed with saturated brine, dried over sodium sulfate, filtered, and concentrated. The residue was purified by column chromatography on silica gel (elution with 95 CHCl$_3$/5 NH$_3$ (2.0M in MeOH) to afford 0.167 g (63%) of N-(2-dimethylamino-ethyl)-3-[5-(2-phenoxy-ethylsulfanylmethyl)-[1,3,4]oxadiazol-2-yl]-benzamide. Recrystallization from Et$_2$O and EtOAc gave 0.079 g (30%) of the title compound.

$^1$H NMR (DMSO-d6) δ8.7 (t, 1H, J=5 Hz), 8.4 (s, 1H), 8.1 (m, 2H), 7.7 (t, 1H, J=8), 7.2 (m, 2H), 6.9 (m, 3H), 4.2 (s, 2H), 4.2 (t, 2H, J=6 Hz), 3.4 (m, 2H), 3.0 (t, 2H, J=6 Hz), 2.4 (t, 2H, J=7 Hz), 2.1 (s, 6H). IR (KBr, cm$^{-1}$) 2952, 2864, 2827, 2785, 1658, 1601, 1498, 1243. MS (ESI) m/e 428, 429, 425. Anal. Calcd for C$_{22}$H$_{26}$N$_4$O$_3$S: C, 61.95; H, 6.14; N, 13.14. Found C, 61.80; H, 6.23; N, 12.92. MP=64° C.

Example 61

Preparation of N-(4-dimethylamino-butyl)-3-[5-(2-phenoxy-ethylsulfanylmethyl)-[1,3,4]oxadiazol-2-yl]-benzamide

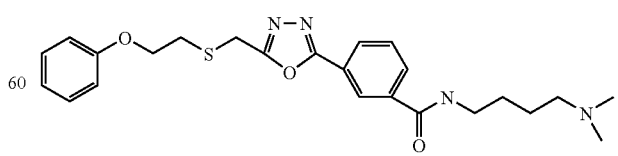

The above compound was prepared in a manner similar to that exemplified for the preparation of Example 60, from 3-[5-(2-phenoxy-ethylsulfanylmethyl)-[1,3,4]oxadiazol-2- yl]-benzoic acid (0.353 g, 1.0 mmol) and N1,N1-dimethyl-butane-$_{1,4}$-diamine (0.230 g, 1.98 mmol) to give 0.346 g (77%) of the title compound.

$^1$H NMR (CDCl$_3$) δ8.4 (s, 1H), 8.1, (d, 1H, J=8 Hz), 8.0 (d, 1H, J=8 Hz), 7.6, (t, 1H, J=8 Hz), 7.2 (m, 3H), 6.9 (m, 2H), 4.2 (t, 2H, J=6 Hz), 4.1 (s, 2H), 3.5 (q, 2H, J=5 Hz), 3.1 (t, 2H, J=6 Hz), 2.4 (t, 2H, J=6 Hz), 2.2 (s, 6H), 1.8 (m, 2H), 1.7 (m, 2H). IR (KBr, cm$^{-1}$) 2940, 2864, 2826, 2784, 1659, 1601, 1549, 1498, 1243. MS (ESI) m/e 455, 453. Anal. Calcd for C$_{24}$H$_{30}$N$_4$O$_3$S: C, 63.41; H, 6.65; N, 12.32. Found C, 63.52; H, 7.17; N, 12.07. MP=38–42° C.

Example 62

Preparation of N-(3-dimethylamino-propyl)-3-[5-(2-phenoxy-ethylsulfanylmethyl)-[1,3,4]oxadiazol-2-yl]-benzamide

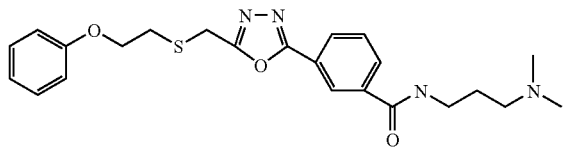

The above compound was prepared in a manner similar to that exemplified for the preparation of Example 60, from 3-[5-(2-phenoxy-ethylsulfanylmethyl)-[1,3,4]oxadiazol-2-yl]-benzoic acid (0.387 g, 1.1 mmol) and N1,N1-dimethyl-propane-1,3-diamine (221 mg, 2.16.mmol) to give 0.046 g (10%) of N-(3-dimethylamino-propyl)-3-[5-(2-phenoxy-ethylsulfanylmethyl)-[1,3,4]oxadiazol-2-yl]-benzamide.

$^1$H NMR (CDCl$_3$) δ9.1 (s, br, 1H), 8.4, (s, 1H), 8.14 (d, 1H, J=8 Hz), 8.1 (d, 1H, J=8 Hz), 7.3 (m, 2H), 6.94 (t, 1H, J=7 Hz), 6.9 (d, 2H, J=8 Hz) 4.2 (t, 2H, J=6 Hz), 4.1 (s, 2H), 3.6 (m, 2H), 3.1), 2H, J=6 Hz), 2.6 (m, 2H), 2.4 (s, 6H), 1.8 (q, 2H, J=6 Hz). IR, (KBr, cm$^{-1}$) 3018, 1653, 1548, 1498, 1243. MS (ESI) m/e 441, 439. HPLC 100%. Anal. Calcd for C$_{23}$H$_{28}$N$_4$O$_3$S: C, 62.70; H, 6.41; N, 12.72. Found C, 61.60; H, 6.19; N, 12.22. MP=88–90° C.

Example 63

Preparation of N-(4-dimethylamino-butyl)-2-[5-(2-phenoxy-ethylsulfanylmethyl)-[1,3,4]oxadiazol-2-yl]-benzamide

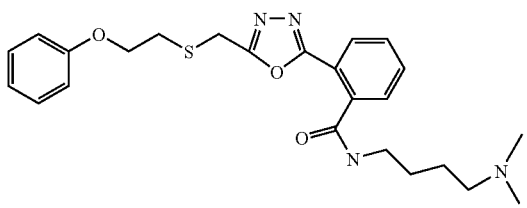

a) 2-(1H-Tetrazol-5-yl)-benzoic acid methyl ester

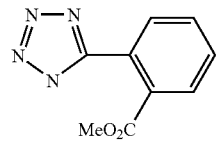

The above compound was prepared in a manner similar to that exemplified for the preparation of Example 60a, from 2-cyano-benzoic acid methyl ester (2.031 g, 12.6 mmol) to give 1.87 g (73%) of 2-(1H-tetrazol-5-yl)-benzoic acid methyl ester.

$^1$H NMR (DMSO-d6) δ7.9 (m, 1H), 7.7 (m, 3H), 3.7 (s, 3H). IR (KBr, cm$^{-1}$) 1715, 1273. MS (ESI) m/e 203. Anal. Calcd for C$_9$H$_8$N$_4$O$_2$: C, 55.04; H, 4.62; N, 25.67. Found C, 53.68; H, 3.89; N, 28.61.

b) 2-[5-(2-Phenoxy-ethylsulfanylmethyl)-[1,3,4]oxadiazol-2-yl]-benzoic acid methyl ester

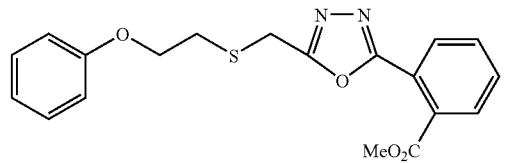

The above compound was prepared in a manner similar to that exemplified for the preparation of Example 60b, from 2-(1H-Tetrazol-5-yl)-benzoic acid methyl ester (0.705 g, 3.45 mmol) to give 0.985 g (73%) of 2-[5-(2-phenoxy-ethylsulfanylmethyl)-[1,3,4]oxadiazol-2-yl]-benzoic acid methyl ester.

$^1$H NMR (CDCl$_3$) δ7.9 (m, 1H), 7.8 (m, 1H), 7.6 (m, 1H), 7.2 (m, 2H), 6.95 (t, 1H, J=7 Hz), 6.9 (d, 2H, J=9 Hz), 4.2 (t, 2H, J=6 Hz), 4.0 (s, 2H), 3.8 (s, 3H), 3.0 (t, 2H, J=6 Hz). IR (KBr, cm$^{-1}$) 1728, 1601, 1498, 1299, 1276, 1243. MS (ESI) m/e 371. Anal. Calcd for C$_{19}$H$_{18}$N$_2$O$_4$S: C, 61.61; H, 4.90; N, 7.56. Found C, 61.41; H, 4.94; N, 7.46.

c) 2-[5-(2-Phenoxy-ethylsulfanylmethyl)-[1,3,4]oxadiazol-2-yl]-benzoic acid

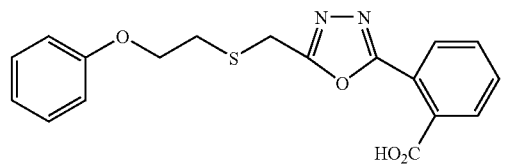

The above compound was prepared in a manner similar to that exemplified for the preparation of Example 60c, from 2-[5-(2-phenoxy-ethylsulfanylmethyl)-[1,3,4]oxadiazol-2-yl]-benzoic acid methyl ester (0.929 g, 2.51 mmol) with the exception that a gold oil formed upon treatment with conc. HCl. This material was titurated with H$_2$O and concentrated to dryness in vacuo to give 0.808 g (90%) of 2-[5-(2-phenoxy-ethylsulfanylmethyl)-[1,3,4]oxadiazol-2-yl]-benzoic acid.

$^1$H NMR(CD$_3$OD) δ8.1 (m, 1H), 7.7 (m, 3H), 7.2 (m, 2H), 6.9 (m, 3H), 4.2 (t, 2H, J=6 Hz) 4.16 (s, 2H), 3.1 (t, 2H, J=6 Hz). IR (KBr, cm$^{-1}$) 3430, 1723, 1635, 1601, 1241. MS (ESI) m/e 357, 355. Anal. Calcd for C$_8$H$_{16}$N$_2$O$_4$S: C, 60.66; H, 4.53; N, 7.86. Found C, 55.74; H, 4.48; N, 7.28.

d) N-(4-Dimethylamino-butyl)-2-[5-(2-phenoxy-ethylsulfanylmethyl)-[1,3,4]oxadiazol-2-yl]-benzamide

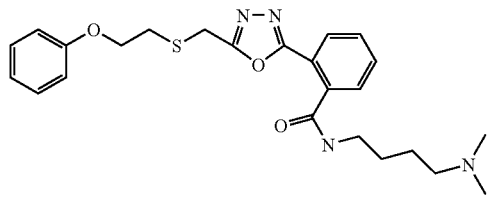

The above compound was prepared in a manner similar to that exemplified for the preparation of Example 60d, from 2-[5-(2-phenoxy-ethylsulfanylmethyl)-[1,3,4]oxadiazol-2-yl]-benzoic acid (0.434 g, 1.22 mmol) and N1,N1-dimethyl-butane-1,4-diamine (0.283 g, 2.44.mmol) to give 0.334 g (60%) of the title compound.

$^1$H NMR (CDCl$_3$) δ8.1 (s (br), 1H), 7.9 (d, 1H, J=7 Hz), 7.5 (m, 3H), 7.3 (m, 2H), 6.95 (t, 1H, J=6 Hz), 6.9 (d, 2H, J=8 Hz), 4.2 (t, 2H, J=6 Hz), 4.0 (s, 2H), 3.4 (q, 2H, J=6 Hz), 3.0 (t, 2H, J=6 Hz), 2.3 (t, 2H, J=6 Hz), 2.0 (s, 6H), 1.66 (m, 2H), 1.6 (m, 2H). IR (KBr, cm$^{-1}$) 3008, 2941, 2864, 2824, 2782, 1721, 1662, 1601, 1588, 1498, 1469, 1243. MS (ESI) m/e 455, 453. Anal. Calcd for C$_{24}$H$_{30}$N$_4$O$_3$S: C, 63.41; H, 6.65; N, 12.32. Found C, 63.38; H, 7.01; N, 11.73. MP=62–65° C.

Example 64

Preparation of N-(2-dimethylamino-ethyl)-2-[5-(2-phenoxy-ethylsulfanylmethyl)-[1,3,4]oxadiazol-2-yl]-benzamide

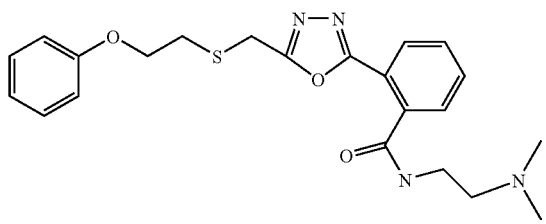

The above compound was prepared in a manner similar to that exemplified for the preparation of Example 60d, from 2-[5-(2-phenoxy-ethylsulfanylmethyl)-[1,3,4]oxadiazol-2-yl]-benzoic acid (0.169 g, 0.474 mmol) and N1,N1-dimethyl-ethane-1,2-diamine (0.084 g, 0.948 mmol) to give 0.082 g (41%) of the title compound.

$^1$H NMR (CDCl$_3$) δ7.8 (d, 1H, J=7 Hz), 7.5 (m, 3H), 7.2 (m, 2H), 6.9 (t, 1H, J=7 Hz), 6.8 (d, 2H, J=8 Hz), 4.1 (t, 2H, J=6 Hz), 3.9 (s, 2H), 3.5 (m, 2H), 3.0 (t, J=6 Hz) 2.5 (s, br, 1H), 2.2 (s, 6H). IR (KBr, cm$^{-1}$) 3009, 1722, 1665, 1601, 1498, 1470, 1402, 1242. MS (ESI) m/e 427, 425. Anal. Calcd for C$_{22}$H$_{26}$N$_4$O$_3$S: C, 61.95; H, 6.14; N, 13.13. Found C, 59.49; H, 5.91; N, 12.18. MP=80–85° C.

Example 65

Preparation of N-(3-dimethylamino-propyl)-2-[5-(2-phenoxy-ethylsulfanylmethyl)-[1,3,4]oxadiazol-2-yl]-benzamide

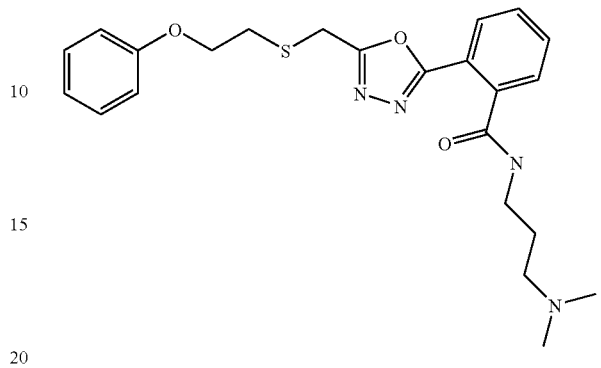

To a solution of 2-[5-(2-phenoxy-ethylsulfanylmethyl)-[1,3,4]oxadiazol-2-yl]-benzoic acid (0.159 g, 0.45 mmol) in 3 mL THF was added 1,1'-carbonyldiimidazole (0.073 g, 0.45 mM) and 0.044 mL DMF. The mixture was heated to 60° C. for 30 min followed by stirring at room temperature for 5 min. N1,N1-Dimethyl-propane-1,3-diamine (0.091 g, 0.89 mmol) was added to the mixture and stirring was continued at room temperature for 2 hours. The mixture was extracted with ethyl acetate and washed with water, brine, dried over sodium sulfate, filtered and concentrated. Purification by column chromatography on silica gel (elution with chloroform and 2M ammonia in methanol gave 0.072 g (37%) of the title compound.

$^1$H NMR (CDCl$_3$) δ 7.9 (d, 1H, J=7 Hz), 7.5 (m, 3H), 7.3 (m, 2H), 7.1 (s, 1H), 6.96 (t, 1H, J=7 Hz), 6.9 (d, 3H, J=39 Hz), 4.2 (7, 2H, J=6 Hz), 4.0 (s, 2H), 3.5 (m, 2H), 3.0 (t, 2H, J=6 Hz), 2.5 (t, 2H, J=6 Hz), 2.2 (s, 6H), 1.7 (m, 2H, J=6 Hz). IR (KBr, cm$^{-1}$) 2928, 2864, 1722, 1684, 1498, 1242. MS (ES) m/e 441. Anal. Calcd for C$_{23}$H$_{28}$N$_4$O$_3$S: C, 62.70; H, 6.41; N, 12.72. Found C, 58.41; H, 6.16; N, 11.47. MP=60–65° C.

Example 66

Preparation of dimethyl-(2-{4-[5-(2-phenoxy-ethyl-sulfanylmethyl)-[1,3,4]oxadiazol-2-yl]-phenoxy}-ethyl)-amine

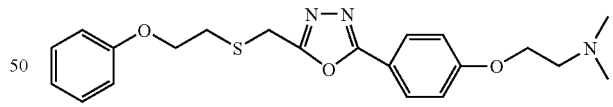

a) 4-Hydroxy-benzoic acid N'-[2-(2-phenoxy-ethyl-sulfanyl)-acetyl]-hydrazide

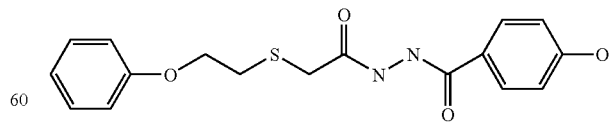

A solution of (2-phenoxy-ethylsulfanyl)-acetic acid (0.848 g, 4.0 mmol) and (2-ethoxy-1-ethoxycarbonyl-1,2-dihdroquinoline, ethyl 1,2-dihydro-2-ethoxy-1-quinolin-ecarboxylate), (EEDQ), (0.989 g, 4.0 mmol) in 20 mL acetonitrile and 5 mL THF were stirred together at room temperature for 1 hr. 4-Hydroxy-benzoic acid hydrazide (0.608 g, 4.0 mmol) was added and the mixture was sonicated for 2 hrs and stirred at room temperature for 16 hrs. The mixture was concentrated to low volume and extracted with ethyl acetate. The organic extract was washed with 1N HCl, H$_2$O, NaHCO$_3$, brine, dried over magnesium sulfate, filtered, and concentrated to dryness to give 1.28 g (92%) of 4-hydroxy-benzoic acid N'-[2-(2-phenoxy-ethylsulfanyl)-acetyl]-hydrazide.

$^1$H NMR (DMSO-d6) δ 10.2 (s, 1H), 10.1 (s, 1H), 10.0 (s, 1H), 7.7 (d, 2H, J=9 Hz), 7.3 (m, 2H), 6.9 (m, 3H), 6.8 (d, 2H, J=9 Hz), 4.2 (t, 2H, J=6 Hz), 3.3 (m, 2H), 3.0 (t, 2H, J=6 Hz). IR (KBr, cm$^{-1}$) 3305, 3201, 3003, 2918, 2867, 1696, 1623, 1609, 1584, 1517, 1287, 1242, 1229. MS (ESI) m/e 347, 345. Anal. Calcd for C$_{17}$H$_{18}$N$_2$O$_4$S: C, 58.95; H, 5.24; N, 8.09. Found C, 58.37; H, 5.51; N, 7.19.

b) 4-[5-(2-phenoxy-ethylsulfanylmethyl)-[1,3,4]oxadiazol-2-yl]-phenol

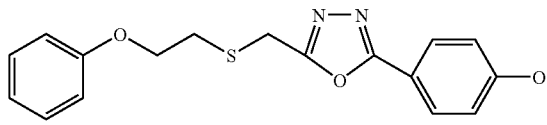

A solution of 4-hydroxy-benzoic acid N-[2-(2-phenoxy-ethylsulfanyl)-acetyl]-hydrazide (4.87 g, 14.1 mmol), triphenylphosphine (7.38 g, 28.1 mmol), and triethylamine (5.14 g, 50.7 mmol) were stirred together in acetonitrile (15 mL). Carbon tetrachloride (9.17 g, 57.9 mmol) was added and the mixture was stirred at room temperature for 3 hrs. The material was concentrated to low volume and diluted with hexane (100 mL), ethyl acetate (6 mL), and ethanol (25 mL). The mixture was sonnicated for 5 minutes and a precipitate formed. The solid was collected and dried in vaccuo (30° C.). The solid was slurried with 1N HCl, collected and dried to give 3.149 g (68%) of the title compound.

$^1$H NMR (DMSO-d6) δ 7.8 (d, 2H, J=9 Hz), 7.2 (t, 2H, J=8 Hz), 6.9 (m, 5H), 4.2 (m, 4H), 3.0 (t, 2H, J=6 Hz). IR (KBr, cm$^{-1}$) 3410, 1762, 1611, 1601, 1498, 1242, 1226, 1174, 752. MS (ESI) m/e 329, 327. Anal. Calcd for C$_{17}$H$_{16}$N$_2$O$_3$S: C, 62.18; H, 4.91; N, 8.53. Found C, 61.99; H, 5.00; N, 7.92. M.P.=172–175° C.

c) Preparation of dimethyl-(2-{4-[5-(2-phenoxy-ethylsulfanylmethyl)-[1,3,4]oxadiazol-2-yl]-phenoxy}-ethyl)-amine

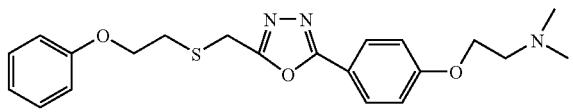

A solution of 4-[5-(2-phenoxy-ethylsulfanylmethyl)-[1,3,4]oxadiazol-2-yl]-phenol (0.214 g, 0.652 mmol) and 60% NaH (0.075 g, 1.95 mmol) was stirred at 5° C. in 10 mL DMF for 2 min. at which time (2-chloro-ethyl)-dimethyl-amine, hydrochloride (0.140 g, 0.978 mmol) was added and the mixture was stirred at 100° C. for 2.5 hours. The resultant mixture was extracted 2 times with ethyl acetate and washed with water, brine, dried over sodium sulfate and concentrated to give 0.243 g of crude product. This was purified directly by column chromatography on silica gel (elution with 1/1 ethyl acetate, toluene followed by chloroform/2M ammonia in methanol) to give a yellow oil which was recrystallized from ethyl ether and ethyl acetate to give 0.098 g (38%) of the title compound.

$^1$H NMR (DMSO-d6) δ 7.9 (d, 2H, J=9 Hz), 7.2 (m, 2H), 7.1 (d, 2H, J=9 Hz), 6.9 (m, 3H), 4.1 (m, 6H), 3.0 (t, 2H, J=6 Hz), 2.6 (t, 2H, J=5 Hz), 2.2 (s, 6H). IR (KBr, cm$^{-1}$) 1616, 1499, 1466, 1253, 1242, 1177, 756. MS ESI) m/e 400.9. Anal. Calcd for C$_{21}$H$_{25}$N$_3$O$_3$S: C, 63.14; H, 6.31; N, 10.52. Found C, 62.92; H, 6.09; N, 10.38. MP=62–64° C.

Example 67

Preparation of dimethyl-(3-{4-[5-(2-phenoxy-ethylsulfanylmethyl)-[1,3,4]oxadiazol-2-yl]-phenoxy}-propyl)-amine

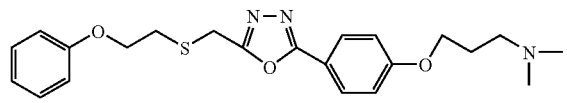

The above compound was prepared in a manner similar to that exemplified for the preparation of Example 66c, from 4-[5-(2-phenoxy-ethylsulfanylmethyl)-[1,3,4]oxadiazol-2-yl]-phenol (0.548 g, 1.67 mmol) and (3-chloro-propyl)-dimethyl-amine, hydrochloride (396 mg, 2.5 mmol) to give 0.288 g (42%) of the title compound.

$^1$H NMR (DMSO-d6) δ 7.9 (d, 2H, J=9 Hz), 7.3 (t, 2H, J=7 Hz), 7.1 (d, 2H, J=9 Hz), 6.9 (m, 3H), 4.2 (m, 4H), 4.1 (t, 2H, J=6 Hz), 3.0 (t, 2H, J=6 Hz), 2.4 (t, 2H, J=7 Hz), 2.1 (s, 6H), 1.9 (m, 2H). IR (KBr, cm$^{-1}$) 2934, 1612, 1601, 1503, 1491, 1466, 1253, 1243, 1178, 762. MS (ESI) m/e 414. Anal. Calcd for C$_{22}$H$_{27}$N$_3$O$_3$S: C, 63.90; H, 6.58; N, 10.16. Found C, 63.55; H, 6.50; N, 10.04. MP=70° C.

Example 68

Preparation of dimethyl-(4-{4-[5-(2-phenoxy-ethylsulfanylmethyl)-[1,3,4]oxadiazol-2-yl]-phenoxy}-butyl)-amine

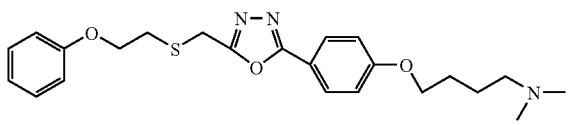

a) 2-[4-(4-Chloro-butoxy)-phenyl]-5-(2-phenoxy-ethylsulfanylmethyl)-[1,3,4]oxadiazole

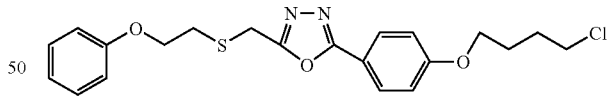

A solution of 4-[5-(2-phenoxy-ethylsulfanylmethyl)-[1,3,4]oxadiazol-2-yl]-phenol (0.202 g, 0.615 mmol), 1-bromo-4-chloro-butane (0.158 g, 0.922 mmol), and potassium carbonate (0.195 g, 1.41 mM) was refluxed in 5 mL acetone overnight. The solid was removed by filtration and the filtrate concentrated to dryness. Recrystallization of the filtrate from ether and ethyl acetate gave 0.127 g (49%) of 2-[4-(4-chloro-butoxy)-phenyl]-5-(2-phenoxy-ethylsulfanylmethyl)-[1,3,4]oxadiazole.

$^1$H NMR (DMSO-d6) δ 7.8 (d, 2H, J=9 Hz), 7.2 (m, 2H), 7.1 (d, 2H, J=9 Hz), 6.9 (m, 3H), 4.2 (m, 4H), 4.1 (t, 2H, J=6 Hz), 3.7 (t, 2H, J=6 Hz), 3.0 (t, 2H, J=6 Hz), 1.9 (m, 4H). IR (KBr, cm$^{-1}$) 1614, 1604, 1586, 1499, 1253, 1242, 1176. MS (ESI) m/e 419, 417. Anal. Calcd for C$_{21}$H$_{23}$ClN$_2$O$_3$S: C, 61.80; H, 6.09; N, 6.26. Found C, 59.82; H, 5.67; N, 6.41.

b) Dimethyl-(4-{4-[5-(2-phenoxy-ethylsulfanylmethyl)-[1,3,4]oxadiazol-2-yl]-phenoxy}-butyl)-amine

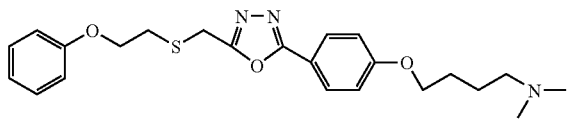

A solution of 2-[4-(4-chloro-butoxy)-phenyl]-5-(2-phenoxy-ethylsulfanylmethyl)-[1,3,4]oxadiazole (0.127 g, 0.303 mmol), dimethyl amine (2M THF, 3.8 mL, 7.58 mmol), NaI (0.004 g, 0.0236 mmol), and NaHCO₃ (0.071 g, 0.84 mmol) in 4 mL DMF was heated to 80° C. overnight in a sealed tube. The mixture was extracted with ethyl acetate followed by washing with water, brine, dried over sodium sulfate and concentrated to dryness. The residue was purified directly by column chromatography on silica gel (elution with ethyl acetate/toluene followed by 90% chloroform/10% 2M ammonia in methanol) to give 0.090 g (70%) of the title compound.

¹H NMR (DMSO-d6) δ7.9 (d, 2h, J=9 Hz), 7.2 (m, 2H), 7.1 (d, 2H, J=9 Hz), 6.9 (m, 3H), 4.2 (m, 4H), 4.0 (t, 2H, J=6 Hz), 3.0 (t, 2H, J=6 Hz), 2.2 (t, 2H, J=7 Hz), 2.1 (s, 6H), 1.7 (m, 2H), 1.5 (m, 2H). IR (KBr, cm⁻¹) 2763, 1612, 1501, 1259, 1246, 1177, 999, 841. MS (ESI) m/e 428. Anal. Calcd for C₂₃H₂₉N₃O₃S: C, 64.61; H, 6.84; N, 9.83. Found C, 64.60; H, 6.85; N, 9.69. MP=62–63° C.

Example 69

Preparation of dimethyl-(5-{4-[5-(2-phenoxy-ethylsulfanylmethyl)-[1,3,4]oxadiazol-2-yl]-phenoxy}-pentyl)-amine a) 2-[4-(5-Chloro-pentyloxy)-phenyl]-5-(2-phenoxy-ethylsulfanylmethyl)-[1,3,4]oxadiazole

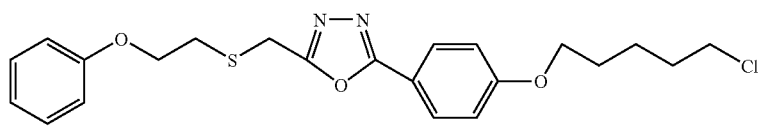

The above compound was prepared in a manner similar to that exemplified for the preparation of Example 68a, from 4-[5-(2-phenoxy-ethylsulfanylmethyl)-[1,3,4]oxadiazol-2-yl]-phenol (0.304 g, 0.926 mmol), and 1-bromo-5-chloro-pentane (0.250 g, 1.38 mmol) to give 0.260 g (65%) of 2-[4-(5-chloro-pentyloxy)-phenyl]-5-(2-phenoxy-ethylsulfanylmethyl)-[1,3,4]oxadiazole.

¹H NMR (DMSO-d6) δ7.9 (d, 2H, J=9 Hz) 7.2 (m, 2H), 7.1 (d, 2H, J=9 Hz), 6.9 (m, 3H), 4.2 (m 4H), 4.0 (t, 2H, J=6 Hz), 3.6 (t, 2H, J=7 Hz), 3.0 (t, 2H, J=6 Hz), 1.8 (m, 4H), 1.5 (m, 2H). IR (KBr, cm⁻¹) 1611, 1503, 1490, 1258, 1244, 1178, 1005, 844, 765. MS (ESI) m/e 433. Anal. Calcd for C₂₂H₂₅N₂ClO₃S: C, 61.03; H, 5.82; N, 6.47. Found C, 59.71; H, 5.75; N, 6.34.

b) Dimethyl-(5-{4-[5-(2-phenoxy-ethylsulfanylmethyl)-[1,3,4]oxadiazol-2-yl]-phenoxy}-pentyl)-amine

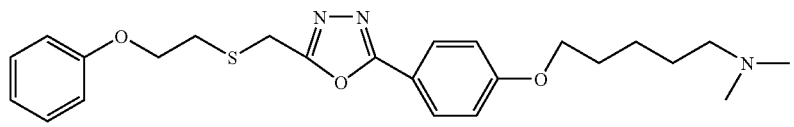

The above compound was prepared in a manner similar to that exemplified for the preparation of Example 68b, from 2-[4-(5-chloro-pentyloxy)-phenyl]-5-(2-phenoxy-ethylsulfanylmethyl)-[1,3,4]oxadiazole (0.210 g, 0.487 mmol) to give 0.111 g (52%) of the title compound.

¹H NMR (DMSO-d6) δ7.8 (d, 2H, J=9 Hz), 7.2 (m, 2H), 7.1 (d, 2H, J=9 Hz), 6.9 (m, 3H), 4.1 (m, 4H), 4.0 (t, 2H, J=6 Hz), 3.0 (t, 2H, J=6 Hz) 2.2 (t, 2H, J=7 Hz), 2.1 (s, 6H), 1.7 (m, 2H), 1.4 (m, 4H). IR (KBr, cm⁻¹) 2941, 1602, 1610, 1500, 1466, 1253, 1175, 1032, 835, 751. MS (ESI) m/e 442. Anal. Calcd for C₂₄H₃₁N₃O₃S: C, 65.28; H, 7.08; N, 9.51. Found C, 65.47; H, 7.03; N, 9.35. MP 51–54° C.

Example 70

Preparation of dimethyl-(6-{4-[5-(2-phenoxy-ethyl-sulfanylmethyl)-[1,3,4]oxadiazol-2-yl]-phenoxy}-hexyl)-amine

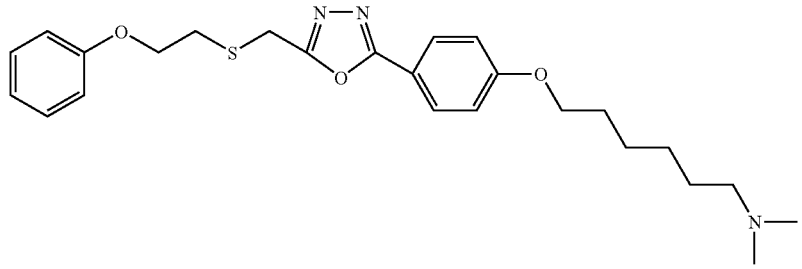

a) 2-[4-(6-Chloro-hexyloxy)-phenyl]-5-(2-phenoxy-ethylsulfanylmethyl)-[1,3,4]oxadiazole

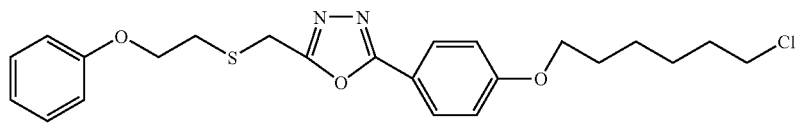

The above compound was prepared in a manner similar to that exemplified for the preparation of Example 68a, from 4-[5-(2-phenoxy-ethylsulfanylmethyl)-[1,3,4]oxadiazol-2-yl]-phenol (0.243 g, 0.739 mmol) and 1-bromo-6-chlorohexane (0.221 g, 1.11 mmol) to give 0.266 g (81%) of 2-[4-(6-chloro-hexyloxy)-phenyl]-5-(2-phenoxy-ethylsulfanylmethyl)-[1,3,4]oxadiazole.

$^1$H NMR (DMSO-d6) δ7.9 (d, 2H, J=9 Hz), 7.2 (m, 2H), 7.1 (d, 2H, J=9 Hz), 6.9 (m, 3H), 4.2 (m, 4H), 4.0 (t, 2H, J=6 Hz), 3.6 (t, 2H, J=7 Hz), 3.0 (t, 2H, J=6 Hz), 1.7 (m, 4H), 1.4 (m, 4H). IR (KBr, cm$^{-1}$) 3456, 2936, 2866, 1615, 1586, 1503, 1466, 1258, 1239, 1176, 1007, 843, 764. MS (ES) m/e 447. Anal. Calcd for $C_{23}H_{27}N_2ClO_3S$: C, 61.80; H, 6.09; N, 6.27. Found C, 61.62; H, 5.55; N, 6.21.

b) Dimethyl-(6-{4-[5-(2-phenoxy-ethylsulfanylmethyl)-[1,3,4]oxadiazol-2-yl]-phenoxy}-hexyl)-amine

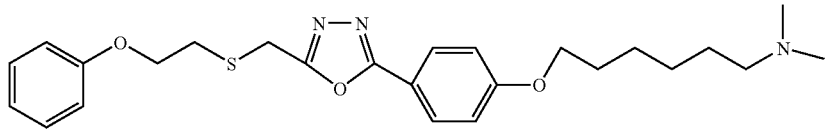

The above compound was prepared in a manner similar to that exemplified for the preparation of Example 68b, from 2-[4-(6-chloro-hexyloxy)-phenyl]-5-(2-phenoxy-ethylsulfanylmethyl)-[1,3,4]oxadiazole (0.266 g, 0.595 mmol) to give 0.116 g (43%) of the title compound.

$^1$H NMR (DMSO-d6) δ7.9 (d, 2H, J=9 Hz), 7.2 (m, 2H), 7.1 (d, 2H, J=9 Hz), 6.9 (m, 3H), 4.2 (m, 4H), 4.0 (t, J=6 Hz), 3.0 (t, 2H, J=6 Hz), 2.2 (t, 2H, J=7 Hz), 2.1 (s, 6H), 1.7 (m, 2H), 1.4 (m, 4H), 1.3 (m, 2H). IR (KBr, cm$^{-1}$) 1611, 1602, 1587, 1500, 1466, 1249, 1175, 1024, 756. MS (ESI) m/e 456. Anal. Calcd for $C_{25}H_{33}N_3O_3S$: C, 65.90; H, 7.30; N, 9.22. Found C, 65.37; H, 7.16; N, 9.08.

Example 71

Preparation of dimethyl-(7-{4-[5-(2-phenoxy-ethyl-sulfanylmethyl)-[1,3,4]oxadiazol-2-yl]-phenoxy}-heptyl)-amine

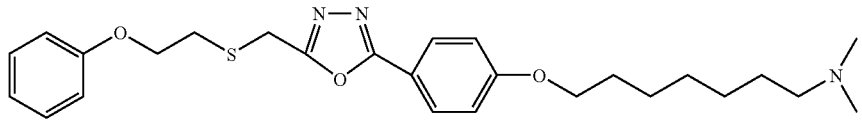

a) 7-{4-[5-(2-phenoxy-ethylsulfanylmethyl)-[1,3,4]oxadiazol-2-yl]-phenoxy}-heptan-1-ol

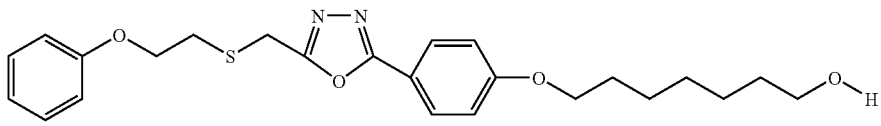

The above compound was prepared in a manner similar to that exemplified for the preparation of Example 68a, from 4-[5-(2-phenoxy-ethylsulfanylmethyl)-[1,3,4]oxadiazol-2-yl]-phenol (0.260 g, 0.792 mmol) and 7-bromo-heptan-1-ol (0.232 g, 1.19 mmol) to give 0.164 g (47%) of 7-{4-[5-(2-phenoxy-ethylsulfanylmethyl)-[1,3,4]oxadiazol-2-yl]-phenoxy}-heptan-1-ol.

$^1$H NMR (DMSO-d6) δ 7.9 (d, 2H, J=9 Hz), 7.2 (m, 2H), 7.1 (d, 2H, 9 Hz), 6.9 (m, 3H), 4.3 (s, 1H) 4.2 (m, 4H), 4.0 t, 2H, J=6 Hz), 3.3 (m, 2H), 3.0 (t, 2H, J=6 Hz), 1.7 (m, 2H), 1.2–1.4 (m, 8H). IR (KBr, cm$^{-1}$) 3622, 3011, 2936, 2861, 1613, 1602, 1499, 1469, 1256, 1224, 1174, 1034. MS (ES) m/e 443. Anal. Calcd for $C_{24}H_{30}N_2O_4S$: C, 65.13; H, 6.83; N, 6.33. Found C, 63.3; H, 6.72; N, 5.91.

b) Dimethyl-(7-{4-[5-(2-phenoxy-ethylsulfanylmethyl)-[1,3,4]oxadiazol-2-yl]-phenoxy}-heptyl)-amine

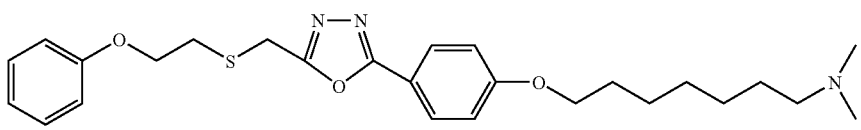

Methanesulfonyl chloride (0.046 g, 0.407 mmol) was added dropwise to a solution of 7-{4-[5-(2-phenoxy-ethylsulfanylmethyl)-[1,3,4]oxadiazol-2-yl]-phenoxy}-heptan-1-ol (0.164 g, 0.374 mmol) and triethylamine (0.045 g, 0.444 mmol) in dichloromethane (20 mL). The mixture was stirred at room temperature for 5 min and concentrated to dryness to give the crude mesylate. The crude solid was dissolved in methanol (10 mL) in a sealed tube and dimethylamine was added (5 mL). The mixture was heated to 80° overnight and concentrated to dryness. The crude solid was dissolved in ethyl acetate and washed with water, brine, dried over sodium sulfate, filtered and concentrated to dryness. The solid was purified directly by column chromatography on silica gel (elution with 1/1 ethyl acetate followed by 90% CHCl$_3$ and 10% 2M NH$_3$ in methanol to give 0.063 g (36%) of the title compound.

$^1$H NMR (DMSO-d6) δ 7.9 (d, 2H, J=9 Hz), 7.2 (m, 2H), 7.1 (d, 2H, J=9 Hz), 6.9 (m, 3H), 4.2 (m, 4H), 4.0 (t, 2H, J=6 Hz), 3.0 (t, 2H, J=6 Hz), 2.2 (t, 2H, J=7 Hz), 2.1 (s, 6H), 1.7 (m, 2H), 1.2–1.4 (m, 8H). IR (KBr, cm$^{-1}$) 2925, 2854, 2762, 1611, 1500, 1254, 1175, 750. MS (ES) m/e 470. Anal. Calcd for $C_{26}H_{35}N_3O_3S$: C, 66.49; H, 7.51; N, 8.95. Found C, 64.78; H, 7.57; N, 8.44. HPLC 90%. MP=39–40° C.

Example 72

Preparation of 1-(2-{4-[5-(2-phenoxy-ethylsulfanylmethyl)-[1,3,4]oxadiazol-2-yl]-phenoxy}-ethyl)-piperidine

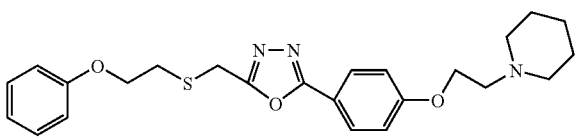

The above compound was prepared in a manner similar to that exemplified for the preparation of Example 66c, from 4-[5-(2-phenoxy-ethylsulfanylmethyl)-[1,3,4]oxadiazol-2-yl]-phenol (0.202 g, 0.615 mmol) and 1-(2-chloroethyl) piperidine monohydrochloride (0.17 g, 0.922 mmol) to give 0.059 g (22%) of the title compound.

$^1$H NMR (DMSO-d6) δ 7.8 (d, 2H, J=9 Hz), 7.2 (t, 2H, J=8 Hz), 7.1 (d, 2H, J=9 Hz), 6.9 (m, 3H) 4.2 (m, 6H), 3.0 (t, 2H, J=6 Hz), 2.6 (m, 2H), 2.4 (m, 4H), 1.5 (m, 4H), 1.4 (m, 2H). IR (KBr, cm$^{-1}$) 2940, 1613, 1499, 1255, 1245, 1175. MS (ESI) m/e 440. Anal. Calcd for $C_{24}H_{29}N_3O_3S$: C, 65.58; H, 6.65; N, 9.56. Found C, 64.56; H, 6.61; N, 9.42. HPLC 100%. MP=70° C.

Example 73

Preparation of diisopropyl-(2-{4-[5-(2-phenoxy-ethylsulfanylmethyl)-[1,3,4]oxadiazol-2-yl]-phenoxy}-ethyl)-amine

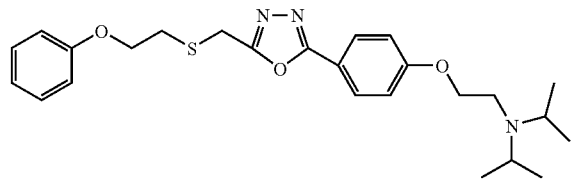

The above compound was prepared in a manner similar to that exemplified for the preparation of Example 66c, from 4-[5-(2-phenoxy-ethylsulfanylmethyl)-[[1,3,4]oxadiazol-2-yl]-phenol (0.223 g, 0.679 mmol) and (2-chloro-ethyl)-diisopropyl-amine, monohydrochloride (0.204 g, 1.02 mmol) to give 0.178 g (58%) of the title compound.

$^1$H NMR (DMSO-d6) δ 7.9 (d, 2H, J=9 Hz), 7.2 (t, 2H, J=8 Hz), 7.1 (d, 2H, J=9 Hz), 6.9 (m, 3H), 4.2 (m, 4H), 4.0 (t, 2H J=7 Hz), 3.0 (m, 4H), 2.8 (t, 2H, J=7 Hz), 1.0 (d, 12H, J=6 Hz). IR (KBr, cm$^{-1}$) 3632, 3432, 3013, 2945, 2838, 1602, 1464, 13333, 1242. MS (ESI) m/e 456. Anal. Calcd for $C_{25}H_{33}N_3O_3S$: C, 65.90; H, 7.30; N, 9.22. Found C, 65.68; H, 7.16; N, 9.17. MP=42–45° C.

Example 74

Preparation of 4-(2-{4-[5-(2-phenoxy-ethylsulfanyl-methyl)-[1,3,4]oxadiazol-2-yl]-phenoxy}-ethyl)-morpholine

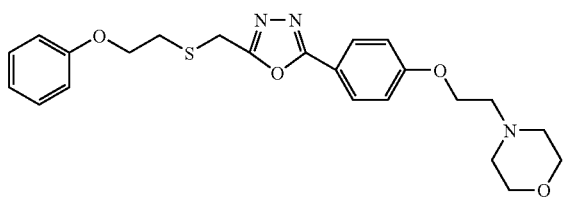

The above compound was prepared in a manner similar to that exemplified for the preparation of Example 66c, from 4-[5-(2-phenoxy-ethylsulfanylmethyl)-[1,3,4]oxadiazol-2-yl]-phenol (0.266 g, 0.81 mM) and 4-(2-chloro-ethyl)-morpholine monohydrochloride (0.226.g, 1.22 mmol) to give 0.225 g (63%) of the title compound.

$^1$H NMR (DMSO-d6) δ 7.9 (d, 2H, J=8 Hz), 7.2 (t, 2H, J=8 Hz), 7.1 (d, 2H, J=9 Hz), 6.9 (m, 3H), 4.2 (m, 6H), 3.6 (t, 4H, J=4 Hz), 3.0 (t, 2H, J=6 Hz), 2.7 (t, 2H, J=6 Hz), 2.5 (m, 4H). IR (KBr, cm$^{-1}$) 1613, 1601, 1588, 1499, 1302, 1253, 1175, 1117. MS (ESI) m/e 442, 440.5. Anal. Calcd for $C_{23}H_{27}N_3O_4S$: C, 62.56; H, 6.16; N, 9.51. Found C, 62.20; H, 6.02; N, 9.39. MP=70–72° C.

Example 75

Preparation of 1-(3-{4-[5-(2-phenoxy-ethylsulfanyl-methyl)-[1,3,4]oxadiazol-2-yl]-phenoxy}-propyl)-piperidine

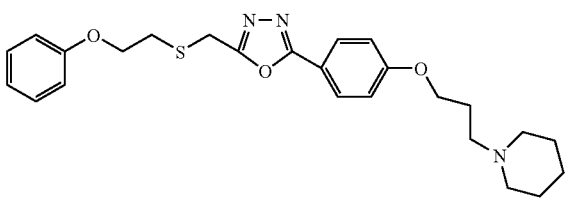

The above compound was prepared in a manner similar to that exemplified for the preparation of Example 66c, from 4-[S-(2-phenoxy-ethylsulfanylmethyl)-1,3,4]oxadiazol-2-yl]-phenol (0.218 g, 0.664 mmol) and 1-(3-chloro-propyl)-piperidine, monohydrochloride (0.197 g, 0.996 mmol) to give 0.055 g (18%) of the title compound.

$^1$H NMR (DMSO-d6) δ 7.9 (d, 2H, J=9 Hz), 7.2 (m, 2H), 7.1 (d, 2H, J=8 Hz), 6.9 (m, 3H), 4.2 (m, 4H), 4.1 (t, 2H, J=7 Hz), 3.0 (t, 2H, J=6 Hz), 2.4–2.3 (m, 6H), 1.9 (t, 2H, J=7 Hz), 1.5 (m, 4H), 1.4 (m, 2H). IR (KBr, cm$^{-1}$) 3008, 2939, 1614, 1601, 1499, 1303, 1256, 1245, 1175, 839. MS (ESI) m/e 454. Anal. Calcd for $C_{25}H_{31}N_3O_4S$: C, 65.58; H, 6.65; N, 9.55. Found C, 65.34; H, 6.65; N, 8.95. MP=65° C.

Example 76

Preparation of 2-(2-phenoxy-ethylsulfanylmethyl)-5-[4-(2-pyrrolidin-1-yl-ethoxy)-phenyl]-[1,3,4]oxadiazole

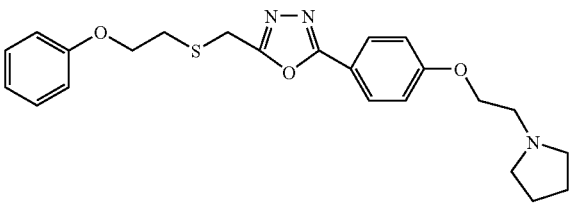

The above compound was prepared in a manner similar to that exemplified for the preparation of Example 66c, from 4-[5-(2-phenoxy-ethylsulfanylmethyl)-[1,3,4]oxadiazol-2-yl]-phenol (0.216 g, 0.658 mmol) and 1-(2-chloro-ethyl)-pyrrolidine, monohydrochloride (0.168 g, 0.987 mmol) to give 0.052 g (18%) of the title compound.

$^1$H NMR (DMSO-d6) δ 7.9 (d, 2H, J=8 Hz), 7.2 (t, 2H, J=8 Hz), 7.1 (d, 2H, J=8 Hz), 6.9 (m, 3H), 4.2 (m, 6H), 3.0 (t, 2H, J=6 Hz), 2.8 (m, 2H), 2.5 (m, 4H), 1.6(m, 4H). IR (KBr, cm$^{-1}$) 1614, 1500, 1246, 1175. MS (ESI) m/e 426. Anal. Calcd for $C_{23}H_{27}N_3O_3S$: C, 64.92; H, 6.40; N, 9.87. Found C, 64.92; H, 6.44; N, 9.76. MP=65° C.

Example 77

Preparation of methyl-(3-{4-[5-(2-phenoxy-ethylsul-fanylmethyl)-[1,3,4]oxadiazol-2-yl]-phenoxy}-propyl)-amine

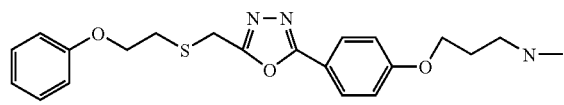

a) 2-[4-(3-Chloro-propoxy)-phenyl]-5-(2-phenoxy-ethylsulfanylmethyl)-[1,3,4]oxadiazole

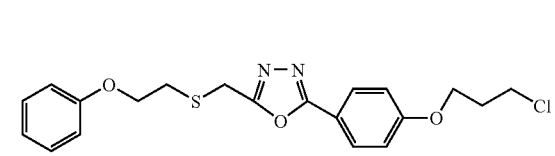

The above compound was prepared in a manner similar to that exemplified for the preparation of Example 68a, from 4-[5-(2-phenoxy-ethylsulfanylmethyl)-[1,3,4]oxadiazol-2-yl]-phenol (2.396 g, 7.30 mmol) and 1-bromo-3-chloro-propane (1.72 g, 10.9 mmol) to give 1.60 g (54%) of 2-[4-(3-chloro-propoxy)-phenyl]-5-(2-phenoxy-ethylsulfa-nylmethyl)-[1,3,4]oxadiazole.

$^1$H NMR (DMSO-d6) δ 7.9 (d, 2H, J=9 Hz), 7.2 (t, 2H, J=8 Hz), 7.1 (d, 2H, J=9 Hz), 6.9 (m, 3H), 4.2 (m, 6H), 3.8 (t, 2H, J=6 Hz), 3.0 (t, 2H, J=6 Hz), 2.2 (m, 2H). MS (ESI) m/e 405.

b) Methyl-(3-{4-[5-(2-phenoxy-ethylsulfanylmethyl)-[1,3,4]oxadiazol-2-yl]-phenoxy}-propyl)-amine

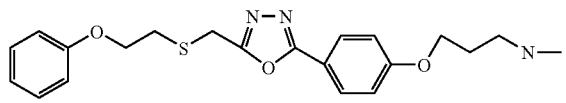

The above compound was prepared in a manner similar to that exemplified for the preparation of Example 68b, from 2-[4-(3-chloro-propoxy)-phenyl]-5-(2-phenoxy-ethylsulfanylmethyl)-[1,3,4]oxadiazole (0.247 g, 0.61 mmol) and methylamine (40% weight in water, 2 mL, 26 mmol). HPLC chromatography on the material previously purified by silica chromatography and combination of various lots gave 190 mg of material as the TFA salt which was desalted to the free amine by washing with 1N NaOH, dried over sodium sulfate, filtered and concentrated to dryness to give 0.088 g (14%) of the title compound.

$^1$H NMR (DMSO-d6) δ7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.0 (t, 2H, J=6 Hz), 2.6 (t, 2H, J=7 Hz), 2.3 (s, 3H), 1.8 (m, 2H). IR (KBr, cm$^{-1}$) 1677, 1611, 1500, 1254, 1205, 1176, 1131, 835, 754, 722. MS (ESI) m/e 400, 398. Anal. Calcd for $C_{21}H_{25}N_3O_3S$: C, 63.14; H, 6.31; N, 10.52. Found C, 61.78; H, 5.92; N, 9.91. MP=40–44° C. HPLC 100%.

Example 78

Preparation of diethyl-(3-{4-[5-(2-phenoxy-ethylsulfanylmethyl)-[1,3,4]oxadiazol-2-yl]-phenoxy}-propyl)-amine

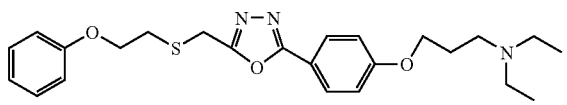

The above compound was prepared in a manner similar to that exemplified for the preparation of Example 68b, from 2-[4-(3-chloro-propoxy)-phenyl]-5-(2-phenoxy-ethylsulfanylmethyl)-[1,3,4]oxadiazole (0.230 g, 0.568 mmol) and diethylamine (1.04 g, 14.2 mmol) to give 0.127 g (50%) of the title compound.

$^1$H NMR (DMSO-d6) δ7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.0 (t, 2H, J=6 Hz), 2.5 (m, 4H), 1.8 (t, 2H, J=6 Hz), 0.9 (t, 6H, J=7 Hz). IR (KBr, cm$^{-1}$) 2973, 1613, 1602, 1499, 1256, 1245, 1174. MS (ESI) m/e 442. Anal. Calcd for $C_{24}H_{31}N_3O_3S$: C, 65.28; H, 7.08; N, 9.52. Found C, 65.19; H, 7.17; N, 9.41. MP=27–31° C.

Example 79

Preparation of 1-(3-{4-[5-(2-phenoxy-ethylsulfanylmethyl)-[1,3,4]oxadiazol-2-yl]-phenoxy}-propyl)-piperazine

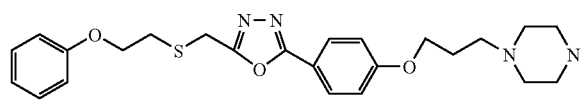

a) 4-(3-{4-[5-(2-Phenoxy-ethylsulfanylmethyl)-[1,3,4]oxadiazol-2-yl]-phenoxy}-propyl)-piperazine-1-carboxylic acid tert-butyl ester

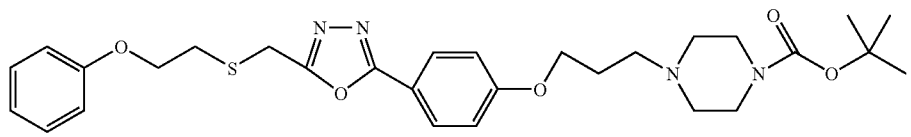

The above compound was prepared in a manner similar to that exemplified for the preparation of Example 68b, from 2-[4-(3-chloro-propoxy)-phenyl]-5-(2-phenoxy-ethylsulfanylmethyl)-[1,3,4]oxadiazole (0.241 g, 0.595.mmol) and piperazine-1-carboxylic acid tert-butyl ester (0.111 g, 0.595 mmol) to give 0.096 g (29%) of 4-(3-{4-[5-(2-phenoxy-ethylsulfanylmethyl)-[1,3,4]oxadiazol-2-yl]-phenoxy}-propyl)-piperazine-1-carboxylic acid tert-butyl ester.

$^1$H NMR (DMSO-d6) δ7.9 (d, 2H, J=9 Hz), 7.2 (m, 2H), 7.1 (d, 2H, J=9 Hz), 6.9 (m, 3H), 4.2 (m, 4H), 4.1 (t, 2H, J=5 Hz), 3.3 (m, 4H), 3.0 (t, 2H, J=6 Hz), 2.4 (m, 2H), 2.3 (m, 4H), 1.9 (m, 2H), 1.4 (s, 9l). MS (ESI) m/e 555. Anal. Calcd for $C_{29}H_{38}N_4O_5S$: C, 62.79; H, 6.90; N, 10.10. Found C, 61.53; H, 6.70; N, 9.73. HPLC 100%.

b) 1-(3-{4-[5-(2-Phenoxy-ethylsulfanylmethyl)-[1,3,4]oxadiazol-2-yl]-phenoxy}-propyl)-piperazine

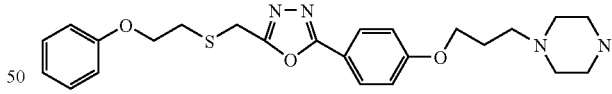

A solution of 4-(3-{4-[5-(2-phenoxy-ethylsulfanylmethyl)-[1,3,4]oxadiazol-2-yl]-phenoxy}-propyl)-piperazine-1-carboxylic acid tert-butyl ester (20a) (0.115 g, 0.20 mmol) and trifluoroacetic acid (5 mL) in 5 mL $CH_2Cl_2$ was stirred at 5° C. for 1 hr. The reaction mixture was concentrated to dryness and extracted into ethyl acetate. The organic extract was washed with $NaHCO_3$, brine, dried over sodium sulfate, filtered and concentrated to give 0.065 g which was purified directly by column chromatography on silica gel (elution with ethyl acetate and toluene followed by 90 chloroform/10 ammonia (2M methanol) to give 0.044 g (47%) of the title product.

$^1$H NMR (DMSO-d6) δ 7.9 (d, 2H, J=9 Hz), 7.2 (t, 2H, J=8 Hz)), 7.1 (d, 2H, J=9 Hz), 6.9 (m, 3H), 4.2 (m, 4H), 4.1 (t, 2H, J=6 Hz), 3.0 (t, 2H, J=6 Hz), 2.6 (m, 4H), 2.4 (t, 2H, J=7 Hz), 2.3 (m, 4H), 1.8 (m, 2H). MS (ESI) m/e 455. HPLC 100%.

Example 80

Preparation of 2-(2-phenoxy-ethylsulfanylmethyl)-5-[4-(4-pyrrolidin-1-yl-butoxy)-phenyl]-[1,3,4]oxadiazole

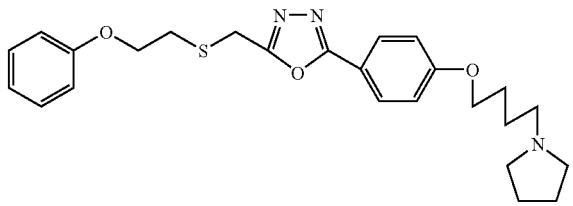

The above compound was prepared in a manner similar to that exemplified for the preparation of Example 68b, from 2-[4-(4-chloro-butoxy)-phenyl]-5-(2-phenoxy-ethylsulfanylmethyl)-[1,3,4]oxadiazole (0.235 g, 0.561 mmol) and pyrrolidine (0.099 g, 1.4 mmol) to give 0.145 g (57%) of the title compound.

$^1$H NMR (DMSO-d6) δ7.9 (d, 2H, J=9 Hz), 7.2 (t, 2H, J=8 Hz)), 7.1 (d, 2H, J=9 Hz), 6.9 (m, 3H), 4.2 (m, 4H), 4.1 (t, 2H, J=6 Hz), 3.0 (t, 2H, J=6 Hz), 2.4 (m, 6H), 1.8 (m, 2H), 1.7 (m, 4H), 1.6 (m, 2H). IR (KBr, cm$^{-1}$) 2932, 2563, 2467, 1617, 1500, 1257, 1248. MS (ESI) m/e 454. Anal. Calcd for $C_{25}H_{31}N_3O_3S$: C, 66.20; H, 6.89; N, 9.26. Found C, 65.98; H, 6.90; N, 9.13. M.P.=45°.

Example 81

Preparation of 1-(4-{4-[5-(2-phenoxy-ethylsulfanylmethyl)-[1,3,4]oxadiazol-2-yl]-phenoxy}-butyl)-piperidine

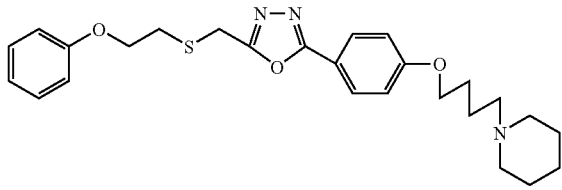

The above compound was prepared in a manner similar to that exemplified for the preparation of Example 68b, from 2-[4-(4-chloro-butoxy)-phenyl]-5-(2-phenoxy-ethylsulfanylmethyl)-[1,3,4]oxadiazole (0.232 g, 0.554 mmol) and piperidine (0.118 g, 1.38 mmol) to give 0.041 g (16%) of the title compound.

$^1$H NMR (DMSO-d6) δ 7.9 (d, 2H, J=9 Hz), 7.2 (t, 2H, J=8 Hz)), 7.1 (d, 2H, J=9 Hz), 6.9 (m, 3H), 4.2 (m, 4H), 4.1 (t, 2H, J=6 Hz), 3.0 (t, 2H, J=6 Hz), 2.3 (m, 6H), 1.7 (m, 2H), 1.6 (m, 2H), 1.5 (m, 4H), 1.4 (m, 2H). IR (KBr, cm$^{-1}$) 2923, 1610, 1601, 1586, 1500, 1467, 1304, 1256, 1248, 1174, 1031. MS (ESI) m/e 470. Anal. Calcd for $C_{26}H_{33}N_3O_3S$: C, 66.78; H, 7.11; N, 8.99. Found C, 66.16; H, 6.91; N, 8.80. M.P.=57–62° C.

Example 82

Preparation of 4-(3-{4-[5-(2-phenoxy-ethylsulfanylmethyl)-[1,3,4]oxadiazol-2-yl]-phenoxy}-propyl)-thiomorpholine

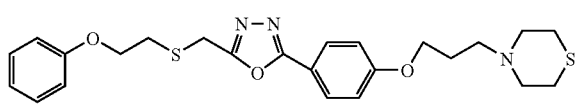

The above compound was prepared in a manner similar to that exemplified for the preparation of Example 68b, from 2-[4-(3-chloro-propoxy)-phenyl]-5-(2-phenoxy-ethylsulfanylmethyl)-[1,3,4]oxadiazole (0.248 g, 0.612 mmol) and thiomorpholine (0.157 g, 1.53 mM) to give 0.136 g (47%) of the title compound.

$^1$H NMR (DMSO-d6) δ7.9 (d, 2H, J=9 Hz), 7.2 (t, 2H, J=8 Hz)), 7.1 (d, 2H, J=9 Hz), 6.9 (m, 3H), 4.2 (m, 4H), 4.1 (t, 2H, J=6 Hz), 3.0 (t, 2H, J=6 Hz), 2.6 (m, 8H), 2.4 (t, 2H, J=7 Hz), 1.9 (m, 2H). IR (KBr, cm$^{-1}$) 2922, 2810, 2775, 1611, 1601, 1590, 1502, 1491, 1468, 1256, 1244, 1176, 837, 766. MS (ESI) m/e 472, 470. Anal. Calcd for $C_{24}H_{29}N_3O_3S_2$: C, 61.12; H, 6.20; N, 8.91. Found C, 60.85; H, 6.26; N, 8.75. M.P.=85° C.

Example 83

Preparation of 1-(3-{4-[5-(2-phenoxy-ethylsulfanylmethyl)-[1,3,4]oxadiazol-2-yl]-phenoxy}-propyl)-azepane

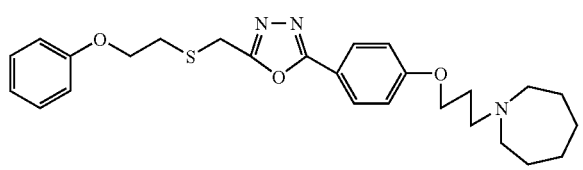

The above compound was prepared in a manner similar to that exemplified for the preparation of Example 68b, from 2-[4-(3-chloro-propoxy)-phenyl]-5-(2-phenoxy-ethylsulfanylmethyl)-[1,3,4]oxadiazole (0.213 g, 0.526 mmol) and azepane (1.30 g, 13.1 mmol) to give 0.103 g (42%) of the title compound.

$^1$H NMR (DMSO-d6) δ 7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.0 (t, 2H, J=6 Hz), 2.6 (m, 6H), 1.8 (m, 2H), 1.5 (m, 8H). IR (KBr, cm$^{-1}$) 2927, 2905, 1614, 1497, 1468, 1251, 1181, 1171, 1036, 1029, 747, 689. MS (ESI) m/e 468. Anal. Calcd for $C_{26}H_{33}N_3O_3S$: C, 66.78; H, 7.11; N, 8.98. Found C, 66.48; H, 6.94; N, 8.91. M.P.=50° C.

Example 84

Preparation of 3-{4-[5-(2-phenoxy-ethylsulfanylmethyl)-[1,3,4]oxadiazol-2-yl]-phenoxy}-propylamine

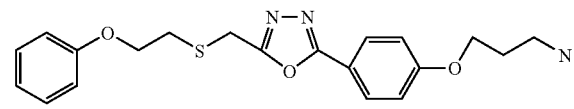

a) (3-{4-[5-(2-Phenoxy-ethylsulfanylmethyl)-[1,3,4]oxadiazol-2-yl]-phenoxy}-propyl)-carbamic acid tert-butyl ester

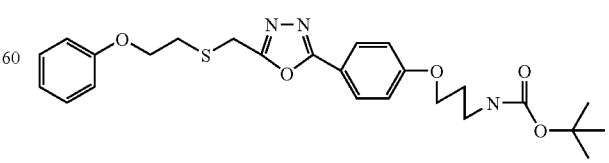

The above compound was prepared in a manner similar to that exemplified for the preparation of Example 68a from 4-[5-(2-phenoxy-ethylsulfanylmethyl)-[1,3,4]oxadiazol-2-yl]-phenol (0.501 g, 1.52 mmol) and (3-bromo-propyl)-carbamic acid tert-butyl ester (0.545 g, 2.28 mmol) to give the BOC protected product which was purified by column chromatography on silica gel (elution with ethyl acetate/toluene) to give 0.617 g (84%) of the (3-{4-[5-(2-phenoxy-ethylsulfanylmethyl)-[1,3,4]oxadiazol-2-yl]-phenoxy}-propyl)-carbamic acid tert-butyl ester.

$^1$H NMR (DMSO-d6) δ7.9 (d, 2H, J=9 Hz), 7.2 (t, 2H, J=8 Hz), 7.1 (d, 2H, J=9 Hz), 6.9 (m, 3H), 4.2 (m, 4H), 4.0 (t, 2H, J=6 Hz), 3.1 (q, 2H, J=6 Hz), 3.0 (t, 2H, J=6 Hz), 1.8 (m, 2H), 1.4 (s, 9H). IR (KBr, cm$^{-1}$) 3400, 1692, 1609, 1524, 1501, 1248, 1242, 1176, 844, 764. MS (ESI) m/e 486. Anal. Calcd for C$_{25}$H$_{31}$N$_3$O$_5$S: C, 70.12; H, 5.23; N, 9.08. Found C, 69.86; H, 5.19; N, 8.92.

b) 3-{4-[5-(2-Phenoxy-ethylsulfanylmethyl)-[1,3,4]oxadiazol-2-yl]-phenoxy}-propylamine

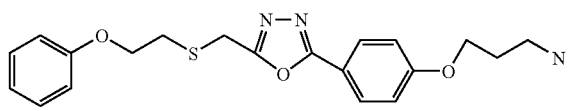

A solution of (3-{4-[5-(2-phenoxy-ethylsulfanylmethyl)-[1,3,4]oxadiazol-2-yl]-phenoxy}-propyl)-carbamic acid tert-butyl ester (0.600 mg, 1.23 mmol) in TFA (7 mL) and CH$_2$Cl$_2$, (5 mL) was stirred at 5° C. for 1 hr. The reaction mixture was concentrated to dryness and extracted into ethyl acetate. The organic extract was washed with NaHCO$_3$, brine, dried over Na$_2$SO$_4$, filtered and concentrated to give 0.300 g. Elemental analysis indicated the presence of fluorine. The material was dissolved in water, ethyl acetate and a minimum amount of methanol to solubilize the material. The mixture was washed with 1N NaOH, dried over sodium sulfate, and concentrated to give 0.183 g, (38%) of the 3-{4-[5-(2-Phenoxy-ethylsulfanylmethyl)-[1,3,4]oxadiazol-2-yl]-phenoxy}-propylamine.

$^1$H NMR (DMSO-d6) δ7.9 (d, 2H, J=9 Hz), 7.2 (t, 2H, J=8 Hz), 7.1 (d, 2H, J=9 Hz), 6.9 (m, 3I), 4.2 (m, 4H), 4.1 (t, 2H, J=6 Hz), 3.0 (t, 2H, J=6 Hz), 2.7 (t, 2H, J=7 Hz), 1.8 (m, 2H). IR (KBr, cm$^{-1}$) 3004, 2972, 2928, 2902, 1616, 1504, 1474, 1252, 1175, 833. MS (ESI) m/e 386. Anal. Calcd for C$_{20}$H$_{23}$N$_3$O$_3$S: C, 62.31; H, 6.01; N, 10.90. Found C, 61.08; H, 5.99; N, 10.49. HPLC 100%. M.P.=30–35°.

Example 85

Preparation of diethyl-(2-{4-[5-(2-phenoxy-ethylsulfanylmethyl)-[1,3,4]oxadiazol-2-yl]-phenoxy}-ethyl)-amine

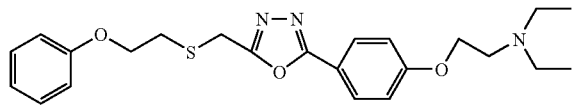

The above compound was prepared in a manner similar to that exemplified for the preparation of Example 68a, from 4-[5-(2-phenoxy-ethylsulfanylmethyl)-[1,3,4]oxadiazol-2-yl]-phenol (0.206 g, 0.627 mmol) and (2-bromo-ethyl)-diethyl-amine hydrobromide to give 0.041 g (15%) of the title compound.

$^1$H NMR (DMSO-d6) δ7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.0 (t, 2H, J=6 Hz), 2.8 (m, 2H), 2.6 (m, 4H), 1.0 (t, 6H, J=7 Hz). IR (KBr, cm$^{-1}$) 1614, 1498, 1258, 1176, 1172, 752. MS (ESI) m/e 429. Anal. Calcd for C$_{23}$H$_{29}$N$_3$O$_3$S: C, 64.61; H, 6.84; N, 9.83. Found C, 64.37; H, 6.85; N, 9.77. M.P.=32–35° C.

Example 86

Preparation of 1-(2-{4-[5-(2-phenoxy-ethylsulfanylmethyl)-[1,3,4]oxadiazol-2-yl]-phenoxy}-ethyl)-azepane

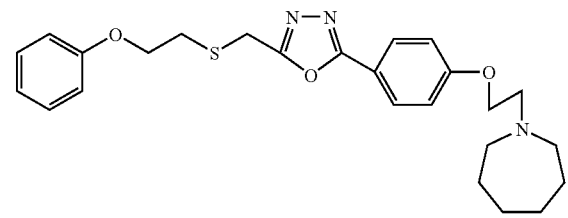

The above compound was prepared in a manner similar to that exemplified for the preparation of Example 68a, from 4-[5-(2-phenoxy-ethylsulfanylmethyl)-[1,3,4]oxadiazol-2-yl]-phenol (0.197 g, 0.599 mmol) and 1-(2-chloro-ethyl)-azepane hydrochloride (0.178 g, 0.899 mmol) to give crude material that was purified directly by column chromatography on silica gel (elution with ethyl acetate/toluene followed by 90% chloroform/10% 2M NH$_3$ in methanol to give 0.216 g (79%) of the title compound.

$^1$H NMR (DMSO-d6) δ 7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.0 (t, 2H, J=6 Hz), 2.9 (m, 2H), 2.7 (m, 4H), 1.5 (m, 8H). IR (KBr, cm$^{-1}$) 2917, 1613, 1604, 1500, 1261, 1247, 1176, 749. MS (ESI) m/e 454. Anal. Calcd for C$_{25}$H$_{31}$N$_3$O$_3$S: C, 66.20; H, 6.89; N, 9.26. Found C, 66.17; H, 6.96; N, 9.16. M.P.=40° C.

Example 87

Preparation of 4-(3-{4-[5-(2-phenoxy-ethylsulfanylmethyl)-[1,3,4]oxadiazol-2-yl]-phenoxy}-propyl)-morpholine

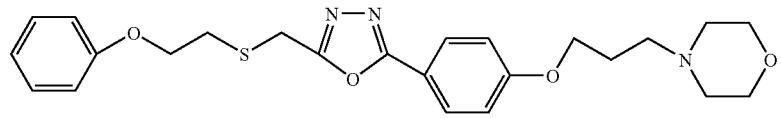

The above compound was prepared in a manner similar to that exemplified for the preparation of Example 68b, from 2-[4-(3-chloro-propoxy)-phenyl]-5-(2-phenoxy-ethylsulfanylmethyl)-[1,3,4]oxadiazole (0.222 g, 0.548 mmol) and morpholine (0.119 g, 1.37 mmol) to give 0.078 g (31%) of the title compound.

$^1$H NMR (DMSO-d6) §7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.6 (t, 4H, J=4 Hz) 3.0 (t, 2H, J=6 Hz), 2.4 (t, 2H, J=7 Hz), 2.3 (m, 4H), 1.9 (m, 2H). IR (KBr, cm$^{-1}$) 3436, 2965, 2943, 2926, 2863, 2810, 1609, 1500, 1468, 1297, 1256, 1242, 1174, 1115, 838, 764. MS (ESI) m/e 456, 454. Anal. Calcd for $C_{24}H_{29}N_3O_4S$: C, 63.27; H, 6.41; N, 9.22. Found C, 63.06; H, 6.60; N, 9.04. M.P.=65° C.

Example 88

Preparation of 2-(2-phenoxy-ethylsulfanylmethyl)-5-[4-(3-pyrrolidin-1-yl-propoxy)-phenyl]-[1,3,4]oxadiazole

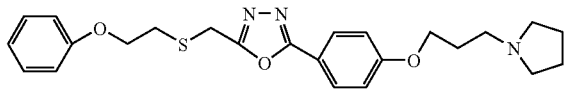

The above compound was prepared in a manner similar to that exemplified for the preparation of Example 68b, from 2-[4-(3-chloro-propoxy)-phenyl]-5-(2-phenoxy-ethylsulfanylmethyl)-[1,3,4]oxadiazole (0.222 g, 0.548 mmol) and pyrrolidine (0.097 g, 1.37 mmol) to give 0.131 g (54%) of the title compound.

$^1$H NMR DMSO-d6) §7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.0 (t, 2H, J=6 Hz), 2.6 (t, 2H, J=7 Hz), 2.5 (m, 4H), 1.9 (m, 2H), 1.7 (m, 4H). IR (KBr, cm$^{-1}$) 2972, 2944, 2928, 2865, 2792, 1613, 1584, 1500, 1478, 1466, 1402, 1253, 1183, 1152, 1006, 849, 757. MS (ESI) m/e 440, 439. Anal. Calcd for $C_{24}H_{29}N_3O_3S$: C, 65.58; H, 6.65; N, 9.56. Found C, 65.28; H, 6.70; N, 9.45. M.P.=70° C.

Example 89

Preparation of 1-(4-{4-[5-(2-phenoxy-ethylsulfanylmethyl)-[1,3,4]oxadiazol-2-yl]-phenoxy}-butyl)-azepane

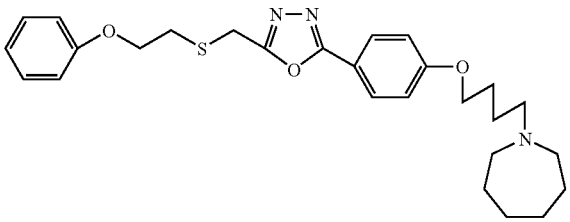

The above compound was prepared in a manner similar to that exemplified for the preparation of Example 68b, from 2-[4-(4-chloro-butoxy)-phenyl]-5-(2-phenoxy-ethylsulfanylmethyl)-[1,3,4]oxadiazole (0.227 g, 0.542 mmol) and azepane (0.56 g, 5.64 mmol) to give 0.091 g (35%) of the title compound.

$^1$H NMR (DMSO-d6) §7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.0 (t, 2H, J=6 Hz), 2.5 (m, 6H), 1.7 (m, 2H), 1.5 (m, 10H). IR (KBr, cm$^{-1}$) 2930, 1610, 1493, 1248, 1175, 837. MS (ESI) m/e 482, 480. Anal. Calcd for $C_{27}H_{35}N_3O_3S$: C, 67.33; H, 7.32; N, 8.72. Found C, 67.35; H, 7.25; N, 8.91. M.P.=35–38° C.

Example 90

Preparation of 4-(2-{4-[5-(2-phenoxy-ethylsulfanyl-methyl)-[1,3,4]oxadiazol-2-yl]-phenoxy}-ethyl)-thiomorpholine

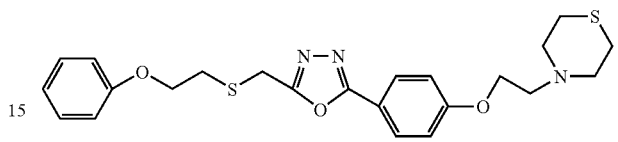

a) 2-[4-(2-Chloro-ethoxy)-phenyl]-5-(2-phenoxy-ethylsulfanylmethyl)-[1,3,4]oxadiazole

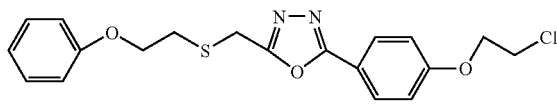

The above compound was prepared in a manner similar to that exemplified for the preparation of Example 68a, from 4-[5-(2-phenoxy-ethylsulfanylmethyl)-[1,3,4]oxadiazol-2-yl]-phenol (1.491 g, (4.54.mmol) and 1-bromo-2-chloro-ethane (0.98 g, 6.81 mmol) to give 1.216 g (68%) of 2-[4-(2-chloro-ethoxy)-phenyl]-5-(2-phenoxy-ethylsulfanylmethyl)-[1,3,4]oxadiazole.

$^1$H NMR (DMSO-d6) §7.9 (d, 2H, J=9 Hz), 7.2 (t, 2H, J=8 Hz), 7.1 (d, 2H, J=9 Hz), 6.9 (m, 3H), 4.3 (t, 2H, J=5 Hz), 4.2 (m, 4H), 4.0 (t, 2H, J=5 Hz), 3.0 (t, 2H, J=6 Hz). IR (KBr, cm$^{-1}$) 3439, 2965, 2929, 2916, 1619, 1603, 1586, 1499, 1465, 1249, 1177, 1088, 1023, 1008, 756. MS (ESI) m/e 391. Anal. Calcd for $C_{19}H_{19}ClN_2O_3S$: C, 58.38; H, 4.90; N, 7.17. Found C, 58.27; H, 5.01; N, 7.07.

b) 4-(2-{4-[5-(2-Phenoxy-ethylsulfanylmethyl)-[1,3,4]oxadiazol-2-yl]-phenoxy}-ethyl)-thiomorpholine

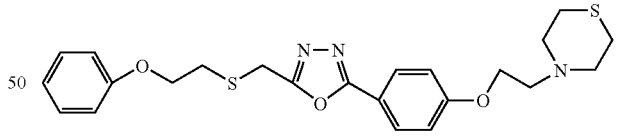

The above compound was prepared in a manner similar to that exemplified for the preparation of Example 68b, from 2-[4-(2-chloro-ethoxy)-phenyl]-5-(2-phenoxy-ethylsulfanylmethyl)-[1,3,4]oxadiazole (0.215 g, 0.55 mmol) and thiomorpholine (0.141 g, 1.37 mmol) to give 0.066 g (26%) of the title product.

$^1$H NMR (DMSO-d6) §7.9 (d, 2H, J=9 Hz), 7.2 (t, 2H, J=8 Hz), 7.1 (d, 2H, J=9 Hz), 6.9 (m, 3H), 4.2 (m, 6H), 3.0 (t, 2H, J=6 Hz) 2.8 (m, 6H), 2.6 (m, 4H). IR (KBr, cm$^{-1}$) 2926, 2807, 1614, 1503, 1459, 1297, 1253, 1173, 834, 754. MS (ES) m/e 458, 456. Anal. Calcd for $C_{23}H_{27}N_3O_3S_2$: C, 60.37; H, 5.95; N, 9.18. Found C, 59.64; H, 5.61; N, 8.94. M.P.=60° C. HPLC 100%.

Example 91

Preparation of 1-(3-{4-[5-(2-phenoxy-ethylsulfanyl-methyl)-[1,3,4]oxadiazol-2-yl]-phenoxy}-propyl)-[1,4]diazepane

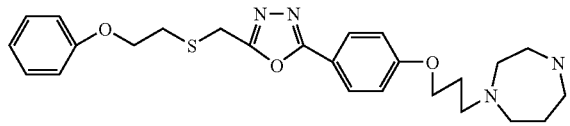

a) 4-(3-{4-[5-(2-Phenoxy-ethylsulfanylmethyl)-[1,3,4]oxadiazol-2-yl]-phenoxy}-propyl)-[1,4]diazepane-1-carboxylic acid tert-butyl ester

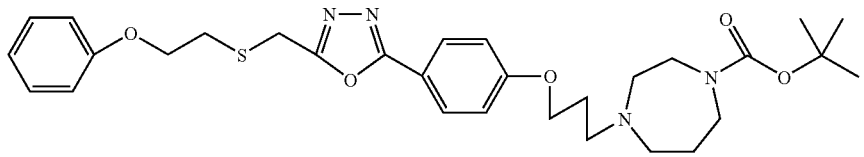

The above compound was prepared in a manner similar to that exemplified for the preparation of Example 68a, from 4-[5-(2-phenoxy-ethylsulfanylmethyl)-[1,3,4]oxadiazol-2-yl]-phenol (0.223 g, 0.679 mmol) and 4-(3-chloro-propyl)-[1,4]diazepane-1-carboxylic acid tert-butyl ester (0.376 g, 1.36 mmol) to give crude material that was purified directly by column chromatography on silica gel (elution with ethyl acetate/toluene followed by 90% chloroform/10% 2M NH$_3$ in methanol) to give 0.49 g (100%) of 4-(3-{4-[5-(2-phenoxy-ethylsulfanylmethyl)-[1,3,4]oxadiazol-2-yl]-phenoxy}-propyl)-[1,4]diazepane-1-carboxylic acid tert-butyl ester.

$^1$H NMR (DMSO-d6) 87.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=7 Hz), 3.6 (t, 2H, J=6 Hz), 3.0 (t, 2H, J=6 Hz) 2.6 (m, 4H), 1.8 (m, 4H), 1.6 (m, 4H), 1.4 (s, 9H). MS (ESI) m/e 569.

b) 1-(3-{4-[5-(2-Phenoxy-ethylsulfanylmethyl)-[1,3,4]oxadiazol-2-yl]-phenoxy}-propyl)-[1,4]diazepane

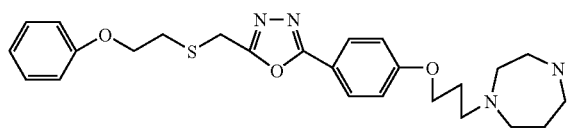

The above compound was prepared in a manner similar to that exemplified for the preparation of Example 79b, from 4-(3-{4-[5-(2-phenoxy-ethylsulfanylmethyl)-[1,3,4]oxadiazol-2-yl]-phenoxy}-propyl)-[1,4]diazepane-1-carboxylic acid tert-butyl ester (0.49 g, 0.862 mmol) and trifluoroacetic acid (5 mL) to give 0.136 g (34%) of the title product.

$^1$H NMR (DMSO-d6) 87.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.3 (m, 2H), 3.0 (t, 2H, J=6 Hz) 2.8 (m, 3H), 2.6 (m, 6H), 1.8 (m, 2H), 1.6 (m, 2H). IR (KBr, cm$^{-1}$) 2337, 1671, 1613, 1499, 1256, 1245, 1175. MS (ESI) m/e 469. Anal. Calcd for C$_{25}$H$_{32}$N$_4$O$_3$S: C, 64.08; H, 6.88; N, 11.95. Found C, 58.41; H, 6.35; N, 10.64. HPLC 100%.

Example 92

Preparation of 4-(4-{4-[5-(2-phenoxy-ethylsulfanyl-methyl)-[1,3,4]oxadiazol-2-yl]-phenoxy}-butyl)-morpholine

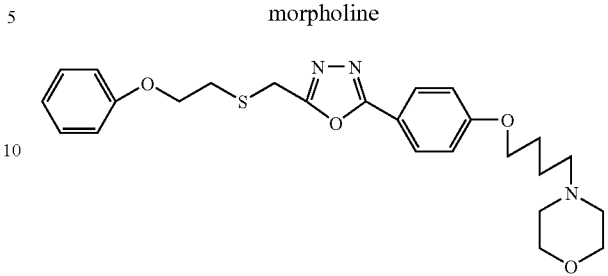

The above compound was prepared in a manner similar to that exemplified for the preparation of Example 68b, from 2-[4-(4-chloro-butoxy)-phenyl]-5-(2-phenoxy-ethylsulfanylmethyl)-[1,3,4]oxadiazole (0.225 g, 0.537 mmol) and morpholine (0.117 g, 1.34 mmol) to give 0.144 g (57%) of the title compound.

$^1$H NMR (DMSO-d6) 87.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.5 (m, 4H), 3.0 (t, 2H, J=6 Hz) 2.3 (m, 6H), 1.8 (m, 2H), 1.6 (m, 2H). IR (KBr, cm$^{-1}$) 2935, 2852, 2811, 1611, 1499, 1303, 1249, 1174, 1118, 836. MS (ESI) m/e 470, 468. Anal. Calcd for C$_{25}$H$_{31}$N$_3$O$_4$S: C, 63.94; H, 6.65; N, 8.95. Found C, 63.83; H, 6.72; N, 8.93. M.P.=64–67° C.

Example 93

Preparation of diethyl-(4-{4-[5-(2-phenoxy-ethylsulfanylmethyl)-[1,3,4]oxadiazol-2-yl]-phenoxy}-butyl)-amine

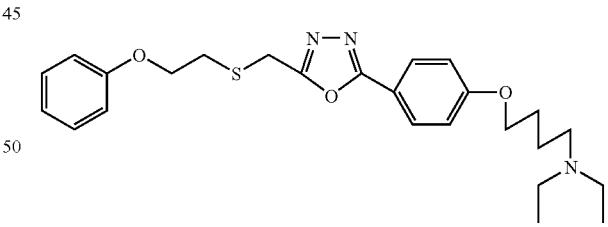

The above compound was prepared in a manner similar to that exemplified for the preparation of Example 68b, from 2-[4-(4-chloro-butoxy)-phenyl]-5-(2-phenoxy-ethylsulfanylmethyl)-[1,3,4]oxadiazole (0.225 g, 0.537 mmol) and diethyl amine (0.989 g, 13.4 mmol) to give 0.090 g (37%) of the title compound.

$^1$H NMR (DMSO-d6) 87.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.0 (t, 2H, J=6 Hz) 2.4 (m, 6H), 1.7 (m, 2H), 1.6 (m, 2H), 1.0 (t, 6H, J=7 Hz). IR (KBr, cm$^{-1}$) 2929, 2799, 1610, 1500, 1248, 1174, 1005, 837. MS (ESI) m/e 456. Anal. Calcd for C$_{25}$H$_{33}$N$_3$O$_3$S: C, 65.90; H, 7.30; N, 9.22. Found C, 63.98; H, 7.08; N, 9.72. M.P.=35–38° C. HPLC 99%.

Example 94

Preparation of 4-(4-{4-[5-(2-phenoxy-ethylsulfanyl-methyl)-[1,3,4]oxadiazol-2-yl]-phenoxy}-butyl)-thiomorpholine

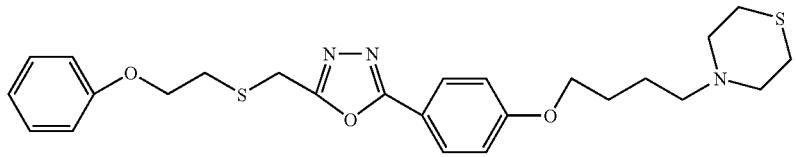

The above compound was prepared in a manner similar to that exemplified for the preparation of Example 68b, from 2-[4-(4-chloro-butoxy)-phenyl]-5-(2-phenoxy-ethylsulfanylmethyl)-[1,3,4]oxadiazole (0.313 g, 0.747 mmol) and thiomorpholine (0.154 g, 1.49 mmol) to give 0.219 g (60%) of the title compound.

$^1$H NMR (DMSO-d6) $\delta$7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.0 (t, 2H, J=6 Hz), 2.6 (m, 8H), 2.3 (m, 2H), 1.8 (m, 2H), 1.6 (m, 2H). IR (KBr, cm$^{-1}$) 3000, 2873, 2816, 1613, 1588, 1499, 1256, 1245, 1174, 1006, 839. MS (ES) m/e 486, 484. Anal. Calcd for $C_{25}H_{31}N_3O_3S_2$: C, 61.83; H, 6.43; N, 8.65. Found C, 61.66; H, 6.44; N, 8.59. M.P.=58° C.

Example 95

Preparation of N-(3-{4-[5-(2-phenoxy-ethylsulfanyl-methyl)-[1,3,4]oxadiazol-2-yl]-phenoxy}-propyl)-methanetriamine, trifluoroacetic acid salt

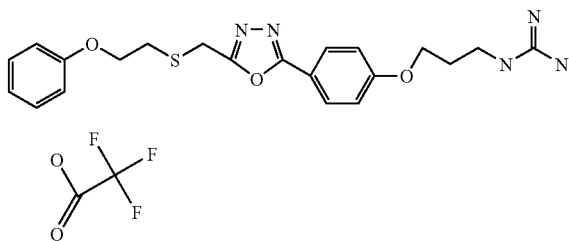

A solution of 3-{4-[5-(2-phenoxy-ethylsulfanylmethyl)-[1,3,4]oxadiazol-2-yl]-phenoxy}-propylamine (Example 85b) (0.142 g, 0.368 mmol) and 1,3-bis(t-butoxycarbonyl)-2-methyl-2-thiopseudourea (0.112 g, 0.387 mmol) in acetonitrile (7 mL) was stirred at room temperature overnight. The mixture was diluted with ethyl acetate and washed with saturated NaHCO$_3$. The aqueous layer was extracted once with ethyl acetate. The combined organics were washed with water, brine, dried over sodium sulfate, filtered, and concentrated. The residue was purified by column chromatography on silica gel (elution with ethyl acetate/toluene) to give 0.119 g (52%) of N-(3-{4-[5-(2-phenoxy-ethylsulfanyl-methyl)-[1,3,4]oxadiazol-2-yl]-phenoxy}-propyl)-methanetriamine, di-carboxylic acid tert-butyl ester (40a).

$^1$H NMR (DMSO-d6) $\delta$8.5 (m, 1H), 7.9 (d, 2H, J=9 Hz), 7.2 (t, 2H, J=8 Hz), 7.1 (d, 2H, J=9 Hz), 6.9 (m, 3H), 4.2 (m, 4H), 4.1 (t, 2H, J=6 Hz), 3.5 (m, 2H), 3.0 (t, 2H, J=6 Hz) 2.0 (m, 2H), 1.5 (s, 9H), 1.4 (s, 9H). MS (ESI) m/e 628.

a) N-(3-{4-[5-(2-phenoxy-ethylsulfanylmethyl)-[1,3,4]oxadiazol-2-yl]-phenoxy}-propyl)-methanetriamine, di-carboxylic acid tert-butyl ester

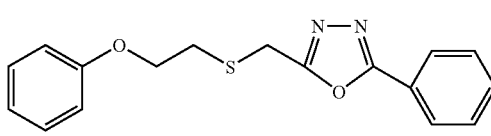

b) N-(3-{4-[5-(2-phenoxy-ethylsulfanylmethyl)-[1,3,4]oxadiazol-2-yl]-phenoxy}-propyl)-methanetriamine, trifluoroacetic acid salt

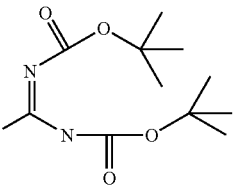

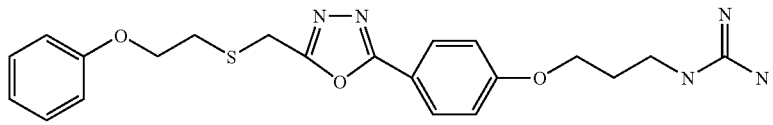

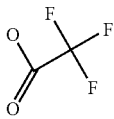

N-(3-{4-[5-(2-phenoxy-ethylsulfanylmethyl)-[1,3,4]oxadiazol-2-yl]-phenoxy}-propyl)-methanetriamine, di-carboxylic acid tert-butyl ester (0.253 g, 0.403 mmol) was dissolved in $CH_2Cl_2$ (5 mL) and cooled to 5° C. Trifluoroacetic acid (5 mL) was added and the mixture was stirred at 5° C. for 1 hr and at room temperature for 1 hr. The mixture was concentrated to dryness, diluted with ethyl acetate and washed with 1N NaOH. The aqueous layer was extracted twice with ethyl acetate. The combined organic extracts were washed with water, brine, dried over sodium sulfate, filtered, and concentrated to 0.073 g. Due to low recovery, the aqueous layer was extracted 4 times with $CH_2Cl_2$ and the combined organic extracts were washed with brine, dried over sodium sulfate, filtered and concentrated to 0.186 g. The combined residues were purified by column chromatography on silica gel (elution with ethyl acetate/toluene followed by 90% chloroform/10% 2M $NH_3$ in methanol) to give 0.106 g that was recrystallized from 1 mL ethyl acetate and 5 mL ethyl ether to give 0.075 g (34%) of the title compound.

$^1$H NMR (DMSO-d6) δ7.9 (d, 2H, J=9 Hz), 7.6 (m, 1H), 7.2 (m, 3H), 7.1 (m, 3H), 7.0 (s, 1H), 6.9 (m, 3H), 4.2 (m, 4H), 4.1 (t, 2H, J=6 Hz), 3.3 (m, 2H), 3.0 (t, 2H, J=6 Hz), 2.0 (m, 2H). IR (KBr, cm$^{-1}$) 3400, 3110, 1674, 1636, 1612, 1500, 1252, 1205, 1176, 1136. MS (ESI) m/e 428. Anal. Calcd for $C_{23}H_{26}N_5F_3O_5S$: C, 51.01; H, 4.84; N, 12.93; F, 10.52. Found C, 45.58; H, 4.91; N, 13.21; F, 11.96. M.P.=100° C. HPLC 100%.

Example 96

Preparation of 2-{4-[2-(1-methyl-pyrrolidin-2-yl)-ethoxy]-phenyl}-5-(2-phenoxy-ethylsulfanylmethyl)-[1,3,4]oxadiazole

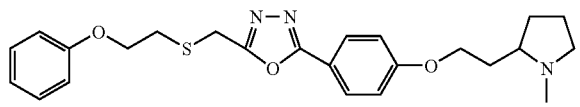

A mixture of 4-[5-(2-phenoxy-ethylsulfanylmethyl)-[1,3,4]oxadiazol-2-yl]-phenol (0.346 g, 1.05 mmol) and 60% NaH (0.121 g, 3.15 mmol) was stirred at 5° C. for 2 minutes in DMF (5 mL). Added 2-(2-chloro-ethyl)-1-methyl-pyrrolidine (0.291 g, 1.58 mmol) and heated the mixture to 100° C. for 10 hrs. Diluted with ethyl acetate and water. The aqueous layer was extracted twice with ethyl acetate. The combined organic extracts were washed 3× water, brine, dried over sodium sulfate, filtered and concentrated. The residue was purified by column chromatography on silica gel (elution with ethyl acetate/toluene followed by 90% chloroform/10% 2M $NH_3$ in methanol) to give 0.054 g, (12%) of the title compound and material that was a mixture of 2 products, one being the title compound and a second product of the reaction Example 97), see procedure for Example 97.

$^1$H NMR (DMSO-d6) δ 7.9 (d, 2H, J=9 Hz), 7.2 (t, 2H, J=8 Hz), 7.1 (d, 2H, J=9 Hz), 6.9 (m, 3H), 4.2 (m, 4H), 4.1 (m, 2H), 3.0 (m, 3H), 2.3 (s, 3H), 2.2 (m, 2H), 2.1 (m, 2H), 2.0 (m, 1H), 1.7 (m, 3H), 1.5 (m, 1H). IR (KBr, cm$^{-1}$) 3410, 3000, 2910, 2800, 1610, 1500, 1468, 1257, 1241, 1173, 764. MS (ESI) m/e 440. Anal. Calcd for $C_{24}H_{29}N_3O_3S$: C, 65.58; H, 6.65; N, 9.56. Found C, 63.09; H, 6.22; N, 8.96. M.P.=46–50° C. HPLC 94%.

Example 97

Preparation of 1-methyl-4-{4-[5-(2-phenoxy-ethylsulfanylmethyl)-[1,3,4]oxadiazol-2-yl]-phenoxy}-azepane

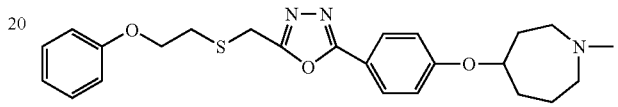

Prepared in the same manner as exemplified in Example 96 and isolated as a by-product of the reaction mixture. The mixture isolated via chromatography from procedure 96 was purified a second time using a Waters Preparatory 2000 with a Kromasil silica column (5×25 cm) (elution with 50/50 ethyl acetate/dichloromethane/1% dimethylethylamine to give 0.209 g (12%) of the title compound and 0.200 g (12%) of the compound of Example 96.

$^1$H NMR (DMSO-d6) δ7.9 (d, 2H, J=9 Hz), 7.2 (t, 2H, J=8 Hz), 7.1 (d, 2H, J=9 Hz), 6.9 (m, 3H), 4.7 (m, 1H), 4.2 (m, 4H), 3.0 (m, 2H), 2.65 (m, 1H), 2.6 (m, 2H), 2.5 (m, 1H), 2.3 (s, 3H), 2.1 (m, 2H), 1.9 (m, 1H), 1.8 (2H), 1.6 (m, 1H). IR (KBr, cm$^{-1}$) 2923, 1612, 1602, 1587, 1499, 1465, 1295, 1237, 1174, 1002. MS (ESI) m/e 440. Anal. Calcd for $C_{24}H_{29}N_3O_3S$: C, 65.58; H, 6.65; N, 9.56. Found C, 66.35; H, 6.83; N, 9.05. M.P.=60–61° C. HPLC 100%.

Example 98

Preparation of 4-{4-[5-(2-phenoxy-ethylsulfanylmethyl)-[1,3,4]oxadiazol-2-yl]-phenoxymethyl}-pyridine

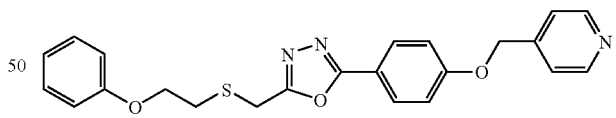

The above compound was prepared in a manner similar to that exemplified for the preparation of Example 96, from 4-[5-(2-phenoxy-ethylsulfanylmethyl)-[1,3,4]oxadiazol-2-yl]-phenol (0.303 g, 0.923 mmol) and 4-bromomethyl-pyridine hydrobromide salt (0.350 g, 1.38 mmol) to give a crude solid which was purified directly by column chromatography on silica gel (elution with ethyl acetate/toluene followed by 90% chloroform/10% 2M $NH_3$ in methanol to give material which was recrystallized from ethyl acetate, methanol, and ethyl ether to give 0.233 g (59%) of the title compound.

$^1$H NMR (DMSO-d6) δ8.6 (d, 2H, J=5 Hz), 7.9 (d, 2H, J=9 Hz), 7.4 (d, 2H, J=5 Hz), 7.2 (m, 4H), 6.9 (m, 3H), 5.3 (s, 2H), 4.2 (m, 4H), 3.0 (t, 2H, J=6 Hz). IR (KBr, cm$^{-1}$)

1603, 1501, 1264, 1249, 1172, 1005, 755. MS (ESI) m/e 420. Anal. Calcd for $C_{23}H_{21}N_3O_3S$: C, 65.85; H, 5.04; N, 10.02. Found C, 65.82; H, 5.11; N, 10.34. M.P.=80–90° C.

Example 99

Preparation of 2-{4-[5-(2-phenoxy-ethylsulfanylmethyl)-[1,3,4]oxadiazol-2-yl]-phenoxymethyl}-pyridine

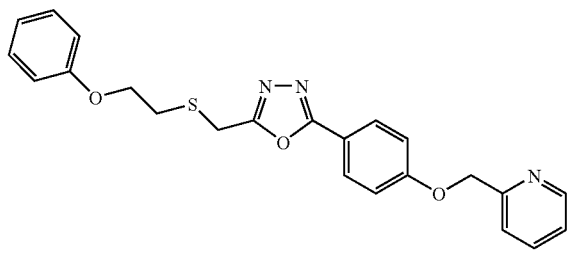

The above compound was prepared in a manner similar to that exemplified for the preparation of Example 96, from 4-[5-(2-phenoxy-ethylsulfanylmethyl)-[1,3,4]oxadiazol-2-yl]-phenol (0.269 g, 0.819 mmol) and 2-bromomethyl-pyridine hydrobromide salt (0.311 g, 1.23 mmol) to give 0.146 g (42%) of the title compound.

$^1$H NMR (DMSO-d6) $\delta$ 8.6 (m, 1H), 7.9 (m, 3H), 7.5 (d, 1H, J=8 Hz), 7.4 (m, 1H), 7.2 (m, 4H), 6.9 (m, 3H), 5.3 (s, 2H), 4.2 (m, 4H), 3.0 (t, 2H, J=6 Hz). IR (KBr, cm$^{-1}$) 1617, 1589, 1498, 1269, 1249, 1172, 1039, 753. MS (ESI) m/e 420. Anal. Calcd for $C_{23}H_{21}N_3O_3S$: C, 65.85; H, 5.04; N, 10.02. Found C, 65.55; H, 4.88; N, 9.88. M.P.=115° C.

Example 100

Preparation of 3-{4-[5-(2-phenoxy-ethylsulfanylmethyl)-[1,3,4]oxadiazol-2-yl]-phenoxymethyl}-pyridine

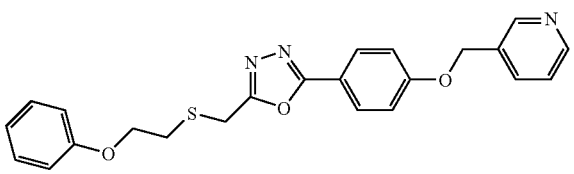

The above compound was prepared in a manner similar to that exemplified for the preparation of Example 96, from 4-[5-(2-phenoxy-ethylsulfanylmethyl)-[1,3,4]oxadiazol-2-yl]-phenol (0.274 g, 0.834 mmol) and 3-bromomethyl-pyridine hydrobromide salt (0.316 g, 1.25 mmol) to give 0.177 g (50%) of the title compound.

$^1$H NMR (DMSO-d6) $\delta$ 8.7 (d, 1H, J=2 Hz), 8.6 (m, 1H), 7.9 (m, 3H), 7.4 (m, 1H), 7.2 (m, 4H), 6.9 (m, 3H), 5.3 (s, 2H), 4.2 (m, 4H), 3.0 (t, 2H, J=6 Hz). IR (KBr, cm$^{-1}$) 1610, 1588, 1498, 1464, 1421, 1299, 1249, 1173, 1006, 758. MS (ESI) m/e 420. Anal. Calcd for $C_{23}H_{21}N_3O_3S$: C, 65.85; H, 5.04; N, 10.02. Found C, 65.83; H, 5.02; N, 10.04. M.P.=111–112° C.

Example 101

Preparation of {4-[5-(2-phenoxy-ethylsulfanylmethyl)-[1,3,4]oxadiazol-2-yl]-phenyl}-urea

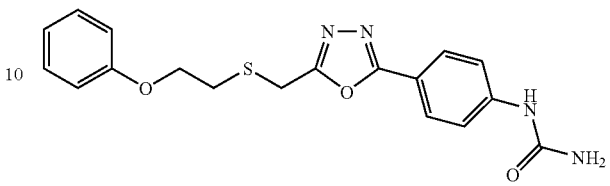

a) 4-Ethoxycarbonylamino-benzoic acid methyl ester

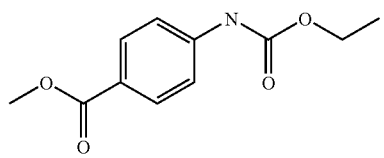

Ethyl chloroformate (16.15 g, 148.85 mmol, 1.5 eq.) was added dropwise via syringe to a solution of methyl 4-aminobenzoate (15.0 g, 99.23 mmol, 1 eq.) in pyridine (400 mL) at 0° C. After addition was complete, the reaction was allowed to stir and gradually warm to room temperature. After 4 hours, the pyridine was removed in vacuo and the residue suspended in water. The aqueous mixture was extracted with 50% Et2O in EtOAc. The combined organic layers were washed with aqueous 1M HCl, saturated sodium bicarbonate, and then brine, dried over MgSO4, filtered, and the solvent removed in vacuo to afford 21.79 g (98%) of 4-ethoxycarbonylamino-benzoic acid methyl ester as a yellow solid.

$^1$H NMR (DMSO-d6) $\delta$ 10.04 (s, 1H), 7.88 (d, 2H, J=9 Hz), 7.59 (d, 2H, J=9 Hz), 4.15 (q, 2H, J=7 Hz), 3.81 (s, 3H), 1.26 (t, 3H, J=7 Hz). IR (KBr, cm$^{-1}$) 3318, 1730, 1692, 1596, 1538, 1415, 1298, 1224, 1180, 1057. MS (ES$^+$) m/e 224. MS (ES$^-$) m/e 222. Anal. Calcd for $C_{11}H_{13}NO_4$ C, 59.19; H, 5.87; N, 6.27. Found C, 59.33; H, 5.92; N, 6.30. MP 159–162° C.

b) (4-Hydrazinocarbonyl-phenyl)-carbamic acid ethyl ester

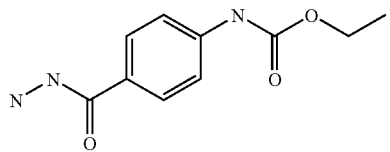

Hydrazine hydrate (3.59 g, 112.0 mmol, 5 eq.) was added to a solution of 4-ethoxycarbonylamino-benzoic acid methyl ester (5.0 g, 22.40 mmol, 1 eq.) in ethanol. The mixture was heated at 76° C. for 16 h. The solvent was removed in vacuo. The resultant white solid was suspended in EtOAc (150 mL)

and heated on a hot plate until ~100 mL remained, then allowed to cool. The resultant precipitate was collected by filtration to give 4.25 g (85%) of (4-hydrazinocarbonyl-phenyl)-carbamic acid ethyl ester as a white solid.

$^1$H NMR (DMSO-d6) δ 9.85 (s, 1H), 9.56 (s, 1H), 7.74 (d, 2H, J=9 Hz), 7.50 (d, 2H, J=9 Hz), 4.52 (br s, 2H), 4.13 (q, 2H, J=7 Hz), 1.25 (t, 3H, J=7 Hz). IR (KBr, cm$^{-1}$) 3303, 3278, 1715, 1631, 1593, 1525, 1503, 1328, 1228, 1067. MS (ES$^+$) m/e 224. Anal. Calcd for C$_{10}$H$_{13}$N$_3$O$_3$ C, 53.81; H, 5.87; N, 18.82. Found C, 53.52; H, 5.86; N, 19.20. MP softening at 186° C. then 193–195° C.

c) (4-{N'-[2-(2-Phenoxy-ethylsulfanyl)-acetyl]-hydrazinocarbonyl}-phenyl)-carbamic acid ethyl ester

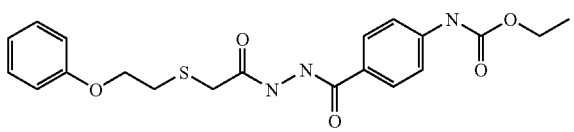

EEDQ (8.30 g, 33.55 mmol, 1.1 eq.) was added as a solid to a solution of (2-Phenoxyethylthio)acetic acid (6.47 g, 30.50 mmol, 1 eq.) in anhydrous 450 mL acetonitrile and 150 mL THF at room temperature. The reaction was stirred at room temperature for 1 h, then (4-hydrazinocarbonyl-phenyl)-carbamic acid ethyl ester (7.49 g, 33.55 mmol, 1.1 eq.) was added as a solid. The mixture was stirred at room temperature for an additional 16 h. The solvent was removed in vacuo to afford a tan solid. The solid was suspended in aqueous 1 M HCl and extracted with EtOAc. The organic extract was washed with water, saturated aqueous sodium bicarbonate, and brine, dried over magnesium sulfate, filtered and concentrated to afford an off-white solid. The resulting solid was recrystallized from EtOAc and collected by filtration to afford 10.01 g (79%) of (4-{N'-[2-(2-phenoxy-ethylsulfanyl)-acetyl]-hydrazinocarbonyl}-phenyl)-carbamic acid ethyl ester as an off-white solid.

$^1$H NMR (DMSO-d6) δ 10.28 (s, 1H), 10.05 (s, 1H), 9.94 (s, 1H), 7.82 (d, 2H, J=9 Hz), 7.55 (d, 2H, J=9 Hz), 7.29 (m, 2H), 6.95 (m, 3H), 4.16 (m, 4H), 3.32 (s, 2H), 3.04 (t, 2H, J=7 Hz), 1.26 (t, 3H, J=7 Hz). IR (CHCl$_3$, cm$^{-1}$) 1737, 1525, 1508, 1498, 1215. MS (ES$^+$) m/e 418. MS (ES$^-$) m/e 416. Anal. Calcd for C$_{20}$H$_{23}$N$_3$O$_5$S C, 57.54; H, 5.55; N, 10.06. Found C, 57.18; H, 5.59; N, 10.10.

d) {4-[5-(2-Phenoxy-ethylsulfanylmethyl)-[1,3,4]oxadiazol-2-yl]-phenyl}-carbamic acid ethyl ester

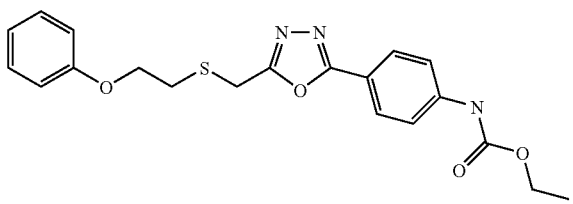

Triphenylphosphine (2.76 g, 10.54 mmol, 1.1 eq.) was added to a suspension of (4-{N'-[2-(2-phenoxy-ethylsulfanyl)-acetyl]-hydrazinocarbonyl}-phenyl)-carbamic acid ethyl ester (4.0 g, 9.58 mmol, 1 eq.) in anhydrous THF (250 mL) at room temerature. Triethylamine (3.49 g, 34.49 mmol, 3.6 eq.) was then added to the mixture via syringe. After stirring for 5 minutes, carbon tetrabromide (3.50 g, 10.54 mmol, 1.1 eq.) was added as a solid with vigorous stirring. The reaction was allowed to stir at room temperature for 16 h. The solvent was removed in vacuo leaving a dark brown solid. The solid was purified via silica gel flash chromatography using a step gradient of EtOAc in hexane as the mobile phase to afford 1.93 g (50%) of {4-[5-(2-phenoxy-ethylsulfanylmethyl)-[1,3,4]oxadiazol-2-yl]-phenyl}-carbamic acid ethyl ester as a yellow solid.

$^1$H NMR (DMSO-d6) δ 10.06 (s, 1H), 7.88 (d, 2H, J=9 Hz), 7.67 (d, 2H, J=9 Hz), 7.27 (m, 2H), 6.93 (m, 3H), 4.18 (m, 6H), 3.02 (t, 2H, J=7 Hz), 1.26 (t, 3H, J=7 Hz). IR (CHCl$_3$, cm$^{-1}$) 3432, 3009, 1737, 1522, 1504, 1242, 1226, 1224, 1216, 1210, 1206, 1182. MS (ES$^+$) m/e 400. MS (ES$^-$) m/e 398. Anal. Calcd for C$_{20}$H$_{21}$N$_3$O$_4$S C, 60.14; H, 5.30; N, 10.52. Found C, 59.78; H, 5.34; N, 10.41.

e) Preparation of {4-[5-(2-phenoxy-ethylsulfanylmethyl)-[1,3,4]oxadiazol-2-yl]-phenyl}-urea

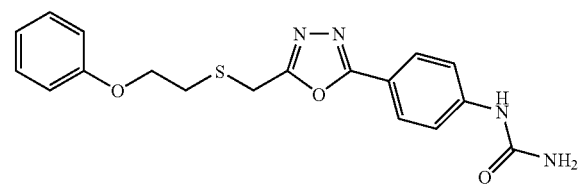

Triethylamine (0.30 g, 3.0 mmol, 1.2 eq.) was added via syringe to a suspension of {4-[5-(2-phenoxy-ethylsulfanylmethyl)-[1,3,4]oxadiazol-2-yl]-phenyl}-carbamic acid ethyl ester (1.0 g, 2.5 mmol, 1 eq.) in anhydrous toluene (10 mL). The mixture was heated to reflux, after 5 minutes, B-chlorocatecholborane (0.46 g, 3.0 mmol, 1.2 eq.) was added as a solid and the reaction allowed to stir at reflux for 15 minutes. The reaction was allowed to cool to about 40° C. and then ammonia in methanol (1.07 mL of 7M NH3 in MeOH) was added via syringe with vigorous stirring (turning the dark brown solution to a yellow suspension). The suspension was allowed to stir at room temperature for 1.5 h. The resultant suspension was filtered to obtain 1.19 g of a yellow solid, which was purified by recrystallization from ethanol to afford 0.67 g (72%) {4-[5-(2-phenoxy-ethylsulfanylmethyl)-[1,3,4]oxadiazol-2-yl]-phenyl}-urea as a light yellow solid.

$^1$H NMR (DMSO-d6) δ 8.97 (s, 1H), 7.82 (d, 2H, J=9 Hz), 7.61 (d, 2H, J=9 Hz), 7.27 (m, 2H), 6.94 (m, 3H), 6.05 (s, 2H), 4.20 (m, 4H), 3.02 (t, 2H, J=7 Hz). IR (KBr, cm$^{-1}$) 3343, 3175, 1699, 1599, 1530, 1497, 1418, 1242, 843. MS (ES$^+$) m/e 371. MS (ES$^-$) m/e 369. Anal. Calcd for C$_{18}$H$_{18}$N$_4$O$_3$S C, 58.36; H, 4.90; N, 15.12. Found C, 58.21; H, 4.95; N, 14.96. MP>220° C.

Example 102

Preparation of 1,1-dimethyl-3-{4-[5-(2-phenoxy-ethylsulfanylmethyl)-[1,3,4]oxadiazol-2-yl]-phenyl}-urea

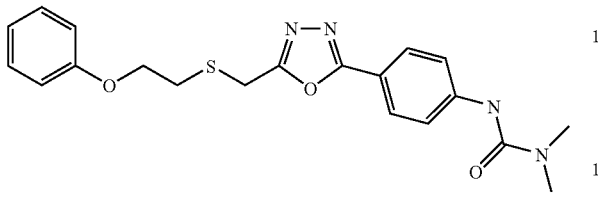

The above compound was prepared in a manner similar to that exemplified for the preparation of Example 101e from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) and dimethylamine (2M in THF, 1.2 mL, 2.4 mmol, 1.2 eq.) to produce 0.53 g (67%) of 1,1-dimethyl-3-{4-[5-(2-phenoxy-ethylsulfanylmethyl)-[1,3,4]oxadiazol-2-yl]-phenyl}-urea as an off-white solid.

$^1$H NMR (DMSO-d6) δ 8.68 (s, 1H), 7.83 (d, 2H, J=9 Hz), 7.71 (d, 2H, J=9 Hz), 7.27 (m, 2H), 6.93 (m, 3H), 4.20 (m, 4H), 3.02 (t, 2H, J=7 Hz), 2.95 (s, 6H). IR (CHCl$_3$, cm$^{-1}$) 3009, 1674, 1598, 1519, 1498, 1415, 1244, 1173. MS (ES$^+$) m/e 399. MS (ES$^-$) m/e 397. Anal. Calcd for C$_{20}$H$_{22}$N$_4$O$_3$S C, 60.28; H, 5.56; N, 14.06. Found C, 60.26; H, 5.47; N, 13.80. Analytical HPLC 97.3% purity. MP softening at 163° C. then 167–169° C.

Example 103

Preparation of pyrrolidine-1-carboxylic acid {4-[5-(2-phenoxy-ethylsulfanylmethyl)-[1,3,4]oxadiazol-2-yl]-phenyl}-amide

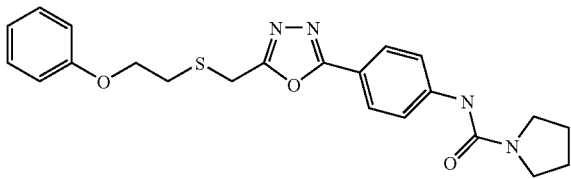

The above compound was prepared in a manner similar to that exemplified for the preparation of Example 101e from {-[5-(2-Phenoxy-ethylsulfanylmethyl)-[1,3,4]oxadiazol-2-yl]-phenyl}-carbamic acid ethyl ester (0.80 g, 2.0 mmol, 1 eq.) and pyrrolidine (0.17 g, 2.4 mmol, 1.2 eq.) to produce 0.50 g (59%) of pyrrolidine-1-carboxylic acid {-[5-(2-phenoxy-ethylsulfanylmethyl)-[1,3,4]oxadiazol-2-yl]-phenyl}-amide as an orange/brown solid.

$^1$H NMR (DMSO-d6) δ 8.51 (s, 1H), 7.83 (d, 2H, J=9 Hz), 7.76 (d, 2H, J=9 Hz), 7.27 (m, 2H), 6.93 (m, 3H), 4.20 (m, 4H), 3.40 (m, 4H), 3.02 (t, 2H, J=7 Hz), 1.86 (m, 4H). IR (KBr, cm$^{-1}$) 3394, 1660, 1595, 1524, 1497, 1252, 835, 759. MS (ES$^+$) m/e 425. MS (ES$^-$) m/e 423. Anal. Calcd for C$_{22}$H$_{24}$N$_4$O$_3$S C, 62.24; H, 5.70; N, 13.20. Found C, 61.85; H, 5.81; N, 12.93. Analytical HPLC>99% purity. MP 184–185° C.

Example 104

Preparation of piperidine-1-carboxylic acid {4-[5-(2-phenoxy-ethylsulfanylmethyl)-[1,3,4]oxadiazol-2-yl]-phenyl}-amide

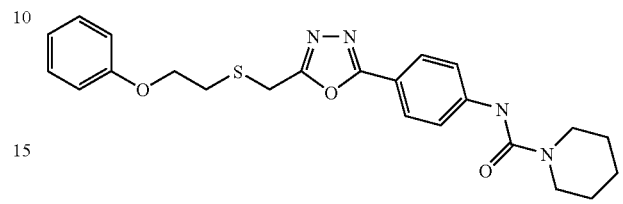

The above compound was prepared in a manner similar to that exemplified for the preparation of Example 101e from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) and piperidine (0.20 g, 2.4 mmol, 1.2 eq.) to produce 0.33 g (38%) of piperidine-1-carboxylic acid {4-[5-(2-phenoxy-ethylsulfanylmethyl)-[1,3,4]oxadiazol-2-yl]-phenyl}-amide as a light yellow solid.

$^1$H NMR (DMSO-d6) δ 8.84 (s, 1H), 7.82 (d, 2H, J=9 Hz), 7.69 (d, 2H, J=9 Hz), 7.27 (m, 2H), 6.93 (m, 3H), 4.20 (m, 4H), 3.44 (m, 4H), 3.02 (t, 2H, J=7 Hz), 1.54 (m, 6H). IR (CHCl$_3$, cm$^{-1}$) 3005, 2944, 2860, 1662, 1599, 1515, 1497, 1420, 1312, 1241, 1181. MS (ES$^+$) m/e 439. MS (ES$^-$) m/e 437. Anal. Calcd for C$_{23}$H$_{26}$N$_4$O$_3$S C, 62.99; H, 5.98; N, 12.78. Found C, 62.59; H, 5.87; N, 12.48. Analytical HPLC 99% purity. MP softening at 128° C. then 132–134° C.

Example 105

Preparation of 1-(2-dimethylamino-ethyl)-3-{4-[5-(2-phenoxy-ethylsulfanylmethyl)-[1,3,4]oxadiazol-2-yl]-phenyl}-urea hydrochloride

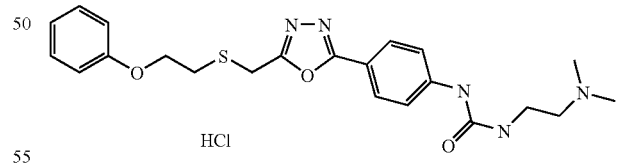

The above compound was prepared in a manner similar to that exemplified for the preparation of Example 101e from {4-[5-(2-Phenoxy-ethylsulfanylmethyl)-[1,3,4]oxadiazol-2-yl]-phenyl}-carbamic acid ethyl ester (1.00 g, 2.5 mmol, 1 eq.) and N,N-dimethylethylenediamine (0.26 g, 3.0 mmol, 1.2 eq.) to afford 0.93 g (85%) of 1-(2-dimethylamino-ethyl)-3-{4-[5-(2-phenoxy-ethylsulfanylmethyl)-[1,3,4] oxadiazol-2-yl]-phenyl}-urea as an orange oil following purification via silica gel flash chromatography using 10%

2M NH3 in methanol in chloroform as the mobile phase. The free base was converted to the hydrochloride salt by adding 1.2 eq. of 4M HCl in 1,4-dioxane (0.33 mL) dropwise to an EtOAc solution of the free base (0.48 g). The resulting white solid was quickly collected by filtration and dried to give 0.26 g of 1-(2-dimethylamino-ethyl)-3-{4-[5-(2-phenoxy-ethylsulfanylmethyl)-[1,3,4]oxadiazol-2-yl]-phenyl}-urea hydrochloride as a white solid.

$^1$H NMR (DMSO-d6) δ 10.06 (s, 1H), 9.70 (s, 1H), 7.84 (d, 2H, J=9 Hz), 7.64 (d, 2H, J=9 Hz), 7.27 (m, 2H), 6.94 (m, 4H), 4.19 (m, 4H), 3.48 (m, 2H), 3.18 (m, 2H), 3.02 (t, 2H, J=7 Hz), 2.82 (s, 6H). IR (CHCl$_3$, cm$^{-1}$) 3302, 3000, 1695, 1602, 1545, 1499, 1318, 1233, 1181. MS (ES$^+$) m/e 442. MS (ES$^-$) m/e 440. Anal. Calcd for C$_{22}$H$_{28}$ClN$_5$O$_3$S C, 55.28; H, 5.90; N, 14.65. Found C, 53.48; H, 5.62; N, 14.60. Analytical HPLC>99% purity.

Example 106

Preparation of 1-{4-[5-(2-phenoxy-ethylsulfanylmethyl)-[1,3,4]oxadiazol-2-yl]-phenyl}-3-(2-pyrrolidin-1-yl-ethyl)-urea oxalate

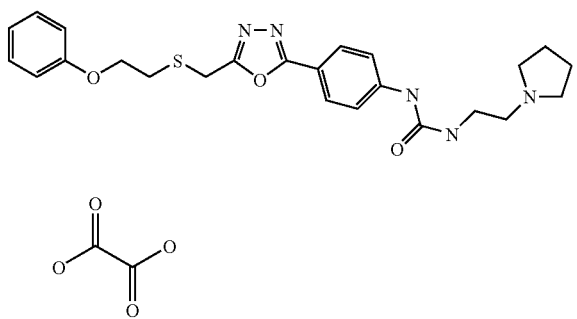

The above compound was prepared in a manner similar to that exemplified for the preparation of Example 101e from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) and 1-(2-aminoethyl)pyrrolidine (0.27 g, 2.4 mmol, 1.2 eq.) to afford 1-{4-[5-(2-phenoxy-ethylsulfanylmethyl)-[1,3,4]oxadiazol-2-yl]-phenyl}-3-(2-pyrrolidin-1-yl-ethyl)-urea as a light brown oil following purification via silica gel flash chromatography using 10% 2M NH3 in methanol in diethyl ether as the mobile phase. The free base was converted to the oxalate salt by adding 1.1 eq. of oxalic acid (0.20 g) in acetone to a warm acetone solution of the amine. After several minutes, a tan solid formed which was collected by filtration leaving 1-{4-[5-(2-phenoxy-ethylsulfanylmethyl)-[1,3,4]oxadiazol-2-yl]-phenyl}-3-(2-pyrrolidin-1-yl-ethyl)-urea oxalate as an off-white solid.

$^1$H NMR DMSO-d6) δ 9.63 (s, 1H), 7.83 (d, 2H, J=9 Hz), 7.65 (d, 2H, J=9 Hz), 7.27 (m, 2H), 7.15 (m, 1H), 6.93 (m, 3H), 4.20 (m, 4H), 3.42 (m, 2H), 3.23 (m, 6H), 3.01 (t, 2H, J=7 Hz), 1.92 (m, 4H). IR (CHCl$_3$, cm$^{-1}$) 3345, 3230, 1689, 1599, 1541, 1498, 1243, 1224. MS (ES$^+$) m/e 468. MS (ES$^-$) m/e 466. Anal. Calcd for C$_{26}$H$_{31}$N$_5$O$_7$S C, 56.00; H, 5.60; N, 12.56. Found C, 55.52; H, 5.65; N, 12.09. Analytical HPLC 100% purity. MP 111–115° C.

Example 107

Preparation of 1-{4-[5-(2-phenoxy-ethylsulfanylmethyl)-[1,3,4]oxadiazol-2-yl]-3-phenyl}-3-(2-piperidin-1-yl-ethyl)-urea The above compound was prepared in a manner similar to that exemplified for the preparation of Example 101 e from {4-[5-(2-Phenoxy-ethylsulfanylmethyl)-[1,3,4]oxadiazol-2-yl]-phenyl}-carbamic acid ethyl ester (0.70 g, 1.75 mmol, 1 eq.) and 1-(2-aminoethyl)piperidine (0.27 g, 2.1 mmol, 1.2 eq.) to afford 0.79 g (94%) of 1-{4-[5-(2-phenoxy-ethylsulfanylmethyl)-[1,3,4]oxadiazol-2-yl]-phenyl}-3-(2-piperidin-1-yl-ethyl)-urea as a yellow oil following purification via silica gel flash chromatography using 10% 2M NH3 in methanol in diethyl ether as the mobile phase. The oil was triturated with diethyl ether/ethyl acetate and the resulting solid collected by filtration leaving 1-{4-[5-(2-phenoxy-ethylsulfanylmethyl)-[1,3,4]oxadiazol-2-yl]-phenyl}-3-(2-piperidin-1-yl-ethyl)-urea (0.50 g) as a yellow solid.

$^1$H NMR (DMSO-d6) δ 9.09 (s, 1H), 7.82 (d, 2H, J=9 Hz), 7.59 (d, 2H, J=9 Hz), 7.27 (m, 2H), 6.93 (m, 3H), 6.20 (br m, 1H), 4.20 (m, 4H), 3.20 (m, 2H), 3.01 (t, 2H, J=7 Hz), 2.35 (m, 6H), 1.51 (m, 4H), 1.38 (m, 2H). IR (CHCl$_3$, cm$^{-1}$) 3418, 3358, 3008, 2942, 1690, 1602, 1499, 1244, 1180. MS (ES$^+$) m/e 482. MS (ES$^-$) m/e 480. Anal. Calcd for C$_{25}$H$_{31}$N$_5$O$_3$S C, 62.35; H, 6.49; N, 14.54. Found C, 62.07; H, 6.39; N, 14.33. Analytical HPLC 100% purity. MP 126–128° C.

Example 108

Preparation of 1-{4-[5-(4-Phenoxy-butyl)-[1,3,4]oxadiazol-2-yl]-phenyl}-3-(3-pyrrolidin-1-yl-propyl)-urea oxalate

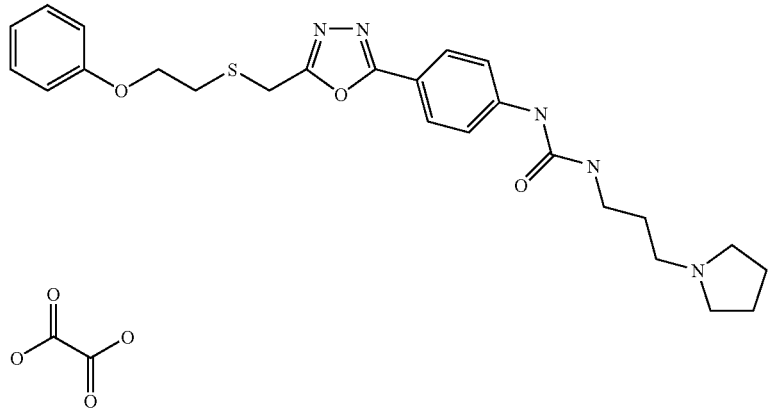

The above compound was prepared in a manner similar to that exemplified for the preparation of Example 101e, from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) and 1-(3-aminopropyl)pyrrolidine (0.31 g, 2.4 mmol, 1.2 eq.) to afford 0.64 g (67%) of 1-{4-[5-(4-phenoxy-butyl)-[1,3,4]oxadiazol-2-yl]-phenyl}-3-(3-pyrrolidin-1-yl-propyl)-urea as a tan foam following purification via silica gel flash chromatography using 10% 2M NH3 in methanol in diethyl ether as the mobile phase. The free base was converted to the oxalate salt by adding 1.1 eq. of oxalic acid (0.13 g) in acetone to an acetone solution of the free base. The resultant solid was collected by filtration and crystallized from methanol to afford 0.39 g of 1-{4-[5-(4-phenoxy-butyl)-[1,3,4]oxadiazol-2-yl]-phenyl}-3-(3-pyrrolidin-1-yl-propyl)-urea oxalate as an off-white solid.

$^1$H NMR (DMSO-d6) δ 9.44 (s, 1H), 7.82 (d, 2H, J=9 Hz), 7.63 (d, 2H, J=9 Hz), 7.27 (m, 2H), 6.93 (m, 4H), 4.20 (m, 4H), 3.17 (m, 8H), 3.01 (t, 2H, J=7 Hz), 1.92 (m, 4H), 1.81 (m, 2H). IR (KBr, cm$^{-1}$) 3364, 3293, 3041, 2932, 2877, 1691, 1600, 1541, 1497, 1417, 1316, 1236, 1179, 843, 757. MS (ES$^+$) m/e 482. MS (ES$^-$) m/e 480. Anal. Calcd for C$_{27}$H$_{33}$N$_5$O$_7$S C, 56.73; H, 5.82; N, 12.25. Found C, 56.24; H, 6.08; N, 12.11. Analytical HPLC 97.8% purity. MP softening at 122° C. then 126–128° C.

Example 109

Preparation of 1-(4-dimethylamino-butyl)-3-{4-[5-(2-phenoxy-ethylsulfanylmethyl)-[1,3,4]oxadiazol-2-yl]-phenyl}-urea oxalate

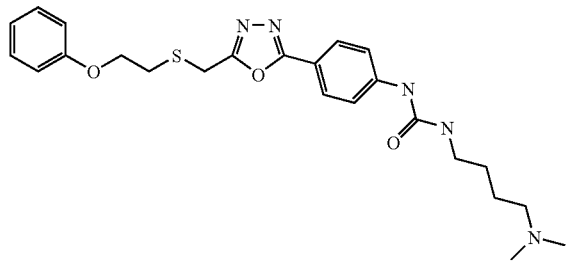

-continued

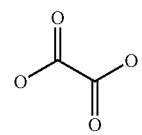

The above compound was prepared in a manner similar to that exemplified for the preparation of Example 101e, from {4-[5-(2-Phenoxy-ethylsulfanylmethyl)-[1,3,4]oxadiazol-2-yl]-phenyl}-carbamic acid ethyl ester (0.87 g, 2.18 mmol, 1 eq.) with 4-dimethylaminobutylamine (0.30 g, 2.62 mmol, 1.2 eq.) to afford 1.0 g (98%) of 1-(4-dimethylamino-butyl)-3-{4-[5-(2-phenoxy-ethylsulfanylmethyl)-[1,3,4]oxadiazol-2-yl]-phenyl}-urea as an orange oil following purification via silica gel flash chromatography using 10% 2M NH3 in methanol in diethyl ether as the mobile phase. The free base was converted to the oxalate salt by adding 1.1 eq of oxalic acid in acetone to an acetone solution of the free base. The 1-(4-dimethylamino-butyl)-3-{4-[5-(2-phenoxy-ethylsulfanylmethyl)-[1,3,4]oxadiazol-2-yl]-phenyl}-urea oxalate (0.74 g) was collected by filtration leaving a yellow solid.

$^1$H NMR (DMSO-d6) δ 9.54 (s, 1H), 7.81 (d, 2H, J=9 Hz), 7.64 (d, 2H, J=9 Hz), 7.27 (m, 2H), 7.11 (br t, 11), 6.93 (m, 3H), 4.20 (m, 4H), 3.13 (m, 2H), 3.02 (m, 4H), 2.74 (s, 6H), 1.65 (m, 2H), 1.47 (m, 2H). IR (CHCl$_3$, cm$^{-1}$) 3311, 3010, 1778, 1693, 1656, 1601, 1499, 1417, 1318, 1241, 1224, 1180. MS (ES$^+$) m/e 470. MS(ES$^-$) m/e 468. Anal. Calcd for C$_{26}$H$_{33}$N$_5$O$_7$S C, 55.80; H, 5.94; N, 12.51. Found C, 54.87; H, 5.63; N, 12.30. Analytical HPLC 100% purity. MP softening at 60° C. then 75–78° C.

Example 110

Preparation of 1-(5-dimethylamino-pentyl)-3-{4-[5-(2-phenoxy-ethylsulfanylmethyl)-[1,3,4]oxadiazol-2-yl]-phenyl}-urea oxalate

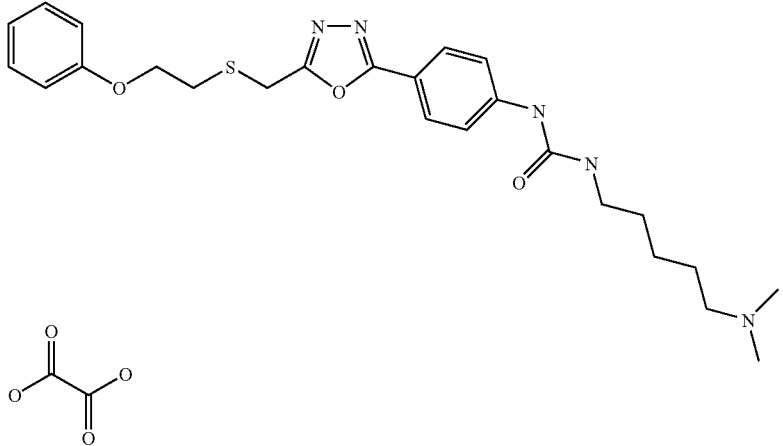

The above compound was prepared in a manner similar to that exemplified for the preparation of Example 101e from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) with 5-(dimethylamino)pentylamine (0.31 g, 2.4 mmol, 1.2 eq.) to afford 0.92 g (95%) of 1-(5-dimethylamino-pentyl)-3-{4-[5-(2-phenoxy-ethylsulfanylmethyl)-[1,3,4]oxadiazol-2-yl]-phenyl}-urea as a dark yellow oil following purification via silica gel flash chromatography using 7.5% 2M NH3 in methanol in diethyl ether as the mobile phase. The oil was converted to the oxalate salt by adding 1.1 eq. of oxalic acid (0.19 g) in acetone to an acetone solution of the free base. The solid that formed was collected by filtration to afford 0.73 g of 1-(5-dimethylamino-pentyl)-3-{4-[5-(2-phenoxy-ethylsulfanylmethyl)-[1,3,4]oxadiazol-2-yl]-phenyl}-urea oxalate as an off-white solid.

$^1$H NMR (DMSO-d6) δ 9.33 (s, 1H), 7.81 (d, 2H, J=9 Hz), 7.62 (d, 2H, J=9 Hz), 7.27 (m, 2H), 6.93 (m, 3H), 6.79 (br t, 1H), 4.19 (m, 4H), 3.10 (m, 2H), 3.01 (m, 4H), 2.73 (s, 6H), 1.63 (m, 2H), 1.47 (m, 2H), 1.31 (m, 2H). IR (KBr, cm$^{-1}$) 3394, 2937, 1696, 1600, 1541, 1499, 1416, 1405, 1318, 1233, 1179, 1083, 1032, 721. MS (ES$^+$) m/e 484. MS (ES$^-$) m/e 482. Anal. Calcd for C$_{27}$H$_{35}$N$_5$O$_7$S C, 56.53; H, 6.15; N, 12.21. Found C, 56.47; H, 6.21; N, 11.98. MP softening at 77° C. then 82–85° C.

Example 111

Preparation of 1-(6-dimethylamino-hexyl)-3-{4-[5-(2-phenoxy-ethylsulfanylmethyl)-[1,3,4]oxadiazol-2-yl]-phenyl}-urea oxalate

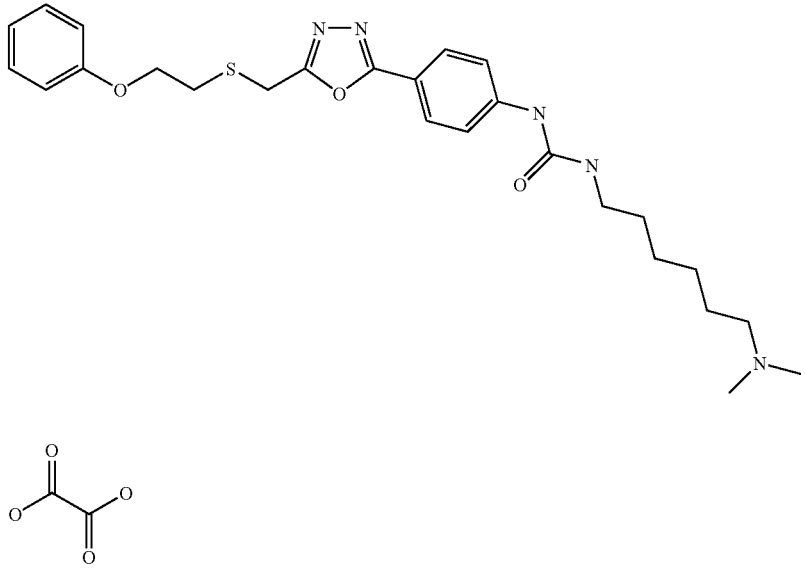

The above compound was prepared in a manner similar to that exemplified for the preparation of Example 101e, from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) with 6-(dimethylamino)hexylamine (0.35 g, 2.4 mmol, 1.2 eq.) to afford 0.97 g (98%) of 1-(6-dimethylamino-hexyl)-3-{4-[5-(2-phenoxy-ethylsulfanylmethyl)-[1,3,4]oxadiazol-2-yl]-phenyl}-urea as a dark yellow oil following purification via silica gel flash chromatography using 7.5% 2M NH3 in methanol in diethyl ether as the mobile phase. The oil was converted to the oxalate salt by adding 1.1 eq. of oxalic acid (0.21 g) in acetone to an acetone solution of the free base. The solid that formed was collected by filtration to afford 0.94 g of 1-(6-dimethylamino-hexyl)-3-{4-[5-(2-phenoxy-ethylsulfanylmethyl)-[1,3,4]oxadiazol-2-yl]-phenyl}-urea oxalate as an off-white solid. The solid was recrystallized from methanol/acetone to give an off-white crystalline solid.

$^1$H NMR (DMSO-d6) δ 9.32 (s, 1H), 7.80 (d, 2H, J=9 Hz), 7.62 (d, 2, J=9 Hz), 7.27 (m, 2H), 6.93 (m, 3H), 6.78 (br t, 1H), 4.20 (m, 4H), 3.09 (m, 2H), 2.99 (m, 4H), 2.72 (s, 6H), 1.59 (m, 2H), 1.44 (m, 2H), 1.31 (m, 4H). IR, (KBr, cm$^{-1}$) 3334, 3041, 2931, 2859, 1690, 1600, 1543, 1498, 1244, 1179. MS (ES$^+$) m/e 498. MS (ES$^-$) m/e 496. Anal. Calcd for $C_{28}H_{37}N_5O_7S$ C, 57.23; H, 6.35; N, 11.92. Found C, 56.55; H, 6.21; N, 11.69. Analytical HPLC 95% purity. MP softening at 100° C. then 105–108° C.

Example 112

Preparation of 1-(2-dimethylamino-ethyl)-1-methyl-3-{4-[5-(2-phenoxy-ethylsulfanylmethyl)-[1,3,4]oxadiazol-2-yl]-phenyl}-urea

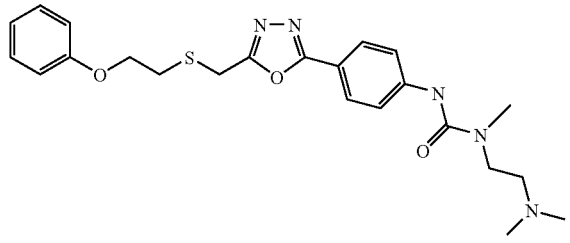

The above compound was prepared in a manner similar to that exemplified for the preparation of Example 101e, from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) and N,N,N'-trimethylethylenediamine (0.25 g, 2.4 mmol, 1.2 eq.) to afford 0.73 g (80%) of 1-(2-dimethylamino-ethyl)-1-methyl-3-{4-[5-(2-phenoxy-ethylsulfanylmethyl)-[1,3,4]oxadiazol-2-yl]-phenyl}-urea as a light yellow solid following purification via silica gel flash chromatography using 10% 2M NH3 in methanol in diethyl ether as the mobile phase.

$^1$H NMR (DMSO-d6) δ 9.63 (s, 1H), 7.83 (d, 2H, J=9 Hz), 7.62 (m, 2H), 7.27 (m, 2H), 6.93 (m, 3H), 4.20 (m, 4H), 3.40 (t, 2H, J=7 Hz), 3.02 (t, 2H, J=7 Hz), 2.95 (s, 3H), 2.45 (m, 2H), 2.24 (s, 6I). IR (CHCl$_3$, cm$^{-1}$) 3008, 2953, 2862, 2791, 1674, 1603, 1542, 1499, 1470, 1390, 1317, 1243, 1180. MS (ES$^+$) m/e 456. MS (ES$^-$) m/e 454. Anal. Calcd for $C_{23}H_{29}N_5O_3S$ C, 60.64; H, 6.42; N, 15.37. Found C, 60.34; H, 6.29; N, 15.17. Analytical HPLC 99% purity. MP softening at 121° C. then 134–135° C.

Example 113

Preparation of 1-benzyl-1-(2-dimethylamino-ethyl)-3-{4-[5-(2-phenoxy-ethylsulfanylmethyl)-[1,3,4]oxadiazol-2-yl]-phenyl}-urea oxalate

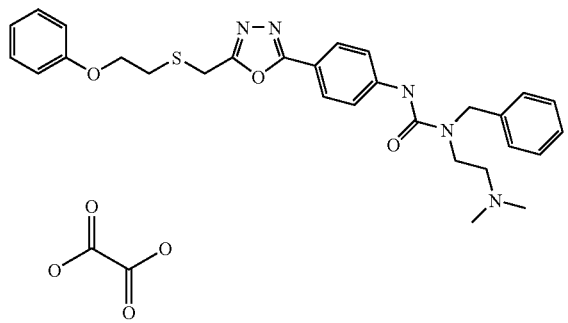

The above compound was prepared in a manner similar to that exemplified for the preparation of Example 101e, from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) and N'-benzyl-N,N-dimethylethylenediamine (0.43 g, 2.4 mmol, 1.2 eq.) to afford 0.89 g (84%) 1-benzyl-1-(2-dimethylamino-ethyl)-3-{4-[5-(2-phenoxy-ethylsulfanylmethyl)-[1,3,4]oxadiazol-2-yl]-phenyl}-urea as a yellow oil following purification via silica gel flash chromatography using 5% 2M NH3 in methanol in diethyl ether as the mobile phase. The free base was converted to the oxalate salt by adding 1.2 eq. of oxalic acid (0.18 g) in acetone to an acetone solution of the free base. Addition of diethyl ether to the cloud point and cooling produced 0.98 g of 1-benzyl-1-(2-dimethylamino-ethyl)-3-{4-[5-(2-phenoxy-ethylsulfanylmethyl)-[1,3,4]oxadiazol-2-yl]-phenyl}-urea oxalate as an off-white solid.

$^1$H NMR (DMSO-d6) δ 9.43 (s, 1H), 7.86 (d, 2H J=9 Hz), 7.73 (d, 2H, J=9 Hz), 7.38 (m, 2H), 7.28 (m, 5H), 6.93 (m, 3H), 4.69 (m, 2H), 4.19 (m, 4H), 3.58 (m, 2H), 3.09 (m, 2H), 3.02 (t, 2H, J=7 Hz), 2.69 (s, 6H). IR (CHCl$_3$, cm$^{-1}$) 3306, 3009, 1777, 1661, 1601, 1499, 1316, 1242, 1224. MS (ES$^+$) m/e 532. MS(ES$^-$) m/e 530. Anal. Calcd for $C_{31}H_{35}N_5O_7S$ C, 59.89; H, 5.67; N, 11.26. Found C, 58.66; H, 5.32; N, 11.23. Analytical HPLC 98% purity. MP softening at 70° C. then 72–76° C.

Example 114

Preparation of 1-(3-dimethylamino-propyl)-1-methyl-3-{4-[5-(2-phenoxy-ethylsulfanylmethyl)-[1,3,4]oxadiazol-2-yl]-phenyl}-urea

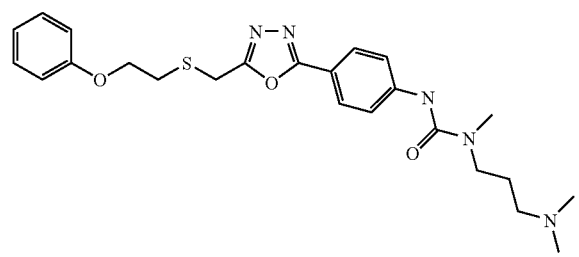

The above compound was prepared in a manner similar to that exemplified for the preparation of Example 101e, from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) and N,N,N'-trimethyl-1,3-propanediamine (0.24 g, 2.1 mmol, 1.2 eq.). to afford 0.51 g (62%) of 1-(3-dimethylamino-propyl)-1-methyl-3-{4-[5-(2-phenoxy-ethylsulfanylmethyl)-[1,3,4]oxadiazol-2-yl]-phenyl}-urea as a crystalline orange solid following purification by silica gel flash chromatography using 10% 2M NH3 in methanol in chloroform as the mobile phase and recrystallization from EtOAc/Et2O.

$^1$H NMR (DMSO-d6) δ 9.66 (s, 1H), 7.83 (d, 2H, J=9 Hz), 7.62 (m, 2H), 7.27 (M, 2H), 6.93 (m, 3H), 4.20 (m, 4H), 3.32 (m, 2H), 3.02 (t, 2H, J=7 Hz), 2.89 (s, 3H), 2.29 (m, 2H), 2.23 (s, 6H), 1.70 (m, 2H). IR (CHCl$_3$, cm$^{-1}$) 3008, 2950, 2827, 2787, 1665, 1604, 1498, 1229, 1179. MS (ES$^+$) m/e 470. MS (ES$^-$) m/e 468. Anal. Calcd for C$_{24}$H$_{31}$N$_5$O$_3$S C, 61.38; H, 6.65; N, 14.91. Found C, 60.75; H, 6.49; N, 14.43. Analytical HPLC 99% yield. MP softening at 114° C. then transition at 116–118° C. then melting at 136–139° C.

Example 115

Preparation of 1-benzyl-1-(3-dimethylamino-propyl)-3-{4-[5-(2-phenoxy-ethylsulfanylmethyl)-[1,3,4]oxadiazol-2-yl]-phenyl}-urea oxalate

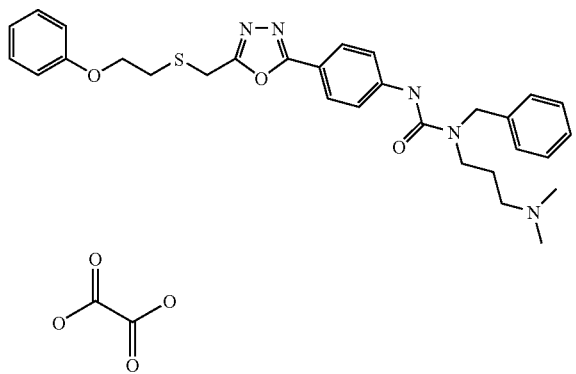

The above compound was prepared in a manner similar to that exemplified for the preparation of Example 101e from {4-[5-(2-Phenoxy-ethylsulfanylmethyl)-[1,3,4]oxadiazol-2-yl]-phenyl}-carbamic acid ethyl ester (0.80 g, 2.0 mmol, 1 eq.) and N'-Benzyl-N,N-dimethyl-propane-1,3-diamine (0.46 g, 2.4 mmol, 1.2 eq.) to afford 0.80 g (73%) of 1-benzyl-1-(3-dimethylamino-propyl)-3-{4-[5-(2-phenoxyethylsulfanylmethyl)-[1,3,4]oxadiazol-2-yl]-phenyl}-urea as an orange oil following purification by silica gel flash chromatography using 5% 2M NH3 in methanol in chloroform as the mobile phase. The free base was converted to the oxalate salt by adding 1.2 eq. of oxalic acid (0.14 g) in acetone to an acetone solution of the free base. Addition of diethyl ether to the resulting yellow solution and cooling produced 0.62 g of 1-benzyl-1-(3-dimethylamino-propyl)-3-{4-[5-(2-phenoxy-ethylsulfanylmethyl)-[1,3,4]oxadiazol-2-yl]-phenyl}-urea oxalate as a tan solid.

$^1$H NMR (DMSO-d6) δ 9.03 (s, 1H), 7.85 (d, 2H, J=9 Hz), 7.75 (d, 2H, J=9 Hz), 7.37 (m, 2H), 7.27 (m, 5H), 6.93 (m, 3H), 4.66 (m, 2H), 4.19 (m, 4H), 3.37 (m, 2H), 3.00 (m, 4H), 2.69 (s, 6H), 1.88 (m, 2H). IR (KBr, cm$^{-1}$) 3435, 1723, 1653, 1599, 1524, 1498, 1234, 838, 703. MS (ES$^+$) 546. MS (ES$^-$) m/e 544. Anal. Calcd for C$_{32}$H$_{37}$N$_5$O$_7$S C, 60.46; H, 5.87; N, 11.02. Found C, 60.14; H, 5.60; N, 10.60. Analytical HPLC 99% purity. MP softening at 117° C. then 159–164° C.

Example 116

Preparation of 4-[5-(2-phenoxy-ethylsulfanylmethyl)-[1,3,4]oxadiazol-2-yl]-phenylamine

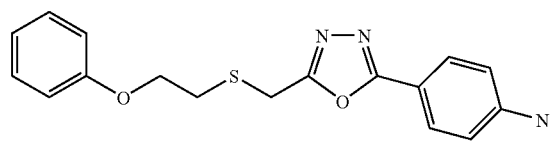

a) 4-Amino-benzoic acid hydrazide

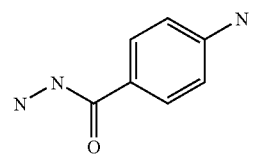

A solution of methyl 4-aminobenzoate (10 g, 66.15 mmol, 1 eq.) and hydrazine hydrate (40 mL) in absolute ethanol (120 mL) was allowed to reflux for 16 h. The solvent was removed in vacuo and the resulting off-white solid was triturated with hot ethyl acetate. The solid was collected by filtration to afford 9.1 g (91%) of 4-amino-benzoic acid hydrazide as an off-white solid.

$^1$H NMR (DMSO-d6) δ 9.25 (s, 1H), 7.53 (d, 2H, J=9 Hz), 6.52 (d, 2H, J=9 Hz), 5.56 (s, 2H), 4.32 (s, 2H). IR (KBr, cm–1) 3428, 3348, 3308, 3233, 1630, 1604, 1504, 1321, 1306, 958, 842. MS (ES+) m/e 152. MS (ES–) m/e 150. Anal. Calcd for C$_7$H$_9$N$_3$O C, 55.62; H, 6.00; N, 27.80. Found C, 55.93; H, 6.21; N, 27.53.

b) 4-Amino-benzoic acid N'-[2-(2-phenoxy-ethylsulfanyl)-acetyl]-hydrazide

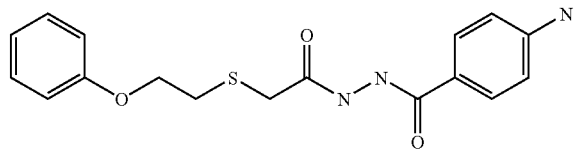

The above compound was prepared in a manner similar to that exemplified. for the preparation of Example 101c, from (2-phenoxyethylthio)acetic acid (4.25 g, 20.0 mmol, 1 eq.) and 4-amino-benzoic acid hydrazide (3.33 g, 22.0 mmol, 1.1 eq.) to afford 5.85 g (85%) of 4-amino-benzoic acid N'-[2-(2-phenoxy-ethylsulfanyl)-acetyl]-hydrazide as a yellow foam following purification by silica gel flash chromatography using a step gradient of acetone in hexane as the mobile phase.

$^1$H NMR (DMSO-d6) δ 9.91 (s, 2H), 7.60 (d, 2H, J=9 Hz), 7.28 (m, 2H), 6.95 (m, 3H), 6.55 (d, 2H, J=9 Hz), 4.19 (t,

2H, J=7 Hz), 3.31 (s, 2H), 3.03 (t, 2H, J=9 Hz). IR (KBr, cm⁻¹) 3450, 3357, 3268, 3214, 1696, 1627, 1611, 1592, 1562, 1482, 1291, 1242, 1173, 837. MS (ES⁺) m/e 346. MS (ES⁻) m/e 344. Anal. Calcd for $C_{17}H_{19}N_3O_3S$ C, 59.11; H, 5.54; N, 12.16. Found C, 59.13; H, 5.79; N, 12.09.

c) 4-[5-(2-Phenoxy-ethylsulfanylmethyl)-[1,3,4]oxadiazol-2-yl]-phenylamine

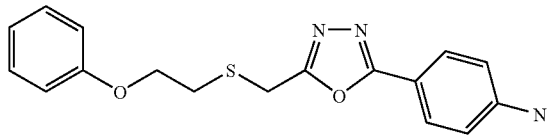

The above compound was prepared in a manner similar to that exemplified for the preparation of Example 101d, from 4-amino-benzoic acid N'-[2-(2-phenoxy-ethylsulfanyl)-acetyl]-hydrazide (11.42 g, 33.06 mmol) to afford 10.77 g (99%) of 4-[5-(2-phenoxy-ethylsulfanylmethyl)-[1,3,4]oxadiazol-2-yl]-phenylamine as a yellow solid following purification by silica gel flash chromatography using a step gradient of ethyl acetate in hexane as the mobile phase.

¹H NMR (DMSO-d6) δ 7.60 (d, 2H, J=9 Hz), 7.27 (m, 2H), 6.93 (m, 3H), 6.66 (d, 2H, J=9 Hz), 5.93 (m, 2H), 4.18 (m, 4H), 3.00 (t, 2H, J=7 Hz). IR (CHCl₃, cm⁻¹) 3011, 1624, 1610, 1501, 1243, 1180. MS (ES+) m/e 328. Anal. Calcd for $C_{17}H_{17}N_3O_2S$ C, 62.37; H, 5.23; N, 12.83. Found C, 61.61; H, 5.12; N, 12.50. Analytical HPLC 97.8% purity. MP 126–130° C.

mmol, 1 eq.) as a solid and stirred at room temperature for 16 h. The solvent was removed in vacuo leaving imidazole-1-carbothioic acid {4-[5-(2-phenoxy-ethylsulfanylmethyl)-[1,3,4]oxadiazol-2-yl]-phenyl}-amide as a brown oil. A portion of one-half of this material (7.96 mmol) was dissolved in anhydrous DMP and treated with N,N-dimethylethylenediamine (0.84 g, 9.55 mmol, 1.2 eq.). The resulting mixture was heated at 100° C. for 1.5 h, cooled, then diluted with EtOAc and washed with 50% brine. The organic layer was collected, dried over MgSO4, filtered, and the solvent removed in vacuo leaving a yellow oil. The residue was purified by preparative HPLC to afford 2.33 g (64%) of 1-(2-dimethylamino-ethyl)-3-{4-[5-(2-phenoxy-ethylsulfanylmethyl)-[1,3,4]oxadiazol-2-yl]-phenyl}-thiourea as a yellow oil which later crystallized. A portion of material was recrystallized from ethyl acetate to afford an off-white solid.

¹H NMR (DMSO-d6) δ 10.06 (s, 1H), 7.84 (m, 5H), 7.27 (m, 2H), 6.93 (m, 3H), 4.20 (m, 4H), 3.56 (m, 2H), 3.02 (t, 2H, J=7 Hz), 2.45 (m, 2H), 2.20 (s, 6H). IR (CHCl₃, cm⁻¹) 3429, 3407, 3007, 2982, 2956, 2829, 2781, 1731, 1614, 1601, 1497, 1337, 1243, 1173. MS (ES⁺) m/e 458. MS (ES⁻) m/e 456 Anal. Calcd for $C_{22}H_{27}N_5O_2S_2$ C, 57.74; H, 5.95; N, 15.30. Found C, 57.60; H, 5.88; N, 14.89. Analytical HPLC 96.9% purity. MP 155–158° C.

Example 118

Preparation of 1-(3-dimethylamino-propyl)-3-{4-[5-(2-phenoxy-ethylsulfanylmethyl)-[1,3,4]oxadiazol-2-yl]-phenyl}-thiourea

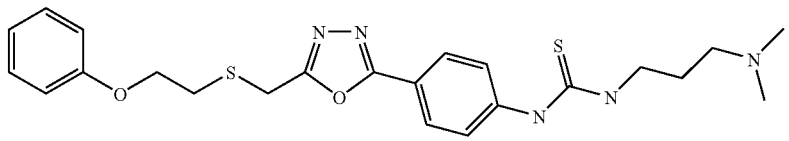

Example 117

Preparation of 1-(2-dimethylamino-ethyl)-3-{4-[5-(2-phenoxy-ethylsulfanylmethyl)-[1,3,4]oxadiazol-2-yl]-phenyl}-thiourea

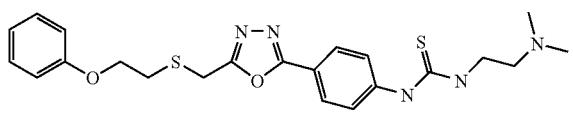

A solution of 4-[5-(2-Phenoxy-ethylsulfanylmethyl)-[1,3,4]oxadiazol-2-yl]-phenylamine (5.21 g, 15.92 mmol, 1 eq., prepared in Example 119) in anhydrous acetonitrile was treated with 1,1'-thiocarbonyldiimidazole (3.15 g, 15.92

The above compound was prepared in a manner similar to that exemplified for the preparation of Example 117, from {4-[5-(2-phenoxy-ethylsulfanylmethyl)-[1,3,4]oxadiazol-2-yl]-phenyl}-amide (7.96 mmol, 1 eq) and 3-dimethylaminopropylamine (0.98 g, 9.55 mmol, 1.2 eq.) to afford 2.87 g (77%) of 1-(3-dimethylamino-propyl)-3-{4-[5-(2-phenoxy-ethylsulfanylmethyl)-[1,3,4]oxadiazol-2-yl]-phenyl}-thiourea as a yellow oil which started to crystallize following purification by preparative HPLC. A small portion was recrystallized from ethyl acetate giving an off-white solid.

¹H NMR (DMSO-d6) δ 9.86 (s, 1H), 8.25 (s, 1H), 7.89 (d, 2H, J=9 Hz), 7.70 (d, 2H, J=9 Hz), 7.27 (m, 2H), 6.93 (m, 3H), 4.20 (m, 4H), 3.50 (m, 2H), 3.02 (t, 2H, J=7 Hz), 2.21 (t, 2H, J=7 Hz), 2.10 (s, 6H), 1.68 (m, 2H). IR (CHCl₃, cm⁻¹) 3411, 2980, 2952, 2862, 2827, 2787, 1615, 1601, 1588, 1532, 1499, 1469, 1307, 1242. MS (ES⁺) m/e 472. MS (ES⁻) m/e 470. Anal. Calcd for $C_{23}H_{29}N_5O_2S_2$ C, 58.57; H, 6.20; N, 14.85. Found C, 59.11; H, 6.49; N, 14.85. Analytical HPLC 97.9% purity. MP 136–139° C.

Example 119

Preparation of N-(2-dimethylamino-ethyl)-N'-{4-[5-(2-phenoxy-ethylsulfanylmethyl)-[1,3,4]oxadiazol-2-yl]-phenyl}-cyanoguanidine oxalate

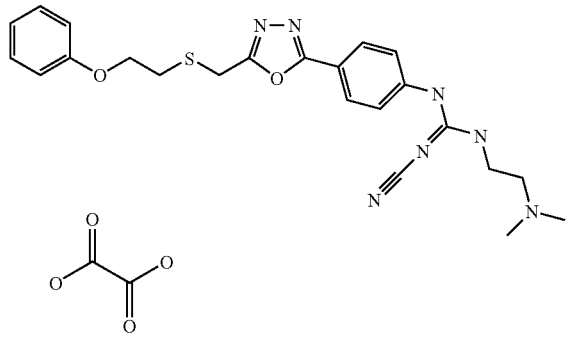

Diphenyl cyanocarbonimidate (1.53 g, 6.42 mmol, 1.05 eq.) was added to a yellow solution of 4-[5-(2-Phenoxy-ethylsulfanylmethyl)-[1,3,4]oxadiazol-2-yl]-phenylamine (2.0 g, 6.11 mmol, 1 eq., prepared in Example 116) in 50 mL of anhydrous acetonitrile. The resultant solution heated at reflux for 16 h. The solvent was removed in vacuo to afford a yellow oil that solidified on standing. The solid was triturated with diethyl ether to afford the corresponding carbamimidic acid phenyl ester (1.78 g, 62% yield) as a yellow solid (MS for carbamimidic acid phenyl ester (ES⁻) m/e 470). N,N-dimethylethylenediamine (1.87 g, 21.2 mmol, 20 eq.) was added to a solution of this carbamimidic acid phenyl ester (0.50 g, 1.06 mmol, 1 eq.) in isopropanol, then heated to reflux. After 5 h, the reaction was cooled, diluted with ethyl acetate, and washed with aqueous sodium bicarbonate. The organic layer was collected, dried over MgSO4, filtered, and the solvent removed in vacuo to afford an orange oil. The oil was purified by silica gel flash chromatography using 10% 2M NH3 in methanol in diethyl ether as the mobile phase to afford 0.14 g (29%) of N-(2-dimethylamino-ethyl)-N-{4-[5-(2-phenoxy-ethylsulfanylmethyl)-[1,3,4]oxadiazol-2-yl]-phenyl}-cyanoguanidine as an off-white solid. The free base was converted to the oxalate salt by adding 1.1 eq. of oxalic acid (0.03 g) in acetone to an acetone solution of the base to afford 0.13 g of N-(2-dimethylamino-ethyl)-N'-{4-[5-(2-phenoxy-ethylsulfanylmethyl)-[1,3,4]oxadiazol-2-yl]-phenyl}-cyanoguanidine oxalate as a tan solid.

$^1$H NMR (DMSO-d6) δ 10.04 (s, 1H), 7.93 (m, 3H), 7.48 (d, 2H, J=9 Hz), 7.27 (m, 2H), 6.93 (m, 3H), 4.19 (m, 4H), 3.02 (m, 4H), 2.81 (t, 2H, J=7 Hz), 2.73 (s, 6H). IR (KBr, cm⁻¹) 3404, 3302, 3040, 2174, 1720, 1618, 1598, 1562, 1500, 1461, 1243, 1010. MS (ES⁺) m/e 466. MS (ES⁻) m/e 464. Anal. Calcd for $C_{25}H_{29}N_7O_6S$ C, 54.04; H, 5.26; N, 17.65. Found C, 51.71; H, 5.70; N, 14.23. Analytical HPLC 95.7% purity. MP softening at 138° C. then decomposition at 145–147° C.

Example 120

Preparation of N-(3-dimethylamino-propyl)-N'-{4-[5-(2-phenoxy-ethylsulfanylmethyl)-[1,3,4]oxadiazol-2-yl]-phenyl}-cyanoguanidine oxalate

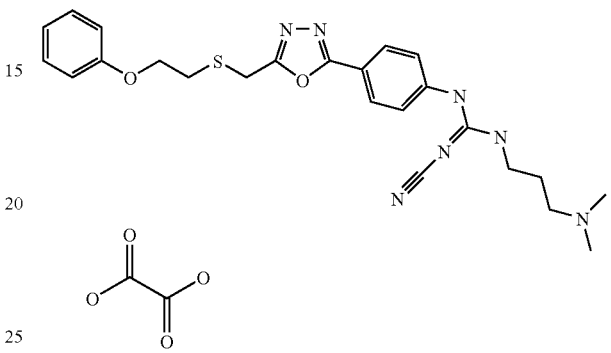

The above compound was prepared in a manner similar to that exemplified for the preparation of Example 119, from the carbamimidic acid phenyl ester (1.2 g, 2.54 mmol, 1 eq.) and 3-dimethylaminopropylamine (5.19 g, 50.8 mmol, 20 eq.) to afford 0.22 g (18%) of N-(3-dimethylamino-propyl)-N'-{4-[5-(2-phenoxy-ethylsulfanylmethyl)-[1,3,4]oxadiazol-2-yl]-phenyl}-cyanoguanidine as an off-white solid. The free base was converted to the oxalate salt as described to afford 0.20 g of N-(3-dimethylamino-propyl)-N'-{4-[5-(2-phenoxy-ethylsulfanylmethyl)-[1,3,4]oxadiazol-2-yl]-phenyl}-cyanoguanidine oxalate as a white solid.

$^1$H NMR (DMSO-d6) δ 9.78 (s, 1H), 7.92 (m, 3H), 7.47 (d, 2H, J=9 Hz), 7.28 (m, 2H), 6.93 (m, 3H), 4.20 (m, 4H), 3.33 (m, 2H), 3.02 (m, 4H), 2.73 (s, 6H), 1.88 (m, 2H). IR (KBr, cm⁻¹) 3316, 3255, 2171, 1720, 1600, 1500, 1237, 755,720. MS (ES⁺) m/e 480. MS (ES⁻) m/e 478. Anal. Calcd for $C_{26}H_{31}N_7O_6S$ C, 54.82; H, 5.49; N, 17.21. Found C, 53.91; H, 5.43; N, 16.76. Analytical HPLC 100% purity. MP softening at 110° C. then decomposition from 130–134° C.

Example 121

Preparation of 2-piperidin-1-yl-ethanesulfonic acid {4-[5-(2-phenoxy-ethylsulfanylmethyl)-[1,3,4]oxadiazol-2-yl]-phenyl}-amide oxalate

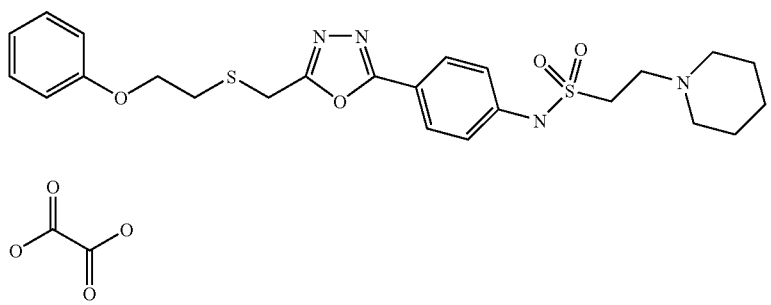

a) Preparation of 2-chloro-ethanesulfonic acid {4-[5-(2-phenoxy-ethylsulfanylmethyl)-[1,3,4]oxadiazol-2-yl]-phenyl}-amide

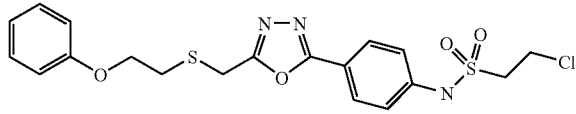

A solution of 4-[5-(2-Phenoxy-ethylsulfanylmethyl)-[1,3,4]oxadiazol-2-yl]-phenylamine (3.0 g, 9.16 mmol, 1 eq.) in anhydrous CH$_2$Cl$_2$ was treated with triethylamine (1.39 g, 13.74 mmol, 1.5 eq.) and 2-chloro-1-ethanesulfonyl chloride (1.79 g, 10.99 mmol, 1.2 eq.). The reaction was allowed to stir at room temperature for 16 h, then was quenched with water and the organic layer removed. The aqueous layer was extracted with CH$_2$Cl$_2$. The combined organic layers were washed with brine, dried over MgSO4, filtered, and concentrated to afford an orange oil. The oil was purified by silica gel flash chromatography using a step gradient of ethyl acetate in hexane as the mobile phase to afford 0.97 g (23%) of 2-chloro-ethanesulfonic acid {4-[5-(2-phenoxy-ethylsulfanylmethyl)-[1,3,4]oxadiazol-2-yl]-phenyl}-amide as an off-white solid.

$^1$H NMR (DMSO-d6) δ 8.06 (d, 2H, J=8 Hz), 7.57 (d, 2H, J=9 Hz), 7.28 (m, 3H), 6.91 (m, 3H), 6.44 and 6.41 (m, 2H total), 6.32 and 6.27 (m, 2H total), 4.25 (s, 2H), 4.18 (t, 2H, J=7 Hz), 3.03 (t, 2H, J=7 Hz). IR (CHCl$_3$, cm$^{-1}$) 1602, 1491, 1384, 1217, 1163, 916. MS (ES$^-$) m/e 416 [M-Cl]$^-$. Anal. Calcd for C$_{19}$H$_{20}$ClN$_3$O$_4$S C, 4.44; N, 9.26. Found C, 49.71; H, 4.15; N, 8.27.

b) Preparation of 2-piperidin-1-yl-ethanesulfonic acid {4-[5-(2-phenoxy-ethylsulfanylmethyl)-[1,3,4]oxadiazol-2-yl]-phenyl}-amide oxalate

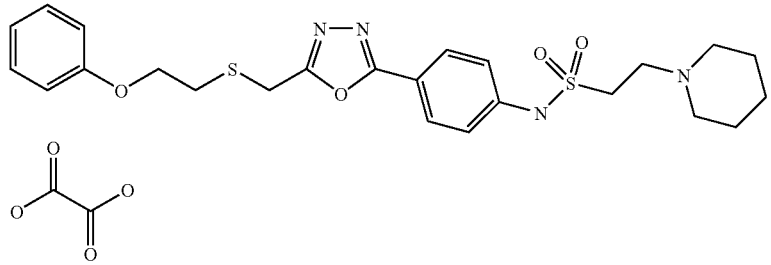

2-Chloro-ethanesulfonic acid {4-[5-(2-phenoxy-ethylsulfanylmethyl)-[1,3,4]oxadiazol-2-yl]-phenyl}-amide (0.91 g, 2.0 mmol, 1 eq.) in anhydrous DMF was treated with sodium bicarbonate (0.50 g, 6.0 mmol, 3 eq.) and sodium iodide (0.03 g, 0.2 mmol, 0.1 eq.) followed by piperidine (0.51 g, 6.0 mmol, 3 eq.). The reaction was then heated to 90° C. and allowed to stir at that temperature for 16 h. The reaction was diluted with water and extracted with ethyl acetate. The combined organic layers were washed with water and brine, dried over MgSO4, filtered, and the solvent removed in vacuo leaving an orange oil which was purified by silica gel flash chromatography using 10% 2M NH3 in methanol in diethyl ether as the mobile phase to afford 0.95 g (94%) of 2-piperidin-1-yl-ethanesulfonic acid {4-[5-(2-phenoxy-ethylsulfanylmethyl)-[1,3,4]oxadiazol-2-yl]-phenyl}-amide as a yellow oil. The free base was converted to the oxalate salt by adding 1.1 eq. of oxalic acid (0.19 g) in acetone dropwise to an acetone solution of the free base. The resulting white precipitate was collected by filtration and crystallized from methanol to afford 0.48 g of 2-piperidin-1-yl-ethanesulfonic acid {4-[5-(2-phenoxy-ethylsulfanylmethyl)-[1,3,4]oxadiazol-2-yl]-phenyl}-amide oxalate as a crystalline white solid.

$^1$H NMR (DMSO-d6) δ 7.93 (d, 2H, J=9 Hz), 7.39 (d, 2H, J=9 Hz), 7.27 (m, 2H), 6.93 (m, 3H), 4.19 (m, 4H), 3.62 (m, 2H), 3.14 (m, 2H), 3.02 (t, 2H, J=7 Hz), 2.82 (m, 4H), 1.57 (m, 4H), 1.41 (m, 2H). IR (KBr, cm-1) 3409, 1617, 1344, 1243, 1159, 916, 759, 705. MS (ES$^+$) m/e 503. MS (ES$^-$) m/e 501. Anal. Calcd for C$_{26}$H$_{32}$N$_4$O$_8$S$_2$ C, 52.69; H, 5.44; N, 9.45. Found C, 52.44; H, 5.46; N, 9.37. Analytical HPLC 99.6% purity. MP softening at 159° C. then 162–166° C.

Example 122

Preparation of 2-{[(2-phenoxyethyl)thio]methyl}-5-{4-[((2-(N-methylpyrrolidin-2-yl)ethyl)amino)carbonyl]phenyl}-1,3,4-oxadiazole

a) 2-{[(2-Phenoxyethyl)thio]methyl}-5-[4-(methoxycarbonyl)phenyl]-1,3,4-oxadiazole

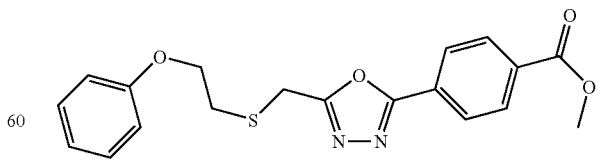

A solution of 2-[(2-phenoxyethyl)thio]acetic acid hydrazide hydrochloride (3.15 g, 12 mmol), triethylamine (4.2 mL, 30 mmol) and terephthalic acid monomethyl ester chloride (1.99 g, 10 mmol) in methylene chloride (100 mL) was stirred at room temperature for 3 h. After filtering the solids, the filtrate was concentrated. The residue was recrystallized from ethanol to yield a pale yellow solid (1.31 g, 3.37 mmol). This solid, 4-(dimethylamino)phenyldiphenylphosphine (2.06 g, 6.74 mmol), triethylamine (1.4 mL, 10 mmol) and carbon tetrachloride (1.6 mL, 16.6 mmol) were stirred in acetonitrile (75 mL) at room temperature for 18 h. The product was filtered from the reaction mixture, washed with acetonitrile (50 mL) and dried to yield 1.13 g (30%) of a pale yellow solid, which was used without further purification.

$^1$H NMR (CDCl$_3$) δ 8.14 (d, 2H, J=9 Hz), 8.06 (d, 2H, J=9 Hz), 7.23 (m, 2H), 6.92 (dd, 1H, J=7 and 8 Hz), 6.86 (d, 2H, J=8 Hz), 4.19 (t, 2H, J=12 Hz), 4.05 (s, 2H), 3.93 (s, 3H), 3.03 (t, 2H, J=12 Hz). MS (ES+) m/e 371 (M+1).

b) 2-{[(2-Phenoxyethyl)thio]methyl}-5-[4-(hydroxycarbonyl)phenyl]-1,3,4-oxadiazole

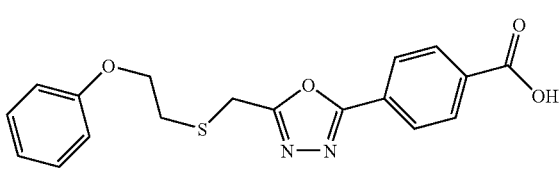

A mixture of 2-{[(2-phenoxyethyl)thio]methyl}-5-[4-(methoxycarbonyl)phenyl]-1,3,4-oxadiazole (1.13 g, 3.0 mmol) and 2N aqueous NaOH (4.5 mL, 9.0 mmol) in THF (20 mL) was stirred at room temperature for 16 h. The mixture was diluted with water (30 mL) and extracted with ethyl ether (50 mL). The aqueous material was acidified with 2N HCl to a pH of 5, then extracted with ethyl ether (3×30 mL). The organic material was dried (MgSO$_4$), filtered and concentrated to yield 803 mg (74%) of a pale yellow solid.

$^1$H NMR (CDCl$_3$) δ 8.20 (d, 2H, J=8 Hz), 8.12 (d, 2H, J=8 Hz), 7.25 (m, 2H), 6.93 (dd, 1H, J=7 and 8 Hz), 6.87 (d, 2H, J=8 Hz), 4.20 (t, 2H, J=12 Hz), 4.08 (s, 2H), 3.05 (t, 2H, J=12 Hz). MS (ES−) m/e 355 (M−1).

c) 2-{[(2-Phenoxyethyl)thio]methyl}-5-{4-[((2-(N-methylpyrrolidin-2-yl)ethyl)amino)carbonyl]phenyl}-1,3,4-oxadiazole

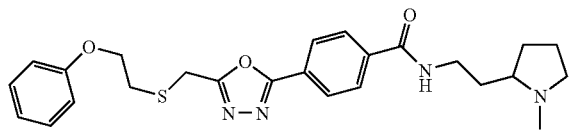

A solution of 2-{[(2-phenoxyethyl)thio]methyl}-5-[4-(hydroxycarbonyl)phenyl]-1,3,4-oxadiazole (300 mg, 0.84 mmol), 2-(2-aminoethyl)-1-methylpyrrolidine (0.18 mL, 1.24 mmol), 1-[3-(dimethylamino)propyl]-3-ethylcarbodiimide hydrochloride (242 mg, 1.26 mmol) and 1-hydroxybenzo-triazole (171 mg, 1.26 mmol) in N,N-dimethylformamide (10 mL) was stirred at room temperature for 16 h. The mixture was diluted with ethyl acetate (50 mL) and extracted with saturated aqueous lithium chloride (2×25 mL), dried (MgSO$_4$), filtered and concentrated to yield 700 mg of a yellow oil. This oil was purified by preparative TLC [90% methylend chloride-5% methanol-5% (2.0 N ammonia in methanol)] to yield 146 mg (37%) of a white solid.

$^1$H NMR (CDCl$_3$) δ 8.75 (br s, 1H), 8.07 (d, 2H, J=8 Hz), 7.88 (d, 2H, J=8 Hz), 7.24 (m, 2H), 6.93 (dd, 1H, J=7 and 8 Hz), 6.87 (d, 2H, J=8 Hz), 4.19 (t, 2H, J=12 Hz), 4.05 (s, 2H), 3.77 (m, 1H), 3.47 (m, 1H), 3.15 (m, 1H), 3.04 (t, 2H, J=12 Hz), 2.57 (m, 1H), 2.40 (s, 3H), 2.31 (m, 1H), 1.90 (m, 2H), 1.75 (m, 4H). IR (film, cm$^{-1}$) 3432, 3335, 2943, 2868, 2778, 2359, 1641, 1584, 1547, 1493, 1456, 1302, 1244, 1082, 1021, 863, 753, 694, 654. MS (ES+) m/e 467 (M+1). Anal. Calcd for C$_{31}$H$_{33}$N$_3$O$_2$S: C, 64.35; H, 6.48; N, 12.01; S, 6.87. Found C, 64.42; H, 6.19; N, 12.45; S, 6.80.

Example 123

Preparation of 2-{[(2-phenoxyethyl)thio]methyl}-5-{4-[((2-piperidinoethyl)amino)carbonyl]phenyl}-1,3,4-oxadiazole

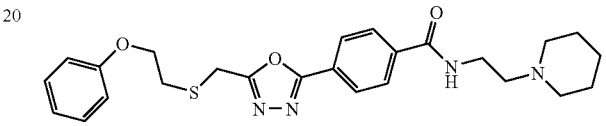

This compound was synthesized similarly to 2-{[(2-Phenoxyethyl)thio]methyl}-5-{4-[((2-(N-methyl pyrrolidin-2-yl)ethyl)amino)carbonyl]phenyl}-1,3,4-oxadiazole using 1-(2-aminoethyl)piperidine (0.12 mL).

$^1$H NMR (CDCl$_3$) δ 8.08 (d, 2H, J=9 Hz), 7.89 (d, 2H, J=9 Hz), 7.24 (m, 2H), 7.15 (br s, 1H), 6.93 (dd, 1H, J=7 and 8 Hz), 6.87 (d, 2H, J=9 Hz), 4.20 (t, 2H, J=12 Hz), 4.06 (s, 2H), 3.53 (dd, 2H, J=6 and 11 Hz), 3.04 (t, 2H, J=12 Hz), 2.57 (dd, 2H, J=6 and 11 Hz), 2.44 (m, 4H), 1.60 (m, 4H), 1.47 (m, 2H). IR (film, cm$^{-1}$) 3313, 2938, 2885, 2851, 2778, 1635, 1552, 1493, 1296, 1239, 1024, 747. MS (ES+) m/e 467 (+1). Anal. Calcd for C$_{25}$H$_{30}$N$_4$O$_3$S: C, 64.35; H, 6.48; N, 12.01; S, 6.87. Found C, 64.02; H, 6.41; N, 12.00; S, 7.02.

Example 124

Preparation of 2-{[(2-phenoxyethyl)thio]methyl}-5-{4-[(N',N'-dimethyl-1,3-propanediamino)carbonyl]phenyl}-1,3,4-oxadiazole

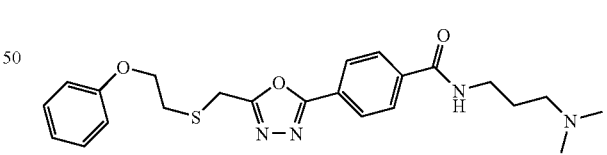

This compound was synthesized similarly to 2-{[(2-Phenoxyethyl)thio]methyl}-5-{4-[((2-(N-methylpyrrolidin-2-yl)ethyl)amino)carbonyl]phenyl}-1,3,4-oxadiazole using 3-(dimethylamino)propylamine (0.11 mL).

$^1$H NMR (CDCl$_3$) δ 8.81 (br s, 1H), 8.07 (d, 2H, J=8 Hz), 7.87 (d, 2H, J=8 Hz), 7.24 (m, 2H), 6.93 (dd, 1H, J=7 and 8 Hz), 6.87 (d, 2H, J=8 Hz), 4.20 (t, 2H, J=12 Hz), 4.05 (s, 2H), 3.58 (dd, 2H, J=6 and 11 Hz), 3.04 (t, 2H, J=12 Hz), 2.54 (dd, 2H, J=6 and 11 Hz), 2.30 (s, 6H), 1.77 (m, 2H). IR (film, cm$^{-1}$) 3431, 3345, 2943, 2867, 2810, 2762, 1641, 1581, 1542, 1494, 1466, 1300, 1246, 1178, 1082, 1026, 750, 693, 651. MS (ES+) m/e 441 (M+1). Anal. Calcd for $C_{23}H_{28}N_4O_3S$: C, 62.70; H, 6.41; N, 12.72; S, 7.28. Found C, 62.13; H, 6.32; N, 12.63; S, 6.99.

Example 125

Preparation of 2-{[(2-Phenoxyethyl)thio]methyl}-5-{4-[5-(N,N-dimethylamino)penten-1-yl]phenyl}-1,3,4-oxadiazole, (E)- and (Z)-isomers

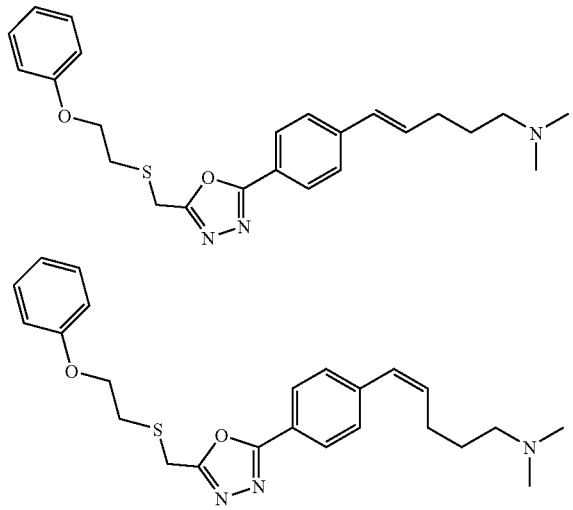

a) Methyl 4-(5-bromopenten-1-yl)benzoate

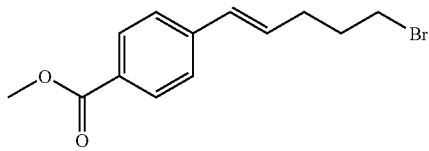

A mixture of methyl 4-formylbenzoate (9.85 g, 60 mmol), 4-bromobutyltriphenylphosphonium bromide (31.56 g, 66 mmol), powdered NaOH (3 g, 75 mmol), and 12 drops of water in methylene chloride (150 mL) was stirred under reflux for 4 h. The mixture was allowed to cool to room temperature and filtered. The filtrate was concentrated and chromatographed on a silica gel column, eluted with ethyl acetate/hexanes 1:50 to 1:30, to give the Z-isomer (colorless oil, 3.68 g, 22%), a mixture of Z- and E-isomers (colorless oil, 2.69 g, 16%), and the E-isomer (white solid, 2.97 g, 17%).

E-isomer: $^1$H NMR (CDCl$_3$) δ 7.94 (d, 2H, J=8.5 Hz), 7.37 (d, 2H, J=8.4 Hz), 6.46 (d, 1H, J=15.8 Hz), 6.28 (dt, 1H, J=15.8, 7.0 Hz), 3.88 (s, 3H), 3.44 (t, 2H, J=6.6 Hz), 2.39 (q, 2H, J=7.0 Hz), 2.03 (quint, 2H 6.6 Hz). MS (ES+) m/e 284 (M+1). Z-isomer: $^1$H NMR (CDCl$_3$) δ 7.98 (d, 2H, J=8.1 Hz), 7.31 (d, 2H, J=8.4 Hz), 6.48 (d, 1H, J=11.7 Hz), 5.70 (dt, 1H, J=11.7, 7.3 Hz), 3.89 (s, 3H), 3.39 (t, 2H, J=6.8 Hz), 2.47 (q, 2H, J=7.3 Hz), 1.99 (quint, 2H, 6.9 Hz). MS (ES+) m/e 284 (M+1).

b) 4-(5-bromopenten-1-yl)benzoic acid

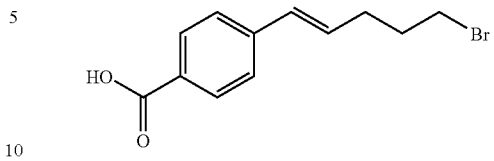

Methyl 4-(5-bromopenten-1-yl)benzoate (1.415 g, 5 mmol) was dissolved in 1,4-dioxane (25 mL) and 2 N NaOH (25 mL, 50 mmol) was added. The mixture was stirred at room temperature for 5 h, cooled in an ice bath, acidified with conc. HCl, and extracted with ether (3×25 mL). The combined ether extracts were dried (MgSO$_4$) and concentrated to give a white solid (1.264, 94%).

E-isomer: $^1$H NMR (CDCl$_3$) δ 8.05 (d, 2H, J=7.7 Hz), 7.43 (d, 2H, J=8.5 Hz), 6.51 (d, 1H, J=16.3 Hz), 6.34 (dt, 1H, J=16.3, 6.9 Hz), 3.47 (t, 2H, J=6.9 Hz), 2.43 (q, 2H, J=6.9 Hz), 2.07 (quint, 2H, 6.8 Hz). MS (ES−) m/e 268 (M−1).

c) 2-{[(2-Phenoxyethyl)thio]methyl}-5-[4-(5-bromopenten-1-yl)phenyl]-1,3,4-oxadiazole

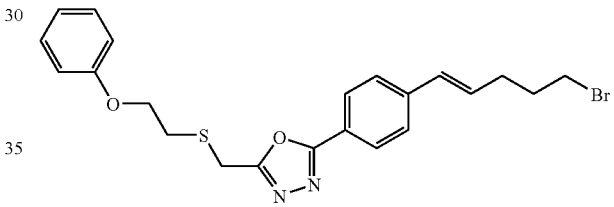

A stirred mixture of 4(5-bromopenten-1-yl)benzoic acid (1.264 g, 4.7 mmol), 2-(2-phenoxyethyl)thioacetylhydrazide hydrochloride (1.314 g, 5 mmol), and 4-(N,N-dimethylamino)phenyldiphenylphosphine (4.58 g, 15 mmol) in acetonitrile (50 mL) was cooled in ice bath and triethylamine (3.04 g, 30 mmol) in carbon tetrachloride (3.85 g, 25 mmol) was added dropwise. The cooling bath was removed after 10 min and stirring was continued for 5 h. The mixture was concentrated to approximately half the original volume and partitioned between ether (150 mL) and 2 N HCl (150 mL). The ether layer was washed with 2 N HCl (4×50 mL), dried (MgSO$_4$), and concentrated. The residue was purified by chromatography (SiO$_2$, ethyl acetate/hexanes 1:5) to give a white solid (1.43 g, 66%).

E-isomer: $^1$H NMR (CDCl$_3$) δ 7.96 (d, 2H, J=8.5 Hz), 7.45 (d, 2H, J=8.5 Hz), 7.27 (m, 2H), 6.96 (t, 1H, J=7.7 Hz), 6.90 (d, 2H, J=8.5 Hz), 6.50 (d, 1H, J=16.2 Hz), 6.32 (dt, 1H, J=16.2, 6.9 Hz), 4.22 (t, 2H, J=6.0 Hz), 4.06 (s, 2H), 3.47 (t, 2H, J=6.9 Hz), 3.06 (t, 2H, J=6.0 Hz), 2.43 (q, 2H, J=6.9 Hz), 2.07 (quint, 2H, 6.9 Hz). MS (ES+) m/e 460 (M+1).

Z-isomer: $^1$H NMR (CDCl$_3$) δ 7.97 (d, 2H, J=8.5 Hz), 7.37 (d, 2H, J=8.5 Hz), 7.22~7.26 (m, 2H), 6.93 (t, 1H, J=7.3 Hz), 6.87 (d, 2H, J=7.7 Hz), 6.48 (d, 1H, J=11.8 Hz), 5.72 (dt, 1H, J=11.7, 7.3 Hz), 4.19 (t, 2H, J=6.2 Hz), 4.04 (s, 2H), 3.41 (t, 2H, J=6.6 Hz), 3.04 (t, 2H, J=6.2 Hz), 2.49 (q, 2H, J=7.3 Hz), 2.01 (quint, 2H, 7.0 Hz). MS (ES+) m/e 460 (M+1).

d) 2-{[(2-Phenoxyethyl)thio]methyl}-5-{4-[5-(N,N-dimethylamino)penten-1-yl]phenyl}-1,3,4-oxadiazole

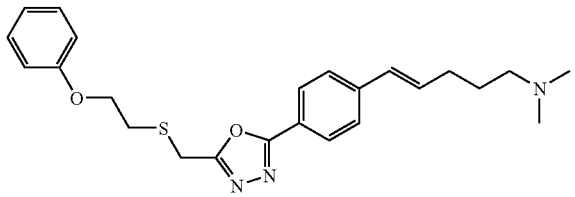

A mixture of 2-{[(2-phenoxyethyl)thio]methyl}-5-[4-(5-bromopenten-1-yl)phenyl]-1,3,4-oxadiazole (300 mg, 0.65 mmol), 2 N dimethylamine in tetrahydrofuran (1.7 mL, 3.4 mmol), and potassium carbonate (903 mg, 6.5 mmol) in acetonitrile (5 mL) was stirred at room temperature for 24 h, diluted with methylene chloride (25 mL) and filtered. The filtrate was concentrated and purified by chromatography (silica gel, methanol/methylene chloride 2% to 10%) to give a white solid (263 mg, 96%).

E-isomer: $^1$H NMR (CDCl$_3$) δ 7.93 (d, 2H, J=8.5 Hz), 7.42 (d, 2H, J=8.4 Hz), 7.22~7.27 (m, 2H), 6.93 (t, 1H, J=7.3 Hz), 6.87 (d, 2H, J=7.7 Hz), 6.42 (d, 1H, J=16.1 Hz), 6.34 (dt, 1H, J=15.7, 6.4 Hz), 4.19 (t, 2H, J=6.2 Hz), 4.03 (s, 2H), 3.03 (t, 2H, J=6.2 Hz), 2.40 (m, 2H), 2.30 (s, 6H), 2.27 (m, 2H), 1.71 (quint, 2×17.3 Hz). IR (KBr, cm$^{-1}$) 3074, 3056, 3038, 2955, 2924, 2856, 1602, 1495, 1237, 1168, 751. MS (ES+) m/e 424 (M+1). Anal. Calcd for C$_{24}$H$_{29}$N$_3$O$_2$S: C, 68.05; H, 6.90; N, 9.92; S, 7.57. Found C, 68.16; H, 6.99; N, 10.23; S, 7.66.

Z-isomer: $^1$H NMR (CDCl$_3$) δ 7.96 (d, 2H, J=8.4 Hz), 7.37 (d, 2H, J=8.4 Hz), 7.22~7.26 (m, 2H), 6.92 (t, 1H, J=7.3 Hz), 6.87 (d, 2H, J=8.0 Hz), 6.44 (d, 1H, J=11.8 Hz), 5.75 (dt, 1H, J=11.4, 7.3 Hz), 4.19 (t, 2H, J=6.2 Hz), 4.03 (s, 2H), 3.04 (t, 2H, J=6.2 Hz), 2.32~2.39 (m, 4H), 2.29 (s, 6H), 1.69 (quint, 2H, 7.3 Hz). IR (KBr, cm$^{-1}$) 3029, 2940, 2863, 2844, 2649, 1598, 1505, 1246, 1174, 752. MS (ES+) m/e 424 (M+1). Anal. Calcd for C$_{24}$H$_{29}$N$_3$O$_2$S: C, 68.05; H, 6.90; N, 9.92; S, 7.57. Found C, 68.45; H, 6.44; N, 10.37; S, 7.41.

Example 126

Preparation of 2-{[(2-Phenoxyethyl)thio]methyl}-5-[4-(5-pyrrolidinopenten-1-yl)phenyl]-1,3,4-oxadiazole

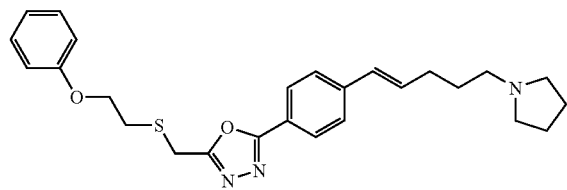

A mixture of 2-{[(2-phenoxyethyl)thio]methyl}-5-[4-(5-bromopenten-1-yl)phenyl]-1,3,4-oxadiazole (150 mg, 0.33 mmol), pyrrolidine (118 mg, 1.65 mmol), and potassium carbonate (457 mg, 3.3 mmol) in acetonitrile (3.5 mL) was stirred at room temperature for 24 h, diluted with methylene chloride (15 mL), filtered, dried (MgSO$_4$), and concentrated. The residue was purified by preparative TLC (silica gel, 10% methanol/methylene chloride) to give a yellow oil (129 mg, 87%).

$^1$H NMR (CDCl$_3$) δ 7.92 (d, 2H, J=8.4 Hz), 7.42 (d, 2H, J=8.4 Hz), 7.22~7.26 (m, 2H), 6.93 (t, 1H, J=7.7 Hz), 6.87 (d, 2H, J=7.7 Hz), 6.41 (d, 1H, J=15.7 Hz), 6.36 (dt, 1H, J=15.7, 6.5 Hz), 4.19 (t, 2H, J=6.2 Hz), 4.03 (s, 2H), 3.03 (t, 2H, J=6.2 Hz), 2.46~2.50 (m, 6H), 2.27 (q, 2H, J=6.9 Hz), 1.67~1.80 (m, 6H). IR (film, cm$^{-1}$) 3070, 3024, 2968, 2841, 2793, 1598, 1506, 1337, 1306, 1229, 1020, 736. MS (ES+) m/e 450 (M+1). Anal. Calcd for C$_{26}$H$_{31}$N$_3$O$_2$S: C, 69.46; H, 6.95; N, 9.35; S, 7.13. Found C, 68.98; H, 7.01; N, 9.73; S, 7.19.

Example 127

Preparation of 2-{[(2-Phenoxyethyl)thio]methyl}-5-[4-(5-piperidinopenten-1-yl)phenyl]-1,3,4-oxadiazole

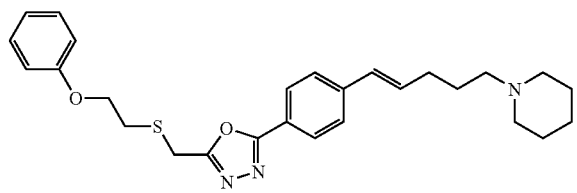

A mixture of 2-{[(2-phenoxyethyl)thio]methyl}-5-[4-(5-bromopenten-1-yl)phenyl]-1,3,4-oxadiazole (150 mg, 0.33 mmol), piperidine (140 mg, 1.65 mmol), and potassium carbonate (458 mg, 3.3 mmol) in acetonitrile (3.5 mL) was stirred at room temperature for 18 h, diluted with methylene chloride (15 mL), filtered, dried (MgSO$_4$), and concentrated. The residue was purified by preparative TLC (silica gel, 10% methanol/methylene chloride) to give yellow oil (136 mg, 89%).

$^1$H NMR (CDCl$_3$) δ 7.92 (d, 2H, J=8.5 Hz), 7.42 (d, 2H, J=8.4 Hz), 7.22~7.26 (m, 2H), 6.93 (t, 1H, J=7.3 Hz), 6.87 (d, 2H, J=8.4 Hz), 6.41 (d, 1H, J=16.1 Hz), 6.34 (dt, 1H, J=16.1, 6.9 Hz), 4.19 (t, 2H, J=6.2 Hz), 4.03 (s, 2H), 3.03 (t, 2H, J=6.2 Hz), 2.38~2.43 (m, 6H), 2.25 (q, 2H, J=6.9 Hz), 1.43~1.74 (m, 8H). R (film, cm$^{-1}$) 3072, 3027, 2945, 2936, 2691, 1600, 1533, 1274, 1196, 1020, 764. MS (ES+) m/e 464 (M+1). Anal. Calcd for C$_{27}$H$_{33}$N$_3$O$_2$S: C, 69.95; H, 7.17; N, 9.06; S, 6.92. Found C, 69.24; H, 7.12; N, 9.68; S, 7.11.

Example 128

Preparation of 2-{[(2-Phenoxyethyl)thio]methyl}-5-{4-[5-(N,N-dimethylamino)pentan-1-yl]phenyl}-1,3,4-oxadiazole

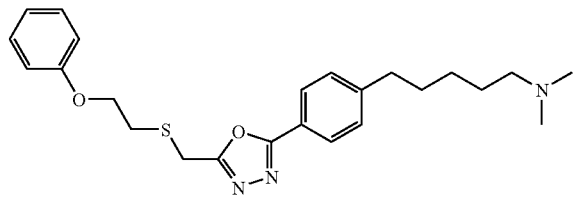

A mixture of (E)- and (Z)-2-{[(2-phenoxyethyl)thio]methyl}-5-{4-[5-(N,N-dimethylamio)penten-1-yl]phenyl}-1,3,4-oxadiazole was made according to the above procedure from 460 mg (1 mmol) of a mixture of (E)- and (Z)-2-{[(2-phenoxyethyl)thio]methyl}-5-[4-(5-bromopenten-1-yl)phenyl]-1,3,4-oxadiazole. Without purification this material was stirred with p-toluenesulfonylhydrazide (2.25 g, 12 mmol) and sodium acetate trihydrate (1.02 g, 7.5 mmol) in tetrahydrofuran (12 mL) and water (12 mL) under reflux for 6 h. 2 N NaOH (20 mL) was added and the mixture was extracted with methylene chloride (2×20 mL). The combined methylene chloride extracts were dried (MgSO$_4$), and concentrated. The residue was purified by column chromatography (silica gel, methanol/methylene chloride 2% to 5% to 10%) to give a colorless oil (333 mg, 78% over two steps).

$^1$H NMR (CDCl$_3$) δ 7.91 (d, 2H, J=8.1 Hz), 7.27 (d, 2H, J=8.4 Hz), 7.22~7.26 (m, 2H), 6.92 (t, 1H, J=7.3 Hz), 6.87 (d, 2H, J=8.5 Hz), 4.18 (t, 2H, J=6.2 Hz), 4.02 (s, 2H), 3.03 (t, 2H, J=6.2 Hz), 2.66 (t, 2H, J=7.7 Hz), 2.24 (t, 2H, J=7.5 Hz), 2.20 (s, 6H), 1.65 (quint, 2H, 7.7 Hz), 1.49 (q, 2H, J=7.5 Hz), 1.34 (q, 2H, J=7.5 Hz). IR (film, cm$^{-1}$) 3034, 3017, 2954, 2883, 2820, 1515, 1357, 1344, 1235, 1137, 1002. MS (ES+) m/e 426 (M+1). Anal. Calcd for C$_{24}$H$_{31}$N$_3$O$_2$S: C, 67.73; H, 7.34; N, 9.87; S, 7.53. Found C, 67.37; H, 7.42; N, 10.06; S, 7.27.

Example 129

Preparation of 2-{[(2-Phenoxyethyl)thio]methyl}-5-{4-[6-(,N-dimethylamino)hexen-1-yl]phenyl}-3-1,3,4-oxadiazole

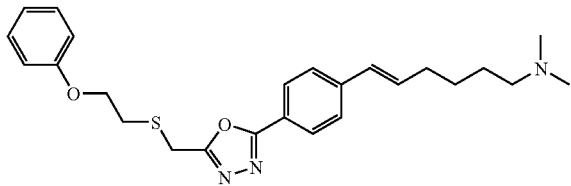

a) 2-{[(2-Phenoxyethyl)thio]methyl}-5-[4-(5-cyanopenten-1-yl)phenyl]-1,3,4-oxadiazole

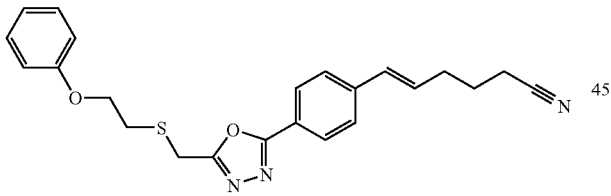

A mixture of 2-{[(2-phenoxyethyl)thio]methyl}-5-[4-(5-bromopenten-1-yl)phenyl]-1,3,4-oxadiazole (460 mg, 1 mmol) and potassium cyanide (195 mg, 3 mmol) in dimethylsulfoxide (6 mL) was stirred at room temperature for 4 h. Water (25 mL) was added and the mixture was extracted with ethyl acetate (3×15 mL). The combined ethyl acetate extracts were washed with water (3×15 mL) and brine (15 mL), dried (MgSO$_4$), and concentrated to give a pale yellow solid (403 mg, 100%).

E-isomer: $^1$H NMR (CDCl$_3$) δ 7.97 (d, 2H, J=7.7 Hz), 7.46 (d, 2H, J=7.7 Hz), 7.28 (m, 2H), 6.96 (t, 1H, J=7.3 Hz), 6.90 (d, 2H, J=7.3 Hz), 6.51 (d, 1H, J=15.4 Hz), 6.29 (dt, 1H, J=15.4, 7.7 Hz), 4.22 (t, 2H, J=6.0 Hz), 4.06 (s, 2H), 3.06 (t, 2H, J=6.0 Hz), 2.41~2.46 (m, 4H), 1.89 (quint, 2H, 6.9 Hz). MS (ES+) m/e 406 (M+1).

Z-isomer: $^1$H NMR (CDCl$_3$) δ 8.01 (d, 2H, J=7.7 Hz), 7.37 (d, 2H, J=8.5 Hz), 7.28 (m, 2H), 6.95 (t, 1H, J=7.7 Hz), 6.90 (d, 2H, J=7.7 Hz), 6.56 (d, 1H, J=1.1 Hz), 5.72 (dt, 1H, J=11.1, 6.8 Hz), 4.22 (t, 2H, J=6.0 Hz), 4.07 (s, 2H), 3.06 (t, 2H, J=6.0 Hz), 2.51 (m, 2H), 2.37 (t, 2H, J=6.8 Hz), 1.85 (m, 2H). MS (ES+) m/e 406 (M+1).

b) 2-{[(2-Phenoxyethyl)thio]methyl}-5-[4-(6-oxohexen-1-yl)phenyl]-1,3,4-oxadiazole

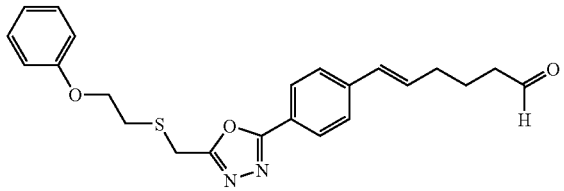

A solution of 2-{[(2-phenoxyethyl)thio]methyl}-5-[4-(5-cyanopenten-1-yl)phenyl]-1,3,4-oxadiazole (400 mg, 1 mmol) in methylene chloride (10 mL) was cooled to −78° C. and 1 M DIBAL-H in hexane (2 mL, 2 mmol) was added dropwise. The mixture was stirred at −78° C. for 2 h, 1 N HCl (20 mL) was added, and the mixture was allowed to warmed to room temperature. The mixture was extracted with methylene chloride (3×10 mL). The combined methylene chloride extracts were dried (MgSO$_4$), concentrated, and purified by chromatography (silica gel, ethyl acetate/hexanes 1:4) to give a white solid (146 mg, 36%).

E-isomer: $^1$H NMR (CDCl$_3$) δ 9.81 (s, 1H), 7.96 (d, 2H, J=7.7 Hz), 7.45 (d, 2H, J=8.6 Hz), 7.28 (m, 2H), 6.96 (t, 1H, J=7.7 Hz), 6.90 (d, 2H, J=7.7 Hz), 6.45 (d, 1H, J=16.3 Hz), 6.33 (dt, 1H, J=16.3, 6.8 Hz), 4.22 (t, 2H, J=6.0 Hz), 4.06 (s, 2H), 3.06 (t, 2H, J=6.0 Hz), 2.53 (t, 2H, J=6.0 Hz), 2.31 (dd, 2H, J=10.8, 7.7 Hz), 1.86 (quint, 2H, 7.7 Hz). MS (ES+) m/e 412 (M+1).

Z-isomer: $^1$H NMR (CDCl$_3$) δ 9.78 (s, 1H), 7.99 (d, 2H, J=8.5 Hz), 7.38 (d, 2H, J=8.6 Hz), 7.26~7.29 (m, 2H), 6.95 (t, 1H, J=7.7 Hz), 6.90 (d, 2H, J=7.7 Hz), 6.49 (d, 1H, J=11.1 Hz), 5.75 (dt, 1H, J=1 1.1, 6.8 Hz), 4.22 (t, 2H, J=6.4 Hz), 4.06 (s, 2H), 3.06 (t, 2H, J=6.0 Hz), 2.48 (t, 2H, J=6.8 Hz), 2.39 (m, 2H), 1.81 (m, 2H). MS (ES+) m/e 412 (M+1).

c) 2-{[(2-Phenoxyethyl)thio]methyl}-5-{4-[6-(N,N-dimethylamino)hexen-1-yl]phenyl}-1,3,4-oxadiazole

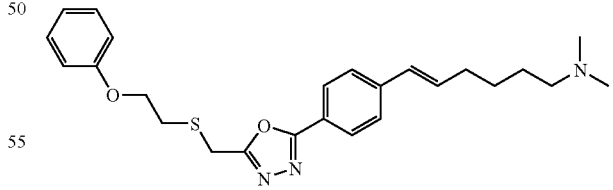

To a stirred mixture of 2-{[(2-phenoxyethyl)thio]methyl}-5-[4-(6-oxohexen-1-yl)phenyl]-1,3,4-oxadiazole (103 mg, 0.25 mmol), 2 M dimethylamine in tetrahydrofuran (0.25 mL, 0.5 mmol), and acetic acid (15 mg, 0.25 mmol) in 1,2-dichloroethane (2 mL) was added sodium triacetoxyborohydride (106 mg, 0.5 mmol) and stirring was continued at room temperature for 2 h. 2N NaOH (10 mL) was added and the mixture was extracted with methylene chloride (3×10 mL). The combined methylene chloride extracts were dried (MgSO4), concentrated, and purified by preparative TLC (silica gel, 10% methanol/methylene chloride) to give a white solid (87 mg, 80%).

E-isomer: $^1$H NMR (CDCl$_3$) δ 7.95 (d, 2H, J=8.6 Hz), 7.44 (d, 2H, J=8.6 Hz), 7.28 (m, 2H), 6.95 (t, 1H, J=7.7 Hz), 6.90 (d, 2H, J=7.7 Hz), 6.43 (d, 1H, J=15.4 Hz), 6.36 (dt, 1H, J=15.4, 6.8 Hz), 4.21 (t, 2H, J=6.4 Hz), 4.05 (s, 2H), 3.06 (t, 2H, J=6.0 Hz), 2.34 (t, 4H, J=6.8 Hz), 2.29 (s, 6H), 2.28 (m, 2H), 1.50~1.59 (m, 4H). IR (KBr, cm$^{-1}$) 3070, 3035, 2954, 2879, 2684, 1599, 1566, 1475, 1339, 1254, 1057, 921, 748. MS (ES+) m/e 438 (M+1). Anal. Calcd for C$_{25}$H$_{31}$N$_3$O$_2$S: C, 68.62; H, 7.14; N, 9.60; S, 7.33. Found C, 68.33; H, 7.21; N, 9.47; S, 7.28.

Z-isomer: $^1$H NMR (CDCl$_3$) δ 7.99 (d, 2H, J=7.7 Hz), 7.39 (d, 2H, J=8.6 Hz), 7.28 (m, 2H), 6.95 (t, 1H, J=7.7 Hz), 6.90 (d, 2H, J=7.7 Hz), 6.45 (d, 1H, J=11.1 Hz), 5.78 (dt, 1H, J=11.1, 7.7 Hz), 4.22 (t, 2H, J=6.4 Hz), 4.06 (s, 2H), 3.06 (t, 2H, J=6.4 Hz), 2.37 (m, 2H), 2.29 (m, 2H), 2.24 (s, 6H), 1.50~1.56 (m, 4H). IR (film, cm$^{-1}$) 3061, 3029, 2943, 2856, 2816, 1600, 1508, 1458, 1248, 1061, 913, 743. MS (ES+) m/e 438 (M+1). Anal. Calcd for C$_{25}$H$_{31}$N$_3$O$_2$S: C, 68.62; H, 7.14; N, 9.60; S, 7.33. Found C, 68.56; H, 7.20; N, 9.81; S, 7.24.

Example 130

Preparation of 2-{[(2-Phenoxyethyl)thio]methyl}-5-{4-[5-(N,N-dimethylamino)pentyn-1-yl]phenyl}-1,3,4-oxadiazole

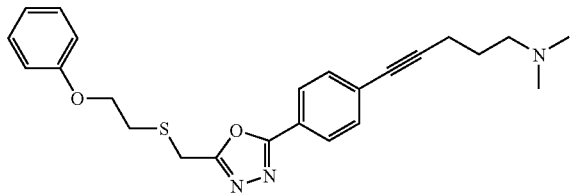

a) 2-{[(2-Phenoxyethyl)thio]methyl}-5-(4-bromophenyl)-1,3,4-oxadiazole

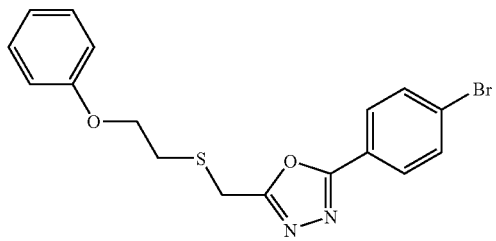

To a mixture of 4-bromobenzoic hydrazide (2.58 g, 12 mmol), 2-{[(2-phenoxyethyl)thio]methyl}acetic acid (2.12 g, 10 mmol), and 4(N,N-dimethylamino)phenyldiphenylphosphine (9.16 g, 30 mmol) in acetonitrile (100 mL) at 0° C. was added triethylamine (5.06 g, 50 mmol) in carbon tetrachloride (7.69 g, 50 mmol).

After 15 min the cooling bath was removed and the mixture was stirred at room temperature overnight. The mixture was concentrated to approximately half the original volume and partitioned between ether (150 mL) and 2 M HCl (100 mL). The ether layer was washed with 2 M HCl (4×30 mL), dried (MgSO$_4$), and concentrated. The residue was triturated from methylene chloride and hexanes to give white powder (2.80 g, 72%)

$^1$H NMR (CDCl$_3$) δ 7.87 (d, 2H, J=8.8 Hz), 7.62 (d, 2H, J=8.8 Hz), 7.23~7.27 (m, 2H), 6.93 (t, 1H, J=7.5 Hz), 6.87 (d, 2H, J=7.7 Hz), 4.19 (t, 2H, J=6.2 Hz), 4.04 (s, 2H), 3.03 (t, 2H, J=6.2 Hz). MS (ES+) m/e 392 (M+1).

b) 2-{[(2-Phenoxyethyl)thio]methyl}-5-[4-(5-hydroxypentyn-1-yl)phenyl]-1,3,4-oxadiazole

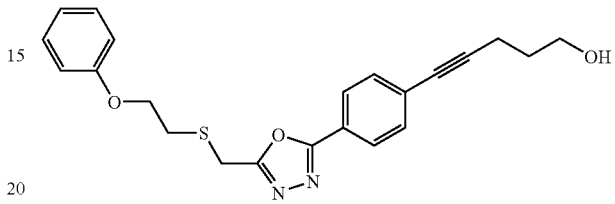

Palladium (II) acetate (30 mg, 0.13 mmol) and copper (I) iodide (30 mg, 0.16 mmol) were added to a solution of 2-{[(2-phenoxyethyl)thio]methyl}-5-(4-bromophenyl)-1,3,4-oxadiazole (782 mg, 2 mmol), 4-pentyn-1-ol (186 mg, 2.2 mmol), triphenylphosphine (104 mg, 0.4 mmol), and diethylamine (438 mg, 6 mmol) in dimethylsulfoxide (15 mL). The mixture was stirred at 90° C. for 5 h, diluted with water (20 mL), and extracted with ethyl acetate (3×15 mL). The combined ethyl acetate extracts were washed with water (2×20 mL) and brine (20 mL), dried (MgSO$_4$), and concentrated. The residue was purified by column chromatography (silica gel, ethyl acetate/hexanes 1:2) to give a yellow oil (704 mg, 89%).

$^1$H NMR (CDCl$_3$) δ 7.92 (d, 2H, J=8.5 Hz), 7.47 (d, 2H, J=8.5 Hz), 7.22~7.26 (m, 2H), 6.93 (t, 1H, J=7.3 Hz), 6.87 (d, 2H, J=7.7 Hz), 4.19 (t, 2H, J=6.0 Hz), 4.03 (s, 2H), 3.81 (t, 2H, J=6.2 Hz), 3.03 (t, 2H, J=6.0 Hz), 2.56 (t, 2H, J=6.9 Hz), 1.86 (quint, 2H, J=6.9 Hz). MS (ES+) m/e 395 (M+1).

c) 2-{[(2-Phenoxyethyl)thio]methyl}-5-{4-[5-(methylsulfonyloxy)pentyn-1-yl]phenyl}-1,3,4-oxadiazole

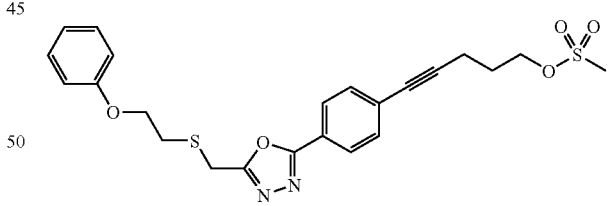

To a solution of 2-{[(2-phenoxyethyl)thio]methyl}-5-[4-(5-hydroxypentyn-1-yl)phenyl]-1,3,4-oxadiazole (205 mg, 0.5 mmol) and triethylamine (250 mg, 2.5 mmol) in methylene chloride (5 mL) was added methanesulfonyl chloride (115 mg, 1 mmol). The mixture was stirred at room temperature overnight, diluted with methylen chloride (10 mL), washed with 2 M NaOH (3×10 mL), dried (MgSO$_4$), and concentrated to give a yellow oil (235, 100%).

$^1$H NMR (CDCl$_3$) δ 7.93 (d, 2H, J=8.4 Hz), 7.48 (d, 2H, J=8.4 Hz), 7.23~7.27 (m, 2H), 6.93 (t, 1H, J=7.3 Hz), 6.87 (d, 2H, J=7.7 Hz), 4.40 (t, 2H, J=6.1 Hz), 4.19 (d, 2H, J=6.0 Hz), 4.04 (s, 2H), 3.03 (t, 2H, J=6.0 Hz), 3.02 (s, 3H), 2.61 (t, 2H, J=6.8 Hz), 2.05 (quint, 2H, J=6.9 Hz). MS (ES+) m/e 473 (M+1).

d) 2-{[(2-Phenoxyethyl)thio]methyl}-5-{4-[5-(N,N-dimethylamino)pentyn-1-yl]phenyl}-1,3,4-oxadiazole

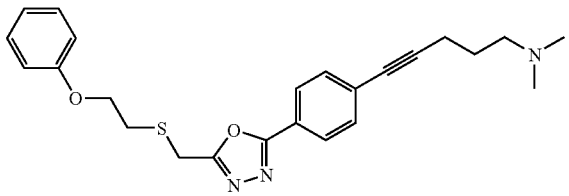

A mixture of 2-{[(2-phenoxyethyl)thio]methyl}-5-{4[5-(methylsulfonyloxy)pentyn-1-yl]phenyl}-1,3,4-oxadiazole (220 mg, 0.5 mmol), 2 M dimethylamine in tetrhydrofuran (1 mL, 2 mmol), and potassium carbonate (690 mg, 5 mmol) in acetonitrile (5 mL) was stirred under reflux overnight. The mixture was cooled to room temperature and filtered. The filtrate was concentrated and purified by preparative TLC (silica gel, 10% methanol/methylene chloride) to give a yellow oil (101 mg, 50%).

$^1$H NMR (CDCl$_3$) δ 7.92 (d, 2H, J=8.4 Hz), 7.47 (d, 2H, J=8.4 Hz), 7.22~7.26 (m, 2H), 6.93 (t, 1H, J=7.3 Hz), 6.87 (d, 2H, J=8.1 Hz), 4.19 (d, 2H, J=6.2 Hz), 4.03 (s, 2H), 3.03 (t, 2H, J=6.2 Hz), 2.47 (t, 2H, J=7.3 Hz), 2.41 (t, 2H, J=7.3 Hz), 1.81 (s, 6H), 1.77 (quint, 2H, J=7.3 Hz). IR (film, cm$^{-1}$) 3020, 2997, 2946, 2885, 2212, 1406, 1347, 1225, 1120, 1088. MS (ES+) m/e 422 (M+1). Anal. Calcd for C$_{24}$H$_{27}$N$_3$O$_2$S: C, 68.38; H, 6.46; N, 9.97; S, 7.61. Found C, 68.26; H, 6.59; N, 9.64; S, 7.69.

Example 131

Preparation of (+)-2-{[(2-Phenoxyethyl)thio]methyl}-5-{4-[3-benzyl-5-(N,N-dimethylamino)pentyn-1-yl]phenyl}-1,3,4-oxadiazole

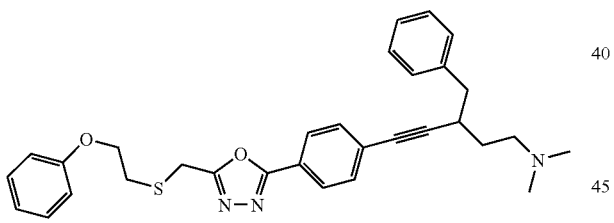

a) (+)-3-Benzyl-5-hydroxy-1-trimethylsilyl-1-pentyne

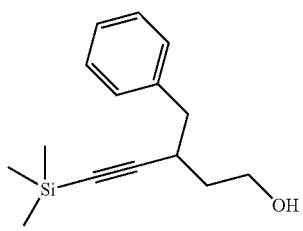

A solution of 5-(trimethylsilyl)-4-pentyn-1-ol (20 g, 128 mmol) and N,N,N',N'-tetramethylethylenediamine (42.5 mL, 282 mmol) in anhydrous THF (650 mL) was stirred under nitrogen and cooled to -30° C. (dry ice/methylene chloride). n-Butyllithium (2.0 M in cyclohexane, 70.5 mL, 141 mmol) and t-butyllithium (1.7 M in pentanes, 82.8 mL, 141 mmol) were sequentially added slowly, while the temperature was maintained between -25° and -35° C. After complete addition, the mixture was stirred for 2 h, within this temperature range. The mixture was then cooled to -78° C. (dry ice/acetone) and benzyl bromide (16 mL, 134 mmol) in tetrahydrofuran (400 mL) was added dropwise while temperature was maintained below -60° C. The reaction was then allowed to warm to room temperature over 3 h. The reaction was quenched with saturated aqueous ammonium chloride (400 mL) and extracted with ethyl ether (2×300 mL). The organic material was dried (Na$_2$SO$_4$), filtered and concentrated to yield 35 g of a yellow liquid. This was purified on silica gel (20% ethyl acetate/hexanes) to yield 23.9 g (76%) of a yellow liquid.

$^1$H NMR (CDCl$_3$) δ 7.28 (m, 3H), 7.22 (d, 2H, J=7 Hz), 3.79 (dd, 2H, J=5 and 6 Hz), 2.74~2.85 (m, 3H), 2.36 (t, 1H, J=14 Hz), 1.64~1.77 (m, 2H). MS (ES+) m/e 247 (M+1).

b) (+)-3-Benzyl-5-hydroxy-1-pentyne

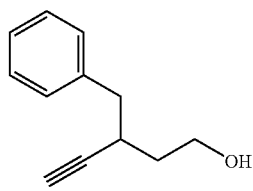

A solution (+)-3-benzyl-5-hydroxy-1-trimethylsilyl-1-pentyne (12.5 g, 50.8 mmol) in methanol (300 mL) saturated with potassium fluoride was refluxed for 1 h. The reaction was cooled to room temperature, diluted with brine (100 mL) and extracted with ethyl ether (3×100 mL). The organic material was washed with brine (2×50 mL), dried (MgSO$_4$), filtered and concentrated to yield a colorless liquid. This was purified by silica gel (33% ethyl acetate/hexanes) to yield 3.68 g (42%) of a colorless liquid.

$^1$H NMR (CDCl$_3$) δ 7.30 (m, 5H), 3.83 (d, 2H, J=4 Hz), 2.77–2.88 (m, 3H), 2.12 (s, 1H), 1.78 (m, 1H), 1.66 (m, 1H), 1.53 (br s, 1H). MS (ES+) m/e 175 (M+1).

c) (+)-2-{[(2-Phenoxyethyl)thio]methyl}-5-[4-(1-(3-benzyl-5-hydroxypentyn-1-yl)phenyl]-1,3,4-oxadiazole

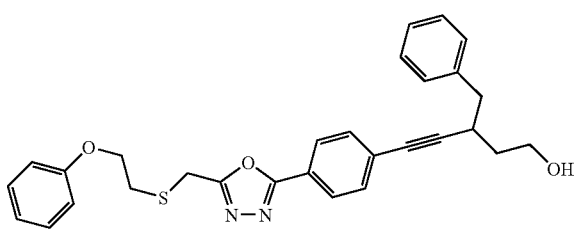

A mixture containing 2-{[(2-phenoxyethyl)thio]methyl}-5-(4-bromophenyl)-1,3,4-oxadiazole (980 mg, 2.5 mmol), triphenyl-phosphine (131 mg, 0.5 mmol) and palladium (II) acetate (56 mg, 0.25 mmol) was stirred in anhydrous DMSO (10 mL) at room temperature under nitrogen. Solutions of (+)-3-benzyl-5-hydroxy-1-pentyne (480 mg, 2.75 mmol) in methyl sulfoxide (2 mL) and diethylamine (0.78 mL, 7.5 mmol) in methyl sulfoxide (5 mL) were subsequently added, followed by copper (I) iodide (5 mg, 0.025 mmol). This mixture was heated to 90° C. for 4 h. The reaction was cooled to room temperature, quenched with water (15 mL) and extracted with methylene chloride (3×40 mL). The organic material was washed with water (20 mL), dried (MgSO$_4$), filtered and concentrated to yield 1.67 g of a brown oil. This oil was purified by silica gel (33% ethyl acetate-hexanes) to yield 856 mg (71%) of a colorless oil.

$^1$H NMR (CDCl$_3$) δ 7.94 (d, 2H, J=9 Hz), 7.44 (d, 2H, J=9 Hz), 7.28 (m, 7H), 6.96 (dd, 1H, J=8 and 9 Hz), 6.89 (d, 2H, J=9 Hz), 4.21 (t, 2H, J=12 Hz), 4.06 (s, 2H), 3.89 (d, 2H, J=4 Hz), 3.09 (m, 1H), 3.06 (t, 2H, J=12 Hz), 2.92 (m, 2H), 1.90 (m, 1H), 1.78 (m, 1H), 1.52 (br s, 1H). MS (ES+) m/e 485 (M+1).

d) (+)-2-{[(2-Phenoxyethyl)thio]methyl}-5-{4-[3-benzyl-5-(N,N-dimethylamino)pentyn-1-yl]phenyl}-1,3,4-oxadiazole

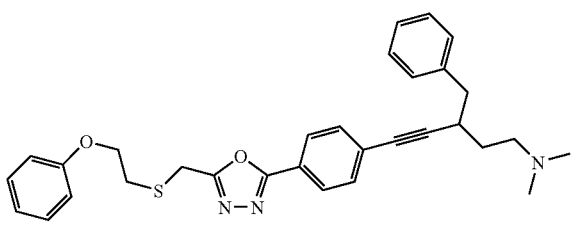

A solution of (+)-2-{[(2-Phenoxyethyl)thio]methyl}-5-[4-(1-(3-benzyl-5-hydroxypentyn-1-yl)phenyl]-1,3,4-oxadiazole (250 mg, 0.52 mmol), triethylamine (0.36 mL, 2.58 mmol) and methanesulfonyl chloride (0.08 mL, 1.04 mmol) were stirred in methylene chloride (5 mL) at room temperature for 16 h. The mixture was diluted with methylene chloride (20 mL), extracted with 2N NaOH (20 mL), dried (MgSO$_4$), filtered and concentrated to yield a quantitative amount of the correspoding mesylate. The mesylate was combined with dimethylamine (2.0 M in THF, 1.03 mL, 2.06 mmol) and potassium carbonate (720 mg, 5.2 mmol) in actonitrile (10 mL) and refluxed for 6 h. Since the reaction was not complete after 6 h., it was allowed to react at room temperature for an additional 16 h. After filtering the solids, the filtrate was concentrated to yield 231 mg of a brown oil. This was purified by preparative TLC (10% methanol/methylene chloride) to yield 73 mg (27%) of a colorless oil.

$^1$H NMR (CDCl$_3$) δ 7.91 (d, 2H, J=8 Hz), 7.41 (d, 2H, J=8 Hz), 7.26 (m, 7H), 6.93 (dd, 1H, J=7 and 8 Hz), 6.87 (d, 2H, J=9 Hz), 4.19 (t, 2H, J=12 Hz), 4.03 (s, 2H), 3.03 (t, 2H, J=12 Hz), 2.93 (m, 1H), 2.85 (m, 2H), 2.47 (m, 2H), 2.21 (s, 6H), 1.74 (m, 1H), 1.65 (m, 1H). MS (ES+) m/e 512 (M+1). IR (film, cm$^{-1}$) 3410, 2936, 1601, 1493, 1462, 1239, 752, 698. Anal. Calcd for C$_{31}$H$_{33}$N$_3$O$_2$S: C, 72.77; H, 6.50; N, 8.21; S, 6.27. Found C, 72.45; H, 6.33; N, 8.16; S, 6.18.

Example 132

Preparation of (E)-(+)-2-{[(2-phenoxyethyl)thio]methyl}-5-{4-[3-benzyl-5-(N,N-dimethylamino)penten-1-yl]phenyl}-1,3,4-oxadiazole

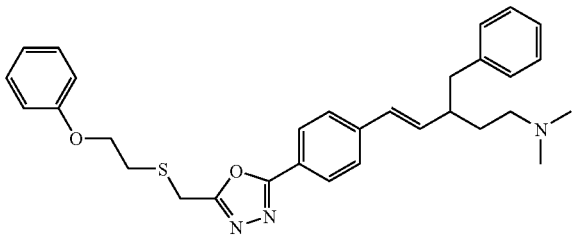

a) (E)-(+)-2-{[(2-phenoxyethyl)thio]methyl}-5-[4-(3-benzyl-5-hydroxypenten-1-yl)phenyl]-1,3,4-oxadiazole

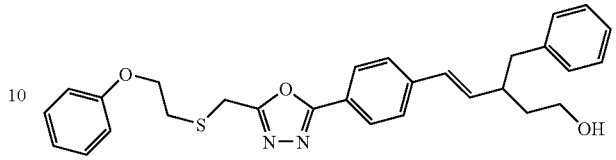

A solution containing Red-Al (65 wt % in toluene, 0.2 mL, 0.67 mmol) in anhydrous tetrahydrofuran (5.5 mL) was stirred in an ice-water bath under nitrogen. A solution of (+)-2-{[(2-phenoxyethyl)thio]methyl}-5-[4-(1-(3-benzyl-5-hydroxypentyn-1-yl)phenyl]-1,3,4-oxadiazole (0.27 g, 0.56 mmol) in anhydrous tetrahydrofuran (10 mL) was added and stirring was continued in the cooling bath until the bubbling due to hydrogen evolution had ceased. The bath was then removed and the reaction was refluxed for 2 h. Since the reaction had not completed, the mixture was again cooled in an ice-water bath and more Red-Al (0.1 mL, 0.33 mmol) was added. The reaction was refluxed for another 1.5 h until starting material was gone. The mixture was then cooled in an ice-water bath and quenched with water (3 mL). The mixture was then extracted with ethyl acetate (2×10 mL). The combined organic material was extracted with brine (2×110 mL), dried (MgSO$_4$), filtered and concentrated to yield 257 mg of a yellow oil.

This material was purified by chromatography (50% ethyl acetate/hexanes) to yield 34 mg (12%) of a white solid. This procedure was repeated twice to generate enough material to continue.

$^1$H NMR (CDCl$_3$) δ 7.92 (d, 2H, J=9 Hz), 7.38 (d, 2H, J=9 Hz), 7.25 (m, 4H), 7.16 (m, 3H), 6.93 (dd, 1H, J=7 and 7 Hz), 6.87 (d, 2H, J=8 Hz), 6.32 (d, 1H, J=6 Hz), 6.16 (dd, 1H, J=6 and 9 Hz), 4.18 (t, 2H, J=12 Hz), 4.03 (s, 2H), 3.68 (m, 2H), 3.03 (t, 2H, J=12 Hz), 2.75 (d, 2H, J=7 Hz), 2.52 (m, 1H), 1.81 (m, 1H), 1.63 (m, 1H), 1.20 (m, 1H). MS (ES+) m/e 487 (M+1).

b) (+)-2-{[(2-Phenoxyethyl)thio]methyl}-5-{4-[3-benzyl-5-(methylsulfonyloxy)penten-1-yl]phenyl}-1,3,4-oxadiazole

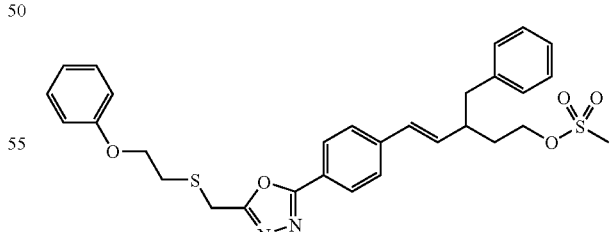

To a solution of (E)-(+)-2-{[(2-phenoxyethyl)thio]methyl}-5-[4-(3-benzyl-5-hydroxypenten-1-yl)phenyl]-1,3,4-oxadiazole (60 mg, 0.12 mmol) and triethylamine (50 mg, 0.5 mmol) in methylene chloride (2 mL) at 0° C. was added methanesulfonyl chloride (29 mg, 0.25 mmol). The resultant mixture was stirred at room temperature overnight, diluted with methylene chloride (20 mL), washed with 2 M HCl (5 mL) and 2 M NaOH (5 mL), dried (MgSO₄), and concentrated to give a yellow oil (61 mg, 90%).

$^{1}$H NMR (CDCl₃) δ 7.93 (d, 2H, J=8.6 Hz), 7.38 (d, 2H, J=8.6 Hz), 7.20~7.31 (m, 4H), 7.18 (t, 1H, J=7.0 Hz), 7.14 (d, 2H, J=7.0 Hz), 6.93 (t, 1H, J=7.8 Hz), 6.87 (d, 2H, J=7.8 Hz), 6.35 (d, 1H, J=15.6 Hz), 6.10 (dd, 1H, J=15.6, 8.9 Hz), 4.20~4.26 (m, 2H), 4.19 (d, 2H, J=6.2 Hz), 4.03 (s, 2H), 3.03 (t, 2H, J=6.2 Hz), 2.91 (s, 3H), 2.76 (d, 2H, J=6.3 Hz), 2.03 (m, 1H), 1.75 (m, 1H), 1.38 (m, 1H). MS (ES+) m/e 565 (M+1).

c) (+)-2-{[(2-Phenoxyethyl)thio]methyl}-5-{4-[3-benzyl-5-(N,N-dimethylamino)penten-1-yl]phenyl}-1,3,4-oxadiazole

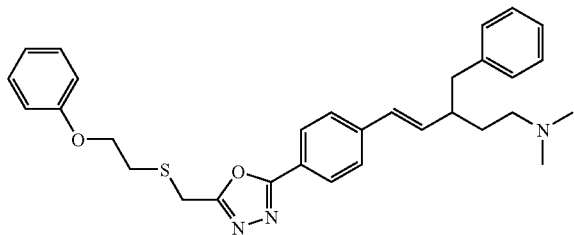

A mixture of (+)-2-{[(2-phenoxyethyl)thio]methyl}-5-{4-[3-benzyl-5-(methylsulfonyloxy)penten-1-yl]phenyl}-1,3,4-oxadiazole (61 mg, 0.11 mmol), 2 M dimethylamine in tetrahydrofuran (0.6 mL, 1.2 mmol), and potassium carbonate (166 mg, 1.2 mmol) in acetonitrile (10 mL) was stirred under reflux for 20 h and filtered. The filtrate was concentrated and purified by preparative TLC (silica gel, 10% methanol/methylene chloride) to give a white solid (32 mg, 57%).

$^{1}$H NMR (CDCl₃) δ 7.92 (d, 2H, J=8.6 Hz), 7.38 (d, 2H, J=8.6 Hz), 7.13~7.26 (m, 7H), 6.93 (t, 1H, J=7.8 Hz), 6.87 (d, 2H, J=7.8 Hz), 6.28 (d, 1H, J=16.4 Hz), 6.13 (dd, 1H, J=16.3, 8.5 Hz), 4.18 (t, 2H, J=6.2 Hz), 4.03 (s, 2H), 3.03 (t, 2H, J=6.2 Hz), 2.74 (d, 2H, J=7.0 Hz), 2.55 (m, 2H), 2.32 (t, 2H, J=7.8 Hz), 2.21 (s, 6H), 1.74 (m, 1H), 1.55 (m, 1H). IR (KBr, cm⁻¹) 3032, 2955, 2906, 1600, 1557, 1476, 1348, 1179, 1126, 747. MS (ES+) m/e 514 (M+1). Anal. Calcd for C₃₁H₃₅N₃O₂S: C, 72.48; H, 6.87; N, 8.18; S, 6.24. Found C, 71.91; H, 6.81; N, 8.23; S, 6.34.

Example 133

Preparation of 2-{[(2-Phenoxyethyl)thio]methyl}-5-{4-[4-(N,N-dimethylamino)buten-1-yl]phenyl}-1,3,4-oxadiazole

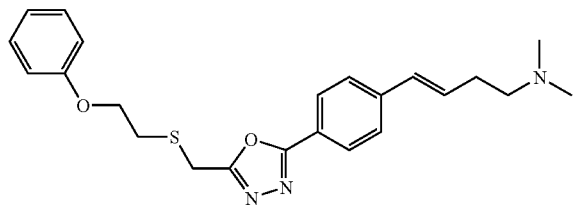

a) 2-{[(2-phenoxyethyl)thio]methyl}-5-[4-(4-hydroxybutyn-1-yl)phenyl]-1,3,4-oxadiazole

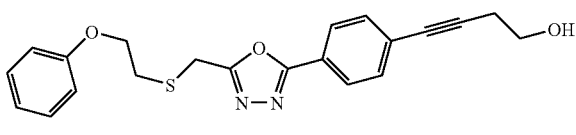

A mixture containing 2-{[(2-phenoxyethyl)thio]methyl}-5-(4-bromophenyl)-1,3,4-oxadiazole (5 g, 12.8 mmol), triphenyl-phosphine (0.67 g, 2.56 mmol) and palladium (II) acetate (287 mg, 1.28 mmol) was stirred in anhydrous dimethylsulfoxide (50 mL) at room temperature under nitrogen. Solutions of 3-butyn-1-ol (1.07 mL, 14.1 mmol) in dimethylsulfoxide (10 mL) and diethylamine (4 mL, 38.4 mmol) in dimethylsulfoxide (10 mL) were subsequently added, followed by copper (I) iodide (25 mg, 0.128 mmol). This mixture was heated to 90° C. for 3 h. The reaction was cooled to room temperature, quenched with water (75 mL) and extracted with ethyl acetate (3×100 mL). The organic material was washed with brine (3×50 mL), dried (MgSO₄), filtered and concentrated to yield 5.92 g of a brown oil. This oil was purified by silica gel (50% ethyl acetate/hexanes) to yield 1.91 g (39%) of a colorless oil.

$^{1}$H NMR (CDCl₃) δ 7.94 (d, 2H, J=8 Hz), 7.50 (d, 2H, J=8 Hz), 7.28 (m, 2H), 6.93 (dd, 1H, J=7 and 8 Hz), 6.87 (d, 2H, J=8 Hz), 4.19 (t, 2H, J=12 Hz), 4.03 (s, 2H), 3.83 (dd, 2H, J=6 and 12 Hz), 3.09 (m, 1H), 3.04 (t, 2H, J=12 Hz), 2.71 (t, 2H, J=12 Hz), 1.76 (t, 1H, J=12 Hz). MS (ES+) m/e 381 (M+1).

b) (E)-2-{[(2-phenoxyethyl)thio]methyl}-5-[4-(4-hydroxybuten-1-yl)phenyl]-1,3,4-oxadiazole

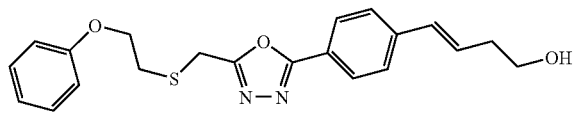

A solution containing Red-Al (0.73 mL, 2.4 mmol) in anhydrous tetrahydrofuran (12 mL) was stirred in an ice-water bath under nitrogen. A solution of 2-{[(2-phenoxyethyl)thio]methyl}-5-[4-(4-hydroxybutyn-1-yl)phenyl]-1,3,4-oxadiazole (0.76 g, 2.0 mmol) in anhydrous tetrahydrofuran (10 mL) was added and stirring was continued in the cooling bath until the bubbling due to hydrogen evolution had ceased. The bath was then removed and the reaction was refluxed for 1 h. Even though some of the alkyne starting material was present, the reaction was stopped here because TLC indicated that the product was decomposing. The mixture was then cooled in an ice-water bath and quenched with water (5 mL). The mixture was diluted with more water (10 mL) and then extracted with ethyl acetate (3×30 mL). The combined organic material was extracted with brine (2×20 mL), dried (MgSO₄), filtered and concentrated to yield 890 mg of a yellow oil which contained products and the alkyne starting material. This material was purified by preparative TLC (50% ethyl acetate/hexanes) to yield 128 mg (22%, based on converted starting material) of a white solid and 187 mg of alkyne starting material.

$^1$H NMR (CDCl$_3$) δ 7.94 (d, 2H, J=8 Hz), 7.45 (d, 2H, J=8 Hz), 7.25 (m, 4H), 7.25 (m, 2H), 6.94 (dd, 1H, J=7 and 8 Hz), 6.87 (d, 2H, J=8 Hz), 6.52 (d, 1H, J=15 Hz), 6.36 (m, 1H), 4.18 (t, 2H, J=12 Hz), 4.03 (s, 21, 3.78 (m, 2H), 3.03 (t, 2H, J=12 Hz), 2.75 (d, 2H, J=7 Hz), 2.52 (m, 2H), 1.43 (m, 1H). MS (ES+) m/e 383 (M+1).

c) (E)-2-{[(2-Phenoxyethyl)thio]methyl}-5-{4-[4-(methylsulfonyloxy)buten-1-yl]phenyl}-1,3,4-oxadiazole

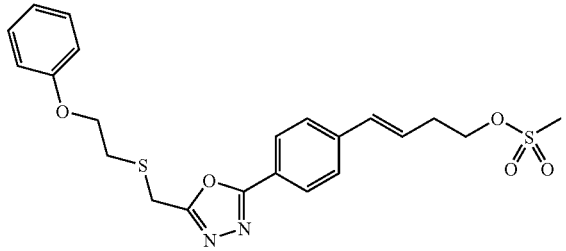

To a solution of (E)-2-{[(2-phenoxyethyl)thio]methyl}-5-[4-(4-hydroxybuten-1-yl)phenyl]-1,3,4-oxadiazole (120 mg, 0.31 mmol) and triethylamine (121 mg, 1.2 mmol) in methylen chloride (3 mL) at 0° C. was added methanesulfonyl chloride (69 mg, 0.6 mmol). The resultant mixture was stirred at room temperature overnight, diluted with methylene chloride (20 mL), washed with 2 M HCl (5 mL) and 2 M NaOH (5 mL), dried (MgSO$_4$), and concentrated to give yellow oil (138 mg, 97%).

$^1$H NMR (CDCl$_3$) δ 7.95 (d, 2H, J=8.6 Hz), 7.44 (d, 2H, J=8.6 Hz), 7.22~7.27 (m, 2H), 6.93 (t, 1H, J=7.8 Hz), 6.87 (d, 2H, J=7.8 Hz), 6.54 (d, 1H, J=16.4 Hz), 6.28 (dt, 1H, J=16.4, 7.0 Hz), 4.34 (t, 2H, J=6.2 Hz), 4.19 (t, 2H, J=6.2 Hz), 4.03 (s, 2H), 3.04 (t, 2H, J=6.2 Hz), 3.01 (s, 3H), 2.68 (m, 2H). MS (ES+) m/e 461 (M+1).

d) (E)-2-{[(2-Phenoxyethyl)thio]methyl}-5-{1[4-(N,N-dimethylamino)buten-1-yl]phenyl}-1,3,4-oxadiazole

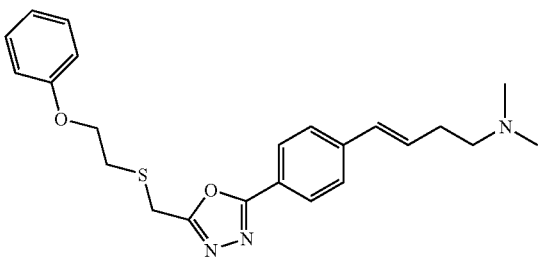

A mixture of (E)-2-{[(2-Phenoxyethyl)thio]methyl}-5-{4-[4-(methylsulfonyloxy)buten-1-yl]phenyl}-1,3,4-oxadiazole (120 mg, 0.29 mmol), 2 M dimethylamine in tetrahydrofuran (1.5 mL, 3 mmol), and potassium carbonate (400 mg, 2.9 mmol) in acetonitrile (15 mL) was stirred under reflux for 20 h and filtered. The filtrate was concentrated and purified by preparative TLC (silica gel, 10% methanol/methylene chloride) to give a white solid (111 mg, 93%).

$^1$H NMR (CDCl$_3$) δ 7.92 (d, 2H, J=7.8 Hz), 7.43 (d, 2H, J=8.6 Hz), 7.22~7.27 (m, 2H), 6.93 (t, 1H, J=7.4 Hz), 6.87 (d, 2H, J=7.6 Hz), 6.46 (d, 1H, J=15.6 Hz), 6.35 (dt, 1H, J=15.6, 6.2 Hz), 4.19 (t, 2H, J=6.2 Hz), 4.03 (s, 2H), 3.03 (t, 2H, J=6.2 Hz), 2.40~2.49 (m, 4H), 2.28 (s, 6H). IR (KBr, cm$^{-1}$) 3032, 2960, 2931, 2880, 1589, 1553, 1499, 1239, 1094, 1042, 746. MS (ES+) m/e 410 (M+1). Anal. Calcd for C$_{23}$H$_{27}$N$_3$O$_2$S: C, 67.45; H, 6.65; N, 10.26; S, 7.83. Found C, 67.32; H, 6.68; N, 10.50; S, 7.88.

Example 134

Preparation of (E)-2-{[(2-Phenoxyethyl)thio]methyl}-5-[4-(3-aminopropen-1-yl)phenyl]-1,3,4-oxadiazole

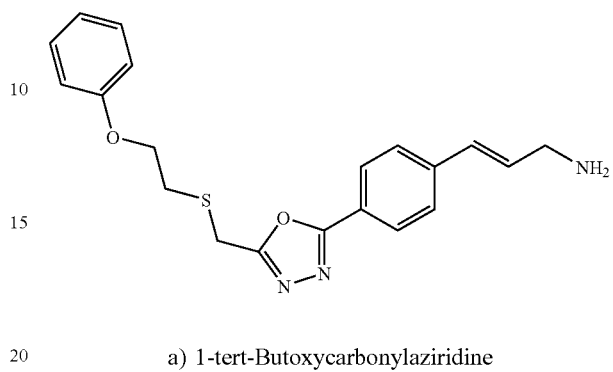

a) 1-tert-Butoxycarbonylaziridine

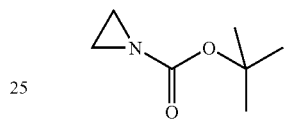

A solution containing ethanolamine (6 g, 98.2 mmol) and di-tert-butyl dicarbonate (23.6 g, 108 mmol) in isopropyl alcohol (40 mL) and dioxane (80 mL) was stirred at room temperature for 3 hr. The mixture was concentrated and dried under vacuum overnight. This material was then combined with p-toluenesulfonyl chloride (22.5 g, 117.8 mmol) and powdered KOH (22.0 g, 392.8 mmol) in ethyl ether (800 mL). The mixture was refluxed for 1.5 days, but only 50% was converted. More KOH (11 g, 146 mmol) was added, the heat was removed and the reaction stirred 2 days at room temperature. The mixture was poured over ice-water (600 mL) and the organic material was separated. The aqueous layer was extracted with ethyl ether (200 mL) and the combined organic extracts were dried (MgSO$_4$), filtered and concentrated at 1 atm to remove most of the ether. The flask was left open in the hood overnight to allow complete evaporation of ether to yield 14 g (99%) of a colorless oil.

$^1$H NMR (CDCl$_3$) δ 2.11 (s, 4H), 1.43 (s, 9H).

b) Methyl 4-{3-[(tert-butoxycarbonyl)amino]propen-1-yl}benzoate

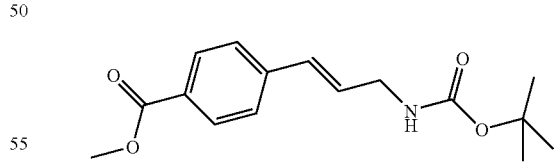

A solution containing methyl 4-formylbenzoate (2.7 g, 16.45 mmol), 1-(tert-butoxycarbonyl)aziridine (7.07 g, 49.4 mmol), and triphenylphosphine (12.9 g, 49.4 mmol) in isopropyl alcohol (150 mL) was refluxed for 3 h. The reaction was concentrated to yield 4.63 g of a colorless oil which contained an approximately 1:3 ratio of Z-olefin (top spot on TLC) to E-olefin (bottom spot). This material was purified on silica gel (20% ethyl acetate/hexanes) to yield 1.24 g (26%) of a white solid (E-isomer). Another 2.2 g (46%) of E/Z mixture was isolated, too.

E-isomer: ¹H NMR (CDCl₃) δ 7.95 (d, 2H, J=8 Hz), 7.38 (d, 2H, J=8 Hz), 6.51 (d, 1H, J=16 Hz), 6.29 (m, 1), 4.68 (br s, 1H), 3.91 (m, 2H), 3.88 (s, 3H), 1.44 (s, 9H). MS (ES+) m/e 292 (M+1).

c) 4-{3-[(tert-butoxycarbonyl)amino]propen-1-yl}benzoic acid, (E)- and (Z)-isomers

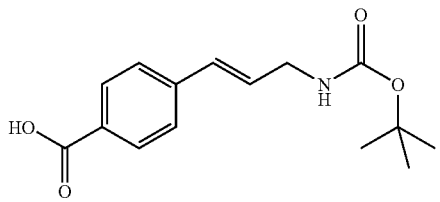

To a solution of methyl 4-{3-[(tert-butoxycarbonyl)amino]propen-1-yl}benzoate (1.46 g, 5 mmol) in 1,4-dioxane (25 mL) was added 2 M NaOH (25 mL, 50 mmol) and the reaction was stirred at room temperature for 3 h. Ice (30 g) was added and the mixture was acidified with 2 M HCl (26 mL) and extracted with methylene chloride (3×30 mL). The combined methylene chloride extracts were washed with water (2×50 mL), dried (MgSO₄), and concentrated to give a white solid (1.20 g, 86%).

E-isomer: ¹H NMR (CDCl₃) δ 7.96 (d, 2H, J=8.6 Hz), 7.52 (d, 2H, J=8.8 Hz), 6.59 (d, 1H, J=15.6 Hz), 6.43 (dt, 1H, J=15.6, 5.5 Hz), 6.19 (br s, 1H), 3.87 (m, 2H), 1.41 (s, 9H). MS (ES−) m/e 276 (M−1).

Z-isomer: ¹H NMR (CDCl₃) δ 8.04 (d, 2H, J=7.8 Hz), 7.29 (d, 2H, J=8.6 Hz), 6.55 (d, 1H, J=11.7 Hz), 5.77 (dt, 1H, J=11.7, 6.0 Hz), 4.64 (br s, 1H), 4.03 (m, 2H), 1.43 (s, 9H). MS (ES−) m/e 276 (M−1).

d) 2-{[(2-Phenoxyethyl)thio]methyl}-5-{4-[3-((tert-butoxycarbonyl)amino)propen-1-yl]phenyl}-1,3,4-oxadiazole, (E)- and (Z)-isomers

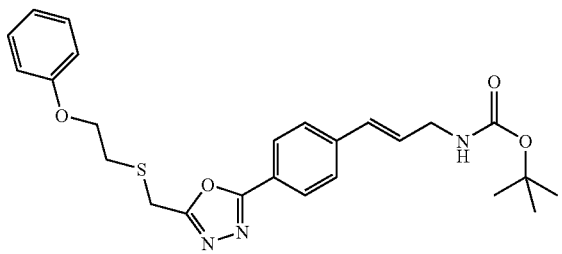

To a stirred mixture of 4-{3-[(tert-butoxycarbonyl)amino]propen-1-yl}benzoic acid (1.11 g, 4 mmol), 2-(2-phenoxyethyl)thioacetic hydrazide hydrochloride (1.16 g, 4.4 mmol), and p-(N,N-dimethylamino)phenyldiphenylphosphine (3.66 g, 12 mmol) in acetonitrile (40 mL) at 0° C. was added a solution of triethylamine (2.43 g, 24 mmol) in carbon tetrachloride (3.08 g, 20 mmol). After 10 min the cooling bath was removed and stirring was continued at room temperature overnight. The mixture was concentrated to approximately half the original volume and partitioned between ether (100 mL) and 2 M HCl (100 mL). The ether layer was washed with 2 M HCl (4×50 mL) and water (50 mL), dried (MgSO₄) and concentrated. The residue was purified by column chromatography (silica gel, ethyl acetate/hexanes 1:2) to give a colorless oil (1.23 g, 66%).

E-isomer: ¹H NMR (CDCl₃) δ 7.95 (d, 2H, J=8.6 Hz), 7.44 (d, 2H, J=7.9 Hz), 7.22~7.26 (m, 2H), 6.92 (t, 1H, J=7.8 Hz), 6.87 (d, 2H, J=7.8 Hz), 6.52 (d, 1H, J=16.4 Hz), 6.31 (dt, 1H, J=16.6, 6.3 Hz), 4.67 (br s, 1H), 4.19 (t, 2H, J=6.2 Hz), 4.03 (s, 2H), 3.93 (m, 2H), 3.03 (t, 2H, J=6.2 Hz), 1.45 (s, 9H). MS (ES+) m/e 468 (M+1).

Z-isomer: ¹H NMR (CDCl₃) δ 7.98 (d, 2H, J=8.6 Hz), 7.32 (d, 2H, J=8.5 Hz), 7.23~7.27 (m, 2H), 6.93 (t, 1H, J=7.8 Hz), 6.86 (d, 2H, J=7.8 Hz), 6.54 (d, 1H, J=11.7 Hz), 5.76 (dt, 1H, J=11.7, 6.3 Hz), 4.62 (br s, 1H), 4.18 (t, 2H, J=6.2 Hz), 4.06 (m, 2H), 4.04 (s, 2H), 3.04 (t, 2H, J=6.2 Hz), 1.43 (s, 9H). MS (ES+) m/e 468 (M+1).

e) 2-{[(2-Phenoxyethyl)thio]methyl}-5-[4-(3-aminopropen-1-yl)phenyl]-1,3,4-oxadiazole, (E)- and (Z)-isomers

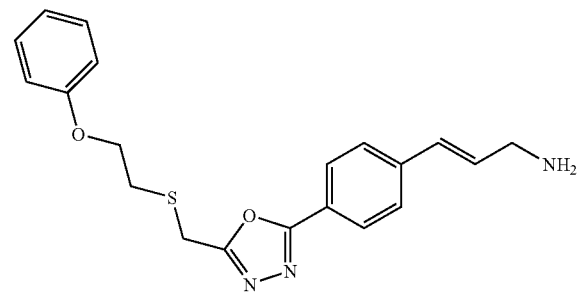

Trifluoroacetic acid (2 mL) was added slowly to a solution of 2-{[(2-phenoxyethyl)thio]methyl}-5-{4-[3-((tert-butoxycarbonyl)amino)propen-1-yl]phenyl}-1,3,4-oxadiazole (467 mg, 1 mmol) in methylene chloride (8 mL). The mixture was stirred at room temperature for 1 h and concentrated. The residue was partitioned between 2 M NaOH (10 mL) and methylene chloride (20 mL), and the aqueous layer was extracted with methylene chloride (15 mL). The combined methylene chloride extracts were dried (MgSO₄) and concentrated. The residue was triturated from methylene and hexanes to give a white powder (323 mg, 88%).

E-isomer: ¹H NMR (CDCl₃) δ 7.95 (d, 2H, J=8.6 Hz), 7.46 (d, 2H, J=8.6 Hz), 7.23~7.26 (m, 2H), 6.93 (t, 1H, J=7.1 Hz), 6.87 (d, 2H, J=7.8 Hz), 6.54 (d, 1H, J=16.3 Hz), 6.44 (dt, 1H, J=15.6, 5.5 Hz), 4.19 (t, 2H, J=6.2 Hz), 4.03 (s, 2H), 3.51 (d, 2H, J=5.5 Hz), 3.04 (t, 2H, J=6.2 Hz). IR (KBr, cm⁻¹) 3430, 3029, 2952, 2945, 2858, 1600, 1563, 1504, 1461, 1244, 1175, 752. MS (ES+) m/e 368 (M+1). Anal. Calcd for $C_{20}H_{21}N_3O_2S$: C, 65.37; H, 5.76; N, 11.43; S, 8.73. Found C, 65.58; H, 6.01; N, 11.20; S, 8.61.

Z-isomer: ¹H NMR (CDCl₃) δ 7.97 (d, 2H, J=8.6 Hz), 7.32 (d, 2H, J=8.7 Hz), 7.22~7.27 (m, 2H), 6.93 (t, 1H, J=7.8 Hz), 6.87 (d, 2H, J=7.8 Hz), 6.47 (d, 1H, J=11.7 Hz), 5.84 (dt, 1H, J=11.7, 5.8 Hz), 4.19 (t, 2H, J=6.2 Hz), 4.04 (s, 2H), 3.60 (d, 2H, J=6.2 Hz), 3.04 (t, 2H, J=6.3 Hz). IR (KBr, cm⁻¹) 3430, 3031, 2950, 2945, 2841, 1599, 1550, 1486, 1410, 1235, 1147, 755. MS (ES+) m/e 368 (M+1). Anal. Calcd for $C_{20}H_{21}N_3O_2S$: C, 65.37; H, 5.76; N, 11.43; S, 8.73. Found C, 64.97; H, 5.94; N, 11.26; S, 8.83.

Example 135

Preparation of 2-{[(2-Phenoxyethyl)thio]methyl}-5-{4-[3-(N,N-dimethylamino)propen-1-yl]phenyl}-1,3,4-oxadiazole, (E)- and (Z)-isomers

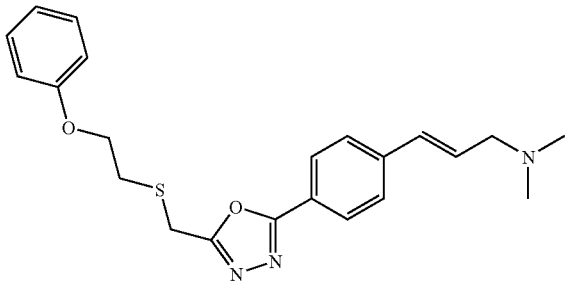

A mixture of 2-{[(2-Phenoxyethyl)thio]methyl}-5-[4-(3-aminopropen-1-yl)phenyl]-1,3,4-oxadiazole (229 mg, 0.62 mmol) and parafomaldehyde (187 mg, 6.2 mmol) in methanol (6 mL) was stirred under reflux for 3 h and then cooled to room temperature. Sodium cyanoborohydride (117 mg, 1.86 mmol) was added in three portions and the resultant mixture was stirred at room temperature for 2 h. The reaction was quenched by addition of water (0.5 mL) and most of the methanol was evaporated. The residue was diluted with saturated sodium bicarbonate (10 mL) and extracted with methylene chloride (3×10 mL). The combined methylene chloride extracts were dried (MgSO$_4$) and concentrated. The residue was purified by preparative TLC (silica gel, 10% methanol/methylene chloride) to give a pale yellow solid (176 mg, 72%).

E-isomer: $^1$H NMR (CDCl$_3$) δ7.95 (d, 2H, J=8.6 Hz), 7.46 (d, 2H, J=8.6 Hz), 7.22~7.27 (m, 2H), 6.93 (t, 1H, J=7.8 Hz), 6.87 (d, 2H, J=7.8 Hz), 6.54 (d, 1H, J=15.6 Hz), 6.38 (dt, 1H, J=16.4, 6.3 Hz), 4.19 (t, 2H, J=6.2 Hz), 4.03 (s, 2H), 3.11 (d, 2H, J=6.3 Hz), 3.04 (t, 2H, J=6.2 Hz), 2.28 (s, 6H). IR (film, cm$^{-1}$) 3030, 2952, 2928, 2884, 1598, 1552, 1481, 1293, 1065, 739. MS (ES+) m/e 396 (M+1). Anal. Calcd for C$_{22}$H$_{25}$N$_3$O$_2$S: C, 66.81; H, 6.37; N, 10.62; S, 8.11. Found C, 67.05; H, 6.28; N, 10.79; S, 8.04.

Z-isomer: $^1$H NMR (CDCl$_3$) δ 7.98 (d, 2H, J=7.8 Hz), 7.35 (d, 2H, J=7.8 Hz), 7.23~7.27 (m, 2H), 6.93 (t, 1H, J=7.4 Hz), 6.87 (d, 2H, J=7.8 Hz), 6.58 (d, 1H, J=11.7 Hz), 5.90 (dt, 1H, J=12.5, 6.2 Hz), 4.18 (t, 2H, J=6.2 Hz), 4.04 (s, 2H), 3.20 (d, 2H, J=6.2 Hz), 3.04 (t, 2H, J=6.2 Hz), 2.25 (s, 6H). IR (film, cm$^{-1}$) 3031, 2980, 2963, 1600, 1552, 1481, 1295, 1055, 983, 750. MS (ES+) m/e 396 (M+1). Anal. Calcd for C$_{22}$H$_{25}$N$_3$O$_2$S: C, 66.81; H, 6.37; N, 10.62; S, 8.11. Found C, 67.37; H, 6.50; N, 10.43; S, 8.03.

Example 136

Preparation of (E)-2-{[(2-phenoxyethyl)thio]methyl}-5-[4-(3-pyrrolidinopropen-1-yl)phenyl]-1,3,4-oxadiazole

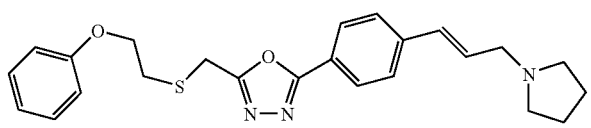

A suspension containing (E)-2-{[(2-phenoxyethyl)thio]methyl}-5-[4-(3-aminopropen-1-yl)phenyl]-1,3,4-oxadiazole (135 mg, 0.367 mmol) and 1,4-butanedial bisulfite adduct (121 mg, 0.367 mmol) was stirred in methanol (4 mL). Sodium cyanoborohydride (46.1 mg, 0.734 mmol) was added and the reaction stirred for 72 h. The reaction was quenched with 2N aqueous NaOH (2 mL), extracted with methylene chloride (3×5 mL), dried (MgSO$_4$) and filtered to yield 147 mg of a yellow oil. This material was purified by preparative TLC (10% methanol/methylene chloride) to yield 55 mg (36%) of a yellow solid.

$^1$H NMR (CDCl$_3$) δ 7.95 (d, 2H, J=8 Hz), 7.46 (d, 2H, J=8 Hz), 7.24 (m, 2H), 6.93 (dd, 1H, J=7 and 8 Hz), 6.87 (d, 2H, J=8 Hz), 6.57 (d, 1H, J=16 Hz), 6.45 (dd, 1H, J=7 and 16 Hz), 4.18 (t, 2H, J=12 Hz), 4.03 (s, 2H), 3.31 (d, 2H, J=6 Hz), 3.03 (t, 2H, J=12 Hz), 2.60 (m, 4H), 1.81 (m, 4H). IR (film, cm$^{-1}$) 3428, 2952, 2930, 2787, 1596, 1493, 1241, 755. MS (ES+) m/e 422 (M+1). Anal. Calcd for C$_{24}$H$_{27}$N$_3$O$_2$S: C, 68.38; H, 6.46; N, 9.97; S, 7.61. Found C, 68.52; H, 6.38; N, 9.89; S, 7.70.

Example 137

Preparation of 2-{[(2-phenoxyethyl)amino]methyl}-5-{4-[(4-(N,N-dimethylamino)butanoyl)amino]phenyl}-1,3,4-oxadiazole

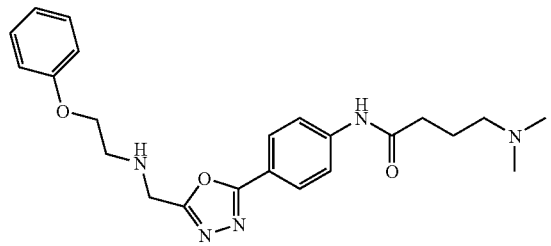

a) 2-(2-Nitrobenzensulfonamido)ethyl phenyl ether

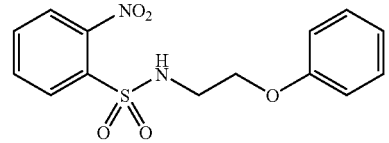

To a stirred mixture of 2-phenoxyethylamine (3.29 g, 24 mmol) and potassium bicarbonate (10 g, 100 mmol) in methylene chloride (200 mL) was added 2-nitrobenzenesulfonyl chloride (4.43 g, 20 mmol) in several portions. The resultant mixture was stirred at room temperature overnight and filtered. The filtrate was washed with 2 M HCl (3×30 mL), dried (MgSO$_4$), and concentrated. The residue was triturated from methylene chloride/hexanes to give a white solid (5.7 g, 88%).

$^1$H NMR (CDCl$_3$) δ 8.13 (d, 1H, J=7.7 Hz), 7.80 (d, 1H, J=7.7 Hz), 7.63~7.71 (m, 2H), 7.18~7.24 (m, 2H), 6.92 (t, 1H, J=7.3 Hz), 6.71 (d, 2H, J=8.0 Hz), 5.90 (br t, 1H, J=5.5 Hz), 4.0 (t, 2H, J=5.1 Hz), 3.52 (t, 2H, 5.5 Hz). MS (ES+) m/e 323 (M+1).

b) N-[(Methoxycarbonyl)methyl]-N-(2-phenoxyethyl)-2-nitrobenzenesulfonamide

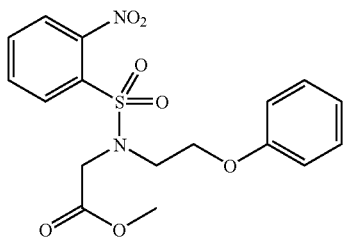

To a stirred mixture of 2-(2-nitrobenzensulfonamido) ethyl phenyl ether (1.61 g, 5 mmol) and potassoum carbonate (6.91 g, 50 mmol) in tetrahydrofuran (50 mL) was added sodium iodide (300 mg, 2 mmol) and methyl bromoacetate (1.53 g, 10 mmol) and stirring was continued at room temperature overnight. The mixture was diluted with ethyl acetate (25 mL), washed with water (2×30 mL) and brine (25 mL), dried (MgSO$_4$), and concentrated to give yellow oil (1.99 g, 100%).

$^1$H NMR (CDCl$_3$) δ 8.08 (d, 1H, J=8.8 Hz), 7.60~7.68 (m, 3H), 7.24 (m, 2H), 6.93 (t, 1H, J=7.3 Hz), 6.77 (d, 2H, J=8.8 Hz), 4.37 (s, 2H), 4.15 (t, 2H, J=4.8 Hz), 3.80 (t, 2H, J=4.8 Hz), 3.56 (s, 3H). MS (ES+) m/e 395 (M+1).

c) 2-[N-(2-phenoxyethyl)-2-nitrobenzenesulonamido]acetic hydrazide

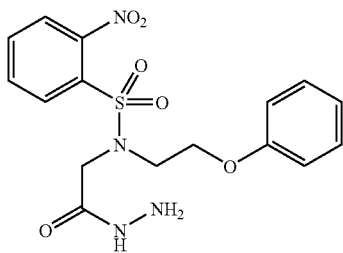

A mixture of methyl N-[(methoxycarbonyl)methyl]-N-(2-phenoxyethyl)-2-nitrobenzenesulfonamide (1.97 g, 5 mmol) and hydrazine monohydrate (2.5 g, 50 mmol) in ethanol was stirred at room temperature overnight and concentrated. Excess hydrazine was also removed under vacuum. The residue was taken up in ethyl acetate (75 mL) and washed with water (2×50 mL), dried (MgSO$_4$), and concentrated to give a yellow oil (1.73 g, 88%).

$^1$H NMR (CDCl$_3$) δ 8.06 (d, 1H, J=7.7 Hz), 7.65~7.74 (m, 3H), 7.23~7.27 (m, 2H), 6.95 (t, 1H, J=7.3 Hz), 6.80 (d, 2H, J=8.4 Hz), 4.15 (t, 2H, J=5.0 Hz), 4.12 (s, 2H), 3.81 (t, 2H, J=5.0 Hz), 3.56 (s, 3H). MS (ES+) m/e 395 (M+1).

d) 2-{[N-(2-nitrobenzenesulfonyl)-(2-phenoxyethyl)amino]methyl}-5-{4-[(tert-butoxycarbonyl)amino]phenyl}-1,3,4-oxadiazole

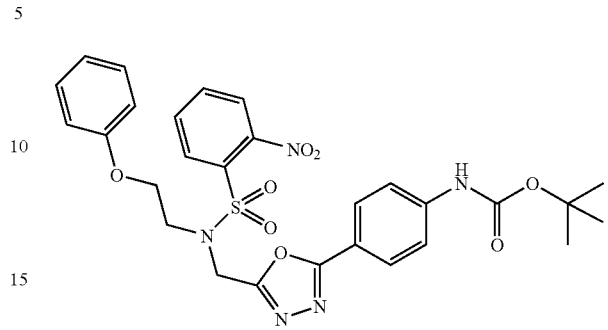

To a stirred mixture of 2-[N-(2-phenoxyethyl)-2-nitrobenzenesulonamido]acetic hydrazide (1.58 g, 4 mmol), 4-(tert-butyloxycarbonyl)bezoic acid (1.19 g, 5 mmol), and 4-(N,N-dimethylamino)phenyldiphenylphosphine (4.58 g, 15 mmol) in acetonitrile (50 mmol), at 0° C., was added a solution of triethylamine (2.56 g, 25 mmol) in carbon tetrachloride (3.85 g, 25 mmol). After 10 min the cooling bath was removed and stirring was continued at room temperature overnight. The resultant mixture was concentrated to approximately half the original volume and partitioned between ether (150 mL) and 2 M HCl (100 mL). The organic layer was washed with 2 M HCl (3×150 mL) and 2 M NaOH (3×50 mL), dried (MgSO$_4$), and concentrated to give a brown oil (1.81 g, 76%).

$^1$H NMR (CDCl$_3$) δ 8.04 (d, 1H, J=8.8 Hz), 7.77 (d, 2H, J=8.8 Hz), 7.43~7.67 (m, 5H), 7.19 (t, 2H, J=8.0 Hz), 6.90 (t, 1H, J=7.3 Hz), 6.71 (d, 2H, J=7.7 Hz), 5.04 (s, 2H), 4.19 (t, 2H, J=5.1 Hz), 3.90 (t, 2H, J=5.1 Hz), 1.51 (s, 9H). MS (ES+) m/e 596 (M+1).

e) 2-{[N-(2-nitrobenzenesulfonyl)-(2-phenoxyethyl)amino]methyl}-5-(4-aminophenyl)-1,3,4-oxadiazole

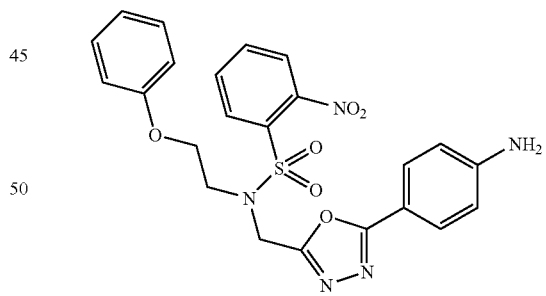

Trifluoroacetic acid (2.5 mL) was added to a solution of 2-{[N-(2-nitrobenzenesulfonyl)-(2-phenoxyethyl)amino]methyl}-5-{4-[(tert-butoxycarbonyl)amino]phenyl}-1,3,4-oxadiazole (1.19 g, 2 mmol) in methylene chloride (7.5 Ml). The mixture was stirred at room temperature for 3 h and concentrated. The residue was dissolved in methylene chloride (15 mL) and washed with 2 M NaOH (15 mL), dired (MgSO$_4$), and concentrated. The residue was purified by column chromatography (silica gel, ethyl acetate/hexanes) to give a pale yellow oil (400 mg, 40%).

$^1$H NMR (CDCl$_3$), δ 8.09 (d, 1H, J=7.4 Hz), 7.57~7.66 (m, 5H), 7.22 (m, 2H), 6.90 (t, 1H, J=7.3 Hz), 6.71 (d, 2H,

J=8.0 Hz), 6.65 (d, 2H, J=8.8 Hz), 5.01 (s, 2H), 4.18 (t, 2H, J=5.0 Hz), 3.90 (t, 2H, J=5.0 Hz). MS (ES+) m/e 496 (M+1).

f) 2-{[N-(2-nitrobenzenesulfonyl)-(2-phenoxyethyl)amino]methyl}-5-{4-[(4-(N,N-dimethylamino)butanoyl)amino]phenyl}-1,3,4-oxadiazole

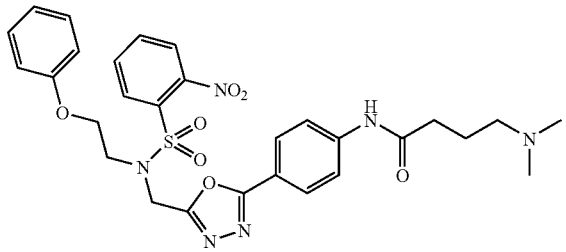

To a stirred mixture of 2-{[N-(2-nitrobenzenesulfonyl)-(2-phenoxyethyl)amino]methyl}-5-(4-aminophenyl)-1,3,4-oxadiazole (248 mg, 0.5 mmol), 4-(N,N-dimethylamino)butanoic acid hydrochloride (168 mg, 1 mmol), and 1-hydroxybenzotriazole (135 mg, 1 mmol) in N,N-dimethylformamide (5 mL) was added diisopropylcarbodiimide (126 mg, 1 mmol) and stirring was continued at room temperature overnight. The mixture was diluted with ethyl acetate (25 mL), washed with 2 M NaOH (3×10 mL), water (2×10 mL), and brine (10 mL), dried (MgSO$_4$), and concentrated. The residue was purified by chromatography (silica gel, 20% methanol/methylene chloride) to give a pale yellow oil (228 mg, 75%).

$^1$H NMR (CDCl$_3$) δ 10.68 (s, 1H), 8.10 (d, 1H, J=9.1 Hz), 7.77 (d, 2H, J=8.8 Hz), 7.58~7.65 (m, 5H), 7.19 (m, 2H), 6.90 (t, 1H, J=7.3 Hz), 6.71 (d, 2H, J=7.7 Hz), 5.04 (s, 2H), 4.19 (t, 2H, J=4.9 Hz), 3.90 (t, 2H, J=4.9 Hz), 2.49~2.56 (m, 4H), 2.36 (s, 6H), 1.86 (m, 2H). MS (ES+) m/e 609 (M+1).

g) 2-{[(2-phenoxyethyl)amino]methyl}-5-{4-[(4-(N,N-dimethylamino)butanoyl)amino]phenyl}-1,3,4-oxadiazole

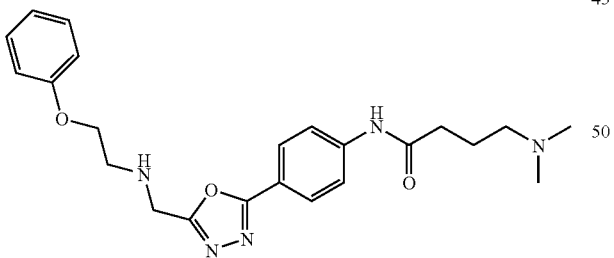

A mixture of 2-{[N-(2-nitrobenzenesulfonyl)-(2-phenoxyethyl)amino]methyl}-5-{4-[(4-(N,N-dimethylamino)butanoyl)amino]phenyl}-1,3,4-oxadiazole (152 mg, 0.25 mmol) and potassium carbonate (104 mg, 0.75 mmol) in N,N-dimethylformamide (1.5 mL) was stirred at room temperature and benzenethiol (33 mg, 0.3 mmol) was added. Stirring was continued for 3 h and the mixture was diluted with water (5 mL) and extracted with ethyl acetate (8 mL). The ethyl acetate extract was loaded to a cation exchange column (Bio-Rad 50W-x2 resin) and eluted with methanol. The basic material was recovered by flushing the column with 2 M ammonia in methanol and further purified by preparative TLC (silica gel, 10% methanol/methylene chloride) to give a pale yellow oil (71 mg, 67%).

$^1$H NMR (CDCl$_3$) δ 10.59 (s, 11, 7.95 (d, 1H, J=8.8 Hz), 7.65 (d, 2H, J=8.8 Hz), 7.22~7.26 (m, 2H), 6.92 (t, 1H, J=7.3 Hz), 6.87 (d, 2H, J=8.1 Hz), 4.16 (s, 2H), 4.08 (t, 2H, J=5.0 Hz), 3.11 (t, 2H, J=5.0 Hz), 2.49~2.56 (m, 41), 2.36 (s, 6H), 1.88 (m, 21). IR (film, cm$^{-1}$) 3483, 3340, 2948, 2925, 1661, 1605, 1500, 1428, 1182, 1067, 1027, 756. MS (ES+) m/e 424 (M+1). Anal. Calcd for C$_{23}$H$_{29}$N$_5$O$_3$: C, 65.23; H, 6.90; N, 16.54. Found C, 65.01; H, 6.96; N, 16.77.

Example 137

Preparation of 2-{[(2-phenoxyethyl)thio]methyl}-5-{4-[(N',N'-dimethyl-1,3-propanediamino)methyl]phenyl}-1,3,4-oxadiazole

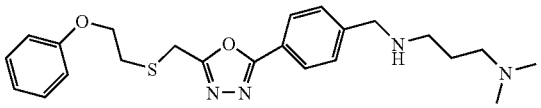

a) 2-[4-(hydroxycarbonyl)phenyl]-1,3-dioxolane

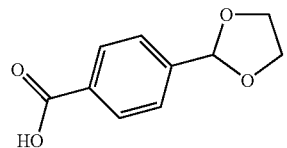

Aluminum oxide (Brockmann I, basic, 150 mesh, 34 g, 0.33 mol) was added to a solution of 4-carboxybenzaldehyde (20 g, 0.13 mol) and ethylene glycol (83 g, 1.3 mol) in toluene (700 mL). The resulting suspension was refluxed for 24 h. After cooling, the solids were filtered and washed with ethyl acetate (300 mL). The filtrate was extracted with water (10×100 mL), dried (MgSO$_4$), filtered and concentrated to yield 15.9 g (61%) of a white solid that required no further purification.

$^1$H NMR (CDCl$_3$) δ 8.09 (d, 2H, J=8 Hz), 7.57 (d, 2H, J=8 Hz), 5.86 (s, H), 4.07 (m, 4H). MS (ES−) m/e 193 (M−1).

b) 2-{[(2-Phenoxyethyl)thio]methyl}-5-[4-(1,3-dioxolan-2-yl)phenyl]-1,3,4-oxadiazole

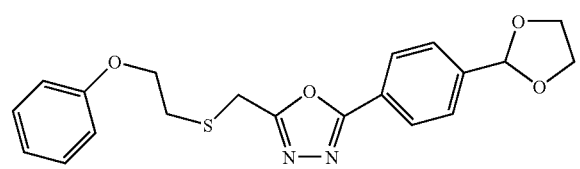

A suspension containing 2-[4-(hydroxycarbonyl)phenyl]-1,3-dioxolane (6.55 g, 33.7 mmol), 2-[(2-phenoxyethyl)thio]acetic acid hydrazide, hydrochloride salt (10.63 g. 40.4 mmol) and 4-(dimethylamino)phenyldiphenylphosphine (30.9 g, 101.1 mmol) was cooled in an ice/water bath.

Triethylamine (28.2 mL, 202.3 mmol) and carbon tetrachloride (16.3 mL, 168.6 mmol) were combined and added dropwise over 5 min. The reaction stirred in the bath for 10 min, then stirred at room temperature for 16 h. The solution was concentrated to about 10% of its original volume and diluted with ethyl ether (300 mL) and 2 NHCl (200 mL). The organic phase was further extracted with 2 N HCl (6×100 mL), dried (MgSO$_4$), filtered and concentrated to yield 8 g (62%) of a yellow solid that was not further purified.

$^1$H NMR (CDCl$_3$) δ 8.03 (d, 2H, J=7 Hz), 7.59 (d, 2H, J=7 Hz), 7.24 (m, 2H), 6.88 (m, 3H), 5.85 (s, 1H), 4.20 (m, 2H), 4.12 (m, 2H), 4.07 (m, 2H), 4.04 (m, 2H), 3.04 (m, 2H). MS (ES+) m/e 385 (M+1).

c) 2-{[(2-Phenoxyethyl)thio]methyl}-5-(4-formylphenyl)-1,3,4-oxadiazole

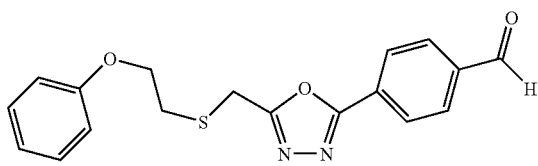

A solution 2-{[(2-phenoxyethyl)thio]methyl}-5-[4-(1,3-dioxolan-2-yl)phenyl]-1,3,4-oxadiazole (8.0 g, 20.8 mmol) and pyridinium p-toluenesulfonate (1.0 g, 4.0 mmol) and water (5 mL) in acetone (200 mL) was refluxed for 6 h, cooled and concentrated. The residue was diluted with ethyl acetate (250 mL) and washed with saturated aqueous sodium bicarbonate (3×60 mL), dried (MgSO$_4$), filtered and concentrated. This residue was purified over silica gel (25% ethyl acetate/hexanes) to yield 2.22 g (31%) of a white solid.

$^1$H NMR (CDCl$_3$) δ 10.08 (s, 1H), 8.18 (d, 2H, J=7 Hz), 7.99 (d, 2H, J=7 Hz), 7.26 (m, 2H), 6.93 (m, 1H), 6.87 (d, 2H, J=8 Hz), 4.20 (t, 2H, J=11 Hz), 4.07 (s, 2H), 3.05 (t, 2H, J=11 Hz). MS (ES+) m/e 341 (M+1).

d) 2-{[(2-Phenoxyethyl)thio]methyl}-5-{4-[(N',N'-dimethyl-1,3-propanediamino)methyl]phenyl}-1,3,4-oxadiazole

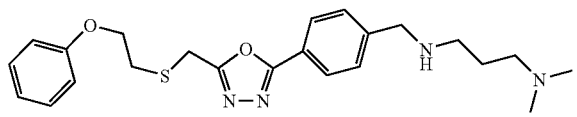

A solution of 2-{[(2-phenoxyethyl)thio]methyl}-5-(4-formylphenyl)-1,3,4-oxadiazole (200 mg, 0.59 mmol), 3-(N,N-dimethylamino)propylamine (0.08 mL, 0.64 mmol) and glacial acetic acid (0.03 mL, 0.59 mmol) in 1,2-dichloroethane (3.0 mL) was stirred under nitrogen at room temperature. Sodium triacetoxyborohydride (190 mg, 0.88 mmol) was added and the reaction stirred for 5 h. The mixture was then diluted with methylene chloride (5 mL), washed with 2 N NaOH (10 mL), dried (MgSO$_4$), filtered and concentrated to yield 0.29 g of a pale yellow oil. This material was purified by preparative TLC [90% methylene chloride/5% methanol/5% (2.0 M ammonia/methanol)] to yield 164 mg (66%) of a colorless oil.

$^1$H NMR (CDCl$_3$) δ 7.97 (d, 2H, J=8 Hz), 7.44 (d, 2H, J=8 Hz), 7.25 (m, 2H), 6.93 (m, 1H), 6.87 (d, 2H, J=8 Hz), 4.19 (t, 2H, J=12 Hz), 4.03 (s, 2H), 3.84 (s, 2H), 3.04 (t, 2H, J=12 Hz), 2.68 (t, 2H, J=14 Hz), 2.34 (t, 2H, J=14 Hz), 2.22 (s, 6H), 1.72 (m, 2H). MS (ES+) m/e 427 (M+1). IR (film, cm$^{-1}$) 3458, 3425, 3397, 1640, 1591, 1491, 1241. Anal. Calcd for C$_{23}$H$_{30}$N$_4$O$_2$S: C, 64.76; H, 7.09; N, 13.13; S, 7.52. Found C, 64.40; H, 6.98; N, 13.29; S, 7.80.

Example 138

Preparation of 2-{[(2-phenoxyethyl)thio]methyl}-5-{[4-[(N,N',N'-trimethyl-1,2-ethanediamino)methyl]phenyl}-1,3,4-oxadiazole

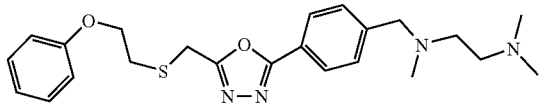

A solution of 2-{[(2-phenoxyethyl)thio]methyl}-5-(4-formylphenyl)-1,3,4-oxadiazole (200 mg, 0.59 mmol), N,N,N'-trimethylethylenediamine (0.15 mL, 1.18 mmol) and glacial acetic acid (0.03 mL, 0.59 mmol) in 1,2-dichloroethane (3.0 mL) was stirred under nitrogen at room temperature. Sodium triacetoxyborohydride (190 mg, 0.88 mmol) was added and the reaction stirred for 3 h. The mixture was then diluted with methylene chloride (5 mL), washed with 2 N NaOH (10 mL), dried (MgSO$_4$), filtered and concentrated to yield 0.31 g of a pale yellow oil. This material was purified by preparative TLC [90% methylene chloride/5% methanol/5% (2.0 M ammonia/methanol)] to yield 172 mg (69%) of a white solid.

$^1$H NMR (CDCl$_3$) δ 7.96 (d, 2H, J=6 Hz), 7.44 (d, 2H, J=6 Hz), 7.25 (m, 2H), 6.93 (1,1H), 6.87 (d, 2H, J=7 Hz), 4.19 (m, 2H), 4.03 (s, 2H), 3.56 (s, 2H), 3.04 (m, 2H), 2.48 (m, 4H), 2.24 (s, 3H), 2.22 (s, 6H). IR (KBr, cm$^{-1}$) 3419, 2945, 2802, 2763, 1594, 1559, 1493, 1460, 1416, 1310, 1237, 1180, 1136, 1083, 1029, 851, 752, 693. MS (ES+) m/e 427 (M+1). Anal. Calcd for C$_{23}$H$_{30}$N$_4$O$_2$S: C, 64.76; H, 7.09; N, 13.13; S, 7.52. Found C, 64.96; H, 7.01; N, 13.47; S, 7.38.

Example 139

Preparation of 2-{[(2-phenoxyethyl)thio]methyl}-5-{4-[(N-benzyl-N',N'-dimethyl-1,2-ethanediamino)methyl]phenyl}-1,3,4-oxadiazole

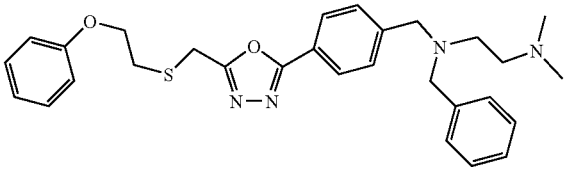

A solution of 2-{[(2-phenoxyethyl)thio]methyl}-5-(4-formylphenyl-1,3,4-oxadiazole (144 mg, 0.42 mmol), N'-benzyl-N,N-dimethylethylenediamine (0.16 mL, 0.85 mmol) and glacial acetic acid (0.025 mL, 0.44 mmol) in 1,2-dichloroethane (3.0 mL) was stirred under nitrogen at room temperature. Sodium triacetoxyborohydride (135 mg, 0.64 mmol) was added and the reaction stirred for 4 h. The mixture was then diluted with methylene chloride (5 mL), washed with 2 N NaOH (10 mL), dried (MgSO$_4$), filtered and concentrated to yield 0.31 g of a pale yellow oil. This material was purified by preparative TLC [90% methylene chloride/5% methanol/5% (2.0 M ammonia/methanol)] to yield 101 mg (47%) of a white solid.

¹H NMR (CDCl₃) δ 7.95 (d, 2H, J=8 Hz), 7.48 (d, 2H, J=8 Hz), 7.32 (m, 5H), 7.27 (m, 2H), 6.92 (m, 1H), 6.87 (d, 2H, J=8 Hz), 4.19 (t, 2H, J=12 Hz), 4.03 (s, 2H), 3.64 (s, 2H), 3.60 (s, 2H), 3.03 (t, 2H, J=12 Hz), 2.58 (dd, 2H, J=7 and 8 Hz), 2.45 (dd, 2H, J=7 and 8 Hz), 2.22 (s, 6H). IR (Kr, cm⁻¹) 3435, 3028, 2970, 2931, 2877, 2793, 1597, 1557, 1496, 1458, 1418, 1364, 1295, 1239, 1170, 1119, 1077, 1018, 971, 836, 746, 694. MS (ES+) m/e 503 (M+1). Anal. Calcd for C₂₉H₃₄N₄O₂S: C, 69.29; H, 6.82; N, 11.15; S, 6.38. Found C, 68.96; H, 6.90; N, 11.15; S, 6.27.

Example 140

Preparation of 2-{[(2-phenoxyethyl)thio]methyl}-5-{4-[(N,N',N'-trimethyl-1,2-propanediamino)methyl]phenyl}-1,3,4-oxadiazole

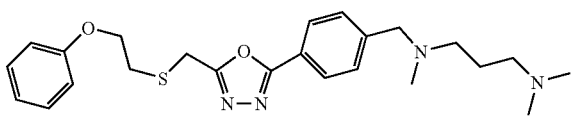

A solution of 2-{[(2-phenoxyethyl)thio]methyl}-5-(4-formylphenyl)-1,3,4-oxadiazole (144 mg, 0.42 mmol), N,N,N'-trimethyl-1,3-propanediamine (0.125 mL, 0.85 mmol) and glacial acetic acid (0.025 mL, 0.44 mmol) in 1,2-dichloro-ethane (3.0 mL) was stirred under nitrogen at room temperature. Sodium triacetoxyborohydride (135 mg, 0.64 mmol) was added and the reaction stirred for 3 h. The mixture was then diluted with methylene chloride (5 mL), washed with 2 N NaOH (10 mL), dried (MgSO₄), filtered and concentrated to yield 0.24 g of a pale yellow oil. This material was purified by preparative TLC [90% methylene chloride/5% methanol/5% (2.0 M ammonia/methanol)] to yield 87 mg (47%) of a colorless oil.

¹H NMR (CDCl₃) δ 7.96 (d, 2H, J=8 Hz), 7.43 (d, 2H, J=8 Hz), 7.25 (m, 2H), 6.92 (m, 1H), 6.87 (d, 2H, J=9 Hz), 4.19 (t, 2H, J=12 Hz), 4.03 (s, 2H), 3.52 (s, 2H), 3.03 (t, 2H, J=12 Hz), 2.40 (dd, 2H, J=7 and 8 Hz), 2.31 (dd, 2H, J=7 and 8 Hz), 2.23 (s, 6H), 2.18 (s, 3H), 1.71 (m, 2H). IR (film, cm⁻¹) 3402, 1595, 1491, 1239, 755, 730. MS (ES+) m/e 442 (M+1). Anal. Calcd for C₂₄H₃₂N₄O₂S: C, 65.42; H, 7.32; N, 12.72; S, 7.28. Found C, 65.68; H, 7.58; N, 12.61; S, 7.23.

Example 141

Preparation of 2-{[(2-phenoxyethyl)thio]methyl}-5-[4-(N-benzyl-N',N'-dimethyl-1,3-propanediamino)phenyl]-1,3,4-oxadiazole

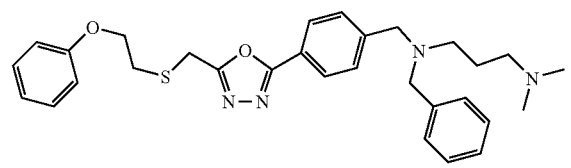

A solution of 2-{[(2-Phenoxyethyl)thio]methyl}-5-{-[(N',N'-dimethyl-1,3-propanediamino)methyl]phenyl}-1,3,4-oxadiazole (110 mg, 0.26 mmol), benzaldehyde (0.03 mL, 0.28 mmol) and glacial acetic acid (0.015 mL, 0.26 mmol) in 1,2-dichloro-ethane (3.0 mL) was stirred under nitrogen at room temperature. Sodium triacetoxyborohydride (82 mg, 0.39 mmol) was added and the reaction stirred for 8 h. The mixture was then diluted with methylene chloride (5 mL), washed with 2 N NaOH (10 mL), dried (MgSO₄), filtered and concentrated to yield 0.15 g of a pale yellow oil. This material was purified by preparative TLC [90% methylene chloride/5% methanol/5% (2.0 M ammonia/methanol)]to yield 52 mg (39%) of a white solid.

¹H NMR (CDCl₃) δ 7.95 (d, 2H, J=8 Hz), 7.47 (d, 2H, J=8 Hz), 7.32 (m, 5H), 7.28 (m, 2H), 6.92 (m, 1H), 6.87 (d, 2H, J=8 Hz), 4.18 (t, 2H, J=12 Hz), 4.03 (s, 2H), 3.59 (s, 2H), 3.56 (s, 2H), 3.03 (t, 2H, J=312 Hz), 2.45 (dd, 2H, J=7 and 8 Hz), 2.24 (m, 2H), 2.17 (s, 6H), 1.68 (m, 2H). IR (KBr, cm⁻¹) 3434, 3026, 2934, 2874, 2785, 2357, 1597, 1558, 1495, 1456, 1419, 1369, 1297, 1239, 1173, 1118, 1075, 1020, 967, 830, 745, 693. MS (ES+) m/e 518 (M+1). Anal. Calcd for C₃₀H₃₆N₄O₂S: C, 69.74; H, 7.02; N, 10.84; S, 6.21. Found C, 69.65; H, 6.96; N, 10.67; S, 6.39.

Example 142

Preparation of 2-{[(2-phenoxyethyl)thio]methyl}-5-{4-[(N,N-bis-(3-N',N'-dimethyl)propyl)amino)methyl]phenyl}-1,3,4-oxadiazole

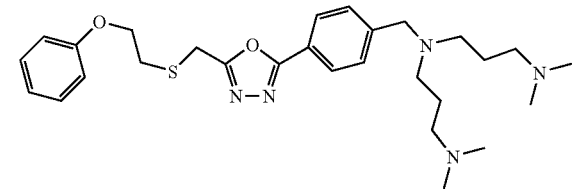

A solution of 2-{[(2-phenoxyethyl)thio]methyl}-5-(4-formylphenyl)-1,3,4-oxadiazole (163 mg, 0.48 mmol), 3,3'-iminobis-(N,N-dimethylpropylamine) (0.22 mL, 0.99 mmol) and glacial acetic acid (0.03 mL, 0.52 mmol) in 1,2-dichloroethane (4.0 mL) was stirred under nitrogen at room temperature. Sodium triacetoxyborohydride (153 mg, 0.72 mmol) was added and the reaction stirred for 16 h. The mixture was then diluted with methylene chloride (10 mL), washed with 2 N NaOH (10 mL), dried (MgSO₄), filtered and concentrated to yield 0.35 g of a pale yellow oil. Half of this material was purified by preparative TLC [90% methylene chloride/5% methanol/5% (2.0 M ammonia-methanol)]to yield 84 mg (34%) of a white solid.

¹H NMR (CDCl₃) δ 7.94 (d, 2H, J=8 Hz), 7.43 (d, 2H, J=8 Hz), 7.25 (m, 2H), 6.90 (m, 1H), 6.88 (d, 2H, J=8 Hz), 4.19 (t, 2H, J=12 Hz), 4.03 (s, 2H), 3.59 (s, 2H), 3.04 (t, 2H, J=12 Hz), 2.44 (t, 4H, J=15 Hz), 2.26 (t, 4H, J=15 Hz), 2.20 (s, 12H), 1.63 (m, 4H). IR (KBr, cm⁻¹) 3430, 2939, 2889, 2863, 2812, 2770, 2720, 1599, 1562, 1497, 1461, 1380, 1297, 1242, 1173, 1082, 1027, 826, 751, 691. MS (ES+) m/e 513 (M+1). Anal. Calcd for C₂₈H₄₁N₅O₂S: C, 65.72; H, 8.08; N, 13.68; S, 6.26. Found C, 65.19; H, 8.10; N, 13.39; S, 6.28.

Example 143

Preparation of 2-{[(2-phenoxyethyl)thio]methyl}-5-{4-[(N',N'-dimethyl-1,2-ethanediamino)methyl]phenyl}-1,3,4-oxadiazole

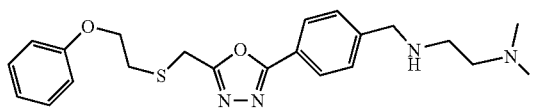

A solution of 2-{[(2-phenoxyethyl)thio]methyl}-5-(4-formylphenyl)-1,3,4-oxadiazole (340 mg, 1.0 mmol), N,N-dimethyl-1,2-ethylenediamine (0.22 mL, 2.0 mmol) and glacial acetic acid (0.06 mL, 1.0 mmol) in 1,2-dichloroethane (6.0 mL) was stirred under nitrogen at room temperature. Sodium triacetoxyborohydride (320 mg, 1.5 mmol) was added and the reaction stirred for 16 h. The mixture was then diluted with methylene chloride (10 mL), washed with 2 N NaOH (10 mL), dried (MgSO$_4$), filtered and concentrated to yield 0.43 g of a pale yellow oil. This material was purified by preparative TLC [90% methylene chloride/5% methanol/5% (2.0 M ammonia/methanol)] to yield 154 mg (37%) of a white solid.

$^1$H NMR (CDCl$_3$) δ 7.97 (d, 2H, J=8 Hz), 7.45 (d, 2H, J=8 Hz), 7.25 (m, 2H), 6.93 (m, 1H), 6.87 (d, 2H, J=8 Hz), 4.19 (t, 2H, J=2 Hz), 4.03 (s, 2H), 3.86 (s, 21), 3.04 (t, 2H, J=12 Hz), 2.67 (t, 2H, J=12 Hz), 2.43 (t, 2H, J=12 Hz), 2.20 (s, 6H). IR (KBr, cm$^{-1}$) 3423, 3318, 2970, 2928, 2856, 2812, 2781, 1595, 1560, 1492, 1461, 1418, 1237, 1079, 1019, 818, 757, 697. MS (ES+) m/e 414 (M+1). Anal. Calcd for C$_{22}$H$_{28}$N$_4$O$_2$S: C, 64.05; H, 6.84; N, 13.58; S, 7.77. Found C, 64.32; H, 6.24; N, 13.52; S, 7.60.

Example 144

Preparation of (+)-2-{[(2-phenoxyethyl)thio]methyl}-5-{4-[((1-benzyl-2-(N,N-dimethylamino)ethyl)amino)methyl]phenyl}-1,3,4-oxadiazole

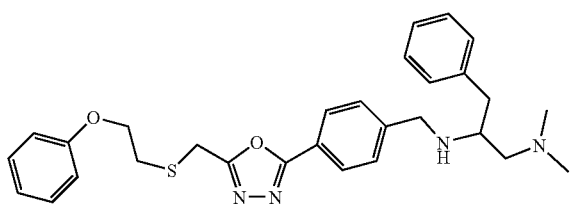

a) (+)-N-(tert-Butyloxycarbonyl)-2-benzylaziridine

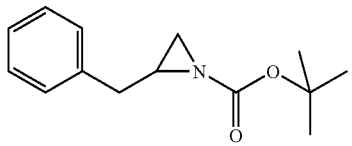

A solution of (+)-2-amino-3-phenylpropanol (6 g, 40 mmol) and di-t-butyl dicarbonate (9.53 g, 44 mmol) in isopropyl alcohol (20 mL) and 1,4-dioxane (40 mL) was stirred at room temperature for 4 h. The reaction was concentrated and vacuum dried. This material, p-toluenesulfonyl chloride (9.2 g, 48 mmol) and potassium hydroxide (9.0 g, 160 mmol) were stirred in ethyl ether (400 mL) at room temperature for 20 h. The mixture was then poured into ice water (400 mL). The aqueous material was extracted with ethyl ether (300 mL) and the combined organic fractions were dried (MgSO$_4$), filtered and concentrated to yield 9.0 g (97%) of a colorless oil.

$^1$H NMR (CDCl$_3$) δ 7.25 (m, 5H), 2.95 (m, 1H), 2.60 (m, 2H), 2.33 (m, 1H), 2.00 (m, 1H), 1.42 (s, 9H). MS (ES+) m/e 134 (M+1-Boc).

b) (+)-N,N-Dimethyl-2-amino-3-phenylpropylamine

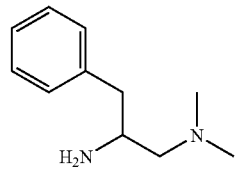

A solution of (+)-N-boc-2-benzylaziridine (3.0 g, 12.9 mmol) and dimethylamine (2.0 M in THF, 50 mL, 100 mmol) in anhydrous acetonitrile (20 mL) was split among three sealed tubes and refluxed for 20 h. The mixture was concentrated to yield 4.0 g of an orange oil. This material was dissolved in methanol (20 mL) and loaded onto a column containing Bio-Rad 50W-X2 cationic exchange resin (60 g, pre-washed with 800 mL of methanol). The column was washed with methanol (800 mL) and methylene chloride (200 mL). The product was eluted with 2.0 N ammonia/methanol (400 mL) and concentrated to yield 3.2 g (89%) of an orange oil. This product was dissolved in 25% trifluoroacetic acid/methylene chloride (40 mL) and stirred at room temperature for 16 h. The reaction was concentrated, dissolved in methanol (5 mL) and added dropwise to 2N HCl in ethyl ether to generate a solid hydrochloride salt, but the result was a thick oil which would not crystallize. This mixture was then concentrated, dissolved in methanol (20 mL) and loaded onto another column of 50W-X2 resin (50 g), described above. The product was, isolated (1.86 g, 91% yield) as a yellow oil.

$^1$H NMR (CDCl$_3$) δ 7.17–7.30 (m, 5H), 3.12 (m, 1H), 2.72 (dd, 1H, J=5 and 9 Hz), 2.45 (dd, 1H, J=5 and 9 Hz), 2.21 (s, 6H), 2.14 (m, 2H). MS (ES+) m/e 179 (M+1).

c) (+)-2-{[(2-Phenoxyethyl)thio]methyl}-5-{4-[((1-benzyl-2-(N,N-dimethylamino)ethyl)amino)methyl]phenyl}-1,3,4-oxadiazole

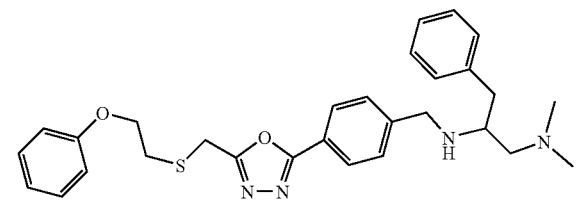

A solution of 2-{[(2-phenoxyethyl)thio]methyl}-5-(4-formylphenyl)-1,3,4-oxadiazole (205 mg, 0.6 mmol), (+)-N, N-dimethyl-2-amino-3-phenylpropylamine hydrochloride salt (430 mg, 2.0 mmol) and glacial acetic acid (0.06 mL, 1 mmol) in 1,2-dichloroethane (8 mL) was stirred under nitrogen at room temperature. Sodium triacetoxyborohydride (191 mg, 0.9 mmol) was added and the reaction stirred for 2 h. The mixture was diluted with methylene chloride (10 mL), extracted with 2 N NaOH (10 mL), dried (MgSO$_4$), filtered and concentrated to yield 483 mg of an orange oil. This oil was purified by preparative TLC [90% methylene chloride/5% methanol/5% (2.0 N ammonia in methanol)] to yield 98 mg (32%) of a solid.

$^1$H NMR (CDCl$_3$) δ 7.94 (d, 2H, J=8 Hz), 7.36 (d, 2H, J=8 Hz), 7.25 (m, 5H), 7.18 (m, 1H), 7.14 (d, 2H, J=8 Hz), 6.93 (dd, 1H, J=7 and 8 Hz), 6.88 (d, 2H, J=9 Hz), 4.19 (t, 2H, J=12 Hz), 4.03 (s, 2H), 3.78 (dd, 2H, J=14 and 14 Hz), 3.04 (t, 2H, J=12 Hz), 2.82 (m, 1H), 2.61 (m, 1H), 2.29 (m, 1H), 2.08 (s, 6H), 2.05 (m, 1H). IR (KBr, cm$^{-1}$) 3027, 2978, 2933, 2885, 2853, 2816, 2777, 1599, 1562, 1495, 1454, 1359, 1289, 1244, 1167, 1121, 1078, 1025, 976, 835, 803, 749, 696, 512. MS (ES+) m/e 503 (M+1). Anal. Calcd for C$_{29}$H$_{34}$N$_4$O$_2$S: C, 69.29; H, 6.82; N, 11.15; S, 6.38. Found C, 69.65; H, 6.84; N, 10.90; S, 6.22.

Example 145

Preparation of (+)-2-{[(2-phenoxyethyl)thio]methyl}-5-{4-[4-(N,N-dimethylamino)-1-hydroxybutyl]phenyl}-1,3,4-oxadiazole

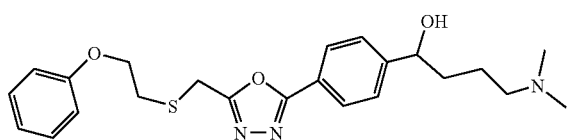

a) (+)-2-{[(2-Phenoxyethyl)thio]methyl}-5-{4-[3-(1,3-dioxolan-2-yl)-1-hydroxypropyl]phenyl}-1,3,4-oxadiazole

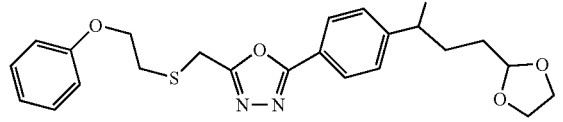

A mixture of 1,2-dibromoethane (0.09 mL, 1 mmol) and magnesium turnings (243 mg, 10 mmol) in anhydrous tetrahydrofuran (5 mL) was cooled in an ice water bath under nitrogen. A solution of 2-(2-bromoethyl)-1,3-dioxolane (1.5 mL, 12.5 mmol) in tetrahydrofuran (1 mL) was added dropwise and the mixture stirred in the cooling bath for 10 min. The mixture was then stirred at room temperature until the magnesium had gone into solution (50 min). After cooling in a dry ice/isopropanol bath, a solution of 2-{[(2-phenoxyethyl)thio]methyl}-5-(4-formylphenyl)-1,3,4-oxadiazole in tetrahydrofuran (5 mL) was added dropwise and stirred for 2 h in the cooling bath. The reaction was quenched with saturated aqueous ammonium chloride (20 mL) and extracted with ethyl acetate (3×20 mL). The organic material was extracted with brine (25 mL), dried (MgSO$_4$), filtered and concentrated to yield 1.56 g of a pale yellow oil. This oil was purified by silica gel (50% ethyl acetate/hexanes) to yield 781 mg (88%) of an oil.

$^1$H NMR (CDCl$_3$) δ 7.98 (d, 2H, J=8 Hz), 7.47 (d, 2H, J=8 Hz), 7.24 (m, 1H), 6.93 (dd, 1H, J=6 and 7 Hz), 6.87 (d, 2H, J=7 Hz), 4.91 (t, 1H, J=8 Hz), 4.81 (m, 1H), 4.19 (t, 2H, J=12 Hz), 4.03 (s, 2H), 3.95 (m, 2H), 3.86 (m, 2H), 3.03 (t, 2H, J=12 Hz), 2.85 (d, 1H, J=4 Hz), 1.89 (m, 2H), 1.82 (m, 2H). MS (ES+) m/e 443 (M+1).

b) (+)-2-{[(2-Phenoxyethyl)thio]methyl}-5-[4-(5-hydroxy-2,3,4,5-tetrahydrofuran-2-yl)phenyl]-1,3,4-oxadiazole, mixture of cis- and trans-isomers

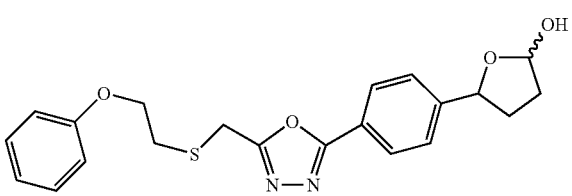

A mixture of (+)-2-{[(2-Phenoxyethyl)thio]methyl}-5-{4-[3-(1,3-dioxolan-2-yl)-1-hydroxypropyl]phenyl}-1,3,4-oxadiazole (658 mg, 1.49 mmol) and iron (III) chloride hexahydrate (1.41 g, 5.21 mmol) in methylene chloride (30 mL) was stirred at room temperature for 1 h. The reaction was quenched with saturated aqueous sodium bicarbonate (25 mL) and extracted with methylene chloride (3×25 mL). The organic material was washed with brine (4×20 mL), dried (MgSO$_4$), filtered and concentrated to yield 498 mg of an orange oil. This oil was purified by preparative TLC (50% ethyl acetate/hexanes to yield 103 mg (17%) of a colorless oil.

$^1$H NMR (CDCl$_3$) δ 7.99 (d, 2H, J=8 Hz), 7.52 (d, 1H, J=8 Hz), 7.42 (d, 1H, J=8 Hz), 7.24 (m, 1H), 6.93 (dd, 1H, J=7 and 8 Hz), 6.87 (d, 2H, J=7 Hz), [cis/trans protons: 5.79 (m, 0.5H), 5.66 (m, 0.5H), 5.29 (m, 0.5H), 5.06 (m, 0.5H)], 4.19 (t, 2H, J=12 Hz), 4.03 (s, 2H), 3.04 (t, 2H, J=12 Hz), 2.73 (br s, 0.5H), 2.56 (br s, 0.5H), 2.33–2.54 (m, 1H), 1.96–2.18 (m, 2H), 1.76 (m, 1H). MS (ES+) m/e 399 (M+1).

c) (+)-2-{[(2-phenoxyethyl)thio]methyl}-5-{4-[4-(N,N-dimethylamino)-1-hydroxybutyl]phenyl}-1,3,4-oxadiazole

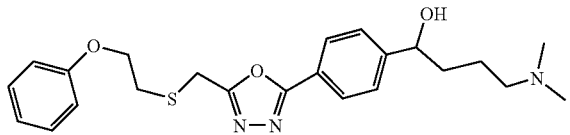

A solution of cis- and trans-(+)-2-{[(2-phenoxyethyl)thio]methyl}-5-[4-(5-hydroxy-2,3,4,5-tetrahydrofuran-2-yl)phenyl]-1,3,4-oxadiazole (100 mg, 0.25 mmol), dimethylamine (2.0 M in THF, 2 mL, 4 mmol) and glacial acetic acid (0.02 mL, 0.35 mmol) in 1,2-dichloroethane was stirred under nitrogen. Sodium triacetoxyborohydride (160 mg, 0.76 mmol) was added and the reaction stirred at room temperature for 16 h. The mixture was diluted with methylene chloride (10 mL) and extracted with 2N NaOH (10 mL), dried (MgSO$_4$), filtered and concentrated to yield 210 mg of an orange oil. This oil was purified by preparative TLC [90% methylene chloride/5% methanol/5% (2.0 N ammonia in methanol)]to yield 35 mg (33%) of a white solid.

$^1$H NMR (CDCl$_3$) δ 7.97 (d, 2H, J=8 Hz), 7.51 (d, 2H, J=8 Hz), 7.24 (m, 2H), 6.92 (dd, 1H, J=7 and 8 Hz), 6.87 (d, 2H, J=8 Hz), 4.72 (d, 1H, J=6 Hz), 4.19 (t, 2H, J=12 Hz), 4.03 (s, 2H), 3.47 (s, 1H), 3.03 (t, 2H, J=12 Hz), 2.42 (m, 2H), 2.32 (s, 6H), 1.99 (m, 2H), 1.75–1.86 (m, 2H). IR (KBr, cm$^{-1}$) 3407, 3167, 3093, 3058, 2916, 2868, 2794, 2734, 1594, 1562, 1493, 1464, 1414, 1293, 1236, 1171, 1078, 1013, 838, 755, 696. MS (ES+) m/e 428 (M+1). Anal. Calcd for C$_{23}$H$_{29}$N$_3$O$_3$S: C, 64.61; H, 6.84; N, 9.83; S, 7.50. Found C, 64.66; H, 6.41; N, 9.31; S, 7.30.

Example 146

Preparation of (E)-2-{[(2-Phenoxyethyl)thio]methyl}-5-[4-(3-amino-3-benzylpropen-1-yl)phenyl]-1,3,4-oxadiazole

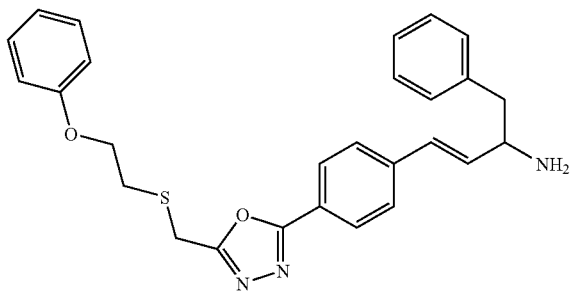

a) 2-{[(2-Phenoxyethyl)thio]methyl}-5-{4-[3-benzyl-3-(tert-butoxycarbonylamino)propen-1-yl]phenyl}-1,3,4-oxadiazole

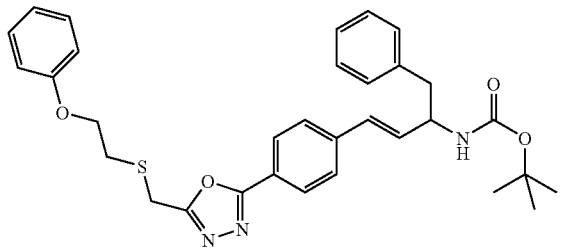

A mixture of 2-{[(2-phenoxyethyl)thio]methyl}-5-(4-formylphenyl)-1,3,4-oxadiazole (510 mg, 1.5 mmol), 1-(terbutoxycarbonyl)-2-benzylaziridine (R- or S-isomer, 933 mg, 4 mmol), and triphenylphosphine (1.05 g, 4 mmol) in 2-propanol (2 mL) was stirred in a sealed tube at 95~100° C. (bath temperature) for 3 days. The reaction mixture was concentrated and purified by chromatography (silica gel, EtOAc/hexanes 1:5). The isolated product was triturated from methylene chloride and haxanes to give pure E-olefines: R-isomer (210 mg, 25%), S-isomer (241 mg, 29%).

$^1$H NMR (CDCl$_3$) δ 7.93 (d, 2H, J=8.4 Hz), 7.40 (d, 2H, J=8.1 Hz), 7.18~7.31 (m, 7H), 6.93 (t, 1H, J=7.3 Hz), 6.87 (d, 2H, J=7.6 Hz) 6.46 (d, 1H, J=16.1 Hz), 6.25 (dd, 1H, J=16.1, 5.6 Hz), 4.52~4.65 (m, 2H), 4.19 (t, 2H, J=6.1 Hz), 4.03 (s, 2H), 3.04 (t, 2H, J=6.1 Hz), 2.93 (d, 2H, J=6.3 Hz), 1.40 (s, 9H). IR (KBr, cm$^{-1}$) 3014, 2949, 2796, 2251, 1688, 1598, 1553, 1326, 1243, 926, 744, 651. MS (ES+) m/e 558 (M+1). Anal. Calcd for C$_{32}$H$_{35}$N$_3$O$_4$S: C, 68.92; H, 6.33; N, 7.53; S, 5.75. Found R-isomer, C, 68.84; H, 6.35; N, 7.44; S, 5.82; S-isomer, C, 68.88; H, 6.27; N, 7.36; S, 5.79.

b) 2-{[(2-Phenoxyethyl)thio]methyl}-5-[4-(3-amino-3-benzylpropen-1-yl)phenyl]-1,3,4-oxadiazole

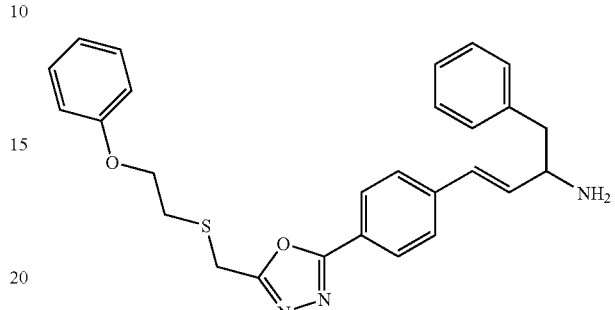

Trifluoroacetic acid (0.5 mL) was added to a solution of 2-{[(2-Phenoxyethyl)thio]methyl}-5-{4-[3-benzyl-3-(tert-butoxycarbonylamino)propen-1-yl]phenyl}-1,3,4-oxadiazole (139 mg, 0.25 mmol) in methylene chloride (2 mL). The resultant mixture was stirred at room temperature overnight, concentrated, and partitioned between methylene chloride (20 mL) and 2 M NaOH (5 mL). The organic layer was dried (MgSO$_4$), concentrated and purified by chromatography (silica gel, 5% methanol/methylene chloride) to give a pale yellow solid: R-isomer, 87 mg, 76%; S-isomer, 80 mg, 70%.

$^1$H NMR (CDCl$_3$) δ 7.93 (d, 2H, J=8.5 Hz), 7.44 (d, 2H, J=8.4 Hz), 7.21~7.32 (m, 7H), 6.93 (t, 1H, J=7.3 Hz), 6.87 (d, 2H, J=7.7 Hz) 6.53 (d, 1H, J=16.1 Hz), 6.36 (dd, 1H, J=15.8, 6.6 Hz), 4.19 (t, 2H, J=6.2 Hz), 4.03 (s, 2H), 3.81 (m, 11H), 3.04 (t, 2H, J=6.2 Hz), 2.93 (dd, 2H, J=13.3, 5.3 Hz), 2.73 (dd, 1H, J=13.3, 8.2 Hz). IR (KBr, cm$^{-1}$) 3028, 2935, 2866, 2830, 1601, 1560, 1494, 1464, 1221, 1050, 915, 733, 700. MS (ES+) m/e 458 (M+1). Anal. Calcd for C$_{27}$H$_{27}$N$_3$O$_2$S: C, 70.87; H, 5.95; N, 9.18; S, 7.01. Found R-isomer, C, 70.52; H, 5.93; N, 9.03; S, 7.28; S-isomer, C, 70.94; H, 5.88; N, 9.12; S, 7.00.

Example 147

Preparation of (E)-2-{[(2-Phenoxyethyl)thio]methyl}-5-{4-[3-benzyl-3-(2-(N,N-dimethylamino)acetamido)propen-1-yl]phenyl}-1,3,4-oxadiazole

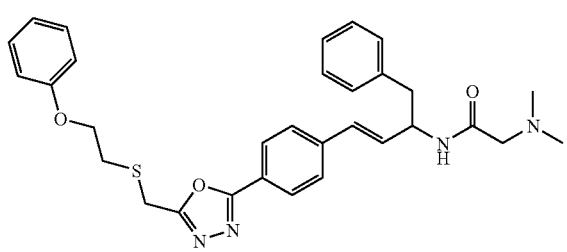

A mixture of 2-{[(2-Phenoxyethyl)thio]methyl}-5-[4-(3-amino-3-benzylpropen-1-yl)phenyl]-1,3,4-oxadiazole (46 mg, 0.1 mmol) and N,N-dimethylglycine (20 mg, 0.2 mmol) in pyridine (1 mL), under nitrogen, was cooled to −10~−5° C. (ice-salt bath) and phosphorus oxychloride (0.05 mL, 0.5 mmol) was added. The mixture was stirred at −10~−5° C. for 90 min and water (2 mL), followed by ethyl acetate (25 mL), was added. The mixture was washed with 2 M NaOH (2×5 mL), water (3×10 mL), and brine (10 mL), dried MgSO$_4$), and concentrated. The residue was co-evaporated with toluene (20 mL) under reduced pressure and purified by preparative TLC (silica gel, 5% methanol/methylene chloride) to give a white solid: R-isomer, 34 mg, 62%; S-isomer, 35 mg, 65%.

$^1$H NMR (CDCl$_3$) δ 7.93 (d, 2H, J=8.5 Hz), 7.41 (d, 2H, J=8.5 Hz), 7.19~7.30 (m, 7H), 6.93 (t, 1H, J=7.3 Hz), 6.87 (d, 2H, J=7.7 Hz) 6.49 (d, 1H, J=16.1 Hz), 6.29 (dd, 1H, J=16.1, 6.2 Hz), 4.95 (m, 1H), 4.19 (t, 2H, J=6.2 Hz), 4.03 (s, 2H), 3.04 (t, 2H, J=6.2 Hz), 2.82~3.06 (m, 4H), 2.18 (s, 6H). IR (KBr, cm$^{-1}$) 3402, 3025, 2958, 2855, 2799, 2776, 1688, 1597, 1550, 1494, 1481, 1239, 1058, 980, 751. MS (ES+) m/e 543 (M+1). Anal. Calcd for C$_{31}$H$_{34}$N$_4$O$_3$S: C, 68.61; H, 6.31; N, 10.32; S, 5.91. Found R-isomer C, 68.88; H, 6.27; N, 10.25; S, 5.74; S-isomer C, 68.78; H, 6.22; N, 10.24; S, 5.92.

Example 148

Preparation of (R)-(E)-2-{[(2-phenoxyethyl)thio]methyl}-5-{4-[3-benzyl-3-(N,N-dimethylamino)propen-1-yl]phenyl}-1,3,4-oxadiazole

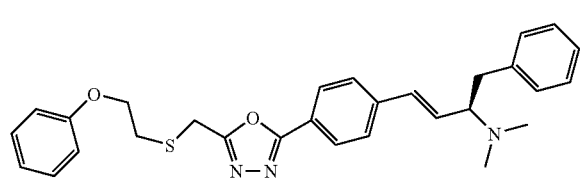

A solution containing (R)-(E)-2-{[(2-phenoxyethyl)thio]methyl}-5-[4-(3-benzyl-3-aminopropen-1-yl)phenyl]-1,3,4-oxadiazole (258 mg, 0.56 mmol) and paraformaldehyde (170 mg, 5.6 mmol) in methanol (6.0 mL) was refluxed for 3 h. The mixture was cooled and sodium cyanoborohydride (107 mg, 1.70 mmol) was added; the reaction stirred at room temperature for 2 h. The mixture was diluted with water (10 mL) and the methanol was removed in vacuo. Saturated aqueous sodium bicarbonate (10 mL) was added and the mixture was extracted with methylene chloride (3×15 mL). The organic material was dried (MgSO$_4$), filtered and concentrated to yield 355 mg of an orange oil. This oil was purified by preparative TLC (10% methanol/methylene chloride) to yield 163 mg (59%) of a pale yellow oil.

$^1$H NMR (CDCl$_3$) δ 7.91 (d, 2H, J=9 Hz), 7.35 (d, 2H, J=8 Hz), 7.24 (m, 5H), 7.13 (m, 2H), 6.93 (dd, 1H, J=7 and 8 Hz), 6.87 (d, 2H, J=8 Hz), 4.18 (t, 2H, J=12 Hz), 4.03 (s, 2H), 3.20 (m, 1H), 3.11 (dd, 2H, J=4 and 9 Hz), 3.03 (t, 2H, J=12 Hz), 2.75 (dd, 2H, J=4 and 9 Hz), 2.37 (s, 6H). IR (film, cm$^{-1}$) 3030, 2935, 2865, 2823, 2779, 1599, 1557, 1494, 1462, 1239, 1078, 1031, 910, 733, 699. MS (ES+) m/e 486 (M+1). Anal. Calcd for C$_{29}$H$_{31}$N$_3$O$_2$S: C, 71.72; H, 6.43; N, 8.65; S, 6.60. Found C, 71.26; H, 6.21; N, 8.54; S, 6.53.

Example 149

Preparation of 2-{[(2-Phenoxyethyl)thio]methyl}-5-{4-[(4-(N,N-dimethylamino)butanoyl)amino]phenyl}-1,3,4-oxadiazole

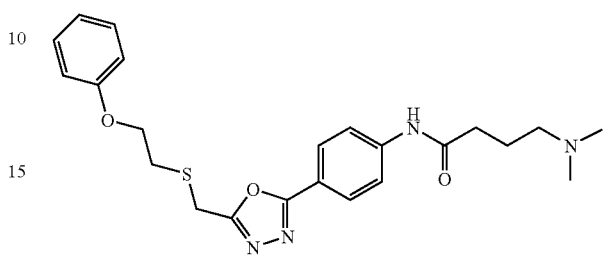

a) 2-{[(2-Phenoxyethyl)thio]methyl}-5-(4-nitrophenyl)-1,3,4-oxadiazole

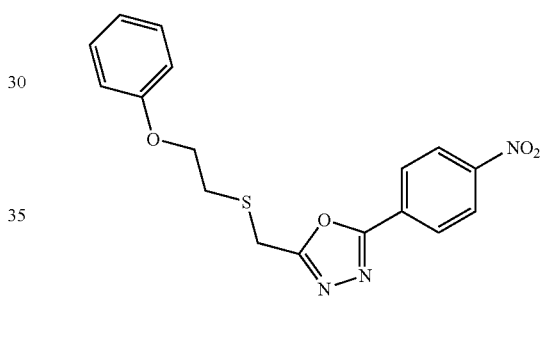

A mixture of 4-nitrobenzoic hydrazide (4.35 g, 24 mmol), 2-(2-phenoxyethylthio)acetic acid (4.25 g, 20 mmol), and (4-N,N-dimethylaminophenyl)diphenylphosphine (18.32 g, 60 mmol) in acetonitrile (200 mL) was stirred and cooled with an ice bath. A mixture of triethylamine (10.12 g, 100 mmol) and carbon tetrachloride (15.38 g, 100 mmol) was added dropwise over 5 min. The cooling was maintained for additional 10 min and removed, and the mixture was allowed to stir overnight. The resultant mixture was concentrated to approximately half the original volume. Diethyl ether (50 mL) and 2 N HCl (300 mL) were added and the mixture was swirled until all solid was dispersed. The solid was collected by filtration and transferred to a beaker. 2 M HCl (300 mL) was added and the mixture was stirred until finely dispersed. The solid was collected by filtration and similarly washed again with 2M HCl (300 mL), followed by water (300 mL). The solid was air-dried to give a light tan powder (5.01 g, 70%).

$^1$H NMR (CDCl$_3$) δ 8.33 (d, 2H, J=9.2 Hz), 8.18 (d, 2H, J=9.2 Hz), 7.22~7.26 (m, 2H), 6.93 (t, 1H, J=7.3 Hz), 6.86 (d, 2H, J=7.7 Hz), 4.20 (t, 2H, J=6.1 Hz), 4.08 (s, 2H), 3.05 (t, 2H, J=6.0 Hz). MS (ES+) m/e 358. (M+1).

b) 2-{[(2-Phenoxyethyl)thio]methyl}-5-(4-aminophenyl)-1,3,4-oxadiazole

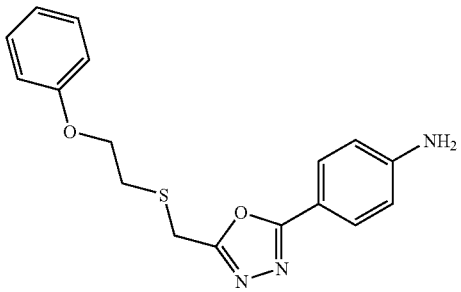

A mixture of 2-{[(2-phenoxyethyl)thio]methyl}-5-(4-nitrophenyl)-1,3,4-oxadiazole (3.57 g, 10 mmol), indium powder (8.03 g, 70 mmol), ethanol (40 mL), and sat. aqueous ammonium chloride (12 mL), added in that order, was stirred under reflux for 2 h. 2 M NaOH (50 mL) was added and the mixture was filtered over Celite. The reaction flask and Celite pad were washed with methylene chloride (50 mL). The combined filtrates were evaporated to remove dichloromethane and most ethanol. The precipitate was collected by filtration, washed with water (15 mL) and ethanol (3 mL), and air-dried to give the desired product (yellow to orange solid, 75~80% yield).

$^1$H NMR (CDCl$_3$) δ 7.79 (d, 2H, J=8.4 Hz), 7.22~7.26 (m, 2H), 6.92 (t, 1H, J=7.3 Hz), 6.87 (d, 2H, J=8.1 Hz), 6.69 (d, 2H, J=8.8 Hz), 4.17 (t, 2H, J=6.2 Hz), 3.99 (s, 2H), 3.02 (t, 2H, J=6.2 Hz). MS (ES+) m/e 328 (M+1).

c) 2-{[(2-Phenoxyethyl)thio]methyl}-5-{4-[(4-(N,N-dimethylamino)butanoyl)amino]phenyl}-1,3,4-oxadiazole

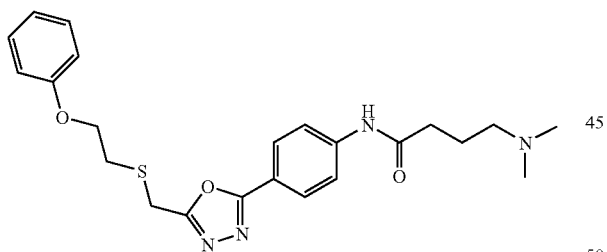

To a suspension of 4-(N,N-dimethylamino)butyric acid hydrochloride (1.67 g, 10 mmol) in N,N-dimethylformamide (0.5 mL) and methylene chloride (50 mL) was added oxalyl chloride (1.48 mL, 17 mmol) dropwise over a period of 10 min. The mixture was stirred at room temperature for 2 h and evaporated under reduced pressure to remove methylene chloride and excess oxalyl chloride. The resultant white solid was dissolved in methylene chloride (5 mL) and added dropwise over 2 min to a solution of 2-{[(2-phenoxyethyl)thio]methyl}-5-(4-aminophenyl)-1,3,4-oxadiazole (982 mg, 3 mmol), 4-(N,N-dimethylamino)pyridine (183 mg, 1.5 mmol), and triethylamine (1.01 g, 10 mmol) in methylene chloride (25 mL) at 0° C. After 20 min the cooling bath was removed, and the mixture was allowed to stir overnight, washed with 2 M NaOH (4×15 mL), dried (MgSO$_4$), and concentrated. The residue was dissolved in methanol (30 mL), diluted with water (5 mL), and concentrated under reduced pressure to remove most methanol. The precipitate was collected by filtration, washed with water (5 mL), redissolved in methylene chloride (30 mL), washed with water (15 mL), dried (MgSO$_4$), and concentrated. The residue was triturated from methylene chloride and hexanes to give an off-white solid (839 mg, 64%).

$^1$H NMR (CDCl$_3$) δ 10.60 (s, 1H), 7.94 (d, 2H, J=8.4 Hz), 7.65 (d, 2H, J=8.8 Hz), 7.22~7.26 (m, 2H), 6.92 (t, 1H, J=7.3 Hz), 6.87 (d, 2H, J=7.7 Hz), 4.18 (t, 2H, J=6.2 Hz), 4.02 (s, 2H), 3.03 (t, 2H, J=6.0 Hz), 2.49~2.57 (m, 4H), 2.36 (s, 6H), 1.87~1.91 (m, 2H). IR (KBr, cm$^{-1}$) 3494, 3456, 3313, 2939, 1666, 1605, 1499, 1465, 1243, 1177, 1035, 760. MS (ES+) m/e 441 (M+1). Anal. Calcd for C$_{23}$H$_{28}$N$_4$O$_3$S: C, 62.70; H, 6.41; N, 12.72; S, 7.28. Found C, 62.59; H, 6.51; N, 12.69; S, 7.23.

Example 150

Preparation of 2-{[(2-Phenoxyethyl)thio]methyl}-5-{4-[2-(N,N',N'-trimethylethylenediamino)acetamido]phenyl}-1,3,4-oxadiazole

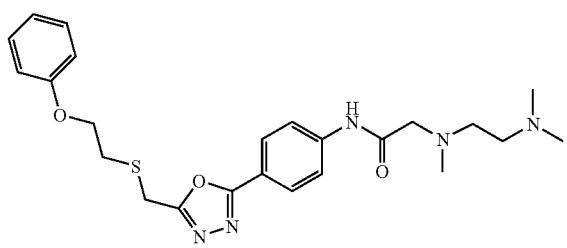

a) 2-{[92-Phenoxyethyl)thio]methyl}-5-[4-(2-chloroacetamido)phenyl]-1,3,4-oxadiazole

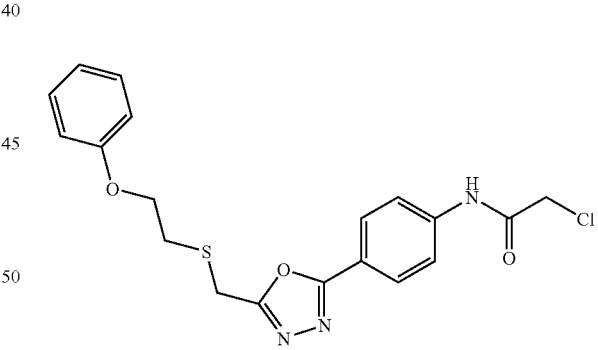

A suspension of 2-{[(2-phenoxyethyl)thio]methyl}-5-(4-aminophenyl)-1,3,4-oxadiazole (1.636 g, 5 mmol) in toluene (30 mL) was heated to approximately 50° C. and chloroacetic chloride (1.636 mL, 20 mmol) was added. The mixture was stirred under reflux for 4 h and allowed to cool to room temperature. The solid was collected by filtration, washed with hexanes and air-dried to give the desired product (1.61 g, 80%).

$^1$H NMR (CDCl$_3$) δ 8.8 (s, 1H), 8.01 (d, 2H, J=8.6 Hz), 7.70 (d, 2H, J=8.6 Hz), 7.23~7.27 (m, 2H), 6.93 (t, 1H, J=7.4 Hz), 6.87 (d, 2H, J=7.8 Hz), 4.21 (s, 2H), 4.19 (t, 2H, J=6.2 Hz), 4.03 (s, 2H), 3.04 (t, 2H, J=6.2 Hz). MS (ES+) m/e 404 (M+1).

b) 2-{[(2-Phenoxyethyl)thio]methyl}-5-{4-[2-(N,N', N'-trimethylethylenediamino)acetamido]phenyl}-1, 3,4-oxadiazole

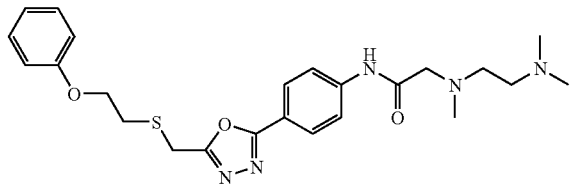

A mixture of 2-{[(2-phenoxyethyl)thio]methyl}-5-[4-(2-chloroacetamido)phenyl]1,3,4-oxadiazole (100 mg, 0.25 mmol) and N,N,N'-trimethylethylenediamine (1.5 mL) was stirred at room temperature overnight and excess N,N,N'-trimethylethylenediamine was evaporated under vacuum. The residue was purified by preparative TLC (silica gel, 10% methanol/methylene chloride) to give a pale yellow oil (100 mg, 85%).

$^1$H NMR (CDCl$_3$) δ 10.41 (s, 1H), 7.96 (d, 2H, J=8.5 Hz), 7.79 (m, 2H), 7.23~7.27 (m, 2H), 6.93 (t, 1H, J=7.3 Hz), 6.88 (d, 2H, J=7.6 Hz), 4.19 (t, 2H, J=6.0 Hz), 4.02 (s, 2H), 3.20 (s, 2H), 3.03 (t, 2H, J=6.0 Hz), 2.60 (m, 2H), 2.44 (s, 6H), 2.27 (m, 5H). IR (film, cm$^{-1}$) 3458, 3321, 2940, 1669, 1602, 1501, 1411, 1257, 1181, 753. MS (ES+) m/e 468 (M+1). Anal. Calcd for C$_{25}$H$_{33}$N$_5$O$_2$S: C, 64.21; H, 7.11; N, 14.98; S, 6.86. Found C, 64.10; H, 7.06; N, 14.79; S, 6.88.

Example 151

Preparation of 2-{[(2-Phenoxyethyl)thio]methyl}-5-{4-[2-(N',N'-dimethylethylenediamino)acetamido] phenyl}-1,3,4-oxadiazole

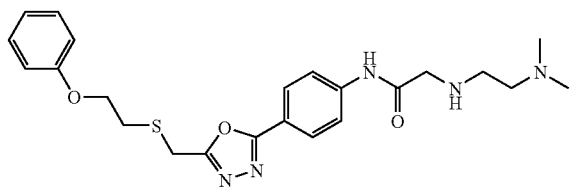

A mixture of 2-{[(2-phenoxyethyl)thio]methyl}-5-[4-(2-chloroacetamido)phenyl]-1,3,4-oxadiazole (50 mg, 0.12 mmol) and N,N-dimethylethylenediamine (1 mL) was stirred at room temperature overnight and excess N,N-dimethylethylenediamine was evaporated under vacuum. The residue was purified by preparative TLC (silica gel, 10% methanol/methylene chloride) to give a pale yellow oil (28 mg, 51%).

$^1$H NMR (CDCl$_3$) δ 7.96 (d, 2H, J=8.7 Hz), 7.79 (d, 2H, J=8.8 Hz), 7.22~7.26 (m, 2H), 6.92 (t, 1H, J=7.7 Hz), 6.87 (d, 2H, J=7.7 Hz), 4.18 (t, 2H, J=6.2 Hz), 4.02 (s, 2H), 3.41 (s, 2H), 3.04 (s, 1H), 3.03 (t, 2H, J=5.9 Hz), 2.79 (t, 2H, J=5.6 Hz), 2.50 (t, 2H, J=5.6 Hz), 2.31 (s, 6H). IR (film, cm$^{-1}$) 3464, 3327, 2959, 1669, 1604, 1521, 1260, 1134, 757. MS (ES+) m/e 454 (M+1). Anal. Calcd for C$_{24}$H$_{31}$N$_5$O$_2$S: C, 63.55; H, 6.89; N, 15.44; S, 7.07. Found C, 63.75; H, 6.91; N, 15.28; S, 7.26.

Example 152

Preparation of 2-{[(2-Phenoxyethyl)thio]methyl}-5-{4-[2-(N-benzyl-N',N'-dimethylethylenediamino) acetamido]phenyl}-1,3,4-oxadiazole

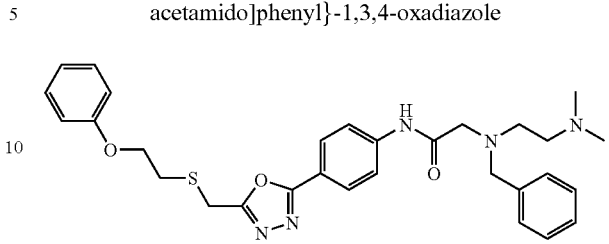

A mixture of 2-{[(2-phenoxyethyl)thio]methyl}-5-[4-(2-chloroacetamido)phenyl]-1,3,4-oxadiazole (202 mg, 0.5 mmol) and N,N-dimethyl-N'-benzylethylenediamine (1.34 g, 7.5 mmol) was stirred at 80~90° C. overnight and excess N,N-dimethyl-N'-benzylethylenediamine was evaporated under vacuum. The residue was purified by preparative TLC (silica gel, 10% methanol/methylene chloride) to give a pale yellow oil (168 mg, 62%).

$^1$H NMR (CDCl$_3$) δ 10.75 (s, 1H), 7.96 (d, 2H, J=8.4 Hz), 7.72 (d, 2H, J=8.3 Hz), 7.24~7.31 (m, 7H), 6.93 (t, 1H, J=7.5 Hz), 6.88 (d, 2H, J=8.0 Hz), 4.19 (t, 2H, J=6.0 Hz), 4.03 (s, 2H), 3.75 (s, 2H), 3.28 (s, 2H), 3.04 (t, 2H, J=6.0 Hz), 2.70 (t, 2H, J=5.4 Hz), 2.33~2.42 (m, 2H), 2.17 (s, 6H). IR (film, cm$^{-1}$) 3455, 3330, 2946, 1670, 1606, 1500, 1420, 1301, 1256, 1177, 758. MS (ES+) m/e 544 (M+1). Anal. Calcd for C$_{31}$H$_{37}$N$_5$O$_2$S: C, 68.48; H, 6.86; N, 12.88; S, 5.90. Found C, 68.53; H, 6.63; N, 12.71; S, 5.82.

Example 153

Preparation of 2-{[(2-Phenoxyethyl)thio]methyl}-5-{4-[2-((2-(N,N-dimethylamino)ethoxy)acetamido] phenyl}-1,3,4-oxadiazole

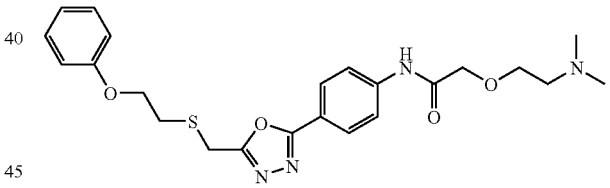

Sodium hydride (60% suspension in oil, 64 mg, 1.6 mmol) was washed with tetrahydrofuran (10 mL), suspended in N,N-dimethylformamide (15 mL) and cooled to 0° C. N,N-dimethylethanolamine (171 mg, 1.92 mmol) was added dropwise over 2 min with stirring, and the mixture was allowed to warm to room temperature and stir for 30 min. 2-{[(2-Phenoxyethyl)thio]methyl}-5-[4-(2-chloroacetamido)phenyl]-1,3,4-oxadiazole (130 mg, 0.32 mmol) was added and stirring was continued for 18 h. The reaction mixture was poured into water (40 mL) and extracted with ethyl acetate (4×15 mL). The combined ethyl acetate extracts were washed with water (2×15 mL) and brine (20 mL), dried (MgSO$_4$), and concentrated. The residue was purified by chromatography (silica gel, 10% methanol/methylene chloride) to give a colorless oil (77 mg, 53%).

$^1$H NMR (CDCl$_3$) δ 10.25 (s, 1H), 7.97 (d, 2H, J=8.8 Hz), 7.78 (d, 2H, J=8.4 Hz), 7.22~7.27 (m, 7H), 6.93 (t, 1H, J=7.3 Hz), 6.87 (d, 2H, J=7.6 Hz), 4.19 (t, 2H, J=6.2 Hz), 4.11 (s, 2H), 4.02 (s, 2H), 3.69 (t, 2H, J=5.0 Hz), 3.03 (t, 2H, J=6.0 Hz), 2.60 (m, 2H), 2.36 (s, 6H). IR (film, cm$^{-1}$) 3470, 3334, 2934, 1669, 1599, 1498, 1412, 1248, 1182, 1036, 756. MS (ES+) m/e 457 (M+1). Anal. Calcd for C₂₃H₂₈N₄O₄S: C, 60.51; H, 6.18; N, 12.27; S, 7.02. Found C, 60.37; H, 6.10; N, 12.17; S, 6.94.

Example 154

Preparation of (+)-2-{[(2-phenoxyethyl)thio]methyl}-5-{4-[2-(2-(N,N-dimethylamino)-1-methylethoxy)acetamido]phenyl}-1,3,4-oxadiazole

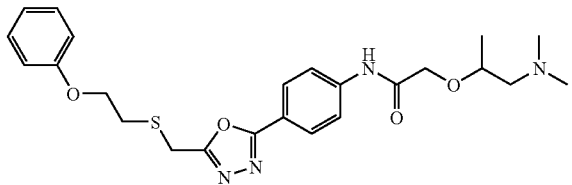

Sodium hydride (60% suspension in oil, 200 mg, 5 mmol) was washed with tetrahydrofuran (10 mL), suspended in N,N-dimethylformamide (5 mL) and cooled to 0° C. with stirring. 1-(N,N-diethylamino)-2-propanol (1.03 g, 10 mmol) in N,N-dimethylformamide (2 mL) was added dropwise, and stirring was continued for 10 min at 0° C. and 30 min at room temperature. 2-{[(2-Phenoxyethyl)thio]methyl}-5-[4-(2-chloroacetamido)phenyl]-1,3,4-oxadiazole (202 mg, 0.5 mmol) was added and the resultant mixture was stirred at room temperature for 2.5 h. The reaction mixture was diluted with ethyl acetate (40 mL), washed with water (5×15 mL) and brine (15 mL), dried (MgSO₄), and concentrated. The residue was purified by chromatography (silica gel, 5% methanol/methylene chloride) to give a colorless oil (120 mg, 51%).

¹H NMR (CDCl₃) δ 10.83 (s, 1H), 7.97 (d, 2H, J=8.8 Hz), 7.73 (d, 2H, J=8.5 Hz), 7.22~7.26 (m, 2H), 6.93 (t, 1H, J=7.7 Hz), 6.87 (d, 2H, J=7.6 Hz), 4.23 (d, 1H, J=16.9 Hz), 4.19 (t, 2H, J=6.2 Hz), 4.03 (s, 2H), 3.95 (d, 1H, J=16.9 Hz), 3.55 (m, 1H), 3.03 (t, 2H, J=6.2 Hz), 2.61 (t, 1H, J=11.5 Hz), 2.31 (s, 6H), 2.15 (m, 1H), 1.13 (d, 3H, J=5.8 Hz). IR (film, cm⁻¹) 3456, 3344, 2931, 1668, 1602, 1503, 1412, 1248, 1172, 1037, 756. MS (ES+) m/e 471 (M+1). Anal. Calcd for C₂₄H₃₀N₄O₄S: C, 61.26; H, 6.43; N, 11.91; S, 6.81. Found C, 61.23; H, 6.27; N, 11.79; S, 6.88.

Example 155

Preparation of (+)-2-{[(2-phenoxyethyl)thio]methyl}-5-{4-[2-(1-benzyl-2-(N,N-dimethylamino)ethoxy)acetamido]phenyl}-1,3,4-oxadiazole

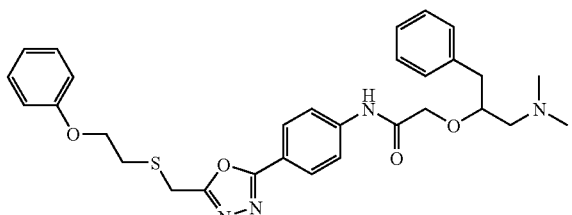

a) (+)-1-Benzyl-2-(N,N-dimethylamino)ethanol

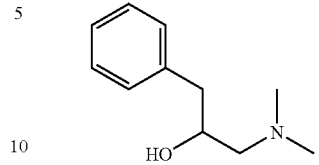

To a solution of 2,3-epoxypropylbenzene (1.34 g, 10 mmol) and lithium perchlorate (1.17 g, 11 mmol) in acetonitrile (10 mL) was added 2 M dimethylamine in tetrahydrofuran (5 mL 10 mmol). The resultant mixture was stirred at room temperature overnight, diluted with ether (20 mL), washed with water (3×10 mL), dried (MgSO₄), and concentrated to give a yellow oil (1.61 g, 90%). This material was used in the next step without further purification.

¹H NMR (CDCl₃) δ 7.16–7.28 (m, 5H), 3.84 (m, 1H), 2.78 (dd, 1H, J=13.5, 7.1 Hz), 2.63 (dd, 1H, J=13.5, 5.6 Hz), 2.30 (dd, 1H, J=11.8, 10.4 Hz), 2.22 (s, 6H), 2.15 (dd, 1H, J=12.1, 3.3 Hz). MS (ES+) m/e 181 (M+1).

b) (+)-2-{[(2-Phenoxyethyl)thio]methyl}-5-{4-[2-(1-benzyl-2-(N,N-dimethylamino)ethoxy)acetamido]phenyl}-1,3,4-oxadiazole

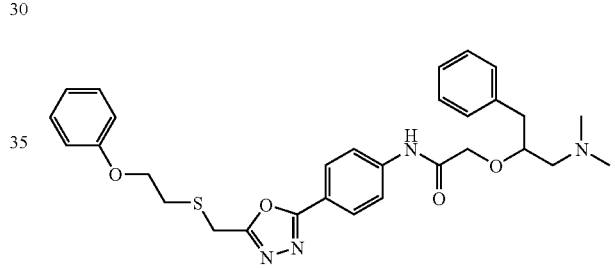

Sodium hydride (60% suspension in oil, 80 mg, 2 mmol) was washed with tetrahydrofuran (10 mL), suspended in N,N-dimethylformamide (4 mL) and cooled to 0° C. with stirring. (+)-1-benzyl-2-(N,N-dimethylamino)ethanol (358 mg, 2 mmol) in N,N-dimethylformamide (3 mL) was added dropwise, and stirring was continued for 10 min at 0° C. and 20 min at room temperature. 2-{[(2-Phenoxyethyl)thio]methyl}-5-[4-(2-chloroacetamido)phenyl]-1,3,4-oxadiazole (202 mg, 0.5 mmol), followed by sodium iodide (149 mg, 1 mmol) was added and the resultant mixture was stirred at room temperature for 3 h. The reaction mixture was diluted with ethyl acetate (50 mL), washed with water (4×25 mL) and brine (25 mL), dried (MgSO₄), and concentrated. The residue was purified by chromatography (silica gel, 5% methanol/methylene chloride) to give a colorless oil (114 mg, 42%).

¹H NMR (CDCl₃) δ 10.87 (s, 1H), 7.98 (d, 2H, J=8.8 Hz), 7.67 (d, 2H, J=8.8 Hz), 7.17~7.32 (m, 7H), 6.92 (t, 1H, J=7.3 Hz), 6.87 (d, 2H, J=8.0 Hz), 4.18 (t, 2H, J=6.2 Hz), 4.11 (d, 1H, J=17.2 Hz), 4.02 (s, 2H), 3.75 (d, 1H, J=17.2 Hz), 3.66 (m, 1H), 3.03 (t, 2H, J=6.2 Hz), 2.76 (m, 2H), 2.62 (dd, 1H, J=13.0, 10.4 Hz), 2.28 (m, 1H), 2.27 (s, 6H). IR (film, cm⁻¹) 3460, 3334, 2934, 1658, 1600, 1501, 1426, 1280, 1175, 1053, 761. MS (ES+) m/e 547 (M+1). Anal. Calcd for C₃₀H₃₄N₄O₄S: C, 65.91; H, 6.27; N, 10.25; S, 5.87. Found C, 66.04; H, 6.25; N, 10.31; S, 5.49.

Example 156

Preparation of 2-{[(2-(4-Fluorophenoxy)ethyl)thio]methyl}-5-{4-[(4-(N,N-dimethylamino)butanoyl)amino]phenyl}-1,3,4-oxadiazole

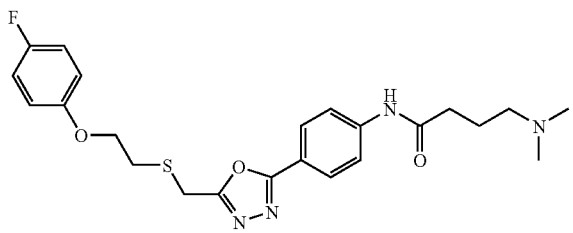

a) Methyl 2-{[2-(tert-butyldimethylsilyloxy)ethyl]thio}acetate

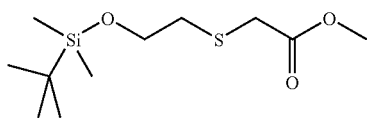

A mixture of methyl thioglycolate (4.78 g, 45 mmol), 2-bromoethoxy-tert-butyldimethylsilane (7.18 g, 30 mmol), and potassium carbonate (10.37 g, 75 mmol) in tetrahydrofuran (150 mL) was stirred under reflux overnight. The resultant mixture was cooled to room temperature, diluted with ether (100 mL), washed with water (3×100 mL) and brine (100 mL), dried ($MgSO_4$), and concentrated to give a colorless oil (7.85 g, 99%).

$^1$H NMR ($CDCl_3$) δ 3.78 (t, 2H, J=6.6 Hz), 3.71 (s, 3H), 3.27 (s, 2H), 2.74 (t, 2H, J=6.6 Hz), 0.87 (s, 9H), 0.04 (s, 6H). MS (ES+) m/e 265 (M+1).

b) 2-{[2-(tert-butyldimethylsilyloxy)ethyl]thio}acetic hydrazide

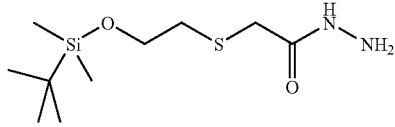

A mixture of methyl 2-{[2-(tert-butyldimethylsilyloxy)ethyl]thio}acetate (2.65 g, 10 mmol) and hydrazine monohydrate (5 g, 100 mmol) in ethanol was stirred at room temperature for 2 h and concentrated. The residue was taken up in ethyl acetate (50 mL), washed with water (5×20 mL), dried ($MgSO_4$), and concentrated to give a colorless oil (2.53 g, 96%).

$^1$H NMR ($CDCl_3$) δ 7.99 (br s, 1H), 3.85 (br s, 2H), 3.79 (t, 2H, J=6.0 Hz), 3.29 (s, 2H), 2.68 (t, 2H, J=6.2 Hz), 0.88 (s, 9H), 0.06 (s, 6H). MS (ES+) m/e 265 (M+1).

c) 4-{[4-(N,N-Dimethylamino)butanoyl]amino}benzoic acid hydrochloride

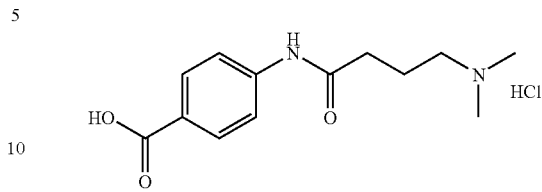

A mixture of methyl 4-aminobenzoate (4.53 g, 30 mmol), 4-(N,N-dimethylamino)butyric acid hydrochloride (6.71 g, 40 mmol), diisopropylcarbodiimide (5.05 g, 40 mmol), and 1-hydroxybenzotriazole (5.41 g, 40 mmol) in N,N-dimethylformamide (200 mL) was stirred at room temperature over the weekend. The reaction mixture was poured into water (600 mL), made basic with 2 M NaOH to pH ~10, and extracted with ethyl acetate (5×150 mL). The combined ethyl acetate extracts were washed with 2 M NaOH (2×150 mL), dried ($MgSO_4$), and concentrated. The residue was purified on a cation exchange column (Bio-Rad 50W-X2 resin) to give colorless oil (6.18 g, 78%). This material (5.28 g, 20 mmol) was dissolved in tetrahydrofuran (30 mL) and stirred with 2 M NaOH (50 mL, 100 mmol) at room temperature overnight. Ether (30 mL) was added and the phases were separated. The aqueous layer was loaded to an anion exchange column (Bio-Rad AG1-X2 resin). The column was eluted with water until the eluent became neutral, followed by 4 M HCl in dioxane to recover the product. Dioxane was evaporated. The resultant solid was washed with dioxane (250 mL) and methylene chloride (200 mL) to give the final product (3.68, 64%).

$^1$H NMR (DMSO-d6) δ 10.40 (s, 1H), 10.0 (br s, 1H), 7.84 (d, 2H, J=8.8 Hz), 7.68 (d, 2H, J=8.8 Hz), 3.03 (m, 2H), 2.72 (s, 6H), 2.45 (m, 2H), 1.92 (m, 2H). MS (ES−) m/e 249 (M−1).

d) 2-{[(2-(tert-Butyldimethylsilyloxy)ethyl)thio]methyl}-5-{4-[(4-(N,N-dimethylamino)butanoyl)amino]phenyl}-1,3,4-oxadiazole

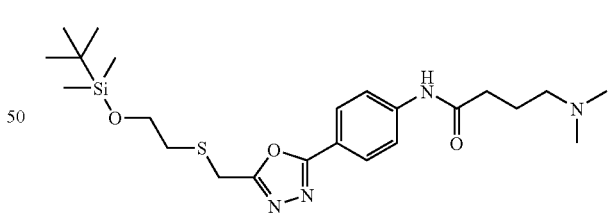

To a stirred mixture of 2-{[2-(tert-butyldimethylsilyloxy)ethyl]thio}acetic hydrazide (2.65 g, 10 mmol), 4-{[4-(N,N-Dimethylamino)butanoyl]amino}benzoic acid hydrochloride (2.86 g, 10 mmol), and 4-(N,N-dimethylaminophenyl)diphenylphosphine (9.16 g, 30 mmol) in acetonitrile (100 mL) at 0° C. was added slowly a solution of triethylamine (6.07 g, 60 mmol) in carbon tetrachloride (7.69 g, 50 mmol). The resultant mixture was stirred at room temperature overnight and concentrated. The residue was taken up in methylene chloride (150 mL), washed with 2 M NaOH (2×50 mL), dried ($MgSO_4$), and concentrated. The residue was purified by chromatography (silica gel, 10% methanol/ methylene chloride to 5% methanol and 5% 7 M methanolic ammonia/methylene chloride) to give a pale yellow oil (1.79 g, 38%).

$^1$H NMR (CDCl$_3$) δ 10.16 (s, 1H), 7.97 (d, 2H, J=8.8 Hz), 7.87 (d, 2H, J=8.8 Hz), 3.96 (s, 2H), 3.81 (t, 2H, J=6.4 Hz), 3.0 (t, 2H, J=5.6 Hz), 2.75~2.85 (m, 4H), 2.76 (s, 6H), 2.15~2.19 (m, 2H), 0.87 (s, 9H), 0.05 (s, 6H). IR (film, cm$^{-1}$) 3473, 3327, 2963, 1659, 1598, 1496, 1245, 1181, 1088, 750. MS (ES+) m/e 479 (M+1). Anal. Calcd for C$_{23}$H$_{38}$N$_4$O$_3$SSi: C, 57.71; H, 8.00; N, 11.70; S, 6.70. Found C, 57.57; H, 8.12; N, 11.52; S, 6.91.

e) 2-{[(2-hydroxyethyl)thio]methyl}-5-{4-[(4-(N,N-dimethylamino)butanoyl)amino]phenyl}-1,3,4-oxadiazole

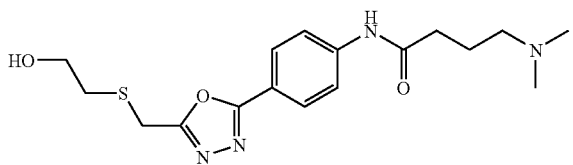

2-{[(2-(tert-Butyldimethylsilyloxy)ethyl)thio]methyl}-5-{4-[(4-(N,N-dimethylamino)butanoyl)amino]phenyl}-1,3,4-oxadiazole (1.47 g, 3 mmol) was stirred in 2 M HCl (15 mL) until it appeared completely dissolved (~30 min). The solution was washed with methylene chloride (3×10 mL), treated with 2 M NaOH to pH ~11, and extracted with methylene chloride (3×10 mL). The combined methylene chloride extracts were dried (MgSO$_4$) and concentrated to give a pale yellow solid (430 mg, 39%).

$^1$H NMR (CDCl$_3$) δ 10.66 (s, 1H), 7.96 (d, 2H, J=7.8 Hz), 7.66 (d, 2H, J=7.8 Hz), 3.94 (s, 2H), 3.81 (t, 2H, J=5.9 Hz), 2.83 (t, 2H, J=5.6 Hz), 2.49~2.56 (m, 4H), 2.36 (s, 6H), 1.88 (m, 2H). IR (KBr, cm$^{-1}$) 3482, 3330, 2957, 1661, 1603, 1501, 1411, 1168, 756. MS (ES+) m/e 365 (M+1). Anal. Calcd for C$_{17}$H$_{24}$N$_4$O$_3$S: C, 56.02; H, 6.64; N, 15.37; S, 8.80. Found C, 56.16; H, 6.74; N, 15.38; S, 8.94.

f) 2-{[(2-(4-Fluorophenoxy)ethyl)thio]methyl}-5-{4-[(4-(N,N-dimethylamino)butanoyl)amino]phenyl}-1,3,4-oxadiazole

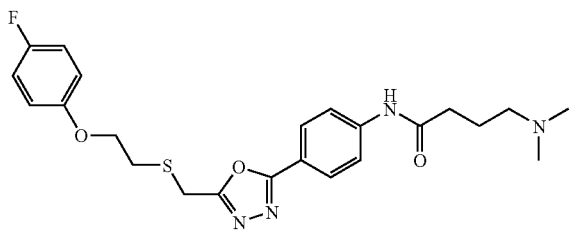

A solution of 2-{[(2-hydroxyethyl)thio]methyl}-5-{4-[(4-(N,N-dimethylamino)butanoyl)amino]phenyl}-1,3,4-oxadiazole (130 mg, 0.36 mmol), 4-fluorophenol (161 mg, 1.44 mmol), and triphenylphosphine (184 mg, 0.7 mmol) in tetrahydrofuran (6 mL) was cooled with an ice bath and diisopropyl azodicarboxylate (142 mg, 0.7 mmol) in tetrahydrofuran (1 mL) was added dropwise. After 5 min the cooling bath was removed and the mixture was stirred at room temperature overnight. The resultant mixture was diluted with ethyl acetate (10 mL), washed with 2 M NaOH (3×10 mL), dried (MgSO$_4$), and concentrated. The residue was purified by preparative TLC (silica gel, 5% methanol and 5% 7 M methanolic ammonia in methylene chloride, twice developed) to give a colorless oil (151 mg, 92%).

$^1$H NMR (CDCl$_3$) δ 10.67 (s, 1H), 7.94 (d, 2H, J=8.8 Hz), 7.65 (d, 2H, J=8.4 Hz), 6.92 (t, 2H, J=8.6 Hz), 6.79~6.82 (m, 2H), 4.13 (t, 2H, J=6.2 Hz), 4.01 (s, 2H), 3.01 (t, 2H, J=6.2 Hz), 2.54 (t, 2H, J=6.4 Hz), 2.49 (t, 2H, J=5.8 Hz), 2.35 (s, 6H), 1.84~1.88 (m, 2H). IR (film, cm$^{-1}$) 3456, 3322, 2957, 1657, 1600, 1446, 1382, 1215, 1177, 755. MS (ES+) m/e 459 (M+1). Anal. Calcd for C$_{23}$H$_{27}$FN$_4$O$_3$S: C, 60.24; H, 5.93; N, 12.22; S, 6.99. Found C, 60.13; H, 5.86; N, 12.36; S, 6.94.

Example 157

Preparation of 2-{[(2-(4-Methoxyphenoxy)ethyl)thio]methyl}-5-{4-[(4-(N,N-dimethylamino)butanoyl)amino]phenyl}-1,3,4-oxadiazole

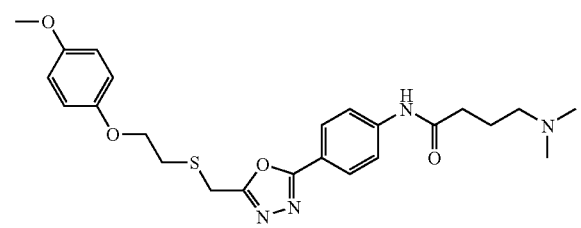

A solution of 2-{[(2-hydroxyethyl)thio]methyl}-5-{4-[(4-(N,N-dimethylamino)butanoyl)amino]phenyl}-1,3,4-oxadiazole (80 mg, 0.22 mmol), 4-methoxyphenol (109 mg, 0.88 mmol), and triphenylphosphine (115 mg, 0.44 mmol) in tetrahydrofuran (8 mL) was cooled with an ice bath and diisopropyl azodicarboxylate (89 mg, 0.44 mmol) in tetrahydrofuran (0.5 mL) was added dropwise. After 5 minutes the cooling bath was removed and the mixture was stirred at room temperature overnight. The resultant mixture was diluted with ethyl acetate (10 mL), washed with 2 M NaOH (3×5 mL), dried (MgSO$_4$), and concentrated. The residue was purified by preparative TLC (silica gel, 5% methanol and 5% 7 M methanolic ammonia in methylene chloride, twice developed) to give a colorless oil (53 mg, 50%).

$^1$H NMR (CDCl$_3$) δ 10.63 (s, 1H), 7.94 (d, 2H, J=8.8 Hz), 7.66 (d, 2H, J=8.7 Hz), 6.81 (d, 2H, J=9.5 Hz), 6.78 (d, 2H, J=9.2 Hz), 4.13 (t, 2H, J=6.2 Hz), 4.01 (s, 2H), 3.73 (s, 3H), 3.0 (t, 2H, J=6.2 Hz), 2.49~2.57 (m, 4H), 2.36 (s, 6H), 1.83~1.91 (m, 2H). IR (film, cm$^{-1}$) 3470, 3341, 2955, 1661, 1606, 1500, 1438, 1388, 1237, 1176, 764. MS (ES+) m/e 471 (M+1). Anal. Calcd for C$_{24}$H$_{30}$N$_4$O$_4$S: C, 61.26; H, 6.43; N, 11.91; S, 6.81. Found C, 61.29; H, 6.45; N, 11.74; S, 6.73.

Example 158

Preparation of 2-{[(2-(4-Benzoyloxyphenoxy)ethyl)thio]methyl-5-{4-[(4-(N,N-dimethylamino)butanoyl)amino]phenyl}-1,3,4-oxadiazole

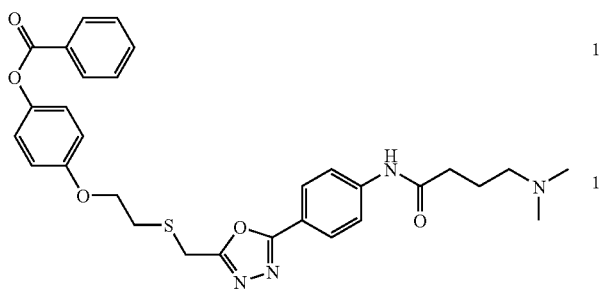

A solution of 2-{[(2-hydroxyethyl)thio]methyl}-5-{4-[(4-(N,N-dimethylamino)butanoyl)amino]phenyl}-1,3,4-oxadiazole (80 mg, 0.22 mmol), 4-hydroxyphenyl benzoate (189 mg, 0.88 mmol), and triphenylphosphine (116 mg, 0.44 mmol) in tetrahydrofuran (8 mL) was cooled with an ice bath and diisopropyl azodicarboxylate (89 mg, 0.44 mmol) in tetrahydrofuran (0.5 mL) was added dropwise. After 5 min the cooling bath was removed and the mixture was stirred at room temperature overnight. The resultant mixture was diluted with ethyl acetate (10 mL), washed with 2 M NaOH (3×5 mL), dried (MgSO$_4$), and concentrated. The residue was purified by preparative TLC (silica gel, 5% methanol and 5% 7 M methanolic ammonia in methylene chloride, twice developed) to give colorless oil (72 mg, 58%).

$^1$H NMR (CDCl$_3$) δ 10.55 (s, 1H), 8.17 (d, 2H, J=7.7 Hz), 7.95 (d, 2H, J=8.4 Hz), 7.67 (d, 2H, J=8.4 Hz), 7.61 (t, 1H, J=7.3 Hz), 7.48 (t, 2H, J=7.6 Hz), 7.09 (d, 2H, J=9.2 Hz), 6.91 (d, 2H, J=8.8 Hz), 4.19 (t, 2H, J=6.0 Hz), 4.02 (s, 2H), 3.05 (t, 2H, J=6.2 Hz), 2.46~2.57 (m, 4H), 2.37 (s, 6H), 1.86~1.90 (m, 2H). IR (film, cm$^{-1}$) 3420, 3035, 2957, 2771, 1763, 1660, 1601, 1499, 1423, 1215, 1170, 755. MS (ES+) m/e 561 (M+1). Anal. Calcd for C$_{30}$H$_{32}$N$_4$O$_5$S: C, 64.27; H, 5.75; N, 9.99; S, 5.72. Found C, 64.40; H, 5.62; N, 10.03; S, 5.74.

Example 159

Preparation of 2-{[(2-(4-Hydroxyphenoxy)ethyl)thio]methyl}-5-{4-[(4-(N,N-dimethylamino)butanoyl)amino]phenyl}-1,3,4-oxadiazole

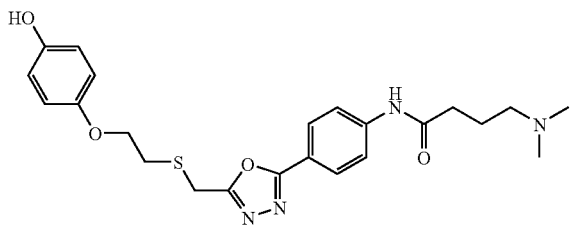

To a solution of 2-{[(2-(4-benzoyloxyphenoxy)ethyl)thio]methyl-5-{4-[(4-(N,N-dimethylamino)butanoyl)amino]phenyl}-1,3,4-oxadiazole (50 mg, 0.1 mmol) in MeOH (1 mL) and tetrahydrofuran (0.5 mL) was added 2M NaOH (1 mL, 2 mmol). The mixture was stirred at room temperature overnight and extracted with methylene chloride (3×5 mL). The combined methylene chloride extracts were washed with water (1 mL), dried (MgSO$_4$), and concentrated to give a colorless oil (30 mg, 66%).

$^1$H NMR (CDCl$_3$) δ 10.60 (s, 1H), 7.86 (d, 2H, J=8.4 Hz), 7.58 (d, 2H, J=8.4 Hz), 6.72 (d, 2H, J=8.8 Hz), 6.67 (d, 1H, J=9.2 Hz), 4.07 (t, 2H, J=6.2 Hz), 4.0 (s, 2H), 3.01 (t, 2H, J=6.2 Hz), 2.44~2.56 (m, 4H), 2.34 (s, 6H), 1.83~1.92 (m, 2H). IR (film, cm$^{-1}$) 3458, 3333, 2965, 1660, 1597, 1500, 1410, 1395, 1264, 1163, 757. MS (ES+) m/e 457 (M+1). Anal. Calcd for C$_{23}$H$_{28}$N$_4$O$_4$S: C, 60.51; H, 6.18; N, 12.27; S, 7.02. Found C, 61.02; H, 6.26; N, 12.09; S, 7.08.

Example 160

Preparation of 2-{[(2-Phenoxyethyl)thio]methyl}-5-{3-hydroxymethyl-4-[((2-piperidinoethyl)amino)carbonyl]phenyl}-1,3,4-oxadiazole

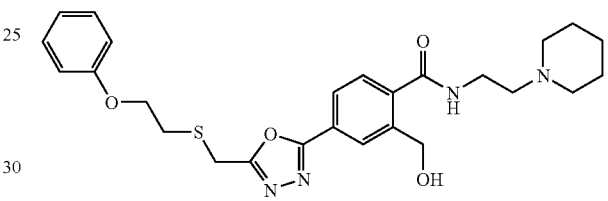

a) 5-{2-[((2-Phenoxyethyl)thio)methyl]-1,3,4-oxadiazol-5-yl}phthalide

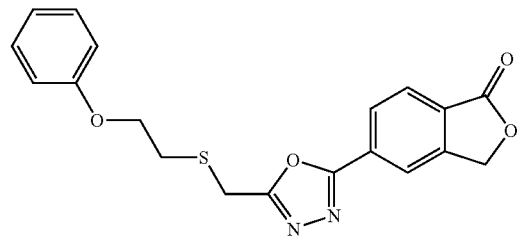

To a mixture of 4-carboxyphthalide (178 mg, 1 mmol), 2-phenoxythioacetic hydrazide hydrochloride (316 mg, 1.2 mmol), 4-(N,N-dimethylamino)phenyldiphenylphosphine (917 mg, 3 mmol), and triethylamine (607 mg, 6 mmol) in acetonitrile (10 mmol) was added carbon tetrachloride (770 mg, 5 mmol). The resultant mixture was stirred at room temperature overnight and concentrated. The residue was partitioned between ether (50 mL) and 2 M HCl (30 mL). The organic layer was washed with 2 M HCl (5×20 mL), dried (MgSO$_4$), and concentrated. The residue was triturated from methylene chloride and hexanes to give a white solid (186 mg, 51%). The reaction was repeated on 3 mmol scale to give the same product (652 mg, 59%).

$^1$H NMR (CDCl$_3$) δ 8.16 (d, 1H, J=8.1 Hz), 8.13 (s, 1H), 8.02 (d, 1H, J=7.8 Hz), 7.22–7.26 (m, 2H), 6.93 (t, 1H, J=7.3 Hz), 6.86 (d, 2H, J=8.0 Hz), 5.37 (s, 2H), 4.20 (t, 2H, J=5.8 Hz), 4.09 (s, 2H), 3.05 (t, 2H, J=5.9 Hz). MS (ES$^+$) m/e 369 (M+1).

b) 2-{[(2-Phenoxyethyl)thio]methyl}-5-{3-hydroxymethyl-4-[((2-piperidinoethyl)amino)carbonyl]phenyl}-1,3,4-oxadiazolo

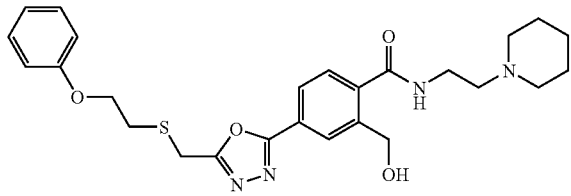

Lithium aluminum hydride (1 M in ether, 1 mL, 1 mmol) was diluted with tetrahydrofuran (1 mL) and N-(2-aminoethyl)piperidine (641 mg, 5 mmol) in tetrahydrofuran (1 mL) was added dropwise over 3 min. The resultant mixture was stirred at room temperature for 2 hr, diluted with tetrahydrofuran (4 mL), and 5-{2-[((2-phenoxyethyl)thio)methyl]-1,3,4-oxadiazol-5-yl}phthalide (368 mg, 1 mmol) was added. Stirring was continued at room temperature overnight and tetrahydrofuran (5 mL), followed by 2 M NaOH (5 mL) was added. The mixture was stirred for 30 min, diluted with water (15 mL), and extracted with ethyl acetate (3×15 mL). The combined ethyl acetate extracts were washed with brine (15 mL), dried ($MgSO_4$), and concentrated. The residue was recrystallized from methylene chloride and hexanes (1:1) to give a white solid (280 mg, 56%).

$^1$H NMR ($CDCl_3$) δ 8.02 (s, 1H), 8.0 (d, 1H, J=8.0 Hz), 7.64 (d, 1H, J=7.7 Hz), 7.22–7.26 (m, 2H), 7.10 (br s, 1H), 6.92 (t, 1H, J=7.3 Hz), 6.87 (d, 2H, J=8.4 Hz), 4.64 (s, 2H), 4.19 (t, 2H, J=6.0 Hz), 4.05 (s, 2H), 3.59 (dd, 2H, J=8.2, 5.5 Hz), 3.04 (t, 2H, J=5.9 Hz), 2.60 (t, 2H, J=5.7 Hz), 2.4~2.52 (m, 4H), 1.60–1.66 (m, 4H), 1.47–1.50 (m, 2l). IR (KBr, $cm^{-1}$) 3465, 3310, 2940, 2888, 2854, 1638, 1556, 1496, 1420, 1297, 1020, 750. MS (ES+) m/e 497 (M+1). Anal. Calcd for $C_{26}H_{32}N_4O_4S$: C, 62.88; H, 6.49; N, 11.28; S, 6.46. Found C, 63.27; Hp 6.46; N, 11.14; S, 6.28.

Example 161

Preparation of 2-{[(2-Phenoxyethyl)thio]methyl}-5-[4-(2-benzyl-2-aminoacetamido)phenyl]-1,3,4-oxadiazole

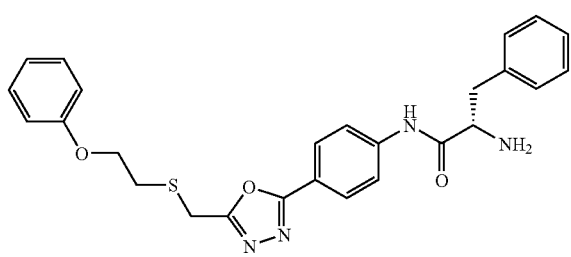

a) 2-{[(2-Phenoxyethyl)thio]methyl}-5-{4-[2-benzyl-2-((tert-butoxycarbonyl)amino)acetamido]phenyl}-1,3,4-oxadiazole

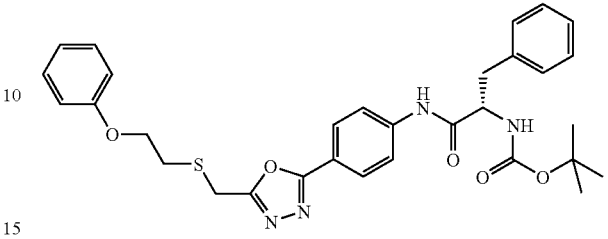

To a mixture of 2-{[(2-phenoxyethyl)thio]methyl}-5-(4-aminophenyl)-1,3,4-oxadiazole (327 mg, 1 mmol), Boc-L-phenylalanine (796 mg, 3 mmol), and 1-hydroxybenzotriazole (405 mg, 3 mmol) in tetrahydrofuran (25 mL) was added diisopropylcarbodiimide (379 mg, 3 mmol) and the mixture was stirred at room temperature overnight. The reaction mixture was diluted with ethyl acetate (25 mL), washed with 2 M NaOH (3×10 mL) and brine (25 mL), dried ($MgSO_4$), and concentrated. The residue was purified by chromatography (silica gel) to give a yellow solid (167 mg, 29%).

$^1$H NMR ($CDCl_3$) δ 7.93 (d, 2H, J=8.4 Hz), 7.80 (d, 2H, J=8.4 Hz), 7.22–7.32 (m, 7H), 6.93 (t, 1H, J=7.5 Hz), 6.87 (d, 2H, J=7.7 Hz), 5.08 (br s, 1H), 4.18 (t, 2H, J=6.2 Hz), 4.02 (s, 2H), 3.78 (t, 1H, J=6.4 Hz), 3.14 (d, 2H, J=6.9 Hz), 3.03 (t, 2H, J=6.2 Hz), 1.12 (s, 9H). MS (ES+) m/e 575 M+1).

b) 2-{[(2-Phenoxyethyl)thio]methyl}-5-[4-(2-benzyl-2-aminoacetamido)phenyl]-1,3,4-oxadiazole

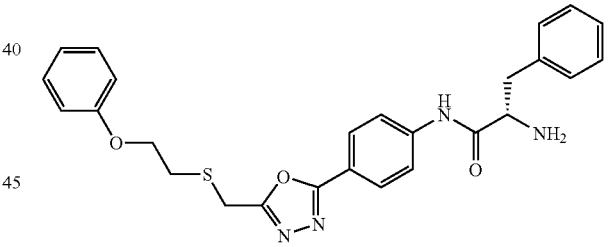

A mixture of 2-{[(2-phenoxyethyl)thio]methyl}-5-{4-[2-benzyl-2-((tert-butoxycarbonyl)amino)acetamido]phenyl}-1,3,4-oxadiazole (144 mg, 0.25 mmol) and 25% trifluoroacetic acid in methylene chloride (2.5 mL) was stirred at room temperature overnight and concentrated. The residue was taken up in methylene chloride (15 mL), washed with 2 M NaOH (2×10 mL), dried ($MgSO_4$), and concentrated. The residue was purified by chromatography (silica gel, 10% methanol/methylene chloride) to give a white solid (74 mg, 60%).

$^1$H NMR ($CDCl_3$) δ 9.69 (s, 1H), 7.98 (d, 2H, J=8.8 Hz), 7.74 (d, 2H, J=8.7 Hz), 7.23–7.34 (m, 7H), 6.93 (t, 1H, J=7.3 Hz), 6.89 (d, 2H, J=8.8 Hz), 4.19 (t, 2H, J=6.2 Hz), 4.03 (s, 2H), 3.75 (dd, 1H, J=9.5, 4.0 Hz), 3.37 (dd, 2H, J=13.9, 3.7 Hz), 3.04 (t, 2H, J=6.2 Hz), 2.80 (dd, 1H, J=13.9, 9.5 Hz). IR (KBr, $cm^{-1}$) 3430, 3060, 2981, 2926, 1681, 1599, 1501, 1426, 1386, 1238, 1094, 744. MS (ES+) m/e 475 (M+1). Anal. Calcd for $C_{26}H_{26}N_4O_3S$: C, 65.80; H, 5.52; N, 11.81; S, 6.76. Found C, 65.70; H, 5.56; N, 11.68; S, 6.61.

Example 162

Preparation of (S)-2-{[(2-Phenoxyethyl)thio]methyl}-5-{4-[2-benzyl-2-(N',N'-dimethylethylenediamino)acetamido]phenyl}-1,3,4-oxadiazole

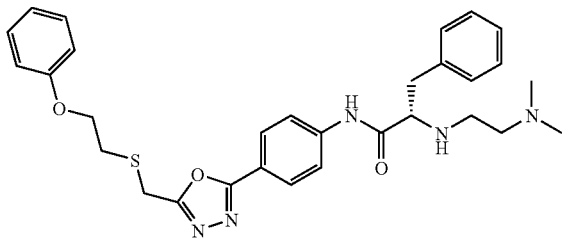

A mixture of 2-{[(2-phenoxyethyl)thio]methyl}-5-[4-(2-benzyl-2-aminoacetamido)phenyl]-1,3,4-oxadiazole (61 mg, 0.125 mmol), 2-(N,N-dimethylamino)ethylchloride hydrochloride (72 mg, 0.5 mmol), sodium carbonate (211 mg, 2 mmol), and sodium iodide (75 mg, 0.5 mmol) in ethanol (5 mL) was stirred under reflux overnight. The reaction mixture was poured into water (20 mL) and extracted with methylene chloride (3×10 mL). The combined methylene cholride extracts were dried (MgSO$_4$) and concentrated. The residue was purified by chromatorgraphy (silica gel, 10% methanol/methylene chloride) to give the desired product (30 mg, 44%) and recovered starting amine (13 mg, 21%).

$^1$H NMR (CDCl$_3$) δ 10.06 (s, 1H), 7.98 (d, 2H, J=8.5 Hz), 7.78 (d, 2H, J=8.8 Hz), 7.23–7.33 (m, 7H), 6.93 (t, 1H, J=7.3 Hz), 6.88 (d, 2H, J=8.4 Hz), 4.20 (t, 2H, J=6.0 Hz), 4.03 (s, 2H), 3.32–3.42 (m, 2H), 3.04 (t, 2H, J=6.2 Hz), 2.74 (dd, 1H, J=13.9, 10.2 Hz), 2.54–2.58 (m, 2H), 2.38 (m, 1H), 2.24 (m, 1H), 2.09 (s, 6H). MS (ES+) m/e 546 (M+1). Anal. Calcd for C$_{30}$H$_{35}$N$_5$O$_3$S: C, 66.03; H, 6.46; N, 12.83; S, 5.88. Found C, 66.18; H, 6.37; N, 12.71; S, 6.01.

Example 163

Preparation of (+)-2-{[(2-Phenoxyethyl)thio]methyl}-5-{4-[2-methyl-2-(N',N'-dimethylethylenediamino)acetamido]phenyl}-1,3,4-oxadiazole

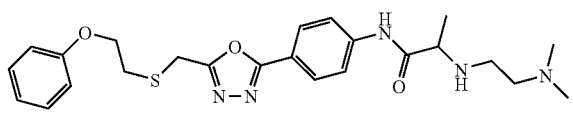

a) (+)-Ethyl 2-[(2-nitrobenzenesulfonyl)amino]propionate

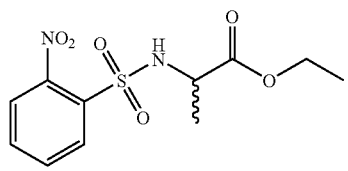

A solution of 2-nitrobenzenesulfonyl chloride (6.0 g, 27.1 mmol) and DL-alanine ethyl ester hydrochloride (5.0 g, 32.5 mmol) in methylene chloride (250 mL) was cooled in an ice/water bath. Triethylamine (9.5 mL, 67.8 mmol) was added dropwise over 3 min. The reaction was stirred for 10 min in the ice/water bath, then at room temperature for 3 h. The mixture was extracted with 2N HCl (3×100 mL), dried (MgSO$_4$), filtered and concentrated to yield 8.1 g (98%) of a yellow solid.

$^1$H NMR (CDCl$_3$) δ 8.05 (m, 1H), 7.89 (m, 1H), 7.69 (m, 2H), 6.07 (d, 1H, J=8 Hz), 4.19 (m, 1H), 3.93 (dd, 2H, J=14 and 14 Hz), 1.45 (dd, 3H, J=3 and 6 Hz), 1.07 (dt, 3H, J=14 and 14 Hz). MS (ES+) m/e 303 (M+1).

b) (+)-Ethyl 2-[N-(2-nitrobenzenesulfonyl)-N-(N',N'-dimethylamino)-1,2-ethanediamino]propionate

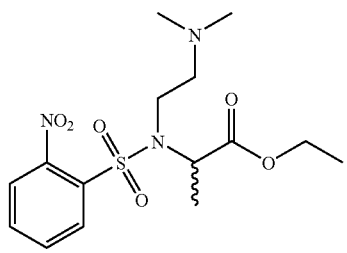

A solution of ethyl (+)-ethyl 2-[(2-nitrobenzenesulfonyl)amino]propionate (3.0 g, 10 mmol), N,N-dimethylethanolamine (2.0 mL, 20 mmol) and triphenylphosphine (6.56 g, 25 mmol) in THF (100 mL) were cooled in an ice/water bath. Diethyl azodicarboxylate (4.0 mL, 25 mmol) was added dropwise over 3 min, stirred another 10 min, then stirred at room temperature for 16 h. The mixture was concentrated, diluted with methanol (20 mL) and loaded onto a column containing Bio-Rad 50W-X2 cation exchange resin (50 g, pre-washed 800 mL of methanol). The column was washed with methanol (800 mL) and methylene chloride (200 mL). The product was then eluted with 2N ammonia/methanol (500 mL) and concentrated to yield 3.34 g of a yellow oil. This material was diluted with ethyl acetate (50 mL), extracted with water (3×50 mL), dried (MgSO$_4$), filtered and concentrated to yield 2.92 g (78%) of a yellow oil.

$^1$H NMR (CDCl$_3$) δ 8.07 (m, 1H), 7.65 (m, 2H), 7.57 (m, 1H), 4.75 (m, 1H), 4.03 (m, 2H, 3.56 (m, 1H), 3.17 (m, 1H), 2.63 (m, 1H), 2.46 (m, 1H), 2.20 (s, 6H), 1.51 (d, 3H, J=7 Hz), 1.12 (t, 3H, J=14 Hz). MS (ES+) m/e 375 (M+1).

c) (+)-2-[N-(2-Nitrobenzenesulfonyl)-N—(N',N'-dimethylamino)-1,2-ethanediamino]propionic acid

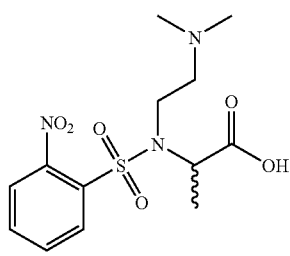

A solution of (+)-ethyl 2-[N-(2-nitrobenzenesulfonyl)-N-(N',N'-dimethylamino)-1,2-ethanediamino]propionate (2.92 g, 7.8 mmol) and aqueous 2 N NaOH (20 mL, 40 mmol) in tetrahydrofuran (14 mL) was stirred at room temperature for 2 h. The mixture was loaded onto a column of Bio-Rad AG1-X2 anionic exchange resin (40 g, pre-washed with 800 mL of water) and allowed to settle for 20 min before it was passed through the column. The column was washed with water (800 mL) and 1,4-dioxane (600 mL). The product was then eluted with 4 N HCl in 1,4-dioxane and concentrated to yield 2.06 g (76%) of a yellow oil.

$^1$H NMR (DMSO-D6) δ 10.00 (br s, 1H), 8.17 (m, 1H), 7.80–7.92 (m, 3H), 4.55 (m, 1H), 4.15 (m, 1H), 3.80 (m, 1H), 3.75 (m, 2H), 2.75 (s, 6H), 1.45 (d, 2H, J=7 Hz). MS (ES–) m/e 344 (M–1).

d) (+)-2-{[(2-Phenoxyethyl)thio]methyl}-5-{4-[(2-(N',N'-dimethyl-N-(2-nitrobenzenesulfonyl)-1,2-ethanediamino)propionyl)amino]phenyl}-1,3,4-oxadiazole

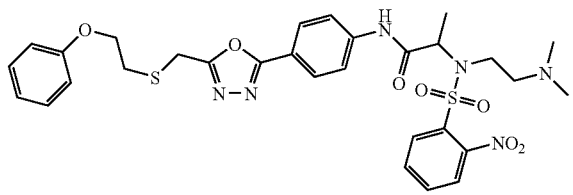

A solution of (+)-2-[N-(2-nitrobenzenesulfonyl)-N-(N',N'-dimethylamino)-1,2-ethanediamino]propionic acid (345 mg, 1 mmol) and 2-{[(2-phenoxyethyl)thio]methyl}-5-(4-aminophenyl)-1,3,4-oxadiazole (327 mg, 1 mmol) in anhydrous pyridine (3.0 mL) was cooled in an ice-salt water bath under nitrogen. Phosphorus oxychloride (0.15 mL, 1.6 mmol) was added dropwise and the cooled reaction stirred for 3 h. The reaction was quenched with water (10 mL) and extracted with ethyl acetate (3×10 mL). The combined organic phase was extracted with saturated aqueous sodium bicarbonate (3×10 mL), water (3×10 mL) and brine (3×10 mL), dried (MgSO$_4$), filtered and concentrated. The residue was co-evaporated with toluene (3×5 mL) to remove any lingering pyridine. This material was purified by preparative TLC (5% methanol/methylene chloride) to yield 147 mg (22%) of a brown oil.

$^1$H NMR (CDCl$_3$) δ 8.59 (br s, 1H), 8.16 (d, 1H, J=9 Hz), 7.97 (d, 2H, J=9 Hz), 7.63–7.75 (m, 5H), 7.25 (m, 2H), 6.93 (m, 1H), 6.87 (d, 2H, J=8 Hz), 4.18 (m, 3H), 4.02 (s, 2H), 3.91 (m, 1H), 3.42 (m, 1H), 3.02 (m, 2H), 2.55 (m, 1H), 2.43 (m, 1H), 2.24 (s, 6H), 1.40 (t, 3H, J=14 Hz). MS (ES+) m/e 655 (M+1).

e) (+)-2-{[(2-Phenoxyethyl)thio]methyl}-5-{4-[2-methyl-2-(N',N'-dimethylethylenediamino)acetamido]phenyl}-1,3,4-oxadiazole

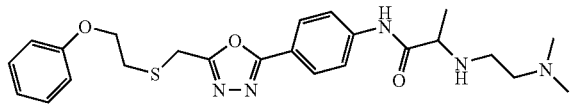

A mixture of (+)-2-{[(2-phenoxyethyl)thio]methyl}-5-{4-[(2-(N',N'-dimethyl-N-(2-nitrobenzenesulfonyl)-1,2-ethanediamino)propionyl)amino]phenyl}-1,3,4-oxadiazole (147 mg, 0.22 mmol), benzenethiol (0.04 mL, 0.39 mmol) and potassium carbonate (93 mg, 0.67 mmol) was stirred in N,N-dimethylformamide (2.0 mL) at room temperature for 1 h. The mixture was diluted with ethyl acetate (40 mL), extracted with water (5×10 mL), dried (MgSO$_4$), filtered and concentrated to yield 182 mg of a brown oil. This residue was purified by preparative TLC (10% methanol/methylene chloride) to yield 35 mg (33%) of a colorless oil.

$^1$H NMR (CDCl$_3$) δ 9.97 (s, 1H), 7.97 (d, 2H, J=8 Hz), 7.76 (d, 2H, J=8 Hz), 7.26 (m, 2H), 6.93 (dd, 1H, J=7 and 8 Hz), 6.88 (d, 2H, J=8 Hz), 4.19 (t, 2H, J=12 Hz), 4.02 (s, 2H), 3.26 (m, 1H), 3.04 (t, 2H, J=12 Hz), 2.81 (m, 1H), 2.64 (m, 1H), 2.47 (m, 1H), 2.37 (m, 1H), 2.24 (s, 6H), 1.40 (d, 2H, J=7). IR (film, cm$^{-1}$) 3421, 3071, 2977, 2938, 1683, 1603, 1499, 1413, 1242, 732. MS (ES+) m/e 470 (M+1). Anal. Calcd for C$_{24}$H$_{31}$N$_5$O$_3$S: C, 61.38; H, 6.65; N, 14.91; S, 6.83. Found C, 61.86; H, 6.62; N, 15.06; S, 6.41.

Example 164

Preparation of (+)-2-{[(2-Phenoxyethyl)thio]methyl}-5-{4-[2-isobutyl-2-(N',N'-dimethylethylenediamino)acetamido]phenyl}-1,3,4-oxadiazole

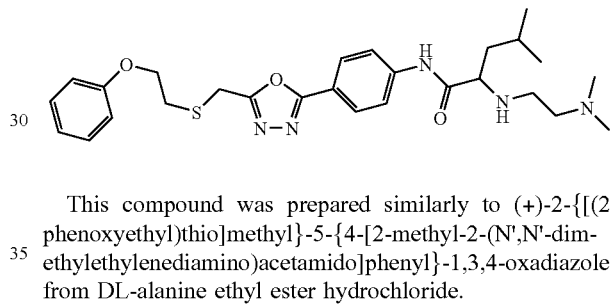

This compound was prepared similarly to (+)-2-{[(2-phenoxyethyl)thio]methyl}-5-{4-[2-methyl-2-(N',N'-dimethylethylenediamino)acetamido]phenyl}-1,3,4-oxadiazole from DL-alanine ethyl ester hydrochloride.

$^1$H NMR (CDCl$_3$) □ 9.98 (s, 1H), 7.96 (d, 2H, J=9 Hz), 7.76 (d, 2H, J=9 Hz), 7.25 (m, 2H), 6.93 (dd, 1H, J=7 and 8 Hz), 6.87 (d, 2H, J=8 Hz), 4.19 (t, 2H, J=12 Hz), 4.02 (s, 2H), 3.18 (m, 1H), 3.04 (t, 2H, J=12 Hz), 2.76 (m, 1H), 2.65 (m, 1), 2.47 (m, 1H), 2.39 (m, 1H), 2.24 (s, 6H), 1.65–1.78 (m, 2H), 1.48 (m, 1H), 0.96 (dd, 6H, J=2 and 9 Hz). IR (film, cm$^{-1}$) 2958, 2867, 2250, 1684, 1601, 1505, 1240, 909, 734, 650. MS (ES+) m/e 512 (M+1). Anal. Calcd for C$_{27}$H$_{37}$N$_5$O$_3$S: C, 63.38; H, 7.29; N, 13.69; S, 6.27. Found C, 63.70; H, 6.73; N, 13.79; S, 5.93.

Example 165

Preparation of N-(3-Dimethylamino-propyl)-4-[5-(3-phenoxy-propoxymethyl)-[1,3,4]oxadiazol-2-yl]-benzamide

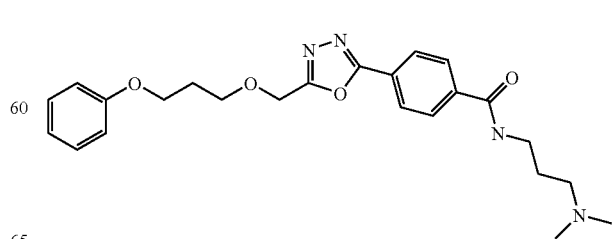

a) (3-Phenoxy-propoxy)-acetic acid tert-butyl ester

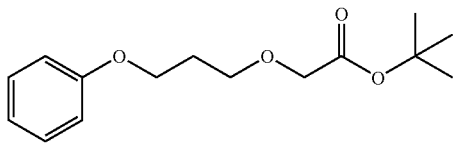

To a solution of 3-phenoxypropanol (5 g, 32.8 mmol) in 30 mL toluene was added tert-butylbromoacetate (19.2 g, 99 mmol) and tetrabutylammonium hydrogen sulfate (2.8 g, 8.2 mmol). The mixture was cooled to 0° C. and treated with 25 mL 50% aqueous NaOH. After stirring for 10 minutes at 0° C. the cooling bath was removed and the reaction was stirred at ambient temperature for 2 hours. It was diluted with 50 mL toluene and the layers were separated. The aqueous layer was extracted with 50 mL toluene and the combined organic layer was dried over MgSO$_4$ before concentrating to dryness. The resulting colorless oil was purified by chromatography using EtOAc in hexanes to recover 6.1 g (23 mmol, 69%) of the desired product as an oil. MS (ES) m/e 378

$^1$H NMR (CDCl$_3$) δ 7.29–7.25 (m, 2H), 6.95–6.89 (m, 3H), 4.11–4.07 (m, 2H), 3.97 (s, 2H), 3.72–3.69 (m, 2H), 2.11–2.08 (m, 2H) and 1.47 (s, 9H).

b) (3-Phenoxy-propoxy)-acetic acid

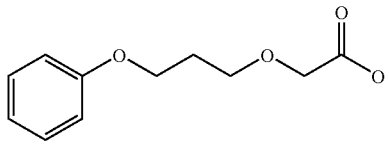

(3-Phenoxy-propoxy)-acetic acid tert-butyl ester (7.6 g, 29 mmol) was mixed with 18 g anisole and 50 mL CH$_2$Cl$_2$ then treated with 25 mL TFA. The mixture was stirred at ambient temp overnight, concentrated to dryness under vacuum and purified by chromatography using MeOH in CHCl$_3$ to recover 5.5 (26 mmol, 90%) of the desired product as an oil. MS (ES) m/e 211

$^1$H NMR (CDCl$_3$) δ 10.55 (bs, 1H), 7.3–7.6 (m, 21), 6.97–6.90 (m, 3H), 4.15 (s, 2H), 4.14–4.10 (m, 2H), 3.78–3.75 (m, 2H), 2.14–2.08 (m, 2H).

c) 4-Hydrazinocarbonyl-benzoic acid methyl ester

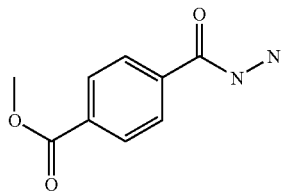

A mixture of dimethyl terephthalate (11 g, 57 mmol) and 350 mL MeOH was treated with 2 mL (62 mmol) of anhydrous hydrazine. The mixture was refluxed for 4 hours, cooled to room temp and filtered. The filtrate was allowed to stand at room temp for several hours then refiltered. The second filtrate was concentrated to dryness, mixed with 200 mL THF, refluxed for several minutes then allowed to stand at room temperature for several hours. The solid was filtered to recover 3.9 g (20 mmol, 35%) product as white crystals. MS (ES) m/e 211

$^1$H NMR (DMSO-d6) δ 9.95 (s, 1H), 8.0–7.98 (m, 2H), 7.92–7.90 (m, 2H), 4.56 (s, 2H), and 3.30 (s, 3H).

d) 4-{N'-[2-(3-Phenoxy-propoxy)-acetyl]-hydrazino}-benzoic acid methyl ester

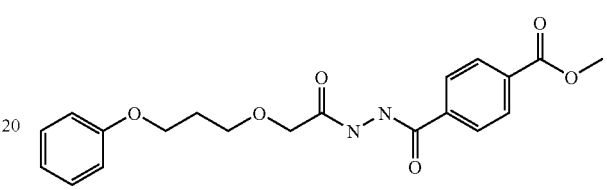

A mixture of (3-phenoxy-propoxy)-acetic acid (3 g, 14.3 mmol) in 25 mL CH$_2$Cl$_2$ was treated with an excess (1 mL) oxalyl chloride and 1 drop of DMF then stirred overnight. After concentration to dryness under vacuum, the residue was dissolved in 10 mL CH$_2$Cl$_2$ and added to a cold (0° C.) mixture of 125 mL pyridine and the 4-hydrazinocarbonyl-benzoic acid methyl ester. The reaction was stirred overnight at ambient temperature, concentrated to dryness under vacuum and purified by chromatography using EtOAc in hexanes to recover 2.7 g of oil which crystallized.

$^1$H NMR (CDCl$_3$) δ 9.36–9.35 (m, 1H), 9.11–9.09 (m, 1H), 8.07–8.03 (m, 2H), 7.82–7.80 (m, 2H), 7.28–7.22 (m, 2H), 6.94–6.86 (m, 3H), 4.12–4.06 (m, 4H), 3.94 (s, 3H), 3.79–3.76 (m, 2H), and 2.15–2.07 (m, 2H).

e) 4-[5-(3-Phenoxy-propoxymethyl)-[1,3,4]oxadiazol-2-yl]-benzoic acid methyl ester

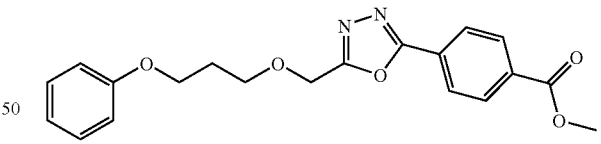

A mixture of 4 {N'-[2-(3-Phenoxy-propoxy)-acetyl]-hydrazino}-benzoic acid methyl ester (2.3 g, 6 mmol) and 25 mL SOCl$_2$ was refluxed overnight and concentrated to dryness under vacuum. Residual SOCl$_2$ was remover by mixing with toluene and reconcentrating to an oil. After dissolving in 16 mL CH$_2$Cl$_2$ and 4 mL MeOH, it was treated with 3 mL 2 M trimethylsilyldiazomethane in hexanes, reconcentrated to dryness and purified by silica gel chromatography using EtOAc in hexanes to recover 0.8 g of product.

$^1$H NMR (CDCl$_3$) δ 8.15–8.08 (m, 4H), 7.24–7.21 (m, 2H), 6.91–6.84 (m, 3H), 4.79 (s, 2H), 4.08–4.06 (m, 2H), 3.96 (s, 3H), 3.82–3.79 (m, 2H), 2.13–2.07 (m, 2H).

f) 4-[5-(3-Phenoxy-propoxymethyl)-[1,3,4]oxadiazol-2-yl]-benzoic acid

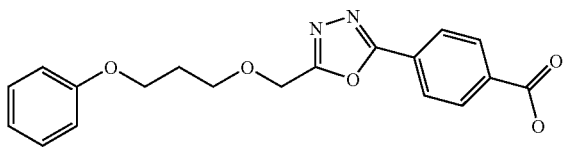

4-[5-(3-Phenoxy-propoxymethyl)-[1,3,4]oxadiazol-2-yl]-benzoic acid methyl ester (0.8 g, 2.3 mmol) was dissolved in 50 mL THF, treated with 3.5 mL 1 M aqueous LiOH, and stirred overnight at ambient temperature. The reaction was neutralized with 3.5 mL 1 N HCl, mixed with 20 mL brine and extracted twice with 20 mL EtOAc. The extracts were dried over MgSO4 and concentrated to 550 mg (1.6 mmol, 68%) of a white solid which was used as isolated in the next procedure.

$^1$H NMR (DMSO-d6) δ 8.15–8.08 (m, 4H), 7.24–7.21 (m, 2H), 6.91–6.84 (m, 3H), 4.08–4.06 (m, 2H), 3–96 (s, 3H), 3.82–3.79 (m, 2H), 2.13–2.07 (m, 2H).

g) N-(3-Dimethylamino-propyl)-4-[5-(3-phenoxy-propoxymethyl)-[1,3,4]oxadiazol-2-yl]-benzamide

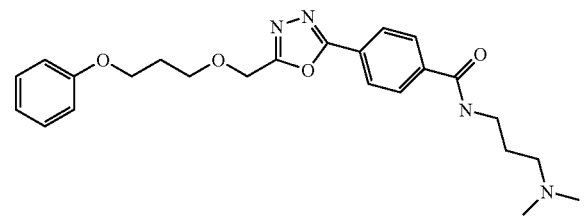

4-[5-(3-Phenoxy-propoxymethyl)-[1,3,4]oxadiazol-2-yl]-benzoic acid (500 mg, 1.4 mmol) was converted to it's acid chloride by mixing with 50 mL CH$_2$Cl$_2$, 2 mL oxalyl chloride and 2 drops of DMF and stirring for 1 hour. After concentration to dryness it was re-dissolved in 10 mL CH$_2$Cl$_2$ and added to a cold mixture of 3-dimethylamino-propylamine (317 mg, 3.1 mmol) in 30 mL CH$_2$Cl$_2$. The reaction was stirred at 0° C. for 1 hour, concentrated to dryness then purified by silica gel chromatography using MeOH in CHCl$_3$ to recover 250 mg white solid.

$^1$H NMR (CDCl$_3$) δ 8.81. (s, 1H), 8.10–8.07 (m, 2H), 7.88–7.86 (m, 2H), 7.25–7.22 (m, 2H), 6.92–6.85 (m, 3H), 4.78 (s, 2H), 4.09–4.06 (m, 2H), 3.82–3.79 (m, 2H), 3.62–3.58 (m, 2H), 2.55–2.52 (m, 2H), 2.3 (s, 6H), 2.13–2.07 (m, 21, 1.81–1.75 (m, 2H).

Anal. Calcd for C$_{24}$H$_{30}$N$_4$O$_4$·0.2C$_4$H$_{10}$O·0.1H$_2$O: C, 65.19; H, 7.15; N, 12.26. Found C, 65.33; H, 6.86; N, 12.60.

Example 166

Preparation of N-(3-Dimethylamino-propyl)-4-{5-[(4-phenoxy-butyrylamino)-methyl]-[1,3,4]oxadiazol-2-yl}-benzamide

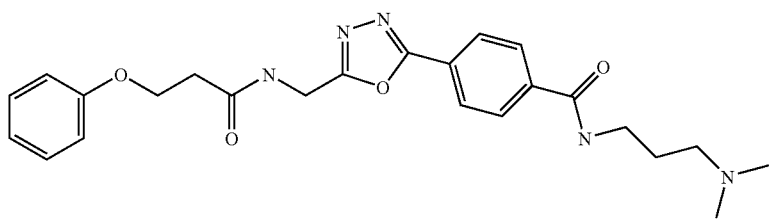

a) 4-{N'-[2-(1,3-Dioxo-1,3-dihydro-isoindol-2-yl)-acetyl]-hydrazinocarbonyl}-benzoic acid methyl ester

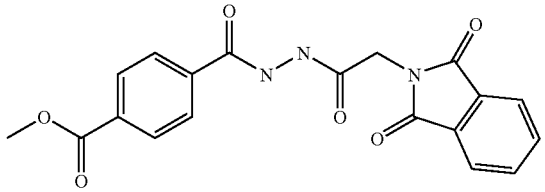

Starting from 4-hydrazinocarbonyl-benzoic acid methyl ester and N-phthaloylglycine, this compound was prepared in 69% yield in a similar manner as exemplified in example 165 d.

$^1$H NMR (DMSO-d6) δ 10.66 (s, 1H), 10.45 (s, 1H), 8.05–8.03 (m, 2H), 7.96–7.91 (m, 4H), 7.88–7.85 (m, 2H), 4.34 (s, 2H), 3.86 (s, 3H) MS (ES) m/e 382.

b) 4-[5-(1,3-Dioxo-1,3-dihydro-isoindol-2-ylmethyl)-[1,3,4]oxadiazol-2-yl]-benzoic acid methyl ester

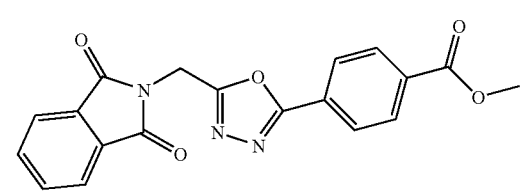

4-{N'-[2-(1,3-Dioxo-1,3-dihydro-isoindol-2-yl)-acetyl]-hydrazinocarbonyl}-benzoic acid methyl ester (5 g, 13.11 mmol) was mixed with 100 mL SOCl$_2$ and refluxed over night. Concentration under vacuum gave a solid which was tritrated with MeOH to recover 3 g (8.3 mmol, 63%) of the product as a white solid.

$^1$H NMR (DMSO-d6) δ 8.14–8.07 (m, 4H), 7.96–7.94 (m, 2H), 7.93–7.87 (m, 2H), 5.15 (s, 2H), 3.87 (s, 3H).

c) 4-[5-(1,3-Dioxo-1,3-dihydro-isoindol-2-ylmethyl)-[1,3,4]oxadiazol-2-yl]-benzoic acid

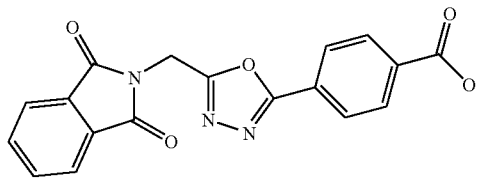

A mixture of 4-[5-(1,3-dioxo-1,3-dihydro-isoindol-2-ylmethyl)-[1,3,4]oxadiazol-2-yl]-benzoic acid methyl ester (6 g, 16.5 mmol), thiophenol (3.6 g, 33 mmol), Potassium fluoride (1.9 g, 33 mmol) and N-methylpyrrolidinone (60 mL) was heated in a sealed tube at 180° C. for 60 hours. The reaction was poured into 200 mL brine, diluted with 40 mL 5N HCl and extracted 3 times with 200 mL EtOAc. The combined extracts was dried over MgSO$_4$ and concentrated to dryness under vacuum. The residue was mixed with 50 mL CHCl$_3$ and filtered to recover 3.5 g solid.

$^1$H NMR (DMSO-d6) δ 12.0 (t, 1H), 8.1–8.0 (m, 2H), 7.95–7.85 (m, 2H), 7.8–7.7 (m, 1H), 7.6–7.5 (m, 1H), 7.4–7.3 (m, 2H), 7.7–7.8 (m, 2H). MS (ES) m/e 350.

d) 4-(5-Aminomethyl-[1,3,4]oxadiazol-2-yl)-N-(3-dimethylamino-propyl)-benzamide

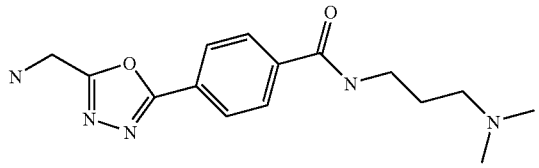

A mixture of 4-[5-(1,3-dioxo-1,3-dihydro-isoindol-2-ylmethyl)-[1,3,4]oxadiazol-2-yl]-benzoic acid (4 g, 11.45 mmol), 3-dimethylaminopropyl amine (1.4 g, 13.7 mmol) and triethylamine (2.3 g, 22.9 mmol) in 100 mL dry DMF was cooled to 0° C. and treated with dicyclohexylcarbodiimide (2.8 g, 13.7 mmol) and hydroxy benzotriazole (1.86 g, 13.7 mmol). The cooling bath was removed and the reaction was stirred for 2 hours before adding an additional 1 g (4.8 mmol) of dicyclohexylcarbodiimide. After stirring an additional 18 hours it was concentrated to dryness under vacuum, mixed with 250 mL CHCl3 and filtered. The filtrate was purified by 2 chromatographies on silica using CHCl3 and MeOH then THF, Hexanes and triethylamine to give 2 g of a solid. This was further purified using an ion exchange column to recover 1.7 g of an oil.

The above oil was dissolved in 50 mL EtOH and treated with 1 mL hydrazine monohydrate. After refluxing for 15 minutes, the reaction was concentrated to dryness, mixed with 30 mL MeOH and filtered. The filtrate was purified by ion exchange chromatography to recover 1.2 g of a solid.

$^1$H NMR (CDCl$_3$) δ 8.75–8.65 (m, 1H), 8.10–8.0 (m, 4H), 3.95 (s, 2H), 3.3–3.25 (m, 4H), 2.3–2.25 (m, 2H), 2.15 (s, 6H), 1.7–1.6 (m, 2H).

Anal. Calcd for $C_{15}H_{21}N_5O_2$: C, 59.39; H, 6.98; N, 23.01. Found C, 59.11; H, 7.04; N, 22.78. MS (ES) m/e 304 e) N-(3-Dimethylamino-propyl)-4-{5-[(4-phenoxybutyrylamino)-methyl]-[1,3,4]oxadiazol-2-yl}-benzamide

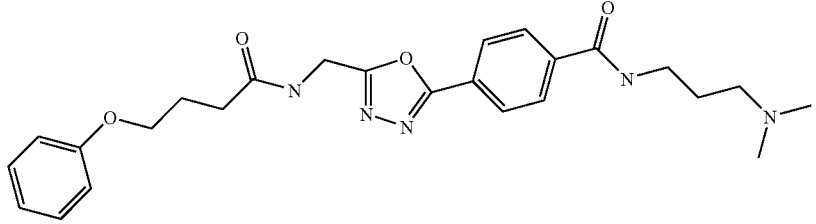

A mixture of the 4-(5-aminomethyl-[1,3,4]oxadiazol-2-yl)-N-(3-dimethylamino-propyl)-benzamide (150 mg, 0.5 mmol), 1-ethyl-3-(3-dimethylaminopropyl)carbodiimide hydrochloride (147 mg, 0.74 mmol), 3-phenoxybutyric acid (133 mg, 0.74 mmol) and triethylamine (200 mg, 2 mmol) in 20 mL dry DMF was stirred for 4 hours. Concentrated to an oil under vacuum, mixed with CHCl$_3$ and purified by chromatography on silica using a mixture of CHCl$_3$, MeOH and ammonium hydroxide to recover 78 mg (0.17 mmol, 33%) of a white solid. MS (ES) m/e 304

$^1$H NMR (CDCl$_3$) δ 8.92 (s, 1H), 8.03–8.01 (m, 2H), 7.84–7.82 (m, 2H), 7.27–7.23 (m, 2H), 6.94–6.86 (m, 3H), 6.63–6.60 (m, 1H), 4.77–4.75 (m, 2H), 4.05–4.02 (m, 2H) 3.60–3.56 (m, 2H), 2.56–2.51 (m, 4H), 2.30 (s, 6H), 2.22–2.15 (m, 2H), 1.8–1.74 (m, 2H). Anal. Calcd for $C_{25}H_{31}N_5O_4$: C, 64.50; H, 6.73; N, 15.22. Found C, 64.50; H, 6.71; N, 15.04.

Example 167

Preparation of N-(3-Dimethylamino-propyl)-4-{5-[(3-phenoxy-propionylamino)-methyl]-[1,3,4]oxadiazol-2-yl}-benzamide

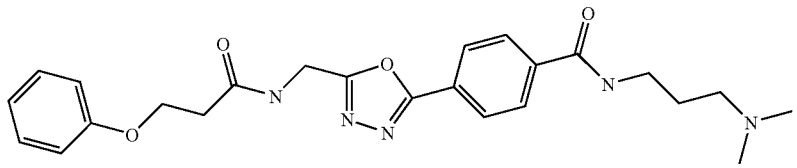

Starting from 3-phenoxy propionic acid and 4-(5-aminomethyl-[1,3,4]oxadiazol-2-yl)-N-(3-dimethylamino-propyl)-benzamide this compound was prepared in 13% yield using the procedure exemplified in Example 166 e.

MS (ES) m/e 452

$^1$H NMR (CDCl$_3$) δ 8.92 (s, 1H), 8.03–8.01 (m, 2H), 7.84–7.82 (m, 2H), 7.29–7.25 (m, 2H), 6.98–6.90 (m, 4H), 4.81–4.79 (m, 2H), 4.32–4.30 (m, 2H), 3.59–3.48 (m, 2H), 2.82–2.79 (m, 2H), 2.54–2.51 (m 2H), 2.31 (s, 6H), 1.80–1.74 (m, 2H). Anal. Calcd for C$_{24}$H$_{30}$N$_4$O$_4$·0.2C$_4$H$_{10}$·0.5H$_2$O: C, 62.59; H, 6.57; N, 15.21. Found C, 62.93; H, 6.27; N, 15.23.

Example 168

Preparation of N-(3-Dimethylamino-propyl)-4-{5-[(5-phenoxy-pentanoylamino)-methyl]-[1,3,4]oxadiazol-2-yl}-benzamide

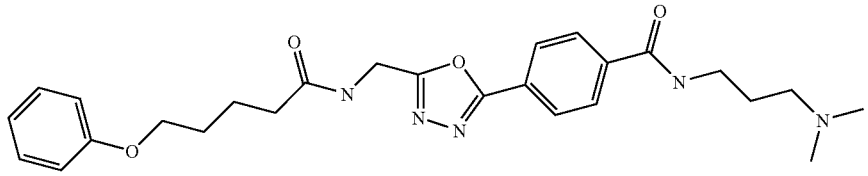

Starting from 3-phenoxybutyric acid and 4-(5-aminomethyl-[1,3,4]oxadiazol-2-yl)-N-(3-dimethylamino-propyl)-benzamide this compound was prepared in 22% yield using the procedure procedure exemplified in Example 166 e.

MS (ES) m/e 480. $^1$H NMR (CDCl$_3$) δ 8.92 (s, 1H), 8.04–8.02 (m, 2H), 7.84–7.82 (m, 2H), 7.28–7.23 (m, 2H), 6.94–6.85 (m, 3H), 6.57 (s, 1H), 4.76–4.75 (m, 2H), 4.00–3.97 (m, 2H), 3.60–3.56 (m, 2), 2.54–2.51 (m, 2H), 2.43–2.40 (m 2), 2.30 (s, 6H), 1.92–1.84 (m, 4H), 1.80–1.74 (m, 2H). Anal. Calcd for C$_{26}$H$_{33}$N$_5$O$_4$·0.2H$_2$O: C, 64.63; H, 6.96; N, 14.50. Found C, 64.37; H, 6.76; N, 14.41.

Example 169

Preparation of Dimethyl-(3-{4-[4-(2-phenoxy-ethylsulfanylmethyl)-oxazol-2-yl]-phenoxy}-propyl)-amine Hydrochloride

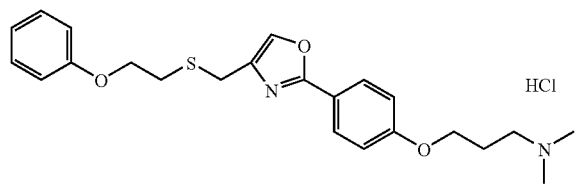

a) 4-(4-Chloromethyl-oxazol-2-yl)-phenol

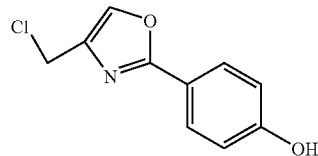

A solution of 4-hydroxy-benzamide (3.20 g, 23.33 mmol) and 1,3-dichloro acetone (5.93 g, 46.66 mmol) in 40 mL dimethylformamide was warmed to 120° C. for 4 h. The reaction mixture was allowed to cool to room temperature and poured into 50 g of ice/water. The resulting precipitate was filtered and dried in vacuo to afford 3.98 g (82%) 2-(4-hydroxyphenyl)-4-chloromethyl-oxazole as a white solid.

$^1$H NMR (DMSO-D$_6$, 300 MHz): δ 10.12 (s, 1H), 8.15 (s, 1H), 7.81 (d, 2H, J=9 Hz), 6.89 (d, 2H, J=9 Hz), 4.70 (s, 2H). MS (MH$^+$) 210.

b) 4-[4-(2-Phenoxy-ethylsulfanylmethyl)-oxazol-2-yl]-phenol

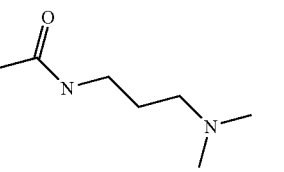

A solution of sodium hydride (200 mg, 8.34 mmol) in ethanol (47 mL) was treated with 2-phenoxy-ethanethiol (1.17 g, 7.59 mmol) in 5 mL ethanol at room temperature and stirred for 10 minutes. 4-(4-Chloromethyl-oxazol-2-yl)-phenol (1.99 g, 9.48 mmol) was added and stirring was continued for 16 hours. The solvent was evaporated in vacuo and the remains were poured into 50 mL water. The precipitate was filtered and dried in vacuo. The solid was stirred in 8 mL solvent mixture of hexane and tert.-butyl methylether (10:1), and dried again in vacuo to afford 2.13 g (86%) 4-[4-(2-phenoxy-ethylsulfanylmethyl)-oxazol-2-yl]-phenol as a white solid.

$^1$H NMR (DMSO-D$_6$, 300 MHz): δ 10.18 (br s, 1H), 7.95 (s, 1H), 7.78 (d, 2H, J=9 Hz), 7.27 (d, 2H, J=12 Hz), 6.96–6.85 (m, 5H), 4.17 (t, 2H, J=7 Hz), 3.76 (s, 2H), 2.92 (t, 2H, J=7 Hz). MS (MH$^+$)328.

c) Dimethyl-(3-{4-[4-(2-phenoxy-ethylsulfanylmethyl)-oxazol-2-yl]-phenoxy}-propyl)-amine Hydrochloride

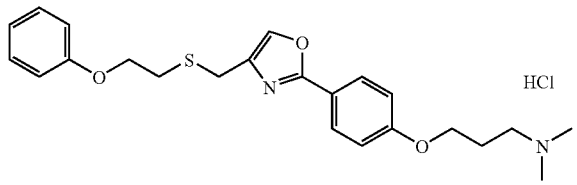

A suspension of 4-[4-(2-phenoxy-ethylsulfanylmethyl)-oxazol-2-yl]-phenol (524 mg, 1.60 mmol), dimethyl 3-chloro-propyl-amine hydrochloride (304 mg, 1.92 mmol), and potassium carbonate (531 mg, 3.84 mmol) in dimethylformamide (20 mL) was heated at 80° C. for 14 hours. The solvent was removed in vacuo and the remains partitioned between water and methylene chloride. The organic layer was dried over sodium sulfate and evaporated. The remaining oil was purified by chromatography on silica gel (elution with gradient methylene chloride/ethanol containing 10% ammonia) to afford a white solid. The solid was dissolved in 10 mL dioxane and treated with 0.1 mL 4M HCl in dioxane and stirred for 10 minutes. Ether was added and the precipitation filtered and dried in vacuo to afford 204 mg (28%) of dimethyl-(3-{4-[4-(2-phenoxy-ethylsulfanylmethyl)-oxazol-2-yl]-phenoxy}-propyl)-amine as a white solid.

$^1$H NMR (DMSO-D$_6$, 300 MHz): δ 10.42 (br s, 1H), 8.01 (s, 1H), 7.90 (d, 2H, J=9 Hz), 7.28 (t, 2H, J=8 Hz), 7.09 (d, 2H, J=9 Hz), 6.99–6.88 (m, 3H), 4.22–4.10 (m, 4H), 3.78 (s, 2H), 3.26–3.17 (m, 2H), 2.93 (t, 2H, J=7 Hz), 2.79 (s, 3H), 2.78 (s, 3H), 2.23–2.12 (m, 2H). MS (MH$^+$) 413.

Example 170

Preparation of Dimethyl-(3-{4-[2-(2-phenoxy-ethylsulfanylmethyl)-oxazol-4-yl]-phenoxy}-propyl)-amine

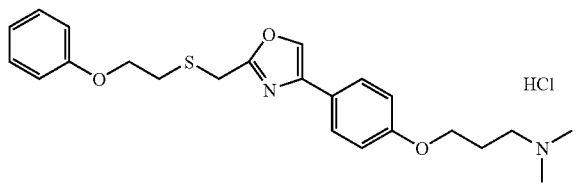

a) 4-(4-Methoxy-phenyl)-2-vinyl-oxazole

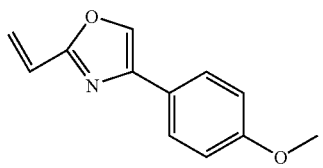

A solution of ω-bromo acetophenone (11.93 g, 52.08 mmol), 2,6 di-tert.-butyl-4-methyl-phenol as a stabilizer (1.15 g, 5.21 mmol), and acryl amide (7.40 g, 104.16 mmol) were dissolved in 360 mL dimethylformamide and heated at 150° C. for 4 hours. The solvent was evaporated and the remaining oil dissolved in 200 mL ethyl acetate and washed with 150 mL water. The organic layer was dried over sodium sulfate and evaporated and the remaining oil purified by chromatography on silica gel (elution with gradient hexane/ethyl acetate) to afford 5.59 g (53%) of 4-(4-methoxy-phenyl)-2-vinyl-oxazole as a white solid.

$^1$H NMR (CDCl$_3$, 300 MHz): δ 7.76 (s, 1H), 7.67 (d, 2H, J=9 Hz), 6.94 (d, 2H, J=9 Hz), 6.65 (dd, 1H, J=18 Hz, J=11 Hz), 6.22 (d, 1H, J=18 Hz), 5.65 (d, 1H, J=11 Hz), 3.34 (s, 3H). MS (MH$^+$)202.

b) 4-(4-Methoxy-phenyl)-oxazole-2-carbaldehyde

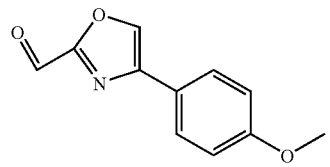

A solution of 4-(4-methoxy-phenyl)-2-vinyl-oxazole (3.06 g, 15.21 mmol), N-methyl-morpholine N-oxide (2.16 g, 15.97 mmol), hydrochinidine-(1,4-phthalazindiyl-diether) (116 mg, 1.49 mmol) in 70 mL acetone: water (4:1) was treated with 4 mL of 0.079 M aqueous osmium tetroxide solution and was stirred at room temperature for 4 hours. The solvent was evaporated in vacuo and remaining oil was dissolved in 150 mL methylene chloride and washed with 50 mL 10% aqueous sodium sulfite solution. The organic layer was dried over sodium sulfate and evaporated. The remaining oil was dissolved in 50 mL tert.-butyl methylether and 50 mL water and treated with sodium meta periodate and stirred for 4 hours. The organic layer was than separated, dried over sodium sulfate and evaporated to afford 1.5 g (49%) of 4-(4-methoxy-phenyl)-oxazole-2-carbaldehyde as a colourless oil.

$^1$H NMR (CDCl$_3$, 300 MHz): δ 9.82 (s, 1H), 8.04 (s, 1H), 7.73 (d, 2H, J=9 Hz), 6.98 (d, 2H, J=9 Hz), 3.87 (s, 3H). MS (MH$^+$) 204.

c) [4-(4-Methoxy-phenyl)-oxazol-2-yl]-methanol

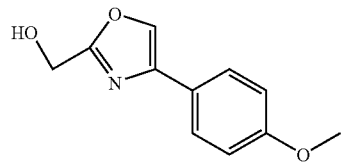

A solution of 4-(4-methoxy-phenyl)-oxazole-2-carbaldehyde (1.27 g, 6.23 mmol) in 50 mL ethanol: water (4:1) was treated with sodium borohydride (236 mg, 6.23 mmol) and stirred at room temperature for 30 minutes. The reaction was quenched with 2 mL acetone and evaporated. The remaining oil was dissolved in 75 mL methylene chloride and washed with 50 mL water. The organic layer was dried over sodium sulfate and evaporated and the remaining oil purified by chromatography on silica gel (elution with gradient hexane/ethyl acetate) to afford 1.17 g (92%) [4-(4-methoxy-phenyl)-oxazol-2-yl]-methanol as white crystals.

$^1$H NMR (CDCl$_3$, 300 MHz): δ 7.78 (s, 1H), 7.63 (d, 2H, J=9 Hz), 6.93 (d, 2H, J=9 Hz), 4.77 (s, 2H), 3.83 (s, 3H). MS (MH$^+$) 206.

d) 2-Chloromethyl-4-(4-methoxy-phenyl)-oxazole

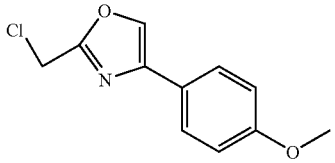

A solution of [4-(4-methoxy-phenyl)-oxazol-2-yl]-methanol (861 mg, 4.2 mmol) in 10 mL carbon tetrachloride was treated with triphenylphosphine (1.18 g, 4.49 mmol) and heated at 80° C. for 7 hours. The solvent was evaporated and the remaining yellow solid purified by chromatography on silica gel (elution with gradient methylene chloride/ethanol) to afford 769 mg (82%) 2-chloromethyl-4-(4-methoxy-phenyl)-oxazole as yellow crystals.

$^1$H NMR (CDCl$_3$, 300 MHz): δ 7.83 (s, 1H), 7.65 (d, 2H, J=9 Hz), 6.94 (d, 2H, J=9 Hz), 4.65 (s, 2H), 3.85 (s, 3H). MS (MH$^+$)224.

e) 4-(2-Chloromethyl-oxazol-4-yl)-phenol

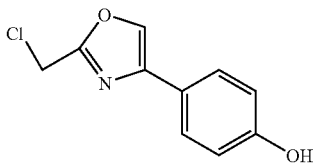

2-Chloromethyl-4-(4-methoxy-phenyl)-oxazole (753 mg, 3.37 mmol) was dissolved in 20 mL methylene chloride, cooled to −70° C. and treated with 6.74 ml 1M boron tribromide solution in methylene chloride. Within 2 hours the reaction mixture was allowed to warm to room temperature and quenched with 15 mL saturated aqueous sodium bicarbonate solution. The organic layer was washed with 10 mL 2M hydrochloric acid, dried over sodium sulfate and evaporated to afford 682 mg (97%) 4-(2-chloromethyl-oxazol-4-yl)-phenol as a white solid.

$^1$H NMR (CDCl$_3$) δ 7.83 (s, 1H), 7.59 (d, 2H, J=9 Hz), 6.87 (d, 2H, J=9 Hz), 5.42 (br S, 1H), 4.65 (s, 2H). MS (MH$^+$) 210.

f) 4-[2-(2-Phenoxy-ethylsulfanylmethyl)-oxazol-4-yl]-phenol

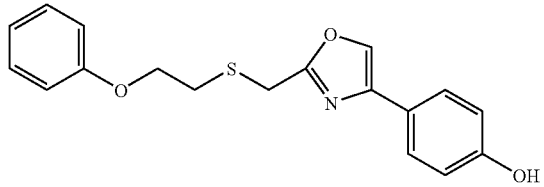

A solution of sodium hydride (82 mg, 3.42 mmol) in 3 mL ethanol was treated with 2-phenoxy-ethanethiol (502 mg, 3.25 mmol) in 2 mL ethanol at room temperature and stirred for 10 minutes. 4-(2-Chloromethyl-oxazol-4-yl)-phenol (682 mg, 3.25 mmol) was added and stirring was continued for 72 hours. The solvent was evaporated in vacuo and the remains were poured into 50 mL water. The precipitate was filtered, dried in vacuo to afford 1.02 g (96%) 4-[2-(2-phenoxy-ethylsulfanylmethyl)-oxazol-4-yl]-phenol as a white solid.

$^1$H NMR (CDCl$_3$, 300 MHz): δ 7.77 (s, 1H), 7.75 (d, 2H, J=9 Hz), 7.26 (t, 2H, J=7 Hz), 6.98–6.82 (m, 5H), 4.16 (t, 2H, J=6 Hz), 3.93 (s, 2H), 3.03 (t, 2H, J=6 Hz). MS (MH$^+$) 328.

g) Dimethyl-(3-{4-[2-(2-phenoxy-ethylsulfanylmethyl)-oxazol-4-yl]-phenoxy}-propyl)-amine

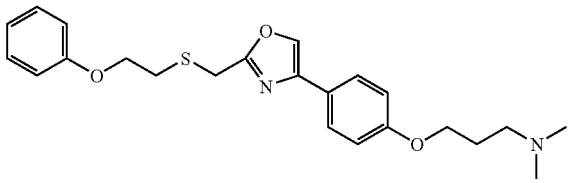

A suspension of 4-[2-(2-phenoxy-ethylsulfanylmethyl)-oxazol-4-yl]-phenol (1.00 g, 3.05 mmol), dimethyl 3-chloropropyl-amine hydrochloride (507 mg, 3.21 mmol), and potassium carbonate (929 mg, 6.72 mmol) in dimethylformamide (20 mL) was heated at 80° C. for 24 hours. The solvent was removed in vacuo and the remains partitioned between water and methylene chloride. The organic layer was dried over sodium sulfate and evaporated. The remaining oil was purified by chromatography on silica gel (elution with gradient methylene chloride/ethanol containing 10% ammonia) to afford 765 mg (61%) of dimethyl-(3-{4-[2-(2-phenoxy-ethylsulfanylmethyl)-oxazol-4-yl]-phenoxy}-propyl)-amine as white solid.

$^1$H NMR (CDCl$_3$, 300 MHz): δ 7.77 (s, 1H), 7.62 (d, 2H, J=9 Hz), 7.26 (t, 2H, J=7 Hz), 6.97–6.86 (m, 5H), 4.17 (t, 2H, J=7 Hz), 4.04 (t, 2H, J=7 Hz), 3.93 (s, 2H), 3.04 (t, 2H, J=7 Hz), 2.46 (t, 2H, J=7 Hz), 2.27 (s, 6H), 2.02–1.92 (m, 2H). MS (MH$^+$) 413.

Example 171

Preparation of Dimethyl-(3-{4-[4-(2-phenoxy-ethylsulfanylmethyl)-thiazol-2-yl]-10 phenoxy}-propyl)-amine Hydrochloride

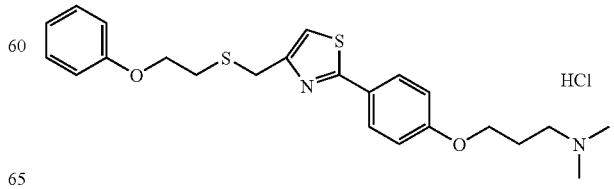

a) 4-Chloromethyl-2-(4-methoxy-phenyl)-thiazole

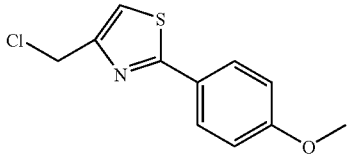

A solution of 4-methoxy-thiobenzamide (1.90 g, 11.33 mmol) and 1,3-dichloro acetone (2.8 g, 22.6 mmol) in 20 mL dimethylformamide was warmed to 100° C. for 2 h. The reaction mixture was allowed to cool to room temperature and poured into 30 g of ice/water. The resulting precipitate was filtered and dried in vacuo to afford 1.60 g (59%) 4-chloromethyl-2-(4-methoxy-phenyl)-thiazole as a white solid.

$^1$H NMR (CDCl$_3$, 300 MHz): δ 7.88 (d, 2H, J=9 Hz), 7.23 (s, 1H), 6.95 (d, 2H, J=9 Hz), 4.72 (s, 2H), 3.83 (s, 3H). MS (MH$^+$) 240.

b) 4-(4-Chloromethyl-thiazol-2-yl)-phenol

4-Chloromethyl-2-(4-methoxy-phenyl)-thiazole (1.0 g, 4.17 mmol) was dissolved in 20 mL methylene chloride, cooled to −70° C. and treated with 8.34 ml 1M boron tribromide solution in methylene chloride. Within 2 hours the reaction mixture was allowed to warm to room temperature and quenched with 15 mL saturated aqueous sodium bicarbonate solution. The organic layer was washed with 10 mL 2M hydrochloric acid, dried over sodium sulfate and evaporated. The solid was stirred with 5 mL methylene chloride. The remaining solid was dried in vacuo to afford 795 mg (85%) 4-(4-chloromethyl-thiazol-2-yl)-phenol as a white solid.

$^1$H NMR (DMSO-D$_6$, 300 MHz): δ 9.80 (br s, 1H), 7.77 (d, 2H, J=9Hz), 7.67 (s, 1H), 6.87 (d, 2H, J=9 Hz), 4.83 (s, 2H). MS (MH$^+$) 226.

c) 4-[4-(2-Phenoxy-ethylsulfanylmethyl)-thiazol-2-yl]-phenol

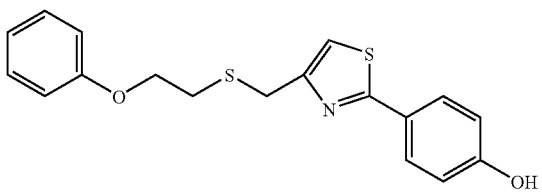

A solution of sodium hydride (80 mg, 3.34 mmol) in 5 mL ethanol was treated with 2-phenoxy-ethanethiol (490 mg, 3.18 mmol) in 2 mL ethanol at room temperature and stirred for 10 minutes. 4-(4-chloromethyl-thiazol-2-yl)-phenol (790 mg, 3.18 mmol) was added and stirring was continued for 16 hours. The solvent was evaporated in vacuo and the remains were poured into 50 mL water and extracted with ethyl acetate. The organic layer was dried over sodium sulfate and evaporated. The remaining oil was purified by chromatography on silica gel (elution with gradient methylene chloride/ethanol containing 10% ammonia) to afford 767 mg (70%) 4-[4-(2-phenoxy-ethylsulfanylmethyl)-thiazol-2-yl]-phenol as a white solid.

$^1$H NMR (CDCl$_3$, 300 MHz): δ 7.80 (d, 2H, J=8 Hz), 7.26 (t, 2H, J=9, Hz), 7.07 (s, 1H), 6.98–6.80 (m, 5H), 5.69 (s, 1H), 4.18 (t, 2H, J=7 Hz), 3.99 (s, 2H), 2.96 (t, 2H, J=7 Hz). MS (MH$^+$) 344.

d) Dimethyl-(3-{4-[4-(2-phenoxy-ethylsulfanylmethyl)-thiazol-2-yl]-phenoxy}-propyl)-amine Hydrochloride

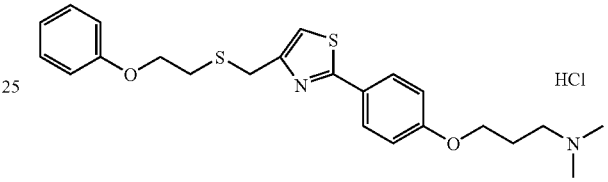

A suspension of 4-[4-(2-phenoxy-ethylsulfanylmethyl)-thiazol-2-yl]-phenol (751 mg, 2.19 mmol), dimethyl 3-chloro-propyl-amine hydrochloride (363 mg, 2.30 mmol), and potassium carbonate (665 mg, 4.81 mmol) in dimethylformamide (15 mL) was heated at 80° C. for 14 hours. The solvent was removed in vacuo and the remains partitioned between water and methylene chloride. The organic layer was dried over sodium sulfate and evaporated. The remaining oil was purified by chromatography on silica gel (elution with gradient methylene chloride/ethanol containing 10% ammonia) to afford a white solid. The solid was dissolved in 10 mL dioxane and treated with 0.5 mL 4M HCl in dioxane and stirred for 10 minutes. Ether was added and the precipitation filtered and dried in vacuo to afford 546 mg (54%) of dimethyl-(3-{4-[4-(2-phenoxy-ethylsulfanylmethyl)-thiazol-2-yl]-phenoxy}-propyl)-amine as a white solid.

$^1$H NMR (DMSO-D$_6$, 300 MHz): δ 10.49 (br s, 1H), 7.86 (d, 2H, J=9 Hz), 7.46 (s, 1H), 7.27 (t, 2H, J=8 Hz), 7.04 (d, 2H, J=9 Hz), 6.97–6.89 (m, 3H), 4.22–3.98 (m, 6H), 3.97 (s, 2H), 3.26–3.17 (m, 2H), 2.94 (t, 2H, J=7 Hz), 2.79 (s, 3H), 2.77 (s, 3H), 2.23–2.11 (m, 2H). MS (MH$^+$) 429.

Example 172

Dimethyl-(3-{4-[2-(2-phenoxy-ethylsulfanylmethyl)-oxazol-5-yl]-phenoxy}-propyl)-amine

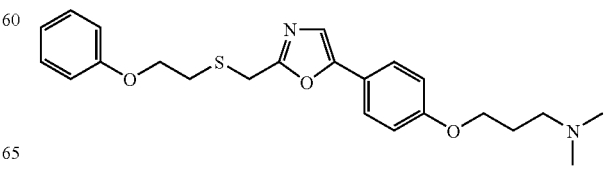

a) 2-Chloro-N-[2-(4-methoxy-phenyl)-2-oxo-ethyl]-acetamide

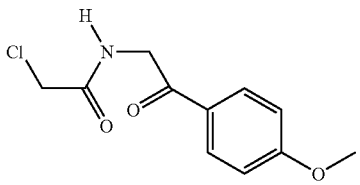

6.30 g (31 mmol) ω-amino-4-methoxy acetophenon hydrochloride was suspended in 70 mL methylene chloride and treated with 8.6 mL (62 mmol) triethylamine. 2.46 ml (31 mmol) of chloro acetylchloride was added drop wise under slight cooling (~10° C.). After complete addition the reaction mixture was stirred at room temperature for 24 h. The reaction was quenched with water (100 mL) and the organic layer was dried over sodium sulfate and evaporated to yield 7.45 g (100%) 2-chloro-N-[2-(4-methoxy-phenyl)-2-oxo-ethyl]-acetamide.

$^1$H NMR (CDCl$_3$, 300 MHz): δ 7.96 (d, 2H, J=7 Hz), 7.68 (br s, 1H), 6.98 (d, 2H, J=7 Hz), 4.73 (d, 2H, J=4 Hz), 4.13 (s, 2H), 3.89 (s, 3H).

b) 2-Chloromethyl-5-(4-methoxy-phenyl)-oxazole

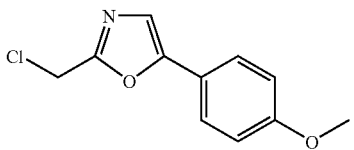

1.7 g (7 mmol) of 2-chloro-N-[2-(4-methoxy-phenyl)-2-oxo-ethyl]-acetamide was treated with 20 ml of phosphorous oxychloride and stirred for 2 h at 100° C. The dark mixture was poured into water cautiously in portions. The temperature was held below 40° C. by addition of ice. After being basification with conc. aequous ammonia the mixture was extracted with tert.-butyl methylether. The organic layer was dried over sodium sulfate and evaporated to yield 1.5 g (96%) of 2-chloromethyl-5-(4-methoxy-phenyl)-oxazole.

$^1$H NMR (CDCl$_3$, 300 MHz): δ 7.58 (d, 2H, J=9 Hz), 7.19 (s, 1H), 6.95 (d, 2H, J=9 Hz), 4.66 (s, 2H), 3.85 (s, 3H).

c) 4-(2-Chloromethyl-oxazol-5-yl)-phenol

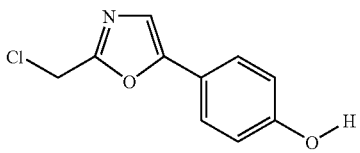

1.4 g (6.2 mmol) of 2-chloromethyl-5-(4-methoxy-phenyl)-oxazole were dissolved in 25 mL methylene chloride, cooled to −70° C., and treated dropwise with 12.4 mL of a borone tribromide solution (1M in methylene chloride). After complete addition the reaction mixture was allowed to warm to room temperature. The mixture was poured into ice/water, basified with saturated aequous sodium carbonate and acidified with aqueous 2M HCl solution. After extraction with methylene chloride, drying over sodium sulfate and evaporation, the crude product was dissolved in 5 mL chloroform filtered and dried to yield 0.79 g (61%) 4-(2-chloromethyl-oxazol-5-yl)-phenol.

$^1$H NMR (DMSO-d$_6$, 300 MHz): δ 9.86 (br s, 1H), 7.54 (d, 2H, J=9 Hz), 7.47 (s, 1H), 6.86 (d, 2H, J=9 Hz), 4.91 (s, 2H).

d) 4-[2-(2-Phenoxy-ethylsulfanylmethyl)-oxazol-5-yl]-phenol

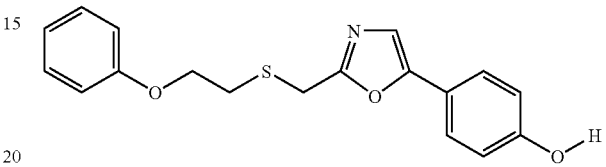

0.54 g (3.5 mmol) of 2-phenoxy-ethanethiol was dissolved in 8 ml of ethanol and treated with 1.75 mL (3.5 mmol) of 2M ethanolic sodium ethoxide solution. After stirring at room temperature for 10 minutes 0.78 g (3.7 mmol) of 4-(2-chloromethyl-oxazol-5-yl)-phenol was added. Stirring at room temperature was continued for 20 hours. The solvent was evaporated and the residue was treated with 100 mL water and 100 mL ethyl acetate. The organic layer was dried over sodium sulfate and evaporated. The remaining oil was purified by chromatography on silica gel (elution with gradient methylene chloride/ethanol) to afford 0.4 g (35%) 4-[2-(2-phenoxy-ethylsulfanylmethyl)-oxazol-5-yl]-phenol.

$^1$H NMR (DMSO-d$_6$, 300 MHz): δ 9.78 (s, 1H), 7.48 (d, 2H, J=8 Hz), 7.36 (s, 1H), 7.27 (t, 3H, J=8 Hz), 6.97–6.90 (m, 3H), 6.83 (d, 2H, J=8 Hz), 4.16 (t, 2H, J=6 Hz), 4.02 (s, 2H), 2.99 (t, 2H, J=6 Hz). MS (MH$^+$) 328.

e) Dimethyl-(3-{4-[2-(2-phenoxy-ethylsulfanylmethyl)-oxazol-5-yl]-phenoxy}-propyl)-amine

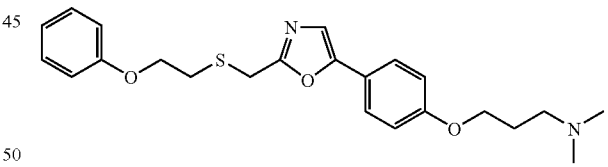

0.39 g (1.2 mmol) of 4-[2-(2-phenoxy-ethylsulfanylmethyl)-oxazol-5-yl]-phenol, 0.28 g (1.8 mmol) of 3-dimethylaminopropyl chloride hydrochloride, and 0.5 g (3.6 mmol) of potassium carbonate were dissolved in 10 mL dimethylformamide and heated to 80° C. for 65 hours. The reaction mixture was poured into 100 mL water and was extracted with tertiarybutyl methylether. The organic layer was dried over sodium sulfate and evaporated. The remaining oil was purified by HPLC to afford 70 mg (14%) dimethyl-(3-{4-[2-(2-phenoxy-ethylsulfanylmethyl)-oxazol-5-yl]-phenoxy}-propyl)-amine.

$^1$H NMR (CDCl$_3$, 300 MHz): δ 7.53 (d, 2H, J=9 Hz), 7.30–7.22 (m, 2H), 7.12 (s, 1H), 6.98–6.85 (m, 5H), 4.17 (t, 2H, J=7 Hz), 4.05 (t, 2H, J=7 Hz), 3.94 (s, 2H), 3.04 (t, 2H, J=7 Hz), 2.47 (t, 2H, J=7 Hz), 2.27 (s, 6H), 2.03–1.92 (m, 2H). MS (MH$^+$) 413.

Example 173

2-(2-Phenoxy-ethylsulfanylmethyl)-5-[4-(2-pyrrolidin-1-yl-ethoxy)-phenyl]-oxazole

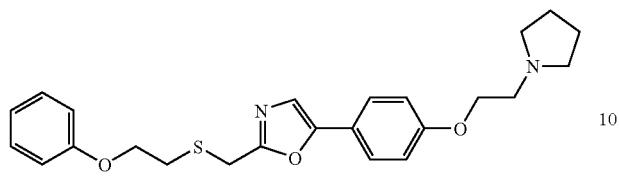

The above compound was prepared in a manner similar to that exemplified for the preparation of Example 172 e, from 300 mg (0.92 mmol) 4-[2-(2-phenoxy-ethylsulfanylmethyl)-oxazol-5-yl]-phenol, 164 mg (0.962 mmol) N-(2-chloro-ethyl)-pyrrolidine hydrochloride, and 278 mg (2.015 mmol) potassium carbonate in 6 mL DMF.

Yield: 209 mg (53%).

$^1$H NMR (CDCl$_3$, 300 MHz): δ 7.53 (d, 2H, J=9 Hz), 7.30–7.22 (m, 2H), 7.12 (s, 1H), 6.98–6.87 (m, 5H), 4.17 (t, 2H, J=7 Hz), 4.14 (t, 2H, J=7 Hz), 3.94 (s, 2H), 3.04 (t, 2H, J=7 Hz), 2.96–2.88 (m, 2H), 2.68–2.61 (m, 4H), 1.86–1.78 (m, 4H). MS (MH$^+$) 425.

Example 174

Dimethyl-(2-{4-[2-(2-phenoxy-ethylsulfanylmethyl)-oxazo-5-yl]-phenoxy}-ethyl)-amine

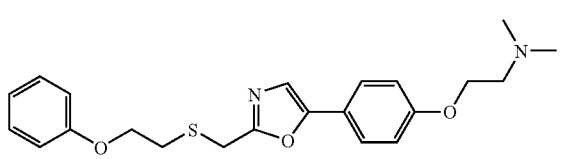

The above compound was prepared in a manner similar to that exemplified for the preparation of Example 172e, from 455 mg (1.39 mmol) of 4-[2-(2-phenoxy-ethylsulfanylmethyl)-oxazol-5-yl]-phenol, 210 mg (1.46 mmol) (2-chloro-ethyl)-dimethyl-amine hydrochloride, and 423 mg (3.06 mmol) of potassium carbonate in 9 mL DMF. Yield: 304 mg (55%).

$^1$H NMR (CDCl$_3$, 300 MHz): δ 7.53 (d, 2H, J=9 Hz), 7.30–7.22 (m, 2H), 7.12 (s, 1H), 6.98–6.87 (m, 5H), 4.17 (t, 2H, J=6 Hz), 4.10 (t, 2H, J=6 Hz), 3.94 (s, 2H), 3.04 (t, 2H, J=6 Hz), 2.75 (t, 2H, J=6 Hz), 2.35 (s, 6H). MS (MH$^+$) 399.

Example 175

1-(2-{4-[2-(2-Phenoxy-ethylsulfanylmethyl)-oxazol-5-yl]-phenoxy}-ethyl)-piperidine

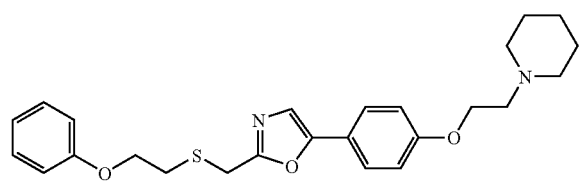

The above compound was prepared in a manner similar to that exemplified for the preparation of Example 172e, from 455 mg (1.39 mmol) 4-[2-(2-phenoxy-ethylsulfanylmethyl)-oxazol-5-yl]-phenol, 269 mg (1.46 mmol), N-(2-chloro-ethyl)-piperidine hydrochloride, and 423 mg (3.06 mmol) of potassium carbonate in 9 mL DMF. Yield: 414 mg (68%).

$^1$H NMR (CDCl$_3$, 300 MHz): δ 7.53 (d, 2H, J=9 Hz), 7.30–7.22 (m, 2H), 7.12 (s, 1H), 6.98–6.87 (m, 5H), 4.17 (t, 2H, J=7 Hz), 4.14 (t, 2H, J=7 Hz), 3.94 (s, 2H), 3.04 (t, 2H, J=6 Hz), 2.79 (t, 2H, J=6 Hz), 2.56–2.48 (m, 4H), 1.67–1.57 (m, 4H), 1.50–1.41 (m, 2H). MS (MH$^+$) 439.

Example 176

1-(3-{4-[2-(2-Phenoxy-ethylsulfanylmethyl)-oxazol-5-yl]-phenoxy}-propyl)-piperidine

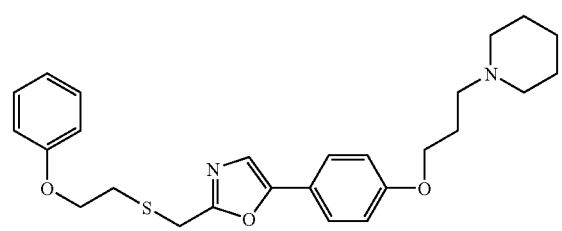

The above compound was prepared in a manner similar to that exemplified for the preparation of Example 172e, from 455 mg (1.39 mmol) 4-[2-(2-phenoxy-ethylsulfanylmethyl)-oxazol-5-yl]-phenol, 289 mg (1.46 mmol) N-(3-chloro-propyl)-piperidine hydrochloride, and 423 mg (3.06 mmol) potassium carbonate in 9 mL DMF. Yield: 525 mg (83%).

$^1$H NMR (CDCl$_3$, 300 MHz): δ 7.52 (d, 2H, J=9 Hz), 7.30–7.22 (m, 2H), 7.12 (s, 1H), 6.98–6.87 (m, 5H), 4.17 (t, 2H, J=6 Hz), 4.04 (t, 2H, J=6 Hz), 3.94 (s, 2H), 3.04 (t, 2H, J=6 Hz), 2.52–2.37 (m, 6H), 2.05–1.93 (m, 2H), 1.66–1.55 (m, 4H), 1.50–1.40 (m, 2H). MS (MH$^+$) 453.

Example 177

2-(2-Phenoxy-ethylsulfanylmethyl)-5-[4-(3-pyrrolidin-1-yl-propoxy)-phenyl]-oxazole

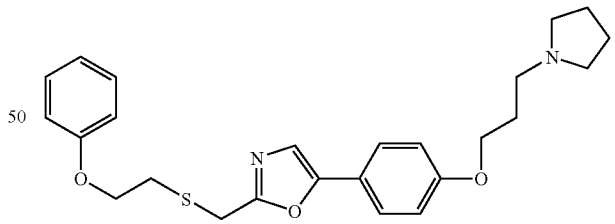

The above compound was prepared in a manner similar to that exemplified for the preparation of Example 172 e, from 455 mg (1.39 mmol) 4-[2-(2-phenoxy-ethylsulfanylmethyl)-oxazol-5-yl]-phenol, 269 mg (1.46 mmol) N-(3-chloro-propyl)-pyrrolidine hydrochloride, and 423 mg (3.06 mmol) potassium carbonate in 9 mL DMF. Yield: 470 mg (77%).

$^1$H NMR (CDCl$_3$, 300 MHz): δ 7.53 (d, 2H, J=9 Hz), 7.30–7.22 (m, 2H), 7.12 (s, 1H), 6.98–6.87 (m, 5H), 4.17 (t, 2H, J=6 Hz), 4.14 (t, 2H, J=6 Hz), 3.94 (s, 2H), 3.04 (t, 2H, J=7 Hz), 2.78 (t, 2H, J=7 Hz), 2.56–2.49 (m, 4H), 1.67–1.58 (m, 4H), 1.50–1.41 (m, 2H). MS (MH$^+$) 439.

Example 178

Preparation of 2-(2-hydroxyethylthio)methyl-5-(4-[3-(dimethylamino)propoxy]-phenyl)-1,3,4-oxadiazole hydrochloride from methyl 4-hydroxy-benzoate

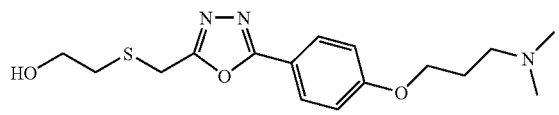

a) Methyl 4-[3-(dimethylamino)propoxy]-benzoate

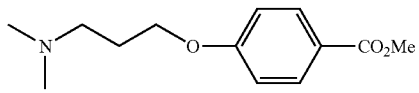

To a solution of 4-hydroxy benzoic acid methyl ester (50.0 g, 328.6 mmol), triphenyl phosphine (130.0 g, 493.5 mmol), and 3-dimethylamino-1-propanol (50.5 g, 57 ml, 493.5 mmol) in 1000 mL of dry THF was added dropwise isopropyl azo dicarboxylate at 0° C. After completed addition the temperature was brought to ambient temperature and the mixture was stirred for 16 h. The mixture was evaporated. It was then dissolved in ethyl acetate and extracted with 2N aqueous HCl. The aqueous phase was made alkaline with solid sodium hydroxide pellets and extracted with ethyl acetate (3 times). The collected organic phases were dried with sodium sulphate and evaporated. The crude material (75 g, 96%) was used directly in the next step.

$^1$H NMR (DMSO-$d_6$) δ 7.95 (d, 2H, J=8 Hz), 7.00 (d, 2H, J=8 Hz), 4.13 (t, 2H, J=6 Hz), 3.83 (s, 3H), 2.32 (t, 2H, J=6 Hz), 2.13 (s 6H), and 1.88 (quint., 2H, J=6 Hz), MS (FD) m/e 238.

b) 4-[3-(dimethylamino)propoxy]-benzoic acid hydrazide

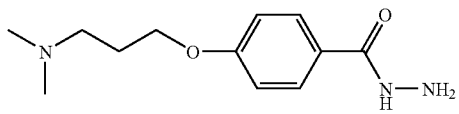

A solution of methyl 4-[3-(dimethylamino)propoxy]-benzoate (108.0 g, 457.0 mmol), in 443 ml (458 g, 9.14 M) of neat hydrazine hydrate was subdivided into ten aliquots and each aliquot was heated in a Teflon bomb in a microwave oven ETHOS 1600 for 1 h to 120° C. After TLC indicated complete conversion the reaction mixture was poured in water and extracted with DCM. The collected organic phases were dried over sodium sulphate, filtered and evaporated. The residue was purified via column chromatography using a DCM/DCM-MeOH/DCM-MeOH-ammonia gradient (100% to 90:10). Yield 32.7 g (42%)

$^1$H NMR (DMSO-$d_6$) δ 9.58 (s, 1H, exch.), 7.80 (d, 2H, J=8 Hz), 6.98 (d, 2H, J=8 Hz), 4.40 (s, 2H, br., exch.), 4.05 (t, 2H, J=6 Hz), 2.35 (t, 2H, J=6 Hz), 2.15 (s 6H), and 1.88 (quint., 2H, J=6 Hz),. MS (FD) m/e 238.

c) 4-[3-(dimethylamino)propoxy]-benzoic acid 2-(chloroacetyl)hydrazide hydrochloride

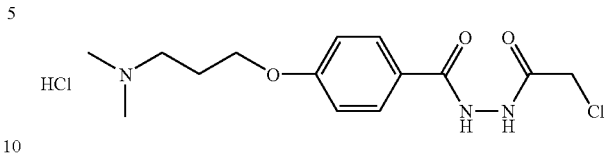

Chloro acetylchloride (2.40 g, 1.68 ml, 21.07 mmol) was slowly added to a solution of 4-[3-(dimethylamino)propoxy]-benzoic acid hydrazide (5.0 g, 21.07 mmol) in 50 ml DCM. After stirring overnight at ambient temperature TLC showed incomplete conversion. After successive addition of chloro acetyl chloride (0.17 ml, additional stirring for 2 h, 0.5 ml additional stirring for 1 h) TLC showed almost complete conversion. The mixture was diluted with 50 ml MTBE and the colorless precipitate thus formed was filtered off and dried in a vacuum oven at 40° C. for 1 h. 6.7 g (91%) of colorless crystals. The material was used in the next step without purification.

d) 2-Chloromethyl-5-(4-[3-(dimethylamino)propoxy]-phenyl)-1,3,4-oxadiazole hydrochloride

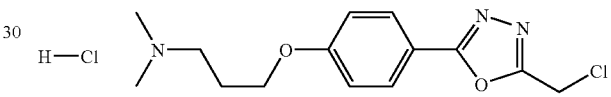

4-[3-(dimethylamino)propoxy]-benzoic acid 2-(chloroacetyl)hydrazide (6.7 g, 19.13 mmol) was added to 34 ml of phosphoryl chloride POCl$_3$ and the mixture was stirred at 95° C. overnight. The mixture was diluted with DCM and evaporated to dryness. The residue was repeatedly triturated with toluene and evaporated to remove remaining traces of POCl$_3$ and HCl. The colorless residue was sufficiently pure for the next step.

$^1$H NMR (DMSO-$d_6$) δ 10.58 (s, 1H, exch.), 7.98 (d, 2H, J=8 Hz), 7.20 (d, 2H, J=8 Hz), 5.12 (s, 2H), 4.18 (t, 2H, J=6 Hz), 3.20 (t, 2H, J=6 Hz), 2.80 (d 6H, J=4 Hz), and 2.20 (quint., 2H, J=6 Hz),. MS (FD) m/e 296.1.

e) 2-(2-hydroxyethylthio)methyl-5-(4-[3-(dimethylamino)propoxy]-phenyl)-1,3,4-oxadiazole hydrochloride

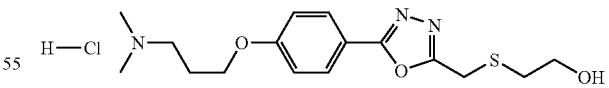

To a solution of sodium ethylate in ethanol, prepared by adding sodium hydride (60% dispersion, 2.1 g, 51.96 mmol) to 90 ml of absolute ethanol was added 2-mercaptoethanol (4.1 g, 51.96 mmol, 3.7 ml). The mixture was stirred at room temperature for 30 min. Then 2-chloromethyl-5-(4-[3-(dimethylamino)propoxy]-phenyl)-1,3,4-oxadiazole hydrochloride (8.6 g, 25.98 mmol) was added as a solid. After 2 h stirring at ambient temperature the mixture was evaporated. The residue was suspended in DCM (dichloromethane) and extracted with aqueous sodium bicarbonate. The organic phase was dried over sodium sulphate and evaporated the residue was purified via flash chromatography on silica gel using DCM-DCM/ethanolic ammonia gradient (100% to 90% DCM) yielding 4.8 g (49%) of pure compound.

$^1$H NMR (DMSO-d$_6$) δ 7.90 (d, 2H, J=8 Hz), 7.12 (d, 2H, J=8 Hz), 4.88 (t, 1H, exch.), 4.10 (m, 2H), 4.10 (s, 2H), 3.57 (q, 2H), 2.72 (t, 2H, J=4 Hz), 2.36 (t, 2H, J=4 Hz), 2.18 (s, 6H) and 1.88 (quint. 2H, J=4 Hz). MS (FD) m/e 338.1.

f) Dimethyl-(3-{4-[5-(2-(4-fluorophenoxy-ethylsulfanylmethyl)-1,3,4-oxadiazol-2-yl]-phenoxy}-propyl)-amine

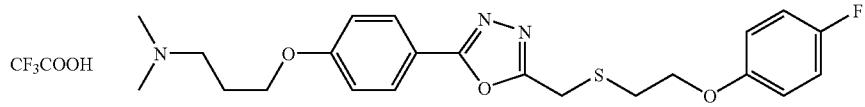

To a mixture of 2-(2-hydroxyethylthio)methyl-5-(4-[3-(dimethylamino)propoxy]-phenyl)-1,3,4-oxadiazole hydrochloride (0.200 g, 0.592 mmol), 4-fluorophenol (0.100 mg, 0.888 mmol) triphenyl phosphine polystyrene resin (0.888 g, 0.888 mmol, 1 meq./g) in 6 ml DCM was added diisopropyl azodicarboxylate (0.180 g, 176 μl, 0.888 mmol) and stirred at ambient temperature for 12 h. The mixture was evaporated and redissolved in methanol. The solution was purified via a SCX-cartidge using 20 ml methanol to remove impurities. The compound was eluted with methanolic ammonia. The residue (206 mg) was finally purified via prep. HPLC (RP-18) using acetonitrile/water/0.1% TFA gradient yielding 44 mg (17%) of the desired compound $^1$H NMR (DMSO-d$_6$) δ 9.50 (s, br, exch) 7.89 (m, 2H), 7.05 (m, 6H), 4.25 (s, 2H), 4.10 (m, 2H), 3.90 (m, br 2H), 3.23 (m, 2H), 3.05 (q, 2H), 2.80 (2 s, 6H), and 2.12 (m, 2H). MS (FD) m/e 432.1.

The following compounds were prepared using the protocol described above, using 2-(2-hydroxyethylthio)methyl-5-(4-[3-(dimethylamino)propoxy]-phenyl)-1,3,4-oxadiazole and the appropriate substituted phenol. After prep. HPLC the appropriate fractions were collected, evaporated and redissolved in methanol. Filtration of the methanolic solution of the trifluoroacetate salts of the desired compounds through SCX cartridges yielded the free bases of the desired compounds:

Example 179

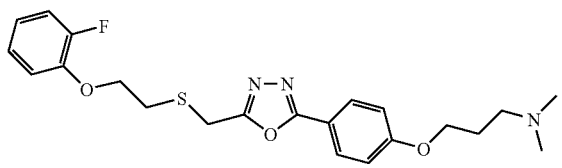

$^1$H NMR (CDCl$_3$) δ 7.97 (d, 2H, J=8 Hz), 7.00 (m, 4H), 6.98 (d, 2H, J=8 Hz), 6.65 (m, 3H), 4.28 (t, 2H), 4.11 (s, 2H), 4.10 (t, 2H), 3.10 (t, 2H), 2.40 (t, 2H), 2.30 (s, 6H), and 2.00 (quint., 2H). MS (FD) m/e 432.1.

Example 180

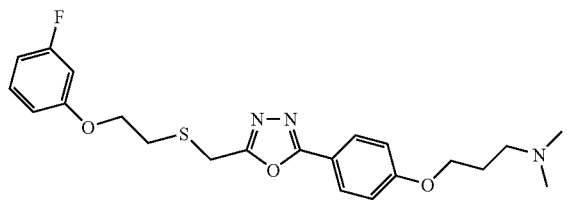

$^1$H NMR (CDCl$_3$) δ 7.95 (d, 2H, J=8 Hz), 7.20 (m, 1H), 6.98 (d, 2H, J=8 Hz), 6.65 (m, 3H), 4.20 (t, 2H), 4.12 (t, 2H), 4.03 (s, 2H), 3.05 (t, 2H), 2.45 (t, 2H), 2.25 (s, 6H), and 2.00 (quint., 2H). MS (FD) m/e 432.1.

Example 181

$^1$H NMR (CDCl$_3$) δ 7.95 (d, 2H, J=8 Hz), 7.12 (d, 2H, J=8 Hz), 7.00 (d, 2H, J=8 Hz), 6.85 (m, 2H), 4.25 (t, 2H), 4.13 (t, 2H), 4.08 (s, 2H), 3.10 (t, 2H), 2.50 (t, 2H), 2.28 (s, 6H), 2.23 (s, 3H), and 1.98 (quint., 2H). MS (FD) m/e 428.1.

Example 182

$^1$H NMR (CDCl$_3$) δ 7.95 (d, 2H, J=8 Hz), 7.15 (t, 1H, J=8 Hz), 7.00 (d, 2H, J=8 Hz), 6.75 (m, 2H), 4.20 (t, 2H), 4.10 (t, 2H), 4.05 (s, 2H), 3.05 (t, 2H), 2.45 (t, 2H), 2.33 (s, 3H), 2.30 (s, 6H), and 1.98 (quint., 2H). MS (FD) m/e 428.1.

Example 183

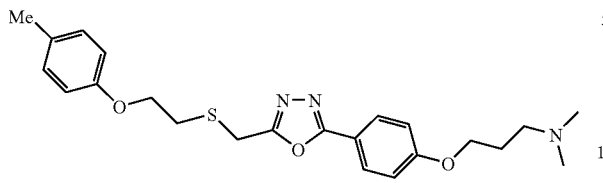

¹H NMR (CDCl₃) δ 7.93 (d, 2H, J=8 Hz), 7.08 (d, 1H, J=8 Hz), 7.20 (t, 1H), 7.00 (d, 2H, J=8 Hz), 6.80 (d, 2H, J=8 Hz), 4.18 (t, 2H), 4.10 (t, 2H), 4.05 (s, 2H), 3.07 (t, 2H), 2.50 (t, 2H), 2.27 (s, 6H), 2.26 (s, 3H), and 2.00 (quint., 21). MS (FD) m/e 428.2.

Example 184

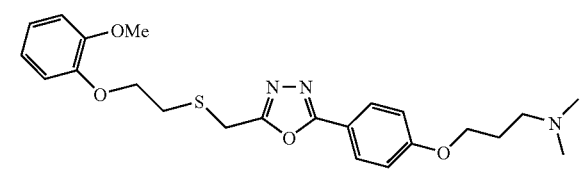

¹H NMR (CDCl₃) δ 7.93 (d, 2H, J=8 Hz), 7.33 (d, 1H, J=8 Hz), 7.20 (t, 1H), 7.00 (d, 2H, J=8 Hz), 6.90 (d, 2H, J=8 Hz), 6.70 (d, 1H), 4.30 (t, 2H), 4.15 (s, 2H), 4.10 (t, 2H), 3.10 (t, 2H), 2.50 (t, 2H), 2.27 (s, 6H), and 2.00 (quint., 2H). MS (FD) m/e 448.1.

Example 185

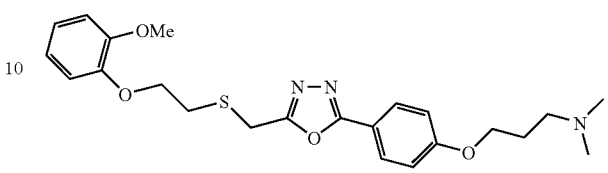

¹H NMR (CDCl₃) δ 7.88 (d, 2H, J=8 Hz), 7.11 (t, 1H, J=8 Hz), 6.90 (d, 2H, J=8 Hz), 6.75 (m, 2H), 6.70 (d, 1H), 4.10 (t, 2H), 4.02 (t, 2H), 3.98 (s, 2H), 3.01 (t, 2H), 2.40, (t, 2H), 2.21 (s, 6H), and 1.90 (quint., 2H). MS (FD) m/e 448.0.

Example 186

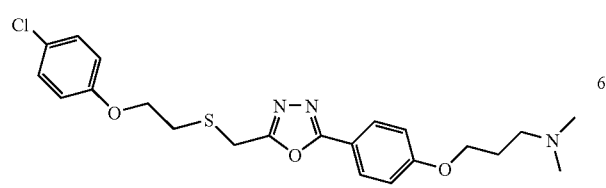

¹H NMR (MeOD) δ 7.39 (d, 2H, J=8 Hz), 7.20 (d, 2.3 J=9 Hz), 7.02 (d, 2H, J=8 Hz), 6.83 (d, 2H, J=9 Hz), 4.20 (t, 21), 4.10 (t, 2H), 4.08 (s, 2H), 3.07 (t, 2H), 2.55 (t, 2H), 2.35 (s, 6H), and 2.05 (quint., 2H). MS (FD) m/e 448.1.

Example 187

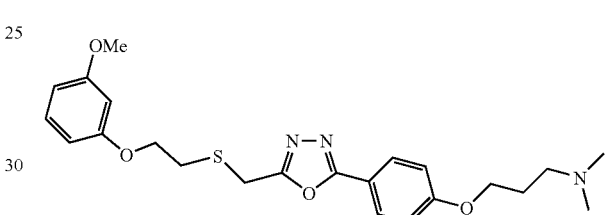

¹H NMR (CDCl₃) δ 7.95 (d, 2H, J=8 Hz), 7.00 (d, 2H, J=8 Hz), 6.90 (m, 4H), 4.20 (t, 2H), 4.10 (t, 2H), 4.05 (s, 2H) 3.78 (s, 3H), 3.07 (t, 2H), 2.45 (t, 2H), 2.25 (s, 6H), and 1.98 (m, 2H). MS (FD) m/e 444.2.

Example 188

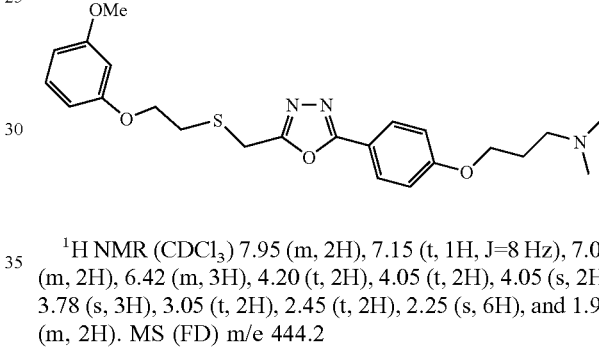

¹H NMR (CDCl₃) 7.95 (m, 2H), 7.15 (t, 1H, J=8 Hz), 7.00 (m, 2H), 6.42 (m, 3H), 4.20 (t, 2H), 4.05 (t, 2H), 4.05 (s, 2H) 3.78 (s, 3H), 3.05 (t, 2H), 2.45 (t, 2H), 2.25 (s, 6H), and 1.98 (m, 2H). MS (FD) m/e 444.2

Example 189

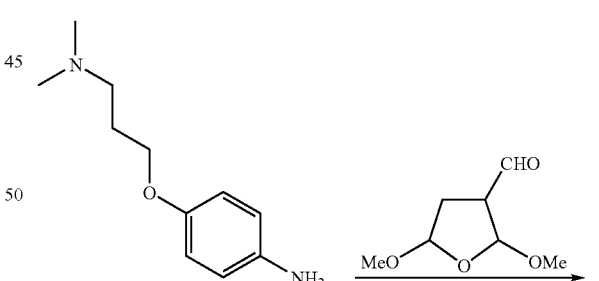

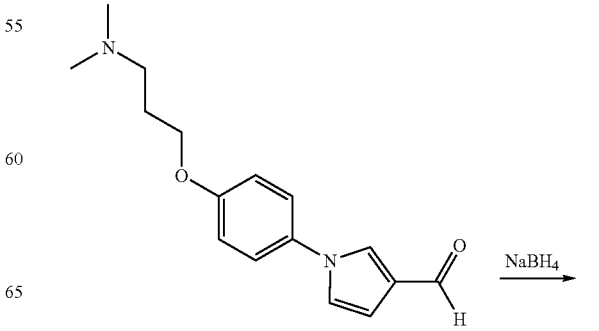

-continued

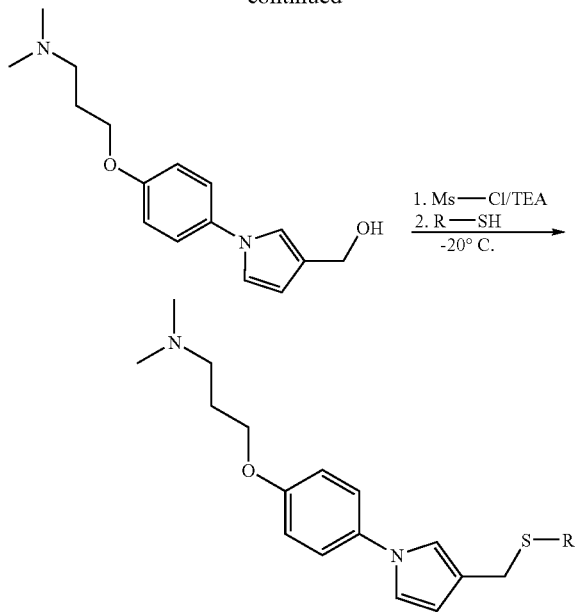

a) 4-[3-(dimethylamino)propoxy]-nitro benzene

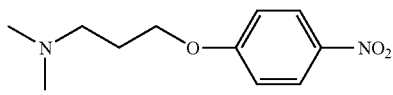

To a suspension of 4-nitro phenol (30.0 g, 216 mmol), anhydrous potassium carbonate (86.7 g, 627 mmol), and potassium iodide (5.5 g, 33 mmol) in 360 ml of dry DMF was added finely ground 3-dimethylamino-1-propyl chloride hydrochloride (51.7 g, 327 mmol). The mixture was stirred at 80° C. for 4 days. Successively another portion of 3-dimethylamino-1-propyl chloride hydrochloride (15.81 g, 100 mmol) and anhydrous potassium carbonate (25.2 g, 200 mmol) was added and stirring at 80° C. was continued for 16 h. After cooling the mixture was diluted with 1.5 l water and extracted with MTBE (2 times 600 ml). The collected organic phases were dried with sodium sulphate and evaporated. The crude yellow oil (31.7 g, 65.6%) was sufficiently pure and used directly in the next step.

$^1$H NMR (CDCl$_3$) δ 8.19 (d, 2H, J=8 Hz), 6.96 (d, 2H, J=8 Hz), 4.13 (t, 2H, J=6 Hz), 2.48 (t, 2H, J=6 Hz), 2.28 (s 6H), and 2.00 (quint, 2H, J=6 Hz),.MS (FD) m/e 225.1.

b) 4-[3-(dimethylamino)propoxy]-aniline

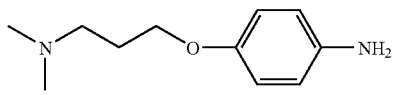

To a solution of 4-[3-(dimethylamino)propoxy]-nitro benzene (12 g, 54 mmol) in 65 ml of absolute ethanol was added 200 mg of Pd(OH)$_2$ on carbon (Pearlman's catalyst). The mixture was hydrogenated at atmospheric hydrogen pressure for 16 h. The mixture was filtered over diatomeous earth and the filter cake rinsed with ethanol. The collected ethanolic filtrates were evaporated. The crude orange oil (10.38 g, 99%) was sufficiently pure and used directly in the next step.

$^1$H NMR (CDCl$_3$) δ 6.83 (d, 2H, J=8 Hz), 6.72 (d, 2H, J=8 Hz), 3.83 (t, 2H, J=6 Hz), 3.40 (s, br, exch. 2H) 2.42 (t, 2H, J=6 Hz), 2.25 (s 6H), and 1.91 (quint., 2H, J=6 Hz),.MS (ED) m/e 195.0.

c) 1-[4-(3-dimethylaminopropoxy)-phenyl)-1H-pyrrole-3-carboxaldehyde

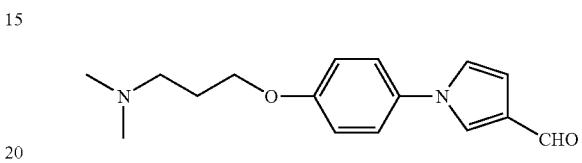

To a solution of 3-formyl-(2,5-dimethoxytetrahydrofuran) (7.5 g, 47 mmol) in 50 ml of glacial acetic acid was added 4-[3-(dimethylamino)propoxy]-aniline (9.8 g, 50 mmol). A slightly exothermic reaction occurred and the mixture darkened. The mixture was stirred at 110° C. for 1 h and poured into 400 ml of crushed ice after cooling to ambient temperature. The aqueous phase was neutralized with solid sodium bicarbonate and exhaustively extracted with DCM. The collected organic phases were dried over sodium sulphate and evaporated. The crude product was purified via flash chromatography on silica gel using a DCM/DCM-ethanolic ammonia gradient 100 to 95:5. A reddish-brown oil was obtained (4.23 g, 33%).

$^1$H NMR (CDCl$_3$) δ 9.84 (s, 1H), 7.58 (t, 2H, J=2 Hz), 7.32 (d, 2H, J=8 Hz), 7.00 (d, 2H, J=8 Hz), 7.00 (m, 1H), 6.77 (m, 1H), 4.08 (t, 2H, J=6 Hz), 2.48 (t, 2H, J=6 Hz), 2.28 (s 6H), and 1.99 (quint., 2H, J=6 Hz),.MS (FD) m/e 273.1.

d) 1-[4-(3-dimethylaminopropoxy)phenyl]-1H-pyrrole-3-methanol

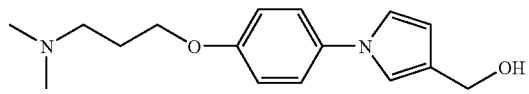

To a stirred solution of DIBAH (17.1 ml, 20% in toluene, 21.2 mmol) was added 1-[4-(3-dimethylaminopropoxy)-phenyl)-1H-pyrrole-3-carboxaldehyde (2.9 g, 10.6 mmol) at 0 to 2° C. After stirring for 1 h at 0° C. the reaction was completed. Excess DIBAH was quenched with 10 ml of toluene/methanol 1:1 under cooling. The gelatinous mixture was solubilized with methanol and evaporated. The residue was extracted successively with DCM and methanol and filtered off. The organic filtrate was evaporated yielding a dark oil (3.0 g, 100%) which solidified in a freezer. According to HPLC the material was approx. 80% pure and was used without further purification.

$^1$H NMR (CDCl$_3$) δ 7.20 (d, 2H, J=8 Hz), 7.32 (d, 2H, J=8 Hz), 7.00 (d, 2H, J=8 Hz), 6.90 (m, 4H), 4.55 (s, 2H), 3.95 (t, 2H, J=6 Hz), 2.40 (t, 2H, J=6 Hz), 2.20 (s 6H), 1.90, (quint., 2H, J=6 Hz), and 1.70 (s, br, exch.1H). MS (FD) m/e 275.2.

2-Phenoxyethanethiol

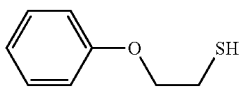

The compound was prepared according to: J. Org. Chem. 1972, 37(10), 1532–37.

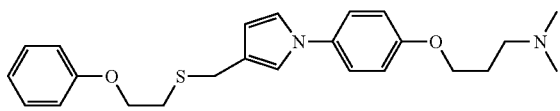

To a stirred solution of 1-[4-(3-dimethylaminopropoxy)phenyl]-1H-pyrrole-3-methanol (360 mg, 1.3 mmol) in 15 ml of dry THF was added triethyl amine (334 mg, 3.3 mmol) and 10 mg DMAP and the mixture was cooled to −8° C. A solution of methane sulfonyl chloride (223 mg, 1.55 mmol) in 2 ml dry THF was added dropwise and the mixture was stirred for 30 min at −5° C. TLC showed almost complete conversion. After stirring for additional 2.5 h at −5 to 0° C. the mixture was quenched with 60% sodium hydride (62 mg, 1.55 mmol) and stirred for 15 min at 0° C. In the meantime a solution of sodium 2-phenoxyethanethiolate was prepared from 2-phenoxy ethanethiol (401 mg, 2.6 mmol) and sodium hydride (60%, 104 mg, 2.6 mmol) in 2 ml dry THF. After 15 min of stirring the solution was cooled to 0° C. and slowly added to the solution of the mesylate. The mixture was stirred at 0° C. for 30 min and then for 16 h at ambient temperature. The mixture was evaporated and the residue purified on an aluminum oxide (neutral) column. The main fraction was isolated as an orange oil (38 mg), which was 73% pure according to HPLC. The crude product was further purified by prep. HPLC (RP-18 acetonitrile/water/0.1% TFA) yielding 24.8 mg of the desired product as the triflate salt (3.6%).

$^1$H NMR (CDCl$_3$) δ 11.8 (s br. 1H), 7.26 (m, 4H), 6.92 (m, 7H,), 6.30 (t, 1H, J=1 Hz), 4.10 (qu, qu, 4H), 3.88 (s, 2H), 3.30 (qu, 2H,), 2.90 (s+m, 8H,), 2.28 (m, 2H). MS (FD) m/e 411.2.

2-Bromo-5-(chloromethyl)-thiophene

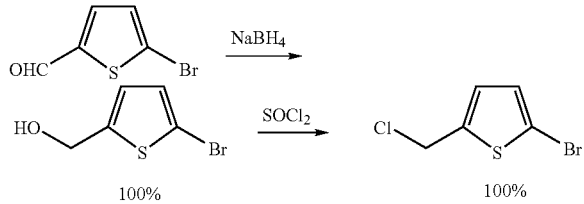

To a suspension of sodium borohydride (400 mg, 10.6 mmol) in 30 ml 2-propanol was added dropwise a solution of 5-bromothiophene-2-carboxaldehyde (2 g, 10.45 mmol) in 5 ml 2-propanol at ambient temperature. After stirring for 1 h at ambient temperature the mixture was carefully hydrolyzed by 2N aqueous hydrochloric acid under ice cooling. The pH value was adjusted to 3 to 4 and the solution was extracted with DCM. The organic phase was dried over sodium sulfate, filtered and evaporated. The residue (1.9 g) was sufficiently pure for the next step.

$^1$H NMR (CDCl$_3$) δ 6.91 (d, 1H, J=4 Hz), 6.75 (d, 1H, J=4 Hz), 4.75 (s, 2H,), 1.90 (s, br., exch.).

A solution of the foregoing 2-bromo-5-thiophene methanol (1.9 g, 10.45 mmol) and thionyl chloride (2.5 g) in 30 ml dry DCM was stirred at ambient temperature for 2 h. The solution was evaporated and the residue repeatedly redissolved in toluene and evaporated to remove traces of thionyl chloride. The crude residue (2.1 g) was directly used in the next step.

$^1$H NMR (CDCl$_3$) δ 6.92 (d, 1H, J=4 Hz), 6.83 (d, 1H, J=4 Hz), 4.70 (s, 2H,). MS (FD) m/e 212.0.

2-Bromo-5-[(2-phenoxy)ethylthio)methyl]-thiophene

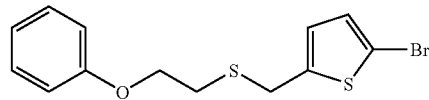

To a 2.5 N solution of sodium ethoxide (prepared from 120 mg, 5 mmol 60% sodium hydride and 20 ml of dry ethanol) was added dropwise 2-phenoxyethanethiol (770 mg, 5 mmol) and stirred for 30 min at ambient temperature. To this solution was added 2-bromo-5-(chloromethyl)-thiophene (1000 mg, 5 mM dropwise and the mixture was stirred over night at ambient temperature. The mixture was carefully hydrolyzed with water and extracted with ethyl acetate. The organic phase was dried, filtered and evaporated. The residue was purified via flash chromatography on silica gel using hexane/ethyl acetate 97.5:2.5 yielding 1.2 g (79%) of the desired compound.

$^1$H NMR (CDCl$_3$) δ 7.30 (m, 2H), 6.92 (m, 4H), 6.71 (d, 2H, J=3 Hz), 4.41 (t, 2H, J=6.5 Hz), 3.97 (s, 2H), 2.88 (t, 2H, J=6.5 Hz). MS (EI) m/e 328.

a) 4-[3-(dimethylamino)propoxy]-iodo benzene

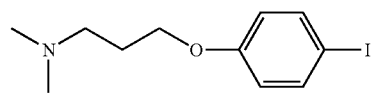

To a suspension of 4-iodo phenol (24.0 g, 110 mmol), anhydrous potassium carbonate (36.0 g, 260 mmol), and potassium iodide (2.2 g, 13 mmol) in 240 ml of dry 2-butanone was added finely ground 3-dimethylamino-1-propyl chloride hydrochloride (13.4 g, 110 mmol). The mixture was stirred under reflux for 48 h. The solvent was distilled off. The residue was dissolved in DCM and extracted with 2N aqueous NaOH twice. The organic phase was separated washed with water twice, dried and evaporated. The crude oil (21.0 g) was purified via flash chromatography on silica gel using a DCM/ethanolic ammonia gradient (100 to 95:5) yielding 12.9 g of the desired compound sufficiently pure for the next step.

$^1$H NMR (CDCl$_3$) δ 7.55 (d, 2H, J=8 Hz), 6.70 (d, 2H, J=8 Hz), 4.00 (t, 2H, J=4 Hz), 2.45 (t, 2H, J=4 Hz), 2.23 (s 6H), and 1.95 (quint., 2H, J=4 Hz),.MS (FD) m/e 306.0.

[4-[3-(dimethylamino)propoxy]phenyl]boronic acid

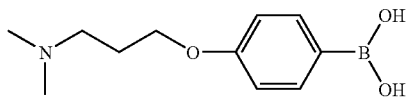

To a solution of 4-[3-(dimethylamino)propoxy]-iodo benzene (1 g, 3.28 mmol) in abs. THF was added a solution of n-butyl lithium in hexane (2.5 ml, 1.6 M solution, 4 mmol) at −78° C. under vigorous stirring within 5 min. After siring at −78° C. for 30 min a solution of trimethyl borate (433 µl, 3.94 mmol) in 10 ml abs. THF was added within 10 min and stirring at −78° C. continued for 2 h. Temperature was increased to −10° C. over 3 h and then to 0° C. The mixture was quenched with 1 ml of water and stirred for 80 h at room temperature. The precipitate thus formed was solubilized with 2 ml of methanol and the solution was evaporated after adding 2.5 g silica gel. The coated silica gel was loaded on an aluminum oxide column and eluted with a DCM/DCM-methanol gradient 100 to 90:10 yielding 200 mg (27%) of the desired compound.

$^1$H NMR (MeOD) δ 7.62 (d, 2H, br), 6.90 (d, 2H, J=8 Hz), 4.06 (t, 2H, J=4 Hz), 2.63 (t, 2H, J=4 Hz), 2.38 (s 6H), and 1.98 (quint., 2H, J=4 Hz),.MS (FD) m/e 224.1.

Example 190

Dimethyl-(3-{4-[5-(2-phenoxy-ethylsulfanylmethyl)-thiophen-2-yl]-phenoxy}-propyl)-amine

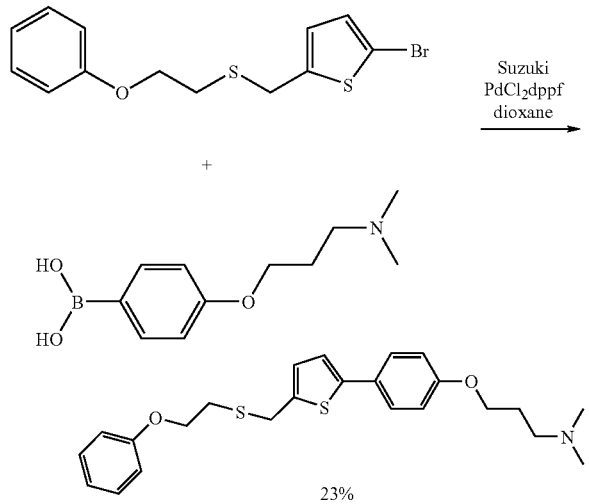

To a solution of 2-bromo-5-[(2-phenoxy)ethylthio)methyl]-thiophene (247 mg, 0,75 mmol) and [4-[3-(dimethylamino)propoxy]phenyl]boronic acid (200 mg, 0.9 mM) in 40 ml of argon flushed dioxane was added tetrakis(triphenylphosphine)palladium (0) (87 mg, 0.75 mmol) and 1,5 ml 2 M aqueous sodium carbonate (3 mmol) under argon. The mixture was heated to 120° C. for 1 h in a microwave oven (MLS ETHOS 1600). TLC showed complete conversion.

The reaction mixture was diluted with water and extracted with DCM. The organic phases were dried over sodium sulphate, filtered and evaporated. The residue was purified via flash chromatography on silica gel using a DCM/methanolic ammonia gradient 99:1–95:5 yielding the desired compound almost pure as the free base after two separations.

Final purification was achieved via HPLC on RP-18 (acetonitrile/water/0.1% TFA gradient) yielding the trifluoro acetic acid salt as an oil.

The methanolic solution of the trifluoro acetate was poured on a SCX column, which was rinsed with DCM/methanol and 7N methanolic ammonia to yield the free base. Yield 23%

Example 191

Alternative Synthesis of dimethyl-(3-{4-[5-(2-phenoxy-ethylsulfanylmethyl)-thiophen-2-yl]-phenoxy}-propyl)-amine

[4-[3-(dimethylamino)propoxy]phenyl]boronic acid pinacolyl ester (not isolated)

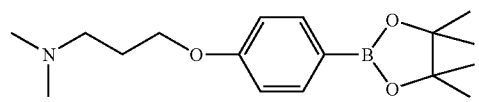

To a solution of 4-[3-(dimethylamino)propoxy]-iodo benzene (610 mg, 2.00 mmol) in degassed 10 ml DMSO was added bis-(pinacolato)-diborane (558 mg, 2.20 mmol), potassium acetate (200 mg, 6.0 mmol) and 1.1-bis-(diphenylphosphino)-ferrocene-palladium(II)chloride DCM complex (200 mg, 0.24 mmol) under argon. The mixture was stirred by 90° C. for 3 h. MS indicated complete conversion according to boron isotope distribution. To this mixture was added a solution of 2-bromo-5-[(2-phenoxy)ethylthio)methyl]-thiophene (790 mg, 2.4 mM) in 5 ml degassed DMSO, PdCl$_2$dppf DCM complex (192 mg, 0.24 mmol) and 2 M aqueous sodium carbonate (2880 µl, 5.76 mmol) under argon. The mixture was heated to 120° C. for 1 h in a microwave oven (MLS ETHOS 1600). After 1 hour mass spectrometry (MS) showed incomplete conversion. Addition of 0.24 mmol of Pd catalyst and prolonged heating for 1 h to 120° C. in the microwave oven gave no major improvements. The reaction mixture was extracted with water, DCM and hexane. The organic layers were dried over sodium sulphate, filtered and evaporated. The residue was dissolved in methanol and poured on a 5 g SCX column, eluted with DCM/methanol and 7N methanolic ammonia and evaporated. The residue was purified via flash chromatography on silica gel using a DCM/methanolic ammonia gradient 99:1–97:3 yielding 250 mg (29%) of the desired compound as free base.

The residue was dissolved in methanol/DCM and poured on a column with 2 g Amberlite 748 (cation exchange resin) to remove Pd traces.

The filtrate was evaporated and purified via flash chromatography and prep HPLC on RP-18 (acetonitrile/water/0.1% TFA gradient) yielding 220 mg (20%) of the desired compound as the trifluoroacetic acid salt as a colorless solid.

Trifluoroacetate $^1$H NMR (CDCl$_3$, 300 MHz) 11.66–11.32 (bs, 1H), 7.52–7.43 (d, 2H, J=9 Hz), 7.31–7.42 (m, 2H), 7.02–6.99 (d, 1H, J=4 Hz), 6.99–6.92 (t, 1H, J=7 Hz), 6.92–6.82 (m, 5H), 4.18–4.06 (t, 2H, J=7 Hz), 4.12–4.06 (t, 2H, 5 Hz), 4.05–4.01 (s, 2H), 3.38–3.28 (m, 2H), 2.96–2.88 (m, 8H) and 2.33–2.22 (m, 2H). IR (CHCl$_3$, cm$^{-1}$) 1243, 1176, 1059 and 832. MS (ES) m/e 428.1.

Base $^1$H NMR (CDCl$_3$, 300 MHz) ☐7.47 (d, 2H, J=9 Hz), 7.32–7.25 (m, 2H), 7.01–6.84 (m, 7H), 4.19–4.10 (t, 2H, J=7 Hz 4.07–3.99 (m, 4H), 2.96–2.87 (t, 2H, J=7 Hz), 2.5–2.40 (t, 2H, J=7 Hz), 2.29–2.21 (s, 6H) and 2.02–1.91 (m, 2H). IR (CHCl$_3$, cm$^{-1}$) 1246, 1176, 1032 and 832. MS (ES) m/e 428.1. Anal. Calcd for C$_{24}$H$_{29}$NO$_2$S$_2$: C, 67.41; H, 6.84; N, 3.28; S 15.00. Found C, 66.42; H, 6.59; N, 3.34; S 14.30.

3-[4-(3-dimethylaminopropoxy)-phenyl)-thiophene-5-carboxaldehyde

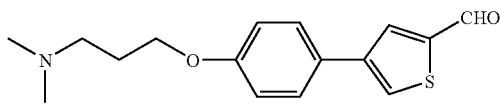

[4-[3-(dimethylamino)propoxy]phenyl]boronic acid pinacolyl ester (not isolated)

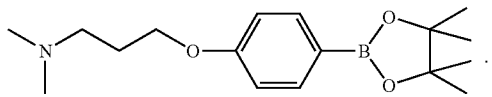

To a solution of 4-[3-(dimethylamino)propoxy]-iodo benzene (1000 mg, 3.28 mmol) in 20 ml DMSO was added bis-(pinacolato)-diborane (922 mg, 3.63 mmol), potassium acetate (980 mg, 10.0 mmol) and 1.1-bis-(diphenylphosphino)-ferrocene-palladium(II)chloride (82 mg, 0.10 mmol). The mixture was stirred by 80° C. for 3 h. MS indicated complete conversion according to boron isotope distribution. This mixture containing the desired compound was directly used in the next step.

c)

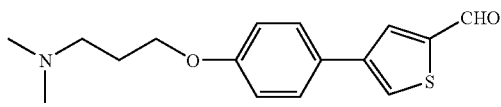

To a solution of 4-bromo thiophene-2-carboxaldehyde (755 mg, 3.96 mmol) and 1.1-bis-(diphenylphosphino)-ferrocene-palladium(II)chloride dichloromethane complex (82 mg, 0.10 mmol) in 6.60 ml 2M aqueous sodium carbonate (1.32 mmol) was added the DMSO solution of the boronic acid derivative described above and the mixture was stirred for 16 h at 80° C. under argon. The mixture was cooled to room temperature and diluted with DCM. The solution was washed with water and brine, dried and evaporated. The residue was purified via flash chromatography on silica gel using a DCM-ethanolic triethyl amine gradient 99:1 to 90:10 yielding 430 mg of the desired compound (45%).

$^1$H NMR (CDCl$_3$) ☐ 9.98 (s, 1H), 7.99 (d, 1H, J=1.5 Hz), 7.75 (d, 1H, J=1.5 Hz), 7.50 (d, 2H, J=8 Hz), 6.86 (d, 2H J=8 Hz), 4.05 (t, 2H, J=4 Hz), 2.50 (t, 2H, J=4 Hz), 2.31 (s, 6H), and 2.00 (quint., 2H, J=4 Hz),.MS (FD) m/e 290.1.

4-[4-(3-dimethylaminopropoxy)phenyl]-thiophene-2-methanol

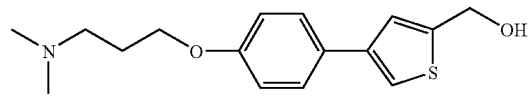

To a solution of 20% DIBAH in toluene (2.97 ml, 3.6 mmol) was added dropwise a solution of 4-[4-(3-dimethylaminopropoxy)-phenyl)-thiophene-2-carboxaldehyde (430 mg, 1.49 mmol) in 25 ml toluene at 0 to 2° C. The mixture was stirred for 2 h at 0 to 2° C. and quenched with 5 ml methanol and evaporated. The solid residue was extracted with DCM and ethanol and the collected organic phases dried over sodium sulfate and evaporated. The residue was purified via flash chromatography on silica gel using a DCM-ethanolic ammonia gradient 99:1 to 90:10 yielding 280 mg (65%) of the desired product.

$^1$H NMR (CDCl$_3$) ☐ 7.48 (d, 2H, J=8 Hz), 7.25 (m 2H), 6.96 (d, 2H J=8 Hz), 4.80 (s, 2H), 4.03 (t, 2H, J=4 Hz), 2.45 (t, 2H, J=4 Hz), 2.28 (s, 6H), 1.95 (quint., 2H, =4 Hz), and 1.70 (s, br., exch. 1H). MS (FD) m/e 292.1.

Dimethyl-(3-{4-[4-(2-phenoxy-ethylsulfanylmethyl)-thiophen-2-yl]-phenoxy}-propyl)-amine

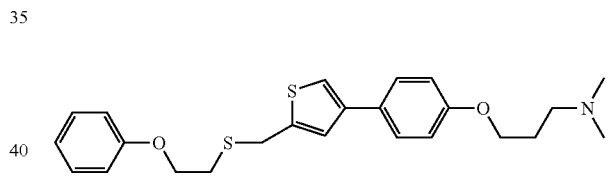

To a stirred suspension of 4-[4-(3-dimethylaminopropoxy)phenyl]-2-thiophene-5-methanol (255 mg, 0.87 mmol) in 10 ml of dry THF was added triethyl amine (223 mg, 2.20 mmol) and 10 mg DMAP and the mixture was cooled to −8 to −10° C. A solution of methane sulfonyl chloride (120 mg, 1.04 mmol) in 2 ml dry THF was added dropwise and the mixture was stirred for 90 min at −5 to −10° C. TLC showed almost complete conversion. The mixture was quenched with 60% sodium hydride (42 mg, 1.04 mmol) and stirred for 15 min at 0° C. In the meantime a solution of sodium 2-phenoxyethanethiolate was prepared from 2-phenoxy ethanethiol (269 mg, 1.74 mmol) and sodium hydride (60%, 71 mg, 1.74 mmol) in 1.5 ml dry THF. After 15 min of stirring the solution was cooled to 0° C. and slowly added to the solution of the mesylate. The mixture was stirred at 0° C. for 30 min and then for 16 h at ambient temperature. The mixture was evaporated and the residue purified by repeated chromatography on a silica gel column (DCM/ethanolic ammonia 99:1) yielding 180 mg of the desired product (48

$^1$H NMR (CDCl$_3$) δ 7.45 (d, 2H, J=8 Hz), 7.27 (m, 2H), 7.20 (m, 2H), 6.91 (m, 5H,), 4.17 (t, 2H, J=4 Hz), 4.05 (t, 2H, J=4 Hz+s 2H), 2.95 (t, 2H, J=4 Hz), 2.52 (t, 2H, J=4 Hz), 2.28 (s, 6H), 1.98 (quint., 2H, J=4 Hz). MS (FD) m/e 428.2 a) 4-[3-(dimethylamino)propoxy]-iodo benzene

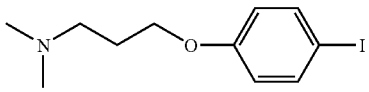

To a suspension of 4-iodo phenol (24.0 g, 110 mmol), anhydrous potassium carbonate (36.0 g, 260 mmol), and potassium iodide (2.2 g, 13 mmol) in 240 ml of dry 2-butanone was added finely ground 3-dimethylamino-1-propyl chloride hydrochloride (13.4 g, 110 mmol). The mixture was stirred under reflux for 48 h. The solvent was distilled off. The residue was dissolved in DCM and extracted with 2N aqueous NaOH twice. The organic phase was separated washed with water twice, dried and evaporated. The crude oil (21.0 g) was purified via flash chromatography on silica gel using a DCM/ethanolic ammonia gradient (100 to 95:5) yielding 12.9 g of the desired compound sufficiently pure for the next step.

$^1$H NMR (CDCl$_3$) δ 7.55 (d, 2H, J=8 Hz), 6.70 (d, 2H, J=8 Hz), 4.00 (t, 2H, J=4 Hz), 2.45 (t, 2H, J=4 Hz), 2.23 (s 6H), and 1.95 (quint., 2H, J=4 Hz),.MS (FD) m/e 306.0.

b) 2-[4-(3-dimethylaminopropoxy)-phenyl)-furan-5-carboxaldehyde

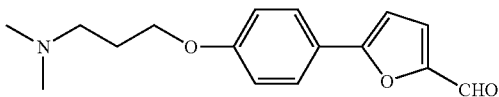

b1) [4-3-(dimethylamino)propoxy]phenyl]boronic acid pinacolyl ester (not isolated)

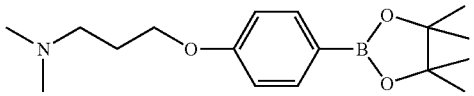

To a solution of 4-[3-(dimethylamino)propoxy]-iodo benzene (1000 mg, 3.28 mmol) in 20 ml DMSO was added bis-(pinacolato)-diborane (922 mg, 3.63 mmol), potassium acetate (980 mg, 10.0 mmol) and 1.1-bis-(diphenylphosphino)-ferrocene-palladium(II)chloride (82 mg, 0.10 mmol). The mixture was stirred by 80° C. for 3 h. MS indicated complete conversion according to boron isotope distribution. This mixture containing the desired compound was directly used in the next step.

c)

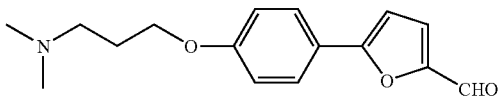

To a solution of 5-bromo furan-2-carboxaldehyde (690 mg, 3.935 mmol) and 1.1-bis-(diphenylphosphino)-ferrocene-palladium(II)chloride dichloromethane complex (82 mg, 0.10 mmol)in 6.60 ml 2M aqueous sodium carbonate (1.32 mmol) was added the DMSO solution of the boronic acid derivative described above and the mixture was stirred for 16 h at 80° C. under argon. The mixture was cooled to room temperature and diluted with DCM. The solution was washed with water and brine, dried and evaporated. The residue was purified via flash chromatography on silica gel using a DCM-ethanolic triethyl amine gradient 99:1 to 90:10 yielding 500 mg of the desired compound (56%).

$^1$H NMR (CDCl$_3$) □ 9.60 (s, 1H), 7.75 (d, 2H, J=6.5 Hz), 7.28 (d, 1H, J=4 Hz), 6.97 (d, 2H J=6.5 Hz), 6.71 (d, 2H, J=4 Hz) 4.07 (t, 2H, J=4 Hz), 2.50 (t, 2H, J=4 Hz), 2.30 (s, 6H,), and 2.00 (quint., 2H, J=4 Hz),.MS (FD) m/e 274.1.

5-[4-(3-dimethylaminopropoxy)phenyl]-furan-2-methanol

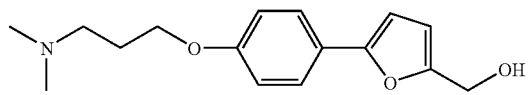

To a solution of 20% DIBAH in toluene (3.6 ml, 4.4 mmol) was added dropwise a solution of 5-[4-(3-dimethylaminopropoxy)-phenyl)-furan-2-carboxaldehyde (500 mg, 1.83 mmol) in 25 ml toluene at 0 to 2° C. The mixture was stirred for 2 h at 0 to 2° C. and quenched with 5 ml methanol and evaporated. The solid residue was extracted with DCM and ethanol and the collected organic phases dried over sodium sulfate and evaporated. The residue was purified via flash chromatography on silica gel using a DCM-ethanolic ammonia gradient 99:1 to 95:5 yielding 460 mg (91%) of the desired product.

$^1$H NMR (CDCl$_3$) δ 7.60 (d, 2H, J=7 Hz), 6.90 (d, 2H J=7 Hz) 6.45 (d, 1H, J=3.5 Hz), 6.33 (d, 1H, J=3.5 Hz), 4.66 (s, 2H), 4.00 (t, 2H, J=4 Hz), 2.43 (t, 2H, J=4 Hz), 2.21 (s, 6H), 1.92 (quint., 2H, J=4 Hz), and 1.80 (s, br, exch 1H). MS (FD) m/e 276.2.

Example 192

Dimethyl-(3-{4-[5-(2-phenoxy-ethylsulfanylmethyl)-furan-2-yl]-phenoxy}-propyl)-amine

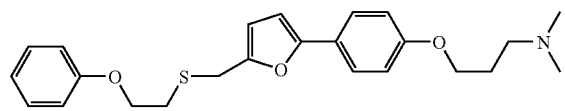

To a stirred solution of 5-[4-(3-dimethylaminopropoxy) phenyl]-2-furan-5-methanol (280 mg, 1.0 mmol) in 16 ml of dry THF was added triethyl amine (258 mg, 2.55 mmol) and 10 mg DMAP and the mixture was cooled to −8 to −10° C. A solution of methane sulfonyl chloride (138 mg, 1.20 mmol) in 3 ml dry THF was added dropwise and the mixture was stirred for 90 min at −5 to 0° C. TLC showed almost complete conversion. The mixture was quenched with 60% sodium hydride (49 mg, 1.20 mmol) and stirred for 15 min at 0° C. In the meantime a solution of sodium 2-phenoxy-ethanethiolate was prepared from 2-phenoxy ethanethiol (309 mg, 2.0 mmol) and sodium hydride (60%, 82 mg, 2.0 mmol) in 2 ml dry THF. After 15 min of stirring the solution

Example 193

Preparation of (3-{4-[5-(1H-indol-2-ylmethylsulfanylmethyl)-[1,3,4]oxadiazol-2-yl]phenoxy}propyl)dimethylamine

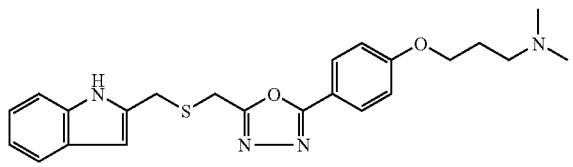

a) Thiobenzoic acid S-(2-{N'-[4-(3-dimethylaminopropoxy)benzoyl]hydrazino}-2-oxo-ethyl) ester

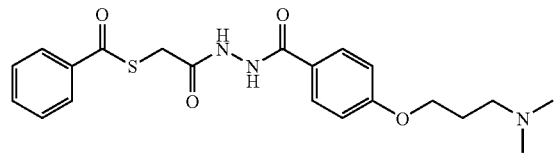

To a solution of benzoylsulfanyl-acetic acid (1.32 g, 6.7 mmol) in 45 ml THF at room temperature was added 1,1'-carbonyldiimidazole. The solution was heated at 60° C. for eighty minutes then stirred at room temperature for forty minutes. Next, a solution of 4-[(3-dimethylamino)propoxy]-benzoic acid hydrazide (1.59 g, 6.7 mmol) in 15 ml CH$_3$CN was added to the reaction. The solution was then stirred at room temperature for approximately 22 hours. The resultant suspension was filtered and the insoluble material was rinsed with CH$_3$CN to afford 1.13 g (40%) of the title compound. The filtrate was concentrated to an oil then treated with water and extracted twice with EtOAc. The combined organic phases were dried over Na$_2$SO$_4$, filtered and concentrated to a solid to afford an additional 2.08 g (74%) of the title compound and two impurities. The second lot containing the impurities was used in subsequent reactions.

$^1$H NMR (DMSO-d6) δ10.28 (bs, 2H), 7.95 (d, 2H, J=7 Hz), 7.83 (d, 2H, J=9 Hz), 7.73 (m, 1H), 7.59 (t, 2H, J=9 Hz), 7.00 (d, 2H, J=9 Hz), 4.06 (t, 2H, J=6 Hz), 3.95 (s, 2H), 2.35 (t, 2H, J=7 Hz), 2.14 (s, 6H), 1.83–1.90 (m, 2H). IR (KBr, cm$^{-1}$) 3280, 2943, 2816, 2769, 1679, 1662, 1654, 1607, 1522, 1497, 1295, 1253, 1211, 919 688. MS (ES$^+$) m/e 416. MS (ES$^-$) m/e 414.

b) Thiobenzoic acid S-{5-[4-(3-dimethylaminopropoxy)phenyl]-[1,3,4]oxadiazol-2-yl}ester

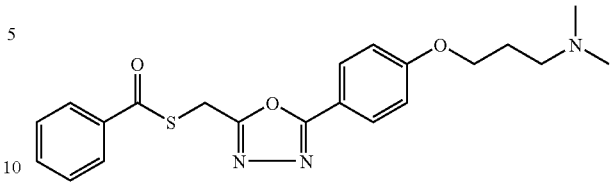

To a solution of Thiobenzoic acid S-(2-{N'-[4-(3-dimethylamino-propoxy)benzoyl]-hydrazino}-2-oxo-ethyl) ester (3.00 g, 7.2 mmol), triphenyl phosphine (3.79 g, 14.4 mmol) and triethylamine (1.46 g, 14.4 mmol) at room temperature was added carbon tetrachloride (2.22 g, 14.4 mmol). After stirring one hour at room temperature, carbon tetrabromide (2.39 g, 7.2 mmol) was added. Additional carbon tetrabromide (0.598 g, 1.8 mmol) was added fifteen minutes later. After stirring for approximately 3.5 hours, the resultant suspension was filtered. The filtrate was concentrated to a semi-solid material. Purification by normal phase chromatography (eluted with 9:1 CH$_3$Cl:MeOH) afforded 2.65 g (92%) of thiobenzoic acid S-{5-[4-(3-dimethylaminopropoxy)phenyl]-[1,3,4]oxadiazol-2-yl}ester s an oil that slowly solidifies.

$^1$H NMR (DMSO-d6) δ7.97 (m, 2H), 7.88 (m, 2H), 7.73 (m, 1H), 7.59 (t, 2H, J=8 Hz) 7.12 (m, 2H), 4.69 (s, 2H), 4.08 (t, 2H, J=6 Hz), 2.37 (t, 2H, J=7 Hz), 2.16 (s, 6H), 1.87 (m, 2H). MS (ES$^+$) m/e 398.

c) (3-{4-[5-(1H-indol-2-ylmethylsulfanylmethyl)-[1,3,4]oxadiazol-2-yl]phenoxy}-propyl)dimethylamine

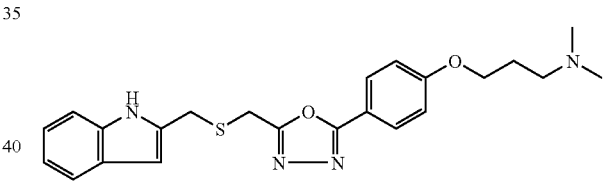

A degassed solution of thiobenzoic acid S-{5-[4-(3-dimethylamino propoxy)-phenyl]-[1,3,4]oxadiazol-2-yl}ester (0.264 g, 0.7 mmol) in 1.65 ml MeOH and 0.85 ml H$_2$O was treated with lithium hydroxide (0.032 g, 1.3 mmol). The reaction was stirred at room temperature for thirty minutes then a mixture of 2-bromomethylindole-1-carboxylic acid methyl ester (0.178 g, 0.7 mmol) in 1 ml MeOH and 2 ml THF was added. After stirring at room temperature for three hours the mixture was concentrated to remove bulk of methanol. The mixture was diluted with EtOAc then washed twice with water and once with brine. The organic layer was dried over Na$_2$SO$_4$, filtered and was concentrated to an oil. Purification by normal phase radial chromatography (eluted with 5% 2M NH3 in MeOH:CHCl$_3$) afforded a solid. Crystallization of the solid from Et2O:MeOH afforded 0.066 g (17%) of (3-{4-[5-(1H-indol-2-ylmethylsulfanylmethyl)-[1,3,4]oxadiazol-2-yl]phenoxy}-propyl)dimethylamine.

$^1$H NMR (DMSO-d6) δ11.11 (bs, 1H), 7.84 (d, 2H, J=9 Hz), 7.44 (d, 1H, J=8 Hz), 7.31 (d, 1H, J=8 Hz), 7.11 (d, 2H, J=9 Hz), 7.04 (t, 1H, J=7 Hz), 6.95 (t, 1H, J=7 Hz), 6.38 (S, 1 h), 4.09 (t, 2H, J=6 Hz), 4.02 (s, 4H), 2.36 (t, 2H, J=7 Hz), 2.15 (s, 6H), 1.87 (m, 2H). IR (KBr, cm$^{-1}$) 3425, 3050, 2942, 2757, 1617, 1499, 1256, 1175, 732. MS (ES$^+$) m/e 423. MS (ES$^-$) m/e 421. Anal. Calcd for C$_{23}$H$_{26}$N$_4$O$_2$S C, 65.38; H, 6.20; N, 13.26. Found C, 65.00; H, 6.17; N, 13.12.

Example 194

Preparation of (3-{4-[5-(1H-Benzoimidazol-2-ylmethylsulfanylmethyl)-[1,3,4]-oxadiazol-2-yl]phenoxy}propyl)dimethyl amine

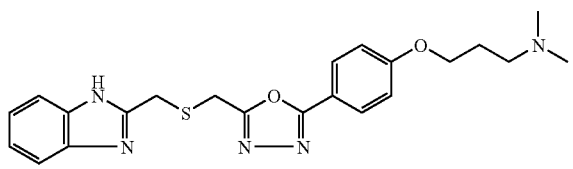

a) 2-Chloromethylbenzoimidazole-1-carboxylic acid tert-butyl ester

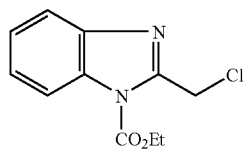

A mixture of 2-(chloromethyl)benzimidazole (4.05 g, 24.3 mmol), 4-dimethylamino pyridine (0.297 g, 2.4 mmol) and di-tert-butyl dicarbonate (6.37 g, 29.2 mmol) in 48 ml $CH_3CN$ was stirred at room temperature for four hours. Next, the suspension was heated at 60 C for 30 minutes. Upon cooling to room temperature the mixture was concentrated to an oil. The mixture was treated with 100 ml each of 1N HCl and $Et_2O$ and the resultant suspension was filtered. The phases from the filtrate were separated and the organic phase was washed with 1N HCl (2×100 ml), brine then concentrated to an oil. Purification by normal phase chromatography (eluted with 70% hexane:EtOAc) afforded 2.23 g (34%) of 2-chloromethylbenzoimidazole-1-carboxylic acid tert-butyl ester as an oil.

H NMR (DMSO-d6) δ8.06 (d, 1H, J=10 Hz), 7.61 (d, 1H, J=8 Hz), 7.21–7.37 (m, 2H), 7.00 (s, 1H), 5.99 (s, 2H), 4.05 (s, 3H). IR (KBr, cm$^{-1}$) 3455, 2980, 2934, 2869, 1709, 1606, 1509, 1454, 1367, 1244, 1169. Anal. Calcd for $C_{13}H_{15}ClN_2O_2$ C, 58.54; H, 5.67; N, 10.50. Found C, 58.55; H, 5.93; N, 10.42.

b) (3-{4-[5-(1H-benzoimidazol-2-ylmethylsulfanylmethyl)-[1,3,4]-oxadiazol-2-yl]phenoxy}propyl)dimethyl amine

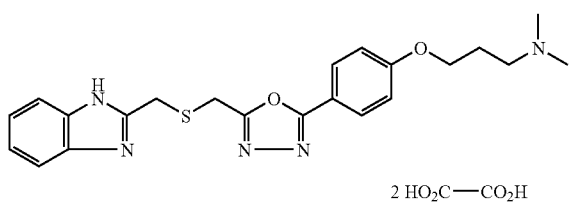

The above compound was prepared in a manner similar to that exemplified for the preparation of 193c, from thiobenzoic acid S-{5-[4-(3-dimethylaminopropoxy)phenyl]-[1,3,4]oxadiazol-2-yl}ester (0.264 g, 0.7 mmol), lithium hydroxide (0.032 g, 1.3 mmol) and 2-chloromethylbenzoimidazole-1-carboxylic acid tert-butyl ester (0.178 g, 0.7 mmol) in 1 ml MeOH to afford 0.118 g of an oil. The oil was dissolved into acetone and treated with 0.038 g of oxalic acid in acetone to afford 0.121 g (36%) of (3-{4-[5-(1H-benzo-imidazol-2-ylmethyl-sulfanylmethyl)-[1,3,4]-oxadiazol-2-yl]phenoxy}propyl)dimethyl amine as the dioxalate salt.

$^1$H NMR (DMSO-d6) δ11.11 (bs, 1H), 7.84 (d, 2H, J=9 Hz), 7.44 (d, 1H, J=8 Hz), 7.31 (d, 1H, J=8 Hz), 7.11 (d, 2H, J=9 Hz), 7.04 (t, 1H, J=7 Hz), 6.95 (t, 1H, J=7 Hz), 6.38 (s, 1H), 4.09 (t, 2H, J=6 Hz), 4.02 (s, 4H), 2.36 (t, 2H, J=7 Hz), 2.15 (s, 6 h), 1.87 (m, 2H). IR (KBr, cm$^{-1}$) 3425, 3050, 2942, 2757, 1617, 1499, 1256, 1175, 732. MS (ES$^+$) m/e 424. MS (ES) m/e 422.

Example 195

Preparation of (3-{4-[5-Benzofuran-3-ylmethylsulfanyl)-[1,3,4]-oxadiazol-2-yl]phenoxy}propyl)dimethylamine

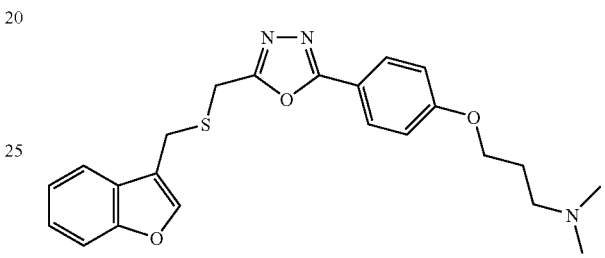

The above compound was prepared in a manner similar to that exemplified for the preparation of 193c, from thiobenzoic acid S-{5-[4-(3-dimethylaminopropoxy)phenyl]-[1,3,4]oxadiazol-2-yl}ester (0.622 g, 1.6 mmol), lithium hydroxide (0.075 g, 3.1 mmol) and 3-bromomethylbenzofuran (0.331 g, 1.6 mmol) in 2.3 ml MeOH. Crystallization from $Et_2O$ afforded 0.202 g (30%) of (3-{4-[5-benzofuran-3-ylmethylsulfanyl)-[1,3,4]-oxadiazol-2-yl]phenoxy}propyl)dimethyl-amine.

$^1$H NMR DMSO-d6) δ7.95 (s, 1H), 7.83 (d, 2H, J=9 Hz), 7.72 (m, 1H), 7.54 (d, 1H, J=8 Hz), 7.23–7.43 (m, 2H), 7.11 (D, 2 h, J=9 Hz), 4.09 (t, 2H, J=7 Hz), 4.03 (s, 2H), 4.01 (s, 2H), 2.36 (t, 2H, J=7 Hz), 2.14 (s, 6H), 1.83–1.92 (m, 2H). IR (KBr, cm$^{-1}$) 2817, 2766, 1611, 1502, 1472, 1452, 1302, 1258, 1179, 1101, 1089, 1004, 839, 746. MS (ES$^+$) m/e 424. Anal. Calcd for $C_{23}H_{25}N_3O_3S$ C, 65.23; H, 5.95; N, 9.92. Found C, 65.27; H, 6.22; N, 9.65. Mp (° C.)=85.

Example 196

Preparation of (3-{4-[5-Benzylsulfanylmethyl)-[1,3,4]-oxadiazol-2-yl]phenoxy}propyl)dimethylamine

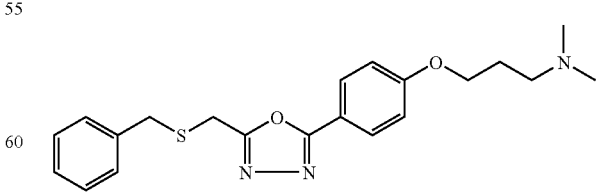

The above compound was prepared in a manner similar to that exemplified for the preparation of 193c, from thiobenzoic acid S-{5-[4-(3-dimethylaminopropoxy)phenyl]-[1,3,4]oxadiazol-2-yl}ester (0.220 g, 0.5 mmol), lithium hydroxide (0.026 g, 1.1 mmol) and benzyl bromide (0.095 g, 0.6 mmol) in 0.9 ml MeOH to afford 0.087 g (41%) of (3-{4-[5-Benzylsulfanylmethyl)-[1,3,4]-oxadiazol-2-yl]phenoxy}propyl)dimethylamine as a crystalline solid.

$^1$H NMR (DMSO-d6) δ7.89 (d, 2H, J=9 Hz), 7.21–7.38 (m, 5H), 7.12 (d, 2H, J=9 Hz), 4.09 (t, 2H, J=6 Hz), 3.95 (s, 2H), 3.86 (s, 2H), 2.36 (t, 2H, J=7 Hz), 2.15 (s, 6H), 1.83–1.92 (m, 2H). IR (KBr, cm$^{-1}$) 2761, 1614, 1565, 1499, 1473, 1246, 1175, 1049, 838, 701. MS (ES$^+$) m/e 384. Anal. Calcd for $C_{21}H_{25}N_3O_3S$ C, 65.77; H, 6.57; N, 10.96. Found C, 65.54; H, 6.50; N, 10.83.

Example 197

Preparation of Dimethyl-(3-{4-[5-(quinolin-2-ylmethylsulfanylmethyl)-[1,3,4]oxadiazol-2-yl]phenoxy}propyl)amine

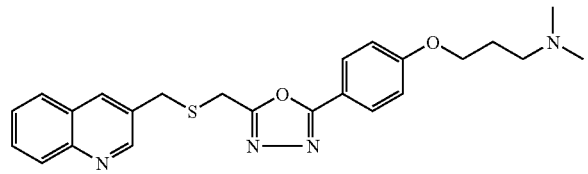

The above compound was prepared in a manner similar to that exemplified for the preparation of 193c, from thiobenzoic acid S-{5-[4-(3-dimethylaminopropoxy)phenyl]-[1,3,4]oxadiazol-2-yl}ester (0.344 g, 0.9 mmol), lithium hydroxide (0.062 g, 2.6 mmol) and 2-chloromethyl quinoline HCl (0.184 g, 0.9 mmol) in 1.4 ml MeOH to afford 0.182 g of an oil. A solution of ethanol (0.194 g, 4.2 mmol) in Et$_2$O was treated with acetyl chloride (0.131 g, 1.7 mmol) to generate HCl in situ. After stirring five minutes this solution was added to a solution of the title compound in Et2O. The resultant suspension was filtered to afford 0.204 g (50%) of dimethyl-(3-{4-[5-(quinolin-2-ylmethylsulfanyl-methyl)-[1,3,4]oxadiazol-2-yl]phenoxy}propyl)amine monohydrochloride salt.

$^1$H NMR (DMSO-d6) δ8.30 (d, 1H, J=8 Hz), 7.90–7.94 (m, 2H), 7.78 (d, 2H, J=9 Hz), 7.69–7.75 (m, 1H), 7.53–7.60 (m, 2H), 7.09 (d, 2H, J=9 Hz), 4.15–4.18 (m, 6H), 3.19–3.24 (m, 2H), 2.78 (s, 6H), 2.13–2.23 (m, 2H). IR (KBr, cm$^{-1}$) 2954, 2632, 2607, 2483, 1615, 1499, 1486, 1473, 1260, 1242, 1183, 837, 827, 759. MS (ES$^+$) m/e 435. Anal. Calcd for $C_{24}H_{26}N_4O_2S$ HCl C, 61.20; H, 5.78; N, 11.89. Found C, 60.86; H, 5.77; N, 11.90. Mp(° C.)=190.

Example 198

Preparation of (3-{4-[5-(Biphenyl-4-ylmethylsulfanylmethyl)-[1,3,4]oxadiazol-2-yl]phenoxy}propyl)dimethylamine

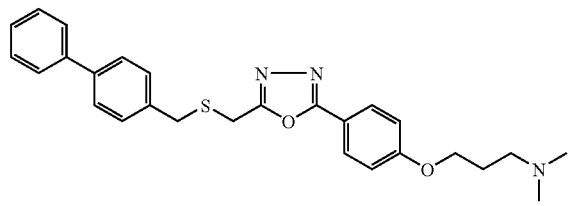

The above compound was prepared in a manner similar to that exemplified for the preparation of 193c, from thiobenzoic acid S-{5-[4-(3-dimethylaminopropoxy)phenyl]-[1,3,4]oxadiazol-2-yl}ester (0.207 g, 0.5 mmol), lithium hydroxide (0.025 g, 1.0 mmol) and 4-bromomethylbiphenyl (0.129 g, 0.5 mmol). After stirring at room temperature for three hours the suspension was filtered. The insoluble material was dissolved into EtOAc:MeOH and purified by normal phase silica gel chromatography (eluted with 5% 2M NH$_3$ in MeOH:CH$_2$Cl$_2$) to afford a white solid. This material was then converted to the HCl as described in Example 5 using the acetyl chloride/EtOH method to generate HCl in situ to afford 0.112 g (43%) of (3-{4-[5-(Biphenyl-4-ylmethylsulfanylmethyl)-[1,3,4]oxadiazol-2-yl]phenoxy}propyl)dimethyl-amine as the hydrochloride salt.

$^1$H NMR (DMSO-d6) δ7.88 (d, 2H, J=9 Hz), 7.59 (d, 4H, J=8 Hz), 7.33–7.47 (m, 5H), 7.11 (d, 2H, J=9 Hz), 4.14 (t, 2H, J=6 Hz), 4.00 (s, 2H), 3.91 (s, 2H), 3.19–3.24 (m, 2H), 2.78 (s, 6H), 2.13–2.22 (m, 2H).IR (KBr, cm$^{-1}$) 3491, 2956, 2599, 2470, 1617, 1587, 1566, 1501, 1484, 1428, 1393, 1308, 1258, 1171, 1087, 1054, 1003, 834, 695. MS (ES$^+$) m/e 460. Analytical HPLC: 100%. Mp(° C.)=191.

Example 199

Preparation of (3-{4-[5-(4-Benzyl-benzylsulfanylmethyl)-[1,3,4]oxadiazol-2-yl]phenoxy}propyl)dimethylamine

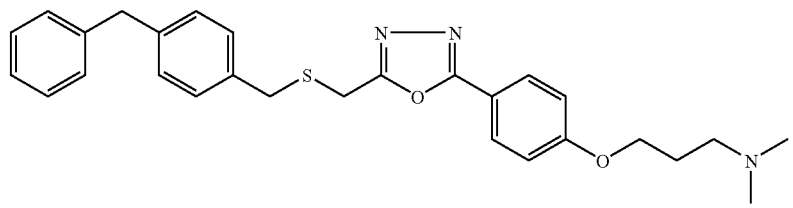

The above compound was prepared in a manner similar to that exemplified for the preparation of 193c, from thiobenzoic acid S-{5-[4-(3-dimethylaminopropoxy)phenyl]-[1,3,4]oxadiazol-2-yl}ester (0.206 g, 0.5 mmol), lithium hydroxide (0.025 g, 1.0 mmol) and 4-benzyl-benzylmethyl bromide (0.135 g, 0.5 mmol) in 1 ml MeOH. Purification by normal phase silica gel chroma-tography (eluted with 5% 2M NH$_3$ in MeOH:CH$_2$Cl$_2$ to 10% 2M NH$_3$ in MeOH:CH$_2$Cl$_2$) afforded an oil. This material was then converted to the HCl as described in Example 5 using the acetyl chloride/EtOH method to generate HCl in situ to afford 0.073 g (28%) of (3-{4-[5-(4-Benzyl-benzylsulfanylmethyl)-[1,3,4]oxadiazol-2-yl]phenoxy}propyl) di-methylamine as the hydrochloride salt.

$^1$H NMR (DMSO-d6) δ7.90 (d, 2H, J=9 Hz), 7.11–7.32 (m, 11H), 4.16 (t, 2H, J=6 Hz) 3.94 (s, 2H), 3.88 (s, 2H), 3.82 (s, 2H), 3.22 (t, 2H, J=8 Hz), 2.77 (s, 6H), 2.13–2.23 (m, 2H). IR (KBr, cm$^{-1}$) 3482, 3024, 2933, 2599, 2475, 1616, 1500, 1428, 1307, 1257, 1173, 1053, 1002, 835, 724, 699. MS (ES$^+$) m/e 474. Mp(° C.)=151.

Example 200

Preparation of (3-{4-[5-(2,2-diphenylethylsulfanylmethyl)-[1,3,4]oxadiazol-2-yl]phenoxy}propyl)dimethylamine

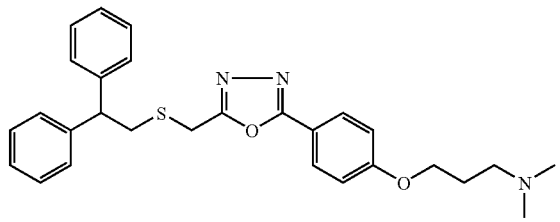

The above compound was prepared in a manner similar to that exemplified for the preparation of 193c, from thiobenzoic acid S-{5-[4-(3-dimethylaminopropoxy)phenyl]-[1,3,4]oxadiazol-2-yl}ester (0.233 g, 0.6 mmol), lithium hydroxide (0.028 g, 1.2 mmol) and 2,2-diphenylethylbromide (0.153 g, 0.6 mmol). The reaction was stirred at room temperature for 3 hours then heated at 60 C for 2 two days. Purification by normal phase silica gel chroma-tography (eluted with 5% 2M NH$_3$ in MeOH:CH$_2$Cl$_2$ to 10% 2M NH$_3$ in MeOH:CH$_2$Cl$_2$) afforded an oil. This material was then converted to the HCl as described in Example 5 using the acetyl chloride/EtOH method to generate HCl in situ to afford 0.104 g (35%) of (3-{4-[5-(2,2-diphenylethylsulfanylmethyl)-[1,3,4]oxadiazol-2-yl]phenoxy}propyl)dimethylamine as the hydrochloride salt.

$^1$H NMR (DMSO-d6) δ7.88 (d, 2H, J=9 Hz), 7.23–7.31 (m, 8H), 7.12–7.18, m, 4H), 4.22 (t, 1H, J=8 Hz), 4.16 (t, 2H, J=6 Hz), 4.09 (s, 2H), 3.35 (d, 2H, J=8 Hz), 3.21 (t, 2H, J=8 Hz), 2.77 (s, 6H), 2.08–2.21 (m, 2H). IR (KBr, cm$^{-1}$) 3436, 3024, 2954, 2594, 2478, 1734, 1613, 1568, 1501, 1452, 1302, 1259, 1176, 1051, 839, 734, 706, 530. MS (ES$^+$) m/e 474. Mp(° C.)=149.

Example 201

Preparation of (3-{4-[5-(Benzofuran-2-ylmethylsulfanylmethyl)-[1,3,4]oxadiazol-2-yl]phenoxy}propyl)dimethylamine

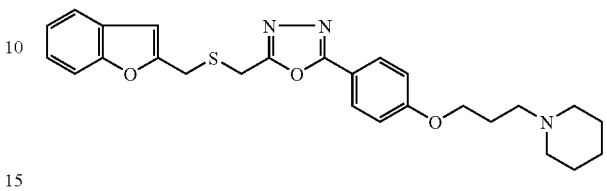

The above compound was prepared in a manner similar to that exemplified for the preparation of 193c, from thiobenzoic acid S-{5-[4-(3-dimethylaminopropoxy)phenyl]-[1,3,4]oxadiazol-2-yl}ester (0.633 g, 1.4 mmol), lithium hydroxide (0.069 g, 2.9 mmol) and benzofuran-2-ylmethyl bromide (0.305 g, 1.4 g). Crystallization of the isolated product from Et$_2$O afforded 0.246 g (37%) of (3-{4-[5-(Benzofuran-2-ylmethyl-sulfanylmethyl)-[1,3,4]oxadiazol-2-yl]phenoxy}propyl)dimethylamine.

$^1$H NMR (DMSO-d6) δ7.79 (d, 2H, J=9 Hz), 7.52 (d, 1H, J=7 Hz), 7.44 (d, 1H, J=8 Hz), 7.16–7.24 (m, 2H), 7.07 (d, 2H, J=9 Hz), 6.78 (s, 1H), 4.07–4.13 (m, 6H), 2.27–2.40 (m, 6H), 1.85–1.91 (m, 2H), 1.45–1.52 (m, 4H), 1.34–1.40 (m, 2H). IR (KBr, cm$^{-1}$) 2933, 2769, 1611, 1501, 1452, 1393, 1300, 1249, 1174, 1130, 1089, 1049, 1005, 950, 839, 815, 761. MS (ES$^+$) m/e 464. Anal. Calcd for C$_{26}$H$_{29}$N$_3$O$_3$S C, 67.36; H, 6.31; N, 9.00. Found C, 67.50; H, 6.52; N, 9.03. Mp(° C.)=114.

Example 202

Preparation of (3-{4-[5-(Benzofuran-2-ylmethoxymethyl)-[1,3,4]oxadiazol-2-yl]phenoxy]propyl)dimethylamine

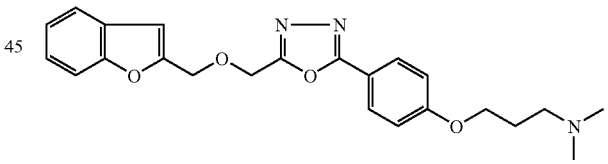

a) {5-[4-(3-Dimethylaminopropoxy)phenyl]-[1,3,4]oxadiazol-2-yl}methanol

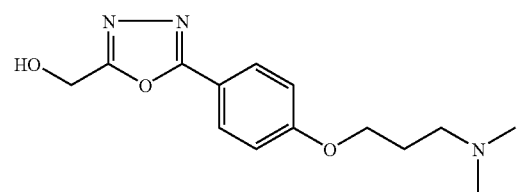

To a solution of acetoxy acetic acid (0.249 g, 2.1 mmol) in 9 ml THF at room temperature was added 1,1'-carbonyldiimidazole (0.342 g, 2.1 mmol). The solution was heated at 60 C for 80 minutes, the stirred at room temperature for 40 minutes. The solution was then treated with 4-[(3-dimethylamino)propoxy]-benzoic acid hydrazide (0.500 g, 2.1 mmol). The resultant light suspension was stirred at room temperature for 1.5 hours. Next, the suspension was treated with triphenyl phosphine (1.11 g, 4.2 mmol) and carbon tetrabromide (1.40 g, 4.2 mmol). The reaction was stirred an additional three hours before being concentrated to a semi-solid material. The crude material was treated with 5.4 ml MeOH and 1.6 ml H$_2$O then lithium hydroxide (0.151 g, 6.3 mol) was added. After stirring at room temperature for 1.45 hours the reaction was concentrated in volume then extracted three times with EtOAc. The combined organic phases were washed with brine, dried over Na$_2$SO$_4$, filtered, then concentrated to an oil. Purification by normal phase silica gel radial chromatography (eluted with 9:1 CHCl$_3$:2M NH$_3$ in MeOH) afforded 0.339 g (58%) of {5-[4-(3-dimethylaminopropoxy)phenyl]-[1,3,4]oxadiazol-2-yl}methanol.

$^1$H NMR (DMSO-d6) δ7.92 (d, 2H, J=9 Hz), 7.13 (d, 2H, J=9 Hz), 5.92 (t, 1H, J=6 Hz), 4.68 (d, 2H, J=6 Hz), 4.09 (t, 2H, J=6 Hz), 2.36 (t, 2H, J=7 Hz), 2.12 (s, 6H), 1.83–1.92 (m, 2H). IR (KBr, cm$^{-1}$) 2873, 2788, 1613, 1588, 1500, 1467, 1309, 1258, 1179, 1055, 1003, 742, 675, 534. MS (ES$^+$) m/e 278.

b) (3-{4-[5-(Benzofuran-2-ylmethoxymethyl)-[1,3,4]oxadiazol-2-yl]phenoxy}propyl)-dimethylamine

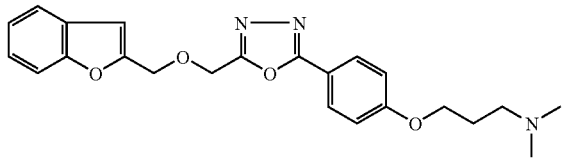

To a solution of {5-[4-(3-dimethylaminopropoxy)phenyl]-[1,3,4]oxadiazol-2-yl}methanol (0.150 g, 0.5 mmol) in 2.5 ml DMF at room temperature was added 60% sodium hydride (0.023 g, 0.6 mmol). After stirring at room temperature for one hour an additional 2 ml DMF was added followed by 2-(bromomethyl)naphthalene (0.120 g, 0.5 mmol). Approximately one hour later additional 60% sodium hydride (0.023 g, 0.6 mmol) was added. The reaction was treated with H$_2$O and extracted three times with EtOAc. The combined organic phases were washed with brine, dried over Na$_2$SO$_4$, filtered, and concentrated to an oil. Purification by normal phase silica gel radial chromatography (eluted with 95:5 CHCl$_3$:2M NH$_3$ in MeOH) to afford an oil. This material was then converted to the HCl as described in Example 5 using the acetyl chloride/EtOH method to generate HCl in situ to afford 0.063 g (26%) of (3-{4-[5-(Benzofuran-2-ylmethoxymethyl)-[1,3,4]oxadiazol-2-yl]phenoxy}propyl)dimethyl-amine as the hydrochloride salt.

$^1$H NMR (DMSO-d6) δ7.88–7.97 (m, 6H), 7.49–7.55 (m, 3H), 7.15 (d, 2H, J=9 Hz), 4.88 (s, 2H), 4.82 (s, 2H), 4.17 (t, 2H, J=6 Hz), 3.22 (t, 2H, J=8 Hz), 2.76 (s, 6H), 2.13–2.23 (m, 2H). IR (KBr, cm$^{-1}$) 2472, 1616, 1500, 1472, 1257, 1089. MS (ES$^+$) m/e 418. Anal. Calcd for C$_{25}$H$_{27}$N$_3$O$_3$ HCl C, 66.14; H, 6.22; N, 9.26. Found C, 65.74; H, 6.11; N, 9.14. Mp(° C.)=173.

Example 203

Preparation of Dimethyl-{3-[4-(5-naphthalene-2-yl-[1,3,4]oxadiazol-2-yl)phenoxy]-25 propyl}amine

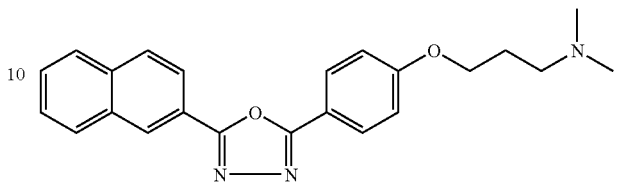

a) 4-Hydroxybenzoic acid N'-(naphthalene-2-carbonyl)hydrazide

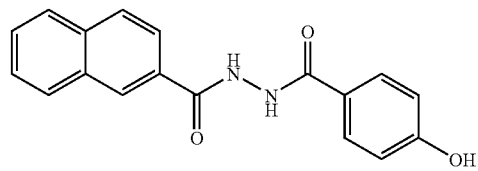

To a solution of 2-naphthaoic acid (2.01 g, 11.7 mmol) in 30 ml DMF at 0 C was added fluoro-N,N,N'-tetramethylformamidinium hexafluoro phosphate (3.08 g, 11.7 mmol). The reaction was stirred at 0 C for fifteen minutes then triethylamine (2.36 g, 23.3 mmol) and a suspension of 4-hydroxybenzoic hydrazide (3.55 g, 23.3 mmol) in 30 ml DMF, were added. The reaction was then stirred at room temperature for thirty minutes. Next, the resultant solution was slowly poured into 600 ml of ice water. The resultant suspension was filtered. The insoluble material was triterated in 500 ml 5N HCl until a fine suspension resulted. The insoluble material was collected by filtration then treated with 300 ml boiling MeOH. The milky suspension was filtered and the filtrate was reduced in volume on a steam bath until crystals started forming. The crystalline material was collected by filtration to afford 1.63 g (46%) of 4-Hydroxybenzoic acid N'-(naphthalene-2-carbonyl)hydrazide.

$^1$H NMR (DMSO-d6) δ10.55 (s, 1H), 10.30 (s, 1H), 10.11 (s, 1H), 8.55 (s, 1H), 7.97–8.08 (m, 4H), 7.82 (d, 2H, J=8 Hz), 7.59–7.68 (m, 2H), 6.86 (d, 2H, J=8 Hz). IR (KBr, cm$^{-1}$) 3339, 1734, 1676, 1645, 1583, 1506, 1437, 1377, 1276, 1238, 1170, 779, 757, 547, 478. MS (ES$^-$) m/e 305.

a) 4-(5-Naphthalen-2-yl-[1,3,4]oxadiazol-2-yl)phenol

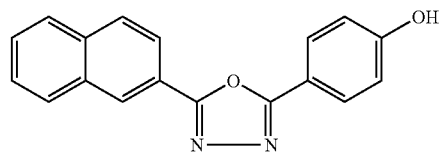

The above compound was prepared in a manner similar to that exemplified for the preparation of Example 19d, from 4-Hydroxybenzoic acid N'-(naphtha-lene-2-carbonyl)hydrazide (1.57 g, 5.1 mmol), triphenylphosphine (2.69 g, 10.3 mmol), triethylamine (1.66 g, 16.4 mmol) and carbon tetrabromide (3.40 g, 10.3 mmol) to afford an oil. The oil was treated with 100 ml EtOAc. The resultant precipitate was collected by filtration and discarded. The filtrate was concentrated to an oil. Purification by normal phase silica gel chromatography (eluted with 3:2 hexane:EtOAc) afforded 0.220 g (15%) of 4-(5-Naphthalen-2-yl-[1,3,4]oxadiazol-2-yl)phenol.

$^1$H NMR (DMSO-d6) δ10.36 (s, 1H), 8.74 (s, 1H), 8.13–8.18 (m, 3H), 8.01–8.08 (m, 3H), 7.64–7.70 (m, 2H), 7.01 (d, 2H, J=9 Hz). IR (KBr, cm$^{-1}$) 1735, 1610, 1589, 1504, 1443, 1292, 1171, 844, 751. MS (ES$^+$) m/e 289, MS (ES$^-$) m/e 287 c) Dimethyl-{3-[4-(5-naphthalene-2-yl-[1,3,4]oxadiazol-2-yl)phenoxy]propyl}amine

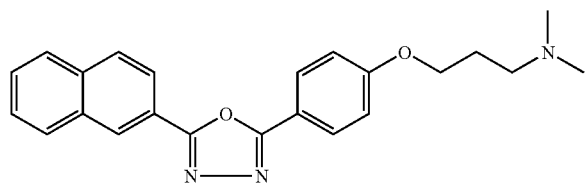

The above compound was prepared in a manner similar to that exemplified for the preparation of Example 19e, from 4-(5-naphthalen-2-yl-[1,3,4]oxadiazol-2-yl)phenol (0.205 g, 0.7 mmol), sodium hydride (0.057 g, 1.4 mmol) and 3-chloro-N,N-dimehtylpropyl amine HCl (0.112 g, 0.7 mmol) to afford the title compound as a crude material. Purification by radial chromatography on silica gel (eluted with 9:1 Et$_2$O: 2M NH$_3$ in MeOH) afforded 0.120 g (45%) of dimethyl-{3-[4-(5-naphthalene-2-yl-[1,3,4]-oxadiazol-2-yl)phenoxy]propyl}amine as a solid.

$^1$H NMR (DMSO-d6) δ8.76 (s, 1H), 8.01–8.21 (m, 6H), 7.64–7.70 (m, 2H), 7.18 (d, 2H, J=9 Hz), 4.13 (t, 2H, J=6 Hz), 2.38 (t, 2H, J=7 Hz), 2.13 (s, 6H), 1.85–1.94 (m, 2H). IR (KBr, cm$^{-1}$) 1613, 1498, 1464, 1257, 1175. MS (ES$^+$) m/e 374. Mp(° C.)=127.

Example 204

Preparation of Dimethyl-{3-[4-(5-naphthalene-2-ylmethyl-[1,3,4]oxadiazol-2-yl)-phenoxy]propyl}amine

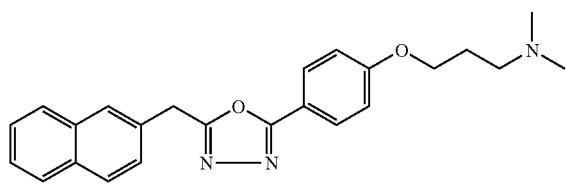

a) 4-(3-Dimethylaminopropoxy)benzoic acid N'-(2-naphthalen-2-ylacetyl)hydrazide

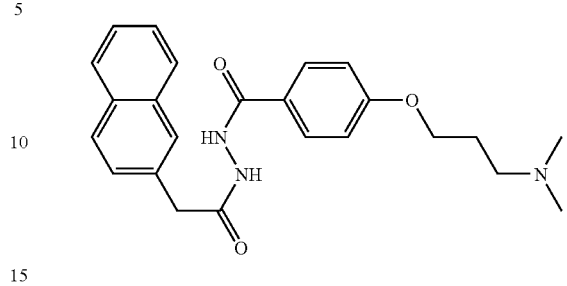

To a solution of 2-naphthyl acetic acid (0.237 g, 1.3 mmol) in 5.6 ml THF at room temperature was added 1,1'-carbonyldiimidazole (0.206 g, 1.3 mmol). The solution was heated at 60 C for one hour. Upon cooling to room temperature, the reaction was treated with 4-[(3-dimethylamino)propoxy]-benzoic acid hydrazide (0.302 g, 1.3 mmol). The reaction was stirred at room temperature for four hours then concentrated to an oil. The oil was treated with 25 ml 0.1 N NaOH and extracted with EtOAc (2×25 ml). A precipitate develop in the aqueous phase. The precipitate was collected by filtration to afford 0.306 g (59%) of 4-(3-Dimethylaminopropoxy)benzoic acid N'-(2-naphthalen-2-ylacetyl)hydrazide.

$^1$H NMR (DMSO-d6) δ10.21 (bs, 2H), 7.81–7.91 (m, 6H), 7.45–7.53 (m, 3H), 6.99 (d, 2H, J=9 Hz), 4.05 (t, 2H, J=6 Hz), 3.71 (s, 2H), 2.34 (t, 2H, J=7 Hz), 2.10 (s, 6H), 1.80–1.89 (m, 2H). IR (CHCl$_3$, cm$^{-1}$) 1682, 1631, 1608, 1510, 1463, 1255, 1174. MS (ES$^+$) m/e 406, MS (ES$^-$) m/e 404.

b) Dimethyl-{3-[4-(5-naphthalene-2-ylmethyl-[1,3,4]oxadiazol-2-yl)-phenoxy]propyl}-amine

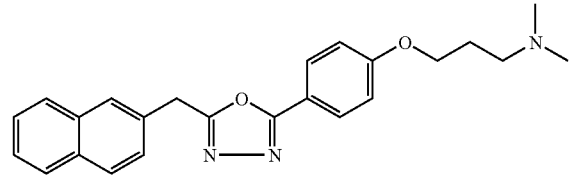

The above compound was prepared in a manner similar to that exemplified for the preparation of Example 19d, from 4-(3-Dimethylaminopropoxy)benzoic acid N'-(2-naphthalen-2-ylacetyl)hydrazide (0.436 g, 1.1 mmol), triphenylphosphine (0.564 g, 2.2 mmol), triethylamine (0.218 g, 2.2 mmol) and carbon tetrabromide (0.713 g, 2.2 mmol) to afford an oil. Purification by normal phase silica gel chromatography (eluted with 9:1 Et$_2$O:2M NH$_3$ in MeOH) followed by conversion to the HCl salt as described in Example 5 using the acetyl chloride/EtOH method to generate HCl in situ afforded 0.235 g (52%) of dimethyl-{3-[4-(5-naphthalene-2-ylmethyl-[1,3,4]oxadiazol-2-yl)phenoxy]propyl}amine as the hydrochloride salt.

$^1$H NMR (DMSO-d6) δ7.87–7.94 (m, 6H), 7.48–7.55 (m, 3H), 7.12 (d, 2H, J=9 Hz), 4.51 (s, 2H), 4.14 (t, 2H, J=6 Hz), 3.20 (t, 2H, 8 Hz), 2.74 (s, 6H), 2.11–2.20 (m, 21). IR (KBr, cm$^{-1}$) 3442, 2954, 2673, 2614, 2476, 1616, 1588, 1501, 1477, 1254, 1178, 1254, 1178, 836, 784, 739, 490. MS (ES$^+$) m/e 388. Mp(° C.)=192.

Example 205

Preparation of Dimethyl-{3-[4-(5-naphthalene-2-ylethyl-[1,3,4]oxadiazol-2-yl)phenoxy]propyl}amine

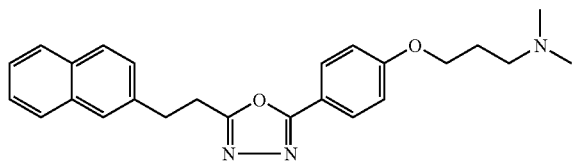

a) 4-Hydroxybenzoic acid N-(3-naphthalen-2-yl-propionyl)hydrazide

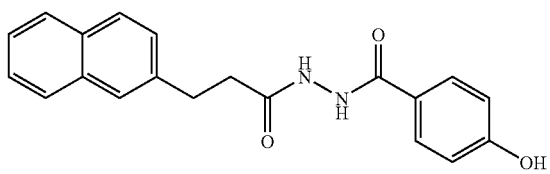

The above compound was prepared in a manner similar to that exemplified for the preparation of Example 26b, from 3-naphthalen-2-yl proprionic acid (1.00 g, 5.0 mmol), 1,1'-carbonyldiimidazole (0.810 g, 5.0 mmol) and 4-hydroxybenzoic hydrazide (0.760 g, 5.0 mmol) to afford an oil that crystallizes out. This material was triterated in EtOAc, filtered to afford 0.320 g (10%) of 4-hydroxybenzoic acid N-(3-naphthalen-2-yl-propionyl)hydrazide along with an impurity.

$^1$H NMR (DMSO-d6) δ7.76–7.90 (m, 6H), 7.40–7.50 (m, 3H), 7.15–7.20 (m, 2H), 3.14–3.18 (m, 2H), 2.56–2.65 (m, 2H). MS (ES$^-$) m/e 333.

b) 4-[5-(2-Naphthalen-2-yl-ethyl)-[1,3,4]oxadizol-2-yl]phenol

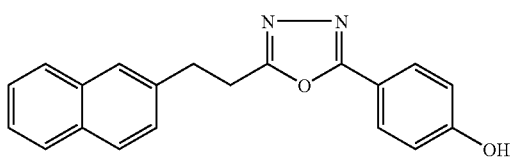

The above compound was prepared in a manner similar to that exemplified for the preparation of Example 19d, from 4-hydroxybenzoic acid N-(3-naphthalen-2-yl-propionyl)hydrazide (0.320 g, 1.0 mmol), triphenylphosphine (0.502 g, 2.0 mmol), triethylamine (0.310 g, 3.1 mmol) and carbon tetrabromide (0.635 g, 2.0 mmol). Purification by normal phase silica gel radial chromatography (eluted with 3:1 EtOAc:hexane) followed by crystallization from EtOAc afforded 0.277 g (91%) of 4-[5-(2-Naphthalen-2-yl-ethyl)-[1,3,4]oxadiazol-2-yl]phenol.

$^1$H NMR (DMSO-d6) δ10.26 (bs, 1H), 7.73–7.88 (m, 6H), 7.43–7.51 (m, 3H), 6.91 (d, 2H, J=8 Hz), 3.23–3.36 (m, 4H). IR (KBr, cm$^{-1}$) 3051, 3016, 1603, 1579, 1505, 1443, 1282, 1239, 1170. MS (ES$^+$) m/e 317, MS (ES) m/e 315. Anal. Calcd for C$_{20}$H$_{16}$N$_2$O$_2$ C, 75.93; H, 5.10; N, 8.85. Found C, 75.60; H, 5.14; N, 8.70.

d) Dimethyl-{3-[4-(5-naphthalene-2-ylethyl)-[1,3,4]oxadiazol-2-yl)phenoxy]propyl}-amine

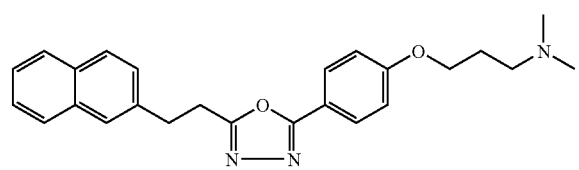

The above compound was prepared in a manner similar to that exemplified for the preparation of Example 19e, from 4-[5-(2-Naphthalen-2-yl-ethyl)-[1,3,4]oxadizol-2-yl]phenol (0.388 g, 1.1 mmol), sodium hydride (0.085 g, 2.1 mmol) and 3-chloro-N,N-dimehtylpropyl amine HCl (0.169 g, 1.1 mmol). Purification by radial chromatography on silica gel (eluted with 9:1 Et$_2$O: 2M NH$_3$ in MeOH) followed by conversion to the HCl salt as described in Example 5 using the acetyl chloride/EtOH method to generate HCl in situ afforded 0.192 g (36%) of dimethyl-{3-[4-(5-naphthalene-2-ylethyl)-[1,3,4]oxadiazol-2-yl)phenoxy]propyl}amine as the hydrochloride salt.

$^1$H NMR (DMSO-d6) δ7.79–7.91 (m, 6H), 7.43–7.51 (m, 3H), 7.13 (d, 2H, J=9 Hz), 4.16 (t, 2H, J=6 Hz), 3.18–3.38 (m, 6H), 2.76 (s, 6H), 2.12–2.21 (m, 2H). IR(CHCl$_3$, cm$^{-1}$) 2969, 1615, 1501, 1475, 1253, 1176. MS (ES$^+$) m/e 402. Mp(° C.)=208–210.

Example 206

Preparation of dimethyl-{3-[4-(5-naphthalene-2-ylpropyl)-[1,3,4]oxadiazol-2-yl)-phenoxy]propyl}amine

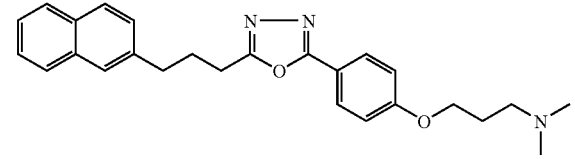

a) 4-Hydroxybenzoic acid N-(4-naphthalen-2-yl-butyryl)hydrazide

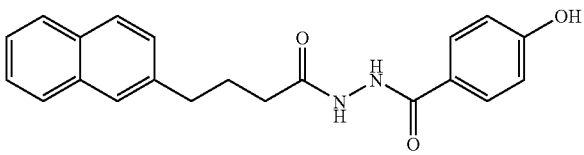

The above compound was prepared in a manner similar to that exemplified for the preparation of Example 19c, from 2-naphthalenebutanoic acid (0.600 g, 2.8 mmol), 2-ethoxy-1-ethoxycarbonyl-1,2-dihydroquinoline (0.692 g, 2.8 mmol) and 4-hydroxybenzoic hydrazide (0.426 g, 2.8 mmol). Crystallization of the isolated crude material from acetone afforded 0.507 g (52%) of 4-Hydroxybenzoic acid N-(4-naphthalen-2-yl-butyryl)hydrazide.

$^1$H NMR (DMSO-d6) δ10.11 (bd, 2H), 9.74 (bs, 1H), 7.84–7.89 (m, 3H), 7.70–7.77 (m, 3H), 7.35–7.50 (m, 3H), 6.81 (d, 2H, J=8 Hz), 2.81 (t, 2H, J=7 Hz), 2.23 (t, 2H, J=7 Hz), 1.93–2.00 (m, 2H). IR (KBr, cm$^{-1}$) 3312, 3270, 3015, 1662, 1624, 1608, 1504, 1321, 1279, 1228, 849, 664, 475. MS (ES$^-$) m/e 347. Anal. Calcd for $C_{21}H_{20}N_2O_3$ C, 72.40; H, 5.79; N, 8.04. Found C, 72.04; H, 5.65; N, 7.92.

b) 4-[5-(3-Naphthalen-2-yl-propyl)-[1,3,4]oxadiazol-2-yl)phenol

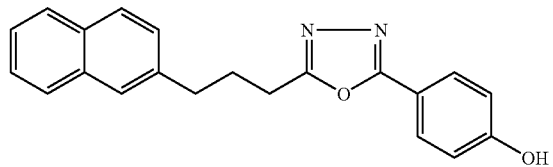

The above compound was prepared in a manner similar to that exemplified for the preparation of Example 19d, from 4-hydroxybenzoic acid N-(4-naph-thalen-2-yl-butyryl)hydrazide (0.464 g, 1.3 mmol), triphenylphosphine (0.699 g, 2.7 mmol), triethylamine (0.270 g, 2.7 mmol) and carbon tetrabromide (0.883 g, 2.7 mmol). Purification by normal phase silica gel radial chromatography (eluted with EtOAc) afforded 4-[5-(3-naphthalen-2-yl-propyl)-[1,3,4]oxadiazol-2-yl)phenol as a solid.

$^1$H NMR (DMSO-d6) δ10.25 (bs, 1H), 7.72–7.88 (m, 6H), 7.41–7.51 (m, 3H), 6.92 (d, 2H, J=9 Hz), 2.86–2.96 (m, 4H), 2.11–2.21 (m, 2H). IR (KBr, cm$^{-1}$) 1613, 1600, 1502, 1285, 1236, 1175, 856, 820, 746, 473. MS (ES$^+$) m/e 331, MS (ES$^-$) m/e 329.

c) Dimethyl-{3-[4-(5-naphthalene-2-ylpropyl)-[1,3,4]oxadiazol-2-yl)-phenoxy]propyl}amine

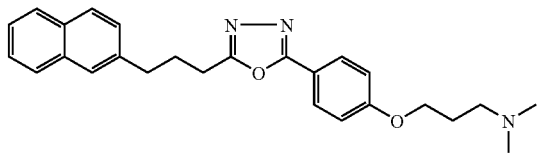

The above compound was prepared in a manner similar to that exemplified for the preparation of Example 21e, from 4-[5-(3-naphthalen-2-yl-propyl)-[1,3,4]oxadiazol-2-yl)phenol (0.252 g, 0.8 mmol), cesium carbonate (0.497 g, 1.5 mmol), and 3-chloro-N,N-dimethylpropylamine HCl (0.121 g, 0.8 mmol). Purification by normal phase silica gel radial chromatography (eluted with 95:5 CHCl$_3$:2M NH$_3$ in MeOH) followed by crystallization from Et$_2$O afforded 0.071 g (22%) of dimethyl-{3-[4-(5-naphthalene-2-ylpropyl)-[1,3,4]oxadiazol-2-yl)-phenoxy]propyl}amine.

$^1$H NMR (DMSO-d6) δ7.84–7.89 (m, 5H), 7.74 (s, 1H), 7.42–7.51 (m, 3H), 7.10 (d, 2H, J=9 Hz), 4.08 (t, 2H, J=6 Hz), 2.86–2.98 (m, 4H), 2.36 (t, 2H, J=7 Hz), 2.11–2.20 (m, 8H), 1.82–1.91 (m, 2H). IR (KBr, cm$^{-1}$) 2950, 2817, 2768, 1916, 1587, 1503, 1255, 1172, 1004, 845, 744. MS (ES$^+$) m/e 416. Anal. Calcd for $C_{26}H_{29}N_3O_2$ C, 75.15; H, 7.03; N, 10.11. Found C, 75.01; H, 6.89; N, 10.02, Mp(° C.)=92.

Example 207

Preparation of dimethyl-{3-[4-(5-naphthalene-2-ylbutyl)-[1,3,4]oxadiazol-2-yl)phenoxy]propyl}amine

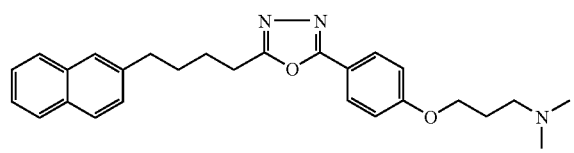

a) 4-(3-Dimethlaminopropoxy)benzoic acid N-(5-naphthalen-2-ylpentanoyl)hydrazide

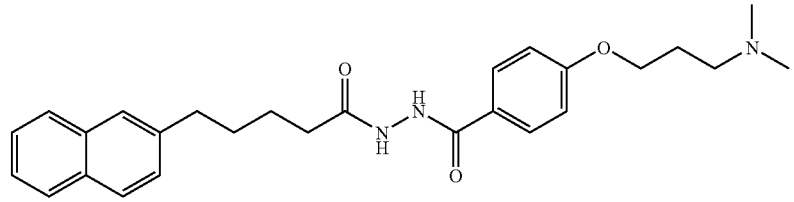

The above compound was prepared in a manner similar to that exemplified for the preparation of Example 204a, from 2-naphthalenepentanoic acid (0.600 g, 2.6 mmol), 1,1'-carbonyldiimidazole (0.426 g, 2.6 mmol) and 4-[(3-dimethylamino)propoxy]-benzoic acid hydrazide (0.624 g, 2.6 mmol). The reaction suspension was filtered to afford 0.417 g (35%) of 4-(3-Dimethlaminopropoxy)benzoic acid N-(5-naphthalen-2-ylpentanoyl)hydrazide.

$^1$H NMR (DMSO-d6) δ10.04 (bs, 1H), 9.74 (bs, 1H), 7.79–7.88 (m, 5H), 7.71 (s, 1H), 7.38–7.50 (m, 3H), 6.99 (d, 2H, J=9 Hz), 4.05 (t, 2H, J=6 Hz), 2.78 (t, 2H, J=7 Hz), 2.34 (t, 2H, J=7 Hz), 2.23 (t, 2H, J=7 Hz), 2.13 (s, 6H), 1.81–1.89 (m, 2H), 1.58–1.76 (m, 4H). IR (KBr, cm$^{-1}$) 3203, 2935, 2855, 2762, 1665, 1598, 1568, 1465, 1256, 1173, 843, 818, 474. MS (ES$^+$) m/e 448, MS (ES) m/e 446. Anal. Calcd for $C_{27}H_{33}N_3O_3$ C, 72.46; H, 7.43; N, 9.39. Found C, 72.51; H, 7.46; N, 9.20.

b) Dimethyl-{3-[4-(5-naphthalene-2-ylbutyl)-[1,3,4]oxadiazol-2-yl)phenoxy]propyl}-amine

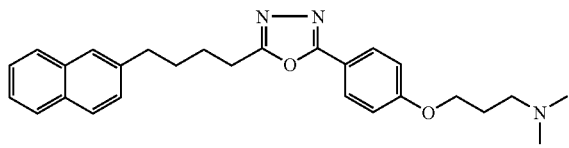

The above compound was prepared in a manner similar to that exemplified for the preparation of Example 19d, from 4-(3-Dimethlaminopropoxy)benzoic acid N-(5-naphthalen-2-ylpentanoyl)hydrazide (0.303 g, 0.68 mmol), triphenylphosphine (0.355 g, 1.4 mmol), triethylamine (0.137 g, 1.4 mmol) and carbon tetrabromide (0.449 g, 1.4 mmol. Purification by normal phase silica gel chromatography (eluted with 9:1 CHCl$_3$:2M NH$_3$ in MeOH) followed by conversion to the HCl salt, as described in Example 5 using the acetyl chloride/EtOH method to generate HCl in situ, afforded the title compound. Crystallization from Et2O: MeOH afforded 0.080 g (7%) of dimethyl-{3-[4-(5-naphthalene-2-ylbutyl)-[1,3,4]oxadiazol-2-yl)phenoxy]propyl}amine.

$^1$H NMR (DMSO-d6) δ 7.82–7.92 (m, 5H), 7.70 (s, 1H), 7.38–7.50 (m, 3H), 7.11 (d, 2H, J=9 Hz), 4.15 (t, 2H, J=6 Hz), 3.21 (t, 2H, J=8 Hz), 2.94–2.99 (m, 2H), 2.76–2.84 (m, 8H), 2.12–2.21 (m, 2H), 1.79–1.81 (m, 4H). R (KBr, cm$^{-1}$) 2936, 1613, 1502, 1256, 1256, 1175. MS (ES$^+$) m/e 430. Mp(° C.)=195.

Example 208

Preparation of 4-{5-[4-(3-Dimethylaminopropoxy)phenyl]-[1,3,4]oxadiazol-2yl}-1-naphthalen-2yl-butan-1-one

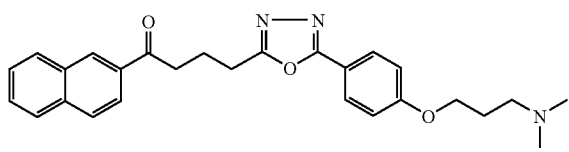

a) 4-(3-Dimethylaminopropoxy)benzoic acid N-(5-naphthalen-2-yl-5-oxopentanoyl)hydrazide

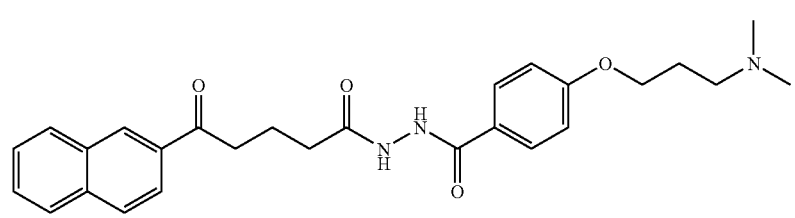

The above compound was prepared in a manner similar to that exemplified for the preparation of Example 204a, from 4-(2-naphthoyl)butyric acid (0.705 g, 2.9 mmol), 1,1'-carbonyldiimidazole (0.472 g, 2.9 mmol) and 4-[(3-dimethylamino)propoxy]-benzoic acid hydrazide (0.691 g, 2.9 mmol). After stirring 6.5 hours at room temperature the reaction mixture was concentrated to an oil. The oil was treated with 25 ml each of EtOAc and H$_2$O. Crystals that formed in this mixture were collected by filtration to afford 0.536 g (40%) of the title compound. The filtrate was concentrated to a solid. Purification by normal phase silica gel radial chromatography (eluted with 9:1 CHCl$_3$:2M NH$_3$ in MeOH) afforded 0.120 g (9%) of the title compound. 0.656 g (49%) of 4-(3-dimethylaminopropoxy)benzoic acid N-(5-naphthalen-2-yl-5-oxopentanoyl)hydrazide was collected.

$^1$H NMR (DMSO-d6) δ10.15 (bs, 1H), 9.84 (bs, 1H), 8.72 (s, 1H), 8.13 (m, 1H), 7.97–8.06 (m, 3H), 7.84 (d, 2H, J=9 Hz), 7.60–7.70 (m, 21), 7.00 (d, 2H, J=9 Hz), 4.06 (t, 2H, J=6 Hz), 3.26–3.32 (m, 2H), 2.30–2.37 (m, 41), 2.11 (s, 6H), 1.93–2.02 (m, 2H), 1.81–1.88 (m, 2H). IR (KBr, cm$^{-1}$) 3422, 3252, 2949, 2792, 1683, 1644, 1604, 1504, 1468, 1251, 1178, 1122, 758. MS (ES$^+$) m/e 462, MS (ES$^-$) m/e 460.

b) 4-{5-[4-(3-Dimethylaminopropoxy)phenyl]-[1,3,4]oxadiazol-2yl}-1-naphthalen-2yl-butan-1-one

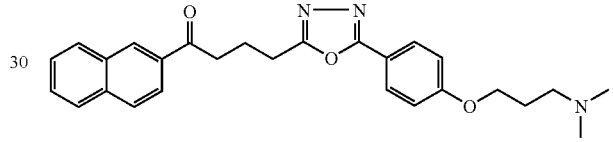

The above compound was prepared in a manner similar to that exemplified for the preparation of Example 19d, from 4-(3-dimethylaminopropoxy)benzoic acid N-(5-naphthalen-2-yl-5-oxopentanoyl)hydrazide (0.334 g, 0.72 mmol), triphenylphosphine (0.380 g, 1.5 mmol), triethylamine (0.146 g, 1.5 mmol) and carbon tetrabromide (0.480 g, 1.5 mmol. Purification by normal phase silica gel chromatography (eluted with 9:1 CHCl$_3$:2M NH$_3$ in MeOH) followed by conversion to the HCl salt, as described in Example 5 using the acetyl chloride/EtOH method to generate HCl in situ, afforded 0.119 g (34%) of 4-{5-[4-(3-dimethylaminopropoxy)-phenyl]-[1,3,4]oxadiazol-2yl}-1-naphthalen-2yl-butan-1-one.

$^1$H NMR (DMSO-d6) δ8.68 (s, 1H), 8.12 (d, 1H, J=7 Hz), 7.97–8.06 (m, 3H), 7.90 (d, 2H, J=9 Hz), 7.60–7.71 (m, 2H), 7.10 (d, 2H, J=9 Hz), 4.15 (t, 2H, J=6 Hz), 3.37 (t, 2H, J=7 Hz), 3.21 (t, 2H, J=8 Hz), 3.05 (t, 2H, J=7 Hz), 2.76 (s, 6H), 2.13–2.24 (m, 4H). IR (CHCl$_3$, cm$^{-1}$) 2969, 1681, 1615, 1501, 1254, 1176. MS (ES$^+$) m/e 444. Mp(° C.)=211.

Example 209

Preparation of (3-{4-[5-Benzofuran-2-ylbutyl)-[1,3,4]oxadiazol-2-yl]phenoxy}-propyl)dimethylamine

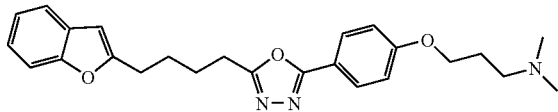

a) 4-Hydroxybenzoic acid N-(5-benzofuran-2-yl pentanoyl)hydrazide

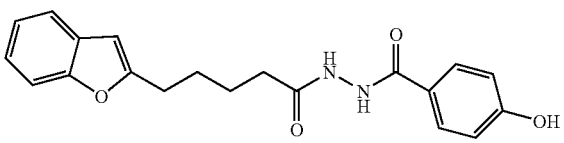

The above compound was prepared in a manner similar to that exemplified for the preparation of Example 19c, from 5-benzofuran-2-yl-pentanoic acid (2.04 g, 9.3 mmol), 2-ethoxy-1-ethoxycarbonyl-1,2-dihydroquinoline (2.31 g, 9.3 mmol) and 4-hydroxybenzoic hydrazide (1.42 g, 9.3 mmol). Purification by normal phase silica gel chromatography (eluted with linear gradient of 2 to 10% 2M $NH_3$ in MeOH:$CH_2Cl_2$) to afford 1.77 g (54%) of 4-hydroxybenzoic acid N-(5-benzofuran-2-yl pentanoyl)hydrazide as a foam.

$^1$H NMR (DMSO-d6) δ10.06 (bs, 1H), 10.00 (bs, 1H), 9.74 (s, 1H), 7.73 (d, 2H, J=9 Hz), 7.45–7.56 (m, 2H), 7.15–7.24 (m, 2H), 6.80 (d, 2H, J=9 Hz), 6.60 (s, 1H), 2.78–2.83 (m, 2H), 2.23 (t, 2H, J=7 Hz), 1.59–1.80 (m, 4H). IR (KBr, cm$^{-1}$) 3238, 2945, 1686, 1643, 608, 1586, 1503, 1455, 1310, 1253, 1173, 752. MS (ES$^+$) m/e 353, MS (ES$^-$) m/e 351.

b) 4-{5-[4-Benzofuran-2-ylbutyl)-[1,3,4]oxadiazol-2-yl]phenol

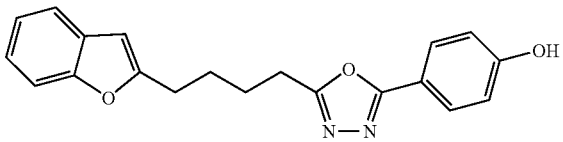

The above compound was prepared in a manner similar to that exemplified for the preparation of Example 19d, from 4-hydroxybenzoic acid N-(5-benzo-furan-2-yl pentanoyl)hydrazide (1.63 g, 4.6 mmol), triphenylphosphine (2.43 g, 9.3 mmol), imidazole (1.01 g, 14.8 mmol) and carbon tetrabromide (3.07 g, 9.3 mmol. Purification by normal phase silica gel chromatography (eluted with 1:1 EtOAc:hexane) followed by crystallization from acetone afforded 0.479 g (31%) of 4-{5-[4-Benzofuran-2-ylbutyl)-[1,3,4]oxadiazol-2-yl]phenol.

$^1$H NMR (DMSO-d6) δ10.26 (bs, 1H), 7.77 (d, 2H, J=8 Hz), 7.45–7.55 (m, 2H), 6.92 (d, 2H, J=8 Hz), 6.61 (s, 1H), 2.96 (t, 2H, J=7 Hz), 2.84 (t, 2H, J=6 Hz), 1.76–1.89 (m, 4H). IR (KBr, cm$^{-1}$) 1616, 1600, 1582, 1447, 1280, 1250, 837, 752, 740. MS (ES$^+$) m/e 335, MS (ES) m/e 333. Anal. Calcd for $C_{20}H_{18}N_2O_3$ C, 71.84; H, 5.43; N, 8.38. Found C, 71.95; H, 5.47; N, 8.41.

c) (3-{4-[5-Benzofuran-2-ylbutyl)-[1,3,4]oxadiazol-2-yl]phenoxy}propyl)dimethylamine

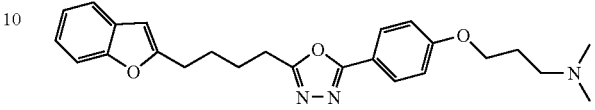

The above compound was prepared in a manner similar to that exemplified for the preparation of Example 19e, from 4-{5-[4-Benzofuran-2-ylbutyl)-[1,3,4]oxadiazol-2-yl]phenol (0.669 g, 2.0 mmol), sodium hydride (0.160 g, 4.0 mmol) and 3-chloro-N,N-dimehtylpropyl amine HCl (0.316 g, 2.0 mmol). Purification by radial chromatography on silica gel (eluted with 9:1 $Et_2O$:2M $NH_3$ in MeOH) followed by conversion to the HCl salt as described in Example 5 using the acetyl chloride/EtOH method to generate HCl in situ afforded 0.132 g (14%) of (3-{4-[5-Benzofuran-2-ylbutyl)-[1,3,4]oxadiazol-2-yl]phenoxy}propyl)dimethylamine as the hydrochloride salt.

$^1$H M (DMSO-d6) δ7.90 (d, 2H, J=9 Hz), 7.40–7.54 (m, 2H), 7.11–7.24 (m, 4H), 6.61 (s, 1H), 4.16 (t, 2H, J=6 Hz), 3.21 (t, 2H, J=8 Hz), 2.98 (t, 2H, J=7 Hz), 2.85 (t, 2H, J=7 Hz), 2.78 (s, 6H), 2.12–2.22 (m, 2H), 1.80–1.99 (m, 4H). IR (CHCl$_3$, cm$^{-1}$) 2967, 1615, 1501, 1474, 1455, 1253, 1176. MS (ES$^+$) m/e 420. Analytical HPLC: 100%. Mp(° C.)=200.

Example 210

Preparation of Dimethyl-(3-{4-[5-(naphthalene-2-ylmethanesulfinylmethyl)-[1,3,4]oxadiazol-2-yl]phenoxy}propyl)amine

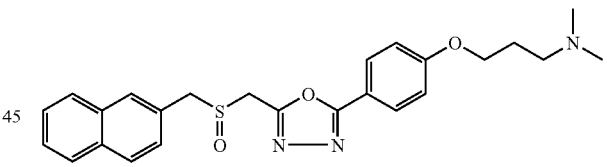

To a solution of dimethyl(3-{4-[5-naphthalen-2-ylmethylsulfanylmethyl)-[1,3,4]oxadiazol-2-yl]phenoxy}propyl)amine (0.187 g, 0.4 mmol) in 4 ml $CH_2Cl_2$ at room temperature was added acetic acid (5.18 g, 86.2 mmol) and m-chloroperbenzoic acid (0.074 g, 0.4 mmol). After stirring thirty minutes the reaction was quenched with $Na_2SO_3$. The mixture was diluted with $H_2O$ then extracted twice with EtOAc. Purification by normal phase silica gel radial chromatography (eluted with 95:5. CHCl$_3$:2M $NH_3$ in MeOH) followed by conversion to the HCl salt as described in Example 5 using the acetyl chloride/EtOH method to generate HCl in situ afforded 0.062 g (30%) of dimethyl-(3-{4-[5-(naphthalene-2-ylmethanesulfinylmethyl)-[1,3,4]oxadiazol-2-yl]phenoxy}propyl)amine.

$^1$H NMR (DMSO-d6) δ7.89–7.97 (m, 6H), 7.53–7.56 (m, 3H), 7.15 (d, 2H, J=9 Hz), 4.60–4.77 (m, 2H), 4.36–4.48 (m, 2H), 4.17 (t, 2H, J=6 Hz), 3.19–3.24 (m, 2H), 2.73 (s, 6H), 2.14–2.23 (m, 2H). IR (KBr, cm$^{-1}$) 3429, 2954, 2601, 2476, 1613, 1498, 1472, 1258, 1177, 1087, 1054, 838, 742. MS (ES$^+$) m/e 450. Mp(° C.)=183.

Example 211

Preparation of Dimethyl(3-{4-[5-(naphthalene-2-ylmethanesulfonylmethyl)-[1,3,4]oxadiazol-2-yl]phenoxy}propyl)amine

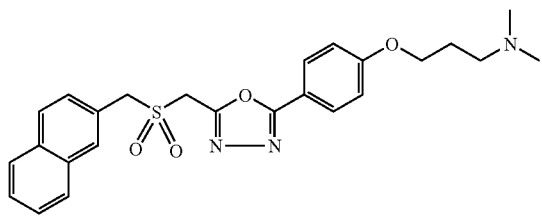

a) 4-[5-(naphthalene-2-ylmethane-sulfonylmethyl)-[1,3,4]oxadiazol-2-yl]phenol

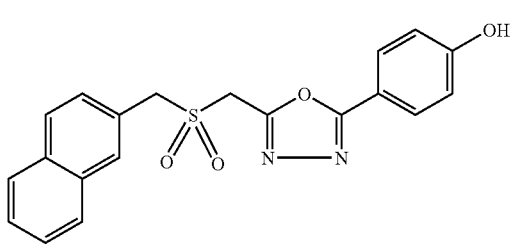

To a solution of 4-[5-(naphthalene-2-ylmethanesulfanylmethyl)-[1,3,4]oxadiazol-2-yl]phenol (0.690 g, 2.0 mmol) in 5 ml DMF at room temperature was added m-chloroperbenzoic acid (1.46 g, 8.5 mmol). The reaction was stirred three hours at room temperature then quenched with aqueous $Na_2SO_3$. The mixture was reduced in volume then diluted with $H_2O$ and extracted with EtOAc. The organic layer was washed with brine, dried over Na2SO4, filtered and concentrated to a solid. Crystallization from $Et_2O$ afforded (0.492 g, 65%) of 4-[5-(naphthalene-2-ylmethanesulfonylmethyl)-[1,3,4]-oxadiazol-2-yl]phenol.

$^1$H NMR (DMSO-d6) δ10.37 (bs, 1H), 7.88–8.01 (m, 4H), 7.77 (d, 2H, J=9 Hz), 7.52–7.59 (m, 3H), 6.94 (d, 2H, J=9 Hz), 5.12 (s, 2H), 4.94 (s, 2H).IR (KBr, cm$^{-1}$) 2986, 1660, 1614, 1598, 1507, 1498, 1443, 1319, 1284, 1241, 1173, 1137, 1120, 839, 751, 484. MS (ES$^+$) m/e 381, MS (ES$^-$) m/e 379.

b) Dimethyl(3-{4-[5-(naphthalene-2-ylmethanesulfonylmethyl)-[1,3,4]oxadiazol-2-yl]phenoxy}propyl)amine

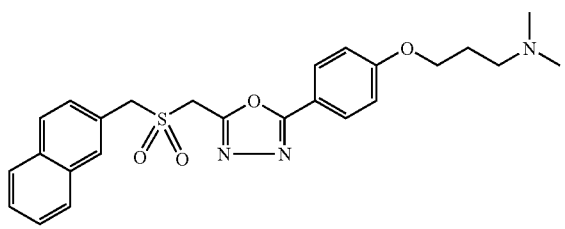

The above compound was prepared in a manner similar to that exemplified for the preparation of Example 21e, from 4-[5-(naphthalene-2-ylmethane-sulfonylmethyl)-[1,3,4]oxadiazol-2-yl]phenol (0.438 g, 1.2 mmol), cesium carbonate (0.750 g, 2.3 mmol), and 3-chloro-N,N-dimethylpropylamine HCl (0.182 g, 1.2 mmol). Purification by normal phase silica gel radial chromatography (eluted with 9:1 CHCl$_3$:2M NH$_3$ in MeOH) followed by treatment with oxailic acid afforded 0.17 mg (3%) of dimethyl(3-{4-[5-(naphthalene-2-ylmethanesulfonylmethyl)-[1,3,4]oxadiazol-2-yl]phenoxy}propyl)amine as the oxalate salt.

$^1$H NMR (DMSO-d6) δ8.01–7.85 (m, 6H), 7.60–7.51 (m, 3H), 7.15–7.20 (m, 2H), 5.14 (s, 2H), 4.93 (s, 2H), 4.10–4.18 (m, 2H), 3.13–3.20 (m, 2H), 2.76 9 (s, 6H), 2.18–2.08 (m, 2H). IR (KBr, cm$^{-1}$) 1614, 1501, 1312, 1260, 1181, 1141, 844, 707, 484. MS (ES$^+$) m/e 466. Mp(° C.)=218.

Example 212

Preparation of Dimethyl(3-{-[5-naphthalen-2-ylsulfanylmethyl)-[1,3,4]oxadiazol-2-yl]phenoxy}propyl)amine

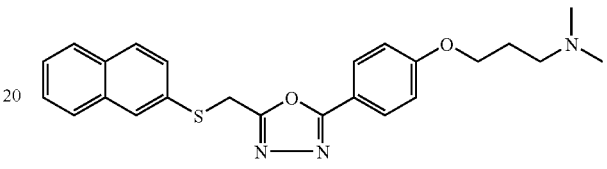

a) 4-hydroxybenzoic acid N-[2-(naphthalene-2-ylsulfanyl)acetyl]hydrazide

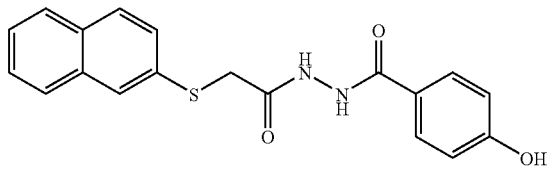

The above compound was prepared in a manner similar to that exemplified for the preparation of Example 26b, from 2-naphthylmercapto acetic acid (1.50 g, 6.9 mmol), 1,1'-carbonyldiimidazole (1.11 g, 6.9 mmol) and 4-hydroxybenzoic hydrazide (1.05 g, 6.9 mmol). Crystallization of the crude material from EtOAc afforded 1.95 g (81%) of 4-hydroxybenzoic acid N-[2-(naphthalene-2-ylsulfanyl)acetyl] hydrazide.

$^1$H NMR DMSO-d6) δ 10.21 (bs, 2H), 10.08 (bs, 1H), 7.95 (s, 1H), 7.85–7.89 (m, 3H), 7.75 (d, 2H, J=9 Hz), 7.42–7.55 (m, 3H), 6.82 (d, 2H, J=9 Hz), 3.89 (s, 2H). IR (KBr, cm$^{-1}$) 3314, 3213, 3006, 1703, 1621, 1605, 1584, 1516, 1282, 1228, 1175, 847, 810, 746, 478. MS (ES$^+$) m/e 353, MS (ES$^-$) m/e 351.

b) 4-[5-naphthalen-2-ylsulfanylmethyl-[1,3,4]oxadiazol-2-yl]phenol

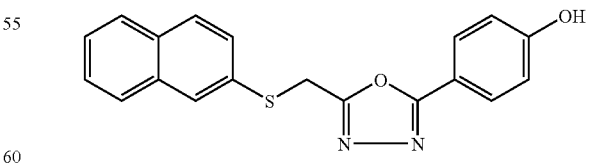

The above compound was prepared in a manner similar to that exemplified for the preparation of Example 19d, from 4-hydroxybenzoic acid N-[2-(naphthalene-2-ylsulfanyl)acetyl]hydrazide (1.81 g, 5.1 mmol), triphenylphosphine (2.69 g, 10.3 mmol), triethylamine (1.87 g, 18.5 mmol) and carbon tetrabromide (3.41 g, 10.3 mmol. Purification by normal phase silica gel chromatography (eluted with 8:1 EtOAc:hexane) followed by crystallization from acetone afforded 0.885 g (51%) of 4-[5-naphthalen-2-ylsulfanylmethyl-[1,3,4]oxadiazol-2-yl]phenol.

$^1$H NMR (DMSO-d6) δ10.29 (bs, 1H), 8.02 (s, 1H), 7.90 (d, 2H, J=9 Hz), 7.83–7.86 (m, 1H), 7.64 (d, 2H, J=9 Hz), 7.48–7.60 (m, 3H), 6.86 (d, 2H, J=9 Hz), 4.62 (s, 2H). IR (KBr, cm$^{-1}$) 1614, 1561, 1497, 1291, 1225, 1175, 1083, 1020, 819, 758, 478. MS (ES$^+$) m/e 335. Anal. Calcd for $C_{19}H_{14}N_2O_2S$ C, 68.25; H, 4.22; N, 8.38. Found C, 68.10; H, 4.02; N, 8.25.

c) Dimethyl(3-{4-[5-naphthalen-2-ylsulfanylmethyl)-[1,3,4]oxadiazol-2-yl]phenoxy}propyl)amine

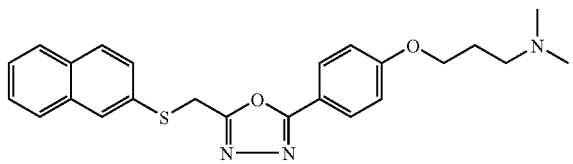

The above compound was prepared in a manner similar to that exemplified for the preparation of Example 19e, from 4-[5-naphthalen-2-ylsulfanylmethyl-[1,3,4]oxadiazol-2-yl] phenol (0.800 g, 2.4 mmol), sodium hydride (0.196 g, 4.9 mmol) and 3-chloro-N,N-dimehtylpropyl amine HCl (0.378 g, 2.4 mmol). Purification by radial chromatography on silica gel (eluted with 9:1 CHCl$_3$:2M NH$_3$ in MeOH) followed by crystallization from Et$_2$O:MeOH afforded 0.204 g (20%) of dimethyl(3-{4-[5-naphthalen-2-ylsulfanylmethyl)-[1,3,4]oxadiazol-2-yl]phenoxy}propyl)amine.

$^1$H NMR (DMSO-d6) δ8.02 (s, 1H), 7.90 (d, 2H, J=9 Hz), 7.83–7.88 (m, 1H), 7.74 (d, 2H, J=9 Hz), 7.49–7.60 (m, 3H), 7.05 (d, 2H, J=9 Hz), 4.87 (s, 2H), 4.06 (t, 2H, J=6 Hz), 2.34 (t, 2H, J=7 Hz), 2.10 (s, 6H), 1.81–1.90 (m, 2H). IR (KBr, cm$^{-1}$) 1607, 1502, 1469, 1299, 1255, 1179, 954, 817, 752, 659, 471. MS (ES$^+$) m/e 420. Anal. Calcd for $C_{24}H_{25}N_3O_2S$ C, 68.71; H, 6.01; N, 10.02. Found C, 68.45; H, 5.87; N, 9.89. Mp(° C.)=106.

Example 213

Preparation of dimethyl(3-{4-[5-naphthalen-2-yloxymethyl)-[1,3,4]oxadiazol-2-yl]phenoxy}propyl)amine

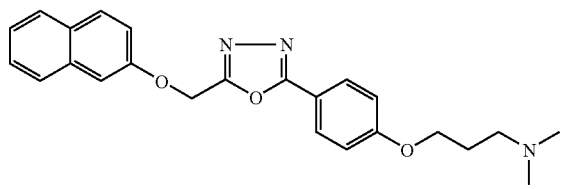

a) 4-(3-dimethylaminopropoxy)benzoic acid N-[2-(naphthalene-2-yloxy)acetyl]hydrazide

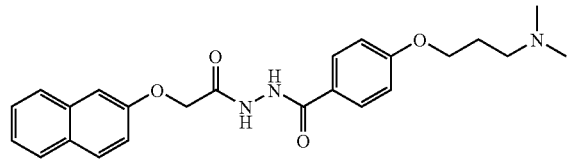

The above compound was prepared in a manner similar to that exemplified for the preparation of Example 204a, from (2-naphthoxy)acetic acid (0.285 g, 1.4 mmol), 1,1'-carbonyldiimidazole (0.228 g, 1.4 mmol) and 4-[(3-dimethylamino)propoxy]-benzoic acid hydrazide (0.334 g, 1.4 mmol). After stirring at room temperature for 24 hours, the insolubles were collected by filtration to afford (0.373 g, 63%) of 4-(3-dimethylaminopropoxy)benzoic acid N-[2-(naphthalene-2-yloxy)acetyl]hydrazide.

$^1$H NMR (DMSO-d6) δ10.26 (bs, 2H), 7.80–7.88 (m, 5H), 7.27–7.51 (m, 4H), 7.01 (d, 2H, J=9 Hz), 4.78 (s, 2H), 4.07 (t, 2H, J=6 Hz), 2.37 (t, 2H, J=7 Hz), 2.15 (s, 6H), 1.82–1.91 (m, 2H). IR (KBr, cm$^{-1}$) 3212, 3058, 2955, 2829, 2777, 1685, 1652, 1607, 1512, 1313, 1260, 1183, 851, 809, 745, 473. MS (ES$^+$) m/e 422, MS (ES$^-$) m/e 420.

b) Dimethyl(3-{4-[5-naphthalen-2-yloxymethyl)-[1, 3,4]oxadiazol-2-yl]phenoxy}propyl)amine

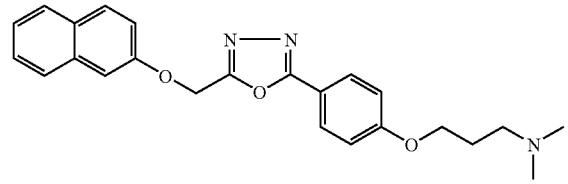

The above compound was prepared in a manner similar to that exemplified for the preparation of Example 19d, from 4-(3-dimethylaminopropoxy)benzoic acid N-[2-(naphthalene-2-yloxy)acetyl]hydrazide (0.322 g, 0.8 mmol), triphenyl-phosphine (0.401 g, 1.5 mmol), triethylamine (0.247 g, 2.4 mmol) and carbon tetra-bromide (0.507 g, 1.5 mmol. Purification by normal phase silica gel chromatography (eluted with 9:1 CH$_2$Cl$_2$:2M NH$_3$ in MeOH) followed by conversion to the HCl salt, as described in Example 5 using the acetyl chloride/EtOH method to generate HCl in situ, afforded 0.136 g (40%) of dmethyl(3-{4-[5-naphthalen-2-yloxymethyl)-[1,3,4]oxadiazol-2-yl]phenoxy}propyl)amine as the hydrochloride salt.

$^1$H NMR (DMSO-d6) δ7.97 9d, 2H, J=9 Hz), 7.82–7.91 (m, 3H), 7.56 (d, 1H, J=3 Hz), 7.50 (t, 1H, J=8 Hz), 7.40 (T, 1H, J=8 Hz), 7.29 (dd, 1H, J=3, 9 Hz), 7.15 (d, 2H, J=9 Hz), 5.59 (s, 2H), 4.17 (t, 2H, J=6 Hz), 3.21 (t, 2H, J=8 Hz), 2.78 (s, 6H), 2.12–2.21 (m 2H). IR (KBr, cm$^{-1}$) 2947, 2555, 2503, 2406, 1618, 1500, 1467, 1393, 1247, 1209, 1178, 1116, 1059, 1012, 957, 839, 805, 749, 472. MS (ES$^+$) m/e 404. Analytical HPLC:100%. Mp(° C.)=Decomposes at 186.

Example 214

Preparation of Dimethyl-(3-{4-{5-(3-phenoxypropoxymethyl)-[1,3,4]oxadiazol-2-yl]phenoxy}propyl)amine

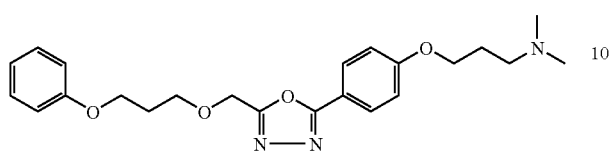

a) 4-hydroxybenzoic acid N-[2-(3-phenoxypropoxy)acetyl]hydrazide

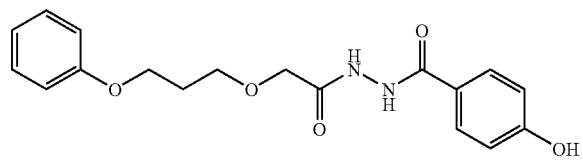

The above compound was prepared in a manner similar to that exemplified for the preparation of Example 19c, from (3-phenoxypropoxy)acetic acid (2.70 g, 12.8 mmol), 2-ethoxy-1-ethoxycarbonyl-1,2-dihydroquinoline (3.18 g, 12.8 mmol) and 4-hydroxybenzoic hydrazide (1.95 g, 12.8 mmol). The resultant crystalline material that formed in the reaction mixture was collected by filtration to afford 2.42 g (55%) of 4-hydroxybenzoic acid N-[2-(3-phenoxypropoxy)acetyl]hydrazide.

$^1$H NMR (DMSO-d6) δ10.06 (bs, 2H), 9.73 (bs, 1H), 7.74 (d, 2H, J=9 Hz), 7.24–7.31 (m, 2H), 6.89–6.95 (m, 3H), 6.81 (d, 2H, J=9 Hz), 4.08 (t, 2H, J=6 Hz), 4.02 (s, 2H), 3.67 (t, 2H, J=6 Hz), 1.98–2.06 (m, 2H). IR (KBr, cm$^{-1}$) 3219, 1686, 1630, 1609, 1498, 1443, 1279, 1242, 1173, 1134, 755. MS (ES$^-$) m/e 343. Anal. Calcd for $C_{18}H_{20}N_2O_5$ C, 62.78; H, 5.85; N, 8.13. Found C, 62.68; H, 5.74; N, 8.01.

b) 4-[-5-(3-Phenoxypropoxymethyl)-[1,3,4]oxadiazol-2-yl]phenol

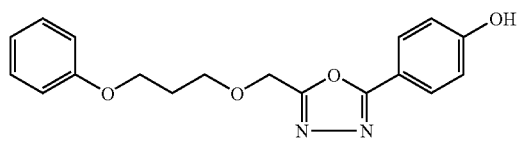

The above compound was prepared in a manner similar to that exemplified for the preparation of Example 19d, from of 4-hydroxybenzoic acid N-[2-(3-phenoxypropoxy)acetyl]hydrazide (2.07 g, 6.0 mmol), triphenylphosphine (3.15 g, 12.0 mmol), triethylamine (2.19 g, 21.6 mmol) and carbon tetrabromide (3.99 g, 12.0 mmol). Purification by chromatography on silica gel (eluted with 1:1 EtOAc:hexane) afforded 1.65 g (85%) of 4-[-5-(3-Phenoxypropoxymethyl)-[1,3,4]oxadiazol-2-yl]phenol as a solid.

$^1$H NMR (DMSO-d6) δ10.32 (bs, 1H), 7.80 (d, 2H, J=9 Hz), 7.21–7.28 (m, 2H), 6.88–6.96 (m, 5H), 4.77 (s, 2H), 4.02 (t, 2H, J=6 Hz), 3.70 (t, 2H, J=6 Hz), 1.95–2.04 (m, 2H). IR (Br, cm$^{-1}$) 3101, 2958, 2871, 1609, 1497, 1470, 1285, 1240, 1172, 1087, 757, 737. MS (ES$^+$) m/e 327, MS (ES$^-$) m/e 325. Anal. Calcd for $C_{18}H_{18}N_2O_4$ C, 66.25; H, 5.56; N, 8.58. Found C, 66.28; H, 5.48; N, 8.54.

c) Dimethyl-(3-{4-{5-(3-phenoxypropoxymethyl)-[1,3,4]oxadiazol-2-yl]phenoxy}propyl)amine

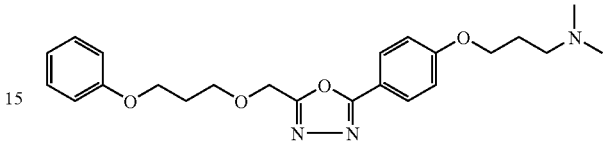

The above compound was prepared in a manner similar to that exemplified for the preparation of Example 21e, from 4-[-5-(3-Phenoxypropoxymethyl)-[1,3,4]oxadiazol-2-yl]phenol (1.42 g, 4.4 mmol), cesium carbonate (2.84 g, 8.7 mmol), and 3-chloro-N,N-dimethylpropylamine HCl (0.688 g, 4.4 mmol). Purification by radial chromatography on silica gel (eluted with a linear gradient of 2 to 5% 2M NH$_3$ in MeOH:CHCl$_3$) followed by conversion to the HCl salt, as described in Example 5 using the acetyl chloride/EtOH method to generate HCl in situ, afforded 0.311 g (16%) of dimethyl-(3-{4-{5-(3-phenoxypropoxymethyl)-[1,3,4]oxadiazol-2-yl]phenoxy}propyl)amine as the hydrochloride salt.

$^1$H NMR (DMSO-d6) δ7.91 (d, 2H, J=9 Hz), 7.21–7.27 (m, 2H), 7.13 (d, 2H, J=9 Hz), 6.88–6.92 (m, 3H), 4.79 (s, 2H), 4.17 (t, 2H, J=6 Hz), 4.03 (t, 2H, J=6 Hz), 3.72 (t, 2H, J=6 Hz), 3.21 (t, 2H, J=8 Hz), 2.78 (s, 6H), 2.14–2.24 (m, 2H), 1.96–2.04 (m, 2H). IR (KBr, cm$^{-1}$) 2474, 1617, 1602, 1499, 1472, 1257, 1171, 1085, 1052, 751. MS (ES$^+$) m/e 412. Mp(° C.)=132.

Example 215

Preparation of Dimethyl-[3-(4-{5-[2-(2-phenxoyethoxy)ethyl]-[1,3,4]oxadiazol-2-yl}phenoxy)propyl]amine

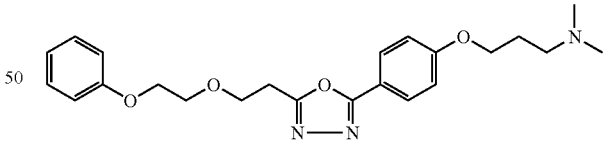

a) 4-Hydroxybenzoic acid N'-[3-(2-phenoxyethoxy)propionyl]hydrazide

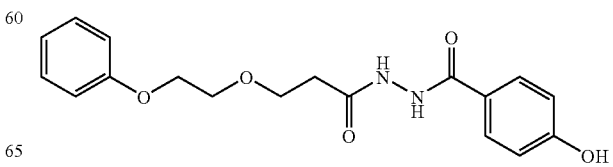

The above compound was prepared in a manner similar to that exemplified for the preparation of Example 19c, from 3-(2-phenoxyethoxy)propionic acid (6.35 g, 30.2 mmol), 2-ethoxy-1-ethoxycarbonyl-1,2-dihydroquinoline (7.47 g, 30.2 mmol) and 4-hydroxybenzoic hydrazide (4.64 g, 30.2 mmol). Purification by chromatography on silica gel (eluted with a linear gradient of 2 to 5% 2M NH$_3$ in MeOH:CHCl$_3$) afforded 4.73 g (70%) of 4-hydroxybenzoic acid N'-[3-(2-phenoxyethoxy)propionyl]hydrazide as a foam.

$^1$H NMR (DMSO-d6) δ10.06 (bs, 2H), 9.82 (bs, 1H), 7.73 (d, 2H, J=9 Hz), 7.23–7.31 (m, 2H), 6.87–6.96 (m, 3H), 6.80 (d, 2H, J=8 Hz), 4.07 (t, 2H, J=5 Hz), 3.64–3.75 (m, 4H), 2.41–2.54 (m, 2H). IR (CHCl$_3$, cm$^{-1}$) 3266, 3012, 2930, 2878, 1688, 1646, 1609, 1497, 1456, 1279, 1245, 1225, 1173, 1122, 849. MS (ES) m/e 345, MS (ES$^-$) m/e 343.

b) 4-{5-[2-(2-phenoxyethoxy)ethyl]-[1,3,4]oxadiazol-2-yl}phenol

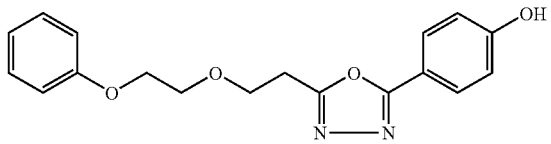

The above compound was prepared in a manner similar to that exemplified for the preparation of Example 19d, from of 4-hydroxybenzoic acid N'-[3-(2-phenoxyethoxy)propionyl]hydrazide (4.71 g, 13.7 mmol), triphenylphosphine (7.17 g, 27.4 mmol), triethylamine (4.98 g, 49.2 mmol) and carbon tetrabromide (9.07 g, 27.4 mmol). Purification by chromatography on silica gel (eluted with 4:1 EtOAc:hexane) afforded 4.40 g (99%) of 4-{5-[2-(2-phenoxyethoxy)ethyl]-[1,3,4]oxadiazol-2-yl}phenol as an oil. Product co-eluted with triphenylphosphine.

$^1$H NM (DMSO-d6) δ10.25 (bs, 1H), 7.78 (d, 2H, J=9 Hz), 7.21–7.27 (m, 2H), 6.88–6.94 (m, 5H), 4.06–4.08 (m, 21), 3.91 (t, 2H, J=6 Hz), 3.76–3.79 (m, 2H), 3.18 (t, 2H, J=6 Hz). IR (CHCl$_3$, cm$^{-1}$) 3006, 1732, 1615, 1600, 1499, 1438, 1375, 1247, 1171, 1121, 1046. MS (ES$^+$) m/e 327, MS (ES$^-$) m/e 325.

c) Dimethyl-[3-(4-{5-[2-(2-phenxoyethoxy)ethyl]-[1,3,4]oxadiazol-2-yl}phenoxy)propyl]amine

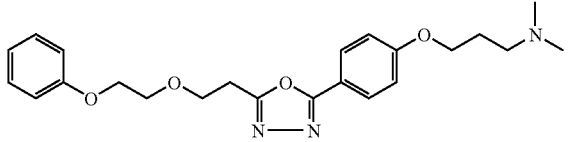

The above compound was prepared in a manner similar to that exemplified for the preparation of Example 21e, from 4-{5-[2-(2-phenoxyethoxy)ethyl]-[1,3,4]oxadiazol-2-yl}phenol (2.02 g, 6.1 mmol), cesium carbonate (3.98 g, 12.2 mmol), and 3-chloro-N,N-dimethylpropylamine HCl (0.966 g, 6.1 mmol). Purification by chromatography on silica gel (eluted with a linear gradient of 2 to 10% 2M NH$_3$ in MeOH:CHCl$_3$) followed by conversion to the oxalate salt afforded 0.053 g (2%) of dimethyl-[3-(4-{5-[2-(2-phenxoyethoxy)ethyl]-[1,3,4]oxadiazol-2-yl}phenoxy)propyl]amine as the oxalate salt.

$^1$H NMR (DMSO-d6) δ7.90 (d, 2H, J=9 Hz), 7.22–7.27 (m, 2H), 7.12 (d, 2H, J=9 Hz), 6.88–6.93 (m, 3H), 4.14 (t, 2H, J=6 Hz), 4.05–4.09 (m, 2H), 3.92 (t, 2H, J=6 Hz), 3.77–3.80 (m, 2H), 3.14–3.22 (m, 4H), 2.76 (s, 6H), 2.08–2.17 (m, 2H). IR (KBr, cm$^{-1}$) 1725, 1614, 1256, 1174, 1046, 840. MS (ES$^+$) m/e 412, Mp (° C.)=116–118.

Example 216

Preparation of {3-[-4-(5-Biphenyl-2-yl-[1,3,4]oxadiazol-2-yl)phenoxy]propyl}dimethylamine

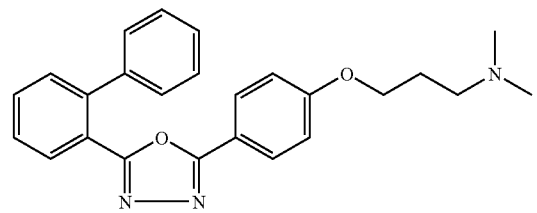

a) 4-Hydroxybenzoic acid N'-(biphenyl-2-caronyl)hydrazide

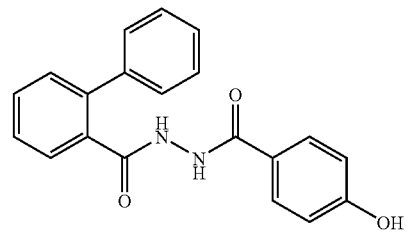

The above compound was prepared in a manner similar to that exemplified for the preparation of Example 19c, from 2-biphenylcarboxylic acid (2.42 g, 12.2 mmol), 2-ethoxy-1-ethoxycarbonyl-1,2-dihydroquinoline (3.02 g, 12.2 mmol) and 4-hydroxybenzoic hydrazide (1.86 g, 12.2 mmol). Purification by chromatography on silica gel (eluted with a linear gradient of 2 to 10% 2M NH$_3$ in MeOH:CHCl$_3$) afforded 0.730 g (18%) of 4-hydroxybenzoic acid N'-(biphenyl-2-caronyl)hydrazide as a solid.

$^1$H NMR (DMSO-d6) δ 10.26 (bs, 1H), 10.20 (bs, 1H), 10.08 (bs, 1H), 7.78 (d, 2H, J=8 Hz), 7.30–7.62 (m, 9H), 6.81 (d, 2H, J=9 Hz). MS (ES$^+$) m/e 333, MS (ES$^-$) m/e 331.

b) 4-(5-biphenyl-2-yl[1,3,4]oxadiazol-2-yl)phenol

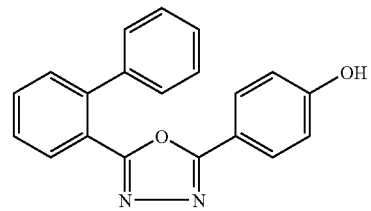

The above compound was prepared in a manner similar to that exemplified for the preparation of Example 19d, from of 4-hydroxybenzoic acid N'-(biphenyl-2-caronyl)hydrazide (0.72 g, 2.2 mmol), triphenylphosphine (1.14 g, 4.3 mmol), triethylamine (0.44 g, 4.3 mmol) and carbon tetrabromide (1.44 g, 4.3 mmol). Purification by radial chromatography on silica gel (eluted with 4:1 EtOAc:hexane) afforded the crude product plus an impurity. The material was triterated in Et₂O then filtered. The insoluble material was collected to afford 0.288 g (42%) of 4-(5-biphenyl-2-yl[1,3,4]oxadiazol-2-yl)phenol.

$^1$H NMR (DMSO-d6) δ10.34 (bs, 1H), 8.05 (d, 1H, J=8 Hz), 7.69–7.74 (m, 1H), 7.59–7.65 (m, 1H), 7.52–7.55 (m, 1H), 7.39–7.44 (m, 5H), 7.28–7.33 (m, 2H), 6.83 (d, 2H, J=9 Hz). MS (ES⁺) m/e 315, MS (ES⁻) m/e 313 c) {3-[-4-(5-Biphenyl-2-yl-[1,3,4]oxadiazol-2-yl)phenoxy]propyl}dimethylamine

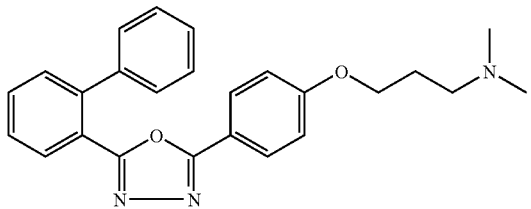

The above compound was prepared in a manner similar to that exemplified for the preparation of Example 19e, from 4-(5-biphenyl-2-yl[1,3,4]oxadiazol-2-yl)phenol (0.233 g, 0.7 mmol), sodium hydride (0.065 g, 1.6 mmol) and 3-chloro-N,N-dimehtylpropyl amine HCl (0.129 g, 8.2 mmol). Purification by radial chromatography on silica gel (eluted with 9:1 CHCl₃: 2M NH₃ in MeOH) followed by conversion to the HCl salt, as described in Example 5 using the acetyl chloride/EtOH method to generate HCl in sit. Crystallization from MeOH:Et₂O afforded 0.058 g (18%) of {3-[-4-(5-Biphenyl-2-yl-[1,3,4]oxadiazol-2-yl)phenoxy]propyl}dimethylamine as the hydrochloride salt.

$^1$H NMR (DMSO-d6) δ10.21 (bs, 1H), 8.06–8.09 (m, 1H), 7.70–7.75 (m, 1H), 7.60–7.66 (m, 1H), 7.51–7.57 (m, 3H), 7.40–7.44 (m, 3H), 7.29–7.33 (m, 2H), 7.05 (d, 2H, J=9 Hz), 4.13 (t, 2H, J=6 Hz), 3.19 (t, 2H, 8 Hz), 2.76 (s, 6H), 2.09–2.17 (m, 2H). IR (KBr, cm⁻¹) 1612, 1498, 1477, 1254, 1178, 1045, 836, 744. MS (ES⁺) m/e 400. Analytical HPLC: 100%. Mp=(° C.)=177.

Example 217

Preparation of {3-[-4-(5-Biphenyl-3-yl-[1,3,4]oxadiazol-2-yl)phenoxy]propyl}dimethylamine

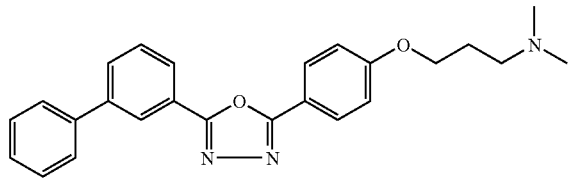

a) 4-Hydroxybenzoic acid N'-(biphenyl-3-caronyl)hydrazide

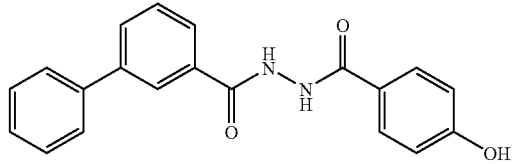

To a suspension of biphenyl-3-carboxylic acid (1.00 g, 5.0 mmol) in 25 ml CH₂Cl₂ at room temperature was added oxalyl chloride (1.92 g, 15.1 mmol) followed by three drops of DMF. The reaction was stirred at room temperature for 1.8 hours then heated at 40 C for four hours. The reaction was then concentrated to an oil. This material was taken up into 41 ml CH₃CN treated with triethylamine (0.510 g, 5.0 mmol), 4-hydroxybenzoic hydrazide (0.786 g, 5.0 mmol) and dimethylamine pyridine (0.062 g, 0.5 mmol). The reaction mixture was heated at 60 C for two days then overnight at room temperature. The suspension was concentrated to a solid. The solid was treated with EtOAc and 5N HCl. The resultant suspension was filtered. The phases from the filtrate were separated. The organic phase was washed with 5N HCl, brine, dried over Na₂SO₄, filtered, concentrated to a semi-solid material. Triteration in CHCl₃ followed by filtration afforded the title compound along with an impurity. This material was taken on to the next step.

MS (ES⁺) m/e 333, MS (ES⁻) m/e 331.

b) 4-(5-biphenyl-3-yl[1,3,4]oxadiazol-2-yl)phenol

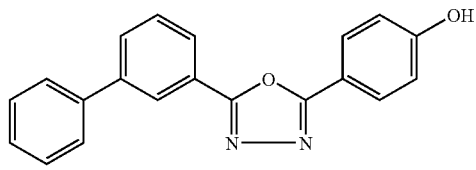

The above compound was prepared in a manner similar to that exemplified for the preparation of Example 19d, from of 4-Hydroxybenzoic acid N'-(biphenyl-3-caronyl)hydrazide (0.604 g, 1.8 mmol), triphenylphosphine (0.953 g, 3.6 mmol), triethylamine (0.368 g, 3.6 mmol) and carbon tetrabromide (1.205 g, 3.6 mmol). Purification by radial chromatography on silica gel (eluted with EtOAc) afforded 0.379 g (66%) of 4-(5-biphenyl-3-yl[1,3,4]oxadiazol-2-yl)phenol.

$^1$H NMR (DMSO-d6) δ10.34 (s, 1H), 8.33 (s, 1H), 8.10 (d, 1H, J=8 Hz), 8.01 (d, 2H, J=8 Hz), 7.93 (d, 1H, J=8 Hz), 7.69–7.80 (m, 3H), 7.43–7.56 (m, 3H), 6.98 (d, 2H, J=9 Hz). IR (KBr, cm⁻¹) 1735, 1612, 1594, 1495, 1439, 1283, 1240, 1203, 1169, 742, 719, 695. MS (ES⁺) m/e 315, MS (ES⁻) m/e 313.

c) {3-[-4-(5-Biphenyl-2-yl-[1,3,4]oxadiazol-3-yl)phenoxy]propyl}dimethylamine

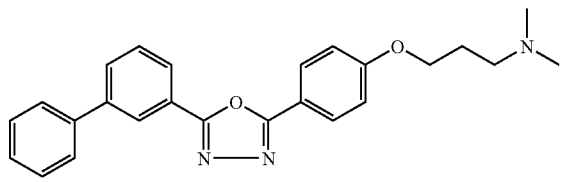

The above compound was prepared in a manner similar to that exemplified for the preparation of Example 19e, from 4-(5-biphenyl-3-yl[1,3,4]oxadiazol-2-yl)phenol (0.0.362 g, 1.2 mmol), sodium hydride (0.101 g, 2.5 mmol) and 3-chloro-N,N-dimehtylpropyl amine HCl (0.200 g, 1.3 mmol). Purification by radial chromatography on silica gel (eluted with 9:1 $CHCl_3$: 2M $NH_3$ in MeOH) followed by crystallization from MeOH:$Et_2O$ afforded 0.083 g (18%) of {3-[-4-(5-Biphenyl-2-yl-[1,3,4]oxadiazol-3-yl)phenoxy]propyl}dimethylamine.

$^1$H NMR (DMSO-d6) δ8.35 (s, 1H), 8.09–8.13 (m, 3H), 7.93 (d, 1H, J=8 Hz), 7.79 (d, 2H, J=8 Hz), 7.72 (t, 1H, J=8 Hz), 7.52–7.57 (m, 2H), 7.43–7.48 (m, 1H), 7.16 (d, 2H, J=9 Hz), 4.12 (t, 2H, J=6 Hz), 2.38 (t, 2H, J=7 Hz), 2.14 (s, 6H), 1.84–1.93 (m, 2H). IR (KBr, $cm^{-1}$) 2755, 1611, 1497, 1257, 1176, 830, 739, 716. MS ($ES^+$) m/e 400. Analytical HPLC: 100%. Mp(° C.)=111.

Example 218

Preparation of Dimethyl-[3-(4-{5-[2-(2-phenoxyethyl)cyclopropylmethyl]-[1,3,4]-oxadiazol-2-yl}phenoxy)propyl]amine

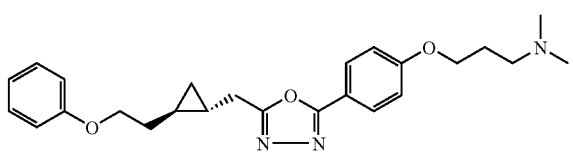

a)
trans-(2-Methoxycarbonylmethylcyclopropyl)acetic acid methyl ester

To a suspension of zinc-copper couple (44.82 g (0.35 mol) in 32 ml $Et_2O$ undergoing sonication was added a solution of trans-3-hexene-1,6-dioic acid methyl ester (29.93 g, 0.17 mol) and methyl iodide (65.18 g (0.24 mol) at a rate of 0.5 ml per ten minutes for the 90 minutes then 1.0 ml per ten minutes for the next 1.5 hours of the addition. At this point the addition was stopped and sonication continued for 1.5 hours. After this the remaining material was added at a rate of 2.0 ml per ten minutes for the remainder of the addition. The reaction was sonicated overnight. The reaction mixture solidified overnight. The mixture was treated with 800 ml EtOAc then heated to 60 C to breakup the solid material. This mixture was treated with filter agent then filtered. The filtrate was concentrated to an oil. The oil was dissolved into $Et_2O$ then washed with 100 ml 10% aqueous HCl, brine, dried over $Na_2SO_4$, filtered concentrated to an oil. Distillation at 115–120 C afforded 9.95 g of a 1:1 mixture of trans-3-hexene-1,6-dioic acid methyl ester and trans-(2-Methoxycarbonylmethylcyclopropyl)acetic acid methyl ester.

b)
trans-(2-Methoxycarbonylmethylcyclopropyl)acetic acid

To a biphasic solution of trans-(2-methoxycarbonylmethylcyclopropyl)acetic acid methyl ester (10.95 g, 58.8 mmol) in 200 ml aqueous potassium phosphate mono basic (2.76 g) was added porcine liver esterase (123 mg, approximately 5,060 units). Next, 58.8 ml 1N LiOH solution was added in portions, maintaining pH between 7.0 and 7.5, over a two-hour period. The reaction was stirred overnight at room temperature. Next, filter aid was added and the reaction was filtered. The filtrate was extracted twice with $Et_2O$ and the organic layer was discarded. The aqueous phase was acidified with 1N HCl then extracted twice with $Et_2O$. The combined organic phases were dried over Na2SO4, filtered, concentrated to afford 6.65 g of a 3:2 ratio of trans-hex-3-enedioic acid monomethyl ester: trans-(2-methoxycarbonylmethylcyclopropyl)acetic acid.

$^1$H NMR of title compound (DMSO-d6) δ3.57 (s, 3H), 2.01–2.33 (m, 4H), 0.76–0.82 (m, 2H), 0.32–0.38 (m, 2H). MS ($ES^-$) m/e 171.

c) trans-[2-(2-hydroxyethyl)cyclopropyl]acetic acid methyl ester

The above compound was prepared in a manner similar to that exemplified for the preparation of Example 22a, from 3:2 ratio of trans-hex-3-enedioic acid monomethyl ester: trans-(2-methoxycarbonylmethylcyclopropyl)acetic acid (8.49 g) to afford 1.47 g mixture of 6-hydroxy-trans-hex-3-enoic acid methyl ester and trans-[2-(2-hydroxyethyl)cyclopropyl]acetic acid methyl ester.

d) trans-[2-(2-phenoxyethyl)cyclopropyl]acetic acid methyl ester

To a mixture of trans-6-hydroxy-hex-3-enoic acid methyl ester and trans-[2-(2-hydroxyethyl)cyclopropyl]acetic acid methyl ester (1.47 g), phenol (0.962 g, 10.2 mmol) and triphenylphosphine (2.68 g, 10.2 mmol) in 28 ml THF at 0 C was added dropwise diisopropylazodicarboxlate (2.07 g, 10.2 mmol). The reaction was stirred overnight at room temperature. The mixture was concentrated to an oil. The oil was diluted with 50 ml EtOAc then washed twice with 1N NaOH, once with brine, dried over Na2SO4, filtered, concentrated to an oil. Purification by chromatography on silica gel (eluted with 25%

EtOAc:hexane) followed by a second purification using chromasil (eluted with linear gradient of 30 to 60% $CH_2Cl_2$:hexane) afforded a 3:2 ratio of trans-[2-(2-phenoxyethyl)cyclopropyl]acetic acid methyl ester and 6-phenoxy-trans-hex-3-enoic acid methyl ester.

The mixture of trans-[2-(2-phenoxyethyl)cyclopropyl]acetic acid methyl ester and 6-phenoxy-trans-hex-3-enoic acid methyl ester (0.954 g) in 3 ml MeOH at −78 C was treated with ozone until a blue haze persisted in the reaction mixture. Nitrogen was then bubbled through the reaction mixture. Next, dimethyl sulfide (0.354 g, 5.7 mmol) was added and stirring continued until the cooling bath warmed to room temperature, approximately 2.5 hours. The solution was then concentrated to an oil.

The oil was dissolved into 25 ml acetone then Jones Reagent (2.5 ml, 8.2 mmol) was added. After stirring at room temperature for five minutes the reaction was quenched with aqueous sodium thiosulfate was added. The product was extracted with $Et_2O$ (2×50 ml), organic phases combined, washed with saturated aqueous sodium bicarbonate (2×50 ml), brine, dried over $Na_2SO_4$, filtered, concentrated to an oil. Purification by radial chromatography on silica gel (eluted with 3:1 hexane:$Et_2O$) afforded 0.395 g of trans-[2-(2-phenoxyethyl)cyclopropyl]acetic acid methyl ester as an oil.

$^1$H NMR (DMSO-d6) δ7.24–7.30 (m, 2H), 6.88–6.93 (m, 3H), 3.99 (t, 2H, J=7 Hz), 3.52 (s, 31), 2.15–2.35 (m, 2H), 1.54–1.73 (m, 2H), 0.66–0.84 (m, 2H), 0.31–0.41 (m, 2H). MS (TOF) m/e 170.

e) trans-[2-(2-phenxoyethyl)cyclopropyl]acetic acid

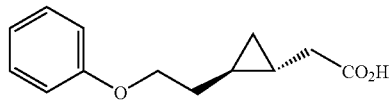

The above compound was prepared in a manner similar to that exemplified for the preparation of Example 1a, from trans[2-(2-phenoxyethyl)cyclopropyl]acetic acid methyl ester (0.371 g, 1.6 mmol) and lithium hydroxide (0.114 g, 4.8 mmol) afforded 0.291 g of trans-[2-(2-phenoxyethyl)cyclopropyl]acetic acid as an oil that crystallizes out.

$^1$H NMR (DMSO-d6) δ7.24–7.30 (m, 2H), 6.88–6.95 (m, 3H), 4.01 (t, 2H, J=7 Hz), 2.06–2.24 (m, 2H), 1.59–1.68 (m, 2H), 0.75–0.84 (m, 1H), 0.63–0.71 (m, 1H), 0.29–0.39 (m, 2H). IR (KBr, cm$^{-1}$) 3038, 2999, 2947, 2928, 1713, 1601, 1499, 1254, 1244, 1225, 1210, 1038, 754, 692. MS (ES$^-$) m/e 219. Anal. Calcd for $C_{13}H_{16}O_3$ C, 70.89; H, 7.32. Found C, 70.75; H, 7.50.

f) 4-(3-Dimethylaminopropoxy)benzoic acid N'-trans-{2-[2-(2-phenoxyethyl)cyclopropyl]acetyl}hydrazide

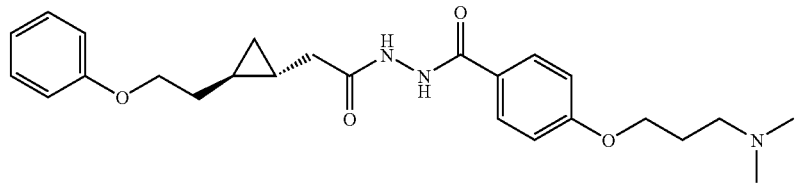

The above compound was prepared in a manner similar to that exemplified for the preparation of Example 19c, from of trans-[2-(2-phenxoyethyl)cyclopropyl]acetic acid (0.274 g, 1.2 mmol), 2-ethoxy-1-ethoxycarbonyl-1,2-dihydroquinoline (0.308 g, 1.2 mmol) and 4-hydroxybenzoic hydrazide (0.295 g, 1.2 mmol). Purification by radial chromatography on silica gel (eluted with 95:5 $CHCl_3$:2M $NH_3$ in MeOH: $CHCl_3$) afforded 0.055 g (10%) of 4-(3-dimethylaminopropoxy)benzoic acid N'-trans-{2-[2-(2-phenoxyethyl)cyclopropyl]acetyl}hydrazide.

g) Dimethyl-[3-(4-{5-[2-(2-phenoxyethyl)cyclopropylmethyl]-[1,3,4]-oxadiazol-2-yl}phenoxy)propyl]amine

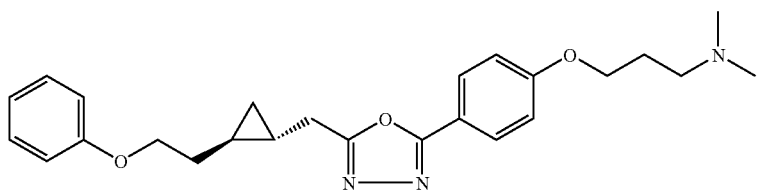

The above compound was prepared in a manner similar to that exemplified for the preparation of Example 19d, from 4-(3-dimethylaminopropoxy)benzoic acid N'-trans-{2-[2-(2-phenoxyethyl)cyclopropyl]acetyl}hydrazide (0.055 g, 0.13 mmol), triphenylphosphine (0.066 g, 0.25 mmol), triethylamine (0.025 g, 0.25 mmol) and carbon tetrabromide (0.083 g, 0.25 mmol). Purification by radial chromatography on silica gel (eluted with 9:1 CHCl$_3$:2M NH$_3$ in MeOH) followed by formation of the oxalate salt afforded 0.061 (95%) g of dimethyl-trans-[3-(4-{5-[2-(2-phenoxyethyl)cyclo propyl methyl]-[1,3,4]-oxadiazol-2-yl}phenoxy)propyl] amine as the oxalate salt.

$^1$H NMR (DMSO-d6) δ 7.90 (d, 2H, J=9 Hz), 7.18–7.23 (m, 21), 7.10 (d, 2H, J=9 Hz), 6.81–6.90 (m, 31), 4.13 (t, 2H, J=6 Hz), 3.94–3.99 (m, 2H), 3.13–3.18 (m, 2H), 2.94–3.01 (m, 1H), 2.73–2.81 (m, 7H), 2.09–2.14 (m, 2H), 1.73–1.79 (m, 1H), 1.51–1.61 (m, 1H), 0.96–1.02 (m, 1H), 0.83–0.93 (m, 1H), 0.45–0.57 (m, 2H). IR (KBr, cm$^{-1}$) 3042, 2937, 2869, 1720, 1615, 1501, 1472, 1257, 1176, 476. MS (ES$^+$) m/e 421. Anal. Calcd for C$_{25}$H$_{31}$N$_3$O$_3$ C$_2$H$_2$O$_4$ C, 63.39; H, 6.50; N, 8.21. Found C, 63.35; H, 6.55; N, 8.22. Mp(° C.)=141.

Example 219

Preparation of 1-{3-[4-(5-Phenylsulfanylmethyl-[1,3,4]oxadiazol-2-yl)phenoxy]propyl}piperidine

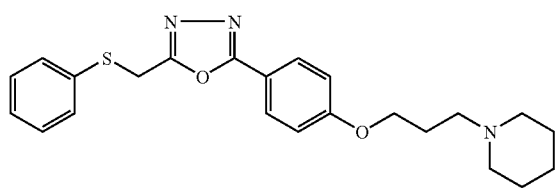

a) Acetic acid 5-(4-hydroxyphenyl)-[1,3,4]oxadiazol-2-ylmethyl ester

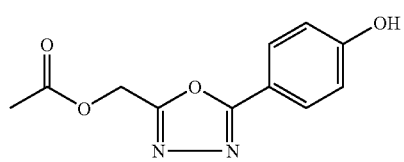

To 4-hydroxybenzoic hydrazide (4.39 g, 28.9 mmole) in 145 ml CH$_3$CN and 35 ml THF at room temperature was added a solution of acetoxyacetyl chloride (3.59 g, 26.3 mmol) in 30 ml CH$_3$CN over a five-minute period. The suspension was then stirred at room temperature for two hours. To this suspension was added triethylamine (6.38 g, 63.0 mmol), triphenylphosphine (8.26 g, 31.5 mmol) and carbon tetrabromide (10.45 g, 31.5 mmol). The resultant red solution was stirred 16 hours at room temperature. The mixture was concentrated to an oil. The oil was diluted with 250 ml EtOAc then washed with 0.1 N HCl (2×250 ml), brine (250 ml), dried over Na$_2$SO$_4$, filtered, concentrated to afford a red oil. Purification from chromatography on silica gel (eluted with EtOAc) afforded a solid. Crystallization from Et$_2$O afforded 1.99 g of the title compound. The filtrate from the crystallization was concentrated to afford an additional 1.06 g of the title compound. A total of 3.05 g (50%) of acetic acid 5-(4-hydroxyphenyl)-[1,3,4]oxadiazol-2-ylmethyl ester was isolated.

$^1$H NMR (DMSO-d6) δ10.33 (bs, 1H), 7.81 (d, 2H, J=9 Hz), 6.93 (d, 2H, J=9 Hz), 5.33 (s, 2H), 2.12 (s, 3H). IR (KBr, cm$^{-1}$) 3147, 1757, 1606, 1590, 1512, 1443, 1411, 1369, 1285, 1211, 1181, 1094, 1066, 968, 846, 741, 626, 521. MS (ES$^+$) m/e 235, MS (ES$^-$) m/e 233.

b) 5-[4-(3-Piperidin-1-yl-propoxy)phenyl]-[1,3,4]oxadiazol-2-yl}methanol

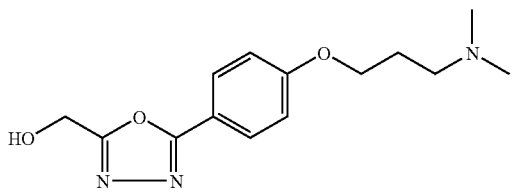

To acetic acid 5-(4-hydroxyphenyl)-[1,3,4]oxadiazol-2-ylmethyl ester (4.96 g, 21.2 mmol), triphenyl phosphine (8.33 g, 31.8 mmol) and 3-N-piperidino-1-propanol (4.79 g, 31.8 mmol) in 65 ml THF at 0 C was added diisopropylazodicarboxylate 6.42 g, 31.8 mmol) over a ten minute period. The resultant orange solution was stirred at room temperature for six hours. Next, 50 ml 1N NaOH was added and the reaction was stirred thirty minutes at room temperature. The reaction mixture was then extracted with EtOAc (2×100 ml). The combined organic layers were washed with brine, dried over Na$_2$SO$_4$, filtered and concentrated to an oil. Purification by chromatography on silica gel (eluted with a step gradient of 5 L CH$_2$Cl$_2$, 5 L 5% 2M NH$_3$ IN MeOH:CH$_2$Cl$_2$, 5 L 7.5% 2M NH$_3$ IN MeOH:CH$_2$Cl$_2$) to afford an oil. Treatment of the oil with Et2O resulted in a suspension. The insoluble material was collected by filtration to afford 4.64 g (69%) of {5-[4-(3-piperidin-1-yl-propoxy)phenyl]-[1,3,4]oxadiazol-2-yl}methanol.

$^1$H NMR (DMSO-d6) δ7.89 (d, 2H, J=9 Hz), 7.10 (d, 2H, J=9 Hz), 5.91 (t, 1H, J=6 Hz), 4.67 (d, 2H, J=6 Hz), 4.09 (t, 2H, J=6 Hz), 2.25–2.42 (m, 6H), 1.85–1.93 (m, 2H), 1.44–1.54 (m, 4H), 1.32–1.41 (m, 2H). IR (KBr, cm$^{-1}$) 3061, 2935, 2811, 1618, 1499, 1464, 1430, 1311, 1260, 1176, 1126, 1053, 839, 780, 738, 679, 528. MS (ES$^+$) m/e 318.

c) 1-{3-[4-(5-Chloromethyl-[1,3,4]oxadiazol-2-yl)phenoxy]propyl}piperidine

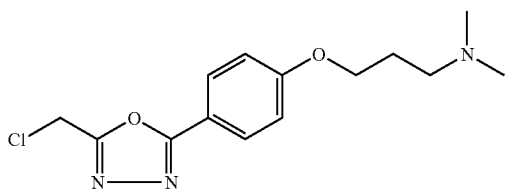

To {5-[4-(3-piperidin-1-yl-propoxy)phenyl]-[1,3,4]oxadiazol-2-yl}methanol (0.159 g, 0.5 mmol) in 5.0 ml CH$_2$Cl$_2$ at room temperature was added thionyl chloride (1.67 g, 14.03 mmol). The reaction was stirred at room temperature for 1.5 hours then concentrated to a solid. This material was dissolved into CH₂Cl₂:H₂O and 1N NaOH added until pH was greater than 12. The phases were separated, aqueous phase extracted with CH₂Cl₂. The organic phases were combined, washed with brine, dried over Na₂SO₄, filtered, concentrated to afford 0.146 g (87%) of 1-{3-[4-(5-chloromethyl-[1,3,4]oxadiazol-2-yl)phenoxy]propyl}piperidine as a crystalline solid.

¹H NMR (DMSO-d6) δ7.90 (d, 2H), 7.13 (d, 2H), 5.09 (s, 2H), 3.08 (t, 2H), 2.26–2.40 (m, 6H), 1.84–1.93 (m, 2H), 1.45–1.51 (m, 4H), 1.33–1.40 (m, 2H). MS (ES⁺) m/e 336.

d) 1-{3-[4-(5-Phenylsulfanylmethyl-[1,3,4]oxadiazol-2-yl)phenoxy]propyl}piperidine

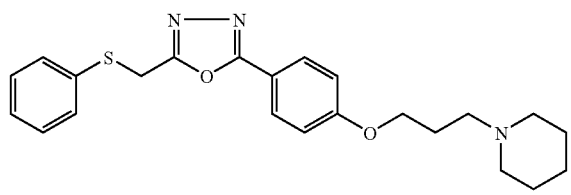

Method A: A suspension of 1-{3-[4-(5-chloromethyl-[1,3,4]oxadiazol-2-yl)phenoxy]propyl}piperidine (0.071 g, 0.21 mmol), cesium carbonate (0.076 g, 0.23 mmol) and benzenethiol (0.026 g, 0.23 mmol) in 1.0 ml acetone was stirred at room temperature for 1.0 hour refluxed for 1.0 hour. After cooling to room temperature the suspension was filtered.

Method B: To benzenethiol (0.026 g, 0.23 mmol) in 1.0 ml THF was added sodium hydride (0.009 g, 0.23 mmol) at room temperature. The mixture was stirred five minutes then 1-{3-[4-(5-chloromethyl-[1,3,4]oxadiazol-2-yl)phenoxy]propyl}piperidine (0.071 g, 0.23 mmol) was added. The reaction mixture was stirred at room temperature for 1.0 hour then refluxed for 1.0 hour. After cooling to room temperature the suspension was filtered.

The filtrates from Method A and Method B were combined, concentrated in vacuo. Purification by radial chromatography (eluted with 5% 2M NH₃ in MeOH:CH₂Cl₂) followed by conversion to the HCl salt, as described in Example 5 using the acetyl chloride/EtOH method to generate HCl in situ, afforded 0.066 g (35%) of 1-{3-[4-(5-Phenylsulfanylmethyl-[1,3,4]oxadiazol-2-yl)phenoxy]propyl}piperidine as the hydrochloride salt.

¹HNMR (DMSO-d6) δ10.10 (bs, 1H), 7.81 (d, 2H, J=9 Hz), 7.44–7.47 (m, 2H), 7.32–7.37 (m, 2H), 7.24–7.28 (m, 1H), 7.12 (d, 2H, J=9 Hz), 4.57 (s, 2H), 4.20 (t, 2H, J=6 Hz), 3.43–3.46 (m, 2H), 3.13–3.20 (m, 2H), 2.81–2.92 (m, 2H), 2.16–2.25 (m, 2H), 1.66–1.82 (m, 5H), 1.33–1.42 (m, 1H). IR (KBr, cm⁻¹) 2940, 2621, 2503, 1615, 1499, 1440, 1393, 1309, 1250, 1178, 1054, 1015, 976, 943, 840, 742, 688. MS (ES⁺) m/e 410. Anal. Calcd for C₂₃H₂₇N₃O₂S HCl C, 61.94; H, 6.33; N, 9.42. Found C, 61.62; H, 6.38; N, 9.28. Analytical HPLC: 100%. Mp(° C.)=152.

Example 220

Preparation of 1-(3-{4-[5-(biphenyl-4-ylsulfanylmethyl)-[1,3,4]oxadiazol-2-yl]phenoxy}propyl)piperdine

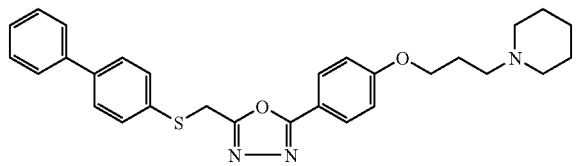

To a solution of biphenyl-4-thiol (0.153 g, 0.82 mmol) in 3.5 ml THF at room temperature was added sodium hydride (0.033 g, 0.82 mmol). The reaction mixture was stirred five minutes then 1-{3-[4-(5-chloromethyl-[1,3,4]oxadiazol-2-yl)phenoxy]propyl}piperidine (0.250 g, 0.74 mmol) was added followed by 2 ml THF. The reaction was heated at 60 C for one hour. After cooling to room temperature the reaction was diluted with 50 ml H₂O and extracted with EtOAc (2×50 ml). The organic phases were washed with brine, dried over Na2SO4, filtered, concentrated in vacuo. Purification by radial chromatography (eluted with 5% 2M NH₃ in MeOH:CH₂Cl₂) followed by conversion to the HCl salt, as described in Example 5 using the acetyl chloride/EtOH method to generate HCl in situ, afforded 0.088 g (23%) of 1-(3-{4-[5-(biphenyl-4-ylsulfanylmethyl)-[1,3,4]oxadiazol-2-yl]phenoxy}propyl)piperdine as the hydrochloride salt.

¹H NMR (DMSO-d6) δ 107.84 (d, 2H, J=9 Hz),7.66 (d, 4H, J=8 Hz), 7.55 (d, 2H, J=8 Hz), 7.44–7.49 (m, 2H), 7.35–7.39 (m, 1H), 7.10 (d, 2H, J=9 Hz), 4.63 (s, 2H), 4.14 (t, 2H, J=6 Hz), 3.39–3.50 (m, 2H), 3.11–3.22 (m, 2H), 2.81–2.92 (m, 2H), 2.11–2.22 (m, 2H), 1.61–1.85 (m, 5H), 1.31–1.42 (m, 1H). IR (KBr, cm⁻¹) 3420, 3053, 3027, 2940, 2612, 2488, 1615, 1500, 1479, 1300, 1254, 1174, 1085, 1005, 948, 835, 761, 698. MS (ES⁺) m/e 486. Mp(° C.)=142.

Example 221

Preparation of 1-(3-{4-[5-(Naphthalen-1-ylsulfanylmethyl)-[1,3,4]oxadiazol-2-yl]phenoxy}propyl)piperdine

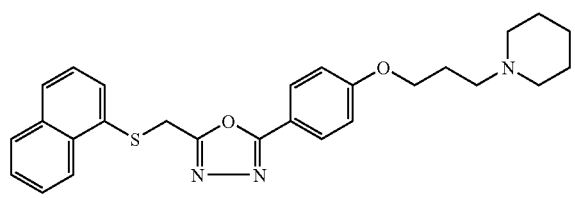

The above compound was prepared in a manner similar to that exemplified for the preparation of Example 220 from 1-naphthalenethiol (0.131 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.162 g (44%) of 1-(3-{4-[5-(naphthalen-1-yl-sulfanylmethyl)-[1,3,4]oxadiazol-2-yl]phenoxy}propyl)piperdine as the hydrochloride salt.

¹H NMR (DMSO-d6) δ8.24–8.29 (m, 1H), 7.91–8.00 (m, 2H), 7.79 (d, 1H, J=7 Hz), 7.70 (d, 2H, J=9 Hz), 7.48–7.58 (m, 3H), 7.08 (d, 2H, J=9 Hz), 4.58 (s, 2H), 4.15 9 t, 2H, J=6 Hz), 3.37–3.45 (m, 2H), 3.13–3.22 (m, 2H), 3.81–3.94 (m, 2H), 2.11–2.34 (m, 2H), 1.65–1.84 (m, 5H), 1.31–1.43 (m, 1H). IR (KBr, cm⁻¹) 3050, 2947, 2462, 2403, 1615, 1591, 1497, 1465, 1427, 1307, 1252, 1171, 1066, 950, 844, 793, 767. MS (ES⁺) m/e 460. Anal. Calcd for $C_{27}H_{29}N_3O_2S$ HCl C, 65.37; H, 6.10; N, 8.47. Found C, 65.13; H, 6.09; N, 8.22. Mp(° C.)=195.

Example 222

Preparation of 2-{5-[4-(3-Piperidin-1-yl-propoxy)phenyl]-[1,3,4]oxadiazol-2-ylmethylsulfanyl}benzothiazole

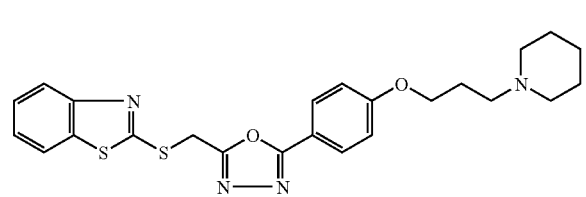

The above compound was prepared in a manner similar to that exemplified for the preparation of Example 220 from 2-mercaptobenzothiazole (0.137 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.170 g (49%/O) of 2-{5-[4-(3-piperidin-1-yl-propoxy)phenyl]-[1,3,4]oxadiazol-2-ylmethylsulfanyl}benzothiazole as the hydrochloride salt.

¹H NMR (DMSO-d6) δ 8.05 (d, 1H, J=8 Hz), 7.85–7.90 (m, 3H), 7.45–7.51 (m, 1H), 7.38–7.44 (m, 1H), 7.12 (d, 2H, J=7 Hz), 5.01 (s, 2H), 4.15 (t, 2H, J=6 Hz), 3.39–3.50 (m, 2H), 3.13–3.22 (m, 2H), 2.81–2.93 (m, 2H), 2.12–2.23 (m, 2H), 1.64–1.84 (m, 5H), 1.31–1.41 (m, 1H). IR (KBr, cm⁻¹) 3431, 2948, 2617, 2486, 1612, 1499, 1457, 1426, 1306, 1253, 1175, 1049, 1004, 942, 835, 753, 724. MS (ES⁺) m/e 467. Mp(° C.)=144.

Example 223

Preparation of 2-{5-[4-(3-piperidin-1-yl-propoxy)phenyl]-[1,3,4]oxadiazol-2-ylmethylsulfanyl}-1H-benzimidazole

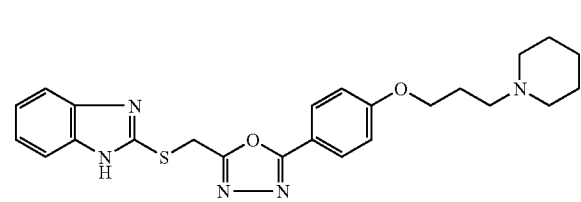

The above compound was prepared in a manner similar to that exemplified for the preparation of Example 220 from 2-mercaptobenzimidazole (0.246 g, 1.64 mmol), 1-{3-[4-(5-chloromethyl-[1,3,4]oxadiazol-2-yl)phenoxy]propyl}piperidine (0.500 g, 1.49 mmol) and sodium hydride (0.066 g, 1.64 mmol) to afford 0.364 g (54%) of 2-{5-[4-(3-piperidin-1-yl-propoxy)phenyl]-[1,3,4]oxadiazol-2-ylmethylsulfanyl}-1H-benzimidazole.

¹H NMR (DMSO-d6) δ7.75 (d, 2H), 7.33–7.54 (m, 2H), 7.10–7.15 (m, 2H), 7.04 (d, 2H), 4.85 (s, 2H), 4.05 (t, 2H), 2.26–2.39 (m, 6H), 1.83–1.91 (m, 2H), 1.45–1.50 (m, 4H), 1.33–1.40 (m, 2H). IR (KBr, cm⁻¹) 3068, 2935, 2878, 2803, 1619, 1500, 1430, 1401, 1352, 1301, 1252, 1179, 1008, 841, 741, 523. MS (ES⁺) m/e 450. Anal. Calcd for $C_{24}H_{27}N_5O_2S$ C, 64.12; H, 6.05; N, 15.58. Found C, 64.07; H, 6.06; N, 15.41. Mp(° C.)=193.

Example 224

Preparation of 1-(3-{4-[5-(1H-Imidazol-2-ylsulfanylmethyl)-[1,3,4]oxadiazol-2-yl]phenoxy}propyl)piperdine

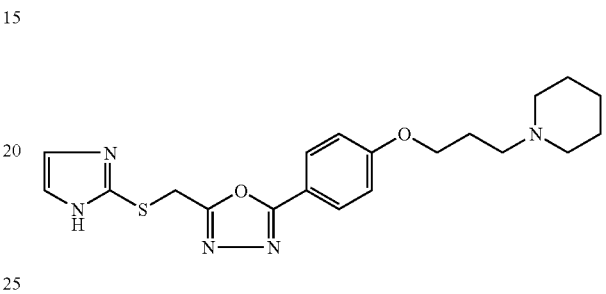

The above compound was prepared in a manner similar to that exemplified for the preparation of Example 220 from 2-mercaptoimidazole (0.082 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.128 g (43%) of 1-(3-{4-[5-(1H-imidazol-2-ylsulfanylmethyl)-[1,3,4]oxadiazol-2-yl]phenoxy}propyl)piperdine.

¹H NMR (DMSO-d6) δ7.79 (d, 2H, J=9 Hz), 7.25 (s, 1H), 7.08 (d, 2H, J=9 Hz), 4.40 (s, 2H), 4.05 (t, 2H, J=6 Hz), 2.24–2.39 (m, 6H), 1.77–1.92 (m, 2H), 1.39–1.52 (m, 4H), 1.30–1.39 (m, 2H). IR (KBr, cm⁻¹) 2992, 2937, 2765, 1616, 1500, 1428, 1329, 1303, 1250, 1179, 1098, 1007, 960, 846, 756, 657. MS (ES⁺) m/e 400. Anal. Calcd for $C_{20}H_{25}N_5O_2S$ C, 60.13; H, 6.31; N, 17.53. Found C, 59.84; H, 6.19; N, 17.27. Mp(° C.)=132.

Example 225

Preparation of 1-(3-{4-[5-([1,3,4]thiadiazol-2-ylsulfanylmethyl)-[1,3,4]oxadiazol-2-yl]phenoxy}propyl)piperdine

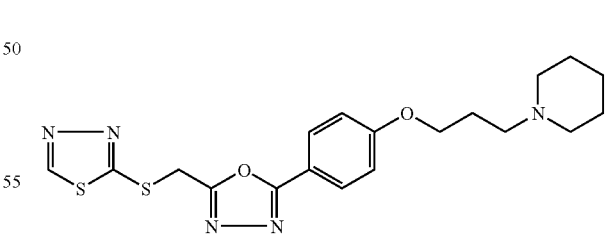

The above compound was prepared in a manner similar to that exemplified for the preparation of Example 220 from 2-mercapto-1,3,4-thiadiazole (0.097 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.154 g (46%) of 1-(3-{4-[5-([1,3,4]thiadiazol-2-ylsulfanylmethyl)-[1,3,4]oxadiazol-2-yl]phenoxy}propyl)piperidine 220 as the hydrochloride salt.

¹H NMR (DMSO-d6) δ9.56 (s, 1H), 7.86 (d, 2H, J=9 Hz), 7.12 (d, 2H, J=9 Hz), 4.92 (s, 2H), 4.15 (t, 2H, J=6 Hz), 3.42–3.48 (m, 2H), 3.14–3.20 (m, 2H), 2.81–2.89 (m, 2H), 2.15–2.22 (m, 2H), 1.66–1.82 (m, 5H), 1.33–1.39 (m, 1H). IR (KBr, cm⁻¹) 2945, 2634, 2508, 1615, 1498, 1429, 1367, 1310, 1254, 1175, 1060, 974, 944, 840, 739. MS (ES⁺) m/e 418, MS (ES⁻) m/e 416. Analytical HPLC: 100%. Anal. Calcd for $C_{19}H_{23}N_5O_2S_2$ HCl C, 50.27; H, 5.33; N, 15.43. Found C, 50.09; H, 5.31; N, 15.17. Mp(° C.)=164.

Example 226

Preparation of 1-(3-{4-[5-(thiazol-2-ylsulfanylmethyl)-[1,3,4]oxadiazol-2-yl]phenoxy}propyl)piperdine

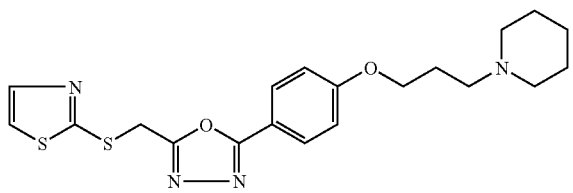

The above compound was prepared in a manner similar to that exemplified for the preparation of Example 220 from 2-mercaptothiazole (0.096 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.154 g (46%) of 1-(3-{4-[5-(thiazol-2-ylsulfanylmethyl)-[1,3,4]oxadiazol-2-yl]phenoxy}propyl)piperdine as the hydrochloride salt.

¹H NMR (DMSO-d6) δ7.85 (d, 2H, J=9 Hz), 7.78 (s, 1H), 7.74 (s, 1H), 7.12 (d, 2H, J=9 Hz), 4.79 (s, 2H), 4.15 (t, 2H, J=6 Hz), 3.41–3.46 (m, 2H), 3.13–3.20 (m, 2H), 2.82–2.90 (m, 2H), 2.12–2.20 (m, 2H), 1.75–1.81 (m, 2H), 1.63–1.72 (m, 2H), 1.32–1.39 (m, 1H). IR (KBr, cm⁻¹) 3074, 2963, 2940, 2918, 2618, 2499, 1614, 1498, 1472, 1430, 1310, 1251, 1180, 1034, 942, 838, 738, 662. MS (ES⁺) m/e 417, MS (ES⁻) m/e 415. Analytical HPLC: 100%. Anal. Calcd for $C_{20}H_{24}N_4O_2S_2$ HCl C, 53.03; H, 5.56; N, 12.37. Found C, 52.92; H, 5.54; N, 12.17. Mp(° C.)=174–176.

Example 227

Preparation of 1-(3-{4-(5-(5-methyl-[1,3,4]thiadiazol-2-ylsulfanylmethyl)-[1,3,4]oxadiazol-2-yl]phenoxy}propyl)piperdine

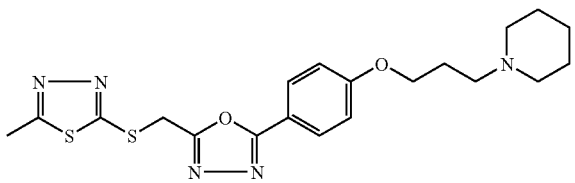

The above compound was prepared in a manner similar to that exemplified for the preparation of Example 220 from 2-mercapto-5-methyl-1,3,4-thiadiazole (0.108 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.163 g (32%) of 1-(3-{4-[5-(5-methyl-[1,3,4]thiadiazol-2-ylsulfanylmethyl)-[1,3,4]oxadiazol-2-yl]phenoxy}propyl)piperdine.

¹H NMR (DMSO-d6) δ7.83 (d, 2H, J=9 Hz), 7.11 (d, 2H, J=9 Hz), 4.85 (s, 2H), 4.08 (t, 2H, J=7 Hz), 2.69 (s, 3H), 2.25–2.39 (m, 6H), 1.81–1.89 (m, 2H), 1.43–1.51 (m, 4H), 1.32–1.39 (m, 2H). IR (KBr, cm⁻¹) 2933, 2807, 1608, 1499, 1421, 1387, 1307, 1262, 1176, 1125, 1068, 1018, 954, 854, 741. MS (ES⁺) m/e 432, MS (ES⁻) m/e 430. Analytical HPLC: 100%. Anal. Calcd for $C_{20}H_{25}N_5O_2S_2$ C, 55.66; H, 5.84; N, 16.23. Found C, 55.75; H, 5.86; N, 16.08. Mp(° C.)=89.

Example 228

Preparation of 1-(3-{4-[5-(4-Phenylthiazol-2-ylsulfanylmethyl)-[1,3,4]oxadiazol-2-yl]phenoxy)propyl)piperdine

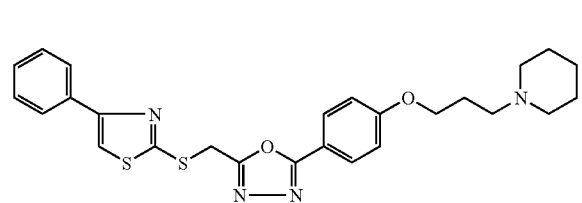

The above compound was prepared in a manner similar to that exemplified for the preparation of Example 220 from 2-mercapto-4-phenylthiazole (0.158 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.080 g (39%) of 1-(3-{4-[5-(4-phenylthiazol-2-ylsulfanylmethyl)-[1,3,4]oxadiazol-2-yl]phenoxy}propyl)piperdine as the hydrochloride salt.

¹H NMR (DMSO-d6) δ8.08 (s, 1H), 7.86–7.88 (m, 4H), 7.29–7.39 (m, 3H), 7.10 (d, 2H, J=9 Hz), 4.86 (s, 2H), 4.14 (t, 2H, J=6 Hz), 3.41–3.47 (m, 2H), 3.13–3.20 (m, 2H), 2.81–2.92 (m, 2H), 2.14–2.22 (m, 2H), 1.65–1.82 (m, 5H), 1.33–1.41 (m, 1H). IR (KBr, cm⁻¹) 2947, 2616, 2468, 2412, 1614, 1498, 1476, 1424, 1306, 1252, 1174, 1034, 839, 729. MS (ES⁺) m/e 493, MS (ES⁻) m/e 491. Analytical HPLC: 100%. Mp(° C.)=141.

Example 229

Preparation of 1-(3-{4-[5-(1-methyl-1H-imidazol-2-ylsulfanylmethyl)-[1,3,4]oxadiazol-2-yl]phenoxy}propyl)piperdine

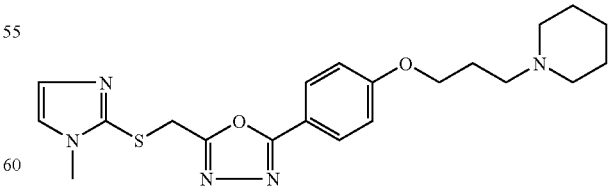

The above compound was prepared in a manner similar to that exemplified for the preparation of Example 220 from 2-mercapto-1-methylimidazole (0.093 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.228 g (37%) of 1-(3-{4-[5-(1-methyl-1H-imidazol-2-ylsulfanylmethyl)-[1,3,4]oxadiazol-2-yl]phenoxy}propyl) piperdine as the hydrochloride salt.

$^1$H NMR (DMSO-d6) δ7.84 (d, 2H, J=9 Hz), 7.57 (s, 1H), 7.36 (s, 1H), 7.13 (d, 2H, J=9 Hz), 4.58 (s, 2H), 4.15 (t, 2H, J=6 Hz), 3.67 (s, 3H), 3.40–3.47 (m, 2H), 3.11–3.47 (m, 2H), 2.82–2.92 (m, 2H), 2.14–2.23 (m, 2H), 1.63–1.82 (m, 5H), 1.31–1.42 (m, 1H). IR (KBr, cm$^{-1}$) 3418, 2946, 2615, 2488, 1899, 1615, 1570, 1499, 1471, 1428, 1299, 1251, 1178, 1056, 943, 837, 736. MS (ES$^+$) m/e 414. Mp(° C.)=173.

Example 230

Preparation of 2-{5-[4-(3-Piperidin-1-yl-propoxy)phenyl]-[1,3,4]oxadiazol-2-ylmethylsulfanyl}benzooxazole

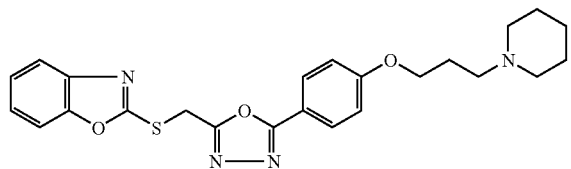

The above compound was prepared in a manner similar to that exemplified for the preparation of Example 220 from 2-mercaptobenzoxazole (0.099 g, 0.66 mmol), 1-{3-[4-(5-chloromethyl-[1,3,4]oxadiazol-2-yl)phenoxy]propyl}piperidine (0.200 g, 0.60 mmol) and sodium hydride (0.026 g, 0.66 mmol) to afford 0.097 g (27%) of 2-{5-[4-(3-Piperidin-1-yl-propoxy)phenyl]-[1,3,4]oxadiazol-2-ylmethylsulfanyl}benzooxazole $^1$H NMR (DMSO-d6) δ7.81 (d, 2H, J=9 Hz), 7.64–7.68 (m, 2H), 7.32–7.37 (m, 2H), 7.08 (d, 2H, J=9 Hz), 4.95 (s, 2H), 4.06 (t, 2H, J=6 Hz), 2.27–2.38 (m, 6H), 1.82–1.89 (m, 2H), 1.44–1.49 (m, 4H), 1.33–1.38 (m, 2H). IR (KBr, cm$^{-1}$) 2930, 2846, 2770, 1613, 1590, 1504, 1453, 1312, 1259, 1180, 1134, 1096, 1014, 955, 846, 807, 741, 702, 657. MS (ES$^+$) m/e 451. Anal. Calcd for $C_{24}H_{26}N_4O_3S$ C, 63.98; H, 5.82; N, 12.43. Found C, 63.95; H, 5.79; N, 12.35. Mp(° C.)=108.

Example 231

Preparation of 1-Methyl-2-{5-[4-(3-piperidin-1-yl-propoxy)phenyl]-[1,3,4]oxadiazol-2-ylmethylsulfanyl}-1H-benzimidazole

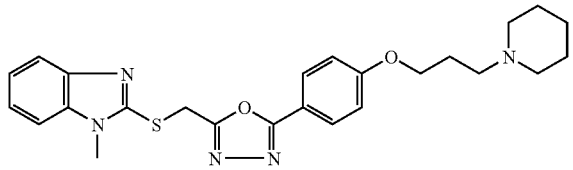

Method A: To a solution of 2-{5-[4-(3-piperidin-1-yl-propoxy)phenyl]-[1,3,4]oxadiazol-2-ylmethylsulfanyl}-1H-benzimidazole (0.066 g, 0.15 mmol) in 3 ml DMF at room temperature was added potassium carbonate (0.022 g, 0.15 mmol), tertabutylammonium bromide (0.005 g, 0.02 mmol) and dimethyl sulfate (0.019 g, 0.15 mmol). The reaction was stirred at room temperature for 5 days.

Method B: To a suspension of 2-{5-[4-(3-piperidin-1-yl-propoxy)phenyl]-[1,3,4]oxadiazol-2-ylmethylsulfanyl}-1H-benzimidazole (0.052 g, 0.12 mmol) in 3 ml acetone was added potassium carbonate (0.018 g, 0.135 mmol), tertabutylammonium bromide (0.004 g, 0.01 mmol) and dimethyl sulfate (0.015 g, 0.12 mmol). The reaction was stirred at room temperature for 6 days.

The reactions were combined and diluted with 25 ml H$_2$O then extracted with EtOAc (2×25 ml). The organic phases were combined, washed with brine, dried over Na2SO4, filtered, concentrated to an oil. Purification by radial chromatography on silica gel (eluted with 5% 2M NH$_3$ in MeOH:CH$_2$Cl$_2$) followed by conversion to the di-HCl salt as described in Example 5 using the acetyl chloride/EtOH method to generate HCl in situ afforded 0.016 g (14%) of 1-methyl-2-{5-[4-(3-piperidin-1-yl-propoxy)phenyl]-[1,3,4]oxadiazol-2-ylmethylsulfanyl}-1H-benzimidazole.

$^1$H NMR (DMSO-d6) δ7.83 (d, 2H), 7.51–7.55 (m, 2H), 7.14–7.25 (m, 2H), 7.08 (d, 2H), 4.90 (s, 2H), 4.14 (t, 2H), 3.73 (s, 3H), 3.41–3.49 (m, 2H), 3.14–3.21 (m, 2H), 2.81–2.93 (m, 2H), 2.14–2.23 (m, 2H), 1.65–1.83 (m, 5H), 1.31–1.45 (m, 1H). MS (ES$^+$) m/e 464. Mp(° C.)=194.

Example 232

Preparation of Dimethyl-{3-[4-(5-phenethylsulfanylmethyl-[1,3,4]oxadiazol-2-yl)phenoxy]propyl}amine

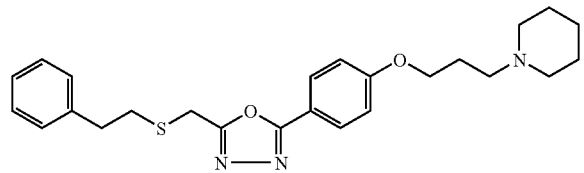

The above compound was prepared in a manner similar to that exemplified for the preparation of Example 193c from thiobenzoic acid S-(2-{N'-[4-(3-dimethylamino propoxy)benzoyl]hydrazino}-2-oxoethyl)ester (0.205 g, 0.5 mmol), (2-bromoethyl) benzene (0.095 g, 0.5 mmol) and lithium hydroxide (0.025 g, 1.0 mmol) to afford 0.139 g (62%) of dimethyl-{3-[4-(5-phenethylsulfanylmethyl-[1,3,4]oxadiazol-2-yl)phenoxy]propyl}amine as the hydrochloride salt.

$^1$H NMR (DMSO-d6) δ790 (d, 2H, J=9 Hz), 7.05–7.23 (m, 7H), 4.15 (t, 2H, J=6 Hz), 4.10 (s, 2H), 3.16–3.22 (m, 2H), 2.86 (s, 4H), 2.79 (s, 6H), 2.09–2.17 (m, 2H). MS (ES$^+$) m/e 398. Analytical HPLC: 100%. Anal. Calcd for $C_{22}H_{27}N_3O_2S$ HCl C, 60.89; H, 6.50; N, 9.68. Found C, 60.64; H, 6.47; N, 9.67. Mp(° C.)=Decomposes at 173.

Example 233

Preparation of 1-(3-{4-[5-Phenyl-1H-tetrazol-5-yl-sulfanylmethyl)-[1,3,4]oxadiazol-2-yl]phenoxy}propyl)piperidine

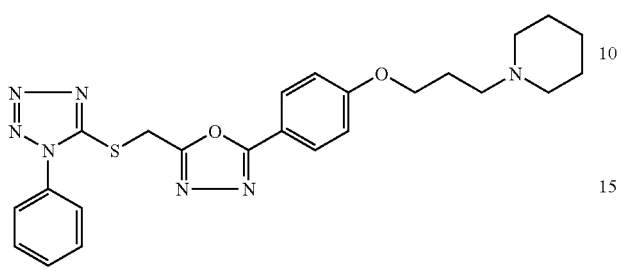

The above compound was prepared in a manner similar to that exemplified for the preparation of Example 28 from 1-phenyl-1H-tetrazole (0.146 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.244 g (64%) of 1-(3-{4-[5-Phenyl-1H-tetrazol-5-yl-sulfanylmethyl)-[1,3,4]oxadiazol-2-yl]phenoxy}propyl)piperidine as the hydrochloride salt.

$^1$HNMR (DMSO-d6) $\delta$7.85 (d, 2H, J=9 Hz), 7.63 (s, 5H), 4.88 (s, 2H), 4.15 (t, 2H, J=6 Hz), 3.41–3.48 (m, 2H), 3.12–3.21 (m, 2H), 2.81–2.92 (m, 2H), 2.12–2.22 (m, 2H), 1.63–1.83 (m, 5H), 1.31–1.41 (m, 1H). IR (KBr, cm$^{-1}$) 2946, 2621, 2499, 2407, 1615, 1499, 1390, 1309, 1252, 1390, 1309, 1252, 1173, 1066, 1015, 838, 767, 738, 696. MS (ES$^+$) m/e 451. Analytical HPLC: 100%. Anal. Calcd for $C_{24}H_{27}N_7O_2S$ HCl C, 56.08; H, 5.49; N, 19.07. Found C, 56.02; H, 5.509; N, 18.86. Mp(° C.)=Decomposes at 182.

Example 234

Preparation of 1-(3-{4-[5-(5-Phenyl-[1,3,4]oxadiazol-2-yl-sulfanylmethyl)-[1,3,4]oxadiazol-2-yl]phenoxy}propyl)piperidine

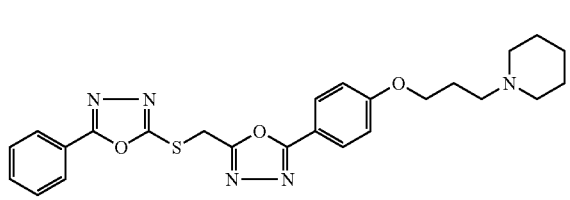

The above compound was prepared in a manner similar to that exemplified for the preparation of Example 220 from 5-phenyl-1,3,4-oxadiazole-2-thiol (0.146 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.259 g (73%) of 1-(3-{4-[5-(5-Phenyl-[1,3,4]oxadiazol-2-yl-sulfanylmethyl)-[1,3,4]oxadiazol-2-yl]phenoxy}propyl)piperidine.

$^1$H NMR (DMSO-d6) $\delta$7.94 (d, 2H, J=8 Hz), 7.82 (d, 2H, J=9 Hz), 7.54–7.64 (m, 3H), 7.07 (d, 2H, J=9 Hz), 4.89 (s, 2H), 4.07 (t, 2H, J=6 Hz), 2.21–2.42 (m, 6H), 1.80–1.91 (m, 2H), 1.41–1.51 (m, 4H), 1.29–1.40 (m, 2H). IR (KBr, cm$^{-1}$) 3067, 2929, 2851, 2752, 1609, 1570, 1480, 1416, 1303, 1253, 1179, 1125, 1065, 1021, 988, 955, 848, 741, 704. MS (ES$^+$) m/e 478, MS (ES$^-$) m/e 476. Anal. Calcd for $C_{25}H_{27}N_5O_3S$ C, 62.87; H, 5.70; N, 14.66. Found C, 62.75; H, 5.63; N, 14.53. Mp(° C.)=118.

Example 235

Preparation of 1-(3-{4-[5-(4-methyl-5-phenyl-4H-[1,2,4]triazol-3-ylsulfanylmethyl)-[1,3,4]oxadiazol-2-yl]phenoxy}propyl)piperidine

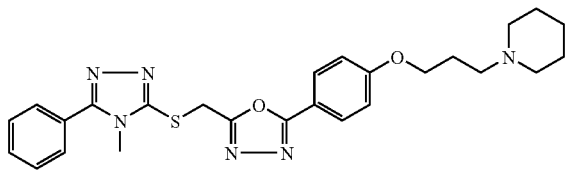

The above compound was prepared in a manner similar to that exemplified for the preparation of Example 220 from 4-methyl-5-phenyl-4H-[1,2,4]triazole-3-thiol (0.157 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.132 g (34%) of 1-(3-{4-[5-(4-methyl-5-phenyl-4H-[1,2,4]triazol-3-ylsulfanylmethyl)-[1,3,4]oxadiazol-2-yl]phenoxy}propyl)piperidine as the hydrochloride salt.

$^1$H NMR (DMSO-d6) $\delta$7.84 9d, 2H, J=9 Hz), 7.65–7.70 (m, 2H), 7.53–7.57 (m, 3H), 7.10 (d, 2H, J=9 Hz), 4.68 (s, 2H), 4.14 (t, 2H, J=6 Hz), 3.40–3.48 (m, 2H), 3.12–3.20 (m, 2H), 2.81–2.91 (m, 2H), 2.15–2.23 (m, 2H), 1.65–1.81 (m, 5H), 1.32–1.40 (m, 1H). IR (KBr, cm$^{-1}$) 3420, 2944, 2623, 2514, 1615, 1501, 1472, 1398, 1252, 1179, 1068, 942, 842, 777, 705. MS (ES$^-$) m/e 489. Analytical HPLC: 100%. Mp(° C.)=Decomposes at 174.

Example 236

Preparation of 2-(4-Methyl-5-{5-[4-(3-piperidin-1-yl-propoxy)phenyl]-[1,3,4]oxadiazol-2-ylmethylsulfanyl}-4H-[1,2,4]triazol-3-yl)pyridine

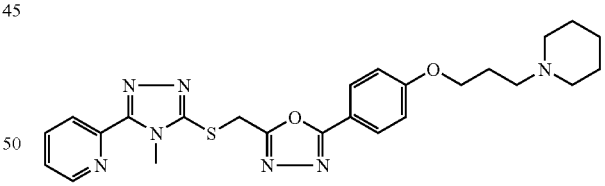

The above compound was prepared in a manner similar to that exemplified for the preparation of Example 220 from 4-methyl-5-pyridin-2-yl-4H-[1,2,4]triazole-3-thiol (0.157 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.161 g (41%) of 2-(4-Methyl-5-{5-[4-(3-piperidin-1-yl-propoxy)phenyl]-[1,3,4]oxadiazol-2-ylmethylsulfanyl}-4H-[1,2,4]triazol-3-yl)pyridine as the dihydrochloride salt.

$^1$H NMR (DMSO-d6) $\delta$8.70 (d, 1H, J=4 Hz), 8.11 (d, 1H, J=8 Hz), 7.97–8.02 (m, 1H), 7.83 (d, 2H, J=9 Hz), 7.51–7.54 (m, 1H), 7.07 (d, 2H, J=9 Hz), 4.69 (s, 2H), 4.15 (t, 2H, J=6 Hz), 3.42–3.49 (m, 2H), 3.14–3.21 (m, 2H), 2.82–2.91 (m, 2H), 2.13–2.20 (m, 2H), 1.76–1.84 (m, 2H), 1.65–1.73 (m, 3H), 1.34–1.40 (m, 1H). IR (KBr, cm$^{-1}$) 3420, 2948, 2619, 2498, 1829, 1613, 1569, 1500, 1469, 1307, 1255, 1176, 1084, 945, 837, 795, 738, 709. MS (ES$^+$) m/e 491. Analytical HPLC: 100%. Mp(° C.)=112.

Example 237

Preparation of 3-(4-Methyl-5-{5-[4-(3-piperidin-1-yl-propoxy)phenyl]-[1,3,4]oxadiazol-2-ylmethylsulfanyl}-4H-[1,2,4]triazol-3-yl)pyridine

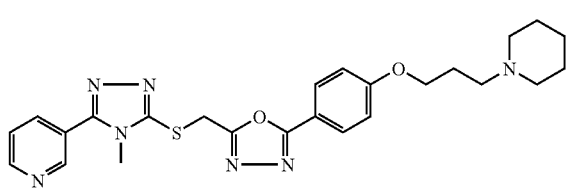

The above compound was prepared in a manner similar to that exemplified for the preparation of Example 220 from 4-methyl-5-pyridin-3-yl-4H-[1,2,4]triazole-3-thiol (0.157 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.138 g (38%) of 3-(4-Methyl-5-{5-[4-(3-piperidin-1-yl-propoxy)phenyl]-[1,3,4]oxadiazol-2-ylmethylsulfanyl}-4H-[1,2,4]triazol-3-yl)pyridine.

$^1$H NMR (DMSO-d6) δ8.87 (s, 1H), 8.72 (d, 1H, J=5 Hz), 7.81 (d, 1H, J=9 Hz), 7.57–7.60 (m, 1H), 7.08 (d, 2H, J=9 Hz), 4.70 (s, 2H), 4.07 (t, 2H, J=6 Hz), 2.26–2.39 (m, 6H), 1.82–1.89 (m, 2H), 1.42–1.52 (m, 4H), 1.30–1.40 (m, 2H). IR (KBr, cm$^{-1}$) 2932, 2761, 1614, 1569, 1500 1422, 1367, 1301, 1255, 1176, 1158, 1093, 1028, 856, 818, 712. MS (ES$^+$) m/e 492, MS (ES$^-$) m/e 490. Analytical HPLC: 100%. Anal. Calcd for $C_{25}H_{29}N_7O_2S$ C, 61.08; H, 5.95; N, 19.94. Found C, 60.93; H, 5.94; N, 19.71. Mp(° C.)=118.

Example 238

Preparation of 1-(3-{4-[5-Phenyl-1H-imidazol-2-ylsulfanylmethyl-[1,3,4]oxadiazol-2-yl]phenoxy}propyl)piperidine

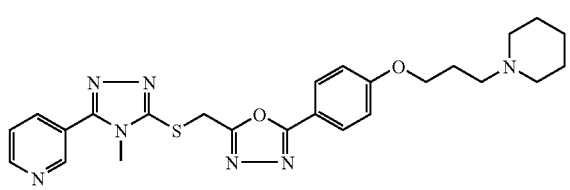

The above compound was prepared in a manner similar to that exemplified for the preparation of Example 220 from 1-phenyl-1H-imidazole-2-thiol (0.144 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.295 g (77%) of 1-(3-{4-[5-Phenyl-1H-imidazol-2-ylsulfanylmethyl-[1,3,4]oxadiazol-2-yl]phenoxy}propyl) piperidine as the dihydrochloride salt.

$^1$H NMR (DMSO-d6) δ7.76–7.84 (m, 3H), 7.59 (s, 1H), 7.35–7.48 (m, 5H), 7.13 (d, 2H, J=9 Hz), 4.56 (s, 2H), 4.16 (t, 2H, J=6 Hz), 3.41–3.48 (m, 2H), 3.13–3.20 (m, 2H), 2.81–2.92 (m, 2H), 2.18–2.27 (m, 2H), 1.74–1.83 (m, 4H), 1.66–1.73 (m, 1H), 1.33–1.43 (m, 1H). IR (KBr, cm$^{-1}$) 3415, 3162, 2944, 2681, 2490, 1731, 1612, 1567, 1500, 1430, 1373, 1304, 1254, 1180, 1088, 1008, 845, 758, 697. MS (ES$^+$) m/e 476. Mp(° C.)=Decomposes at 177.

Example 239

Preparation of 1-(3-{4-[5-(1-Naphthalen-1-yl-1H-imidazol-2-ylsulfanylmethyl)-[1,3,4]oxadiazol-2-yl]phenoxy}propyl)piperidine

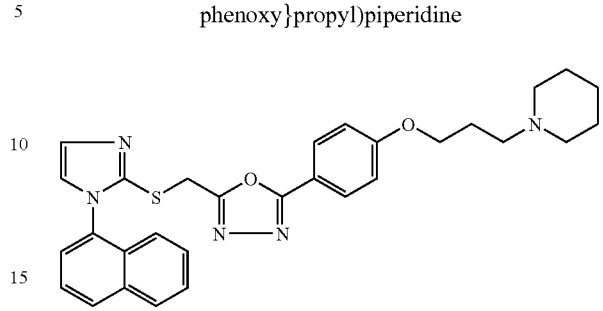

The above compound was prepared in a manner similar to that exemplified for the preparation of Example 220 from 1-naphthalene-1yl-1H-imidazole-2-thiol (0.185 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.358 g (86%) of 1-(3-{4-[5-(1-Naphthalen-1-yl-1H-imidazol-2-ylsulfanylmethyl)-[1,3,4]oxadiazol-2-yl]phenoxy}propyl)piperidine as the dihydrochloride salt.

$^1$H NMR (DMSO-d6) δ8.10 (d, 1H, J=7 Hz), 8.03 (d, 1H, J=8 Hz), 7.75–7.80 (m, 3H), 7.48–7.59 (m, 41), 7.34–7.39 (m, 1H), 7.13 (d, 2H, J=9 Hz), 7.05 (d, 1H, J=8 Hz), 4.40–4.60 (m, 2H), 4.18 (t, 2H, J=6 Hz), 3.42–3.48 (m, 2H), 3.14–3.21 (m, 2H), 2.82–2.92 (m, 2H), 2.17–2.25 (m, 2H), 1.67–1.82 (m, 5H), 1.34–1.42 (m, 1H). IR (KBr, cm$^{-1}$) 3416, 3058, 2944, 2638, 2538, 1612, 1568, 1499, 1474, 1397, 1304, 1255, 1176, 1086, 1017, 841, 807, 776. MS (ES$^+$) m/e 526. Anal. Calcd for $C_{30}H_{31}N_5O_2S$ 2HCl C, 60.20; H, 5.57; N, 11.70. Found C, 60.08; H, 5.63; N, 11.49. Mp(° C.)=Decomposes at 120.

Example 240

Preparation of 1-(3-{4-[5-(4-Phenoxyphenylsulfanylmethyl)-[1,3,4]oxadiazol-2-yl]phenoxy}propyl)piperidine

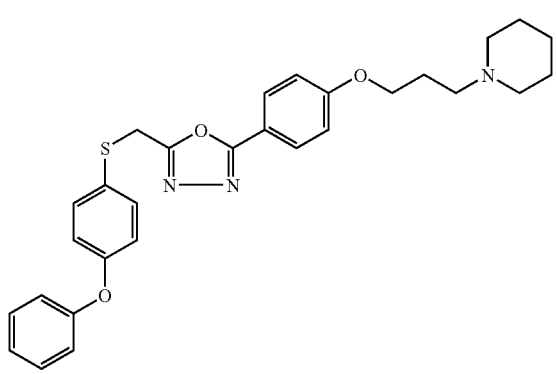

The above compound was prepared in a manner similar to that exemplified for the preparation of Example 220 from 4-phenoxybenzene thiol (0.166 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.161 g (40%) of 1-(3-{4-[5-(4-phenoxyphenylsulfanylmethyl)-[1,3,4]oxadiazol-2-yl]phenoxy}propyl)piperidine as the hydrochloride salt.

¹H NMR (DMSO-d6) δ 7.82 (d, 2H, J=9 Hz), 7.45 (d, 2H, J=9 Hz), 7.34–7.39 (m, 2H), 7.09–7.16 (m, 3H), 6.93–7.00 (m, 4H), 4.48 (s, 2H), 4.15 (t, 2H, J=6 Hz), 3.41–3.48 (m, 2H), 3.13–3.20 (m, 2H), 2.82–2.91 (m, 2H), 2.15–2.22 (m, 2H), 1.65–1.83 (m, 5H), 1.33–1.41 (m, 1H). IR (KBr, cm⁻¹) 2936, 2863, 2620, 2499, 2418, 1612, 1582, 1498, 1422, 1232, 1171, 1090, 1038, 1005, 961, 833, 758, 693, 503. MS (ES⁺) m/e 502. Anal. Calcd for $C_{29}H_{31}N_3O_3S$ HCl C, 64.73; H, 5.99; N, 7.81. Found C, 64.49; H, 6.01; N, 7.75. Mp(° C.)=169.

Example 241

1-(3-{4-[5-(2-Phenoxyphenylsulfanylmethyl)-[1,3,4]oxadiazol-2-yl]phenoxy}propyl)piperidine

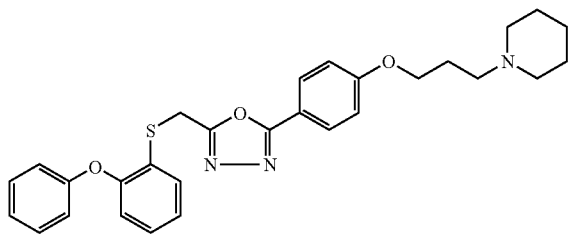

The above compound was prepared in a manner similar to that exemplified for the preparation of Example 220 from 2-phenoxybenzene thiol (0.166 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.166 g (41%) of 1-(3-{4[5-(4-phenoxyphenylsulfanylmethyl)-[1,3,4]oxadiazol-2-yl]phenoxy}propyl)piperidine as the hydrochloride salt.

¹H NMR (DMSO-d6) δ7.79 (d, 2H, J=9 Hz), 7.61 (dd, 1H, J=8 Hz), 7.25–7.31 (m, 3H), 7.15–7.19 (m, 1H), 7.03–7.12 (m, 3H), 6.90 (dd, 1H, J=2, 8 Hz), 6.84 (d, 2H, J=7 Hz), 4.54 (s, 2H), 4.14 (t, 2H, J=6 Hz), 3.42–3.48 (m, 2H), 3.14–3.19 (m, 2H), 2.82–2.91 (m, 2H), 2.14–2.21 (m, 2H), 1.66–1.82 (m, 5H), 1.43–1.42 (m, 1H). IR (KBr, cm⁻¹) 2949, 2618, 2488, 1612, 1570, 1499, 1470, 1298, 1253, 1230, 1175, 1069, 941, 834, 755. MS (ES⁺) m/e 502. Anal. Calcd for $C_{29}H_{31}N_3O_3S$ HCl C, 64.73; H, 5.99; N, 7.81. Found C, 64.44; H, 5.94; N, 7.68. Mp(° C.)=132.

Example 242

1-(3-{4-[5-(Benzofuran-2-ylmethoxymethyl)-[1,3,4]oxadiazol-2-yl]phenoxy}propyl)piperidine

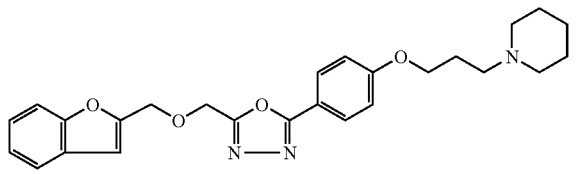

The above compound was prepared in a manner similar to that exemplified for the preparation of Example 202b from {5-[4-(3-piperidin-2-yl-propoxy)phenyl][1,3,4]oxadiazol-2-yl}methanol (0.216 g, 0.7 mmol), 2-chloromethlybenzofuran (0.113 g, 0.7 mmol) and sodium hydride (0.027 g, 0.7 mmol). Purification by radial chromatography (eluted with 5% NH₃ in MeOH:CH₂Cl₂) afforded 0.129 g of the title compound as an oil that slowly crystallizes out. This material was combined with 0.021 g from a previous run, then converted to the HCl salt as described in Example 5 using the acetyl chloride/EtOH method to generate HCl in situ afforded 0.091 g of 1-(3-{4-[5-(benzofuran-2-ylmethoxymethyl)-[1,3,4]oxadiazol-2-yl]phenoxy}propyl)piperidine.

¹H NMR (DMSO-d6) δ7.88 (d, 2H), 7.81 (d, 1H), 7.73 (d, 1H), 7.20–7.33 (m, 2H), 7.11 (d, 2H), 6.95 (s, 1H), 4.86 (s, 2H), 4.79 (s, 2H), 4.15 (t, 2H), 3.43–3.50 (m, 2H), 3.15–3.23 (m, 2H), 2.83–2.94 (m, 2H), 2.15–2.23 (m, 2H), 1.65–1.85 (m, 5H), 1.33–1.45 (m, 1H). MS (ES⁺) m/e 448. Mp(° C.)=138.

Example 243

1-(3-{4-[5-(Biphenyl-2-ylsulfanylmethyl)-[1,3,4]oxadiazol-2-yl]phenoxy}propyl)piperidine

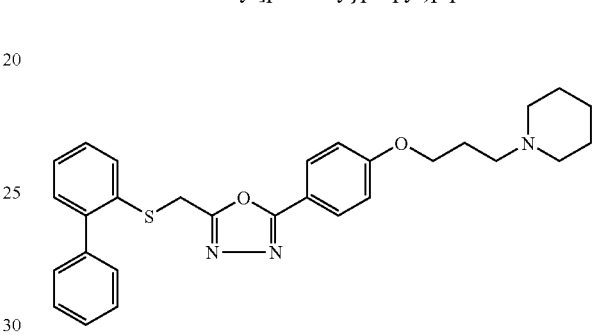

The above compound was prepared in a manner similar to that exemplified for the preparation of Example 220 from biphenyl-2-thiol (0.152 g, 0.82 mmol), 1-{3-[4-(5-chloromethyl-[1,3,4]oxadiazol-2-yl)phenoxy]propyl}piperidine (0.250 g, 0.74 mmol) and sodium hydride (0.033 g, 0.82 mmol) to afford 0.213 g (55%) of 1-(3-{4-[5-(biphenyl-2-ylsulfanylmethyl)-[1,3,4]oxadiazol-2-yl]phenoxy}propyl)piperidine as the hydrochloride salt.

¹H NMR (DMSO-d6) δ 7.78 (d, 2H, J=9 Hz), 7.66 (d, 1H, J=8 Hz), 7.29–7.40 (m, 5H, 7.20–7.25 (m, 3H), 7.11 (d, 2H, J=9 Hz), 4.39 (s, 2H), 4.15 (t, 2H, J=6 Hz), 3.40–3.48 (m, 2H), 3.12–3.21 (m, 2H), 2.81–2.91 (m, 2H), 2.12–2.23 (m, 2H), 1.65–1.83 (m, 5H), 1.32–1.41 (m, 1H). IR (KBr, cm⁻¹) 3435, 3058, 2947, 2632, 2496, 1614, 1586, 1497, 1466, 1428, 1309, 1249, 1176, 1084, 1052, 839, 746, 700. MS (ES⁺) m/e 486. Analytical HPLC: 100%. Mp(° C.)=165.

Example 244

3-{5-[4-(3-Piperidine-1-yl-propoxy)phenyl]-[1,3,4]oxadiazol-2-ylmethylsulfanyl}-1H-indole

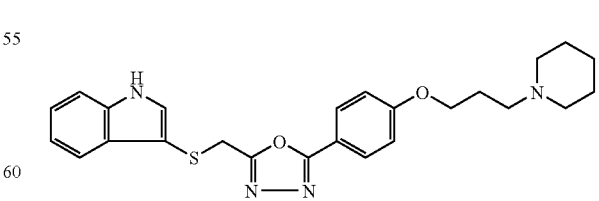

The above compound was prepared in a manner similar to that exemplified for the preparation of Example 220 from 3-mercaptoindole (0.252 g, 1.69 mmol), 1-{3-[4-(5-chloromethyl-[1,3,4]oxadiazol-2-yl)phenoxy]propyl}piperidine (0.515 g, 1.53 mmol) and sodium hydride (0.067 g, 1.69 mmol) to afford 0.2963 g (43%) of 3-{5-[4-(3-piperidine-1-yl-propoxy)phenyl]-[1,3,4]oxadiazol-2-ylmethylsulfanyl}-1H-indole.

¹H NMR (DMSO-d6) δ7.767 (d, 2H, J=Hz), 7.38–7.47 (m, 3H), 7.04–7.11 (m, 3H), 6.93–6.97 (m, 1H), 4.12 (s, 2H), 4.07 (t, 2H, J=6 Hz), 2.28–2.39 (m, 6H), 1.83–1.90 (m, 21), 1.43–1.52 (m, 4H), 1.32–1.40 (m, 2H). IR (KBr, cm⁻¹) 3221, 3097, 2933, 2850, 2765, 1609, 1567, 1500, 1463, 1423, 1302, 1256, 1173, 1127, 1017, 839, 738. MS (ES⁺) m/e 449, MS (ES⁻) m/e 447. Mp(° C.)=155.

Example 245

1-(3-{4-[5-(Benzofuran-2-ylsulfanylmethyl)-[1,3,4]oxadiazol-2-yl]phenoxy}propyl)piperidine

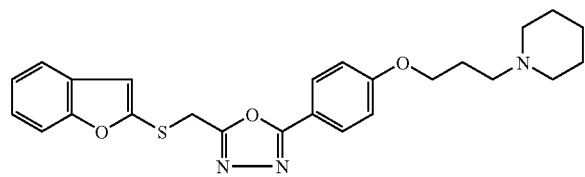

A suspension of 2-[1,2,3]thiazol-4-yl-phenol (0.0.082 g, 0.46 mmol), 1-{3-[4-(5-chloromethyl-[1,3,4]oxadiazol-2-yl)phenoxy]propyl}piperidine (0.154 g, 0.46 mmol) and potassium carbonate (0.076 g, 0.55 mmol) was refluxed for 48 hours then concentrated to an oil. The oil was treated with H₂O then extracted twice with EtOAc. The combined organic phases were washed with brine, dried over Na₂SO₄, filtered, concentrated to an oil. Purification by radial chromatography on silica gel (eluted with 5% 2M NH₃ in MeOH:CH₂Cl₂) followed by conversion to the HCl salt as described in Example 5 using the acetyl chloride/EtOH method to generate HCl in situ afforded 0.074 g (33%) of 1-(3-{4-[5-(benzofuran-2-ylsulfanylmethyl)-[1,3,4]oxadiazol-2-yl]phenoxy}propyl)piperidine as the hydrochloride salt.

¹HNMR (DMSO-d6) δ7.71 (d, 2H, J=9 Hz), 7.58 (d, 1H, J=7 Hz), 7.51 (d, 1H, J=7 Hz), 7.31–7.35 (m, 2H), 7.14 (s, 1H), 7.05 (d, 2H, J=9 Hz), 4.56 (s, 2H), 4.13 (t, 2H, J=6 Hz), 3.39–3.48 (m, 2H), 3.12–3.20 (m, 2H), 2.80–2.92 (m, 2H), 2.13–2.22 (m, 2H), 1.65–1.83 (m, 5H), 1.33–1.40 (m, 1H). IR (KBr, cm⁻¹) 2943, 2619, 2503, 1615, 1499, 1446, 1252, 1178, 1055, 944, 840, 750, 415. MS (ES⁺) m/e 450.

Example 246

Preparation of (3-{4-[4-benzyl-5-(2-phenoxyethylsulfanylmethyl)-4H-[1,2,4]triazol-3-yl]-phenoxy}-propyl)-dimethyl-amine, oxalic acid salt

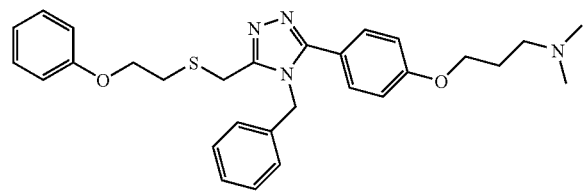

-continued

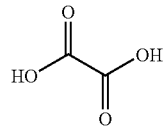

a) 4-Hydroxy-benzoic acid N'-[2-(2-phenoxy-ethylsulfanyl)-acetyl]-hydrazide

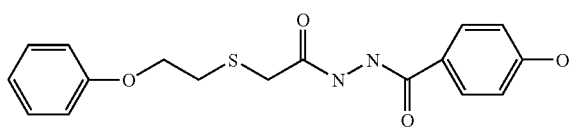

A solution of (2-phenoxy-ethylsulfanyl)-acetic acid (0.848 g, 4.0 mM) and (2-ethoxy-1-ethoxycarbonyl-1,2-dihdroquinoline, ethyl 1,2-dihydro-2-ethoxy-1-quinolinecarboxylate), (EEDQ), (0.989 g, 4.0 mM) in 20 mL acetonitrile and 5 mL THF were stirred together at room temperature for 1 hr. 4-Hydroxy-benzoic acid hydrazide (0.608 g, 4.0 mM) was added and the mixture was sonicated for 2 hrs and stirred at room temperature for 16 hrs. The mixture was concentrated to low volume and extracted with ethyl acetate. The organic extract was washed with 1N HCl, H₂O, NaHCO₃, brine, dried over magnesium sulfate, filtered, and concentrated to dryness to give 1.28 g (92%) of 4-hydroxy-benzoic acid N'-[2-(2-phenoxy-ethylsulfanyl)-acetyl]-hydrazide.

¹H NMR (DMSO-d6) δ 10.2 (s, 1H), 10.1 (s, 1H), 10.0 (s, 1H), 7.7 (d, 2H, J=9 Hz), 7.3 (m, 2H), 6.9 (m, 3H), 6.8 (d, 2H, J=9 Hz), 4.2 (t, 2H, J=6 Hz), 3.3 (m, 2H), 3.0 (t, 2H, J=6 Hz). IR (KBr, cm⁻¹) 3305, 3201, 3003, 2918, 2867, 1696, 1623, 1609, 1584, 1517, 1287, 1242, 1229. MS (ESI) m/e 347, 345. Anal. Calcd for C₁₇H₁₈N₂O₄S: C, 58.95; H, 5.24; N, 8.09. Found C, 58.37; H, 5.51; N, 7.19.

b) 4-[5-(2-phenoxy-ethylsulfanylmethyl)-[1,3,4]oxadiazol-2-yl]-phenol

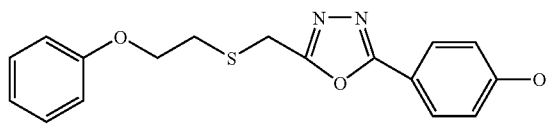

A solution of 4-hydroxy-benzoic acid N'-[2-(2-phenoxy-ethylsulfanyl)-acetyl]-hydrazide (4.87 g, 14.1 mM), triphenyl phosphine (7.38 g, 28.1 mM), and triethylamine (5.14 g, 50.7 mM) were stirred together in acetonitrile (15 mL). Carbon tetrachloride (9.17 g, 57.9 mM) was added and the mixture was stirred at room temperature for 3 hrs. The material was concentrated to low volume and diluted with hexane (100 mL), ethyl acetate (6 mL), and ethanol (25 mL). The mixture was sonnicated for 5 minutes and a precipitate formed. The solid was collected and dried in vaccuo (30° C.). The solid was slurried with 1N HCl, collected and dried to give 3.149 g (68%) of the title compound.

¹H NMR (DMSO-d6) δ 7.8 (d, 2H, J=9 Hz), 7.2 (t, 2H, J=8 Hz), 6.9 (m, 5H), 4.2 (m, 4H), 3.0 (t, 2H, J=6 Hz). IR (KBr, cm$^{-1}$) 3410, 1762, 1611, 1601, 1498, 1242, 1226, 1174, 752. MS (ESI) m/e 329, 327. Anal. Calcd for $C_{17}H_{16}N_2O_3S$: C, 62.18; H, 4.91; N, 8.53. Found C, 61.99; H, 5.00; N, 7.92. M.P.=172–175° C.

c) 4-[4-Benzyl-5-(2-phenoxy-ethylsulfanylmethyl)-4H-[1,2,4]triazol-3-yl]-phenol

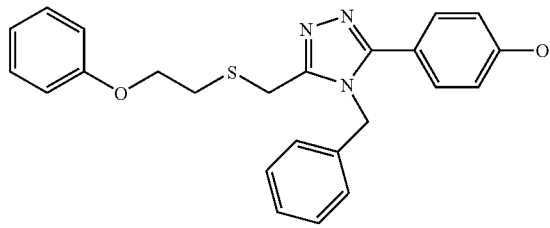

A heterogeneous mixture of 4-[5-(2-phenoxyethylsulfanylmethyl)-[1,3,4]oxadiazol-2-yl]-phenol (0.657 g, 2.0 m) in neat benzylamine (2.0 mL, 18.0 mM) was stirred at 120° C. for 18 h and at 150° C. for 6 h. The reaction mixture was allowed to cool to room temperature, diluted with ethyl acetate, and the organic layer washed with 1N HCl, water and brine, dried over anhydrous magnesium sulfate, filtered, and concentrated in vacuo to afford 0.903 g of a yellow gum. Purification by column chromatography on silica gel (isocratic elution with ethyl acetate) afforded 0.383 g (46%) of 4-[4-Benzyl-5-(2-phenoxy-ethylsulfanylmethyl)-4H-[1,2,4]triazol-3-yl]-phenol as a white foam (MP 64–66° C., MW 417.53).

$^1$H NMR (DMSO-$d_6$) δ 9.87 (s, 1H), 7.32 (d, 2H, J=8 Hz), 7.27 (m, 5H), 6.92 (d, 2H, J=8 Hz), 6.88 (m, 3H), 6.78 (d, 2H, J=9 Hz), 5.34 (s, 2H), 4.07 (t, 2H, J=7 Hz), 3.92 (s, 2H), and 2.91 (t, 2H, J=7 Hz). IR (KBr, cm$^{-1}$) 3050–2470, 1612, 1496, 1453, 1282, 1241, 1172, 840, 754, and 692. MS (ESI) m/e 418, 416. Anal. Calcd for $C_{24}H_{23}N_3O_2S$: C, 69.04; H, 5.55; N, 10.06; S, 7.68. Found C, 68.39; H, 5.45; N, 9.77; S, 7.52.

d) (3-{4-[4-benzyl-5-(2-phenoxyethylsulfanylmethyl)-4H-[1,2,4]triazol-3-yl]-phenoxy}-propyl)-dimethyl-amine, oxalic acid salt

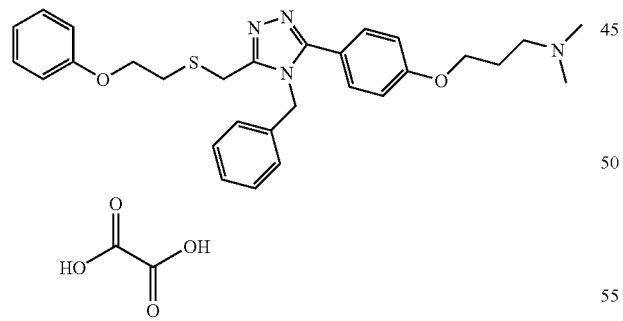

A heterogeneous mixture of 4-[4-Benzyl-5-(2-phenoxyethylsulfanylmethyl)-4H-[1,2,4]triazol-3-yl]-phenol (0.152 g, 0.36 mM), 3-chloro-N,N-dimethylpropylamine hydrochloride (0.063 g, 0.396 mM), and cesium carbonate (0.142 g, 0.432 mM) in 3 mL DMF was stirred at 90–100° C. for 7 h. Triton B (40 weight % in CH$_3$OH, 0.082 mL, 0.18 mM, 0.5 eq) was then added, and the reaction mixture heated at 90° C. for an additional 1.5 h. The reaction mixture was allowed to cool to room temperature and diluted with ethyl acetate/H$_2$O. The solvent layers were separated, the aqueous layer back extracted with ethyl acetate, the combined organic extracts washed with water, saturated NaHCO$_3$ solution, 1N NaOH, and brine, dried over anhydrous sodium sulfate, filtered, and concentrated in vacuo to afford 0.136 g of a yellow gum. Purification by column chromatography on silica gel (isocratic elution with ethyl acetate followed by 9:1 CHCl$_3$/2.0 M ammonia in methanol) afforded 0.101 g (55%) of (3-{4-[4-benzyl-5-(2-phenoxyethylsulfanylmethyl)-4H-[1,2,4]triazol-3-yl]-phenoxy}-propyl)-dimethylamine as an oily gum. The gum (0.099 g, 0.196 mM) was dissolved in 2 mL acetone, and oxalic acid (0.019 g, 0.216 mM), dissolved in 1 mL acetone, was added with rapid stirring at room temperature followed by the addition of diethyl ether/hexane (1:1, 2 mL). Filtered the resultant thick precipitate, washed the collected solid with acetone and diethyl ether, and dried in vacuo at 40° C. to afford 0.104 g (89%) of (3-{4-[4-benzyl-5-(2-phenoxyethylsulfanylmethyl)-4H-[1,2,4]triazol-3-yl]-phenoxy}-propyl)-dimethylamine, oxalic acid salt as an off-white solid (MP 88–92° C., MW oxalate salt 592.72, MW free amine 502.68).

$^1$H NMR (DMSO-$d_6$) δ 7.46 (d, 2H, J=9 Hz), 7.26 (m, 5H), 6.98 (d, 2H, J=9 Hz), 6.92 (m, 3H), 6.88 (d, 2H, J=9 Hz), 5.37 (s, 2H), 4.06 (m, 4H), 3.95 (s, 2H), 3.13 (m, 2H), 2.91 (t, 2H, J=6 Hz), 2.74 (s, 6H), and 2.06 (m, 2H). IR (KBr, cm$^{-1}$) 3037–2870, 2700–2500, 1721, 1611, 1478, 1248, 1176, 1036, 704, and 475. MS (ESI) m/e 503. Anal. Calcd for $C_{29}H_{34}N_4O_2S \cdot C_2H_2O_4$: C, 62.82; H, 6.12; N, 9.45; S, 5.41. Found C, 56.37; H, 5.27; N, 8.26; S, 5.37. Analytical HPLC: 88% purity.

Example 247

Preparation of Dimethyl-(3-{4-[5-(2-phenoxy-ethylsulfanylmethyl)-4-phenyl-4H-[1,2,4]triazol-3-yl]-phenoxy}-propyl)-amine, oxalic acid salt

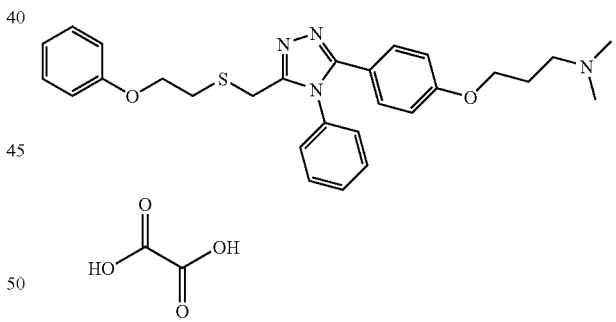

a) 4-Hydroxy-benzoic acid M-[2-(2-phenoxyethylsulfanyl)-acetyl]-hydrazide

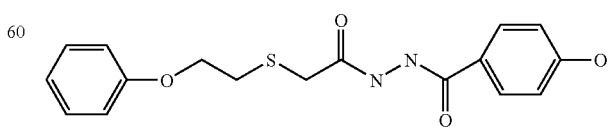

The above compound was prepared in an identical manner as exemplified in Example 246a.

b) 4-[5-(2-phenoxy-ethylsulfanylmethyl)-[1,3,4]oxadiazol-2-yl]-phenol

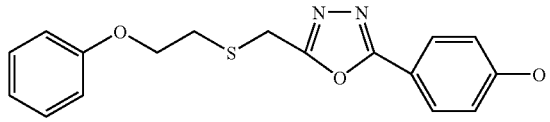

The above compound was prepared in an identical manner as exemplified in Example 246b.

c) 4-[5-(2-Phenoxy-ethylsulfanylmethyl)-4-phenyl-4H-[1,2,4]triazol-3-yl]-phenol

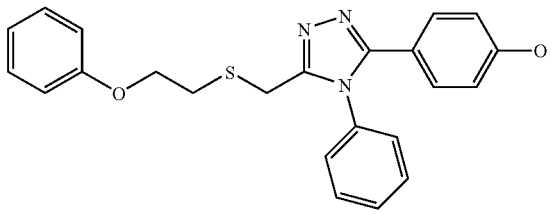

A heterogeneous mixture of 4-[5-(2-phenoxyethylsulfanylmethyl)-[1,3,4]oxadiazol-2-yl]-phenol (0.985 g, 3.0 mM) in neat aniline (2.0 mL, 22.0 mM) was stirred at 150° C. for 12 h. The reaction mixture was allowed to cool to room temperature, diluted with ethyl acetate, and the organic layer washed with 1N HCl, water and brine, dried over anhydrous magnesium sulfate, filtered, and concentrated in vacuo to afford a light tan solid. Added ethyl acetate and diethyl ether to the solid, sonicated, filtered, washed the collected solid with ethyl acetate and diethyl ether, and dried in vacuo at 40° C. to afford 0.99 g (82%) of 4-[5-(2-Phenoxy-ethylsulfanylmethyl)-4-phenyl-4H-[1,2,4]triazol-3-yl]-phenol as a light lavender solid (MP 214–216° C., MW 403.51.

$^1$H NMR (DMSO-d$_6$) δ 9.83 (s, 1H), 7.51 (m, 3H), 7.38 (m, 2H), 7.26 (t, 2H, J=7 Hz), 7.12 (d, 2H, J=9 Hz), 6.91 (t, 1H, J=7 Hz), 6.87 (d, 2H, J=10 Hz), 6.66 (d, 2H, J=9 Hz), 4.02 (t, 2H, J=6 Hz), 3.80 (s, 2H), and 2.85 (t, 2H, J=7 Hz). IR (KBr, cm$^{-1}$) 3050–2487, 1607, 1585, 1499, 1469, 1285, 1244, 1176, 1037, and 691. MS (ESI) m/e 404, 402. Anal. Calcd for C$_{23}$H$_{21}$N$_3$O$_2$S: C, 68.46; H, 5.25; N, 10.41; S, 7.95. Found C, 68.58; H, 5.26; N, 10.40; S, 7.94.

d) Dimethyl-(3-{4-[5-(2-phenoxy-ethylsulfanylmethyl)-4-phenyl-4H-[1,2,4]triazol-3-yl]-phenoxy}-propyl)-amine, oxalic acid salt

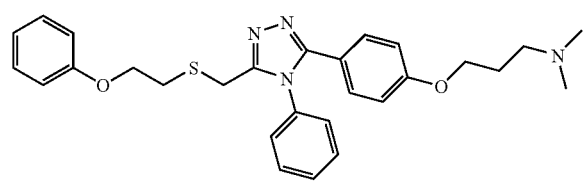

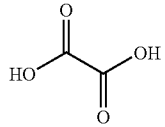

A heterogeneous mixture of 4-[5-(2-Phenoxy-ethylsulfanylmethyl)-4-phenyl-4H-[1,2,4]triazol-3-yl]-phenol (0.161 g, 0.4 mM), 3-chloro-N,N-dimethylpropylamine hydrochloride (0.07 g, 0.44 mM), and Triton B (40 weight % in CH$_3$OH, 0.418 mL, 0.92 mM) in 3 mL DMF was stirred at 90° C. for 4.5 h. Cesium carbonate (0.099 g, 0.3 mM, 0.75 eq) was then added, and the reaction mixture heated at 90° C. for an additional 2.5 h. The reaction mixture was allowed to cool to room temperature and diluted with ethyl acetate/H$_2$O. The solvent layers were separated, the aqueous layer back extracted with ethyl acetate, the combined organic extracts washed with water, saturated NaHCO$_3$ solution, 1N NaOH, and brine, dried over anhydrous sodium sulfate, filtered, and concentrated in vacuo to afford 0.155 g of a lavender gum. Purification by column chromatography on silica gel (isocratic elution with ethyl acetate followed by 95:5 CHCl$_3$/2.0 M ammonia in methanol) afforded 0.137 g (70%) of Dimethyl-(3-{4-[5-(2-phenoxy-ethylsulfanylmethyl)-4-phenyl-4H-[1,2,4]triazol-3-yl]-phenoxy}-propyl)-amine as an off-white. The gum (0.135 g, 0.276 mM) was dissolved in 2 mL acetone, and oxalic acid (0.028 g, 0.304 mM), dissolved in 1 mL acetone, was added with rapid stirring at room temperature followed by the addition of diethyl ether/hexane (1:2, 3 mL). Filtered the resultant thick precipitate, washed the collected solid with diethyl ether and hexane, and dried in vacuo at 40° C. to afford 0.153 g (96%) of Dimethyl-(3-{4-[5-(2-phenoxy-ethylsulfanylmethyl)-4-phenyl-4H-[1,2,4]triazol-3-yl]-phenoxy}-propyl)-amine, oxalic acid salt as a white solid (MP 120–123° C., MW oxalate salt 578.70, MW free amine 488.66).

$^1$H NMR (DMSO-d6) δ 7.51 (m, 3H), 7.41 (m, 2H), 7.34 (m, 2H), 7.25 (d, 2H, J=9 Hz), 6.91 (t, 1H, J=7 Hz), 6.88 (d, 2H, J=9 Hz), 6.87 (d, 2H, J=7 Hz), 4.01 (m, 4H), 3.81 (s, 2H), 3.10 (m, 2H), 2.86 (t, 2H, J=6 Hz), 2.72 (s, 6H), and 2.03 (m, 2H). IR (KBr, cm$^{-1}$) 2950–2870, 2700–2500, 1612, 1600, 1586, 1497, 1477, 1403, 1258, 1246, 1181, 704, and 694. MS (ESI) m/e 489. Anal. Calcd for C$_{28}$H$_{32}$N$_4$O$_2$S.C$_2$H$_2$O$_4$: C, 62.27; H, 5.92; N, 9.68; S, 5.54. Found C, 60.86; H, 5.40; N, 9.40; S, 5.61. Analytical HPLC: 94% purity.

Example 248

Preparation of Dimethyl-(3-{4-[5-(4-phenoxy-phenyl)-[1,3,4]oxadiazol-2-yl]-phenoxy}-propyl)-amine

a) 4-Hydroxy-benzoic acid N'-(4-phenoxy-benzoyl)-hydrazide

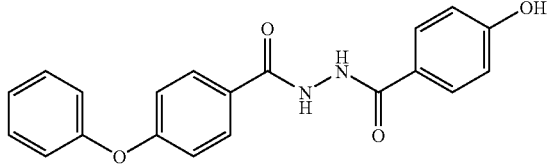

The above compound was prepared in a manner similar to that exemplified for the preparation of Example 51a, from 4-phenoxybenzoic acid (1.09 g, 5.0 mM) to afford 1.01 g (58%) of 4-Hydroxy-benzoic acid N'-(4-phenoxy-benzoyl)-hydrazide as a white solid (MP 203–205° C., MW 348.36).

$^1$HNMR (DMSO-d$_6$) δ 10.32 (s, 1H), 10.19 (s, 1H), 10.08 (s, 1H), 7.93 (d, 2H, J=9 Hz), 7.78 (d, 2H, J=Hz), 7.44 (t, 2H, J=8 Hz), 7.22 (t, 1H, J=8 Hz), 7.10 (d, 2H, J=8 Hz), 7.06 (d, 2H, J=9 Hz), and 6.83 (d, 2H, J=9 Hz). IR (KBr, cm$^{-1}$) 3216, 1656, 1614, 1586, 1573, 1515, 1488, 1284, 1247, 1169, 844, 753, and 693. MS (ESI) m/e 349, 347. Anal. Calcd for C$_{20}$H$_{16}$N$_2$O$_4$: C, 68.96; H, 4.63; N, 8.04. Found C, 68.65; H, 4.68; N, 8.00.

b) 4-[5-(4-phenoxy-phenyl)-[1,3,4]oxadiazol-2-yl]-phenol

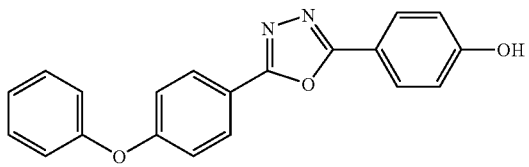

The above compound was prepared in a manner similar to that exemplified for the preparation of Example 49e, from 4-hydroxy-benzoic acid N'-(4-phenoxy-benzoyl)-hydrazide (1.01 g, 2.9 mM), triphenylphosphine (1.54 g, 5.8 mM), and triethylamine (1.46 mL, 10.44 mM) to afford 0.65 g (68%) of 4-[5-(4-phenoxy-phenyl)-[1,3,4]oxadiazol-2-yl]-phenol as a white solid (MP 204–206° C., MW 330.35).

$^1$H NMR (DMSO-d6) δ 10.31 (s, 1H), 8.07 (d, 2H, J=9 Hz), 7.92 (d, 2H, J=9 Hz), 7.45 (t, 2H, J=8 Hz), 7.23 (t, 1H, J=7 Hz), 7.15 (d, 2H, J=9 Hz), 7.13 (d, 2H, J=9 Hz), and 6.95 (d, 2H, J=9 Hz). IR (KBr, cm$^{-1}$) 3125, 1740, 1612, 1588, 1492, 1379, 1287, 1240, 1167, 1099, 1068, 868, 847, 746, 695, and 510. MS (ESI) m/e 331, 329. Anal. Calcd for C$_{20}$H$_{14}$N$_2$O$_3$: C, 72.72; H, 4.27; N, 8.48. Found C, 70.35; H, 4.66; N, 7.27.

c) Dimethyl-(3-{4-[5-(4-phenoxy-phenyl)-[1,3,4]oxadiazol-2-yl]-phenoxy}-propyl)-amine

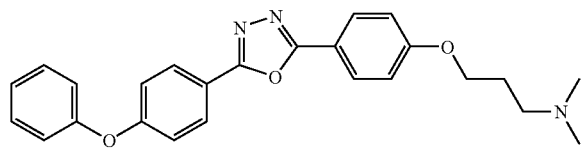

The above compound was prepared in a manner similar to that exemplified for the preparation of Example 50f, from 4-[5-(4-phenoxy-phenyl)-[1,3,4]oxadiazol-2-yl]-phenol (0.298 g, 0.9 mM) and purified by Chromatotron radial chromatography on silica gel (isocratic elution with 95:5 CH$_2$Cl$_2$/2.0 M ammonia in methanol) to afford 0.295 g (780%) of Dimethyl-(3-{4-[5-(4-phenoxy-phenyl)-[1,3,4]oxadiazol-2-yl]-phenoxy}-propyl)-amine as a white solid (MP 95° C., MW 415.50).

$^1$H NMR (CDCl$_3$) δ 8.07 (d, 2H, J=9 Hz), 8.04 (d, 2H, J=9 Hz), 7.40 (t, 2H, J=8 Hz), 7.20 (t, 1H, J=8 Hz), 7.10 (d, 2H, J=9 Hz), 7.09 (d, 2H, J=9 Hz), 7.02 (d, 2H, J=9 Hz), 4.12 (t, 2H, J=6 Hz), 2.61 (t, 2H, J=7 Hz), 2.38 (s, 6H), and 2.08 (m, 2H). IR (KBr, cm$^{-1}$) 2954, 2821, 2764, 1610, 1488, 1417, 1298, 1246, 1171, 1068, 996, 871, 835, 742, 689, 670, and 510. MS (ESI) m/e 416. Anal. Calcd for C$_{25}$H$_{25}$N$_3$O$_3$: C, 72.27; H, 6.06; N, 10.11. Found C, 71.99; H, 6.29; N, 9.94. Analytical HPLC: 100% purity.

Example 249

Preparation of {3-[4-(5-Biphenyl-4-yl-methyl-[1,3,4]oxadiazol-2-yl)-phenoxy]-propyl}-dimethyl-amine

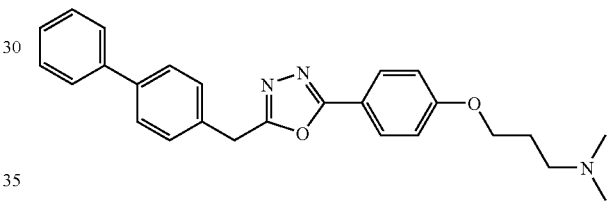

a) 4-Hydroxy-benzoic acid N-(2-biphenyl-4-yl-acetyl)-hydrazide

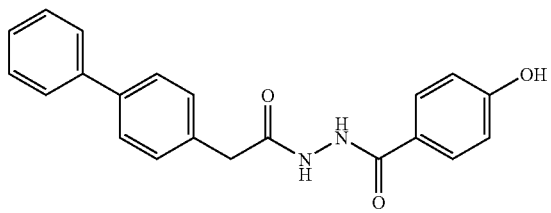

The above compound was prepared in a manner similar to that exemplified for the preparation of Example 51a, from 4-biphenylacetic acid (1.08 g, 5.0 m) to afford 1.58 g (91%) of 4-Hydroxy-benzoic acid N'-(2-biphenyl-4-yl-acetyl)-hydrazide as a white solid (MP 234–239° C. dec, MW 346.13).

$^1$H NMR (DMSO-d$_6$) δ 10.10 (s, 1H), 10.09 (s, 1H), 10.05 (s, 1H), 7.73 (d, 2H, J=9 Hz), 7.64 (d, 2H, J=7 Hz), 7.60 (d, 2H, J=8 Hz), 7.44 (t, 2H, J=8 Hz), 7.43 (d, 2H, J=8 Hz), 7.34 (t, 1H, J=7 Hz), 6.80 (d, 2H, J=9 Hz), and 3.56 (s, 2H). IR (KBr, cm$^{-1}$) 3265, 1663, 1605, 1572, 1485, 1281, 1230, 847, 740, and 497. MS (ESI) m/e 347, 345. Anal. Calcd for C$_{21}$H$_{18}$N$_2$O$_3$: C, 72.82; H, 5.24; N, 8.09. Found C, 71.83; H, 5.35; N, 8.31.

b) 4-(5-Biphenyl-4-yl-methyl-[1,3,4]oxadiazol-2-yl)-phenol

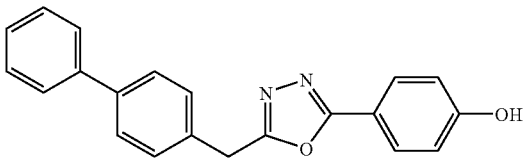

The above compound was prepared in a manner similar to that exemplified for the preparation of Example 49e, from 4-Hydroxy-benzoic acid N'-(2-biphenyl-4-yl-acetyl)-hydrazide (1.56 g, 4.5 mM), triphenylphosphine (2.38 g, 9.0 mM), and triethylamine (2.26 mL, 16.2 mM) to afford 0.798 g (54%) of 4-(5-Biphenyl-4-yl-methyl-[1,3,4]oxadiazol-2-yl)-phenol as a light yellow solid (MP 252–255° C., MW 328.37).

$^1$H NMR (DMSO-d$_6$) δ 10.24 (s, 1H), 7.76 (d, 2H, J=9 Hz), 7.63 (m, 4H), 7.43 (m, 4H), 7.33 (t, 1H, J=7 Hz), 6.90 (d, 2H, J=9 Hz), and 4.34 (s, 2H). IR (KBr, cm$^{-1}$) 3055, 1612, 1569, 1497, 1431, 1370, 1285, 1238, 1173, 1087, 1030, 862, 819, 757, 692, and 522. MS (ESI) m/e 329, 327. Anal. Calcd for C$_{21}$H$_{16}$N$_2$O$_2$: C, 76.81; H, 4.91; N, 8.53. Found C, 76.41; H, 5.03; N, 8.19.

c) {3-[4-(5-Biphenyl-4-yl-methyl-[1,3,4]oxadiazol-2-yl)-phenoxy]-propyl}-dimethyl-amine

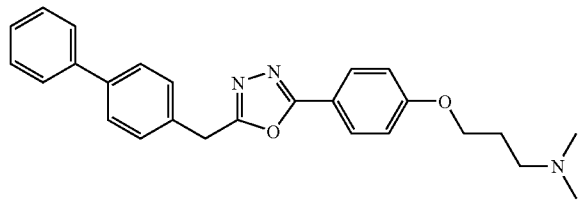

The above compound was prepared in a manner similar to that exemplified for the preparation of Example 50f, from 4-(5-Biphenyl-4-yl-methyl-[1,3,4]oxadiazol-2-yl)-phenol (0.328 g, 1.0 mM), 3-chloro-N,N-dimethylpropylamine hydrochloride (0.174 g, 1.1 mM), and sodium hydride (0.092 g, 2.3 mM) in 7 mL DMF to afford 0.461 g of a brown gum. A second lot of the above compound was prepared in a manner similar to that exemplified for the preparation of Example 50f, from 4-(5-Biphenyl-4-yl-methyl-[1,3,4]oxadiazol-2-yl)-phenol (0.164 g, 0.5 mM), 3-chloro-N,N-dimethylpropylamine hydrochloride (0.087 g, 0.55 mM), and cesium carbonate (0.197 g, 0.6 mM) in 3 mL DMF to afford 0.173 g of a yellow-orange solid. The combined lots were purified by Chromatotron radial chromatography on silica gel (isocratic elution with 97:3 Et$_2$O/2.0 M ammonia in methanol) to afford 0.113 g (18%) of {3-[4-(5-Biphenyl-4-yl-methyl-[1,3,4]oxadiazol-2-yl)-phenoxy]-propyl}-dimethyl-amine as a white solid (95–97° C., MW 413.52).

$^1$H NMR (CDCl$_3$) δ 7.94 (d, 2H, J=9 Hz), 7.58 (d, 2H, J=8 Hz), 7.57 (d, 2H, J=7 Hz), 7.44 (t, 2H, J=8 Hz), 7.43 (d, 2H, J=8 Hz), 7.34 (t, 1H, J=7 Hz), 6.96 (d, 2H, J=9 Hz), 4.31 (s, 2H), 4.12 (t, 2H, J=6 Hz), 2.81 (m, 2H), 2.53 (bs, 6H), and 2.20 (m, 2H). IR (KBr, cm$^{-1}$) 2943, 2857, 2813, 2762, 1613, 1568, 1501, 1473, 1249, 1174, 1035, 832, 757, 739, and 699. MS (ESI) m/e 414, 412. Anal. Calcd for C$_{26}$H$_{27}$N$_3$O$_2$: C, 75.52; H, 6.58; N, 10.16. Found C, 75.12; H, 6.54; N, 10.01. Analytical HPLC: 100% purity.

Example 250

Preparation of 1-(2-Dimethylamino-ethyl)-3-{4-[2-(2-phenoxy-ethylsulfanylmethyl)-oxazol-5-yl]-phenyl}-urea maleate

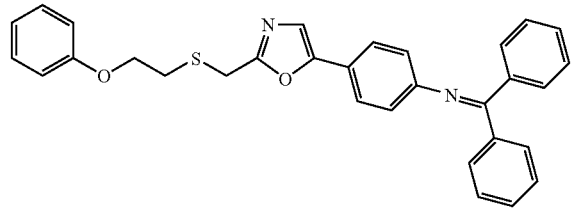

a) Benzhydrylidene-{4-[2-(2-phenoxy-ethylsulfanylmethyl)-oxazol-5-yl]-phenyl}-amine

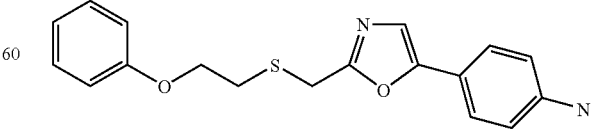

Combined 5-(4-bromo-phenyl)-2-(2-phenoxy-ethylsulfanylmethyl)-oxazole (0.5 g, 1.28 mmol, 1 eq., Example 268f), benzophenone imine (0.30 g, 1.54 mmol, 1.2 eq.), tris(dibenzylideneacetone)dipalladium(0) (3 mg, 3.2 pmol, 0.25%), (±)-BINAP (6 mg, 9.60 □mol, 0.75%), and sodium tert-butoxide (0.17 g, 1.79 mmol, 1.4 eq.) in toluene (10 mL) and heated to 105° C. overnight. Diluted the cooled reaction with EtOAc and washed with water. The organic layer was collected, dried over MgSO$_4$, filtered, and the solvent removed leaving an orange oil which was purified via normal phase chromatography using 25% EtOAc in hexanes as the mobile phase leaving benzhydrylidene-{4-[2-(2-phenoxy-ethylsulfanylmethyl)-oxazol-5-yl]-phenyl}-amine (0.63 g, 100% yield) as a yellow oil.

$^1$H NMR (DMSO-d6) δ 7.67 (m, 2H), 7.48 (m, 7H), 7.25 (m, 6H), 6.93 (m, 3H), 6.77 (m, 2H), 4.16 (t, 2H, J=7 Hz), 4.01 (s, 2H), 2.98 (t, 2H, J=7 Hz). IR (CHCl$_3$, cm$^{-1}$) 3003.6, 1600.7, 1570.8, 1494.6, 1293.1, 1241. MS(ES$^+$) m/e 491 [M+H]$^+$. Anal. Calcd. for C$_{31}$H$_{26}$N$_2$O$_2$S C, 75.89; H, 5.34; N, 5.71. Found C, 75.50; H, 5.42; N, 5.63. M.P.=86–90° C.

b) 4-[2-(2-Phenoxy-ethylsulfanylmethyl)-oxazol-5-yl]-phenylamine

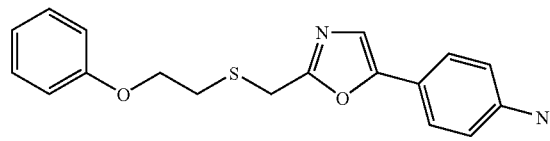

A THF solution (15 mL) of benzhydrylidene-{4-[2-(2-phenoxy-ethylsulfanylmethyl)-oxazol-5-yl]-phenyl}-amine (2.0 g, 4.08 mmol, 1 eq.) was treated with 0.75 mL of 2 M aqueous HCl and the solution allowed to stir at room temperature for 1 hour. Diluted with 0.5 M aqueous HCl and extracted with EtOAc. Collected the organic layer, dried over MgSO$_4$, filtered, and removed the solvent in vacuo leaving an orange oil which was purified via normal phase chromatography using a step gradient of EtOAc in hexanes as the mobile phase resulting in 4-[2-(2-phenoxy-ethylsulfanylmethyl)-oxazol-5-yl]-phenylamine (1.2 g, 90% yield) as yellow solid after removal of the solvent.

$^1$H NMR (DMSO-d6) δ 7.27 (m, 4H), 6.93 (m, 3H), 6.60 (m, 21), 4.16 (t, 2H, J=7 Hz), 4.0 (s, 2H), 2.98 (t, 2H, J=7 Hz). IR (KBr, cm$^{-1}$) 3461.7, 3339, 1627.5, 1613.9, 1601, 1505.7, 1488.7, 1299, 1242, 1231.3, 1175, 1099.3, 828.1, 757.8, 749.9. MS(ES$^+$) m/e 327 [M+H]$^+$. Anal. Calcd. for C$_{18}$H$_{18}$N$_2$O$_2$S C, 66.23; H, 5.56; N, 8.58. Found C, 65.98; H, 5.56; N, 8.45. M.P.=110–111° C.

c) {-[2-(2-Phenoxy-ethylsulfanylmethyl)-oxazol-5-yl]-phenyl}-carbamic acid ethyl ester

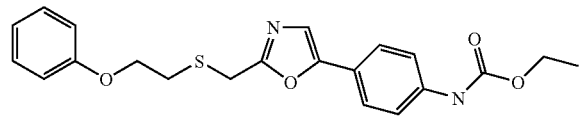

The above compound was prepared in a manner similar to that exemplified for the preparation of Example 101a from 4-[2-(2-phenoxy-ethylsulfanylmethyl)-oxazol-5-yl]-phenylamine (1.63 g, 4.99 mmol, 1 eq.) and ethyl chloroformate (0.81 g, 7.49 mmol, 1.5 eq.) to produce {4-[2-(2-phenoxy-ethylsulfanylmethyl)-oxazol-5-yl]-phenyl}-carbamic acid ethyl ester (1.99 g, 100% yield) as a yellow solid.

$^1$H NMR (DMSO-d6) δ 9.81 (s, 1H), 7.57 (m, 4H), 7.47 (s, 1H), 7.27 (m, 2H), 6.93 (m, 3H), 4.15 (m, 4H), 4.04 (s, 2H), 3.0 (t, 2H, J=7 Hz), 1.25 (t, 3H, J=7 Hz). MS(ES$^+$) m/e 399 [M+H]$^+$. MS(ES$^-$) m/e 397 [M-H]$^-$.

d) Preparation of 1-(2-dimethylamino-ethyl)-3-{4-[2-(2-phenoxy-ethylsulfanylmethyl)-oxazol-5-yl]-phenyl}-urea maleate

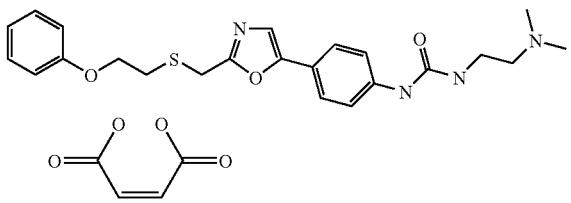

The above compound was prepared in a manner similar to that exemplified for the preparation of Example 101e from {4-[2-(2-phenoxy-ethylsulfanylmethyl)-oxazol-5-yl]-phenyl}-carbamic acid ethyl ester (1.0 g, 2.5 mmol, 1 eq.) and N,N-dimethylethylenediamine (0.26 g, 3.0 mmol, 1.2 eq.) to produce 1-(2-dimethylamino-ethyl)-3-{4-[2-(2-phenoxy-ethylsulfanylmethyl)-oxazol-5-yl)-phenyl}-urea (1.05 g, 95% yield) as a yellow oil.

An EtOAc solution of 1-(2-dimethylamino-ethyl)-3-{4-[2-(2-phenoxy-ethylsulfanylmethyl)-oxazol-5-yl]-phenyl}-urea (0.51 g, 1.16 mmol, 1 eq.) was treated dropwise with an EtOAc solution of maleic acid (0.15 g, 1.28 mmol, 1.1 eq.). Removed the EtOAc in vacuo and added Et$_2$O and boiled the resulting gum until 1-(2-dimethylamino-ethyl)-3-{4-[2-(2-phenoxy-ethylsulfanylmethyl)-oxazol-5-yl]-phenyl}-urea maleate (0.43 g, 68% yield) was obtained as a yellow solid.

$^1$H NMR (DMSO-d6) δ 8.98 (s, 1H), 7.54 (m, 4H), 7.44 (s, 1H), 7.27 (m, 2H), 6.93 (m, 3H), 6.41 (t, 1H, J=6 Hz), 6.03 (s, 2H), 4.17 (t, 2H, J=7 Hz), 4.04 (s, 2), 3.44 (m, 2H), 3.15 (m, 2H), 2.99 (t, 2H, J=7 Hz), 2.82 (s, 6H). IR (KBr, cm$^{-1}$) 3402.4, 1695.6, 1607.6, 1547.2, 1498.6, 1465, 1359.6, 1322.2, 1227.1, 867.3, 754.4. MS(ES$^+$) m/e 441 [M+H]$^+$. MS(ES$^-$) m/e 439 [M-H]$^-$. Anal. Calcd. for C$_{27}$H$_{32}$N$_4$O$_7$S C, 58.26; H, 5.79; N, 10.07. Found C, 57.68; H, 5.58; N, 9.88. Analytical LC/MS 100% (diode array detector). M.P.=105–107° C.

Example 251

Preparation of 1-{4-[2-(2-phenoxy-ethylsulfanylmethyl)-oxazol-5-yl]-phenyl}-3-pyrrolidin-1-ylmethyl-urea oxalate

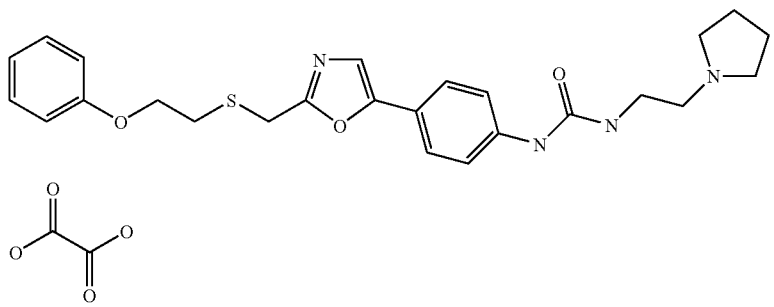

The above compound was prepared in a manner similar to that exemplified for the preparation of Example 101e from {4-[2-(2-phenoxy-ethylsulfanylmethyl)-oxazol-5-yl]-phenyl}-carbamic acid ethyl ester (1.0 g, 2.5 mmol, 1 eq.) and 1-(2-aminoethyl)pyrrolidine (0.34 g, 3.0 mmol, 1.2 eq.) to produce 1-{4-[2-(2-phenoxy-ethylsulfanylmethyl)-oxazol-5-yl]-phenyl}-3-pyrrolidin-1-ylmethyl-urea (1.14 g, 97% yield) as a yellow oil.

An EtOAc solution of the urea was treated with an EtOAc solution of oxalic acid (0.20 g, 1.1 eq.) producing 1-{4-[2-(2-phenoxy-ethylsulfanylmethyl)-oxazol-5-yl]-phenyl}-3-pyrrolidin-1-ylmethyl-urea oxalate (0.57 g) as an off-white solid that was collected by filtration.

Hz), 4.03 (s, 2H), 3.19 (m, 2H), 2.99 (t, 2H, J=7 Hz), 2.34 (m, 6H), 1.51 (m, 4H), 1.38 (m, 2H). IR (CHCl$_3$, cm$^{-1}$) 2941.6, 1684.5, 1601, 1587.4, 1520.3, 1504.9, 1498.4, 1243.7. MS(ES$^+$) m/e 481 [M+H]$^+$. MS(ES$^-$) m/e 479 [M−H]$^-$. Analytical LC/MS 100% purity (diode array detector). M.P.=84–87° C.

Example 253

Preparation of 1-{4-[2-(2-Phenoxy-ethylsulfanylmethyl)-oxazol-5-yl]-phenyl}-3-(3-pyrrolidin-1-yl-propyl)-urea oxalate

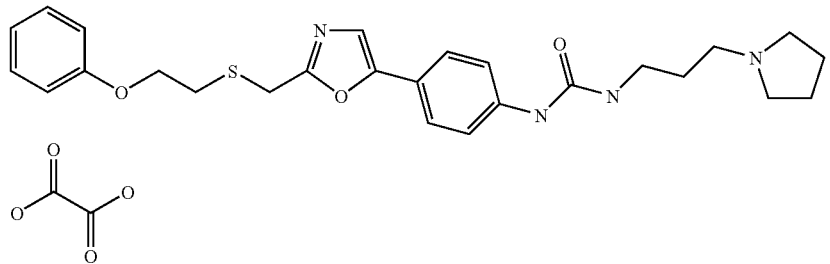

$^1$H NMR (DMSO-d6) δ 9.37 (s, 1H), 7.53 (bs, 4H), 7.43 (s, 1H), 7.27 (m, 2H), 7.09 (bs, 1H), 6.93 (m, 3H), 4.17 (t, 2H, J=7 Hz), 4.04 (s, 2H), 3.41 (bs, 2H), 3.22 (m, 6H), 2.99 (t, 2H, J=7 Hz), 1.92 (bs, 4H). IR (KBr, cm1) 3367.2, 3283.3, 1733.7, 1688.4, 1587.2, 1536, 1504.2, 1317.2, 1233.3, 711.6. MS(ES$^+$) m/e 467 [M+H]$^+$. MS(ES$^-$) m/e 465 [M−H]$^-$. Anal. Calcd. for C$_{27}$H$_{32}$N$_4$O$_7$S C, 58.26; H, 5.79; N, 10.07. Found C, 57.82; H, 5.76; N, 9.86. Analytical LC/MS 95% purity (diode array detector). M.P.=124–126° C.

Example 252

Preparation of 1-{4-[2-(2-Phenoxy-ethylsulfanylmethyl)-oxazol-5-yl]-phenyl}-3-piperidin-1-ylmethyl-urea

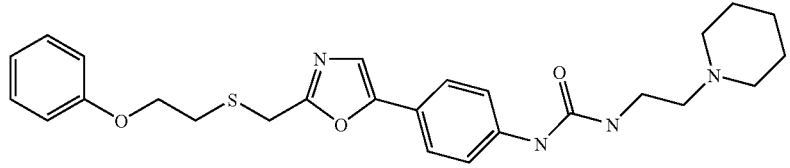

The above compound was prepared in a manner similar to that exemplified for the preparation of Example 101e from {4-[2-(2-phenoxy-ethylsulfanylmethyl)-oxazol-5-yl]-phenyl}-carbamic acid ethyl ester (1.75 g, 4.39 mmol, 1 eq.) and 1-(2-aminoethyl)piperidine (0.68 g, 5.27 mmol, 1.2 eq.) to obtain 1-{4-[2-(2-phenoxy-ethylsulfanylmethyl)-oxazol-5-yl]-phenyl}-3-piperidin-1-ylmethyl-urea (0.88 g, 42% yield) as a yellow solid.

$^1$H NMR (DMSO-d6) δ 8.85 (s, 1H), 7.50 (m, 5H), 7.27 (m, 2H), 6.92 (m, 3H), 6.10 (t, 1H, J=6 Hz), 4.17 (t, 2H, J=7

The above compound was prepared in a manner similar to that exemplified for the preparation of Example 101e from {4-[2-(2-phenoxy-ethylsulfanylmethyl)-oxazol-5-yl]-phenyl}-carbamic acid ethyl ester (0.55 g, 1.38 mmol, 1 eq.) and 1-(3-aminopropyl)pyrrolidine (0.21 g, 1.66 mmol, 1.2 eq.) to produce 1-{4-[2-(2-phenoxy-ethylsulfanylmethyl)-oxazol-5-yl]-phenyl}-3-(3-pyrrolidin-1-yl-propyl)-urea (0.42 g, 64% yield) as a yellow oil.

An EtOAc solution of the free base was treated with an EtOAc solution of oxalic acid (0.09 g, 1.1 eq.) producing 1-{4-[2-(2-phenoxy-ethylsulfanylmethyl)-oxazol-5-yl]-phenyl}-3-(3-pyrrolidin-1-yl-propyl)-urea oxalate (0.46 g) as a light yellow solid.

$^1$H NMR (DMSO-d6) δ 9.25 (s, 1H), 7.53 (bs, 4H), 7.42 (s, 1H), 7.27 (m, 2), 6.93 (m, 4H), 4.17 (t, 2H, J=7 Hz), 4.04 (s, 2H), 3.24 (b, 4H), 3.16 (m, 4H), 2.99 (t, 2H, J=7 Hz), 1.92 (bs, 4H), 1.81 (m, 2H). IR (KBr, cm$^{-1}$) 3383, 3039.7, 1688.7, 1586.4, 1535.5, 1504.4, 1413.8, 1317.3, 1236.1, 840, 756.6, 694.7. MS(ES$^+$) m/e 481 [M+H]$^+$. MS(ES$^-$) m/e 479 [M−H]$^-$. Analytical LC/MS 85% purity (diode array detector).

Example 254

Preparation of 1-{4-[2-(benzofuran-2-ylmethoxymethyl)-oxazol-5-yl]-phenyl}-3-(2-dimethylaminoethyl)-urea

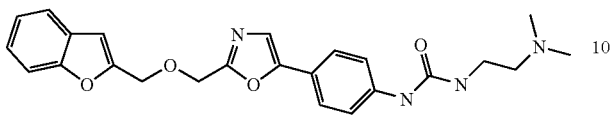

a) 2-(Benzofuran-2-ylmethoxymethyl)-5-(4-bromophenyl)-oxazole

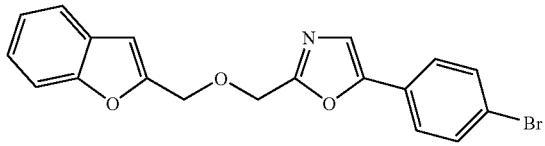

A THF solution of 1-benzofuran-2-ylmethanol (2.2 g, 14.85 mmol, 1 eq.) was treated with NaH (0.65 g, 60% in oil, 16.34 mmol, 1.1 eq.) and stirred at room temperature for 5 minutes before 5-(4-bromo-phenyl)-2-chloromethyl-oxazole (4.05 g, 14.85 mmol, 1 eq.) was added as a solid. The reaction was allowed to stir overnight at room temperature. The solvent was removed in vacuo and the oil dissolved in EtOAc and washed with water and brine. The organic layer was collected, dried over MgSO$_4$, filtered, and the solvent removed leaving a brown oil that was purified by normal phase chromatography using a step gradient of EtOAc in hexanes as the mobile phase. Removal of the solvent and recrystallization from Et$_2$O/hexanes left 2-(benzofuran-2-ylmethoxymethyl)-5-(4-bromo-phenyl)-oxazole (3.82 g, 67% yield) as a yellow solid.

$^1$H NMR (DMSO-d6) δ 7.74 (s, 1H), 7.65 (m, 5H), 7.55 (m, 1H), 7.27 (m, 2H), 6.95 (s, 1H), 4.76 (s, 2H), 4.71 (s, 2H). IR (KBr, cm$^{-1}$) 3096.5, 1480.8, 1405, 1067.7, 1009.9, 940.5, 821.4, 759.5, 503.6. MS(FAB$^+$) m/e 384, 386 [M+H]$^+$. Analytical LC/MS 100% purity (diode array detector). M.P.=80–82° C.

b) Benzhydrylidene-{4-[2-(benzofuran-2-ylmethoxymethyl)-oxazol-5-yl]-phenyl}-amine

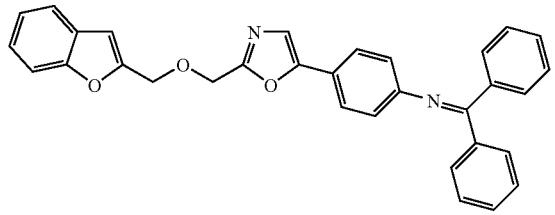

The above compound was prepared in a manner similar to that exemplified in example 250a from 2-(benzofuran-2-ylmethoxymethyl)-5-(4-bromo-phenyl)-oxazole (4.0 g, 10.41 mmol, 1 eq.), benzophenone imine (2.26 g, 12.49 mmol, 1.2 eq.), and sodium tert-butoxide (1.40 g, 14.57 mmol, 1.4 eq.) to produce benzhydrylidene-{4-[2-(benzofuran-2-ylmethoxymethyl)-oxazol-5-yl]-phenyl}-amine (4.72 g, 94% yield) as a yellow foam.

$^1$H NMR (DMSO-d6) δ 7.64 (m, 3H), 7.51 (m, 7H), 7.26 (m, 7H), 6.95 (s, 1H), 6.77 (m, 2H), 4.73 (s, 2H), 4.66 (s, 2H). MS(ES$^+$) m/e 485 [M+H]$^+$.

c) 4-[2-(Benzofuran-2-ylmethoxymethyl)-oxazol-5-yl]-phenylamine

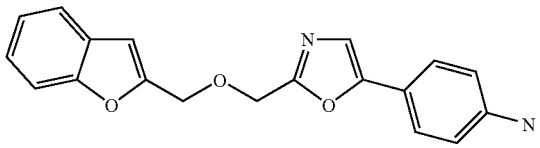

The above compound was prepared in a manner similar to that exemplified in Example 250b from benzhydrylidene-{4-[2-(benzofuran-2-ylmethoxymethyl)-oxazol-5-yl]-phenyl}-amine (4.6 g, 9.49 mmol, 1 eq.) and 2M aqueous HCl (1.5 mL) to produce 4-[2-(benzofuran-2-ylmethoxymethyl)-oxazol-5-yl]-phenylamine (2.78 g, 91% yield) as a yellow solid.

$^1$H NMR (DMSO-d6) δ 7.63 (m, 1H), 7.56 (m, 1H), 7.28 (m, 5H), 6.95 (s, 1H), 6.61 (m, 2H), 5.46 (s, 2H), 4.73 (s, 2H), 4.64 (s, 2H). IR (KBr, cm$^{-1}$) 3322, 3222.3, 2909.7, 1610, 1502.3, 1451.8, 1437.7, 1363.7, 1281.9, 1236.9, 1129.5, 1077.6, 943.7, 808.1, 755.2, 687.4, 520.2. MS(ES$^+$) m/e 321 [M+H]$^+$, 131. Anal. Calcd. for C$_{19}$H$_{16}$N$_2$O$_3$ C, 71.24; H, 5.03; N, 8.74. Found C, 71.07; H, 5.03; N, 8.72. Analytical LC/MS 100% purity (diode array detector). M.P.=96–98° C.

d) {4-[2-Benzofuran-2-ylmethoxymethyl)-oxazol-5-yl]-phenyl}-carbamic acid ethyl ester

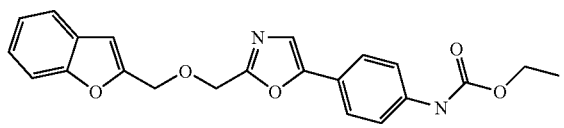

This above compound was prepared in a manner similar to that exemplified in Example 101a from 4-[2-(benzofuran-2-ylmethoxymethyl)-oxazol-5-yl]-phenylamine (2.54 g, 7.93 mmol, 1 eq.) and ethyl chloroformate (1.29 g, 11.9 mmol, 1.5 eq.) to produce {4-[2-(benzofuran-2-yl-methoxymethyl)-oxazol-5-yl]-phenyl}-carbamic acid ethyl ester (3.08 g, 99% yield) as a yellow solid.

$^1$H NMR (DMSO-d6) δ 9.82 (s, 1H), 7.58 (m, 7H), 7.27 (m, 2H), 6.96 (s, 1H), 4.75 (s, 2H), 4.69 (s, 2H), 4.14 (q, 2H, J=7 Hz), 1.25 (t, 3H, J=7 Hz). IR (CHCl$_3$, cm$^{-1}$) 3434, 3010.7, 1733, 1600.3, 1586.6, 1521.5, 1453.9, 1416.2, 1316.6, 1255.1, 1224.7, 1205.9, 1135, 1069.2, 943.6, 838.8, 818.4. MS(ES$^+$) m/e 393 [M+H]$^+$, 131. MS(ES$^-$) m/e 391 [M−H]$^-$, 131. Anal. Calcd. for C$_{22}$H$_{20}$N$_2$O$_5$ C, 67.34; H, 5.14; N, 7.14. Found C, 67.65; H, 5.08; N, 7.10. Analytical LC/MS 100% purity (diode array detector).

e) Preparation of 1-{4-[2-(benzofuran-2-yl-methoxymethyl)-oxazol-5-yl]-phenyl}-3-(2-dimethylamino-ethyl)-urea

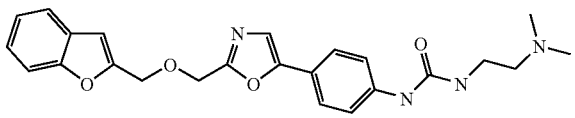

The above compound was prepared in a manner similar to that exemplified in Example 101e from {4-[2-(benzofuran-2-ylmethoxymethyl)-oxazol-5-yl]-phenyl}-carbamic acid ethyl ester (1.0 g, 2.55 mmol, 1 eq.) and N,N-dimethylethylenediamine (0.27 g, 3.06 mmol, 1.2 eq.) to produce 1-{4-[2-(benzofuran-2-ylmethoxymethyl)-oxazol-5-yl]-phenyl}-3-(2-dimethylamino-ethyl)-urea (0.72 g, 65% yield) as an off-white solid when triturated with hot EtOAc and cooled.

$^1$H NMR (DMSO-d6) δ 8.83 (s, 1H), 7.63 (m, 1H), 7.5 (m, 6H), 7.27 (2H), 6.96 (s, 1H), 6.14 (t, 1H, J=6 Hz), 4.75 (s, 2H), 4.68 (s, 2H), 3.18 (m, 2H), 2.32 (t, 2H, J=7 Hz), 2.17 (s, 6H). IR (KBr, cm$^{-1}$) 3311.1, 2938.4, 2902.9, 2860.3, 2819.1, 1631.2, 1585.8, 1504.6, 1455.8, 1417.7, 1310.7, 1256.1, 1131.2, 1074, 989.8, 943.2, 839.1, 805.3, 749.9. MS(ES$^+$) m/e 435 [M+H]$^+$. MS(ES$^-$) m/e 433 [M–H]$^-$. Anal. Calcd. for C$_{24}$H$_{26}$N$_4$O$_4$ C, 66.34; H, 6.03; N, 12.89. Found C, 66.55; H, 5.99; N, 12.68. Analytical LC/MS 100% purity (diode array detector). M.P.=150–154° C.

Example 255

Preparation of 1-{4-[2-(Benzofuran-2-ylmethoxymethyl)-oxazol-5-yl]-phenyl}-3-(2-pyrrolidin-1-yl-ethyl)-urea

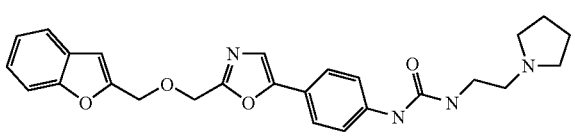

The above compound was prepared in a manner similar to that exemplified in Example 101e from {4-[2-(benzofuran-2-ylmethoxymethyl)-oxazol-5-yl]-phenyl}-carbamic acid ethyl ester (1.0 g, 2.55 mmol, 1 eq.) and N-(2-aminoethyl)pyrrolidine (0.35 g, 3.06 mmol, 1.2 eq.) to produce 1-{4-[2-(benzofuran-2-ylmethoxymethyl)-oxazol-5-yl]-phenyl}-3-(2-pyrrolidin-1-yl-ethyl)-urea (0.86 g, 73% yield) as a white solid.

$^1$H NMR (DMSO-d6) δ 8.84 (s, 1H), 7.63 (m, 1H), 7.5 (m, 6H), 7.27 (m, 2H), 6.96 (s, 1H), 6.17 (t, 1H, J=6 Hz), 4.75 (s, 2H), 4.68 (s, 2H), 3.2 (m, 2H), 2.46 (m, 6H), 1.70 (bs, 4H). IR (KBr, cm$^{-1}$) 3346, 2962.2, 2798.2, 1649.4, 1558.4, 1525.5, 1453.9, 1413.1, 1313.4, 1242.1, 1079.8, 754.1. MS(ES$^+$) m/e 461 [M+H]$^+$. MS(ES$^-$) m/e 459 [M–H]$^-$. Analytical LC/MS 100% purity (diode array detector). M.P.=124–126° C.

Example 256

Preparation of 1-{4-[2-(benzofuran-2-ylmethoxymethyl)-oxazol-5-yl]-phenyl}-3-(2-piperidin-1-yl-ethyl)-urea

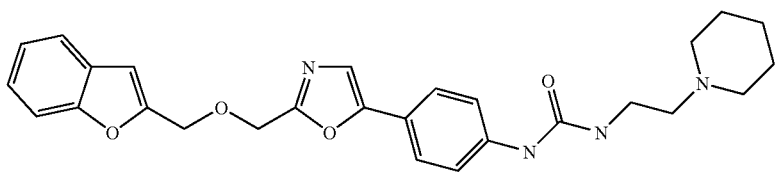

The above compound was prepared in a manner similar to that exemplified in Example 101 e from {4-[2-(benzofuran-2-ylmethoxymethyl)-oxazol-5-yl]-phenyl}-carbamic acid ethyl ester (1.0 g, 2.55 mmol, 1 eq.) and N-(2-aminoethyl)piperidine (0.39 g, 3.06 mmol, 1.2 eq.) to produce 1-{4-[2-(benzofuran-2-ylmethoxymethyl)-oxazol-5-yl]-phenyl}-3-(2-piperidin-1-yl-ethyl)-urea (0.60 g, 50% yield) as a light yellow solid on tituration with Et$_2$O.

$^1$H NMR (DMSO-d6) δ 8.86 (s, 1H), 7.63 (m, 1H), 7.5 (m, 6H), 7.27 (m, 2H), 6.96 (s, 1H), 6.1 (t, 1H, J=6 Hz), 4.75 (s, 2H), 4.68 (s, 2H), 3.19 (m, 2H), 2.34 (m, 6H), 1.51 (m, 4H), 1.39 (m, 2H). IR (KBr, cm$^{-1}$) 3323.1, 2923.8, 2856, 2786.8, 1656.3, 1554.3, 1452.8, 1410.3, 1309.8, 1232.5, 1136.1, 1069.6, 941.7, 839.6, 742.2. MS(ES$^+$) 475 [M+H]$^+$. MS(ES$^-$) 473 [M–H]$^-$. Anal. Calcd. for C$_{27}$H$_{30}$N$_4$O$_4$ C, 68.34; H, 6.37; N, 11.81. Found C, 68.05; H, 6.12; N, 11.69. Analytical LC/MS 100% purity (diode array detector). M.P.=102–104° C.

Example 257

Preparation of 1-{4-[5-(2-phenoxy-ethylsulfanylmethyl)-[1,3,4]oxadiazol-2-yl]-phenyl}-3-(2-pyrrolidin-1-yl-ethyl)-imidazolidin-2-one

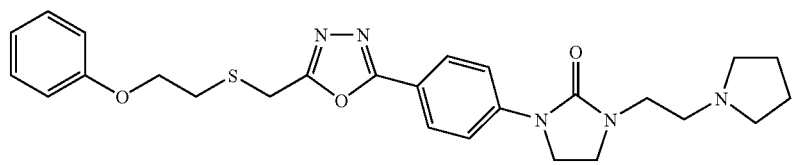

a) 4-[3-(2-Chloro-ethyl)-ureido]-benzoic acid methyl ester

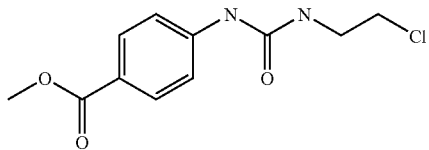

A THF solution of methyl 4-aminobenzoate (14.05 g, 92.91 mmol, 1 eq.) was treated with 2-chloroethyl isocyanate (10 g, 94.77 mmol, 1.02 eq.) and stirred overnight at room temperature. Removed the solvent and recrystallized the orange solid from EtOAc leaving 4-[3-(2-chloro-ethyl)-ureido]-benzoic acid methyl ester (16.41 g, 69% yield) as a yellow solid.

$^1$H NMR (DMSO-d6) δ 9.08 (s, 1H), 7.84 (d, 2H, J=9 Hz), 7.52 (d, 2H, J=9 Hz), 6.55 (t, 1H, J=6 Hz), 3.8 (s, 3H), 3.67 (t, 2H, J=7 Hz), 3.44 (m, 2H). IR (KBr, cm$^{-1}$) 3339.2, 3288.1, 1714.6, 1639.2, 1596, 1565.3, 1438, 1282.8, 1243.6, 1170.3, 1108.2. MS(ES$^+$) m/e 257, 259 [M+H]$^+$. Analytical LC/MS 100% purity (light scattering). M.P.=163–165° C.

b) 4-(2-Oxo-imidazolidin-1-yl)-benzoic acid methyl ester

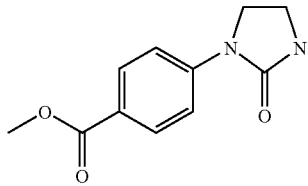

A suspension of NaH (5.24 g, 60% in oil, 130.89 mmol, 2.1 eq.) in THF was treated dropwise with a THF solution of 4-[3-(2-chloro-ethyl)-ureido]-benzoic acid methyl ester (16 g, 62.33 mmol, 1 eq.) and stirred for 1 hour at room temperature and then 1 hour at reflux. The solvent was removed in vacuo and the residue dissolved in CH$_2$Cl$_2$ and washed with water. The organic layer was collected, dried over MgSO$_4$, and the solvent removed leaving a tan solid which was recrystallized from EtOAc/MeOH to produce 4-(2-oxo-imidazolidin-1-yl)-benzoic acid methyl ester (8.22 g, 60% yield) as an off-white solid.

$^1$H NMR (DMSO-d6) δ 7.9 (d, 2H, J=9 Hz), 7.69 (d, 2H, J=9 Hz), 7.23 (s, 1H), 3.9 (m, 2H), 3.81 (s, 3H), 3.43 (t, 2H, J=8 Hz). IR (KBr, cm$^{-1}$) 3241.8, 3100.1, 1721.5, 1680.8, 1431.8, 1284.6, 1264.4, 1182.2, 1109.9, 853.4. MS(ES$^+$) m/e 221 [M+H]$^+$. Anal. Calcd. for C$_{11}$H$_{12}$N$_2$O$_3$ C, 59.99; H, 5.49; N, 12.72. Found C, 60.16; H, 5.38; N, 12.64. Analytical LC/MS 100% purity (diode array and light scattering detection). M.P.>200° C.

c) 4-(2-Oxo-imidazolidin-1-yl)-benzoic acid hydrazide

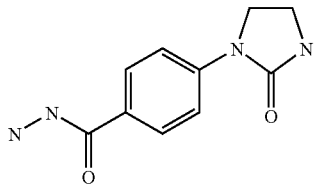

The above compound was prepared in a manner similar to that exemplified for the preparation of Example 101b from 4-(2-oxo-imidazolidin-1-yl)-benzoic acid methyl ester (8.18 g, 37.14 mmol, 1 eq.) and hydrazine (11.90 g, 371.4 mmol, 10 eq.) except that MeOH and THF were used as solvents to produce 4-(2-oxo-imidazolidin-1-yl)-benzoic acid hydrazide (3.36 g, 41% yield) as an off-white solid.

$^1$H NMR (DMSO-d6) δ 9.61 (s, 1H), 7.79 (d, 2H, J=9 Hz), 7.6 (d, 2H, J=9 Hz), 7.1 (s, 1H), 4.41 (s, 2H), 3.87 (t, 2H, J=8 Hz), 3.41 (t, 2H, J=8 Hz). IR (KBr, cm$^{-1}$) 3298.7, 3213.8, 3198.1, 1700.3, 1635.3, 1606, 1487.2, 1443.8, 1429.2, 1407.1, 1311.1, 1261.5, 940.1, 843.7, 745.4. MS(ES$^+$) m/e 221 [M+H]$^+$. M.P.>200° C.

d) 4-(2-Oxo-imidazolidin-1-yl)-benzoic acid N'-[2-(2-phenoxy-ethylsulfanyl)-acetyl]-hydrazide

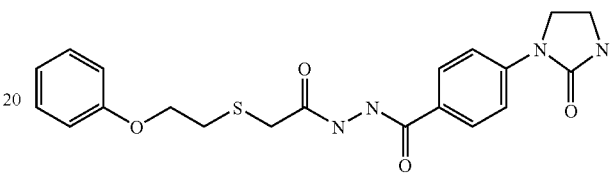

The above compound was prepared in a manner similar to that exemplified for the preparation of Example 101c from 4-(2-oxo-imidazolidin-1-yl)-benzoic acid hydrazide (2.0 g, 9.08 mmol, 1 eq.) and (2-phenoxyethylthio)acetic acid (1.93 g, 9.08 mmol, 1 eq.) to produce 4-(2-oxo-imidazolidin-1-yl)-benzoic acid N'-[2-(2-phenoxy-ethylsulfanyl)-acetyl]-hydrazide (2.79 g, 74% yield) as a tan solid.

$^1$H NMR (DMSO-d6) δ 10.3 (s, 1H), 10 (s, 1H), 7.86 (d, 2H, J=9 Hz), 7.66 (d, 2H, J=9 Hz), 7.29 (m, 2H), 7.16 (s, 1H), 6.95 (m, 3H), 4.2 (t, 2H, J=7 Hz), 3.9 (m, 2H), 3.43 (m, 4H), 3.05 (m, 2H). IR (KBr, cm$^{-1}$) 3300.6, 1696.1, 1656.6, 1611.3, 1484, 1241, 1032.7, 745.4. MS(ES$^+$) m/e 415 [M+H]$^+$. Anal. Calcd. for C$_{20}$H$_{22}$N$_4$O$_4$S C, 57.96; H, 5.35; N, 13.52. Found C, 57.57; H, 5.4; N, 13.41.

e) 1-{4-[5-(2-Phenoxy-ethylsulfanylmethyl)-[1,3,4]oxadiazol-2-yl]-phenyl}-imidazolidin-2-one

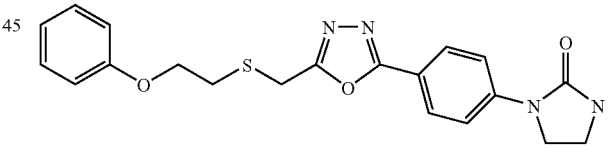

The above compound was prepared in a similar manner to that exemplified for the preparation of Example 101d from 4-(2-oxo-imidazolidin-1-yl)-benzoic acid N'-[2-(2-phenoxy-ethylsulfanyl)-acetyl]-hydrazide (2.6 g, 6.27 mmol, 1 eq.) to produce 1-{4-[5-(2-phenoxy-ethylsulfanylmethyl)-[1,3,4]oxadiazol-2-yl]-phenyl}-imidazolidin-2-one (1.02 g, 41% yield) as a brown solid.

$^1$H NMR (DMSO-d6) δ 7.89 (d, 2H, J=9 Hz), 7.77 (d, 2H, J=9 Hz), 7.25 (m, 3H), 6.93 (m, 3H), 4.2 (m, 4H), 3.92 (m, 2H), 3.44 (m, 2H), 3.0 (t, 2H, J=7 Hz). IR (KBr, cm$^{-1}$) 3265, 1707.8, 1585.2, 1505, 1496.2, 1487.2, 1408.7, 1268.1, 1233.5, 845.65, 754. MS(ES$^+$) m/e 397 [M+H]$^+$. MS(ES$^-$) m/e 395 [M−H]$^-$. Anal. Calcd. for C$_{20}$H$_{20}$N$_4$O$_3$S C, 60.59; H, 5.08; N, 14.13. Found C, 60.23; H, 5.08; N, 13.66. Analytical LC/MS 100% purity (diode array detector). M.P.=108–181° C.

f) 1-{4-[5-(2-Phenoxy-ethylsulfanylmethyl)-[1,3,4]oxadiazol-2-yl]-phenyl}-3-(2-pyrrolidin-1-yl-ethyl)-imidazolidin-2-one

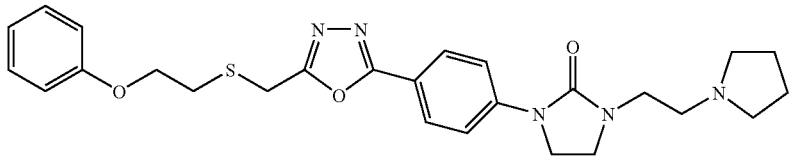

A DMF suspension of 1-{4-[5-(2-phenoxy-ethylsulfanyl-methyl)-[1,3,4]oxadiazol-2-yl]-phenyl}-imidazolidin-2-one (0.76 g, 1.92 mmol, 1 eq.) and 1-(chloroethyl)pyrrolidine hydrochloride (0.34 g, 2.02 mmol, 1.05 eq.) was treated with NaH (0.16 g, 60% in oil, 4.03 mmol, 2.1 eq.) and the reaction heated to 85° C. overnight. The reaction was diluted with EtOAc and washed with water. The organic layer was collected, dried over MgSO$_4$, and the solvent removed leaving an orange/brown oil that was purified by normal phase chromatography using a step gradient of 2M NH3 in MeOH in chloroform as the mobile phase leaving a yellow oil which produced 1-{4-[5-(2-phenoxy-ethylsulfanylmethyl)-[1,3,4]oxadiazol-2-yl]-phenyl}-3-(2-pyrrolidin-1-yl-ethyl)-imidazolidin-2-one (0.28 g, 29% yield) as a yellow solid on trituration with ether.

$^1$H NMR (DMSO-d6) δ 7.9 (d, 2H, J=9 Hz), 7.77 (d, 2H, J=9 Hz), 7.27 (m, 2H), 6.93 (m, 3H), 4.19 (m, 4H), 3.87 (m, 2H), 3.56 (m, 2H), 3.32 (m, 6H), 3.02 (t, 2H, J=7 Hz), 2.6 (bt, 2H), 1.68 (m, 4H). IR (KBr, cm$^{4}$") 3403.8, 2948.7, 2922.6, 2769.3, 1688.4, 1613.2, 1507.1, 1485.9, 1424.2, 1268, 1242, 740.5. MS(ES$^+$) m/e 494 [M+H]$^+$. Analytical LC/MS 100% (diode array and light scattering detection). M.P.=125–129° C.

Example 258

Preparation of N,N-dimethyl-M-{5-[5-(2-phenoxy-ethylsulfanylmethyl)-[1,3,4]oxadiazol-2-yl]-pyridin-2-yl}-ethane-1,2-diamine

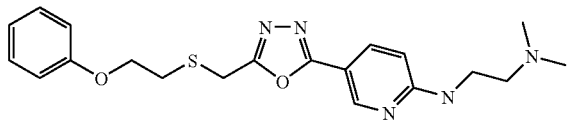

a) 6-Chloro-nicotinic acid N'-[2-(2-phenoxy-ethylsulfanyl)-acetyl]-hydrazide

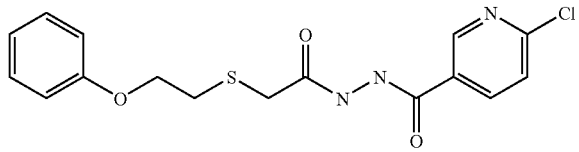

The above compound was prepared in a similar manner to that exemplified for the preparation of Example 101c from 2-chloropyridine-5-carboxylic acid (Aldrich, 2.0 g, 12.69 mmol, 1 eq.), (2-phenoxy-ethylsulfanyl)-acetic acid hydrazide (Maybridge, 2.87 g, 12.69 mmol, 1 eq.), and EEDQ (3.45 g, 13.96 mmol, 1.1 eq.). The reaction was worked up as described and the brown oil purified by silica gel chromatography using a step gradient of EtOAc in hexanes as the mobile phase. Removal of the solvent in vacuo left 6-chloro-nicotinic acid N'-[2-(2-phenoxy-ethylsulfanyl)-acetyl]-hydrazide (3.95 g, 85% yield) as a white solid.

$^1$HNMR (DMSO-d6) δ 10.76 (s, 1H), 10.26 (s, 1H), 8.87 (m, 1H), 8.26 (m, 1H), 7.69 (d, 1H, J=8 Hz), 7.29 (m, 2H), 6.95 (m, 3H), 4.2 (t, 2H, J=7 Hz), 3.35 (s, 2H), 3.04 (t, 2H, J=7 Hz). IR (KBr, cm$^{-1}$) 3222.8, 1605.3, 1493, 1459.5, 1253.7, 1174.2, 1110.4, 1035.5, 756.3, 599.8. MS(ES$^+$) m/e 366 [M+H]$^+$, 272 [M–OPh]$^+$. MS(ES$^-$) m/e 364 [M–H]$^-$. Analytical LC/MS 100% (diode array detection). M.P.=136–138° C.

b) 2-Chloro-5-[5-(2-phenoxy-ethylsulfanylmethyl)-[1,3,4]oxadiazol-2-yl]-pyridine

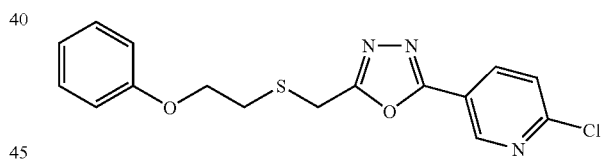

The above compound was prepared in a similar manner to that exemplified for the preparation of Example 101d from 6-chloro-nicotinic acid N'-[2-(2-phenoxy-ethylsulfanyl)-acetyl]-hydrazide (3.48 g, 9.51 mmol, 1 eq.). The crude material was purified by silica gel chromatography using a step gradient of EtOAc in hexanes as the mobile phase. The solvent was removed in vacuo leaving 2-chloro-5-[5-(2-phenoxy-ethylsulfanylmethyl)-[1,3,4]oxadiazol-2-yl]-pyridine (2.50 g, 76% yield) as an off-white solid.

$^1$H NMR (DMSO-d6) δ 8.97 (m, 1H), 8.36 (m, 1H), 7.75 (d, 1H, J=8 Hz), 7.26 (m, 2H), 6.92 (m, 3H), 4.25 (s, 2H), 4.19 (t, 2H, J=6 Hz), 3.04 (t, 2H, J=6 Hz). IR (KBr, cm$^{-1}$) 2924, 1602.7, 1570.5, 1499, 1465.5, 1385, 1248.7, 1176.5, 1136.6, 1114.2, 1035.7, 1004.6, 843.9, 750.5. MS(ES$^-$) 346 [M–H]$^-$. Analytical LC/MS 100% (diode array detection). M.P.=113–115° C.

c) N,N-Dimethyl-M-{5-[5-(2-phenoxy-ethylsulfanylmethyl)-[1,3,4]oxadiazol-2-yl]-pyridin-2-yl}-ethane-1,2-diamine

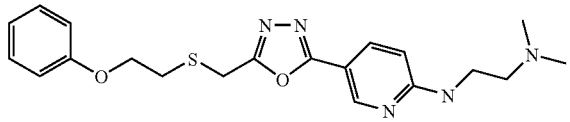

2-Chloro-5-[5-(2-phenoxy-ethylsulfanylmethyl)-[1,3,4]oxadiazol-2-yl]-pyridine (0.72 g, 2.07 mmol, 1 eq.) was suspended in N,N-dimethylethylenediamine (5 mL) and the reaction heated to 100° C. for three hours. The reaction was diluted with EtOAc and washed two times with water and then brine. The organic layer was collected, dried over MgSO$_4$, filtered, and the solvent removed in vacuo leaving an orange oil that was purified by silica gel chromatography using 10% 2M NH$_3$ in MeOH in Et$_2$O as the mobile phase. Removal of the solvent in vacuo left and orange oil which was triturated with diethyl ether producing N,N-dimethyl-2-chloro-5-[5-(2-phenoxy-ethylsulfanylmethyl)-[1,3,4]oxadiazol-2-yl]-pyridine (0.75 g, 2.16 mmol, 1 eq.) and 3-dimethylaminopropylamine (6 mL). Purification and trituration as described left N,N-dimethyl-N-{5-[5-(2-phenoxy-ethylsulfanylmethyl)-[1,3,4]oxadiazol-2-yl]-pyridin-2-yl}-propane-1,3-diamine (0.31 g, 35% yield) as a white solid.

$^1$H NMR (DMSO-d6) δ 8.54 (m, 1H), 7.82 (m, 1H), 7.39 (m, 1H), 7.27 (m, 2H), 6.93 (m, 3H), 6.58 (d, 1H, J=9 Hz), 4.17 (m, 4H), 3.33 (m, 2H), 3.01 (t, 2H, J=7 Hz), 2.27 (t, 2H, J=7 Hz), 2.13 (s, 6H), 1.67 (m, 2H). IR (CHCl$_3$, cm$^{-1}$) 3007.1, 2949.9, 2864.7, 2824.4, 1613.1, 1498.5, 1411.8, 1344.5, 1299, 1243.4, 1223.4, 1173.1, 1145.4, 1081.8, 1034.6. MS (ES$^+$) m/e 414 [M+H]$^+$. MS (ES$^-$) m/e 412 [M−H]$^-$. Anal. Calcd. for C$_{21}$H$_{27}$N$_5$O$_2$S C, 60.99; H, 6.58; N, 16.93. Found C, 60.94; H, 6.61; N, 16.60. Analytical LC/MS 100% purity (diode array detection). M.P.=94–96° C.

Example 260

Preparation of 1-(3-{4-[5-(2-Phenoxy-ethylsulfanylmethyl)-[1,3,4]oxadiazol-2-yl]-phenoxy}-propyl)-piperidin-4-one

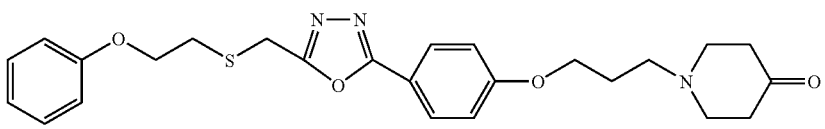

Prepared in a similar manner as 68b from 2-[4-(3-chloropropoxy)-phenyl]-5-(2-phenoxy-ethylsulfanylmethyl)-[1,3,4]oxadiazole (0.350 g, 0.864 mM), piperidin-4-one, trifluoroacetic acid (0.921 g, 4.32 mM), NaI (0.065 g, 0.432 mM), and NaHCO$_3$ (0.399 g, 0.475 mM) in 3 mL DMF. The mixture was heated to 950 overnight in a sealed tube and worked up to give 0.304 g brown oil which was purified by column chromatography to give 0.139 g of material which was combined with another lot and repurified on normal phase chromatography with 50:50 ethyl acetate:dichloromethane with 1% 2M ammonia in methanol to give 0.097 g (19%) of the title compound $^1$H NMR (DMSO-d6) δ 7.9 (d, 2H, J=9 Hz), 7.2 (t, 2H, J=8 Hz), 7.1 (d, 2H, J=9 Hz), 6.9 (m, 3H), 4.2 (m, 6H), 3.0 (t, 2H, J=6 Hz), 2.7 (m, 4H), 2.6 (t, 2H, J=7 Hz), 2.3 (m, 4H), 1.9 (m, 2H). IR (KBr, cm$^{-1}$) 2930, 1704, 1613, 1499, 1392, 1303, 1249, 1170, 1083, 1031, 847, 758, 694. MS (ESI) m/e 468.3, 500.3. Anal. Calcd for C$_{25}$H$_{29}$N$_3$O$_4$S$_1$: C, 64.22; H, 6.25; N, 8.98. Found C, 64.10; H, 6.27; N, 8.92. M.P.=55–57° C.

M-{5-[5-(2-phenoxy-ethylsulfanylmethyl)-[1,3,4]oxadiazol-2-yl]-pyridin-2-yl}-ethane-1,2-diamine (0.28 g, 34% yield) as an off-white solid.

$^1$H NMR (DMSO-d6) δ 8.54 (m, 1H), 7.82 (m, 1H), 7.27 (m, 3H), 6.93 (m, 3H), 6.64 (d, 1H, J=9 Hz), 4.17 (m, 4H), 3.41 (m, 2H), 3.01 (t, 2H, J=7 Hz), 2.42 (t, 2H, J=7 Hz), 2.18 (s, 6H). IR (CHCl$_3$, cm$^{-1}$) 3388.1, 3007.6, 2864.4, 2825.5, 2777.3, 1612.7, 1498.6, 1406.2, 1343.1, 1299.4, 1224.9, 1173.2, 1144.7, 1034.3, 957.4, 823.5. MS(ES$^+$) m/e 400 [M+H]$^+$. MS(ES$^-$) m/e 398 [M−H]$^-$. Analytical LC/MS 100% purity (diode array detection). M.P.=97–98° C.

Example 259

N,N-Dimethyl-N'-{5-[5-(2-phenoxy-ethylsulfanylmethyl)-[1,3,4]oxadiazol-2-yl]-pyridin-2-yl}-propane-1,3-diamine

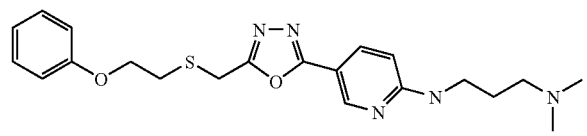

The above compound was prepared in a similar manner to that exemplified for the preparation of Example 258 from Example 261

Preparation of diisopropyl-(3-{4-[5-(2-phenoxy-ethylsulfanylmethyl)-[1,3,4]oxadiazol-2-yl]-phenoxy}-propyl)-amine

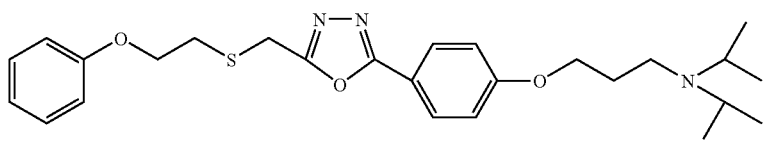

Prepared in a similar manner as 68b from 2-[4-(3-chloro-propoxy)-phenyl]-5-(2-phenoxy-ethylsulfanylmethyl)-[1,3,4]oxadiazole (0.477 g, 1.2 mM), diisopropylamine (8.66 g. 86 mM), NaI (0.088 g, 0.59 mM), and NaHCO$_3$ (0.297 g, 3.54 mM) in 3 mL DMF. The solution was heated to 95° overnight in a sealed tube and worked up to give 0.417 g brown oil, which was purified by column chromatography as in 68b and recrystallized from ethyl ether and ethyl acetate to give 0.266 g (48%) of the title compound.

$^1$H NMR (DMSO-d6) δ7.9 (d, 2H, J=9 Hz), 7.2 (t, 2H, J=8 Hz), 7.1 (d, 2H, J=9 Hz), 6.9 (m, 3H), 4.2 (m, 4H), 4.1 (m, 2H), 3.0 (m, 4H), 2.6 (m, 2H), 1.8 (m, 2H), 0.9 (m, 12H). IR (KBr, cm$^{-1}$) 2965, 1616, 1501, 1265, 1242, 1176, 751. MS (ESI) m/e 470. Anal. Calcd for C$_{26}$H$_{35}$N$_3$O$_3$S$_1$: C, 66.49; H, 7.51; N, 8.95. Found C, 66.08; H, 7.57; N, 8.76. M.P.=30–33° C. HPLC 100%.

Example 262

Preparation of diisopropyl-(4-{4-[5-(2-phenoxy-ethylsulfanylmethyl)-[1,3,4]oxadiazol-2-yl]-phenoxy}-butyl)-amine

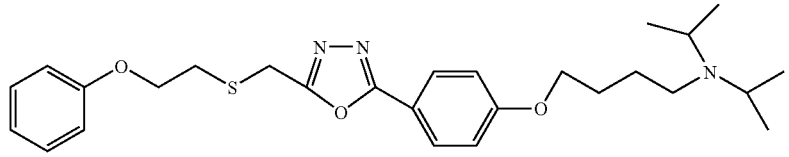

Prepared in a similar manner as 68b from 2-[4-(4-chlorobutoxy)-phenyl]-5-(2-phenoxy-ethylsulfanylmethyl)-[1,3,4]oxadiazole (0.458 g, 1.09 mM), diisopropylamine (8.00 g. 79 mM), NaI (0.082 g, 0.55 mM), and NaHCO$_3$ (0.275 g, 3.27 mM) in 5 mL DMF. The solution was heated to 95° overnight in a sealed tube. Chromatography gave 0.238 g (45%) of diisopropyl-(4-{4-[5-(2-phenoxy-ethylsulfanylmethyl)-[1,3,4]oxadiazol-2-yl]-phenoxy}-butyl)-amine.

$^1$H NMR (DMSO-d6) δ7.9 (d, 2H, J=9 Hz), 7.2 (t, 2H, J=8 Hz), 7.1 (d, 2H, J=9 Hz), 6.9 (m, 3H), 4.2 (m, 4H), 4.1 (m, 2H), 3.0 (m, 4H), 2.4 (m, 2H), 1.7 (m, 2H), 1.5 (m, 2H), 0.9 (m, 12H). IR (KBr, cm$^{-1}$) 1615, 1504, 1255, 1174, 833. MS (ESI) m/e 484. Anal. Calcd for C$_{27}$H$_{37}$N$_3$O$_3$S$_1$: C, 67.05; H, 7.71; N, 8.68. Found C, 66.20; H, 7.53; N, 8.57. M.P.=42–44° C. HPLC 100%.

Example 263

Preparation of 2-[4-(3-azetidin-1-yl-propoxy)-phenyl]-5-(2-phenoxy-ethylsulfanylmethyl)-[1,3,4]oxadiazole

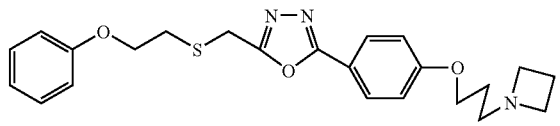

Prepared in a similar manner as 68b from 2-[4-(3-chloropropoxy)-phenyl]-5-(2-phenoxy-ethylsulfanylmethyl)-[1,3,4]oxadiazole (0.348 g, 0.86 mM), azetidine, monohydrochloride, (0.402 g, 4.3 mM), NaI (0.064 g, 0.43 mM), NaHCO$_3$ (0.433 g, 5.15 mM) in 3 mL DMF. The solution was heated to 95° overnight in a sealed tube. Chromatography and recrystallization from ethyl ether and ethyl acetate gave 30 mg (8%) of the title compound.

$^1$H NMR (CDCl$_3$-d6) δ7.9 (d, 2H, J=9 Hz), 7.2 (m, 2H), 7.0 (m, 3), 6.9 (d, 2H, J=8 Hz), 4.2 (t, 2H, J=6 Hz), 4.0 (m, 4H), 3.2 (t, 4H, J=7 Hz), 3.0 (t, 2H, J=6 Hz), 2.6 (t, 2H, J=7 Hz), 2.1 (m, 2H), 1.9 (m, 2H). IR (KBr, cm$^{-1}$) 2926, 1622, 1603, 1499, 1250, 753. MS (ESI) m/e 426. M.P.=60° C. HPLC 100%.

Example 264

Preparation of 4-{4-[5-(2-phenoxy-ethylsulfanylmethyl)-[1,3,4]oxadiazol-2-yl]-phenoxy}-butyronitrile

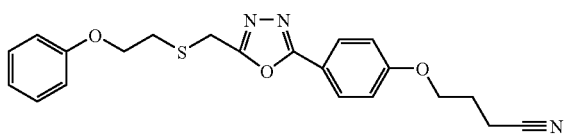

A solution of 4-[5-(2-phenoxy-ethylsulfanylmethyl)-[1,3,4]oxadiazol-2-yl]-phenol (0.435 g, 1.32 mM), K$_2$CO$_3$ (0.492 g, 3.56 mM) and 4-chlorobutyronitrile (0.293 g, 1.98 mM) was heated to 70° in 10 mL DMF for 4 hrs. The resultant mixture was extracted 2 times with ethyl acetate and washed with water, brine, dried over sodium sulfate and concentrated to give 0.452 g crude product. The mixture was purified directly by column chromatography on silica gel (elution with 1/1 ethyl acetate, toluene followed by chloroform/2 m ammonia in methanol to give 0.378 g (72%) of the title compound.

$^1$H NMR (DMSO-d6) δ7.9 (d, 2H, J=9 Hz), 7.2 (t, 2H, J=8 Hz), 7.1 (d, 2H, J=9 Hz), 6.9 (m, 3H), 4.2 (m, 6H), 3.0 (t, 2H, J=6 Hz), 2.6 (t, 2H, J=7 Hz), 2.0 (m, 2H). IR (KBr, cm$^{-1}$) 2930, 1610, 1499, 1464, 1425, 1303, 1253, 1179, 1051, 842, 755. MS (ESI) m/e 396. Anal. Calcd for C$_{21}$H$_{21}$N$_3$O$_3$S$_1$: C, 63.78; H, 5.35; N, 10.62. Found C, 60.25; H, 5.13; N, 9.89. M.P.=67–68° C. HPLC 93%.

Example 265

Preparation of 1-(2-{4-[2-(2-phenoxy-ethylsulfanylmethyl)-oxazol-5-yl]-phenoxy}-ethyl)-azepane

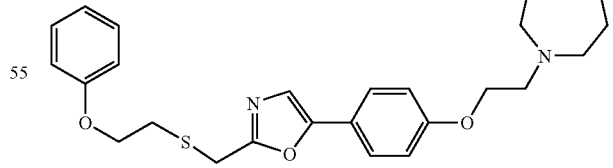

Prepared in a similar manner as 66c from 4-[2-(2-phenoxy-ethylsulfanylmethyl)-oxazol-5-yl]-phenol (0.461 g, 1.41 mM) and 1-(2-chloro-ethyl)-azepane, monohydrochloride (0.419 g, 2.11 mM to give 0.196 g (31%) of the title compound.

$^1$H NMR (DMSO-d6) δ7.6 (d, 2H, J=9 Hz), 7.4 (s, 1H), 7.2 (t, 2H, J=8 Hz), 7.0 (d, 2H, J=9 Hz), 6.9 (m, 3H), 4.1 (t,

2H, J=7 Hz), 4.0 (m, 4H), 3.0 (t, 2H, J=6 Hz), 2.8 (m, 2H), 2.7 (m, 4H), 1.5 (m, 8H). IR (KBr, cm$^{-1}$) 2924, 2822, 1604, 1550, 1502, 1465, 1299, 1251, 1173, 1106, 1029, 818, 750. MS (ESI m/e 453. Anal. Calcd for C$_{26}$H$_{32}$N$_2$O$_3$S$_1$: C, 68.99; H, 7.13; N, 6.19. Found C, 68.84; H, 7.03; N, 6.21. M.P.=35–38° C. HPLC 100%.

Example 266

Preparation of 1-(3-{4-[2-(2-phenoxy-ethylsulfanyl-methyl)-oxazol-5-yl]-phenoxy}-propyl)-azepane

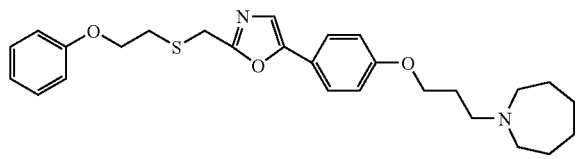

54a) 5-[4-(3-Chloro-propoxy)-phenyl]-2-(2-phenoxy-ethylsulfanylmethyl)-oxazole

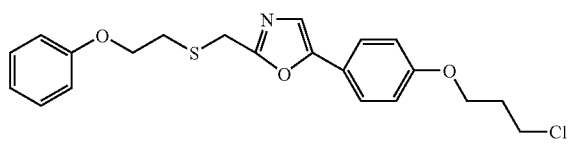

Prepared in a similar manner as 68a from 4-[2-(2-phenoxy-ethylsulfanylmethyl)-oxazol-5-yl]-phenol (1.186 g, 3.62 mM) and 1-bromo-3-chloro-propane (0.855 g, 5.43 mM) to give 0.904 g (62%) of 5-[4-(3-chloro-propoxy)-phenyl]-2-(2-phenoxy-ethylsulfanylmethyl)-oxazole.

$^1$H NMR (DMSO-d6) δ7.6 (d, 2H, J=9 Hz), 7.4 (s, 1H), 7.2 (t, 2H, J=8 Hz), 7.0 (d, 2H, J=9 Hz), 6.9 (m, 3H), 4.1 (m, 4H), 4.0 (s, 2H), 3.8 (t, 2H, J=6 Hz), 3.0 (t, 2H, J=6 Hz), 2.2 (m, 2H). IR (KBr, cm$^{-1}$) 2972, 2922, 1603, 1506, 1466, 1295, 1243, 1175, 1105, 1031, 943, 834, 805, 761. MS (ESI) m/e 404. Anal. Calcd for C$_{21}$H$_{22}$C$_{11}$N$_1$O$_3$S$_1$: C, 62.44; H, 5.49; N, 3.47. Found C, 60.66; H, 5.24; N, 3.39. M.P.=71–73° C. HPLC 100%.

54b) 1-(3-{4-[2-(2-phenoxy-ethylsulfanylmethyl)-oxazol-5-yl]-phenoxy}-propyl)-azepane

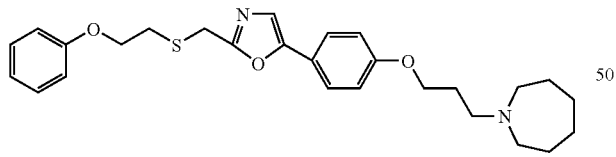

Prepared in a similar manner as 68b from 5-[4-(3-chloro-propoxy)-phenyl]-2-(2-phenoxy-ethylsulfanylmethyl)-oxazole (0.400 g, 0.99 mM), azepane (2.45 g, 24.7 mM), NaI (0.074 g, 0.495 mM), and NaHCO$_3$ (0.22 g, 2.77 mM) in 3 mL DMF. The solution was heated to 90° overnight in a sealed tube. Chromatography and recrystallization from hexane and ethyl ether gave 0.178 g (38%) of the title compound.

$^1$H NMR (DMSO-d6) δ7.6 (d, 2H, J=9 Hz), 7.4 (s, 1H), 7.2 (t, 2H, J=8 Hz), 7.0 (d, 2H, J=9 Hz), 6.9 (m, 3H), 4.1 (t, 2H, J=7 Hz), 4.0 (m, 4H), 3.0 (t, 2H, J=6 Hz), 2.6 (m, 6H), 1.8 (m, 2H), 1.5 (m, 8H). IR (KBr, cm$^{-1}$) 2923, 2850, 1602, 1551, 1507, 1465, 1255, 1176, 1110, 1033, 941, 832, 751, 691. MS (ESI) m/e 467. Anal. Calcd for C$_{27}$H$_{34}$N$_2$O$_3$S$_1$: C, 69.49; H, 7.34; N, 6.00. Found C, 69.78; H, 7.43; N, 4.09. M.P.=32–35° C. HPLC 100%.

Example 267

Preparation of 1-(3-{4-[2-(2-phenoxy-ethylsulfanyl-methyl)-oxazol-5-yl]-phenoxy}-propyl)-azocane oxalic acid salt

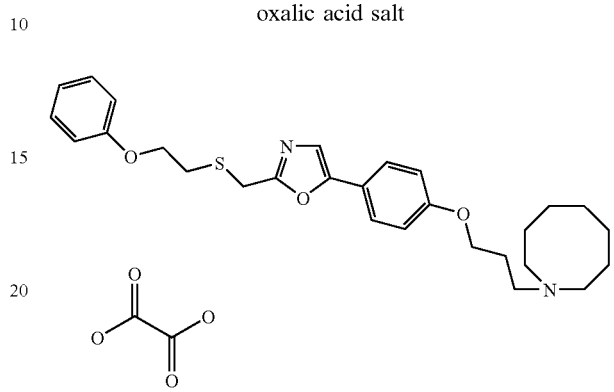

Prepared in a similar manner as 68b from 5-[4-(3-chloro-propoxy)-phenyl]-2-(2-phenoxy-ethylsulfanylmethyl)-oxazole (0.488 g, 1.21 mM), azocane (3.42 g, 30 mM), NaI (0.091 g, 0.495 mM), and NaHCO$_3$ (0.28 g, 3.39 mM) in 3 mL DMF. The solution was heated to 90° overnight in a sealed tube. Chromatography was followed by formation of the oxalic acid salt. The product mixture was dissolved in acetone (3 mL) and to that was added dropwise a solution of oxalic acid (0.063 g, 0.7 mM) in acetone (2 mL). The mixture was concentrated to low volume and to this was added ethyl ether (5 mL). Upon cooling, a solid precipitated and was collected by filtration and dried under vacuum (40°) to give 0.194 g (28%) of the title compound.

$^1$H NMR (DMSO-d6) δ7.6 (d, 2H, J=9 Hz), 7.4 (s, 1H), 7.2 (m, 2H), 7.0 (d, 2H, J=9 Hz), 6.9 (m, 3H), 4.2 (t, 2H, J=7 Hz), 4.1 (t, 2H, J=6 Hz), 4.0 (s, 2H) 3.0 (t, 2H, J=6 Hz), 2.1 (m, 2H), 1.5–1.9 (m, 10H). IR (KBr, cm$^{-1}$) 2934, 1717, 1601, 1506, 1245, 1203, 1035, 836, 759, 705. MS (ESI) m/e 481. Anal. Calcd for C$_{30}$H$_{38}$N$_2$O$_7$S$_1$: C, 63.14; H, 6.71; N, 4.91. Found C, 60.25; H, 6.40; N, 4.64. M.P.=89–94° C. HPLC 80%.

Example 268

Preparation of 2-(2-phenoxy-ethylsulfanylmethyl)-5-[4-(3-pyrrolidin-1-yl-propenyl)-phenyl]-oxazole

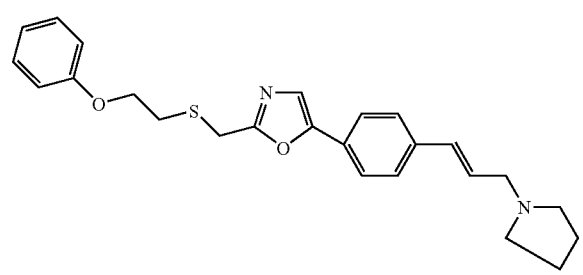

a) (2-Thiocyanato-ethoxy)-benzene

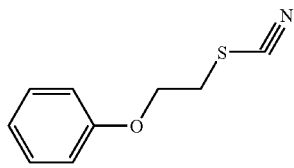

A solution of (2-bromo-ethoxy)-benzene (18.0 g, 89.5 mM) and KSCN (26.1 g, 268 mM) were added together in a nitrogen flushed round bottom flask. The mixture was heated for 3 hours at 100° C., followed by dilution with $H_2O$ (300 mL), and extraction twice with EtOAc. The combined organic extracts were washed with $H_2O$ (10×100 mL), brine (2×100 mL)), dried over sodium sulfate and concentrated to dryness to give 12.8 g (yellow oil) (80%) of the title compound.

$^1$H NMR (DMSO-d6) δ7.3 (t, 2H, J=8 Hz), 6.9 (m, 3H), 4.3 (t, 2H, J=5 Hz), 3.5 (t, 2H, J=5 Hz). IR ($CHCl_3$, $cm^{-1}$) 3669, 3520, 3016, 2923, 2870, 2158, 1670, 1601, 1497, 1465, 1385, 1303, 1236, 1083, 1038. MS (ESI) m/e 179. Anal calcd. $C_9H_9NOS$: C, 60.31; H, 5.06; N, 7.81. Found C, 60.11; H, 5.06; N, 7.53. HPLC 100%.

b) Dimer of 2-phenoxy-ethanethiol

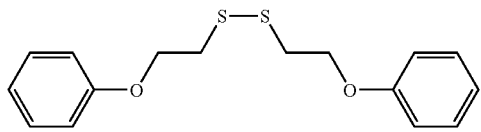

To a solution of (2-thiocyanato-ethoxy)-benzene (12.8 g, 71.4 mM) in MeOH (200 mL) was added a dropwise solution of NaOMe (70 mL, 321 mM, 25% NaOMe in MeOH) over 25 min. The reaction mixture was stirred for 2.5 hours. The mixture was then filtered and the collected solid was dried under vacuum overnight to give a white solid, 7.9 g (72%)

$^1$H NMR (DMSO-d6) δ 7.3 (t, 2H, J=8 Hz), 6.9 (m, 3H), 4.2 (t, 2H, J=6 Hz), 3.1 (m, 2H). IR ($CHCl_3$, $cm^{-1}$) 1600, 1587, 1497, 1243, 1225, 1173, 1032, 1016. MS (ESI) m/e 306. Anal. Calcd for $C_{16}H_{18}O_2S_2$: C, 62.71; H, 5.92; N, 0.00. Found C, 61.28; H, 5.76; N, 0.72. M.P.=72–75° C. HPLC 100%.

c) 2-Phenoxy-ethanethiol

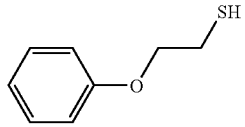

A solution of the dimer of 2-phenoxy-ethanethiol (6.3 g, 20.4 mM) and Zn dust (12 g, 184 mM) was refluxed in acetic acid (120 mL) for 2 hours. The mixture was diluted with $H_2O$ (300 mL), extracted with dichloromethane, dried over sodium sulfate, filtered and concentrated to dryness to give 5.2 g (83%) of 2-phenoxy-ethanethiol.

$^1$H NMR (DMSO-d6) δ7.3 (t, 2H, J=8 Hz), 6.9 (m, 3H), 4.0 (t, 2H, J=6 Hz), 2.8 (m, 2H).

d) N-[2-(4-Bromo-phenyl)-2-oxo-ethyl]-2-chloro-acetamide

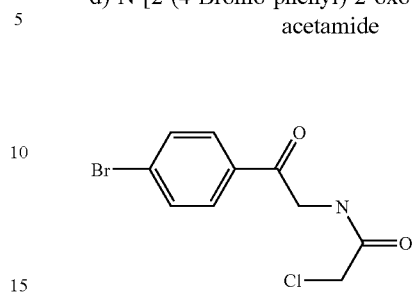

A $CH_2Cl_2$ suspension (100 mL) of 4-bromophenacylamine hydrochloride (10 g, 39.92 mmol, 1 eq.) and chloroacetyl chloride (6.76 g, 59.88 mmol, 1.5 eq.) was treated with 100 mL of triethylamine (12.12 g, 119.76 mmol, 3 eq.) in $CH_2Cl_2$ dropwise over 1.5 hours. After addition had ceased, the reaction was allowed to stir overnight at room temperature.

The reaction was washed with 0.1 M aqueous HCl and then brine. The organic layer was collected, dried over $MgSO_4$, filtered, and the solvent removed in vacuo leaving a dark brown oil which was purified via normal phase chromatography using a step gradient of EtOAc in hexanes as the mobile phase giving 8.38 g (72% yield) of a yellow solid.

$^1$H NMR (DMSO-d6) δ 8.56 (t, 1H, J=5 Hz), 7.93 (d, 2H, J=8 Hz), 7.76 (d, 2H, J=8 Hz), 4.66 (m, 2H), 4.20 (s, 2H). IR ($CHCl_3$, $cm^{-1}$) 3397, 3009, 1672, 1590, 1526, 1074, 987. MS (ES$^+$) m/z 290, 292 [M+H]$^+$. MS (ES$^-$) m/z 288, 290 [M−H]$^-$. Anal. Calcd for $C_{10}H_9BrClNO_2$: C, 41.34; H, 3.12; N, 4.82. Found C, 41.23; H, 2.95; N, 4.75. M.P.=145–146° C.

e) 5-(4-Bromo-phenyl)-2-chloromethyl-oxazole

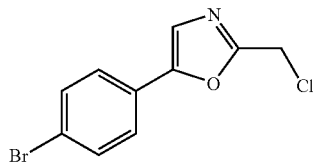

A $POCl_3$ suspension (70 mL) of N-[2-(4-bromo-phenyl)-2-oxo-ethyl]-2-chloro-acetamide (7.38 g, 25.4 mmol, 1 eq) was refluxed for 2 hours. The cooled solution was poured into ice and stirred for several hours. The aqueous layer was extracted with EtOAc. The organic layer was collected, dried over $MgSO_4$, filtered, and the solvent removed in vacuo leaving a dark brown oil which was purified by normal phase chromatography using a gradient of EtOAc in hexanes as the mobile phase leaving 5-(4-bromo-phenyl)-2-chloromethyl-oxazole (5.85 g, 85% yield) as a light brown solid.

$^1$H (DMSO-d6) δ 7.8 (s, 1H), 7.7 (m, 4H), 4.9 (s, 2H). IR ($CHCl_3$, $cm^{-1}$) 3005, 1481, 1405, 1216, 1119, 1074, 1011, 823. MS (ES$^+$) m/z 272, 274 [M+H]$^+$. Anal. calcd. for $C_{10}H_7BrClNO$ C, 44.07; H, 2.59; N, 5.14. Found C, 44.06; H, 2.41; N, 5.04.

f) 5-(4-Bromo-phenyl)-2-(2-phenoxy-ethylsulfanyl-methyl)-oxazole

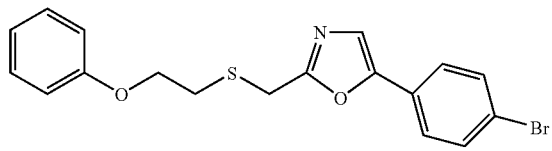

A solution of 2-phenoxy-ethanethiol (3.3 g, 21.39 mmol, 1 eq.) and 5-(4-bromo-phenyl)-2-chloromethyl-oxazole (5.83 g, 21.39 mmol, 1 eq.) in anhydrous DMF was treated with solid potassium carbonate (8.87 g, 64.17 mmol, 3 eq.) and allowed to stir overnight. Diluted the reaction with water and extracted 2×250 mL with EtOAc. The organic layers were combined, washed with 50% brine, collected, dried over MgSO$_4$, filtered, and the solvent removed in vacuo leaving a tan solid which was purified by normal phase chromatography using a step gradient of EtOAc in hexanes as the mobile phase leaving 8.16 g (98% yield) of a tan solid.

$^1$H NMR (DMSO-d6) δ 7.65 (m, 5H), 7.27 (m, 2H), 6.93 (m, 3H), 4.16 (t, 2H, J=7 Hz), 4.06 (s, 2H), 3.00 (t, 2H, J=7 Hz). IR (CHCl$_3$, cm$^{-1}$) 3009, 2930, 2871, 1601, 1497, 1481, 1243, 1073, 822. MS (ES$^+$) m/z 390, 392 [M+H]$^+$. Anal. Calcd. for C$_{18}$H$_{16}$BrNO$_2$S C, 55.39; H, 4.13; N, 3.59. Found C, 55.31; H, 4.03; N, 3.60. M.P.=82–84° C.

g) 3-{4-[2-(2-Phenoxy-ethylsulfanylmethyl)-oxazol-5-yl]-phenyl}-acrylic acid ethyl ester

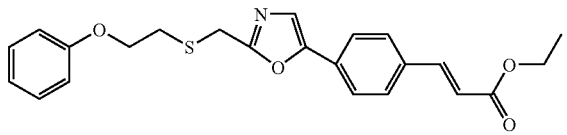

To a closed reaction vessel was added 5-(4-bromo-phenyl)-2-(2-phenoxy-ethylsulfanylmethyl)-oxazole (1.372 g, 3.52 mM), triethylamine (0.427 g, 4.22 mM), Hartwig's ligand$^1$ (0.126 g, 0.178 mM), bis(dibenzylideneacetone)palladium (0.051 g, 0.088 mM), and ethyl acrylate (0.49 g, 4.93 mM) in DMF (5 mL). The mixture was heated overnight at 80° C., filtered through celite, and concentrated to low volume. The crude reaction mixture was diluted with ethyl acetate and water and separated. The aqueous mixture was extracted with ethyl acetate and the organic extracts combined, which were then washed with water, brine, dried over sodium sulfate, and concentrated to dryness. The residue was purified directly by column chromatography on silica gel (elution with 20% ethyl acetate/hexane followed by 30% ethyl acetate/hexane to give 1.097 g (76%) 55 g.

$^1$H NMR (DMSO-d6) δ7.8 (d, 2H, J=8 Hz), 7.7–7.6 (m, 4H), 7.3 (t, 2H, J=8 Hz), 6.9 (m, 3H), 6.7 (d, 1H, J=16 Hz), 4.2 (m, 4H), 4.1 (s, 2H), 3.0 (t, 2H, J=7 Hz), 1.3 (t, 3H, J=7 Hz). MS (ESI) m/e 409.8. Anal. Calcd for C$_{23}$H$_{23}$N$_1$O$_4$S$_1$: C, 67.46; H, 5.66; N, 3.42. Found C, 66.03; H, 5.54; N, 3.28. M.P.=65–67° C. HPLC 100%.

h) 3-{4-[2-(2-Phenoxy-ethylsulfanylmethyl)-oxazol-5-yl]-phenyl}-acrylic acid

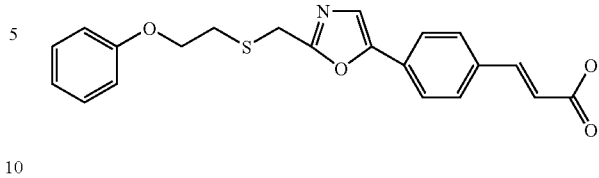

A solution of 3-{4-[2-(2-phenoxy-ethylsulfanylmethyl)-oxazol-5-yl]-phenyl}-acrylic acid ethyl ester (2.323 g (5.67 mM), in 1N NaOH (12 mL, 11.9 mM), EtOH (19 mL), and THF (20 mL) was stirred overnight at room temperature. The reaction mixture was concentrated to low volume and diluted with ethyl acetate/H$_2$O. The aqueous material was acidified with 1N HCl and extracted with ethyl acetate (4×100 mL). The combined organic extracts were washed with brine, dried over sodium sulfate and concentrated to dryness to give 1.082 g (50%) of 3-{4-[2-(2-phenoxy-ethylsulfanylmethyl)-oxazol-5-yl]-phenyl}-acrylic acid $^1$H NMR (DMSO-d6) δ7.3 (t, 2H, J=8 Hz), 6.9 (m, 3H), 4.2 (t, 2H, J=6 Hz), 3.1 (m, 2H). IR (KBr, cm$^{-1}$) 3437, 2928, 1681, 1604, 1499, 1422, 1258, 1220, 1171, 829, 747. MS (ESI) m/e 382. Anal. Calcd for C$_{21}$H$_{19}$NO$_4$S$_1$: C, 66.12; H, 5.02; N, 3.67. Found C, 65.99; H, 5.21; N, 3.35. M.P.=150–153° C. HPLC 100%.

i)

ii) 3-{4-[2-(2-Phenoxy-ethylsulfanylmethyl)-oxazol-5-yl]-phenyl}-prop-2-en-1-ol

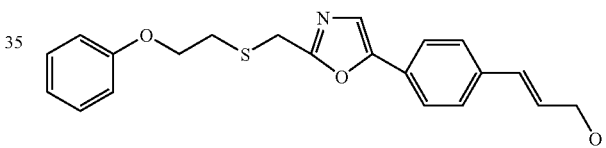

A solution of 3-{4-[2-(2-phenoxy-ethylsulfanylmethyl)-oxazol-5-yl]-phenyl}-acrylic acid (1.9 g, 4.98 mM), diethyl chlorophosphate, (1.031 g, 5.98 mM), and triethylamine (1.0 g, 9.96 mM was stirred at room temperature in THF (155 mL) for 22 hours. The mixture was filtered, washed with THF, and the filtrate concentrated to dryness. The filtrate was redissolved in 120 mL THF and to this mixture was added dropwise over 3 min. a solution of NaBH$_4$ (0.378 g, 9.96 mM) dissolved in H$_2$O (5 mL) and THF (20 mL). After stirring at room temperature for 2.5 hours, 1N HCl (10 mL) was added dropwise and the mixture was stirred overnight at room temperature. The mixture was concentrated to low volume, diluted with ethyl acetate, washed with water, 1N HCl, water, sodium bicarbonate, water, brine, dried over sodium sulfate, and concentrated to dryness. The residue was purified directly by column chromatography (elution with ethyl acetate/toluene followed by 95% chloroform/5% 2M ammonia in methanol) to give 0.331 g (18%) of 3-{4-[2-(2-phenoxy-ethylsulfanylmethyl)-oxazol-5-yl]-phenyl}-prop-2-en-1-ol.

$^1$H NMR (DMSO-d6) δ7.6 (d, 3H, J=8 Hz), 7.5 (d, 2H, J=8 Hz), 7.2 (t, 2H, J=8 Hz), 6.9 (m, 3H), 6.5 (d, 1H, J=16 Hz), 6.4 (tt, 1H, J=5 Hz), 4.2 (m, 4H), 4.0 (s, 2H), 3.0 (t, 2H, J=7 Hz). IR (KBr, cm$^{-1}$) 3431, 2916, 1653, 1601, 1496, 1247, 968, 750. MS (ESI) m/e 368. Anal. Calcd for C$_{21}$H$_{21}$NO$_3$S$_1$: C, 68.64; H, 5.76; N, 3.81. Found C, 64.83; H, 5.36; N, 3.57. M.P.=73–74° C.

j) 5-[4-(3-Bromo-propenyl)-phenyl]-2-(2-phenoxy-ethylsulfanylmethyl)-oxazole

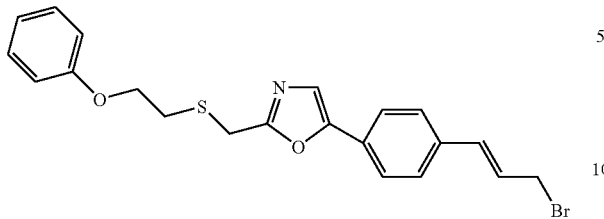

To a solution of triphenylphosphine (0.247 g, 0.943 mM) dissolved in dichloromethane (3 mL) was added bromine (0.151 g, 0.0943 mM) dropwise and the mixture was stirred for 10 min at room temperature. The mixture was cooled to +5° C. and a solution of 3-{4-[2-(2-phenoxy-ethylsulfanyl-methyl)-oxazol-5-yl]-phenyl}-prop-2-en-1-ol (0.333 g, 0.898 mM) and imidazole (0.122 g, 1.8 mM) in dichloromethane (5 mL) was added dropwise. The mixture was stirred at room temperature for 3 hours and washed with water, sodium bicarbonate, water, brine, dried over sodium sulfate and concentrated to dryness. The residue was purified directly by column chromatography on silica gel (elution with 1/3 ethyl acetate/hexane followed by ethyl acetate/tolune to give 0.165 g (43%) of 5-[4-(3-bromo-propenyl)-phenyl]-2-(2-phenoxy-ethylsulfanylmethyl)-oxazole.

$^1$H NMR (DMSO-d6) δ7.6 (d, 3H, J=7 Hz), 7.5 (d, 2H, J=8 Hz), 7.3 (t, 2H, J=8 Hz), 6.9 (m, 3H), 6.8 (d, 1H, J=16 Hz), 6.6 (m, 1H), 4.4 (d, 2H, J=8 Hz), 4.2 (t, 2H, J=6 Hz), 4.0 (s, 2H), 3.0 (t, 2H, J=7 Hz). IR (KBr, cm$^{-1}$) 3447, 2923, 2862, 1601, 1546, 1491, 1468, 1241, 1204, 1106, 1033, 965, 944, 821, 764, 694, 519. MS (S]) m/e 432. Anal. Calcd for $C_{21}H_{20}BrNO_2S_1$: C, 58.61; H, 4.68; N, 3.25. Found C, 59.30; H, 5.03; N, 3.05. M.P.=88–91° C.

k) 2-(2-phenoxy-ethylsulfanylmethyl)-5-[4-(3-pyrrolidin-1-yl-propenyl)-phenyl]-oxazole

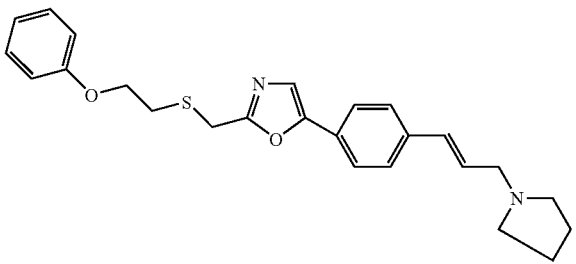

Prepared in a similar manner as 68b from 5-[4-(3-bromo-propenyl)-phenyl]-2-(2-phenoxy-ethylsulfanylmethyl)-oxazole (0.150 g, 0.348 mM), pyrrolidine (1.73 g, 24.4 mM), NaI (0.026 g, 0.174 mM), and NaHCO$_3$ (0.088 g, 1.04 mM) in 3 mL DMF. Chromatography and recrystallization from ethyl ether and hexane gave 0.044 g (30%) of the title compound.

$^1$H NMR (DMSO-d6) δ7.6 (d, 3H, J=7 Hz), 7.5 (d, 2H, J=8 Hz), 7.2 (t, 2H, J=8 Hz), 6.9 (m, 3H), 6.6 (d, 1H, J=16 Hz), 6.4 (m, 1H), 4.2 (t, 2H, J=7 Hz), 4.1 (s, 2H), 3.2 (d, 2H, J=7 Hz), 3.0 (t, 2H, J=7 Hz), 1.7 (m, 4H). IR (KBr, cm$^{-1}$) 2957, 2912, 2778, 1604, 1501, 1463, 1255, 1107, 1056, 973, 944, 822, 754, 693. MS (ESI) m/e 421. Anal. Calcd for $C_{25}H_{28}N_2O_2S_1$: C, 71.40; H, 6.71; N, 6.66. Found C, 70.88; H, 6.68; N, 6.57. M.P.=73–75° C.

Example 269

Preparation of Dimethyl-(3-{4-[5-(4-phenoxy-benzyl)-[1,3,4]oxadiazol-2-yl]-phenoxy}-propyl)-amine, oxalic acid salt

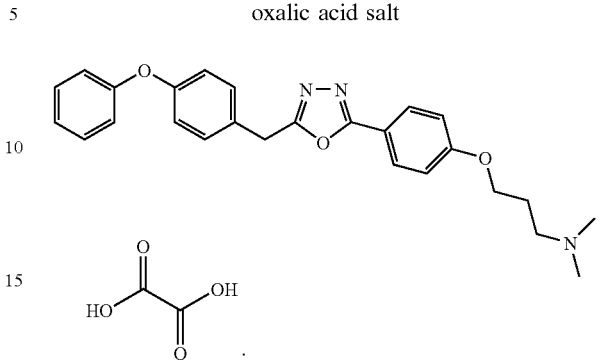

a) 4-Hydroxy-benzoic acid N'-[2-(4-phenoxy-phenyl)-acetyl]-hydrazide

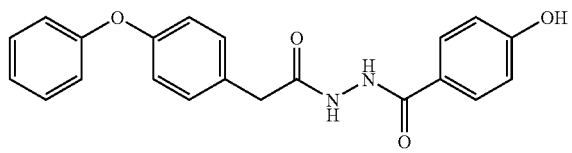

The above compound was prepared in a manner similar to that exemplified for the preparation of Example 51a, from 4-phenoxyphenylacetic acid (1.16 g, 5.0 mM) to afford 1.59 g (87%) of 4-Hydroxy-benzoic acid N'-[2-(4-phenoxy-phenyl)-acetyl]-hydrazide as a white solid (MP 181–183° C., MW 362.39).

$^1$H NMR DMSO-d6) δ 10.04 (m, 3H), 7.72 (d, 2H, J=8 Hz), 7.35 (d, 2H, J=8 Hz), 7.33 (d, 2H, J=9 Hz), 7.11 (t, 1H, J=8 Hz), 6.96 (m, 4H), 6.79 (d, 2H, J=9 Hz), and 3.50 (s, 2H). IR (KBr, cm$^{-1}$) 3292, 1607, 1576, 1510, 1490, 1311, 1279, 1245, 1172, 848, 755, 693, and 507. MS (ESI) m/e 363, 361. Anal. Calcd for $C_{21}H_{18}N_2O_4$: C, 69.60; H, 5.01; N, 7.73. Found C, 69.08; H, 4.99; N, 7.73.

b) 4-[5-(4-phenoxy-benzyl)-[1,3,4]oxadiazol-2-yl]-phenol

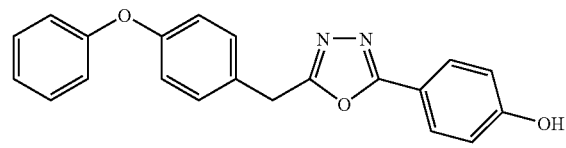

The above compound was prepared in a manner similar to that exemplified for the preparation of Example 49e, from 4-Hydroxy-benzoic acid N'-[2-(4-phenoxy-phenyl)-acetyl]-hydrazide (1.53 g, 4.22 mM), triphenylphosphine (2.24 g, 8.44 mM, and triethylamine (2.12 mL, 15.19 mM) to afford 0.835 g (57%) of 4-[5-(4-phenoxy-benzyl)-[1,3,4]oxadiazol-2-yl]-phenol as a white solid (MP 202–203° C., MW 344.37).

$^1$H NMR (DMSO-d6) δ 10.24 (s, 1H), 7.77 (d, 2H, J=9 Hz), 7.37 (m, 4H), 7.12 (t, 1H, J=7 Hz), 6.98 (m, 4H), 6.91 (d, 2H, J=9 Hz), and 4.29 (s, 2H). IR (KBr, cm$^{-1}$) 3124, 2803, 1889, 1610, 1500, 1426, 1366, 1284, 1250, 1172, 1083, 1021, 857, 816, 780, 735, and 691. MS (ESI) m/e 345, 343. Anal. Calcd for $C_{21}H_{16}N_2O_3$: C, 73.24; H, 4.68; N, 8.13. Found C, 73.08; H, 4.86; N, 8.06.

c) Dimethyl-(3-{4-[5-(4-phenoxy-benzyl)-[1,3,4]oxadiazol-2-yl]-phenoxy}-propyl)-amine, oxalic acid salt

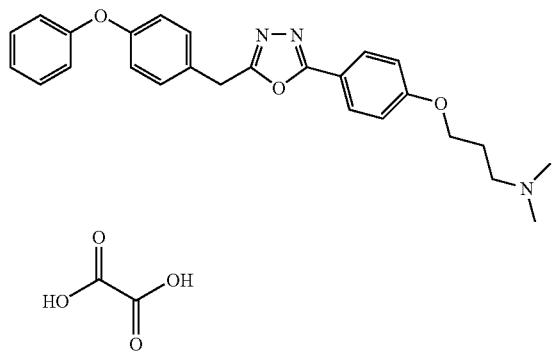

A solution of 4-[5-(4-phenoxy-benzyl)-[1,3,4]oxadiazol-2-yl]-phenol (0.344 g, 1.0 mM), 3-chloro-N,N-dimethylpropylamine hydrochloride (0.174 g, 1.1 mM), and Triton B (40 weight % in $CH_3OH$, 1.05 mL, 2.3 mM) in 5 mL DMF was stirred at 50–90° C. for 5.5 h. Cesium carbonate (0.066 g, 0.2 mM, 0.4 eq) was then added, and the reaction mixture heated at 90° C. for an additional 4.5 h. The reaction mixture was allowed to cool to room temperature and diluted with ethyl acetate/$H_2O$. The solvent layers were separated, the aqueous layer back extracted with ethyl acetate, the combined organic extracts washed with water, saturated $NaHCO_3$ solution, 1N NaOH, and brine, dried over anhydrous sodium sulfate, filtered, and concentrated in vacuo to afford 0.297 g (69%) of a gold gum. Purification by Chromatotron radial chromatography on silica gel (isocratic elution with 95:5 $CH_2Cl_2$/2.0 M ammonia in methanol) afforded 0.147 g (34%) of Dimethyl-(3-{4-[5-(4-phenoxy-benzyl)-[1,3,4]oxadiazol-2-yl]-phenoxy}-propyl)-amine as a colorless gum. The gum (0.143 g, 0.33 mM) was dissolved in 2 mL acetone, and oxalic acid (0.033 g, 0.36 mM), dissolved in 1 mL acetone, was added with rapid stirring at room temperature followed by the addition of diethyl ether/hexane (1:2, 3 mL). Filtered the resultant thick precipitate, washed the collected solid with diethyl ether and hexane, and dried in vacuo at 40° C. to afford 0.167 g (97%) of Dimethyl-(3-{4-[5-(4-phenoxy-benzyl)-[1,3,4]oxadiazol-2-yl]-phenoxy}-propyl)-amine, oxalic acid salt as a white solid (MP 156–158° C., MW oxalate salt 519.56, MW free amine 429.21).

$^1$H NMR DMSO-d6) δ 7.89 (d, 2H, J=9 Hz), 7.38 (d, 2H, J=8 Hz), 7.36 (d, 2H, J=9 Hz), 7.12 (t, 1H, J=8 Hz), 7.11 (d, 2H, J=9 Hz), 6.99 (d, 2H, J=8 Hz), 6.98 (d, 2H, J=9 Hz), 4.31 (s, 2H), 4.12 (t, 2H, J=6 Hz), 3.15 (t, 2H, J=7 Hz), 2.74 (s, 6H), and 2.09 (m, 2H). IR (KBr, cm$^{-1}$) 3435, 3034, 2931, 2659, 2562, 1722, 1612, 1589, 1496, 1475, 1428, 1309, 1256, 1169, 1053, 961, 872, 841, 739, 692, and 482. MS (ESI) m/e 430. Anal. Calcd for $C_{26}H_{27}N_3O_3$—$C_2H_2O_4$: C, 64.73; H, 5.63; N, 8.09. Found C, 64.11; H, 5.68; N, 7.80. Analytical HPLC: 100% purity.

Example 270

Preparation of 1-{3-[4-(5-Benzofuran-2-yl-methyl-[1,3,4]oxadiazol-2-yl)-phenoxy]-propyl}-piperidine

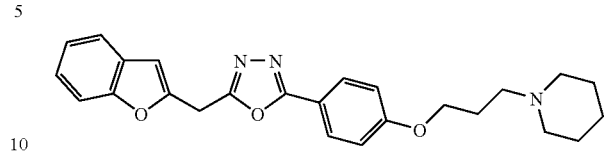

a) 4-(3-Piperidin-1-yl-propoxy)-benzoic acid N'-(2-benzofuran-2-yl-acetyl)-hydrazide

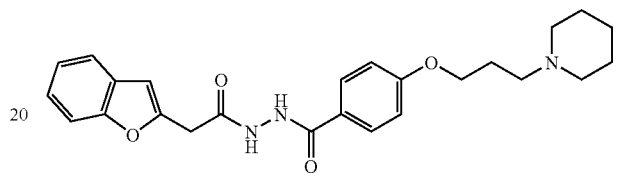

The above compound was prepared in a manner similar to that exemplified for the preparation of Example 51a, from 2-benzofurylacetic acid (0.529 g, 3.0 mM) and 4-(3-piperidin-1-yl-propoxy)-benzoic acid hydrazide (0.749 g, 3.0 mM) followed by purification by column and Chromatotron radial chromatography on silica gel (isocratic elution with 95:5 $CH_2Cl_2$/2.0 M ammonia in methanol) to afford 0.437 g (33%) of 4-(3-Piperidin-1-yl-propoxy)-benzoic acid N'-(2-benzofuran-2-yl-acetyl)-hydrazide as an off-white solid (MW 435.53).

$^1$H NMR (DMSO-d$_6$) δ 10.28 (s, 1H), 10.21 (s, 1H), 7.83 (d, 2H, J=9 Hz), 7.57 (d, 1H, J=8 Hz), 7.50 (d, 1H, J=8 Hz), 7.22 (m, 2H), 6.99 (d, 2H, J=9 Hz), 6.78 (s, 1H), 4.04 (t, 2H, J=6 Hz), 3.80 (s, 2H), 2.36 (t, 2H, J=7 Hz), 2.31 (m, 4H), 1.86 (m, 2H), 1.47 (m, 4H), and 1.36 (m, 2H). IR (KBr, cm$^{-1}$) 3234, 2933, 1646, 1606, 1500, 1453, 1304, 1252, 1175, and 750. MS (ESI) m/e 436, 434. Anal. Calcd for $C_{25}H_{29}N_3O_4$: C, 68.95; H, 6.71; N, 9.65. Found C, 67.82; H, 6.71; N, 9.59.

b) 1-{3-[4-(5-Benzofuran-2-yl-methyl-[1,3,4]oxadiazol-2-yl)-phenoxy]-propyl}-piperidine

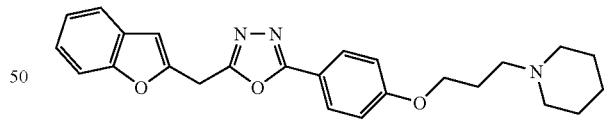

The above compound was prepared in a manner similar to that exemplified for the preparation of Example 49e, from 4-(3-Piperidin-1-yl-propoxy)-benzoic acid N'-(2-benzofuran-2-yl-acetyl)-hydrazide (0.422 g, 0.97 mM), triphenylphosphine (0.514 g, 1.94 mM), and triethylamine (0.487 mL, 3.49 mM) followed by column chromatography purification on silica gel (isocratic elution with ethyl acetate followed by 95:5 $CH_2Cl_2$/2.0 M ammonia in methanol) to afford 0.129 g (31%) of 1-{3-[4-(5-Benzofuran-2-yl-methyl-[1,3,4]oxadiazol-2-yl)-phenoxy]-propyl}-piperidine as a tan solid (MP 76–79° C., MW 417.51).

$^1$H NMR (CDCl$_3$) δ 7.96 (d, 2H, J=9 Hz), 7.53 (d, 1H, J=8 Hz), 7.45 (d, 1H, J=8 Hz), 7.24 (m, 2H), 6.95 (d, 2H, J=9 Hz), 6.69 (s, 1H), 4.47 (s, 2H), 4.15 (t, 2H, J=6 Hz), 3.09 (m,

2H), 2.47 (m, 2H), and 1.58 (m, 10H). IR (KBr, cm$^{-1}$) 3439, 2935, 2852, 2806, 2767, 2633, 2545, 1614, 1589, 1500, 1455, 1415, 1305, 1257, 1176, 1123, 1009, 955, 833, 739, 523, and 435. MS (ESI) m/e 418, 416. Anal. Calcd for $C_{25}H_{27}N_3O_3$: C, 71.92; H, 6.52; N, 10.06. Found C, 67.92; H, 6.28; N, 9.26. Analytical HPLC: 100% purity.

Example 271

Preparation of 5-(2-Phenoxy-ethylsulfanylmethyl)-2-[4-(2-pyrrolidin-1-yl-ethoxy)-phenyl]-oxazole

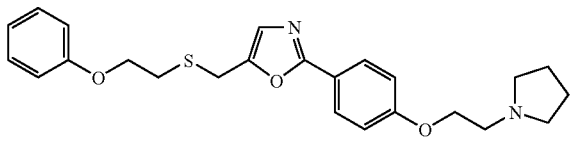

a)
4-Benzyloxy-N-(2,3-dihydroxy-propyl)-benzamide

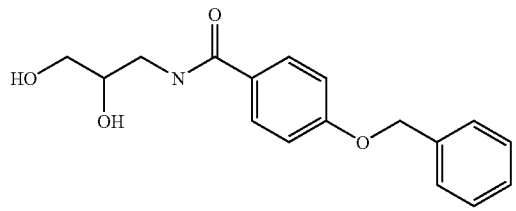

A solution of 4-benzyloxy-benzoic acid (9.08 g, 39.8 mM) and (2,2-dimethyl-[1,3]dioxolan-4-yl)-methylamine (4.97 g, 37.9 mM) in 75 mL methylene chloride was treated with dicyclohexylcarbodiimide (8.21 g, 39.8 mM) and stirred for 36 h at room temperature. After evaporation of the solvent in vacuo the remaining solid was dissolved in 250 mL acidic acid:water (4:1) and warmed to 50° C. for 6 h. The solvents were evaporated and the remaining oil purified by chromatography on silica gel (elution with gradient ethyl acetate/ethanol) to afford a white solid as a mixture of 4-benzyloxy-N-(2,3-dihydroxy-propyl)-benzamide and dicyclohexyl urea. The latter crystallized out of 40 mL ethanol at 5° C. After evaporation of the solvent 4.0 g (33%)4-benzyloxy-N-(2,3-dihydroxy-propyl)-benzamide was obtained as an oil.

$^1$H NMR (DMSO-d$_6$, 300 MHz) δ 8.23 (t, J=5 Hz, 1H), 7.83 (t, J=8 Hz, 2H), 7.49–7.30 (m, 5H), 7.07 (t, J=8 Hz, 2H), 5.18 (s, 2H), 4.80 (br s, 1H), 4.65 (br s, 1H), 3.68–3.53 (m, 1H), 3.42–3.12 (m, 4H). MS (ESI): m/e=302 (MH)$^+$.

b) 4-Methoxy-benzoic acid 3-(4-benzyloxy-benzoylamino)-2-hydroxy-propyl ester

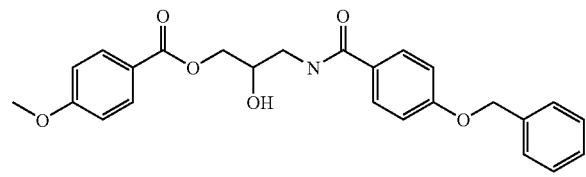

A solution of 4-benzyloxy-N-(2,3-dihydroxy-propyl)-benzamide (4.0 g, 13.27 mM) and triethylamine (4.02 g, 39.82 mM) in 150 mL methylene chloride was cooled to 5° C. and treated with a solution of 4-methoxy-benzoic acid chloride (2.26 g, 13.27 mM) in 50 mL methylene chloride. Within 14 h the reaction mixture was allowed to warm to room temperature and was than quenched with 150 mL water. The organic layer was washed with 10 mL 2M hydrochloric acid, dried over sodium sulfate and evaporated. The remaining oil was purified by chromatography on silica gel (elution with gradient methylene chloride/ethanol) to afford 2.2 g (38%) 4-methoxy-benzoic acid 3-(4-benzyloxy-benzoylamino)-2-hydroxy-propyl ester as a white solid.

$^1$H NMR (DMSO-d$_6$, 300 MHz) δ 8.38 (t, J=5 Hz, 1H), 7.96 (t, J=8 Hz, 2H), 7.83 (t, J=8 Hz, 2H), 7.49–7.28 (m, 5H), 7.10–7.02 (m, 4H), 5.26 (br s, 1H), 5.18 (s, 2H), 4.25–3.95 (m, 3H), 3.85 (s, 3H), 3.40–3.25 (m, 2H). MS (ESI): m/e=436 (MH)$^+$.

c) 4-Methoxy-benzoic acid 3-(4-benzyloxy-benzoylamino)-2-oxo-propyl ester

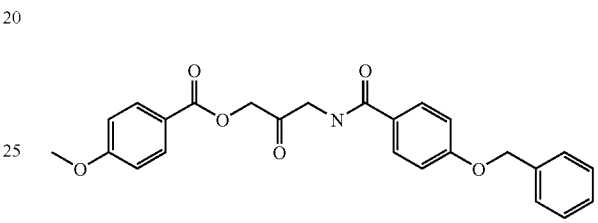

A solution of 4-methoxy-benzoic acid 3-(4-benzyloxy-benzoylamino)-2-hydroxy-propyl ester (1.2 g, 2.76 mM) in 30 mL methylene chloride was cooled to 5° C. and treated with 7.8 mL of a solution of 1,1-dihydro-1,1,1-triacetoxy-1,2-benziodoxol-3(1H)-one in methylene chloride (Dess-Martin reagent, 15 wt % in methylene chloride, from Acros). After 2 h the reaction mixture was allowed to warm to room temperature and the solvent was removed in vacuo. The remains were vigorously stirred with 50 mL of ethyl acetate/tert-butylmethyl ether (5:1) and filtered. The solution was washed with 20 mL water, dried over sodium sulfate and evaporated to afford 1.0 g (84%) 4-methoxy-benzoic acid 3-(4-benzyloxy-benzoylamino)-2-oxo-propyl ester as a white solid.

$^1$H NMR (CDCl$_3$, 300 MHz) δ 8.06 (t, J=8 Hz, 2H), 7.82 (t, J=8 Hz, 2H), 7.47–7.28 (m, 5H), 7.02 (t, J=8 Hz, 2H), 6.96 (t, J=8 Hz, 2H), 6.82 (br s, 1H), 5.18 (s, 2H), 5.00 (s, 2H), 4.52 (s, 2H), 3.88 (s, 3H). MS (ES): m/e=434 (MH)$^+$.

d) 4-Methoxy-benzoic acid 2-(4-benzyloxy-phenyl)-oxazol-5-ylmethyl ester

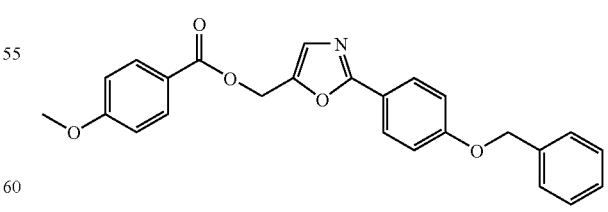

A solution of 4-methoxy-benzoic acid 3-(4-benzyloxy-benzoylamino)-2-oxo-propyl ester (1.0 g, 2.3 mM) in 150 mL anhydrous dioxane in an Argon atmosphere was treated with (methoxycarbonylsulfamoyl)-triethylammonium hydroxide (1.1 g, 4.6 mM) in one portion and heated to 68°

C. for 30 minutes. The reaction mixture was poured into 50 mL of water and extracted with 70 mL ethyl acetate.

The organic layer was dried over sodium sulfate and evaporated. The remaining oil was purified by chromatography on silica gel (elution with gradient ethyl acetate/hexane) to afford 320 mg (31%) 4-methoxy-benzoic acid 2-(4-benzyloxy-phenyl)-oxazol-5-ylmethyl ester as a white solid.

¹H NMR (CDCl₃, 300 MHz) δ 8.01 (t, J=9 Hz, 2H), 7.98 (t, J=9 Hz, 2H), 7.47–7.33 (m, 5H), 7.23 (s, 1H), 7.05 (t, J=8 Hz, 2H), 6.92 (t, J=8 Hz, 2H), 5.28 (s, 2H), 5.15 (s, 2H), 3.88 (s, 3H). MS (ESI): m/e=416 (MH)⁺.

e) 4-Methoxy-benzoic acid 2-(4-hydroxy-phenyl)-oxazol-5-ylmethyl ester

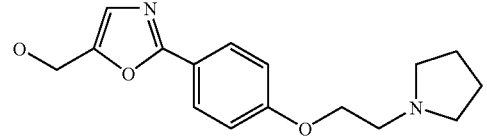

A solution of 4-methoxy-benzoic acid 2-(4-benzyloxy-phenyl)-oxazol-5-ylmethyl ester (320 mg, 7.7 mM) in methanol was filled in an autoclave and treated with 10% Palladium on charcoal (32 mg, 3.0·10⁻⁵ M). The autoclave was charged with hydrogen (8 bar) and the reaction mixture stirred at 50° C. of 6 h. The pressure was released and the suspension filtered and evaporated to afford 226 mg (90%) of 4-methoxy-benzoic acid 2-(4-hydroxy-phenyl)-oxazol-5-ylmethyl ester as a white solid.

¹H NMR (CDCl₃, 300 MHz) δ 8.02 (t, J=9 Hz, 2H), 7.93 (t, J=9 Hz, 2H), 7.25 (s, 1H), 6.94–6.87 (m, 4H), 5.38 (s, 2H), 3.88 (s, 3H). MS (ESI): m/e=326 (MH)⁺.

f) 4-Methoxy-benzoic acid 2-[4-(2-pyrrolidin-1-yl-ethoxy)-phenyl]-oxazol-5-ylmethyl ester

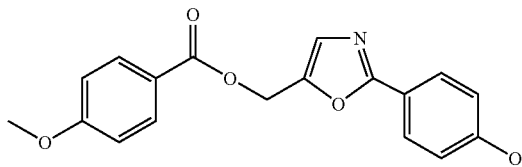

A suspension of 4-methoxy-benzoic acid 2-(4-hydroxy-phenyl)-oxazol-5-ylmethyl ester (220 mg, 0.68 mM), N-(2-chloro-ethyl)-pyrrolidine hydrochloride (115 mg, 0.68 mM), and potassium carbonate (929 mg, 6.72 mM) in 20 mL dimethylformamide was heated at 60° C. for 3 h. The solvent was removed in vacuo and the remains partitioned between 10 mL water and 30 mL methylene chloride. The organic layer was dried over sodium sulfate and evaporated. The remaining oil was purified by chromatography on silica gel (elution with gradient methylene chloride/ethanol containing 10% ammonia) to afford 100 mg (35%) of 4-methoxy-benzoic acid 2-[4-(2-pyrrolidin-1-yl-ethoxy)-phenyl]-oxazol-5-ylmethyl ester s a white solid.

¹H NMR (CDCl₃, 300 MHz) δ 7.97–7.82 (m, 4H), 7.15 (s, 1H), 6.94–6.82 (m, 4H), 5.38 (s, 2H), 4.39 (t, J=6 Hz, 2H), 3.88 (s, 3H), 2.85 (t, J=6 Hz, 2H), 2.63–2.52 (m, 4H), 1.80–1.70 (m, 4H). MS (ESI): m/e=423(MH)⁺.

g) {2-[4-(2-Pyrrolidin-1-yl-ethoxy)-phenyl]-oxazol-5-yl}-methanol

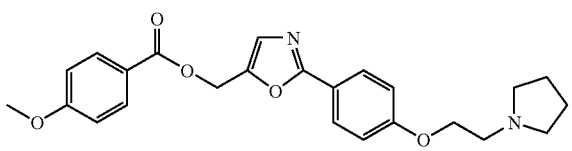

A solution of 4-methoxy-benzoic acid 2-[4-(2-pyrrolidin-1-yl-ethoxy)-phenyl]-oxazol-5-ylmethyl ester (95 mg, 0.23 mM) in anhydrous tetrahydrofuran was treated with lithium aluminium hydride (2 mg, 5.6×10⁻⁵ M) at 5° C. and stirred for 30 minutes. The reaction was quenched with 0.2 mL acetone and evaporated. The remaining oil was dissolved in 75 mL methylene chloride and washed with 50 mL water. The organic layer was dried over sodium sulfate and evaporated and the remaining oil purified by chromatography on silica gel (elution with gradient methylene chloride/ethanol containing 10% ammonia) to afford 15 g (23%) of {2-[4-(2-pyrrolidin-1-yl-ethoxy)-phenyl]-oxazol-5-yl}-methanol as a white solid.

¹H NMR (CDCl₃, 300 MHz) δ 7.99 (d, J=9 Hz, 2H), 7.12 (s, 1H), 6.98 (d, J=9 Hz, 2H), 4.75 (s, 2H), 4.45 (t, J=6 Hz, 2H), 4.00–3.90 (m, 2H), 3.55 (t, J=6 Hz, 2H), 3.05–2.90 (m, 2H), 2.20–2.10 (m, 4H). MS (ESI): m/e=289 (MH)⁺.

h) 5-(2-Phenoxy-ethylsulfanylmethyl)-2-[4-(2-pyrrolidin-1-yl-ethoxy)-phenyl]-oxazole

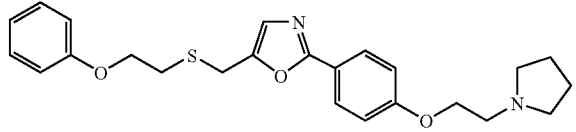

A solutuion of {2-[4-(2-pyrrolidin-1-yl-ethoxy)-phenyl]-oxazol-5-yl}-methanol (6.5 mg, 2.26×10⁻⁵ M) and triethylamine (8.2 mg, 8.11×10⁻⁵ M) in 2 mL methylene chloride was cooled to 5° C., treated with methane sulfonyl chloride (2.8 mg, 2.48×10⁻⁵ M) in 1 mL methylene chloride and stirred for 30 minutes.

In a separate flask 3 mL ethanol were treated with sodium hydride (8.2 mg, 0.34 mM) at 5° C., stirred for 10 minutes before 2-phenoxy-ethanethiol (50.2 mg, 0.325 mM) was added. This solution was stirred for further 10 minutes at 5° before it was added to the first solution at 5° C. Stirring of the combined solutions was continued for 72 h. The solvent was evaporated in vacuo and the remains were poured into 10 mL water. The aqueous phase was extracted twice with 10 mL methylene chloride. The organic layer was dried over sodium sulfate and evaporated and the remaining oil purified by chromatography on silica gel (elution with gradient methylene chloride/ethanol containing 10% ammonia) to afford 1.5 mg (16%) of 5-(2-phenoxy-ethylsulfanylmethyl)-2-[4-(2-pyrrolidin-1-yl-ethoxy)-phenyl]-oxazole as a white solid.

¹H NMR (CDCl₃, 300 MHz) δ 7.93 (d, J=9 Hz, 2H), 7.30–7.27 (m, 2H), 7.01–6.88 (m, 6H), 4.25–4.14 (m, 4H), 3.95 (s, 2H), 2.98–2.89 (m, 4H), 2.72–2.60 (m, 4H), 1.88–1.78 (m, 4H). MS (ESI): m/e=425 (MH)⁺.

Example 272

Preparation of 4-Methyl-5-(2-phenoxy-ethylsulfanylmethyl)-2-[4-(2-pyrrolidin-1-yl-ethoxy)-phenyl]-oxazole

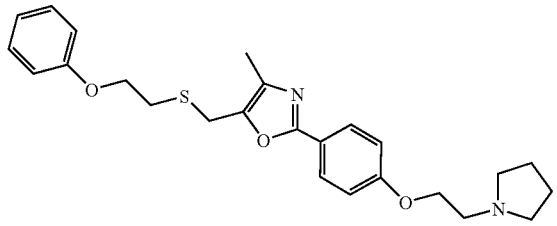

a) 2-(4-Methoxy-benzoylamino)-propionic acid methyl ester

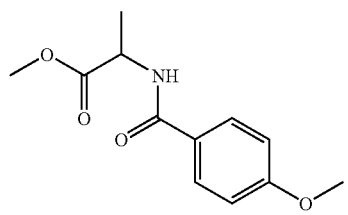

A solution of 4-methoxy-benzoic acid (5.20 g, 34.2 mM) in 35 mL dimethylformamide was cooled to 0° C. and treated with N,N'-carbonyl di-imidazole (5.55 g, 34.2 mM). Stirring was continued for 30 minutes before L-alanine methyl ester hydrochloride (4.68 g, 33.5 mM) was added. The reaction mixture was allowed to warm to room temperature and stirred for 16 h. The solvent was removed in vacuo and the remaining oil poured into 200 mL of 2N HCl and extracted twice with 30 mL methylene chloride. The organic layer was washed twice with 50 mL 5% aqueous Na₂CO₃ solution, dried over sodium sulfate and evaporated to afford 4.28 g (53%) of 2-(4-methoxy-benzoylamino)-propionic acid methyl ester as a white solid.

$^1$H NMR (CDCl$_3$, 300 MHz) δ 7.78 (d, J=9 Hz, 2H), 6.94 (d, J=9 Hz, 2H), 6.67 (br s, 1H), 4.80 (q, J=8 Hz, 1H), 3.88 (s, 3H), 3.80 (s, 3H), 1.55 (d, J=8 Hz, 3H). MS (ESI): m/e=238 (MH)$^+$.

b) 2-(4-Methoxy-benzoylamino)-propionic acid

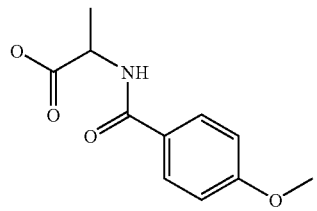

A solution of 2-(4-methoxy-benzoylamino)-propionic acid methyl ester (4.20 g, 17.7 mM) in 20 mL tetrahydrofuran and water (1:1) was treated with lithium hydroxide (0.43 g, 35 mM) and stirred for 20 h at room temperature. The reaction mixture was diluted with 2N HCl until a pH=1 was reached. The precipitation was filtered and dried to afford 2.5 g (63%) 2-(4-methoxy-benzoylamino)-propionic acid as a white solid.

$^1$H NMR (DMSO-d$_6$, 300 MHz) δ 12.50 (br s, 1H), 8.48 (d, J=7 Hz, 1H), 7.88 (d, J=9 Hz, 2H), 7.00 (d, J=9 Hz, 2H), 4.42 (q, J=8 Hz, 1H), 3.82 (s, 3H), 1.45 (d, J=8 Hz, 3H). MS (ESI): m/e=224 (MH)$^+$.

c) 2-(4-Methoxy-phenyl)-4-methyl-oxazole-5-carboxylic acid methyl ester

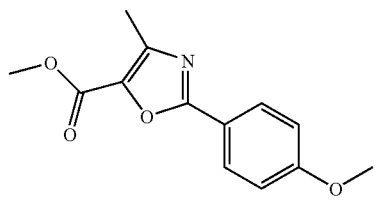

A suspension of 2-(4-methoxy-benzoylamino)-propionic acid (1.8 g, 8.0 mM) in 32 mL benzene and 120 mL methylene chloride was treated with oxalyl chloride (10 g, 80 mM) and stirred for 18 h at room temperature. During that time, the suspension turned into a solution. The volatiles were removed in vacuo, the remaining oil was cooled to 0° C. and treated with triethylamine (1.2 g, 12 mM) followed by addition of 60 mL methanol and stirred for 2 h at room temperature. The solvents were removed in vacuo. The remains were extracted with tert-butyl methyl ether. The ether layer was evaporated and the remaining oil was purified by chromatography on silica gel with methylene chloride to afford 0.82 g (42%) 2-(4-methoxy-phenyl)-4-methyl-oxazole-5-carboxylic acid methyl ester as a white solid.

$^1$H NMR (CDCl$_3$, 300 MHz) δ 8.07 (d, J=9 Hz, 2H), 6.98 (d, J=9 Hz, 2H), 3.95 (s, 3H), 3.87 (s, 3H), 2.55 (s, 3H),). MS (ESI): m/e=248 (MH)$^+$.

d) [2-(4-Methoxy-phenyl)-4-methyl-oxazol-5-yl]-methanol

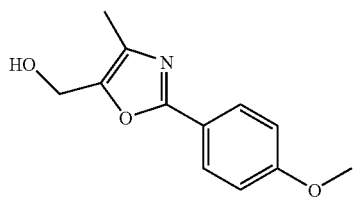

A solution of 4-(4-methoxy-phenyl)-4-methyl-oxazole-2-carboxylic acid methyl ester (0.79 g, 3.19 mM) in 40 mL toluene was cooled to 0° C. and treated with 7.9 mL di-isobutyl aluminium hydride solution (20% in toluene, 9.58 mM) and stirred for 2 h. The reaction mixture was allowed to warm to room temperature quenched with 5 mL methanol and evaporated. The remaining oil was dissolved in 15 mL methanol and filtered. The methanolic layer was evaporated and the remaining oil purified by chromatography on silica gel (elution with gradient methylene chloride/ethanol) to afford 0.29 g (42%) [2-(4-methoxy-phenyl)-4-methyl-oxazol-5-yl]-methanol as a solid.

$^1$H NMR (DMSO-d$_6$, 300 MHz) δ 7.88 (d, J=9 Hz, 2H), 7.06 (d, J=9 Hz, 2H), 5.28 (t, J=7 Hz, 1H), 4.50 (d, J=7 Hz, 2H), 3.95 (s, 3H), 2.25 (s, 3). MS (ESI): m/e=220 (MH)$^+$.

e) 2-(4-Methoxy-phenyl)-4-methyl-oxazole-5-carbaldehyde

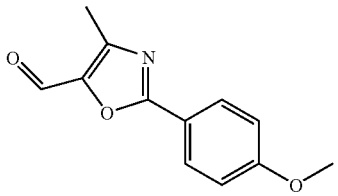

A solution of [2-(4-methoxy-phenyl)-4-methyl-oxazol-5-yl]-methanol (0.18 g, 0.79 mM) in 3 mL methylene chloride was cooled to 5° C. and treated with 2.5 g of a solution of 1,1-dihydro-1,1,1-triacetoxy-1,2-benziodoxol-3(1H)-one in methylene chloride (Dess-Martin reagent in solution, 15 wt %, from Acros). After 2.5 h the reaction mixture was allowed to warm to room temperature and the solvent was removed in vacuo. The remains were vigorously stirred with 50 mL tert-butylmethyl ether and filtered. The solution was washed with 10 mL water, dried over sodium sulfate and evaporated to afford 0.16 g (92%) 2-(4-methoxy-phenyl)-4-methyl-oxazole-5-carbaldehyde as an oil.

$^1$H NMR (CDCl$_3$, 300 MHz) δ 9.88 (s, 1H), 8.10 (d, J=9 Hz, 2H), 7.00 (d, J=9 Hz, 2H), 3.90 (s, 3H), 2.58 (s, 3H). MS (ESI): m/e=218 (MH)$^+$.

f) 2-(4-Hydroxy-phenyl)-4-methyl-oxazole-5-carbaldehyde

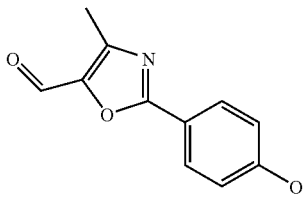

2-(4-Methoxy-phenyl)-4-methyl-oxazole-5-carbaldehyde (0.16 g, 0.73 mM) was dissolved in 4 mL methylene chloride, cooled to −20° C. and treated with 2.58 mL 1M boron tribromide solution in methylene chloride. Within 2 h the reaction mixture was allowed to warm to room temperature and stirred for 28 h. The reaction mixture was quenched with 3 mL water. The organic layer was dried over sodium sulfate and evaporated. The remaining was oil purified by chromatography on silica gel (elution with gradient methylene chloride/ethanol) to afford 63 mg (42%) 2-(4-hydroxy-phenyl)-4-methyl-oxazole-5-carbaldehyde as a white solid.

$^1$HNMR (CDCl$_3$, 300 MHz) δ 9.85 (s, 1H), 8.06 (d, J=9 Hz, 2H), 6.95 (d, J=9 Hz, 2H), 2.60 (s, 3H). MS (ESI): m/e=204 (M)$^+$.

g) Acetic acid 4-(5-formyl-4-methyl-oxazol-2-yl)-phenyl ester

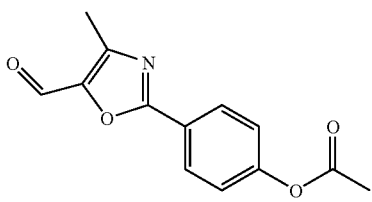

A solution of 2-(4-hydroxy-phenyl)-4-methyl-oxazole-5-carbaldehyde (63 mg, 0.31 mM) in 1 mL tetrahydrofuran was treated with triethylamine (31.5 mg, 0.31 nM) and acetyl chloride (24.5 mg, 0.31 mM) and stirred at room temperature for 2 h. The solvent was evaporated and the remains dissolved in 4 mL methylene chloride and 4 mL water. The organic layer was dried over sodium sulfate and evaporated to afford 56 mg (74%)acetic acid 4-(5-formyl-4-methyl-oxazol-2-yl)-phenyl ester as a white solid.

$^1$H NMR (CDCl$_3$, 300 MHz) δ 9.85 (s, 1H), 8.18 (d, J=9 Hz, 2H), 7.27 (d, J=9 Hz, 2H), 2.58 (s, 3H), 2.35 (s, 3H). MS (ESI): m/e=246 (MH)$^+$.

h) Acetic acid 4-(5-hydroxymethyl-4-methyl-oxazol-2-yl)-phenyl ester

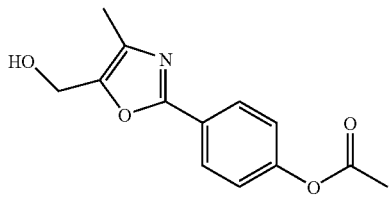

A solution of acetic acid 4-(5-formyl-4-methyl-oxazol-2-yl)-phenyl ester (56 mg, 0.23 mM) in 5 mL methanol and water (4:1) was treated with sodium borohydride (0.33 mg, 8.6×10$^{-5}$ M) at 0° C. and stirred for 30 minutes. The reaction was quenched with 0.2 mL acetone and evaporated. The remaining oil was dissolved in 7 mL methylene chloride and washed with 5 mL water. The organic layer was dried over sodium sulfate and evaporated and the remaining oil purified by chromatography on silica gel (elution with gradient methylene chloride/ethanol) to afford 31.5 mg (55%) acetic acid 4-(5-hydroxymethyl-4-methyl-oxazol-2-yl)-phenyl ester as a white solid.

$^1$H NMR (CDCl$_3$, 300 MHz) δ 8.05 (d, J=9 Hz, 2H), 7.18 (d, J=9 Hz, 2H), 4.70 (s, 2H), 2.48 (s, 3H), 2.27 (s, 3H). MS (ESI): m/e=248 (MH)$^+$.

i) 4-[4-Methyl-5-(2-phenoxy-ethylsulfanylmethyl)-oxazol-2-yl]-phenol

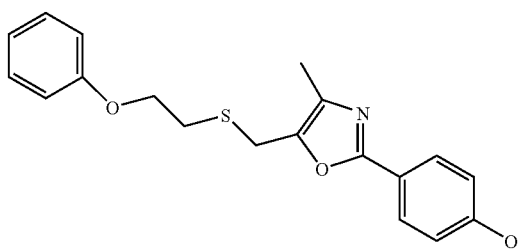

A solution of acetic acid 4-(5-hydroxymethyl-4-methyl-oxazol-2-yl)-phenyl ester (120 mg, 0.49 mm) and triethylamine (54 mg, 0.53 mM) in 2 mL methylene chloride was cooled to 5° C., treated with methane sulfonyl chloride (61 mg, 0.53 mM) in 1 mL methylene chloride and stirred for 30 minutes.

In a separate second flask 8 mL ethanol were treated with sodium hydride (42 mg, 1.75 mM) at 5° C., stirred for 10 minutes before 2-phenoxy-ethanethiol (270 mg, 1.75 mM) was added. This solution was stirred for further 10 minutes at 5° before the two separate solutions were combined at that temperature through addition of second solution to the first one. Stirring of the combined solutions was continued for 72 h. The solvent was evaporated in vacuo and the remains were poured into 10 mL water. The aqueous phase was extracted with methylene chloride. The organic layer was dried over sodium sulfate and evaporated and the remaining oil purified by chromatography on silica gel (elution with gradient methylene chloride/ethanol) to afford 96 mg (53%) 4-[4-methyl-5-(2-phenoxy-ethylsulfanylmethyl)-oxazol-2-yl]-phenol as a white solid.

$^1$H NMR (CDCl$_3$, 300 MHz) δ 7.83 (d, J=9 Hz, 2H), 7.32–7.22 (m, 2H9, 7.00–6.80 (m, 5H), 4.20 (t, J=7 Hz, 2H), 3.92 (s, 2H), 2.92 (t, J=7 Hz, 2H), 2.27 (s, 3H). MS (ESI): m/e=342 (MH)$^+$.

j) 4-Methyl-5-(2-phenoxy-ethylsulfanylmethyl)-2-[4-(2-pyrrolidin-1-yl-ethoxy)-phenyl]-oxazole

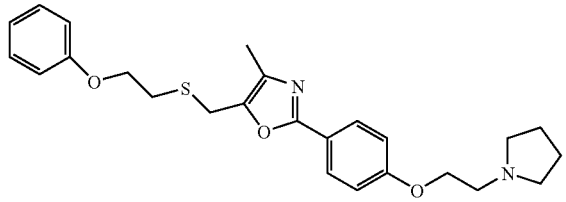

A suspension of 4-[4-methyl-5-(2-phenoxy-ethylsulfanyl-methyl)-oxazol-2-yl]-phenol (57 mg, 0.17 mM), N-(2-chloro-ethyl)-pyrrolidine hydrochloride (31 mg, 0.18 mM), and potassium carbonate (51 mg, 0.37 mM) in S mL dimethylformamide was heated at 80° C. for 16 h. The solvent was removed in vacuo and the remains partitioned between 2 mL water and 5 mL methylene chloride. The organic layer was dried over sodium sulfate and evaporated. The remaining oil was purified by chromatography on silica gel (elution with gradient methylene chloride/ethanol containing 10% ammonia) to afford 39 mg (53%) 4-methyl-5-(2-phenoxy-ethylsulfanylmethyl)-2-[4-(2-pyrrolidin-1-yl-ethoxy)-phenyl]-oxazole as a white solid.

$^1$H NMR (CDCl$_3$, 300 MHz) δ 7.93 (d, J=9 Hz, 2H), 7.33–7.25 (m, 2H), 7.01–6.88 (m, 5H), 4.25–4.10 (m, 4H), 3.95 (s, 2H), 2.98–2.89 (m, 4H), 2.70–2.55 (m, 4H), 2.23 (s, 3H), 1.88–1.77 (m, 4H). MS (ESI): m/e=439 (MH)$^+$.

Example 273

Preparation of Dimethyl-(3-{4-[4-methyl-5-(2-phenoxy-ethylsulfanylmethyl)-oxazol-2-yl]-phenoxy}-propyl)-amine

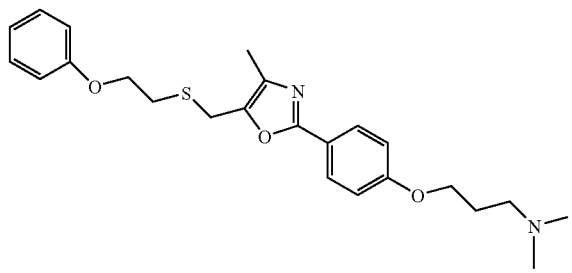

A suspension of 4-[4-methyl-5-(2-phenoxy-ethylsulfanyl-methyl)-oxazol-2-yl]-phenol (26 mg, 0.08 mM), (3-chloropropyl)-dimethyl-amine hydrochloride (13.2 mg, 0.08 mM), and potassium carbonate (23 mg, 0.17 mM) in 5 mL dimethylformamide was heated at 80° C. for 16 h. The solvent was removed in vacuo and the remains partitioned between 2 mL water and 5 mL methylene chloride. The organic layer was dried over sodium sulfate and evaporated. The remaining oil was purified by chromatography on silica gel (elution with gradient methylene chloride/ethanol containing 10% ammonia) to afford 17 mg (52%) dimethyl-(3-{4-[4-methyl-5-(2-phenoxy-ethylsulfanylmethyl)-oxazol-2-yl]-phenoxy}-propyl)-amine as a white solid.

$^1$H NMR (CDCl$_3$, 300 MHz) δ 7.91 (d, J=9 Hz, 2H), 7.33–7.24 (m, 2H), 7.00–6.87 (m, 5H), 4.20 (t, J=7 Hz, 2H), 4.08 (t, J=7 Hz, 2H), 3.92 (s, 2H), 2.95 (t, J=7 Hz, 2H), 2.48 (t, J=7 Hz, 2H), 2.28 (s, 6H), 2.22 (s, 3H), 2.02–1.92 (m, 2H). MS (ESI): m/e=428 (MH)$^{30}$.

Example 274

Preparation of [3-(4-{5-[2-(4-trifluoromethoxy-phenoxy)-ethylsulfanylmethyl]-[1,3,4]oxadiazol-2-yl}-phenoxy)-propyl]-dimethyl-amine

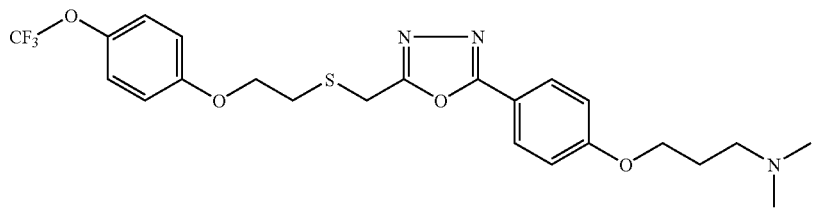

a) Methyl 4-(3-dimethylamino-propoxy)-benzoate

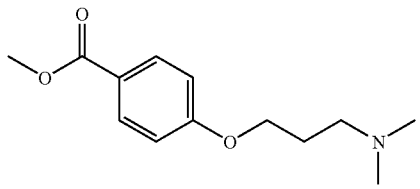

To a cold mixture (0° C.) of methyl 4-hydroxybenzoate (33.93 g, 223 mmol), triphenylphosphine (53.29 g, 203 mmol), and 3-dimethylaminopropanol-1 (20.88 g, 202 mmol) in anhydrous THF (180 mL) was added diisopropylazodicarboxylate (44 mL, 223 mmol) over 5 minutes with stirring. The stirring continued at 0° C. for 30 minutes and then 23° C. overnight. After removal of solvent, the residue was submitted to a flash filtration chromatography on silica gel (elution with ethyl acetate, then 20% 2M $NH_3$-MeOH in $CH_2Cl_2$). A yellowish oil was obtained (44.83 g, 94%).

$^1$H NMR ($CDCl_3$) δ 7.95 (d, 2H, J=8.85 Hz), 6.88 (d, 2H, J=8.85 Hz), 4.04 (t, 2H, J=6.55 Hz), 3.85 (s, 3H), 2.42 (t, 2H, J=7.26 Hz), 2.22 (s, 6H), 1.94 (m, 2H, J=6.55, 7.26 Hz). MS ($ES^+$) m/e 238.

b) 4-(3-Dimethylamino-propoxy)-benzoic hydrazide

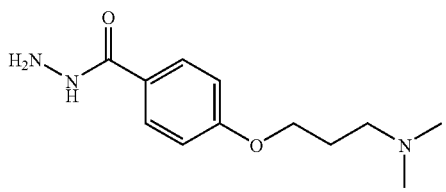

A mixture of methyl 4-(3-dimethylamino-propoxy)-benzoate (44.83 g, 189 mmol) and hydrazine monohydrate (100 g, 2000 mmol) was stirred at 80° C. overnight; then it was allowed to cool to 23° C. A white solid formed. The solid was collected by filtration, washed with hexanes (3×50 mL), and dried in vacuum to afford a white powder (32.01 g, 71%).

$^1$H NMR ($CDCl_3$) δ 7.67 (d, 2H, J=8.85 Hz), 6.90 (d, 2H, J=8.85 Hz), 7.36 (s, b, 1H), 4.02 (t, 2H, J=6.37 Hz), 4.00 (s, b, 2H), 2.42 (t, 2H, J=7.26 Hz), 2.22 (s, 6H), 1.93 (m, 2H, J=6.37, 7.26 Hz). MS ($ES^+$) m/e 238. mp 79.5–81.0° C. Anal. Calcd for $C_{12}H_{19}N_3O_2$: C, 60.74; H, 8.07; N, 17.71. Found C, 60.39; H, 7.97; N, 17.63.

c) Ethylene glycol mono-p-toluate

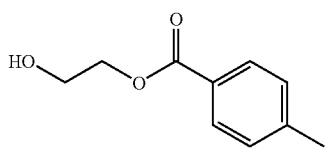

To a cold solution (0° C.) of triethylamine (40 mL, 287 mmol) and ethylene glycol (60 mL, 1080 mol) in dichloromethane (300 mL) was added p-toluoyl chloride (27 mL, 200 mmol) with stirring. After 30 minutes, cooling bath was removed and stirring continued overnight at 23° C. The reaction mixture was distributed between diethyl ether (300 mL) and water (300 mL). The organic phase was isolated and washed subsequently with 0.3 N HCl (aq, 200 mL), sat. $NaHCO_3$ (aq, 200 mL), and sat. NaCl (aq, 200 mL). After removal of solvent, the residue was purified on a silica gel column with hexanes-ethyl acetate (3:1) to give a white solid (29.34 g, 81.4%).

$^1$H NMR ($CDCl_3$) δ 7.92 (d, 2H, J=8.49 Hz), 7.22 (d, 2H, J=7.78 Hz), 4.41–4.45 (m, 2H), 3.94 (q, 2H, J=5.83, 9.37 Hz), 2.39 (s, 3H), 2.03 (t, 2H, J=5.83 Hz). MS ($ES^+$) m/e 181. mp 44.5–45.0° C.

d) 2-(4-Trifluoromethoxy-phenoxy)-ethyl p-toluate

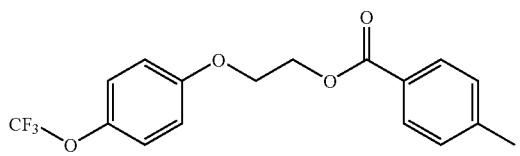

To a cold mixture (0° C.) of ethylene glycol mono-p-toluate (1.80 g, 10 mmol), triphenylphosphine (2.88 g, 11 mmol), and 4-trifluoromethoxyphenol (1.87 g, 10.5 mmol) in anhydrous THF (10 mL) was added diisopropylazodicarboxylate (2.2 mL, 10.5 mmol) with stirring. The reaction mixture was stirred at 0° C. for 30 minutes and then 23° C. overnight. After removal of solvent, the residue was purified by chromatography on silica gel (elution with 5% ethyl acetate in hexanes) to provide a white solid (3.06 g, 90%).

$^1$H NMR ($CDCl_3$) δ 7.91 (d, 2H, J=8.14 Hz), 7.21 (d, 2H, J=8.14 Hz), 7.13 (d, 2H, J=8.85 Hz), 6.91 (d, 2H, J=8.85 Hz), 4.63 (t, 2H, J=4.77 Hz), 4.27 (t, 2H, J=4.77 Hz), 2.38 (s, 3H). MS ($ES^+$) m/e 341. mp 76.0–77.5° C.

e) 2-(4-Trifluoromethoxy-phenoxy)-ethanol-1

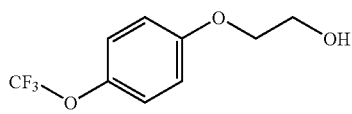

A solution of 2-(4-trifluoromethoxy-phenoxy)-ethyl p-toluate (3.06 g, 9 mmol) in 2 N LiOH (20 mL, 40 mmol), THF (15 mL), and MeOH (15 mL) was stirred at 23° C. overnight. After neutralized with sat. $NaHCO_3$ (aq, 100 mL), the reaction mixture was extracted with diethyl ether (3×100 mL). The combined organic phases were dried over anhydrous sodium sulfate. After removal of solvent, a colorless oil was obtained (2.00 g, 100%)

$^1$H NMR ($CDCl_3$) δ 7.13 (d, 2H, J=9.20 Hz), 6.89 (d, 2H, J=9.20 Hz), 4.05 (t, 2H, J=4.42 Hz), 3.95 (m, b, 2H), 1.96 (t, b, 1H). MS ($ES^+$) m/e 223.

f) 2-(4-Trifluoromethoxy-phenoxy)-ethyl tosylate

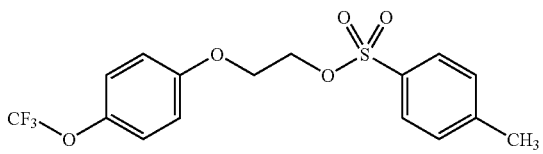

A cold solution of 2-(4-trifluoromethoxy)-ethanol-1 (667 mg, 3 mmol), pyridine (0.5 mL, 6 mmol), and p-toluenesulfonyl chloride (860 mg, 4.5 mmol) in chloroform (5 mL) was stirred at 0° C. After 6 hours, solvent was removed and the residue was submitted to a silica gel chromatography (elution with 20% ethyl acetate in hexanes) to afford a white solid (858 mg, 76%).

$^1$H NMR (CDCl$_3$) δ 7.79 (d, 2H, J=8.14 Hz), 7.31 (d, 2H, J=8.14 Hz), 7.08 (d, 2H, J=9.20 Hz), 6.75 (d, 2H, J=9.20 Hz), 4.34–4.38 (m, 2H), 4.10–4.14 (m, 2H), 2.42 (s, 3H). MS (ES$^+$) m/e 377. mp 35.0–36.0° C.

g) Methyl 2-(4-trifluoromethoxy-phenoxy)-ethylsulfanyl-acetate

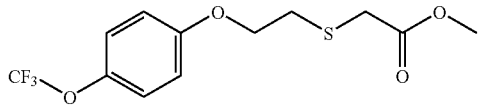

A mixture of 2-(4-trifluoromethoxy-phenoxy)-ethyl tosylate (753 mg, 2 mmol), methyl thioglycolate (0.4 mL, 7 mmol), and potassium carbonate (875 mg, 6 mmol) in THF (5 mL) was stirred at 65° C. overnight. The reaction mixture was filtered and washed with diethyl ether (3×6 mL) and dichloromethane (2×6 mL). After evaporation of solvent, the residue was purified by chromatography on silica gel (elution with 20% ethyl acetate in hexanes) to deliver a colorless oil (619 mg, 100%).

$^1$H NMR (CDCl$_3$) δ 7.12 (d, 2H, J=9.20 Hz), 6.86 (d, 2H, J=9.20 Hz), 4.15 (t, 2H, J=6.37 Hz), 3.71 (s, 3H), 3.33 (s, 2H), 3.01 (t, 2H, J=6.37 Hz). MS (ES$^+$) m/e 311.

h) 2-(4-Trifluoromethoxy-phenoxy)-ethylsulfanyl acetic acid

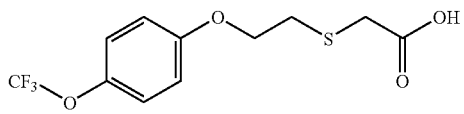

A solution of methyl 2-(4-trifluoromethoxy-phenoxy)-ethylsulfanyl-acetate (619 mg, 2.0 mmol) in 2 N LiOH (aq, 3 mL), MeOH (3 mL), and THF (3 mL) was stirred at 23° C. After one hour, the reaction mixture was acidified with 3 N HCl (aq, 4 mL). The aqueous layer was isolated and extracted twice with dichloromethane (25 mL each). The combined organic phases were dried with anhydrous magnesium sulfate. After removal of solvent, a colorless oil was obtained (580 mg, 98%).

$^1$H NMR (CDCl$_3$) δ 7.12 (d, 2H, J=9.20 Hz), 6.86 (d, 2H, J=9.20 Hz), 4.17 (t, 2H, J=6.01 Hz), 3.37 (s, 2H), 3.03 (t, 2H, J=6.01 Hz). MS (ES$^−$) m/e 295.

i) [3-(4-{5-[2-(4-Trifluoromethoxy-phenoxy)-ethylsulfanylmethyl]-[1,3,4]oxadiazol-2-yl}-phenoxy)-propyl]-dimethyl-amine

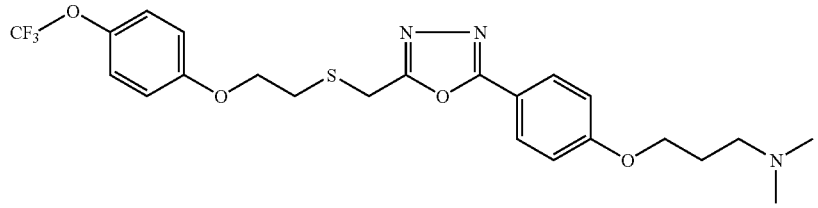

To a cold solution (0° C.) of 2-(4-trifluoromethoxy-phenoxy)-ethylsulfanyl acetic acid (296 mg, 1 mmol), 4-(3-dimethylamino-propoxy)-benzoic hydrazide (237 mg, 1 mmol), and triphenylphosphine (1.31 g, 5 mmol) in anhydrous acetonitrile (10 mL) was added a mixture of carbon tetrachloride (0.58 mL, 6 mmol) and triethylamine (0.97 mL, 7 mmol) with stirring. The stirring continued at 0° C. for 30 minutes and then 23° C. overnight. After evaporation of solvent, the residue was distributed between 1N NaOH (30 mL) and dichloromethane (25 mL). The aqueous layer was isolated and extracted twice with dichloromethane (25 mL each). The combined organic phases were dried with anhydrous sodium sulfate. After removal of solvent, the residue was submitted for purification on silica gel (elution with ethyl acetate, then 4% 2 M NH$_3$—MeOH in dichloromethane) to yield a white solid (267 mg, 54%).

$^1$H NMR (CDCl$_3$) δ 7.92 (d, 2H, J=8.85 Hz), 7.09 (d, 2H, J=8.86 Hz), 6.97 (d, 2H, J=8.85 Hz), 6.85 (d, 2H, J=8.86 Hz), 4.15 (t, 2H, J=6.19 Hz), 4.07 (t, 2H, J=6.37 Hz), 4.00 (s, 2H), 3.02 (t, 2H, J=6.19 Hz), 2.45 (t, 2H, J=7.08 Hz), 2.24 (s, 6H), 1.97 (m, 2H, J=6.37, 7.08 Hz). MS (ES$^+$) m/e 498. mp 92.5–93.5° C. Anal. Calcd for C$_{23}$H$_{26}$F$_3$N$_3$O$_4$S: C, 55.52; H, 5.27; N, 8.45; S, 6.44; F, 11.46. Found C, 55.29; H, 5.14; N, 8.38; S, 6.28; F, 11.38.

Example 275

Preparation of [3-(4-{5-[2-(2-trifluoromethoxy-phenoxy)-ethylsulfanylmethyl]-[1,3,4]oxadiazol-2-yl}-phenoxy)-propyl]-dimethyl-amine

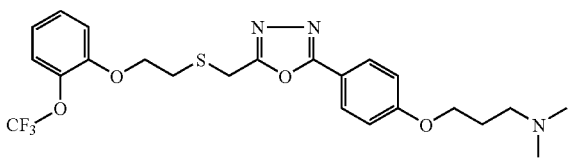

397 a) 2-(2-Trifluoromethoxy-phenoxy)-ethyl p-toluate

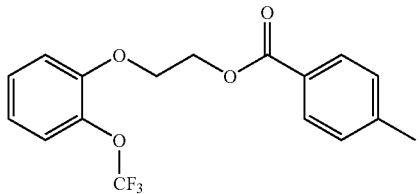

In a similar manner as exemplified in Example 274 part d), 2-trifluoromethoxy-phenol (1.87 g, 10.5 mmol) was converted into 2-(2-trifluoromethoxy-phenoxy)-ethyl p-toluate (3.10 g, 87%) as a colorless oil.

$^1$H NMR (CDCl$_3$) δ 7.91 (d, 2H, J=8.14 Hz), 7.17–7.26 (m, 4H), 7.02 (dd, 1H, J=1.42, 8.85 Hz), 6.95 (td, 1H, J=1.42, 7.78 Hz), 4.65 (t, 2H, J=4.78 Hz), 4.34 (t, 2H, J=4.78 Hz), 2.38 (s, 3H). MS (ES$^+$) m/e 341.

b) 2-(2-Trifluoromethoxy-phenoxy)-ethanol-1

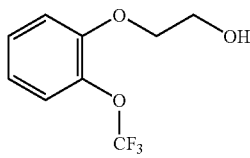

In a similar manner as exemplified in Example 274 part e), 2-(2-trifluoromethoxy-phenoxy)-ethyl p-toluate (2.72 g, 8 mmol) was converted into 2-(2-trifluoromethoxy-phenoxy)-ethanol-1 (1.74 g, 98%) as a colorless oil.

$^1$H NMR (CDCl$_3$) δ 7.20–7.27 (m, 2H), 7.69–7.02 (m, 2H), 4.12 (t, 2H, J=4.42 Hz), 3.96 (q, 2H, J=4.95, 9.20), 2.06 (m, b, 1H). MS (ES$^+$) m/e 223.

c) 2-(2-Trifluoromethoxy-phenoxy)-ethyl tosylate

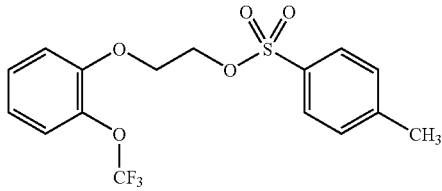

In a similar manner as exemplified in Example 274 part f), 2-(2-trifluoromethoxy-phenoxy)-ethanol-1 (666 mg, 2 mmol) was converted into 2-(2-trifluoromethoxy-phenoxy)-ethyl tosylate (926 mg, 82%) as a colorless oil.

$^1$H NMR (CDCl$_3$) δ 7.79 (d, 2H, J=8.14 Hz), 7.31 (d, 2H, J=8.14 Hz), 7.16–7.22 (m, 2H), 6.95 (t, 1H, J=7.78 Hz), 6.90 (d, 1H, J=7.78 Hz), 4.32–4.36 (m, 2H), 4.18–4.23 (m, 2H), 2.42 (s, 3H). MS (ES$^+$) m/e 377.

398 d) Methyl 2-(2-trifluoromethoxy-phenoxy)-ethylsulfanyl-acetate

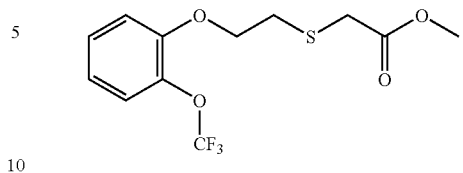

In a similar manner as exemplified in Example 274 part g), 2-(2-trifluoromethoxy-phenoxy)-ethyl tosylate (753 mg, 2 mmol) was converted into methyl 2-(2-trifluoromethoxy-phenoxy)-ethylsulfanyl-acetate (620 mg, 100%) as a colorless oil.

$^1$H NMR (CDCl$_3$) δ 7.18–7.25 (m, 2H), 6.89–7.00 (m, 2H), 4.22 (t, 2H, J=6.37 Hz), 3.71 (s, 3H), 3.39 (s, 2H), 3.04 (t, 2H, J=6.37 Hz). MS (ES$^+$) m/e 311.

e) 2-(2-Trifluoromethoxy-phenoxy)-ethylsulfanyl acetic acid

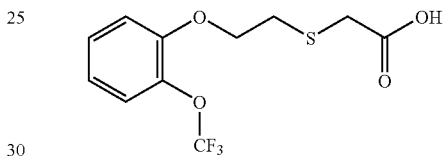

In a similar manner as exemplified in Example 274 part h), methyl 2-(2-trifluoromethoxy-phenoxy)-ethylsulfanyl-acetate (620 mg, 2 mmol) was converted into 2-(2-trifluoromethoxy-phenoxy)-ethylsulfanyl acetic acid (592 mg, 100%) as a white solid.

$^1$H NMR (CDCl$_3$) δ 7.18–7.26 (m, 2H), 6.92–6.99 (m, 2H), 4.24 (t, 2H, J=6.01 Hz), 3.44 (s, 2H), 3.07 (t, 2H, J=6.01 Hz). MS (ES$^{31}$) m/e 295. mp 41.5–42.5° C.

f) [3-(4-{5-[2-(2-Trifluoromethoxy-phenoxy)-ethyl-sulfanylmethyl]-[1,3,4]oxadiazol-2-yl}-phenoxy)-propyl]-dimethyl-amine

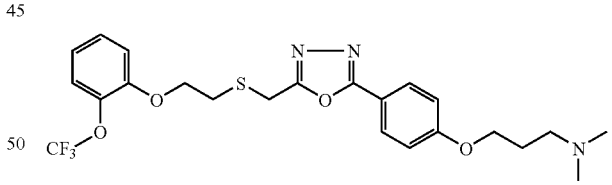

In a similar manner as exemplified in Example 274 part i), 2-(2-trifluoromethoxy-phenoxy)-ethylsulfanyl acetic acid (296 mg, 1 mmol) was converted into [3-(4-{5-[2-(2-trifluoromethoxy-phenoxy)-ethylsulfanylmethyl]-[1,3,4]oxadiazol-2-yl}-phenoxy)-propyl]-dimethyl-amine (320 mg, 64%) as a white solid.

$^1$H NMR (CDCl$_3$) δ 7.93 (d, 2H, J=9.20 Hz), 7.18–7.25 (m, 2H), 6.97 (d, 2H, J=9.20 Hz), 6.91–6.96 (m, 2H), 4.24 (t, 2H, J=6.19 Hz), 4.07 (t, 2H, J=6.55 Hz), 4.05 (s, 2H), 3.07 (t, 2H, J=6.19 Hz), 2.45 (t, 2H, J=7.08 Hz), 2.25 (s, 6H), 1.97 (m, 2H, J=6.55, 7.08 Hz). MS (ES$^+$) m/e 498. mp 55.0–55.5° C. Anal. Calcd for C$_{23}$H$_{26}$F$_3$N$_3$O$_4$S: C, 55.52; H, 5.27; N, 8.45; S, 6.44; F, 11.46. Found C, 55.28; H, 5.32; N, 8.26; S, 6.48; F, 11.76.

Example 276

Preparation of [3-(4-{5-[2-(3-trifluoromethoxy-phenoxy)-ethylsulfanylmethyl]-[1,3,4]oxadiazol-2-yl}-phenoxy)-propyl]-dimethyl-amine

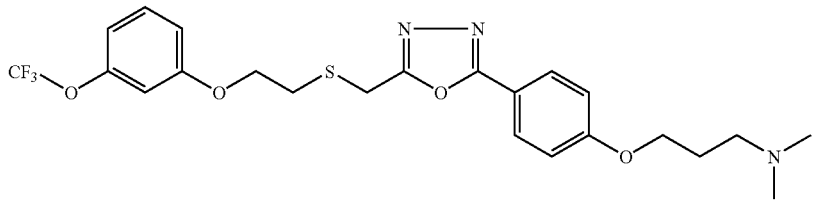

$^1$H NMR (CDCl$_3$) δ 7.79 (d, 2H, J=8.49 Hz), 7.82 (d, 2H, J=8.49 Hz), 7.23 (t, 1H, J=8.49 Hz), 6.80 (d, 1H, J=8.49 Hz), 6.70 (d, 1H, J=8.49 Hz), 6.58 (s, 1H), 4.34–4.38 (m, 2H), 4.10–4.14 (m, 2H), 2.42 (s, 3I). MS (ES$^+$) m/e 377. mp 58.5–59.5° C.

a) 2-(3-Trifluoromethoxy-phenoxy)-ethyl p-toluate

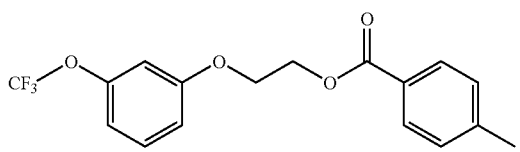

In a similar manner as exemplified in Example 274 part d), 3-trifluoromethoxy-phenol (1.87 g, 10.5 mmol) was converted into 2-(3-trifluoromethoxy-phenoxy)-ethyl p-toluate (3.31 g, 93%) as a white solid.

$^1$H NMR (CDCl$_3$) δ 7.92 (d, 2H, J=8.14 Hz), 7.27 (t, 1H, J=8.32 Hz), 7.22 (d, 2H, J=8.14 Hz), 6.77–6.87 (m, 3H), 4.63 (t, 2H, J=4.77 Hz), 4.28 (t, 2H, J=4.77 Hz), 2.39 (s, 3H). MS (ES$^+$) m/e 341. mp 63.0–64.0° C.

b) 2-(3-Trifluoromethoxy-phenoxy)-ethanol-1

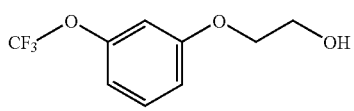

In a similar manner as exemplified in Example 274 part e), 2-(3-trifluoromethoxy-phenoxy)-ethyl p-toluate (2.72 g, 8 mmol) was converted into 2-(3-trifluoromethoxy-phenoxy)-ethanol-1 (1.78 g, 100%) as a colorless oil.

$^1$H NMR (CDCl$_3$) δ 7.13 (d, 2H, J=8.85 Hz), 6.85–6.94 (m, 2H), 4.05 (t, 2H, J=4.42 Hz), 3.95 (s, b, 2H), 1.96 (s, b, 1H). MS (ES$^+$) m/e 223.

c) 2-(3-Trifluoromethoxy-phenoxy)-ethyl tosylate

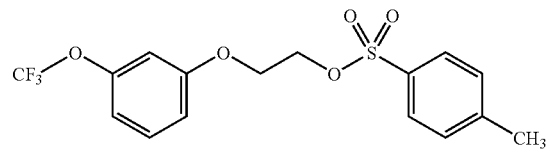

In a similar manner as exemplified in Example 274 part f), 2-(3-trifluoromethoxy-phenoxy)-ethanol-1 (666 mg, 2 mmol) was converted into 2-(3-trifluoromethoxy-phenoxy)-ethyl tosylate (1.00 g, 89%) as a white solid.

d) Methyl 2-(3-trifluoromethoxy-phenoxy)-ethylsulfanyl-acetate

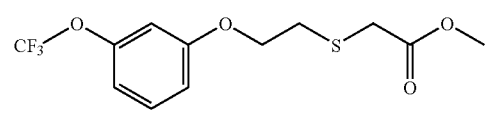

In a similar manner as exemplified in Example 274 part g), 2-(3-trifluoromethoxy-phenoxy)-ethyl tosylate (753 mg, 2 mmol) was converted into methyl 2-(3-trifluoromethoxy-phenoxy)-ethylsulfanyl-acetate (625 mg, 100%) as a colorless oil.

$^1$H NMR (CDCl$_3$) δ 7.26 (t, 1H, J=8.49 Hz), 6.80 (d, 2H, J=8.49 Hz), 6.73 (s, 1H), 4.16 (t, 2H, J=6.37 Hz), 3.71 (s, 3H), 3.34 (s, 2H), 3.01 (t, 2H, J=6.37 Hz). MS (ES) m/e 311.

e) 2-(3-Trifluoromethoxy-phenoxy)-ethylsulfanyl acetic acid

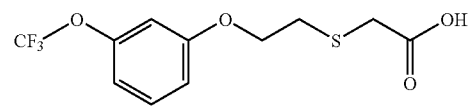

In a similar manner as exemplified in Example 274 part h), methyl 2-(3-trifluoromethoxy-phenoxy)-ethylsulfanyl-acetate (620 mg, 2 mmol) was converted into 2-(3-trifluoromethoxy-phenoxy)-ethylsulfanyl acetic acid (513 mg, 87%) as a colorless oil.

$^1$H NMR (CDCl$_3$) δ 7.26 (t, 1H, J=8.14 Hz), 6.81 (d, 2H, J=8.14 Hz), 6.73 (s, 1H), 4.18 (t, 2H, J=6.01 Hz), 3.38 (s, 2H), 3.04 (t, 2H, J=6.01 Hz). MS (ES) m/e 295.

f) [3-(4-{5-[2-(3-Trifluoromethoxy-phenoxy)-ethylsulfanylmethyl]-[1,3,4]oxadiazol-2-yl}-phenoxy)-propyl]-dimethyl-amine

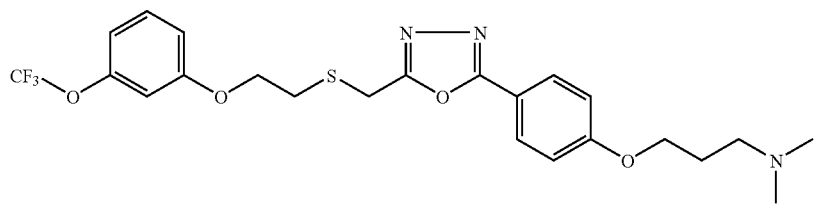

In a similar manner as exemplified in Example 274 part i), 2-(3-trifluoromethoxy-phenoxy)-ethylsulfanyl acetic acid (296 mg, 1 mmol) was converted into [3-(4-{5-[2-(3-trifluoromethoxy-phenoxy)-ethylsulfanylmethyl]-[1,3,4]oxadiazol-2-yl}-phenoxy)-propyl]-dimethyl-amine (280 mg, 56%) as a yellowish solid.

$^1$H NMR (CDCl$_3$) δ 7.93 (d, 2H, J=8.85 Hz), 7.24 (t, 1H, J=8.14 Hz), 6.97 (d, 2H, J=8.85 Hz), 6.79 (d, 2H, J=8.14 Hz), 6.72 (s, 1H), 4.16 (t, 2H, J=6.02 Hz), 4.07 (t, 2H, J=6.37 Hz), 4.00 (s, 2H), 3.03 (t, 2H, J=6.02 Hz), 2.45 (t, 2H, J=7.08 Hz), 2.25 (s, 6H), 1.97 (m, 2H, J=6.37, 7.08 Hz). MS (ES$^+$) m/e 498. mp 46.0–46.5° C. Anal. Calcd for C$_{23}$H$_{26}$F$_3$N$_3$O$_4$S: C, 55.52; H, 5.27; N, 8.45; S, 6.44; F, 11.46. Found C, 55.55; H, 5.18; N, 8.32; S, 6.49; F, 11.66.

Example 277

Preparation of [3-(4-{5-[2-(4-methoxy-phenoxy)-ethylsulfanylmethyl]-[1,3,4]oxadiazol-2-yl}-phenoxy)-propyl]-dimethyl-amine

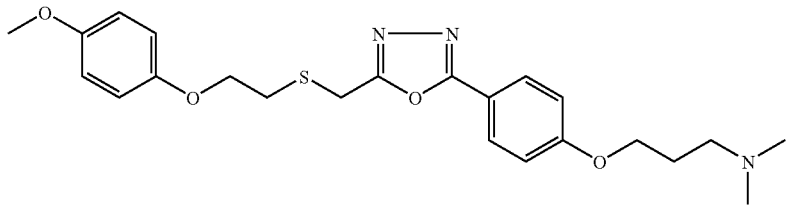

a) 2-(4-Methoxy-phenoxy)-ethyl p-toluate

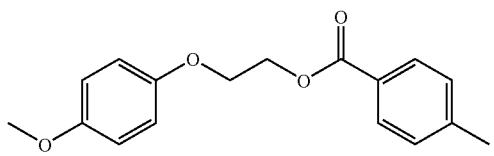

In a similar manner as exemplified in Example 274 part d), 4-methoxy-phenol (1.30 g, 10.5 mmol) was converted into 2-(4-methoxy-phenoxy)-ethyl p-toluate (2.74 g, 91%) as a white solid.

$^1$HNMR (CDCl$_3$) δ 7.92 (d, 2H, J=8.14 Hz), 7.21 (d, 2H, J=8.14 Hz), 6.87 (d, 2H, J=9.20 Hz), 6.81 (d, 2H, J=9.20 Hz), 4.60 (t, 2H, J=4.95 Hz), 4.23 (t, 2H, J=4.95 Hz), 3.75 (s, 3H), 2.38 (s, 3H). MS (ES$^+$) m/e 287. mp 40.5–42.5° C.

b) 2-(4-Methoxy-phenoxy)-ethanol-1

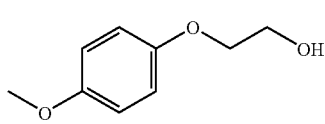

In a similar manner as exemplified in Example 274 part e), 2-(4-methoxy-phenoxy)-ethyl p-toluate (2.29 g, 8 mmol) was converted into 2-(4-methoxy-phenoxy)-ethanol-1 (1.28 g, 95%) as a white solid.

$^1$H NMR (CDCl$_3$) δ 6.83 (m, 4H), 4.01 (m, 2H), 3.91 (m, 2H), 3.75 (s, 3H), 2.07 (s, b, 1H). MS (ES$^+$) m/e 169. mp 68.5–69.0° C.

c) 2-(4-Methoxy-phenoxy)-ethyl tosylate

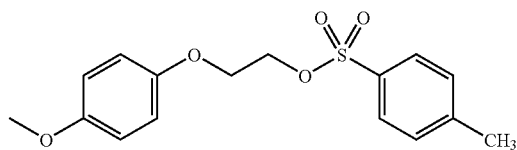

In a similar manner as exemplified in Example 274 part f), 2-(4-methoxy-phenoxy)-ethanol-1 (504 mg, 2 mmol) was converted into 2-(4-methoxy-phenoxy)-ethyl tosylate (245 mg, 25%) as a white solid.

$^1$H NMR (CDCl$_3$) δ 7.79 (d, 2H, J=8.14 Hz), 7.31 (d, 2H, J=8.14 Hz), 6.68–6.79 (m, 4H), 4.29–4.34 (m, 2H), 4.05–4.11 (m, 2H), 3.73 (s, 3H), 2.42 (s, 3H). MS (ES$^+$) m/e 323. mp 87.0–88.0° C.

d) Methyl 2-(4-Methoxy-phenoxy)-ethylsulfanyl-acetate

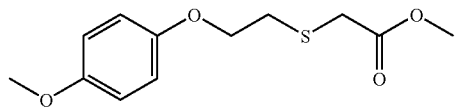

In a similar manner as exemplified in Example 274 part g), 2-(4-methoxy-phenoxy)-ethyl tosylate (245 mg, 0.76 mmol) was converted into methyl 2-(4-methoxy-phenoxy)-ethylsulfanyl-acetate (191 mg, 98%) as a colorless oil.

$^1$H NMR (CDCl$_3$) δ 6.81 (m, 4H), 4.11 (t, 2H, J=6.37 Hz), 3.74 (s, 3H), 3.71 (s, 3H), 3.34 (s, 2H), 2.98 (t, 2H, J=6.37 Hz). MS (ES$^+$) m/e 257.

e) 2-(4-Methoxy-phenoxy)-ethylsulfanyl acetic acid

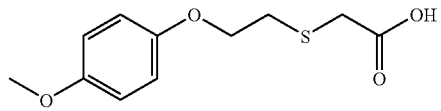

In a similar manner as exemplified in Example 274 part h), methyl 2-(4-methoxy-phenoxy)-ethylsulfanyl-acetate (191 mg, 0.76 mmol) was converted into 2-(4-methoxyphenoxy)-ethylsulfanyl acetic acid (144 mg, 79%) as a white solid.

$^1$H NMR (CDCl$_3$) δ 6.81 (s, 4H), 4.14 (t, 2H, J=6.01 Hz), 3.74 (s, 3H), 3.39 (s, 2H), 3.01 (t, 2H, J=6.01 Hz). MS (ES$^+$) m/e 241. mp 68.5–69.0° C.

f) [3-(4-{5-[2-(4-Methoxy-phenoxy)-ethylsulfanyl-methyl]-[1,3,4]oxadiazol-2-yl}-phenoxy)-propyl]-dimethyl-amine

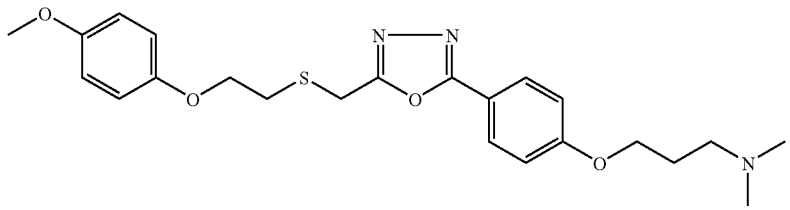

In a similar manner as exemplified in Example 274 part i), 2-(4-methoxy-phenoxy)-ethylsulfanyl acetic acid (121 mg, 0.5 mmol) was converted into [3-(4-{5-[2-(4-methoxy-phenoxy)-ethylsulfanylmethyl]-[1,3,4]oxadiazol-2-yl}-phenoxy)-propyl]-dimethyl-amine (85 mg, 39%) as a white solid.

$^1$H NMR (CDCl$_3$) δ 7.92 (d, 2H, J=8.85 Hz), 6.97 (d, 2H, J=8.85 Hz), 6.75–6.84 (m, 4H), 4.12 (t, 2H, J=6.19 Hz), 4.07 (t, 2H, J=6.37 Hz), 4.00 (s, 2H), 3.73 (s, 3H), 3.00 (t, 2H, J=6.19 Hz), 2.45 (t, 2H, J=7.25 Hz), 2.25 (s, 6H), 1.97 (m, 2H, J=6.37, 7.25 Hz). MS (ES$^+$) m/e 444. mp 77.5–78.0° C. Anal. Calcd for C$_{23}$H$_{29}$N$_3$O$_4$S: C, 62.28; H, 6.59; N, 9.47; S, 7.23. Found C, 62.01; H, 6.60; N, 9.35; S, 7.26.

Example 278

Preparation of [3-(4-{5-[2-(1-naphthoxy)-ethylsulfanylmethyl]-[1,3,4]oxadiazol-2-yl}-phenoxy)-propyl]-dimethyl-amine

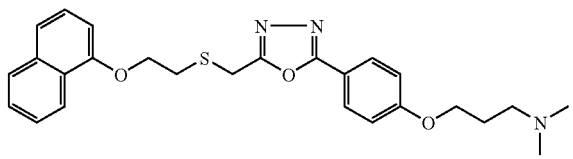

a) 2-(1-Naphthoxy)-ethyl tosylate

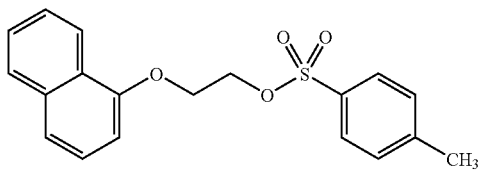

In a similar manner as exemplified in Example 274 part f), 2-(1-naphthoxy)-ethanol-1 (565 mg, 2 mmol) was converted into 2-(1-naphthoxy)-ethyl tosylate (757 mg, 74%) as a white solid.

$^1$H NMR (CDCl$_3$) δ 7.81 (d, 2H, J=8.49 Hz), 7.73 (d, 1H, J=8.14 Hz), 7.69 (d, 1H, J=9.91 Hz), 7.67 (t, 1H, J=8.32 Hz), 7.41 (t, 1H, J=8.14 Hz), 7.33 (d, 1H, J=8.14), 7.30 (d, 2H, J=7.78 Hz), 6.97–7.02 (m, 2H), 4.40–4.44 (m, 2H), 4.22–4.28 (m, 2H), 2.40 (s, 3H). MS (ES$^+$) m/e 343. mp 93.0–94.0° C.

b) Methyl 2-(1-naphthoxy)-ethylsulfanyl-acetate

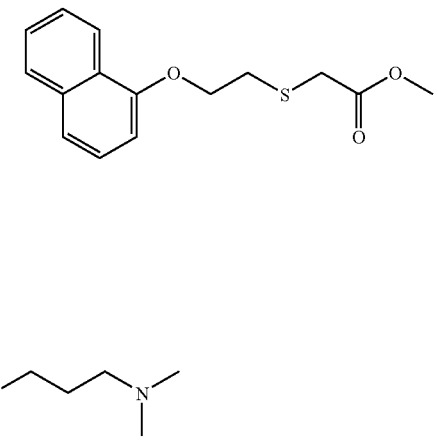

In a similar manner as exemplified in Example 274 part g), 2-(1-naphthoxy)-ethyl tosylate (685 mg, 2 mmol) was converted into methyl 2-(1-naphthoxy)-ethylsulfanyl-acetate (552 mg, 100%) as a colorless oil.

$^1$H NMR (CDCl$_3$) δ 8.21–8.27 (m, 1H), 7.74–7.81 (m, 1H), 7.39–7.51 (m, 3H), 7.34 (t, 1H, J=7.79 Hz), 6.79 (t, 1H, J=7.08 Hz), 4.36 (t, 2H, J=6.37 Hz), 3.71 (s, 3H), 3.39 (s, 2H), 3.17 (t, 2H, J=6.37 Hz). MS (ES$^+$) m/e 277.

c) 2-(1-Naphthoxy)-ethylsulfanyl acetic acid

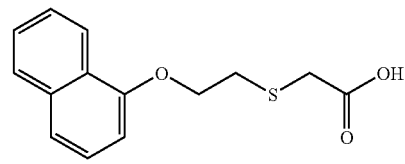

In a similar manner as exemplified in Example 274 part h), methyl 2-(1-naphthoxy)-ethylsulfanyl-acetate (552 mg, 2 mmol) was converted into 2-(1-naphthoxy)-ethylsulfanyl acetic acid (500 mg, 95%) as a white solid.

$^1$H NMR (CDCl$_3$) δ 8.20–8.28 (m, 1H), 7.74–7.82 (m, 1H), 7.44–7.50 (m, 2H), 7.42 (d, 1H, J=8.49 Hz), 7.84 (dd, 1H, J=7.78, 8.49 Hz), 6.79 (d, 1H, J=7.78 Hz), 4.37 (t, 2H, J=6.01 Hz), 3.42 (s, 2H), 3.20 (t, 2H, J=6.01 Hz). MS (ES) m/e 261. mp 64.5–65.5° C.

d) [3-(4-{5-[2-(1-Naphthoxy)-ethylsulfanylmethyl]-[1,3,4]oxadiazol-2-yl}-phenoxy)-propyl]-dimethyl-amine

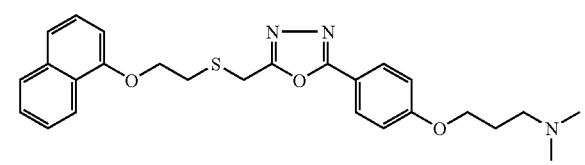

In a similar manner as exemplified in Example 274 part i), 2-(1-naphthoxy)-ethylsulfanyl acetic acid (262 mg, 1 mmol) was converted into [3-(4-{5-[2-(1-naphthoxy)-ethylsulfanylmethyl]-[1,3,4]oxadiazol-2-yl}-phenoxy)-propyl]-dimethyl-amine (344 mg, 74%) as a white solid.

$^1$H NMR (CDCl$_3$) δ 8.23–8.28 (m, 1H), 7.88–7.95 (m, 2H), 7.73–7.78 (m, 1H), 7.38–7.49 (m, 3H), 7.33 (t, 1H, J=8.02 Hz), 6.92–6.98 (m, 2H), 6.78 (d, 1H, J=7.43 Hz), 4.37 (t, 2H, J=6.01 Hz), 4.06 (t, 2H, J=6.37 Hz), 4.05 (s, 2H), 3.18 (t, 2H, J=6.01 Hz), 2.46 (t, 2H, J=7.80 Hz), 2.25 (s, 6H), 1.97 (m, 2H, J=6.37, 7.80 Hz). MS (ES$^+$) m/e 464. mp 101.0–102.0° C. Anal. Calcd for C$_{26}$H$_{29}$N$_3$O$_3$S: C, 67.36; H, 6.31; N, 9.06; S, 6.92. Found C, 67.07; H, 6.23; N, 8.98; S, 6.61.

Example 279

Preparation of [3-(4-{5-[2-(2-naphthoxy)-ethylsulfanylmethyl]-[1,3,4]oxadiazol-2-yl}-phenoxy)-propyl]-dimethyl-amine

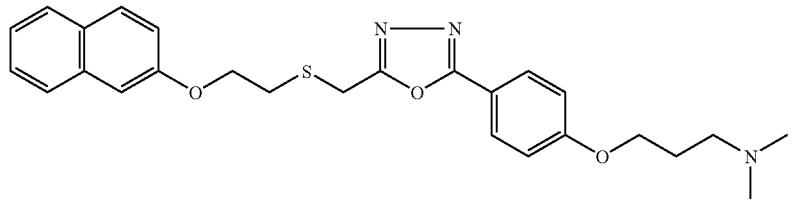

a) 2-(2-Naphthoxy)-ethyl tosylate

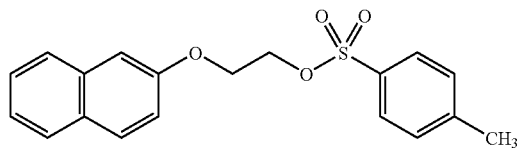

In a similar manner as exemplified in Example 274 part f), 2-(2-naphthoxy)-ethanol-1 (565 mg, 2 mmol) was converted into 2-(2-naphthoxy)-ethyl tosylate (646 mg, 63%) as a white solid.

$^1$H NMR (CDCl$_3$) δ 8.01 (d, 1H, J=8.85 Hz), 7.80 (d, 2H, J=8.49 Hz), 7.76 (d, 1H, J=7.78 Hz), 7.46 (t, 1H, J=8.14 Hz), 7.40 (t, 2H, J=8.49 Hz), 7.29 (t, 1H, J=7.78 Hz), 7.24–7.28 (m, 2H), 6.67 (d, 1H, J=7.43 Hz), 4.50 (t, 2H, J=4.60 Hz), 4.31 (t, 2H, J=4.60 Hz), 2.39 (s, 3H). MS (ES$^+$) m/e 343. mp 79.0–80.0° C.

b) Methyl 2-(2-naphthoxy)-ethylsulfanyl acetate

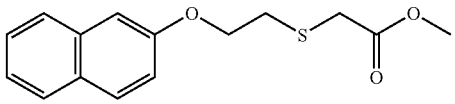

In a similar manner as exemplified in Example 274 part g), 2-(2-naphthoxy)-ethyl tosylate (514 mg, 1.5 mmol) was converted into methyl 2-(1-naphthoxy)-ethylsulfanyl-acetate (414 mg, 100%) as a colorless oil.

$^1$H NMR (CDCl$_3$) δ 7.68–7.76 (m, 3H), 7.42 (q, 1H, J=6.72, 8.14 Hz), 7.32 (q, 1H, J=6.72, 7.08 Hz), 7.12 (d, 1H, J=8.14 Hz), 7.11 (s, 1H), 4.29 (t, 2H, J=6.37 Hz), 3.72 (s, 3H), 3.38 (s, 2H), 3.08 (t, 2H, J=6.37 Hz). MS (ES$^+$) m/e 277.

c) 2-(2-Naphthoxy)-ethylsulfanyl acetic acid

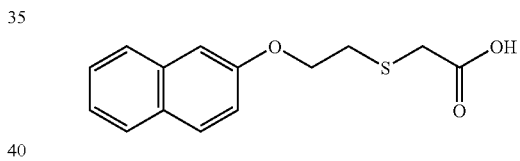

In a similar manner as exemplified in Example 274 part h), methyl 2-(2-naphthoxy)-ethylsulfanyl-acetate (414 mg, 1.5 mmol) was converted into 2-(2-naphthoxy)-ethylsulfanyl acetic acid (345 mg, 88%) as a white solid.

$^1$H NMR (CDCl$_3$) δ 7.66–7.77 (m, 3H), 7.42 (t, 1H, J=8.14 Hz), 7.32 (t, 1H, J=8.14 Hz), 7.08–7.15 (m, 2H), 4.30 (t, 2H, J=6.01 Hz), 3.38 (s, 2H), 3.08 (t, 2H, J=6.01 Hz). MS (ES$^-$) m/e 261. mp 99.5–100.5° C.

d) [3-(4-{5-[2-(2-Naphthoxy)-ethylsulfanylmethyl]-[1,3,4]oxadiazol-2-yl}-phenoxy)-propyl]-dimethyl-amine

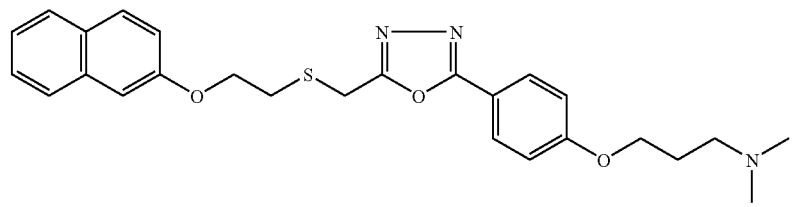

In a similar manner as exemplified in Example 274 part i), 2-(2-naphthoxy)-ethylsulfanyl acetic acid (262 mg, 1 mmol) was converted into [3-(4-{5-[2-(2-naphthoxy)-ethylsulfanylmethyl]-[1,3,4]oxadiazol-2-yl}-phenoxy)-propyl]-dimethyl-amine (291 mg, 63%) as a white solid.

¹H NMR (CDCl₃) δ 7.89 (d, 2H, J=8.85 Hz), 7.73 (d, 1H, J=8.14 Hz), 7.69 (t, 2H, J=8.14 Hz), 7.41 (q, 1H, J=7.08, 7.78 Hz), 7.31 (q, 1H, J=6.72, 7.08 Hz), 7.09–7.14 (m, 2H), 6.91 (d, 2H, J=8.85 Hz), 4.30 (t, 2H, J=6.01 Hz), 4.05 (s, 2H), 4.04 (t, 2H, J=6.37 Hz), 3.10 (t, 2H, J=6.01 Hz), 2.44 (t, 2H, J=7.16 Hz), 2.24 (s, 6H), 1.96 (m, 2H, J=6.37, 7.16 Hz). MS (ES⁺) m/e 464. mp 97.0–98.0° C. Anal. Calcd for C₂₆H₂₉N₃O₃S: C, 67.36; H, 6.31; N, 9.06; S, 6.92. Found C, 66.89; H, 6.41; N, 8.95; S, 6.89.

Example 280

Preparation of (3-{4-[5-(2-tert-butoxy-ethylsulfanylmethyl)-[1,3,4]oxadiazol-2-yl]-phenoxy}-propyl)-dimethyl-amine

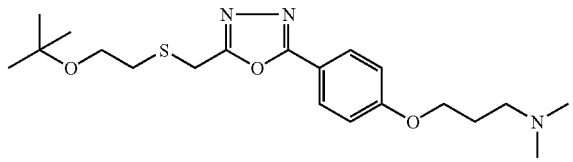

a) 2-tert-Butoxy-ethyl tosylate

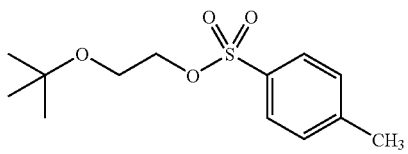

In a similar manner as exemplified in Example 274 part f), 2-tert-butoxy-ethanol-1 (2.36 g, 20 mmol) was converted into 2-tert-butoxy-ethyl tosylate (5.21 g, 96%) as a colorless oil.

¹H NMR (CDCl₃) δ 7.78 (d, 2H, J=8.14 Hz), 7.31 (d, 2H, J=8.14 Hz), 4.09 (t, 2H, J=5.13 Hz), 3.52 (t, 2H, J=5.13 Hz), 2.42 (s, 3H), 1.10 (s, 9H). MS (ES⁺) m/e 273.

b) Methyl 2-(2-tert-butoxy)-ethylsulfanyl-acetate

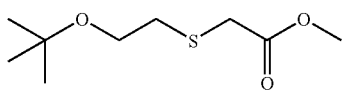

In a similar manner as exemplified in Example 274 part g), 2-tert-butoxy-ethyl tosylate (5.21 g, 19 mmol) was converted into methyl 2-tert-butoxy-ethylsulfanyl-acetate (3.94 g, 100%) as a colorless oil.

¹H NMR (CDCl₃) δ 3.71 (s, 3H), 3.54 (t, 2H, J=6.55 Hz), 3.30 (s, 2H), 2.75 (t, 2H, J=6.55 Hz), 1.17 (s, 9H). MS (ES⁺) m/e 207.

c) 2-tert-Butoxy-ethylsulfanyl acetic acid

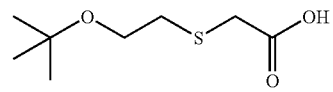

In a similar manner as exemplified in Example 274 part h), methyl 2-(2-tert-butoxy)-ethylsulfanyl-acetate (3.94 g, 19 mmol) was converted into 2-tert-butoxy-ethylsulfanyl acetic acid (3.30 g, 90%) as a colorless oil.

¹H NMR (CDCl₃) δ 3.63 (t, 2H, J=6.01 Hz), 3.35 (s, 2H), 2.80 (t, 2H, J=6.01 Hz), 1.20 (s, 9H). MS (ES⁻) m/e 191.

d) (3-{4-[5-(2-tert-Butoxy-ethylsulfanylmethyl)-[1,3,4]oxadiazol-2-yl]-phenoxy}-propyl)-dimethyl-amine

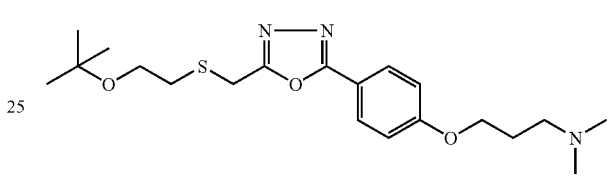

In a similar manner as exemplified in Example 274 part i), 2-tert-butoxy-ethylsulfanyl acetic acid (777 mg, 4 mmol) was converted into (3-{4-[5-(2-tert-Butoxy-ethylsulfanylmethyl)-[1,3,4]oxadiazol-2-yl]-phenoxy}-propyl)-dimethyl-amine (590 mg, 37%) as a brown oil.

¹H NMR (CDCl₃) δ 7.95 (d, 2H, J=8.85 Hz), 6.97 (d, 2H, J=8.85 Hz), 4.06 (t, 2H, J=6.37 Hz), 3.97 (s, 2H), 3.55 (t, 2H, J=6.29 Hz), 2.78 (t, 2H, J=6.29 Hz), 2.44 (t, 2H, J=7.26 Hz), 2.24 (s, 6H), 1.96 (m, 2H, J=6.37, 7.26 Hz), 1.16 (s, 9H). MS (ES⁺) m/e 394.

e) (3-{4-[5-(2-tert-Butoxy-ethylsulfanylmethyl)-[1,3,4]oxadiazol-2-yl]-phenoxy}-propyl)-dimethyl-amine maleate

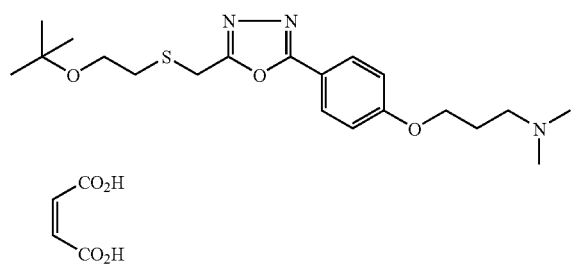

To a hot solution of maleic acid (193 mg, 1.7 mmol) in ethyl acetate (1 mL) was added a solution of (3-{4-[5-(2-tert-Butoxy-ethylsulfanylmethyl)-[1,3,4]oxadiazol-2-yl]-phenoxy}-propyl)-dimethyl-amine (590 mg, 1.5 mmol) in ethyl acetate with stirring. After 10 minutes, solvent was removed on a rotary evaporator. The oily residue was dissolved in dichloromethane (1 mL) followed by addition of diethyl ether (20 mL). The mixture was rapidly stirred at 23° C. till solid formed. The solid was collected by filtration, washed with diethyl ether (3×5 mL), and dried in vacuum to provide a light brown solid (300 mg, 39%).

¹H NMR (CDCl₃) δ 7.96 (d, 2H, J=8.85 Hz), 6.94 (d, 2H, J=8.85 Hz), 6.22 (s, 2H), 4.13 (t, 2H, J=5.48 Hz), 3.97 (s, 2H), 3.56 (t, 2H, J=6.19 Hz), 3.27 (t, 2H, J=7.96 Hz), 2.87 (s, 6H), 2.77 (t, 2H, J=6.19 Hz), 2.22–2.34 (m, 2H), 1.16 (s, 9H). MS (ES⁺) m/e 394. mp 84.5–85.5° C. Anal. Calcd for C₂₄H₃₅N₃O₇S: C, 56.56; H, 6.92; N, 8.25; S, 6.29. Found C, 56.33; H, 6.85; N, 8.36; S, 6.03.

Example 281

Preparation of (3-{4-[5-(2-methoxy-ethylsulfanylmethyl)-[1,3,4]oxadiazol-2-yl]-phenoxy}-propyl)-dimethyl-amine

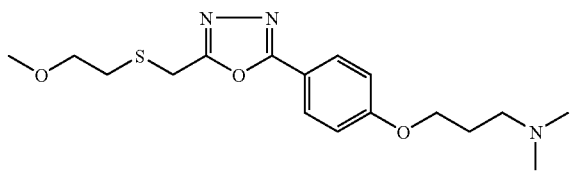

a) Methyl 2-(2-methoxy)-ethylsulfanyl-acetate

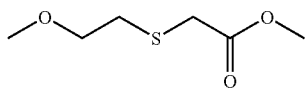

In a similar manner as exemplified in Example 274 part g), 2-bromoethyl methyl ether (1.39 g, 10 mmol) was converted into methyl 2-(2-methoxy)-ethylsulfanyl-acetate (1.06 g, 64%) as a colorless oil.

¹H NMR (CDCl₃) δ 3.71 (s, 3H), 3.57 (t, 2H, J=6.37 Hz), 3.33 (s, 3H), 3.27 (s, 2H), 2.80 (t, 2H, J=6.37 Hz). MS (ES⁺) m/e 165.

b) 2-Methoxy-ethylsulfanyl acetic acid

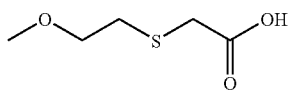

In a similar manner as exemplified in Example 274 part h), methyl 2-(2-methoxy)-ethylsulfanyl-acetate (1.06 g, 19 mmol) was converted into 2-methoxy-ethylsulfanyl acetic acid (0.84 g, 87%) as a colorless oil.

¹H NMR (CDCl₃) δ 3.62 (t, 2H, J=6.01 Hz), 3.36 (s, 3H), 3.32 (s, 2H), 2.84 (t, 2H, J=6.01 Hz). MS (ES⁻) m/e 149.

c) (3-{4-[S-(2-Methoxy-ethylsulfanylmethyl)-[1,3,4]oxadiazol-2-yl]-phenoxy}-propyl)-dimethyl-amine

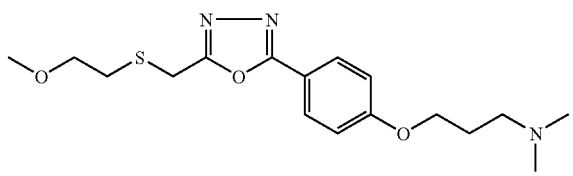

In a similar manner as exemplified in Example 274 part i), 2-methoxy-ethylsulfanyl acetic acid (549 mg, 3.7 mmol) was converted into (3-{4-[5-(2-methoxy-ethylsulfanylmethyl)-[1,3,4]oxadiazol-2-yl]-phenoxy}-propyl)-dimethyl-amine (900 mg, 69%) as a white solid.

¹H NMR (CDCl₃) δ 7.96 (d, 2H, J=8.85 Hz), 6.95 (d, 2H, J=8.85 Hz), 4.15 (t, 2H, J=5.66 Hz), 3.94 (s, 2H), 3.58 (t, 2H, J=6.01 Hz), 3.32 (s, 3H), 3.19–3.26 (m, 2H), 2.83 (s, 6H), 2.81 (m, 2H, J=6.01 Hz), 2.37–2.46 (m, 2H). MS (ES⁺) m/e 352.

d) (3-{4-[5-(2-Methoxy-ethylsulfanylmethyl)-[1,3,4]oxadiazol-2-yl]-phenoxy}-propyl)-dimethyl-amine maleate

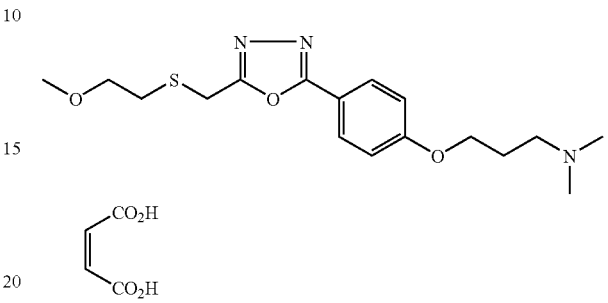

In a similar manner as exemplified in Example 280 part e), (3-{4-[5-(2-methoxy-ethylsulfanylmethyl)-[1,3,4]oxadiazol-2-yl]-phenoxy}-propyl)-dimethyl-amine (300 mg, 0.85 mmol) was converted (3-{4-[5-(2-methoxy-ethylsulfanylmethyl)-[1,3,4]oxadiazol-2-yl]-phenoxy}-propyl)-dimethyl-amine maleate (278 mg, 70%) as a white solid.

¹H NMR (CDCl₃) δ 7.97 (d, 2H, J=8.85 Hz), 6.95 (d, 2H, J=8.85 Hz), 6.23 (s, 2H), 4.13 (t, 2H, J=5.66 Hz), 3.95 (s, 2H), 3.59 (t, 2H, J=6.01 Hz), 3.33 (s, 3H), 3.26 (t, 2H, J=7.96 Hz), 2.86 (s, 6H), 2.82 (t, 2H, J=6.01 Hz), 2.24–2.84 (m, 2H). MS (ES³⁰) m/e 352. mp 97.5–99.0° C. Anal. Calcd for C₂₁H₂₉N₃O₇S: C, 53.95; H, 6.25; N, 8.99; S, 6.86. Found C, 53.83; H, 6.26; N, 8.92; S, 6.99.

Example 282

Preparation of (3-{4-[5-(2-phenylmethoxy-ethylsulfanylmethyl)-[1,3,4]oxadiazol-2-yl]-phenoxy}-propyl)-dimethyl-amine

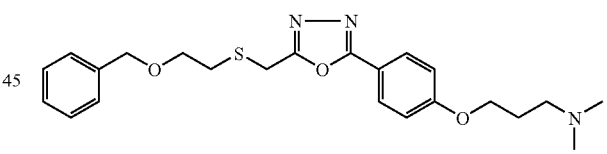

a) Methyl 2-(2-phenylmethoxy)-ethylsulfanyl-acetate

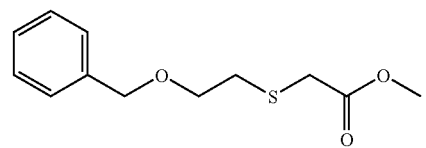

In a similar manner as exemplified in Example 274 part g), benzyl 2-bromoethyl ether (2.15 g, 10 mmol) was converted into methyl 2-(2-phenylmethoxy)-ethylsulfanyl-acetate (2.19 g, 91%) as a colorless oil.

¹H NMR (CDCl₃) δ 7.21–7.39 (m, 5H), 4.52 (s, 2H), 3.69 (s, 3H), 3.66 (t, 2H, J=6.37 Hz), 3.28 (s, 2H), 2.85 (t, 2H, J=6.37 Hz). MS (ES⁺) m/e 241.

b) 2-Phenylmethoxy-ethylsulfanyl acetic acid

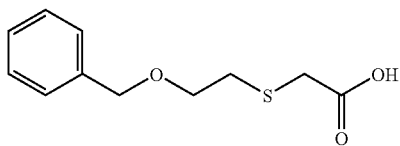

In a similar manner as exemplified in Example 274 part h), methyl 2-(2-phenylmethoxy)-ethylsulfanyl-acetate (2.16 g, 9 mmol) was converted into 2-phenylmethoxy-ethylsulfanyl acetic acid (1.89 g, 92%) as a colorless oil.

$^1$H NMR (CDCl$_3$) δ 7.23–7.36 (m, 5H), 4.53 (s, 2H), 3.69 (t, 2H, J=6.19 Hz), 3.32 (s, 2H), 2.87 (t, 2H, J=6.19 Hz). MS (ES$^-$) m/e 225.

c) (3-{4-[5-(2-Phenylmethoxy-ethylsulfanylmethyl)-[1,3,4]oxadiazol-2-yl]-phenoxy}-propyl)-dimethyl-amine

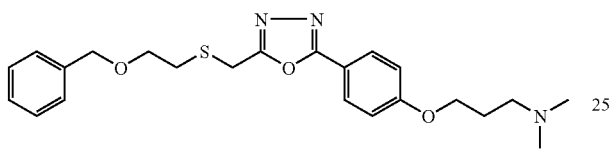

In a similar manner as exemplified in Example 274 part i), 2-phenylmethoxy-ethylsulfanyl acetic acid (675 mg, 3 mmol) was converted into (3-{4-[5-(2-phenymethoxy-ethylsulfanylmethyl)-[1,3,4]oxadiazol-2-yl]-phenoxy}-propyl)-dimethyl-amine (994 mg, 78%) as a white solid.

$^1$H NMR (CDCl$_3$) δ 7.93 (d, 2H, J=8.85 Hz), 7.21–7.34 (m, 5H), 6.97 (d, 2H, J=8.85 Hz), 4.52 (s, 2H), 4.06 (t, 2H, J=6.37 Hz), 3.94 (s, 2H), 3.67 (t, 2H, J=6.37 Hz), 2.86 (t, 2H, J=6.37 Hz), 2.44 (t, 2H, J=7.26 Hz), 2.24 (s, 6H), 1.96 (m, 2H, J=6.37, 7.26 Hz). MS (ES$^+$) m/e 428.

d) (3-{4-[5-(2-Phenylmethoxy-ethylsulfanylmethyl)-[1,3,4]oxadiazol-2-yl]-phenoxy}-propyl)-dimethyl-amine maleate

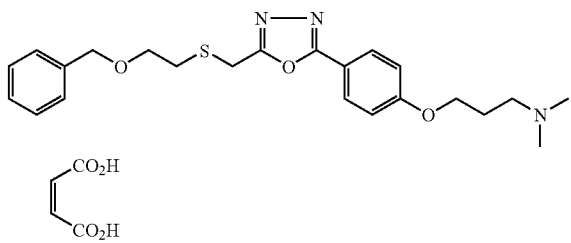

In a similar manner as exemplified in Example 280 part e), (3-{4-[5-(2-phenylmethoxy-ethylsulfanylmethyl)-[1,3,4]oxadiazol-2-yl]-phenoxy}-propyl)-dimethyl-amine (497 mg, 1.16 mmol) was converted (3-{4-[5-(2-phenylmethoxy-ethylsulfanylmethyl)-[1,3,4]oxadiazol-2-yl]-phenoxy}-propyl)-dimethyl-amine maleate (537 mg, 85%) as a white solid.

$^1$H NMR (CDCl$_3$) δ 7.95 (d, 2H, J=8.85 Hz), 7.20–7.34 (m, 5H), 6.94 (d, 2H, J=8.85 Hz), 6.25 (s, 2H), 4.52 (s, 2H), 4.13 (t, 2H, J=5.48 Hz), 3.95 (s, 2H), 3.68 (t, 2H, J=6.37 Hz), 3.27 (t, 2H, J=7.96 Hz), 2.87 (s, 6H), 2.86 (t, 2H, J=6.37 Hz), 2.30 (m, 2H, J=5.48, 7.96 Hz). MS (ES$^+$) m/e 428. mp 71.5–72.0° C. Anal. Calcd for C$_{27}$H$_{33}$N$_3$O$_7$S: C, 59.65; H, 6.12; N, 7.73; S, 5.90. Found C, 59.52; H, 6.07; N, 7.73; S, 5.99.

Example 283

Preparation of (3-{2,6-dichloro-4-[5-(2-phenoxy-ethylsulfanylmethyl)-[1,3,4]oxadiazol-2-yl]-phenoxy}-propyl)-dimethyl-amine; fumaric acid salt

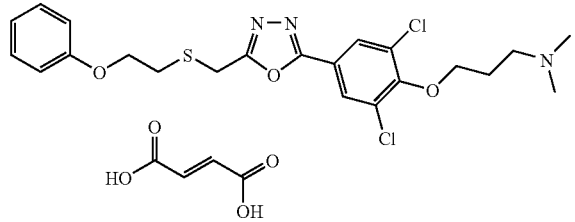

a) Methyl 3,5-dichloro-4-(3-dimethylamino-propoxy)-benzoate

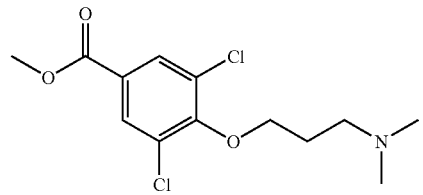

17.05 gm (77.1 mmol) of methyl 3,5-dichloro-4-hydroxy-benzoate, 22.26 gm (84.9 mmol) of triphenylphosphine, and 10.0 mL (84.9 mmol) of 3-dimethylaminopropan-1-ol were dissolved in 100 mL of dry THF and with stirring under dry nitrogen cooled to 0° C. 16.7 ml (84.9 mmol) of diisopropylazodicarboxylate was then slowly added over 5 minutes. Stirring was continued at 0° C. for 2 hours and then at room temperature for a further 2 hours. The solvents were then removed under reduced pressure to yield an oil. This was diluted with about 100 mL of ethylacetate which was then extracted 3 times with 3N HCl. The aqueous extracts were combined, cooled to 0° C. and solid sodium hydroxide was added until the aqueous phase was at least pH 10. The basified aqueous fraction was then extracted twice with 50 ml portions of methylene chloride which were then combined, dried over magnesium sulfate, filtered, and evaporated to give 16.3 gm (70%) of methyl 3,5-dichloro-4-(3-dimethylamino-propoxy)-benzoate as a thick syrup.

$^1$H NMR (CHCl$_3$-d1) δ 7.91 (s, 1H), 4.09 (t, 2H, J=6.37 Hz), 3.86 (s, 3H), 2.49 (t, 2H, J=7.78 Hz), 2.22 (s, 6H), 1.95–2.02 (m, 2H).

b) 3,5-Dichloro-4-(3-dimethylamino-propoxy)-benzoic acid hydrazide

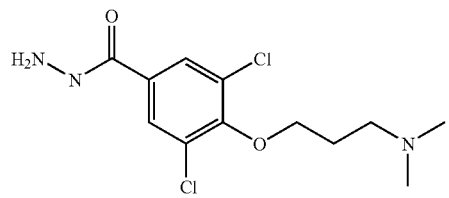

5.01 gm (16.43 mmol) of methyl 3,5-dichloro-4-(3-dimethylamino-propoxy)-benzoate was dissolved in 15 mL of ethanol and 15 ml of hydrazine hydrate were added. The mixture was heated at 90° C. for 5.5 h and then cooled to room temperature. The mixture was diluted with about 100 mL of methylene chloride, which was then washed with about 30 mL of water. The aqueous layer was washed once with about 30 ml of ethylacetate and then the organic fractions were combined, dried over magnesium sulfate, filtered, and evaporated to yield 3.56 gm (71%) of 3,5-dichloro-4-(3-dimethylamino-propoxy)-benzoic acid hydrazide as a waxy solid.

$^1$H NMR (CHCl$_3$-d1) δ 7.69 (s, 2H), 4.08 (t, 2H, J=6.72 Hz), 2.50 (t, 2H, J=7.78 Hz), 2.23 (s, 6H), 1.95–2.02 (m, 2H).

c) (3-{2,6-Dichloro-4-[5-(2-phenoxy-ethylsulfanyl-methyl)-[1,3,4]oxadiazol-2-yl]-phenoxy}-propyl)-dimethyl-amine; fumaric acid salt

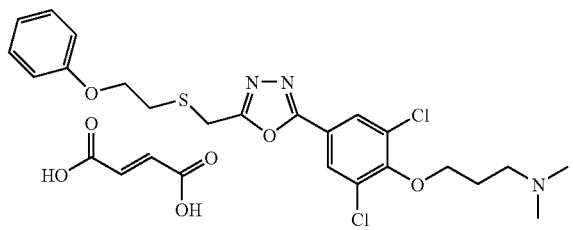

3.05 gm (10.0 mmol) of 3,5-dichloro-4-(3-dimethylamino-propoxy)-benzoic acid hydrazide, 2.12 gm (10.0 mmol) of (2-phenoxy-ethylsulfanyl)-acetic acid, 7.87 gm (30.0 mmol) of triphenylphosphine, 8.3 ml (60.0 mmol) of triethylamine, were suspended in 25 mL of dry acetonitrile and stirred at room temperature. 4.8 mL (50.0 mmol) of carbon tetrachloride was then slowly added. The resultant mixture was stirred at room temperature for about 5 hours and then the solvent was removed under reduced pressure. The resultant oil was diluted with about 50 mL of ethylacetate which was then extracted with two portions of about 15 mL 3N HCl. The combined acidic extracts were basified with solid sodium hydroxide and then extracted with two approximately 30 mL portions of methylene chloride. The methylene chloride extracts were dried over magnesium sulfate, filtered, and then evaporated to yield 3.94 gm of a dark red oil. The oil was chromatographed on about 100 gm of silica gel using sequentially 500 mL of ethylacetate, a 1,000 mL gradient of from 0 to 40% methanol in ethylacetate and then 1,000 mL of 40% methanol in methylene chloride to give 1.45 gm of the desired free base. This was dissolved in a mixture of ethylacetate and methylene chloride and 344 mg of fumaric acid was added. The solvents were evaporated and the residue was triturated in diethyl ether to give 1.48 gm of (3-{2,6-dichloro-4-[5-(2-phenoxy-ethylsulfanylmethyl)-[1,3,4]oxadiazol-2-yl]-phenoxy}-propyl)-dimethyl-amine; fumaric acid salt as a solid. mp=95–99° C.

$^1$H NMR (CH$_3$OH-d4) δ 7.97 (s, 2H), 7.18 (t, 2H, J=8.14 Hz), 6.81–6.87 (m, 3H), 6.66 (s, 2H), 4.21 (t, 2H, J=5.66 Hz), 4.13–4.17 (m, 4H), 3.40–3.46 (m, 2H), 3.03 (t, 2H, J=6.01 Hz), 2.91 (s, 6H), 2.23–2.32 (m, 2H).

Anal. Calcd for C$_{26}$H$_{29}$Cl$_2$N$_3$O$_7$S: C, 52.18; H, 4.88; N, 7.02; Cl, 11.85. Found C, 52.20; H, 4.74; N, 7.88; Cl, 11.86.

Example 284

Preparation of (3-{2-methoxy-4-[5-(2-phenoxy-ethylsulfanylmethyl)-[1,3,4]oxadiazol-2-yl]-phenoxy}-propyl)-dimethyl-amine; maleic acid salt

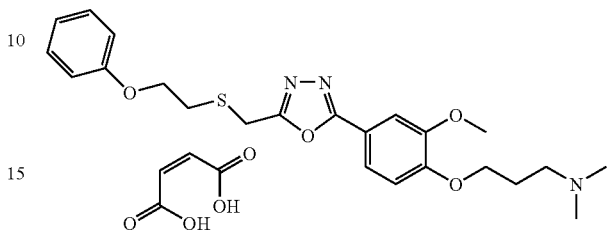

a) Methyl 4-(3-dimethylamino-propoxy)-3-methoxy benzoate

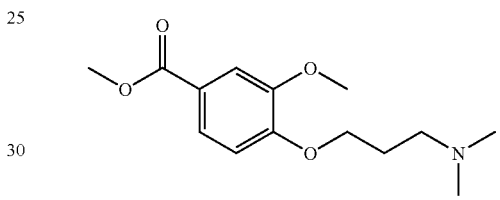

In a similar manner as exemplified in Example 283 part a), 10.0 gm of methyl 4-hydroxy-3-methoxybenzoate was converted into 16.08 gm of methyl 4-(3-dimethylamino-propoxy)-3-methoxy benzoate as a yellow oil.

$^1$H NMR (CHCl$_3$-d1) δ 7.60 (dd, 1H, J=8.49, 2.12 Hz), 7.50 (d, 1H, J=2.12 Hz), 6.86 (d, 1H, J=8.49 Hz), 4.09 (t, 2H, J=6.72 Hz), 3.87 (s, 3H), 3.84 (s, 3H), 2.41 (t, 2H, J=7.08 Hz), 2.20 (s, 6H), 1.94–2.04 (m, 2H).

b) 4-(3-Dimethylamino-propoxy)-3-methoxy benzoic acid hydrazide

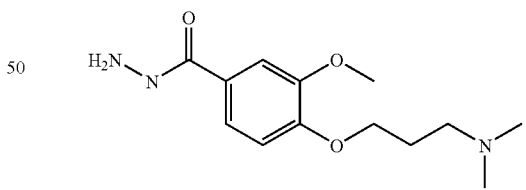

In a similar manner as exemplified in Example 283 part b), 16 gm of methyl 4-(3-dimethylamino-propoxy)-3-methoxy benzoate was converted into 4-(3-dimethylamino-propoxy)-3-methoxy benzoic acid hydrazide a portion of which was purified by chromatography on silica gel using a 6% 2N ammonia in methanol mixture in methylene chloride to yield 1.35 gm of a white solid.

$^1$H NMR (CHCl$_3$-d1) δ 8.06 (bs, 1H), 7.83 (d, 1H, J=2.12 Hz), 7.22 (dd, 1H, J=8.40 Hz), 6.80 (d, 1H, J=8.49 Hz), 4.02 (t, 2H, J=6.72 Hz), 3.81 (s, 3H), 2.38 (t, 2H, J=7.43 Hz, 2.17 (s, 6H), 1.90–1.99 (m, 2H).

c) (3-{2-Methoxy-4-[5-(2-phenoxy-ethylsulfanylmethyl)-[1,3,4]oxadiazol-2-yl]-phenoxy}-propyl)-dimethyl-amine; maleic acid salt

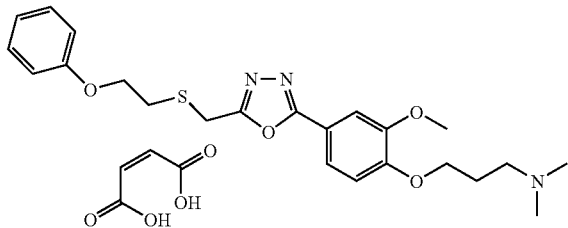

In a similar manner as exemplified in Example 283 part c), 1.37 gm of 4-(3-dimethylamino-propoxy)-3-methoxy benzoic acid hydrazide was converted into 1.62 gm of (3-{2-methoxy-4-[5-(2-phenoxy-ethylsulfanylmethyl)-[1,3,4]oxadiazol-2-yl]-phenoxy}-propyl)-dimethyl-amine; maleic acid salt except: The initial reaction mixture was evaporated to dryness, taken up in ethyl acetate, and washed with saturated sodium bicarbonate. The organic phase was dried over magnesium sulfate, filtered, and evaporated to yield a solid which was chromatographed on about 100 gm of silica gel using 500 mL of ethylacetate, a 500 mL gradient of a 0 to 5% 2N ammonia in methanol mixture in methylene chloride, and 1,500 mL of a 5% 2N ammonia in methanol mixture in methylene chloride. The free base was converted into the maleic acid salt by addition of an equivalent of maleic acid to the free base in hot ethyl acetate. The desired salt precipitated from solution as a white solid which was collected by filtration. mp=114–116° C.

$^1$H NMR (CH$_3$OH-d4) δ 7.54–7.58 (m, 2H), 7.19 (t, 2H, J=8.14 Hz), 7.09 (d, 1H, J=8.85 Hz), 6.84–6.90 (m, 2H), 6.20 (s, 2H), 4.22 (t, 2H, J=5.66 Hz), 4.17 (t, 2H, J=6.01 Hz), 4.13 (s, 2H), 3.90 (s, 3H), 3.38 (t, 2H, J=7.08 Hz), 3.03 (t, 2H, J=6.01 Hz), 2.96 (s, 6H), 2.23–2.31 (m, 2H).

Anal. Calcd for C$_{27}$H$_{33}$N$_3$O$_8$S: C, 57.95; H, 5.94; N, 7.51. Found C, 58.02; H, 5.89; N, 7.49.

Example 285

Preparation of (3-{2,6-dimethoxy-4-[5-(2-phenoxy-ethylsulfanylmethyl)-[1,3,4]oxadiazol-2-yl]-phenoxy}-propyl)-dimethyl-amine; maleic acid salt

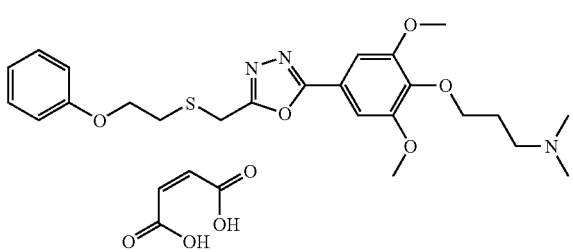

a) Methyl 3,5-dimethoxy-4-(3-dimethylamino-propoxy)-benzoate

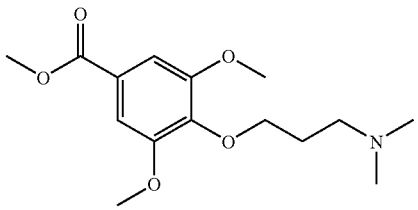

In a similar manner as exemplified for Example 283, part a), 5.0 gm (23.56 mmol) of methyl 3,5-dimethoxy-4-hydroxybenzoate was converted into 6.96 gm (100%) of methyl 3,5-dimethoxy-4-(3-dimethylamino-propoxy)-benzoate as a yellow oil.

$^1$H NMR (CHCl$_3$-d1) δ 7.25 (s, 2H), 4.05 (t, 2H, J=6.72 Hz), 3.86 (s, 3H), 3.85 (s, 6H), 2.44 (t, 2H, J=7.08 Hz), 2.20 (s, 6H), 1.84–1.93 (m, 2H).

b) 3,5-dimethoxy-4-(3-dimethylamino-propoxy)-benzoic acid hydrazide

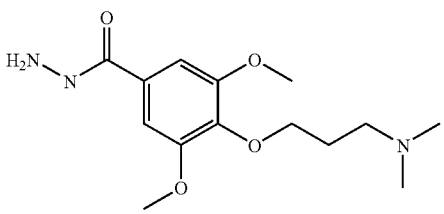

In a similar manner as exemplified for Example 283, part b), 2.49 gm of methyl 3,5-dimethoxy-4-(3-dimethylamino-propoxy)-benzoate was converted into 1.99 gm (80%) of 3,5-dimethoxy-4-(3-dimethylamino-propoxy)-benzoic acid hydrazide as a white waxy solid excepting that the reaction was carried out at room temperature for 24 h. mp=95–96° C.

$^1$H NMR (CHCl$_3$-d1) δ 6.93 (s, 2H), 4.02 (t, 2H, J=6.72 Hz), 3.84 (s, 6H), 2.44 (t, 2H, J=7.08 Hz, 2.21 (s, 6H), 1.84–1.93 (m, 2H).

c) (3-{2,6-Dimethoxy-4-[5-(2-phenoxy-ethylsulfanylmethyl)-[1,3,4]oxadiazol-2-yl]-phenoxy}-propyl)-dimethyl-amine; maleic acid salt

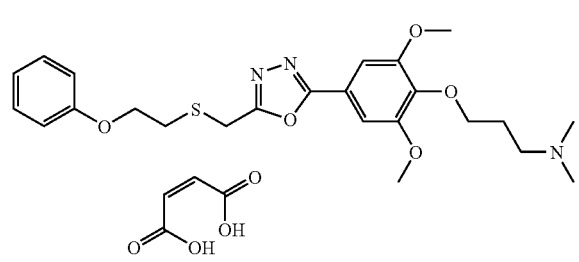

In a similar manner as exemplified for Example 284 part c), 1.06 gm of 3,5-dimethoxy-4-(3-dimethylamino-propoxy)-benzoic acid hydrazide was converted into 1.20 gm of (3-{2,6-dimethoxy-4-[5-(2-phenoxy-ethylsulfanylmethyl)-[1,3,4]oxadiazol-2-yl]-phenoxy}-propyl)-dimethyl-amine; maleic acid salt as a white solid except that 2N sodium hydroxide was substituted for the saturated sodium bicarbonate in the ethyl acetate wash. mp=103–104° C.

$^1$H NMR (CH$_3$OH-d4) δ 7.30 (s, 2H), 7.19 (t, 2H, J=7.78 Hz), 6.84–6.89 (m, 2H), 6.22 (s, 2H), 4.13–4.19 (m, 6H), 3.91 (s, 6H), 3.45 (t, 2H, J=6.72 Hz), 3.04 (t, 2H, J=6.01 Hz), 2.96 (s, 6H), 2.12–2.19 (m, 2H).

Anal. Calcd for C$_{28}$H$_{35}$N$_3$O$_9$S: C, 57.03; H, 5.98; N, 7.13. Found C, 57.01; H, 5.84; N, 7.10.

Example 286

Preparation of (3-{2-chloro-4-[5-(2-phenoxy-ethylsulfanylmethyl)-[1,3,4]oxadiazol-2-yl]-phenoxy}-propyl)-dimethyl-amine; maleic acid salt

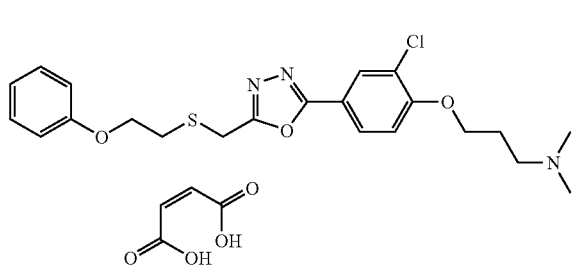

a) Methyl 3-chloro-4-(3-dimethylamino-propoxy)-benzoate

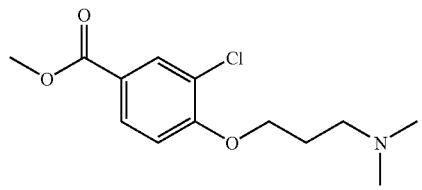

In a similar manner as exemplified for Example 283, part a), 5.01 gm of methyl 3-chloro-4hydroxybenzoate was converted into 6.39 gm of methyl 3-chloro-4-(3-dimethylamino-propoxy)-benzoate as a yellow oil.

$^1$H NMR (CHCl$_3$-d1) δ 8.00 (d, 1H, J=2.12 Hz), 7.86 (dd, 1H, J=8.49, 2.12 Hz), 6.91 (d, 1H, J=8.85 Hz), 4.11 (t, 2H, J=6.72 Hz), 3.85 (s, 3H), 2.45 (t, 2H, J=7.08 Hz), 2.22 (s, 6H), 1.94–2.03 (m, 2H).

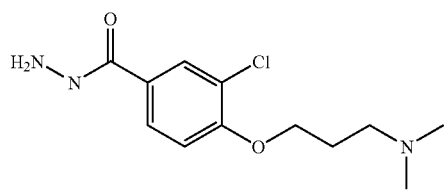

b) 3-Chloro-4-(3-dimethylamino-propoxy)-benzoic acid hydrazide

In a similar manner as exemplified for example 285 part b), 6.35 gm of methyl 3-chloro-4-(3-dimethylamino-propoxy)-benzoate was converted into 5.81 gm of 3-chloro-4-(3-dimethylamino-propoxy)-benzoic acid hydrazide as a white waxy solid.

$^1$H NMR (CHCl$_3$-d1) δ 8.06 (bs, 1H), 7.79 (d, 1H, J=2.12 Hz), 7.61 (dd, 1H, J=8.40, 2.48 Hz), 6.88 (d, 1H, J=8.85 Hz), 4.07 (t, 2H, J=6.37 Hz), 2.44 (t, 2H, J=7.08 Hz), 2.21 (s, 6H), 1.92–2.01 (m, 2H).

c) (3-{2-Chloro-4-[5-(2-phenoxy-ethylsulfanylmethyl)-[1,3,4]oxadiazol-2-yl]-phenoxy}-propyl)-dimethyl-amine; maleic acid salt

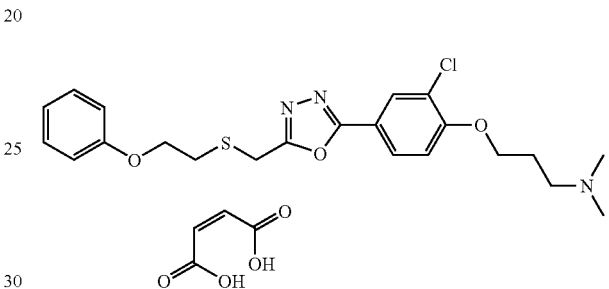

In a similar manner as exemplified for example 284 part c), 2.49 gm of 3-chloro-4-(3-dimethylamino-propoxy)-benzoic acid hydrazide was converted into 1.84 gm of (3-{2-chloro-4-[5-(2-phenoxy-ethylsulfanylmethyl)-[1,3,4]oxadiazol-2-yl]-phenoxy}-propyl)-dimethyl-amine; maleic acid salt as a white solid.

$^1$H NMR (CH$_3$OH-d4) δ 7.99 (d, 1H, J=2.12 Hz), 7.90 (dd, 1H, J=8.85, 2.12 Hz), 7.16–7.26 (m, 3H), 6.83–6.89 (m, 3H), 6.21 (s, 2H), 4.27 (t, 2H, J=5.66 Hz), 4.17 (t, 2H, J=6.01 Hz), 4.13 (s, 2H), 3.38 (t, 2H, J=7.43), 3.03 (t, 2H, J=6.01 Hz), 2.95 (s, 6H), 2.26–2.85 (m, 2H).

Anal. Calcd for C$_{26}$H$_{30}$ClN$_3$O$_7$S: C, 55.36; H, 5.36; N, 7.45; Cl, 6.29. Found C, 55.50; H, 5.24; N, 7.37, Cl, 6.29.

Example 287

Preparation of (3-{2-fluoro-4-[5-(2-phenoxy-ethylsulfanylmethyl)-[1,3,4]oxadiazol-2-yl]-phenoxy}-propyl)-dimethyl-amine; maleic acid salt

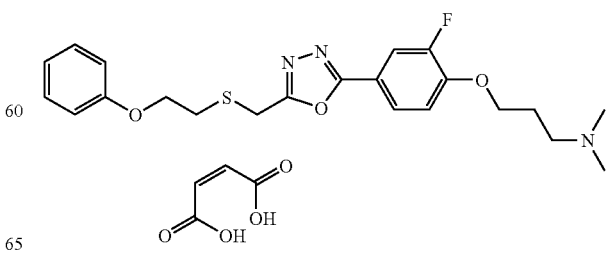

a) Methyl 4-(3-dimethylamino-propoxy)-3-fluoro benzoate

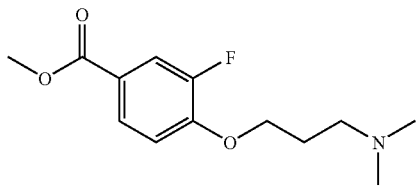

In a similar manner as exemplified in Example 283 part a), 2.82 gm of methyl 3-fluoro-4-hydroxybenzoate was converted into 3.95 gm of methyl 4-(3-dimethylamino-propoxy)-3-fluoro benzoate as a yellow oil.

¹H NMR (CHCl₃-d1) δ 7.74 (d, 1H, J=9.20 Hz), 7.69 (d, 1H, J=9.55 Hz), 4.11 (t, 2H, J=6.37 Hz), 3.84 (s, 3H), 2.42 (t, 2H, 6.72 Hz), 2.21 (s, 6H), 1.92–2.01 (m, 2H).

b) 4-(3-Dimethylamino-propoxy)-3-fluoro benzoic acid hydrazide

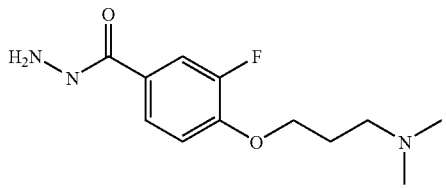

In a similar manner as exemplified in Example 285 part b), 3.84 gm of methyl 4-(3-dimethylamino-propoxy)-3-fluoro benzoate was converted into 3.51 gm of 4-(3-dimethylamino-propoxy)-3-fluoro benzoic acid hydrazide as a white solid. mp=109–111° C.

¹H NMR (CHCl₃-d1) δ 7.41–7.51 (m, 2H), 6.97 (t, 1H, J=8.49), 4.10 (t, 2H, J=6.72 Hz), 2.43 (t, 2H, J=7.08 Hz), 2.22 (s, 6H), 1.93–2.02 (m, 2H).

c) (3-{2-Fluoro-4-[5-(2-phenoxy-ethylsulfanylmethyl)-[1,3,4]oxadiazol-2-yl]-phenoxy}-propyl)-dimethyl-amine; maleic acid salt

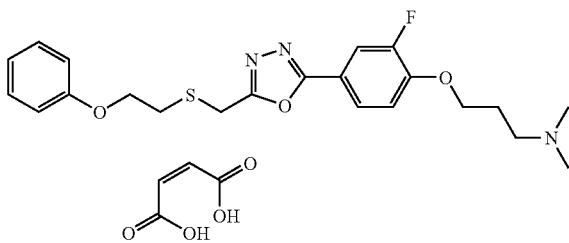

In a similar manner as exemplified in example 284 part c), 1.01 gm of 4-(3-dimethylamino-propoxy)-3-fluoro benzoic acid hydrazide was converted into 448 mg of (3-{2-fluoro-4-[5-(2-phenoxy-ethylsulfanylmethyl)-[1,3,4]oxadiazol-2-yl]-phenoxy}-propyl)-dimethyl-amine; maleic acid salt as a beige solid. mp=70–72° C.

¹H NMR (CH₃OH-d4) δ 7.76 (d, 1H, J=8.85 Hz), 7.72 (d, 1H, J=11.32 Hz), 7.26 (t, 1H, J=8.49 Hz), 7.19 (t, 2H, J=8.85 Hz), 6.84–6.90 (m, 3H), 6.22 (s, 2H), 4.26 (t, 2H, J=5.66 Hz), 4.18 (t, 2H, J=6.01 Hz), 4.13 (s, 2H), 3.35 (t, 2H, J=7.43 Hz), 3.03 (t, 2H, J=6.37 Hz), 2.93 (s, 6H), 2.23–2.32 (m, 2H).

Anal. Calcd for C₂₆H₃₀FN₃O₇S: C, 57.03; H, 5.52; N, 7.67. Found C, 56.68; H, 5.32; N, 7.71.

Example 288

Preparation of dimethyl-(3-{5-[5-(2-phenoxy-ethyl-sulfanylmethyl)-[1,3,4]oxadiazol-2-yl]-pyridin-2-yloxy}-propyl)-amine

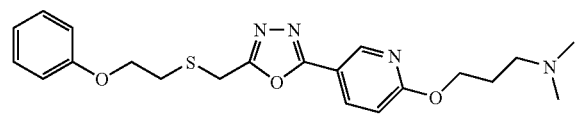

a) 6-(3-Dimethylamino-propoxy)-nicotinic acid benzyl ester

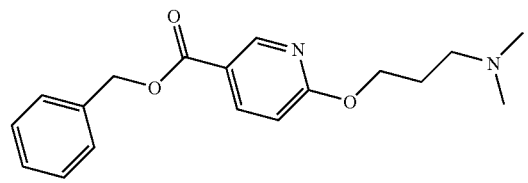

In a similar manner as exemplified for Example 283, part a), 5.0 gm of benzyl 6-hydroxynicotinate was converted into a 50:50 mixture of 6-(3-dimethylamino-propoxy)-nicotinic acid benzyl ester and it's N-alkylated isomer as a light yellow oil.

b) 6-(3-Dimethylamino-propoxy)-nicotinic acid hydrazide

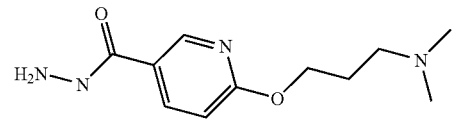

In a similar manner as exemplified in example 285 part b), 7.0 gm of a 50:50 mixture of 6-(3-dimethylamino-propoxy)-nicotinic acid benzyl ester and it's N-alkylated isomer were converted into a mixture of N- and O-alkylated hydrazides which was separated by chromatography on silica gel using a 0 to 10% gradient of a 2N ammonia in methanol mixture in methylene chloride. 1.96 gm of 6-(3-dimethylamino-propoxy)-nicotinic acid hydrazide was obtained as a white solid. mp=81–83° C.

¹H NMR (CHCl₃-d1) δ 8.50 (s, 1H), 7.93 (d, 1H, J=10.61 Hz), 7.86 (bs, 1H), 6.73 (d, 1H, J=8.85 Hz), 4.35 (t, 2H, J=6.72 Hz), 2.45 (t, 2H, J=7.08 Hz), 2.25 (s, 6H), 1.87–2.00 (m, 2H).

c) Dimethyl-(3-{5-[5-(2-phenoxy-ethylsulfanylmethyl)-[1,3,4]oxadiazol-2-yl]-pyridin-2-yloxy}-propyl)-amine

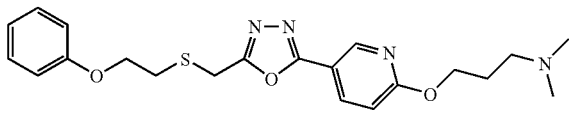

In a similar manner as exemplified in example 284, part c), 1.00 gm of 6-(3-dimethylamino-propoxy)-nicotinic acid hydrazide was converted into 774 mg of the free base dimethyl-(3-{5-[5-(2-phenoxy-ethylsulfanylmethyl)-[1,3,4]oxadiazol-2-yl]-pyridin-2-yloxy}-propyl)-amine as a white solid. mp=69–70° C.

$^1$H NMR (CHCl$_3$-d1) δ 8.67 (d, 1H, J=1.77 Hz), 8.13 (dd, 1H, J=8.85, 2.48 Hz), 7.24 (t, 2H, J=8.85), 6.92 (t, 1H, J=7.43 Hz), 6.92 (t, 1H, J=7.43 Hz), 6.86 (d, 2H, J=7.78 Hz), 6.80 (d, 1H, J=8.85 Hz), 4.40 (t, 2H, J=6.72 Hz), 4.18 (t, 2H, J=6.37 Hz), 4.03 (s, 2H), 3.03 (t, 2H, J=6.01 Hz), 2.42 (t, 2H, J=7.08 Hz), 2.24 (s, 6H), 1.91–1.99 (m, 2H). Anal. Calcd for C$_{21}$H$_{26}$N$_4$O$_3$S: C, 60.85; H, 6.32; N, 13.52. Found C, 61.07; H, 6.28; N, 13.46.

Example 289

Preparation of dimethyl-(3-{6-[5-(2-phenyl-sulfanylmethyl)-[1,3,4]oxadiazol-2-yl]-pyridin-3-yloxy}-propyl)-amine

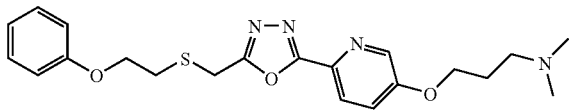

a)
5-(3-Dimethylamino-propoxy)-pyridine-2-carboxylic acid methyl ester

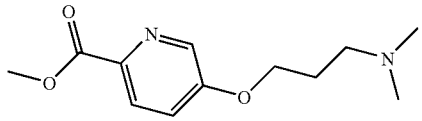

504.4 mg (3.29 mmol) of 5-hydroxy-pyridine-2-carboxylic acid methyl ester, 864 mg (3.29 mmol) of triphenylphosphine, and 390 uL of 3-dimethylaminopropan-1-ol were combined and stirred under dry nitrogen in 10 mL of dry THF at 0° C. 650 uL (3.29 mmol) of diisopropylazodicarboxylate was then slowly added over 3 minutes with continued stirring at 0° C. for 1 hour and then at room temperature for a further 3 hours. The solvents were removed under reduced pressure and the resultant oil was chromatographed on about 100 gm of silica gel using 240 ml of ethylacetate, then 500 ml of a gradient of from 0 to 5% of a 2N ammonia in methanol mixture in methylene chloride, and then 1 L of a 5% 2N ammonia in methanol mixture in methylene chloride to give 602.3 mg (77%) of 5-(3-dimethylamino-propoxy)-pyridine-2-carboxylic acid methyl ester as a yellow waxy solid. mp 44–45° C.

$^1$H NMR (CHCl$_3$-d1) δ 8.36 (d, 1H, J=2.48 Hz), 8.07 (d, 1H, J=8.85 Hz), 7.23 (dd, 1H, J=8.84, 2.83 Hz), 4.11 (t, 2H, J=6.37 Hz), 3.95 (s, 2H), 2.43 (t, 2H, J=7.08 Hz), 2.23 (s, 6H), 1.93–2.01 (m, 2H).

b)
5-(3-Dimethylamino-propoxy)-pyridine-2-carboxylic acid hydrazide

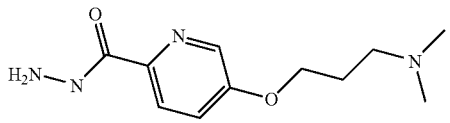

In a similar manner as exemplified in example 285 part b), 1.4 gm of 5-(3-dimethylamino-propoxy)-pyridine-2-carboxylic acid methyl ester was converted into 1.38 gm of 5-(3-dimethylamino-propoxy)-pyridine-2-carboxylic acid hydrazide as a light brown waxy solid. mp=82–83° C.

$^1$H NMR (CHCl$_3$-d1) δ 8.67 (bs, 1H), 8.16 (d, 1H, J=2.48 Hz), 8.05 (d, 1H, J=8.85 Hz), 7.25 (dd, 1H, J=8.49, 2.83 Hz), 4.08 (t, 2H, J=6.37 Hz), 2.42 (t, 2H, J=7.08 Hz), 2.22 (s, 6H), 1.91–2.00 (m, 2H).

c) Dimethyl-(3-{6-[5-(2-phenoxy-ethylsulfanylmethyl)-[1,3,4]oxadiazol-2-yl]-pyridin-3-yloxy}-propyl)-amine

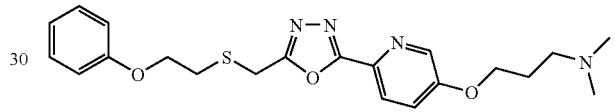

In a similar manner as exemplified for Example 283, part c), 1.00 gm of 5-(3-dimethylamino-propoxy)-pyridine-2-carboxylic acid hydrazide was converted into 712 mg of the free base dimethyl-(3-{6-[5-(2-phenoxy-ethylsulfanylmethyl)-[1,3,4]oxadiazol-2-yl]-pyridin-3-yloxy}-propyl)-amine as a beige solid. mp=47–49° C.

$^1$H NMR (CHCl$_3$-d1) δ 8.40 (d, 1H, J=2.83 Hz), 8.12 (d, 1H, J=8.84 Hz), 7.80 (dd, 1H, J=8.85, 2.83 Hz), 7.18 (t, 2H, J=8.85 Hz), 6.92 (t, 1H, J=7.43 Hz), 6.87 (d, 2H, J=7.78 Hz), 4.18 (t, 2H, J=6.01 Hz), 4.13 (t, 2H, J=6.37 Hz), 4.04 (s, 2H), 3.04 (t, 2H, J=6.37 Hz), 2.45 (t, 2H, J=7.08 Hz), 2.24 (s, 6H), 1.94–2.03 (m, 2H).

Anal. Calcd for C$_{21}$H$_{26}$N$_4$O$_3$S: C, 60.85; H, 6.32; N, 13.52. Found C, 60.82; H, 6.24; N, 13.51.

Example 290

Preparation of 1-methyl-3-{4-[5-(2-phenoxy-ethylsulfanylmethyl)-[1,3,4]oxadiazol-2-yl]-phenoxymethyl}-piperidine; maleic acid salt

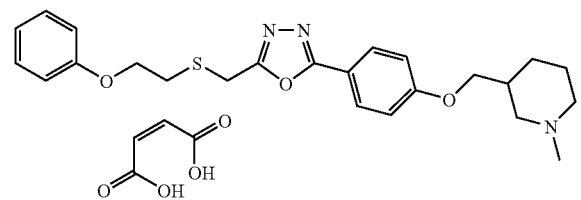

a) 4-(1-Methyl-piperidin-3-ylmethoxy)-benzoic acid methyl ester

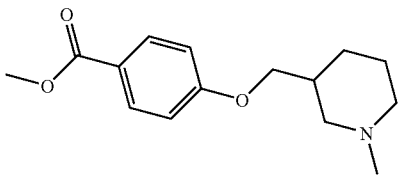

In a similar manner as exemplified for Example 283 part a), excepting that 3-hydroxymethyl-1-methyl-piperidine was substituted for the 3-dimethylaminopropan-1-ol and that the resultant material was purified by chromatography on about 100 gm of silica gel using 500 mL of ethylacetate, then 500 mL of a gradient of from 0 to 5% of a 2N ammonia in methanol mixture in methylene chloride, and then 1.8 L of a 5% 2N ammonia in methanol mixture in methylene chloride, 1.5 gm of methyl 4-hydroxybenzoate was converted into 1.792 gm of 4-(1-methyl-piperidin-3-yl-methoxy)-benzoic acid methyl ester as a white waxy solid. mp=55–56° C.

$^1$H NMR (CHCl$_3$-d1) δ 7.93 (d, 2H, J=8.85 Hz), 6.86 (d, 2H, J=8.85 Hz), 3.77–3.90 (m, 5H), 2.90 (d, 1H, J=9.91 Hz), 2.71 (d, 1H, J=10.97 Hz), 2.24 (s, 3H), 2.05–2.17 (m, 1H), 1.92 (bt, 1H), 1.53–1.84 (m, 4H), 1.07 (dq, 1H, J=12.03, 3.54 Hz).

b) 4-(1-Methyl-piperidin-3-ylmethoxy)-benzoic acid hydrazide

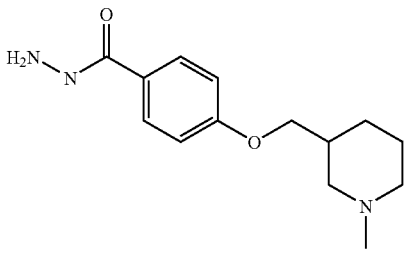

In a similar manner as exemplified for Example 285, part b), 1.7 gm of 4-(1-methyl-piperidin-3-ylmethoxy)-benzoic acid methyl ester was converted into 1.7 gm of 4-(1-methyl-piperidin-3-ylmethoxy)-benzoic acid hydrazide as a white solid. mp=170–172° C.

$^1$H NMR (CHCl$_3$-d1) δ 7.67 (d, 2H, J=8.84 Hz), 6.89 (d, 2H, J=8.84 Hz), 4.04 (bs, 2H), 3.76–3.89 (m, 2H), 2.91 (bd, 1H, J=10.61 Hz), 2.73 (bd, 1H, J=10.97 Hz), 2.25 (s, 3H), 2.05–2.18 (m, 1H), 1.94 (bt, 1H, J=10.97 Hz), 1.54–1.86 (m, 4H), 1.08 (dq, 1H, J=11.32 Hz).

1-Methyl-3-{4-[5-(2-phenoxy-ethylsulfanylmethyl)-[1,3,4]oxadiazol-2-yl]-phenoxymethyl}-piperidine; maleic acid salt

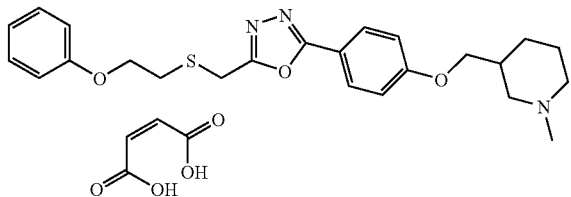

In a similar manner as exemplified for Example 285, part c), 800 mg of 4-(1-methyl-piperidin-3-ylmethoxy)-benzoic acid hydrazide was converted into 620 mg of 1-methyl-3-{4-[5-(2-phenoxy-ethylsulfanylmethyl)-[1,3,4]oxadiazol-2-yl]-phenoxymethyl}-piperidine; maleic acid salt as a white solid. mp=115–116° C.

$^1$H NMR (CHCl$_3$-d1) δ 7.95 (d, 2H, J=8.84 Hz), 7.25 (t, 2H, J=8.85 Hz), 6.90–6.98 (m, 3H), 6.87 (d, 2H, J=8.85 Hz), 6.27 (s, 2H), 4.19 (t, 2H, J=6.37 Hz), 3.99–4.05 (m, 3H), 3.86–3.93 (m, 1H), 3.68 (bd, 1H, J=12.38 Hz), 3.60 (bd, 1H, J=11.32 Hz), 3.03 (t, 2H, J=6.01 Hz), 2.82 (s, 3H), 2.50–2.73 (m, 3H), 1.91–2.15 (m, 3H), 1.48 (dq, 2H, J=13.44, 4.60).

Anal. Calcd for $C_{28}H_{33}N_3O_7S$: C, 60.53; H, 5.99; N, 7.56. Found C, 60.76; H, 5.90; N, 7.62.

Example 291

Preparation of 1-methyl-4-{4-[5-(2-phenoxy-ethyl-sulfanylmethyl)-[1,3,4]oxadiazol-2-yl]-phenoxy}-piperidine; maleic acid salt

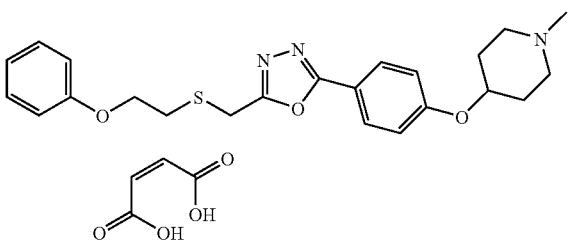

a) 4-(1-Methyl-piperidin-4-yloxy)-benzoic acid methyl ester

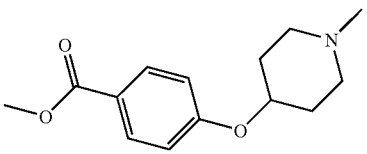

In a similar manner as exemplified in example 290, part a), except that 4-hydroxy-1-methyl-piperidine was substituted for 3-hydroxymethyl-1-methyl-piperidine, 1.5 gm of methyl 4-hydroxybenzoate was converted into 743 mg of 4-(1-methyl-piperidin-4-yloxy)-benzoic acid methyl ester.

$^1$H NMR (CHCl$_3$-d1) δ 7.93 (d, 2H, J=9.20 Hz), 6.87 (d, 2H, J=9.20 Hz), 4.33–4.42 (m, 1H), 3.84 (s, 3H), 2.59–2.71 (m, 21), 2.21–2.32 (m, 5H), 1.93–3.02 (m, 2H), 1.76–1.88 (m, 2H).

b) 4-(1-Methyl-piperidin-4-yloxy)-benzoic acid hydrazide

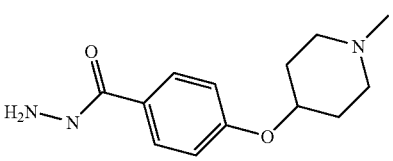

740 mg of 4-(1-methyl-piperidin-4-yloxy)-benzoic acid methyl ester was stirred in 3 ml of hydrazine hydrate and 3 ml of ethanol for 24 h. The solvents were removed under reduced pressure to yield 740 mg of 4-(1-methyl-piperidin-4-yloxy)-benzoic acid hydrazide as a white solid. mp=110–112° C.

$^1$H NMR (CHCl$_3$-d1) δ 7.66 (d, 2H, J=8.85 Hz), 6.90 (d, 2H, J=8.49 Hz), 4.31–4.41 (m, 1H), 4.04 (bs, 2H), 2.60–2.72 (m, 2H), 2.22–2.33 (m, 5H), 1.94–2.05 (m, 2H), 1.77–1.89 (m, 2H).

c) 1-Methyl-4-{4-[5-(2-phenoxy-ethylsulfanylmethyl)-[1,3,4]oxadiazol-2-yl]-phenoxy}-piperidine; maleic acid salt

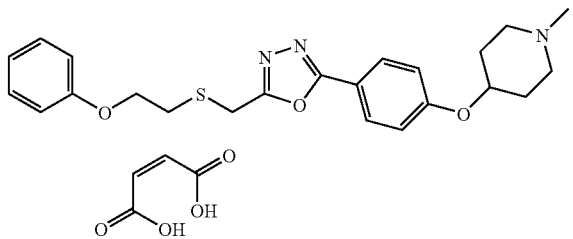

In a similar manner as exemplified for example 284, part c), 684 mg of 4-(1-methyl-piperidin-4-yloxy)-benzoic acid hydrazide was converted into 897 mg of 1-methyl-4-{4-[5-(2-phenoxy-ethylsulfanylmethyl)-[1,3,4]oxadiazol-2-yl]-phenoxy}-piperidine; maleic acid salt as a yellow solid. mp=149–150° C.

$^1$H NMR (CHCl$_3$-d1) δ 7.98 (d, 2H, J=8.85 Hz), 7.25 (t, 2H, J=7.43 Hz), 6.98 (d, 2H, J=8.85 Hz), 6.93 (t, 1H, J=7.08 Hz), 6.87 (d, 2H, J=7.78 Hz), 6.28 (s, 2H), 4.78 (bs, 1H), 4.19 (t, 2H, J=6.01 Hz), 4.03 (s, 2H), 3.37–3.49 (m, 2H), 3.07–3.21 (m, 2H), 3.03 (t, 2H, J=6.01 Hz), 2.82 (s, 3H), 2.35 (bt, 2H, J=13.44 Hz), 2.20 (bd, 2H, J=15.21 Hz).

Anal. Calcd for C$_{27}$H$_{32}$N$_3$O$_7$S: C, 59.88; H, 5.77; N, 7.76. Found C, 59.85; H, 5.66; N, 7.63.

Example 292

Preparation of (3-{3-methoxy-4-[5-(2-phenoxy-ethylsulfanylmethyl)-[1,3,4]oxadiazol-2-yl]-phenoxy}-propyl)-dimethyl-amine

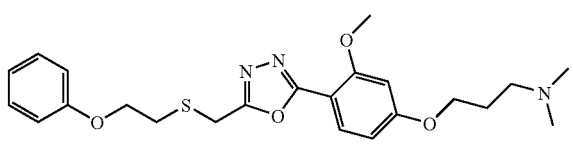

a) Methyl 4-(3-dimethylamino-propoxy)-2-methoxy benzoate

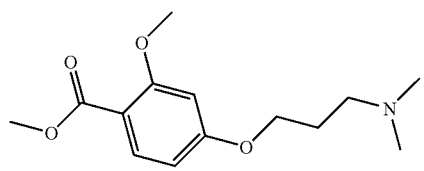

In a similar manner as exemplified for example 291, part a), 1.0 gm of methyl 2-methoxybenzoate was converted into 1.12 gm of methyl 4-(3-dimethylamino-propoxy)-2-methoxy benzoate as a clear oil.

$^1$H NMR (CHCl$_3$-d1) δ 7.80 (d, 1H, J=9.20 Hz), 6.43–6.47 (m, 2H), 4.02 (t, 2H, J=6.37 Hz), 3.85 (s, 3H), 3.81 (s, 3H), 2.41 (t, 2H, J=7.07 Hz), 2.22 (s, 6H), 1.88–1.97 (m, 2H).

b) 4-(3-Dimethylamino-propoxy)-2-methoxy benzoic acid hydrazide

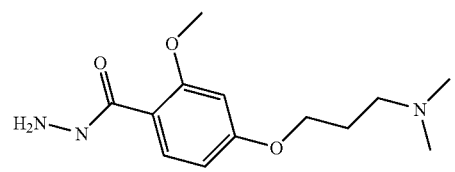

In a similar manner as exemplified in example 291, part b, 1.12 gm of methyl 4-(3-dimethylamino-propoxy)-2-methoxy benzoate was converted into 1.028 gm of 4-(3-dimethylamino-propoxy)-2-methoxy benzoic acid hydrazide as a white waxy solid. mp=47–52° C.

$^1$H NMR (CHCl$_3$-d1) δ 7.98 (d, 1H, J=8.49 Hz), 6.51 (dd, 1H, J=8.85, 2.48 Hz), 6.42 (d, 1H, J=2.48 Hz), 3.98 (t, 2H, J=6.01 Hz), 3.87 (s, 3H), 2.48 (t, 2H, J=7.43 Hz), 2.25 (s, 6H), 1.88–1.97 (m, 2H).

c) (3-{3-Methoxy-4-[5-(2-phenoxy-ethylsulfanylmethyl)-[1,3,4]oxadiazol-2-yl]-phenoxy}-propyl)-dimethyl-amine

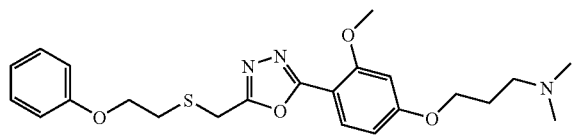

In a similar manner as exemplified for example 284, part c), 726 mg of 4-(3-dimethylamino-propoxy)-2-methoxy benzoic acid hydrazide was converted into 720 mg (3-{3-methoxy-4-[5-(2-phenoxy-ethylsulfanylmethyl)-[1,3,4]oxadiazol-2-yl]-phenoxy}-propyl)-dimethyl-amine as the free base.

$^1$H NMR (CHCl$_3$-d1) δ 7.80 (d, 1H, J=8.85 Hz), 7.24 (t, 2H, J=7.43 Hz), 6.92 (t, 1H, J=7.43 Hz), 6.86 (d, 2H, J=8.85 Hz), 6.52–6.58 (m, 2H), 4.17 (t, 2H, J=6.37 Hz), 4.06 (t, 2H, J=6.37 Hz), 4.00 (s, 2H), 3.89 (s, 3H), 3.04 (t, 2H, J=6.37 Hz), 2.44 (t, 2H, J=7.08 Hz), 2.24 (s, 6H), 1.91–2.00 (m, 2H).

Example 293

Preparation of 1-methyl-4-{5-[5-(2-phenoxy-ethylsulfanylmethyl)-[1,3,4]oxadiazol-2-yl]-pyridin-2-yl}-piperazine; maleic acid salt

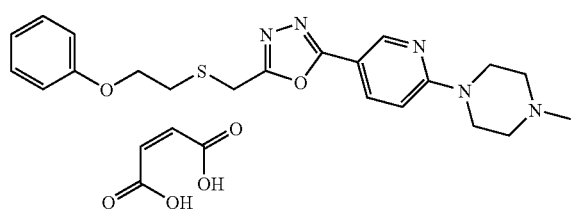

a) 6-(4-Methyl-piperazin-1-yl)-nicotinic acid methyl ester

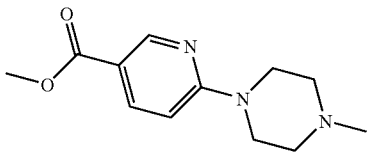

803.7 mg (4.69 mmol) of methyl 6-chloronicotinate, 570 uL (5.16 mmol) of N-methyl-piperidine, and 980 uL of diisopropylethylamine were and heated to 50° C. in 10 mL of dry DMF for 24 h. The mixture was then cooled and diluted with about 100 mL of ethylacetate which was then washed with about 30 mL of 2N NaOH, about 30 mL of brine. The organic fraction was dried over magnesium sulfate and then evaporated under reduced pressure to yield 1.1 gm of 6-(4-methyl-piperazin-1-yl)-nicotinic acid methyl ester as a yellow solid.

$^1$H NMR (CHCl$_3$-d1) δ 8.76 (d, 1H, J=2.12 Hz), 7.99 (dd, 1H, J=8.85, 2.48 Hz), 6.56 (d, 1H, J=9.20 Hz), 3.84 (s, 3H), 3.68 (t, 4H, J=4.95 Hz), 2.48 (t, 4H, J=4.95 Hz), 2.32 (s, 3H).

b) 6-(4-Methyl-piperazin-1-yl)-nicotinic acid hydrazide

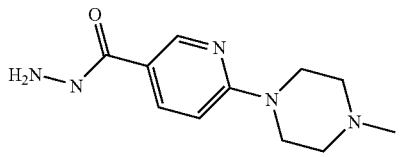

In a similar manner as exemplified for example 291, part b), 1.05 gm of 6-(4-methyl-piperazin-1-yl)-nicotinic acid methyl ester was converted into 1.05 gm of 6-(4-methyl-piperazin-1-yl)-nicotinic acid hydrazide as a waxy solid.

$^1$H NMR (CHCl$_3$-d1) δ 8.50 (d, 1H, J=2.12 Hz), 7.84 (dd, 1H, J=8.85, 2.48 Hz), 7.13 (bs, 1H), 6.60 (d, 1H, J=8.85 Hz), 4.02 (bs, 1H), 3.65 (t, 4H, J=5.81 Hz), 2.48 (t, 4H, J=4.95 Hz), 2.32 (s, 3H).

c) 1-Methyl-4-{5-[5-(2-phenoxy-ethylsulfanylmethyl)-[1,3,4]oxadiazol-2-yl]-pyridin-2-yl}-piperazine; maleic acid salt

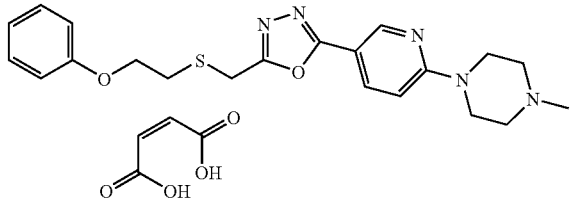

In a similar manner as exemplified for example 284, part c), 1.00 gm of 6-(4-methyl-piperazin-1-yl)-nicotinic acid hydrazide was converted into 1.00 gm of 1-methyl-4-{5-[5-(2-phenoxy-ethylsulfanylmethyl)-[1,3,4]oxadiazol-2-yl]-pyridin-2-yl}-piperazine; maleic acid salt as a white solid. mp=146–147° C.

$^1$H NMR (CH$_3$OH-d4) δ 8.74 (d, 1H, J=1.77 Hz), 8.09 (dd, 1H, J=9.20, 2.12 Hz), 7.20 (t, 2H, J=8.14 Hz), 7.02 (d, 1H, J=8.85 Hz), 6.83–6.90 (m, 3H), 6.23 (s, 2H), 4.17 (t, 2H, J=6.01 Hz), 4.13 (s, 2H), 3.33 (bs, 2H), 3.03 (t, 2H, J=6.37 Hz), 2.91 (s, 3H). Anal. Calcd for C$_{25}$H$_{29}$N$_5$O$_6$S: C, 56.91; H, 5.54; N, 13.27. Found C, 56.85; H, 5.36; N, 13.19.

Example 294

Preparation of 1-methyl-4-{4-[5-(2-phenoxy-ethylsulfanylmethyl)-[1,3,4]oxadiazol-2-yl]-phenyl}-piperazine; maleic acid salt

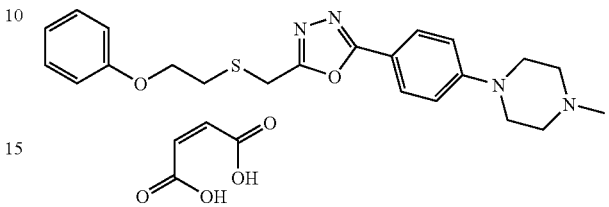

a) 4-(4-Methyl-piperazin-1-yl)-benzoic acid hydrazide

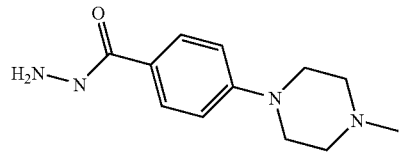

800 mg (3.41 mmol) of methyl 4-(4-methylpiperazino)benzenecarboxylate, 3 mL of hydrazine hydrate and 6 mL of ethanol were heated at 55° C. for 24 hours at which time another 1 mL of hydrazine hydrate was added and heating was continued for another 24 hours. The solvents were then removed under reduced pressure and the resultant solid was purified on about 100 gm of silica gel using a 0 to 10% gradient of a 2N ammonia in methanol mixture in methylene chloride, and then 1.8 L of a 10% 2N ammonia in methanol mixture in methylene chloride to give 620 mg of 4-(4-methyl-piperazin-1-yl)-benzoic acid hydrazide as a yellow waxy solid.

$^1$H NMR (CHCl$_3$-d1) δ 7.63 (d, 2H, J=9.20 Hz), 7.27 (bs, 1H), 6.86 (d, 2H, J=9.20 Hz), 4.03 (bs, 2H), 3.28 (t, 4H, J=4.95 Hz), 2.53 (t, 4H, J=4.95 Hz), 2.32 (s, 3H).

b) 1-Methyl-4-{4-[5-(2-phenoxy-ethylsulfanylmethyl)-[1,3,4]oxadiazol-2-yl]-phenyl}-piperazine; maleic acid salt

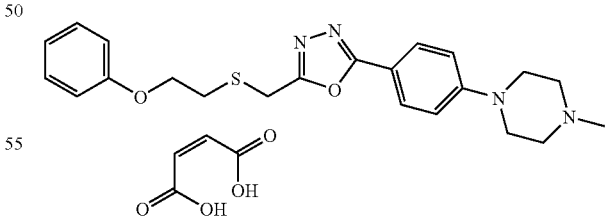

In a similar manner as exemplified in example 284, part c), 621 mg of 4-(4-methyl-piperazin-1-yl)-benzoic acid hydrazide was converted into 1.08 gm of 1-methyl-4-{4-[5-(2-phenoxy-ethylsulfanylmethyl)-[1,3,4]oxadiazol-2-yl]-phenyl}-piperazine; maleic acid salt as a yellow solid. mp=151–152° C.

$^1$H NMR (CHCl$_3$-d1) δ 7.93 (d, 2H, J=8.85 Hz), 7.25 (t, 2H, J=8.49 Hz), 6.90–6.98 (m, 3H), 6.87 (d, 2H, J=7.78 Hz), 6.27 (s, 2H), 4.18 (t, 2H, J=6.19 Hz), 4.02 (s, 2H), 3.2–3.9 (bs, 6H), 3.03 (t, 2H, J=6.19 Hz), 2.86 (s, 3H).

Example 295

Preparation of 5-(2-Phenoxy-ethylsulfanylmethyl)-3-[4-(2-pyrrolidin-1-yl-ethoxy)-phenyl]-isoxazole

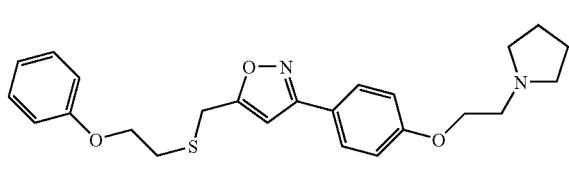

a) 4-(Tetrahydro-pyran-2-yloxy)-benzaldehyde

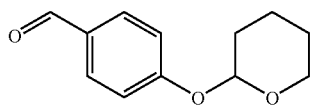

A round bottom flask was charged with 4-hydroxy-benzaldehyde (1.32 g, 10.8 mmol), evacuated by vacuum pump and filled with N₂. The aldehyde was diluted with CH₂Cl₂ (15 mL) giving a cloudy mixture. 3,4-Dihydro-2H-pyran (1.5 mL, 16.2 mmol) was added by syringe, pyridinium p-toluenesulfonate (0.27 g, 1.1 mmol) was added neat and the reaction stirred at rt under N₂ for one hour. A reflux condensor was attached and the mixture stirred in a 45° C. oil bath overnight. The reaction was quenched with sat. aq. NaHCO₃, the organic layer removed and the aqueous phase extracted with EtOAc (2×). The combined organics were dried over MgSO₄, filtered and concentrated. The crude product was purified by flash chromatography on silica gel (gradient EtOAc/Hexane 0%-80%) to give the title compound (0.87 g, 39%): ¹H NMR (CDCl₃): δ 9.88 (s, 1H), 7.82 (ap d, J=8.8 Hz, 2H), 7.15 (ap d, J=8.8 Hz, 2H), 5.54 (t, J=3.1 Hz, 1H), 3.89–3.81 (m, 1H), 3.67–3.60 (m, 1H), 2.08–1.96 (m, 1H), 1.93–1.87 (m, 2H), 1.79–1.52 (m, 3H); TLC (30% EtOAc/hexane) Rƒ 0.36.

b) 4-(Tetrahydro-pyran-2-yloxy)-benzaldehyde oxime

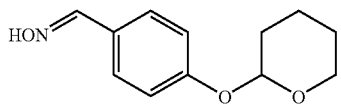

To a solution of 4-(tetrahydro-pyran-2-yloxy)-benzaldehyde (0.87 g, 4.2 mmol) in EtOH was added NaOAc³⁰ 3H₂O (2.3 g, 16.9 mmol) and hydroxylamine hydrochloride (0.44 g, 6.3 mmol). The mixture was stirred at rt for 30 min, concentrated, diluted with sat. aq. NaHCO₃, and extracted with EtOAc (3×). The combined organics were dried over MgSO₄, filtered and concentrated. The crude product was purified by flash chromatography on silica gel (gradient EtOAc/Hexane 0%–80%) to give predominantly one diastereomer as the title compound (0.63 g, 68%): ¹H NMR (CDCl₃): δ 8.08 (s, 1H), 7.50 (ap d, J=8.9 Hz, 2H), 7.06 (ap d, J=8.9 Hz, 2H), 5.46 (t, J=3.2 Hz, 1H), 3.92–3.85 (m, 1H), 3.65–3.59 (m, 1H), 2.07–1.96 (m, 1H), 1.91–1.85 (m, 2H), 1.77–1.57 (m, 3H); TLC (30% EtOAc/hexane) Rƒ 0.29.

c) 4-(Tetrahydro-pyran-2-yloxy)-benzaldehyde chloro-oxime

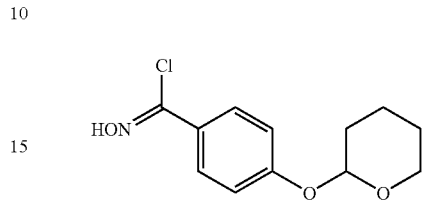

To a solution of 4-(Tetrahydro-pyran-2-yloxy)-benzaldehyde oxime (2.23 g, 10.1 mmol) in DMF at rt was added in one portion N-chlorosuccinimide (1.88 g, 14.1 mmol). After heating with a heat gun for 1 minute, the reaction went from a clear colorless solution to a clear light yellow solution. The reaction was stirred for 78 hours at rt, quenched with 50% sat. aq. NaCl, extracted with ether (3×), dried over MgSO₄, filtered and concentrated. The crude product was azeotroped with xylenes (2×) on the Rotovap to remove DMF and purified by flash chromatography on silica gel (gradient EtOAc/Hexane 0%–70%) to give the title compound contaminated with starting material (1.25 g): ¹H NMR (CDCl₃): δ 7.49–7.41 (m, 2H), 7.12–7.05 (m, 2H), 5.47 (ap q, 4H), 3.93–3.80 (m, 1H), 2.05–1.96 (m, 1H), 1.92–1.85 (m, 2H), 1.75–1.54 (m, 3H).

d) 5-Chloromethyl-3-[4-(tetrahydro-pyran-2-yloxy)-phenyl]-isoxazole

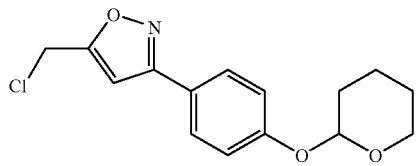

To a solution of 4-(tetrahydro-pyran-2-yloxy)-benzaldehyde chloro-oxime (1.25 g, 4.9 mmol) and 3-chloro-propyne (0.42 mL, 5.9 mmol) in ethyl acetate, DIPEA (1.02 mL, 5.9 mmol) was added slowly at rt, giving a cloudy suspension. The reaction was stirred for 16 hours then quenched with 80% sat. aq. NH₄Cl. After removal of the organic phase, the aqeuous phase was extracted with EtOAc (2×) and the combined organics dried over MgSO₄, filtered and concentrated. The crude product was purified by flash chromatography on silica gel (gradient EtOAc/Hexane 0%–70%) giving the title compound as the only regioisomer (1.10 g): ¹H NMR (CDCl₃): δ7.72 (ap d, J=8.9 Hz, 2H), 7.45 (m, 2H), 7.14–7.07 (m, 2H), 6.58 (s, 1H), 5.50–5.45 (m, 1H), 4.65 (s, 2H), 3.93–3.85 (m, 1H), 3.66–3.60 (m, 1H), 2.07–1.98 (m, 1H), 1.92–1.86 (m, 2H), 1.77–1.59 (m, 3H); TLC (30% EtOAc/Hexane) Rf 0.36.

e) 5-(2-Phenoxy-ethylsulfanylmethyl)-3-[4-(tetrahydro-pyran-2-yloxy)-phenyl]-isoxazole

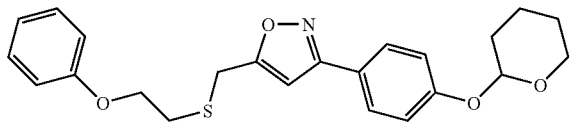

An oven-dried round bottom flask was charged with NaH (60% in mineral oil, 0.13 g, 3.1 mmol), evacuated with a vacuum pump and filled with $N_2$. After dilution with anhydrous THF (10 mL), the flask was set in an ice-water bath and 2-phenoxy-ethanethiol (0.32 g, 2.09 mmol) in THF (5 mL) added slowly by syringe under $N_2$. The reaction was stirred 30 minutes at 0° C., then removed from the bath and stirred 20 minutes at ambient temperature. 5-Chloromethyl-3-[4-(tetrahydro-pyran-2-yloxy)-phenyl]-isoxazole (0.68 g, 2.30 mmol) in THF (10 mL) was added by syringe, causing the reaction to change from colorless to yellow after 30 minutes. The reaction was stirred overnight then quenched with $H_2O$, diluted with hexane and the organic phase removed. The aqueous phase was extracted with EtOAc (2×), the combined organic phases were dried over $MgSO_4$, filtered and concentrated. The crude product was purified by flash chromatography on silica gel (gradient EtOAc/Hexane 10%–50%) to give the title compound (0.51 g): ES-MS 412.1 (M+1), $^1$H NMR (CDCl$_3$): δ 7.70 (ap d, J=8.9 Hz, 2H), 7.31–7.25 (m, 2H), 7.11 (ap d, J=8.9 Hz, 2H), 6.96 (ap t, 1H), 6.90 (ap d, J=8.1 Hz, 2H), 6.44 (s, 1H), 5.49 (t, J=3.3 Hz, 1H), 4.20 (t, J=6.2 Hz, 2H), 3.96 (s, 2H), 3.94–3.86 (m, 1H), 3.66–3.60 (m, 1H), 2.99 (t, J=6.2 Hz, 2H), 2.08–1.98 (m, 1H), 1.92–1.86 (m, 2H), 1.77–1.58 (m, 3H).

f) 4-[5-(2-Phenoxy-ethylsulfanylmethyl)-isoxazol-3-yl]-phenol

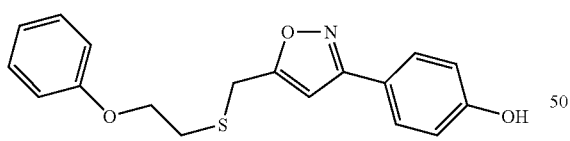

To a mixture of 5-(2-phenoxy-ethylsulfanylmethyl)-3-[4-(tetrahydro-pyran-2-yloxy)-phenyl]-isoxazole (0.51 g, 1.23 mmol) in ethanol was added pyridinium p-toluenesulfonate (0.03 g, 0.12 mmol). A reflux condensor was attached and the reaction stirred in a 50° C. oil bath for 3 hours. The mixture was concentrated and the crude product purified by flash chromatography on silica gel (10% EtOAc/Hexane) to give the title compound as a clear, colorless oil (0.39 g, 97%): ES-MS 328.1 (M+1), $^1$H NMR (CDCl$_3$): δ 7.66 (ap d, J=8.7 Hz, 2H), 7.30–7.25 (m, 2H), 6.99–6.88 (m, 5H), 6.44 (s, 1H), 5.33 (br s, 1H), 4.21 (t, J=6.2 Hz, 2H), 3.96 (s, 2H), 3.00 (t, J=6.2 Hz, 2H).

g) 5-(2-Phenoxy-ethylsulfanylmethyl)-3-[4-(2-pyrrolidin-1-yl-ethoxy)-phenyl]-isoxazole

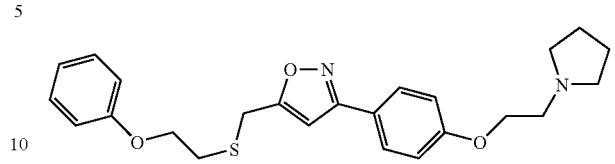

An oven-dried round bottom flask was charged with 4-[5-(2-phenoxy-ethylsulfanylmethyl)-isoxazol-3-yl]-phenol (0.282 g, 0.86 mmol), evacuated with a vacuum pump and filled with $N_2$. Anhydrous DMF (5 mL) was added by syringe and after dissolution of the phenol the reaction was set in an ice-water bath and stirred 5 minutes. NaH (60% in mineral oil, 0.09 g, 2.24 mmol) was added neat. The mixture was stirred 5 minutes at 0° C., then removed from the bath and allowed to warn to rt. 1-(2-Chloro-ethyl)-pyrrolidine hydrochloride (0.176 g, 1.03 mmol) was added neat. A reflux condensor was attached and the mixture stirred 6 hours in a 50° C. oil bath. The reaction was quenched with 50% sat. aq. $NaHCO_3$ and the mixture extracted with EtOAc (3×). The combined organics were washed with brine, dried over $MgSO_4$, filtered and concentrated, then azeotroped with xylenes on the Rotovap (2×) to remove DMF. The crude product was purified by flash chromatography on silica gel (gradient EtOAc/Hexane 30%–85%, 2N $NH_3$ in MeOH/ EtOAc 5%) then crystallized in $CH_2Cl_2$/Ether/Hexane to give the title compound as fine white crystals (0.197 g, 54%): ES–MS 425.1 (M+1), $^1$H NMR (CDCl$_3$): δ 7.69 (ap d, J=8.8 Hz, 2H), 7.30–7.25 (m, 2H), 7.00–6.94 (m, 3H), 6.91–6.88 (m, 2H), 6.44 (s, 1H), 4.22–4.17 (m, 4H), 3.96 (s, 2H), 3.02–2.93 (m, 4H), 2.70 (br s, 4H), 1.88–1.83 (m, 4H). Anal. calcd. for $C_{24}H_{28}N_2O_3S$: C, 67.90; H, 6.65; N, 6.60. Found: C, 67.97; H, 6.61; N, 6.67.

Example 296

Preparation of 4-[5-(2-Phenoxy-ethylsulfanylmethyl)-[1,2,4]oxadiazol-3-yl]-phenol

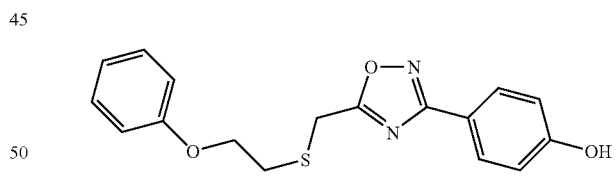

a) 4-(Tetrahydro-pyran-2-yloxy)-benzonitrile

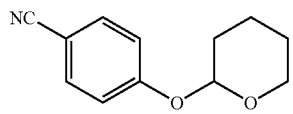

A solution of 4-cyanophenol (2.73 g, 22.9 mmol) in $CH_2Cl_2$ (15 mL) was treated with 3,4-dihydro-2H-pyran (4.19 mL, 45.8 mmol) and pyridinium p-toluenesulfonate (0.57 g, 2.29 mmol). A reflux condensor was attached and the mixture stirred in a 50° C. oil bath for 3 hours. After concentrating on the RotoVap, the crude product was purified by flash chromatography on silica gel (gradient EtOAc/Hexane 0%–50%) to give a clear oil, which crystallized neat to give the title compound as fine white crystals (4.35 g, 93%): $^1$H NMR (CDCl$_3$): δ 7.57 (dt, J=8.7, 2.4 Hz, 2H), 7.10 (dt, J=8.7, 24 Hz, 2H), 5.49 (t, J=3.0 Hz, 1H), 3.85–3.77 (m, 1H), 3.65–3.59 (m, 1H), 2.04–1.92 (m, 1H), 1.90–1.84 (m, 2H), 1.77–1.50 (m, 3H); TLC (30% EtOAc/Hexane) Rf 0.47.

b) N-{Amino-[4-(tetrahydro-pyran-2-yloxy)-phenyl]-methyl}-hydroxylamine

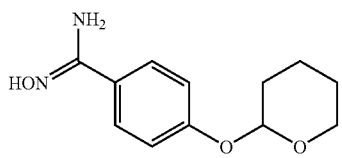

A CEM reaction vial (for microwave reactions) with stir-bar was charged with 4-(tetrahydro-pyran-2-yloxy)-benzonitrile (3.14 g, 15.4 mmol). The nitrile was diluted with anhydrous ethanol (25 mL) and treated with hydroxylamine hydrochloride (1.61 g, 23.2 mmol) and ground NaOH (0.93 g, 23.2 mmol). A septum was attached and the reaction microwaved in the CEM Discover reactor at 80° C. for 40 minutes (cooling on, average power 40 watts). The mixture was concentrated, diluted with H$_2$O, and extracted with EtOAc (3×). The combined organics were washed with brine, dried over MgSO$_4$, filtered and concentrated. The crude product was purified by flash chromatography on silica gel (gradient EtOAc/Hexane 20%–100%) to give the title compound as a white foam (1.89 g, 52%): ES-MS 237.1 (M+1); $^1$H NMR (CDCl$_3$): δ 7.55 (dt, J=8.8, 2.5 Hz, 2H), 7.06 (dt, J=8.8, 2.5 Hz, 2H), 5.46 (t, J=3.0 Hz, 1H), 4.85 (br s, 2H), 3.92–3.85 (m, 1H), 3.65–3.58 (m, 1H), 2.05–1.96 (m, 1H), 1.91–1.85 (m, 2H), 1.76–1.57 (m, 3H).

c) (2-Phenoxy-ethylsulfanyl)-acetyl chloride

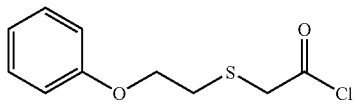

An oven-dried round-bottom flask with stir-bar was charged with (2-phenoxy-ethylsulfanyl)-acetic acid (Maybridge, 5.57 g, 26.2 mmol). The flask was evacuated and filled with N$_2$. Anhydrous CH$_2$Cl$_2$ (20 mL) and DMF (4 drocl) was added by syringe and the flask was set in an ice-water bath. Oxalyl chloride (2M/CH$_2$Cl$_2$, 26.2 mL, 52.4 mmol) was added dropwise by syringe and the reaction stirred for 2 hours while the bath expired. The reaction mixture was concentrated then azeotroped with xylenes (remove DMF) on the RotoVap to give the title compound as a brown oil (6.57 g, 109%). $^1$H NMR (CDCl$_3$): δ 7.32–7.27 (m, 2H), 7.01–6.96 (m, 2H), 6.92–6.88 (m, 2H), 4.23 (t, 15.8 Hz, 2H), 3.91 (s, 2H), 3.05 (t, J=5.8 Hz, 2H).

d) 4-[5-(2-Phenoxy-ethylsulfanylmethyl)-[1,2,4]oxadiazol-3-yl]-phenol

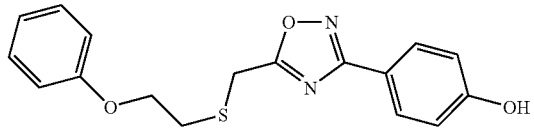

In a CEM reaction vial with stir-bar a solution of N-{Amino-[4-(tetrahydro-pyran-2-yloxy)-phenyl]-methyl}-hydroxylamine (1.52 g, 6.43 mmol) in pyridine was treated with (2-phenoxy-ethylsulfanyl)-acetyl chloride (1.78 g, 7.72 mmol). The reaction was stirred at rt for 15 minutes, then microwaved in the CEM Discover reactor at 65° C. (cooling on) for 20 minutes and 80° C. (cooling on) for 30 minutes. The reaction mixture was transferred to a rb flask, concentrated then azeotroped with heptane on the RotoVap (2×) to remove pyridine. The mixture was dissolved in ethanol, transferred to a CEM reaction vial and treated with pyridinium p-toluenesulfonate (0.16 g, 0.64 mmol). A septum was attached and the reaction microwaved at 55° C. (cooling on) for 10 minutes then 75° C. (cooling on) for 10 minutes. The mixture was concentrated on the RotoVap and purified by flash chromatography on silica gel (gradient EtOAc/Hexane 0–70%) to give the title compound as a clear yellow oil (1.37 g, 65%): ES-MS 329.1 (M+1), $^1$H NMR (CDCl$_3$): δ 7.96 (dt, J=8.9, 2.4 Hz, 2H), 7.30–7.25 (m, 2H), 6.98–6.88 (m, 5H), 5.49 (br s, 1H), 4.24 (t, J=6.2 Hz, 2H), 4.05 (s, 2H), 3.11 (t, J=6.2 Hz, 2H).

Example 297

1-(2-{4-[5-(2-Phenoxy-ethylsulfanylmethyl)-[1,2,4]oxadiazol-3-yl]-phenoxy}-ethyl)-piperidine hydrochloride

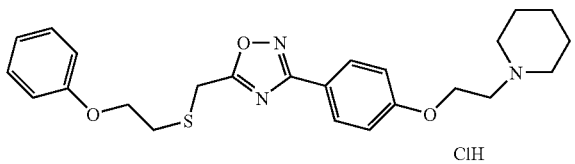

In oven-dried round bottom flask was charged with 4-[5-(2-phenoxy-ethylsulfanylmethyl)-[1,2,4]oxadiazol-3-yl]-phenol (0.258 g, 0.78 mmol), evacuated with a vacuum pump and filled with N$_2$. Anhydrous DMF (5 mL) was added by syringe and after dissolution of the phenol the reaction was set in an ice-water bath. NaH (60% in mineral oil, 0.08 g, 2.0 mmol) was added neat. The mixture was stirred 1 minute at 0° C., removed from the bath and stirred 5 minutes at rt. 1-(2-Chloro-ethyl)-piperidine hydrochloride (0.173 g, 0.94 mmol) was added neat, a reflux condenser was attached and the mixture stirred 1.5 hours in a 50° C. oil bath. The reaction was quenched with 50% sat. aq. NaHCO$_3$ and extracted with EtOAc (3×). The combined organics were washed with brine, dried over MgSO$_4$, filtered and concentrated, then azeotroped with xylenes on the Rotovap (2×) to remove DMF. The crude product was purified by flash chromatography on silica gel (gradient EtOAc/Hexane 30%–85%, 2N NH$_3$ in MeOH/EtOAc 5%) to give the free base as a clear oil. The free base was dissolved in ethanol and treated with 1M HCl/ether to give the title compound as white crystals. ES-MS 440.1 (M+1), $^1$H NMR (DMSO d6): δ 10.56 (s, 1H), 7.94 (dt, J=8.8, 2.4 Hz, 2H), 7.25 (ap t, 2H), 7.16 (dt, J=8.8 Hz, 2.4 Hz, 2H), 6.94–6.89 (m, 3H), 4.49 (t, J=5.0 Hz, 2H), 4.26 (s, 2H), 4.20 (t, J=6.3 Hz, 2H), 3.53–3.45 (m, 4M), 3.06 (t, J=6.3 Hz, 2H), 3.03–2.94 (m, 2H), 1.84–1.76 (m, 4H), 1.69 (m, 1H), 1.44–1.33 (m, 1H). Anal. calcd. for $C_{24}H_{30}ClN_3O_3S$: C, 60.55; H, 6.35; N, 8.83. Found: C, 59.91; H, 5.90; N, 8.57.

Example 298

Dimethyl-(2-{4-[5-(2-phenoxy-ethylsulfanylmethyl)-[1,2,4]oxadiazol-3-yl]-phenoxy}-ethyl)-amine hydrochloride

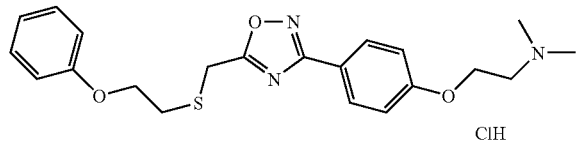

A CEM reaction vessel was charged with NaH (60% in mineral oil, 0.15 g, 3.8 mmol). The vessel was capped with a septum and evacuated by a vacuum pump. DMF (3 mL) was added by syringe, the vessel filled with $N_2$ and set in an ice-water bath. 4-[5-(2-phenoxy-ethylsulfanylmethyl)-[1,2,4]oxadiazol-3-yl]-phenol (0.422 g, 1.28 mmol) in DMF (2 mL) was added dropwise by syringe. The mixture was stirred 5 minutes at 0° C., removed from the bath and stirred 15 minutes at rt. The septum was removed, (2-chloro-ethyl)-dimethyl-amine hydrochloride (0.222 g, 1.54 mmol) was added neat, a new septum cap was attached and the reaction stirred 5 minutes at rt. The reaction was microwaved in the CEM Discover reactor at 70° C. (cooling on) for 20 minutes, then quenched with $H_2O$ and extracted with EtOAc (3×). The combined organics were washed with brine, dried over $MgSO_4$, filtered and concentrated, then azeotroped with xylenes on the Rotovap (2×) to remove DMF. The crude product was purified by flash chromatography on silica gel (gradient EtOAc/Hexane 30%–85%, 2N $NH_3$ in MeOH/EtOAc 5%). The free base was dissolved in ethanol and treated with 1M HCl/ether to give the title compound as white crystals (0.230 g, 41%). ES-MS 400.1 (M+1), $^1H$ NMR (DMSO $d_6$): δ 10.26 (s, 1H), 7.95 (dt, J==8.8, 2.5 Hz, 2H), 7.25 (ap t, 2H), 7.16 (dt, J=8.8 Hz, 2.5 Hz, 2H), 6.94–6.89 (m, 3H), 4.43 (t, J=5.0 Hz, 2H), 4.27 (s, 2H), 4.20 (t, J=6.3 Hz, 2H), 3.52 (t, J=5.0 Hz, 2H), 3.06 (t, J=6.3 Hz, 2H), 2.85 (s, 6H). Anal. calcd. for $C_{21}H_{26}ClN_3O_3S$: C, 57.85; H, 6.01; N, 9.64. Found: C, 57.72; H, 5.90; N, 9.46.

e) 5-(2-Phenoxy-ethylsulfanylmethyl)-3-[4-(2-pyrrolidin-1-yl-ethoxy)-phenyl]-[1,2,4]oxadiazole hydrochloride

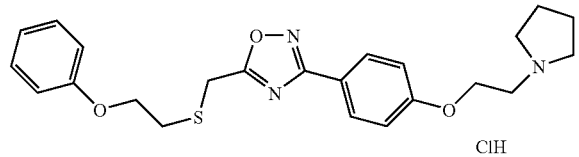

The title compound was synthesized from 4-[5-(2-phenoxy-ethylsulfanylmethyl)-[1,2,4]oxadiazol-3-yl]-phenol using a method similar to that described for dimethyl-(2-{4-[5-(2-phenoxy-ethylsulfanylmethyl)-[1,2,4]oxadiazol-3-yl]-phenoxy}-ethyl)-amine hydrochloride: ES-MS 426.1 (M+1), $^1H$ NMR (DMSO $d_6$): δ 10.39 (s, 1H), 7.95 (dt, J=8.8, 2.5 Hz, 2H), 7.25 (ap t, 2H), 7.15 (dt, J=8.8 Hz, 2.5 Hz, 2H), 6.94–6.89 (m, 3H), 4.40 (t, J=5.0 Hz, 2H), 4.26 (s, 2H), 4.19 (t, J=6.3 Hz, 2H), 3.63–3.54 (m, 4l, 3.16–3.03 (m, 4H), 2.05–1.96 (m, 2H), 1.94–1.83 (m, 2H). Anal. calcd. for $C_{23}H_{28}ClN_3O_3S$: C, 59.79; H, 6.11; N, 9.09. Found: C, 59.55; H, 6.15; N, 8.94.

e) 3-{4-[2-(1-Methyl-pyrrolidin-2-yl)-ethoxy]-phenyl}-5-(2-phenoxy-ethylsulfanylmethyl)-[1,2,4]oxadiazole hydrochloride

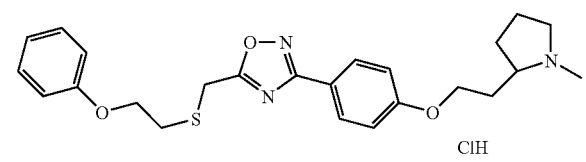

The title compound was synthesized from 4-[5-(2-phenoxy-ethylsulfanylmethyl)-[1,2,4]oxadiazol-3-yl]-phenol using a method similar to that described for dimethyl-(2-{4-[5-(2-phenoxy-ethylsulfanylmethyl)-[1,2,4]oxadiazol-3-yl]-phenoxy}-ethyl)-amine hydrochloride: ES-MS 440.1 (M+1), $^1H$ NMR (DMSO $d_6$): δ 10.69 (m, 1H), 7.91 (ap t, 2H), 7.25 (ap t, 2H), 7.13–7.08 (m, 2H), 6.94–6.88 (m, 3), 4.26 (s, 2H), 4.19 (t, J=6.2 Hz, 2H), 3.48–3.29 (m, 1H), 3.18–2.99 (m, 4H), 2.82–2.73 (m, 3H), 2.46–1.69 (m, 7H).

Example 299

Preparation of 4-[5-(2-Phenoxy-ethylsulfanylmethyl)-isoxazol-3-yl]-N-(2-pyrrolidin-1-yl-ethyl)-benzamide

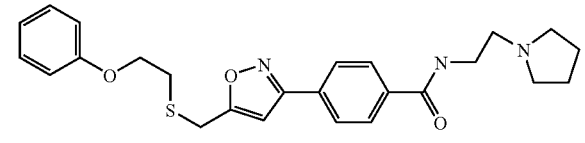

a) 4-Hydroxyaminomethyl-benzoic acid methyl ester

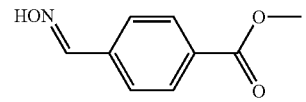

To a solution of 4-formyl-benzoic acid methyl ester (4.18 g, 25.5 mmol) in EtOH was added NaOAc·$3H_2O$ (6.93 g, 50.9 mmol) and hydroxylamine hydrochloride (2.65 g, 38.2 mmol). The mixture was stirred at rt for 1 hour, concentrated on the Rotovap, diluted with $H_2O$, and extracted with EtOAc (3×). The combined organics were dried over $MgSO_4$, filtered and the solvent removed under vacuum to give a white residue as crude (4.02 g, 88%): $^1H$ NMR ($CDCl_3$): δ 8.17 (s, 1H), 8.05 (ap d, J=8.5 Hz, 2H), 7.65 (ap d, J=8.5 Hz, 2H), 3.94 (s, 3H); TLC (20% EtOAc/Hexane) Rf 0.18 b) 4-(Chloro-hydroxyamino-methyl)-benzoic acid methyl ester

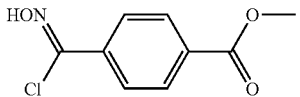

To a solution of 4-hydroxyaminomethyl-benzoic acid methyl ester (4.02 g) in DMF at rt was added in five portions N-chlorosuccinimide (4.24 g, 31.7 mmol). After addition of the first portion, the reaction was heated with a heat gun for 10 seconds, giving a cloudy mixture. The remaining portions were added over 2 minutes. The reaction was stirred for 1 hour at rt, quenched with 70% sat. aq. NaCl, extracted with ether (3×), dried over MgSO$_4$, filtered and concentrated. The crude product was azeotroped with xylenes (2×) to remove residual DMF, giving a white residue as crude product (5.56 g): $^1$H NMR (CDCl$_3$): δ 9.04 (br s, 1H), 8.05 (ap d, J=8.8 Hz, 2H), 7.92 (ap d, J=8.8 Hz, 2H), 3.94 (s, 3H); TLC (20% EtOAc/Hexane) Rf 0.18 c) 4-(5-Chloromethyl-isoxazol-3-yl)-benzoic acid methyl ester

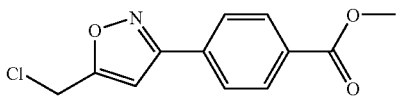

To a solution of 4-(chloro-hydroxyimino-methyl)-benzoic acid methyl ester (1.14 g, 5.35 mmol) and 3-chloro-propyne (0.46 mL, 6.42 mmol) in ethyl acetate TEA (0.89 mL, 6.42 mmol) was added slowly at rt, giving a cloudy mixture. The reaction was stirred for 16 hours then quenched with 75% sat. aq. NH$_4$Cl. After removal of the organic phase, the aqeuous phase was extracted with EtOAc (2×) and the combined organics dried over MgSO$_4$, filtered and concentrated. The crude product was purified by flash chromatography on silica gel (gradient EtOAc/Hexane 0%–80%) giving the title compound as the only regioisomer (0.84 g, 62%). The structure of the regioisomer was confirmed by 1-D NOESY analysis: ES-MS 252.0 (M+1), $^1$H NMR (CDCl$_3$): δ 8.13 (ap d, J=8.7 Hz, 2H), 7.88 (ap d, J=8.7 Hz, 2H), 6.69 (s, 1H), 4.68 (d, J=0.8 Hz, 2H), 3.96 (s, 3H).

d) 4-[5-(2-Phenoxy-ethylsulfanylmethyl)-isoxazol-3-yl]-benzoic acid methyl ester

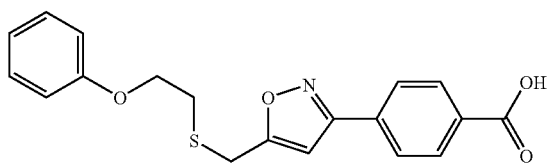

An oven-dried round bottom flask was charged with NaH (60% in mineral oil, 0.10 g, 2.5 mmol), evacuated with a vacuum pump and filled with N$_2$. After dilution with anhydrous THF (10 mL), the reaction was set in an ice-water bath and 2-phenoxy-ethanethiol (0.25 g, 1.6 mmol) in THF (20 mL) added slowly by syringe. The reaction was stirred 30 minutes at 0° C., then removed from bath and allowed to warm to rt. 4-(5-Chloromethyl-isoxazol-3-yl)-benzoic acid methyl ester (0.45 g, 1.8 mmol) in THF (10 mL) was added by syringe, giving a cloudy yellow mixture. The reaction was stirred overnight then neutralized with 0.25 N HCl and extracted with EtOAc (3×). The combined organic phases were dried over MgSO$_4$, filtered and concentrated. The crude product was purified by flash chromatography on silica gel (gradient EtOAc/Hexane 30%–85%, MeOH/EtOAc 5%) to give the methyl ester of the title compound (0.16 g) and the title compound (0.20 g): ES-MS 356.0 (M+1), $^1$H NMR (CDCl$_3$): δ 13.14 (br s, 1H), 8.07–7.93 (m, 5H), 7.29–7.21 (m, 2H), 7.01 (s, 1H), 6.94–6.88 (m, 2H), 4.16 (t, J=6.4 Hz, 2H), 4.11 (s, 2H), 2.96 (t, J=6.4 Hz, 2H).

e) 4-[5-(2-Phenoxy-ethylsulfanylmethyl)-isoxazol-3-yl]-N-(2-pyrrolidin-1-yl-ethyl)-benzamide

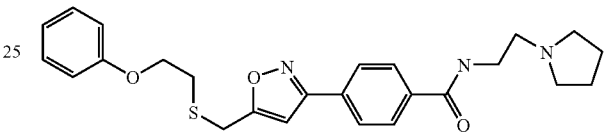

To a mixture of 4-[5-(2-phenoxy-ethylsulfanylmethyl)-isoxazol-3-yl]-benzoic acid (0.20 g, 0.55 mmol) in CH$_2$Cl$_2$ was added neat HOBt (0.11 g, 0.83 mmol), EDCI-HCl (0.16 g, 0.83 mmol), and DIPEA (0.19 mL, 1.11 mmol) at rt. 2-Pyrrolidin-1-yl-ethylamine (0.11 mL, 0.83 mmol) was added by syringe and the reaction stirred 1 hour. The reaction was quenched with 50% sat. aq. NaHCO$_3$ and the organic phase removed. The aqueous phase was extracted with EtOAc (2×) and the combined organics dried over MgSO$_4$, filtered and concentrated. The crude product was purified by radial chromatography on silica gel (gradient EtOAc/Hexane 30%–85%, 2N NH$_3$ in MeOH/EtOAc 5%–20%) then repurified by RP-HPLC to give the TFA salt. The salt was free-based with NaHCO$_3$ and crystallized in CH$_2$Cl$_2$/ether/hexane. The title compound was recovered as fine white crystals (0.029 g): ES-MS 452.3 (M+1), $^1$H NMR (CDCl$_3$): δ 7.91–7.82 (m, 4H), 7.31–7.25 (m, 2H), 6.96 (ap t, J=7.5 Hz, 1H), 6.90 (ap d, J=8.0 Hz, 2H), 6.67 (s, 1H), 4.22 (t, J=6.1 Hz, 2), 3.99 (s, 2H), 3.64 (ap q, 2H), 3.01 (t, J=6.1 Hz, 2H), 2.86 (br s, 2H), 2.74 (br s, 4H), 1.89 (br s, 4H). Anal. calcd. for C$_{25}$H$_{29}$N$_3$O$_3$S: C, 66.49; H, 6.47; N, 9.30. Found: C, 65.04; H, 6.20; N, 9.10.

Example 300

Preparation of Dimethyl-(3-{4-[5-(2-phenoxy-ethylsulfanylmethyl)-[1,3,4]oxadiazol-2-yl]-phenyl}-isoxazol-5-ylmethyl)-amine

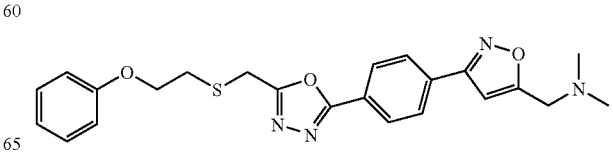

a) 4-(Hydroxyimino-methyl)-benzoic acid methyl ester

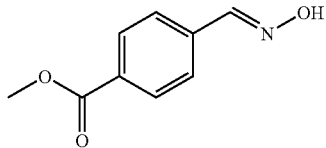

To a solution of 4-Formyl-benzoic acid methyl ester (Aldrich, 4.94 g, 30.1 mmol) in EtOH was added NaOAc[19] 3H$_2$O (8.19 g, 60.2 mmol) and hydroxylamine hydrochloride (3.14 g, 45.1 mmol). The mixture was stirred at rt for 90 minutes, concentrated on the Rotovap, diluted with H$_2$O, and extracted with EtOAc (3×). The combined organics were dried over MgSO$_4$, and the solvent removed under vacuum to give a white residue as crude (5.17 g): $^1$H NMR (CDCl$_3$): δ 8.17 (s, 1H), 8.06 (ap d, J=8.4 Hz, 2), 7.85 (br s, 1H), 7.65 (ap d, J=8.4 Hz, 2H), 3.93 (s, 3H).

b) 4-(Chloro-hydroxyimino-methyl)-benzoic acid methyl ester

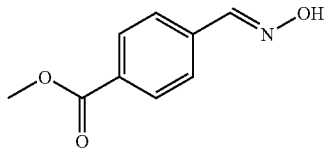

To a solution of 4-(Hydroxyimino-methyl)-benzoic acid methyl ester (5.17 g, 28.8 mmol) in DMF at rt was added in two portions N-chlorosuccinimide (4.24 g, 31.7 mmol). After addition of first portion, the reaction was heated with a heat gun for 10 seconds to give a cloudy mixture. The remaining portion was added and reaction became hotter (exotherm) for several minutes then slowly cooled. The reaction was stirred for 15 minutes at rt, quenched with 50% sat. aq. NaCl, extracted with ether (3×), dried over MgSO$_4$, filtered and concentrated. The crude product was azeotroped with xylenes (2×) to remove DMF, giving a white residue as the title compound (7.17 g): ES-MS 195.1 (M+1), $^1$H NMR (CDCl$_3$): δ 9.10 (s, 1H), 8.06 (ap d, J=8.5 Hz, 2H), 7.93 (ap d, J=8.4 Hz, 2H), 3.93 (s, 3H).

c) 4-(5-Diethoxymethyl-isoxazol-3-yl)-benzoic acid methyl ester

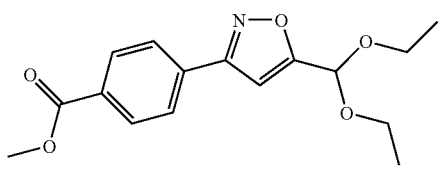

To a solution of 4-(Chloro-hydroxyimino-methyl)-benzoic acid methyl ester (7.17 g, 28.8 mmol) and 3,3-diethoxy-propyne (4.95 mL, 34.6 mmol) in ethyl acetate, TEA (4.82 mL, 34.6 mmol) was added slowly over 20 minutes at rt, giving a thick suspension. The reaction was stirred for 16 hours then quenched with H$_2$O. After removal of the organic phase, the aqeuous phase was extracted with CH$_2$Cl$_2$ (2×) and the combined organics dried over MgSO$_4$, filtered and concentrated. The crude product was purified by flash chromatography on silica gel (gradient EtOAc/Hexane 10%–85%, 5% MeOH/EtOAc) giving the title compound (4.26 g): ES-MS 306.2 (M+1), $^1$H NMR (CDCl$_3$): δ 8.12 (ap d, 2H), 7.89 (ap d, 2H), 6.71 (s, 1H), 5.69 (s, 1H), 3.69 (m, 4H), 1.28 (t, J=7.0 Hz, 6H).

d) 4-(5-Diethoxymethyl-isoxazol-3-yl)-benzoic acid hydrazide

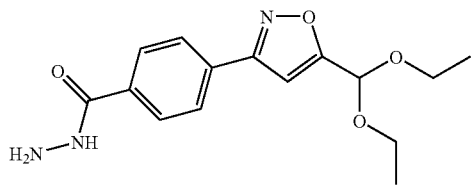

4-(5-Diethoxymethyl-isoxazol-3-yl)-benzoic acid methyl ester (4.26 g, 13.9 mmol) was diluted with isopropanol (25 mL) and hydrazine (2.0 mL, 70 mmol) was added by syringe under N$_2$. The mixture was refluxed in a 100° C. oil bath for 16 hours. The reaction was concentrated, then diluted with CH$_2$Cl$_2$ and concentrated (2×) on Rotovap, then placed on high vacuum for 2 hours, giving the title compound as a thick oil (4.24 g): $^1$H NMR (DMSO-d$_6$): δ 9.88 (br s, 1H), 7.95 (m, 4H), 7.14 (s, 1H), 5.80 (s, 1H), 3.63 (q, J=7.1 Hz, 4H), 3.32 (br s, 2H), 1.19 (t, J=7.1 Hz, 6H).

e) 4-(5-Diethoxymethyl-isoxazol-3-yl)-benzoic acid N'-[2-(2-phenoxy-ethylsulfanyl)-acetyl]-hydrazide

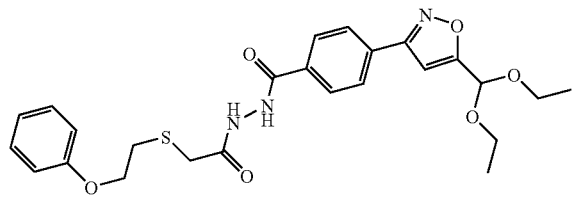

A mixture of (2-phenoxy-ethylsulfanyl)-acetic acid (Maybridge, 2.95 g, 13.9 mmol) and N,N'-carbonyldiimidazole (2.25 g, 13.9 mmol) in THF/MeCN 1:1 (15 mL) was heated at 60° C. for one hour, then allowed to cool to rt. 4-(5-Diethoxymethyl-isoxazol-3-yl)-benzoic acid hydrazide (4.24 g, 13.9 mmol) was added in one portion and the mixture stirred at rt under N$_2$ for 16 hours, then stirred at 50° C. for 4 hours. The reaction was poured into H$_2$O and extracted with EtOAc (1×) and CH$_2$Cl$_2$ (2×). The combined organics were dried over MgSO$_4$, filtered and concentrated. The crude product was purified by flash chromatography on silica gel (gradient EtOAc/Hexane 10%–85%, MeOH/EtOAc 5%–10%) to give the title compound (2.75 g): ES-MS 500.2 (M+1), $^1$H NMR (CDCl$_3$): δ 9.54 (ap d, 1H), 9.06 (ap t, 1H), 7.84 (m, 4H), 7.30–7.23 (m, 2H), 6.98–6.87 (m, 3H), 6.69 (s, 1H), 5.69 (s, 1H), 4.25 (t, J=5.8 Hz, 2H), 3.69 (m, 4H), 3.51 (s, 2H), 3.10 (t, J=5.8 Hz, 2H), 1.29 (t, J=7.0 Hz, 6H).

f) 2-[4-(5-Diethoxymethyl-isoxazol-3-yl)-phenyl]-5-(2-phenoxy-ethylsulfanylmethyl)-[1,3,4]oxadiazole

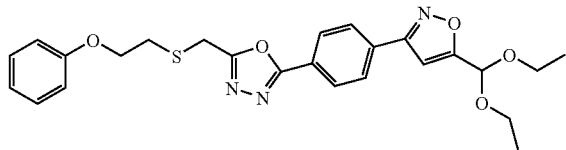

A mixture of 4-(5-diethoxymethyl-isoxazol-3-yl)-benzoic acid N'-[2-(2-phenoxy-ethylsulfanyl)-acetyl]-hydrazide (2.75 g, 5.5 mmol), triphenylphosphine (1.73 g, 6.6 mmol), and TEA (2.67 mL, 19.3 mmol) in THF was treated with carbon tetrabromide (2.19 g, 19.3 mmol) and stirred at rt under $N_2$. After 1 hour, the reaction was heated to 50° C. and stirred 3 hours. The reaction was removed from heat and additional triphenylphosphine (0.29 g, 1.1 mmol) and carbon tetrabromide (0.36 g, 1.1 mmol) was added, then returned to heat and stirred for 16 hours. The mixture was concentrated, neutralized with sat. aq. $NH_4Cl$ and extracted with EtOAc (3×), dried over $MgSO_4$, filtered and concentrated. The resulting crude was purified by flash chromatography on silica gel (gradient $CH_2Cl_2$/Hexane 50%–100%, MeOH/$CH_2Cl_2$ 2%–110%) then repurified (gradient EtOAc/Hexane 10%–50%) to give the title compound as an off-white residue (0.80 g): ES-MS 482.2 (M+1), $^1$H NMR ($CDCl_3$): δ 8.12 (ap d, J=8.5 Hz, 2H), 7.96 (ap d, J=8.5 Hz, 2H), 7.29–7.25 (m, 2H), 6.98–6.88 (m, 3H), 6.73 (s, 1H), 5.72 (s, 1H), 4.23 (t, J=6.1 Hz, 2H), 4.09 (s, 2H), 3.70 (m, 4H), 3.08 (t, J=6.1 Hz, 2H), 1.30 (t, J=7.0 Hz, 6H).

g) 3-{4-[5-(2-Phenoxy-ethylsulfanylmethyl)-[1,3,4]oxadiazol-2-yl]-phenyl}-isoxazole-5-carbaldehyde

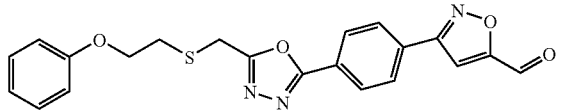

To a solution of 2-[4-(5-diethoxymethyl-isoxazol-3-yl)-phenyl]-5-(2-phenoxy-ethylsulfanylmethyl)-[1,3,4]oxadiazole (0.80 g, 1.7 mmol) in acetic acid/$H_2O$ (4:1, 25 mL) was added slowly 1 N aq. HCl (3 mL), giving a thick suspension. The mixture was stirred 5 minutes at rt, concentrated, diluted with acetone and concentrated (2×), then placed on high vacuum to give the title compound: ES-MS 482.2 (M+33 consistent with aldehyde), $^1$H NMR ($CDCl_3$): δ 10.06 (s, 1), 8.16 (ap d, J=8.4 Hz, 2H), 7.98 (ap d, J=8.4 Hz, 2H), 7.35 (s, 1H), 7.30–7.24 (m, 2H), 6.98–6.87 (m, 3H), 4.23 (t, J=6.2 Hz, 2H), 4.10 (s, 2H), 3.08 (t, J=6.2 Hz, 2H).

h) Dimethyl-(3-{4-[5-(2-phenoxy-ethylsulfanylmethyl)-[1,3,4]oxadiazol-2-yl]-phenyl}-isoxazol-5-ylmethyl)-amine

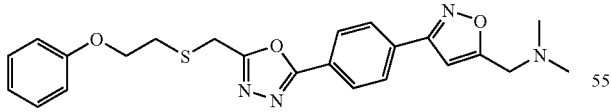

To a solution of 3-{4-[5-(2-phenoxy-ethylsulfanylmethyl)-[1,3,4]oxadiazol-2-yl]-phenyl}-isoxazole-5-carbaldehyde (0.14 g, 0.34 mmol) in 1,2-dichloroethane was added dimethylamine (2 M/MeOH, 0.7 mL, 1.37 mmol) and finely ground $NaBH(OAc)_3$ (0.15 g, 0.69 mmol). The reaction was stirred 16 hours at rt, then heated to 60° C. and stirred 2 hours. Additional $NaBH(OAc)_3$ (0.08 g, 0.35 mmol) was added and the reaction stirred at 60° C. for 16 hours, then stirred at rt for 6 days. The reaction was quenched with $H_2O$ and extracted with $CH_2Cl_2$ (2×) and EtOAc (1×), dried over $MgSO_4$, filtered and concentrated. The crude product was purified by radial chromatography on silical gel (gradient EtOAc/Hexane 20%–85%), then crystallized in $CH_2Cl_2$/ether/hexane to give the title compound as fine, off-white crystals: ES-MS 437.2 (M+1), $^1$H NMR ($CDCl_3$): δ 8.12 (ap d, J=8.3 Hz, 2H), 7.94 (ap d, J=8.4 Hz, 2), 7.29–7.25 (m, 2H), 6.95 (ap t, J=7.4 Hz, 1H), 6.90 (ap d, J=8.3 Hz, 2H), 6.57 (s, 1H), 4.23 (t, J=6.0 Hz, 2H), 4.09 (s, 2H), 3.71 (s, 2H), 3.08 (t, J=6.0 Hz, 2H), 2.38 (s, 6H). Anal. calcd. for $C_{23}H_{24}N_4O_3S$: C, 63.28; H, 5.54; N, 12.83; O, 11.00; S, 7.35. Found: C, 62.95; H, 5.49; N, 12.70, O, 11.20; S, 7.60.

Example 301

Preparation of 3-{4-[5-(2-Phenoxy-ethylsulfanylmethyl)-[1,3,4]oxadiazol-2-yl]-phenyl}-propenal

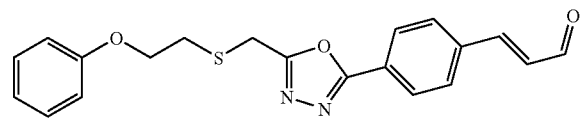

a) 4-(1-Hydroxy-allyl)-benzoic acid methyl ester

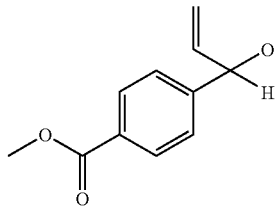

To a solution of 4-Formyl-benzoic acid methyl ester (Aldrich) (15.0 g, 91.40 mM) in 300 mL of THF at −78° C. was added vinyl Grignard (Aldrich)(95.94 mL of a 1.0 molar solution in THF, 95.94 mM) dropwise via an addition funnel. The mixture was stirred at −78° C. for 3 h then warmed to RT and stirred for 18 h. The excess Grignard was quenched with 100 mL of sat $NH_4Cl$ and diluted with 300 mL of methylene chloride and extracted three times with methylene chloride, one time with ethyl acetate and the combined organics were dried over $MgSO_4$. The material was filtered through paper and concentrated to a yellow liquid. The material was applied to a 65 mm Biotage flash columb and eluted with a gradient of 1 L hexanes, 2 L 10% EtOAc in hexanes, 3 L 20% EtOAc in hexanes and 2 L 30% EtOAc in hexanes which upon concentrating provided 9.72 g of the 4-(1-Hydroxy-allyl)-benzoic acid methyl ester as a yellow liquid. $^1$H NMR ($CDCl_3$, 300 MHz): δ 8.10 (d, 2H, J=8.1 Hz), 7.54 (d, 2H, J=8.1 Hz), 6.11 (ddd, 1H, J=18.0, 9.0, 6.6 Hz), 5.29–5.50 (m, 2H), 4.01 (s, 3H), 2.40 (s, 1H). TLC (50% EtOAC/50% Hexanes) $R_f$ 0.49.

b) 4-(1-Acetoxy-allyl)-benzoic acid methyl ester

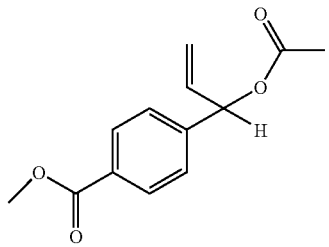

To a solution of 4-(1-Hydroxy-allyl)-benzoic acid methyl ester (2.3 g, 11.9 mM) in 36 m L of $CH_2Cl_2$ at rt was added pyridine (6 mL, 74 mmol), acetic anhydride (Aldrich)(3 mL, 32.0 mM) dropwise via a syringe and N,N-Dimethyl amino pyridine (20 mg, 0.16 mmol). The mixture was stirred at rt for 18 h. The material was diluted with 100 mL of methylene chloride and extracted three times with methylene chloride, one time with ethyl acetate and the combined organics were dried over MgSO$_4$. The material was filtered through paper and concentrated to a yellow liquid. The material was applied to a 40 mm Biotage flash column and eluted with a gradient of 1 L hexanes, 1 L 10% EtOAc in hexanes, 2 L 20% EtOAc in hexanes and 1 L 30% EtOAc in hexanes which upon concentrating provided 2.7 g of the 4-(1-Acetoxy-allyl)-benzoic acid methyl ester as a yellow liquid. $^1$H NMR (CDCl$_3$, 300 MHz): δ 8.03 (d, 2H, J=8.0 Hz), 7.42 (d, 2H, J=8.0 Hz), 6.32 (d, 1H, J=6.8 Hz), 6.0 (ddd, 1H, J=15.6, 8.3, 5.9 Hz), 5.25–5.38 (m, 2H), 5.95 (s, 3H), 2.37 (s, 3). TLC (50% EtOAC/50% Hexanes) R$_f$ 0.60.

c) 4-(1-Acetoxy-allyl)-benzoic acid methyl ester

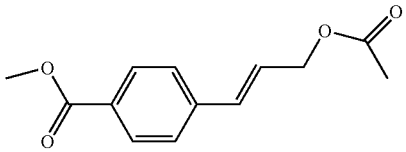

A solution of 4-(1-Hydroxy-allyl)-benzoic acid methyl ester (11.83 g, 50.73 mM) in THF (150 mL) was treated with Bis(benzonitrile)dichloropalladium(II) (329 mg, 1.26 mM) at room temperature and stirred for 19 h. The material was poured through a plug of Celite 2 cm and silica 2 cm., concentrated and the crude yellow liquid solid was used directly (12 g).

1H NMR (CDCl$_3$, 300 MHz): δ 8.02 (d, 2H, J=7.2 Hz), 7.46 (d, 2H, J=7.2 Hz), 6.70 (d, 1H, J=15 Hz), 6.41 (dt, 1H, J=15, 7.0 Hz), 4.78 (dd, 2H, J=6.8, 0.5 Hz), 3.93 (s, 3H), 2.14 (s, 3H). TLC (50% EtOAC/50% Hexanes) R$_f$ 0.60.

d) 4-(3-Hydroxy-propenyl)-benzoic acid methyl ester

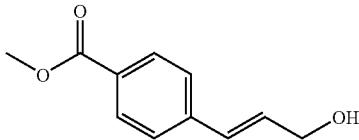

To a solution of 4-(3-acetoxy-propenyl)-benzoic acid methyl ester (6.85 g, 20.5 mmol) in MeOH was added p-toluenesulfonic acid monohydrate (0.55 g, 2.92 mmol). The mixture was stirred at 60° C. for 16 hours, concentrated on the Rotovap, neutralized with sat aq. NaHCO$_3$, and extracted with EtOAc (3×). The combined organics were washed with brine, dried over MgSO$_4$, and the solvent removed under vacuum to give a white residue as crude (5.34 g).

ES-MS 193.1 (M+1), $^1$H NMR (CDCl$_3$): δ 7.98 (ap d, J=8.4 Hz, 2H), 7.44 (ap d, J=8.4 Hz, 2H), 6.67 (ap d, J=15.9 Hz, 1H), 6.48 (dt, J=15.9, 5.9 Hz, 1H), 4.37 (t, J=5.1 Hz, 2H), 3.91 (s, 3H), 1.52 (ap t, 1H).

e) 4-[3-(tert-Butyl-diphenyl-silanyloxy)-propenyl]-benzoic acid methyl ester

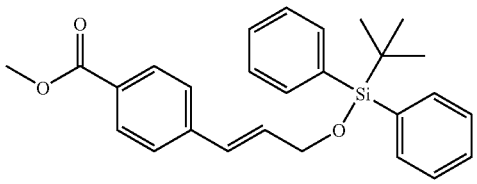

To a solution of 4-(3-hydroxy-propenyl)-benzoic acid methyl ester (5.85 g, 30.44 mmol) in DMF (60 mL) was added imidazole (4.14 g, 60.9 mmol) and t-butyl-chlorodiphenylsilane (8.7 mL, 33.5 mmol). The mixture was stirred at rt for 1 hour and poured into 80% sat. aq. NH$_4$Cl (60 mL) and extracted with ether (3×). The combined organics were dried over MgSO$_4$, filtered and concentrated under vacuuum. The product was azeotroped with xylenes on the Rotovap to remove residual DMF, giving the title compound (14.76 g) as crude, which was used in the next step without further purification: $^1$H NMR (CDCl$_3$): δ 7.98 (ap d, J=8.4 Hz, 2H), 7.73–7.69 (m, 4H), 7.44–7.36 (m, 8H), 6.71 (ap d, J=16.0 Hz, 1H), 6.39 (dt J=16.0, 4.5 Hz, 1H), 4.40 (dd, J=4.5, 1.9 Hz, 2H), 3.92 (s, 3H), 1.11 (s, 9H); TLC (30% EtOAc/Hexane) Rf 0.56.

f) 4-[3-(tert-Butyl-diphenyl-silanyloxy)-propenyl]-benzoic acid

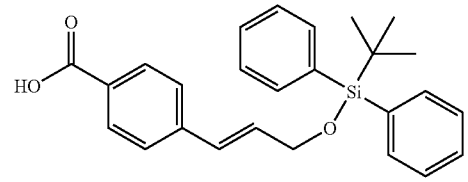

4-[3-(tert-Butyl-diphenyl-silanyloxy)-propenyl]-benzoic acid methyl ester (17.49 g, 40.6 mmol) was diluted with ethanol (50 mL) and stirred for 10 minutes, then treated with 1.7 N NaOH (60 mL) and stirred at 45° C. for 4 hours, then 50° C. for 30 minutes. The mixture was concentrated, neutralized with 5 N HCl to pH 7 and 1 N HCl to pH 3, and extracted with EtOAc (3×). The combined organics were washed with brine, dried over MgSO$_4$, filtered and concentrated. The resulting crude was crystallized in MeOH/CH$_2$Cl$_2$/ether/hexane to remove desilylated byproduct. The supernatant was concentrated and purified by flash chromatography on silica gel (gradient EtOAc/hexane 10%–100%) to give the title compound (9.52 g): $^1$H NMR (CDCl$_3$): δ 8.06 (ap d, J=8.4 Hz, 2H), 7.71 (m, 4H), 7.47–7.37 (m, 8H), 6.73 (ap d, J=15.9 Hz, 1H), 6.42 (dt, J=15.9, 4.6 Hz, 1H), 4.41 (dd, J=4.6, 1.8 Hz, 2H), 1.11 (s, 9H).

g) 4-[3-(tert-Butyl-diphenyl-silanyloxy)-propenyl]-benzoic acid hydrazide

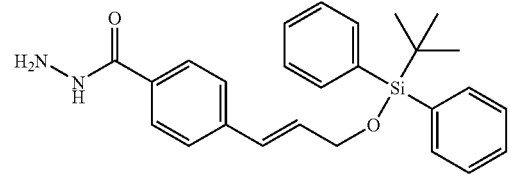

A solution of 4-[3-(tert-butyl-diphenyl-silanyloxy)-propenyl]-benzoic acid (9.52 g, 22.8 mmol) in THF/MeCN 1:1 (100 mL) was treated with N,N'-carbonyldiimidazole (3.89 g, 24.0 mmol) and heated at 60° C. for one hour. After cooling to rt, hydrazine (0.73 mL, 25.0 mmol) was added by syringe. The mixture was stirred for 1 hour at rt, concentrated, diluted with 75% sat. aq. NH$_4$Cl, and extracted with EtOAc (3×). The combined organics were washed with brine, dried over MgSO$_4$, filtered, and the solvent removed under vacuum to give the title compound (10.96 g) as crude, which was used in the next step without further purification: $^1$H NMR (CDCl$_3$): δ 7.70 (m, 6H), 7.44–7.36 (m, 8H), 7.14 (s, 1H), 6.69 (ap d, J=15.9 Hz, 1H), 6.37 (dt, J=15.9, 4.6 Hz, 1H), 4.40 (dd, J=4.6, 1.8 Hz, 2H), 1.11 (s, 9H).

h) 4-[3-(tert-Butyl-diphenyl-silanyloxy)-propenyl]-benzoic acid N-[2-(2-phenoxy-ethylsulfanyl)-acetyl]-hydrazide

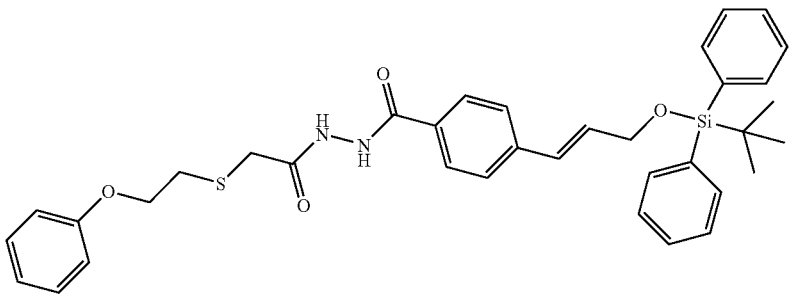

A solution of (2-phenoxy-ethylsulfanyl)-acetic acid (Maybridge, 4.84 g, 22.8 mmol) in THF/MeCN 1:1 (60 mL) was treated with N,N'-carbonyldiimidazole (3.88 g, 23.9 mmol) then heated at 60° C. for one hour. After cooling to rt, 4-[3-(tert-Butyl-diphenyl-silanyloxy)-propenyl]-benzoic acid hydrazide (10.96 g, 22.8 mmol) was added neat. The mixture was stirred for 2 hours at rt, concentrated, diluted with 75% sat. aq. NH₄Cl, and extracted with EtOAc (3×). The combined organics were washed with brine, dried over MgSO₄, filtered, and concentrated. The crude oil was purified by flash chromatography on silica gel (gradient EtOAc/Hexane 10%–50%) to give the title compound (12.09 g): ES-MS 625.4 (M+1); ¹H NMR (CDCl₃): δ 9.42 (d, J=5.8 Hz, 1H), 8.59 (d, J=5.8 Hz, 1H), 7.70 (m, 6H), 7.44–7.36 (m, 8H), 7.29–7.24 (m, 2H), 6.96–6.90 (m, 3H), 6.69 (ap d, J=15.9 Hz, 1H), 6.38 (dt, J=15.9, 4.6 Hz, 1H), 4.40 (dd, J=4.7, 1.8 Hz, 2H), 4.26 (t, J=5.9 Hz, 2H), 3.51 (s, 2H), 3.10 (t, J=5.9 Hz, 2H), 1.11 (s, 9H).

i) 2-{4-[3-(tert-Butyl-diphenyl-silanyloxy)-propenyl]-phenyl}-5-(2-phenoxy-ethylsulfanylmethyl)-[1,3,4]oxadiazole

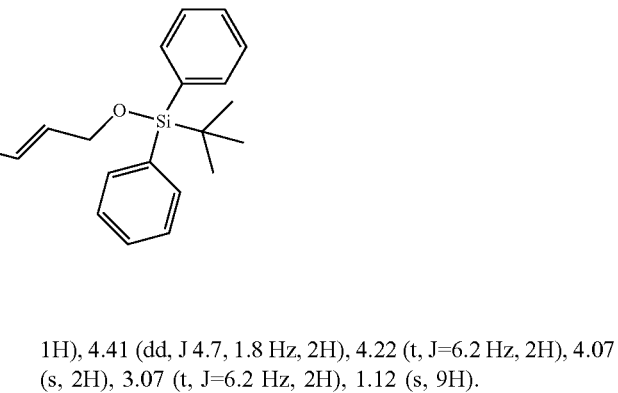

To a mixture of 4-[3-(tert-Butyl-diphenyl-silanyloxy)-propenyl]-benzoic acid N'-[2-(2-phenoxy-ethylsulfanyl)-acetyl]-hydrazide (12.09 g, 19.3 mmol) and 2-chloro-1,3-dimethyl-2-imidazolinium hexafluorophosphate (5.66 g, 20.3 mmol) in anhydrous CH₂Cl₂ was slowly added DIPEA (7.4 mL, 42.6 mmol) by syringe. The mixture was stirred at rt for 72 hours, then quenched with 80% sat aq. NH₄Cl (120 mL). The organic phase was removed and the aqueous phase extracted with CH₂Cl₂ (1×) and EtOAc (1×). The combined organic phases were dried over MgSO₄, filtered and concentrated. The crude oil was purified by flash chromatography on silica gel (gradient EtOAc/Hexane 10%–50%) to give the title compound (9.09 g): ES-MS 607.4 (M+1); ¹H NMR (CDCl₃): δ 7.97 (ap d, J=8.4 Hz, 2H), 7.71 (m, 4H), 7.48–7.37 (m, 8H), 7.30–7.25 (m, 2H), 6.95 (ap t, 1H), 6.90 (m, 2H), 6.71 (ap d, J=15.9 Hz, 1H), 6.40 (dt, J=15.9, 4.6 Hz, 1H), 4.41 (dd, J 4.7, 1.8 Hz, 2H), 4.22 (t, J=6.2 Hz, 2H), 4.07 (s, 2H), 3.07 (t, J=6.2 Hz, 2H), 1.12 (s, 9H).

j) 3-{4-[5-(2-Phenoxy-ethylsulfanylmethyl)-[1,3,4]oxadiazol-2-yl]-phenyl}-prop-2-en-1-ol

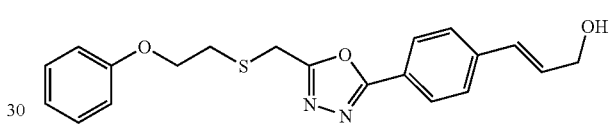

2-{4-[3-(tert-Butyl-diphenyl-silanyloxy)-propenyl]-phenyl}-5-(2-phenoxy-ethylsulfanylmethyl)-[1,3,4]oxadiazole (9.09 g, 15.0 mmol) in anhydrous THF (100 mL) was treated with tetrabutylammonium flouride (1M/THF, 18.7 mL, 18.7 mmol). The reaction was stirred at rt for 2.5 hours, then poured into water (80 mL). Hexane (25 mL) was added, the organic phase removed, and the aqueous phase extracted with EtOAc (2×). The combined organics were washed with brine, dried over MgSO₄, filtered and concentrated. The resulting oil was purified by flash chromatography on silica gel (gradient EtOAc/Hexane 10%–60%) to give the title compound (4.25 g) as a white residue: ES-MS 369.1 (M+1); ¹H NMR (CDCl₃): δ 7.98 (ap d, J=8.4 Hz, 2H), 7.50 (ap d, J=8.4 Hz, 2H), 7.29–7.24 (m, 2H), 6.97–6.88 (m, 3H), 6.68 (ap d, J=15.9 Hz, 1H), 6.50 (dt, J=15.9, 4.6 Hz, 1H), 4.39 (dd, J=5.3, 1.6 Hz, 2H), 4.22 (t, J=6.1 Hz, 2H), 4.06 (s, 2H), 3.07 (t, J=6.2 Hz, 2H).

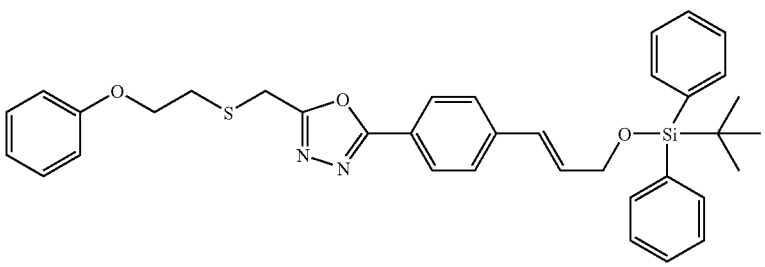

k) 3-{4-[5-(2-Phenoxy-ethylsulfanylmethyl)-[1,3,4]oxadiazol-2-yl]-phenyl}-propenal

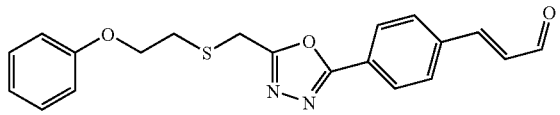

In an oven-dried round-bottom flask, a mixture of anhydrous $CH_2Cl_2$ (20 mL) and oxalyl chloride (2M/$CH_2Cl_2$, 3.93 mL, 7.86 mmol) was chilled to −78° C. in a dry ice/acetone bath and treated with DMSO (1.50 mL, 21.4 mmol) by slow addition with syringe. The mixture was stirred 20 minutes and 3-{4-[5-(2-phenoxy-ethylsulfanylmethyl)-[1,3,4]oxadiazol-2-yl]-phenyl}-prop-2-en-1-ol (2.63 g, 7.14 mmol) in $CH_2Cl_2$ (60 mL) was added slowly by syringe. The mixture was stirred 45 minutes at −78° C. and DIPEA (6.2 mL, 35.7 mmol) was added slowly by syringe. The mixture was stirred an additional 30 minutes, removed from bath and stirred 2 hours as it warmed to room temperature (rt). The reaction was neutralized with sat. aq. $NH_4Cl$ (75 mL) and the organic layer removed. The aqueous phase was extracted with $CH_2Cl_2$ (1×) and EtOAc (1×), dried over $MgSO_4$, filtered and concentrated. The crude product was purified by chromatography on silica gel (gradient EtOAc/Hexane 10%–85%) to give the title compound (2.43 g): ES-MS 367.1 (M+1); $^1H$ NMR ($CDCl_3$): δ 9.76 (d, J=7.7 Hz, 1H), 8.09 (ap d, J=8.4 Hz, 2H), 7.69 (ap d, J=8.4 Hz, 2H), 7.51 (d, J=16.0 Hz, 1H), 7.29–7.24 (m, 2H), 6.98–6.88 (m, 3H), 6.80 (dd, J=16.0, 7.5 Hz, 1H), 4.23 (t, J=6.1 Hz, 2H), 4.09 (s, 2H), 3.08 (t, J=6.1 Hz, 2H).

Example 302

Ethyl-isopropyl-(3-{4-[5-(2-phenoxy-ethylsulfanylmethyl)-[1,3,4]oxadiazol-2-yl]-phenyl}-allyl)-amine

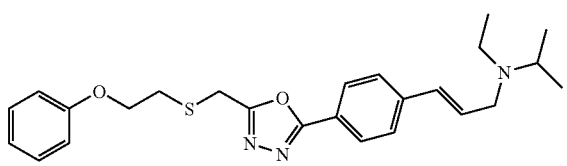

To a solution of 3-{4-[5-(2-Phenoxy-ethylsulfanylmethyl)-[1,3,4]oxadiazol-2-yl]-phenyl}-propenal (0.282 g, 0.77 mmol) in 1,2-dichloroethane was added ethyl-isopropyl-amine (0.11 mL, 0.92 mmol) and finely ground NaBH(OAc)$_3$ (0.20 g, 0.92 mmol). The reaction was stirred 2 hours at rt, quenched with $H_2O$ and the organic phase removed and passed through a $Na_2SO_4$ drying tube. The aqueous phase was extracted with EtOAc (2×), the organic phases dried in the same manner and the combined organics concentrated. The crude product was purified by flash chromatography on silica gel (gradient EtOAc/Hexane 50%–85%, 2N $NH_3$ in MeOH/EtOAc 15%), then crystallized in $CH_2Cl_2$/ether/hexane to give the title compound as fine, white crystals (0.125 g): ES-MS 438.2 (M+1), $^1H$ NMR ($CDCl_3$): δ 7.96 (ap d, J=8.4 Hz, 2H), 7.48 (ap d, J=8.4 Hz, 2H), 7.29–7.25 (m, 2H), 6.98–6.88 (m, 3H), 6.57 (d, J=16.0 Hz, 1H), 6.45–6.37 (m, 1H), 4.22 (t, J=6.2 Hz, 2H), 4.06 (s, 2H), 3.28 (d, J=5.9 Hz, 2H), 3.06 (t, J=6.2 Hz, 2H), 2.55 (ap q, 2H), 1.11–1.02 (m, 9H). Anal. calcd. for $C_{23}H_{24}N_4O_3S_1$: C, 68.62; H, 7.14; N, 9.60. Found: C, 68.44; H, 7.05; N, 9.55.

Example 303

Diethyl-(3-{4-[5-(2-phenoxy-elthylsulfanylmethyl)-[1,3,4]oxadiazol-2-yl]-phenyl}-allyl)-amine

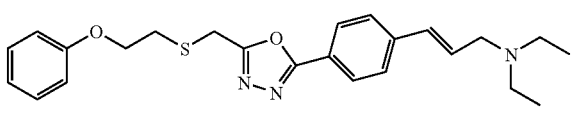

The title compound was synthesized from 3-{4-[5-(2-phenoxy-ethylsulfanylmethyl)-[1,3,4]oxadiazol-2-yl]-phenyl}-propenal using a method similar to that described for ethyl-isopropyl-(3-{4-[5-(2-phenoxy-ethylsulfanylmethyl)-[1,3,4]oxadiazol-2-yl]-phenyl}-allyl)-amine: ES-MS 424.2 (M+1), $^1H$ NMR ($CDCl_3$): δ 7.97 (ap d, J=8.4 Hz, 2H), 7.48 (ap d, J=8.4 Hz, 2H), 7.29–7.25 (m, 2H), 6.97–6.88 (m, 3H), 6.57 (d, J=16.0 Hz, 1H), 6.48–6.39 (m, 1H), 4.22 (t, J=6.0 Hz, 2H), 4.06 (s, 2), 3.30 (d, J=6.0 Hz, 2H), 3.07 (t, J=6.0 Hz, 2), 2.61 (q, J=7.1 Hz, 4H), 1.09 (t, J=7.1 Hz, 6H). Anal. calcd. for $C_{24}H_{29}N_3O_2S$: C, 68.05; H, 6.90; N, 9.92. Found: C, 67.94; H, 6.88; N, 9.73.

Example 304

1-(3-{4-[5-(2-Phenoxy-ethylsulfanylmethyl)-[1,3,4]oxadiazol-2-yl]-phenyl}-allyl)-piperidine

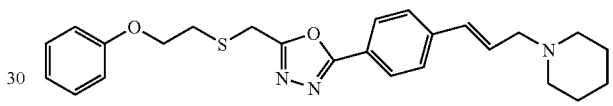

The title compound was synthesized from 3-{4-[5-(2-phenoxy-ethylsulfanylmethyl)-[1,3,4]oxadiazol-2-yl]-phenyl}-propenal using a method similar to that described for Ethyl-isopropyl-(3-{4-[5-(2-phenoxy-ethylsulfanylmethyl)-[1,3,4]oxadiazol-2-yl]-phenyl}-allyl)-amine: ES-MS 436.2 (M+1), $^1H$ NMR ($CDCl_3$): δ 7.96 (ap d, J=8.4 Hz, 2H), 7.48 (ap d, J=8.4 Hz, 2H), 7.29–7.24 (m, 2H), 6.95 (ap t, 1H), 6.90 (ap d, 2H), 6.57 (d, J=16.0 Hz, 1H), 6.48–6.41 (m, 1H), 4.22 (t, J=6.1 Hz, 2H), 4.06 (s, 2H), 3.17 (d, J=6.1 Hz, 2H), 3.07 (t, J=6.1 Hz, 2H), 2.47 (br s, 4H), 1.64 (m, 4H), 1.58 (br s, 2H). Anal. calcd. for $C_{25}H_{29}N_3O_2S$: C, 68.93; H, 6.71; N, 9.65. Found: C, 68.33; H, 6.56; N, 9.42.

Example 305

Cyclohexyl-ethyl-(3-{4-[5-(2-phenoxy-ethylsulfanylmethyl)-[1,3,4]oxadiazol-2-yl]-phenyl}-allyl)-amine

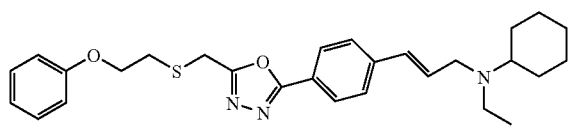

The title compound was synthesized from 3-{4-[5-(2-phenoxy-ethylsulfanylmethyl)-[1,3,4]oxadiazol-2-yl]-phenyl}-propenal using a method similar to that described for ethyl-isopropyl-(3-{4-[5-(2-phenoxy-ethylsulfanylmethyl)-[1,3,4]oxadiazol-2-yl]-phenyl}-allyl)-amine: ES-MS 478.3 (M+1), $^1H$ NMR ($CDCl_3$): δ 7.96 (ap d, J=8.4 Hz, 2H), 7.48 (ap d, J=8.4 Hz, 2H), 7.29–7.24 (m, 2H), 6.95 (ap t, 1H), 6.90 (ap d, 2H), 6.55 (d, J=16.1 Hz, 1H), 6.41 (m, 1H), 4.22 (t, J=6.1 Hz, 2l1), 4.06 (s, 2H), 3.33 (d, J=5.8 Hz, 2H), 3.07 (t, J=6.1 Hz, 2H), 2.64–2.53 (m, 3H), 1.88–1.75 (m, 4H), 1.64 (ap d, J=11.5 Hz, 2H), 1.25 (m, 4H), 1.06 (t, J=7.1 Hz, 3H). Anal. calcd. for $C_{28}H_{35}N_3O_2S$: C, 70.41; H, 7.39; N, 8.80; Found: C, 69.92; H, 7.32; N, 8.65.

Example 306

4-(3-{4-[5-(2-Phenoxy-ethylsulfanylmethyl)-[1,3,4]oxadiazol-2-yl]-phenyl}-allyl)-morpholine

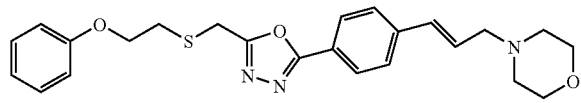

The title compound was synthesized from 3-{4-[5-(2-phenoxy-ethylsulfanylmethyl)-[1,3,4]oxadiazol-2-yl]-phenyl}-propenal using a method similar to that described for ethyl-isopropyl-(3-{4-[5-(2-phenoxy-ethylsulfanylmethyl)-[1,3,4]oxadiazol-2-yl]-phenyl}-allyl)-amine: ES-MS 438.3 (M+1), $^1$H NMR (CDCl$_3$): δ 7.97 (ap d, J=8.2 Hz, 2H), 7.48 (ap d, J=8.2 Hz, 2H), 7.29–7.24 (m, 2H), 6.95 (ap t, 1H), 6.89 (ap d, 2H), 6.59 (d, J=16.0 Hz, 1H), 6.40 (m, 1H), 4.22 (t, J=6.1 Hz, 2H), 4.06 (s, 2H), 3.76 (ap t, J=4.5 Hz, 4H), 3.20 (d, J=6.6 Hz, 2H), 3.07 (t, I=6.2 Hz, 2H), 2.53 (br s, 4H). Anal. calcd. for C$_{24}$H$_{27}$N$_3$O$_3$S: C, 65.88; H, 6.22; N, 9.60. Found: C, 65.61; H, 6.18; N, 9.56.

Example 307

Benzyl-methyl-(3-{4-[5-(2-phenoxy-ethylsulfanylmethyl)-[1,3,4]oxadiazol-2-yl]-phenyl}-20 allyl)-amine

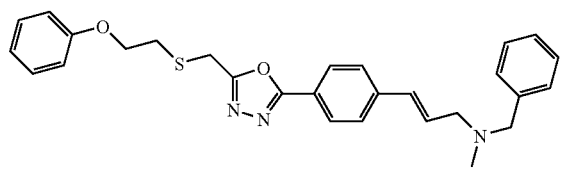

The title compound was synthesized from 3-{4-[5-(2-phenoxy-ethylsulfanylmethyl)-[1,3,4]oxadiazol-2-yl]-phenyl}-propenal using a method similar to that described for ethyl-isopropyl-(3-{4-[5-(2-phenoxy-ethylsulfanylmethyl)-[1,3,4]oxadiazol-2-yl]-phenyl}-allyl)-amine: ES-MS 472.3 (M+1), $^1$H NMR (CDCl$_3$): δ 7.97 (ap d, J=8.6 Hz, 2H), 7.48 (ap d, J=8.5 Hz, 2H), 7.36–7.31 (m, 4H), 7.29–7.24 (m, 3H), 6.98–6.87 (m, 3H), 6.59 (d, J=16.1 Hz, 1H), 6.48–6.40 (m, 1H), 4.22 (t, J=6.2 Hz, 2H), 4.06 (s, 2H), 3.58 (br s, 2H), 3.23 (d, J=6.2 Hz, 2H), 3.06 (t, J=6.2 Hz, 2H), 2.28 (s, 3H). Anal. calcd. for C$_{28}$H$_{29}$N$_3$O$_2$S: C, 71.31; H, 6.20; N, 8.91. Found: C, 70.81; H, 6.20; N, 8.75.

Example 308

1-(3-{4-[5-(2-Phenoxy-ethylsulfanylmethyl)-[1,3,4]oxadiazol-2-yl]-phenyl}-allyl)-4-phenyl-piperazine

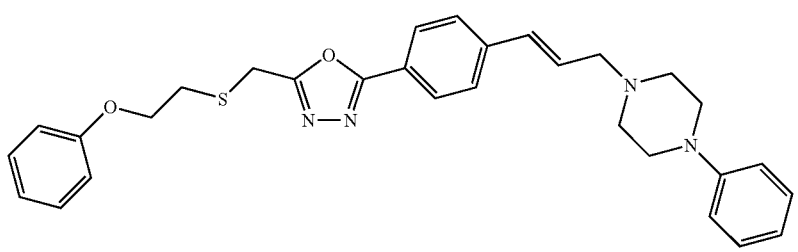

The title compound was synthesized from 3-{4-[5-(2-phenoxy-ethylsulfanylmethyl)-[1,3,4]oxadiazol-2-yl]-phenyl}-propenal using a method similar to that described for ethyl-isopropyl-(3-{4-[5-(2-phenoxy-ethylsulfanylmethyl)-[1,3,4]oxadiazol-2-yl]-phenyl}-allyl)-amine: ES-MS 513.3 (M+1), $^1$H NMR (CDCl$_3$): δ 7.98 (ap d, J=8.4 Hz, 2H), 7.50 (ap d, J=8.4 Hz, 2H), 7.29–7.24 (m, 4H), 6.98–6.84 (m, 6H), 6.62 (d, J=16.0 Hz, 1H), 6.45 (m, 1H), 4.22 (t, J=6.2 Hz, 2H), 4.06 (s, 2H), 3.26 (m, 6H), 3.07 (t, J=6.2 Hz, 2H), 2.70 (ap t, 4H). Anal. calcd. for C$_{30}$H$_{32}$N$_4$O$_2$S: C, 70.28; H, 6.29; N, 10.93. Found: C, 70.26; H, 6.28; N, 10.92.

Example 309

1-Methyl-(3-{4-[5-(2-phenoxy-ethylsulfanylmethyl)-[1,3,4]oxadiazol-2-yl]-phenyl}-allyl)-piperazine

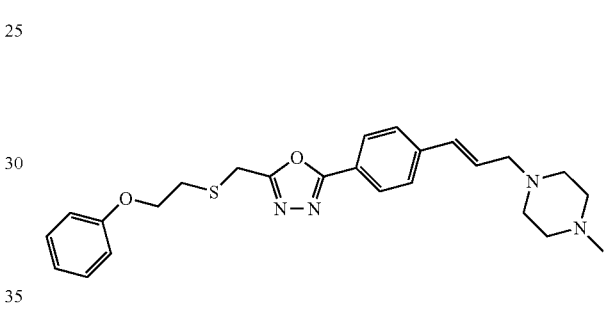

The title compound was synthesized from 3-{4-[5-(2-phenoxy-ethylsulfanylmethyl) [1,3,4]oxadiazol-2-yl]-phenyl}-propenal using a method similar to that described for ethyl-isopropyl-(3-{4-[5-(2-phenoxy-ethylsulfanylmethyl)-[1,3,4]oxadiazol-2-yl]-215 phenyl}-allyl)-amine: ES-MS 451.3 (M+1), $^1$H NMR (CDCl$_3$): δ 7.97 (ap d, J=8.4 Hz, 2H), 7.47 (ap d, J=8.4 Hz, 2H), 7.29–7.24 (m, 2H), 6.95 (ap t, 1H), 6.90 (ap d, 2H), 6.58 (d, J=15.8 Hz, 1H), 6.41 (m, 1H), 4.22 (t, J=6.3 Hz, 2H), 4.06 (s, 2H), 3.22 (d, J=6.8 Hz, 2H), 3.07 (t, J=6.2 Hz, 2H), 2.54 (br s, 8H), 2.33 (s, 3H). Anal. calcd. for C$_{25}$H$_{30}$N$_4$O$_2$S: C, 66.64; H, 6.71; N, 12.43. Found: C, 66.08; H, 6.71; N, 12.17.

Example 310

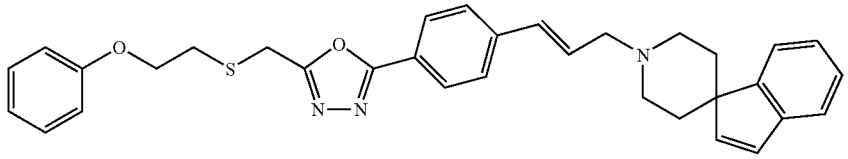

The title compound was synthesized from 3-{4-[5-(2-phenoxy-ethylsulfanylmethyl)-[1,3,4]oxadiazol-2-yl]-phenyl}-propenal using a method similar to that described for ethyl-isopropyl-(3-{4-[5-(2-phenoxy-ethylsulfanylmethyl)-[1,3,4]oxadiazol-2-yl]-phenyl}-allyl)-amine: ES-MS 536.4 (M+1), $^1$H NMR (CDCl$_3$): δ 7.98 (ap d, J=8.5 Hz, 2H), 7.51 (ap d, J=8.5 Hz, 2H), 7.39 (d, J=7.0 Hz, 1H), 7.34–7.18 (m, 5H), 6.98–6.85 (m, 3H), 6.76 (d, J=5.7 Hz, 1H), 6.63 (d, J=15.8 Hz, 1H), 6.56–6.41 (m, 1H), 4.22 (t, J=6.2 Hz, 2H), 4.06 (s, 2H), 3.35 (ap d, 2H), 3.12–3.05 (m, 4H), 2.43 (ap t, 2H), 2.25 (ap t, 2H), 1.42 (ap d, 2H). Anal. calcd. for C$_{33}$H$_{33}$N$_3$O$_2$S: C, 73.99; H, 6.21; N, 7.84. Found: C, 72.89; H, 6.04; N, 7.69.

Example 311

1-(3-{4-[5-(2-Phenoxy-ethylsulfanylmethyl)-[1,3,4]oxadiazol-2-yl]-phenyl}-allyl)-4-phenyl-piperidine-4-carbonitrile

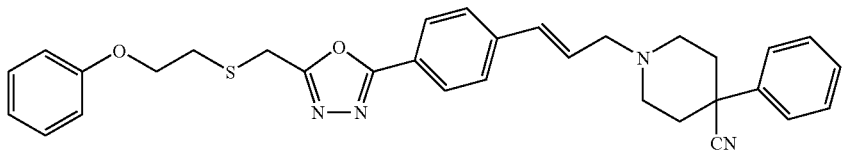

The title compound was synthesized from 3-{4-[5-(2-phenoxy-ethylsulfanylmethyl)-[1,3,4]oxadiazol-2-yl]-phenyl}-propenal using a method similar to that described for ethyl-isopropyl-(3-{4-[5-(2-phenoxy-ethylsulfanylmethyl)-[1,3,4]oxadiazol-2-yl]-phenyl}-allyl)-amine: ES-MS 537.2 (M+1), $^1$H NMR (CDCl$_3$): δ 7.99 (ap d, J=8.4 Hz, 2H), 7.51 (m, 4H), 7.41 (ap t, 2H), 7.35 (ap d, 1H), 7.30–7.24 (m, 2H), 6.95 (ap t, J=7.4 Hz, 1H), 6.90 (ap d, 21), 6.63 (d, J=15.9 Hz, 1H), 6.42 (m, 1H), 4.22 (t, J=6.1 Hz, 2H), 4.07 (s, 2H), 3.32 (d, J=6.2 Hz, 2H), 3.13 (d, J=12.1 Hz, 2H), 3.07 (t, J=6.2 Hz, 2H), 2.58 (m, 2H), 2.16 (m, 4H). Anal. calcd. for C$_{32}$H$_{32}$N$_4$O$_2$S: C, 71.61; H, 6.01; N, 10.44. Found: C, 71.10; H, 6.07; N 10.22.

Example 312

Cyclopentyl-methyl-(3-{4-[5-(2-phenoxy-ethylsulfanylmethyl)-[1,3,4]oxadiazol-2-yl]-phenyl}-allyl)-amine

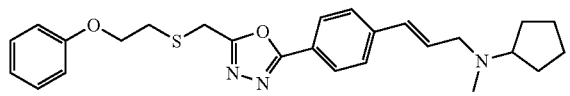

The title compound was synthesized from 3-{4-[5-(2-phenoxy-ethylsulfanylmethyl)-[1,3,4]oxadiazol-2-yl]-phenyl}-propenal using a method similar to that described for ethyl-isopropyl-(3-{4-[5-(2-phenoxy-ethylsulfanylmethyl)-[1,3,4]oxadiazol-2-yl]-phenyl}-allyl)-amine: ES-MS 450.3 (M+1), $^1$H NMR (CDCl$_3$): δ 7.97 (ap d, J=8.3 Hz, 2H), 7.47 (ap d, J=8.3 Hz, 2H), 7.29–7.24 (m, 2H), 6.95 (ap t, 1H), 6.90 (m, 2H), 6.56 (d, J=16.1 Hz, 1H), 6.50–6.42 (m, 1H), 4.22 (t, J=6.1 Hz, 2H), 4.06 (s, 2H), 3.28 (ap d, 2H), 3.05 (t, J=6.2 Hz, 2H), 2.76 (m, 1H), 2.30 (br s, 3H), 1.90 (m, 2H), 1.73 (m, 2H), 1.64–1.43 (m, 4H). Anal. calcd. for C$_{26}$H$_{31}$N$_3$O$_2$S: C, 69.46; H, 6.95; N, 9.35. Found: C, 69.24; H, 6.83; N, 9.25.

Example 313

Preparation of 2-[4-(1H-Imidazol-4-yl)-phenyl]-5-(2-phenoxy-ethylsulfanylmethyl)-[1,3,4]oxadiazole

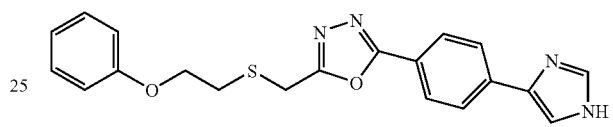

a) 2-(2-Phenoxy-ethylsulfanylmethyl)-5-{4-[4-(toluene-4-sulfonyl)-4,5-dihydro-oxazol-5-yl]-phenyl}-[1,3,4]oxadiazole

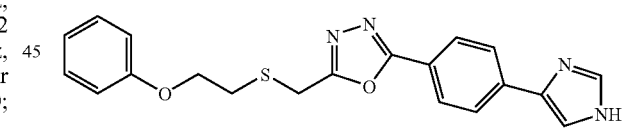

A solution of 4-[5-(2-Phenoxy-ethylsulfanylmethyl)-[1,3,4]oxadiazol-2-yl]-benzaldehyde (1.53 g, 4.50 mmol) in anhydrous ethanol (10 mL) was treated with tosylmethyl isocyanide (0.70 g, 5.40 mmol) and KCN (0.30 g, 0.45 mmol) and stirred under N$_2$ at rt for 1 hour, giving a thick slurry. The mixture was diluted with ether and filtered through paper. The precipitate was triturated with ether and filtered again, and the remaining solvent removed under vacuum to give the title compound as an amorphous brown solid:

$^1$H NMR (CDCl$_3$): δ 8.06 (ap d, J=8.4 Hz, 2H), 7.85 (ap d, J=8.4 Hz, 2H), 7.48 (ap d, J=8.5 Hz, 2H), 7.39 (ap d, J=8.0 Hz, 2H), 7.28–7.23 (m, 3H), 6.95–6.87 (m, 3H), 6.12 (d, J=6.2 Hz, 1H), 5.01 (ap d, J=6.2 Hz, 1H), 4.21 (t, J=6.0 Hz, 2H), 4.07 (s, 2H), 3.06 (t, J=6.0 Hz, 2H), 2.47 (s, 3H).

b) 2-[4-(1H-Imidazol-4-yl)-phenyl]-5-(2-phenoxy-ethylsulfanylmethyl)-[1,3,4]oxadiazole

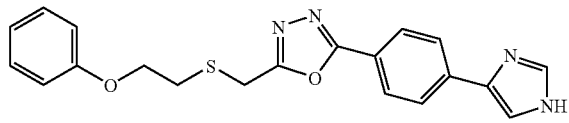

In a sealed vial, a solution of 2-(2-Phenoxy-ethylsulfanylmethyl)-5-{4-[4-(toluene-4-sulfonyl)-4,5-dihydro-oxazol-5-yl]-phenyl}-[1,3,4]oxadiazole (0.405 g, 0.75 mmol) in 7N NH₃/MeOH (5 mL, 35 mmol) was microwaved at 100° C. for 15 minutes. The mixture was concentrated, diluted with H₂O, extracted with EtOAc (3×), dried over MgSO₄, filtered and concentrated. The crude product was purified by radial chromatography on silica gel (gradient EtOAc/Hexane 10%–100%; MeOH/EtOAC 10%) to give the title compound: ES-MS 379.3 (M+1), ¹H NMR (CDCl₃): δ 8.04 (ap d, J=8.4 Hz, 2H), 7.89 (ap d, J=8.4 Hz, 2H), 7.82 (s, 1H), 7.46 (s, 1H), 7.29–7.24 (m, 2H), 6.97–6.87 (m, 3H), 4.22 (t, J=6.1 Hz, 2H), 4.07 (s, 2H), 3.07 (t, J=6.1 Hz, 2H).

Example 314

Preparation of 4-[5-(2-Phenoxy-ethylsulfanylmethyl)-[1,3,4]oxadiazol-2-yl]-benzaldehyde

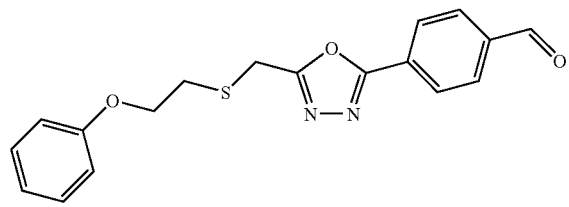

a) 4-Dimethoxymethyl-benzoic acid methyl ester

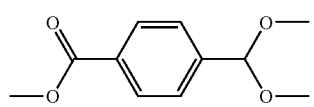

To a solution of 4-formyl-benzoic acid methyl ester (31.9 g, 194 mmol) in methanol (150 mL) was added p-toluenylsulfonic acid (36.9 g, 194 mmol), trimethyl orthoformate (42 mL, 388 mmol), and oven-dried 4 A mol sieves (20 g). The mixture was stirred at 70° C. for 16 h, concentrated on the Rotovap, diluted with ether, vacuum filtered through paper and the filtrate neutralized with sat. aq. NaHCO₃. The organic phase was set aside, the aqueous phase was extracted with EtOAc (2×) and the combined organics washed with sat. aq. NaHCO₃, dried over MgSO₄, filtered and concentrated to give the title compound (21.55 g): ¹H NMR (CDCl₃): δ 8.40 (ap d, J=8.4 Hz, 2H), 7.54 (ap d, J=8.1 Hz, 2H), 3.93 (s, 3H), 3.34 (s, 6H); TLC (30% EtOAc/Hexane) 0.44.

b) 4-Dimethoxymethyl-benzoic acid hydrazide

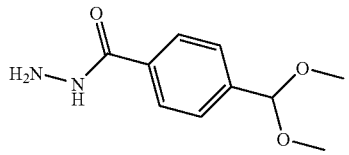

To a solution of 4-dimethoxymethyl-benzoic acid methyl ester (21.55 g, 102 mmol) in isopropanol (70 mL) under N₂ was added hydrazine (7.5 mL, 256 mmol) by syringe. The mixture was stirred at 100° C. for 16 hours, allowed to cool to rt and concentrated on the Rotovap. The crude product was redissolved in CH₂Cl₂, concentrated, and placed on high vacuum for 4 hours to give the title compound (21.37 g): ¹H NMR (DMSO-d₆): δ 9.75 (s, 1H), 7.80 (ap d, J=8.4 Hz, 2H), 7.42 (ap d, J=8.4 Hz, 2H), 4.51 (br s, 2H), 3.23 (s, 6H); TLC (EtOAc) 0.09.

c) 4-Dimethoxymethyl-benzoic acid NM-[2-(2-phenoxy-ethylsulfanyl)-acetyl]-hydrazide

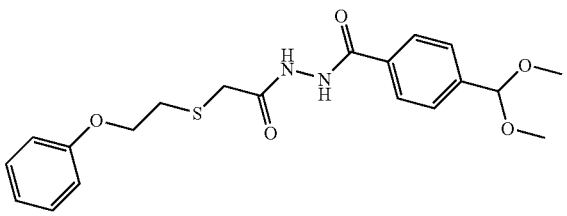

A solution of (2-phenoxy-ethylsulfanyl)-acetic acid (23.83 g, 112 mmol) in THF/MeCN 1:1 (100 mL) was treated with N,N'-carbonyldiimidazole (18.20 g, 112 mmol) then heated at 60° C. for one hour. After cooling to rt, 4-dimethoxymethyl-benzoic acid hydrazide (23.60 g, 112 mmol) was added neat. The mixture was stirred for 2 hours at rt, concentrated, diluted with 65% sat. aq. NaHCO₃, extracted with EtOAc (3×), washed with brine, dried over MgSO₄, filtered, and the solvent removed under vacuum to give the title compound. This crude product was used in the next step without further purification: ES-MS 387.1 (M+1), ¹H NMR (DMSO-d₆): δ 10.47 (s, 1H), 10.13 (s, 1H), 7.88 (ap d, J=8.4 Hz, 2H), 7.48 (ap d, J=8.4 Hz, 2H), 7.29–7.25 (m, 2H), 6.96–6.89 (m, 3H), 4.18 (t, J=6.6 Hz, 2H), 3.32 (s, 2H), 3.25 (s, 6H), 3.04 (t, J=6.6 Hz, 2H).

d) 4-[5-(2-Phenoxy-ethylsulfanylmethyl)-[1,3,4]oxadiazol-2-yl]-benzaldehyde

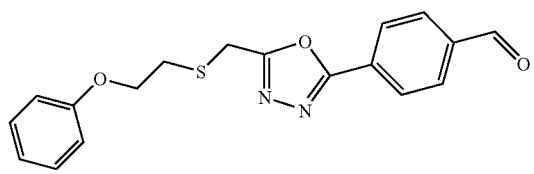

A mixture of 4-dimethoxymethyl-benzoic acid N'-[2-(2-phenoxy-ethylsulfanyl)-acetyl]-hydrazide (112 mmol), triphenylphosphine (32.3 g, 123 mmol), and TEA (55 mL, 392 mmol) in THF was chilled in an ice bath and treated with carbon tetrabromide (40.8 g, 331.6 mmol) in 3 portions over 10 minutes. After 30 minutes, the reaction was removed from the bath and stirred 3 hours at rt, then diluted with EtOAc (200 mL) and 2N HCl (250 mL) and stirred overnight. The mixture was poured into EtOAc (200 mL), shaken, and the organic phase removed. The aqueous phase was extracted with EtOAc (2×) and the combined organic phases were washed with brine, dried over MgSO$_4$, filtered and concentrated. The resulting crude was purified by flash chromatography on silica gel (gradient EtOAc/Hexane 10%–100%) to give the title compound as a white residue (23.92 g): ES-MS 341.0 (M+1), $^1$H NMR (CDCl$_3$): δ 10.09 (s, 1H), 8.21 (ap d, J=8.4 Hz, 2H), 8.01 (ap d, J=8.4 Hz, 2H), 7.29–7.24 (m, 2H), 6.98–6.87 (m, 3H), 4.23 (t, J=6.0 z, 2H), 4.11 (s, 2H), 3.08 (t, J=6.0 Hz, 2H).

dehyde using a method similar to that described for 4-{4-[5-(2-phenoxy-ethylsulfanylmethyl)-[1,3,4]oxadiazol-2-yl]-benzyl}-morpholine: ES-MS 425.2 (M+1), $^1$H NMR (CDCl$_3$): δ 7.99 (ap d, J=8.3 Hz, 2H), 7.47 (ap d, J=8.4 Hz, 2H), 7.30–7.25 (m, 2H), 6.96 (ap t, 1H), 6.90 (m, 2H), 4.22 (t, J=6.1 Hz, 2H), 4.07 (s, 2H), 3.59 (s, 2H), 3.07 (t, J=6.1 Hz, 2H), 2.52 (br s, 8H), 2.33 (s, 3H). Anal. calcd. for C$_{23}$H$_{28}$N$_4$O$_2$S: C, 65.07; H, 6.65; N, 13.20. Found: C, 64.23; H, 6.51; N, 12.96.

Example 317

1'-{4-[5-(2-Phenoxy-ethylsulfanylmethyl)-[1,3,4] oxadiazol-2-yl]-benzyl}-[1,4']bipiperidinyl

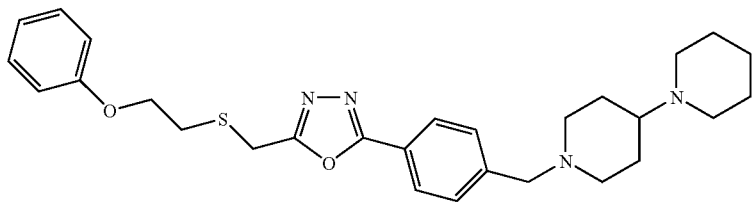

Example 315

4-{4-[5-(2-Phenoxy-ethylsulfanylmethyl)-[1,3,4] oxadiazol-2-yl]-benzyl}-morpholine

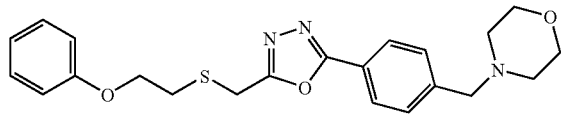

To a solution of 4-[5-(2-phenoxy-ethylsulfanylmethyl)-[1,3,4]oxadiazol-2-yl]-benzaldehyde (0.533 g, 1.57 mmol) in 1,2-dichloroethane (10 mL) was added morpholine (0.27 mL, 3.13 mmol) and finely ground NaBH(OAc)$_3$ (0.50 g, 2.35 mmol). The reaction was stirred 2 hours at rt, quenched with H$_2$O (10 mL) and the organic phase removed. The aqueous phase was extracted with EtOAc (2×) and the combined organic phases dried over MgSO$_4$, filtered and concentrated. The crude product was purified by flash chromatography on silica gel (gradient EtOAc/Hexane 30%–85%) to give the title compound as an amorphous white solid (0.415 g): ES-MS 412.2 (M+1), $^1$H NMR (CDCl$_3$): δ 7.99 (ap d, J=8.4 Hz, 2H), 7.47 (ap d, J=8.4 Hz, 2H), 7.29–7.24 (m, 2H), 6.95 (ap t, 1H), 6.89 (m, 2H), 4.21 (t, J=6.2 Hz, 2H), 4.06 (s, 2H), 3.73 (t, J=4.6 Hz, 4H), 3.57 (s, 2H), 3.06 (t, J=6.2 Hz, 2H), 2.47 (ap t, 4H). Anal. calcd. for C$_{22}$H$_{25}$N$_3$O$_3$S: C, 64.21; H, 6.12; N, 10.21; O, 11.66; S, 7.79. Found: C, 64.84; H, 5.86; N, 9.15; O, 11.39; S, 7.99.

Example 316

1-Methyl-4-{4-[5-(2-phenoxy-ethylsulfanylmethyl)-[1,3,4]oxadiazol-2-yl]-benzyl}-piperazine

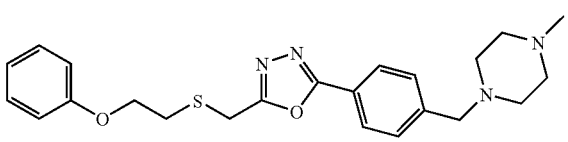

The title compound was synthesized from 4-[5-(2-phenoxy-ethylsulfanylmethyl)-[1,3,4]oxadiazol-2-yl]-benzaldehyde The title compound was synthesized from 4-[5-(2-phenoxy-ethylsulfanylmethyl)-[1,3,4]oxadiazol-2-yl]-benzaldehyde using a method similar to that described for 4-{4-[5-(2-phenoxy-ethylsulfanylmethyl)-[1,3,4]oxadiazol-2-yl]-benzyl}-morpholine: ES-MS 493.2 (M+1), $^1$H NMR (CDCl$_3$): δ 7.97 (ap d, J=8.3 Hz, 2H), 7.45 (ap d, J=8.3 Hz, 2H), 7.29–7.24 (m, 2H), 6.97–6.88 (m, 3H), 4.21 (t, J=6.2 Hz, 2H), 4.06 (s, 2H), 3.54 (s, 2H), 3.06 (t, J=6.2 Hz, 2H), 2.93 (d, J=11.9 Hz, 2H), 2.53 (br s, 4H), 2.29 (ap t, 1H), 2.00 (ap t, 2H), 1.80 (ap d, 2H), 1.68–1.56 (m, 6H), 1.45, (m, 2H). Anal. calcd. for C$_{28}$H$_{36}$N$_4$O$_2$S: C, 68.26; H, 7.37; N, 11.37. Found: C, 67.68; H, 7.19; N, 11.22.

Example 318

{4-[5-(2-Phenoxy-ethylsulfanylmethyl)-[1,3,4]oxadiazol-2-yl]-benzyl}-pyridin-2-yl-amine

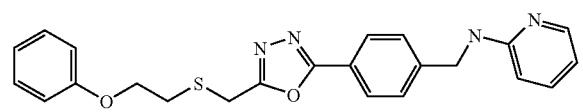

The title compound was synthesized from 4-[5-(2-phenoxy-ethylsulfanylmethyl)-[1,3,4]oxadiazol-2-yl]-benzaldehyde using a method similar to that described for 4-{4-[5-(2-phenoxy-ethylsulfanylmethyl)-[1,3,4]oxadiazol-2-yl]-benzyl}-morpholine: ES-MS 419.2 (M+1), $^1$H NMR (CDCl$_3$): δ 8.09 (ap d, J=8.4 Hz, 1H), 8.00 (ap d, J=8.4 Hz, 2H), 7.51–7.43 (m, 3H), 7.29–7.23 (m, 2H), 6.97–6.87 (m, 3H), 6.65 (m, 1H), 6.41 (ap d, J=8.3 Hz, 1H), 4.63 (d, J=6.3 Hz, 2H), 4.21 (t, J=6.1 Hz, 2H), 4.06 (s, 2H), 3.07 (t, J=6.2 Hz, 2H). Anal. calcd. for C$_{23}$H$_{22}$N$_4$O$_2$S: C, 66.01; H, 5.30; N, 13.39. Found: C, 65.23; H, 5.36; N, 12.71.

Example 319

{4-[5-(2-Phenoxy-ethylsulfanylmethyl)-[1,3,4]oxadiazol-2-yl]-benzyl}-pyridin-2-ylmethyl-amine

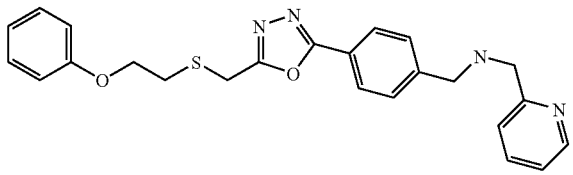

The title compound was synthesized from 4-[5-(2-phenoxy-ethylsulfanylmethyl)-[1,3,4]oxadiazol-2-yl]-benzaldehyde using a method similar to that described for 4-{4-[5-(2-phenoxy-ethylsulfanylmethyl)-[1,3,4]oxadiazol-2-yl]-benzyl}-morpholine: ES-MS 433.3 (M+1), $^1$H NMR (CDCl$_3$): δ 8.58 (ap d, 1H), 8.00 (ap d, J=8.2 Hz, 2H), 7.67 (td, J=7.7, 1.8 Hz, 2H), 7.53 (d, J=8.4 Hz, 2H), 7.33–7.24 (m, 3H), 7.20 (m, 1H) 6.97–6.88 (m, 3H), 4.22 (t, J=6.2 Hz, 2H), 4.06 (s, 2I), 3.99 (s, 2H), 3.97 (s, 2H), 3.07 (t, J=6.2 Hz, 2H).

Example 320

{4-[5-(2-Phenoxy-ethylsulfanylmethyl)-[1,3,4]oxadiazol-2-yl]-benzyl}-pyrimidin-4-ylmethyl-amine

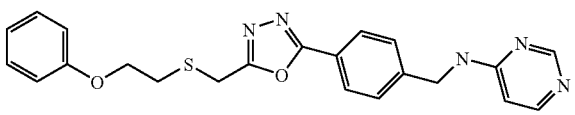

The title compound was synthesized from 4-[5-(2-phenoxy-ethylsulfanylmethyl)-[1,3,4]oxadiazol-2-yl]-benzaldehyde using a method similar to that described for 4-{4-[5-(2-phenoxy-ethylsulfanylmethyl)-[1,3,4]oxadiazol-2-yl]-benzyl}-morpholine: ES-MS 420.1 (M+1), $^1$H NMR (CDCl$_3$): δ 8.60 (br s, 1H), 8.20 (br s, 1H), 8.00 (ap d, J=8.3 Hz, 2H), 7.45 (d, J=8.2 Hz, 2H), 7.28–7.23 (m, 2H), 6.97–6.86 (m, 3H), 6.37 (d, J=5.9 Hz, 1H), 4.66 (d, J=5.9 Hz, 2H), 4.21 (t, J=6.1 Hz, 2H), 4.06 (s, 2H), 3.06 (t, J=6.2 Hz, 2H).

Example 321

{4-[5-(2-Phenoxy-ethylsulfanylmethyl)-[1,3,4]oxadiazol-2-yl]-benzyl}-pyrazin-2-yl-amine

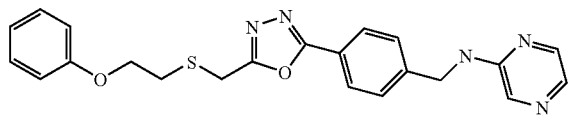

The title compound was synthesized from 4-[5-(2-phenoxy-ethylsulfanylmethyl)-[1,3,4]oxadiazol-2-yl]-benzaldehyde using a method similar to that described for 4-{4-[5-(2-phenoxy-ethylsulfanylmethyl)-[1,3,4]oxadiazol-2-yl]-benzyl}-morpholine: ES-MS 420.1 (M+1), $^1$H NMR (CDCl$_3$): δ 8.01–7.83 (m, 5H), 7.46 (d, J=8.5 Hz, 2H), 7.27–7.22 (m, 2H), 6.95–6.86 (m, 3H), 5.12 (ap t, 1H), 4.66 (d, J=5.9 Hz, 2H), 4.21 (t, J=6.1 Hz, 2H), 4.06 (s, 2H), 3.06 (t, J=6.2 Hz, 2H).

Example 322

{4-[5-(2-Phenoxy-ethylsulfanylmethyl)-[1,3,4]oxadiazol-2-yl]-benzyl}-pyridin-4-ylmethyl-amine

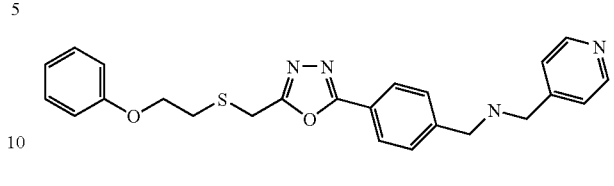

The title compound was synthesized from 4-[5-(2-phenoxy-ethylsulfanylmethyl)-[1,3,4]oxadiazol-2-yl]-benzaldehyde using a method similar to that described for 4-{4-[5-(2-phenoxy-ethylsulfanylmethyl)-[1,3,4]oxadiazol-2-yl]-benzyl}-morpholine: ES-MS 433.3 (M+1), $^1$H NMR (CDCl$_3$): δ 8.57 (dd, J=4.0, 1.5 Hz, 21, 8.01 (ap d, J=8.4 Hz, 2H), 7.49 (ap d, J=8.4 Hz, 2H), 7.32–7.24 (m, 4H), 6.98–6.88 (m, 3H), 4.22 (t, J=6.1 Hz, 2H), 4.07 (s, 2H), 3.90 (s, 2H), 3.85 (s, 2H), 3.07 (t, J=6.1 Hz, 2H).

Example 323

{4-[5-(2-Phenoxy-ethylsulfanylmethyl)-[1,3,4]oxadiazol-2-yl]-benzyl}-(2-pyrrolidin-1-yl-ethyl)-amine

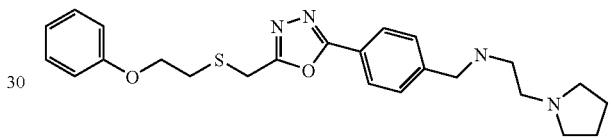

The title compound was synthesized from 4-[5-(2-phenoxy-ethylsulfanylmethyl)-[1,3,4]oxadiazol-2-yl]-benzaldehyde using a method similar to that described 4-{4-[5-(2-phenoxy-ethylsulfanylmethyl)-[1,3,4]oxadiazol-2-yl]-benzyl}-morpholine: ES-MS 439.3 (M+1), $^1$H NMR (CDCl$_3$): δ 7.99 (ap d, J=8.4 Hz, 2H), 7.48 (ap d, J=8.4 Hz, 2H), 7.29–7.24 (m, 2H), 6.98–6.88 (m, 3H), 4.22 (t, J=6.1 Hz, 2H), 4.06 (s, 2H), 3.90 (s, 2H), 3.07 (t, J=6.1 Hz, 2H), 2.85–2.60 (m, 6H), 1.83 (m, 6H). Anal. calcd. for C$_{24}$H$_{30}$N$_4$O$_2$S: C, 65.72; H, 6.89; N, 12.77; 0, 7.30; S, 7.31. Found: C, 65.54; H, 6.91; N, 12.65; O, 7.62; S, 7.31.

Example 324

2-(2-Phenoxy-ethylsulfanylmethyl)-5-(4-pyrrolidin-1-ylmethyl-phenyl)-[1,3,4]oxadiazole

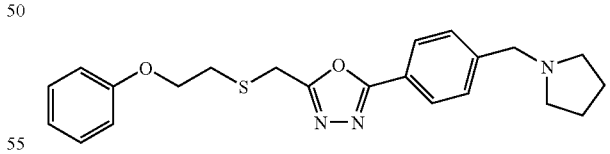

The title compound was synthesized from 4-[5-(2-phenoxy-ethylsulfanylmethyl)-[1,3,4]oxadiazol-2-yl]-benzaldehyde using a method similar to that described 4-{4-[5-(2-phenoxy-ethylsulfanylmethyl)-[1,3,4]oxadiazol-2-yl]-benzyl}-morpholine:

Exact Mass 395.17: MS (aspci): m/z=396.2 (M+1); $^1$H NMR (CDCl$_3$, 300 MHz): δ 8.00 (d, 2H, J=7.65 Hz), 7.47 (d, 2H, J=7.60), 6.28 (app t, 2H, J=7.6 Hz), 6.86–7.00 (m, 3H), 4.23 (t, 2H, J=6.3 Hz), 4.07 (s, 2H), 3.71 (s, 2H), 3.06 (t, 2H, J=6.9 Hz), 2.48–2.62 (m, 4H), 1.75–1.90 (m, 4H). TLC (EtOAc) R$_f$ 0.02.

Example 325

Diethyl-{4-[5-(2-phenoxy-ethylsulfanylmethyl)-[1,3,4]oxadiazol-2-yl]-benzyl}-amine

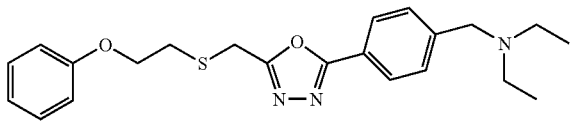

The title compound was synthesized from 4-[5-(2-phenoxy-ethylsulfanylmethyl)-[1,3,4]oxadiazol-2-yl]-benzaldehyde using a method similar to that described 4-{4-[5-(2-phenoxy-ethylsulfanylmethyl)-[1,3,4]oxadiazol-2-yl]-benzyl}-morpholine:

Exact Mass 397.18: MS (aspci): m/z=398.2 (M+1);
$^1$H NMR (CDCl$_3$, 300 MHz): δ 7.99 (d, 2H, J=7.5 Hz), 7.50 (d, 2H, J=7.5), 7.27 (t, 3H, J 37.4 Hz), 6.86–7.00 (m, 4H), 4.22 (t, 2H, 6.0 Hz), 4.07 (s, 2H), 3.07 (t, 2H, J=6.6 Hz), 2.57 (q, 4H, J=7.5 Hz), 1.07 (t, 6H, J=7.0 Hz). TLC (EtOAc) R$_f$ 0.01.

Example 326

1-{4-[5-(2-Phenoxy-ethylsulfanylmethyl)-[1,3,4]oxadiazol-2-yl]-benzyl}-piperidine

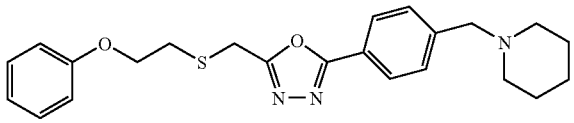

The title compound was synthesized from 4-[5-(2-phenoxy-ethylsulfanylmethyl)-[1,3,4]oxadiazol-2-yl]-benzaldehyde using a method similar to that described 4-{4-[5-(2-phenoxy-ethylsulfanylmethyl)-[1,3,4]oxadiazol-2-yl]-benzyl}-morpholine:

Exact Mass 409.18: MS (aspci): m/z=410.1 (M+1);
$^1$H NMR (CDCl$_3$, 300 MHz): δ 7.90–8.10 (m, 2H), 7.42–7.58 (m, 2H), 7.15–7.45 (m, 3H), 6.85–7.00 (m, 4H), 4.22 (t, 2H, J=5.95 Hz), 4.07 (s, 2H), 3.55 (b s, 2H), 3.08 (t, 2H, J=6.3 Hz), 2.30–2.49 (m, 4H), 1.38–1.70 (m, 6H). TLC (EtOAc) R$_f$ 0.02.

Example 327

N-{4-[5-(2-Phenoxy-ethylsulfanylmethyl)-[1,3,4]oxadiazol-2-yl]-benzyl}-N-(2-pyrrolidin-1-yl-ethyl)-acetamide

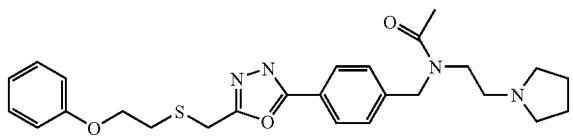

A mixture of {4-[5-(2-phenoxy-ethylsulfanylmethyl)-[1,3,4]oxadiazol-2-yl]-benzyl}-(2-pyrrolidin-1-yl-ethyl)-amine (0.505 g, 1.14 mmol) and pyridine (1.8 mL, 23 mmol) in CH$_2$Cl$_2$ (8 mL) was treated with acetic anhydride (1.1 mL, 11.4 mmol) and stirred at rt overnight. The mixture was poured into sat. aq. NaHCO$_3$ and extracted with EtOAc (3×). The combined organics were dried over MgSO$_4$, filtered and concentrated. The crude product was purified by radial chromatography (gradient EtOAc/Hexane 20%–100%; 7N NH$_3$ in MeOH/EtOAc 10%–20%) and recrystallized in CH$_2$Cl$_2$/ether/hexane to give the title compound as a white powder (0.288 g): ES-MS 481.3 (M+1), $^1$H NMR (CDCl$_3$): δ 8.00 (m, 2), 7.39–7.24 (m, 4H), 6.98–6.88 (m, 3H), 4.70 (s, 2H), 4.22 (ap t, J=6.1 Hz, 2H), 4.07 (d, J=4.3 Hz, 2H), 3.60–3.40 (m, 2H), 3.02 (m, 2H), 2.62 (t, J=7.5 Hz, 2H), 2.51 (ap t, 4H), 2.24, 2.14 (s, 3H), 1.85–1.76 (m, 4H). Anal. calcd. for C$_{26}$H$_{32}$N$_4$O$_3$S: C, 64.97; H, 6.71; N, 11.66; 0, 9.99; S, 6.67. Found: C, 65.08; H, 6.75; N, 11.70; O, 9.88; S, 6.77.

We claim:
1. A compound of formula I:

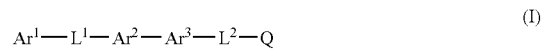

or a pharmaceutically acceptable salt, solvate, enantiomer, diastereomer or mixture of diastereomers thereof wherein:
Ar$^1$ is a phenyl or benzofuranyl optionally substituted with one to five groups selected from C$_1$–C$_8$ alkyl, C$_2$–C$_8$ alkenyl, C$_2$–C$_8$ alkynyl, hydroxy, C$_1$–C$_8$ alkoxy, C$_1$–C$_8$ alkylaryl, phenyl,
—O-aryl, heteroaryl, cycloalkyl, C$_1$–C$_8$ alkylcycloalkyl, cyano, —(CH$_2$)$_n$NR$^6$R$^6$, C$_1$–C$_8$ haloalkyl, C$_1$–C$_8$ haloalkoxy, halo, (CH$_2$)$_n$COR$^6$, (CH$_2$)$_n$NR$^5$SO$_2$R$^6$, —(CH$_2$)$_n$C(O)NR$^6$R$^6$, heterocyclic, and C$_1$–C$_8$ alkylheterocyclic; wherein the cycloalkyl, phenyl, aryl, and heterocyclic; L$^1$ is a bond or represented by the formula X$_2$—(CR$^3$R$^4$)$_m$—X$_3$ where X$_2$ is attached to Ar$^1$ and X$_3$ is attached to Ar$^2$ wherein R$^3$ and R$^4$ are independently selected from a bond, hydrogen, C$_1$–C$_8$ alkyl, C$_2$–C$_8$ alkylene, C$_2$–C$_8$ alkynyl, phenyl, aryl, C$_1$–C$_8$ alkylaryl;
X$_2$ is independently —CH, —(CR$^3$R$^4$)$_m$, or O(CR$^3$R4)$_m$;
X$_3$ is —S(CR$^3$R$^4$)$_m$, —O(CR$^3$R$^4$)$_m$, or —S(CR$^3$R$^4$)$_m$;
Ar$^2$ is oxazole; and optionally substituted with one to three substitutents independently selected from C$_1$–C$_8$ alkyl, C$_2$–C$_8$ alkenyl, C$_2$–C$_8$ alkynyl, hydroxy, C$_1$–C$_8$ alkoxy, C$_1$–C$_8$ alkylaryl, phenyl, aryl, C$_3$–C$_8$ cycloalkyl, C$_1$–C$_8$ alkylcycloalkyl, cyano, C$_1$–C$_8$ haloalkyl, halo, (CH$_2$)$_n$C(O)R$^6$, (CH$_2$)$_n$C(O)OR$^6$, (CH$_2$)$_n$NR$^5$SO$_2$R$^6$, (CH$_2$)$_n$C(O)NR$^6$R$^6$, and C$_1$–C$_8$ alkylheterocyclic;
Ar$^3$ is phenyl optionally substituted with one to three substituents independently selected from C$_1$–C$_8$ alkyl, C$_2$–C$_8$ alkenyl, C$_2$–C$_8$ alkynyl, halo, —NHR$^5$, C$_1$–C$_8$ haloalkyl, C$_3$–C$_8$ cycloalkyl, hydroxy, alkoxy, (CH$_2$)$_n$C(O)R$^6$, (CH$_2$)$_n$C(O)OR$^6$, (CH$_2$)$_n$NR$^5$SO$^2$R$^6$, (CH$_2$)$_n$C(O)NR$^6$R$^6$, phenyl, C$_1$–C$_8$ alkylaryl, and aryl;
L$^2$ is represented by the formula:

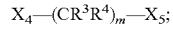

wherein X$_4$ is attached to Ar$^3$ and is selected from the group consisting of —CH, NHCO, NR$^6$'C(O)NR$^6$;
X$_5$ is selected from the group consisting of —CH$_2$, —CH$_2$CH$_2$—, —CH$_2$CH$_2$CH$_2$—, NR$^3$(CR$^3$R$^4$)$_m$;
Q is a group represented by —NR$^1$R$^2$; wherein R$^1$ and R$^2$ combine together, and with the nitrogen atom to which they are attached or with 0, 1, 2 or 3 atoms adjacent to the nitrogen atom to form a four, five, six or seven member nitrogen containing monocyclic heterocycle which may have 1, or 2 substituents independently selected from $C_1$–$C_8$ alkyl, $C_2$–$C_8$ alkenyl, $C_3$–$C_8$ cycloalkane, $C_1$–$C_8$ alkylaryl, —C(O)$C_1$–$C_8$ alkyl, —C(O)O$C_1$–$C_8$ alkyl, $C_1$–$C_8$ alkylcycloalkane, oxo, halo amino, and $(CH_2)_nC(O)NR^6R^{6'}$;

$R^5$ is hydrogen, CN, $C_1$–$C_8$ alkyl, $C_2$–$C_8$ alkenyl, $C_5$–$C_8$ alkylaryl, $(CH_2)_nNSO_2C_1$–$C_8$ alkyl, $(CH_2)_n$ $NSO_2$phenyl, $(CH_2)_nNSO_2$aryl, —C(O)$C_1$–$C_8$ alkyl, or —C(O)O$C_1$–$C_8$ alkyl; and $R^6$ and $R^{6'}$ are each independently hydrogen, $C_1$–$C_8$ alkyl, phenyl, aryl, $C_1$–$C_8$alkylaryl, or $C_3$–$C_8$cycloalkyl;

$R^7$ is hydrogen, $C_1$–$C_8$ alkyl, phenyl, aryl, $C_1$–$C_8$alkylaryl, or $C_3$–$C_8$cycloalkyl, and wherein m is an integer from 1 to 8; and n is an integer from 0 to 8.

2. A compound according to claim 1 wherein the $Ar^1$ is benzofuranyl or phenyl; $L^1$ is —$CH_2OCH_2$—, or —$OCH_2CH_2SCH_2$; Ar is oxazole: $Ar^3$ is phenyl; $L^2$ is $NHCONHCH_2CH_2$; and $R^1$ and $R^2$ combine with each other and with the nitrogen atom to which they are attached to form a nitrogen containing monocyclic ring selected from the group consisting of pyrrolidinyl, piperidinyl, morpholinyl, thiomorpholinyl and azepanyl.

3. A compound according to claim 1 wherein the group $L^1$ is a divalent linker selected from the group consisting of: —$SCH_2$—, —$OCH_2$—, —$CH_2OCH_2$—, —$OCH_2CH_2OCH_2$—, —$OCH_2CH_2SCH_2$— and —$O(CH_2)_3SCH_2$.

4. A compound according to claim 1 wherein the linker $L^2$ is: —$OCH_2CH_2$—, —$O(CH_2)_3$—, —$NHCONHCH_2CH_2$—, —$NHCON(CH_3)CH_2CH_2$—, —$NHCON(CH_3)CH_2CH_2CH_2$—, or —$NHCONHCH_2CH_2CH_2$—.

5. A compound selected from the group consisting of:
1-{4-[2-(Benzofuran-2-ylmethoxymethyl)-oxazol-5-yl]-phenyl}-3-(2-dimethylamino-ethyl)-urea,
1-{4-[2-(Benzofuran-2-ylmethoxymethyl)-oxazol-5-yl]-phenyl}-3-(2-pyrrolidin-1-yl-ethyl)-urea,
1-{4-[2-(Benzofuran-2-ylmethoxymethyl)-oxazol-5-yl]-phenyl}-3-(2-piperidin-1-yl-ethyl)-urea,
1-(3-{4-[2-(2-Phenoxy-ethylsulfanylmethyl)-oxazol-5-yl]-phenoxy}-propyl)-azepane,
1-(3-{4-[2-(2-Phenoxy-ethylsulfanylmethyl)-oxazol-5-yl]-phenoxy}-propyl)-azepane,
1-{4-[2-(2-Phenoxy-ethylsulfanylmethyl)-oxazol-5-yl]-phenyl}-3-(2-pyrrolidin-1-yl-ethyl)-urea,
1-{4-[2-(2-Phenoxy-ethylsulfanylmethyl)-oxazol-5-yl]-phenyl}-3-(3-pyrrolidin-1-yl-propyl)-urea,
1-{4-[2-(2-Phenoxy-ethylsulfanylmethyl)-oxalol-5-yl]-phenyl-}-3-(3-pyrrolidin-1-yl-propyl)-urea,
and pharmaceutically acceptable salts, solvates, enantiomers, diastereomers or mixture of diastereomers thereof.

6. The compound of claim 1 which is the hydrochloride salt or the bisulfate salt.

7. A method of treating obesity comprising administering to a patient in need thereof a compound of claim 1.

8. A method of treating Type II Diabetes comprising administering to a patient in need thereof a compound of claim 1.

9. A pharmaceutical formulation comprising a compound of claim 1 and a pharmaceutical acceptable carrier for the treatment of obesity.

* * * * *